US007264926B2

(12) United States Patent
Meyers

(10) Patent No.: US 7,264,926 B2
(45) Date of Patent: Sep. 4, 2007

(54) NUCLEOSIDE PHOSPHATASE

(75) Inventor: Rachel E. Meyers, Newton, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 731 days.

(21) Appl. No.: 10/160,501

(22) Filed: May 30, 2002

(65) Prior Publication Data

US 2003/0059919 A1    Mar. 27, 2003

Related U.S. Application Data

(63) Continuation-in-part of application No. 09/945,327, filed on Aug. 31, 2001, now abandoned, and a continuation-in-part of application No. 09/907,509, filed on Jul. 16, 2001, now abandoned, and a continuation-in-part of application No. 09/870,110, filed on May 29, 2001, now abandoned, and a continuation-in-part of application No. 09/870,383, filed on May 29, 2001, now abandoned, and a continuation-in-part of application No. 09/870,130, filed on May 29, 2001, now abandoned, and a continuation-in-part of application No. 09/870,133, filed on May 29, 2001, now abandoned, and a continuation-in-part of application No. 09/862,535, filed on May 21, 2001, now abandoned, and a continuation-in-part of application No. 09/860,821, filed on May 18, 2001, now abandoned, and a continuation-in-part of application No. 09/838,573, filed on Apr. 18, 2001, now abandoned.

(60) Provisional application No. 60/318,581, filed on Sep. 10, 2001, provisional application No. 60/229,425, filed on Aug. 31, 2000, provisional application No. 60/218,385, filed on Jul. 14, 2000, provisional application No. 60/207,650, filed on May 26, 2000, provisional application No. 60/205,449, filed on May 19, 2000, provisional application No. 60/207,506, filed on May 26, 2000, provisional application No. 60/205,961, filed on May 19, 2000, provisional application No. 60/207,640, filed on May 26, 2000, provisional application No. 60/207,649, filed on May 26, 2000, provisional application No. 60/197,747, filed on Apr. 18, 2000.

(51) Int. Cl.
*C12N 9/16* (2006.01)
*C12N 15/55* (2006.01)
*C12N 15/63* (2006.01)
*C12Q 1/68* (2006.01)

(52) U.S. Cl. .............. 435/6; 435/196; 435/252.3; 435/325; 435/320.1; 536/23.2

(58) Field of Classification Search ............... 435/195, 435/320.1, 252.3, 6; 536/23.2
See application file for complete search history.

(56) References Cited

U.S. PATENT DOCUMENTS 6,004,808 A * 12/1999 Negulescu et al. ......... 435/325
2002/0147140 A1   10/2002 Rosen et al.

FOREIGN PATENT DOCUMENTS

| WO | WO 01/34629 A1 | | 5/2001 |
| WO | WO 01/70979 | * | 9/2001 |
| WO | WO 01/70979 A2 | | 9/2001 |

OTHER PUBLICATIONS

Shi, J-D., et al. (2001) J. Biol. Chem. 276(20), 17474-17478.*
Blast results and background information of 62088 SEQ ID No. 1 of 10/160501 versus cDNA encoding musculoskeletal system antigens #1497 and #1508 from U.S. 2002/0147140 A1. This result is also found from sequences in other applications in this patent family.
Simpson, A.J.G., "PM1-HT0422-090100-004-h10 HT0422 Homo sapiens cDNA, mRNA sequence," Mar 17, 2000, (sequence) EMBL [online], Hinxton, Cambridge, UK: European Bioinformatics Institute [retrieved on Nov. 24, 2004] Retrieved from internet: URL: http://srs.ebi.ac.uk. EMBL Accession No. AW580249.
Wray, P., "Human DNA sequence from clone RP11-483F11 on chromosome 10, complete sequence," Mar. 4, 2003 (sequence), GenBank [online] Bethesda, MD, USA: [retrieved on Nov. 24, 2004] National Center for Biotechnology Information. Retrieved from the internet: URL: http://www.nchi.nlm.nih.gov. GenBank Accession No. AL133353.

(Continued)

*Primary Examiner*—Rebecca Prouty

(57) ABSTRACT

The invention provides isolated nucleic acids molecules, designated 39228, 21956, 25856, 22244, 8701, 32263, 50250, 55158, 47765, 62088, 50566, and 48118 nucleic acid molecules, which encode novel GTPase activating molecules, cadherin molecules, and ankyrin containing family members. The invention also provides antisense nucleic acid molecules, recombinant expression vectors containing 39228, 21956, 25856, 22244, 8701, 32263, 50250, 55158, 47765, 62088, 50566, and 48118 nucleic acid molecules, host cells into which the expression vectors have been introduced, and non-human transgenic animals in which a 39228, 21956, 25856, 22244, 8701, 32263, 50250, 55158, 47765, 62088, 50566, or 48118 gene has been introduced or disrupted. The invention still further provides isolated 39228, 21956, 25856, 22244, 8701, 32263, 50250, 55158, 47765, 62088, 50566, and 48118 polypeptides, fusion polypeptides, antigenic peptides and anti-39228, 21956, 25856, 22244, 8701, 32263, 50250, 55158, 47765, 62088, 50566, and 48118 antibodies. Diagnostic and therapeutic methods utilizing compositions of the invention are also provided.

23 Claims, 100 Drawing Sheets

OTHER PUBLICATIONS

Wang, C., et al., "Homo sapiens lysosomal apyrase-like protein 1 (LALP1) mRNA, complete cds," May 14, 2001 (sequence), GenBank [online] Bethesda, MD, USA: [retrieved on Nov. 24, 2004] National Center for Biotechnology Information. Retrieved from the internet: URL: http://www.ncbi.nlm.nih.gov. GenBank Accession No. AF269255.

* cited by examiner

Input file Fbh39228FL.seq; Output File 39228.trans
Sequence length 1808

```
GGAGTCGACCCACGCGTCCGGGAGCAGCGGCCGGGGCGGCAGCGGTCCCCAGGCCGGGACACCCGGGGTGGTGCGCCCG
GGTTCGCGGGGGCTGCGCCGGCGCCGGGGAGGCGGGGGGAGCGGGAGCGGGCGACGCGGGGAAGGGGGGAGCCAGGGGG
AGGGCGCCGGCCGGAGGAGGGGCGGACCCGCCGCCCTAGCCGAGCAGAGCACAGCCGAGCCGAGCGGCCCGGGCGGGGG
```

| | | | | | | | | M | L | R | L | V | P | T | G | 8 |
|---|---|---|---|---|---|---|---|---|---|---|---|---|---|---|---|---|

CCGACCCCGGCCAGCGTCGGCGCAGAGAGCGGGCGGAGGCGCAGGCC ATG CTG CGG CTG GTG CCC ACC GGG  24

| A | R | A | I | V | D | M | S | Y | A | R | H | F | L | D | F | Q | G | S | A | 28 |
|---|---|---|---|---|---|---|---|---|---|---|---|---|---|---|---|---|---|---|---|---|

GCC CGG GCC ATC GTG GAC ATG TCG TAC GCC CGC CAC TTC CTG GAC TTC CAG GGC TCC GCC  84

| I | P | Q | A | M | Q | K | L | V | V | T | R | L | S | P | N | F | R | E | A | 48 |

ATT CCC CAA GCC ATG CAG AAG CTG GTG GTG ACC CGG CTG AGC CCC AAC TTC CGC GAG GCC  144

| V | T | L | S | R | D | C | P | V | P | L | P | G | D | G | D | L | L | V | R | 68 |

GTC ACC CTG AGC CGG GAC TGC CCG GTG CCG CTC CCC GGG GAC GGA GAC CTC CTC GTC CGG  204

| N | R | F | V | G | V | N | A | S | D | I | N | Y | S | A | G | R | Y | D | P | 88 |

AAC CGA TTT GTT GGT GTT AAC GCA TCT GAC ATC AAC TAT TCA GCA GGC CGC TAT GAC CCC  264

| S | V | K | P | P | F | D | I | G | F | E | G | I | G | E | V | V | A | L | G | 108 |

TCA GTT AAG CCT CCC TTT GAC ATA GGT TTC GAA GGC ATT GGG GAG GTG GTG GCC CTA GGC  324

| L | S | A | S | A | R | Y | T | V | G | Q | A | V | A | Y | M | A | P | G | S | 128 |

CTC TCT GCT AGT GCC AGA TAC ACA GTT GGC CAA GCT GTG GCT TAC ATG GCA CCT GGT TCT  384

| F | A | E | Y | T | V | V | P | A | S | I | A | T | P | V | P | S | V | K | P | 148 |

TTT GCT GAG TAC ACA GTT GTG CCT GCC AGC ATT GCA ACT CCA GTG CCC TCA GTG AAA CCC  444

| E | Y | L | T | L | L | V | S | G | T | T | A | Y | I | S | L | K | E | L | G | 168 |

GAG TAT CTT ACC CTG CTG GTA AGT GGC ACC ACC GCA TAC ATC AGC CTG AAA GAG CTC GGA  504

| G | L | S | E | G | K | K | V | L | V | T | A | A | A | G | G | T | G | Q | F | 188 |

GGA CTG TCG GAA GGG AAA AAA GTT TTG GTG ACA GCA GCA GCT GGG GGA ACG GGC CAG TTT  564

| A | M | Q | L | S | K | K | A | K | C | H | V | I | G | T | C | S | S | D | E | 208 |

GCC ATG CAG CTT TCA AAG AAG GCA AAG TGC CAT GTA ATT GGA ACC TGC TCT TCT GAT GAA  624

| K | S | A | F | L | K | S | L | G | C | D | R | P | I | N | Y | K | T | E | P | 228 |

AAG TCT GCT TTT CTG AAA TCT CTT GGC TGT GAT CGT CCT ATC AAC TAT AAA ACT GAA CCC  684

| V | G | T | V | L | K | Q | E | Y | P | E | G | V | D | V | V | Y | E | S | V | 248 |

GTA GGT ACC GTC CTT AAG CAG GAG TAC CCT GAA GGT GTC GAT GTG GTC TAT GAA TCT GTT  744

| G | G | A | M | F | D | L | A | V | D | A | L | A | T | K | G | R | L | I | V | 268 |

GGG GGA GCC ATG TTT GAC TTG GCT GTA GAC GCC CTG GCT ACG AAA GGG CGC TTG ATA GTA  804

| I | G | F | I | S | G | Y | Q | T | P | T | G | L | S | P | V | K | A | G | T | 288 |

ATA GGG TTT ATC TCT GGC TAC CAA ACT CCT ACT GGC CTT TCG CCT GTG AAA GCA GGA ACA  864

| L | P | A | K | L | L | K | K | S | A | S | V | Q | G | F | F | L | N | H | Y | 308 |

TTG CCA GCC AAA CTG CTC AAG AAA TCT GCC AGC GTA CAG GGC TTC TTC CTG AAC CAT TAC  924

Fig. 1A

```
L   S   K   Y   Q   A   A   M   S   H   L   L   E   M   C   V   S   G   D   L    328
CTT TCT AAG TAT CAA GCA GCC ATG AGC CAC TTG CTC GAG ATG TGT GTG AGC GGA GAC CTG  984

V   C   E   V   D   L   G   D   L   S   P   E   G   R   F   T   G   L   E   S    348
GTT TGT GAG GTG GAC CTT GGA GAT CTG TCT CCA GAG GGC AGG TTT ACT GGC CTG GAG TCC 1044

I   F   R   A   V   N   Y   M   Y   M   G   K   N   T   G   K   I   V   V   E    368
ATA TTC CGT GCT GTC AAT TAT ATG TAC ATG GGA AAA AAC ACT GGA AAA ATT GTA GTT GAA 1104

L   P   H   S   V   N   S   K   L   *                                            378
TTA CCT CAC TCT GTC AAC AGT AAG CTG TAA                                         1134

AAACAGAACAATGACATAAATCAAGGGAGAAAGAAAATGGGCACTTTATGTCTCAGAATTACTCAAATCAATTTATTTT

TAGTTGGTAATGGATATAATATTTCTTAAAACAAAAGTAAGGTGTTAATGAATAGGTCTCTCCTTCTCCTCCTCCTCCT

CCTCTTCCCTTGGGGGAAAAAAAAAAATGTGCTAATAAAACTTCCCTCCATGGCTAAGAGGGAAAACGCTTACATTCAA

TTCTTTAGTCATGGATGGTCTCGTTCCAGATGTTATTGTTCCAGGGAACTAAATTCATTCCTGATGCCAGATCTGATCG

AGKCAGTATGTCTTCAGCTTGGATCAGGATTTTAAAATCAGTTTTGAAAGTGGGTTCCCGACTTCTTTGGCTTT
```

Fig. 1B

Searching for complete domains in PFAM
hmmpfam - search a single seq against HMM database
HMMER 2.1.1 (Dec.1998)

Copyright (C) 1992-1998 Washington University School of Medicine
HMMER is freely distributed under the GNU General Public License (GPL).
- - - - - - - - - - - - - - - - - - - - - - - - - - - - - - - - - - - -
HMM file:              /prod/ddm/seqanal/PFAM/pfam5.0/Pfam
Sequence file:         /prod/ddm/wspace/orfanal/oa-script.28923.seq
- - - - - - - - - - - - - - - - - - - - - - - - - - - - - - - - - - - -
Query: 39228

Scores for sequence family classification (score includes all domains):
Model        Description                                  Score    E-value  N
------       -----------                                  -----    -------  ---
adh_zinc     Zinc-binding dehydrogenases                   -6.8    2.2e-09  1
Lipase_GDSL  Lipase/Acylhydrolase with GDSL-like motif    -20.4        5.5  1

Parsed for domains:
Model        Domain  seq-f  seq-t   hmm-f  hmm-t       score   E-value
---------    ------  -----  -----   -----  -----       -----   -------
Lipase_GDSL   1/1     103    189 ..    1    146 []     -20.4       5.5
adh_zinc      1/1      47    368 ..    1    384 []      -6.8    2.2e-09

Alignments of top-scoring domains:
Lipase_GDSL: domain 1 of 1, from 103 to 189: score -20.4, E = 5.5
                *->kvvalGDSLtdgggngsestklkdnyrqyrglspssvgdgnfsngtv
                   vvalG S ++ +  g                       ++g+f+++tv
      39228  103 EVVALGLSASARYTVGQAV---------------AYMAPGSFAEYTV 134 lpdilakalgiklgVgikeksilfrvgklqengsltglNfAvgGataedl
                +p+ +a+  ++                      +  +l+  v+G ta
      39228  135 VPASIATPVPSV-------------------KPEYLTLLVSGTTAYIS 163 lkrlpnlldqvikksqykmygksrkksqkdpdlvtielGgNDlcdyfrd<
                lk+l  1                      s+ ++ lvt + Gg   ++ +
      39228  164 LKELGGL----------------SEGKKVLVTAAAGG----TGQFA 189

```
adh_zinc: domain 1 of 1, from 47 to 368: score -6.8, E = 2.2e-09
                *->aavaweagKPLsieeievpppkahEVlvkIkatGiChtDlHtlkggw
                   av +         + +vp p++++  lv+ +++G+  +D+ +  g
     39228    47     EAVTLS------RDCPVPLPGDGDLLVRNRFVGVNASDINYSAGRY  86 pggpiGfiikyPmVlGHEgaGvVveVGsgV.tslKpGDRvViplptpsCg
                ++     +k P  +G Eg+G+Vv+ G + +  ++ +G+
     39228    87  -DPS----VKPPFDIGFEGIGEVVALGLSAsARYTVGQ------------ 119 eCeyCksGkenlCpknrftqgkGvmpDgtSRFtckGkkiyhFmGdGtFse
                                      ++    +m+                 G F+e
     39228   120  ------------------AVA--YMA------------------PGSFAE 131

YtvvdedDfvakiPdnaplEeaAplgCggsTgyhAaknagkvpGstVaV
                Ytvv++  ++++P  p E  +l   g+T+y ++k  g    G++V+V
     39228   132  YTVVPAS-IATPVPSVKP-EYLTLLVS-GTTAYISLKELGGLSEGKKVLV 178 fGaGgGvGllavqgAKAmGAariiavDvnpeklelAkelGAtdfiNpree
                 a gG G  a+q+ K +   +++i++ +++ek ++  k+lG++   iN+
     39228   179  TAAAGGTGQFAMQLSKKAK-CHVIGTCSSDEKSAFLKSLGCDRPINY--- 224 keekdsdkdpiqevlkeltggGvDvvietsGnpkameqAleslkpgWGtl
                     + + p+  vlk+    GvDvv e +G  + ++ A+++l   G+l
     39228   225  -----KTE-PVGTVLKQEYPEGVDVVYESVG-GAMFDLAVDALATK-GRL 266

VlVGlppagells........tvpllllltgrtikGsavGgfkdsrdtvek
                +++G  + + +++ ++ + +t p  ll+ ++ ++   ++ +  + + +
     39228   267  IVIGFISGYQTPTglspvlagTLPAKLLK-KSASVQGFFLNHY-LSKYQA 314 lvflyaeGkvkpdPpLITH..........rfplfdeineAfelmekGkvs
                +++ ++e  v  d L+ + + ++  ++++rf +++  i  A  m  Gk
     39228   315  AMSHLLEMCVSGD--LVCEvdlgdlspegRFTGLESIFRAVNYMYMGKNT 362 iRvVld<-*
                +++V+
     39228   363  GKIVVE    368
```

Fig. 3B

>74 p99.2 (363) AD (27) ADH3(13) ADH2(12) // OXIDOREDUCTASE ZINC
  DEHYDROGENASE ALCOHOL NAD PROTEIN FAMILY MULTIGENE NADP FORMALDEHYDE
  Length = 421

Score = 175 (66.7 bits), Expect = 6.8e-11, P = 6.8e-11
Identities = 95/350 (27%), Positives = 150/350 (42%)

```
Query:    54 DCPVPLPGDGDLLVRNRFVGVNASDINYSAGRYD-PSV-------KPPFDIGFEGIGEVV 105
             + P P PG+ ++L++ + G+ SD++ + G  P        KP +G E G V
Sbjct:    20 EVPPPKPGEDEVLIKVKACGICHSDLHMAHGEGGGPEAPFPVWGSKYPLVLGHEAAGVVE 79

Query:   106 ALGLSASARYTVGQ--AVAYMAPGSFAEYT-VVPASIATPVPSVK-PEYLTLLVSGTTAY 161
             +G ++++ VG  AVAY A  AEY  + ++  E T+ V+ TAY
Sbjct:    80 EVGEGVTSKFKVGDRVAVAYTASCGQAEYCEACKSGMENLCDNMSFEEAATVPVAYLTAY 139

Query:   162 ISLKEL--GGLSEGKKVLVTAAAGGTGQFAMQLSKK---AKCHVIGT----C--SSDEKSA 211
             L   GL G+ V V AAAGG G +A+Q++K   A    V T   C   S  +
Sbjct:   140 YGLSRFTANGLKGGESVFVHAAAGGVGMYAVQIAKSLAAADPEVAATDKVCLLGSGVTTG 199

Query:   212 FLKSL--GCDRPINYKTE-----PVGTVLKQEYPEGVDVVYESVGGA-MFDLAVDALATK 263
             ++  G D P +Y       VG + Q   G DVV +VGG+ M + ++
Sbjct:   200 LAAAMNTGADEPGSYVAVFGAFGGVGLMAVQGAKAGGDVVIIAVGGSDMMEEKLELAKEM 259

Query:   264 GRLIVIGFISGYQTPTGLSPVKAGTLPAKLLKKSASVQGFFLNHYLSKYQAAMSHLLEMC 323
             G  +VIG S    +  PV  + ++ KAV  ++  +  +A   +M
Sbjct:   260 GATVVIGSTSDQDDSS--KPVVEELV--EMTTKGAGVSADYVIECVGTAASASPDRYQM- 314

Query:   324 VSGDLVCEVDLGDLS----PEGRFTGLESIFRAVNYMYMG--KNTGKIVV 367
             +S L + G +   P + LE+  A  M MG K TGK+V+
Sbjct:   315 MSALLAALMGEGKIVVVGVPSSSYP-LETAPEAFQVM-MGRAKVTGKVVL 362
```

>4561 p99.2 (12) QOR(5) // QUINONE OXIDOREDUCTASE NADPH:QUINONE NADP REDUCTASE
  ZINC PROTEIN CRYSTALLIN ZETA- NADPH
  Length = 58

Score = 90 (36.7 bits), Expect = 0.00070, P = 0.00070
Identities = 21/52 (40%), Positives = 29/52 (55%)

```
Query:    33 MQKLVVTRLSPNFREAVTLSRDCPVPLPGDGDLLVRNRFVGVNASDINYSAG 84
             M+ +VVT    E +   D VP PG G++LVRNR +GVN D + +G
Sbjct:     8 MRAIVVTEFGGP--EVLKYREDYDVPQPGPGEVLVRNRAIGVNYIDTYFRSG 57
```

Fig. 4

```
Input file Fbh21956a.seq; Output File 21956.trans
Sequence length 3238

GCACGAGGAACAGAAGCAGCAGAAGCAACAGCAGTAGCAGCGGCAGCAGCAACAGCAGCAGCCCCTACTGAAGTCCAAT
                                                                          M   N      2
AGAGGAGACTTGATCTCTAGTTCATTCTGGAACTCCGCCTGGGATTGTGCACTGTCCAGGGTCCTGAAAC ATG AAC    6

Q   T   A   S   V   S   H   H   I   K   C   Q   P   S   K   T   I   K   E   L      22
CAA ACT GCC AGC GTG TCC CAT CAC ATC AAG TGT CAA CCC TCA AAA ACA ATC AAG GAA CTG     66

G   S   N   S   P   P   Q   R   N   W   K   G   I   A   I   A   L   L   V   I      42
GGA AGT AAC AGC CCT CCA CAG AGA AAC TGG AAG GGA ATT GCT ATT GCT CTG CTG GTG ATT    126

L   V   V   C   S   L   I   T   M   S   V   I   L   L   T   P   D   E   L   T      62
TTA GTT GTA TGC TCA CTC ATC ACT ATG TCA GTC ATC CTC TTA ACC CCA GAT GAA CTC ACA    186

N   S   S   E   T   R   L   S   L   E   D   L   F   R   K   D   F   V   L   H      82
AAT TCG TCA GAA ACC AGA TTG TCT TTG GAA GAC CTC TTT AGG AAA GAC TTT GTG CTT CAC    246

D   P   E   A   R   W   I   N   D   T   D   V   V   Y   K   S   E   N   G   H     102
GAT CCA GAG GCT CGG TGG ATC AAT GAT ACA GAT GTG GTG TAT AAA AGC GAG AAT GGA CAT    306

V   I   K   L   N   I   E   T   N   A   T   L   L   L   E   N   T   T   F         122
GTC ATT AAA CTG AAT ATA GAA ACA AAT GCT ACC ACA TTA TTA TTG GAA AAC ACA ACT TTT    366

V   T   F   K   A   S   R   H   S   V   S   P   D   L   K   Y   V   L   L   A     142
GTA ACC TTC AAA GCA TCA AGA CAT TCA GTT TCA CCA GAT TTA AAA TAT GTC CTT CTG GCA    426

Y   D   V   K   Q   I   F   H   Y   S   Y   T   A   S   Y   V   I   Y   N   I     162
TAT GAT GTC AAA CAG ATT TTT CAT TAT TCG TAT ACT GCT TCA TAT GTG ATT TAC AAC ATA    486

H   T   R   E   V   W   E   L   N   P   P   E   V   E   D   S   V   L   Q   Y     182
CAC ACT AGG GAA GTT TGG GAG TTA AAT CCT CCA GAA GTA GAG GAC TCC GTC TTG CAG TAC    546

A   A   W   G   V   Q   G   Q   Q   L   I   Y   I   F   E   N   N   I   Y   Y     202
GCG GCC TGG GGT GTC CAA GGG CAG CAG CTG ATT TAT ATT TTT GAA AAT AAT ATC TAC TAT    606

Q   P   D   I   K   S   S   S   L   R   L   T   S   S   G   K   E   E   I   I     222
CAA CCT GAT ATA AAG AGC AGT TCA TTG CGA CTG ACA TCT TCT GGA AAA GAA GAA ATA ATT    666

F   N   G   I   A   D   W   L   Y   E   E   L   L   H   S   H   I   A   H         242
TTT AAT GGG ATT GCT GAC TGG TTA TAT GAA GAG GAA CTC CTG CAT TCT CAC ATC GCC CAC    726

W   W   S   P   D   G   E   R   L   A   F   L   M   I   N   D   S   L   V   P     262
TGG TGG TCA CCA GAT GGA GAA AGA CTT GCC TTC CTG ATG ATA AAT GAC TCT TTG GTA CCC    786

T   M   V   I   P   R   F   T   G   A   L   Y   P   K   G   K   Q   Y   P   Y     282
ACC ATG GTT ATC CCT CGG TTT ACT GGA GCG TTG TAT CCC AAA GGA AAG CAG TAT CCG TAT    846

P   K   A   G   Q   V   N   P   T   I   K   L   Y   V   V   N   L   Y   G   P     302
CCT AAG GCA GGT CAA GTG AAC CCA ACA ATA AAA TTA TAT GTT GTA AAC CTG TAT GGA CCA    906

T   H   T   L   E   L   M   P   P   D   S   F   K   S   R   E   Y   Y   I   T     322
ACT CAC ACT TTG GAG CTC ATG CCA CCT GAC AGC TTT AAA TCA AGA GAA TAC TAT ATC ACT    966

```
        M   V   K   W   V   S   N   T   K   T   V   V   R   W   L   N   R   P   Q   N
      ATG GTT AAA TGG GTA AGC AAT ACC AAG ACT GTG GTA AGA TGG TTA AAC CGA CCT CAG AAC  1026
        I   S   I   L   T   V   C   E   T   T   T   G   A   C   S   K   K   Y   E   M   362
      ATC TCC ATC CTC ACA GTC TGT GAG ACC ACT ACA GGT GCT TGT AGT AAA AAA TAT GAG ATG  1086
        T   S   D   T   W   L   S   Q   Q   N   E   E   P   V   F   S   R   D   G   S   382
      ACA TCA GAT ACG TGG CTC TCT CAG CAG AAT GAG GAG CCC GTG TTT TCT AGA GAC GGC AGC  1146
        K   F   F   M   T   V   P   V   K   Q   G   G   R   G   E   F   H   H   I   A   402
      AAA TTC TTT ATG ACA GTG CCT GTT AAG CAA GGG GGA CGT GGA GAA TTT CAC CAC ATA GCT  1206
        M   F   L   I   Q   S   K   S   E   Q   I   T   V   R   H   L   T   S   G   N   422
      ATG TTC CTC ATC CAG AGT AAA AGT GAG CAA ATT ACC GTG CGG CAT CTG ACA TCA GGA AAC  1266
        W   E   V   I   K   I   L   A   Y   D   E   T   T   Q   K   I   Y   F   L   S   442
      TGG GAA GTG ATA AAG ATC TTG GCA TAC GAT GAA ACT ACT CAA AAA ATT TAC TTT CTG AGC  1326
        T   E   S   S   P   R   G   R   Q   L   Y   S   A   S   T   E   G   L   L   N   462
      ACT GAA TCT TCT CCC AGA GGA AGG CAG CTG TAC AGT GCT TCT ACT GAA GGA TTA TTG AAT  1386
        R   Q   C   I   S   C   N   F   M   K   E   Q   C   T   Y   F   D   A   S   F   482
      CGC CAA TGC ATT TCA TGT AAT TTC ATG AAA GAA CAA TGT ACA TAT TTT GAT GCC AGT TTT  1446
        S   P   M   N   Q   H   F   L   L   F   C   E   G   P   R   V   P   V   V   S   502
      AGT CCC ATG AAT CAA CAT TTC TTA TTA TTC TGT GAA GGT CCA AGG GTC CCA GTG GTC AGC  1506
        L   H   S   T   D   N   P   A   K   Y   F   I   L   E   S   N   S   M   L   K   522
      CTA CAT AGT ACG GAC AAC CCA GCA AAA TAT TTT ATA TTG GAA AGC AAT TCT ATG CTG AAG  1566
        E   A   I   L   K   K   K   I   G   K   P   E   I   K   I   L   H   I   D   D   542
      GAA GCT ATC CTG AAG AAG AAG ATA GGA AAG CCA GAA ATT AAA ATC CTT CAT ATT GAC GAC  1626
        Y   E   L   P   L   Q   L   S   L   P   K   D   F   M   D   R   N   Q   Y   A   562
      TAT GAA CTT CCT TTA CAG TTG TCC CTT CCC AAA GAT TTT ATG GAC CGA AAC CAG TAT GCT  1686
        L   L   L   I   M   D   E   E   P   G   G   Q   L   V   T   D   K   F   H   I   582
      CTT CTG TTA ATA ATG GAT GAA GAA CCA GGA GGC CAG CTG GTT ACA GAT AAG TTC CAT ATT  1746
        D   W   D   S   V   L   I   D   M   D   N   V   I   V   A   R   F   D   G   R   602
      GAC TGG GAT TCC GTA CTC ATT GAC ATG GAT AAT GTC ATT GTA GCA AGA TTT GAT GGC AGA  1806
        G   S   G   F   Q   G   L   K   I   L   Q   E   I   H   R   R   L   G   S   V   622
      GGA AGT GGA TTC CAG GGT CTG AAA ATT TTG CAG GAG ATT CAT CGA AGA TTA GGT TCA GTA  1866
        E   V   K   D   Q   I   T   A   V   K   F   L   L   K   L   P   Y   I   D   S   642
      GAA GTA AAG GAC CAA ATA ACA GCT GTG AAA TTT TTG CTG AAA CTG CCT TAC ATT GAC TCC  1926
        K   R   L   S   I   F   G   K   G   Y   G   G   Y   I   A   S   M   I   L   K   662
      AAA AGA TTA AGC ATT TTT GGA AAG GGT TAT GGT GGC TAT ATT GCA TCA ATG ATC TTA AAA  1986
        S   D   E   K   L   F   K   C   G   S   V   V   A   P   I   T   D   L   K   L   682
      TCA GAT GAA AAG CTT TTT AAA TGT GGA TCC GTG GTT GCA CCT ATC ACA GAC TTG AAA TTG  2046
        Y   A   S   A   F   S   E   R   Y   L   G   M   P   S   K   E   E   S   T   Y   702
      TAT GCC TCA GCT TTC TCT GAA AGA TAC CTT GGG ATG CCA TCT AAG GAA GAA AGC ACT TAC  2106
        Q   A   A   S   V   L   H   N   V   H   G   L   K   E   E   N   I   L   I   I   722
```

FIG. 6B

```
      CAG GCA GCC AGT GTG CTA CAT AAT GTT CAT GGC TTG AAA GAA GAA AAT ATA TTA ATA ATT  2166
       H   G   T   A   D   T   K   V   H   F   Q   H   S   A   E   L   I   K   H   L    742
      CAT GGA ACT GCT GAC ACA AAA GTT CAT TTC CAA CAC TCA GCA GAA TTA ATC AAG CAC CTA  2226
       I   K   A   G   V   N   Y   T   M   Q   V   Y   P   D   E   G   H   N   V   S    762
      ATA AAA GCT GGA GTG AAT TAT ACT ATG CAG GTC TAC CCA GAT GAA GGT CAT AAC GTA TCT  2286
       E   K   S   K   Y   H   L   Y   S   T   I   L   K   F   F   S   D   C   L   K    782
      GAG AAG AGC AAG TAT CAT CTC TAC AGC ACA ATC CTC AAA TTC TTC AGT GAT TGT TTG AAG  2346
       E   E   I   S   V   L   P   Q   E   P   E   E   D   E   *                         797
      GAA GAA ATA TCT GTG CTA CCA CAG GAA CCA GAA GAA GAT GAA TAA                        2391
      TGGACCGTATTTATACAGAACTGAAGGGAATATTGAGGCTCAATGAAACCTGACAAAGAGACTGTAATATTGTAGTTGC
      TCCAGAATGTCAAGGGCAGCTTACGGAGATGTCACTGGAGCAGCACGCTCAGAGACAGTGAACTAGCATTTGAATACAC
      AAGTCCAAGTCTACTGTGTTGCTAGGGGTGCAGAACCCGTTTCTTTGTATGAGAGAGGTCAAAGGGTTGGTTTCCTGGG
      AGAAATTAGTTTTGCATTAAAGTAGGAGTAGTGCATGTTTTCTTCTGTTATCCCCCTGTTTGTTCTGTAACTAGTTGCT
      CTCATTTTAATTTCACTGGCCACCATCATCTTTGCATATAATGCACAATCTATCATCTGTCCTACAGTCCCTGATCTTT
      CATGGCTGAGCTGCAATCTAACACTTTACTGTACCTTTATAATAAGTGCAATTCTTTCATTGTCTATTATTATGCTTAA
      GAAAATATTCAGTTAATAAAAAACAGAGTATTTTATGTAATTTCTGTTTTTAAAAAGACATTATTAAATGGGTCAAAGG
      ACATATAGAAATGTGGRWTTCAGCACCTTCCAAAGTTCAGCCAGTTATCAGTAGATACAATATCTTTAAATGAACACAC
      GAGTGTATGTCTCACAATATATATACACCAGTGTGCATATACAGTTAATGAAACTATCTTTAAATG
```

FIG. 6C

```
Input file Fbh25856FL.seq; Output File 25856.trans
Sequence length 1626

AGGTCCCGGGATCCGGTGGGTGGTGCAAATCAAAGAACCTGCTCCTCAGTGGATGTTGCCCTTTACTTTCTAGGCCTTG

TCCGGGAAGTGTTACTTTCTGCTCTAAAAGCTGCGGAATTCTAATACGNCTCACTATAGGGAGTCGACCACGCGTCCGC

M   D   S   Q   P     5
CGGCCGCTGGGCCGCTGCCTGAGCCAGGGAGGCGCAGCGCGAGCTCCCACTTCGTCTTC ATG GAT TCC CAG CCC    15

S   C   V   V   V   T   G   F   G   P   F   R   Q   H   L   V   N   S   S   W    25
AGC TGC GTG GTG GTG ACT GGT TTT GGG CCC TTC CGG CAG CAC TTG GTG AAT TCC AGC TGG    75

E   A   V   K   E   L   S   K   L   G   L   G   N   E   T   V   V   Q   L   R    45
GAA GCA GTG AAG GAG CTC TCC AAG CTG GGC CTG GGG AAT GAA ACA GTG GTG CAG CTG CGG   135

T   L   E   L   P   V   D   Y   R   E   A   K   R   R   V   T   G   I   W   E    65
ACT CTG GAG CTG CCT GTA GAT TAC AGG GAG GCT AAG CGG AGG GTC ACC GGA ATC TGG GAA   195

D   H   Q   P   Q   L   V   V   H   V   G   M   D   T   A   A   K   A   I   I    85
GAT CAT CAG CCG CAA CTC GTC GTG CAT GTG GGC ATG GAC ACC GCC GCC AAG GCG ATC ATT   255

L   E   Q   S   G   K   N   Q   G   Y   R   D   A   D   I   R   S   F   W   P   105
CTG GAA CAG TCT GGC AAG AAC CAA GGC TAC CGG GAC GCC GAC ATC CGC AGC TTC TGG CCC   315

E   G   G   V   C   L   P   G   S   P   D   V   L   E   S   G   V   C   M   K   125
GAG GGC GGC GTG TGC CTA CCT GGC AGC CCA GAC GTG CTG GAG TCA GGG GTC TGC ATG AAG   375

A   V   C   K   R   V   A   V   E   G   V   D   V   I   F   S   R   D   A   G   145
GCA GTC TGC AAG CGC GTA GCT GTG GAG GGT GTC GAC GTG ATC TTT TCC CGA GAT GCA GGC   435

R   Y   V   C   D   Y   T   Y   Y   L   S   L   H   H   G   K   G   C   A   A   165
AGA TAC GTC TGT GAT TAT ACC TAT TAC CTG TCT CTG CAT CAT GGA AAG GGC TGC GCG GCA   495

L   I   H   V   P   P   L   S   R   G   L   P   A   S   L   L   G   R   A   L   185
CTC ATC CAT GTC CCT CCA CTA TCG CGC GGG CTC CCG GCC AGC CTG CTG GGA AGA GCC TTG   555

R   G   H   H   P   A   N   A   G   R   G   *                                    197
AGA GGT CAT CAT CCA GCA AAT GCT GGA AGA GGG TGA                                    591

TTGTGAACATCTGGTGAGAGAATGGATGTGAAGGTCTTTTTAGCAACATTAGAACACTACAAAAATCACACATCTGAAT

GATTTAATGGAGGGAGAAACAGATAGCTTCCCTGTCGTCTTTACTGGCAATTTGCATGCTGAGAAAGCTCAGCTGTCAG

AGAAGAGGCAATGCTTTTCTGGAGAACGCTTCCAGGCAACATGCGTGAACACACGTGCCCCACATAGCTCAGCTTCCCT

GCCACCAAAGTGTAGTGATGCTTCCAGGAGGGACAAAACCAAACCAGAGACAGAAATGCATACAGAATTATTTTATTTA

ACTTAAACCATGTAGTACTTTACTAGAAAAAAGCAGAGTAAGAGAAACTAACGTTGCCTTAGCTTCAGCCATTCAAAAT

AGACAGTTTCTTTTTTCCATTATGTAAAGAATCCAGAGTATATCGCAATAACAGGAATAAATTCTTACAACAGAATATA

CAAAAACATTTTGAAATTTTTTTCATCTACTGATTTTTTATATAAACAGGATTTTTTAGGAATAATTTATACACAGAAA

GTCATTTTATGTAACAAATTGGCCATGTTATTACCTTTTTTTTTCTTACTTAAAAAAATTTTTTTTTAACAAGAAAACT

CAGAAAATGCATTATTTGCGGNGCATCCATTCCATCCCGCCTTCTGGTTTGATTTTTTTATCCCAGACAAAGGGATAC
```

FIG. 7A

CCAGAGGTAGACAAACTCTGGCAAACCCTNTCACCTTAACCTCACTGGGCTTAAAAAAGCAGACAGGGGGTTTTCACCC

GGGCGGTCTCTTCCACCCGGTGGATGTG

FIG. 7B

Input file Fbh22244F1.seq; Output File 22244.trans
Sequence length 1498

```
GCCGCGCGGGTCTGGCGGGACCGGTTTGGAAGACTTTGCCGGCCTGCAGATTGGCCTTAAGAGAAGGACGGAGCCACAT

M   A   A   V   D   S   F   Y   L   L    10
ACTGCTGACGGCCCAGAACTGGCAGAGAGAAGGTTGCC    ATG GCT GCT GTT GAC AGT TTC TAC CTC TTG  30

Y   R   E   I   A   R   S   C   N   C   Y   M   E   A   L   A   L   V   G   A    30
TAC AGG GAA ATC GCC AGG TCT TGC AAT TGC TAT ATG GAA GCT CTA GCT TTG GTT GGA GCC    90

W   Y   T   A   R   K   S   I   T   V   I   C   D   F   Y   S   L   I   R   L    50
TGG TAT ACG GCC AGA AAA AGC ATC ACT GTC ATC TGT GAC TTT TAC AGC CTG ATC AGG CTG    150

H   F   I   P   R   L   G   S   R   A   D   L   I   K   Q   Y   G   R   W   A    70
CAT TTT ATC CCC CGC CTG GGG AGC AGA GCA GAC TTG ATC AAG CAG TAT GGA AGA TGG GCC    210

V   V   S   G   A   T   D   G   I   G   K   A   Y   A   E   E   L   A   S   R    90
GTT GTC AGC GGT GCA ACA GAT GGG ATT GGA AAA GCC TAC GCT GAA GAG TTA GCA AGC CGA    270

G   L   N   I   I   L   I   S   R   N   E   E   K   L   Q   V   V   A   K   D    110
GGT CTC AAT ATA ATC CTG ATT AGT CGG AAC GAG GAG AAG TTG CAG GTT GTT GCT AAA GAC    330

I   A   D   T   Y   K   V   E   T   D   I   I   V   A   D   F   S   S   G   R    130
ATA GCC GAC ACG TAC AAA GTG GAA ACT GAT ATT ATA GTT GCG GAC TTC AGC AGC GGT CGT    390

E   I   Y   L   P   I   R   E   A   L   K   D   K   D   V   G   I   L   V   N    150
GAG ATC TAC CTT CCA ATT CGA GAA GCC CTG AAG GAC AAA GAC GTT GGC ATC TTG GTA AAT    450

N   V   G   V   F   Y   P   Y   P   Q   Y   F   T   Q   L   S   E   D   K   L    170
AAC GTG GGT GTG TTT TAT CCC TAC CCG CAG TAT TTC ACT CAG CTG TCC GAG GAC AAG CTC    510

W   D   I   I   N   V   N   I   A   A   A   S   L   M   V   H   V   V   L   P    190
TGG GAC ATC ATA AAT GTG AAC ATT GCC GCC GCT AGT TTG ATG GTC CAT GTT GTG TTA CCG    570

G   M   V   E   R   K   K   G   A   I   V   T   I   S   S   G   S   C   C   K    210
GGA ATG GTG GAG AGA AAG AAA GGT GCC ATC GTC ACG ATC TCT TCT GGC TCC TGC TGC AAA    630

P   T   P   Q   L   A   A   F   S   A   S   K   A   Y   L   D   H   F   S   R    230
CCC ACT CCT CAG CTG GCT GCA TTT TCT GCT TCT AAG GCT TAT TTA GAC CAC TTC AGC AGA    690

A   L   Q   Y   E   Y   A   S   K   G   I   F   V   Q   S   L   I   P   F   Y    250
GCC TTG CAA TAT GAA TAT GCC TCT AAA GGA ATC TTT GTA CAG AGT CTA ATC CCT TTC TAT    750

V   A   T   S   M   T   A   P   S   N   F   L   H   R   C   S   W   L   V   P    270
GTA GCC ACC AGC ATG ACA GCA CCC AGC AAC TTT CTG CAC AGG TGC TCG TGG TTG GTG CCT    810

S   P   K   V   Y   A   H   H   A   V   S   T   L   G   I   S   K   R   T   T    290
TCG CCA AAA GTC TAT GCA CAT CAT GCT GTT TCT ACT CTT GGG ATT TCC AAA AGG ACC ACA    870

G   Y   W   S   H   S   I   Q   F   L   F   A   Q   Y   M   P   E   W   L   W    310
GGA TAT TGG TCC CAT TCT ATT CAG TTT CTT TTT GCA CAG TAT ATG CCT GAA TGG CTC TGG    930

V   W   G   A   N   I   L   N   R   S   L   R   K   E   A   L   S   C   T   A    330
GTG TGG GGA GCA AAT ATT CTC AAC CGT TCA CTA CGT AAG GAA GCC TTA TCC TGC ACA GCC    990
```

FIG. 18A

```
     *                                                                                  331
    TGA                                                                                 993

GTCTGGATGGCCACTTGAGAAGTTTTGCCAACTCCTGGGAACCTCGATATTCTGACATTTGGAAAAACACATTTAATTT

ATCTCCTGTGTTTCATTGCTGATTATTCAGCATACTGTTGATTCGTCATTTGCAAAACACACATAATACCGTCAGAGTG

CTGTGAAAAACCTTAAGGGTGTGTGGATGGCACAGGATCAATAATGCCTGAGGCTGATTGACGACATCTACATTTCGGT

GCTTTTTCCCTAAGCTGTTTGAAAGTTACGCTTTTCTGTTGTTCTAGAGCCACAGCAGTCTAATATTGAAATATAATAT

GATTTGTCAGGTCTTATAAAAAAAAAAAAAAAAAAAAAATTGCGGCCGCAAGCTTATTCCCTTTAGTRRGGGT
```

FIG. 18B

```
Input file Fbh8701FL.seq; Output File 8701.trans
Sequence length 1981
```

|                                                                                                                  |      |
|------------------------------------------------------------------------------------------------------------------|------|
|              M  A  A  A  A  R  A  R  V  A  Y  L  L  R  Q  L | 16 |

```
                    M   A   A   A   A   R   A   R   V   A   Y   L   L   R   Q   L    16
GGACTCCAAGCGCC     ATG GCC GCT GCC GCC CGA GCC CGG GTC GCG TAC TTG CTG AGG CAA CTG    48

Q   R   A   A   C   Q   C   P   T   H   S   H   T   Y   S   Q   A   P   G   L       36
CAA CGC GCA GCG TGC CAG TGC CCA ACT CAT TCT CAT ACT TAC TCC CAA GCC CCT GGA CTT     108

S   P   S   G   K   T   T   D   Y   A   F   E   M   A   V   S   N   I   R   Y       56
TCA CCT TCT GGG AAA ACA ACA GAT TAT GCC TTT GAG ATG GCT GTT TCA AAT ATT AGA TAT     168

G   A   A   V   T   K   E   V   G   M   D   L   K   N   M   G   A   K   N   V       76
GGA GCA GCA GTT ACA AAG GAA GTA GGA ATG GAC CTA AAA AAC ATG GGT GCT AAA AAT GTG     228

C   L   M   T   D   K   N   L   S   K   L   P   P   V   Q   V   A   M   D   S       96
TGC TTG ATG ACA GAC AAG AAC CTC TCC AAG CTC CCT CCT GTG CAA GTA GCT ATG GAT TCC     288

L   V   K   N   G   I   P   F   T   V   Y   D   N   V   R   V   E   P   T   D      116
CTA GTG AAG AAT GGC ATC CCC TTT ACG GTT TAT GAT AAT GTG AGA GTG GAA CCA ACG GAT     348

S   S   F   M   E   A   I   E   F   A   Q   K   G   A   F   D   A   Y   V   A      136
TCA AGC TTC ATG GAA GCT ATT GAG TTT GCC CAA AAG GGA GCT TTT GAT GCC TAT GTT GCT     408

V   G   G   G   S   T   M   D   T   C   K   A   A   N   L   Y   A   S   S   P      156
GTC GGT GGT GGC TCT ACC ATG GAC ACC TGT AAG GCT GCT AAT CTG TAT GCA TCC AGC CCT     468

H   S   D   F   L   D   Y   V   S   A   P   I   G   K   G   K   P   V   S   V      176
CAT TCT GAT TTC CTA GAT TAT GTC AGT GCC CCC ATT GGC AAG GGA AAG CCT GTG TCT GTG     528

P   L   K   P   L   I   A   V   P   T   T   S   G   T   G   S   E   T   T   G      196
CCT CTT AAG CCT CTG ATT GCA GTG CCA ACT ACC TCA GGA ACC GGG AGT GAA ACT ACT GGG     588

V   A   I   F   D   Y   E   H   L   K   V   K   I   G   I   T   S   R   A   I      216
GTT GCC ATT TTT GAC TAT GAA CAC TTG AAA GTA AAA ATT GGC ATC ACT TCG AGA GCC ATC     648

K   P   T   L   G   L   I   D   P   L   H   T   L   H   M   P   A   R   V   V      236
AAA CCC ACA CTG GGA CTG ATT GAT CCT CTG CAC ACC CTC CAC ATG CCT GCC CGA GTG GTC     708

A   N   S   G   F   D   V   L   C   H   A   L   E   S   Y   T   T   L   P   Y      256
GCC AAC AGT GGC TTT GAT GTG CTT TGC CAT GCC CTG GAG TCA TAC ACC ACC CTG CCC TAC     768

H   L   R   S   P   C   P   S   N   P   I   T   R   P   A   Y   Q   G   S   N      276
CAC CTG CGG AGC CCC TGC CCT TCA AAT CCC ATC ACA CGG CCT GCG TAC CAG GGC AGC AAC     828

P   I   S   D   I   W   A   I   H   A   L   R   I   V   A   K   Y   L   K   R      296
CCA ATC AGT GAC ATT TGG GCT ATC CAC GCG CTG CGG ATC GTG GCT AAG TAT CTG AAG AGG     888

A   V   R   N   P   D   D   L   E   A   R   S   H   M   H   L   A   S   A   F      316
GCT GTC AGA AAT CCC GAT GAT CTT GAA GCA AGG TCT CAT ATG CAC TTG GCA AGT GCT TTT     948

A   G   I   G   F   G   N   A   G   V   H   L   C   H   G   M   S   Y   P   I      336
GCT GGC ATC GGC TTT GGA AAT GCT GGT GTT CAT CTG TGC CAT GGA ATG TCT TAC CCA ATT    1008

S   G   L   V   K   M   Y   K   A   K   D   Y   N   V   D   H   P   L   V   P      356
TCA GGT TTA GTG AAG ATG TAT AAA GCA AAG GAT TAC AAT GTG GAT CAC CCA CTG GTG CCC    1068
```

FIG. 19A

```
      H   G   L   S   V   V   L   T   S   P   A   V   F   T   F   T   A   Q   M   F   376
     CAT GGC CTT TCT GTG GTG CTC ACG TCC CCA GCG GTG TTC ACT TTC ACG GCC CAG ATG TTT 1128

P   E   R   H   L   E   M   A   E   I   L   G   A   D   T   R   T   A   R   I   396
     CCA GAG CGA CAC CTG GAG ATG GCA GAA ATA CTG GGA GCC GAC ACC CGC ACT GCC AGG ATC 1188

Q   D   A   G   L   V   L   A   D   T   L   R   K   F   L   F   D   L   D   V   416
     CAA GAT GCA GGG CTG GTG TTG GCA GAC ACG CTC CGG AAA TTC TTA TTC GAT CTG GAT GTT 1248

D   D   G   L   A   A   V   G   Y   S   K   A   D   I   P   A   L   V   K   G   436
     GAT GAT GGC CTA GCA GCT GTT GGT TAC TCC AAA GCT GAT ATC CCC GCA CTA GTG AAA GGA 1308

T   L   P   Q   E   R   V   T   K   L   A   P   C   P   Q   S   E   E   D   L   456
     ACG CTG CCC CAG GAA AGG GTC ACC AAG CTT GCA CCC TGT CCC CAG TCA GAA GAG GAT CTG 1368

A   A   L   F   E   A   S   M   K   L   Y   *                                    468
     GCT GCT CTG TTT GAA GCT TCA ATG AAA CTG TAT TAA                                   1404
```

TTGTCATTTTAACTGAAAGAATTACCGCTGGCCATTGTAGTGCTGAGAGCAAGAGCTGATCTAGCTAGGGCTTTGTCTT

TTCATCTTTGCGCATAACTTACCTGTTACCAGTATAGGTGGGATATACATTTATCTTGCAGGAAATTCCCCAAAGCTCA

GAGTCCAGTTCCTTCCATAAAACAGGCTGGACAAATGACCACTATGTTAGACCCCCAGGCTCGACTTCAGGGGTCAGTG

TTCCTGTCCCAAACCCCACACAGAATACTCTGCCTCTGYTTCATGTAGCAAATGAGCAAAAACTCAGTATCTATCAAAA

GTGTAAATTATATTTCCTATGCCTAGTAATTCACTTCATGTCTAAAAATTTATCTGATAGAAACACTAGCACCAGTACA

TACAGAAGCATGGCAAGGATGTTTCTGGCAGCACTTTTCTAATAATAAAAGATTTGAAACAACMWWAARWAWWMAWWAW

WRRWAWAWARAKSACTTATAGTATACTAGACAGTGGAATACTATGGTACTGTTAATAAAGATGAAGTAAATCTCTTGGA

AAAAAAAAAA

FIG. 19B

PROTEIN FAMILY / DOMAIN MATCHES, HMMer VERSION 2
Searching for complete domains in PFAM
hmmpfam - search a single seq against HMM database
HMMER 2.1.1
Copyright (C)              Washington University School of Medicine
HMMER is freely distributed under the GNU General Public License (GPL).

```
- - - - - - - - - - - - - - - - - - - - - - - - - - - - - - - - - - -
HMM file:             /prod/ddm/seqanal/PFAM/pfam5.2/Pfam
Sequence file:        /prod/ddm/wspace/orfanal/oa-script.3827.seq
- - - - - - - - - - - - - - - - - - - - - - - - - - - - - - - - - - -
    Query: 22244

Scores for sequence family classification (score includes all domains):
Model         Description                              Score     E-value  N
--------      -----------                              -----     -------  ---
adh_short     short chain dehydrogenase                117.6     2.4e-31  1
Shikimate_DH  Shikimate / quinate 5-dehydrogenase     -123.7         6   1

Parsed for domains:
Model          Domain   seq-f  seq-t    hmm-f  hmm-t     score   E-value
--------       ------   -----  -----    -----  -----     -----   -------
Shikimate_DH   1/1       10    189 ..     1    261 []   -123.7        6
adh_short      1/1       68    254 ..     1    203 []    117.6   2.4e-31

Alignments of top-scoring domains:
Shikimate_DH: domain 1 of 1, from 10 to 189: score -123.7, E = 6
                   *->lHNaafeqlGlnhvYlafevppddLlagavegffalgfrGanVTiPf
                      l++  ++++         +++  + l ga + ++
         22244    10  LYREIARSCNC------YMEALA-LVGAWYTARKSI----------  38

KeeampllDelterAkliGAVNTLiregDGkrklrGdNTDgiGilkaLee
                      + ++++         li+    L+++   +l         G +++L +
         22244    39 -TVICDFY-------SLIR----LHFI--P--RL--------GSRADLIK  64 gGlgarvrkgktaLvlGA.GGAaRAviyaLlklGvskIyIaNRTveKaee
                      +g         + a+v GA+ G ++A + +L++ G  +I+++ R+ eK++
         22244    65  Q-YG------RWAVVSGAtDGIGKAYAEELASRG-LNIILISRNEEKLQV 106

LaerfgsgygaisvvsvselegqeglaagalkafDiiinaTsvgmkpeid
                      a+   ++            +e              Dii++ +s g +
         22244   107  VAKDIAD--------TYKVET-----------DIIVADFSSGRE---I 132 dpplslsllfkenptggvvlDmvYkPlt.ptTfLlreAqergwkvidGle
                      p++ +l  k+   +g+++  v    + p+  ++++ +++ w +i+
         22244   133  YLPIREALKDKD---VGILVNNVGVFYPyPQ-YFTQLSEDKLWDIIN--- 175

MLveQGaeqFelWtGv<-*
                      v  +a++       +
         22244   176 --VNIAAASLMVHVVL     189
```

FIG. 21A

```
adh_short: domain 1 of 1, from 68 to 254: score 117.6, E = 2.4e-31
                *->KvaLvTGassGIGlaiAkrLakeGakVvvadrneeklekGavakelk
                   ++a+v Ga+ GIG+a+A++La++G +++++ rneekl+   vak ++
      22244   68  RWAVVSGATDGIGKAYAEELASRGLNIILISRNEEKLQV--VAKDIA  112 elGgndkdralaiqlDvtdeesvaaveqaverlGr..lDvLVNNAGgiil
                   +    ++   i++D ++   +  ++   ++e+l ++++ +LVNN+G++
      22244  113  DTYK---VETDIIVADFSSGRE--IYLPIREALKDkdVGILVNNVGVFY-  156 lrpgpfaelsrtmeedwdrvidvNltgvflltravlplmamkkrggGrIv
                  ++p  f  ls    e+   ++i+vN+ ++ l++  vlp +m++r++G Iv
      22244  157  PYPQYFTQLS---EDKLWDIINVNIAAASLMVHVVLP--GMVERKKGAIV  201

NiSSvaGrkeg.glvgvpggsaYsASKaAvigltrsLAlElaphgIrVna
                  +iSS        g++ ++ p+ +a sASKa + +++r+L+ E+a +gI V +
      22244  202  TISS------GsCCKPTPQLAAFSASKAYLDHFSRALQYEYASKGIFVQS  245 vaPGgvdTd<-*
                   P +v+T
      22244  246  LIPFYVATS   254
```

FIG. 21B

```
PROTEIN FAMILY / DOMAIN MATCHES, HMMer VERSION 2
Searching for complete domains in PFAM
hmmpfam - search a single seq against HMM database
HMMER 2.1.1 (Dec 1998)
Copyright (C) 1992-1998 Washington University School of Medicine
HMMER is freely distributed under the GNU General Public License (GPL).
- - - - - - - - - - - - - - - - - - - - - - - - - - - - - - - - - - -
HMM file:                /prod/ddm/seqanal/PFAM/pfam5.2/Pfam
Sequence file:           /prod/ddm/wspace/orfanal/oa-script.22103.seq
- - - - - - - - - - - - - - - - - - - - - - - - - - - - - - - - - - -
Query:  8701

Scores for sequence family classification (score includes all domains):
Model     Description                                     Score    E-value   N
--------  -----------                                     -----    -------  ---
Fe-ADH    Iron-containing alcohol dehydrogenases          183.6    1.2e-51   2

Parsed for domains:
Model     Domain   seq-f  seq-t    hmm-f  hmm-t     score   E-value
--------  ------   -----  -----    -----  -----     -----   -------
Fe-ADH    1/2       52    253  ..    1    209  [.   119.3   3e-33
Fe-ADH    2/2      276    338  ..   215    282  ..   64.1   1.9e-17

Alignments of top-scoring domains:
Fe-ADH: domain 1 of 2, from 52 to 253: score 119.3, E = 3e-33
                   *->PavylfGkGalteageelkklGfkkaLIVtDeflikinGavdkvlkk
                      + + +G ++ +e+g++lk+ G+k++ ++tD+ l k+  v + ++
          8701    52    -SNIRYGAAVTKEVGMDLKNMGAKNVCLMTDKNLSKL-PPVQVAMDS 96

LkeagIavavfdgvepnPtittVkkGleilreencDivIAiGGGSphDcA
                   L ++gI ++v+d v  +Pt++   +++e +++ + D  +A+GGGS++D++
          8701    97 LVKNGIPFTVYDNVRVEPTDSSFMEAIEFAQKGAFDAYVAVGGGSTMDTC 146

Kaiallatnp.gdtfDye.....gikFMDIRKriYtfpklkpklplvAIp
                   Ka  l+a  p+ d  +Dy++  +  +++k           p+ +p +pl+A+p
          8701   147 KAANLYASSPhSDFLDYVsapigKGK-----------PVSVPLKPLIAVP 185

TTAGTgSEvTafaVItdeatgvKmviadyhltPdvavvDpelmagmPpsL
                   TT+GTgSE+T +a+   e  +vK +i ++ + P++   +Dp+ +  mP+++
          8701   186 TTSGTGSETTGVAIFDYEHLKVKIGITSRAIKPTLGLIDPLHTLHMPARV 235 tAatGmDALtHAiEAYvS<-*
                   A +G D L HA E+Y++
          8701   236 VANSGFDVLCHALESYTT    253

Fe-ADH: domain 2 of 2, from 276 to 338: score 64.1, E = 1.9e-17
                   *->tpvTDalaikAielIakyLpkAvekeGddaeeAREamayAsaLAGNG
                      +p++D  ai A++++akyL++Av +   dd+e AR  m++Asa AG
          8701   276    NPISDIWAIHALRIVAKYLKRAVRN-PDDLE-ARSHMHLASAFAG-- 318

LmAFaNAgLGlvHaMAHqLGg<-*
                   ++F+NAg+  l+H+M+++++g
          8701   319 -IGFGNAGVHLCHGMSYPISG    338
```

```
GTAGCGAGGCTTGGGTGGCGAACTCGGCACGAGGCCCAAAGGTAGGCTCAGGCTCCGACGGTGGCCGGCGGGGTCACG
AGGCTTCGTAGTGGAGGAACGGGTTTGGCGTGTGGGACGCAGCTGCCTCTGTACTGGGAGTCACGGAGTGGCCGGGCT

M   A   A   A   S   A   V   S   L   L   V   A   A   E   R   N        17
CCAGGGAC ATG GCG GCG GCC TCT GCG GTG TCG CTG CTG GTG GCG GCG GAG AGG AAC        51

R   W   H   R   L   P   S   L   L   P   P   R   T   W   V   R   Q   R   37
CGG TGG CAT CGT CTC CCG AGC CTG CTC CCG AGG ACA TGG GTG TGG AGG CAA AGA        111

T   M   K   Y   T   A   T   G   R   N   I   T   K   V   L   I   A   N   R   57
ACC ATG AAG TAC ACA ACA GCC ACA GGA AGA AAC ATT ACC AAG GTC CTC ATT GCA AAC AGA  171

G   E   I   A   C   R   V   M   R   T   A   K   K   L   G   V   Q   T   V   A   77
GGA GAA ATT GCC TGC AGG GTG ATG CGC ACA GCC AAA AAA CTG GGT GTA CAG ACT GTG GCG  231

V   Y   S   E   A   D   R   N   S   Q   S   M   H   V   D   M   A   E   A   Y   S   97
GTT TAT AGT GAG GCT GAC AGA AAT TCC CAG AGC ATG CAT GTA GAT ATG GCA GAT GCA TAT TCC  291

I   G   P   A   P   Q   A   I   H   P   G   C   G   F   L   S   E   N   M   E  117
ATC GGC CCC GCT CCC CAG CAG GCT ATC CAT CCA GGA TGC GGT TTT CTT TCA GAA AAC ATG GAA  351

K   T   S   A   Q   K   E   G   I   F   I   G   P   P   P   S   A   I  137
AAG ACC TCT GCA CAG AAG GAA GGA ATT TTT ATA GGC CCT CCA TCT GCA ATT              411

F   A   E   L   C   K   Q   I                                                  157
TTT GCT GAA CTT TGT AAG CAA                                                      471
```

FIG. 33B

```
R   D   M   G   I   K   S   T   S   K   I   M   A   A   A   G   V   P   V       177
AGA GAC ATG GGT ATA AAG AGC ACA TCC AAA ATA ATG GCT GCT GCT GGA GTA CCT GTT     531

V   E   G   Y   H   G   E   D   Q   S   Q   L   K   A   E   H   A   R           197
GTG GAG GGT TAT CAT GGT GAG GAC CAA TCA CAA CTG AAG GAA CAC GCC AGG AGA         591

I   G   Y   P   Y   M   V   I   K   A   G   G   K   G   M   R                   217
ATT GGC TAT CCT TAT ATG GTC ATT AAA GCC GGT GGA AAA GGA ATG AGG                 651

V   R   S   E   Q   V   R   A   R   S   A   R   E   A   R   R   I               237
GTT AGA TCA GAA CAA GTC CGG GCA TCA GCA CGG GAG GCA AGG AGG ATT                 711

S   F   N   D   A   M   L   E   K   F   V   Y   E   Q   R   H   K               257
TCT TTC AAT GAT GCT ATG CTG GAG AAG TTT GTA TAC GAG CAG AGG CAT AAG             771

V   Q   V   F   G   D   H   I   G   N   A   Y   L   F   E   R   P   V   E       277
GTC CAG GTG TTT GGT GAT CAT ATC GGC AAT GCT TAC TTG TTT GAA AGA CCG GTA GAA     831

V   R   K   L   H   Q   K   I   E   A   P   A   K   S   G   I   K   V           297
GTG CAG AGG CTG CAT CAG AAG ATT GAG GCC CCA GCG AAA TCT GGT ATT AAA GAA         891

V   K   E   I   G   E   A   V   R   A   A   K   N   Y   V   G                   317
GTA AAG GAA ATT GGA GAG GCT GCA AGA GCT GCT AAA TAT GTT GGA                     951

A   G   T   V   E   F   I   M   D   S   K   H   N   F   C   E   M   N           337
GCA GGG ACT GTG GAG TTT ATT ATG GAC TCA AAA CAT AAT TTC TGT GAG ATG AAT         1011
```

FIG. 33C

```
T   R   L   Q   V   E   T   E   M   I   T   G   T   D   L   V   E                              357
ACA AGG CTG CAA GTT ACT GAG ATG ATC ACA GGA ACT GAC TTG GTG GAG                                 1071

W   Q   L   R   I   A   E   K   I   P   L   S   Q   E   I   T   L                              377
TGG CAG CTT AGA ATT GCA GAA AAG ATT CCT TTG AGC CAG GAA ATA ACT CTG                             1131

Q   G   H   A   F   E   A   R   I   Y   A   E   N   N   F   M   P                              397
CAG GGC CAT GCC TTC GAA GCT AGA ATA TAT GCA GAA AAT AAC TTC ATG CCT                             1191

V   A   G   P   L   V   H   L   S   T   P   R   A   D   I   E                                  417
GTG GCA GGC CCA TTA GTG CAC CTC TCT ACT CCT CGA GCA GAC ATT GAA                                 1251

T   G   R   Q   A   V   S   E   D   Y   P   R   A   T   I   L                                  437
ACT GGA CGG CAA GCA GTA TCC GAA GAC TAT CCT CGA GCA ACC ATT CTG                                 1311

V   W   A   A   D   R   Q   T   A   L   D   A   L   P   Y   S   M   R   Q                      457
GTG TGG GCA GCA GAT CGC CAG CAG GCG TTG GAC GCG CTG CCC TAC AGC ATG CGT CAG                     1371

Y   N   I   V   G   L   P   T   N   I   D   F   K   L   L   N   L   S   G   H   P              477
TAC AAT ATT GTT GGA CTG CCC ACC AAC ATT GAC TTC AAA CTC CTC AAC CTG TCT GGC CAC CCA             1431

E   F   A   G   N   V   H   T   D   F   I   P   Q   H   K   Q   L                              497
GAA TTT GCT GGG AAC GTG CAC ACT GAT TTC ATC CCT CAA CAC AAA CAG TTG                             1491

L   S   R   K   A   A   A   Q   C   L   E   S   K   G   A   L   I   L                          517
CTC AGT CGG AAG GCT GCA GCC CAG TGC TTA GAG TCT AAA GGT GCA CTG ATC CTC                         1551
```

FIG. 33D

| | | | | | | | | | | | | | | | | | | | | |
|---|---|---|---|---|---|---|---|---|---|---|---|---|---|---|---|---|---|---|---|---|
| K | E | K | A | M | T | D | T | F | L | Q | A | H | D | Q | F | S | P | F | | 537 |
| AAG | GAG | AAA | GCC | ATG | ACC | GAC | ACT | TTC | CTT | CAG | GCA | CAT | GAT | CAA | TTC | TCT | CCA | TTT | | 1611 |
| S | S | S | G | R | R | L | N | I | Y | T | T | R | N | M | F | L | K | D | | 557 |
| TCG | AGC | AGT | GGA | AGA | AGA | CTG | AAT | ATC | TCG | TAT | ACC | AGA | AAC | ATG | ACT | CTT | AAA | GAT | | 1671 |
| G | K | N | V | A | I | A | V | T | Y | N | H | D | G | Y | T | S | M | Q | | 577 |
| GGT | AAC | AAT | GTA | GCC | ATA | GCT | GTA | ACG | TAT | AAC | CAT | GAT | GGG | TAT | AGC | TCT | ATG | CAG | | 1731 |
| I | D | K | T | F | Q | V | L | G | N | L | A | Y | S | E | G | D | C | Y | | 597 |
| ATT | GAT | AAA | ACT | TTC | CAA | GTC | CTT | GGT | AAT | CTT | TAC | AGC | GAG | GGA | GAT | TGC | ACT | TAC | | 1791 |
| L | K | C | S | V | N | G | V | A | S | K | A | L | I | I | L | E | N | T | | 617 |
| CTG | AAA | TGT | TCT | GTT | AAT | GGA | GTT | GCT | AGT | AAA | GCG | CTG | ATT | ATC | CTG | GAA | AAC | ACT | | 1851 |
| I | Y | L | F | S | I | E | K | Q | I | D | P | V | P | K | T | G | T | L | | 637 |
| ATT | TAC | CTA | TTT | TCC | AGT | ATT | GAG | CAA | ATT | GAC | ATT | CCA | CCC | AAA | ACT | GGA | ACT | TTA | | 1911 |
| S | V | S | Q | S | E | T | P | L | A | P | M | D | S | Y | K | T | T | I | | 657 |
| TCT | GTG | AGC | CAA | TCA | GAA | ACT | CCC | TTA | GCT | CCT | ATG | GAT | TCC | TAC | AAA | ACT | ACC | ATT | | 1971 |
| E | K | V | F | V | K | A | K | G | D | K | V | A | G | S | L | M | V | M | | 677 |
| GAA | AAG | GTG | TTT | GTC | AAA | GCT | AAA | GGA | GAC | AAA | GTG | GCG | GGA | TCC | CTC | ATG | GTT | ATG | | 2031 |
| I | A | M | K | M | E | H | T | I | K | S | P | K | D | G | T | V | K | V | | 697 |
| ATC | GCC | ATG | AAG | ATG | GAG | CAT | ACC | ATA | AAG | TCT | CCA | AAG | GAT | GGC | ACA | GTA | AAG | GTG | | 2091 |

FIG. 33E

```
  F   Y   R   E   G   A   Q   A   N   R   H   T   P   L   V   E   F   E   E   E   E      717
TTC TAC AGA GAA GGT GCT CAG GCC AAC AGA CAC ACT CCT TTA GTC GAG TTT GAG GAG GAA GAA     2151

E   S   D   K   R   E   S   E   *                                                      726
GAA TCA GAC AAA AGG GAA TCG GAA TAA                                                     2178

ACTCCAGCAAGGAAATGGCCAGTTAAGTAGTGTCTTCTCTCCACCAAAAAGAGGAAGTGCCTCCAGCTTTTCTGGGG
GTCTCATAAAGAGCAGTTTTACTAAATGATTGTATGCTTATGCTGAACACCTTTCATATTGGAGAATCATGCATTTGGG
TCACTAATTATCTCAAAATATTTCATACTAATAAAGTTGAATTATTTTTATTGGAAGCCAAAAAAAAAAAAAAAGG
```

FIG. 34A

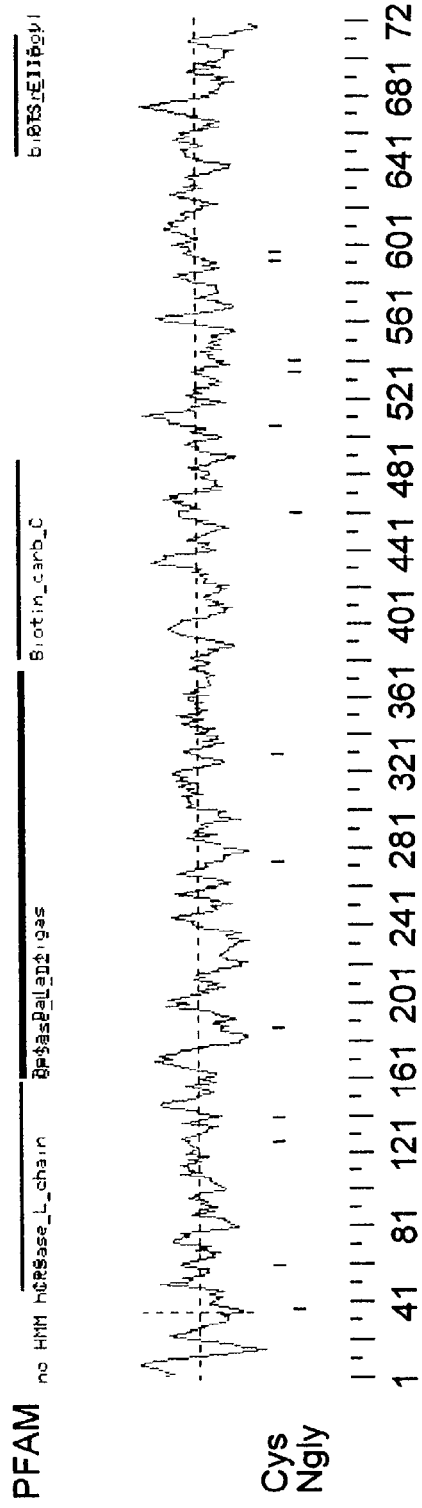

FIG. 34B

>32263
MAAASAVSVLLVAAERNRWHRLPSLLLPPRTWVWRQRTMKYTTATGRNITKVLIANRGEI
ACRVMRTAKKLGVQTVAVYSEADRNSMHVDMADEAYSIGPAPSQQSYLSMEKIIQVAKTS
AAQAIHPGCGFLSENMEFAELCKQEGIIFIGPPPSAIRDMGIKSTSKSIMAAAGVPVVEG
YHGEDQSDQCLKEHARRIGYPVMIKAVRGGGGKGMRIVRSEQEFQEQLESARREAKKSFN
DDAMLIEKFVDTPRHVEVQVFGDHHGNAVYLFERDCSVQRRHQKIIEEAPAPGIKSEVRK
KLGEAAVRAAKAVNYVGAGTVEFIMDSKHNFCFMEMNTRLQVEHPVTEMITGTDLVEWQL
RIAAGEKIPLSQEEITLQGHAFEARIYAEDPSNNFMPVAGPLVHLSTPRADPSTRIETGV
RQGDEVSVHYDPMIAKLVVWAADRQAALTKLRYSLRQYNIVGLPTNIDFLLNLSGHPEFE
AGNVHTDFIPQHHKQLLSRKAAAKESLCQAALGLILKEKAMTDTFTLQAHDQFSPFSSS
SGRRLNISYTRNMTLKDGKNNVAIAVTYNHDGSYSMQIEDKTFQVLGNLYSEGDCTYLKC
SVNGVASKAKLIILENTIYLFSKEGSIEIDIPVPKYLSSVSSQETQGGPLAPMTGTIEKV
FVKAGDKVKAGDSLMVMIAMKMEHTIKSPKDGTVKKVFYREGAQANRHTPLVEFEEESD
KRESE

FIG. 35A

```
Scores for sequence family classification (score includes all domains):
Model            Description                                          Score    E-value   N
-------          -----------                                          -----    -------   -
CPSase_L_chain   Carbamoyl-phosphate synthase (CPSase)                586.6    1.5e-172  1
biotin_lipoyl    Biotin-requiring enzymes                              67.8    2.3e-16   1
Dala_Dala_ligas  D-ala D-ala ligase                                    11.1    0.047     1
PTS_EIIA_1       phosphoenolpyruvate-dependent sugar p                  5.7    3.1       1
GARS             Phosphoribosylglycinamide synthetase                -337.1    8.6       1

Parsed for domains:
Model            Domain   seq-f  seq-t    hmm-f  hmm-t       score    E-value
-------          ------   -----  -----    -----  -----       -----    -------
Dala_Dala_ligas  1/1      163    233 ..   146    223 ..       11.1    0.047
GARS             1/1      108    411 ..     1    445 []     -337.1    8.6
CPSase_L_chain   1/1       51    419 ..     1    433 []      586.6    1.5e-172
PTS_EIIA_1       1/1      661    674 ..    69     82 ..        5.7    3.1
biotin_lipoyl    1/1      650    714 ..     1     75 []       67.8    2.3e-16

Alignments of top-scoring domains:
Dala_Dala_ligas: domain 1 of 1, from 163 to 233: score 11.1, E = 0.047
                   *->KvltKlllkaaGipvvPyilltrkdwknepdskefiekveekLgyPv
                      K+ K +++aaG+pvv    +   + ++ +++      + gyPv
     32263    163    KSTSKSIMAAAGVPVVEGYHGEDQSDQCLKEH------ARRIGYPV 202

FVKPAnaGSSvGiskVtseeELqsAleeAfq<-*
                   ++K  + G  +G+ +V+se E q+ le A++
     32263    203  MIKAVRGGGKGMRIVRSEQEFQEQLESARR   233
```

FIG. 35B

```
GARS: domain 1 of 1, from 108 to 411: score -337.1, E = 8.6

*->mkVLvIGsGGREHALAwkLaQSPlVkkvyvAPGkNgGtarleKcskl
                    +    + +v k  +A     +G    +l+
    32263    108 -----------------LSMEKIIQVAKTSAAQAIHPGCGFLS-----       133 envailvtDfealveFAkkkkidLVvvGPEaPLvlGlvDaleaaGipvFG
                en +           te++k+++i     ++GP  P      a + +GI
    32263    134 ENMEF-------AELCKQEGI---IFIGP-PP-----SAIRDMGI----       162

PskaAAqLEgSKsFaKdFmkrhgIPGTAeYetFtdp..eeAksyireaga
                          Ks +K  m+++g+P     e    +d ++  +k+ r+ g+
    32263    163 -------KSTSKSIMAAAGVP--VVEGYHGEDQsdQCLKEHARRIGY--       200

PAGDieiVVKADGLAAGKGViVamtkeE......AieAvdeilvdkkFG
                P      + +KA++ +GKG     +++++++E   +++ ++A+++++ + d
    32263    201 P-----VMIKAVRGGGGKGMRIVRSEQEfqeqlesARREAKKSFND---       241 eAGetVVIEEfLe...GeEvSvlAfvDGktviplppAQDHKRlgeGD...
                      +IE f+++++   Ev v++  G+ v+         1+e D +
    32263    242 ---DAMLIEKFVDtprHVEVQVFGDHHGNAVY--------LFERDcsv       278

........tGPNTGGMGAYsPaPvispelTekldkikeeIlqPTvdglr
                +++++++      ++          +PaP I  e+     +k  e  +  +++++
    32263    279 qrrhqkiieE--------APAPGIKSEV---RKKLGEAAV-RAAKA--       312
```

FIG. 35C

```
32263  313  kEgipykGvlYAGlMLtkdGpevLiPKVLEFNcRFGDPETQvilpLL.De
             +y+G   ++++    ++       E N R          L+ e
             ---VNYVGAGTVEFIMDSKHNF----CFMEMNTR----------LqVE  343

32263  344  SDLaevlLAavegkLdsvdllfskdddkaAVgVVlAagGYPesyrKGdeIt
              e  +     dl +                             + + G++I
             HPVTEMITGT-------------DLVEWQ---------------LRIAAGEKIP  369

32263  370  gleeaekkgggnvivFHAGtakdngvvTnGGRVLaVtAlgddleeArekA
              + e    +g          HA                  eAe    A
             LSQEEITLQG---------HAF----------------------EARIYA  388

32263  389  ykavqk...IkFpGmfYRKDIGyrAl<-*
              +       ++ +p +        rA
             EDPSNNfmpVAGPLVHLS---TPRAD 411

CPSase_L_chain: domain 1 of 1, from 51 to 419: score 586.6, E = 1.5e-172
      *->kvLianrGeiaigqarefdysGYEtFderigavaalseedLantilv
         kvLianrGeia++++r+++++G          +q+va++se+d +n+++v
32263  51  KVLIANRGEIACRVMRTAKKLG---------VQTVAVYSEAD-RNSMHV  89 npadatvqtgpgLADkvyflpktylnvdkIIeaarpdgvlathgGyGfLn
      +ad+++ +gp++       + ++yl+++kII   a+  +++a+h+G GfL+
32263  90  DMADEAYSIGPAP-------SQQSYLSMEKIIQVAKTSAAQAIHPGCGFLS  133
```

FIG. 35D

```
              enaeLaeagvleeygvkflGppaeaIramGDKisfkaamkeagvptvPss
              en e+ae + +e   g++f+Gpp+ aIr+mG k ++k++m+ agvp+v++
32263   134   ENMEFAELCKQE--GIFIGPPPSAIRDMGIKSTSKSIMAAAGVPVVEGY   181 agPrvDtvhvDktlvsVpddlYkGlvesaeeAlaaAkeiGYPViiKAAfg
                    s   +   + A++iGYPV+IKA    g
32263   182   HG-----------------------------EDQSDQCLKEHARRIGYPVMIKAVRG   209 gGGkGmriarneeelielfaqAlaeapaAFGnpqvlvEKslkgpkhiEyq
              gGGkGmri+r e e++e   ++A++ea++F  ++ +l+EK+++ p+h+E+q
32263   210   GGGKGMRIVRSEQEFQEQLESARREAKKSFNDDAMLIEKFVDTPRHVEVQ   259

VlaDahGNcItlcnrECsdgrGiRtQkslevAPsqtLtdeergmlreaAv
              V  D hGN++++l+++r+Cs+qr R+Qk+Ie+AP+++++e+r+++l+eaAv
32263   260   VFGDHHGNAVYLFERDCSVQR--RHQKIIEEAPAGIKSEVRKKLGEAAV    307 kiarhvGyvGaGTVefl1dpdsgefyfIEvnpRlqVehplteka TGypLa
              ++a++v+yvGaGTVef+ d+ + +f+f+E+N+RlqVehp+te++TG +L+
32263   308   RAAKAVNYVGAGTVEFIMDS-KHNFCFMEMNTRLQVEHPVTEMITGTDLV   356 keqakIAlGipLpelkNivTggttAcFEPsLDYvvvKiprwdlpkGhave
              ++q++IA+G++ p+                           Gha  e
32263   357   EWQLRIAAGEKIPLS-----------------------QEEITLQGHAFE   383 cRIgsedpsvgFvPsiGRvfeesfpkAgrgVrvdss<-*
              +RI++edps++F+P  G++ ++s p A ++ r++ +
32263   384   ARIYAEDPSNNFMPVAGPLVHLSTPRADPSTRIETG   419
```

FIG. 35E

```
PTS_EIIA_1: domain 1 of 1, from 661 to 674: score 5.7, E = 3.1
               *->hVeeGdkVkqGDkL<-*
                  +V++GdkVk+GD L
      32263   661 FVKAGDKVKAGDSL     674 biotin_lipoyl: domain 1 of 1, from 650 to 714: score 67.8, E = 2.3e-16
               *->keiksPmiGesvkegtPvaevlVkvGDkVkaGqvlcevEaMKmemei
                  +Pm G+++k          v+Vk+GDkVkaG++l++  aMKme++i
      32263   650 ---LAPMTGIEK-------VFVKAGDKVKAGDSLMVMIAMKMEHTI     686 pApvaGvvkeilvkeGdtVevGdpLaki<-*
               +p++G+vk++    eG+    +pL+++
      32263   687 KSPKDGTVKKVFYREGAQANRHTPLVEF     714
```

FIG. 35F

```
Searching for complete domains in SMART
hmmpfam - search a single seq against HMM database
HMMER 2.1.1 (Dec 1998)
Copyright (C) 1992-1998 Washington University School of Medicine
HMMER is freely distributed under the GNU General Public License (GPL).
- - - - - - - - - - - - - - - - - - - - - - - - - - - - - - - - - - - - - - -
HMM file:          /ddm/robison/smart/smart/smart.all.hmms
Sequence file:     /prod/ddm/wspace/orfanal/oa-script.29777.seq
- - - - - - - - - - - - - - - - - - - - - - - - - - - - - - - - - - - - - - -
Query: 32263

Scores for sequence family classification (score includes all domains):
Model    Description                                         Score    E-value    N
-----    -----------                                         -----    -------    ---
        [no hits above thresholds]

Parsed for domains:
Model    Domain   seq-f   seq-t    hmm-f   hmm-t    score   E-value
-----    ------   -----   -----    -----   -----    -----   -------
        [no hits above thresholds]

Alignments of top-scoring domains:
        [no hits above thresholds]
```

FIG. 36A

```
                    1                                                          60
thal.PRO            M-SMMT-VWAL----RRNVRRKNHSMLVR---YISGSASMK---PKEQCIEKILVANRGE
celegans.PRO        MLRAASSIRAVANRGLATAAVARPGVPLDEREGKEIYTTVGID-YNEPKFDKILIANRGE
human.PRO           MLSA------ALRTLKHVLYYSRQCLMVSRN----LGSVGYD-PNEKTFDKILVANRGE
32263.pro           M-AAASAVSVLLVAAERNRWHRLPSLLLPPRTWVWRQRTMKYTTATGRNITKVLIANRGE 61                                                         120
thal.PRO            IACRIMRTAKRLGIQTVAVYSDADRDSLHVKSADEADRIGPPSAKRLSYLSGVTIMEAAA
celegans.PRO        IACRVIKTARAMGIKTVAVHSDVDSNSLHVKMADEAVCVGEAPTAK-SYLRADRILQAVE
human.PRO           IACRVIRTCKKMGIKTVAIHSDVDASSVHVKMADEAVCVGPAPTSK-SYLNMDAIMEAIK
32263.pro           IACRVMRTAKKLGVQTVAVYSEADRNSMHVDMADEAYSIGPAPSQQ-SYLSMEKIIQVAK 121                                                        180
thal.PRO            RTGAQAIHPGYGFLSESSDFAQLCEDSGLTFIGPPASAIRDMGDKSASKRIMGAAGVPLV
celegans.PRO        DTGAQAVHPGYGFLSENTKFAAELEKAGAKFIGPNSKAILDMGDKIHSKKIATAARVSMI
human.PRO           KTRAQAVHPGYGFLSENKEFARCLAAEDVVFIGPDTHAIQAMGDKIESKLLAKKAEVNTI
32263.pro           TSAAQAIHPGCGFLSENMEFAELCKQEGIIFIGPPPSAIRDMGIKSTSKSIMAAAGVPVV 181                                                        240
thal.PRO            PGYHGHEQDIDHMKSEAEKIGYPIIIKPTHGGGGKGMRIVQSGKDFEADSFLGAQREAAAS
celegans.PRO        PGYDGEIADEDMCVKVSRDIGYPVMIKASAGGGGKGMRVAWNDKQAREGYRLSKQEAASS
human.PRO           PGFDGVVKDAEEAVRIAREIGYPVMIKASAGGGKGMRIAWDDEETRDGFRLSSQEAASS
32263.pro           EGYHGEDQSDQCLKEHARRIGYPVMIKAVRGGGGKGMRIVRSEQEFQELESARREAKKS
```

FIG. 36B

```
              241                                                           300
thal.PRO      FGVNTILLEKYITRPRHIEVQIFGDKHGNVLHLHLYERDCSVQRRHQKIIEEAPA-------
celegans.PRO  FGDDRMLVEKFIDNPRHIEMQVLCDKHGNALWLNERECSIQRRNQKVIEEAPSSFVPPEM
human.PRO     FGDDRLLIEKFIDNPRHIEIQVLGDKHGNALWLNERECSIQRRNQKVVEEAPSIFLDAET
32263.pro     FNDDAMLIEKFVDTPRHVEVQVFGDHHGNAVYLFERDCSVQRRHQKIIEEAPAPGIKSEV 301                                                           360
thal.PRO      -------------AVGYYNAGTVEFIVDTESDQFYFMEMNTRLQVEHPVTEMIVGQDLVE
celegans.PRO  RRKMGEQAVQLAKAVGYDSAGTVEFLVDSQ-RNFYFLEMNTRLQVEHPITECITGIDIVQ
human.PRO     RRAMGEQAVALARAVKYSSAGTVEFLVDSK-KNFYFLEMNTRLQVEHPVTECITGLDLVQ
32263.pro     RKKLGEAAVRAAKAVNYVGAGTVEFIMDSK-HNFCFMEMNTRLQVEHPVTEMITGTDLVE 361                                                           420
thal.PRO      WQIRVANGEPLPLSQSEVPMSGHAFEARIYAENVPKGF-LPATGVLNHYRPVAVSPSVRV
celegans.PRO  QMLRVSYGHPLPITQEQVPLNGWAFESRVYAEDPYKGFGLPSVGRLSRYVEPKHVDGVRC
human.PRO     EMIRVAKGYPLRHKQADIRINGWAVECRVYAEDPYKSFGLPSIGRLSQYQEPLHLPGVRV
32263.pro     WQLRIAAGEKIPLSQEEITLQHAFEARIYAEDPSNNF-MPVAGPLVHLSTPRADPSTRI 421                                                           480
thal.PRO      ETGVEQGDTVSMHYDPMIAKLVVLGGNRGEALVKLKDCLSNFQVAGVPTNINFLQKLASH
celegans.PRO  DSGIREGSEISIYYDPLICKLVTHGDNREQALNRMQEALDNYVIRGVTHNIPLLRDIVQE
human.PRO     DSGIQPGSDISIYYDPMISKLITYGSDRTEALKRMADALDNYVIRGVTHNIALLREVIIN
32263.pro     ETGVRQGDEVSVHYDPMIAKLVWDPMIAKLVVWAADRQAALTKLRYSLRQYNIVGLPTNIDFLLNLSGH
```

FIG. 36C

```
              481                                                        540
thal.PRO      KEFAVGNVETHFIEHHKSDLFADESNPAATEVAYKAVKHSAALVAACISTIEHSTWNESN
celegans.PRO  KRFRTGDITTKYLPEVYPEGFQGTSLSPKEQD--VVIAFASALNARKLARANQFLNQNKQ
human.PRO     SRFVKGDISTKFLSDVYPDGFKGHMLTKSEKN--QLLAIASSLFVAFQLRAQHFQENSRM
32263.pro     PEFEAGNVHTDFIPQHHKQLLLSRKAAAKESLC----QAALGLILEKAMTDTFTLQAHD 541                                                        600
thal.PRO      HGKVPSIWYSNPPFRVHHEAKQTIELEWNNECEGTGSNLISLGVRYQPDGSYLIEEGNDS
celegans.PRO  R--STHVASFSKTYKFVSSLPVKEG-------ERPTEHAVEVEFVEGSANKAQVRIGGKT
human.PRO     PVIKPDIANWE--------LSVKLH------DK-----VHTVVASNNGSVFSVEVDGSK
32263.pro     Q-------FS--PFSSSSGRRLNISYTRNMTLKD-GKNNVAIAVTYNHDGSYSMQIEDKT 601                                                        660
thal.PRO      PSLELRVTRAGKCDF-RVEAAGLSMNVSLAAYLKDGYKHIHIWHGSEHHQFKQKVGIEFS
celegans.PRO  VTISGDLNLSH--PVNSIEVDGEHITTQIVGKRAG-EITVLYKGTP-----FKVKV---LP
human.PRO     LNVTSTWNLAS--PLLSVSVDGTQRTVQCLSREAGGNMSIQFLGTV-----YKVNI---LI
32263.pro     FQVLGNLYSEGDCTYLKCSVNGVASKAKLILENTIY------------LFSKEGSIEI-
```

FIG. 36D

```
             661                                                        720
thal.PRO     EDEEGVQHRTSSETSSHPPGTIVAPMAGLVVKVLVENEAKVDQGQPIILVLEAMKMEHVVK
celegans.PRO EQAVKYLQYMKEKAKVDLSTVVLSPMPGAIKNVNVKPGDMVSEGQELVVMEAMKMQNSLH
human.PRO    RLAAELNKFMLEKVTEDTSSVLRSPMPGVVVAVSVKPGDAVAEGQEICVIEAMKMQNSMT
32263.pro    --DIPVPKYLSSVSSQETQGGPLAPMTGTIEKVFVKAGDKVKAGDSLMVMIAMKMEHTIK 721                          758
thal.PRO     APSSGSIQDLKVKAGQQVSDGSALF------RIKG
celegans.PRO AGKTGRVKAVNVKVGATVDEGEVLVELE-------
human.PRO    AGKTGTVKSVHCQAGDTVGEGDLIVELE-------
32263.pro    SPKDGTVKKVFYREGAQANRHTPLVEFEEEESDKRESE
```

Input file Fbh50250f1.seq; Output File 50250all.trans
Sequence length 2031

```
     T   R   P   P   T   R   P   R   P   A   P   P   G   C   S   M   A   L   C    19
    CC ACG CGT CCG CCC ACG CGT CCG CGC CCC GCC CCG CCC GGC TGC TCC ATG GCG CTG TGC   57

E   A   A   G   C   G   S   A   L   L   W   P   R   L   L   F   G   D   S    39
    GAG GCC GCG GGC TGC GGG AGT GCC CTG CTC TGG CCT CGC TTG TTG CTC TTC GGG GAC TCC  117

I   T   Q   F   S   F   Q   Q   G   G   W   G   A   S   L   A   D   R   L   V    59
    ATC ACC CAG TTT TCC TTC CAG CAG GGT GGA TGG GGA GCA TCG CTG GCT GAC AGG CTG GTC  177

R   K   C   D   V   L   N   R   G   F   S   G   Y   N   T   R   W   A   K   I    79
    AGA AAA TGT GAT GTT CTG AAT CGT GGA TTT TCA GGT TAC AAT ACC AGG TGG GCC AAA ATT  237

I   L   P   R   L   I   R   K   G   N   S   L   D   I   P   V   A   V   T   I    99
    ATC CTT CCA AGA TTA ATC AGG AAA GGA AAC AGT TTG GAC ATC CCA GTA GCA GTT ACA ATT  297

F   F   G   A   N   D   S   A   L   K   D   E   N   P   K   Q   H   I   P   L   119
    TTC TTT GGG GCC AAT GAC AGT GCA CTA AAA GAT GAG AAT CCC AAG CAG CAC ATT CCC CTG  357

E   E   Y   A   A   N   L   K   S   M   V   Q   Y   L   K   S   V   D   I   P   139
    GAG GAG TAC GCT GCG AAC CTA AAG AGC ATG GTG CAG TAC CTG AAG TCC GTG GAC ATC CCT  417

E   N   R   V   I   L   I   T   P   T   P   L   C   E   T   A   W   E   E   Q   159
    GAG AAT CGA GTC ATT CTC ATC ACG CCG ACC CCA CTT TGT GAA ACA GCC TGG GAA GAA CAG  477

C   I   I   Q   G   C   K   L   N   R   L   N   S   V   V   G   E   Y   A   N   179
    TGC ATC ATA CAA GGT TGC AAA CTA AAT CGC CTG AAC TCT GTT GTT GGT GAA TAT GCC AAT  537

A   C   L   Q   V   A   Q   D   C   G   T   D   V   L   D   L   W   T   L   M   199
    GCG TGT TTA CAA GTG GCC CAA GAC TGT GGG ACT GAC GTA CTT GAC CTG TGG ACC CTG ATG  597

Q   D   S   Q   D   F   S   S   Y   L   S   D   G   L   H   L   S   P   K   G   219
    CAG GAC AGC CAG GAC TTC TCA TCT TAT TTA TCA GAT GGA CTA CAT TTG TCT CCA AAG GGG  657

N   E   F   L   F   S   H   L   W   P   L   I   E   K   K   V   S   S   L   P   239
    AAT GAA TTT TTG TTC TCG CAT CTC TGG CCT TTG ATA GAG AAA AAG GTC TCT TCT CTA CCT  717

L   L   L   P   Y   W   R   D   V   A   E   A   K   P   E   L   S   L   L   G   259
    TTG CTG CTT CCT TAC TGG CGG GAT GTA GCA GAA GCA AAA CCT GAA TTA AGT CTG CTG GGA  777

D   G   D   H   *                                                              264
    GAT GGA GAC CAT TAG                                                              792
```

CCAATCACAGGAGACCCAAATCTGCTTGTTATCTACAGAACTCAAAGTTGTCAATACGTAGAGGTACGCTTTTTTCCTC

AGGCTTAAACCTTTGCCACTGATATTAATAATAAAAGTATTAGATGATTTTTCAGGGAAGTTTTATACTTAGGTCCATT

GTGTTTCGACAGTATTTATTAATGCAGATATCAGTGCTACAGCTATAAAATATACCCTGAGCAGCTTGTTAATTCTATA

AATGACAAAGACTATGTTTTTAAAAAGTCACAATTTTATAAAAATGGTTTTTCTTACATTCTTTTGAGAACTGTTTCAC

TCATACATACACCCACACACCCCACTCAACCTTGTATCAAATTCCAAAAGTGTAACTAAAGTATAAGAATATCATGACT

AGTTAAAAGATAGCAAATACCATAAGGTACAAGTTCAAGTATTAGTATAACAAGTATCTGAGTAACAAATGTCCTTGGA

FIG. 37A

```
AATGGGGGGTAGGAGGAGATATGATTAGTCACAGGTTTGGTTAACTGCCCTCAAAATTTACAAGTTAAAATGTTTTGGC
TGGTGAGCACATTTCAGTTCTTAGGGGAAAAAAAGCTTTTAATGGCAATTTATAGAAATCAGAATCCAGGCTAATGATT
TTTATCCTTCACACAGTAAATGCAGCCCATCCAGAATCCTGGAGCAATAAAGTAAGAAGTAATTCAAATATCTGCTTGT
GGGTCAATAAAAAGGGTTTCTGAAGTATCAAGTCTTGTGGGGACAGCCCCCAACCCTAAGGGCAGGTAGTATTCTATCT
CCTGGCTGGCTCATCACATTCAAAACAACCTGNNTTTTTTNTTGTTGTTGTTGTTGTTAAGAAATATCTCACCCTCTTA
TTCAATAGTGTTTGAAAACAGGCAATCTTTGTATTTTAAATATTCTAGGTTTGTAGATAGTGAATTTTTTTTTTTTTTT
TTTTTTTTTGAGGCAGAGTCTCACTCTGTCACCCAGGCTGGAGTGTAGTGGCGCAACCTCAGCCTCTCCAAGTGCTGGG
ATTACAGGCATGAGCCACCACTCCCAGCCAATAGTGAATTTTCTAAGAGCATGTATCCCTATCAGTAACAGGGATACAT
GAAGATACTTATAAAATACAGAAAAACTGCCCAGCAAATCAGGGCCCTAAACAGTTGGTAGATTCCATAAATTCAACTG
GCTACCATGTATAGCCCTCACTGTAAGGTAGGTGGTTAGGTTTCTAGAGAGC
```

FIG. 37B

```
Input file Fbh50250fl.seq; Output File 50250.trans
Sequence length 2031
                                                        M   A   L   C   E   A   A   G     8
CCACGCGTCCGCCCACGCGTCCGCGCCCCGCCCCGCCCGGCTGCTCC ATG GCG CTG TGC GAG GCC GCG GGC    24

C   G   S   A   L   L   W   P   R   L   L   L   F   G   D   S   I   T   Q   F    28
TGC GGG AGT GCC CTG CTC TGG CCT CGC TTG TTG CTC TTC GGG GAC TCC ATC ACC CAG TTT    84

S   F   Q   Q   G   G   W   G   A   S   L   A   D   R   L   V   R   K   C   D    48
TCC TTC CAG CAG GGT GGA TGG GGA GCA TCG CTG GCT GAC AGG CTG GTC AGA AAA TGT GAT   144

V   L   N   R   G   F   S   G   Y   N   T   R   W   A   K   I   I   L   P   R    68
GTT CTG AAT CGT GGA TTT TCA GGT TAC AAT ACC AGG TGG GCC AAA ATT ATC CTT CCA AGA   204

L   I   R   K   G   N   S   L   D   I   P   V   A   V   T   I   F   F   C   A    88
TTA ATC AGG AAA GGA AAC AGT TTG GAC ATC CCA GTA GCA GTT ACA ATT TTC TTT GGG GCC   264

N   D   S   A   L   K   D   E   N   P   K   Q   H   I   P   L   E   E   Y   A   108
AAT GAC AGT GCA CTA AAA GAT GAG AAT CCC AAG CAG CAC ATT CCC CTG GAG GAG TAC GCT   324

A   N   L   K   S   M   V   Q   Y   L   K   S   V   D   I   P   E   N   R   V   128
GCG AAC CTA AAG AGC ATG GTG CAG TAC CTG AAG TCC GTG GAC ATC CCT GAG AAT CGA GTC   384

I   L   I   T   P   T   P   L   C   E   T   A   W   E   E   Q   C   I   I   Q   148
ATT CTC ATC ACG CCG ACC CCA CTT TGT GAA ACA GCC TGG GAA GAA CAG TGC ATC ATA CAA   444

G   C   K   L   N   R   L   N   S   V   V   G   E   Y   A   N   A   C   L   Q   168
GGT TGC AAA CTA AAT CGC CTG AAC TCT GTT GTT GGT GAA TAT GCC AAT GCG TGT TTA CAA   504

V   A   Q   D   C   G   T   D   V   L   D   L   W   T   L   M   Q   D   S   Q   188
GTG GCC CAA GAC TGT GGG ACT GAC GTA CTT GAC CTG TGG ACC CTG ATG CAG GAC AGC CAG   564

D   F   S   S   Y   L   S   D   G   L   H   L   S   P   K   G   N   E   F   L   208
GAC TTC TCA TCT TAT TTA TCA GAT GGA CTA CAT TTG TCT CCA AAG GGG AAT GAA TTT TTG   624

F   S   H   L   W   P   L   I   E   K   K   V   S   S   L   P   L   L   L   P   228
TTC TCG CAT CTC TGG CCT TTG ATA GAG AAA AAG GTC TCT TCT CTA CCT TTG CTG CTT CCT   684

Y   W   R   D   V   A   E   A   K   P   E   L   S   L   L   G   D   G   D   H   248
TAC TGG CGG GAT GTA GCA GAA GCA AAA CCT GAA TTA AGT CTG CTG GGA GAT GGA GAC CAT   744

*
TAG

CCAATCACAGGAGACCCAAATCTGCTTGTTATCTACAGAACTCAAAGTTGTCAATACGTAGAGGTACGCTTTTTTCCTC

AGGCTTAAACCTTTGCCACTGATATTAATAATAAAAGTATTAGATGATTTTTCAGGGAAGTTTTATACTTAGGTCCATT

GTGTTTCGACAGTATTTATTAATGCAGATATCAGTGCTACAGCTATAAAATATACCCTGAGCAGCTTGTTAATTCTATA

AATGACAAAGACTATGTTTTTAAAAAGTCACAATTTTTATAAAAATGGTTTTTCTTACATTCTTTTGAGAACTGTTTCAC

TCATACATACACCCACACACCCCACTCAACCTTGTATCAAATTCCAAAAGTGTAACTAAAGTATAAGAATATCATGACT

AGTTAAAAGATAGCAAATACCATAAGGTACAAGTTCAAGTATTAGTATAACAAGTATCTGAGTAACAAATGTCCTTGGA
```

FIG. 38A

AATGGGGGGTAGGAGGAGATATGATTAGTCACAGGTTTGGTTAACTGCCCTCAAAATTTACAAGTTAAAATGTTTTGGC

TGGTGAGCACATTTCAGTTCTTAGGGGAAAAAAAGCTTTTAATGGCAATTTATAGAAATCAGAATCCAGGCTAATGATT

TTTATCCTTCACACAGTAAATGCAGCCCATCCAGAATCCTGGAGCAATAAAGTAAGAAGTAATTCAAATATCTGCTTGT

GGGTCAATAAAAAGGGTTTCTGAAGTATCAAGTCTTGTGGGGACAGCCCCCAACCCTAAGGGCAGGTAGTATTCTATCT

CCTGGCTGGCTCATCACATTCAAAACAACCTGNNTTTTTTNTTGTTGTTGTTGTTGTTAAGAAATATCTCACCCTCTTA

TTCAATAGTGTTTGAAAACAGGCAATCTTTGTATTTTAAATATTCTAGGTTTGTAGATAGTGAATTTTTTTTTTTTTTT

TTTTTTTTTGAGGCAGAGTCTCACTCTGTCACCCAGGCTGGAGTGTAGTGGCGCAACCTCAGCCTCTCCAAGTGCTGGG

ATTACAGGCATGAGCCACCACTCCCAGCCAATAGTGAATTTTCTAAGAGCATGTATCCCTATCAGTAACAGGGATACAT

GAAGATACTTATAAAATACAGAAAAACTGCCCAGCAAATCAGGGCCCTAAACAGTTGGTAGATTCCATAAATTCAACTG

GCTACCATGTATAGCCCTCACTGTAAGGTAGGTGGTTAGGTTTCTAGAGAGC

FIG. 38B

```
Input file Fbh55158FL.seq; Output File 55158.trans
Sequence length 1855
                                                             M   E   I   V   W     5
AANTCGAGAAATTNTAATANNCACTCACTATAGGGAGTCGACCCACGCGACCGCAGAGG ATG GAA ATA GTC TGG    15

E   V   L   F   L   L   Q   A   N   F   I   V   C   I   S   A   Q   Q   N   S    25
GAG GTG CTT TTT CTT CTT CAA GCC AAT TTC ATC GTC TGC ATA TCA GCT CAA CAG AAT TCA    75

P   K   I   H   E   G   W   W   A   Y   K   E   V   V   Q   G   S   F   V   P    45
CCA AAA ATC CAT GAA GGC TGG TGG GCA TAC AAG GAG GTG GTC CAG GGA AGC TTT GTT CCA   135

V   P   S   F   W   G   L   V   N   S   A   W   N   L   C   S   V   G   K   R    65
GTT CCT TCT TTC TGG GGA TTG GTG AAC TCA GCT TGG AAT CTT TGC TCT GTG GGG AAA CGG   195

Q   S   P   V   N   I   E   T   S   H   M   I   F   D   P   F   L   T   P   L    85
CAG TCG CCA GTC AAC ATA GAG ACC AGT CAC ATG ATC TTC GAC CCC TTT CTG ACA CCT CTT   255

R   I   N   T   G   G   R   K   V   S   G   T   M   Y   N   T   G   R   H   V   105
CGC ATC AAC ACG GGG GGC AGG AAG GTC AGT GGG ACC ATG TAC AAC ACT GGA AGA CAC GTA   315

S   P   R   L   D   K   E   H   L   V   N   I   S   G   G   P   M   T   Y   S   125
TCC CCT CGC CTG GAC AAG GAG CAC TTG GTC AAC ATA TCT GGA GGG CCC ATG ACA TAC AGC   375

H   R   L   E   E   I   R   L   H   F   G   S   E   D   S   Q   G   S   E   H   145
CAC CGG CTG GAG GAG ATC CGA CTA CAC TTT GGG AGT GAG GAC AGC CAA GGG TCG GAG CAC   435

L   L   N   G   Q   A   F   S   G   E   V   Q   L   I   H   Y   N   H   E   L   165
CTC CTC AAT GGA CAG GCC TTC TCT GGG GAG GTG CAG CTC ATC CAC TAT AAC CAT GAG CTA   495

Y   T   N   V   T   E   A   A   K   S   P   N   G   L   V   V   S   I   F   185
TAT ACG AAT GTC ACA GAA GCT GCA AAG AGT CCA AAT GGA TTG GTG GTA GTT TCT ATA TTT   555

I   K   V   S   D   S   S   N   P   F   L   N   R   M   L   N   R   D   T   I   205
ATA AAA GTT TCT GAT TCA TCA AAC CCA TTT CTT AAT CGA ATG CTC AAC AGA GAT ACT ATC   615

T   R   I   T   Y   K   N   D   A   Y   L   L   Q   G   L   N   I   E   E   L   225
ACA AGA ATA ACA TAT AAA AAT GAT GCA TAT TTA CTA CAG GGG CTT AAT ATA GAG GAA CTA   675

Y   P   E   T   S   S   F   I   T   Y   D   G   S   M   T   I   P   P   C   Y   245
TAT CCA GAG ACC TCT AGT TTC ATC ACT TAC GAT GGG TCG ATG ACT ATC CCA CCC TGC TAT   735

E   T   A   S   W   I   I   M   N   K   P   V   Y   I   T   R   M   Q   M   H   265
GAG ACA GCA AGT TGG ATC ATA ATG AAC AAA CCT GTC TAT ATA ACC AGG ATG CAG ATG CAT   795

S   L   R   L   L   S   Q   N   Q   P   S   Q   I   F   L   S   M   S   D   N   285
TCC TTG CGC CTG CTC AGC CAG AAC CAG CCA TCT CAG ATC TTT CTG AGC ATG AGT GAC AAC   855

F   R   P   V   Q   P   L   N   N   R   C   I   R   T   N   I   N   F   S   L   305
TTC AGG CCT GTC CAG CCA CTC AAC AAC CGC TGC ATC CGC ACC AAT ATC AAC TTC AGT TTA   915

Q   G   K   D   C   P   N   N   R   A   Q   K   L   Q   Y   R   V   N   E   W   325
CAG GGG AAG GAC TGT CCA AAC AAC CGA GCC CAG AAG CTT CAG TAT AGA GTA AAT GAA TGG   975

L   L   K   *                                                                    329
CTC CTC AAG TAG                                                                    987
                                  FIG. 44A
```

```
GGAACAAAGCCAAGAAGAATCCCACCTCAGTGAAATGCTACAACTGTGAATTGACGTAACCTAGAATGTCCCCCTTCTT
GCTTCTCTCTCCTTCTTTCCCCCAAGCCTCATTCATTCTTGGGATTGGCCCTTTCTTCATGAAAAGTGTCTGCAAAACC
ATGGCAGAGGAATACATCTCTCACACATACTCACAAACACACACACAAGCACTTGCACATACATACAAACACATGCAAA
CATACCTACACACACACACTCTTACAACCTCCATCATGGGAAGTCAAGTTTCAGAAACAAAAGTCTCATTCATAAGA
GGTCTTAGAAGAAAATAACCAGTTAACCTGATTTCAATTTTGATACCGTTTTCCTGAACTAATAAATCTACCCAATGAG
ACTTTTCAGCCTTTGTACATACAAAATTCTTCCAAAAGAGAGAGGAGAAAATACAGCTCTGATGGCATCAAACGGACTT
TGCATCAAGTAATTTCAGATAGTGTCCTAGGATCCTTTGAGGGTGCTGGTAGCAGGTGAGCAGGACAAAGTTGACCAAG
GACACTTATTTCTAGATTATGATTCTTCTGTTTACTCAACAATTTACAAAGAAAAAAAAGACAGACATTGAAGAGCTAC
ACATTGTATATATATCACCACAGACTATAAGGAAATGGAATTATTTCCCTCTTTGTCACATATCTGTAGTAGGATTTGC
CAAGATCAGAAATGATCCATTTGCTGTTTCTTGTTTTCCAAAGGTCATACATTGTGTTTGGTTATTGTTACCAGCTCAA
TAAATGTGTTTAACGAGTT
```

FIG. 44B

```
Protein family / Domain Matches, HMMer version 2

Searching for complete domains in PFAM
hmmpfam - search a single seq against HMM database
HMMER 2.1.1 (Dec 1998)
Copyright (C) 1992-1998 Washington University School of Medicine
HMMER is freely distributed under the GNU General Public License (GPL)
- - - - - - - - - - - - - - - - - - - - - - - - - - - - - - - -
HMM file:              /prod/ddm/seqanal/PFAM/pfam6.2/Pfam
Sequence file:         /prod/ddm/wspace/orfanal/oa-script.732.seq
- - - - - - - - - - - - - - - - - - - - - - - - - - - - - - - -
Query:  55158

Scores for sequence family classification (score includes all domains):
Model           Description                              Score    E-value  N
--------        -----------                              -----    -------  ---
carb_anhydrase  Eukaryotic-type carbonic anhydrase       170.6    2.6e-47  1

Parsed for domains:
Model           Domain  seq-f  seq-t   hmm-f  hmm-t    score   E-value
--------        ------  -----  -----   -----  -----    -----   -------
carb_anhydrase  1/1     63     301 ..   33    283 .]   170.6   2.6e-47

Alignments of top-scoring domains:
carb_anhydrase: domain 1 of 1, from 63 to 301: score 170.6, E = 2.6e-47
               *->GerQSPInIqtkeakyDPsLkpLsl.SYdaatakefeivNnGHsfqV
                  G rQSP+nI t+     DP L pL+++++  ++++  ++ N+G+ +
       55158  63 GKRQSPVNIETSHMIFDPFLTPLRInTGGRKVSG--TMYNTGRHVSP 107 eFdDsddksvlsGGPLpaGhpYRLkQfHFHWGGAssddqGSEHTVDGkkY
                  +d       +sGGP +   + RL + ++H G  s+d qGSEH ++G ++
       55158 108 RLDK-EHLVNISGGPMTY--SHRLEEIRLHFG--SEDSQGSEHLLNGQAF 152 aaELHLVHWNstKYgsykeAvskpDGLAV1GvFlkvGdyqenpglqkvv.
                  + E L+H+N  Y ++ eA++ p+GL V+ +F kv    np l++ ++
       55158 153 SGEVQLIHYNHELYTNVTEAAKSPNGLVVVSIFIKVS-DSSNPFLNRMLN 201

.DaLssIktKGksatftnFDPstLLPseklrDYWTYpGSLTTPPLtEsVt
                  +D   I +K    + +++++ L P+     + TY GS T+PP++E
       55158 202 rDTITRITYKNDAYLLQGLNIEELYPE--TSSFITYDGSMTIPPCYETAS 249

WiVlkepIsvSseQllkFRsLlfnaegeeevpGCdGimvdNyRPtQPLkg
                  Wi+   p+ + + Q+ +R L n       +      m dN+RP QPL++
       55158 250 WIIMNKPVYITRMQMHSLRLLSQNQPSQIFLS-----MSDNFRPVQPLNN 294

RVVRASF<-*
                  R +R +
       55158 295 RCIRTNI      301
```

> Fbh47765F1 - Import - vector trimmed

```
CACGGGTCCGCGGCTGCTCCGCGGCGGCCGCCGCCCAGCCCCGGACTGTCCGCGCCTCCATCTGGTATCTTGGCCTCAGCT

L   L   L   L   L      16
        M   A   W   S   P   P   A   T   L   F   L   F   L   L   L   L   L           
GTCCTTGAAGTCACC ATG GCG TGG TCC CCA CCA GCC ACC CTC TTT CTG TTC CTG CTG CTG CTA       48

G   Q   P   P   S   R   P   Q   S   L   G   T   T   K   L   R   L   V   G            36
GGC CAG CCC CCT AGC AGG CCA CAG TCA CTG GGC ACC ACT AAG CTC CGG CTG GTG GGC          108

P   E   S   K   P   E   E   R   L   E   V   H   Q   Q   G   W   G   T                56
CCA GAG AGC AAG CCA GAG GAG CGC CTG GAG GTG CAC CAG CAG GGC TGG GGC ACC              168

V   C   D   D   N   F   A   I   Q   E   A   T   V   G   Y   R   Q   L   G   F        76
GTG TGT GAT GAC AAC TTT GCT ATC CAG GAG GCC ACA GTG GGC TAC CGC CAG CTG GGC TTC      228

E   A   A   L   T   W   A   H   S   A   K   Y   G   Q   E   G   P   I   W            96
GAA GCT GCC TTG ACC TGG GCC CAC AGT GCC AAG TAC GGC CAA GAG GGA CCC ATC TGG          288

L   D   N   V   R   C   V   C   T   E   S   D   Q   C   S   N   G              116
CTG GAC AAT GTG CGC TGT GTG TGT ACA GAG AGC GAC CAG TGC TCT AAT GGC                  348

W   G   V   S   D   D   C   S   H   E   D   V   G   I   H   P   R   R              136
TGG GGA GTC AGT GAC GAC TGC AGT CAC GAA GAC GTA GGG ATA CAC CCC CGG CGC              408

H   R   G   Y   L   S   E   T   V   S   N   A   L   Q   P   Q   R   R   L          156
CAT CGT GGC TAC CTT TCT GAA ACT GTC TCC AAT GCC CTT CCC CAG CGG CGG CTG              468

E   V   R   L   K   P   I   L   A   S   A   K   Q   H   S   P   V   T   E          176
GAG GAG GTG CGG CTC AAG CCC ATC CTT GCC AGT GCC AAG CAG CAT AGC CCA GTG ACC GAG      528
```

FIG. 53B

| | | | | | | | | | | | | | | | | | | | | |
|---|---|---|---|---|---|---|---|---|---|---|---|---|---|---|---|---|---|---|---|---|
| G | A | V | E | V | K | Y | E | G | H | W | R | Q | V | C | D | Q | G | W | T | 196 |
| GGA | GCC | GTG | GAG | GTG | AAG | TAT | GAG | GGC | CAC | TGG | CGG | CAG | GTG | TGT | GAC | CAG | GGC | TGG | ACC | 588 |
| M | N | N | S | R | V | V | C | L | M | L | G | F | P | S | E | V | P | V | D | 216 |
| ATG | AAC | AAC | AGC | AGG | GTG | GTG | TGC | CTG | ATG | CTG | GGC | TTC | CCC | AGC | GAG | GTG | CCT | GTC | GAC | 648 |
| S | H | Y | Y | R | K | N | V | W | D | K | M | R | D | P | K | S | R | L | K | 236 |
| AGC | CAC | TAC | TAC | AGG | AAA | AAC | GTC | TGG | GAT | AAG | ATG | AGG | GAC | CCT | AAG | TCT | AGG | CTG | AAG | 708 |
| S | L | T | N | N | Q | S | F | W | I | H | Q | V | T | C | L | G | T | E | P | 256 |
| AGC | CTG | ACG | AAT | AAC | CAG | TCC | TTC | TGG | ATC | CAC | CAG | GTC | ACC | TGC | CTG | GGG | ACA | GAG | CCC | 768 |
| H | M | A | N | C | Q | A | V | C | A | P | R | G | R | L | K | F | R | R | A | 276 |
| CAC | ATG | GCC | AAC | TGC | CAG | GCT | GTG | TGC | GCC | CCA | CGG | GGG | AAG | CTG | TTC | CGG | CGG | ACA | GCC | 828 |
| P | G | M | H | A | V | C | V | S | W | A | E | E | P | R | P | R | L | G | C | 296 |
| CCA | GGT | ATG | CAC | GCT | GTG | TGT | GTC | AGC | TGG | GCA | GAG | GAG | CCG | AGG | CCT | CGG | CTG | GGC | TGC | 888 |
| T | K | R | G | E | R | V | E | S | A | L | M | N | R | Q | R | W | G | T | K | 316 |
| ACA | AAG | CGC | GGC | GAG | GGC | GTG | GAA | GGG | GCC | CTC | ATG | AAC | CGC | CAG | CGC | TGG | GGC | ACG | AAG | 948 |
| A | Q | V | G | L | I | S | A | S | V | V | C | R | Q | L | Q | G | L | G | C | 336 |
| GCC | CAG | GTG | GGC | CTC | ATC | TCT | GCC | AGT | GTC | GTG | TGT | CGT | CAG | CTG | CAG | GGC | CTG | GGC | TGT | 1008 |
| D | H | R | W | N | L | I | G | L | G | G | Q | G | L | G | G | F | G | G | S | 356 |
| GAC | CAC | AGG | TGG | AAC | CTC | ATC | GGC | CTG | GGC | GGC | CAA | GGG | CTG | GGC | GGC | TTT | GGC | GGC | TCT | 1068 |
| A | R | E | A | L | F | G | A | R | L | G | G | Q | L | P | I | H | L | H | S | 376 |
| GCT | CGG | GAG | GCC | CTC | TTT | GGG | GCC | CGG | CTG | GGG | CAA | CTA | GGG | CCC | ATC | CAC | CTG | CAC | AGT | 1128 |

FIG. 53C

```
E   V   R   C   R   G   Y   E   R   T   L   S   D   C   P   A   L   E   G   S   396
GAG GTG CGC TGC AGG GGA TAT GAG CGG ACC CTC AGC GAC TGC CCT GCC CTG GAA GGG TCC  1188

Q   N   G   C   Q   H   E   N   D   A   A   V   S   D   R   C   N   V   M   G   416
CAG AAT GGT TGC CAA CAT GAG AAT GAT GCT GCT GTC AGC GAC AGG TGC AAT GTC ATG GGC  1248

F   Q   N   Q   V   R   L   A   G   G   R   I   P   E   E   P   L   L   E   V   436
TTT CAG AAT CAG GTG CGC TTG GCT GGT GGT CGT ATC CCT GAG GAG CCT CTA TTG GAG GTG  1308

Q   V   N   G   R   P   V   S   A   G   S   V   C   F   E   S   V   H   D   L   456
CAG GTG AAC GGG CGC CCA GTC AGC AGT GGG AGT GTG TGC TTT GAG AGT GTG CAC CTA CTC  1368

T   E   A   M   V   A   C   R   Q   L   G   F   A   I   H   S   W   G   A   K   476
ACC GAA GCC ATG GTG GCC TGC CGA CAG CTG GGC TTT GCC ATC CAT AGT TGG GGG GCC TAC  1428

E   T   W   F   S   R   A   R   V   E   V   M   H   V   P   G   V   D   L   R   496
GAA ACC TGG TTC TCG AGG GCC AGG GTG GAG GTG ATG CAC GTG CCG GGG GTG GAC CTG CGC  1488

C   S   G   G   L   F   L   Q   Q   C   S   V   H   P   A   D   S   C   516
TGC TCA GGC GGG CTG TTC CTG CAG CAG TGC TCC GTG CAC CCA GCA GAC AGC TGC TCC  1548

H   G   G   R   L   F   V   Q   V   G   T   L   E   D   P   R   L   V   536
CAC GGC GGG CGC TTC CTG GTG CAG GTG GGA ACG CTG GAG GAC CCG CGC CTG CTG GTG  1608

M   N   A   Q   V   E   T   A   Y   L   C   L   S   Q   L   556
ATG AAC GCC CAG GTG GAG ACG GCC TAC CTC TGC AGC AGC CTC CAG CTG  1668

Y   C   A   H   E   E   N   C   L   T   S   K   S   A   D   H   M   D   W   P   Y   576
TAT TGT GCC CAC GAG GAG AAC TGC CTC ACC TCC AAG TCT GCA GAT CAC ATG GAC TGG CCC TAC  1728
```

FIG. 53D

| G GGA | Y TAC | R CGC | L CTA | L TTG | R CGC | F TTC | S TCC | T ACA | Q CAG | I ATC | Y TAC | N AAT | L CTG | G GGC | R CGG | T ACT | D GAC | F TTT | 596 1788 |
|---|---|---|---|---|---|---|---|---|---|---|---|---|---|---|---|---|---|---|---|
| R CGT | P CCA | K AAG | T ACT | G GGA | R CGC | D GAT | S AGC | W TGG | V GTT | H CAC | Q CAG | C TGC | H CAC | R AGG | H CAT | Y TAC | H CAC | S AGC | 616 1848 |
| I ATT | E GAG | V GTC | F TTC | T ACC | H CAC | Y TAC | D GAC | L CTC | L CTC | T ACT | N AAT | G GGC | S TCC | K AAG | R AGG | Y TAC | A GCT | G GGG | 636 1908 |
| H CAC | K AAG | A GCC | S AGC | F TTC | C TGT | L CTG | E GAA | Q CAG | N AAC | P CCC | C TGC | G GGC | L CTG | V GTG | K AAG | Q CAG | R CGC | Y TAC | 656 1968 |
| A GCA | C TGC | A GCC | N AAC | F TTT | G GGA | E GAA | V GTG | D GAT | T ACA | T ACT | N AAT | G GGG | W TGG | G GGA | M ATG | T ACC | Y TAC | H CAT | 676 2028 |
| D GAC | I ATT | D GAT | C TGC | Q CAG | W TGG | V GTG | E GAA | A GCA | E GAG | S TCA | D GAT | V GTG | G GGC | G GGC | P CCC | F TTC | I ATC | Q CAG | 696 2088 |
| V GTG | I ATT | V GTG | N AAC | P CCC | Y TAT | E GAA | R CGG | V GTC | A GCA | E GAG | W TGG | L CTG | H CAC | N AAC | S TCC | N AAT | M ATG | L CTG | 716 2148 |
| C TGC | R CGC | C TGC | K AAG | D GAT | G GGG

FIG. 53E

AGCTGTCACTGCACACTCCTAGCTGCTGCCGATACACCAGATACCTCAGCTTATTGGAGCCATGCCCCTTCACAGAGTCC

CAACTCAGAGGAAAAGGGCCAGTGCCAAGGGCACCAAGAACCTGCTCAGGAAGCCTTTTGATGGCAAGATCACCAATC

CAGATGGTATTGCTCCCTCAGGATGGCTCTGGGCCTGCCCCTAAGGGCCTATGGAATATGTCCTCCAGGCTT

TGCTTAGCTGAGCTCCTCTTCTGTAAGGAAAACCCAGTCATCCCTGAATCTTGCCACAGAGATCCGGGATTCAGGAGCTC

TCAGTTTCTTAGGGATGGACTATGGCCCCAGTCCCCCATCTAAGTGGTGCTTTGCAAATGTCTTGGAGGAGTATAGGACA

GAGGACCAAAATACACAGCAGGTAGTGKTAGCTCTCTGCTAGGAGCTCAAAGCAACACAACTTGTATCAAAATCACAAC

TGGCAGAAAAACTGGGTGGATCCAATCCTTTCTTTCATCTGTGTATTTAAGAAYYAACCYTTAMACTCTGGTCTTTAGG

GGCCTTAMCTTTATTTWMCACAMAMAATNGGNGGTTTATTATCYTTGGAAGCACAAA

FIG. 55A

Input file Fbh62088FL.seq; Output File 62088.trans
Sequence length 3296

CGCGTNCGCGTGGGCGYCCSCGNMCGSGYSGGCCCCCGCGTCCGGGAGCAGCTCGGGACT

GAACCGAGAGGTGCCGAAGGAACCGGGCGGGCCGCTTGATCCCGCTGCAGACGTAGGAGATGCCTGGGACAAGGAGGCCA

```
                                              M   A   R   I   S                5
CCTTCTCAGGGCAAAGAAAAAGAAGGTGACAGGCGTTGAGACCACCGAAGGGAACCC ATG GCT AGG ATC AGT     15

F   S   Y   L   C   P   A   S   W   Y   F   T   V   P   T   V   S   P   F   L    25
TTT TCC TAC CTC TGC CCA GCC TCC TGG TAC TTC ACT GTG CCC ACA GTG AGT CCA TTT CTC    75

R   Q   R   V   A   F   L   G   L   F   F   I   S   C   L   L   M   L            45
CGT CAG CGG GTG GCA TTC CTG GGA CTC TTC TTC ATA TCC TGT CTC CTT TTA CTT ATG TTA   135

I   D   F   R   H   W   S   A   S   L   P   R   D   R   Q   Y   E   R   Y        65
ATC ATA GAC TTT CGA CAT TGG AGT GCT TCA TTA CCA CGA GAT AGG CAA TAC GAA AGG TAT   195

L   A   R   V   G   C   E   L   E   A   T   D   T   E   D   P   N   L   G        85
TTG GCT CGA GTA GGG TGT GAG CTT GAA GCT ACT GAC ACT GAA GAC CCA AAT CTG GGA       255

L   V   D   C   H   L   S   G   S   R   I   F   V   Y   F   W   P   R   H       105
CTT GTT GAC TGT CAT TTG AGC AGT GGT GAT ATT TTT GTT TAT TGG CCA AGA CAT           315

N   G   N   P   H   D   L   D   I   K   Q   M   R   D   R   N   S   Q   P       125
AAT GGG AAC CCC CAT GAC TTG CTG GAC ATC AAA CAG ATG AGA GAC CGC AAC AGC CAA CCA   375
```

FIG. 55B

| | | | | | | | | | | | | | | | | | | | | | |
|---|---|---|---|---|---|---|---|---|---|---|---|---|---|---|---|---|---|---|---|---|---|
| V | V | K | I | K | P | G | I | S | A | M | A | D | T | P | E | H | A | S | | 145 |
| GTG | GTT | AAA | ATC | AAG | CCA | GGA | ATC | TCT | GCA | ATG | GCA | GAC | ACT | CCA | GAA | CAT | GCC | AGT | | 435 |
| D | Y | L | R | P | L | S | F | A | A | H | V | P | K | H | A | K | | | | 165 |
| GAT | TAC | CTT | CGT | CCT | CTG | AGC | TTT | GCT | GCT | CAT | GTG | CCT | AAG | CAC | GCA | AAG | | | | 495 |
| E | T | P | L | Y | I | L | C | T | A | G | M | R | L | P | E | R | K | Q | | 185 |
| GAG | ACC | CCT | CTT | TAC | ATC | CTC | TGC | ACA | GCA | GGC | ATG | AGG | CTC | CCT | GAG | AGG | AAG | CAG | | 555 |
| L | I | A | L | D | V | K | T | P | L | E | F | D | F | L | | | | | | 205 |
| TTG | ATC | GCT | TTG | GAC | CTA | GTG | AAA | CCA | TTA | GAG | CTG | GAG | TTT | CTC | TTT | TCA | | | | 615 |
| Q | S | Q | E | A | V | I | S | E | Q | G | E | D | Y | A | W | I | G | | | 225 |
| CAG | TCT | CAA | GAA | GCA | GTG | ATC | TCT | GAA | CAG | GGG | GAA | GAT | TAT | GCA | TGG | ATT | GGA | | | 675 |
| N | F | V | L | G | R | F | D | H | E | T | R | A | E | A | T | Q | E | | | 245 |
| AAC | TTT | GTT | TTG | GGA | AGA | TTC | GAC | CAC | GAG | ACA | AGG | GCT | GAG | GCT | ACC | CAG | GAA | | | 735 |
| L | A | A | G | R | R | R | T | M | D | I | L | G | G | A | S | E | Q | | | 265 |
| TTG | GCA | GCA | GGA | CGG | AGA | AGG | ACA | ATG | GAT | ATA | CTG | GGA | GGA | GCC | TCT | GAA | CAA | | | 795 |
| I | A | Y | E | V | P | T | S | V | L | P | A | K | Q | E | E | A | A | | | 285 |
| ATT | GCT | TAT | GAA | GTT | CCT | ACC | TCA | GTC | CTT | CCT | GCA | AAG | CAG | GAA | GAA | GCT | GCC | | | 855 |
| K | I | L | L | F | N | L | G | C | D | V | Q | H | T | E | H | V | Y | | | 305 |
| AAG | ATC | CTG | CTG | GAG | TTC | AAC | CTG | TGT | GGC | GAT | GTG | CAA | ACT | GAA | CAC | GTG | TAC | | | 915 |

FIG. 55C

```
    R   V   Y   V   T   T   F   L   G   F   G   N   F   A   R   Q   R   Y   E       325
    AGG GTT TAT GTC ACA ACT TTT CTG GGT TTC GGA GGC AAC TTT GCC CGG CAG CGC TAC GAA   975
    D   L   V   L   N   E   T   L   N   K   N   R   L   G   Q   K   T   G   L        345
    GAC CTT GTT CTG AAT GAA ACT CTT AAC AAA AAC AGA TTG CTT CAG AAG ACA GGT CTG       1035
    S   P   N   D   P   F   L   D   P   C   L   G   Q   T   D   K   V   A   M        365
    AGT CCC AAT GAC CCA TTT CTG GAT CCC TGC CTG GGA CAG ACA GAT GTG GCA ATG           1095
    R   N   S   Q   V   L   H   V   R   G   R   A   G   W   S   C   G   A   E        385
    AGG AAC AGC CAA GTC CAT GTC CGA GGA AGA TGG TCA GAC CAG TCT TGT GGG GCA GAG       1155
    L   S   P   I   L   D   F   R   A   S   N   T   S   Q   L   N   G   I   Y   Q    405
    CTG AGC CCC CTG CTG GAC TTC CGC GCT TCC AAC ACC AGC CAG CTC AAT GGC ATA TAT CAA   1215
    S   P   D   L   R   N   N   S   E   Y   F   S   E   F   A   F   Y   C   T        425
    TCG CCT ATT GAC TTC AAC AAC AGC GAG TAC TTC TCT GAG TTT TTT TAT TGT ACA           1275
    E   D   V   G   M   A   W   I   G   R   Y   H   G   P   T   F   A   K   A   Q    445
    GAG GAT GTG GGC ATG GCT GCT ATT GGT GGC TAC CAT GGG CCA ACA TTT GCC AAG GCT CAG   1335
    D   Y   C   G   M   A   W   S   V   L   T   Y   Q   R   F   K   N   G   L   F    465
    GAT TAC TGT GGC ATG GCT TGG TCG GTA CTA ACT TAC CAG AGA TTC AAG AAT GGC CTC TTT   1395
    S   H   A   D   E   H   R   L   K   Y   L   Y   Q   C   F   K   S   A   M   Y  Q 485
    TCA CAT GCA GAT GAG CAT CGA CTC AAA TAT CAG TGT TTT AAA TCG GCT ATG TAC CAA       1455
```

FIG. 55D

```
V   L   H   E   G   F   H   F   P   Y   D   Y   P   N   L   R   T   A   Q   L       505
GTC TTA CAT GAA GGA TTC CAC TTT CCC TAT GAC TAC CCA AAC CTG CGG ACA GCC CAG CTG     1515

V   Y   D   R   E   V   Q   T   L   G   A   I   L   Y   K   T   R   F   L          525
GTG TAT GAC CGA GAG GTT CAG TGG CTG GGA GCC ATT CTA TAT AAA ACA CGA TTC TTA         1575

P   L   R   D   L   Q   R   Q   E   G   V   R   Q   A   H   Q   C   I   L   R   L   545
CCA CTC AGG GAT CTT CAG CGG CAG GAA GGT GTC CGA CAA GCC CAT CAA TGT ATC CTG CGT CTC 1635

S   F   V   N   Y   H   Y   L   F   A   C   I   L   V   V   T   R   Q   A   I      565
TCC TTT GTA AAC TAC CAC TAT CTC TTT GCC TGT CTG GTG GTG ACA CGA CAA GCC ATC         1695

F   L   Y   L   L   R   L   R   I   H   H   Q   T   R   A   S   A   P              585
TTC CTA TAC CTT CTG CGG CTA CGC ATT CAC CAC CAA CGA GCC TCA GCT CCA                 1755

L   D   L   L   W   L   E   E   V   P   M   M   G   V   Q   V   G   P   *          605
TTG GAC TTG CTG TGG CTT GAA GAG GTG CCC ATG ATG GGA GTA CAG GTG GGG CCG TGA         1815
```

GGCTGGACCAGGACTAGAGAAGCTTGAGCACCCCGAGTTGCTGCTCATTGAATTCCTCCACTTTCTTATATAGCCTCA

GATGCTGTGATGTCTGACCTTGTGTGGATATTTGCCCTTGGAATTTCTACTTTACTTTCTACCGTAATTCCTTCTCCGTAC

CCAGGTCTTCTCTGAGAGAAGCTATAATTTAATCTGTGAGGAACTAAATGACAGGAGATTGGTGCTAATACGGGGGACC

AAGCTTTGTCCAAGTGAAGCAGGCTTCGACTCCTTCGAGAGGTCTGGTGTGTTCCTAGAATCTCACCTTTTCTTCCCT

TGCTAAAGCATGAAGTTTGGCACACTGAAGCCTGGTTGAAATGAAATTTGTAGCATCTGATACAAAGCCAG

FIG. 55E

AGACATTCTAGCAAGTGCAGCAGCCCCTTCTTTCTCTGTAACAGAGATATCATTTATGTGGAGATCCACAACCTTTAAC

AGGGATCCAAGATCTTTGCAGTTCAATCGACCACACATAGGAATTTCCAGGCACCACAAATGATATAACTTCCTGCTTCCT

TGACAAAGAAGCCATCATGGGTGTGATCCAAGATCCCTGTCGTAGTGTTGATGATGTTAGTACATGATTTAAAGGTTA

GAACCCCTTCTAAATGAATGGTCTGTGGAAGATTTAGTATCTTATCTGATGCCTGGTATGATGAGGATAGAAAATTTT

TCCATTTTTATGTGCCTCACAGGCTGTTTGGGCATTAATTTTGCTTTTTGAGCCTTAAGTGTGTTAGTAGGATGGAGAA

ACTGTGATGGGGACTGGGAACCTGGATTTGTCTGATTTAGGTCACTGTTCCCTGGGCCTGTTTTTGTGAGCCCTTACA

CAGGAAGATATAAAGAGAGTTCTTTCATTTCACTGCTAAAATCAGTATGTAGTATGGGAATGTATTTGGGTTGTTTTT

AAAGAAAAGGGGAACAGAATCAGGAGAGTGGGCAAAGGCAATAAAATCAAAGTTCTTATTAATTATTCTGAGAAATAG

AAGTTCTCAATTTATGACTCTTGGAATGTCTGAAAGGGAGCAAATTTGGAATAGATCAATCTGTTAATAAGCCATCTG

GCAACTTTCAGAACCTCTATTAAGAGACTGCTGAGTCACAAACAGCACTTCCATTAATGAAGCGAGAGGAAAAGCCATA

ATAATTACATCTTCACCCACTACCCTTCCTTCCTCCACATTAGCCATTAAATTGCATGAGGATTTC

FIG. 57A

Protein Family Domain Matches, HMMer version 2

Searching for complete domains in PFAM
hmmpfam -search a single seq against HMM database
HMMER 2.1.1 (Dec 1998)
Copyright (C) 1992-1998 Washington University School of Medicine
HMMER is freely distributed under the GNU General Public License (GPL).

HMM file:      /prod/ddm/seqanal/PFAM/pfam5.3/Pfam
Sequence file: /prod/ddm/wspace/orfanal/oa-script.28431.seq

Query: 62088

Scores for sequence family classification (score includes all domains):
```
Model       Description                                        Score    E-value   N
-----       -----------                                        -----    -------   ---
GDA1_CD39   GDA1/CD39(nucleoside phosphatase) family           324.9    9e-94     1
```

Parsed for domains:
```
Model       Domain   seq-f  seq-t     hmm-f  hmm-t      score    E-value
-----       ------   -----  -----     -----  -----      -----    -------
GDA1_CD39   1/1      75     536  ..   1      566 []     324.9    9e-94
```

FIG. 57B

```
Alignments of top-scoring domains:
GDA1_CD39: domain 1 of 1, from 75 to 536: score 324.9, E = 9e-94

*->vlachenvkYgVviDAGSsGtRlhvVykwkdesslnkgrsididlqi
                      +++ n+ Yg v D GSsG+R++VY w ++   + g+  dl ++
         62088  75  TDTEDPNLNYGLVVDCGSSGRIFVYFW-PR---HNGNPHDLLDIK-    116 vplieeekpvfkkłePGLSsFatKpwESRPVDARLLFQYVPQmeeaakyL
                   +  + pv+kk+ PG+S  a+ p                    e a   yL
         62088  117 QMRDRNSQPVVKKIKPGISAMADTP-------------------EHASDYL  148 tPLLefAeevIPesqrseKQKVQVKALGTPVflgATAGmRLLpedYrdak
                   +PLL  fA    ++P +++ e              TP+++  TAGmRLLpe  ++
         62088  149 RPLLSFAAAHVPVKKHKE-----------------TPLYILCTAGMRLLPER---KQ  185 ekilkaLrnglksistfpvddnsqgvrIIdGaeEGlYgWItvNYLLGrfg
                   +iL  L   1+    f   ++  ++ +I G++EG+Y+WI++N  LGrf+
         62088  186 LAILADLVKDLPLEFDFLFSQ--SQAEVISGKQEGVYAWIGINFVLGRFD  233 kdnawlsidey.peqsrqkTvGviDlGGAStQIaFapqneesviaskve
                   +          +      +   TvG +D+GGAS  QIa++++  +sv++ k e
         62088  234 HEDESDAEATQeLAAGRRRTVGILDMGGASLQIAYEVP-TSTSVLPAKQE  282
```

FIG. 57C

```
           din.eylqqerlk......gekYPSAdvYvhsfLgYGanealrkyl.akL
           + ++++l  ++l+ + +++   Y    vYv++fLg+G n a+ +y++ +L
62088  283 EAAkILLAEFNLGcdvqhtEHVY---RVYVTTFLGFGGNFARQRYEdLVL    329 isnasndgkilkgDddtktri......LsDPClppGlnktvevsevevtPCT
           ++++++    +   +kt+ +++++   DPClp Gl  +ve
62088  330 NETLNKN----RLLGQKTGLspdnpFLDPCLPVGLTDVVERNSQ-----    369

KrfskelpfkvfairgtgnyeqCsnsirelinkkanavCpyeqakCtFNG
                  v + rg g++    C  +  ++11         + +q    ++NG
62088  370 --------VLHVRGRGDWVSCGAMLSPLLA-----RSNTSQ--ASLNG    402

VhaPsiglalqkknigaSsyfYttgdffglvgeyepilvaspekltkkake
            + + +i+++++ +++g+S++fY t d++ ++g y   +    ++k+a+
62088  403 IYQSPIDFNNSEFYGFSEFFYCTEDVLRIGGRY-----HGPTFAKAAQD    446 aCsGfknWediksgypkt1dkn.vseerLktaCfd1ayilsLLhdGFdld
           +C    W+    ++ +l+ ++++e rLk++Cf++a+ + +Lh+GF+++
62088  447 YCG--MAWSVLTQRFKNGLFSShADEHRLKYQCFKSAWMYQVLHEGFHFP    494
```

FIG. 57D

```
62088  495  ktswDAEnvnDReligsvkkIagsEvlVeagWtLGamlyltsalplqknD
             +   ++++ + ++E        ++WtLGa+ly t++lpl++           529
             YD-Y-------PNLRTAQLVYDRE----VQWTLGAILYKTRFLPLRD--

62088  530  DFmvGiAPsERRtKLtGkerLsvk<-*
             +++     v                    536
             ----------LRQEGVR
```

FIG. 58

Transmembrane Segments Predicted by MEMSAT

| Start | End | Orient | Score |
|---|---|---|---|
| 29 | 47 | Out-->ins | 6.0 |
| 84 | 102 | ins-->out | 0.7 |
| 552 | 570 | Out-->ins | 6.8 |

>62088
MARISFSYLCPASWYFTVPTVSPFLRQRVAFLGLFFISCLLLLMLIIDFRHWSASLPRDR
QYERYLARVGELEATDTEDPNLNYGLVVDCGSSGSRIFVYFWPRHNGNPHDLLDIKQMRD
RNSQPVVKKIKPGISAMADTPEHASDYLRPLLSFAAAHVPVKKHKETPLYILCTAGMRLL
PERKQLAILADLVKDLPLEFDFLFSQSQAEVISGKQEGVYAWIGINFVLGRFDHEDESDA
EATQELAAGRRRTVGILDMGGASLQIAYEVPTSTSVLPAKQEEAAKILLAEFNLGCDVQH
TEHVYRVYVTTFLGFGGNFARQRYEDLVLNETLNKNRLLGQKTGLSPDNPFLDPCLPVGL
TDVVERNSQVLHVRGRGDWVSCGAMLSPLLARSNTSQASLNGIYQSPIDFNNSEFYGFSE
FFYCTEDVLRIGGRYHGPTFAKAAQDYCGMAWSVLTQRFKNGLFSSHADEHRLKYQCFKS
AWMYQVLHEGFHFPYDYPNLRTAQLVYDREVQWTLGAILYKTRFLPLRDLRQEGVRQAHG
SWFRLSFVYNHYLFFACILVVLLAIFLYLLRLRRIHHRQTRASAPLDLLWLEEVVPMMGV
QVGP

Transmembrane Segments for presumed mature peptides

| Start | End | Orient | Score |
|---|---|---|---|
| 30 | 48 | ins-->out | 0.7 |
| 498 | 516 | out-->ins | 6.8 |

>62088
SLPRDRQYERYLARVGELEATDTEDPNLNYGLVVDCGSSGSRIFVYFWPRHNGNPHDLLD
IKQMRDRNSQPVVKKIKPGISAMADTPEHASDYLRPLLSFAAAHVPVKKHKETPLYILCT
AGMRLLPERKQLAILADLVKDLPLEFDFLFSQSQAEVISGKQEGVYAWIGINFVLGRFDH
EDESDAEATQELAAGRRRTVGILDMGGASLQIAYEVPTSTSVLPAKQEEAAKILLAEFNL
GCDVQHTEHVYRVYVTTFLGFGGNFARQRYEDLVLNETLNKNRLLGQKTGLSPDNPFLDP
CLPVGLTDVVERNSQVLHVRGRGDWVSCGAMLSPLLARSNTSQASLNGIYQSPIDFNNSE
FYGFSEFFYCTEDVLRIGGRYHGPTFAKAAQDYCGMAWSVLTQRFKNGLFSSHADEHRLK
YQCFKSAWMYQVLHEGFHFPYDYPNLRTAQLVYDREVQWTLGAILYKTRFLPLRDLRQEG
VRQAHGSWFRLSFVYNHYLFFACILVVLLAIFLYLLRLRRIHHRQTRASAPLDLLWLEEV
VPMMGVQVGP

```
Input file Fbh50566FL.seq; Output File 50566.trans
Sequence length 1154
                      M   K   V   K   V   I   P   V   L   E   D   N   Y   M    14
CGGACGCGTGGGTCCGTGACC ATG AAG GTC AAG GTC ATC CCC GTG CTC GAG GAC AAC TAC ATG   42

Y   L   V   I   E   E   L   T   R   E   A   V   A   V   D   V   A   V   P   K    34
TAC CTG GTC ATC GAG GAG CTC ACG CGC GAG GCG GTG GCC GTG GAC GTG GCT GTG CCC AAG 102

R   L   L   E   I   V   G   R   E   G   V   S   L   T   A   V   L   T   T   H    54
AGG CTG CTG GAG ATC GTG GGC CGG GAG GGG GTG TCT CTG ACC GCT GTG CTG ACC ACC CAC 162

H   H   W   D   H   A   R   G   N   P   E   L   A   R   L   R   P   G   L   A    74
CAT CAC TGG GAC CAC GCG CGG GGA AAC CCG GAG CTG GCG CGG CTT CGT CCC GGG CTG GCG 222

V   L   G   A   D   E   R   I   F   S   L   T   R   R   L   A   H   G   E   E    94
GTG CTG GGC GCG GAC GAG CGC ATC TTC TCG CTG ACG CGC AGG CTG GCG CAC GGC GAG GAG 282

L   R   F   G   A   I   H   V   R   C   L   L   T   P   G   H   T   A   G   H   114
CTG CGG TTC GGG GCC ATC CAC GTG CGT TGC CTC CTG ACG CCC GGC CAC ACC GCC GGC CAC 342

M   S   Y   F   L   W   E   D   D   C   P   D   P   P   A   L   F   S   G   D   134
ATG AGC TAC TTC CTG TGG GAG GAC GAT TGC CCG GAC CCA CCC GCC CTG TTC TCG GGC GAC 402

A   L   S   V   A   G   C   G   S   C   L   E   G   S   A   Q   Q   M   Y   Q   154
GCG CTG TCG GTG GCC GGC TGC GGC TCG TGC CTG GAG GGC AGC GCC CAG CAG ATG TAC CAG 462

S   L   A   E   L   G   T   L   P   P   E   T   K   V   F   C   G   H   E   H   174
AGC CTG GCC GAG CTG GGT ACC CTG CCC CCC GAG ACG AAG GTG TTC TGC GGC CAC GAG CAC 522

T   L   S   N   L   E   F   A   Q   K   V   E   P   C   N   D   H   V   R   A   194
ACG CTT AGC AAC CTG GAG TTT GCC CAG AAA GTG GAG CCC TGC AAC GAC CAC GTG AGA GCC 582

K   L   S   W   A   K   K   R   D   E   D   D   V   P   T   V   P   S   T   L   214
AAG CTG TCC TGG GCT AAG AAG AGG GAT GAG GAT GAC GTG CCC ACT GTG CCG TCG ACT CTG 642

G   E   E   R   L   Y   N   P   F   L   R   V   A   E   E   P   V   R   K   F   234
GGC GAG GAG CGC CTC TAC AAC CCC TTC CTG CGG GTG GCA GAG GAG CCG GTG CGC AAG TTC 702

T   G   K   A   V   P   A   D   V   L   E   A   L   C   K   E   R   A   R   F   254
ACG GGC AAG GCG GTC CCC GCC GAC GTC CTG GAG GCG CTA TGC AAG GAG CGG GCG CGC TTC 762

E   Q   A   G   E   P   R   Q   P   Q   A   R   L   L   A   L   Q   W   G   274
GAA CAG GCG GGC GAG CCG CGG CAG CCA CAG GCG CGG GCC CTC CTT GCG CTG CAG TGG GGG 822

L   L   S   A   A   P   H   D   *                                              283
CTC CTG AGT GCA GCC CCA CAC GAC TGA                                             849

GCCACCCAGACCCTCACAGGGCTGGGGCCTGCGTCCCTCCTCGTGACCTCGGCCAGCTGGACCCACATGAGGGCCACCT

CTGGAACCTTCTTCGAGGCCCTGGCCAGCCATCTGCCCAGCCTCGGAGGGTGGGCAACCTGGTGCTTCCCGGGTGGACA

CACAGGACCACTCAGTGGGGCCTGTGTGGGCGCCGAGACCTGGGTGTCTGGGAAGTGGGGCACACGGGGCCTCCGAACT

ATGAATAAAGCTTTGAAAGCCGTTGTCAAAAAAAAAAAAAAAAAAAAA
```

FIG. 59

Analysis of 50566 (282 aa)

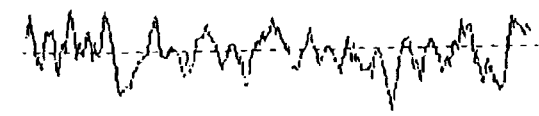

>50566
MKVKVIPVLEDNYMYLVIEELTREAVAVDVAVPKRLLEIVGREGVSLTAVLTTHHHWDHA
RGNPELARLRPGLAVLGADERIFSLTRRLAHGEELRFGAIHVRCLLTPGHTAGHMSYFLW
EDDCPDPPALFSGDALSVAGCGSCLEGSAQQMYQSLAELGTLPPETKVFCGHEHTLSNLE
FAQKVEPCNDHVRAKLSWAKKRDEDDVPTVPSTLGEERLYNPFLRVAEEPVRKFTGKAVP
ADVLEALCKERARFEQAGEPRQPQARALLALQWGLLSAAPHD

Transmembrane Segments Predicted by MEMSAT

| Start | End | Orient | Score |
|-------|-----|--------|-------|
| 129 | 145 | out-->ins | 0.8 |

FIG. 60

```
Scores for sequence family classification (score includes all domains):
Model       Description                                Score    E-value   N
--------    -----------                                -----    -------  ---
lactamase_B Metallo-beta-lactamase superfamily         133.3    4.4e-36   1

Parsed for domains:
Model       Domain  seq-f  seq-t    hmm-f  hmm-t     score   E-value
--------    ------ ------ ------   ------ ------    ------  --------
lactamase_B 1/1       7    172  ..    1    218 []   133.3   4.4e-36

Alignments of top-scoring domains:
lactamase_B: domain 1 of 1, from 7 to 172: score 133.3, E = 4.4e-36
                *->pglvdsnaylvedddggPgeaaliDpGttapaaeallrllkdggple
                    p l d+++ylv+ + +  +ea+ +D + +    + ++++ ++
      50566    7    PVLEDNYMYLVIEELT--REAVAVDVAVPKR-LLEIVGREG------  44 nikkidaiilTHaHaDHiGGapaellekfgvpvaahaaevyaskdylgyg
                   ++a++ TH+H+DH+ G+p el+++ +    + v         +++
      50566   45  --VSLTAVLTTHHHWDHARGNP-ELARLRP------GLAV-------LGA 78 edrlk..dealkdgdltfliviee1rvglgvelevihtPGtHTpgsivyy
                   ++r+ + ++ l++g+         elr+g ++++++ tPG HT g+++y+
      50566   79  DERIFs1TRRLAHGE--------ELRFG-AIHVRCLLTPG-HTAGHMSYF 118 lpeekggespkivvLftGDtlfsggcpdgetdlplgrtdllggdpaelie
                   l+e+    +p   +Lf+GD+l  +gc          g   l+g++ +++
      50566  119  LWEDDCPDPP---ALFSGDALSVAGC---------GS--CLEGSAQQMYQ 154 sleqsesllklllpddtvvypGH<-*
                   sl     +l  +lp++t v++GH
      50566  155  SLA----ELG-TLPPETKVFCGH      172
```

FIG. 61

```
GAAAACTGAAAGCCGGACCCCAGGCCGCCGCGCTGCCGCCCGGCCTCCCCGCCAGCGCGCCACCATGGGCAGTCCCGGT
                                                                 M   T   V   R   N   I   A      7
TTCCCCTTGTAAAGATGGCGGTGAGGGATCGCTGCAACCTTTAGACTA ATG ACT GTC CGA AAC ATC GCC      21

S   I   C   N   M   G   T   N   A   S   A   L   E   K   D   I   G   P   E   Q     27
TCC ATC TGT AAT ATG GGC ACC AAT GCC TCT GCT CTG GAA AAA GAC ATT GGT CCA GAG CAG    81

F   P   I   N   E   H   Y   F   G   L   V   N   F   G   N   T   C   Y   C   N     47
TTT CCA ATC AAT GAA CAC TAT TTC GGA TTG GTC AAT TTT GGA AAC ACA TGC TAC TGT AAC    141

S   V   L   Q   A   L   Y   F   C   R   P   F   R   E   N   V   L   A   Y   K     67
TCC GTG CTT CAG GCA TTG TAC TTC TGC CGT CCA TTC CGG GAG AAT GTG TTG GCA TAC AAG    201

A   Q   Q   K   K   K   E   N   L   L   T   C   L   A   D   L   F   H   S   I     87
GCC CAG CAA AAG AAG AAG GAA AAC TTG CTG ACG TGC CTG GCG GAC CTT TTC CAC AGC ATT    261

A   T   Q   K   K   K   V   G   V   I   P   P   K   K   F   I   S   R   L   R    107
GCC ACA CAG AAG AAG AAG GTT GGC GTC ATC CCA CCA AAG AAG TTC ATT TCA AGG CTG AGA    321

K   E   N   D   L   F   D   N   Y   M   Q   Q   D   A   H   E   F   L   N   Y    127
AAA GAG AAT GAT CTC TTT GAT AAC TAC ATG CAG CAG GAT GCT CAT GAA TTT TTA AAT TAT    381

L   L   N   T   I   A   D   I   L   Q   E   E   K   K   Q   E   K   Q   N   G    147
TTG CTA AAC ACT ATT GCG GAC ATC CTT CAG GAG GAG AAG AAA CAG GAA AAA CAA AAT GGA    441

K   L   K   N   G   N   M   N   E   P   A   E   N   N   K   P   E   L   T   W    167
AAA TTA AAA AAT GGC AAC ATG AAC GAA CCT GCG GAA AAT AAT AAA CCA GAA CTC ACC TGG    501

V   H   E   I   F   Q   G   T   L   T   N   E   T   R   C   L   N   C   E   T    187
GTC CAT GAG ATT TTT CAG GGA ACG CTT ACC AAT GAA ACT CGA TGC TTG AAC TGT GAA ACT    561

V   S   S   K   D   E   D   F   L   D   L   S   V   D   V   E   Q   N   T   S    207
GTT AGT AGC AAA GAT GAA GAT TTT CTT GAC CTT TCT GTT GAT GTG GAG CAG AAT ACA TCC    621

I   T   H   C   L   R   D   F   S   N   T   E   T   L   C   S   E   Q   K   Y    227
ATT ACC CAC TGT CTA AGA GAC TTC AGC AAC ACA GAA ACA CTG TGT AGT GAA CAA AAA TAT    681

Y   C   E   T   C   C   S   K   Q   E   A   Q   K   R   M   R   V   K   K   L    247
TAT TGT GAA ACA TGC TGC AGC AAA CAA GAA GCC CAG AAA AGG ATG AGG GTA AAA AAG CTG    741

P   M   I   L   A   L   H   L   K   R   F   K   Y   M   E   Q   L   H   R   Y    267
CCC ATG ATC TTG GCC CTG CAC CTA AAG CGG TTC AAG TAC ATG GAG CAG CTG CAC AGA TAC    801

T   K   L   S   Y   R   V   V   F   P   L   E   L   R   L   F   N   T   S   S    287
ACC AAG CTG TCT TAC CGT GTG GTC TTC CCT CTG GAA CTC CGG CTC TTC AAC ACC TCC AGT    861

D   A   V   N   L   D   R   M   Y   D   L   V   A   V   V   H   C   G   S        307
GAT GCA GTG AAC CTG GAC CGC ATG TAT GAC TTG GTT GCG GTG GTC GTT CAC TGT GGC AGT    921

G   P   N   R   G   H   Y   I   T   I   V   K   S   H   G   F   W   L   L   F    327
GGT CCT AAT CGT GGG CAT TAT ATC ACT ATT GTG AAA AGT CAC GGC TTC TGG CTT TTG TTT    981

D   D   D   I   V   E   K   I   D   A   Q   A   I   E   E   F   Y   G   L   T    347
GAT GAT GAC ATT GTA GAG AAA ATA GAT GCT CAA GCT ATT GAA GAA TTC TAT GGC CTG ACG    1041

S   D   I   S   K   N   S   E   S   G   Y   I   L   F   Y   Q   S   R   E   *    367
TCA GAT ATA TCA AAA AAT TCA GAA TCT GGA TAT ATT TTA TTC TAT CAG TCA AGA GAG TAA   1101

CTGAAAGACCTGCGGGACTGATTCACGTGGGGAGAATGTTCACAGCACTGTCACCCGGCTTCTCCGCAGGCTTTCCTCT

TCCCCAGTGGCCCACTAATGGTATCACTCCGAGTCTCAATGGTCTGGCTGTGTTAGACTCTCTCCTTTTGTGTTTTTAC

ATGCAGCACTACTCTTGGTTTTATTTCAGTCTGACATAGAGTTAACTGCAATCAGATTGTAGTCTGATTTATATGAATA

ACGGTTGCTAATTTTAGGACTGGGTGAAAGCTATGCCATTCATTATGTCTGGCTGTATTAGAATGACATTTCCTATGAA

TGTCTACGGTCTGTTTTAGGTGTTTGCTAAACTTCTATGGCTTCCAGGGTCTTCTTACAATGCATTCCTTTAACTTGTC

CCTGGAAGCATTGCTACCCATTTTCAGCTTCTCTGCCTCTCTTCTGATACAAGGACAGAAGAATTGGGTAGATATTCAC

CTTTTAGGGGTGCAAGTATAGCTTTAAGTTTGTGCAAGTGAAAATGTTGAAAAGTGAGTAACCTCGATATTAAAATCAT

CCTTGACATG
```

FIG. 63

Analysis of Fbh48118fl (367 aa)

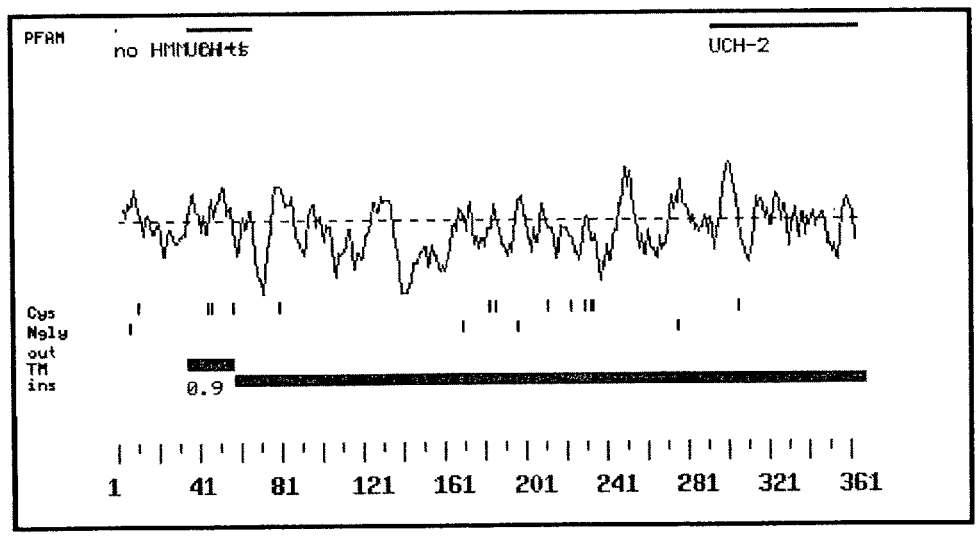

```
>Fbh48118fl
MTVRNIASICNMGTNASALEKDIGPEQFPINEHYFGLVNFGNTCYCNSVLQALYFCRPFR
ENVLAYKAQQKKKENLLTCLADLFHSIATQKKKVGVIPPKKFISRLRKENDLFDNYMQQD
AHEFLNYLLNTIADILQEEKKQEKQNGKLKNGNMNEPAENNKPELTWVHEIFQGTLTNET
RCLNCETVSSKDEDFLDLSVDVEQNTSITHCLRDFSNTETLCSEQKYYCETCCSKQEAQK
RMRVKKLPMILALHLKRFKYMEQLHRYTKLSYRVVFPLELRLFNTSSDAVNLDRMYDLVA
VVVHCGSGPNRGHYITIVKSHGFWLLFDDDIVEKIDAQAIEEFYGLTSDISKNSESGYIL
FYQSRE*
```

FIG. 64

Transmembrane Segments Predicted by MEMSAT

| Start | End | Orient | Score |
|---|---|---|---|
| 34 | 56 | out-->ins | 0.9 |

```
>Fbh48118f1
MTVRNIASICNMGTNASALEKDIGPEQFPINEHYFGLVNFGNTCYCNSVLQALYFCRPFR
ENVLAYKAQQKKKENLLTCLADLFHSIATQKKKVGVIPPKKFISRLRKENDLFDNYMQQD
AHEFLNYLLNTIADILQEEKKQEKQNGKLKNGNMNEPAENNKPELTWVHEIFQGTLTNET
RCLNCETVSSKDEDFLDLSVDVEQNTSITHCLRDFSNTETLCSEQKYYCETCCSKQEAQK
RMRVKKLPMILALHLKRFKYMEQLHRYTKLSYRVVFPLELRLFNTSSDAVNLDRMYDLVA
VVVHCGSGPNRGHYITIVKSHGFWLLFDDDIVEKIDAQAIEEFYGLTSDISKNSESGYIL
FYQSRE
```

FIG. 65

Protein Family / Domain Matches, HMMer version 2

```
Searching for complete domains in PFAM
hmmpfam - search a single seq against HMM database
HMMER 2.1.1 (Dec 1998)
Copyright (C) 1992-1998 Washington University School of Medicine
HMMER is freely distributed under the GNU General Public License (GPL).
- - - - - - - - - - - - - - - - - - - - - - - - - - - - - - - - - - - - -
HMM file:                  /prod/ddm/seqanal/PFAM/pfam6.4/Pfam
Sequence file:             /prod/ddm/wspace/orfanal/oa-script.20454.seq
- - - - - - - - - - - - - - - - - - - - - - - - - - - - - - - - - - - - -
Query:   Fbh48118f1

Scores for sequence family classification (score includes all domains):
Model    Description                                      Score    E-value   N
--------  -----------                                     -----    -------  ---
UCH-2    Ubiquitin carboxyl-terminal hydrolase family     106.4    5.6e-28   1
UCH-1    Ubiquitin carboxyl-terminal hydrolases famil      60.8    2.9e-14   1

Parsed for domains:
Model    Domain  seq-f  seq-t    hmm-f  hmm-t    score   E-value
-------- ------- -----  -----    -----  -----    -----   -------
UCH-1     1/1      35     66 ..     1     32 []   60.8   2.9e-14
UCH-2     1/1     292    364 ..     1     69 []  106.4   5.6e-28

Alignments of top-scoring domains:
UCH-1: domain 1 of 1, from 35 to 66: score 60.8, E = 2.9e-14
                   *->tGLiNlGNTCYmNSvLQcLfsipplrdyllldi<-*
                      +GL+N+GNTCY+NSvLQ+L++++p+r+ +l +
    Fbh48118f1     35 FGLVNFGNTCYCNSVLQALYFCRPFRENVLAY       66

UCH-2: domain 1 of 1, from 292 to 364: score 106.4, E = 5.6e-28
                   *->gpgkYeLyaVvvHsGsslsgGHYtayvkken.WykFDDdkVsrvtee
                      +++Y+L+aVvvH+Gs++++GHY++ vk+++ W++FDDd+V+ ++
    Fbh48118f1    292 LDRMYDLVAVVVHCGSGPNRGHYITIVKSHGfWLLFDDDIVEKIDAQ  338 evlkesgg...esgdtssAYiLfYer<-*
                    ++++ g ++++s++++s+YiLfY+
    Fbh48118f1    339 AIEEFYGLtsdISKNSESGYILFYQS       364
```

FIG. 66

NUCLEOSIDE PHOSPHATASE

RELATED APPLICATIONS

This application is a continuation-in-part of U.S. patent application Ser. No. 09/838,573, filed Apr. 18, 2001 (now abandoned), which claims the benefit of U.S. Provisional Application Ser. No. 60/197,747, filed Apr. 18, 2000.

This application is also a continuation-in-part of U.S. patent application Ser. No. 09/870,133, filed May 29, 2001 (now abandoned), which claims the benefit of U.S. Provisional Application Ser. No. 60/207,649, filed May 26, 2000.

This application is also a continuation-in-part of U.S. patent application Ser. No. 09/870,130, filed May 29, 2001 (now abandoned), which claims the benefit of U.S. Provisional Application Ser. No. 60/207,640, filed May 26, 2000.

This application is also a continuation-in-part of U.S. patent application Ser. No. 09/862,535, filed May 21, 2001 (now abandoned), which claims the benefit of U.S. Provisional Application Ser. No. 60/205,961, filed May 19, 2000.

This application is also a continuation-in-part of U.S. patent application Ser. No. 09/870,383, filed May 29, 2001 (now abandoned), which claims the benefit of U.S. Provisional Application Ser. No. 60/207,506, filed May 26, 2000.

This application is also a continuation-in-part of U.S. patent application Ser. No. 09/860,821, filed May 18, 2001 (now abandoned), which claims the benefit of U.S. Provisional Application Ser. No. No. 60/205,449, filed May 19, 2000.

This application is also a continuation-in-part of U.S. patent application Ser. No. 09/870,110, filed May 29, 2001 (now abandoned), which claims the benefit of U.S. Provisional Application Ser. No. 60/207,650, filed May 26, 2000.

This application is also a continuation-in-part of U.S. patent application Ser. No. 09/907,509, filed Jul. 16, 2001 (now abandoned), which claims the benefit of U.S. Provisional Application Ser. No. 60/218,385, filed Jul. 14, 2000.

This application is also a continuation-in-part of U.S. patent application Ser. No. 09/945,327, filed Aug. 31, 2001 (now abandoned), which claims the benefit of U.S. Provisional Application Ser. No. 60/229,425, filed Aug. 31, 2000.

This application also claims the benefit of U.S. Provisional Application Ser. No. 60/318,581, filed Sep. 10, 2001.

The entire contents of each of the above-referenced patent applications are incorporated herein by this reference.

Index

| Chapter | Page | Title |
|---------|------|-------|
| I. | 2 | 39228, A NOVEL HUMAN ALCOHOL DEHYDROGENASE AND USES THEREFOR |
| II. | 88 | 21956 AND 25856, NOVEL HUMAN AMINIOPEPTIDASES AND USES THEREOF |
| III. | 171 | 22244 AND 8701, NOVEL HUMAN DEHYDROGENASES AND USES THEREOF |
| IV. | 255 | 32263, A NOVEL HUMAN BIOTIN ENZYME AND USES THEREOF |
| V. | 336 | 50250, A NOVEL HUMAN LIPASE AND USES THEREOF |
| VI. | 415 | 55158, A NOVEL HUMAN CARBONIC ANHYDRASE AND USES THEREOF |
| VII. | 495 | 47765, A NOVEL HUMAN LYSYL OXIDASE AND USES THEREOF |
| VIII. | 572 | 62088, A NOVEL HUMAN NUCLEOSIDE PHOSPHATASE FAMILY MEMBER AND USES THEREOF |

-continued

| Chapter | Page | Title |
|---------|------|-------|
| IX. | 655 | 50566, A NOVEL HUMAN GLYOXALASE II RELATED FACTOR AND USES THEREOF |
| X. | 734 | 48118, A HUMAN UBIQUITIN CARBOXYL TERMINAL HYDROLASE AND USES THEREFOR |

I. 39228, a Novel Human Alcohol Dehydrogenase and Uses Therefor

BACKGROUND OF THE INVENTION

The oxidation and reduction of molecules which contain alcohol and aldehyde groups is of critical importance in many metabolic and catabolic pathways in cells. A large family of enzymes which facilitate many of these molecular alterations, termed alcohol dehydrogenases (Adh), has been identified. In the forward reaction, these enzymes catalyze the transfer of a hydride ion from the target alcohol group to the enzyme or a cofactor of the enzyme (e.g., $NAD^+$), thereby forming an aldehyde group on the substrate. These enzymes are also able to participate in the reverse reaction, wherein a carbonyl group on the target aldehyde is reduced to an alcohol by the transfer of a hydride group from the enzyme.

Members of the alcohol dehydrogenase family are found in nearly all organisms, from microbes to *Drosophila* to humans. Both between species and within the same species, alcohol dehydrogenase isozymes vary widely. For example, members of the human Adh family are encoded by at least seven genes. These isozymes can be divided into at least 4 classes which are all found in the liver and can be distributed differentially throughout other human tissues according to function. Class I Adh isozymes appear to have the widest range of substrates by virtue of their integral involvement with hepatic processing of ethanol, bile compounds, testosterone, neurotransmitters, retinol, peroxidic aldehydes, congeners, and mevalonate. Class II Adh isozymes are involved with many of the same processing pathways as Class I, but appear to play at most a minor role in ethanol processing. Class III Adh isozymes are not able to oxidize ethanol, but function in formaldehyde and fatty acid metabolism. Class IV Adh isozymes are particularly important for retinol to vitamin A metabolism and "first pass" processing of dietary alcohol. As such, their activity is highest in the stomach and cornea (Holmes (1994) *Alcohol Alcohol Suppl* 2:127–130;).

The importance of Adh isozymes in such a wide array of metabolic pathways implicates them in many important biological processes, including embryological development (Duester, *Experimental Biology Symposium*—Apr. 9, 1997: *Functional Metabolism of Vitamin A in Embryonic Development*, Editor: M. H. Zile, pp 459S–462S); the ability of the cell to grow and differentiate, to generate and store energy, and to communicate and interact with other cells. Alcohol dehydrogenases also are important in the detoxification of compounds to which an organism is exposed, such as alcohols, toxins, carcinogens, and mutagens. Links between the variability of Adh activity and predisposition to alcoholism have been proposed (Whitfield (1994) *Alcohol Alcohol Suppl* 2:59–65; Jornvall (1994) *EXS* 71:221–229).

SUMMARY OF THE INVENTION

The present invention is based, at least in part, on the discovery of a novel family of Adh related proteins, referred to herein interchangeably as "Alcohol Dehydrogenase-Related Protein-1," "Adh-Related Protein-1," or "Adhr-1" nucleic acid and protein molecules. The Adhr-1 molecules of the present invention are useful as targets for developing modulating agents to regulate a variety of cellular processes which are influenced by the regulated metabolic interconversion between alcoholic groups and aldehyde groups. These processes include the cellular metabolism (e.g., for energy production, energy storage, detoxification,) transduction of intracellular signaling, embryological development, progression through the cell cycle and visual systems. Accordingly, in one aspect, this invention provides isolated nucleic acid molecules encoding Adhr-1 proteins or biologically active portions thereof, as well as nucleic acid fragments suitable as primers or hybridization probes for the detection of Adhr-1-encoding nucleic acids.

In one embodiment, an Adhr-1 nucleic acid molecule of the invention is at least 50%, 55%, 60%, 65%, 70%, 75%, 80%, 85%, 86%, 87%, 88%, 89%, 90%, 94%, 95%, 96%, 97%, 98%, 99%, 99.5% or more identical to the nucleotide sequence (e.g., to the entire length of the nucleotide sequence) shown in SEQ ID NO:1 or 3, or a complement thereof.

In a preferred embodiment, the isolated nucleic acid molecule includes the nucleotide sequence shown SEQ ID NO:1 or 3, or a complement thereof. In another embodiment, the nucleic acid molecule includes SEQ ID NO:3 and nucleotides 1–284 of SEQ ID NO:1. In another embodiment, the nucleic acid molecule includes SEQ ID NO:3 and nucleotides 1419–1808 of SEQ ID NO:1. In another preferred embodiment, the nucleic acid molecule consists of the nucleotide sequence shown in SEQ ID NO:1 or 3. In another preferred embodiment, the nucleic acid molecule includes a fragment of at least 50, 100, 200, 300, 400, 500, 600, 700, 800, 900, 1000, 1100, 1200, 1300, 1400, 1500, 1600, 1700, 1800, or more nucleotides (e.g., contiguous nucleotides) of the nucleotide sequence of SEQ ID NO:1 or 3, or a complement thereof.

In another embodiment, an Adhr-1 nucleic acid molecule includes a nucleotide sequence encoding a protein having an amino acid sequence sufficiently identical to the amino acid sequence of SEQ ID NO:2. In a preferred embodiment, an Adhr-1 nucleic acid molecule includes a nucleotide sequence encoding a protein having an amino acid sequence at least 50%, 55%, 60%, 65%, 70%, 75%, 80%, 85%, 86%, 87%, 88%, 89%, 90%, 91%, 92%, 93%, 94%, 95%, 96%, 97%, 99.5% or more identical to the entire length of the amino acid sequence of SEQ ID NO:2.

In another preferred embodiment, an isolated nucleic acid molecule encodes the amino acid sequence of human Adhr-1. In yet another preferred embodiment, the nucleic acid molecule includes a nucleotide sequence encoding a protein having the amino acid sequence of SEQ ID NO:2.

Another embodiment of the invention features nucleic acid molecules, preferably Adhr-1 nucleic acid molecules, which specifically detect Adhr-1 nucleic acid molecules relative to nucleic acid molecules encoding non-Adhr-1 proteins. For example, in one embodiment, such a nucleic acid molecule is at least 50–100, 100–500, 500–1000, 1000–1500, 1500–1800, or more nucleotides in length and hybridizes under stringent conditions to a nucleic acid molecule comprising the nucleotide sequence shown in SEQ ID NO:1, or a complement thereof.

In other preferred embodiments, the nucleic acid molecule encodes a naturally occurring allelic variant of a polypeptide comprising the amino acid sequence of SEQ ID NO:2, wherein the nucleic acid molecule hybridizes to a nucleic acid molecule comprising SEQ ID NO:1 or 3 under stringent conditions.

Another embodiment of the invention provides an isolated nucleic acid molecule which is antisense to an Adhr-1 nucleic acid molecule, e.g., the coding strand of an Adhr-1 nucleic acid molecule.

Another aspect of the invention provides a vector comprising an Adhr-1 nucleic acid molecule. In certain embodiments, the vector is a recombinant expression vector. In another embodiment, the invention provides a host cell containing a vector of the invention. In yet another embodiment, the invention provides a host cell containing a nucleic acid molecule of the invention. The invention also provides a method for producing a protein, preferably an Adhr-1 protein family member, by culturing a host cell in a suitable medium, e.g., a mammalian host cell such as a non-human mammalian cell, of the invention containing a recombinant expression vector, such that the protein is produced.

Another aspect of this invention features isolated or recombinant Adhr-1 proteins and polypeptides. In preferred embodiments, the isolated Adhr-1 protein family member includes at least one or more of the following domains: a zinc-containing alcohol dehydrogenase signature domain, (referred to hereafter as an "ADH-Zn" domain), a serine-containing active domain of the "G-D-S-L" family of lipases (referred to hereafter as a "Lipase-SER" domain), and/or a transmembrane domain.

In a preferred embodiment, the Adhr-1 protein family member has an amino acid sequence at least about 50%, 55%, 60%, 65%, 70%, 75%, 80%, 85%, 86%, 87%, 88%, 89%, 90%, 91%, 92%, 93%, 94%, 95%, 96%, 97%, 98%, 99%, 99.5% or more identical to the amino acid sequence of SEQ ID NO:2, and includes at least one or more of the following domains: an ADH-Zn domain, a Lipase-SER domain, a transmembrane domain.

In another preferred embodiment, the Adhr-1 protein family member modulates Adh activity, and includes at least one or more of the following domains: an ADH-Zn domain, a Lipase-SER domain, and/or a transmembrane domain.

In yet another preferred embodiment, the Adhr-1 protein family member is encoded by a nucleic acid molecule having a nucleotide sequence which hybridizes under stringent hybridization conditions to a nucleic acid molecule comprising the nucleotide sequence of SEQ ID NO:1 or 3, and includes at least one or more of the following domains: an ADH-Zn domain, a Lipase-SER domain, and/or a transmembrane domain.

In another embodiment, the invention features fragments of the protein having the amino acid sequence of SEQ ID NO:2, wherein the fragment comprises at least 15, 20, 30, 40, 50, 60, 70, 80, 90, or 100 amino acids (e.g., contiguous amino acids) of the amino acid sequence of SEQ ID NO:2. In another embodiment, the protein, preferably an Adhr-1 protein, has the amino acid sequence of SEQ ID NO:2.

In another embodiment, the invention features an isolated Adhr-1 protein family member which is encoded by a nucleic acid molecule consisting of a nucleotide sequence at least about 50%, 55%, 60%, 65%, 70%, 75%, 80%, 85%, 86%, 87%, 88%, 89%, 90%, 91%, 92%, 93%, 94%, 95%, 96%, 97%, 98%, 99%, 99.5% or more identical to a nucleotide sequence of SEQ ID NO:1 or 3, or a complement thereof. This invention further features an isolated protein, preferably an Adhr-1 protein, which is encoded by a nucleic acid molecule consisting of a nucleotide sequence which hybridizes under stringent hybridization conditions to a nucleic acid molecule comprising the nucleotide sequence of SEQ ID NO:1 or 3, or a complement thereof.

The proteins of the present invention or portions thereof, e.g., biologically active portions thereof, can be operatively linked to a non-Adhr-1 polypeptide (e.g., heterologous amino acid sequences) to form fusion proteins. The invention further features antibodies, such as monoclonal or polyclonal antibodies, that specifically bind proteins of the invention, preferably Adhr-1 proteins. In addition, the Adhr-1 proteins or biologically active portions thereof can be incorporated into pharmaceutical compositions, which optionally include pharmaceutically acceptable carriers.

In another aspect, the present invention provides a method for detecting the presence of an Adhr-1 nucleic acid molecule, protein or polypeptide in a biological sample by contacting the biological sample with an agent capable of detecting an Adhr-1 nucleic acid molecule, protein or polypeptide such that the presence of an Adhr-1 nucleic acid molecule, protein or polypeptide is detected in the biological sample.

In another aspect, the present invention provides a method for detecting the presence of Adhr-1 activity in a biological sample by contacting the biological sample with an agent capable of detecting an indicator of Adhr-1 activity such that the presence of Adhr-1 activity is detected in the biological sample.

In another aspect, the invention provides a method for modulating Adhr-1 activity comprising contacting a cell capable of expressing Adhr-1 with an agent that modulates Adhr-1 activity such that Adhr-1 activity in the cell is modulated. In one embodiment, the agent inhibits Adhr-1 activity. In another embodiment, the agent stimulates Adhr-1 activity.

In one embodiment, the agent is an antibody that specifically binds to an Adhr-1 protein. In another embodiment, the agent modulates expression of Adhr-1 by modulating transcription of an Adhr-1 gene or translation of an Adhr-1 mRNA. In yet another embodiment, the agent is a nucleic acid molecule having a nucleotide sequence that is antisense to the coding strand of an Adhr-1 mRNA or an Adhr-1 gene.

In one embodiment, the methods of the present invention are used to treat a subject having a disorder characterized by aberrant or unwanted Adhr-1 protein or nucleic acid expression or activity (e.g., an Adh-associated disorder or a disorder related to lipid metabolism) by administering an agent which is an Adhr-1 modulator to the subject. In one embodiment, the Adhr-1 modulator is an Adhr-1 protein. In another embodiment the Adhr-1 modulator is an Adhr-1 nucleic acid molecule. In yet another embodiment, the Adhr-1 modulator is a peptide, peptidomimetic, or other small molecule. In a preferred embodiment, the disorder characterized by aberrant or unwanted Adhr-1 protein or nucleic acid expression is an Adh-related disorder, e.g., alcohol-related disorder (e.g. alcoholism, cirrhosis), a developmental disorder, a cell signaling disorder, or a retinoid-related disorder. In another preferred embodiment, the disorder is related to lipid metabolism The present invention also provides diagnostic assays for identifying the presence or absence of a genetic alteration characterized by at least one of (i) aberrant modification or mutation of a gene encoding an Adhr-1 protein; (ii) mis-regulation of the Adhr-1 gene; and (iii) aberrant post-translational modification of an Adhr-1 protein, wherein a wild-type form of the gene encodes a protein with an Adhr-1 activity.

In another aspect the invention provides methods for identifying a compound that binds to or modulates the activity of an Adhr-1 protein, by providing an indicator composition comprising an Adhr-1 protein having Adhr-1 activity, contacting the indicator composition with a test compound, and determining the effect of the test compound on Adhr-1 activity in the indicator composition to identify a compound that modulates the activity of an Adhr-1 protein.

Other features and advantages of the invention will be apparent from the following detailed description and claims.

BRIEF DESCRIPTION OF THE DRAWINGS

FIGS. 1A–B depict the cDNA sequence and predicted amino acid sequence of the human Adhr-1. The nucleotide sequence corresponds to nucleic acids 1 to 1808 of SEQ ID NO:1. The amino acid sequence corresponds to amino acids 1 to 377 of SEQ ID NO:2. The coding region of the human Adhr-1 corresponds to SEQ ID NO:3.

FIGS. 3A–B depict the results of a search which was performed against the HMM database using the amino acid sequence of human Adhr-1. This search resulted in the identification of an ADH-Zn domain and a Lipase-SER domain in the human Adhr-1 protein.

FIG. 4 depicts the results of a search performed against the ProDom database using the amino acid sequence of human Adhr-1.

FIGS. 6A–C depict the cDNA sequence and predicted amino acid sequence of human AP21956 (clone Fbh21956). The nucleotide sequence corresponds to nucleic acids 1–3238 of SEQ ID NO:4. The amino acid sequence corresponds to amino acids 1–796 of SEQ ID NO:5. The coding region without the 5' or 3' untranslated regions of the human AP21956 gene is shown in SEQ ID NO:6.

FIGS. 7A–B depict the cDNA sequence and predicted amino acid sequence of human AP25856 (clone Fbh25856). The nucleotide sequence corresponds to nucleic acids 1–1626 of SEQ ID NO:7. The amino acid sequence corresponds to amino acids 1–196 of SEQ ID NO:8. The coding region without the 5' or 3' untranslated region of the human AP25856 gene is shown in SEQ ID NO:9.

FIGS. 18A–B depict the cDNA sequence and predicted amino acid sequence of human DHDR-5 (clone FBH22244). The nucleotide sequence corresponds to nucleic acids 1–1498 of SEQ ID NO:10. The amino acid sequence corresponds to amino acids 1–330 of SEQ ID NO:11. The coding region without the 5' or 3' untranslated regions of the human DHDR-5 gene is shown in SEQ ID NO:12.

FIGS. 19A–B depict the cDNA sequence and predicted amino acid sequence of human DHDR-6 (clone FBH8701). The nucleotide sequence corresponds to nucleic acids 1–1981 of SEQ ID NO:13. The amino acid sequence corresponds to amino acids 1–467 of SEQ ID NO:14. The coding region without the 5' or 3' untranslated region of the human DHDR-6 gene is shown in SEQ ID NO:15.

FIGS. 21A–B depict the results of a search which was performed against the HMM database using the amino acid sequence of human DHDR-5 (SEQ ID NO:11). This search resulted in the identification of a Shikimate/quinate 5-dehydrogenase domain and a short chain dehydrogenase domain in the human DHDR-5 protein.

(15) normal skin; (16) normal spinal cord; (17) normal brain cortex; (18) brain—hypothalamus; (19) nerve; (20) dorsal root ganglion (DRG); (21) glial cells (astrocytes); (22) glioblastoma; (23) normal breast; (24) breast tumor; (25) normal ovary; (26) ovary tumor; (27) normal prostate; (28) prostate tumor; (29) epithelial cells (prostate); (30) normal colon; (31) colon tumor; (32) normal lung; (33) lung tumor; (34) lung—chronic obstructive pulmonary disease (COPD); (35) colon—inflammatory bowel disease (IBD); (36) normal liver; (37) liver fibrosis; (38) dermal cells—fibroblasts; (39) normal spleen; (40) normal tonsil; (41) lymph node; (42) small intestine; (43) skin—decubitus; (44) synovium; (45) bone marrow—mononuclear cells (BM-MNC); (46) activated peripheral blood mononuclear cells (PBMC).

Figure 24:
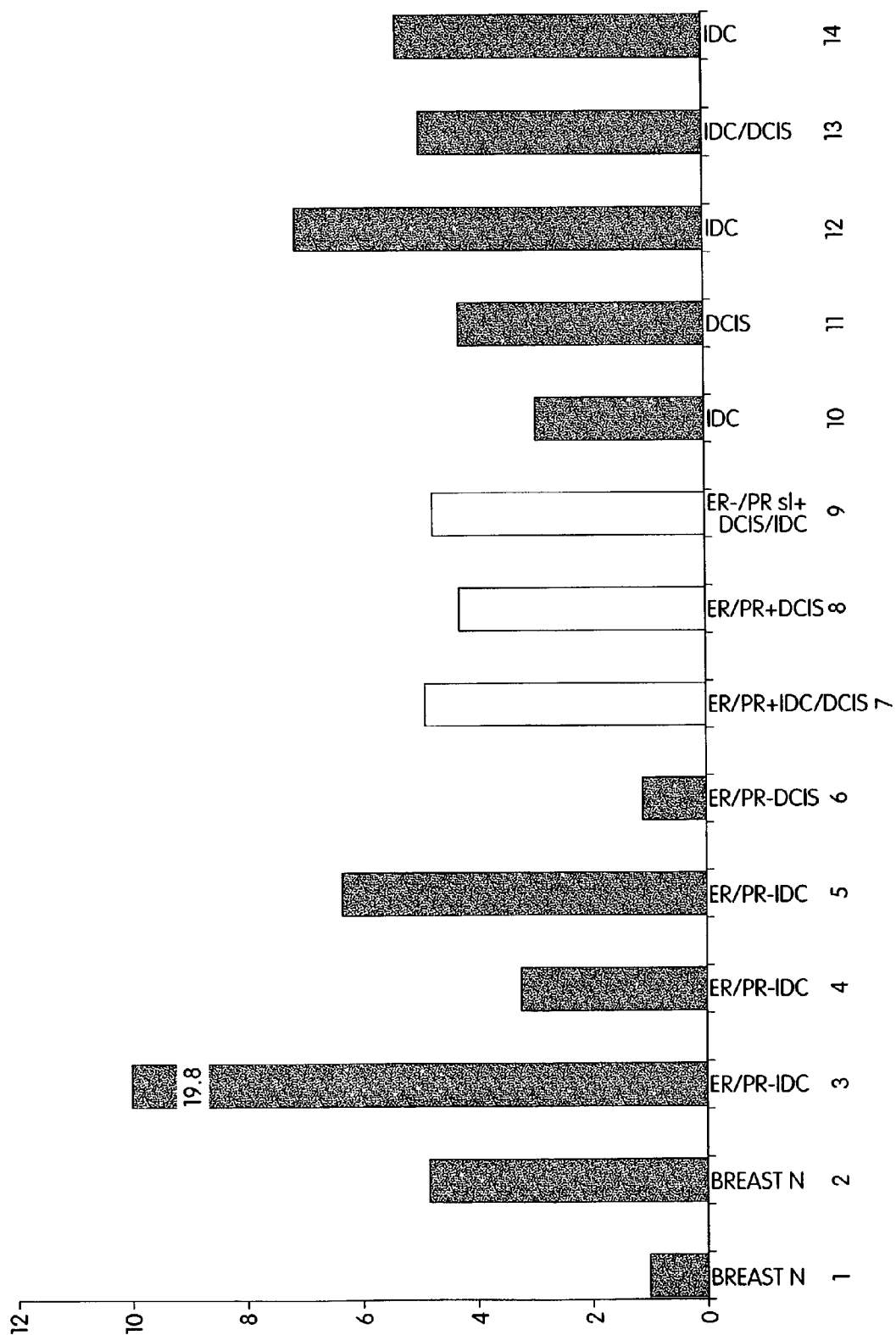

FIG. 24 depicts expression levels of human DHDR-5 in human breast tumor samples, as determined by Taqman analysis. Sample No.: (1–2) normal breast; (3–5) ER/PR– infiltrating ductal carcinoma (IDC); (6) ER/PR– ductal carcinoma in situ (DCIS); (7–9) ER/PR+ ductal carcinoma in situ (DCIS); (10) infiltrating ductal carcinoma (IDC); (11) ductal carcinoma in situ (DCIS); (12) infiltrating ductal carcinoma (IDC); (13) infiltrating ductal carcinoma (IDC)/ ductal carcinoma in situ (DCIS); (14) infiltrating ductal carcinoma (IDC).

Figure 25:
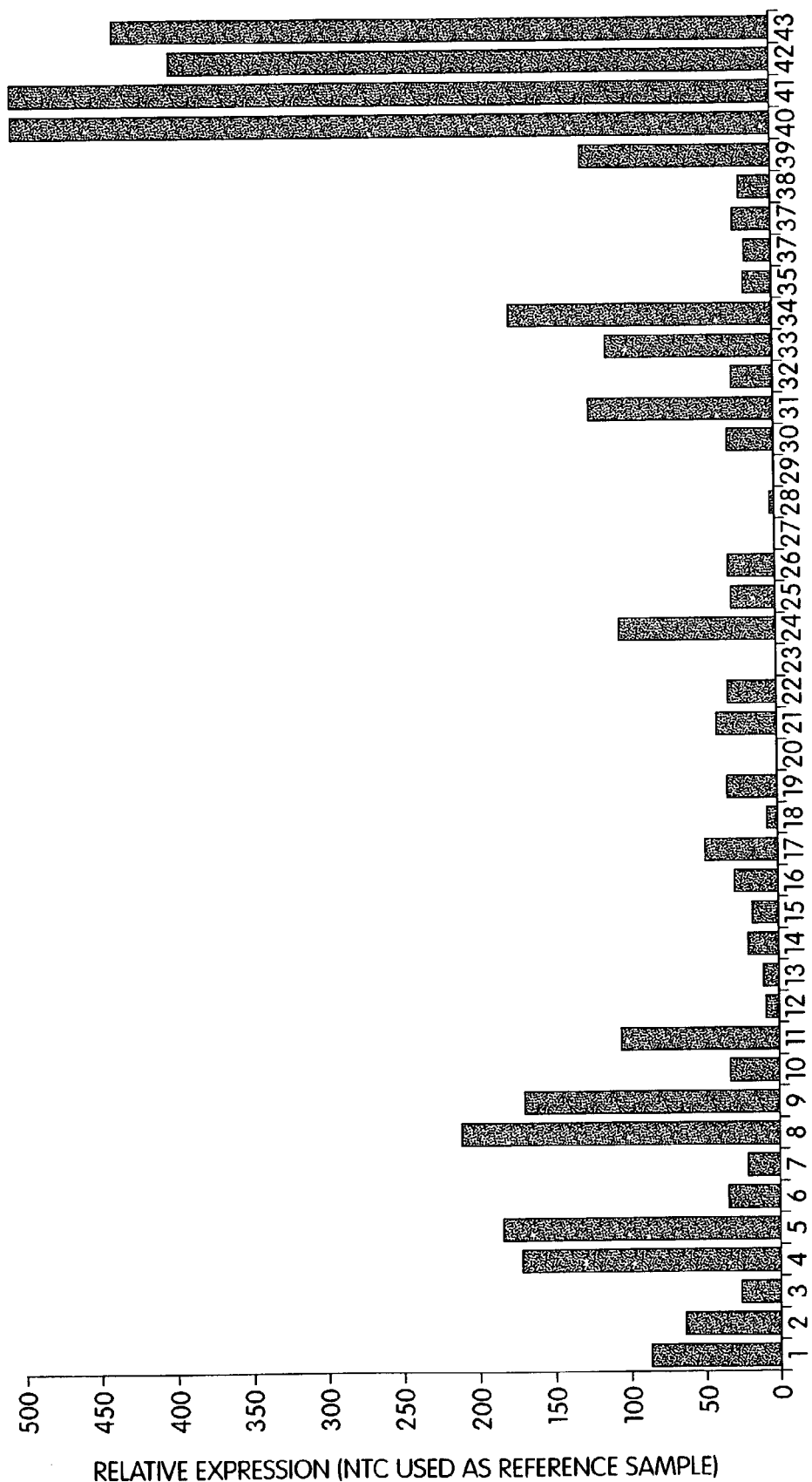

FIG. 25 depicts expression levels of human DHDR-5 in cell lines and tissue types, as determined by Taqman analysis. Sample No.: (1) heart; (2) lung; (3) lung pool; (4) fetal liver; (5) spleen; (6) grans.; (7) normal human dermal fibroblasts (NHDF)—mock; (8) normal human lung fibroblasts (NHLF)—mock; (9) normal human lung fibroblasts (NHLF)—treated with TGF; (10) NC heps; (11) pass stell; (12–13) control liver; (14–16) LF; (17) tonsil; (18) LN; (19) TH224 hours; (20–21) TH124 hours; (22) TH224 hours; (23) CD4; (24) CD8; (25) CD3 rest; (26) CD14; (27) peripheral blood mononuclear cells (PBMC)—mock; (28) bone marrow mononuclear cells (BM MNC); (29) ABM CD34+; (30) MPB CD34+; (31) bone marrow (BM) GPA+; (32) cord blood; (33) erythroid; (34) meg; (35) Neut d14; (36) CD14–/CD15+; (37) MBM CD11b–; (38) MAI 01; (39) HL60; (40) K562; (41) Molt 4; (42) Hep3B normoxia; (43) Hep3B hypoxia.

Figure 26:
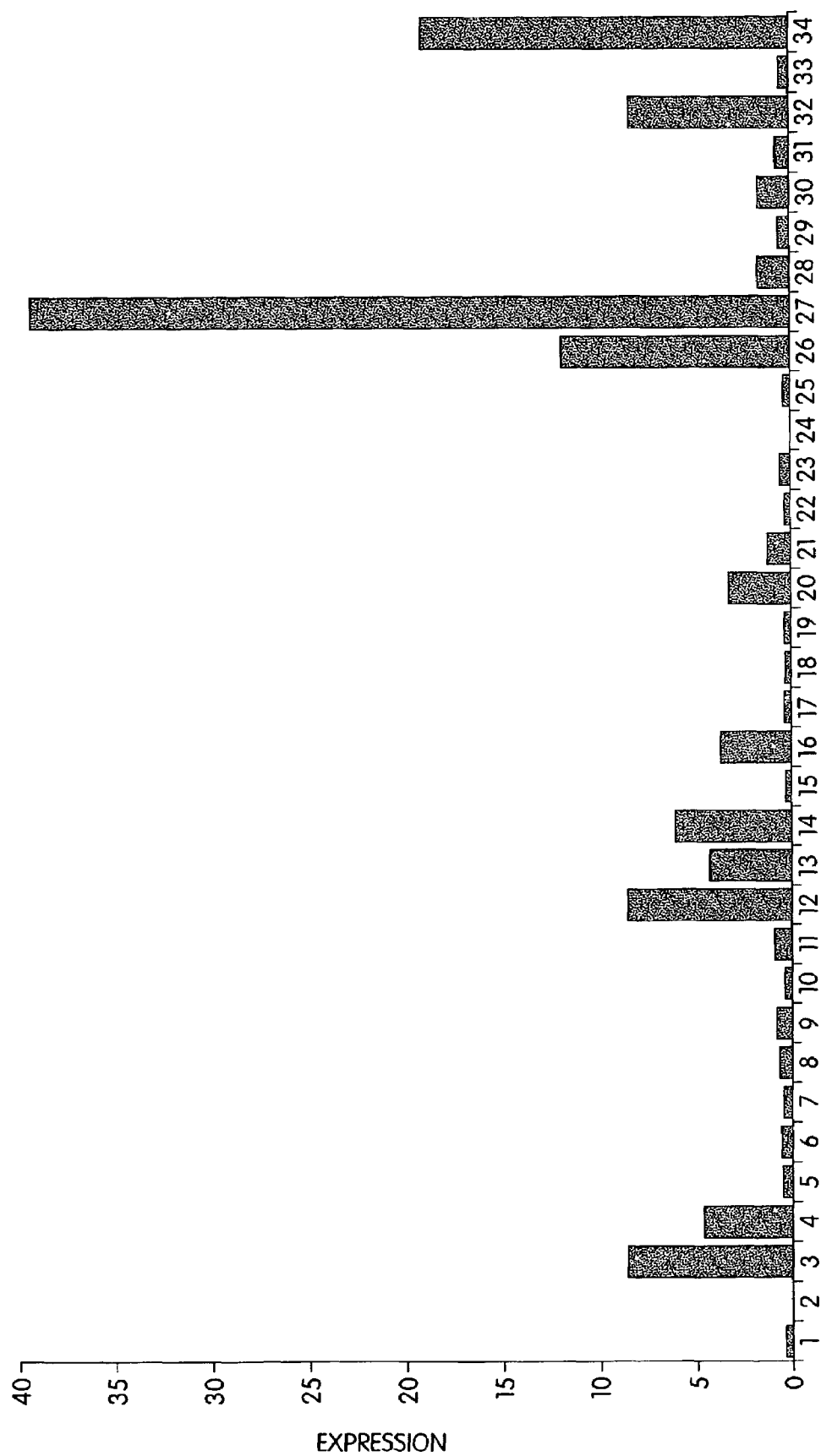

FIG. 26 depicts expression levels of human DHDR-5 in human breast, ovary, and lung tumors, as determined by Taqman analysis. Sample No.: (1–3) normal breast; (4–11) breast tumor; (12–14) normal ovary; (15–21) ovary tumor; (22–25) normal lung; (26) lung tumor—SmC; (27–29) lung tumor—poorly differentiated non-small cell carcinoma of the lung (PDNSCCL); (30) lung tumor—small cell carcinoma (SCC); (31) lung tumor—ACA; (32) lung tumor— small cell carcinoma (SCC); (33) lung tumor—AC; (34) normal human bronchial epithelial (NHBE) cells.

Figure 27:
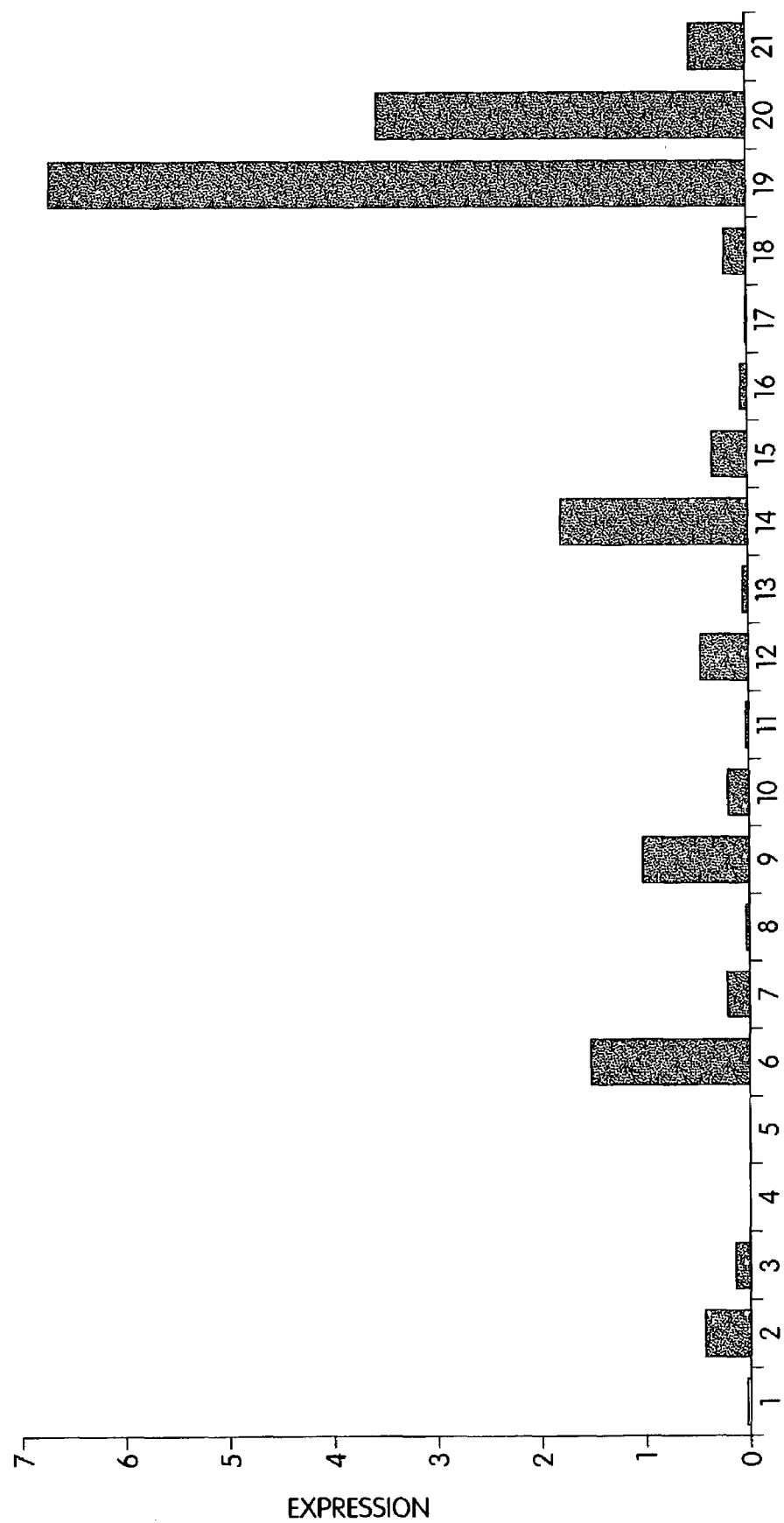

FIG. 27 depicts expression levels of human DHDR-5 in colon tumors, as determined by Taqman analysis. Sample No.: (1–4) normal colon; (5–12) colon tumor; (13–16) liver metastasis; (17–18) normal liver; (19) human microvascular endothelial cells (HMVEC)—arrested; (20) human microvascular endothelial cells (HMVEC)—proliferating; (21) placenta.

Figure 28:
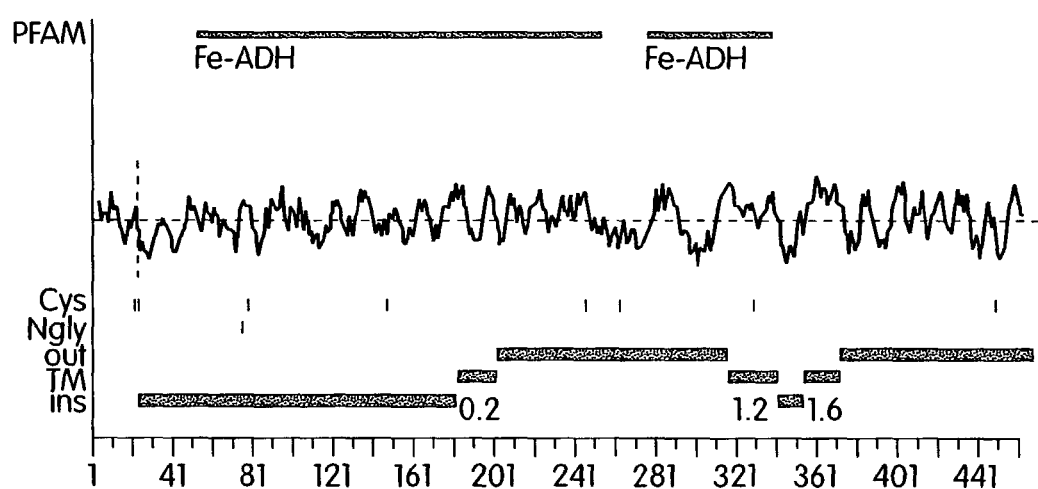

FIG. 28 depicts a hydrophobicity plot of the human DHDR-6 protein.

FIG. 29 depicts the results of a search which was performed against the HMM database using the amino acid sequence of human DHDR-6 (SEQ ID NO:14). This search resulted in the identification of an Iron-containing alcohol dehydrogenase domain in the human DHDR-6 protein.

Figure 30:
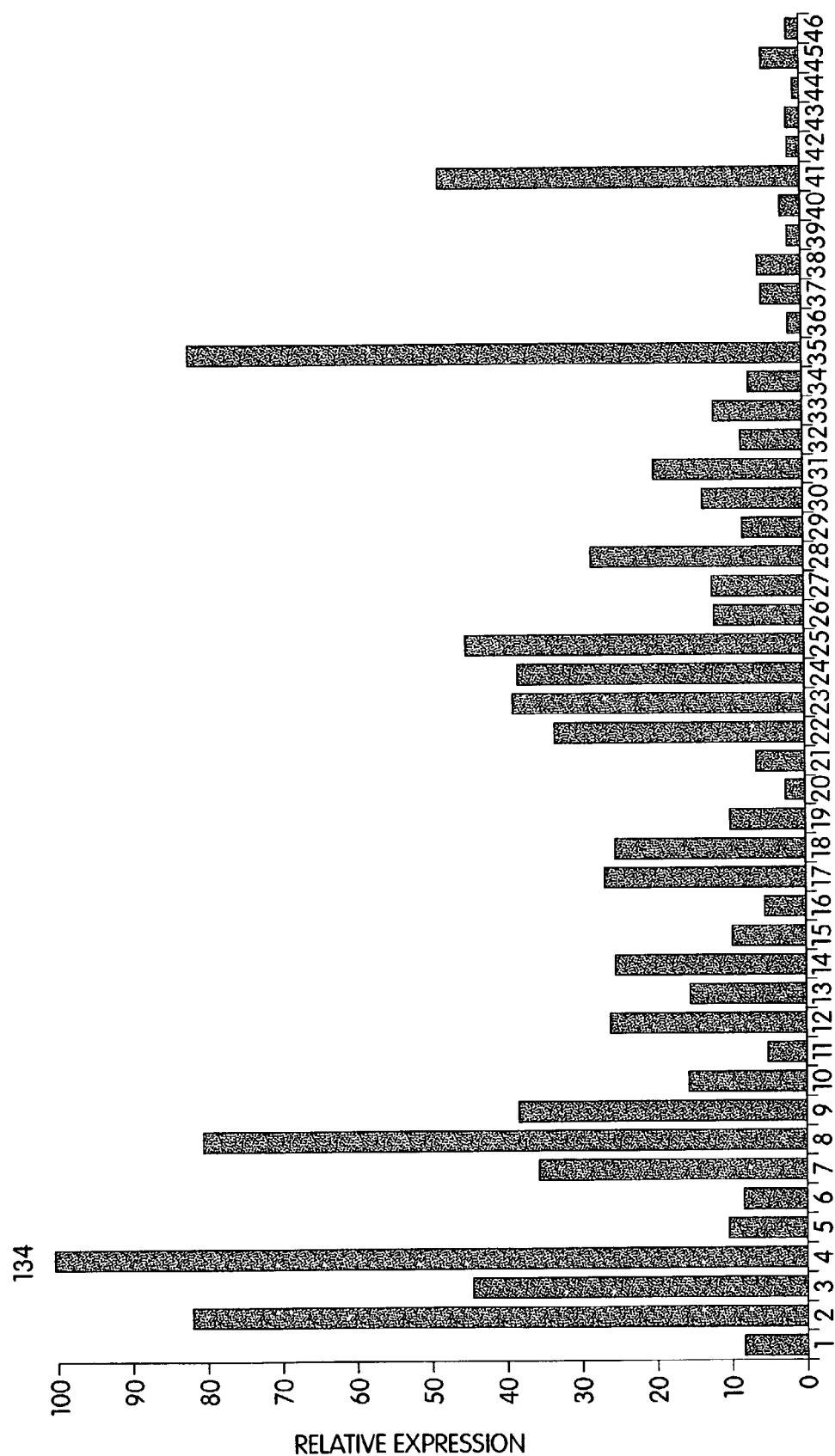

FIG. 30 depicts expression levels of human DHDR-6 in various cells and tissues, as determined by Taqman analysis. Sample No.: (1) normal aorta; (2) normal fetal heart; (3) normal heart; (4) heart—congestive heart failure (CHF); (5) normal vein; (6) aortic smooth muscle cells (SMC); (7) normal spinal cord; (8) normal brain cortex; (9) brain— hypothalamus; (10) glial cells (astrocytes); (11) brain— glioblastoma; (12) normal breast; (13) breast tumor—infiltrating ductal carcinoma (IDC); (14) normal ovary; (15) ovary tumor; (16) pancreas; (17) normal prostate; (18) prostate tumor; (19) normal colon; (20) colon tumor; (21) colon—inflammatory bowel disease (IBD); (22) normal kidney; (23) normal liver; (24) liver fibrosis; (25) normal fetal liver; (26) normal lung; (27) lung tumor; (28) lung— chronic obstructive pulmonary disease (COPD); (29) normal spleen; (30) normal tonsil; (31) normal lymph node; (32) normal thymus; (33) epithelial cells; (34) endothelial cells; (35) skeletal muscle cells; (36) dermal fibroblasts; (37) normal skin; (38) normal adipose tissue; (39) primary osteoblasts; (40) osteoblasts (undifferentiated); (41) osteoblasts (differentiated); (42) osteoclasts; (43) early aorta; (44) late aorta; (45) human umbilical vein endothelial cells (HUVEC); (46) human microvascular endothelial cells (HMVEC).

Figure 31:
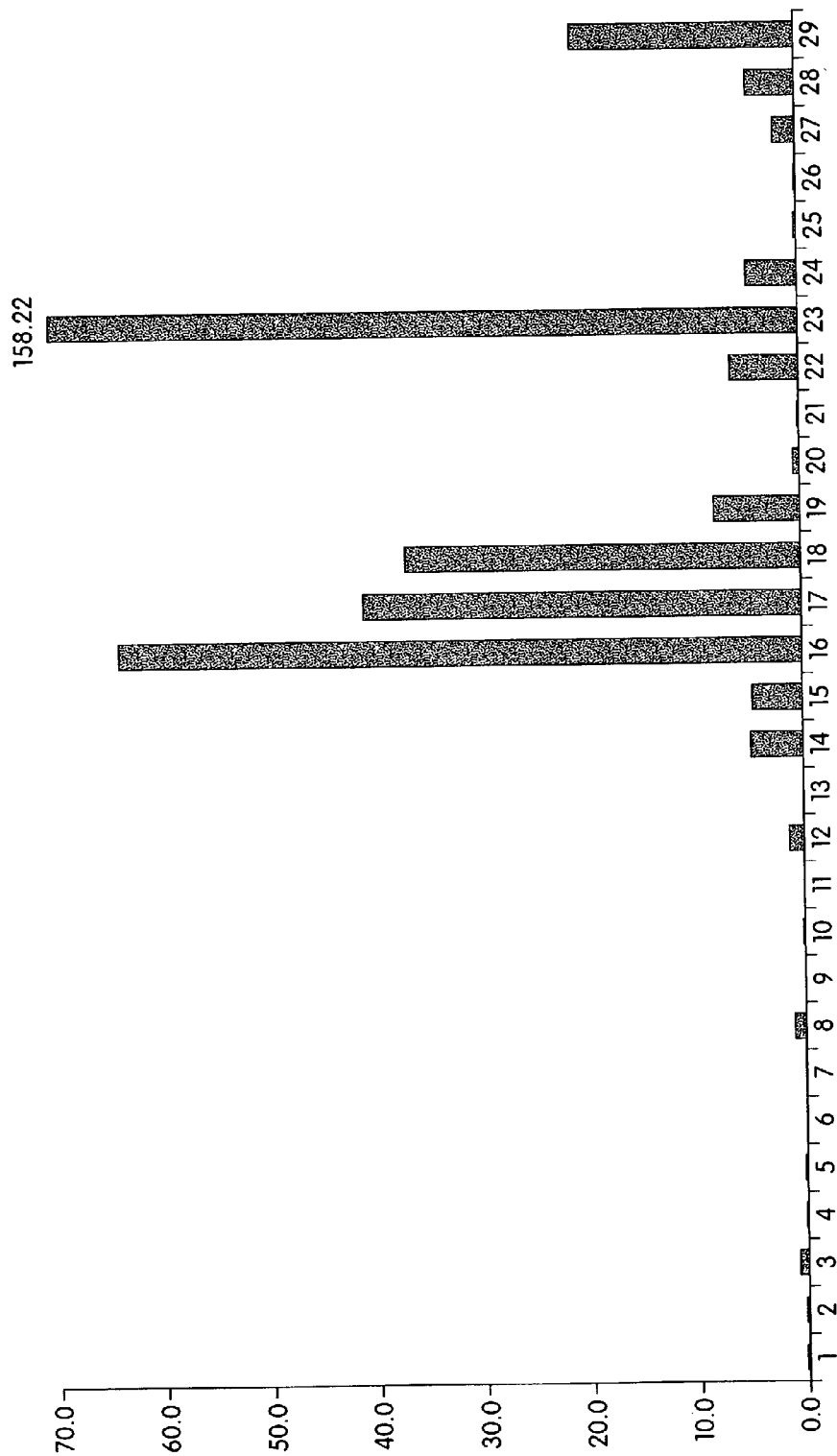

FIG. 31 depicts expression levels of human DHDR-6 in colon and brain tumors, as determined by Taqman analysis. Sample No.: (1–4) normal colon; (5–10) colon tumor; (11–14) liver metastasis; (15) normal liver; (16–18) normal brain; (19) astrocytes; (20–24) brain tumor; (25) human microvascular endothelial cells (HMVEC)—arrested; (26) human microvascular endothelial cells (HMVEC)—proliferating; (27) fetal adrenal gland; (28–29) fetal liver.

Figure 32:
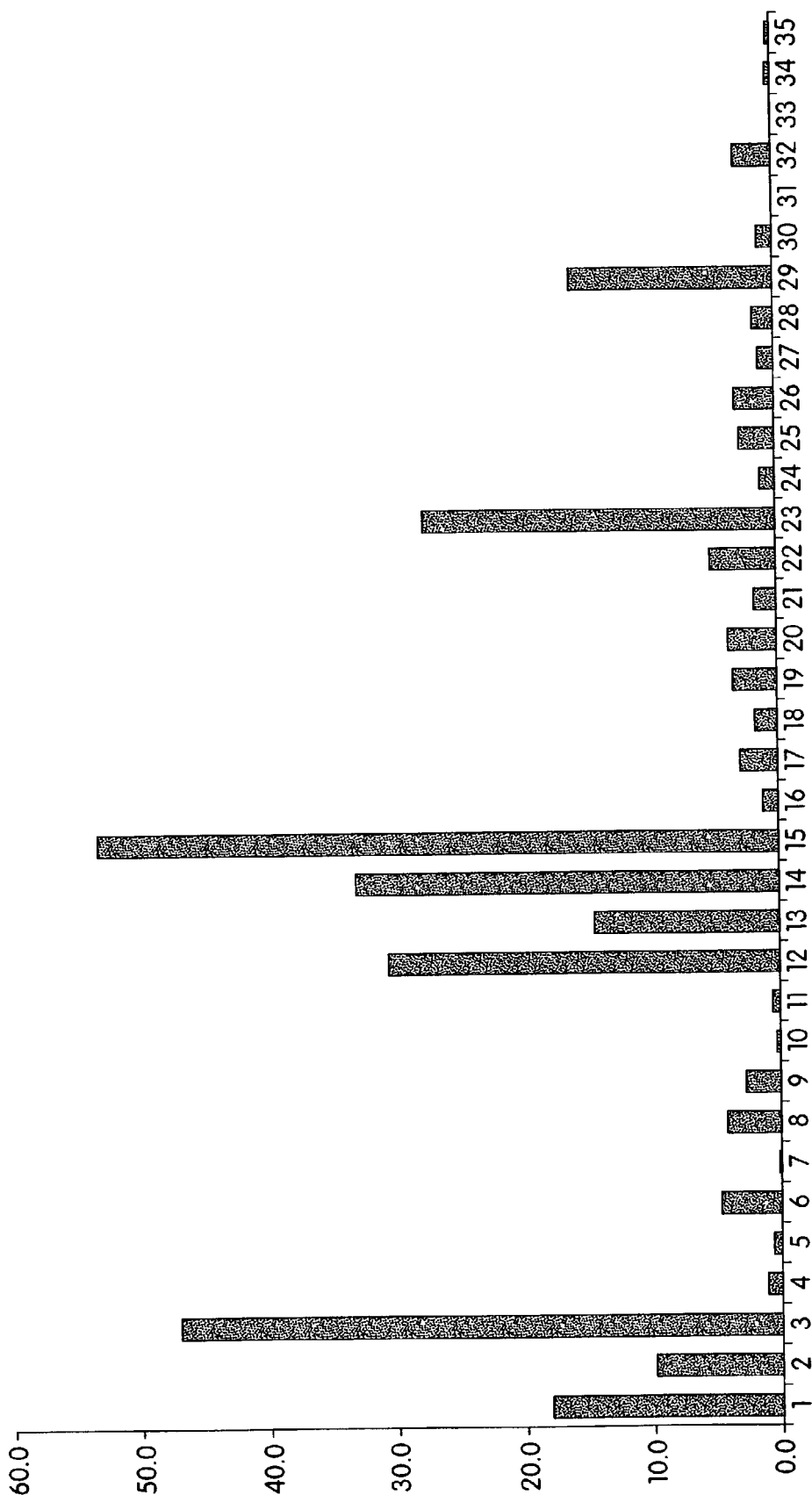

FIG. 32 depicts expression levels of human DHDR-6 in breast, ovary, and lung tumors, as determined by Taqman analysis. Sample No.: (1–3) normal breast; (4–11) breast tumor; (12–15) normal ovary; (16–23) ovary tumor; (24–27) normal lung; (28–35) lung tumor.

FIGS. 33A–E depict the cDNA sequence and predicted amino acid sequence of human BRE (clone Fbh32263). The nucleotide sequence corresponds to nucleic acids 1 to 2577 of SEQ ID NO:16. The amino acid sequence corresponds to amino acids 1 to 725 of SEQ ID NO:17. The coding region without the 3' untranslated region of the human BRE gene is shown in SEQ ID NO:18.

FIGS. 34A–B depict a structural, hydrophobicity, and antigenicity analysis of the human Fbh32263 protein.

FIGS. 35A–F depict the results of a search which was performed against the HMM database and which resulted in the identification of a "CPSase domain" and a "biotin requiring enzyme domain".

FIGS. 36A–D depict an alignment of human BRE (SEQ ID NO:17, depicted as "32263.pro") with known transcarboxylases. These are 3-methylcrotonyl-CoA carboxylase precursor from *Arabidopsis* (GenBank No. AAA67356; depicted as "thal.pro"); a protein similar to propionyl-CoA carboxylase alpha chain from *C. elegans* (GenBank No. AAA93384; depicted as "celegans.pro"); and propionyl-CoA carboxylase alpha chain precursor from *H. sapiens* (GenBank No. P05165; depicted as "human.pro"). The CPSase domain of the human BRE is indicated in italics. The biotin-requiring enzyme domain of the human BRE is underlined. The alignment was performed using the Clustal algorithm which is part of the MEGALIGN program (e.g., version 3.1.7) which is part of the DNASTAR sequence analysis software package. The pairwise alignment parameters are as follows: K-tuple=1; Gap Penalty=3; Window=5; Diagonals saved=5. The multiple alignment parameters are as follows: Gap Penalty=10; and Gap length penalty=10.

FIGS. 37A–B depict the cDNA sequence and predicted amino acid sequence of human LP (clone Fbh50250). The nucleotide sequence corresponds to nucleic acids 1 to 2031 of SEQ ID NO:19. The amino acid sequence corresponds to amino acids 1 to 263 of SEQ ID NO:20. The coding region without the 3' or 5' untranslated region of the human LP gene is shown in SEQ ID NO:21.

FIGS. 38A–B depicts the cDNA sequence and predicted amino acid sequence of a fragment of human LP (clone Fbh50250), $LP_{48-794}$. The nucleotide sequence corresponds to nucleic acids 1 to 2031 of SEQ ID NO:22. The amino acid sequence corresponds to amino acids 1 to 248 of SEQ ID NO:23. The coding region without the 3' untranslated or 5' untranslated region of the human $LP_{48-794}$ gene is shown in SEQ ID NO:24.

Figure 39:
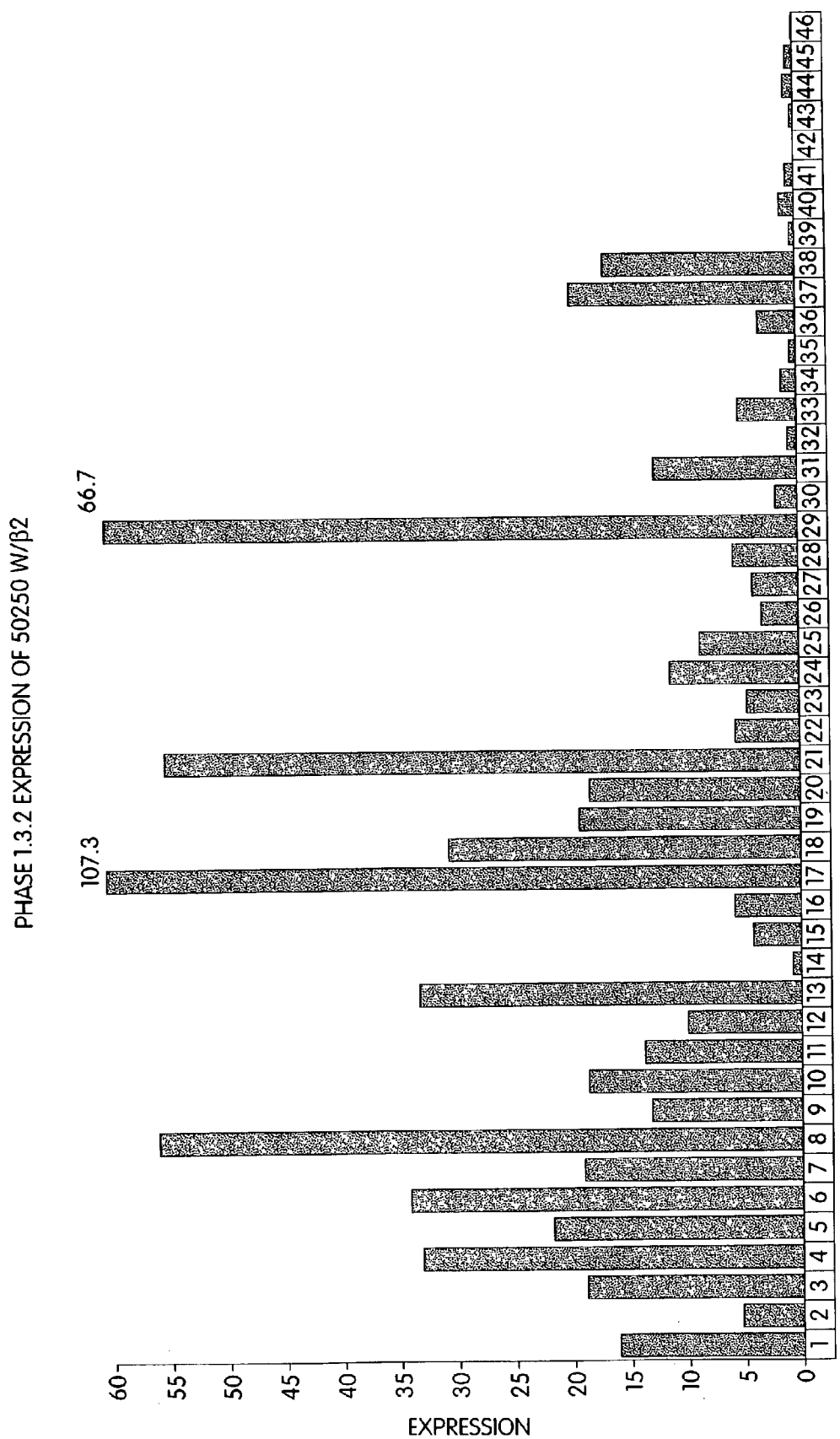

FIG. 39 depicts the results of an analysis of the expression pattern of LP in a panel of human tissues as determined by quantitative PCR using the TaqMan™ procedure.

Figure 40:
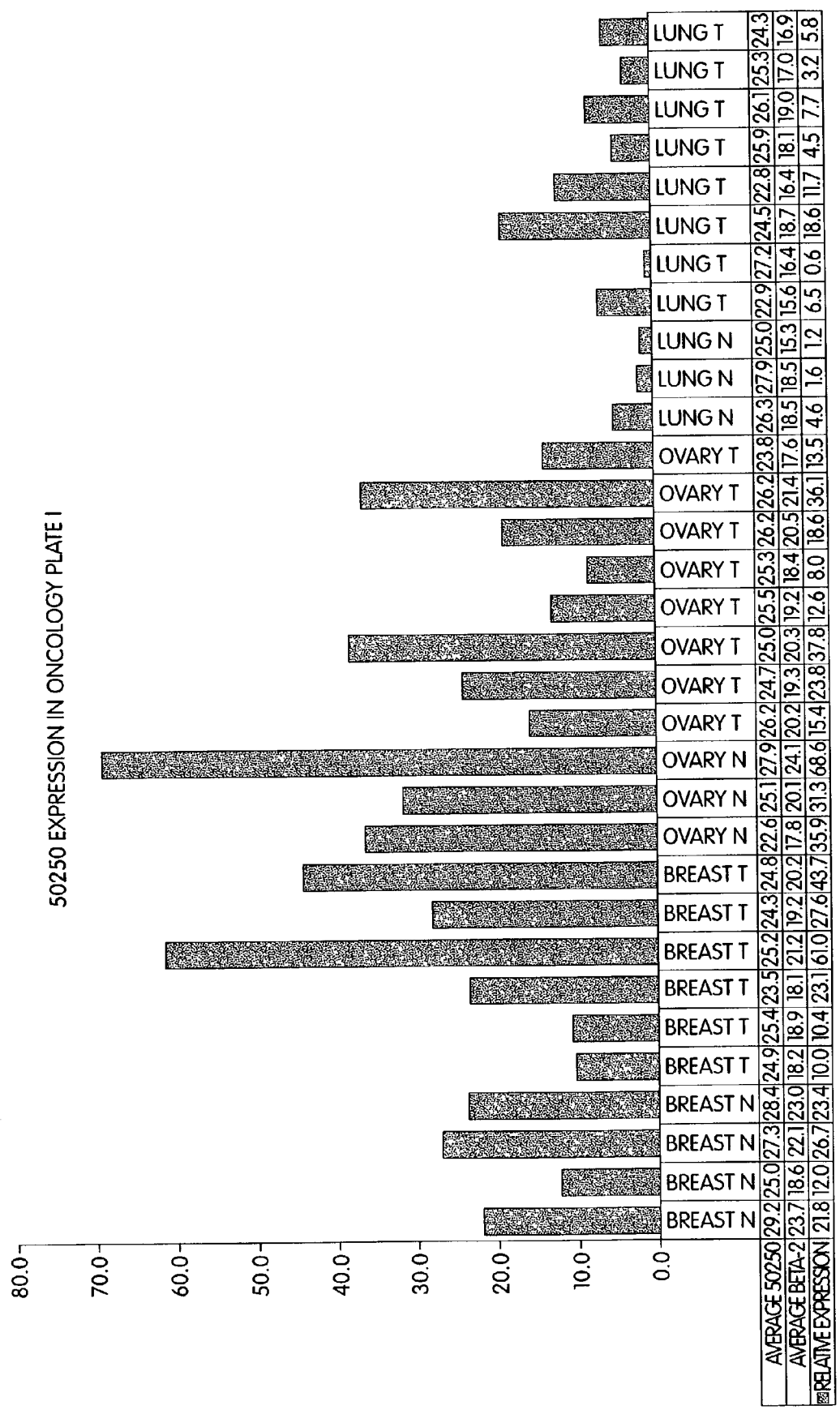

FIG. 40 depicts the results of an analysis of the expression pattern of LP in a panel of breast, ovary and lung tumors as compared to normal breast, ovary and lung samples as determined by quantitative PCR using the TaqMan™ procedure.

Figure 41:
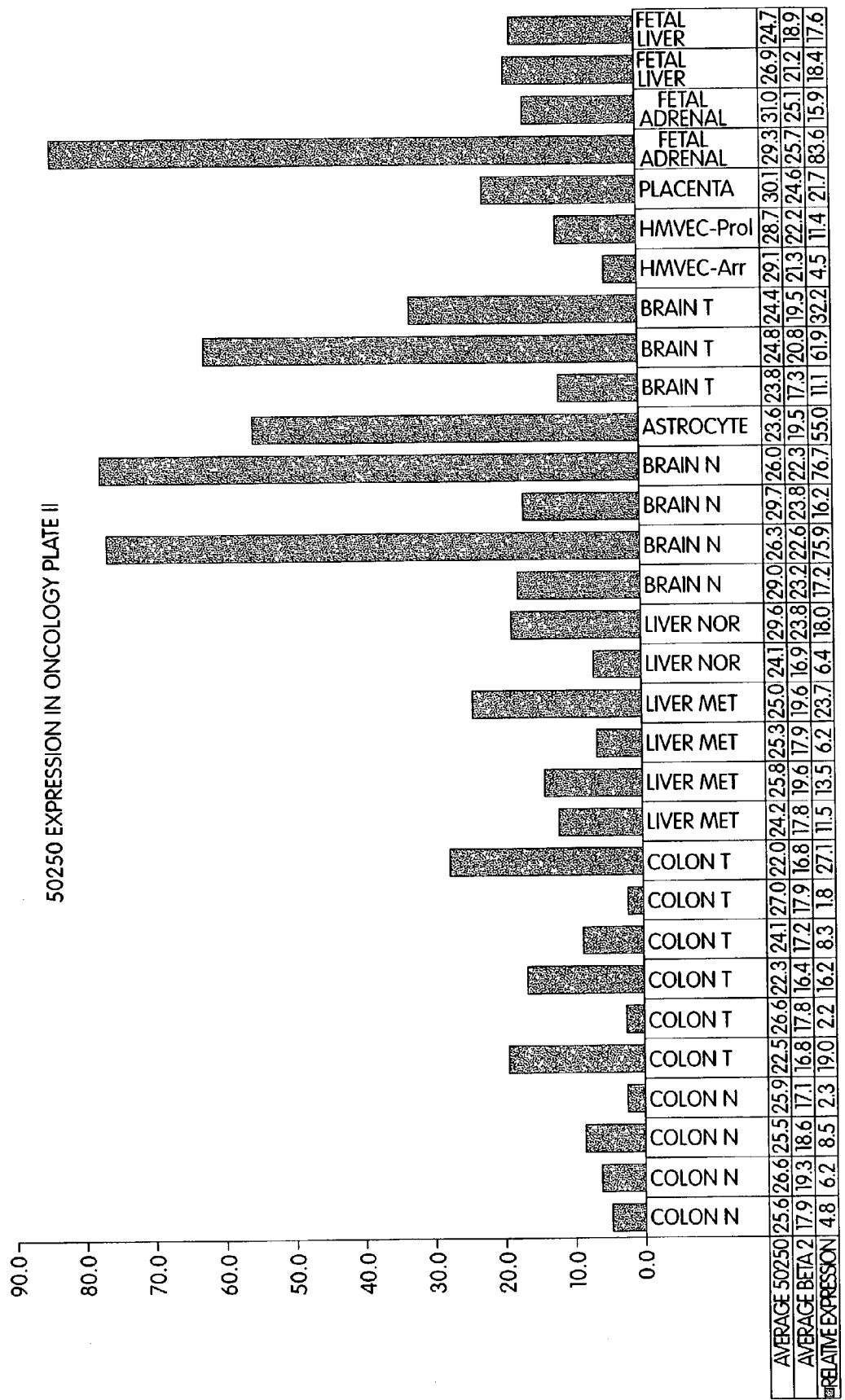

FIG. 41 depicts the results of an analysis of the expression pattern of LP in a panel of colon, brain and liver tumors as compared to normal colon, brain and liver samples as determined by quantitative PCR using the TaqMan™ procedure.

Figure 42:
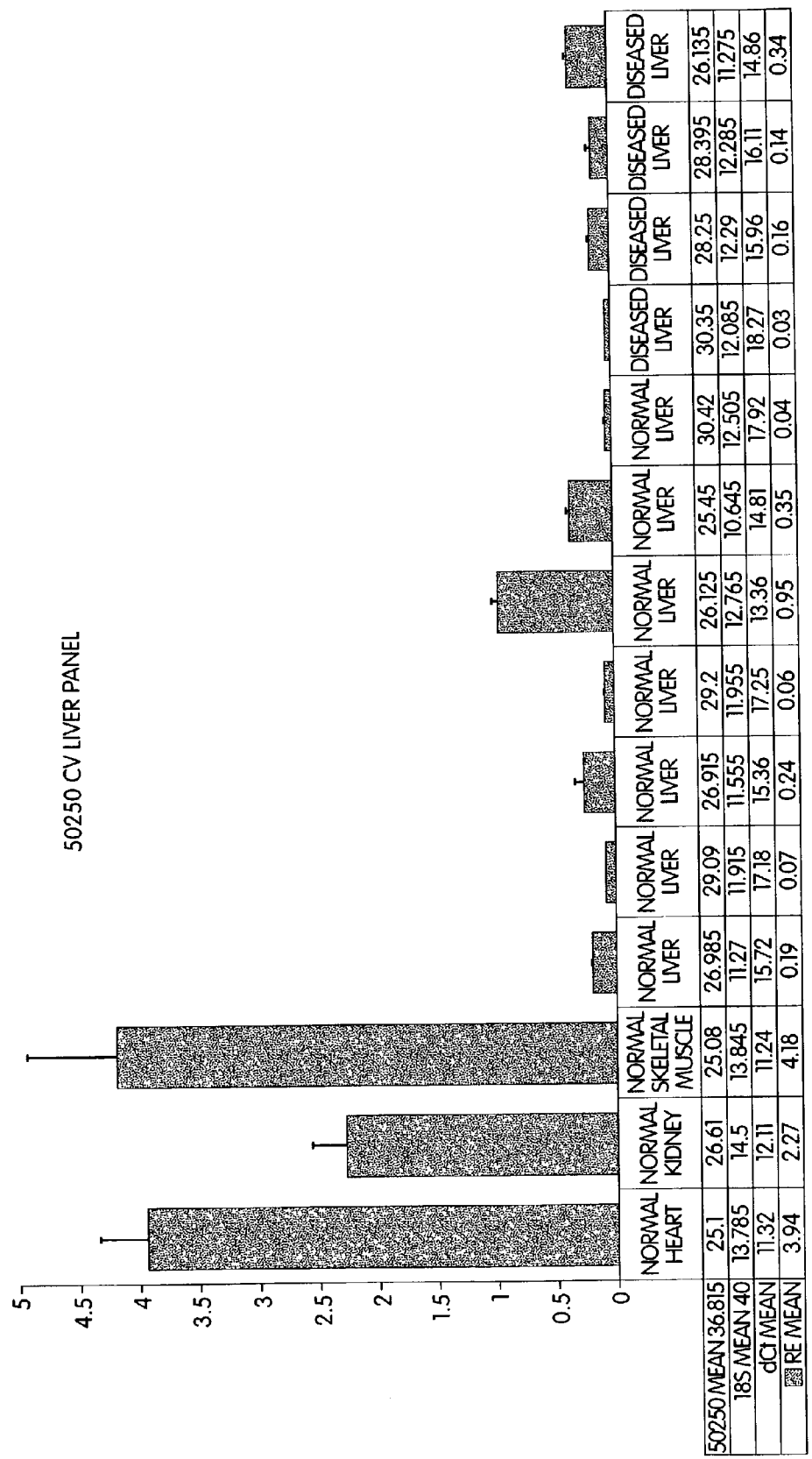

FIG. 42 depicts the results of an analysis of the expression pattern of LP in a panel of various normal and diseased liver samples as determined by quantitative PCR using the TaqMan™ procedure.

Figure 43:
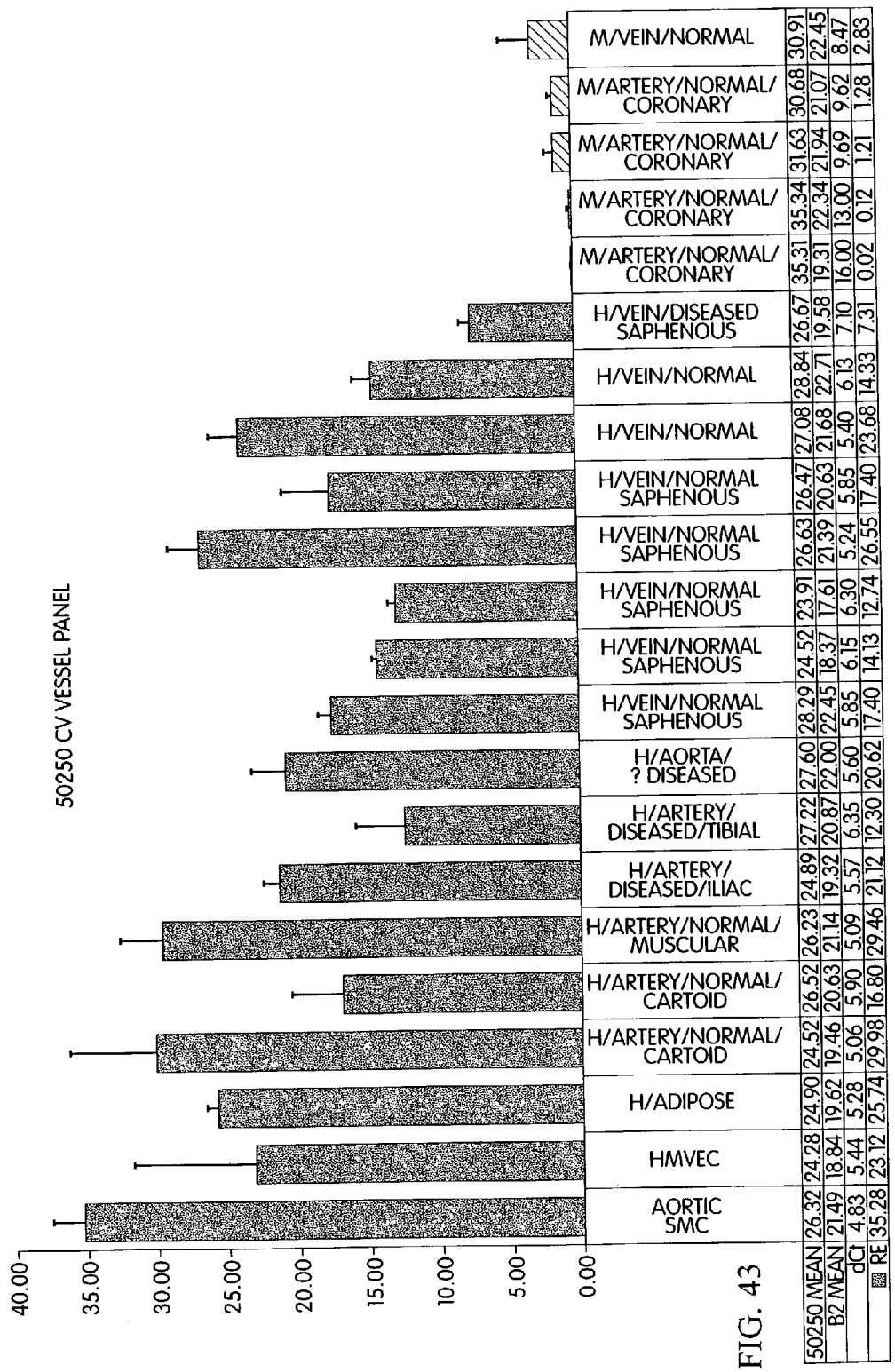

FIG. 43 depicts the results of an analysis of the expression pattern of LP in a panel of normal and diseased cardiovascular vessels as determined by quantitative PCR using the TaqMan™ procedure.

FIGS. 44A–B depict the cDNA sequence and predicted amino acid sequence of human CAH (clone Fbh55158). The nucleotide sequence corresponds to nucleic acids 1 to 1855 of SEQ ID NO:26. The amino acid sequence corresponds to amino acids 1 to 328 of SEQ ID NO:27. The coding region without the 3' untranslated region of the human CAH gene is shown in SEQ ID NO:28.

Figure 45:
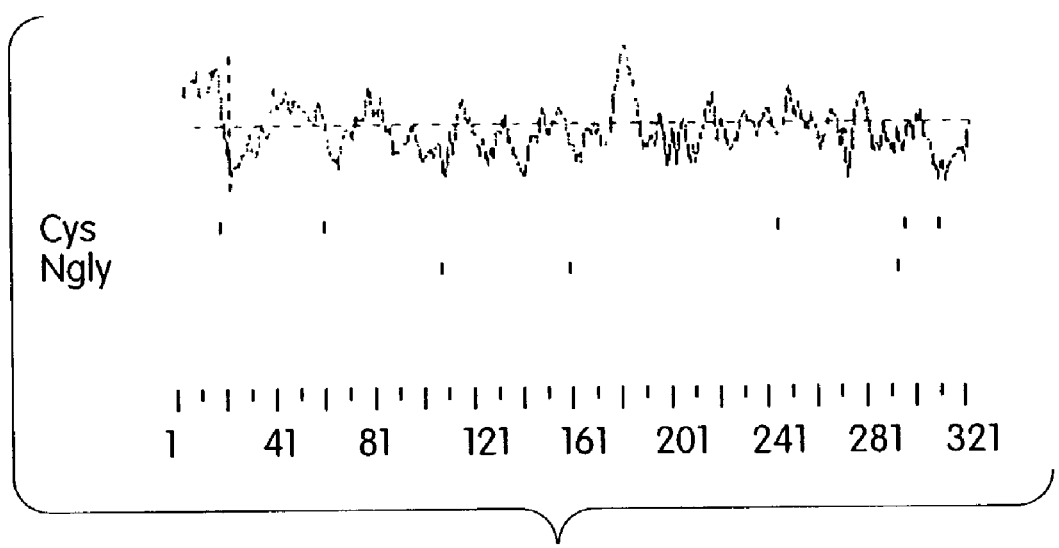

FIG. 45 depicts a hydrophobicity analysis of the human CAH protein.

FIG. 46 depicts the results of a search which was performed against the HMM database using the amino acid sequence of human CAH (SEQ ID NO:27) and which resulted in the identification of a "eukaryotic-type carbonic anhydrase domain" in the human CAH protein.

Figure 47:

FIG. 47 is a graphic depiction of the relative levels of human CAH mRNA expression in a human tissue panel, as determined using Taqman™ analysis (1=normal artery, 2=normal vein, 3=early aortic smooth muscle cells, 4=coronary smooth muscle cells, 5=static HUVEC, 6=shear HUVEC, 7=normal heart tissue, 8=congestive heart failure (CHF) heart tissue, 9=kidney tissue, 10=skeletal muscle, 11=normal adipose, 12=pancreas, 13=primary osteoblasts, 14 differentiated osteoclasts, 15=normal skin tissue, 16=normal spinal cord, 17=normal brain cortex, 18=brain hypothalamus, 19=nerve tissue, 20=dorsal root ganglia (DRG), 21=glial cells, 22=glioblastoma tissue, 23=normal breast tissue, 24=berate tumor tissue, 25=normal ovary tissue, 26=ovary tumor tissue, 27=normal prostate tissue, 28=prostate tumor tissue, 29=prostate epithelial cells, 30=normal colon tissue, 31=colon tumor tissue, 32=normal lung, 33=lung tumor tissue, 34=chronic obstructive pulmonary disease (COPD) lung tissue, 35=inflammatory bowel disease (IBD) colon tissue, 36=normal liver tissue, 37=liver fibrosis tissue, 38=dermal cells-fibroblasts, 39=normal spleen tissue, 40=normal tonsil tissue, 41=lymph node tissue, 42=small intestine tissue, 43=skin-decubitus, 44=synovium, 45=bone marrow, 46=activated PBMC).

Figure 48:
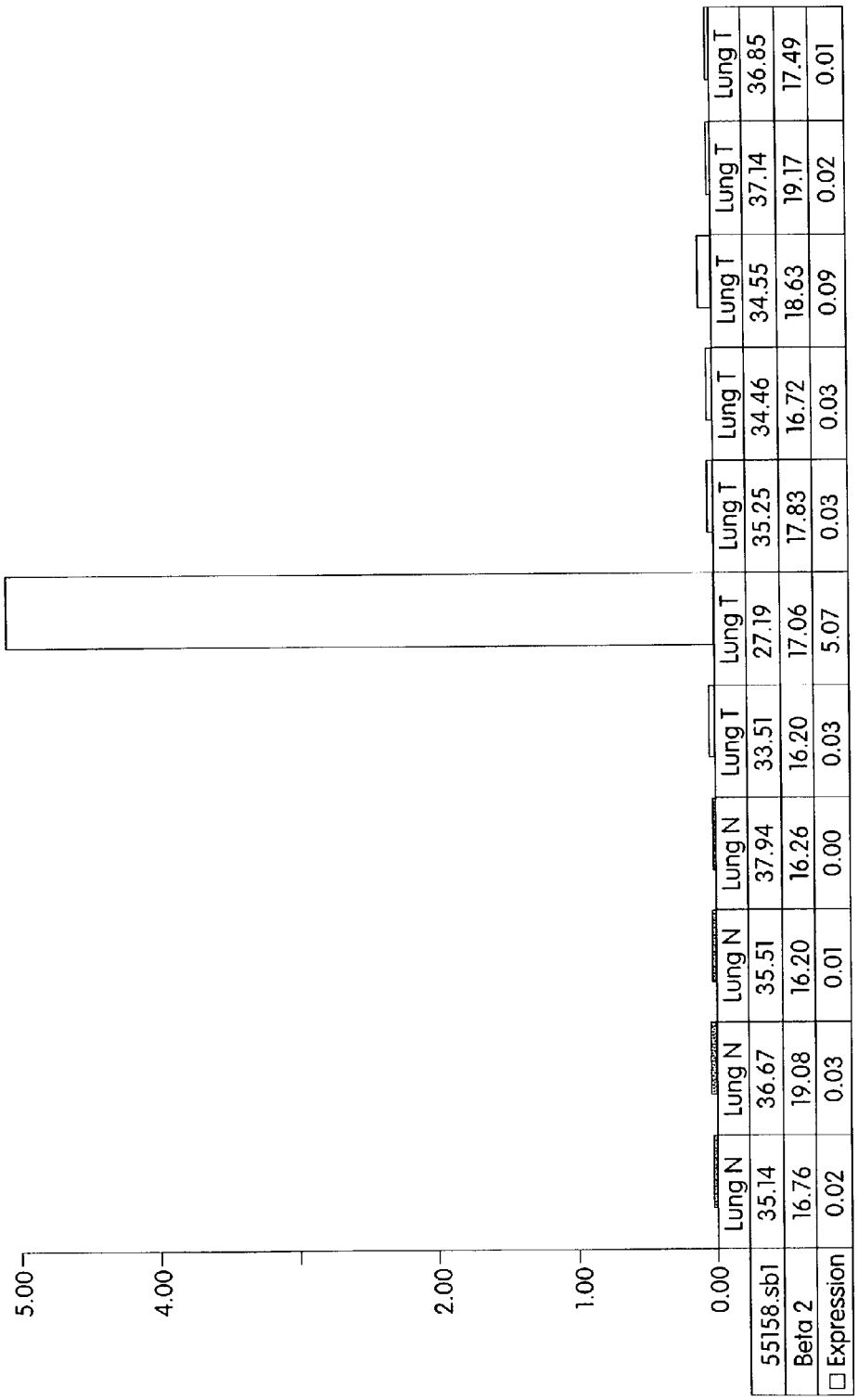

FIG. 48 is a graphic depiction of the relative levels of human CAH mRNA expression in a panel containing human normal (N) and tumor (T) lung tissue, as determined using Taqman™ analysis.

Figure 49:
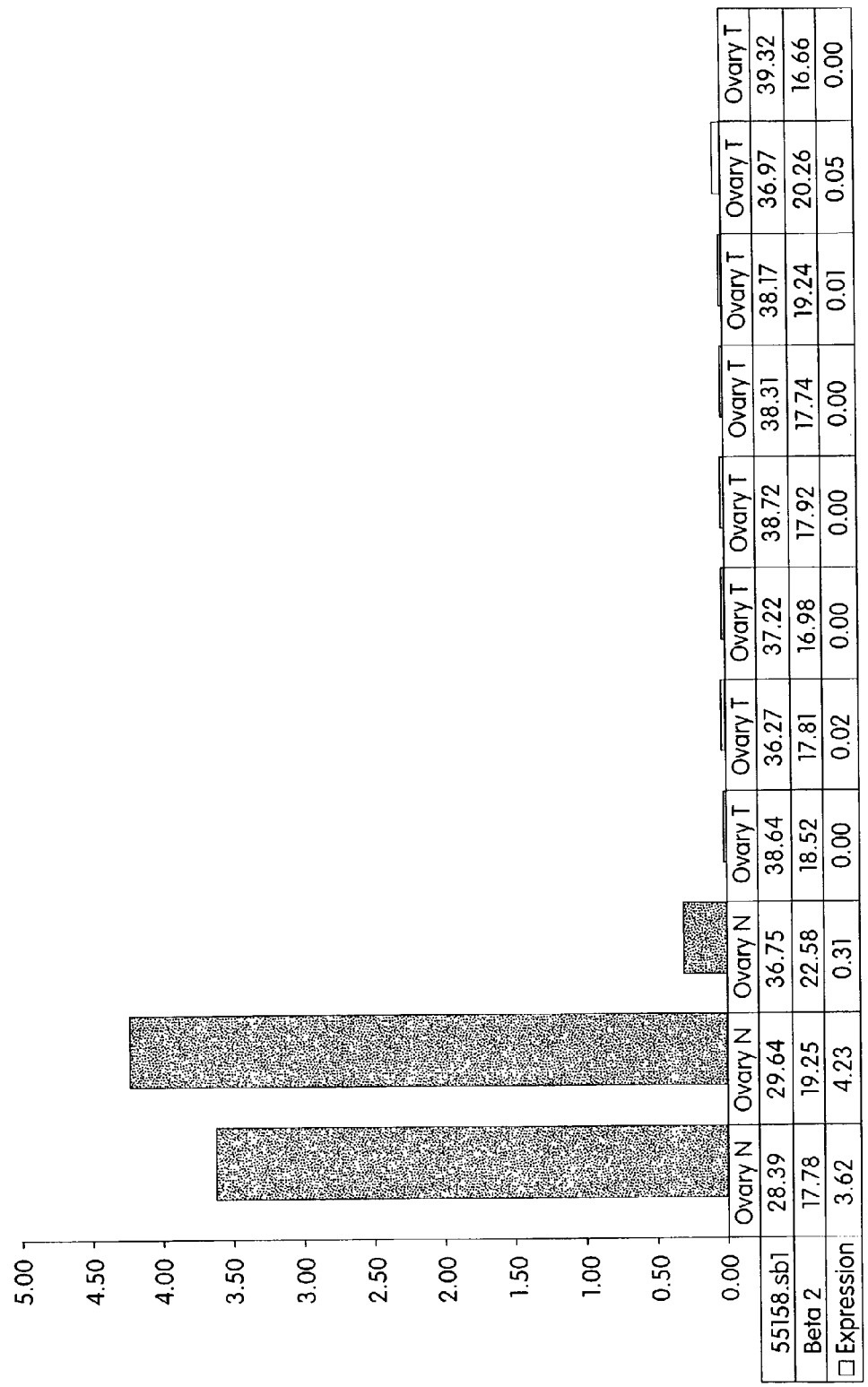

FIG. 49 is a graphic depiction of the relative levels of human CAH mRNA expression in a panel containing human normal (N) and tumor (T) ovary tissue, as determined using Taqman™ analysis.

Figure 50:
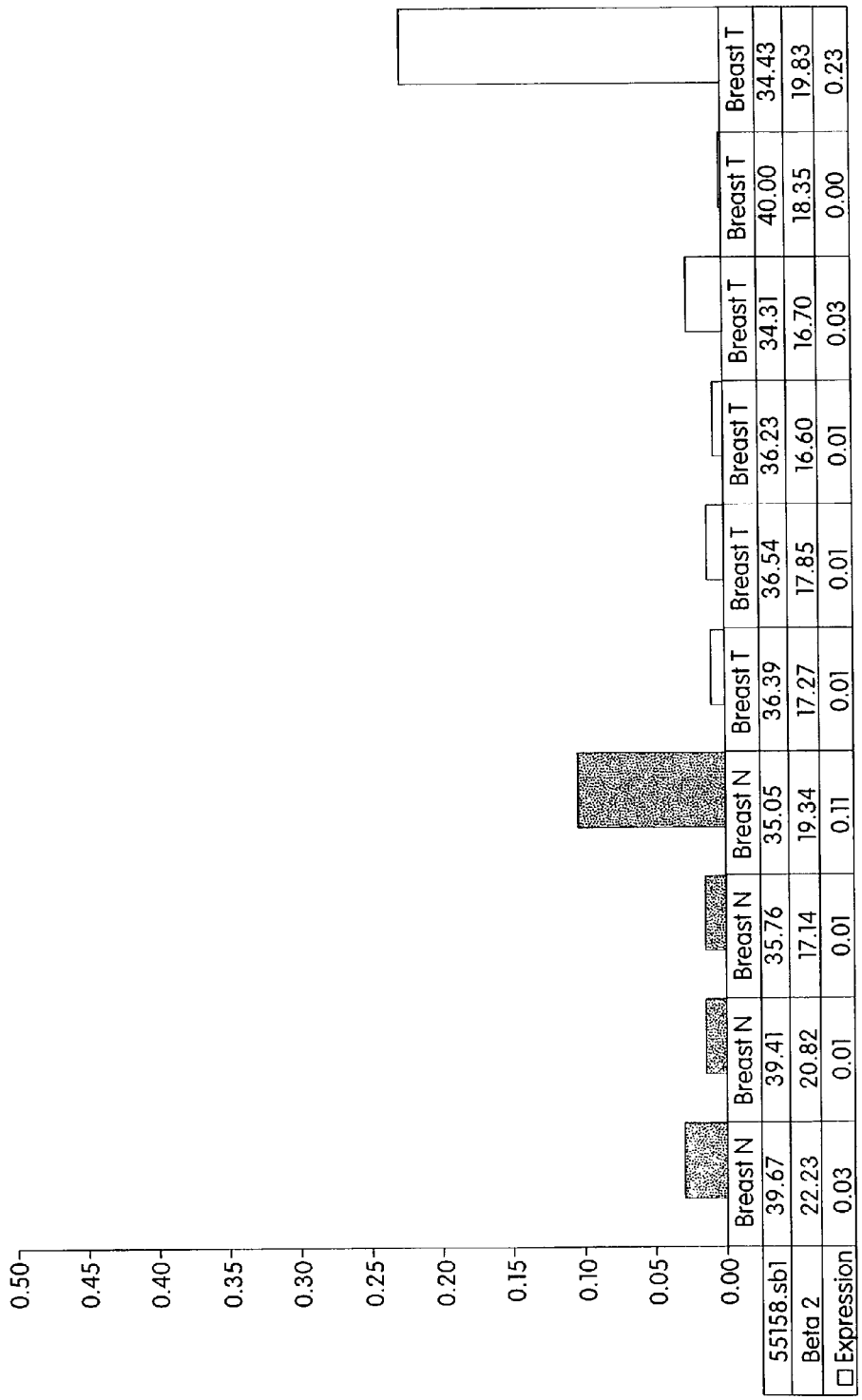

FIG. 50 is a graphic depiction of the relative levels of human CAH mRNA expression in a panel containing human normal (N) and tumor (T) breast tissue, as determined using Taqman™ analysis.

Figure 51:
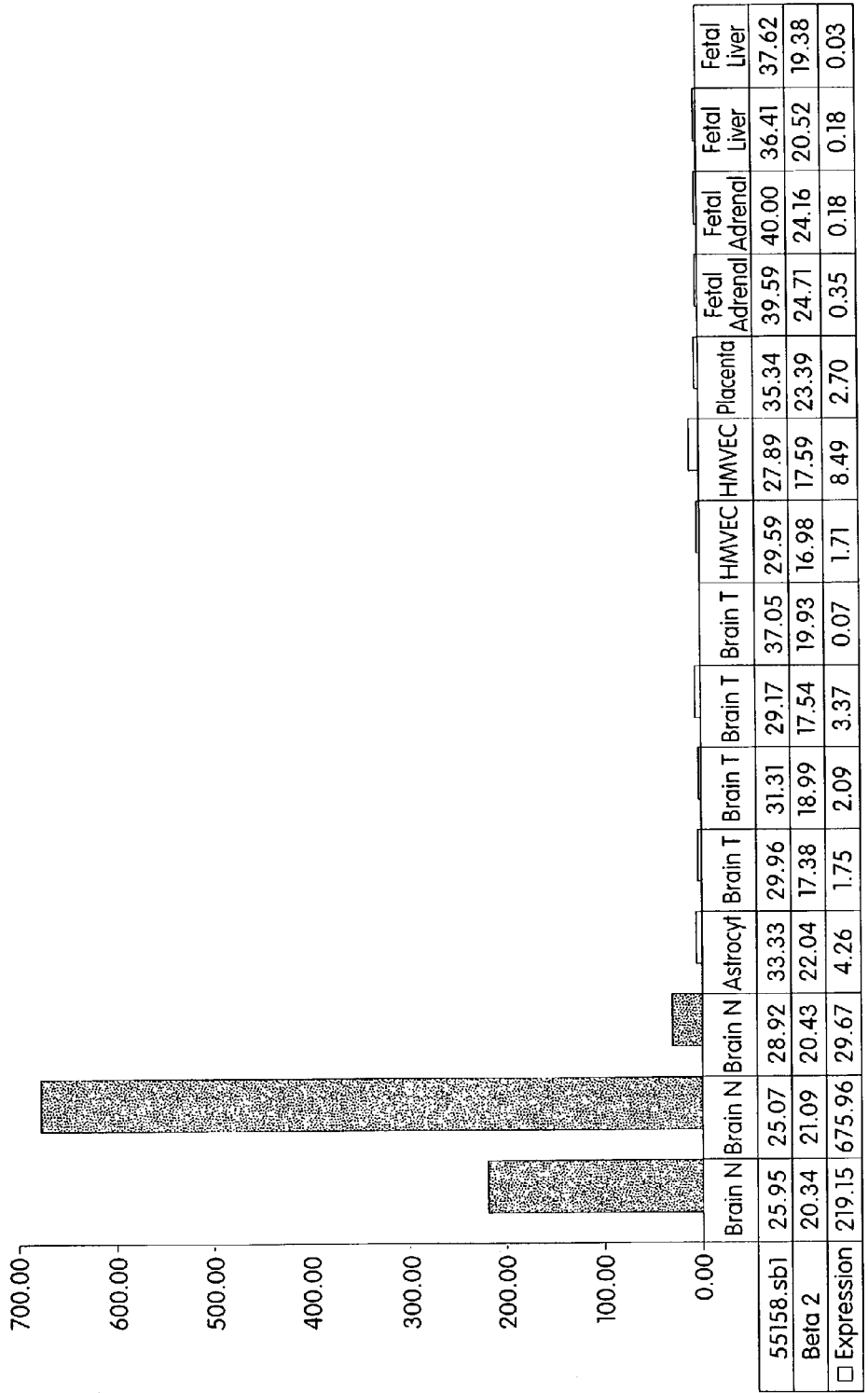

FIG. 51 is a graphic depiction of the relative levels of human CAH mRNA expression in a panel containing human normal (N) and tumor (T) brain tissue, as determined using Taqman™ analysis.

Figure 52:

FIG. 52 is a graphic depiction of the relative levels of human CAH mRNA expression in a human normal (N) and tumor (T) colon tissue panel, including colon tumor metastases to the liver, (liver met), as determined using Taqman™ analysis.

FIGS. 53A–E depict the cDNA sequence and predicted amino acid sequence of human LSO (clone Fbh47765). The nucleotide sequence corresponds to nucleic acids 1 to 2976 of SEQ ID NO:29. The amino acid sequence corresponds to amino acids 1 to 756 of SEQ ID NO:30. The coding region without the 3' untranslated region of the human LSO gene is shown in SEQ ID NO:31.

Figure 54:
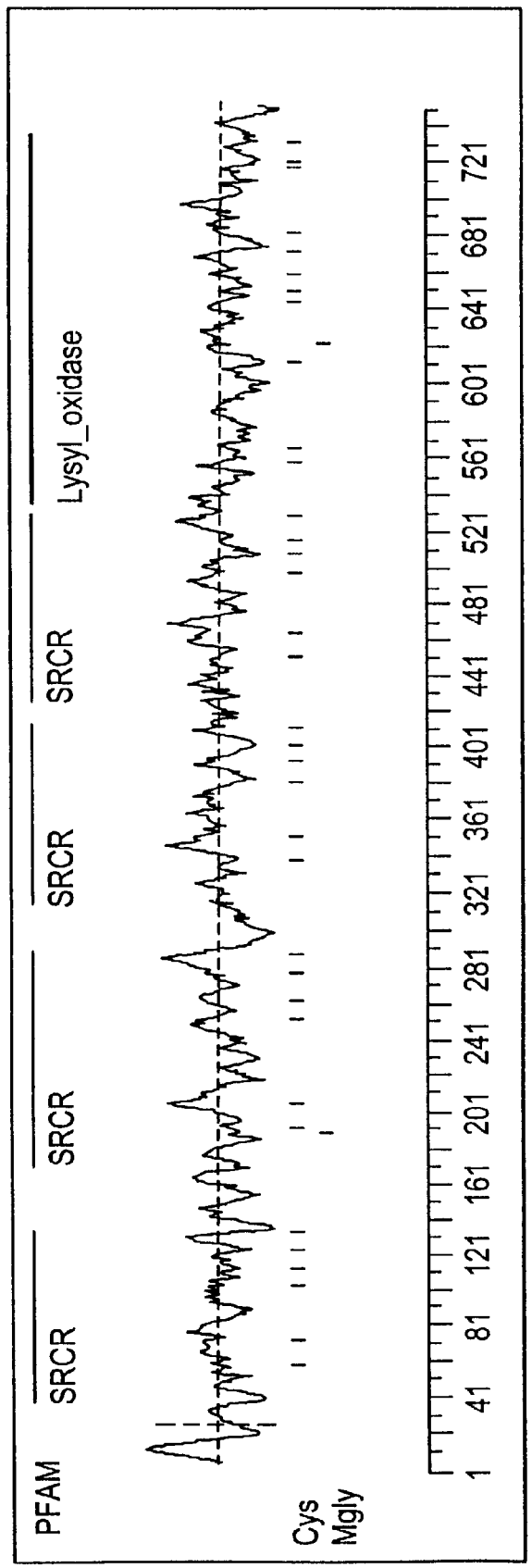

FIG. 54 depicts a structural, hydrophobicity, and antigenicity analysis of the human LSO protein (SEQ ID NO:30).

FIGS. 55A–E depict the cDNA sequence and predicted amino acid sequence of human NPM-1. The nucleotide sequence corresponds to nucleic acids 1 to 3296 of SEQ ID NO:33. The amino acid sequence corresponds to amino acids 1 to 604 of SEQ ID NO:34. The coding region without the 5' and 3' untranslated regions of the human NPM-1 gene is shown in SEQ ID NO:35.

Figure 56:
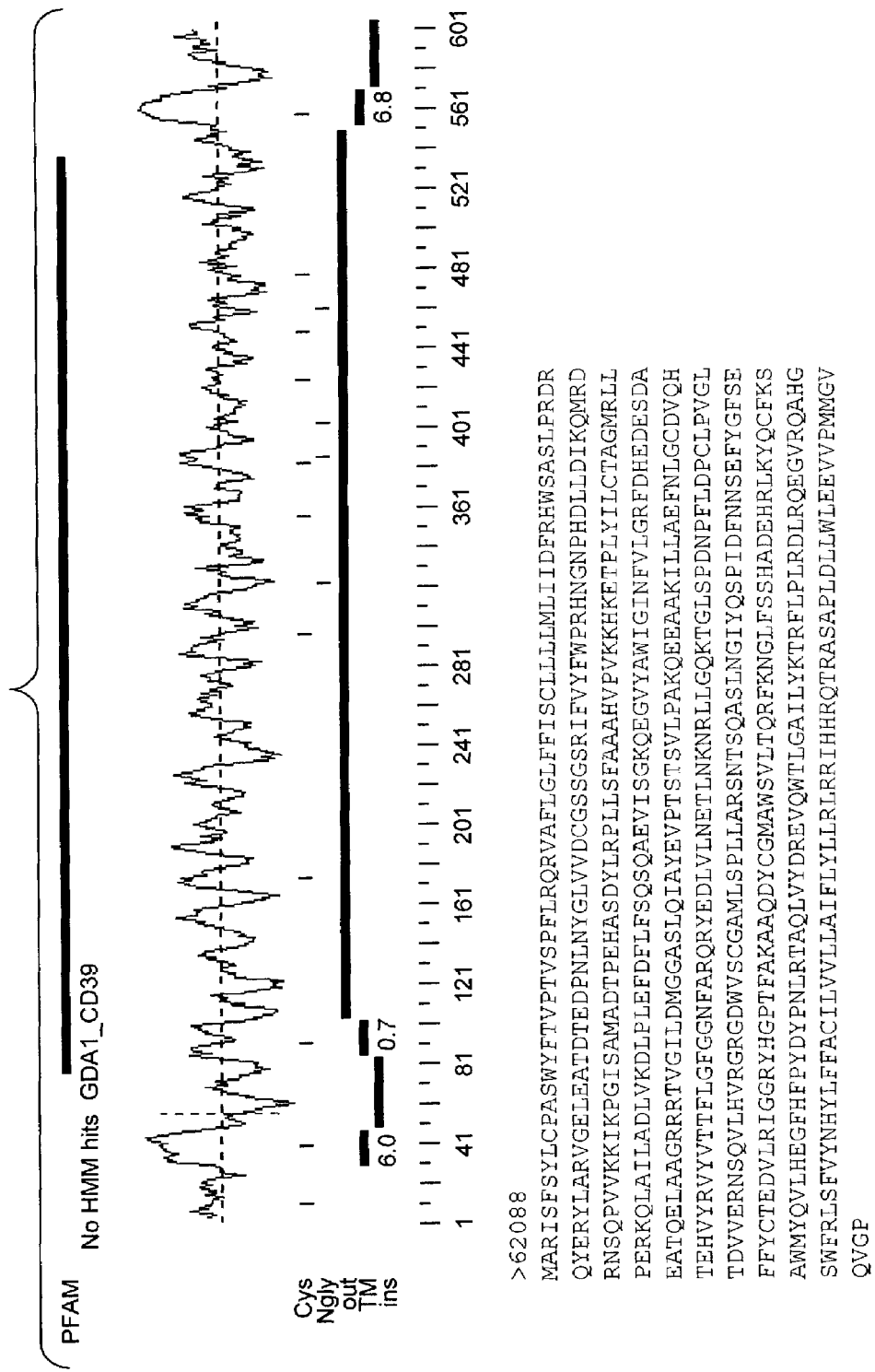

FIG. 56 depicts a structural, hydrophobicity, and antigenicity analysis of the human NPM-1 polypeptide.

FIGS. 57A–D depict the results of a search which was performed against the HMM database in PFAM and which resulted in the identification of one "nucleoside phosphatase family domain" in the human NPM-1 polypeptide (SEQ ID NO:34).

FIG. 58 depicts the results of a MEMSAT analysis and which assisted in the identification of two "transmembrane domains" in the human NPM-1 polypeptide (SEQ ID NO:34).

FIG. 59 depicts the cDNA sequence and predicted amino acid sequence of human G2RF. The nucleotide sequence corresponds to nucleic acids 1 to 1154 of SEQ ID NO:36. The amino acid sequence corresponds to amino acids 1 to 282 of SEQ ID NO:37. The coding region without the 5' and 3' untranslated regions of the human G2RF gene is shown in SEQ ID NO:38.

FIG. 60 depicts a structural, hydrophobicity, and antigenicity analysis of the human G2RF polypeptide. The results of a MEMSAT analysis, which identified one "transmembrane domain" in the human G2RF polypeptide (SEQ ID NO:37), are also shown.

FIG. 61 depicts the results of a search which was performed against the HMM database in PFAM and which resulted in the identification of one "metallo-beta lactamase superfamily domain" in the human G2RF polypeptide (SEQ ID NO:37).

Figure 62:
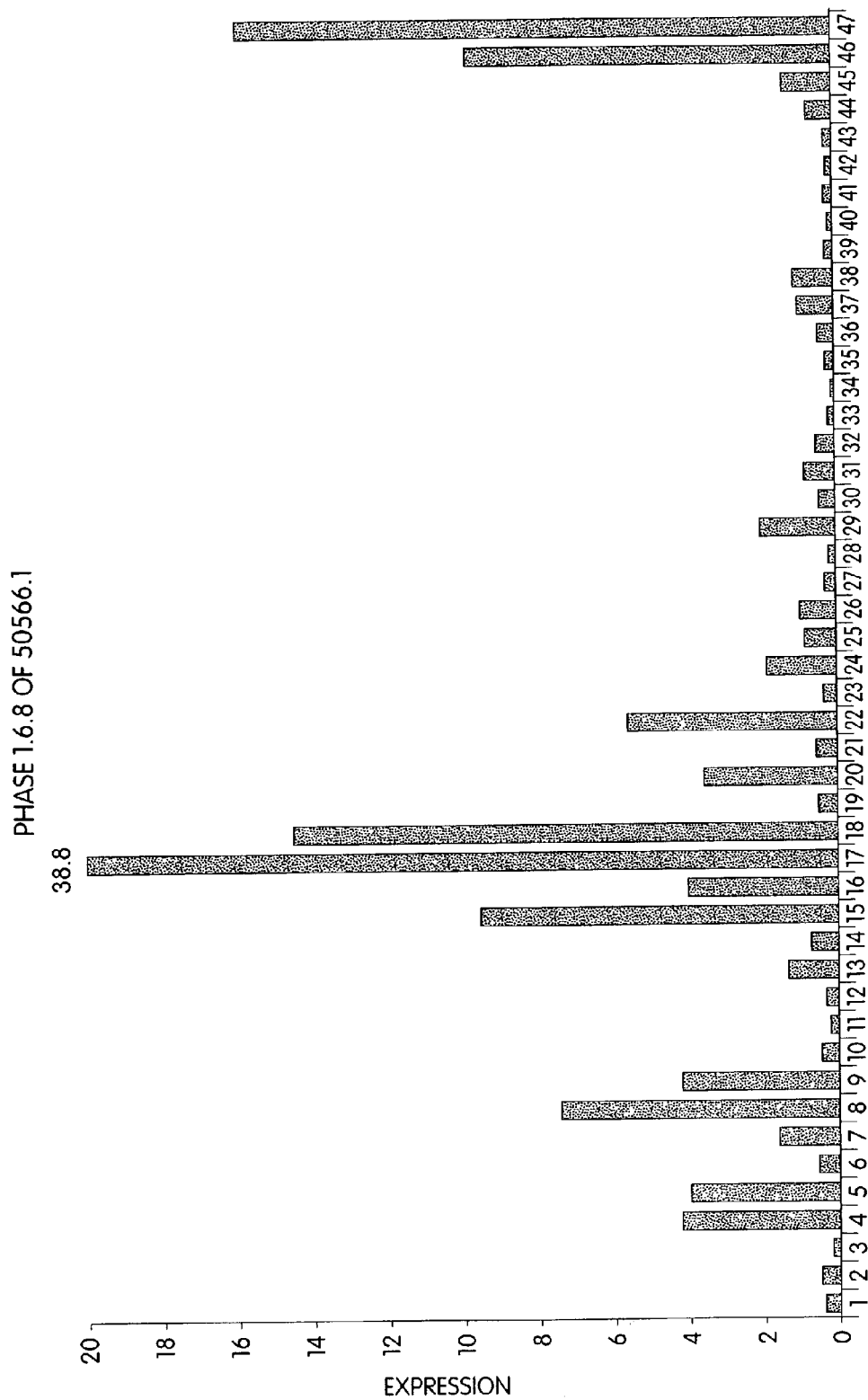

FIG. 62 depicts the results of tissue expression analysis of G2RF mRNA using Taqman analysis.

FIG. 63 depicts the cDNA sequence and predicted amino acid sequence of HUCH-1 (clone Fbh48118fl). The nucleotide sequence corresponds to nucleic acids 1 to 1791 of SEQ ID NO:39. The amino acid sequence corresponds to amino acids 1 to 366 of SEQ ID NO:40. The coding region without the 5' and 3' untranslated regions of the HUCH-1 gene is shown in SEQ ID NO:41.

FIG. 64 depicts a structural, hydrophobicity, and antigenicity analysis of the HUCH-1 protein.

FIG. 65 depicts the results of a search which was performed against the MEMSAT database and which resulted in the identification of one "transmembrane domain" in the HUCH-1 protein (SEQ ID NO:40).

FIG. 66 depicts the results of a search which was performed against the HMM database and which resulted in the identification of two "ubiquitin carboxyl-terminal hydrolase family domains" in the HUCH-1 protein.

DETAILED DESCRIPTION OF THE INVENTION

The present invention is based, at least in part, on the discovery of novel molecules, referred to herein interchangeably as "Alcohol Dehydrogenase-Related Protein-1," "Adh-Related Protein-1," or "Adhr-1" nucleic acid and protein molecules, which are novel members of a family of enzymes possessing alcohol dehydrogenase (Adh) activity. These novel molecules are capable of oxidizing alcohol groups, or reducing aldehyde groups, by catalyzing the transfer of a hydride moiety and, thus, play a role in or function in a variety of cellular processes, e.g., energy-related metabolism, proliferation, differentiation, visual systems, hormonal responses, and inter- or intra-cellular communication.

As used herein, the terms "alcohol dehydrogenase" and "Adh" include a molecule which is involved in the oxidation or reduction of a biochemical molecule (e.g., metabolic precursor which contains an alcohol group or an aldehyde group) by catalyzing the transfer of a hydride ion to or from the biochemical molecule. Alcohol dehydrogenase molecules are involved in the metabolism and catabolism of biochemical molecules necessary for energy production or storage, for intra- or intercellular signaling, for metabolism or catabolism of metabolically important biomolecules, and for detoxification of potentially harmful compounds (e.g., ethanol). Thus, the Adhr-1 molecules of the present invention provide novel diagnostic targets and therapeutic agents to control Adh-associated disorders and/or lipid metabolism-associated disorders.

As used herein, the term "Adh-associated disorder" includes a disorder, disease or condition which is caused or characterized by a misregulation (e.g., downregulation or upregulation) of Adh activity. Adh-associated disorders can detrimentally affect cellular functions such as cellular proliferation, growth, differentiation, inter- and intra-cellular communication, energy production and energy storage; tissue function, such as cardiac function, CNS function, or musculoskeletal function; systemic responses in an organism, such as nervous system responses or digestive responses; and protection of cells from toxic compounds (e.g., alcohols, carcinogens, toxins, or mutagens). Examples of Adh-associated disorders include metabolic disorders (e.g., hyper- or hypolipoproteinemias, diabetes mellitus, and familial hypercholesterolemia); disorders related to toxins and/or alcohol consumption (e.g., alcoholism, cirrhosis, or depression); disorders related to the CNS (e.g., cognitive and neurodegenerative disorders stemming from aberrant metabolism of neurotransmitters or degradation resulting from alcohol damage); disorders related to retinol metabolism (e.g., embryological disorders, visual disorders or night blindness).

The present invention also provides methods and compositions for the diagnosis and treatment of tumorigenic disease, e.g., lung tumors, ovarian tumors, colon tumors, prostate tumors, breast tumors, and cervical squamous cell carcinoma. The present invention is based, at least in part, on the discovery that "Adhr-1 is differentially expressed in tumor tissue samples relative to its expression in normal tissue samples.

"Differential expression", as used herein, includes both quantitative as well as qualitative differences in the temporal and/or tissue expression pattern of a gene. Thus, a differentially expressed gene may have its expression activated or inactivated in normal versus tumorigenic disease conditions (for example, in an experimental tumorigenic disease system). The degree to which expression differs in normal versus tumorigenic disease or control versus experimental states need only be large enough to be visualized via standard characterization techniques, e.g., quantitative PCR, Northern analysis, or subtractive hybridization. The expression pattern of a differentially expressed gene may be used as part of a prognostic or diagnostic tumorigenic disease evaluation, or may be used in methods for identifying compounds useful for the treatment of tumorigenic disease. In addition, a differentially expressed gene involved in a tumorigenic disease may represent a target gene such that modulation of the level of target gene expression or of target gene product activity may act to ameliorate a tumorigenic disease condition. Compounds that modulate target gene expression or activity of the target gene product can be used in the treatment of tumorigenic disease. Although the Adhr-1 genes described herein may be differentially expressed with respect to tumorigenic disease, and/or their products may interact with gene products important to tumorigenic disease, the genes may also be involved in mechanisms important to additional cell processes, e.g., muscle cell processes.

The Adhr-1 molecules of the present invention further provide novel diagnostic targets and therapeutic agents for treating musculo-skeletal disorders as this gene is highly expressed in skeletal muscle tissue. Alcohol Dehydrogenase has been shown to serve as a substrate for the chaperon like molecule alpha B-crystallin, a member of the small heat shock protein family. AlphaB-crystallin is a major lens protein and is also expressed in skeletal and cardiac muscle (Bova M. P., et al. (1999) *Proc Natl Acad Sci USA* 96: 6137). One of the many functions of molecular chaperons is to prevent mis-associations and to promote proper folding of proteins. Thus, the Adhr-1 molecules of the present invention may provide a means of treating diseases such as cataract; desmin related myopathy and other potential diseases that arise from misfolding of the Adhr-1 protein.

Moreover, it has been demonstrated that when mice are subjected to ultraviolet radiation (UVR) exposure and monitored for ocular aldehyde dehydrogenase (ALDH) and alcohol dehydrogenase (ADH) activity, dramatic reductions in ALDH and ADH activities were observed by 4–6 days post-exposure, resulting in enzyme levels of 15–16% of control animals. Major decreases in corneal enzyme levels were predominantly responsible for these changes (Downes J. E., et al., (1993) *Cornea* 12: 241). Expression of Adhr-1 in the retina suggests that the Adhr-1 molecules of the present invention may be used in assisting the cornea to protect the eye against UVR-induced tissue damage.

The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics.

Figure 2:
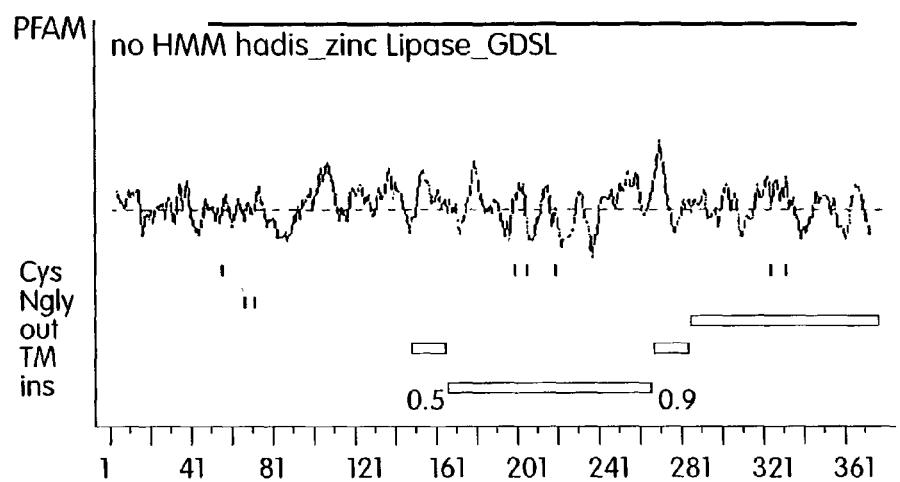
FIG. 2 depicts a structural, hydrophobicity, and antigenicity analysis of the human Adhr-1 protein.

For example, the family of Adhr-1 proteins comprise at least one, and preferably two or more "transmembrane domains." As used herein, the term "transmembrane domain" includes an amino acid sequence of about 15 amino acid residues in length which spans the plasma membrane. More preferably, a transmembrane domain includes at least 10, 15, 20, 25, 30, 35, 40, 45 or more amino acid residues and spans the plasma membrane. Transmembrane domains are rich in hydrophobic residues, and typically have a helical structure. In one embodiment, at least 50%, 60%, 70%, 80%, 90%, 95% or more of the amino acid residues of a transmembrane domain are hydrophobic, e.g., leucines, isoleucines, tyrosines, or tryptophans. Transmembrane domains are described in, for example, Zagotta W. N. et al., (1996) *Annual Rev. Neurosci.* 19:235–63, the contents of which are incorporated herein by reference. Amino acid residues 148–164 and 266–282 of the human Adhr-1 polypeptide (SEQ ID NO:2) comprise transmembrane domains (FIG. 2).

In another embodiment, an Adhr-1 molecule of the present invention is identified based on the presence of an "ADH-Zn domain" (also referred to above as "Zinc-containing alcohol dehydrogenase signature domain") in the protein or corresponding nucleic acid molecule. As used herein, the term "ADH-Zn domain" includes a protein domain having an amino acid sequence of about 322 amino acid residues and having a bit score for the alignment of the sequence to the ADH-Zn domain (HMM) of about 1, 5, 10, 20, 30, 40, 50 or greater. Preferably, an ADH-Zn domain includes at least about 275–375, more preferably about 300–350 amino acid residues, or most preferably about 315–335 amino acids and has a bit score for the alignment of the sequence to the ADH-Zn domain (HMM) of at least about 1, 5, 10, 20, 30, 40, 50 or greater. The ADH-Zn domain has been assigned the PFAM label "ADH_ZINC" under Accession number PS00059 (found at Pfam website, genome.wustl.edu/Pfam). ADH-Zn domains are involved in Adh activity and are described in, for example, Joernvall et al. (1987) *Eur. J. Biochem.* 167:195–201; Joernvall et al. (1993) *FEBS Letters* 322:240–244, the contents of which are incorporated herein by reference.

In another embodiment, an Adhr-1 molecule of the present invention is identified based on the presence of a "Lipase-SER domain" (also referred to above as "serine-containing active domain of the 'G-D-S-L' family of lipases") in the protein or corresponding nucleic acid molecule. As used herein, the term "Lipase-SER domain" includes a protein domain having an amino acid sequence of about 86 amino acid residues and having a bit score for the alignment of the sequence to the Lipase-SER domain (HMM) of about 1, 5, 10, 20, 30, 40, 50 or greater. Preferably, an Lipase-SER domain includes at least about 40–125, more preferably about 60–105 amino acid residues, or most preferably about 75–95 amino acids and has a bit score for the alignment of the sequence to the ADH-Zn domain (HMM) of at least about 1, 5, 10, 20, 30, 40, 50 or greater. The Lipase-SER domain has been assigned the PFAM label "LIPASE_GDSL_SER" under Accession number PS01098 (http://genome.wustl.edu/Pfam.html). Lipase-SER domains are involved in lipase and/or phospholipase activity and are described in, for example, Upton and Buckley (1995) *TIBS* 20:178–179, the contents of which are incorporated herein by reference.

To identify the presence of an ADH-Zn and/or a Lipase-SER domain in an Adhr-1 protein and make the determination that a protein of interest has a particular profile, the amino acid sequence of the protein is searched against a database of HMMs (e.g., the Pfam database, release 2.1) using the default parameters see the Pfam website maintained in several locations, e.g. by the Sanger Institute (pfam.sanger.ac.uk/Software/Pfam/HMM_search). A description of the Pfam database can be found in Sonhammer et al. (1997) *Proteins* 28(3)405–420 and a detailed description of HMMs can be found, for example, in Gribskov et al. (1990) *Meth. Enzymol.* 183:146–159; Gribskov et al. (1987) *Proc. Natl. Acad. Sci. USA* 84:4355–4358; Krogh et al. (1994) *J. Mol. Biol.* 235:1501–1531; and Stultz et al. (1993) *Protein Sci.* 2:305–314, the contents of which are incorporated herein by reference. A search was performed against the HMM database resulting in the identification of an ADH-Zn domain and a Lipase-SER domain in the amino acid sequence of SEQ ID NO:2 (at about residues 47–368 and 103–189, respectively). The results of this search are set forth in FIGS. 3A–B.

Isolated Adhr-1 proteins of the present invention, have an amino acid sequence sufficiently identical to the amino acid sequence of SEQ ID NO:2, or are encoded by a nucleotide sequence sufficiently identical to SEQ ID NO:1 or 3. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%–80%, and even more preferably 90–95% homology across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70–80%, or 90–95% homology and share a common functional activity are defined herein as sufficiently identical.

As used interchangeably herein, a "Adhr-1 activity", "biological activity of Adhr-1," or "functional activity of Adhr-1," includes an activity exerted by an Adhr-1 protein, polypeptide or nucleic acid molecule on an Adhr-1-responsive cell or tissue, or on an Adhr-1 protein substrate, as determined in vivo, or in vitro, according to standard techniques. In one embodiment, an Adhr-1 activity is a direct activity, such as an association with an Adhr-1-target molecule. As used herein, a "target molecule" or "binding partner" is a molecule with which an Adhr-1 protein binds or interacts in nature, such that Adhr-1-mediated function is achieved. An Adhr-1 target molecule can be a non-Adhr-1 molecule or an Adhr-1 accessory polypeptide or molecule of the present invention (e.g., $NAD^+$, a $Zn^+$ molecule, or other cofactor). As used herein, an "accessory" peptide or molecule refers to a peptide or molecule whose presence is may be needed for the proper activity of a protein (e.g., a cofactor or a metal ion that is needed by an enzyme). In an exemplary embodiment, an Adhr-1 target molecule is an Adhr-1 ligand (e.g., an alcohol, an aldehyde, a retinol or a lipid). Alternatively, an Adhr-1 activity is an indirect activity, such as a cellular signaling activity mediated by interaction of the Adhr-1 protein with an Adhr-1 ligand. The biological activities of Adhr-1 are described herein. For example, the Adhr-1 proteins of the present invention can have one or more of the following activities: 1) modulate metabolism and catabolism of biochemical molecules necessary for energy production or storage, 2) modulate or facilitate intra- or intercellular signaling, 3) modulate metabolism or catabolism of metabolically important biomolecules, and 4) modulate detoxification of potentially harmful compounds.

Accordingly, another embodiment of the invention features isolated Adhr-1 proteins and polypeptides having an Adhr-1 activity. Other preferred proteins are Adhr-1 proteins having one or more of the following domains: a transmembrane domain, an ADH-Zn domain, a Lipase-SER domain, and, preferably, an Adhr-1 activity. Additional preferred Adhr-1 proteins have at least one ADH-Zn, and/or at least one Lipase-SER, and/or at least one transmembrane domain and are, preferably, encoded by a nucleic acid molecule having a nucleotide sequence which hybridizes under stringent hybridization conditions to a nucleic acid molecule comprising the nucleotide sequence of SEQ ID NO:1 or 3.

The nucleotide sequence of the isolated human Adhr-1 cDNA and the predicted amino acid sequence of the human Adhr-1 polypeptide are shown in FIGS. 1A–B and in SEQ ID NO:1 and SEQ ID NO:2, respectively.

These deposits will be maintained under the terms of the Budapest Treaty on the International Recognition of the Deposit of Microorganisms for the Purposes of Patent Procedure. These deposits was made merely as a convenience for those of skill in the art and are not an admission that a deposit is required under 35 U.S.C. §112.

The human Adhr-1 gene, which is approximately 1808 nucleotides in length, encodes a protein having a molecular weight of approximately 41.5 kD and which is approximately 377 amino acid residues in length.

Various aspects of the invention are described in further detail in the following subsections:

I. Isolated Nucleic Acid Molecules

One aspect of the invention pertains to isolated nucleic acid molecules that encode Adhr-1 proteins or biologically active portions thereof, as well as nucleic acid fragments sufficient for use as hybridization probes to identify Adhr-1-encoding nucleic acid molecules (e.g., Adhr-1 mRNA) and fragments for use as PCR primers for the amplification or mutation of Adhr-1 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated Adhr-1 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1 or 3, or a portion thereof, can be isolated using standard molecular biology techniques and the sequence information provided herein. Using all or portion of the nucleic acid sequence of SEQ ID NO:1 or 3, as a hybridization probe, Adhr-1 nucleic acid molecules can be isolated using standard hybridization and cloning techniques (e.g., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO:1 or 3 can be isolated by the polymerase chain reaction (PCR) using synthetic oligonucleotide primers designed based upon the sequence of SEQ ID NO:1 or 3.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to Adhr-1 nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1. The sequence of SEQ ID NO:1 corresponds to the human Adhr-1 cDNA. This cDNA comprises sequences encoding the human Adhr-1 protein (i.e., "the coding region", from nucleotides 285–1418), as well as 5' untranslated sequences (nucleotides 1–284) and 3' untranslated sequences (nucleotides 1419–1808). Alternatively, the nucleic acid molecule can comprise only the coding region of SEQ ID NO:1 (e.g., nucleotides 285–1418, corresponding to SEQ ID NO:3).

In another preferred embodiment, an isolated nucleic acid molecule of the invention comprises a nucleic acid molecule which is a complement of the nucleotide sequence shown in SEQ ID NO:1 or 3, or a portion of any of these nucleotide sequences. A nucleic acid molecule which is complementary to the nucleotide sequence shown in SEQ ID NO:1 or 3, is one which is sufficiently complementary to the nucleotide sequence shown in SEQ ID NO:1 or 3, such that it can hybridize to the nucleotide sequence shown in SEQ ID NO:1 or 3, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 86%, 87%, 88%, 89%, 90%, 91%, 92%, 93%, 97%, 98%, 99%, 99.5% or more identical to the entire length of the nucleotide sequence shown in SEQ ID NO:1 or 3, or a portion of any of these nucleotide sequences.

Moreover, the nucleic acid molecule of the invention can comprise only a portion of the nucleic acid sequence of SEQ ID NO:1 or 3, for example, a fragment which can be used as a probe or primer or a fragment encoding a portion of an Adhr-1 protein, e.g., a biologically active portion of an Adhr-1 protein. The nucleotide sequence determined from the cloning of the Adhr-1 gene allows for the generation of probes and primers designed for use in identifying and/or cloning other Adhr-1 family members, as well as Adhr-1 homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1 or 3, of an anti-sense sequence of SEQ ID NO:1 or 3, or of a naturally occurring allelic variant or mutant of SEQ ID NO:1 or 3. In one embodiment, a nucleic acid molecule of the present invention comprises a nucleotide sequence which is greater than 50, 100, 200, 300, 400, 500, 600, 700, 800, 900, 1000, 1100, 1200, 1300, 1400, 1500, 1600, 1700, 1800 or more nucleotides in length and hybridizes under stringent hybridization conditions to a nucleic acid molecule of SEQ ID NO:1 or 3.

Probes based on the Adhr-1 nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress an Adhr-1 protein, such as by measuring a level of an Adhr-1-encoding nucleic acid in a sample of cells from a subject, e.g., detecting Adhr-1 mRNA levels or determining whether a genomic Adhr-1 gene has been mutated or deleted.

A nucleic acid fragment encoding a "biologically active portion of an Adhr-1 protein" can be prepared by isolating a portion of the nucleotide sequence of SEQ ID NO:1 or 3, which encodes a polypeptide having an Adhr-1 biological activity (the biological activities of the Adhr-1 proteins are described herein), expressing the encoded portion of the Adhr-1 protein (e.g., by recombinant expression in vitro) and assessing the activity of the encoded portion of the Adhr-1 protein.

The invention further encompasses nucleic acid molecules that differ from the nucleotide sequence shown in SEQ ID NO:1 or 3, due to degeneracy of the genetic code and, thus, encode the same Adhr-1 proteins as those encoded by the nucleotide sequence shown in SEQ ID NO:1 or 3. In another embodiment, an isolated nucleic acid molecule of the invention has a nucleotide sequence encoding a protein having an amino acid sequence shown in SEQ ID NO:2.

In addition to the Adhr-1 nucleotide sequences shown in SEQ ID NO:1 or 3, it will be appreciated by those skilled in the art that DNA sequence polymorphisms that lead to changes in the amino acid sequences of the Adhr-1 proteins may exist within a population (e.g., the human population). Such genetic polymorphism in the Adhr-1 genes may exist among individuals within a population due to natural allelic variation. As used herein, the terms "gene" and "recombinant gene" refer to nucleic acid molecules which include an open reading frame encoding an Adhr-1 protein, preferably a mammalian Adhr-1 protein, and can further include non-coding regulatory sequences, and introns.

Allelic variants of human Adhr-1 include both functional and non-functional Adhr-1 proteins. Functional allelic variants are naturally occurring amino acid sequence variants of the human Adhr-1 protein that maintain the ability to bind an Adhr-1 ligand or substrate (e.g., an alcohol, an aldehyde, a retinol or a lipid) and/or modulate Adh activity and/or Adh-associated signaling mechanisms, and/or Adh-associated disorders. Functional allelic variants will typically contain only conservative substitution of one or more amino acids of SEQ ID NO:2, or substitution, deletion or insertion of non-critical residues in non-critical regions of the protein.

Non-functional allelic variants are naturally-occurring amino acid sequence variants of the human Adhr-1 proteins that do not have the ability to either bind an Adhr-1 ligand or substrate (e.g., an alcohol, an aldehyde, a retinol, or a lipid) and/or modulate Adh activity and/or Adh-associated signaling mechanisms, and/or Adh-associated disorders. Non-functional allelic variants will typically contain a non-conservative substitution, a deletion, or insertion or premature truncation of the amino acid sequence of SEQ ID NO:2, or a substitution, insertion or deletion in critical residues or critical regions.

The present invention further provides non-human orthologues of the human Adhr-1 protein. Orthologues of the human Adhr-1 protein are proteins that are isolated from non-human organisms and possess the same ability to bind an Adhr-1 ligand or substrate (e.g., an alcohol, an aldehyde, a retinol or a lipid) and/or modulate Adh activity and/or Adh-associated signaling mechanisms, and/or Adh-associated disorders. Orthologues of the human Adhr-1 protein can readily be identified as comprising an amino acid sequence that is substantially identical to SEQ ID NO:2.

Moreover, nucleic acid molecules encoding other Adhr-1 family members and, thus, which have a nucleotide sequence which differs from the Adhr-1 sequences of SEQ ID NO:1 or 3 are intended to be within the scope of the invention. For example, another Adhr-1 cDNA can be identified based on the nucleotide sequence of human Adhr-1. Moreover, nucleic acid molecules encoding Adhr-1 proteins from different species, and which, thus, have a nucleotide sequence which differs from the Adhr-1 sequences of SEQ ID NO:1 or 3 are intended to be within the scope of the invention. For example, a mouse Adhr-1 cDNA can be identified based on the nucleotide sequence of a human Adhr-1.

Nucleic acid molecules corresponding to natural allelic variants and homologues of the Adhr-1 cDNAs of the invention can be isolated based on their homology to the Adhr-1 nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the Adhr-1 cDNAs of the invention can further be isolated by mapping to the same chromosome or locus as the Adhr-1 gene.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1 or 3. In other embodiment, the nucleic acid is at least 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4, and 6. Additional stringent conditions can be found in *Molecular Cloning. A Laboratory Manual*, Sambrook et al., Cold Spring Harbor Press, Cold Spring Harbor, N.Y. (1989), chapters 7, 9, and 11. A preferred, non-limiting example of stringent hybridization conditions includes hybridization in 4×sodium chloride/sodium citrate (SSC), at about 65–70° C. (or alternatively hybridization in 4×SSC plus 50% formamide at about 42–50° C.) followed by one or more washes in 1×SSC, at about 65–70° C. A preferred, non-limiting example of highly stringent hybridization conditions includes hybridization in 1×SSC, at about 65–70° C. (or alternatively hybridization in 1×SSC plus 50% formamide at about 42–50° C.) followed by one or more washes in 0.3×SSC, at about 65–70° C. A preferred, non-limiting example of reduced stringency hybridization conditions includes hybridization in 4×SSC, at about 50–60° C. (or alternatively hybridization in 6×SSC plus 50% formamide at about 40–45° C.) followed by one or more washes in 2×SSC, at about 50–60° C. Ranges intermediate to the above-recited values, e.g., at 65–70° C. or at 42–50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m(° C.)=2(\# \text{ of A+T bases})+4(\# \text{ of G+C bases})$. For hybrids between 18 and 49 base pairs in length, $T_m(° C.)=81.5+16.6(\log_{10}[Na^+])+0.41(\% \text{ G+C})-(600/N)$, where N is the number of bases in the hybrid, and $[Na^+]$ is the concentration of sodium ions in the hybridization buffer ($[Na^+]$ for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25–0.5M $NaH_2PO_4$, 7% SDS at about 65° C., followed by one or more washes at 0.02M $NaH_2PO_4$, 1% SDS at 65° C. (see e.g., Church and Gilbert (1984) *Proc. Natl. Acad. Sci. USA* 81:1991–1995), or alternatively 0.2×SSC, 1% SDS. Preferably, an isolated nucleic acid molecule of the invention that hybridizes under stringent conditions to the sequence of SEQ ID NO:1 or 3 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the Adhr-1 sequences that may exist in the population, the skilled artisan will further appreciate that changes can be introduced by mutation into the nucleotide sequences of SEQ ID NO:1 or 3, thereby leading to changes in the amino acid sequence of the encoded Adhr-1 proteins, without altering the functional ability of the Adhr-1 proteins. For example, nucleotide substitutions leading to amino acid substitutions at "non-essential" amino acid residues can be made in the sequence of SEQ ID NO:1 or 3. A "non-essential" amino acid residue is a residue that can be altered from the wild-type sequence of Adhr-1 (e.g., the sequence of SEQ ID NO:2) without altering the biological activity, whereas an "essential" amino acid residue is required for biological activity. For example, amino acid residues that are conserved among the Adhr-1 proteins of the present invention, e.g., those present in the ADH-Zn domain(s) or the Lipase-SER domain(s) or the transmembrane domain(s), are predicted to be particularly unamenable to alteration. Furthermore, additional amino acid residues that are conserved between the Adhr-1 proteins of the present invention and other members of the Adh family are not likely to be amenable to alteration.

Accordingly, another aspect of the invention pertains to nucleic acid molecules encoding Adhr-1 proteins that contain changes in amino acid residues that are not essential for activity. Such Adhr-1 proteins differ in amino acid sequence from SEQ ID NO:2, yet retain biological activity. In one embodiment, the isolated nucleic acid molecule comprises a nucleotide sequence encoding a protein, wherein the protein comprises an amino acid sequence at least 50%, 55%, 60%, 65%, 70%, 75%, 80%, 85%, 86%, 87%, 88%, 89%, 90%, 91%, 92%, 93%, 94%, 95%, 96%, 97%, 98%, 99%, 99.5% or more identical to SEQ ID NO:2.

An isolated nucleic acid molecule encoding an Adhr-1 protein identical to the protein of SEQ ID NO:2, can be created by introducing one or more nucleotide substitutions, additions or deletions into the nucleotide sequence of SEQ ID NO:1 or 3, such that one or more amino acid substitutions, additions or deletions are introduced into the encoded protein. Mutations can be introduced into SEQ ID NO:1 or 3 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in an Adhr-1 protein is preferably replaced with another amino acid residue from the same side chain family. Alternatively, in another embodiment, mutations can be introduced randomly along all or part of an Adhr-1 coding sequence, such as by saturation mutagenesis, and the resultant mutants can be screened for Adhr-1 biological activity to identify mutants that retain activity. Following mutagenesis of SEQ ID NO:1 or 3, the encoded protein can be expressed recombinantly and the activity of the protein can be determined.

In another preferred embodiment, a mutant Adhr-1 protein can be assayed for the ability to metabolize or catabolize biochemical molecules necessary for energy production or storage, permit intra- or intercellular signaling, metabolize or catabolize metabolically important biomolecules, and to detoxify potentially harmful compounds.

In addition to the nucleic acid molecules encoding Adhr-1 proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire Adhr-1 coding strand, or to only a portion thereof. In one embodiment, an antisense nucleic acid molecule is antisense to a "coding region" of the coding strand of a nucleotide sequence encoding Adhr-1. The term "coding region" refers to the region of the nucleotide sequence comprising codons which are translated into amino acid residues (e.g., the coding region of human Adhr-1 corresponds to SEQ ID NO:3). In another embodiment, the antisense nucleic acid molecule is antisense to a "noncoding region" of the coding strand of a nucleotide sequence encoding Adhr-1. The term "noncoding region" refers to 5' and 3' sequences which flank the coding region that are not translated into amino acids (i.e., also referred to as 5' and 3' untranslated regions).

Given the coding strand sequences encoding Adhr-1 disclosed herein (e.g., SEQ ID NO:3), antisense nucleic acids of the invention can be designed according to the rules of Watson and Crick base pairing. The antisense nucleic acid molecule can be complementary to the entire coding region of Adhr-1 mRNA, but more preferably is an oligonucleotide which is antisense to only a portion of the coding or noncoding region of Adhr-1 mRNA. For example, the antisense oligonucleotide can be complementary to the region surrounding the translation start site of Adhr-1 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an Adhr-1 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff and Gerlach (1988) *Nature* 334:585–591)) can be used to catalytically cleave Adhr-1 mRNA transcripts to thereby inhibit translation of Adhr-1 mRNA. A ribozyme having specificity for an Adhr-1-encoding nucleic acid can be designed based upon the nucleotide sequence of an Adhr-1 cDNA disclosed herein (i.e., SEQ ID NO:1 or 3. For example, a derivative of a Tetrahymena L-19 IVS RNA can be constructed in which the nucleotide sequence of the active site is complementary to the nucleotide sequence to be cleaved in an Adhr-1-encoding mRNA. See, e.g., Cech et al. U.S. Pat. No. 4,987,071; and Cech et al. U.S. Pat. No. 5,116,742. Alternatively, Adhr-1 mRNA can be used to select a catalytic RNA having a specific ribonuclease activity from a pool of RNA molecules. See, e.g., Bartel, D. and Szostak, J. W. (1993) *Science* 261:1411–1418.

Alternatively, Adhr-1 gene expression can be inhibited by targeting nucleotide sequences complementary to the regulatory and/or 5' untranslated region of the Adhr-1 nucleotides (e.g., the Adhr-1 promoter and/or enhancers; e.g., nucleotides 1–126 of SEQ ID NO:1) to form triple helical structures that prevent transcription of the Adhr-1 gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12):807–15.

In yet another embodiment, the Adhr-1 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. *Proc. Natl. Acad. Sci.* 93: 14670–675.

PNAs of Adhr-1 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of Adhr-1 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. (1996) supra; Perry-O'Keefe supra).

In another embodiment, PNAs of Adhr-1 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of Adhr-1 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3'PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

II. Isolated Adhr-1 Proteins and Anti-Adhr-1 Antibodies

One aspect of the invention pertains to isolated Adhr-1 proteins, and biologically active portions thereof, as well as polypeptide fragments suitable for use as immunogens to raise anti-Adhr-1 antibodies. In one embodiment, native Adhr-1 proteins can be isolated from cells or tissue sources by an appropriate purification scheme using standard protein purification techniques. In another embodiment, Adhr-1 proteins are produced by recombinant DNA techniques. Alternative to recombinant expression, an Adhr-1 protein or polypeptide can be synthesized chemically using standard peptide synthesis techniques.

An "isolated" or "purified" protein or biologically active portion thereof is substantially free of cellular material or other contaminating proteins from the cell or tissue source from which the Adhr-1 protein is derived, or substantially free from chemical precursors or other chemicals when chemically synthesized. The language "substantially free of cellular material" includes preparations of Adhr-1 protein in which the protein is separated from cellular components of the cells from which it is isolated or recombinantly produced. In one embodiment, the language "substantially free of cellular material" includes preparations of Adhr-1 protein having less than about 30% (by dry weight) of non-Adhr-1 protein (also referred to herein as a "contaminating protein"), more preferably less than about 20% of non-Adhr-1 protein, still more preferably less than about 10% of non-Adhr-1 protein, and most preferably less than about 5% non-Adhr-1 protein. When the Adhr-1 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of Adhr-1 protein in which the protein is separated from chemical precursors or other chemicals which are involved in the synthesis of the protein. In one embodiment, the language "substantially free of chemical precursors or other chemicals" includes preparations of Adhr-1 protein having less than about 30% (by dry weight) of chemical precursors or non-Adhr-1 chemicals, more preferably less than about 20% chemical precursors or non-Adhr-1 chemicals, still more preferably less than about 10% chemical precursors or non-Adhr-1 chemicals, and most preferably less than about 5% chemical precursors or non-Adhr-1 chemicals.

As used herein, a "biologically active portion" of an Adhr-1 protein includes a fragment of an Adhr-1 protein which participates in an interaction between an Adhr-1 molecule and a non-Adhr-1 molecule, e.g., an alcohol, an aldehyde, or a lipid. Biologically active portions of an Adhr-1 protein include peptides comprising amino acid sequences sufficiently identical to or derived from the amino acid sequence of the Adhr-1 protein, e.g., the amino acid sequence shown in SEQ ID NO:2, which include less amino acids than the full length Adhr-1 proteins, and exhibit at least one activity of an Adhr-1 protein. Typically, biologically active portions comprise a domain or motif with at least one activity of the Adhr-1 protein, e.g., the ability to bind an Adhr-1 ligand or substrate (e.g., an alcohol, an aldehyde, or a lipid), the ability to metabolize an Adhr-1 ligand or substrate (e.g., an alcohol, an aldehyde, a retinol, or a lipid), the ability to modulate Adh activity, or the ability to modulate Adh-associated disorders. A biologically active portion of an Adhr-1 protein can be a polypeptide which is, for example, 10, 25, 50, 100, 200, 300, or more amino acids in length. Biologically active portions of an Adhr-1 protein can be used as targets for developing agents which modulate an Adhr-1 mediated activity, e.g., the ability to bind an Adhr-1 ligand or substrate (e.g., an alcohol, an aldehyde, a retinol, or a lipid); the ability to metabolize an Adhr-1 ligand or substrate (e.g., an alcohol, an aldehyde, a retinol, or a lipid), the ability to modulate Adh activity, or the ability to modulate Adh-associated disorders.

In one embodiment, a biologically active portion of an Adhr-1 protein comprises at least one ADH-Zn domain, and/or at least one Lipase-SER domain, and/or at least one transmembrane domain. It is to be understood that a preferred biologically active portion of an Adhr-1 protein of the present invention may contain at least one ADH-Zn domain. Another preferred biologically active portion of an Adhr-1 protein may contain at least one Lipase-SER domain. Yet another preferred biologically active portion of an Adhr-1 protein may contain at least one transmembrane domain. Moreover, other biologically active portions, in which other regions of the protein are deleted, can be prepared by recombinant techniques and evaluated for one or more of the functional activities of a native Adhr-1 protein.

In a preferred embodiment, the Adhr-1 protein has an amino acid sequence shown in SEQ ID NO:2. In other embodiments, the Adhr-1 protein is substantially identical to SEQ ID NO:2, and retains the functional activity of the protein of SEQ ID NO:2, yet differs in amino acid sequence due to natural allelic variation or mutagenesis, as described in detail in subsection I above. Accordingly, in another embodiment, the Adhr-1 protein is a protein which comprises an amino acid sequence at least about 50%, 55%, 60%, 65%, 70%, 75%, 80%, 85%, 86%, 87%, 88%, 89%, 90%, 91%, 92%, 93%, 94%, 95%, 96%, 97%, 98%, 99%, 99.5% or more identical to SEQ ID NO:2.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the Adhr-1 amino acid sequence of SEQ ID NO:2 having 377 amino acid residues, at least 113, preferably at least 151, more preferably at least 188, even more preferably at least 226, and even more preferably at least 264, 302 or 340 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at the bioinformatics page of the website maintained by Accelrys, Inc., San Diego, Calif., USA), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (Myers and Miller, 1988, *Comput. Appl. Biosci.* 4:11–17) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to Adhr-1 nucleic acid molecules of the invention. BLAST protein searches can be performed with the XBLAST program, score=100, wordlength=3 to obtain amino acid sequences homologous to Adhr-1 protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used (accesible at the website maintained by National Center for Biotechnology Information, Bethesda, Md., USA).

The invention also provides Adhr-1 chimeric or fusion proteins. As used herein, an Adhr-1 "chimeric protein" or "fusion protein" comprises an Adhr-1 polypeptide operatively linked to a non-Adhr-1 polypeptide. A "Adhr-1 polypeptide" includes a polypeptide having an amino acid sequence corresponding to Adhr-1, whereas an "non-Adhr-1 peptide" includes a polypeptide having an amino acid sequence corresponding to a protein which is not substantially homologous to an Adhr-1 protein, e.g., a protein which is different from the Adhr-1 protein and which is derived from the same or a different organism. Within an Adhr-1 fusion protein the Adhr-1 polypeptide can correspond to all or a portion of an Adhr-1 protein. In a preferred embodiment, an Adhr-1 fusion protein comprises at least one biologically active portion of an Adhr-1 protein. In another preferred embodiment, an Adhr-1 fusion protein comprises at least two biologically active portions of an Adhr-1 protein. Within the fusion protein, the term "operatively linked" is intended to indicate that the Adhr-1 polypeptide and the non-Adhr-1 polypeptide are fused in-frame to each other. The non-Adhr-1 polypeptide can be fused to the N-terminus or C-terminus of the Adhr-1 polypeptide.

For example, in one embodiment, the fusion protein is a GST-Adhr-1 fusion protein in which the Adhr-1 sequences are fused to the C-terminus of the GST sequences. Such fusion proteins can facilitate the purification of recombinant Adhr-1.

In another embodiment, the fusion protein is an Adhr-1 protein containing a heterologous signal sequence at its N-terminus. In certain host cells (e.g., mammalian host cells), expression and/or secretion of Adhr-1 can be increased through use of a heterologous signal sequence.

The Adhr-1 fusion proteins of the invention can be incorporated into pharmaceutical compositions and administered to a subject in vivo. The Adhr-1 fusion proteins can be used to affect the bioavailability of an Adhr-1 ligand or substrate. Use of Adhr-1 fusion proteins may be useful therapeutically for the treatment of disorders caused by, for example, (i) aberrant modification or mutation of a gene encoding an Adhr-1 protein; (ii) mis-regulation of the Adhr-1 gene; and (iii) aberrant post-translational modification of an Adhr-1 protein.

Moreover, the Adhr-1-fusion proteins of the invention can be used as immunogens to produce anti-Adhr-1 antibodies in a subject, to purify Adhr-1 ligands and in screening assays to identify molecules which inhibit the interaction of Adhr-1 with an Adhr-1 ligand or substrate.

Preferably, an Adhr-1 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). An Adhr-1-encoding nucleic acid can be cloned into such an expression vector such that the fusion moiety is linked in-frame to the Adhr-1 protein.

The present invention also pertains to variants of the Adhr-1 proteins which function as either Adhr-1 agonists (mimetics) or as Adhr-1 antagonists. Variants of the Adhr-1 proteins can be generated by mutagenesis, e.g., discrete point mutation or truncation of an Adhr-1 protein. An agonist of the Adhr-1 proteins can retain substantially the same, or a subset, of the biological activities of the naturally occurring form of an Adhr-1 protein. An antagonist of an Adhr-1 protein can inhibit one or more of the activities of the naturally occurring form of the Adhr-1 protein by, for example, competitively modulating an Adhr-1-mediated activity of an Adhr-1 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the Adhr-1 protein.

In one embodiment, variants of an Adhr-1 protein which function as either Adhr-1 agonists (mimetics) or as Adhr-1 antagonists can be identified by screening combinatorial libraries of mutants, e.g., truncation mutants, of an Adhr-1 protein for Adhr-1 protein agonist or antagonist activity. In one embodiment, a variegated library of Adhr-1 variants is generated by combinatorial mutagenesis at the nucleic acid level and is encoded by a variegated gene library. A variegated library of Adhr-1 variants can be produced by, for example, enzymatically ligating a mixture of synthetic oligonucleotides into gene sequences such that a degenerate set of potential Adhr-1 sequences is expressible as individual polypeptides, or alternatively, as a set of larger fusion proteins (e.g., for phage display) containing the set of Adhr-1 sequences therein. There are a variety of methods which can be used to produce libraries of potential Adhr-1 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential Adhr-1 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of an Adhr-1 protein coding sequence can be used to generate a variegated population of Adhr-1 fragments for screening and subsequent selection of variants of an Adhr-1 protein. In one embodiment, a library of coding sequence fragments can be generated by treating a double stranded PCR fragment of an Adhr-1 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the Adhr-1 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of Adhr-1 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify Adhr-1 variants (Arkin and Youvan (1992) *Proc. Natl. Acad. Sci. USA* 89:7811–7815; Delagrave et al. (1993) *Protein Engineering* 6(3):327–331).

In one embodiment, cell based assays can be exploited to analyze a variegated Adhr-1 library. For example, a library of expression vectors can be transfected into a cell line, e.g., a neuronal cell line, which ordinarily responds to Adhr-1 in a particular Adhr-1 ligand-dependent manner. The transfected cells are then contacted with an Adhr-1 ligand and the effect of expression of the mutant on signaling by the Adhr-1 ligand can be detected, e.g., by monitoring Adhr-1 activity, changes in concentration of metabolites of Adhr-1 (e.g. an alcohol, an aldehydes, or a lipids), signaling mechanisms which rely on the activity of Adhr-1, or the activity of an Adhr-1-regulated transcription factor. Plasmid DNA can then be recovered from the cells which score for inhibition, or alternatively, potentiation of signaling by the Adhr-1 ligand, and the individual clones further characterized. In related cell-based assays, changes in ligands or target proteins of Adhr-1 (e.g. an alcohol, an aldehyde, or a lipid) can be measured in live cells which express Adhr-1 molecules of the invention. Such an assay can be used for screening compound libraries for useful ligands which interact with Adhr-1, or can be used to identify variants of Adhr-1 which have useful properties. Other cell-based assays include those which can monitor fluxes in intracellular alcohol, aldehyde, lipid, or retinoid levels which result from Adhr-1 activity, e.g., cellular staining or flow cytometry (Valet and Raffael, 1985, *Naturwiss.*, 72:600–602). Also within the scope of the invention are assays and models which utilize Adhr-1 nucleic acids to create transgenic organisms for identifying useful pharmaceutical compounds or variants of the Adhr-1 molecules.

An isolated Adhr-1 protein, or a portion or fragment thereof, can be used as an immunogen to generate antibodies that bind Adhr-1 using standard techniques for polyclonal and monoclonal antibody preparation. A full-length Adhr-1 protein can be used or, alternatively, the invention provides antigenic peptide fragments of Adhr-1 for use as immunogens. The antigenic peptide of Adhr-1 comprises at least 8 amino acid residues of the amino acid sequence shown in SEQ ID NO:2 and encompasses an epitope of Adhr-1 such that an antibody raised against the peptide forms a specific immune complex with Adhr-1. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of Adhr-1 that are located on the surface of the protein, e.g., hydrophilic regions, as well as regions with high antigenicity (see, for example, FIG. 2).

An Adhr-1 immunogen typically is used to prepare antibodies by immunizing a suitable subject, (e.g., rabbit, goat, mouse or other mammal) with the immunogen. An appropriate immunogenic preparation can contain, for example, recombinantly expressed Adhr-1 protein or a chemically synthesized Adhr-1 polypeptide. The preparation can further include an adjuvant, such as Freund's complete or incomplete adjuvant, or similar immunostimulatory agent. Immunization of a suitable subject with an immunogenic Adhr-1 preparation induces a polyclonal anti-Adhr-1 antibody response.

Accordingly, another aspect of the invention pertains to anti-Adhr-1 antibodies. The term "antibody" as used herein refers to immunoglobulin molecules and immunologically active portions of immunoglobulin molecules, i.e., molecules that contain an antigen binding site which specifically binds (immunoreacts with) an antigen, such as Adhr-1. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind Adhr-1. The term "monoclonal antibody" or "monoclonal antibody composition", as used herein, refers to a population of antibody molecules that contain only one species of an antigen binding site capable of immunoreacting with a particular epitope of Adhr-1. A monoclonal antibody composition thus typically displays a single binding affinity for a particular Adhr-1 protein with which it immunoreacts.

Polyclonal anti-Adhr-1 antibodies can be prepared as described above by immunizing a suitable subject with an Adhr-1 immunogen. The anti-Adhr-1 antibody titer in the immunized subject can be monitored over time by standard techniques, such as with an enzyme linked immunosorbent assay (ELISA) using immobilized Adhr-1. If desired, the antibody molecules directed against Adhr-1 can be isolated from the mammal (e.g., from the blood) and further purified by well known techniques, such as protein A chromatography to obtain the IgG fraction. At an appropriate time after immunization, e.g., when the anti-Adhr-1 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255: 4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with an Adhr-1 immunogen as described above, and the culture supernatants of the resulting hybridoma cells are screened to identify a hybridoma producing a monoclonal antibody that binds Adhr-1.

Any of the many well known protocols used for fusing lymphocytes and immortalized cell lines can be applied for the purpose of generating an anti-Adhr-1 monoclonal antibody (see, e.g., G. Galfre et al. (1977) *Nature* 266:55052; Gefter et al. *Somatic Cell Genet.*, cited supra; Lerner, *Yale J.*

Biol. Med., cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC (Manassas, Va.). Typically, HAT-sensitive mouse myeloma cells are fused to mouse splenocytes using polyethylene glycol ("PEG"). Hybridoma cells resulting from the fusion are then selected using HAT medium, which kills unfused and unproductively fused mycloma cells (unfused splenocytes die after several days because they are not transformed). Hybridoma cells producing a monoclonal antibody of the invention are detected by screening the hybridoma culture supernatants for antibodies that bind Adhr-1, e.g., using a standard ELISA assay.

Alternative to preparing monoclonal antibody-secreting hybridomas, a monoclonal anti-Adhr-1 antibody can be identified and isolated by screening a recombinant combinatorial immunoglobulin library (e.g., an antibody phage display library) with Adhr-1 to thereby isolate immunoglobulin library members that bind Adhr-1. Kits for generating and screening phage display libraries are commercially available (e.g., the Pharmacia *Recombinant Phage Antibody System*, Catalog No. 27–9400–01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1369–1372; Hay et al. (1992) *Hum. Antibod. Hybridomas* 3:81–85; Huse et al. (1989) *Science* 246:1275–1281; Griffiths et al. (1993) *EMBO J.* 12:725–734; Hawkins et al. (1992) *J. Mol. Biol.* 226:889–896; Clackson et al. (1991) *Nature* 352:624–628; Gram et al. (1992) *Proc. Natl. Acad. Sci. USA* 89:3576–3580; Garrard et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-Adhr-1 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *Biotechniques* 4:214; Winter U.S. Pat. No. 5,225,539; Jones et al. (1986) *Nature* 321:552–525; Verhoeyen et al. (1988) *Science* 239:1534; and Beidler et al. (1988) *J. Immunol.* 141:4053–4060.

An anti-Adhr-1 antibody (e.g., monoclonal antibody) can be used to isolate Adhr-1 by standard techniques, such as affinity chromatography or immunoprecipitation. An anti-Adhr-1 antibody can facilitate the purification of natural Adhr-1 from cells and of recombinantly produced Adhr-1 expressed in host cells. Moreover, an anti-Adhr-1 antibody can be used to detect Adhr-1 protein (e.g., in a cellular lysate or cell supernatant) in order to evaluate the abundance and pattern of expression of the Adhr-1 protein. Anti-Adhr-1 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid encoding an Adhr-1 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., Adhr-1 proteins, mutant forms of Adhr-1 proteins, fusion proteins, and the like).

The recombinant expression vectors of the invention can be designed for expression of Adhr-1 proteins in prokaryotic or eukaryotic cells. For example, Adhr-1 proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in Adhr-1 activity assays, (e.g., direct assays or competitive assays described in detail below), or to generate antibodies specific for Adhr-1 proteins, for example. In a preferred embodiment, an Adhr-1 fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the Adhr-1 expression vector is a yeast expression vector. Examples of vectors for expression in yeast *S. cerevisiae* include pYepSec1 (Baldari, et al., (1987) *EMBO J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (Invitrogen Corporation, San Diego, Calif.).

Alternatively, Adhr-1 proteins can be expressed in insect cells using baculovirus expression vectors. Baculovirus vectors available for expression of proteins in cultured insect cells (e.g., Sf9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular*

*Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The expression characteristics of an endogenous Adhr-1 gene within a cell line or microorganism may be modified by inserting a heterologous DNA regulatory element into the genome of a stable cell line or cloned microorganism such that the inserted regulatory element is operatively linked with the endogenous Adhr-1 gene. For example, an endogenous Adhr-1 gene which is normally "transcriptionally silent", i.e., an Adhr-1 gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous Adhr-1 gene may be activated by insertion of a promiscuous regulatory element that works across cell types.

A heterologous regulatory element may be inserted into a stable cell line or cloned microorganism, such that it is operatively linked with an endogenous Adhr-1 gene, using techniques, such as targeted homologous recombination, which are well known to those of skill in the art, and described, e.g., in Chappel, U.S. Pat. No. 5,272,071; PCT publication No. WO 91/06667, published May 16, 1991.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to Adhr-1 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which an Adhr-1 nucleic acid molecule of the invention is introduced, e.g., an Adhr-1 nucleic acid molecule within a recombinant expression vector or an Adhr-1 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an Adhr-1 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding an Adhr-1 protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) an Adhr-1 protein. Accordingly, the invention further provides methods for producing an Adhr-1 protein using the host cells of the invention. In one embodiment, the method comprises culturing the host cell of the invention (into which a recombinant expression vector encoding an Adhr-1 protein has been introduced) in a suitable medium such that an Adhr-1 protein is produced. In another embodiment, the method further comprises isolating an Adhr-1 protein from the medium or the host cell.

The host cells of the invention can also be used to produce non-human transgenic animals. For example, in one embodiment, a host cell of the invention is a fertilized oocyte or an embryonic stem cell into which Adhr-1-coding sequences have been introduced. Such host cells can then be used to create non-human transgenic animals in which exogenous Adhr-1 sequences have been introduced into their genome or homologous recombinant animals in which endogenous Adhr-1 sequences have been altered. Such animals are useful for studying the function and/or activity of an Adhr-1 and for identifying and/or evaluating modulators of Adhr-1 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous Adhr-1 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing an Adhr-1-encoding nucleic acid into the male pronuclei of a fertilized oocyte, e.g., by microinjection, retroviral infection, and allowing the oocyte to develop in a pseudopregnant female foster animal. The Adhr-1 cDNA sequence of SEQ ID NO:1 or 3 can be introduced as a transgene into the genome of a non-human animal. Alternatively, a nonhuman homologue of a human Adhr-1 gene, such as a mouse or rat Adhr-1 gene, can be used as a transgene. Alternatively, an Adhr-1 gene homologue, such as another Adhr-1 family member, can be isolated based on hybridization to the Adhr-1 cDNA sequences of SEQ ID NO:1 or 3 (described further in subsection I above) and used as a transgene. Intronic sequences and polyadenylation signals can also be included in the transgene to increase the efficiency of expression of the transgene. A tissue-specific regulatory sequence(s) can be operably linked to an Adhr-1 transgene to direct expression of an Adhr-1 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of an Adhr-1 transgene in its genome and/or expression of Adhr-1 mRNA in tissues or cells of the animals. A transgenic founder animal can then be used to breed additional animals carrying the transgene. Moreover, transgenic animals carrying a transgene encoding an Adhr-1 protein can further be bred to other transgenic animals carrying other transgenes.

To create a homologous recombinant animal, a vector is prepared which contains at least a portion of an Adhr-1 gene into which a deletion, addition or substitution has been introduced to thereby alter, e.g., functionally disrupt, the Adhr-1 gene. The Adhr-1 gene can be a human gene (e.g., the cDNA of SEQ ID NO:1, 3, 4, or 6), but more preferably, is a non-human homologue of a human Adhr-1 gene (e.g., a cDNA isolated by stringent hybridization with the nucleotide sequence of SEQ ID NO:1, 3, 4, or 6). For example, a mouse Adhr-1 gene can be used to construct a homologous recombination nucleic acid molecule, e.g., a vector, suitable for altering an endogenous Adhr-1 gene in the mouse genome.

In a preferred embodiment, the homologous recombination nucleic acid molecule is designed such that, upon homologous recombination, the endogenous Adhr-1 gene is functionally disrupted (i.e., no longer encodes a functional protein; also referred to as a "knock out" vector). Alternatively, the homologous recombination nucleic acid molecule can be designed such that, upon homologous recombination, the endogenous Adhr-1 gene is mutated or otherwise altered but still encodes functional protein (e.g., the upstream regulatory region can be altered to thereby alter the expression of the endogenous Adhr-1 protein). In the homologous recombination nucleic acid molecule, the altered portion of the Adhr-1 gene is flanked at its 5' and 3' ends by additional nucleic acid sequence of the Adhr-1 gene to allow for homologous recombination to occur between the exogenous Adhr-1 gene carried by the homologous recombination nucleic acid molecule and an endogenous Adhr-1 gene in a cell, e.g., an embryonic stem cell. The additional flanking Adhr-1 nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced Adhr-1 gene has homologously recombined with the endogenous Adhr-1 gene are selected (see e.g., Li, E. et al. (1992) *Cell* 69:915). The selected cells can then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The Adhr-1 nucleic acid molecules, fragments of Adhr-1 proteins, and anti-Adhr-1 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR® EL solubilizer (BASF, Florham Park, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of an Adhr-1 protein or an anti-Adhr-1 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography. As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, an Adhr-1 protein of the invention has one or more of the following activities: the ability to bind an Adhr-1 ligand or substrate (e.g., an alcohol, an aldehyde, a retinol or a lipid); the ability to metabolize an Adhr-1 ligand or substrate (e.g., an alcohol, an aldehyde, a retinol or a lipid); the ability to modulate an Adh-associated signaling mechanism; the ability to modulate Adh-associated disorders or lipid metabolism-associated disorders. Thus, an Adhr-1 protein of the invention can be used to, for example, modulate the ability to bind an Adhr-1 ligand or substrate (e.g., an alcohol, an aldehyde, a retinol or a lipid); modulate the ability to metabolize an Adhr-1 ligand or substrate (e.g., an alcohol, an aldehyde, a retinol or a lipid); modulate an Adh-associated signaling mechanism; to ameliorate one or more Adh-associated disorders or lipid metabolism-associated disorders.

The isolated nucleic acid molecules of the invention can be used, for example, to express Adhr-1 protein (e.g., via a recombinant expression vector in a host cell in gene therapy applications), to detect Adhr-1 mRNA (e.g., in a biological sample) or a genetic alteration in an Adhr-1 gene, and to modulate Adhr-1 activity, as described further below. The Adhr-1 proteins can be used to treat disorders characterized by insufficient or excessive production of an Adhr-1 ligand or substrate or production of Adhr-1 inhibitors. In addition, the Adhr-1 proteins can be used to screen for naturally occurring Adhr-1 ligands or substrates to screen for drugs or compounds which modulate Adhr-1 activity, as well as to treat disorders characterized by insufficient or excessive production of Adhr-1 protein or production of Adhr-1 protein forms which have decreased, aberrant or unwanted activity compared to Adhr-1 wild type protein (e.g., Adh-associated disorders). Moreover, the anti-Adhr-1 antibodies of the invention can be used to detect and isolate Adhr-1 proteins, regulate the bioavailability of Adhr-1 proteins, and modulate Adhr-1 activity.

A. Screening Assays:

The invention provides a method (also referred to herein as a "screening assay") for identifying modulators, i.e., candidate or test compounds or agents (e.g., peptides, peptidomimetics, small molecules or other drugs) which bind to Adhr-1 proteins, have a stimulatory or inhibitory effect on, for example, Adhr-1 expression or Adhr-1 activity, or have a stimulatory or inhibitory effect on, for example, the expression or activity of an Adhr-1 ligand or substrate.

In one embodiment, the invention provides assays for screening candidate or test compounds which are substrates or ligands of an Adhr-1 protein or polypeptide or biologically active portion thereof. In another embodiment, the invention provides assays for screening candidate or test compounds which bind to or modulate the activity of an Adhr-1 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses an Adhr-1 protein or biologically active portion thereof is contacted with a test compound and the ability of the test compound to modulate Adhr-1 activity is determined. Determining the ability of the test compound to modulate Adhr-1 activity can be accomplished by monitoring, for example, changes in intracellular calcium concentration by, e.g., flow cytometry, or by the activity of an Adhr-1-regulated transcription factor. The cell, for example, can be of mammalian origin, e.g., a neuronal cell.

The ability of the test compound to modulate Adhr-1 binding to a ligand or substrate or to bind to Adhr-1 can also be determined. Determining the ability of the test compound to modulate Adhr-1 binding to a ligand or substrate can be accomplished, for example, by coupling the Adhr-1 ligand or substrate with a radioisotope or enzymatic label such that binding of the Adhr-1 ligand or substrate to Adhr-1 can be determined by detecting the labeled Adhr-1 ligand or substrate in a complex. Determining the ability of the test compound to bind Adhr-1 can be accomplished, for example, by coupling the compound with a radioisotope or enzymatic label such that binding of the compound to Adhr-1 can be determined by detecting the labeled Adhr-1 compound in a complex. For example, compounds (e.g., Adhr-1 ligands or substrates) can be labeled with $^{125}I$, $^{35}S$, $^{14}C$, or $^{3}H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., an Adhr-1 ligand or substrate) to interact with Adhr-1 without the labeling of any of the interactants. For example, a microphysiometer can be used to detect the interaction of a compound with Adhr-1 without the labeling of either the compound or the Adhr-1. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and Adhr-1.

In another embodiment, an assay is a cell-based assay comprising contacting a cell expressing an Adhr-1 target molecule (e.g., an Adhr-1 ligand or substrate) with a test compound and determining the ability of the test compound to modulate (e.g., stimulate or inhibit) the activity of the Adhr-1 target molecule. Determining the ability of the test compound to modulate the activity of an Adhr-1 target molecule can be accomplished, for example, by determining the ability of the Adhr-1 protein to bind to or interact with the Adhr-1 target molecule.

Determining the ability of the Adhr-1 protein or a biologically active fragment thereof, to bind to or interact with an Adhr-1 target molecule or ligand (e.g., an alcohol, an aldehyde, a retinol, or a lipid) can be accomplished by one of the methods described above for determining direct binding. In a preferred embodiment, determining the ability of the Adhr-1 protein to bind to or interact with an Adhr-1 target molecule or ligand can be accomplished by determining the activity of the target molecule. For example, the activity of the target molecule (e.g., catalytic/enzymatic activity) can be determined of the target on an appropriate substrate (e.g. an alcohol, an aldehyde, a retinol, or a lipid), detecting the induction of a reporter gene (comprising a target-responsive regulatory element operatively linked to a nucleic acid encoding a detectable marker, e.g., luciferase), or detecting a target-regulated cellular response such as changes in cytoskeletal structure or nuclear transport.

In yet another embodiment, an assay of the present invention is a cell-free assay in which an Adhr-1 protein or biologically active portion thereof is contacted with a test compound and the ability of the test compound to bind to the Adhr-1 protein or biologically active portion thereof is determined. Preferred biologically active portions of the Adhr-1 proteins to be used in assays of the present invention include fragments which participate in interactions with non-Adhr-1 molecules, e.g., fragments with high surface probability scores (see, for example, FIG. 2). Binding of the test compound to the Adhr-1 protein can be determined either directly or indirectly as described above. In a preferred embodiment, the assay includes contacting the Adhr-1 protein or biologically active portion thereof with a known compound which binds Adhr-1 to form an assay mixture, contacting the assay mixture with a test compound, and determining the ability of the test compound to interact with an Adhr-1 protein, wherein determining the ability of the test compound to interact with an Adhr-1 protein comprises determining the ability of the test compound to preferentially bind to Adhr-1 or biologically active portion thereof as compared to the known compound.

In another embodiment, the assay is a cell-free assay in which an Adhr-1 protein or biologically active portion thereof is contacted with a test compound and the ability of the test compound to modulate (e.g., stimulate or inhibit) the activity of the Adhr-1 protein or biologically active portion thereof is determined. Determining the ability of the test compound to modulate the activity of an Adhr-1 protein can be accomplished, for example, by determining the ability of the Adhr-1 protein to bind to an Adhr-1 target molecule by one of the methods described above for determining direct binding. Determining the ability of the Adhr-1 protein to bind to an Adhr-1 target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIACORE™). Changes in the optical phenomenon of surface plasmon resonance (SPR) can be used as an indication of real-time reactions between biological molecules.

In an alternative embodiment, determining the ability of the test compound to modulate the activity of an Adhr-1 protein can be accomplished by determining the ability of the Adhr-1 protein to further modulate the activity of a downstream effector of an Adhr-1 target molecule. For example, the activity of the effector molecule on an appropriate target can be determined or the binding of the effector to an appropriate target can be determined as previously described.

In yet another embodiment, the cell-free assay involves contacting an Adhr-1 protein or biologically active portion thereof with a known compound which binds the Adhr-1 protein to form an assay mixture, contacting the assay mixture with a test compound, and determining the ability of the test compound to interact with the Adhr-1 protein, wherein determining the ability of the test compound to interact with the Adhr-1 protein comprises determining the ability of the Adhr-1 protein to preferentially bind to or modulate the activity of an Adhr-1 target molecule.

In more than one embodiment of the above assay methods of the present invention, it may be desirable to immobilize either Adhr-1 or its target molecule to facilitate separation of complexed from uncomplexed forms of one or both of the proteins, as well as to accommodate automation of the assay. Binding of a test compound to an Adhr-1 protein, or interaction of an Adhr-1 protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/Adhr-1 fusion proteins or glutathione-S-transferase/target fusion proteins can be adsorbed onto glutathione SEPHAROSE™ beads (Sigma Chemical, St. Louis, Mo.) or glutathione derivatized microtitre plates, which are then combined with the test compound or the test compound and either the non-adsorbed target protein or Adhr-1 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of Adhr-1 binding or activity determined using standard techniques.

Other techniques for immobilizing proteins on matrices can also be used in the screening assays of the invention. For example, either an Adhr-1 protein or an Adhr-1 target molecule can be immobilized utilizing conjugation of biotin and streptavidin. Biotinylated Adhr-1 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with Adhr-1 protein or target molecules but which do not interfere with binding of the Adhr-1 protein to its target molecule can be derivatized to the wells of the plate, and unbound target or Adhr-1 protein trapped in the wells by antibody conjugation. Methods for detecting such complexes, in addition to those described above for the GST-immobilized complexes, include immunodetection of complexes using antibodies reactive with the Adhr-1 protein or target molecule, as well as enzyme-linked assays which rely on detecting an enzymatic activity associated with the Adhr-1 protein or target molecule.

In another embodiment, modulators of Adhr-1 expression are identified in a method wherein a cell is contacted with a candidate compound and the expression of Adhr-1 mRNA or protein in the cell is determined. The level of expression of Adhr-1 mRNA or protein in the presence of the candidate compound is compared to the level of expression of Adhr-1 mRNA or protein in the absence of the candidate compound. The candidate compound can then be identified as a modulator of Adhr-1 expression based on this comparison. For example, when expression of Adhr-1 mRNA or protein is greater (statistically significantly greater) in the presence of the candidate compound than in its absence, the candidate compound is identified as a stimulator of Adhr-1 mRNA or protein expression. Alternatively, when expression of Adhr-1 mRNA or protein is less (statistically significantly less) in the presence of the candidate compound than in its absence, the candidate compound is identified as an inhibitor of Adhr-1 mRNA or protein expression. The level of Adhr-1 mRNA or protein expression in the cells can be determined by methods described herein for detecting Adhr-1 mRNA or protein.

In yet another aspect of the invention, the Adhr-1 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with Adhr-1 ("Adhr-1-binding proteins" or "Adhr-1-bp") and are involved in Adhr-1 activity. Such Adhr-1-binding proteins are also likely to be involved in the propagation of signals by the Adhr-1 proteins or Adhr-1 targets as, for example, downstream elements of an Adhr-1-mediated signaling pathway. Alternatively, such Adhr-1-binding proteins are likely to be Adhr-1 inhibitors.

The two-hybrid system is based on the modular nature of most transcription factors, which consist of separable DNA-binding and activation domains. Briefly, the assay utilizes two different DNA constructs. In one construct, the gene that codes for an Adhr-1 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an Adhr-1-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the Adhr-1 protein.

In another aspect, the invention pertains to a combination of two or more of the assays described herein. For example, a modulating agent can be identified using a cell-based or a cell free assay, and the ability of the agent to modulate the activity of an Adhr-1 protein can be confirmed in vivo, e.g., in an animal such as an animal model.

This invention further pertains to novel agents identified by the above-described screening assays. Accordingly, it is within the scope of this invention to further use an agent identified as described herein in an appropriate animal model. For example, an agent identified as described herein (e.g., an Adhr-1 modulating agent, an antisense Adhr-1 nucleic acid molecule, an Adhr-1-specific antibody, or an Adhr-1-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

Animal based models for studying tumorigenesis in vivo are well known in the art (reviewed in Animal Models of Cancer Predisposition Syndromes, Hiai, H and Hino, O (eds.) 1999, *Progress in Experimental Tumor Research*, Vol. 35; Clarke A R *Carcinogenesis* (2000) 21:435–41) and include, for example, carcinogen-induced tumors (Rithidech, K et al. *Mutat Res* (1999) 428:33–39; Miller, M L et al. *Environ Mol Mutagen* (2000) 35:319–327), injection and/or transplantation of tumor cells into an animal, as well as animals bearing mutations in growth regulatory genes, for example, oncogenes (e.g., ras) (Arbeit, J M et al. *Am J Pathol* (1993) 142:1187–1197; Sinn, E et al. *Cell* (1987) 49:465–475; Thorgeirsson, S S et al. *Toxicol Lett* (2000) 112–113:553–555) and tumor suppressor genes (e.g., p53) (Vooijs, M et al. *Oncogene* (1999) 18:5293–5303; Clark A R *Cancer Metast Rev* (1995) 14:125–148; Kumar, T R et al. *J. Intern Med* (1995) 238:233–238; Donehower, L A et al. (1992) *Nature* 356215–221). Furthermore, experimental model systems are available for the study of, for example, ovarian cancer (Hamilton, T C et al. *Semin Oncol* (1984) 11:285–298; Rahman, N A et al. *Mol Cell Endocrinol* (1998) 145:167–174; Beamer, W G et al. *Toxicol Pathol* (1998) 26:704–710), gastric cancer (Thompson, J et al. *Int J. Cancer* (2000) 86:863–869; Fodde, R et al. *Cytogenet Cell Genet* (1999) 86:105–111), breast cancer (Li, M et al. *Oncogene* (2000) 19:1010–1019; Green, J E et al. *Oncogene* (2000) 19:1020–1027), melanoma (Satyamoorthy, K et al. *Cancer Metast Rev* (1999) 18:401–405), and prostate cancer (Shirai, T et al. *Mutat Res* (2000) 462:219–226; Bostwick, D G et al. *Prostate* (2000) 43:286–294).

Additionally, gene expression patterns may be utilized to assess the ability of a compound to ameliorate tumorigenic disease symptoms. For example, the expression pattern of one or more genes may form part of a "gene expression profile" or "transcriptional profile" which may be then be used in such an assessment. "Gene expression profile" or "transcriptional profile", as used herein, includes the pattern of mRNA expression obtained for a given tissue or cell type under a given set of conditions. Such conditions may include, but are not limited to, cell proliferation, differentiation, transformation, tumorigenesis, metastasis, and carcinogen exposure. Other conditions may include, for example, cataract, desmin related myopathy, UV damage to tissues, like cornea, or diseases related to the musculoskeletal system (the bones, joints, muscles, ligaments and connective tissue), including any of the control or experimental conditions described herein, for example, skeletal muscle cells treated under conditions of laminar sheer stress (LSS), cytokine stimulation, growth on Matrigel, and proliferation.

Gene expression profiles may be generated, for example, by utilizing a differential display procedure, Northern analysis and/or RT-PCR. In one embodiment, Adhr-1 gene sequences may be used as probes and/or PCR primers for the generation and corroboration of such gene expression profiles.

Gene expression profiles may be characterized for known states, such as, tumorigenic disease or normal, within the cell- and/or animal-based model systems. Subsequently, these known gene expression profiles may be compared to ascertain the effect a test compound has to modify such gene expression profiles, and to cause the profile to more closely resemble that of a more desirable profile.

For example, administration of a compound may cause the gene expression profile of a tumorigenic disease model system to more closely resemble the control system. Administration of a compound may, alternatively, cause the gene expression profile of a control system to begin to mimic a tumorigenic disease state. Such a compound may, for example, be used in further characterizing the compound of interest, or may be used in the generation of additional animal models.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the Adhr-1 nucleotide sequences, described herein, can be used to map the location of the Adhr-1 genes on a chromosome. The mapping of the Adhr-1 sequences to chromosomes is an important first step in correlating these sequences with genes associated with disease.

Briefly, Adhr-1 genes can be mapped to chromosomes by preparing PCR primers (preferably 15–25 bp in length) from the Adhr-1 nucleotide sequences. Computer analysis of the Adhr-1 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the Adhr-1 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220: 919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the Adhr-1 nucleotide sequences to design oligonucleotide primers, sublocalization can be achieved with panels of fragments from specific chromosomes. Other mapping strategies which can similarly be used to map an Adhr-1 sequence to its chromosome include in situ hybridization (described in Fan, Y. et al. (1990) *Proc. Natl. Acad. Sci. USA,* 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature,* 325:783–787.

Moreover, differences in the DNA sequences between individuals affected and unaffected with a disease associated with the Adhr-1 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The Adhr-1 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the Adhr-1 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The Adhr-1 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can comfortably provide positive individual identification with a panel of perhaps 10 to 1,000 primers which each yield a noncoding amplified sequence of 75–100 bases. If predicted coding sequences, such as those in SEQ ID NO:3 are used, a more appropriate number of primers for positive individual identification would be 500–2,000.

If a panel of reagents from Adhr-1 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial Adhr-1 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the Adhr-1 nucleotide sequences or portions thereof, e.g., fragments derived from the noncoding regions of SEQ ID NO:1, having a length of at least 20 bases, preferably at least 30 bases.

The Adhr-1 nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such Adhr-1 probes can be used to identify tissue by species and/or by organ type.

In a similar fashion, these reagents, e.g., Adhr-1 primers or probes can be used to screen tissue culture for contamination (i.e. screen for the presence of a mixture of different types of cells in a culture).

C. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining Adhr-1 protein and/or nucleic acid expression as well as Adhr-1 activity, in the context of a biological sample (e.g., blood, serum, cells, tissue) to thereby determine whether an individual is afflicted with a disease or disorder, or is at risk of developing a disorder, associated with aberrant or unwanted Adhr-1 expression or activity. The invention also provides for prognostic (or predictive) assays for determining whether an individual is at risk of developing a disorder associated with Adhr-1 protein, nucleic acid expression or activity. For example, mutations in an Adhr-1 gene can be assayed in a biological sample. Such assays can be used for prognostic or predictive purpose to thereby prophylactically treat an individual prior to the onset of a disorder characterized by or associated with Adhr-1 protein, nucleic acid expression or activity.

Another aspect of the invention pertains to monitoring the influence of agents (e.g., drugs, compounds) on the expression or activity of Adhr-1 in clinical trials.

These and other agents are described in further detail in the following sections.

1. Diagnostic Assays

An exemplary method for detecting the presence or absence of Adhr-1 protein or nucleic acid in a biological sample involves obtaining a biological sample from a test subject and contacting the biological sample with a compound or an agent capable of detecting Adhr-1 protein or nucleic acid (e.g., mRNA, or genomic DNA) that encodes Adhr-1 protein such that the presence of Adhr-1 protein or nucleic acid is detected in the biological sample. A preferred agent for detecting Adhr-1 mRNA or genomic DNA is a labeled nucleic acid probe capable of hybridizing to Adhr-1 mRNA or genomic DNA. The nucleic acid probe can be, for example, the Adhr-1 nucleic acid set forth in SEQ ID NO:1 or 3, or a portion thereof, such as an oligonucleotide of at least 15, 30, 50, 100, 250 or 500 nucleotides in length and sufficient to specifically hybridize under stringent conditions to Adhr-1 mRNA or genomic DNA. Other suitable probes for use in the diagnostic assays of the invention are described herein.

A preferred agent for detecting Adhr-1 protein is an antibody capable of binding to Adhr-1 protein, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect Adhr-1 mRNA, protein, or genomic DNA in a biological sample in vitro as well as in vivo. For example, in vitro techniques for detection of Adhr-1 mRNA include Northern hybridizations and in situ hybridizations. In vitro techniques for detection of Adhr-1 protein include enzyme linked immunosorbent assays (ELISAs), Western blots, immunoprecipitations and immunofluorescence. In vitro techniques for detection of Adhr-1 genomic DNA include Southern hybridizations. Furthermore, in vivo techniques for detection of Adhr-1 protein include introducing into a subject a labeled anti-Adhr-1 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting Adhr-1 protein, mRNA, or genomic DNA, such that the presence of Adhr-1 protein, mRNA or genomic DNA is detected in the biological sample, and comparing the presence of Adhr-1 protein, mRNA or genomic DNA in the control sample with the presence of Adhr-1 protein, mRNA or genomic DNA in the test sample.

The invention also encompasses kits for detecting the presence of Adhr-1 in a biological sample. For example, the kit can comprise a labeled compound or agent capable of detecting Adhr-1 protein or mRNA in a biological sample; means for determining the amount of Adhr-1 in the sample; and means for comparing the amount of Adhr-1 in the sample with a standard. The compound or agent can be packaged in a suitable container. The kit can further comprise instructions for using the kit to detect Adhr-1 protein or nucleic acid.

2. Prognostic Assays

The diagnostic methods described herein can furthermore be utilized to identify subjects having or at risk of developing a disease or disorder associated with aberrant or unwanted Adhr-1 expression or activity. As used herein, the term "aberrant" includes an Adhr-1 expression or activity which deviates from the wild type Adhr-1 expression or activity. Aberrant expression or activity includes increased or decreased expression or activity, as well as expression or activity which does not follow the wild type developmental pattern of expression or the subcellular pattern of expression. For example, aberrant Adhr-1 expression or activity is intended to include the cases in which a mutation in the Adhr-1 gene causes the Adhr-1 gene to be under-expressed or over-expressed and situations in which such mutations result in a non-functional Adhr-1 protein or a protein which does not function in a wild-type fashion, e.g., a protein which does not interact with an Adhr-1 ligand (e.g., an alcohol, an aldehyde, a retinol, or a lipid), or one which interacts with a non-Adhr-1 ligand (e.g. a molecule or moiety other than an alcohol, an aldehyde, a retinol, or a lipid). As used herein, the term "unwanted" includes an unwanted phenomenon involved in a biological response such as aberrant metabolism of Adhr-1 substrates or aberrant cellular functions and processes in which Adhr-1 participates. For example, the term unwanted includes an Adhr-1 expression or activity which is undesirable in a subject. Examples of Adh-associated disorders include metabolic disorders, disorders related to toxins and/or alcohol consumption (e.g. alcoholism, cirrhosis, or depression); disorders related to the CNS (e.g. cognitive and neurodegenerative disorders stemming from aberrant metabolism of neurotransmitters or degradation resulting from alcohol damage); disorders related to retinol metabolism (e.g. embryological disorders, visual disorders or night blindness). Examples of lipid-metabolism-associated disorders include hyper- or hypolipoproteinemias, diabetes mellitus, and familial hypercholesterolemia.

The assays described herein, such as the preceding diagnostic assays or the following assays, can be utilized to identify a subject having or at risk of developing a disorder associated with a misregulation in Adhr-1 protein activity or nucleic acid expression. Such disorders include the disorders listed above.

Alternatively, the prognostic assays can be utilized to identify a subject having or at risk for developing a disorder associated with a misregulation in Adhr-1 protein activity or nucleic acid expression, such as the disorders listed above Thus, the present invention provides a method for identifying a disease or disorder associated with aberrant or unwanted Adhr-1 expression or activity in which a test sample is obtained from a subject and Adhr-1 protein or nucleic acid (e.g., mRNA or genomic DNA) is detected, wherein the presence of Adhr-1 protein or nucleic acid is diagnostic for a subject having or at risk of developing a disease or disorder associated with aberrant or unwanted Adhr-1 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted Adhr-1 expression or activity. For example, such methods can be used to determine whether a subject can be effectively treated with an agent for a Adh-associated disorder or a lipid metabolism-associated disorder. Thus, the present invention provides methods for determining whether a subject can be effectively treated with an agent for a disorder associated with aberrant or unwanted Adhr-1 expression or activity in which a test sample is obtained and Adhr-1 protein or nucleic acid expression or activity is detected (e.g., wherein the abundance of Adhr-1 protein or nucleic acid expression or activity is diagnostic for a subject that can be administered the agent to treat a disorder associated with aberrant or unwanted Adhr-1 expression or activity).

The methods of the invention can also be used to detect genetic alterations in an Adhr-1 gene, thereby determining if a subject with the altered gene is at risk for a disorder characterized by misregulation in Adhr-1 protein activity or nucleic acid expression, such as an Adh-associated disorder or a lipid metabolism-related disorder. In preferred embodiments, the methods include detecting, in a sample of cells from the subject, the presence or absence of a genetic alteration characterized by at least one of an alteration affecting the integrity of a gene encoding an Adhr-1 protein, or the mis-expression of the Adhr-1 gene. For example, such genetic alterations can be detected by ascertaining the existence of at least one of 1) a deletion of one or more nucleotides from an Adhr-1 gene; 2) an addition of one or more nucleotides to an Adhr-1 gene; 3) a substitution of one or more nucleotides of an Adhr-1 gene, 4) a chromosomal rearrangement of an Adhr-1 gene; 5) an alteration in the level of a messenger RNA transcript of an Adhr-1 gene, 6) aberrant modification of an Adhr-1 gene, such as of the methylation pattern of the genomic DNA, 7) the presence of a non-wild type splicing pattern of a messenger RNA transcript of an Adhr-1 gene, 8) a non-wild type level of an Adhr-1 protein, 9) allelic loss of an Adhr-1 gene, and 10) inappropriate post-translational modification of an Adhr-1 protein. As described herein, there are a large number of assays known in the art which can be used for detecting alterations in an Adhr-1 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the Adhr-1 gene (see Abravaya et al. (1995) *Nucleic Acids Res.*23:675–682). This method can include the steps of collecting a sample of cells from a subject, isolating nucleic acid (e.g., genomic, mRNA or both) from the cells of the sample, contacting the nucleic acid sample with one or more primers which specifically hybridize to an Adhr-1 gene under conditions such that hybridization and amplification of the Adhr-1 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an Adhr-1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in Adhr-1 can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in Adhr-1 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the Adhr-1 gene and detect mutations by comparing the sequence of the sample Adhr-1 with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the Adhr-1 gene include methods in which protection from cleavage agents is used to detect mismatched bases in RNA/RNA or RNA/DNA heteroduplexes (Myers et al. (1985) *Science* 230: 1242). In general, the art technique of "mismatch cleavage" starts by providing heteroduplexes of formed by hybridizing (labeled) RNA or DNA containing the wild-type Adhr-1 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in Adhr-1 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on an Adhr-1 sequence, e.g., a wild-type Adhr-1 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in Adhr-1 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125–144; and Hayashi (1992) *Genet. Anal. Tech. Appl.* 9:73–79). Single-stranded DNA fragments of sample and control Adhr-1 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an Adhr-1 gene.

Furthermore, any cell type or tissue in which Adhr-1 is expressed may be utilized in the prognostic assays described herein.

3. Monitoring of Effects During Clinical Trials

Monitoring the influence of agents (e.g., drugs) on the expression or activity of an Adhr-1 protein (e.g., the metabolism and catabolism of biochemical molecules necessary for energy production or storage, the modulation or facilitation of intra- or intercellular signaling, the metabolism or catabolism of metabolically important biomolecules, the detoxification of potentially harmful compounds) can be applied not only in basic drug screening, but also in clinical trials. For example, the effectiveness of an agent determined by a screening assay as described herein to increase Adhr-1 gene expression, protein levels, or upregulate Adhr-1 activity, can be monitored in clinical trials of subjects exhibiting decreased Adhr-1 gene expression, protein levels, or downregulated Adhr-1 activity. Alternatively, the effectiveness of an agent determined by a screening assay to decrease Adhr-1 gene expression, protein levels, or suppress Adhr-1 activity, can be monitored in clinical trials of subjects exhibiting increased Adhr-1 gene expression, protein levels, or upregulated Adhr-1 activity. In such clinical trials, the expression or activity of an Adhr-1 gene, and preferably, other genes that have been implicated in, for example, an Adhr-1-associated disorder can be used as a "read out" or markers of the phenotype of a particular cell.

For example, and not by way of limitation, genes, including Adhr-1, that are modulated in cells by treatment with an agent (e.g., compound, drug or small molecule) which modulates Adhr-1 activity (e.g., identified in a screening assay as described herein) can be identified. Thus, to study the effect of agents on Adhr-1-associated disorders (e.g., Adh-associated disorder, a disorders related to lipid metabolism), for example, in a clinical trial, cells can be isolated and RNA prepared and analyzed for the levels of expression of Adhr-1 and other genes implicated in the Adhr-1-associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of Adhr-1 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of an Adhr-1 protein, mRNA, or genomic DNA in the preadministration sample; (iii) obtaining one or more post-administration samples from the subject; (iv) detecting the level of expression or activity of the Adhr-1 protein, mRNA, or genomic DNA in the post-administration samples; (v) comparing the level of expression or activity of the Adhr-1 protein, mRNA, or genomic DNA in the pre-administration sample with the Adhr-1 protein, mRNA, or genomic DNA in the post administration sample or samples; and (vi) altering the administration of the agent to the subject accordingly. For example, increased administration of the agent may be desirable to increase the expression or activity of Adhr-1 to higher levels than detected, i.e., to increase the effectiveness of the agent. Alternatively, decreased administration of the agent may be desirable to decrease expression or activity of Adhr-1 to lower levels than detected, i.e. to decrease the effectiveness of the agent. According to such an embodiment, Adhr-1 expression or activity may be used as an indicator of the effectiveness of an agent, even in the absence of an observable phenotypic response.

D. Methods of Treatment

The present invention provides for both prophylactic and therapeutic methods of treating a subject at risk of (or susceptible to) a disorder or having a disorder associated with aberrant or unwanted Adhr-1 expression or activity, e.g., an Adh-associated disorder or a lipid metabolism-associated disorder. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the Adhr-1 molecules of the present invention or Adhr-1 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted Adhr-1 expression or activity, by administering to the subject an Adhr-1 or an agent which modulates Adhr-1 expression or at least one Adhr-1 activity. Subjects at risk for a disease which is caused or contributed to by aberrant or unwanted Adhr-1 expression or activity can be identified by, for example, any or a combination of diagnostic or prognostic assays as described herein. Administration of a prophylactic agent can occur prior to the manifestation of symptoms characteristic of the Adhr-1 aberrancy, such that a disease or disorder is prevented or, alternatively, delayed in its progression. Depending on the type of Adhr-1 aberrancy, for example, an Adhr-1, Adhr-1 agonist or Adhr-1 antagonist agent can be used for treating the subject. The appropriate agent can be determined based on screening assays described herein.

2. Therapeutic Methods

Another aspect of the invention pertains to methods of modulating Adhr-1 expression or activity for therapeutic purposes. Accordingly, in an exemplary embodiment, the modulatory method of the invention involves contacting a cell with an Adhr-1 or agent that modulates one or more of the activities of Adhr-1 protein activity associated with the cell. An agent that modulates Adhr-1 protein activity can be an agent as described herein, such as a nucleic acid or a protein, a naturally-occurring target molecule of an Adhr-1 protein (e.g., an Adhr-1 ligand or substrate), an Adhr-1 antibody, an Adhr-1 agonist or antagonist, a peptidomimetic of an Adhr-1 agonist or antagonist, or other small molecule. In one embodiment, the agent stimulates one or more Adhr-1 activities. Examples of such stimulatory agents include active Adhr-1 protein and a nucleic acid molecule encoding Adhr-1 that has been introduced into the cell. In another embodiment, the agent inhibits one or more Adhr-1 activities. Examples of such inhibitory agents include antisense Adhr-1 nucleic acid molecules, anti-Adhr-1 antibodies, and Adhr-1 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of an Adhr-1 protein or nucleic acid molecule such as an Adh-associated disorder or a lipid metabolism-associated disorder. In one embodiment, the method involves administering an agent (e.g., an agent identified by a screening assay described herein), or combination of agents that modulates (e.g., upregulates or downregulates) Adhr-1 expression or activity. In another embodiment, the method involves administering an Adhr-1 protein or nucleic acid molecule as therapy to compensate for reduced, aberrant, or unwanted Adhr-1 expression or activity.

Stimulation of Adhr-1 activity is desirable in situations in which Adhr-1 is abnormally downregulated and/or in which increased Adhr-1 activity is likely to have a beneficial effect. Likewise, inhibition of Adhr-1 activity is desirable in situations in which Adhr-1 is abnormally upregulated and/or in which decreased Adhr-1 activity is likely to have a beneficial effect.

3. Pharmacogenomics

The Adhr-1 molecules of the present invention, as well as agents, or modulators which have a stimulatory or inhibitory effect on Adhr-1 activity (e.g., Adhr-1 gene expression) as identified by a screening assay described herein can be administered to individuals to treat (prophylactically or therapeutically) Adhr-1-associated disorders (e.g., Adh-associated disorder, a disorder related to lipid metabolism) associated with aberrant or unwanted Adhr-1 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an Adhr-1 molecule or Adhr-1 modulator as well as tailoring the dosage and/or therapeutic regimen of treatment with an Adhr-1 molecule or Adhr-1 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11): 983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., an Adhr-1 protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C 19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., an Adhr-1 molecule or Adhr-1 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with an Adhr-1 molecule or Adhr-1 modulator, such as a modulator identified by one of the exemplary screening assays described herein.

E. Electronic Apparatus Readable Media and Arrays

Electronic apparatus readable media comprising Adhr-1 sequence information is also provided. As used herein, "Adhr-1 sequence information" refers to any nucleotide and/or amino acid sequence information particular to the Adhr-1 molecules of the present invention, including but not limited to full-length nucleotide and/or amino acid sequences, partial nucleotide and/or amino acid sequences, polymorphic sequences including single nucleotide polymorphisms (SNPs), epitope sequences, and the like. Moreover, information "related to" said Adhr-1 sequence information includes detection of the presence or absence of a sequence (e.g., detection of expression of a sequence, fragment, polymorphism, etc.), determination of the level of a sequence (e.g., detection of a level of expression, for example, a quantitative detection), detection of a reactivity to a sequence (e.g., detection of protein expression and/or levels, for example, using a sequence-specific antibody), and the like. As used herein, "electronic apparatus readable media" refers to any suitable medium for storing, holding, or containing data or information that can be read and accessed directly by an electronic apparatus. Such media can include, but are not limited to: magnetic storage media, such as floppy discs, hard disc storage medium, and magnetic tape; optical storage media such as compact discs; electronic storage media such as RAM, ROM, EPROM, EEPROM and the like; and general hard disks and hybrids of these categories such as magnetic/optical storage media. The medium is adapted or configured for having recorded thereon Adhr-1 sequence information of the present invention.

As used herein, the term "electronic apparatus" is intended to include any suitable computing or processing apparatus or other device configured or adapted for storing data or information. Examples of electronic apparatus suitable for use with the present invention include stand-alone computing apparatuses; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the Adhr-1 sequence information.

A variety of software programs and formats can be used to store the sequence information on the electronic apparatus readable medium. For example, the sequence information can be represented in a word processing text file, formatted in commercially-available software such as WordPerfect and Microsoft Word, represented in the form of an ASCII file, or stored in a database application, such as DB2, Sybase, Oracle, or the like, as well as in other forms. Any number of dataprocessor structuring formats (e.g., text file or database) may be employed in order to obtain or create a medium having recorded thereon the Adhr-1 sequence information.

By providing Adhr-1 sequence information in readable form, one can routinely access the sequence information for a variety of purposes. For example, one skilled in the art can use the sequence information in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has a Adhr-1 associated disease or disorder or a pre-disposition to a Adhr-1 associated disease or disorder, wherein the method comprises the steps of determining Adhr-1 sequence information associated with the subject and based on the Adhr-1 sequence information, determining whether the subject has a Adhr-1 associated disease or disorder or a pre-disposition to a Adhr-1 associated disease or disorder, and/or recommending a particular treatment for the disease, disorder, or pre-disease condition.

The present invention further provides in an electronic system and/or in a network, a method for determining whether a subject has a Adhr-1 associated disease or disorder or a pre-disposition to a disease associated with Adhr-1 wherein the method comprises the steps of determining Adhr-1 sequence information associated with the subject, and based on the Adhr-1 sequence information, determining whether the subject has a Adhr-1 associated disease or disorder or a pre-disposition to a Adhr-1 associated disease or disorder, and/or recommending a particular treatment for the disease, disorder or pre-disease condition. The method may further comprise the step of receiving phenotypic information associated with the subject and/or acquiring from a network phenotypic information associated with the subject.

The present invention also provides in a network, a method for determining whether a subject has a Adhr-1 associated disease or disorder or a pre-disposition to a Adhr-1 associated disease or disorder associated with Adhr-1, said method comprising the steps of receiving Adhr-1 sequence information from the subject and/or information related thereto, receiving phenotypic information associated with the subject, acquiring information from the network corresponding to Adhr-1 and/or a Adhr-1 associated disease or disorder, and based on one or more of the phenotypic information, the Adhr-1 information (e.g., sequence information and/or information related thereto), and the acquired information, determining whether the subject has a Adhr-1 associated disease or disorder or a pre-disposition to a Adhr-1 associated disease or disorder. The method may further comprise the step of recommending a particular treatment for the disease, disorder or pre-disease condition.

The present invention also provides a business method for determining whether a subject has a Adhr-1 associated disease or disorder or a pre-disposition to a Adhr-1 associated disease or disorder, said method comprising the steps of receiving information related to Adhr-1 (e.g., sequence information and/or information related thereto), receiving phenotypic information associated with the subject, acquiring information from the network related to Adhr-1 and/or related to a Adhr-1 associated disease or disorder, and based on one or more of the phenotypic information, the Adhr-1 information, and the acquired information, determining whether the subject has a Adhr-1 associated disease or disorder or a pre-disposition to a Adhr-1 associated disease or disorder. The method may further comprise the step of recommending a particular treatment for the disease, disorder or pre-disease condition.

The invention also includes an array comprising a Adhr-1 sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, one of which can be Adhr-1. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a Adhr-1 associated disease or disorder, progression of Adhr-1 associated disease or disorder, and processes, such a cellular transformation associated with the Adhr-1 associated disease or disorder.

The array is also useful for ascertaining the effect of the expression of a gene on the expression of other genes in the same cell or in different cells (e.g., ascertaining the effect of Adhr-1 expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including Adhr-1) that could serve as a molecular target for diagnosis or therapeutic intervention.

This invention is further illustrated by the following examples which should not be construed as limiting. The contents of all references, patents and published patent applications cited throughout this application, as well as the Figures and the Sequence Listing, are incorporated herein by reference.

EXAMPLES

Example 1

Identification and Characterization of Human Adhr-1 cDNA

In this example, the identification and characterization of the gene encoding human Adhr-1 (clone Fbh39228) is described.

Isolation of the human Adhr-1 cDNA

The invention is based, at least in part, on the discovery of a human gene encoding a novel protein, referred to herein as Adhr-1. The entire sequence of the human clone Fbh39228 was determined and found to contain an open reading frame termed human "Adhr-1." The nucleotide sequence encoding the human Adhr-1 protein is shown in FIGS. 1A–B and is set forth as SEQ ID NO:1. The protein encoded by this nucleic acid comprises about 377 amino acids and has the amino acid sequence shown in FIGS.

1A–B and set forth as SEQ ID NO:2. The coding region (open reading frame) of SEQ ID NO:1 is set forth as SEQ ID NO:3.

Analysis of the Human Adhr-1 Molecule

A search for domain consensus sequences was performed using the amino acid sequence of Adhr-1 and a database of HMMs (the Pfam database, release 2.1) using the default parameters (described above). The search revealed an ADH-Zn domain (Pfam label ADH_ZINC; Pfam Accession Number PS00059) within SEQ ID NO:2 at residues 47–368 and an Lipase-SER domain (Pfam label LIPASE_GDSL_ser; Pfam Accession Number PS01098) within SEQ ID NO:2 at residues 103–189 (see FIGS. 3A–B).

A search was performed against the ProDom database resulting in the identification of a portion of the deduced amino acid sequence of human Adhr-1 (SEQ ID NO:2) which has a 27% identity to ProDom Accession Number PD000104 ("Oxidoreductase zinc dehydrogenase alcohol NAD protein family multigene NADP formaldehyde") over residues 54 to 367. In addition, human Adhr-1 is 40% identical to ProDom entry "Quinone oxidoreductase NADPH:quinone NADP reductase zinc protein crystallin zeta-NADPH" over residues 33 to 84. The results of this analysis are set forth in FIG. 4.

A search was also performed against the Prosite database, and resulted in the identification of several possible N-glycosylation sites within the human Adhr-1 protein at residues 75–78 and 80–83. In addition, protein kinase C phosphorylation sites were identified within the human Adhr-1 protein at residues 89–91, 112–114, 145–147, 163–165, 193–195, and 362–364. This search also identified casein kinase II phosphorylation sites at residues 128–131, 163–166, 205–208, and 344–347 of human Adhr-1. A tyrosine phosphorylation site motif was also identified in the human Adhr-1 protein at residues 10–17. The search also identified the presence of N-myristoylation site motifs at residues 73–78, 108–113, 118–123, 169–174, 202–207, and 287–292. In addition, the search identified an amidation site at residues 172–175, and a microbody C-terminal targeting signal at residues 375–377 of human Adhr-1.

An analysis of the possible cellular localization of the Adhr-1 protein based on its amino acid sequence was performed using the methods and algorithms described in Nakai and Kanehisa (1992) *Genomics* 14:897–911, and at the PSORT website maintained by the Human Genome Center at the Institute of Medical Science in the University of Tokyo, Japan (psort.nibb.ac.jp). The results from this analysis predict that the Adhr-1 protein is found in the peroxisomes, in the cytoplasm, and in the mitochondria.

Example 2

Expression of Recombinant Adhr-1 Protein in Bacterial Cells

In this example, Adhr-1 is expressed as a recombinant glutathione-S-transferase (GST) fusion polypeptide in *E. coli* and the fusion polypeptide is isolated and characterized.

Specifically, Adhr-1 is fused to GST and this fusion polypeptide is expressed in *E. coli*, e.g., strain PEB199. Expression of the GST-Adhr-1 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant Adhr-1 Protein in COS Cells

To express the Adhr-1 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire Adhr-1 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the Adhr-1 DNA sequence is amplified by PCR using two primers. The 5' primer contains the restriction site of interest followed by approximately twenty nucleotides of the Adhr-1 coding sequence starting from the initiation codon; the 3' end sequence contains complementary sequences to the other restriction site of interest, a translation stop codon, the HA tag or FLAG tag and the last 20 nucleotides of the Adhr-1 coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the Adhr-1 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the Adhr-1-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989. The expression of the Adhr-1 polypeptide is detected by radiolabeling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S -methionine (or $^{35}$S -cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the Adhr-1 coding sequence is cloned directly into the polylinker of the pcDNA/Amp vector using the appropriate restriction sites. The resulting plasmid is transfected into COS cells in the manner described above, and the expression of the Adhr-1 polypeptide is detected by radiolabeling and immunoprecipitation using an Adhr-1 specific monoclonal antibody.

Example 4

Tissue Distribution of Human Adhr-1 mRNA Using Taq-man™ Analysis

This example describes the tissue distribution of human ADHR-1 mRNA in a variety of cells and tissues, as determined using the TaqMan™ procedure. The Taqman™ procedure is a quantitative, reverse transcription PCR-based approach for detecting mRNA. The RT-PCR reaction exploits the 5' nuclease activity of AmpliTaq Gold™ DNA Polymerase to cleave a TaqMan™ probe during PCR. Briefly, cDNA was generated from the samples of interest, e.g., various human tissue samples, and used as the starting material for PCR amplification. In addition to the 5' and 3' gene-specific primers, a gene-specific oligonucleotide probe (complementary to the region being amplified) was included in the reaction (i.e., the Taqman™ probe). The TaqMan™ probe includes the oligonucleotide with a fluorescent reporter dye covalently linked to the 5' end of the probe (such as FAM (6-carboxyfluorescein), TET (6-carboxy-4,7,2',7'-tetrachlorofluorescein), JOE (6-carboxy-4,5-dichloro-2,7-dimethoxyfluorescein), or VIC) and a quencher dye (TAMRA (6-carboxy-N,N,N',N'-tetramethylrhodamine) at the 3' end of the probe.

During the PCR reaction, cleavage of the probe separates the reporter dye and the quencher dye, resulting in increased fluorescence of the reporter. Accumulation of PCR products is detected directly by monitoring the increase in fluorescence of the reporter dye. When the probe is intact, the proximity of the reporter dye to the quencher dye results in suppression of the reporter fluorescence. During PCR, if the target of interest is present, the probe specifically anneals between the forward and reverse primer sites. The 5'-3' nucleolytic activity of the AmpliTaq™ Gold DNA Polymerase cleaves the probe between the reporter and the quencher only if the probe hybridizes to the target. The probe fragments are then displaced from the target, and polymerization of the strand continues. The 3' end of the probe is blocked to prevent extension of the probe during PCR. This process occurs in every cycle and does not interfere with the exponential accumulation of product. RNA was prepared using the trizol method and treated with DNase to remove contaminating genomic DNA. cDNA was synthesized using standard techniques. Mock cDNA synthesis in the absence of reverse transcriptase resulted in samples with no detectable PCR amplification of the control gene confirms efficient removal of genomic DNA contamination.

Figure 5:
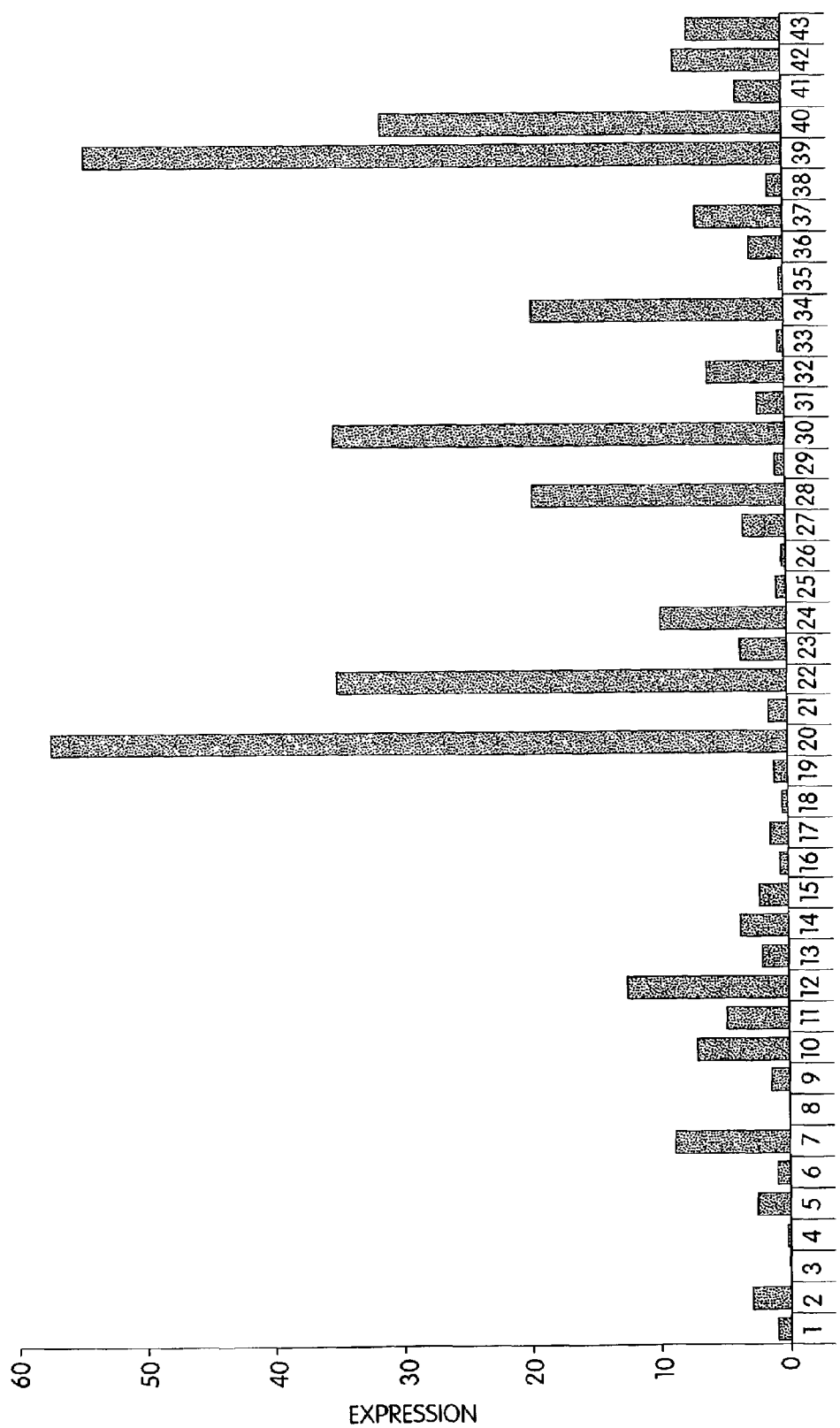
FIG. 5 is a graph depicting the results of the expression profile of Adhr-1 in various human tumors and normal tissues as determined by a TaqMan® Quantitative Polymerase Chain Reaction analysis.

As indicated in FIG. 5, expression of ADHR-1 mRNA was upregulated in various tumors, e.g., 100% of lung tumor samples analyzed had a higher level of expression as compared to normal lung tissues. Similarly, the expression of this gene was found to be upregulated in 100% of the prostate tumor samples analyzed, 75% of the colon tumor samples analyzed, 100% of the colon to liver metastasis samples analyzed, 25% of the breast tumor samples analyzed, and 20% of the ovarian tumor samples analyzed, as compared to their normal tissue counterparts.

Expression of Adhr-1 was also detected in tumor derived cell lines such as insulinoma (HepG-2), acute promyelocytic leukemia (HL-60), melanoma (G361), erythroleukemia cells, mast cells (HMC-1), cervical squamous cell carcinomas, ovarian cancer cell lines (e.g., SKOV3/Var which are a variant of the parental SKOV3 ovarian cancer cell line that are cisplatin resistant, A2780, A2780/ADR, OVCAR-3, HEY, MDA2774, and ES2 cell lines). Furthermore, it was found that the expression of Adhr-1 was upregulated in SKOV3/var cells when this cell line was treated with the growth factor heregulin, demonstrating that Adhr-1 may be acting in the same signaling pathway as the epidermal growth factor receptor (EGFR) family which includes EGFR, Her2, Her3 and Her4.

Strong expression of Adhr-1 was detected in skeletal muscle tissues and in tissues derived from normal brain cortex. In addition, weak to intermediate expression of Adhr-1 was detected in normal tissues like keratinocytes, mammary gland, thymus, spleen small intestine, retina, retinal pigmentosa epithelia, normal ovarian epithelia, normal megakaryocyte, placenta, aortic endothelial, Th-1 and Th-2-induced T cells, HUVEC (untreated) and HUVEC (hypoxia), and in fetal tissues derived from the heart, kidney, lung, and dorsal spinal chord.

II. 21956 and 25856, Novel Human Aminiopeptidases and Uses Thereof

BACKGROUND OF THE INVENTION

The degradation, inactivation, and/or activation of proteins is of critical importance in most metabolic pathways in cells and within the various systems of the body. A large family of closely related enzymes which catalyze the hydrolysis of amino acid residues from the amino-terminus of protein or peptide substrates, termed aminopeptidases, has been identified. Members of the aminopeptidase family are found in nearly all organisms, from microbes to plants to humans. They are widely distributed in many tissues and cells. Some aminopeptidases are secreted, while others are cytosolic or membrane-bound. Aminopeptidases can also be found in many subcellular organelles (Taylor (1993) *FASEB* 7:290; Sanderink et al. (1988) *J. Clin. Chem. Clin. Biochem.* 26:795–807; Taylor (1993) *Trends Biochem. Sci.* 18:167–171).

Different classes of aminopeptidases have been identified and are classified, in part, based on their specificity as to the amino acid residues to be removed (e.g., leucine aminopeptidase, X-prolyl aminopeptidase, arginyl-aminopeptidase, alanyl-aminopeptidase, glutamyl-aminopeptidase, and aspartyl-aminopeptidase). Aminopeptidases are also classified based on the number of amino acid residues that are cleaved from the amino-terminus of peptides or proteins (e.g., aminodipeptidases and aminotripeptidases). Most, but not all aminopeptidases are identified as metalloenzymes, and contain one or more $Zn^{2+}$ binding sites (Taylor (1993) *FASEB* 7:290; Taylor (1993) *Trends Biochem. Sci.* 18:167–171).

Aminopeptidases play important roles in the degradation of nearly all proteins and polypeptides in a cell. Therefore, their activity contributes to the ability of the cell to grow and differentiate, to proliferate, to adhere and move, and to interact and communicate with other cells. Aminopeptidases participate in the metabolism of secreted regulatory molecules such as hormones and neurotransmitters and are also important in protein maturation (e.g., the conversion of pro-proteins and pro-hormones to their active forms), the inactivation of peptides, antigen presentation, the regulation of the cell cycle, and the regulation of synaptic transmission. In addition, aminopeptidases supply amino acids during starvation and degrade exogenous peptides to amino acids for nutrition (Taylor (1993) *FASEB* 7:290).

Aminopeptidases have been associated with several human disease states and conditions including cataracts, cystic fibrosis, cancer, leukemia, asthma, hypertension, and aging and may play a role in inflammation. Aminopeptidases have also been identified as indicators of several human diseases including liver disease, renal disease, thyroid disease, and Alzheimer's disease (Jung et al. (1987) *Clin. Chem. Acta*.168:187; Kuda et al. (1997) *Biochem. Biophys. Res. Commun.* 231:526; van der Velden et al. (1998) *Clin. Exp. Allergy* 28:110; Ramirez, et al. (1997) *Regul. Pept.* 72:155; Janas, et al. (1999) *Dig. Dis. Sci*.44:170; Taylor (1993) *FASEB* 7:290).

SUMMARY OF THE INVENTION

The present invention is based, at least in part, on the discovery of novel members of the family of aminopeptidase molecules, referred to herein as AP (for aminopeptidases) e.g., AP21956 and AP25856 nucleic acid and protein molecules. The AP nucleic acid and protein molecules of the present invention are useful as modulating agents in regulating a variety of cellular processes, e.g., cellular proliferation, growth, differentiation, or migration. Accordingly, in one aspect, this invention provides isolated nucleic acid molecules encoding AP proteins or biologically active portions thereof, as well as nucleic acid fragments suitable as primers or hybridization probes for the detection of AP-encoding nucleic acids.

In one embodiment, an AP nucleic acid molecule of the invention is at least 50%, 55%, 60%, 65%, 70%, 75%, 80%, 85%, 90%, 91%, 92%, 93%, 94%, 95%, 99% or more identical to the nucleotide sequence (e.g., to the entire length of the nucleotide sequence) shown in SEQ ID NO:4, 6, 7, or 9, or a complement thereof. In a preferred embodiment, the isolated nucleic acid molecule includes the nucleotide sequence shown in SEQ ID NO:4, 6, 7, or 9, or a complement thereof. In another embodiment, the nucleic acid molecule includes SEQ ID NO:6 and nucleotides 1–149 of SEQ ID NO:4. In a further embodiment, the nucleic acid molecule includes SEQ ID NO:6 and nucleotides 2540–3238 of SEQ ID NO:4. In yet another embodiment, the nucleic acid molecule includes SEQ ID NO:9 and nucleotides 1–217 of SEQ ID NO:7. In yet a further embodiment, the nucleic acid molecule includes SEQ ID NO:9 and nucleotides 809–1626 of SEQ ID NO:7. In another preferred embodiment, the nucleic acid molecule consists of the nucleotide sequence shown in SEQ ID NO:4, 6, 7, or 9. In yet another embodiment, the nucleic acid molecule comprises nucleotide residues 12432–3238 or 74–342 of SEQ ID NO:4. In yet another embodiment, the nucleic acid molecule consists of nucleotide residues 12432–3238 or 74–342 of SEQ ID NO:4. In yet another embodiment, the nucleic acid molecule comprises nucleotide residues 803–1101 or 1547–1626 of SEQ ID NO:7. In yet another embodiment, the nucleic acid molecule consists of nucleotide residues 803–1101 or 1547–1626 of SEQ ID NO:7.

In another embodiment, an AP nucleic acid molecule includes a nucleotide sequence encoding a protein having an amino acid sequence sufficiently identical to the amino acid sequence of SEQ ID NO:5 or 8. In a preferred embodiment, an AP nucleic acid molecule includes a nucleotide sequence encoding a protein having an amino acid sequence at least 50%, 55%, 60%, 65%, 70%, 75%, 80%, 85%, 90%, 91%, 92%, 93%, 94%, 95%, 96%, 97%, 98%, 99% or more identical to the entire length of the amino acid sequence of SEQ ID NO:5 or 8.

In another preferred embodiment, an isolated nucleic acid molecule encodes the amino acid sequence of a human AP, e.g., AP21956 or AP25856. In yet another preferred embodiment, the nucleic acid molecule includes a nucleotide sequence encoding a protein having the amino acid sequence of SEQ ID NO:5 or 8. In yet another preferred embodiment, the nucleic acid molecule is at least 21, 30, 40, 45, 50, 97, 100, 150, 200, 250, 300, 350, 400, 445, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250 or more nucleotides in length. In a further preferred embodiment, the nucleic acid molecule is at least 21, 30, 40, 45, 50, 97, 100, 150, 200, 250, 300, 350, 400, 445, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250 or more nucleotides in length and encodes a protein having an AP activity (as described herein).

Another embodiment of the invention features nucleic acid molecules, preferably AP nucleic acid molecules, which specifically detect AP nucleic acid molecules relative to nucleic acid molecules encoding non-AP proteins. For example, in one embodiment, such a nucleic acid molecule is at least 21, 30, 40, 45, 50, 97, 100, 150, 200, 250, 300, 350, 400, 445, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250 or more nucleotides in length and hybridizes under stringent conditions to a nucleic acid molecule comprising the nucleotide sequence shown in SEQ ID NO:4, 6, 7, or 9, or a complement thereof.

In preferred embodiments, the nucleic acid molecules are at least 15 (e.g., 15 contiguous) nucleotides in length and hybridize under stringent conditions to the nucleotide molecules set forth in SEQ ID NO:4, 6, 7, or 9, or a complement thereof.

In other preferred embodiments, the nucleic acid molecule encodes a naturally occurring allelic variant of a polypeptide comprising the amino acid sequence of SEQ ID NO:5 or 8, wherein the nucleic acid molecule hybridizes to a complement of a nucleic acid molecule comprising SEQ ID NO:4, 6, 7, or 9, respectively, under stringent conditions.

Another embodiment of the invention provides an isolated nucleic acid molecule which is antisense to an AP nucleic acid molecule, e.g., the coding strand of an AP nucleic acid molecule.

Another aspect of the invention provides a vector comprising an AP nucleic acid molecule. In certain embodiments, the vector is a recombinant expression vector. In another embodiment, the invention provides a host cell containing a vector of the invention. In yet another embodiment, the invention provides a host cell containing a nucleic acid molecule of the invention. The invention also provides a method for producing a protein, preferably an AP protein, by culturing in a suitable medium, a host cell, e.g., a mammalian host cell such as a non-human mammalian cell, of the invention containing a recombinant expression vector, such that the protein is produced.

Another aspect of this invention features isolated or recombinant AP proteins and polypeptides. In one embodiment, an isolated AP protein includes at least one or more of the following domains: a transmembrane domain, a signal peptide domain, a dipeptidyl peptidase IV N-terminal domain, a prolyl oligopeptidase domain, and/or a dienelactone hydrolase domain.

In a preferred embodiment, an AP protein includes at least one or more of the following domains: a transmembrane domain, a signal peptide domain, a dipeptidyl peptidase IV N-terminal domain, a prolyl oligopeptidase domain, and/or a dienelactone hydrolase domain, and has an amino acid sequence at least about 50%, 55%, 60%, 65%, 67%, 68%, 70%, 75%, 80%, 85%, 90%, 91%, 92%, 93%, 94%, 95%, 96%, or more identical to the amino acid sequence of SEQ ID NO:5 or 8. In another preferred embodiment, an AP protein includes at least one or more of the following domains: a transmembrane domain, a signal peptide domain, a dipeptidyl peptidase IV N-terminal domain, a prolyl oligopeptidase domain, and/or a dienelactone hydrolase domain, and has an AP activity ( as described herein).

In yet another preferred embodiment, an AP protein includes at least one or more of the following domains: a transmembrane domain, a signal peptide domain, a dipeptidyl peptidase IV N-terminal domain, a prolyl oligopeptidase domain, and/or a dienelactone hydrolase domain, and is encoded by a nucleic acid molecule having a nucleotide sequence which hybridizes under stringent hybridization conditions to a complement of a nucleic acid molecule comprising the nucleotide sequence of SEQ ID NO:4, 6, 7, or 9.

In another embodiment, the invention features fragments of the protein having the amino acid sequence of SEQ ID NO:5 or 8, wherein the fragment comprises at least 32 amino acids (e.g., contiguous amino acids) of the amino acid sequence of SEQ ID NO:5 or 8. In another embodiment, an AP protein has the amino acid sequence of SEQ ID NO:5 or 8.

In another embodiment, the invention features an AP protein which is encoded by a nucleic acid molecule consisting of a nucleotide sequence at least about 50%, 55%, 60%, 65%, 70%, 75%, 80%, 85%, 90%, 91%, 92%, 93%, 94%, 95%, 96%, 97%, 98%, 99% or more identical to a nucleotide sequence of SEQ ID NO:4, 6, 7, or 9, or a complement thereof. This invention further features an AP protein which is encoded by a nucleic acid molecule consisting of a nucleotide sequence which hybridizes under stringent hybridization conditions to a complement of a nucleic acid molecule comprising the nucleotide sequence of SEQ ID NO:4, 6, 7, or 9.

The proteins of the present invention or portions thereof, e.g., biologically active portions thereof, can be operatively linked to a non-AP polypeptide (e.g., heterologous amino acid sequences) to form fusion proteins. The invention further features antibodies, such as monoclonal or polyclonal antibodies, that specifically bind proteins of the invention, preferably AP proteins. In addition, the AP proteins or biologically active portions thereof can be incorporated into pharmaceutical compositions, which optionally include pharmaceutically acceptable carriers.

In another aspect, the present invention provides a method for detecting the presence of an AP nucleic acid molecule, protein, or polypeptide in a biological sample by contacting the biological sample with an agent capable of detecting an AP nucleic acid molecule, protein, or polypeptide such that the presence of an AP nucleic acid molecule, protein or polypeptide is detected in the biological sample.

In another aspect, the present invention provides a method for detecting the presence of AP activity in a biological sample by contacting the biological sample with an agent capable of detecting an indicator of AP activity such that the presence of AP activity is detected in the biological sample.

In another aspect, the invention provides a method for modulating AP activity comprising contacting a cell capable of expressing AP with an agent that modulates AP activity such that AP activity in the cell is modulated. In one embodiment, the agent inhibits AP activity. In another embodiment, the agent stimulates AP activity. In one embodiment, the agent is an antibody that specifically binds to an AP protein. In another embodiment, the agent modulates expression of AP by modulating transcription of an AP gene or translation of an AP mRNA. In yet another embodiment, the agent is a nucleic acid molecule having a nucleotide sequence that is antisense to the coding strand of an AP mRNA or an AP gene.

In one embodiment, the methods of the present invention are used to treat a subject having a disorder characterized by aberrant or unwanted AP protein or nucleic acid expression or activity by administering an agent which is an AP modulator to the subject. In one embodiment, the AP modulator is an AP protein. In another embodiment the AP modulator is an AP nucleic acid molecule. In yet another embodiment, the AP modulator is a peptide, peptidomimetic, or other small molecule. In a preferred embodiment, the disorder characterized by aberrant or unwanted AP protein or nucleic acid expression is a aminopeptidase-associated disorder, e.g., a CNS disorder, a cellular proliferation, growth, differentiation, or migration disorder, a metabolic disorder, an inflammatory disorder, an immune disorder, a hormonal disorder, a cardiovascular disorder, or a digestive disorder.

The present invention also provides diagnostic assays for identifying the presence or absence of a genetic alteration characterized by at least one of (i) aberrant modification or mutation of a gene encoding an AP protein; (ii) misregulation of the gene; and (iii) aberrant post-translational modification of an AP protein, wherein a wild-type form of the gene encodes a protein with an AP activity.

In another aspect the invention provides methods for identifying a compound that binds to or modulates the activity of an AP protein, by providing an indicator composition comprising an AP protein having AP activity, contacting the indicator composition with a test compound, and determining the effect of the test compound on AP activity in the indicator composition to identify a compound that modulates the activity of an AP protein.

Other features and advantages of the invention will be apparent from the following detailed description and claims.

DETAILED DESCRIPTION OF THE INVENTION

The present invention is based, at least in part, on the discovery of novel molecules, referred to herein as "AP" (for aminopeptidases) e.g., AP21956 and AP25856 nucleic acid and protein molecules, which are novel members of a family of enzymes possessing aminopeptidase activity. These novel molecules are capable of catalyzing the hydrolysis of amino acids from protein or peptide substrates, and, thus, play a role in or function in a variety of cellular processes, e.g., proliferation, growth, differentiation, migration, immune responses, hormonal responses, metabolic regulation, and inter- or intra-cellular communication.

As used herein, the term "aminopeptidase" includes a molecule which is involved in catalyzing the hydrolysis of amino acids from protein or peptide substrates (e.g., the hydrolysis of proline, arginine, lysine, and the like). Aminopeptidase molecules are involved in the metabolism and catabolism of biochemical molecules necessary for energy production or storage, for intra- or inter-cellular signaling, and in the metabolism or catabolism of metabolically important biomolecules. Examples of aminopeptidases include dipeptidylpeptidases, leucine aminopeptidases, X-prolyl aminopeptidases, arginyl-aminopeptidases, alanyl-aminopeptidases, glutamyl-aminopeptidases, and aspartyl-aminopeptidases. Thus, the AP molecules of the present invention provide novel diagnostic targets and therapeutic agents to control aminopeptidase-associated disorders.

As used herein, an "aminopeptidase-associated disorder" includes a disorder, disease or condition which is caused or characterized by a misregulation (e.g., downregulation or upregulation) of aminopeptidase activity. Aminopeptidase-associated disorders can detrimentally affect cellular functions such as cellular proliferation, growth, differentiation, or migration, inter- or intra-cellular communication; tissue function, such as cardiac function or musculoskeletal function; systemic responses in an organism, such as nervous system responses, hormonal responses (e.g., insulin response), or immune responses. Examples of aminopeptidase-associated disorders include CNS disorders such as cognitive and neurodegenerative disorders, examples of which include, but are not limited to, Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis, progressive supranuclear palsy, epilepsy, and Jakob-Creutzfieldt disease; autonomic function disorders such as hypertension and sleep disorders, and neuropsychiatric disorders, such as depression, schizophrenia, schizoaffective disorder, korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), and bipolar affective neurological disorders, e.g., migraine and obesity. Further CNS-related disorders include, for example, those listed in the American Psychiatric Association's Diagnostic and Statistical manual of Mental Disorders (DSM), the most current version of which is incorporated herein by reference in its entirety.

Further examples of aminopeptidase-associated disorders include cardiac-related disorders. Cardiovascular system disorders in which the AP molecules of the invention may be directly or indirectly involved include arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrillation, Jervell syndrome, Lange-Nielsen syndrome, long-QT syndrome, congestive heart failure, sinus node dysfunction, angina, heart failure, hypertension, atrial fibrillation, atrial flutter, dilated cardiomyopathy, idiopathic cardiomyopathy, myocardial infarction, coronary artery disease, coronary artery spasm, and arrhythmia. AP-mediated or related disorders also include disorders of the musculoskeletal system such as paralysis and muscle weakness, e.g., ataxia, myotonia, and myokymia.

Aminopeptidase disorders also include cellular proliferation, growth, differentiation, or migration disorders. Cellular proliferation, growth, differentiation, or migration disorders include those disorders that affect cell proliferation, growth, differentiation, or migration processes. As used herein, a "cellular proliferation, growth, differentiation, or migration process" is a process by which a cell increases in number, size or content, by which a cell develops a specialized set of characteristics which differ from that of other cells, or by which a cell moves closer to or further from a particular location or stimulus. The AP molecules of the present invention are involved in signal transduction mechanisms, which are known to be involved in cellular growth, differentiation, and migration processes. Thus, the AP molecules may modulate cellular growth, differentiation, or migration, and may play a role in disorders characterized by aberrantly regulated growth, differentiation, or migration. Such disorders include cancer, e.g., carcinoma, sarcoma, or leukemia; tumor angiogenesis and metastasis; skeletal dysplasia; hepatic disorders; and hematopoietic and/or myeloproliferative disorders.

AP-associated or related disorders also include hormonal disorders, such as conditions or diseases in which the production and/or regulation of hormones in an organism is aberrant. Examples of such disorders and diseases include type I and type II diabetes mellitus, pituitary disorders (e.g., growth disorders), thyroid disorders (e.g., hypothyroidism or hyperthyroidism), and reproductive or fertility disorders (e.g., disorders which affect the organs of the reproductive system, e.g., the prostate gland, the uterus, or the vagina; disorders which involve an imbalance in the levels of a reproductive hormone in a subject; disorders affecting the ability of a subject to reproduce; and disorders affecting secondary sex characteristic development, e.g., adrenal hyperplasia).

AP-associated or related disorders also include inflammatory or immune system disorders, examples of which include, but are not limited to viral infection, inflammatory bowel disease, ulcerative colitis, Crohn's disease, leukocyte adhesion deficiency II syndrome, peritonitis, chronic obstructive pulmonary disease, lung inflammation, asthma, acute appendicitis, septic shock, nephritis, amyloidosis, rheumatoid arthritis, chronic bronchitis, sarcoidosis, scleroderma, lupus, polymyositis, Reiter's syndrome, psoriasis, pelvic inflammatory disease, inflammatory breast disease, orbital inflammatory disease, immune deficiency disorders (e.g., HIV, common variable immunodeficiency, congenital X-linked infantile hypogammaglobulinemia, transient hypogammaglobulinemia, selective IgA deficiency, chronic mucocutaneous candidiasis, severe combined immunodeficiency, common variable immunodeficiency, or chronic mucocutaneous candidiasis), autoimmune disorders.

An AP associated disorder also includes a hematopoietic or thrombotic disorder, for example, disseminated intravascular coagulation, thromboembolic vascular disease, anemia, lymphoma, leukemia, neutrophilia, neutropenia, myeloproliferative disorders, thrombocytosis, thrombocytopenia, von Willebrand disease, and hemophilia.

In addition, AP associated disorders include gastrointestinal and digestive disorders including, but not limited to, esophageal disorders such as atresia and fistulas, stenosis, achalasia, esophageal rings and webs, hiatal hernia, lacerations, esophagitis, diverticula, systemic sclerosis (scleroderma), varices, esophageal tumors such as squamous cell carcinomas and adenocarcinomas, stomach disorders such as diaphragmatic hernias, pyloric stenosis, dyspepsia, gastritis, acute gastric erosion and ulceration, peptic ulcers, stomach tumors such as carcinomas and sarcomas, small intestine disorders such as congenital atresia and stenosis, diverticula, Meckel's diverticulum, pancreatic rests, ischemic bowel disease, infective enterocolitis, Crohn's disease, tumors of the small intestine such as carcinomas and sarcomas, disorders of the colon such as malabsorption, obstructive lesions such as hernias, megacolon, diverticular disease, melanosis coli, ischemic injury, hemorrhoids, angiodysplasia of right colon, inflammations of the colon such as ulcerative colitis, and tumors of the colon such as polyps and sarcomas; as well as metabolic disorders (e.g., lysosomal storage disease, type II glycogenolysis, Fabry's disease, enzyme deficiencies, and inborn errors of metabolism); hepatic disorders and renal disorders (e.g., renal failure and glomerulonephritis).

AP-associated or related disorders also include disorders affecting tissues in which AP protein is expressed.

As used herein, a "aminopeptidase-mediated activity" includes an activity which involves catalyzing the hydrolysis of amino acids from protein or peptide substrates, e.g., biochemical molecules in a neuronal cell, a muscle cell, or a liver cell associated with the regulation of one or more cellular processes. Aminopeptidase-mediated activities include the catalyzing the hydrolysis of amino acids from protein or peptide substrates necessary, e.g., for energy production or storage, for intra- or inter-cellular signaling, for metabolism or catabolism of metabolically important biomolecules, immune responses, hormonal responses, and cell proliferation, growth, differentiation, and migration.

The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin, e.g., monkey proteins. Members of a family may also have common functional characteristics.

For example, in one embodiment of the invention, the family of AP proteins of the present invention comprises at least one "transmembrane domain." As used herein, the term "transmembrane domain" includes an amino acid sequence of about 20 amino acid residues in length which spans the plasma membrane. More preferably, a transmembrane domain includes about at least 15, 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta, W. N. et al., (1996) *Annual Rev. Neurosci.* 19: 235–263, the contents of which are incorporated herein by reference. Amino acid residues 34–56 and 251–274 of the native AP21956 protein are predicted to comprise transmembrane domains. Accordingly, AP proteins having at least 50–60% homology, preferably about 60–70%, more preferably about 70–80%, or about 80–90% homology with a transmembrane domain of human AP are within the scope of the invention.

In another embodiment of the invention, an AP protein of the present invention is identified based on the presence of a signal peptide. The prediction of such a signal peptide can be made, for example, by using the computer algorithm SignalP (Henrik et al. (1997) *Protein Engineering* 10:1–6).

As used herein, a "signal sequence" or "signal peptide" includes a peptide containing about 50 or more amino acids which occurs at the N-terminus of secretory and membrane bound proteins and which contains a large number of hydrophobic amino acid residues. For example, a signal sequence contains at least about 30–60 amino acid residues, preferably about 35–55 amino acid residues, more preferably about 50–55 amino acid residues, and more preferably about 53 amino acid residues, and has at least about 35–65%, preferably about 38–50%, and more preferably about 40–45% hydrophobic amino acid residues (e.g., Valine, Leucine, Isoleucine or Phenylalanine). Such a "signal sequence", also referred to in the art as a "signal peptide," serves to direct a protein containing such a sequence to a lipid bilayer, and is cleaved in secreted and membrane bound proteins. A possible signal sequence was identified in the amino acid sequence of human AP21956 at about amino acids 1–53 of SEQ ID NO:5.

In another embodiment, an AP molecule of the present invention is identified based on the presence of a "dipeptidyl peptidase IV N-terminal domain" in the protein or corresponding nucleic acid molecule. As used herein, the term "dipeptidyl peptidase IV N-terminal domain" includes a protein domain having an amino acid sequence of about 400–600 amino acid residues and a bit score of 100, 200, 300, 400, 500, 600 or more. Preferably, a dipeptidyl peptidase IV N-terminal domain includes at least about 450–550, or more preferably about 509 amino acid residues, and a bit score of at least 588.2. To identify the presence of a dipeptidyl peptidase IV N-terminal domain in an AP protein, and make the determination that a protein of interest has a particular profile, the amino acid sequence of the protein is searched against a database of known protein domains (e.g., the HMM database). The dipeptidyl peptidase IV N-terminal domain (HMM) has been assigned the PFAM Accession number PF00930 (found at Pfam website, sanger.ac.uk). A search was performed against the HMM database resulting in the identification of a dipeptidyl peptidase IV N-terminal domain in the amino acid sequence of human AP21956 (SEQ ID NO:5) at about residues 69–578 of SEQ ID NO:5.

In another embodiment, an AP molecule of the present invention is identified based on the presence of a "prolyl oligopeptidase domain" in the protein or corresponding nucleic acid molecule. As used herein, the term "prolyl oligopeptidase domain" includes a protein domain having an amino acid sequence of about 40–120 amino acid residues and a bit score of 20, 30, 40, 50, 60, 80, 100 or more. Preferably, a prolyl oligopeptidase domain includes at least about 50–90, or more preferably about 76 amino acid residues and a bit score of 71.7. To identify the presence of a prolyl oligopeptidase domain in an AP protein, and make the determination that a protein of interest has a particular profile, the amino acid sequence of the protein is searched against a database of known protein domains (e.g., the HMM database). The prolyl oligopeptidase domain (HMM) has been assigned the PFAM Accession number PF00326 (found at Pfam website, sanger.ac.uk). A search was performed against the HMM database resulting in the identification of a prolyl oligopeptidase domain in the amino acid sequence of human AP21956 (SEQ ID NO:5) at about residues 580–656 of SEQ ID NO:5.

In another embodiment, an AP molecule of the present invention is identified based on the presence of a "dienelactone hydrolase domain" in the protein or corresponding nucleic acid molecule. As used herein, the term "dienelactone hydrolase domain" includes a protein domain having an amino acid sequence of about 20–60 amino acid residues and a bit score of 5, 6, 7, 8, 9, 10, 11, 12 or more. Preferably, a dienelactone hydrolase domain includes at least about 30–50, or more preferably about 40 amino acid residues, and a bit score of 9.6. To identify the presence of a dienelactone hydrolase domain in an AP protein, and make the determination that a protein of interest has a particular profile, the amino acid sequence of the protein is searched against a database of known protein domains (e.g., the HMM database). The dienelactone hydrolase domain (HMM) has been assigned the PFAM Accession number PF01738 (found at Pfam website, sanger.ac.uk). A search was performed against the HMM database resulting in the identification of an dienelactone hydrolase domain in the amino acid sequence of human AP21956 (SEQ ID NO:5) at about residues 719–759.

In a preferred embodiment, the AP molecules of the invention include at least one or more of the following domains: a transmembrane domain, a signal peptide domain, a dipeptidyl peptidase IV N-terminal domain, a prolyl oligopeptidase domain, and/or a dienelactone hydrolase domain.

Isolated proteins of the present invention, preferably AP proteins, have an amino acid sequence sufficiently identical to the amino acid sequence of SEQ ID NO:5 or 8, or are encoded by a nucleotide sequence sufficiently identical to SEQ ID NO:4, 6, 7, or 9. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%–80%, and even more preferably 90–95% homology across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70–80%, or 90–95% homology and share a common functional activity are defined herein as sufficiently identical.

As used interchangeably herein, "AP activity", "biological activity of AP" or "functional activity of AP," refers to an activity exerted by an AP protein, polypeptide or nucleic acid molecule on an AP responsive cell or tissue, or on an AP protein substrate, as determined in vivo, or in vitro, according to standard techniques. In one embodiment, an AP activity is a direct activity, such as an association with an AP-target molecule. As used herein, a "target molecule" or "binding partner" is a molecule with which an AP protein binds or interacts in nature, such that AP-mediated function is achieved. An AP target molecule can be a non-AP molecule or an AP protein or polypeptide of the present invention. In an exemplary embodiment, an AP target molecule is an AP ligand (e.g., a hormone or a neurotransmitter). Alternatively, an AP activity is an indirect activity, such as a cellular signaling activity mediated by interaction of the AP protein with an AP ligand. The biological activities of AP are described herein. For example, the AP proteins of the present invention can have one or more of the following activities: 1) modulate metabolism and catabolism of biochemical molecules necessary for energy production or storage, 2) modulate intra- or inter-cellular signaling, 3) modulate metabolism or catabolism of metabolically important biomolecules, 4) modulate metabolism of secreted biochemical molecules necessary for cell regulation (e.g., hormones or neurotransmitters), and 5) modulate degradation of peptides.

Accordingly, another embodiment of the invention features isolated AP proteins and polypeptides having an AP activity. Other preferred proteins are AP proteins having one or more of the following domains: a transmembrane domain, a signal peptide domain, a dipeptidyl peptidase IV N-terminal domain, a prolyl oligopeptidase domain, and/or a dienelactone hydrolase domain, and, preferably, an AP activity.

Additional preferred proteins have at least one of a transmembrane domain, a signal peptide domain, a dipeptidyl peptidase IV N-terminal domain, a prolyl oligopeptidase domain, and/or a dienelactone hydrolase domain, and are, preferably, encoded by a nucleic acid molecule having a nucleotide sequence which hybridizes under stringent hybridization conditions to a complement of a nucleic acid molecule comprising the nucleotide sequence of SEQ ID NO:4, 6, 7, or 9.

The nucleotide sequence of the isolated human AP21956 cDNA and the predicted amino acid sequence of the human AP21956 polypeptide are shown in FIGS. 6A–C and in SEQ ID NO:4 and 5, respectively. The nucleotide sequence of the isolated human AP25856 cDNA and the predicted amino acid sequence of the human AP25856 polypeptide are shown in FIGS. 7A–B and in SEQ ID NO:7 and 8, respectively.

The human AP21956 gene, which is approximately 3238 nucleotides in length, encodes a protein having a molecular weight of approximately 87.56 kD and which is approximately 796 amino acid residues in length. The human AP25856 gene, which is approximately 1626 nucleotides in length, encodes a protein having a molecular weight of approximately 21.56 kD and which is approximately 196 amino acid residues in length.

Various aspects of the invention are described in further detail in the following subsections:

I. Isolated Nucleic Acid Molecules

One aspect of the invention pertains to isolated nucleic acid molecules that encode AP proteins or biologically active portions thereof, as well as nucleic acid fragments sufficient for use as hybridization probes to identify AP-encoding nucleic acid molecules (e.g., AP mRNA) and fragments for use as PCR primers for the amplification or mutation of AP nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated AP nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium, when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:4, 6, 7, or 9, or a portion thereof, can be isolated using standard molecular biology techniques and the sequence information provided herein. Using all or portion of the nucleic acid sequence of SEQ ID NO:4, 6, 7, or 9 as a hybridization probe, AP nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:4, 6, 7, or 9 can be isolated by the polymerase chain reaction (PCR) using synthetic oligonucleotide primers designed based upon the sequence of SEQ ID NO:4, 6, 7, or 9.

A nucleic acid of the invention can be amplified using cDNA, mRNA or, alternatively, genomic DNA as a template and appropriate oligonucleotide primers according to standard PCR amplification techniques. The nucleic acid so amplified can be cloned into an appropriate vector and characterized by DNA sequence analysis.

Furthermore, oligonucleotides corresponding to AP nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:4, 6, 7, or 9. This cDNA may comprise sequences encoding the human AP21956 protein (i.e., "the coding region", from nucleotides 150–2539), as well as 5' untranslated sequences (nucleotides 1–149) and 3' untranslated sequences (nucleotides 2540–3238) of SEQ ID NO:4. This cDNA may comprise sequences encoding the human AP25856 protein (i.e., "the coding region", from nucleotides 218–808), as well as 5' untranslated sequences (nucleotides 1–217) and 3' untranslated sequences (nucleotides 809–1626) of SEQ ID NO:7. Alternatively, the nucleic acid molecule can comprise only the coding region of SEQ ID NO:4 (e.g., nucleotides 150–2539, corresponding to SEQ ID NO:6) or only the coding region of SEQ ID NO:7 (e.g., nucleotides 218–808, corresponding to SEQ ID NO:9). In another embodiment, the isolated nucleic acid molecule of the invention consists of SEQ ID NO:4, 6, 7, or 9.

In another preferred embodiment, an isolated nucleic acid molecule of the invention comprises a nucleic acid molecule which is a complement of the nucleotide sequence shown in SEQ ID NO:4, 6, 7, or 9, or a portion of any of these nucleotide sequences. A nucleic acid molecule which is complementary to the nucleotide sequence shown in SEQ ID NO:4, 6, 7, or 9, is one which is sufficiently complementary to the nucleotide sequence shown in SEQ ID NO:4, 6, 7, or 9 such that it can hybridize to the nucleotide sequence shown in SEQ ID NO:4, 6, 7, or 9, respectively, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 90%, 91%, 92%, 93%, 94%, 95%, 96%, 97%, 98%, 99% or more identical to the entire length of the nucleotide sequence shown in SEQ ID NO:4, 6, 7, or 9, or a portion of any of these nucleotide sequences.

Moreover, the nucleic acid molecule of the invention can comprise only a portion of the nucleic acid sequence of SEQ ID NO:4, 6, 7, or 9, for example, a fragment which can be used as a probe or primer or a fragment encoding a portion of an AP protein, e.g., a biologically active portion of an AP protein. The nucleotide sequences determined from the cloning of the AP21956 and AP25856 genes allow for the generation of probes and primers designed for use in identifying and/or cloning other AP family members, as well as AP homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:4, 6, 7, or 9 of an anti-sense sequence of SEQ ID NO:4, 6, 7, or 9 or of a naturally occurring allelic variant or mutant of SEQ ID NO:4, 6, 7, or 9 In one embodiment, a nucleic acid molecule of the present invention comprises a nucleotide sequence which is greater than 21, 30, 40, 45, 50, 97, 100, 150, 200, 250, 300, 350, 400, 445, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250 or more nucleotides in length and hybridizes under stringent hybridization conditions to a nucleic acid molecule of SEQ ID NO:4, 6, 7, or 9.

Probes based on the AP nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress an AP protein, such as by measuring a level of an AP-encoding nucleic acid in a sample of cells from a subject e.g., detecting AP mRNA levels or determining whether a genomic AP gene has been mutated or deleted.

A nucleic acid fragment encoding a "biologically active portion of an AP protein" can be prepared by isolating a portion of the nucleotide sequence of SEQ ID NO:4, 6, 7, or 9, which encodes a polypeptide having an AP biological activity (the biological activities of the AP proteins are described herein), expressing the encoded portion of the AP protein (e.g., by recombinant expression in vitro) and assessing the activity of the encoded portion of the AP protein.

The invention further encompasses nucleic acid molecules that differ from the nucleotide sequence shown in SEQ ID NO:4, 6, 7, or 9, due to degeneracy of the genetic code and thus encode the same AP proteins as those encoded by the nucleotide sequence shown in SEQ ID NO:4, 6, 7, or 9. In another embodiment, an isolated nucleic acid molecule of the invention has a nucleotide sequence encoding a protein having an amino acid sequence shown in SEQ ID NO:5 or 8.

In addition to the AP nucleotide sequences shown in SEQ ID NO:4, 6, 7, or 9, it will be appreciated by those skilled in the art that DNA sequence polymorphisms that lead to changes in the amino acid sequences of the AP proteins may exist within a population (e.g., the human population). Such genetic polymorphism in the AP genes may exist among individuals within a population due to natural allelic variation. As used herein, the terms "gene" and "recombinant gene" refer to nucleic acid molecules which include an open reading frame encoding an AP protein, preferably a mammalian AP protein, and can further include non-coding regulatory sequences, and introns.

Allelic variants of human AP include both functional and non-functional AP proteins. Functional allelic variants are naturally occurring amino acid sequence variants of the human AP protein that maintain the ability to bind an AP ligand or substrate and/or modulate cell proliferation and/or migration mechanisms. Functional allelic variants will typically contain only conservative substitution of one or more amino acids of SEQ ID NO:5 or 8, or substitution, deletion or insertion of non-critical residues in non-critical regions of the protein.

Non-functional allelic variants are naturally occurring amino acid sequence variants of the human AP protein that do not have the ability to either bind an AP ligand and/or modulate any of the AP activities described herein. Non-functional allelic variants will typically contain a non-conservative substitution, deletion, or insertion or premature truncation of the amino acid sequence of SEQ ID NO:5 or 8, or a substitution, insertion or deletion in critical residues or critical regions of the protein.

The present invention further provides non-human orthologues of the human AP protein. Orthologues of the human AP protein are proteins that are isolated from non-human organisms and possess the same AP ligand binding and/or modulation of membrane excitability activities of the human AP protein. Orthologues of the human AP protein can readily be identified as comprising an amino acid sequence that is substantially identical to SEQ ID NO:5 or 8.

Moreover, nucleic acid molecules encoding other AP family members and, thus, which have a nucleotide sequence which differs from the AP sequences of SEQ ID NO:4, 6, 7, or 9 are intended to be within the scope of the invention. For example, another AP cDNA can be identified based on the nucleotide sequence of human AP. Moreover, nucleic acid molecules encoding AP proteins from different species, and which, thus, have a nucleotide sequence which differs from the AP sequences of SEQ ID NO:4, 6, 7, or 9, are intended to be within the scope of the invention. For example, a mouse AP cDNA can be identified based on the nucleotide sequence of a human AP.

Nucleic acid molecules corresponding to natural allelic variants and homologues of the AP cDNAs of the invention can be isolated based on their homology to the AP nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the AP cDNAs of the invention can further be isolated by mapping to the same chromosome or locus as the AP gene.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:4, 6, 7, or 9. In other embodiment, the nucleic acid is at least 21, 30, 40, 45, 50, 97, 100, 150, 200, 250, 300, 350, 400, 445, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in Current Protocols in Molecular Biology, Ausubel et al., eds., John Wiley & Sons, Inc. (1995), sections 2, 4 and 6. Additional stringent conditions can be found in Molecular Cloning: A Laboratory Manual, Sambrook et al., Cold Spring Harbor Press, Cold Spring Harbor, N.Y. (1989), chapters 7, 9 and 11. A preferred, non-limiting example of stringent hybridization conditions includes hybridization in 4×sodium chloride/sodium citrate (SSC), at about 65–70° C. (or hybridization in 4×SSC plus 50% formamide at about 42–50° C.) followed by one or more washes in 1×SSC, at about 65–70° C. A preferred, non-limiting example of highly stringent hybridization conditions includes hybridization in 1×SSC, at about 65–70° C. (or hybridization in 1×SSC plus 50% formamide at about 42–50° C.) followed by one or more washes in 0.3×SSC, at about 65–70° C. A preferred, non-limiting example of reduced stringency hybridization conditions includes hybridization in 4×SSC, at about 50–60° C. (or alternatively hybridization in 6×SSC plus 50% formamide at about 40–45° C.) followed by one or more washes in 2×SSC, at about 50–60° C. Ranges intermediate to the above-recited values, e.g., at 65–70° C. or at 42–50° C. are also intended to be encompassed by the present invention. SSPE (1×SSPE is 0.1 5M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m$(° C.)=2(# of A+T bases)+4(# of G+C bases). For hybrids between 18 and 49 base pairs in length, $T_m$(° C.)=81.5+16.6($\log_{10}$[$Na^+$])+0.41(% G+C)−(600/N), where N is the number of bases in the hybrid, and [$Na^+$] is the concentration of sodium ions in the hybridization buffer ([$Na^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25–0.5M $NaH_2PO_4$, 7% SDS at about 65° C., followed by one or more washes at 0.02M $NaH_2PO_4$, 1% SDS at 65° C., see e.g., Church and Gilbert (1984) Proc. Natl. Acad. Sci. USA 81:1991–1995, (or alternatively 0.2×SSC, 1% SDS).

Preferably, an isolated nucleic acid molecule of the invention that hybridizes under stringent conditions to the sequence of SEQ ID NO:4, 6, 7, or 9, and corresponds to a naturally-occurring nucleic acid molecule. As used herein, a "naturally-occurring" nucleic acid molecule refers to an RNA or DNA molecule having a nucleotide sequence that occurs in nature (i.e., encodes a natural protein).

In addition to naturally-occurring allelic variants of the AP sequences that may exist in the population, the skilled artisan will further appreciate that changes can be introduced by mutation into the nucleotide sequences of SEQ ID NO:4, 6, 7, or 9, thereby leading to changes in the amino acid sequence of the encoded AP proteins, without altering the functional ability of the AP proteins. For example, nucleotide substitutions leading to amino acid substitutions at "non-essential" amino acid residues can be made in the sequence of SEQ ID NO:4, 6, 7, or 9. A "non-essential" amino acid residue is a residue that can be altered from the wild-type sequence of AP (e.g., the sequence of SEQ ID NO:5 or 8) without altering the biological activity, whereas an "essential" amino acid residue is required for biological activity. For example, amino acid residues that are conserved among the AP proteins of the present invention, e.g., those present in a transmembrane domain, are predicted to be particularly unamenable to alteration. Furthermore, additional amino acid residues that are conserved between the AP proteins of the present invention and other members of the AP family are not likely to be amenable to alteration.

Accordingly, another aspect of the invention pertains to nucleic acid molecules encoding AP proteins that contain changes in amino acid residues that are not essential for activity. Such AP proteins differ in amino acid sequence from SEQ ID NO:5 or 8, yet retain biological activity. In one embodiment, the isolated nucleic acid molecule comprises a nucleotide sequence encoding a protein, wherein the protein comprises an amino acid sequence at least about 50%, 55%, 60%, 65%, 70%, 75%, 80%, 85%, 90%, 91%, 92%, 93%, 94%, 95%, 96%, 97%, 98%, 99% or more identical to SEQ ID NO:5 or 8.

An isolated nucleic acid molecule encoding an AP protein identical to the protein of SEQ ID NO:5 or 8 can be created by introducing one or more nucleotide substitutions, additions or deletions into the nucleotide sequence of SEQ ID NO:4, 6, 7, or 9 such that one or more amino acid substitutions, additions or deletions are introduced into the encoded protein. Mutations can be introduced into SEQ ID NO:4, 6, 7, or 9 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in an AP protein is preferably replaced with another amino acid residue from the same side chain family. Alternatively, in another embodiment, mutations can be introduced randomly along all or part of an AP coding sequence, such as by saturation mutagenesis, and the resultant mutants can be screened for AP biological activity to identify mutants that retain activity. Following mutagenesis of SEQ ID NO:4, 6, 7, or 9, the encoded protein can be expressed recombinantly and the activity of the protein can be determined.

In a preferred embodiment, a mutant AP protein can be assayed for the ability to metabolize or catabolize biochemical molecules necessary for energy production or storage, permit intra- or inter-cellular signaling, metabolize or catabolize metabolically important biomolecules, or detoxify potentially harmful compounds.

In addition to the nucleic acid molecules encoding AP proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire AP coding strand, or to only a portion thereof. In one embodiment, an antisense nucleic acid molecule is antisense to a "coding region" of the coding strand of a nucleotide sequence encoding an AP. The term "coding region" refers to the region of the nucleotide sequence comprising codons which are translated into amino acid residues (e.g., the coding region of human AP corresponds to SEQ ID NO:6 or 9). In another embodiment, the antisense nucleic acid molecule is antisense to a "noncoding region" of the coding strand of a nucleotide sequence encoding AP. The term "noncoding region" refers to 5' and 3' sequences which flank the coding region that are not translated into amino acids (also referred to as 5' and 3' untranslated regions).

Given the coding strand sequences encoding AP disclosed herein (e.g., SEQ ID NO:6 or 9), antisense nucleic acids of the invention can be designed according to the rules of Watson and Crick base pairing. The antisense nucleic acid molecule can be complementary to the entire coding region of AP mRNA, but more preferably is an oligonucleotide which is antisense to only a portion of the coding or noncoding region of AP mRNA. For example, the antisense oligonucleotide can be complementary to the region surrounding the translation start site of AP mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an AP protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff and Gerlach (1988) *Nature* 334:585–591)) can be used to catalytically cleave AP mRNA transcripts to thereby inhibit translation of AP mRNA. A ribozyme having specificity for an AP-encoding nucleic acid can be designed based upon the nucleotide sequence of an AP cDNA disclosed herein (i.e., SEQ ID NO:4, 6, 7, or 9. For example, a derivative of a Tetrahymena L-19 IVS RNA can be constructed in which the nucleotide sequence of the active site is complementary to the nucleotide sequence to be cleaved in an AP-encoding mRNA. See, e.g., Cech et al. U.S. Pat. No. 4,987,071; and Cech et al. U.S. Pat. No. 5,116,742. Alternatively, AP mRNA can be used to select a catalytic RNA having a specific ribonuclease activity from a pool of RNA molecules. See, e.g., Bartel, D. and Szostak, J. W. (1993) *Science* 261:1411–1418.

Alternatively, AP gene expression can be inhibited by targeting nucleotide sequences complementary to the regulatory region of the AP (e.g., the AP promoter and/or enhancers; e.g., nucleotides 1–117 of SEQ ID NO:4 or nucleotides 1–14 of SEQ ID NO:7) to form triple helical structures that prevent transcription of the AP gene in target cells. See generally, Helene, C. (1991) *Anticancer Drug Des.* 6(6): 569–84; Helene, C. et al. (1992) *Ann. N.Y. Acad. Sci.* 660:27–36; and Maher, L. J. (1992) *Bioassays* 14(12): 807–15.

In yet another embodiment, the AP nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. (1996) *Proc. Natl. Acad. Sci.* 93:14670–675.

PNAs of AP nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of AP nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-O'Keefe et al. (1996) supra).

In another embodiment, PNAs of AP can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of AP nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. et al. (1996) supra). The synthesis of PNA-DNA chimeras can be performed as described in Hyrup B. et al. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

Alternatively, the expression characteristics of an endogenous AP gene within a cell line or microorganism may be modified by inserting a heterologous DNA regulatory element into the genome of a stable cell line or cloned microorganism such that the inserted regulatory element is operatively linked with the endogenous AP gene. For example, an endogenous AP gene which is normally "transcriptionally silent", i.e., an AP gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous AP gene may be activated by insertion of a promiscuous regulatory element that works across cell types.

A heterologous regulatory element may be inserted into a stable cell line or cloned microorganism, such that it is operatively linked with an endogenous AP gene, using techniques, such as targeted homologous recombination, which are well known to those of skill in the art, and described, e.g., in Chappel, U.S. Pat. No. 5,272,071; PCT publication No. WO 91/06667, published May 16, 1991.

II. Isolated AP Proteins and Anti-AP Antibodies

One aspect of the invention pertains to isolated AP proteins, and biologically active portions thereof, as well as polypeptide fragments suitable for use as immunogens to raise anti-AP antibodies. In one embodiment, native AP proteins can be isolated from cells or tissue sources by an appropriate purification scheme using standard protein purification techniques. In another embodiment, AP proteins are produced by recombinant DNA techniques. Alternative to recombinant expression, an AP protein or polypeptide can be synthesized chemically using standard peptide synthesis techniques.

An "isolated" or "purified" protein or biologically active portion thereof is substantially free of cellular material or other contaminating proteins from the cell or tissue source from which the AP protein is derived, or substantially free from chemical precursors or other chemicals when chemically synthesized. The language "substantially free of cellular material" includes preparations of AP protein in which the protein is separated from cellular components of the cells from which it is isolated or recombinantly produced. In one embodiment, the language "substantially free of cellular material" includes preparations of AP protein having less than about 30% (by dry weight) of non-AP protein (also referred to herein as a "contaminating protein"), more preferably less than about 20% of non-AP protein, still more preferably less than about 10% of non-AP protein, and most preferably less than about 5% non-AP protein. When the AP protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of AP protein in which the protein is separated from chemical precursors or other chemicals which are involved in the synthesis of the protein. In one embodiment, the language "substantially free of chemical precursors or other chemicals" includes preparations of AP protein having less than about 30% (by dry weight) of chemical precursors or non-AP chemicals, more preferably less than about 20% chemical precursors or non-AP chemicals, still more preferably less than about 10% chemical precursors or non-AP chemicals, and most preferably less than about 5% chemical precursors or non-AP chemicals.

As used herein, a "biologically active portion" of an AP protein includes a fragment of an AP protein which participates in an interaction between an AP molecule and a non-AP molecule. Biologically active portions of an AP protein include peptides comprising amino acid sequences sufficiently identical to or derived from the amino acid sequence of the AP protein, e.g., the amino acid sequence shown in SEQ ID NO:5 or 8, which include fewer amino acids than the full length AP proteins, and exhibit at least one activity of an AP protein. Typically, biologically active portions comprise a domain or motif with at least one activity of the AP protein, e.g., hydrolyis of amino acid residues. A biologically active portion of an AP protein can be a polypeptide which is, for example, 25, 32, 50, 75, 100, 125, 150, 175, 200, 250, 300 or more amino acids in length. Biologically active portions of an AP protein can be used as targets for developing agents which modulate an AP mediated activity, e.g., inter-cellular interaction.

In one embodiment, a biologically active portion of an AP protein comprises at least one transmembrane domain. It is to be understood that a preferred biologically active portion of an AP protein of the present invention may contain at least one transmembrane domain and one or more of the following domains: a signal peptide domain, a dipeptidyl peptidase IV N-terminal domain, a prolyl oligopeptidase domain, and/or a dienelactone hydrolase domain. Moreover, other biologically active portions, in which other regions of the protein are deleted, can be prepared by recombinant techniques and evaluated for one or more of the functional activities of a native AP protein.

In a preferred embodiment, the AP protein has an amino acid sequence shown in SEQ ID NO:5 or 8. In other embodiments, the AP protein is substantially identical to SEQ ID NO:5 or 8, and retains the functional activity of the protein of SEQ ID NO:5 or 8, yet differs in amino acid sequence due to natural allelic variation or mutagenesis, as described in detail in subsection I above. Accordingly, in another embodiment, the AP protein is a protein which comprises an amino acid sequence at least about 50%, 55%, 60%, 65%, 70%, 75%, 80%, 85%, 90%, 91%, 92%, 93%, 94%, 95%, 96%, 97%, 98%, 99% or more identical to SEQ ID NO:5 or 8.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the AP amino acid sequence of SEQ ID NO:5 or 8 having 500 amino acid residues, at least 75, preferably at least 150, more preferably at least 225, even more preferably at least 300, and even more preferably at least 400 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* 48:444–453 (1970)) algorithm which has been incorporated into the GAP program in the GCG software package (available at the bioinformatics page of the website maintained by Accelrys, Inc., San Diego, Calif., USA), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*Comput. Appl. Biosci.* 4:11–17 (1988)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403–10. BLAST nucleotide searches can be performed with the NBLAST program, score=100, wordlength=12 to obtain nucleotide sequences homologous to AP nucleic acid molecules of the invention. BLAST protein searches can be performed with the XBLAST program, score=100, wordlength=3 to obtain amino acid sequences homologous to AP protein molecules of the invention. To obtain gapped alignments for comparison purposes, Gapped BLAST can be utilized as described in Altschul et al. (1997) *Nucleic Acids Res.* 25(17):3389–3402. When utilizing BLAST and Gapped BLAST programs, the default parameters of the respective programs (e.g., XBLAST and NBLAST) can be used (accessible at the website maintained by National Center for Biotechnology Information, Bethesda, Md., USA).

The invention also provides AP chimeric or fusion proteins. As used herein, an AP "chimeric protein" or "fusion protein" comprises an AP polypeptide operatively linked to a non-AP polypeptide. An "AP polypeptide" refers to a polypeptide having an amino acid sequence corresponding to an AP molecule, whereas a "non-AP polypeptide" refers to a polypeptide having an amino acid sequence corresponding to a protein which is not substantially homologous to the AP protein, e.g., a protein which is different from the AP protein and which is derived from the same or a different organism. Within an AP fusion protein the AP polypeptide can correspond to all or a portion of an AP protein. In a preferred embodiment, an AP fusion protein comprises at least one biologically active portion of an AP protein. In another preferred embodiment, an AP fusion protein comprises at least two biologically active portions of an AP protein. Within the fusion protein, the term "operatively linked" is intended to indicate that the AP polypeptide and the non-AP polypeptide are fused in-frame to each other. The non-AP polypeptide can be fused to the N-terminus or C-terminus of the AP polypeptide.

For example, in one embodiment, the fusion protein is a GST-AP fusion protein in which the AP sequences are fused to the C-terminus of the GST sequences. Such fusion proteins can facilitate the purification of recombinant AP.

In another embodiment, these fusion protein is an AP protein containing a heterologous signal sequence at its N-terminus. In certain host cells (e.g., mammalian host cells), expression and/or secretion of AP can be increased through use of a heterologous signal sequence.

The AP fusion proteins of the invention can be incorporated into pharmaceutical compositions and administered to a subject in vivo. The AP fusion proteins can be used to affect the bioavailability of an AP substrate. Use of AP fusion proteins may be useful therapeutically for the treatment of disorders caused by, for example, (i) aberrant modification or mutation of a gene encoding an AP protein; (ii) mis-regulation of the AP gene; and (iii) aberrant post-translational modification of an AP protein.

Moreover, the AP-fusion proteins of the invention can be used as immunogens to produce anti-AP antibodies in a subject, to purify AP ligands and in screening assays to identify molecules which inhibit the interaction of AP with an AP substrate.

Preferably, an AP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). An AP-encoding nucleic acid can be cloned into such an expression vector such that the fusion moiety is linked in-frame to the AP protein.

The present invention also pertains to variants of the AP proteins which function as either AP agonists (mimetics) or as AP antagonists. Variants of the AP proteins can be generated by mutagenesis, e.g., discrete point mutation or truncation of an AP protein. An agonist of the AP proteins can retain substantially the same, or a subset, of the biological activities of the naturally occurring form of an AP protein. An antagonist of an AP protein can inhibit one or more of the activities of the naturally occurring form of the AP protein by, for example, competitively modulating an AP-mediated activity of an AP protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the AP protein.

In one embodiment, variants of an AP protein which function as either AP agonists (mimetics) or as AP antagonists can be identified by screening combinatorial libraries of mutants, e.g., truncation mutants, of an AP protein for AP protein agonist or antagonist activity. In one embodiment, a variegated library of AP variants is generated by combinatorial mutagenesis at the nucleic acid level and is encoded by a variegated gene library. A variegated library of AP variants can be produced by, for example, enzymatically ligating a mixture of synthetic oligonucleotides into gene sequences such that a degenerate set of potential AP sequences is expressible as individual polypeptides, or alternatively, as a set of larger fusion proteins (e.g., for phage display) containing the set of AP sequences therein. There are a variety of methods which can be used to produce libraries of potential AP variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential AP sequences. Methods for synthesizing degenerate oligonucleotides are known in the art (see, e.g., Narang, S. A. (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

In addition, libraries of fragments of an AP protein coding sequence can be used to generate a variegated population of AP fragments for screening and subsequent selection of variants of an AP protein. In one embodiment, a library of coding sequence fragments can be generated by treating a double stranded PCR fragment of an AP coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the AP protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of AP proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify AP variants (Arkin and Youvan (1992) Proc. Natl. Acad. Sci. USA 89:7811–7815; Delagrave et al. (1993) Protein Engineering 6(3):327–331).

In one embodiment, cell based assays can be exploited to analyze a variegated AP library. For example, a library of expression vectors can be transfected into a cell line, e.g., a neuronal cell line, which ordinarily responds to an AP ligand in a particular AP ligand-dependent manner. The transfected cells are then contacted with an AP ligand and the effect of expression of the mutant on, e.g., membrane excitability of AP can be detected. Plasmid DNA can then be recovered from the cells which score for inhibition, or alternatively, potentiation of signaling by the AP ligand, and the individual clones further characterized.

An isolated AP protein, or a portion or fragment thereof, can be used as an immunogen to generate antibodies that bind AP using standard techniques for polyclonal and monoclonal antibody preparation. A full-length AP protein can be used or, alternatively, the invention provides antigenic peptide fragments of AP for use as immunogens. The antigenic peptide of AP comprises at least 8 amino acid residues of the amino acid sequence shown in SEQ ID NO:5 or 8 and encompasses an epitope of AP such that an antibody raised against the peptide forms a specific immune complex with the AP protein. Preferably, the antigenic peptide comprises at least 10 amino acid residues, more preferably at least 15 amino acid residues, even more preferably at least 20 amino acid residues, and most preferably at least 30 amino acid residues.

Figure 8:
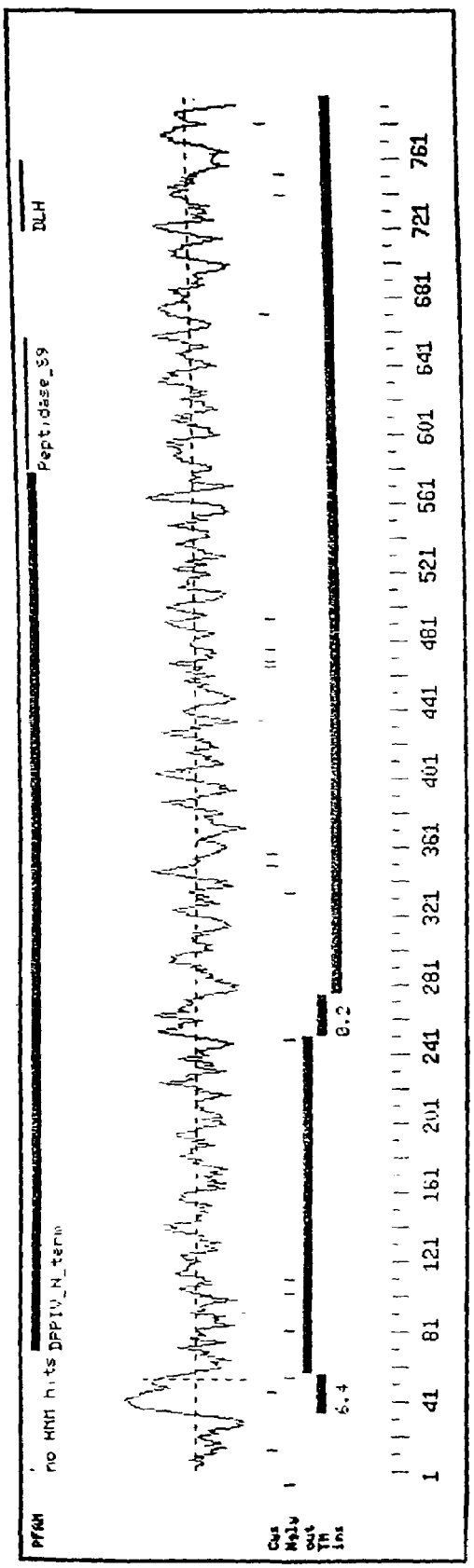
FIG. 8 depicts a hydrophobicity analysis of the human AP21956 protein.
Figure 9:
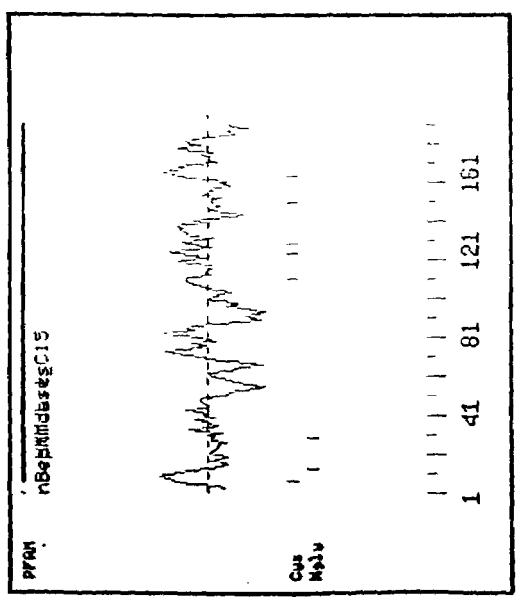
FIG. 9 depicts a hydrophobicity analysis of the human AP25856 protein.

Preferred epitopes encompassed by the antigenic peptide are regions of AP that are located on the surface of the protein, e.g., hydrophilic regions, as well as regions with high antigenicity (see FIGS. 8 and 9).

An AP immunogen typically is used to prepare antibodies by immunizing a suitable subject, (e.g., rabbit, goat, mouse, or other mammal) with the immunogen. An appropriate immunogenic preparation can contain, for example, recombinantly expressed AP protein or a chemically synthesized AP polypeptide. The preparation can further include an adjuvant, such as Freund's complete or incomplete adjuvant, or similar immunostimulatory agent. Immunization of a suitable subject with an immunogenic AP preparation induces a polyclonal anti-AP antibody response.

Accordingly, another aspect of the invention pertains to anti-AP antibodies. The term "antibody" as used herein refers to immunoglobulin molecules and immunologically active portions of immunoglobulin molecules, i.e., molecules that contain an antigen binding site which specifically binds (immunoreacts with) an antigen, such as an AP. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind AP molecules. The term "monoclonal antibody" or "monoclonal antibody composition", as used herein, refers to a population of antibody molecules that contain only one species of an antigen binding site capable of immunoreacting with a particular epitope of AP. A monoclonal antibody composition thus typically displays a single binding affinity for a particular AP protein with which it immunoreacts.

Polyclonal anti-AP antibodies can be prepared as described above by immunizing a suitable subject with an AP immunogen. The anti-AP antibody titer in the immunized subject can be monitored over time by standard techniques, such as with an enzyme linked immunosorbent assay (ELISA) using immobilized AP. If desired, the antibody molecules directed against AP can be isolated from the mammal (e.g., from the blood) and further purified by well known techniques, such as protein A chromatography to obtain the IgG fraction. At an appropriate time after immunization, e.g., when the anti-AP antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985) *Monoclonal Antibodies and Cancer Therapy*, Alan R. Liss, Inc., pp. 77–96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387–402; Gefter, M. L. et al. (1977) *Somatic Cell Genet.* 3:231–36). Briefly, an immortal cell line (typically a myeloma) is fused to lymphocytes (typically splenocytes) from a mammal immunized with an AP immunogen as described above, and the culture supernatants of the resulting hybridoma cells are screened to identify a hybridoma producing a monoclonal antibody that binds AP.

Any of the many well known protocols used for fusing lymphocytes and immortalized cell lines can be applied for the purpose of generating an anti-AP monoclonal antibody (see, e.g., G. Galfre et al. (1977) *Nature* 266:55052; Gefter et al. (1977) supra; Lerner (1981) supra; and Kenneth (1980) supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC (Manassas, Va.). Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind AP, e.g., using a standard ELISA assay.

Alternative to preparing monoclonal antibody-secreting hybridomas, a monoclonal anti-AP antibody can be identified and isolated by screening a recombinant combinatorial immunoglobulin library (e.g., an antibody phage display library) with AP to thereby isolate immunoglobulin library members that bind AP. Kits for generating and screening phage display libraries are commercially available (e.g., the Pharmacia *Recombinant Phage Antibody System*, Catalog No. 27–9400–01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1369–1372; Hay et al. (1992) *Hum. Antibod. Hybridomas* 3:81–85; Huse et al. (1989) *Science* 246:1275–1281; Griffiths et al. (1993) *EMBO J.* 12:725–734; Hawkins et al. (1992) *J. Mol. Biol.* 226: 889–896; Clackson et al. (1991) *Nature* 352:624–628; Gram et al. (1992) *Proc. Natl. Acad. Sci. USA* 89:3576–3580; Garrard et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. (1990) *Nature* 348:552–554.

Additionally, recombinant anti-AP antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171, 496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; Shaw et al. (1988) *J. Natl. Cancer Inst.* 80:1553–1559; Morrison, S. L. (1985) *Science* 229:1202–1207; Oi et al. (1986) *BioTechniques* 4:214; Winter U.S. Pat. No. 5,225, 539; Jones et al. (1986) *Nature* 321:552–525; Verhoeyen et al. (1988) *Science* 239:1534; and Beidler et al. (1988) *J. Immunol.* 141:4053–4060.

An anti-AP antibody (e.g., monoclonal antibody) can be used to isolate AP by standard techniques, such as affinity chromatography or immunoprecipitation. An anti-AP antibody can facilitate the purification of natural AP from cells and of recombinantly produced AP expressed in host cells.

Moreover, an anti-AP antibody can be used to detect AP protein (e.g., in a cellular lysate or cell supernatant) in order to evaluate the abundance and pattern of expression of the AP protein. Anti-AP antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

III. Recombinant Expression Vectors and Host Cells

Another aspect of the invention pertains to vectors, preferably expression vectors, containing a nucleic acid encoding an AP protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) *Methods Enzymol.* 185:3–7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., AP proteins, mutant forms of AP proteins, fusion proteins, and the like).

The recombinant expression vectors of the invention can be designed for expression of AP proteins in prokaryotic or eukaryotic cells. For example, AP proteins can be expressed in bacterial cells such as *E. coli*, insect cells (using baculovirus expression vectors), yeast cells, or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in AP activity assays, (e.g., direct assays or competitive assays described in detail below), or to generate antibodies specific for AP proteins, for example. In a preferred embodiment, an AP fusion protein expressed in a retroviral expression vector of the present invention can be utilized to infect bone marrow cells which are subsequently transplanted into irradiated recipients. The pathology of the subject recipient is then examined after sufficient time has passed (e.g., six weeks).

Examples of suitable inducible non-fusion *E. coli* expression vectors include pTrc (Amann et al. (1988) *Gene* 69:301–315) and pET 11d (Studier et al. (1990) *Methods Enzymol.* 185:60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in E. coli is to express the protein in a host bacteria with an impaired capacity to proteolytically cleave the recombinant protein (Gottesman, S. (1990) Methods Enzymol. 185:119–128). Another strategy is to alter the nucleic acid sequence of the nucleic acid to be inserted into an expression vector so that the individual codons for each amino acid are those preferentially utilized in E. coli (Wada et al. (1992) Nucleic Acids Res. 20:2111–2118). Such alteration of nucleic acid sequences of the invention can be carried out by standard DNA synthesis techniques.

In another embodiment, the AP expression vector is a yeast expression vector. Examples of vectors for expression in yeast S. cerevisiae include pYepSec1 (Baldari et al. (1987) EMBO J. 6:229–234), pMFa (Kurjan and Herskowitz (1982) Cell 30:933–943), pJRY88 (Schultz et al. (1987) Gene 54:113–123), pYES2 (Invitrogen Corporation, San Diego, Calif.), and picZ (Invitrogen Corp, San Diego, Calif.).

Alternatively, AP proteins can be expressed in insect cells using baculovirus expression vectors. Baculovirus vectors available for expression of proteins in cultured insect cells (e.g., Sf 9 cells) include the pAc series (Smith et al. (1983) Mol. Cell Biol. 3:2156–2165) and the pVL series (Lucklow and Summers (1989) Virology 170:31–39).

In yet another embodiment, a nucleic acid of the invention is expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al., Molecular Cloning: A Laboratory Manual. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268–277), lymphoid-specific promoters (Calame and Eaton (1988) Adv. Immunol. 43:235–275), particular promoters of T cell receptors (Winoto and Baltimore (1989) EMBO J. 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) Proc. Natl. Acad. Sci. USA 86:5473–5477), pancreas-specific promoters (Edlund et al. (1985) Science 230:912–916), and mammary gland-specific promoters (e.g., milk whey promoter; U.S. Pat. No. 4,873,316 and European Application Publication No. 264,166). Developmentally-regulated promoters are also encompassed, for example by the murine hox promoters (Kessel and Gruss (1990) Science 249:374–379) and the α-fetoprotein promoter (Campes and Tilghman (1989) Genes Dev. 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to AP mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub, H. et al., Antisense RNA as a molecular tool for genetic analysis, Reviews—Trends in Genetics, Vol. 1(1) 1986.

Another aspect of the invention pertains to host cells into which an AP nucleic acid molecule of the invention is introduced, e.g., an AP nucleic acid molecule within a recombinant expression vector or an AP nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an AP protein can be expressed in bacterial cells such as E. coli, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (Molecular Cloning: A Laboratory Manual. 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding an AP protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) an AP protein. Accordingly, the invention further provides methods for producing an AP protein using the host cells of the invention. In one embodiment, the method comprises culturing the host cell of the invention (into which a recombinant expression vector encoding an AP protein has been introduced) in a suitable medium such that an AP protein is produced. In another embodiment, the method further comprises isolating an AP protein from the medium or the host cell.

The host cells of the invention can also be used to produce non-human transgenic animals. For example, in one embodiment, a host cell of the invention is a fertilized oocyte or an embryonic stem cell into which AP-coding sequences have been introduced. Such host cells can then be used to create non-human transgenic animals in which exogenous AP sequences have been introduced into their genome or homologous recombinant animals in which endogenous AP sequences have been altered. Such animals are useful for studying the function and/or activity of an AP and for identifying and/or evaluating modulators of AP activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous AP gene has been altered by homologous recombination between the endogenous gene and an exogenous DNA molecule introduced into a cell of the animal, e.g., an embryonic cell of the animal, prior to development of the animal.

A transgenic animal of the invention can be created by introducing an AP-encoding nucleic acid into the male pronuclei of a fertilized oocyte, e.g., by microinjection, retroviral infection, and allowing the oocyte to develop in a pseudopregnant female foster animal. The AP cDNA sequence of SEQ ID NO:7 or 9 can be introduced as a transgene into the genome of a non-human animal. Alternatively, a nonhuman homologue of a human AP gene, such as a mouse or rat AP gene, can be used as a transgene. Alternatively, an AP gene homologue, such as another AP family member, can be isolated based on hybridization to the AP cDNA sequences of SEQ ID NO:4, 6, 7, or 9 (described further in subsection I above) and used as a transgene. Intronic sequences and polyadenylation signals can also be included in the transgene to increase the efficiency of expression of the transgene. A tissue-specific regulatory sequence(s) can be operably linked to an AP transgene to direct expression of an AP protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of an AP transgene in its genome and/or expression of AP mRNA in tissues or cells of the animals. A transgenic founder animal can then be used to breed additional animals carrying the transgene. Moreover, transgenic animals carrying a transgene encoding an AP protein can further be bred to other transgenic animals carrying other transgenes.

To create a homologous recombinant animal, a vector is prepared which contains at least a portion of an AP gene into which a deletion, addition or substitution has been introduced to thereby alter, e.g., functionally disrupt, the AP gene. The AP gene can be a human gene (e.g., the cDNA of SEQ ID NO:6 or 9), but more preferably, is a non-human homologue of a human AP gene (e.g., a cDNA isolated by stringent hybridization with the nucleotide sequence of SEQ ID NO:4 or 7). For example, a mouse AP gene can be used to construct a homologous recombination nucleic acid molecule, e.g., a vector, suitable for altering an endogenous AP gene in the mouse genome. In a preferred embodiment, the homologous recombination nucleic acid molecule is designed such that, upon homologous recombination, the endogenous AP gene is functionally disrupted (i.e., no longer encodes a functional protein; also referred to as a "knock out" vector). Alternatively, the homologous recombination nucleic acid molecule can be designed such that, upon homologous recombination, the endogenous AP gene is mutated or otherwise altered but still encodes functional protein (e.g., the upstream regulatory region can be altered to thereby alter the expression of the endogenous AP protein). In the homologous recombination nucleic acid molecule, the altered portion of the AP gene is flanked at its 5' and 3' ends by additional nucleic acid sequence of the AP gene to allow for homologous recombination to occur between the exogenous AP gene carried by the homologous recombination nucleic acid molecule and an endogenous AP gene in a cell, e.g., an embryonic stem cell. The additional flanking AP nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced AP gene has homologously recombined with the endogenous AP gene are selected (see e.g., Li, E. et al. (1992) *Cell* 69:915). The selected cells can then be injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 1113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *S. cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to the morula or blastocyte stage and then transferred to pseudopregnant female foster animal. The offspring borne of this female foster animal will be a clone of the animal from which the cell, e.g., the somatic cell, is isolated.

IV. Pharmaceutical Compositions

The AP nucleic acid molecules, fragments of AP proteins, and anti-AP antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR® EL solubilizer (BASF, Florham Park, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of an AP protein or an anti-AP antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, the AP proteins of the invention have one or more of the following activities: 1) they modulate metabolism or catabolism of biochemical molecules necessary for energy production or storage, 2) they modulate intra- or inter-cellular signaling, 3) they modulate metabolism or catabolism of metabolically important biomolecules, 4) they modulate metabolism of secreted biochemical molecules necessary for cell regulation (e.g., hormones or neurotransmitters), and 5) they modulate the degradation of peptides.

In a preferred embodiment, the AP molecules of the invention are useful for catalyzing the hydrolysis of amino acid residues from the amino acid terminus of peptides. As such, these molecules may be employed in small or large-scale synthesis of amino acid residues, or in chemical processes that require the production or interconversion of these compounds. Such processes are known in the art (see, e.g., Ullmann et al. (1999) Ullmann's Encyclopedia of Industrial Chemistry, $6^{th}$ ed. VCH: Weinheim; Gutcho (1983) Chemicals by Fermentation. Park ridge, N.J.: Noyes Data Corporation (ISBN 0818805086); Rehm et al. (eds.) (1993) Biotechnology, $2^{nd}$ ed. VCH: Weinheim; and Michal, G. (1999) Biochemical Pathways: An Atlas of Biochemistry and Molecular Biology. New York: John Wiley & Sons, and references contained therein.)

The isolated nucleic acid molecules of the invention can be used, for example, to express AP protein (e.g., via a recombinant expression vector in a host cell in gene therapy applications), to detect AP mRNA (e.g., in a biological sample) or a genetic alteration in an AP gene, and to modulate AP activity, as described further below. The AP proteins can be used to treat disorders characterized by insufficient or excessive production of an AP substrate or production of AP inhibitors. In addition, the AP proteins can be used to screen for naturally occurring AP substrates, to screen for drugs or compounds which modulate AP activity, as well as to treat disorders characterized by insufficient or excessive production of AP protein or production of AP protein forms which have decreased, aberrant or unwanted activity compared to AP wild type protein (e.g., aminopeptidase-associated disorders), such as CNS disorders (e.g., Alzheimer's disease, dementias related to Alzheimer's disease, such as Pick's disease), Parkinson's and other Lewy diffuse body diseases, senile dementia, Huntington's disease, Gilles de la Tourette's syndrome, multiple sclerosis, amyotrophic lateral sclerosis, progressive supranuclear palsy, epilepsy, and Jakob-Creutzfieldt disease; autonomic function disorders such as hypertension and sleep disorders, and neuropsychiatric disorders, such as depression, schizophrenia, schizoaffective disorder, korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, and bipolar affective disorder (e.g., severe bipolar affective (mood) disorder (BP-1) and bipolar affective neurological disorders (e.g., migraine and obesity)); cardiac disorders (e.g., arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrillation, Jervell syndrome, Lange-Nielsen syndrome, long-QT syndrome, congestive heart failure, sinus node dysfunction, angina, heart failure, hypertension, atrial fibrillation, atrial flutter, dilated cardiomyopathy, idiopathic cardiomyopathy, myocardial infarction, coronary artery disease, coronary artery spasm, and arrhythmia); muscular disorders (e.g., paralysis, muscle weakness (e.g., ataxia, myotonia, and myokymia), muscular dystrophy (e.g., Duchenne muscular dystrophy or myotonic dystrophy), spinal muscular atrophy, congenital myopathies, central core disease, rod myopathy, central nuclear myopathy, Lambert-Eaton syndrome, denervation, and infantile spinal muscular atrophy (Werdnig-Hoffman disease); cellular growth, differentiation, or migration disorders (e.g., cancer, e.g., carcinoma, sarcoma, or leukemia; tumor angiogenesis and metastasis; skeletal dysplasia; neuronal deficiencies resulting from impaired neural induction and patterning); hepatic disorders; hematopoietic and/or myeloproliferative disorders; neurological disorders (e.g., Sjogren-Larsson syndrome, disorders in GABA processing or reception), immune disorders (e.g., autoimmune disorders or immune deficit disorders); hormonal disorders (e.g., pituitary, insulin-dependent, thyroid, or fertility or reproductive disorders); inflammatory or immune system disorders (e.g. viral infection, inflammatory bowel disease, ulcerative colitis, Crohn's disease, leukocyte adhesion deficiency II syndrome, peritonitis, chronic obstructive pulmonary disease, lung inflammation, asthma, acute appendicitis, septic shock, nephritis, amyloidosis, rheumatoid arthritis, chronic bronchitis, sarcoidosis, scleroderma, lupus, polymyositis, Reiter's syndrome, psoriasis, pelvic inflammatory disease, inflammatory breast disease, orbital inflammatory disease); immune deficiency disorders (e.g., HIV, common variable immunodeficiency, congenital X-linked infantile hypogammaglobulinemia, transient hypogammaglobulinemia, selective IgA deficiency, chronic mucocutaneous candidiasis, severe combined immunodeficiency); autoimmune disorders; a hematopoietic or thrombotic disorder (e.g., disseminated intravascular coagulation, thromboembolic vascular disease, anemia, lymphoma, leukemia, neutrophilia, neutropenia, myeloproliferative disorders, thrombocytosis, thrombocytopenia, von Willebrand disease, and hemophilia); gastrointestinal and digestive disorders (e.g., esophageal disorders such as atresia and fistulas, stenosis, achalasia, esophageal rings and webs, hiatal hernia, lacerations, esophagitis, diverticula, systemic sclerosis (scleroderma), varices, esophageal tumors such as squamous cell carcinomas and adenocarcinomas, stomach disorders such as diaphragmatic hernias, pyloric stenosis, dyspepsia, gastritis, acute gastric erosion and ulceration, peptic ulcers, stomach tumors such as carcinomas and sarcomas, small intestine disorders such as congenital atresia and stenosis, diverticula, Meckel's diverticulum, pancreatic rests, ischemic bowel disease, infective enterocolitis, Crohn's disease, tumors of the small intestine such as carcinomas and sarcomas, disorders of the colon such as malabsorption, obstructive lesions such as hernias, megacolon, diverticular disease, melanosis coli, ischemic injury, hemorrhoids, angiodysplasia of right colon, inflammations of the colon such as ulcerative colitis, and tumors of the colon such as polyps and sarcomas); or metabolic disorders, e.g., lysosomal storage disease, type II glycogenolysis, Fabry's disease, enzyme deficiencies, and inborn errors of metabolism; hepatic disorders and renal disorders, e.g., renal failure and glomerulonephritis. Moreover, the anti-AP antibodies of the invention can be used to detect and isolate AP proteins, regulate the bioavailability of AP proteins, and modulate AP activity.

A. Screening Assays:

The invention provides a method (also referred to herein as a "screening assay") for identifying modulators, i.e., candidate or test compounds or agents (e.g., peptides, peptidomimetics, small molecules or other drugs) which bind to AP proteins, have a stimulatory or inhibitory effect on, for example, AP expression or AP activity, or have a stimulatory or inhibitory effect on, for example, the expression or activity of AP substrate.

In one embodiment, the invention provides assays for screening candidate or test compounds which are substrates of an AP protein or polypeptide or biologically active portion thereof (e.g., proteins or peptides). In another embodiment, the invention provides assays for screening candidate or test compounds which bind to or modulate the activity of an AP protein or polypeptide or biologically active portion thereof (e.g., hormones or neurotransmitters). The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or phage (Scott and Smith (1990) *Science* 249:386–390; Devlin (1990) *Science* 249:404–406; Cwirla et al. (1990) *Proc. Natl. Acad. Sci.* 87:6378–6382; Felici (1991) *J. Mol. Biol.* 222:301–310; Ladner supra.).

In one embodiment, an assay is a cell-based assay in which a cell which expresses an AP protein or biologically active portion thereof is contacted with a test compound and the ability of the test compound to modulate AP activity is determined. Determining the ability of the test compound to modulate AP activity can be accomplished by monitoring, for example, the production of one or more specific metabolites in a cell which expresses AP (see, e.g., Saada et al. (2000) *Biochem Biophys. Res. Commun.* 269: 382–386). The cell, for example, can be of mammalian origin, e.g., a neuronal cell. The ability of the test compound to modulate AP binding to a substrate (e.g., an alcohol or an aldehyde) or to bind to AP can also be determined. Determining the ability of the test compound to modulate AP binding to a substrate can be accomplished, for example, by coupling the AP substrate with a radioisotope or enzymatic label such that binding of the AP substrate to AP can be determined by detecting the labeled AP substrate in a complex. Alternatively, AP could be coupled with a radioisotope or enzymatic label to monitor the ability of a test compound to modulate AP binding to an AP substrate in a complex. Determining the ability of the test compound to bind AP can be accomplished, for example, by coupling the compound with a radioisotope or enzymatic label such that binding of the compound to AP can be determined by detecting the labeled AP compound in a complex. For example, compounds (e.g., AP substrates) can be labeled with $^{125}I$, $^{35}S$, $^{14}C$, or $^{3}H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., an AP substrate) to interact with AP without the labeling of any of the interactants. For example, a microphysiometer can be used to detect the interaction of a compound with AP without the labeling of either the compound or the AP (McConnell, H. M. et al. (1992) *Science* 257:1906–1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and AP.

In another embodiment, an assay is a cell-based assay comprising contacting a cell expressing an AP target molecule (e.g., an AP substrate) with a test compound and determining the ability of the test compound to modulate (e.g., stimulate or inhibit) the activity of the AP target molecule. Determining the ability of the test compound to modulate the activity of an AP target molecule can be accomplished, for example, by determining the ability of the AP protein to bind to or interact with the AP target molecule.

Determining the ability of the AP protein, or a biologically active fragment thereof, to bind to or interact with an AP target molecule can be accomplished by one of the methods described above for determining direct binding. In a preferred embodiment, determining the ability of the AP protein to bind to or interact with an AP target molecule can be accomplished by determining the activity of the target molecule. For example, the activity of the target molecule can be determined by detecting induction of a cellular response (e.g., changes in intracellular $K^+$ levels), detecting catalytic/enzymatic activity of the target on an appropriate substrate, detecting the induction of a reporter gene (comprising a target-responsive regulatory element operatively linked to a nucleic acid encoding a detectable marker, e.g., luciferase), or detecting a target-regulated cellular response.

In yet another embodiment, an assay of the present invention is a cell-free assay in which an AP protein or biologically active portion thereof is contacted with a test compound and the ability of the test compound to bind to the AP protein or biologically active portion thereof is determined. Preferred biologically active portions of the AP proteins to be used in assays of the present invention include fragments which participate in interactions with non-AP molecules, e.g., fragments with high surface probability scores. Binding of the test compound to the AP protein can be determined either directly or indirectly as described above. In a preferred embodiment, the assay includes contacting the AP protein or biologically active portion thereof with a known compound which binds AP to form an assay mixture, contacting the assay mixture with a test compound, and determining the ability of the test compound to interact with an AP protein, wherein determining the ability of the test compound to interact with an AP protein comprises determining the ability of the test compound to preferentially bind to AP or biologically active portion thereof as compared to the known compound.

In another embodiment, the assay is a cell-free assay in which an AP protein or biologically active portion thereof is contacted with a test compound and the ability of the test compound to modulate (e.g., stimulate or inhibit) the activity of the AP protein or biologically active portion thereof is determined. Determining the ability of the test compound to modulate the activity of an AP protein can be accomplished, for example, by determining the ability of the AP protein to bind to an AP target molecule by one of the methods described above for determining direct binding. Determining the ability of the AP protein to bind to an AP target molecule can also be accomplished using a technology such as real-time Biomolecular Interaction Analysis (BIA) (Sjolander, S. and Urbaniczky, C. (1991) *Anal. Chem.* 63:2338–2345; Szabo et al. (1995) *Curr. Opin. Struct. Biol.* 5:699–705). As used herein, "BIA" is a technology for studying biospecific interactions in real time, without labeling any of the interactants (e.g., BIACORE™). Changes in the optical phenomenon of surface plasmon resonance (SPR) can be used as an indication of real-time reactions between biological molecules.

In an alternative embodiment, determining the ability of the test compound to modulate the activity of an AP protein can be accomplished by determining the ability of the AP protein to further modulate the activity of a downstream effector of an AP target molecule. For example, the activity of the effector molecule on an appropriate target can be determined or the binding of the effector to an appropriate target can be determined as previously described.

In yet another embodiment, the cell-free assay involves contacting an AP protein or biologically active portion thereof with a known compound which binds the AP protein to form an assay mixture, contacting the assay mixture with a test compound, and determining the ability of the test compound to interact with the AP protein, wherein determining the ability of the test compound to interact with the AP protein comprises determining the ability of the AP protein to preferentially bind to or catalyze the transfer of a hydride moiety to or from the target substrate.

In more than one embodiment of the above assay methods of the present invention, it may be desirable to immobilize either AP or its target molecule to facilitate separation of complexed from uncomplexed forms of one or both of the proteins, as well as to accommodate automation of the assay. Binding of a test compound to an AP protein, or interaction of an AP protein with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/AP fusion proteins or glutathione-S-transferase/target fusion proteins can be adsorbed onto glutathione SEPHAROSE™ beads (Sigma Chemical, St. Louis, Mo.) or glutathione derivatized microtitre plates, which are then combined with the test compound or the test compound and either the non-adsorbed target protein or AP protein, and the mixture incubated under conditions conducive to complex formation (e.g., at physiological conditions for salt and pH). Following incubation, the beads or microtitre plate wells are washed to remove any unbound components, the matrix is immobilized in the case of beads, and complex formation is determined either directly or indirectly, for example, as described above. Alternatively, the complexes can be dissociated from the matrix, and the level of AP binding or activity determined using standard techniques.

Other techniques for immobilizing proteins on matrices can also be used in the screening assays of the invention. For example, either an AP protein or an AP target molecule can be immobilized utilizing conjugation of biotin and streptavidin. Biotinylated AP protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies which are reactive with AP protein or target molecules but which do not interfere with binding of the AP protein to its target molecule can be derivatized to the wells of the plate, and unbound target or AP protein is trapped in the wells by antibody conjugation. Methods for detecting such complexes, in addition to those described above for the GST-immobilized complexes, include immunodetection of complexes using antibodies reactive with the AP protein or target molecule, as well as enzyme-linked assays which rely on detecting an enzymatic activity associated with the AP protein or target molecule.

In another embodiment, modulators of AP expression are identified in a method wherein a cell is contacted with a candidate compound and the expression of AP mRNA or protein in the cell is determined. The level of expression of AP mRNA or protein in the presence of the candidate compound is compared to the level of expression of AP mRNA or protein in the absence of the candidate compound. The candidate compound can then be identified as a modulator of AP expression based on this comparison. For example, when expression of AP mRNA or protein is greater (statistically significantly greater) in the presence of the candidate compound than in its absence, the candidate compound is identified as a stimulator of AP mRNA or protein expression. Alternatively, when expression of AP mRNA or protein is less (statistically significantly less) in the presence of the candidate compound than in its absence, the candidate compound is identified as an inhibitor of AP mRNA or protein expression. The level of AP mRNA or protein expression in the cells can be determined by methods described herein for detecting AP mRNA or protein.

In yet another aspect of the invention, the AP proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with AP ("AP-binding proteins" or "AP25856-bp or AP21956-bp") and are involved in AP activity. Such AP-binding proteins are also likely to be involved in the propagation of signals by the AP proteins or AP targets as, for example, downstream elements of an AP-mediated signaling pathway. Alternatively, such AP-binding proteins are likely to be AP inhibitors.

The two-hybrid system is based on the modular nature of most transcription factors, which consist of separable DNA-binding and activation domains. Briefly, the assay utilizes two different DNA constructs. In one construct, the gene that codes for an AP protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an AP-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the AP protein.

In another aspect, the invention pertains to a combination of two or more of the assays described herein. For example, a modulating agent can be identified using a cell-based or a cell free assay, and the ability of the agent to modulate the activity of an AP protein can be confirmed in vivo, e.g., in an animal such as an animal model for cellular transformation, cancer, and/or tumorigenesis.

Animal based models for studying tumorigenesis in vivo are well known in the art (reviewed in Animal Models of Cancer Predisposition Syndromes, Hiai, H and Hino, O (eds.) 1999, *Progress in Experimental Tumor Research*, Vol. 35; Clarke A R *Carcinogenesis* (2000) 21:435–41) and include, for example, carcinogen-induced tumors (Rithidech, K et al. *Mutat Res* (1999) 428:33–39; Miller, M L et al. *Environ Mol Mutagen* (2000) 35:319–327), injection and/or transplantation of tumor cells into an animal, as well as animals bearing mutations in growth regulatory genes, for example, oncogenes (e.g., ras) (Arbeit, J M et al. *Am J*

*Pathol* (1993) 142:1187–1197; Sinn, E et al. *Cell* (1987) 49:465–475; Thorgeirsson, S S et al. *Toxicol Lett* (2000) 112–113:553–555) and tumor suppressor genes (e.g., p53) (Vooijs, M et al. *Oncogene* (1999) 18:5293–5303; Clark A R *Cancer Metast Rev* (1995) 14:125–148; Kumar, T R et al. *J. Intern Med* (1995) 238:233–238; Donehower, L A et al. (1992) Nature 356215–221). Furthermore, experimental model systems are available for the study of, for example, colon cancer (Heyer J, et al. (1999) *Oncogene* 18(38): 5325–33), ovarian cancer (Hamilton, T C et al. *Semin Oncol* (1984) 11:285–298; Rahman, N A et al. *Mol Cell Endocrinol* (1998) 145:167–174; Beamer, W G et al. *Toxicol Pathol* (1998) 26:704–710), gastric cancer (Thompson, J et al. *Int J. Cancer* (2000) 86:863–869; Fodde, R et al. *Cytogenet Cell Genet* (1999) 86:105–111), breast cancer (Li, M et al. *Oncogene* (2000) 19:1010–1019; Green, J E et al. *Oncogene* (2000) 19:1020–1027), melanoma (Satyamoorthy, K et al. *Cancer Metast Rev* (1999) 18:401–405), and prostate cancer (Shirai, T et al. *Mutat Res* (2000) 462:219–226; Bostwick, D G et al. *Prostate* (2000) 43:286–294).

This invention further pertains to novel agents identified by the above-described screening assays. Accordingly, it is within the scope of this invention to further use an agent identified as described herein in an appropriate animal model. For example, an agent identified as described herein (e.g., an AP modulating agent, an antisense AP nucleic acid molecule, an AP-specific antibody, or an AP binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

In one embodiment, the invention features a method of treating a subject having a cellular growth or proliferation disorder that involves administering to the subject a AP modulator such that treatment occurs. In another embodiment, the invention features a method of treating a subject having cancer that involves treating a subject with a AP modulator, such that treatment occurs. Preferred AP modulators include, but are not limited to, AP proteins or biologically active fragments, AP nucleic acid molecules, AP antibodies, ribozymes, and AP antisense oligonucleotides designed based on the AP nucleotide sequences disclosed herein, as well as peptides, organic and non-organic small molecules identified as being capable of modulating AP expression and/or activity, for example, according to at least one of the screening assays described herein.

Any of the compounds, including but not limited to compounds such as those identified in the foregoing assay systems, may be tested for the ability to ameliorate cellular growth or proliferation disorder symptoms. Cell-based and animal model-based assays for the identification of compounds exhibiting such an ability to ameliorate cellular growth or proliferation disorder systems are described herein.

In one aspect, cell-based systems, as described herein, may be used to identify compounds which may act to ameliorate cellular growth or proliferation disorder symptoms, for example, reduction in tumor burden, tumor size, tumor cell growth, differentiation, and/or proliferation, and invasive and/or metastatic potential before and after treatment. For example, such cell systems may be exposed to a compound, suspected of exhibiting an ability to ameliorate cellular growth or proliferation disorder symptoms, at a sufficient concentration and for a time sufficient to elicit such an amelioration of cellular growth or proliferation disorder symptoms in the exposed cells. After exposure, the cells are examined to determine whether one or more of the cellular growth or proliferation disorder cellular phenotypes has been altered to resemble a more normal or more wild type, non-cellular growth or proliferation disorder phenotype. Cellular phenotypes that are associated with cellular growth and/or proliferation disorders include aberrant proliferation, growth, and migration, anchorage independent growth, and loss of contact inhibition.

In addition, animal-based cellular growth or proliferation disorder systems, such as those described herein, may be used to identify compounds capable of ameliorating cellular growth or proliferation disorder symptoms. Such animal models may be used as test substrates for the identification of drugs, pharmaceuticals, therapies, and interventions which may be effective in treating cellular growth or proliferation disorders. For example, animal models may be exposed to a compound, suspected of exhibiting an ability to ameliorate cellular growth or proliferation disorder symptoms, at a sufficient concentration and for a time sufficient to elicit such an amelioration of cellular growth or proliferation disorder symptoms in the exposed animals. The response of the animals to the exposure may be monitored by assessing the reversal of cellular growth or proliferation disorders, or symptoms associated therewith, for example, reduction in tumor burden, tumor size, and invasive and/or metastatic potential before and after treatment.

With regard to intervention, any treatments which reverse any aspect of cellular growth or proliferation disorder symptoms should be considered as candidates for human cellular growth or proliferation disorder therapeutic intervention. Dosages of test compounds may be determined by deriving dose-response curves.

Additionally, gene expression patterns may be utilized to assess the ability of a compound to ameliorate cellular growth and/or proliferation disorder symptoms. For example, the expression pattern of one or more genes may form part of a "gene expression profile" or "transcriptional profile" which may be then be used in such an assessment. "Gene expression profile" or "transcriptional profile", as used herein, includes the pattern of mRNA expression obtained for a given tissue or cell type under a given set of conditions. Such conditions may include, but are not limited to, cell growth, proliferation, differentiation, transformation, tumorigenesis, metastasis, and carcinogen exposure. Gene expression profiles may be generated, for example, by utilizing a differential display procedure, Northern analysis and/or RT-PCR. In one embodiment, AP gene sequences may be used as probes and/or PCR primers for the generation and corroboration of such gene expression profiles.

Gene expression profiles may be characterized for known states within the cell- and/or animal-based model systems. Subsequently, these known gene expression profiles may be compared to ascertain the effect a test compound has to modify such gene expression profiles, and to cause the profile to more closely resemble that of a more desirable profile.

For example, administration of a compound may cause the gene expression profile of a cellular growth or proliferation disorder model system to more closely resemble the control system. Administration of a compound may, alternatively, cause the gene expression profile of a control system to begin to mimic a cellular growth and/or proliferation disorder state. Such a compound may, for example, be used in further characterizing the compound of interest, or may be used in the generation of additional animal models.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the AP nucleotide sequences, described herein, can be used to map the location of the AP genes on a chromosome. The mapping of the AP sequences to chromosomes is an important first step in correlating these sequences with genes associated with disease.

Briefly, AP genes can be mapped to chromosomes by preparing PCR primers (preferably 15–25 bp in length) from the AP nucleotide sequences. Computer analysis of the AP sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the AP sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio, P. et al. (1983) Science 220: 919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the AP nucleotide sequences to design oligonucleotide primers, sublocalization can be achieved with panels of fragments from specific chromosomes. Other mapping strategies which can similarly be used to map an AP sequence to its chromosome include in situ hybridization (described in Fan, Y. et al. (1990) Proc. Natl. Acad. Sci. USA, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results in a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridization during chromosomal mapping.

Once a sequence has been mapped to a precise chromosomal location, the physical position of the sequence on the chromosome can be correlated with genetic map data. (Such data are found, for example, in McKusick, V., Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) Nature, 325:783–787.

Moreover, differences in the DNA sequences between individuals affected and unaffected with a disease associated with the AP gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The AP sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the AP nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The AP nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:4 or 7 can comfortably provide positive individual identification with a panel of perhaps 10 to 1,000 primers which each yield a noncoding amplified sequence of 100 bases. If predicted coding sequences, such as those in SEQ ID NO:6 or 9 are used, a more appropriate number of primers for positive individual identification would be 500–2000.

If a panel of reagents from AP nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of AP Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:4 or 7 are particularly appropriate for this use as greater numbers of polymorphisms occur in the noncoding regions, making it easier to differentiate individuals using this technique. Examples of polynucleotide reagents include the AP nucleotide sequences or portions thereof, e.g., fragments derived from the noncoding regions of SEQ ID NO:4 or 7 having a length of at least 20 bases, preferably at least 30 bases.

The AP nucleotide sequences described herein can further be used to provide polynucleotide reagents, e.g., labeled or labelable probes which can be used in, for example, an in situ hybridization technique, to identify a specific tissue, e.g., osteoclasts or trachea tissue. This can be very useful in cases where a forensic pathologist is presented with a tissue of unknown origin. Panels of such AP probes can be used to identify tissue by species and/or by organ type.

In a similar fashion, these reagents, e.g., AP primers or probes can be used to screen tissue culture for contamination (i.e. screen for the presence of a mixture of different types of cells in a culture).

C. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining AP protein and/or nucleic acid expression as well as AP activity, in the context of a biological sample (e.g., blood, serum, cells, or tissue) to thereby determine whether an individual is afflicted with a disease or disorder, or is at risk of developing a disorder, associated with aberrant or unwanted AP expression or activity. The invention also provides for prognostic (or predictive) assays for determining whether an individual is at risk of developing a disorder associated with AP protein, nucleic acid expression or activity. For example, mutations in an AP gene can be assayed in a biological sample. Such assays can be used for prognostic or predictive purpose to thereby prophylactically treat an individual prior to the onset of a disorder characterized by or associated with AP protein, nucleic acid expression or activity.

Another aspect of the invention pertains to monitoring the influence of agents (e.g., drugs, compounds) on the expression or activity of AP in clinical trials.

These and other agents are described in further detail in the following sections.

1. Diagnostic Assays

An exemplary method for detecting the presence or absence of AP protein or nucleic acid in a biological sample involves obtaining a biological sample from a test subject and contacting the biological sample with a compound or an agent capable of detecting AP protein or nucleic acid (e.g., mRNA or genomic DNA) that encodes AP protein such that the presence of AP protein or nucleic acid is detected in the biological sample. A preferred agent for detecting AP mRNA or genomic DNA is a labeled nucleic acid probe capable of hybridizing to AP mRNA or genomic DNA. The nucleic acid probe can be, for example, the AP nucleic acid set forth in SEQ ID NO:4, 6, 7, or 9, or a portion thereof, such as an oligonucleotide of at least 15, 30, 50, 100, 250 or 500 nucleotides in length and sufficient to specifically hybridize under stringent conditions to AP mRNA or genomic DNA. Other suitable probes for use in the diagnostic assays of the invention are described herein.

A preferred agent for detecting AP protein is an antibody capable of binding to AP protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells, and biological fluids isolated from a subject, as well as tissues, cells, and fluids present within a subject. That is, the detection method of the invention can be used to detect AP mRNA, protein, or genomic DNA in a biological sample in vitro as well as in vivo. For example, in vitro techniques for detection of AP mRNA include Northern hybridizations and in situ hybridizations. In vitro techniques for detection of AP protein include enzyme linked immunosorbent assays (ELISAs), Western blots, immunoprecipitations and immunofluorescence. In vitro techniques for detection of AP genomic DNA include Southern hybridizations. Furthermore, in vivo techniques for detection of AP protein include introducing into a subject a labeled anti-AP antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting AP protein, mRNA, or genomic DNA, such that the presence of AP protein, mRNA or genomic DNA is detected in the biological sample, and comparing the presence of AP protein, mRNA or genomic DNA in the control sample with the presence of AP protein, mRNA or genomic DNA in the test sample.

The invention also encompasses kits for detecting the presence of AP in a biological sample. For example, the kit can comprise a labeled compound or agent capable of detecting AP protein or mRNA in a biological sample; means for determining the amount of AP in the sample; and means for comparing the amount of AP in the sample with a standard. The compound or agent can be packaged in a suitable container. The kit can further comprise instructions for using the kit to detect AP protein or nucleic acid.

2. Prognostic Assays

The diagnostic methods described herein can furthermore be utilized to identify subjects having or at risk of developing a disease or disorder associated with aberrant or unwanted AP expression or activity. As used herein, the term "aberrant" includes an AP expression or activity which deviates from the wild type AP expression or activity. Aberrant expression or activity includes increased or decreased expression or activity, as well as expression or activity which does not follow the wild type developmental pattern of expression or the subcellular pattern of expression. For example, aberrant AP expression or activity is intended to include the cases in which a mutation in the AP gene causes the AP gene to be under-expressed or over-expressed and situations in which such mutations result in a non-functional AP protein or a protein which does not function in a wild-type fashion, e.g., a protein which does not interact with an AP substrate, or one which interacts with a non-AP substrate. As used herein, the term "unwanted" includes an unwanted phenomenon involved in a biological response such as cellular proliferation. For example, the term unwanted includes an AP expression or activity which is undesirable in a subject.

The assays described herein, such as the preceding diagnostic assays or the following assays, can be utilized to identify a subject having or at risk of developing a disorder associated with a misregulation in AP protein activity or nucleic acid expression, such as a CNS disorder (e.g., a cognitive or neurodegenerative disorder), a cellular proliferation, growth, differentiation, or migration disorder, a cardiovascular disorder, musculoskeletal disorder, an immune disorder, or a hormonal disorder. Alternatively, the prognostic assays can be utilized to identify a subject having or at risk for developing a disorder associated with a misregulation in AP protein activity or nucleic acid expression, such as a CNS disorder, a cellular proliferation, growth, differentiation, or migration disorder, a metabolic disorder, an inflammatory disorder, an immune disorder, a hormonal disorder, a cardiovascular disorder, or a digestive disorder. Thus, the present invention provides a method for identifying a disease or disorder associated with aberrant or unwanted AP expression or activity in which a test sample is obtained from a subject and AP protein or nucleic acid (e.g., mRNA or genomic DNA) is detected, wherein the presence of AP protein or nucleic acid is diagnostic for a subject having or at risk of developing a disease or disorder associated with aberrant or unwanted AP expression or activity. As used herein, a "test sample" refers to a biological sample obtained from a subject of interest. For example, a test sample can be a biological fluid (e.g., cerebrospinal fluid or serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted AP expression or activity. For example, such methods can be used to determine whether a subject can be effectively treated with an agent for a such as a CNS disorder, a cellular proliferation, growth, differentiation, or migration disorder, e.g., cancer, a metabolic disorder, an inflammatory disorder, an immune disorder, a hormonal disorder, a cardiovascular disorder, or a digestive disorder. Thus, the present invention provides methods for determining whether a subject can be effectively treated with an agent for a disorder associated with aberrant or unwanted AP expression or activity in which a test sample is obtained and AP protein or nucleic acid expression or activity is detected (e.g., wherein the abundance of AP protein or nucleic acid expression or activity is diagnostic for a subject that can be administered the agent to treat a disorder associated with aberrant or unwanted AP expression or activity).

The methods of the invention can also be used to detect genetic alterations in an AP gene, thereby determining if a subject with the altered gene is at risk for a disorder characterized by misregulation in AP protein activity or nucleic acid expression such as a CNS disorder, a cellular proliferation, growth, differentiation, or migration disorder, e.g., cancer, a metabolic disorder, an inflammatory disorder, an immune disorder, a hormonal disorder, a cardiovascular disorder, or a digestive disorder. In preferred embodiments, the methods include detecting, in a sample of cells from the subject, the presence or absence of a genetic alteration characterized by at least one alteration affecting the integrity of a gene encoding an AP-protein, or the mis-expression of the AP gene. For example, such genetic alterations can be detected by ascertaining the existence of at least one of 1) a deletion of one or more nucleotides from an AP gene, 2) an addition of one or more nucleotides to an AP gene, 3) a substitution of one or more nucleotides of an AP gene, 4) a chromosomal rearrangement of an AP gene, 5) an alteration in the level of a messenger RNA transcript of an AP gene, 6) aberrant modification of an AP gene, such as of the methylation pattern of the genomic DNA, 7) the presence of a non-wild type splicing pattern of a messenger RNA transcript of an AP gene, 8) a non-wild type level of an AP-protein, 9) allelic loss of an AP gene, and 10) inappropriate post-translational modification of an AP-protein. As described herein, there are a large number of assays known in the art which can be used for detecting alterations in an AP gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in an AP gene (see Abravaya et al. (1995) *Nucleic Acids Res.* 23:675–682). This method can include the steps of collecting a sample of cells from a subject, isolating nucleic acid (e.g., genomic, mRNA or both) from the cells of the sample, contacting the nucleic acid sample with one or more primers which specifically hybridize to an AP gene under conditions such that hybridization and amplification of the AP gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) *Proc. Natl. Acad. Sci. USA* 87:1874–1878), transcriptional amplification system (Kwoh, D. Y. et al. (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an AP gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in AP can be identified by hybridizing a sample and control nucleic acids, e.g., DNA or RNA, to high density arrays containing hundreds or thousands of oligonucleotide probes (Cronin, M. T. et al. (1996) *Human Mutation* 7:244–255; Kozal, M. J. et al. (1996) *Nature Medicine* 2:753–759). For example, genetic mutations in AP can be identified in two dimensional arrays containing light-generated DNA probes as described in Cronin, M. T. et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the AP gene and detect mutations by comparing the sequence of the sample AP with the corresponding wild-type (control) sequence. Examples of sequencing reactions include those based on techniques developed by Maxam and Gilbert (1977) *Proc. Natl. Acad. Sci. USA* 74:560) or Sanger (1977) *Proc. Natl. Acad. Sci. USA* 74:5463). It is also contemplated that any of a variety of automated sequencing procedures can be utilized when performing the diagnostic assays (Naeve, C. W. (1995) *Biotechniques* 19:448–53), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the AP gene include methods in which protection from cleavage agents is used to detect mismatched bases in RNA/RNA or RNA/DNA heteroduplexes (Myers et al. (1985) *Science* 230: 1242). In general, the art technique of "mismatch cleavage" starts by providing heteroduplexes formed by hybridizing (labeled) RNA or DNA containing the wild-type AP sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad Sci USA* 85:4397 and Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in AP cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on an AP sequence, e.g., a wild-type AP sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in AP genes. For example, single strand conformation polymorphism (SSCP)

may be used to detect differences in electrophoretic mobility between mutant and wild type nucleic acids (Orita et al. (1989) *Proc Natl. Acad. Sci USA:* 86:2766; see also Cotton (1993) Mutat. Res. 285:125–144 and Hayashi (1992) *Genet. Anal. Tech. Appl.* 9:73–79). Single-stranded DNA fragments of sample and control AP nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an AP gene.

Furthermore, any cell type or tissue in which AP is expressed may be utilized in the prognostic assays described herein.

3. Monitoring of Effects During Clinical Trials

Monitoring the influence of agents (e.g., drugs) on the expression or activity of an AP protein (e.g., the modulation of cell proliferation and/or migration) can be applied not only in basic drug screening, but also in clinical trials. For example, the effectiveness of an agent determined by a screening assay as described herein to increase AP gene expression, protein levels, or upregulate AP activity, can be monitored in clinical trials of subjects exhibiting decreased AP gene expression, protein levels, or downregulated AP activity. Alternatively, the effectiveness of an agent determined by a screening assay to decrease AP gene expression, protein levels, or downregulate AP activity, can be monitored in clinical trials of subjects exhibiting increased AP gene expression, protein levels, or AP activity. In such clinical trials, the expression or activity of an AP gene, and preferably, other genes that have been implicated in, for example, an AP-associated disorder can be used as a "read out" or marker of the phenotype of a particular cell.

For example, and not by way of limitation, genes, including AP, that are modulated in cells by treatment with an agent (e.g., compound, drug or small molecule) which modulates AP activity (e.g., identified in a screening assay as described herein) can be identified. Thus, to study the effect of agents on AP-associated disorders (e.g., a CNS disorder, a cellular proliferation, growth, differentiation, or migration disorder, e.g., cancer, a metabolic disorder, an inflammatory disorder, an immune disorder, a hormonal disorder, a cardiovascular disorder, or a digestive disorder), for example, in a clinical trial, cells can be isolated and RNA prepared and analyzed for the levels of expression of AP and other genes implicated in the AP-associated disorder, respectively. The levels of gene expression (e.g., a gene expression pattern) can be quantified by Northern blot analysis or RT-PCR, as described herein, or alternatively by measuring the amount of protein produced, by one of the methods as described herein, or by measuring the levels of activity of AP or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of an AP protein, mRNA, or genomic DNA in the preadministration sample; (iii) obtaining one or more post-administration samples from the subject; (iv) detecting the level of expression or activity of the AP protein, mRNA, or genomic DNA in the post-administration samples; (v) comparing the level of expression or activity of the AP protein, mRNA, or genomic DNA in the pre-administration sample with the AP protein, mRNA, or genomic DNA in the post administration sample or samples; and (vi) altering the administration of the agent to the subject accordingly. For example, increased administration of the agent may be desirable to increase the expression or activity of AP to higher levels than detected, i.e., to increase the effectiveness of the agent. Alternatively, decreased administration of the agent may be desirable to decrease expression or activity of AP to lower levels than detected, i.e. to decrease the effectiveness of the agent. According to such an embodiment, AP expression or activity may be used as an indicator of the effectiveness of an agent, even in the absence of an observable phenotypic response.

D. Methods of Treatment

The present invention provides for both prophylactic and therapeutic methods of treating a subject at risk of (or susceptible to) a disorder or having a disorder associated with aberrant or unwanted AP expression or activity, e.g., a aminopeptidase-associated disorder such as a CNS disorder, a cellular proliferation, growth, differentiation, or migration disorder, e.g., cancer, a metabolic disorder, an inflammatory disorder, an immune disorder, a hormonal disorder, a cardiovascular disorder, or a digestive disorder.

"Treatment", as used herein, is defined as the application or administration of a therapeutic agent to a patient, or application or administration of a therapeutic agent to an isolated tissue or cell line from a patient, who has a disease or disorder, a symptom of disease or disorder or a predisposition toward a disease or disorder, with the purpose of curing, healing, alleviating, relieving, altering, remedying, ameliorating, improving or affecting the disease or disorder, the symptoms of disease or disorder or the predisposition toward a disease or disorder. A therapeutic agent includes, but is not limited to, small molecules, peptides, antibodies, ribozymes and antisense oligonucleotides.

With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the AP molecules of the present invention or AP modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted AP expression or activity, by administering to the subject an AP or an agent which modulates AP expression or at least one AP activity. Subjects at risk for a disease which is caused or contributed to by aberrant or unwanted AP expression or activity can be identified by, for example, any or a combination of diagnostic or prognostic assays as described herein. Administration of a prophylactic agent can occur prior to the manifestation of symptoms characteristic of the AP aberrancy, such that a disease or disorder is prevented or, alternatively, delayed in its progression. Depending on the type of AP aberrancy, for example, an AP, AP agonist or AP antagonist agent can be used for treating the subject. The appropriate agent can be determined based on screening assays described herein.

2. Therapeutic Methods

Another aspect of the invention pertains to methods of modulating AP expression or activity for therapeutic purposes. Accordingly, in an exemplary embodiment, the modulatory method of the invention involves contacting a cell with an AP or agent that modulates one or more of the activities of AP protein activity associated with the cell. An agent that modulates AP protein activity can be an agent as described herein, such as a nucleic acid or a protein, a naturally-occurring target molecule of an AP protein (e.g., an AP substrate), an AP antibody, an AP agonist or antagonist, a peptidomimetic of an AP agonist or antagonist, or other small molecule. In one embodiment, the agent stimulates one or more AP activities. Examples of such stimulatory agents include active AP protein and a nucleic acid molecule encoding AP that has been introduced into the cell. In another embodiment, the agent inhibits one or more AP activities. Examples of such inhibitory agents include antisense AP nucleic acid molecules, anti-AP antibodies, and AP inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of an AP protein or nucleic acid molecule. In one embodiment, the method involves administering an agent (e.g., an agent identified by a screening assay described herein), or combination of agents that modulates (e.g., upregulates or downregulates) AP expression or activity. In another embodiment, the method involves administering an AP protein or nucleic acid molecule as therapy to compensate for reduced, aberrant, or unwanted AP expression or activity.

Stimulation of AP activity is desirable in situations in which AP is abnormally downregulated and/or in which increased AP activity is likely to have a beneficial effect. Likewise, inhibition of AP activity is desirable in situations in which AP is abnormally upregulated and/or in which decreased AP activity is likely to have a beneficial effect.

3. Pharmacogenomics

The AP molecules of the present invention, as well as agents, or modulators which have a stimulatory or inhibitory effect on AP activity (e.g., AP gene expression) as identified by a screening assay described herein can be administered to individuals to treat (prophylactically or therapeutically) AP-associated disorders (e.g., a CNS disorder, a cellular proliferation, growth, differentiation, or migration disorder, a metabolic disorder, an inflammatory disorder, an immune disorder, a hormonal disorder, a cardiovascular disorder, or a digestive disorder) associated with aberrant or unwanted AP activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an AP molecule or AP modulator as well as tailoring the dosage and/or therapeutic regimen of treatment with an AP molecule or AP modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11): 983–985 and Linder, M. W.

et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate aminopeptidase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach" can be utilized to identify genes that predict drug response. According to this method, if a gene that encodes a drug target is known (e.g., an AP protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and the cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling" can be utilized to identify genes that predict drug response. For example, the gene expression of an animal dosed with a drug (e.g., an AP molecule or AP modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with an AP molecule or AP modulator, such as a modulator identified by one of the exemplary screening assays described herein.

VI. Electronic Apparatus Readable Media and Arrays

Electronic apparatus readable media comprising AP sequence information is also provided. As used herein, "AP sequence information" refers to any nucleotide and/or amino acid sequence information particular to the AP molecules of the present invention, including but not limited to full-length nucleotide and/or amino acid sequences, partial nucleotide and/or amino acid sequences, polymorphic sequences including single nucleotide polymorphisms (SNPs), epitope sequences, and the like. Moreover, information "related to" said AP sequence information includes detection of the presence or absence of a sequence (e.g., detection of expression of a sequence, fragment, polymorphism, etc.), determination of the level of a sequence (e.g., detection of a level of expression, for example, a quantitative detection), detection of a reactivity to a sequence (e.g., detection of protein expression and/or levels, for example, using a sequence-specific antibody), and the like. As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon AP sequence information of the present invention.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the AP sequence information.

A variety of software programs and formats can be used to store the sequence information on the electronic apparatus readable medium. For example, the sequence information can be represented in a word processing text file, formatted in commercially-available software such as WordPerfect and Microsoft Word, or represented in the form of an ASCII file, stored in a database application, such as DB2, Sybase, Oracle, or the like, as well as in other forms. Any number of data processor structuring formats (e.g., text file or database) may be employed in order to obtain or create a medium having recorded thereon the AP sequence information.

By providing AP sequence information in readable form, one can routinely access the sequence information for a variety of purposes. For example, one skilled in the art can use the sequence information in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has a AP-associated disease or disorder or a pre-disposition to a AP-associated disease or disorder, wherein the method comprises the steps of determining AP sequence information associated with the subject and based on the AP sequence information, determining whether the subject has a AP-associated disease or disorder or a pre-disposition to a AP-associated disease or disorder and/or recommending a particular treatment for the disease, disorder or pre-disease condition.

The present invention further provides in an electronic system and/or in a network, a method for determining whether a subject has a AP-associated disease or disorder or a pre-disposition to a disease associated with a AP wherein the method comprises the steps of determining AP sequence information associated with the subject, and based on the AP sequence information, determining whether the subject has a AP-associated disease or disorder or a pre-disposition to a AP-associated disease or disorder, and/or recommending a particular treatment for the disease, disorder or pre-disease condition. The method may further comprise the step of receiving phenotypic information associated with the subject and/or acquiring from a network phenotypic information associated with the subject.

The present invention also provides in a network, a method for determining whether a subject has a AP-associated disease or disorder or a pre-disposition to a AP associated disease or disorder associated with AP, said method comprising the steps of receiving AP sequence information from the subject and/or information related thereto, receiving phenotypic information associated with the subject, acquiring information from the network corresponding to AP and/or a AP-associated disease or disorder, and based on one or more of the phenotypic information, the AP information (e.g., sequence information and/or information related thereto), and the acquired information, determining whether the subject has a AP-associated disease or disorder or a pre-disposition to a AP-associated disease or disorder (e.g., a carbonic anhydrase-associated disorder such as a CNS disorder, a cellular proliferation, growth, differentiation, or migration disorder, a metabolic disorder, an inflammatory disorder, an immune disorder, a hormonal disorder, a cardiovascular disorder, or a digestive disorder. The method may further comprise the step of recommending a particular treatment for the disease, disorder or pre-disease condition.

The present invention also provides a business method for determining whether a subject has a AP-associated disease or disorder or a pre-disposition to a AP-associated disease or disorder, said method comprising the steps of receiving information related to AP (e.g., sequence information and/or information related thereto), receiving phenotypic information associated with the subject, acquiring information from the network related to AP and/or related to a AP-associated disease or disorder, and based on one or more of the phenotypic information, the AP information, and the acquired information, determining whether the subject has a AP-associated disease or disorder or a pre-disposition to a AP-associated disease or disorder. The method may further comprise the step of recommending a particular treatment for the disease, disorder or pre-disease condition.

The invention also includes an array comprising a AP sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, one of which can be AP. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a AP-associated disease or disorder, progression of AP-associated disease or disorder, and processes, such a cellular transformation associated with the AP-associated disease or disorder.

The array is also useful for ascertaining the effect of the expression of a gene on the expression of other genes in the same cell or in different cells (e.g., ascertaining the effect of AP expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including AP) that could serve as a molecular target for diagnosis or therapeutic intervention. This invention is further illustrated by the following examples which should not be construed as limiting. The contents of all references, patents and published patent applications cited throughout this application, as well as the Figures and the Sequence Listing, are incorporated herein by reference.

EXAMPLES

Example 1

Identification and Characterization of Human AP cDNA

In this example, the identification and characterization of the genes encoding human AP21956 (clone Fbh21956) and human AP25856 (clone Fbh25856) is described.

Isolation of the AP cDNA

The invention is based, at least in part, on the discovery of human genes encoding novel proteins, referred to herein as AP, e.g., AP21956 and AP25856. The entire sequences of human clones Fbh21956 and Fbh25856 were determined and found to contain open reading frames termed human "AP21956" and "AP25856", respectively.

The nucleotide sequence encoding the human AP21956 is shown in FIGS. 6A–C and is set forth as SEQ ID NO:4. The protein encoded by this nucleic acid comprises about 796 amino acids and has the amino acid sequence shown in FIGS. 6A–C and set forth as SEQ ID NO:5. The coding region (open reading frame) of SEQ ID NO:4 is set forth as SEQ ID NO:6.

The nucleotide sequence encoding the human AP25856 is shown in FIGS. 7A–B and is set forth as SEQ ID NO:7. The protein encoded by this nucleic acid comprises about 196 amino acids and has the amino acid sequence shown in FIGS. 7A–B and set forth as SEQ ID NO:8. The coding region (open reading frame) of SEQ ID NO:7 is set forth as SEQ ID NO:9.

Analysis of the Human AP Molecules

The amino acid sequences of human AP21956 and AP25856 were analyzed using the program PSORT (see the PSORT website maintained by the Human Genome Center at the Institute of Medical Science in the University of Tokyo, Japan (psort.nibb.ac.jp)) to predict the localization of the proteins within the cell. This program assesses the presence of different targeting and localization amino acid sequences within the query sequence. The results of the analyses show the possibility of human AP21956 being localized to the golgi, to the mitochondria, to the cytoplasm, to secretory vesicles, to the endoplasmic reticulum, or extracellularly, including the cell wall. The results of the analyses further show the possibility of human AP25856 being localized to the cytoplasm, to the nucleus, to the mitochondria, or to the golgi.

Each of the amino acid sequences of AP21956 and AP25856 was analyzed by the SignalP program (Henrik, et al. (1997) *Protein Engineering* 10:1–6) for the presence of a signal peptide. These analyses revealed the possible presence of a signal peptide in the amino acid sequence of AP21956 (SEQ ID NO:5) from residues 1–53.

Searches of each of the amino acid sequences of AP21956 and AP25856 were performed against the Memsat database. These searches resulted in the identification of two transmembrane domains in the amino acid sequence of human AP21956 (SEQ ID NO:5) at about residues 34–56 and 251–274.

Searches of each of the amino acid sequences of AP21956 and AP25856 were also performed against the HMM database. These searches resulted in the identification of a dipeptidyl peptidase IV N-terminal domain, at about residues 69–578 (score=588.2) a prolyl oligopeptidase domain at about residues 580–656 (score=71.7), a dienelactone hydrolase domain at about residues 719–759 (score=9.6), and a phospholipase/carboxylesterase domain at about residues 556–773 (score=–96.8) in the amino acid sequence of AP21956 (SEQ ID NO:5). These searches also resulted in the identification of a pyroglutamyl peptidase domain at about residues 6–190 (score=–63.6) in the amino acid sequence of AP25856 (SEQ ID NO:8).

Searches of the amino acid sequences of AP21956 and AP25856 were also performed against the ProDom database. These searches resulted in the identification of a "peptidase aminopeptidase glycoprotein protease transmembrane serine signal-anchor hydrolase domain" at about amino acid residues 22–185, a "peptidase aminopeptidase glycoprotein transmembrane protease hydrolase domain" at about amino acid residues 183–275, a "aminopeptidase signal-anchor serine dipeptidyl hydrolase dipeptidase glycoprotein domain" at about amino acid residues 266–382, a "peptidase aminopeptidase glycoprotein hydrolase protease transmembrane signal-anchor serine domain" at about amino acid residues 280–530, a "hydrolase IV peptidase aminopeptidase glycoprotein enzyme acylamino-acid-releasing protease transmembrane domain" at about residues 552–632, a "dipeptidyl IV-related peptidase domain" at about amino acid residues 626–781, a "ATTS peptidase domain" at about amino acid residues 628–742, a "dipeptidyl protease peptidase IV serine endopeptidase aminopeptidase enzyme domain" at about amino acid residues 639–742, a "dipeptidyl related transmembrane like signal-anchor dipeptidylpeptidase splicing domain" at about amino acid residues 743–796, a "hydrolase domain" at about amino acid residues 475–606, and a hydrolase family plasmid predicted CT149 Trax-RTXA dienelasctone domain" at about amino acid residues 594–740 of the AP21956 protein sequence (SEQ ID NO:5). These searches also resulted in the identification of a "peptidase pyrrolidone-carboxylate" domain at about amino acid residues 8–172 of the AP25856 protein sequence (SEQ ID NO:8).

Search of the amino acid sequences of AP21956 and AP25856 were also performed against the ProSite database. These searches resulted in the identification of several "N-glycosylation sites" at about amino acid residues 2–5, 63–66, 90–93, 111–114, 119–122, 257–260, 342–345, 748–751, and 760–763, one "cAMP- and cGMP-dependent protein kinase phosphorylation site" at about amino acid residues 643–646, several "protein kinase C phosphorylation sites" at about amino acid residues 18–20, 124–126, 210–212, 216–218, 291–293, 313–315, 357–359, 414–416, 435–437, 446–448, 577–579, 642–644, 688–690, and 762–764, several "casein kinase II phosphorylation sites" at about amino acid residues 18–21, 57–60, 70–73, 216–219, 347–350, 408–411, 476–479, and 696–699, a "tyrosine kinase phosphorylation site" at about amino acid residues 553–561, and several "N-myristoylation sites" at about amino acid residues 34–39, 573–578, 653–658, 724–729, and 746–751 of the AP21956 protein sequence (SEQ ID NO:5). These searches also resulted in the identification of two "N-glycosylation sites" at about amino acid residues 22–25 and 38–41, a "cAMP- and cGMP-dependent protein kinase phosphorylation site" at about residues 58–61, a "protein kinase C phosphorylation site" at about amino acid residues 89–91, a "casein kinase II phosphorylation site" at about amino acid residues 23–26, a "tyrosine kinase phosphorylation site" at about residues 146–154, and a "N-myristoylation site" at about amino acid residues 76–81 of the AP25856 protein sequence (SEQ ID NO:8).

BLAST searches were also performed using the nucleotide sequences of AP21956 and AP25856.

Tissue Distribution of AP mRNA as Determined by Northern Blot Analysis

This example describes the tissue distribution of human AP, e.g., human AP21956 or human AP25856 mRNA, as determined by Northern analysis.

Northern blot hybridizations with the various RNA samples are performed under standard conditions and washed under stringent conditions, i.e., 0.2×SSC at 65° C. The DNA probe is radioactively labeled with $^{32}$P-dCTP using the Prime-It kit (Stratagene, La Jolla, Calif.) according to the instructions of the supplier. Filters containing human mRNA (MultiTissue Northern I and MultiTissue Northern II from Clontech, Palo Alto, Calif.) are probed in ExpressHyb hybridization solution (Clontech) and washed at high stringency according to manufacturer's recommendations.

AP expression in normal human and monkey tissues is assessed by PCR using the Taqman™ system (PE Applied Biosystems) according to the manufacturer's instructions.

Tissue Distribution of AP mRNA as Determined by in situ Analysis

This example describes the tissue distribution of human AP, e.g., human AP21956 or human AP25856 mRNA, as determined by Northern in situ hybridization analysis.

For in situ analysis, various tissues, e.g., tissues obtained from brain, are first frozen on dry ice. Ten-micrometer-thick sections of the tissues are postfixed with 4% formaldehyde in DEPC-treated 1× phosphate-buffered saline at room temperature for 10 minutes before being rinsed twice in DEPC 1× phosphate-buffered saline and once in 0.1 M triethanolamine-HCl (pH 8.0). Following incubation in 0.25% acetic anhydride-0.1 M triethanolamine-HCl for 10 minutes, sections are rinsed in DEPC 2×SSC (1×SSC is 0.15 M NaCl plus 0.015 M sodium citrate). Tissue is then dehydrated through a series of ethanol washes, incubated in 100% chloroform for 5 minutes, and then rinsed in 100% ethanol for 1 minute and 95% ethanol for 1 minute and allowed to air dry.

Hybridizations are performed with $^{35}$S-radiolabeled (5×10$^7$ cpm/ml) cRNA probes. Probes are incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1× Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides are washed with 2×SSC. Sections are then sequentially incubated at 37° C. in TNE (a solution containing 10 mM Tris-HCl (pH 7.6), 500 mM NaCl, and 1 mM EDTA), for 10 minutes, in TNE with 10% g of RNase A per ml for 30 minutes, and finally in TNE for 10 minutes. Slides are then rinsed with 2×SSC at room temperature, washed with 2×SSC at 50° C. for 1 hour, washed with 0.2×SSC at 55° C. for 1 hour, and 0.2×SSC at 60° C. for 1 hour. Sections are then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

Tissue Distribution of AP mRNA by Taqman™ Analysis

This example describes the tissue distribution of human AP mRNA in a variety of cells and tissues, as determined using the TaqMan™ procedure. The Taqman™ procedure is a quantitative, reverse transcription PCR-based approach for detecting mRNA. The RT-PCR reaction exploits the 5' nuclease activity of AmpliTaq Gold™ DNA Polymerase to cleave a TaqMan™ probe during PCR. Briefly, cDNA was generated from the samples of interest, e.g., various human and monkey normal and tumor tissues, cell lines, and the like, and used as the starting material for PCR amplification. In addition to the 5' and 3' gene-specific primers, a gene-specific oligonucleotide probe (complementary to the region being amplified) was included in the reaction (i.e., the Taqman™ probe). The TaqMan™ probe includes the oligonucleotide with a fluorescent reporter dye covalently linked to the 5' end of the probe (such as FAM (6-carboxyfluorescein), TET (6-carboxy-4,7,2',7'-tetrachlorofluorescein), JOE (6-carboxy-4,5-dichloro-2,7-dimethoxyfluorescein), or VIC) and a quencher dye (TAMRA (6-carboxy-N,N,N',N'-tetramethylrhodamine) at the 3' end of the probe.

During the PCR reaction, cleavage of the probe separates the reporter dye and the quencher dye, resulting in increased fluorescence of the reporter. Accumulation of PCR products is detected directly by monitoring the increase in fluorescence of the reporter dye. When the probe is intact, the proximity of the reporter dye to the quencher dye results in suppression of the reporter fluorescence. During PCR, if the target of interest is present, the probe specifically anneals between the forward and reverse primer sites. The 5'-3' nucleolytic activity of the AmpliTaq™ Gold DNA Polymerase cleaves the probe between the reporter and the quencher only if the probe hybridizes to the target. The probe fragments are then displaced from the target, and polymerization of the strand continues. The 3' end of the probe is blocked to prevent extension of the probe during PCR. This process occurs in every cycle and does not interfere with the exponential accumulation of product. RNA was prepared using the trizol method and treated with DNase to remove contaminating genomic DNA. cDNA was synthesized using standard techniques. Mock cDNA synthesis in the absence of reverse transcriptase resulted in samples with no detectable PCR amplification of the control gene confirms efficient removal of genomic DNA contamination.

Human AP21956

Figure 10:
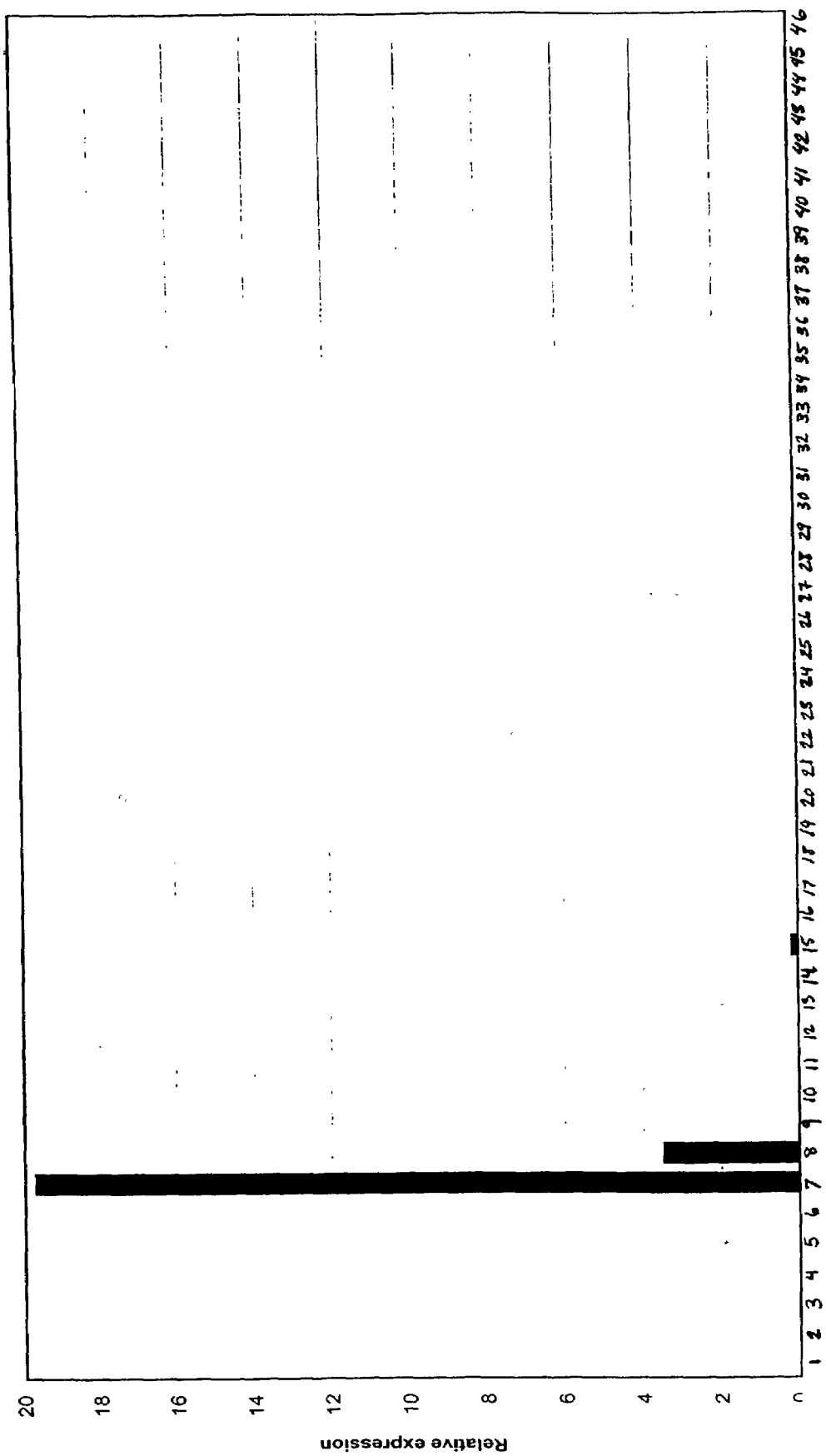
FIG. 10 is a graphic depiction of the relative levels of human AP21956 mRNA expression in a human tissue panel containing normal and tumor tissue samples, as determined using Taqman™ analysis (1=normal aortic tissue, 2=normal fetal heart tissue, 3=normal heart tissue, 4=congestive heart failure (CHF) heart tissue, 5=normal vein, 6=normal spinal cord, 7=normal brain cortex, 8=normal brain hypothalamus, 9=glial cells, 10=glioblastoma tissue, 11=normal breast tissue, 12=breast tumor tissue, 13=normal ovary tissue, 14=ovary tumor tissue, 15=pancreas, 16=normal prostate tissue, 17=prostate tumor tissue, 18=normal colon tissue, 19=colon tumor tissue, 20=inflammatory bowel disease (IBD) colon tissue, 21=normal kidney tissue, 22=normal liver tissue, 23=liver fibrosis, 24=normal fetal liver tissue, 25=normal lung tissue, 26=lung tumor tissue, 27=chronic obstructive pulmonary disease (COPD) lung tissue, 28=spleen normal tissue, 29=normal tonsil tissue, 30=normal lymph node tissue, 31=normal thymus tissue, 32=prostate epithelial cells, 33=aortic endothelial cells, 34=normal skeletal muscle, 35=dermal fibroblasts, 36=normal skin tissue, 37=normal adipose tissue, 38=primary osteoblasts, 39=undifferentiated osteoblasts, 40=differentiated osteoblasts, 41=osteoclasts, 42=aortic smooth muscle cells, early, 43=aortic smooth muscle cells, late, 44=shear HUVEC, 45=static HUVEC, 46=undifferentiated osteoclasts).

The results of the Taqman analysis of human AP21956 mRNA expression are as follows. A human tissue panel was tested revealing highest expression of human AP21956 mRNA in normal brain cortex, normal brain hypothalamus, and pancreas (see FIG. 10).

Figure 11:
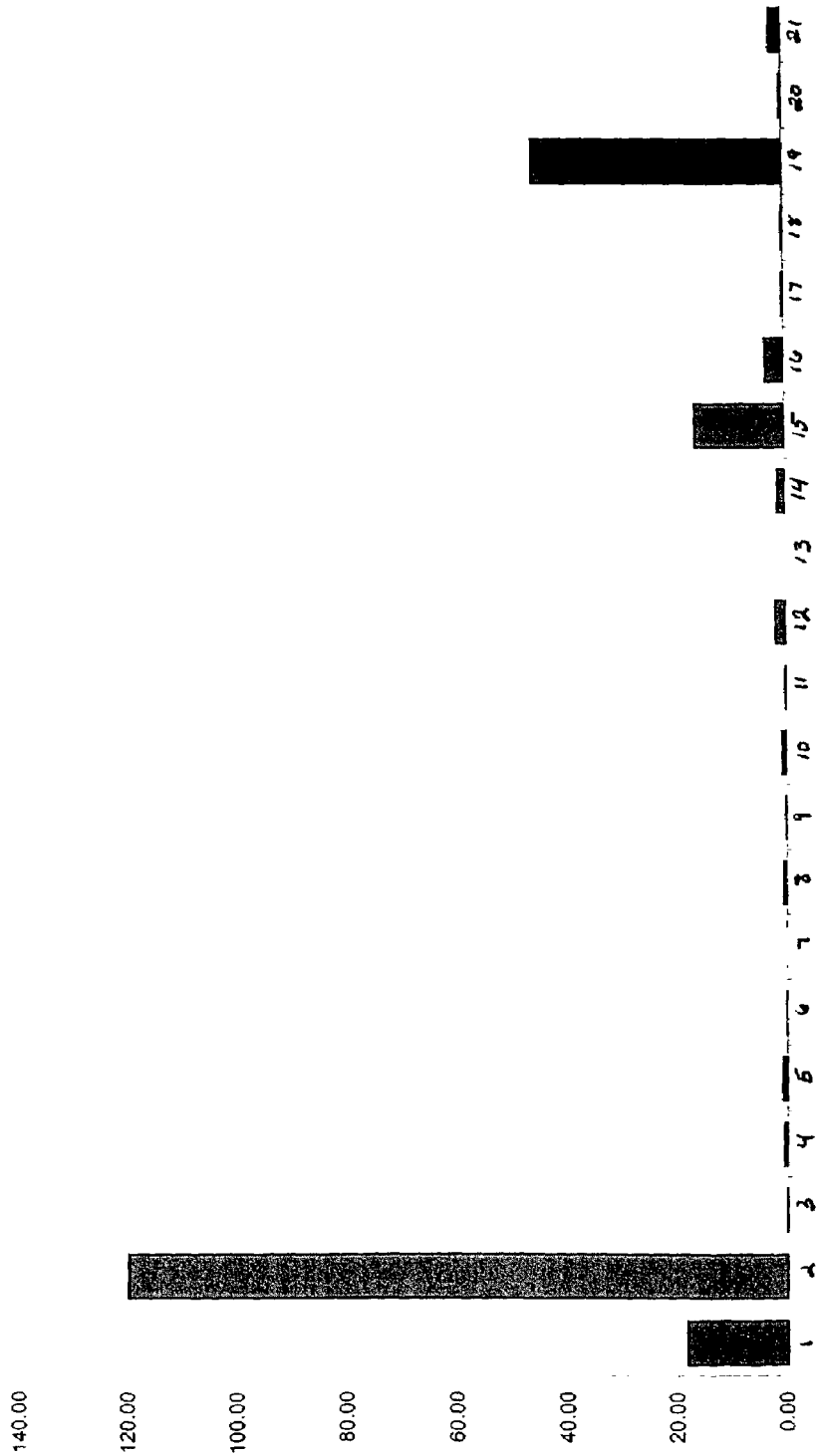
FIG. 11 is a graphic depiction of the relative levels of human AP21956 mRNA expression in a panel containing normal human tissue samples, as determined using Taqman™ analysis (1=adrenal gland, 2=brain tissue, 3=heart tissue, 4=kidney tissue, 5=liver tissue, 6=lung tissue, 7=mammary gland tissue, 8=placental tissue, 9=prostate tissue, 10=pituitary gland tissue, 11=muscle tissue, 12=small intestine tissue, 13=spleen tissue, 14=stomach tissue, 15=testes tissue, 16=thymus tissue, 17=trachea tissue, 18=uterine tissue, 19=spinal cord tissue, 20=skin tissue, 21=dorsal root ganglia (DRG)).

A second human panel containing various normal human tissues indicated highest expression of human AP21956 mRNA in brain tissue, spinal cord tissue, adrenal gland, and testes. Weaker expression was also detected in the thymus, dorsal root ganglia (DRG), stomach tissue, and small intestine (see FIG. 11).

Figure 12:
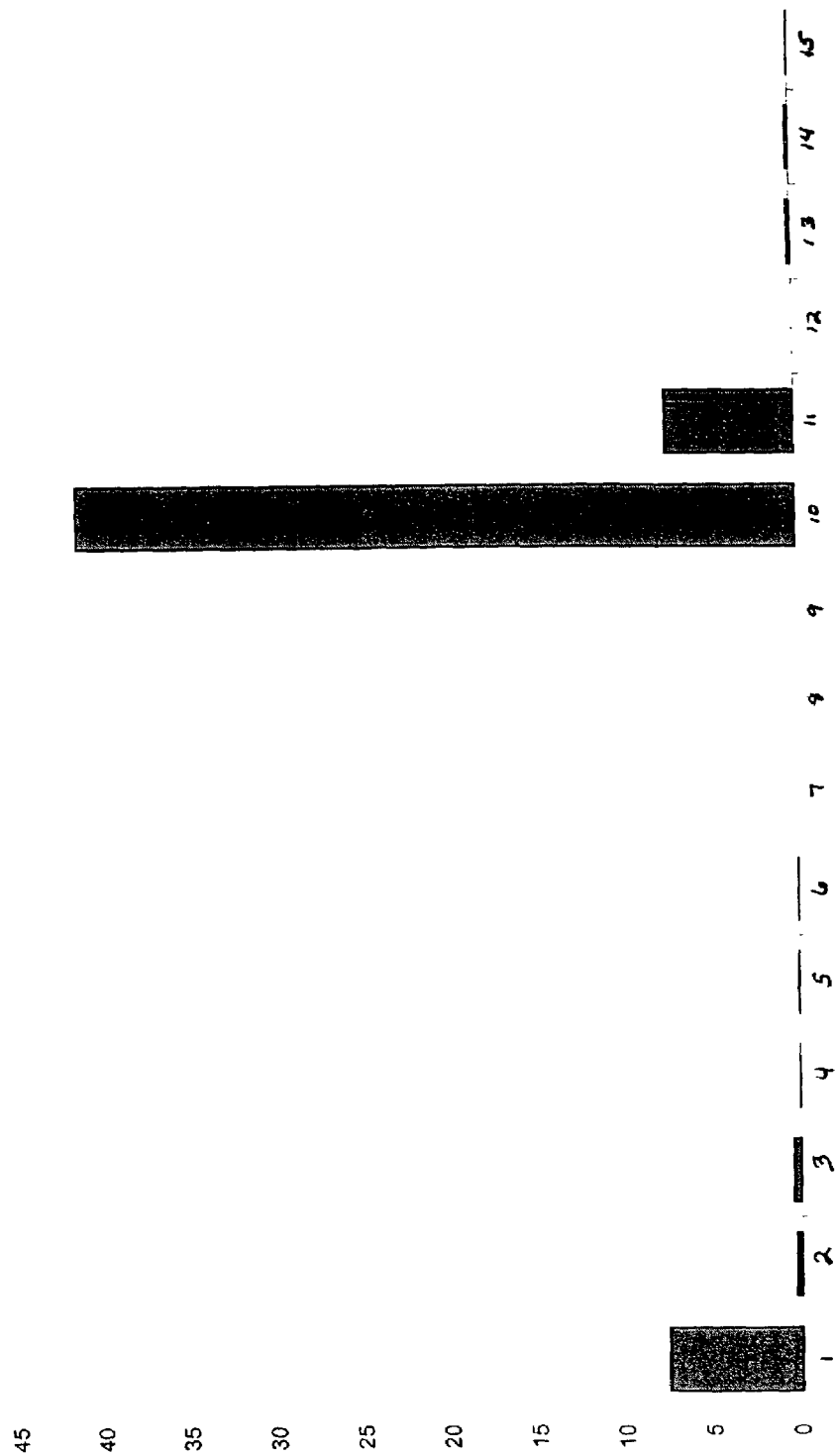
FIG. 12 is a graphic depiction of the relative levels of human AP21956 mRNA expression in a panel containing human and monkey tissue samples, as determined using Taqman™ analysis (1=monkey cortex, 2=monkey dorsal root ganglia (DRG), 3=monkey spinal cord tissue, 4=monkey kidney tissue, 5=monkey hairy skin tissue, 6=monkey heart, left ventricle tissue, 7=monkey gastro muscle tissue, 8=monkey liver tissue, 9=human brain tissue, 10=human 11=spinal cord tissue, 12=human heart tissue, 13=human kidney tissue, 14=human liver tissue, 15=human lung tissue).

A panel containing monkey and human tissues was also tested indicating highest expression of human AP21956 mRNA in human brain, human spinal cord, and monkey cortex (see FIG. 12).

Figure 13:
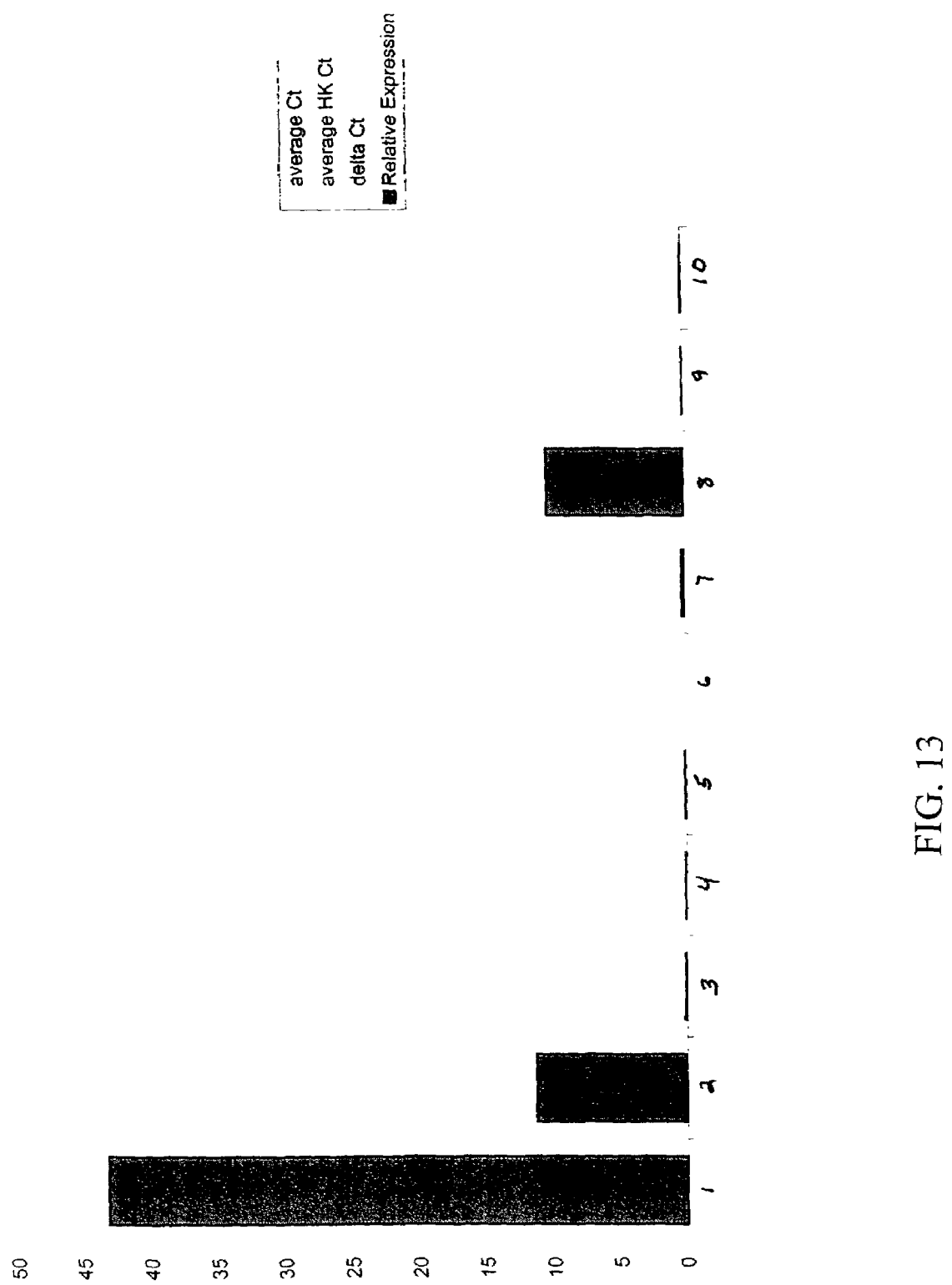
FIG. 13 is a graphic depiction of the relative levels of human AP21956 mRNA expression in a panel containing normal human tissue samples, as determined using Taqman™ analysis (1=human brain tissue, 2=human spinal cord tissue, 3=human heart tissue, 4=human kidney tissue, 5=human liver tissue, 6=human lung tissue, 7=human dorsal root ganglia (WU), 8=human spinal cord (WU), 9=human spinal cord tissue, 10=human skin tissue).

A panel containing various human tissues indicated highest expression of human AP21956 mRNA in human brain and human spinal cord (see FIG. 13).

Figure 14:
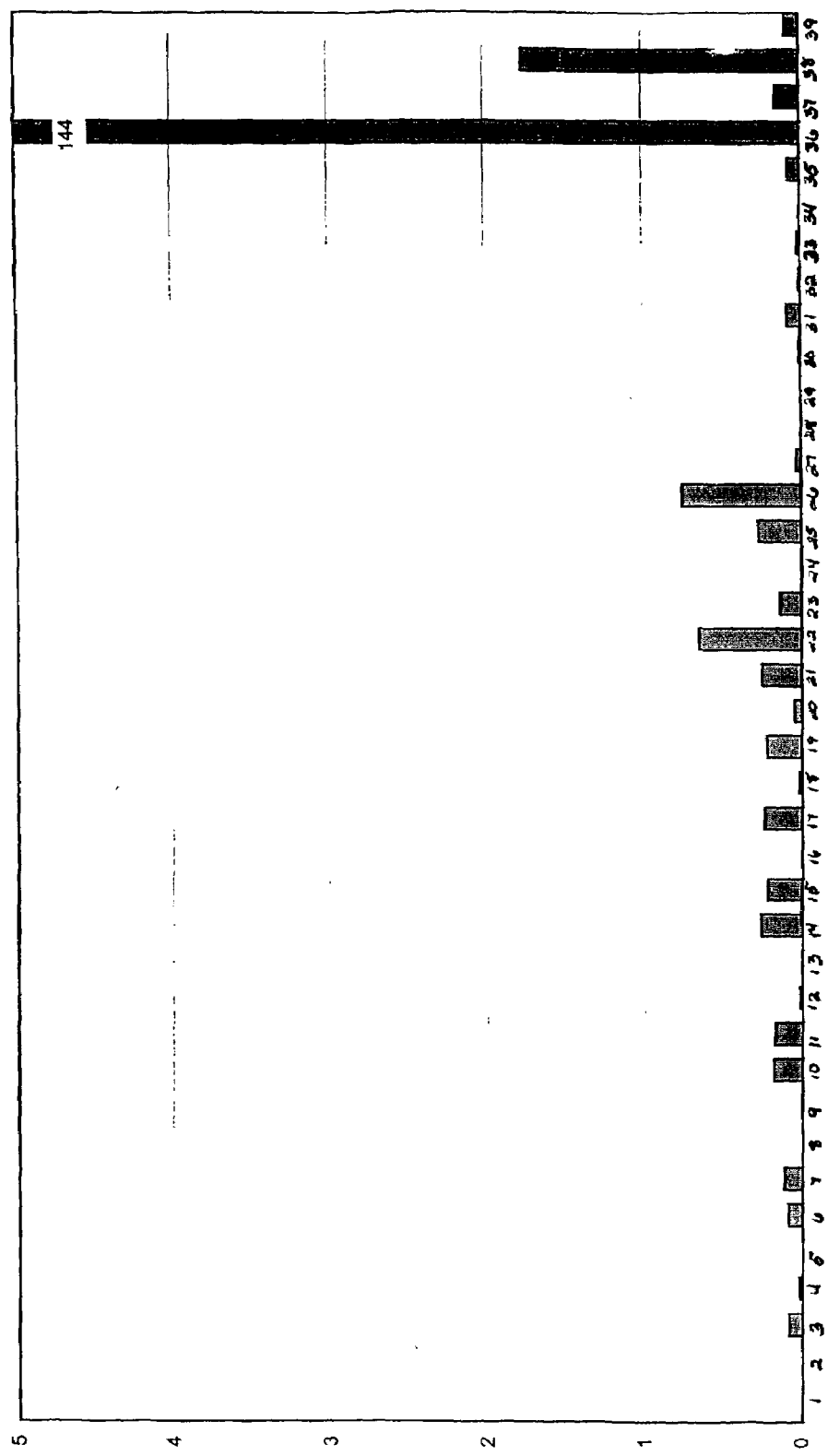
FIG. 14 is a graphic depiction of the relative levels of human AP21956 mRNA expression in a panel containing human normal and tumor tissue samples, as determined using Taqman™ analysis (1–10=breast tumor tissue samples, 11–13=lung tumor tissue samples, 14–20=lung tumor tissue samples, 21–23=colon normal tissue samples, 24–31=colon tumor tissue samples, 32–34=colon metastases to the liver, 35=normal liver tissue, 36=normal brain tissue, 37–39=brain tumor tissue).

A panel containing human breast, lung, colon, liver, and brain normal and tumor tissue samples indicated highest expression of human AP21956 mRNA in normal brain tissue, with comparatively weaker expression in brain tumor tissue. Expression of human AP21956 mRNA was higher in breast tumor tissue compared to normal breast tissue. Expression was also detected in a normal liver tissue sample, with weaker expression detected in colon tumor metastases to the liver. Human AP21956 mRNA expression was also detected in colon tumor tissue and colon normal tissue, and lung tumor tissue and normal lung tissue (see FIG. 14).

Human AP25856

Figure 15:
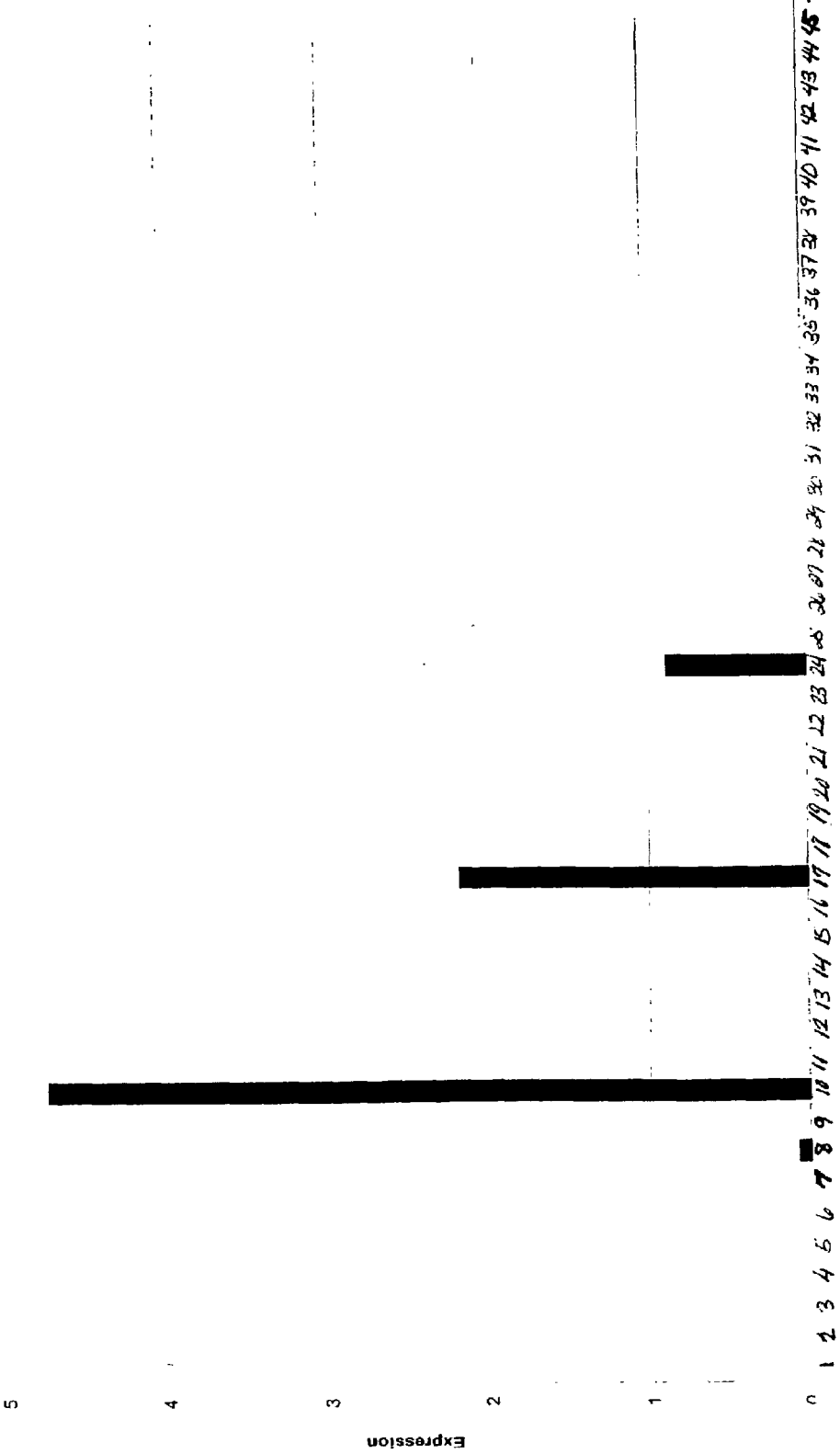
FIG. 15 is a graphic depiction of the relative levels of human AP25856 mRNA expression in a human tissue panel, as determined using Taqman™ analysis (1=normal artery, 2=normal vein, 3=early aortic smooth muscle cells, 4=coronary smooth muscle cells, 5=static HUVEC, 6=shear HUVEC, 7=normal heart tissue, 8=congestive heart failure (CHF) heart tissue, 9=kidney tissue, 10=skeletal muscle, 11=normal adipose, 12=pancreas, 13=primary osteoblasts, 14=differentiated osteoclasts, 15=normal skin tissue, 16=normal spinal cord tissue, 17=normal brain cortex, 18=brain hypothalamus, 19=nerve tissue, 20=dorsal root ganglia (DRG), 21=glial cells, 22=glioblastoma tissue, 23=normal breast tissue, 24=breast tumor tissue, 25=normal ovary tissue, 26=ovary tumor tissue, 27=normal prostate tissue, 28=prostate tumor tissue, 29=prostate epithelial cells, 30=normal colon tissue, 31=colon tumor tissue, 32=normal lung tissue, 33=lung tumor tissue, 34=chronic obstructive pulmonary disease (COPD) lung tissue, 35=inflammatory bowel disease (IBD) colon tissue, 36=normal liver tissue, 37=liver fibrosis tissue, 38=dermal cells-fibroblasts, 39=normal spleen tissue, 40=normal tonsil tissue, 41=lymph node tissue, 42=small intestine tissue, 43=skin-decubitus, 44=synovium, 45=bone marrow, 46=activated PBMC).

The results of the Taqman analysis of Human AP25856 mRNA expression are as follows. A human tissue panel was tested revealing highest expression of human AP25856 mRNA in normal skeletal muscle tissue, normal brain cortex tissue, and breast tumor tissue (see FIG. 15).

Figure 16:
FIG. 16 is a graphic depiction of the relative levels of human AP25856 mRNA expression in a human tissue panel containing human normal and tumor tissue samples, as determined using Taqman™ analysis (1–3=breast normal tissue, 4–9=breast tumor tissue, 10–11=normal ovary, 12–16=ovary tumor, 17–19=normal lung, 20–26=lung tumor, 27=NHBE, 28–30=normal colon, 31–34=colon tumor, 35–36=colon metastases to the liver, 37=normal liver (female), 38=hemangioma, 39=HMVEC, arrested, 40=HMVEC, prolific).

A tissue panel containing various human normal and tumor tissues was also tested revealing highest expression of human AP25856 mRNA in breast tumor tissue. By contract, expression of human AP25856 mRNA was higher in normal ovary tissue as compared to ovary tumor samples. Expression of AP25856 mRNA was also detected in two lung tumor samples and two normal lung tissue samples. Expression was also detected in a normal colon tumor tissue sample and a colon tumor sample, with higher expression in the tumor tissue sample (see FIG. 16).

Figure 17:
FIG. 17 is a graphic depiction of the relative levels of human AP25856 mRNA expression in a human tissue panel containing human normal and tumor tissue samples, as determined using Taqman™ analysis (1–3=hemangioma, 4=normal kidney, 5=renal cell carcinoma, 6–7=Wilms tumor, 8=skin tissue, 9=uterine adenocarcinoma, 110=neuroblastoma, 11=fetal adrenal gland, 12=fetal kidney, 13=fetal heart, 14=normal heart, 15=cartilage, 16=spinal cord, 17=lymphangioma, 18=endometrial polyps, 19=synovium (RA), 20=hyperkeratotic skin).

To further investigate an underlying cause of the change in expression in cancerous tissue, e.g., angiogenesis, AP25856 expression levels were measured in an angiogenesis panel containing various tissues. The relative levels of AP25856 expression in various samples are depicted in FIG. 17. Highest expression of human AP25856 mRNA was detected in normal kidney tissue. Expression was also detected in fetal kidney tissue, fetal heart, normal heart, spinal cord, Wilms tumor, fetal adrenal gland, neuroblastoma, and hemangioma (see FIG. 17).

Example 2

Expression of Recombinant AP Protein in Bacterial Cells

In this example, human AP, e.g., human AP21956 or human AP25856, is expressed as a recombinant glutathione-S-transferase (GST) fusion polypeptide in *E. coli* and the fusion polypeptide is isolated and characterized. Specifically, AP is fused to GST and this fusion polypeptide is expressed in *E. coli*, e.g., strain PEB 199. Expression of the GST-AP fusion protein in PEB199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant AP Protein in COS Cells

To express a human AP, e.g., human AP21956 or human AP25856, gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire AP protein and an HA tag (Wilson et al. (1984) *Cell* 37:767) or a FLAG tag fused in-frame to its 3' end is cloned into the polylinker region of the vector, thereby placing the expression of the recombinant protein under the control of the CMV promoter.

To construct the plasmid, the AP DNA sequence is amplified by PCR using two primers. The 5' primer contains the restriction site of interest followed by approximately twenty nucleotides of the AP coding sequence starting from the initiation codon; the 3' end sequence contains complementary sequences to the other restriction site of interest, a translation stop codon, the HA tag or FLAG tag and the last 20 nucleotides of the AP coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably, the two restriction sites chosen are different so that the AP gene is inserted in the correct orientation. The ligation mixture is transformed into *E. coli* cells (strains HB101, DH5α, or SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the AP-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J. et al., *Molecular Cloning: A Laboratory Manual.* 2nd, ed., Cold Spring Harbor Laboratory, Cold Spring Harbor Laboratory Press, Cold Spring Harbor, N.Y., 1989. The expression of the AP polypeptide is detected by radiolabeling ($^{35}$S-methionine or $^{35}$S-cysteine, available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA- or FLAG-specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA- or FLAG-specific monoclonal antibody. Precipitated polypeptides are then analyzed by SDS-PAGE.

Alternatively, DNA containing the AP coding sequence is cloned directly into the polylinker of the pcDNA/Amp vector using the appropriate restriction sites. The resulting plasmid is transfected into COS cells in the manner described above, and the expression of the AP polypeptide is detected by radiolabeling and immunoprecipitation using an AP-specific monoclonal antibody.

III. 22244 and 8701, Novel Human Dehydrogenases and Uses Thereof

BACKGROUND OF THE INVENTION

The oxidation and reduction of molecules is of critical importance in most metabolic and catabolic pathways in cells. A large family of enzymes which facilitate these molecular alterations, termed dehydrogenases, have been identified. In the forward reaction, these enzymes catalyze the transfer of a hydride ion from the target substrate to the enzyme or a cofactor of the enzyme (e.g., NAD$^+$ or NADP$^+$), thereby forming a carbonyl group on the substrate. These enzymes are also able to participate in the reverse reaction, wherein a carbonyl group on the target molecule is reduced by the transfer of a hydride group from the enzyme. Members of the dehydrogenase family are found in nearly all organisms, from microbes to *Drosophila* to humans. Both between species and within the same species, dehydrogenases vary widely, and structural similarities between distant dehydrogenase family members are most frequently found in the cofactor binding site of the enzyme. Even within a particular subclass of dehydrogenase molecules, e.g., the short-chain dehydrogenase molecules, members typically display only 15–30% amino acid sequence identity, and this is limited to the cofactor binding site and the catalytic site (Jornvall et al. (1995) *Biochemistry* 34:6003–6013).

Different classes of dehydrogenases are specific for an array of biological and chemical substrates. For example, there exist dehydrogenases specific for alcohols, for aldehydes, for steroids, and for lipids, with particularly important classes of dehydrogenases including the short-chain dehydrogenase/reductases, the medium-chain dehydrogenases, the aldehyde dehydrogenases, the alcohol dehydrogenases, and the steroid dehydrogenases. Within each of these classes, each enzyme is specific for a particular substrate (e.g., ethanol or isopropanol, but not both with equivalent affinity). This exquisite specificity permits tight regulation of the metabolic and catabolic pathways in which these enzymes participate, without affecting similar but separate biochemical pathways in the same cell or tissue. The short-chain dehydrogenases, part of the alcohol oxidoreductase superfamily (Reid et al. (1994) *Crit. Rev. Microbiol.* 20:13–56), are $Zn^{++}$-independent enzymes with an N-terminal cofactor binding site and a C-terminal catalytic domain (Persson et al. (1995) *Adv. Exp. Med. Biol.* 372:383–395; Jornvall et al. (1995) supra), whereas the medium chain dehydrogenases are $Zn^{++}$-dependent enzymes with an N-terminal catalytic domain and a C-terminal coenzyme binding domain (Jornvall et al. (1995) supra; Jornvall et al. (1999) *FEBS Lett.* 445:261–264). The steroid dehydrogenases are a subclass of the short-chain dehydrogenases, and are known to be involved in a variety of biochemical pathways, affecting mammalian reproduction, hypertension, neoplasia, and digestion (Duax et al. (2000) *Vitamins and Hormones* 58:121–148). Aldehyde dehydrogenases show heterogeneity in the placement of these domains, and also heterogeneity in their substrates, which include toxic substances, retinoic acid, betaine, biogenic amine, and neurotransmitters (Hsu et al. (1997) *Gene* 189:89–94). It is common in higher organisms for different dehydrogenase molecules to be expressed in different tissues, according to the localization of the substrate for which the enzyme is specific. For example, different mammalian aldehyde dehydrogenases are localized to different tissues, e.g., salivary gland, stomach, and kidney (Hsu et al. (1999) supra).

Dehydrogenases play important roles in the production and breakdown of nearly all major metabolic intermediates, including amino acids, vitamins, energy molecules (e.g., glucose, sucrose, and their breakdown products), signaling molecules (e.g., transcription factors and neurotransmitters), and nucleic acids. As such, their activity contributes to the ability of the cell to grow and differentiate, to proliferate, and to communicate and interact with other cells. Dehydrogenases also are important in the detoxification of compounds to which the organism is exposed, such as alcohols, toxins, carcinogens, and mutagens.

SUMMARY OF THE INVENTION

The present invention is based, at least in part, on the discovery of novel members of the family of dehydrogenase molecules, referred to herein as DHDR nucleic acid and protein molecules (e.g., DHDR-5 and DHDR-6). The DHDR nucleic acid and protein molecules of the present invention are useful as modulating agents in regulating a variety of cellular processes, e.g., cellular proliferation, growth, differentiation, or migration. The present invention is also based, at least in part, on the discovery that the DHDR molecules of the present invention are differentially expressed (e.g., upregulated and/or downregulated) in different types of tumor cells, e.g., ovary, lung, colon, brain, and breast tumor cells. Accordingly, in one aspect, this invention provides isolated nucleic acid molecules encoding DHDR polypeptides or biologically active portions thereof, as well as nucleic acid fragments suitable as primers or hybridization probes for the detection of DHDR-encoding nucleic acids.

In one embodiment, a DHDR nucleic acid molecule of the invention is at least 50%, 55%, 60%, 65%, 70%, 75%, 80%, 84%, 85%, 86%, 90%, 91%, 92%, 93%, 97%, 98%, 99%, 99.1%, 99.2%, 99.3%, 99.4%, 99.5%, 99.6%, 99.7%, 99.8%, 99.9% or more identical to the nucleotide sequence (e.g., to the entire length of the nucleotide sequence) shown in SEQ ID NO:10, 12, 13, or 15, or a complement thereof.

In a preferred embodiment, the isolated nucleic acid molecule includes the nucleotide sequence shown in SEQ ID NO:10, 12, 13, or 15, or a complement thereof. In another embodiment, the nucleic acid molecule includes SEQ ID NO:12 and nucleotides 1–117 of SEQ ID NO:10. In a further embodiment, the nucleic acid molecule includes SEQ ID NO:12 and nucleotides 1108–1498 of SEQ ID NO:10. In yet another embodiment, the nucleic acid molecule includes SEQ ID NO:15 and nucleotides 1–14 of SEQ ID NO:13. In yet a further embodiment, the nucleic acid molecule includes SEQ ID NO:15 and nucleotides 1416–1981 of SEQ ID NO:13. In another preferred embodiment, the nucleic acid molecule consists of the nucleotide sequence shown in SEQ ID NO:10, 12, 13, or 15.

In another embodiment, a DHDR nucleic acid molecule includes a nucleotide sequence encoding a protein having an amino acid sequence sufficiently identical to the amino acid sequence of SEQ ID NO:11 or 14. In a preferred embodiment, a DHDR nucleic acid molecule includes a nucleotide sequence encoding a protein having an amino acid sequence at least 50%, 55%, 60%, 65%, 70%, 75%, 80%, 84%, 85%, 86%, 90%, 91%, 92%, 93%, 94%, 95%, 96%, 97%, 99.1%, 99.2%, 99.3%, 99.4%, 99.5%, 99.6%, 99.7%, 99.8%, 99.9% or more identical to the entire length of the amino acid sequence of SEQ ID NO:11 or 14.

In another preferred embodiment, an isolated nucleic acid molecule encodes the amino acid sequence of human DHDR-5 or DHDR-6. In yet another preferred embodiment, the nucleic acid molecule includes a nucleotide sequence encoding a protein having the amino acid sequence of SEQ ID NO:11 or 14. In yet another preferred embodiment, the nucleic acid molecule is at least 50, 100, 150, 200, 250, 300, 350, 400, 450, 500, 550, 600, 650, 700, 750, 800, 850, 900, 950, 1000, 1050, 1100, 1150, 1200, 1250, 1281, 1300, 1350, 1400, 1450, 1500, 1550, 1600, 1650, 1700, 1750, 1800, 1850, 1900, 1950 or more nucleotides in length. In a further preferred embodiment, the nucleic acid molecule is at least 50, 100, 150, 200, 250, 300, 350, 400, 450, 500, 550, 600, 650, 700, 750, 800, 850, 900, 950, 1000, 1050, 1100, 1150, 1200, 1250, 1281, 1300, 1350, 1400, 1450, 1500, 1550, 1600, 1650, 1700, 1750, 1800, 1850, 1900, 1950 or more nucleotides in length and encodes a protein having a DHDR activity (as described herein).

Another embodiment of the invention features nucleic acid molecules, preferably DHDR nucleic acid molecules, which specifically detect DHDR nucleic acid molecules relative to nucleic acid molecules encoding non-DHDR proteins. For example, in one embodiment, such a nucleic acid molecule is at least 20, 30, 40, 50, 100, 150, 200, 250, 300, 350, 400, 450, 500, 550, 600, 650, 700, 750, 800, 850, 900, 950, 1000, 1050, 1100, 1150, 1200, 1250, 1281, 1300, 1350, 1400, 1450, 1500, 1550, 1600, 1650, 1700, 1750, 1800, 1850, 1900, 1950 or more nucleotides in length and hybridizes under stringent conditions to a nucleic acid molecule comprising the nucleotide sequence shown in SEQ ID NO:10, 12, 13, or 15, or a complement thereof.

In preferred embodiments, the nucleic acid molecules are at least 15 (e.g., 15 contiguous) nucleotides in length and hybridize under stringent conditions to the nucleotide molecules set forth in SEQ ID NO:10, 12, 13, or 15, or a complement thereof.

In other preferred embodiments, the nucleic acid molecule encodes a naturally occurring allelic variant of a polypeptide comprising the amino acid sequence of SEQ ID NO:11 or 14, wherein the nucleic acid molecule hybridizes to a complement of a nucleic acid molecule comprising SEQ ID NO:10, 12, 13, or 15, respectively, under stringent conditions.

Another embodiment of the invention provides an isolated nucleic acid molecule which is antisense to a DHDR nucleic acid molecule, e.g., the coding strand of a DHDR nucleic acid molecule.

Another aspect of the invention provides a vector comprising a DHDR nucleic acid molecule. In certain embodiments, the vector is a recombinant expression vector. In another embodiment, the invention provides a host cell containing a vector of the invention. In yet another embodiment, the invention provides a host cell containing a nucleic acid molecule of the invention. The invention also provides a method for producing a protein, preferably a DHDR protein, by culturing in a suitable medium, a host cell, e.g., a mammalian host cell such as a non-human mammalian cell, of the invention containing a recombinant expression vector, such that the protein is produced.

Another aspect of this invention features isolated or recombinant DHDR proteins and polypeptides. In one embodiment, an isolated DHDR protein includes at least one or more of the following domains: a transmembrane domain, a signal peptide domain, a short chain dehydrogenase domain, a shikimate/quinate 5-dehydrogenase domain, and/or an iron-containing alcohol dehydrogenase domain.

In a preferred embodiment, a DHDR protein includes at least one or more of the following domains: a transmembrane domain, a signal peptide domain, a short chain dehydrogenase domain, a shikimate/quinate 5-dehydrogenase domain, and/or an iron-containing alcohol dehydrogenase domain, and has an amino acid sequence at least about 50%, 55%, 60%, 65%, 67%, 68%, 70%, 75%, 80%, 84%, 85%, 86%, 90%, 94%, 95%, 96%, 97%, 98%, 99%, 99.1%, 99.2%, 99.3%, 99.4%, 99.5%, 99.6%, 99.8%, 99.9% or more identical to the amino acid sequence of SEQ ID NO:11 or 14. In another preferred embodiment, a DHDR protein includes at least one or more of the following domains: a transmembrane domain, a signal peptide domain, a short chain dehydrogenase domain, a shikimate/quinate 5-dehydrogenase domain, and/or an iron-containing alcohol dehydrogenase domain, and has a DHDR activity (as described herein).

In yet another preferred embodiment, a DHDR protein includes at least one or more of the following domains: a transmembrane domain, a signal peptide domain, a short chain dehydrogenase domain, a shikimate/quinate 5-dehydrogenase domain, and/or an iron-containing alcohol dehydrogenase domain, and is encoded by a nucleic acid molecule having a nucleotide sequence which hybridizes under stringent hybridization conditions to a complement of a nucleic acid molecule comprising the nucleotide sequence of SEQ ID NO:10, 12, 13, or 15.

In another embodiment, the invention features fragments of the protein having the amino acid sequence of SEQ ID NO:11 or 14, wherein the fragment comprises at least 15 amino acids (e.g., contiguous amino acids) of the amino acid sequence of SEQ ID NO:11 or 14. In another embodiment, a DHDR protein has the amino acid sequence of SEQ ID NO:11 or 14.

In another embodiment, the invention features a DHDR protein which is encoded by a nucleic acid molecule consisting of a nucleotide sequence at least about 50%, 55%, 60%, 65%, 70%, 75%, 80%, 84%, 85%, 86%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to a nucleotide sequence of SEQ ID NO:10, 12, 13, or 15, or a complement thereof. This invention further features a DHDR protein which is encoded by a nucleic acid molecule consisting of a nucleotide sequence which hybridizes under stringent hybridization conditions to a complement of a nucleic acid molecule comprising the nucleotide sequence of SEQ ID NO:10, 12, 13, or 15.

The proteins of the present invention or portions thereof, e.g., biologically active portions thereof, can be operatively linked to a non-DHDR polypeptide (e.g., heterologous amino acid sequences) to form fusion proteins. The invention further features antibodies, such as monoclonal or polyclonal antibodies, that specifically bind proteins of the invention, preferably DHDR proteins. In addition, the DHDR proteins or biologically active portions thereof can be incorporated into pharmaceutical compositions, which optionally include pharmaceutically acceptable carriers.

In another aspect, the present invention provides a method for detecting the presence of a DHDR nucleic acid molecule, protein, or polypeptide in a biological sample by contacting the biological sample with an agent capable of detecting a DHDR nucleic acid molecule, protein, or polypeptide such that the presence of a DHDR nucleic acid molecule, protein or polypeptide is detected in the biological sample.

In another aspect, the present invention provides a method for detecting the presence of DHDR activity in a biological sample by contacting the biological sample with an agent capable of detecting an indicator of DHDR activity such that the presence of DHDR activity is detected in the biological sample.

In another aspect, the invention provides a method for modulating DHDR activity comprising contacting a cell capable of expressing DHDR with an agent that modulates DHDR activity such that DHDR activity in the cell is modulated. In one embodiment, the agent inhibits DHDR activity. In another embodiment, the agent stimulates DHDR activity. In one embodiment, the agent is an antibody that specifically binds to a DHDR protein. In another embodiment, the agent modulates expression of DHDR by modulating transcription of a DHDR gene or translation of a DHDR mRNA. In yet another embodiment, the agent is a nucleic acid molecule having a nucleotide sequence that is antisense to the coding strand of a DHDR mRNA or a DHDR gene.

In one embodiment, the methods of the present invention are used to treat a subject having a disorder characterized by aberrant or unwanted DHDR protein or nucleic acid expression or activity by administering an agent which is a DHDR modulator to the subject. In one embodiment, the DHDR modulator is a DHDR protein. In another embodiment the DHDR modulator is a DHDR nucleic acid molecule. In yet another embodiment, the DHDR modulator is a peptide, peptidomimetic, or other small molecule. In a preferred embodiment, the disorder characterized by aberrant or unwanted DHDR protein or nucleic acid expression is a dehydrogenase-associated disorder, e.g., a cell proliferation, growth, differentiation, and/or migration disorder, or a CNS disorder, a cardiovascular disorder, or a muscular disorder.

The present invention also provides diagnostic assays for identifying the presence or absence of a genetic alteration characterized by at least one of (i) aberrant modification or mutation of a gene encoding a DHDR protein; (ii) misregulation of the gene; and (iii) aberrant post-translational modification of a DHDR protein, wherein a wild-type form of the gene encodes a protein with a DHDR activity.

In another aspect the invention provides methods for identifying a compound that binds to or modulates the activity of a DHDR protein, by providing an indicator composition comprising a DHDR protein having DHDR activity, contacting the indicator composition with a test compound, and determining the effect of the test compound on DHDR activity in the indicator composition to identify a compound that modulates the activity of a DHDR protein.

In other embodiments, the invention provides methods for identifying a subject having a cellular proliferation, growth, differentiation, and/or migration disorder, or at risk for developing a cellular proliferation, growth, differentiation, and/or migration disorder; methods for identifying a compound capable of treating a cellular proliferation, growth, differentiation, and/or migration disorder characterized by aberrant DHDR nucleic acid expression or DHDR polypeptide activity; and methods for treating a subject having a cellular proliferation, growth, differentiation, and/or migration disorder characterized by aberrant DHDR polypeptide activity or aberrant DHDR nucleic acid expression Other features and advantages of the invention will be apparent from the following detailed description and claims.

DETAILED DESCRIPTION OF THE INVENTION

The present invention is based, at least in part, on the discovery of novel molecules, referred to herein as "dehydrogenase" or "DHDR" nucleic acid and protein molecules, which are novel members of a family of enzymes possessing dehydrogenase activity. These novel molecules are capable of oxidizing or reducing biological molecules by catalyzing the transfer of a hydride moiety and, thus, play a role in or function in a variety of cellular processes, e.g., proliferation, growth, differentiation, migration, immune responses, hormonal responses, and inter- or intra-cellular communication. The DHDR molecules of the present invention are differentially expressed (e.g., upregulated and/or downregulated) in different types of tumor cells, e.g., ovary, lung, colon, brain, and breast tumor cells, and thus may play a role in modulating the ability of tumor cells to proliferate.

As used herein, the term "dehydrogenase" includes a molecule which is involved in the oxidation or reduction of a biochemical molecule (e.g., an amino acid, a vitamin, or a nucleic acid), by catalyzing the transfer of a hydride ion to or from the biochemical molecule. Dehydrogenase molecules are involved in the metabolism and catabolism of biochemical molecules necessary for energy production or storage, for intra- or inter-cellular signaling, for metabolism or catabolism of metabolically important biomolecules, and for detoxification of potentially harmful compounds. Dehydrogenase molecules are also involved in the regulation of cellular proliferation, growth, differentiation, and/or migration. Examples of dehydrogenases include alcohol dehydrogenases, aldehyde dehydrogenases, steroid dehydrogenases, and lipid dehydrogenases. Thus, the DHDR molecules of the present invention provide novel diagnostic targets and therapeutic agents to control dehydrogenase-associated disorders.

As used herein, a "dehydrogenase-associated disorder" includes a disorder, disease or condition which is caused or characterized by a misregulation (e.g., downregulation or upregulation) of dehydrogenase activity. Dehydrogenase-associated disorders can detrimentally affect cellular functions such as cellular proliferation, growth, differentiation, or migration, inter- or intra-cellular communication; tissue function, such as cardiac function or musculoskeletal function; systemic responses in an organism, such as nervous system responses, hormonal responses (e.g., insulin response), or immune responses; and protection of cells from toxic compounds (e.g., carcinogens, toxins, or mutagens).

The DHDR molecules of the present invention are differentially expressed (e.g., upregulated and/or downregulated) in different types of tumor cells. Accordingly, examples of dehydrogenase-associated disorders include cellular proliferation, growth, differentiation, and/or migration disorders. As used herein, "cellular proliferation, growth, differentiation, and/or migration disorders" include those disorders that affect cellular proliferation, growth, differentiation, and/or migration processes. As used herein, a "cellular proliferation, growth, differentiation, and/or migration process" is a process by which a cell increases in number, size or content, by which a cell develops a specialized set of characteristics which differ from that of other cells, or by which a cell moves closer to or further from a particular location or stimulus. Examples of cellular proliferation, growth, differentiation, and/or migration disorders include cancer, e.g., ovarian cancer, breast cancer, colon cancer, lung cancer, brain cancer, as well as other types of carcinomas, sarcomas, lymphomas, and/or leukemias; tumor angiogenesis and metastasis; skeletal dysplasia; hepatic disorders; and hematopoietic and/or myeloproliferative disorders.

Further examples of dehydrogenase associated disorders include CNS disorders such as cognitive and neurodegenerative disorders, including, but not limited to, Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis, progressive supranuclear palsy, epilepsy, and Jakob-Creutzfieldt disease; autonomic function disorders such as hypertension and sleep disorders, and neuropsychiatric disorders, such as depression, schizophrenia, schizoaffective disorder, korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), and bipolar affective neurological disorders, e.g., migraine and obesity. Further CNS-related disorders include, for example, those listed in the American Psychiatric Association's Diagnostic and Statistical manual of Mental Disorders (DSM), the most current version of which is incorporated herein by reference in its entirety.

Additional examples of dehydrogenase-associated disorders include cardiac-related disorders. Cardiovascular system disorders in which the DHDR molecules of the invention may be directly or indirectly involved include arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrillation, Jervell syndrome, Lange-Nielsen syndrome, long-QT syndrome, congestive heart failure, sinus node dysfunction, angina, heart failure, hypertension, atrial fibrillation, atrial flutter, dilated cardiomyopathy, idiopathic cardiomyopathy, myocardial infarction, coronary artery disease, coronary artery spasm, and arrhythmia. Dehydrogenase associated disorders also include disorders of the musculoskeletal system such as paralysis and muscle weakness, e.g., ataxia, myotonia, and myokymia.

Dehydrogenase associated disorders further include hormonal disorders, such as conditions or diseases in which the production and/or regulation of hormones in an organism is aberrant. Examples of such disorders and diseases include type I and type II diabetes mellitus, pituitary disorders (e.g., growth disorders), thyroid disorders (e.g., hypothyroidism or hyperthyroidism), and reproductive or fertility disorders (e.g., disorders which affect the organs of the reproductive system, e.g., the prostate gland, the uterus, or the vagina; disorders which involve an imbalance in the levels of a reproductive hormone in a subject; disorders affecting the ability of a subject to reproduce; and disorders affecting secondary sex characteristic development, e.g., adrenal hyperplasia).

Dehydrogenase associated disorders also include immune disorders, such as autoimmune disorders or immune deficiency disorders, e.g., congenital X-linked infantile hypogammaglobulinemia, transient hypogammaglobulinemia, common variable immunodeficiency, selective IgA deficiency, chronic mucocutaneous candidiasis, or severe combined immunodeficiency.

Dehydrogenase associated disorders also include disorders affecting tissues in which DHDR molecules are expressed, e.g., osteoclasts, breast, brain, heart, trachea, thyroid, testis, and fetal heart (see working examples for further examples of tissues in which the DHDR molecules of the present invention are expressed).

As used herein, a "dehydrogenase-mediated activity" includes an activity which involves the oxidation or reduction of one or more biochemical molecules, e.g., biochemical molecules in a tumor cell, a breast cell, an ovary cell, a neuronal cell, a muscle cell, or a liver cell associated with the regulation of one or more cellular processes. Dehydrogenase-mediated activities include the oxidation or reduction of biochemical molecules necessary for energy production or storage, for intra- or inter-cellular signaling, for metabolism or catabolism of metabolically important biomolecules, and for detoxification of potentially harmful compounds. Dehydrogenase-mediated activities also include modulation of cellular proliferation, growth, differentiation, and/or migration.

The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin, e.g., mouse or monkey proteins. Members of a family may also have common functional characteristics.

For example, the family of DHDR proteins of the present invention comprises at least one "transmembrane domain". As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta, W. N. et al. (1996) *Annu. Rev. Neurosci.* 19:235–263, the contents of which are incorporated herein by reference. Amino acid residues 173–193 and 240–257 of the native DHDR-5 protein are predicted to comprise transmembrane domains (see FIG. 20). Amino acid residues 181–200, 316–340, and 354–371 of the native DHDR-6 protein and residues 295–319 and 333–350 of the presumed mature DHDR-6 protein are predicted to comprise transmembrane domains (see FIG. 28). Accordingly, DHDR proteins having at least 50–60% homology, preferably about 60–70%, more preferably about 70–80%, or about 80–90% homology with a transmembrane domain of human DHDR are within the scope of the invention.

In another embodiment of the invention, a DHDR protein of the present invention is identified based on the presence of a signal peptide. The prediction of such a signal peptide can be made, for example, by using the computer algorithm SignalP (Henrik et al. (1997) *Protein Eng.* 10:1–6). As used herein, a "signal sequence" or "signal peptide" includes a peptide containing about 15 or more amino acids which occurs at the N-terminus of secretory and membrane bound proteins and which contains a large number of hydrophobic amino acid residues. For example, a signal sequence contains at least about 10–30 amino acid residues, preferably about 15–25 amino acid residues, more preferably about 18–20 amino acid residues, and more preferably about 19 amino acid residues, and has at least about 35–65%, preferably about 38–50%, and more preferably about 40–45% hydrophobic amino acid residues (e.g., Valine, Leucine, Isoleucine or Phenylalanine). Such a "signal sequence", also referred to in the art as a "signal peptide", serves to direct a protein containing such a sequence to a lipid bilayer, and is cleaved in secreted and membrane bound proteins. A possible signal sequence was identified in the amino acid sequence of human DHDR-6 at about amino acids 1–21 of SEQ ID NO:14.

In another embodiment, a DHDR molecule of the present invention is identified based on the presence of a "short chain dehydrogenase domain" in the protein or corresponding nucleic acid molecule. As used herein, the term "short chain dehydrogenase domain" includes a protein domain having an amino acid sequence of about 100–300 amino acid residues and a bit score of 50, 60, 70, 80, 90, 100, 110, 120, 130, 140 or more. Preferably, a short chain dehydrogenase domain includes at least about 140–240, or more preferably about 187 amino acid residues, and a bit score of at least 117.6. To identify the presence of a short chain dehydrogenase domain in a DHDR protein, and make the determination that a protein of interest has a particular profile, the amino acid sequence of the protein is searched against a database of known protein domains (e.g., the HMM database). The short chain dehydrogenase domain (HMM) has been assigned the PFAM Accession number PF00106 (see the PFAM website, available online through Washington University in Saint Louis). A search was performed against the HMM database resulting in the identification of a short chain dehydrogenase domain in the amino acid sequence of human DHDR-5 (SEQ ID NO:11) at about residues 68–254 of SEQ ID NO:11. The results of the search are set forth in FIGS. 21A–B.

In another embodiment, a DHDR molecule of the present invention is identified based on the presence of a "shikimate/quinate 5-dehydrogenase domain" in the protein or corresponding nucleic acid molecule. As used herein, the term "shikimate/quinate 5-dehydrogenase domain" includes a protein domain having an amino acid sequence of about 100–300 amino acid residues. Preferably, a shikimate/quinate 5-dehydrogenase domain includes at least about 130–230, or more preferably about 180 amino acid residues. To identify the presence of a shikimate/quinate 5-dehydrogenase domain in a DHDR protein, and make the determination that a protein of interest has a particular profile, the amino acid sequence of the protein is searched against a database of known protein domains (e.g., the HMM database). The shikimate/quinate 5-dehydrogenase domain (HMM) has been assigned the PFAM Accession number PF01488 (see the PFAM website, available online through Washington University in Saint Louis). A search was performed against the HMM database resulting in the identification of a shikimate/quinate 5-dehydrogenase domain in the amino acid sequence of human DHDR-5 (SEQ ID NO:11) at about residues 10–189 of SEQ ID NO:11. The results of the search are set forth in FIGS. 21A–B.

In another embodiment, a DHDR molecule of the present invention is identified based on the presence of an "iron-containing alcohol dehydrogenase domain" in the protein or corresponding nucleic acid molecule. As used herein, the term "iron-containing alcohol dehydrogenase domain" includes a protein domain having an amino acid sequence of about 40–300 amino acid residues and a bit score of 50, 60, 70, 80, 90, 100, 110, 120 or more. Preferably, an iron-containing alcohol dehydrogenase domain includes at least about 50–250, or more preferably about 63–202 amino acid residues, and a bit score of 64.1–119.3. To identify the presence of an iron-containing alcohol dehydrogenase domain in a DHDR protein, and make the determination that a protein of interest has a particular profile, the amino acid sequence of the protein is searched against a database of known protein domains (e.g., the HMM database). The iron-containing alcohol dehydrogenase domain (HMM) has been assigned the PFAM Accession number PF00465 (see the PFAM website, available online through Washington University in Saint Louis). A search was performed against the HMM database resulting in the identification of iron-containing alcohol dehydrogenase domains in the amino acid sequence of human DHDR-6 (SEQ ID NO:14) at about residues 52–253 and 276–338 of SEQ ID NO:14. The results of the search are set forth in FIG. 29.

A description of the PFAM database can be found in Sonhammer et al. (1997) *Proteins* 28:405–420, and a detailed description of HMMs can be found, for example, in Gribskov et al. (1990) *Methods Enzymol.* 183:146–159; Gribskov et al. (1987) *Proc. Natl. Acad. Sci. USA* 84:4355–4358; Krogh et al. (1994) *J. Mol. Biol.* 235:1501–1531; and Stultz et al. (1993) *Protein Sci.* 2:305–314, the contents of which are incorporated herein by reference.

In a preferred embodiment, the DHDR molecules of the invention include at least one or more of the following domains: a transmembrane domain, a signal peptide domain, a short chain dehydrogenase domain, a shikimate/quinate 5-dehydrogenase domain, and/or an iron-containing alcohol dehydrogenase domain.

Isolated proteins of the present invention, preferably DHDR proteins, have an amino acid sequence sufficiently identical to the amino acid sequence of SEQ ID NO:11 or 14, or are encoded by a nucleotide sequence sufficiently identical to SEQ ID NO:10, 12, 13, or 15. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%–80%, and even more preferably 90–95% homology across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70–80%, or 90–95% homology and share a common functional activity are defined herein as sufficiently identical.

As used interchangeably herein, "DHDR activity", "biological activity of DHDR" or "functional activity of DHDR", refers to an activity exerted by a DHDR protein, polypeptide or nucleic acid molecule on a DHDR responsive cell or tissue, or on a DHDR protein substrate, as determined in vivo, or in vitro, according to standard techniques. In one embodiment, a DHDR activity is a direct activity, such as an association with a DHDR-target molecule. As used herein, a "target molecule" or "binding partner" is a molecule with which a DHDR protein binds or interacts in nature, such that DHDR-mediated function is achieved. A DHDR target molecule can be a non-DHDR molecule or a DHDR protein or polypeptide of the present invention (e.g., NAD+, NADP+, or other cofactor). In an exemplary embodiment, a DHDR target molecule is a DHDR ligand (e.g., an alcohol, an aldehyde, a lipid, or a steroid). Alternatively, a DHDR activity is an indirect activity, such as a cellular signaling activity mediated by interaction of the DHDR protein with a DHDR ligand. The biological activities of DHDR are described herein. For example, the DHDR proteins of the present invention can have one or more of the following activities: 1) modulate metabolism and catabolism of biochemical molecules necessary for energy production or storage, 2) modulate intra- or inter-cellular signaling, 3) modulate metabolism or catabolism of metabolically important biomolecules, 4) modulate detoxification of potentially harmful compounds, and 5) modulate cellular proliferation, growth, differentiation, and/or migration.

Accordingly, another embodiment of the invention features isolated DHDR proteins and polypeptides having a DHDR activity. Other preferred proteins are DHDR proteins having one or more of the following domains: a transmembrane domain, a signal peptide domain, a short chain dehydrogenase domain, a shikimate/quinate 5-dehydrogenase domain, and/or an iron-containing alcohol dehydrogenase domain, and, preferably, a DHDR activity.

Additional preferred proteins have at least one transmembrane domain, and one or more of a signal peptide domain, a short chain dehydrogenase domain, a shikimate/quinate 5-dehydrogenase domain, and/or an iron-containing alcohol dehydrogenase domain, and are, preferably, encoded by a nucleic acid molecule having a nucleotide sequence which hybridizes under stringent hybridization conditions to a complement of a nucleic acid molecule comprising the nucleotide sequence of SEQ ID NO:10, 12, 13, or 15.

The nucleotide sequence of the isolated human DHDR-5 cDNA and the predicted amino acid sequence of the human DHDR-5 polypeptide are shown in FIGS. 18A–B and in SEQ ID NO:10 and 11, respectively. The nucleotide sequence of the isolated human DHDR-6 cDNA and the predicted amino acid sequence of the human DHDR-6 polypeptide are shown in FIGS. 19A–B and in SEQ ID NO:13 and 14, respectively.

The human DHDR-5 gene, which is approximately 1498 nucleotides in length, encodes a protein having a molecular weight of approximately 36.3 kD and which is approximately 330 amino acid residues in length. The human DHDR-6 gene, which is approximately 1981 nucleotides in length, encodes a protein having a molecular weight of approximately 51.4 kD and which is approximately 467 amino acid residues in length.

Various aspects of the invention are described in further detail in the following subsections:

I. Isolated Nucleic Acid Molecules

One aspect of the invention pertains to isolated nucleic acid molecules that encode DHDR proteins or biologically active portions thereof, as well as nucleic acid fragments sufficient for use as hybridization probes to identify DHDR-encoding nucleic acid molecules (e.g., DHDR mRNA) and fragments for use as PCR primers for the amplification or mutation of DHDR nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated DHDR nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium, when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:10, 12, 13, or 15, or a portion thereof, can be isolated using standard molecular biology techniques and the sequence information provided herein. Using all or portion of the nucleic acid sequence of SEQ ID NO:10, 12, 13, or 15, as a hybridization probe, DHDR nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:10, 12, 13, or 15 can be isolated by the polymerase chain reaction (PCR) using synthetic oligonucleotide primers designed based upon the sequence of SEQ ID NO:10, 12, 13, or 15.

A nucleic acid of the invention can be amplified using cDNA, mRNA or, alternatively, genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to DHDR nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:10, 12, 13, or 15. This cDNA may comprise sequences encoding the human DHDR-5 protein (i.e., "the coding region", from nucleotides 118–1107), as well as 5' untranslated sequences (nucleotides 1–117) and 3' untranslated sequences (nucleotides 1108–1498) of SEQ ID NO:10. This cDNA may comprise sequences encoding the human DHDR-6 protein (i.e., "the coding region", from nucleotides 15–1415), as well as 5' untranslated sequences (nucleotides 1–14) and 3' untranslated sequences (nucleotides 1416–1981) of SEQ ID NO:13. Alternatively, the nucleic acid molecule can comprise only the coding region of SEQ ID NO:10 (e.g., nucleotides 118–1107, corresponding to SEQ ID NO:12) or only the coding region of SEQ ID NO:13 (e.g., nucleotides 15–1415, corresponding to SEQ ID NO:15). In another embodiment, the nucleic acid molecule can comprise the coding region of SEQ ID NO:10 (e.g., nucleotides 118–1107, corresponding to SEQ ID NO:12), as well as a stop codon (e.g., nucleotides 1108–1110 of SEQ ID NO:10). In yet another embodiment, the nucleic acid molecule can comprise the coding region of SEQ ID NO:13 (e.g., nucleotides 15–1415, corresponding to SEQ ID NO:15), as well as a stop codon (e.g., nucleotides 1416–1418 of SEQ ID NO:13). In another embodiment, the nucleic acid molecule can comprise nucleotides 1–26 of SEQ ID NO:10. In yet another embodiment, and isolated nucleic acid molecule of the invention consists of the nucleic acid sequence of SEQ ID NO:10, 12, 13, or 15.

In another preferred embodiment, an isolated nucleic acid molecule of the invention comprises a nucleic acid molecule which is a complement of the nucleotide sequence shown in SEQ ID NO:10, 12, 13, or 15, or a portion of any of these nucleotide sequences. A nucleic acid molecule which is complementary to the nucleotide sequence shown in SEQ ID NO:10, 12, 13, or 15, is one which is sufficiently complementary to the nucleotide sequence shown in SEQ ID NO:10, 12, 13, or 15, such that it can hybridize to the nucleotide sequence shown in SEQ ID NO:10, 12, 13, or 15, respectively, thereby forming a stable duplex.

In still another preferred embodiment, an isolated nucleic acid molecule of the present invention comprises a nucleotide sequence which is at least about 50%, 55%, 60%, 65%, 70%, 75%, 80%, 84%, 85%, 86%, 90%, 91%, 92%, 93%, 94%, 95%, 99%, 99.1%, 99.2%, 99.3%, 99.4%, 99.5%, 99.6%, 99.7%, 99.8%, 99.9% or more identical to the entire length of the nucleotide sequence shown in SEQ ID NO:10, 12, 13, or 15, or a portion of any of these nucleotide sequences.

Moreover, the nucleic acid molecule of the invention can comprise only a portion of the nucleic acid sequence of SEQ ID NO:10, 12, 13, or 15, for example, a fragment which can be used as a probe or primer or a fragment encoding a portion of a DHDR protein, e.g., a biologically active portion of a DHDR protein. The nucleotide sequences determined from the cloning of the DHDR-5 and DHDR-6 genes allow for the generation of probes and primers designed for use in identifying and/or cloning other DHDR family members, as well as DHDR homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:10, 12, 13, or 15, of an anti-sense sequence of SEQ ID NO:10, 12, 13, or 15, or of a naturally occurring allelic variant or mutant of SEQ ID NO:10, 12, 13, or 15. In one embodiment, a nucleic acid molecule of the present invention comprises a nucleotide sequence which is greater than 50–100, 100–150, 150–200, 200–250, 250–300, 300–350, 350–400, 400–450, 450–500, 500–550, 550–600, 600–650, 650–700, 700–750, 750–800, 800–850, 850–900, 900–950, 950–1000, 1000–1050, 1050–1100, 1100–1150, 1150–1200, 1200–1250, 1250–1281, 1281–1300, 1300–1350, 1350–1400, 1400–1450, 1450–1500, 1500–1550, 1550–1600, 1600–1650, 1650–1700, 1700–1750, 1750–1800, 1800–1850, 1850–1900, 1900–1950 or more nucleotides in length and hybridizes under stringent hybridization conditions to a nucleic acid molecule of SEQ ID NO:10, 12, 13, or 15.

Probes based on the DHDR nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a DHDR protein, such as by measuring a level of a DHDR-encoding nucleic acid in a sample of cells from a subject e.g., detecting DHDR mRNA levels or determining whether a genomic DHDR gene has been mutated or deleted.

A nucleic acid fragment encoding a "biologically active portion of a DHDR protein" can be prepared by isolating a portion of the nucleotide sequence of SEQ ID NO:10, 12, 13, or 15, which encodes a polypeptide having a DHDR biological activity (the biological activities of the DHDR proteins are described herein), expressing the encoded portion of the DHDR protein (e.g., by recombinant expression in vitro) and assessing the activity of the encoded portion of the DHDR protein.

The invention further encompasses nucleic acid molecules that differ from the nucleotide sequence shown in SEQ ID NO:10, 12, 13, or 15, due to degeneracy of the genetic code and thus encode the same DHDR proteins as those encoded by the nucleotide sequence shown in SEQ ID NO:10, 12, 13, or 15. In another embodiment, an isolated nucleic acid molecule of the invention has a nucleotide sequence encoding a protein having an amino acid sequence shown in SEQ ID NO:11 or 14.

In addition to the DHDR nucleotide sequences shown in SEQ ID NO:10, 12, 13, or 15, it will be appreciated by those skilled in the art that DNA sequence polymorphisms that lead to changes in the amino acid sequences of the DHDR proteins may exist within a population (e.g., the human population). Such genetic polymorphism in the DHDR genes may exist among individuals within a population due to natural allelic variation. As used herein, the terms "gene" and "recombinant gene" refer to nucleic acid molecules which include an open reading frame encoding a DHDR protein, preferably a mammalian DHDR protein, and can further include non-coding regulatory sequences, and introns.

Allelic variants of human DHDR include both functional and non-functional DHDR proteins. Functional allelic variants are naturally occurring amino acid sequence variants of the human DHDR protein that maintain the ability to bind a DHDR ligand or substrate and/or modulate cell proliferation and/or migration mechanisms. Functional allelic variants will typically contain only conservative substitution of one or more amino acids of SEQ ID NO:11 or 14, or substitution, deletion or insertion of non-critical residues in non-critical regions of the protein.

Non-functional allelic variants are naturally occurring amino acid sequence variants of the human DHDR protein that do not have the ability to either bind a DHDR ligand and/or modulate any of the DHDR activities described herein. Non-functional allelic variants will typically contain a non-conservative substitution, deletion, or insertion or premature truncation of the amino acid sequence of SEQ ID NO:11 or 14, or a substitution, insertion or deletion in critical residues or critical regions of the protein.

The present invention further provides non-human orthologues of the human DHDR protein. Orthologues of the human DHDR protein are proteins that are isolated from non-human organisms and possess the same DHDR ligand binding and/or modulation of membrane excitability activities of the human DHDR protein. Orthologues of the human DHDR protein can readily be identified as comprising an amino acid sequence that is substantially identical to SEQ ID NO:11 or 14.

Moreover, nucleic acid molecules encoding other DHDR family members and, thus, which have a nucleotide sequence which differs from the DHDR sequences of SEQ ID NO:10, 12, 13, or 15, are intended to be within the scope of the invention. For example, another DHDR cDNA can be identified based on the nucleotide sequence of human DHDR. Moreover, nucleic acid molecules encoding DHDR proteins from different species, and which, thus, have a nucleotide sequence which differs from the DHDR sequences of SEQ ID NO:10, 12, 13, or 15, are intended to be within the scope of the invention. For example, a mouse DHDR cDNA can be identified based on the nucleotide sequence of a human DHDR.

Nucleic acid molecules corresponding to natural allelic variants and homologues of the DHDR cDNAs of the invention can be isolated based on their homology to the DHDR nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the DHDR cDNAs of the invention can further be isolated by mapping to the same chromosome or locus as the DHDR gene.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:10, 12, 13, or 15. In other embodiment, the nucleic acid is at least 50–100, 100–150, 150–200, 200–250, 250–300, 300–350, 350–400, 400–450, 450–500, 500–550, 550–600, 600–650, 650–700, 700–750, 750–800, 800–850, 850–900, 900–950, 950–1000, 1000–1050, 1050–1100, 1100–1150, 1150–1200, 1200–1250, 1250–1281, 1281–1300, 1300–1350, 1350–1400, 1400–1450, 1450–1500, 1500–1550, 1550–1600, 1600–1650, 1650–1700, 1700–1750, 1750–1800, 1800–1850, 1850–1900, 1900–1950 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A preferred, non-limiting example of stringent hybridization conditions includes hybridization in 4× or 6× sodium chloride/sodium citrate (SSC), at about 65–70° C. (or hybridization in 4×SSC plus 50% formamide at about 42–50° C.) followed by one or more washes in 1×SSC, at about 65–70° C. A further preferred, non-limiting example of stringent hybridization conditions includes hybridization at 6×SSC at 45° C., followed by one or more washes in 0.2×SSC, 0.1% SDS at 65° C. A preferred, non-limiting example of highly stringent hybridization conditions includes hybridization in 1×SSC, at about 65–70° C. (or hybridization in 1×SSC plus 50% formamide at about 42–50° C.) followed by one or more washes in 0.3×SSC, at about 65–70° C. A preferred, non-limiting example of reduced stringency hybridization conditions includes hybridization in 4× or 6×SSC, at about 50–60° C. (or alternatively hybridization in 6×SSC plus 50% formamide at about 40–45° C.) followed by one or more washes in 2×SSC, at about 50–60° C. Ranges intermediate to the above-recited values, e.g., at 65–70° C. or at 42–50° C. are also intended to be encompassed by the present invention. SSPE (1×SSPE is 0.15M NaCl, 10 mM NaH$_2$PO$_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m(° C.)=2(\# \text{ of A+T bases})+4(\# \text{ of G+C bases})$. For hybrids between 18 and 49 base pairs in length, $T_m(° C.)=81.5+16.6(\log_{10}[Na^+])+0.41(\% \text{ G+C})-(600/N)$, where N is the number of bases in the hybrid, and [Na$^+$] is the concentration of sodium ions in the hybridization buffer ([Na$^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25–0.5M NaH$_2$PO$_4$, 7% SDS at about 65° C., followed by one or more washes at 0.02M NaH$_2$PO$_4$, 1% SDS at 65° C., see e.g., Church and Gilbert (1984) *Proc. Natl. Acad. Sci. USA* 81:1991–1995, (or alternatively 0.2×SSC, 1% SDS).

Preferably, an isolated nucleic acid molecule of the invention that hybridizes under stringent conditions to the sequence of SEQ ID NO:10, 12, 13, or 15, and corresponds to a naturally-occurring nucleic acid molecule. As used herein, a "naturally-occurring" nucleic acid molecule refers to an RNA or DNA molecule having a nucleotide sequence that occurs in nature (i.e., encodes a natural protein).

In addition to naturally-occurring allelic variants of the DHDR sequences that may exist in the population, the skilled artisan will further appreciate that changes can be introduced by mutation into the nucleotide sequences of SEQ ID NO:10, 12, 13, or 15, thereby leading to changes in the amino acid sequence of the encoded DHDR proteins, without altering the functional ability of the DHDR proteins. For example, nucleotide substitutions leading to amino acid substitutions at "non-essential" amino acid residues can be made in the sequence of SEQ ID NO:10, 12, 13, or 15. A "non-essential" amino acid residue is a residue that can be altered from the wild-type sequence of DHDR (e.g., the sequence of SEQ ID NO:11 or 14) without altering the biological activity, whereas an "essential" amino acid residue is required for biological activity. For example, amino acid residues that are conserved among the DHDR proteins of the present invention, e.g., those present in a transmembrane domain, are predicted to be particularly unamenable to alteration. Furthermore, additional amino acid residues that are conserved between the DHDR proteins of the present invention and other members of the DHDR family are not likely to be amenable to alteration.

Accordingly, another aspect of the invention pertains to nucleic acid molecules encoding DHDR proteins that contain changes in amino acid residues that are not essential for activity. Such DHDR proteins differ in amino acid sequence from SEQ ID NO:11 or 14, yet retain biological activity. In one embodiment, the isolated nucleic acid molecule comprises a nucleotide sequence encoding a protein, wherein the protein comprises an amino acid sequence at least about 50%, 55%, 60%, 65%, 70%, 75%, 80%, 84%, 85%, 86%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to SEQ ID NO:11 or 14.

An isolated nucleic acid molecule encoding a DHDR protein identical to the protein of SEQ ID NO:11 or 14 can be created by introducing one or more nucleotide substitutions, additions or deletions into the nucleotide sequence of SEQ ID NO:10, 12, 13, or 15, such that one or more amino acid substitutions, additions or deletions are introduced into the encoded protein. Mutations can be introduced into SEQ ID NO:10, 12, 13, or 15, by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a DHDR protein is preferably replaced with another amino acid residue from the same side chain family. Alternatively, in another embodiment, mutations can be introduced randomly along all or part of a DHDR coding sequence, such as by saturation mutagenesis, and the resultant mutants can be screened for DHDR biological activity to identify mutants that retain activity. Following mutagenesis of SEQ ID NO:10, 12, 13, or 15, the encoded protein can be expressed recombinantly and the activity of the protein can be determined.

In a preferred embodiment, a mutant DHDR protein can be assayed for the ability to metabolize or catabolize biochemical molecules necessary for energy production or storage, permit intra- or inter-cellular signaling, metabolize or catabolize metabolically important biomolecules, or detoxify potentially harmful compounds. In a further preferred embodiment, a mutant DHDR protein can be assayed for the ability to modulate cellular proliferation, growth, differentiation, and/or migration.

In addition to the nucleic acid molecules encoding DHDR proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire DHDR coding strand, or to only a portion thereof. In one embodiment, an antisense nucleic acid molecule is antisense to a "coding region" of the coding strand of a nucleotide sequence encoding a DHDR. The term "coding region" refers to the region of the nucleotide sequence comprising codons which are translated into amino acid residues (e.g., the coding region of human DHDR corresponds to SEQ ID NO:12 or 15). In another embodiment, the antisense nucleic acid molecule is antisense to a "noncoding region" of the coding strand of a nucleotide sequence encoding DHDR. The term "noncoding region" refers to 5' and 3' sequences which flank the coding region that are not translated into amino acids (also referred to as 5' and 3' untranslated regions).

Given the coding strand sequences encoding DHDR disclosed herein (e.g., SEQ ID NO:12 or 15), antisense nucleic acids of the invention can be designed according to the rules of Watson and Crick base pairing. The antisense nucleic acid molecule can be complementary to the entire coding region of DHDR mRNA, but more preferably is an oligonucleotide which is antisense to only a portion of the coding or noncoding region of DHDR mRNA. For example, the antisense oligonucleotide can be complementary to the region surrounding the translation start site of DHDR mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5- oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a DHDR protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al.

(1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff and Gerlach (1988) *Nature* 334:585–591)) can be used to catalytically cleave DHDR mRNA transcripts to thereby inhibit translation of DHDR mRNA. A ribozyme having specificity for a DHDR-encoding nucleic acid can be designed based upon the nucleotide sequence of a DHDR cDNA disclosed herein (i.e., SEQ ID NO:10, 12, 13, or 15. For example, a derivative of a Tetrahymena L-19 IVS RNA can be constructed in which the nucleotide sequence of the active site is complementary to the nucleotide sequence to be cleaved in a DHDR-encoding mRNA. See, e.g., Cech et al. U.S. Pat. No. 4,987,071; and Cech et al. U.S. Pat. No. 5,116,742. Alternatively, DHDR mRNA can be used to select a catalytic RNA having a specific ribonuclease activity from a pool of RNA molecules. See, e.g., Bartel, D. and Szostak, J. W. (1993) *Science* 261:1411–1418.

Alternatively, DHDR gene expression can be inhibited by targeting nucleotide sequences complementary to the regulatory region of the DHDR (e.g., the DHDR promoter and/or enhancers; e.g., nucleotides 1–117 of SEQ ID NO:10 or nucleotides 1–14 of SEQ ID NO:12) to form triple helical structures that prevent transcription of the DHDR gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioessays* 14(12):807–15.

In yet another embodiment, the DHDR nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup, B. and Nielsen, P. E. (1996) *Bioorg. Med. Chem.* 4(1):5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup and Nielsen (1996) supra and Perry-O'Keefe et al. (1996) *Proc. Natl. Acad. Sci. USA* 93:14670–675.

PNAs of DHDR nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of DHDR nucleic acid molecules can also be used in the analysis of single base pair mutations in a gene (e.g., by PNA-directed PCR clamping); as 'artificial restriction enzymes' when used in combination with other enzymes (e.g., S1 nucleases (Hyrup and Nielsen (1996) supra)); or as probes or primers for DNA sequencing or hybridization (Hyrup and Nielsen (1996) supra; Perry-O'Keefe et al. (1996) supra).

In another embodiment, PNAs of DHDR can be modified (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of DHDR nucleic acid molecules can be generated which may combine the advantageous properties of PNA and DNA. Such chimeras allow DNA recognition enzymes (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup and Nielsen (1996) supra). The synthesis of PNA-DNA chimeras can be performed as described in Hyrup and Nielsen (1996) supra and Finn, P. J. et al. (1996) *Nucleic Acids Res.* 24(17):3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acids Res.* 17:5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5:1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) *Biotechniques* 6:958–976) or intercalating agents (see, e.g., Zon (1988) *Pharm. Res.* 5:539–549). To this end, the oligonucleotide may be conjugated to another molecule (e.g., a peptide, hybridization triggered cross-linking agent, transport agent, or hybridization-triggered cleavage agent).

Alternatively, the expression characteristics of an endogenous DHDR gene within a cell line or microorganism may be modified by inserting a heterologous DNA regulatory element into the genome of a stable cell line or cloned microorganism such that the inserted regulatory element is operatively linked with the endogenous DHDR gene. For example, an endogenous DHDR gene which is normally "transcriptionally silent", i.e., a DHDR gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous DHDR gene may be activated by insertion of a promiscuous regulatory element that works across cell types.

A heterologous regulatory element may be inserted into a stable cell line or cloned microorganism, such that it is operatively linked with an endogenous DHDR gene, using techniques, such as targeted homologous recombination, which are well known to those of skill in the art, and described, e.g., in Chappel, U.S. Pat. No. 5,272,071; PCT publication No. WO 91/06667, published May 16, 1991.

II. Isolated DHDR Proteins and Anti-DHDR Antibodies

One aspect of the invention pertains to isolated DHDR proteins, and biologically active portions thereof, as well as polypeptide fragments suitable for use as immunogens to raise anti-DHDR antibodies. In one embodiment, native DHDR proteins can be isolated from cells or tissue sources by an appropriate purification scheme using standard protein purification techniques. In another embodiment, DHDR proteins are produced by recombinant DNA techniques. Alternative to recombinant expression, a DHDR protein or polypeptide can be synthesized chemically using standard peptide synthesis techniques.

An "isolated" or "purified" protein or biologically active portion thereof is substantially free of cellular material or other contaminating proteins from the cell or tissue source from which the DHDR protein is derived, or substantially free from chemical precursors or other chemicals when chemically synthesized. The language "substantially free of cellular material" includes preparations of DHDR protein in which the protein is separated from cellular components of the cells from which it is isolated or recombinantly produced. In one embodiment, the language "substantially free of cellular material" includes preparations of DHDR protein having less than about 30% (by dry weight) of non-DHDR protein (also referred to herein as a "contaminating protein"), more preferably less than about 20% of non-DHDR protein, still more preferably less than about 10% of non-DHDR protein, and most preferably less than about 5% non-DHDR protein. When the DHDR protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of DHDR protein in which the protein is separated from chemical precursors or other chemicals which are involved in the synthesis of the protein. In one embodiment, the language "substantially free of chemical precursors or other chemicals" includes preparations of DHDR protein having less than about 30% (by dry weight) of chemical precursors or non-DHDR chemicals, more preferably less than about 20% chemical precursors or non-DHDR chemicals, still more preferably less than about 10% chemical precursors or non-DHDR chemicals, and most preferably less than about 5% chemical precursors or non-DHDR chemicals.

As used herein, a "biologically active portion" of a DHDR protein includes a fragment of a DHDR protein which participates in an interaction between a DHDR molecule and a non-DHDR molecule. Biologically active portions of a DHDR protein include peptides comprising amino acid sequences sufficiently identical to or derived from the amino acid sequence of the DHDR protein, e.g., the amino acid sequence shown in SEQ ID NO:11 or 14, which include fewer amino acids than the full length DHDR proteins, and exhibit at least one activity of a DHDR protein. Typically, biologically active portions comprise a domain or motif with at least one activity of the DHDR protein, e.g., modulating membrane excitability. A biologically active portion of a DHDR protein can be a polypeptide which is, for example, 25, 50, 75, 100, 125, 150, 175, 200, 250, 300, 310 or more amino acids in length. Biologically active portions of a DHDR protein can be used as targets for developing agents which modulate a DHDR mediated activity, e.g., a proliferative response.

In one embodiment, a biologically active portion of a DHDR protein comprises at least one transmembrane domain. It is to be understood that a preferred biologically active portion of a DHDR protein of the present invention may contain at least one transmembrane domain and one or more of the following domains: a signal peptide domain, a short chain dehydrogenase domain, a shikimate/quinate 5-dehydrogenase domain, and/or an iron-containing alcohol dehydrogenase domain. Moreover, other biologically active portions, in which other regions of the protein are deleted, can be prepared by recombinant techniques and evaluated for one or more of the functional activities of a native DHDR protein.

In a preferred embodiment, the DHDR protein has an amino acid sequence shown in SEQ ID NO:11 or 14. In other embodiments, the DHDR protein is substantially identical to SEQ ID NO:11 or 14, and retains the functional activity of the protein of SEQ ID NO:11 or 14, yet differs in amino acid sequence due to natural allelic variation or mutagenesis, as described in detail in subsection I above. Accordingly, in another embodiment, the DHDR protein is a protein which comprises an amino acid sequence at least about 50%, 55%, 60%, 65%, 70%, 75%, 80%, 84%, 85%, 86%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to SEQ ID NO:11 or 14.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the DHDR-5 amino acid sequence of SEQ ID NO:11 having 330 amino acid residues, at least 99, preferably at least 132, more preferably at least 165, more preferably at least 198, and even more preferably at least 231, 264, 297 or more amino acid residues are aligned; when aligning a second sequence to the DHDR-6 amino acid sequence of SEQ ID NO:14 having 467 amino acid residues, at least 140, preferably at least 187, more preferably at least 234, more preferably at least 280, and even more preferably at least 327, 374, 420 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* 48:444–453 (1970)) algorithm which has been incorporated into the GAP program in the GCG software package (available online through the Genetics Computer Group), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online through the Genetics Computer Group), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*Comput. Appl. Biosci.* 4:11–17 (1988)) which has been incorporated into the ALIGN program (version 2.0 or 2.0U), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403–10. BLAST nucleotide searches can be performed with the NBLAST program, score=100, wordlength=12 to obtain nucleotide sequences homologous to DHDR nucleic acid molecules of the invention. BLAST protein searches can be performed with the XBLAST program, score=100, wordlength=3 to obtain amino acid sequences homologous to DHDR protein molecules of the invention. To obtain gapped alignments for comparison purposes, Gapped BLAST can be utilized as described in Altschul et al. (1997) *Nucleic Acids Res.* 25(17):3389–3402. When utilizing BLAST and Gapped BLAST programs, the default parameters of the respective programs (e.g., XBLAST and NBLAST) can be used. See the website for the National Center for Biotechnology Information.

The invention also provides DHDR chimeric or fusion proteins. As used herein, a DHDR "chimeric protein" or "fusion protein" comprises a DHDR polypeptide operatively linked to a non-DHDR polypeptide. A "DHDR polypeptide" refers to a polypeptide having an amino acid sequence corresponding to a DHDR molecule, whereas a "non-DHDR polypeptide" refers to a polypeptide having an amino acid sequence corresponding to a protein which is not substantially homologous to the DHDR protein, e.g., a protein which is different from the DHDR protein and which is derived from the same or a different organism. Within a DHDR fusion protein the DHDR polypeptide can correspond to all or a portion of a DHDR protein. In a preferred embodiment, a DHDR fusion protein comprises at least one biologically active portion of a DHDR protein. In another preferred embodiment, a DHDR fusion protein comprises at least two biologically active portions of a DHDR protein. Within the fusion protein, the term "operatively linked" is intended to indicate that the DHDR polypeptide and the non-DHDR polypeptide are fused in-frame to each other. The non-DHDR polypeptide can be fused to the N-terminus or C-terminus of the DHDR polypeptide.

For example, in one embodiment, the fusion protein is a GST-DHDR fusion protein in which the DHDR sequences are fused to the C-terminus of the GST sequences. Such fusion proteins can facilitate the purification of recombinant DHDR.

In another embodiment, the fusion protein is a DHDR protein containing a heterologous signal sequence at its N-terminus. In certain host cells (e.g., mammalian host cells), expression and/or secretion of DHDR can be increased through use of a heterologous signal sequence.

The DHDR fusion proteins of the invention can be incorporated into pharmaceutical compositions and administered to a subject in vivo. The DHDR fusion proteins can be used to affect the bioavailability of a DHDR substrate. Use of DHDR fusion proteins may be useful therapeutically for the treatment of disorders caused by, for example, (i) aberrant modification or mutation of a gene encoding a DHDR protein; (ii) mis-regulation of the DHDR gene; and (iii) aberrant post-translational modification of a DHDR protein.

Moreover, the DHDR-fusion proteins of the invention can be used as immunogens to produce anti-DHDR antibodies in a subject, to purify DHDR ligands and in screening assays to identify molecules which inhibit the interaction of DHDR with a DHDR substrate.

Preferably, a DHDR chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A DHDR-encoding nucleic acid can be cloned into such an expression vector such that the fusion moiety is linked in-frame to the DHDR protein.

The present invention also pertains to variants of the DHDR proteins which function as either DHDR agonists (mimetics) or as DHDR antagonists. Variants of the DHDR proteins can be generated by mutagenesis, e.g., discrete point mutation or truncation of a DHDR protein. An agonist of the DHDR proteins can retain substantially the same, or a subset, of the biological activities of the naturally occurring form of a DHDR protein. An antagonist of a DHDR protein can inhibit one or more of the activities of the naturally occurring form of the DHDR protein by, for example, competitively modulating a DHDR-mediated activity of a DHDR protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the DHDR protein.

In one embodiment, variants of a DHDR protein which function as either DHDR agonists (mimetics) or as DHDR antagonists can be identified by screening combinatorial libraries of mutants, e.g., truncation mutants, of a DHDR protein for DHDR protein agonist or antagonist activity. In one embodiment, a variegated library of DHDR variants is generated by combinatorial mutagenesis at the nucleic acid level and is encoded by a variegated gene library. A variegated library of DHDR variants can be produced by, for example, enzymatically ligating a mixture of synthetic oligonucleotides into gene sequences such that a degenerate set of potential DHDR sequences is expressible as individual polypeptides, or alternatively, as a set of larger fusion proteins (e.g., for phage display) containing the set of DHDR sequences therein. There are a variety of methods which can be used to produce libraries of potential DHDR variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential DHDR sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of a DHDR protein coding sequence can be used to generate a variegated population of DHDR fragments for screening and subsequent selection of variants of a DHDR protein. In one embodiment, a library of coding sequence fragments can be generated by treating a double stranded PCR fragment of a DHDR coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the DHDR protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of DHDR proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify DHDR variants (Arkin and Youvan (1992) *Proc. Natl. Acad. Sci. USA* 89:7811–7815; Delagrave et al. (1993) *Protein Eng.* 6(3): 327–331).

In one embodiment, cell based assays can be exploited to analyze a variegated DHDR library. For example, a library of expression vectors can be transfected into a cell line, e.g., a neuronal cell line, which ordinarily responds to a DHDR ligand in a particular DHDR ligand-dependent manner. The transfected cells are then contacted with a DHDR ligand and the effect of expression of the mutant on, e.g., membrane excitability of DHDR can be detected. Plasmid DNA can then be recovered from the cells which score for inhibition, or alternatively, potentiation of signaling by the DHDR ligand, and the individual clones further characterized.

An isolated DHDR protein, or a portion or fragment thereof, can be used as an immunogen to generate antibodies that bind DHDR using standard techniques for polyclonal and monoclonal antibody preparation. A full-length DHDR protein can be used or, alternatively, the invention provides antigenic peptide fragments of DHDR for use as immunogens. The antigenic peptide of DHDR comprises at least 8 amino acid residues of the amino acid sequence shown in SEQ ID NO:11 or 14 and encompasses an epitope of DHDR such that an antibody raised against the peptide forms a specific immune complex with the DHDR protein. Preferably, the antigenic peptide comprises at least 10 amino acid residues, more preferably at least 15 amino acid residues, even more preferably at least 20 amino acid residues, and most preferably at least 30 amino acid residues.

Figure 20:
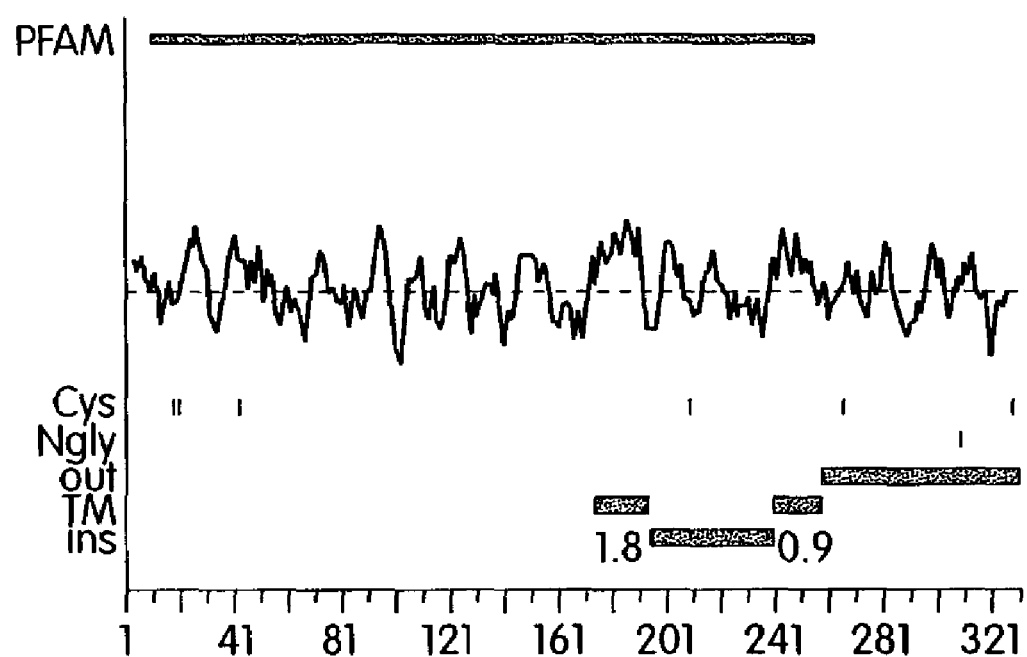
FIG. 20 depicts a hydrophobicity plot of the human DHDR-5 protein.

Preferred epitopes encompassed by the antigenic peptide are regions of DHDR that are located on the surface of the protein, e.g., hydrophilic regions, as well as regions with high antigenicity (see, for example, FIGS. 20 and 28).

A DHDR immunogen typically is used to prepare antibodies by immunizing a suitable subject (e.g., rabbit, goat, mouse, or other mammal) with the immunogen. An appropriate immunogenic preparation can contain, for example, recombinantly expressed DHDR protein or a chemically synthesized DHDR polypeptide. The preparation can further include an adjuvant, such as Freund's complete or incomplete adjuvant, or similar immunostimulatory agent. Immunization of a suitable subject with an immunogenic DHDR preparation induces a polyclonal anti-DHDR antibody response.

Accordingly, another aspect of the invention pertains to anti-DHDR antibodies. The term "antibody" as used herein refers to immunoglobulin molecules and immunologically active portions of immunoglobulin molecules, i.e., molecules that contain an antigen binding site which specifically binds (immunoreacts with) an antigen, such as a DHDR. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind DHDR molecules. The term "monoclonal antibody" or "monoclonal antibody composition", as used herein, refers to a population of antibody molecules that contain only one species of an antigen binding site capable of immunoreacting with a particular epitope of DHDR. A monoclonal antibody composition thus typically displays a single binding affinity for a particular DHDR protein with which it immunoreacts.

Polyclonal anti-DHDR antibodies can be prepared as described above by immunizing a suitable subject with a DHDR immunogen. The anti-DHDR antibody titer in the immunized subject can be monitored over time by standard techniques, such as with an enzyme linked immunosorbent assay (ELISA) using immobilized DHDR. If desired, the antibody molecules directed against DHDR can be isolated from the mammal (e.g., from the blood) and further purified by well known techniques, such as protein A chromatography to obtain the IgG fraction. At an appropriate time after immunization, e.g., when the anti-DHDR antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.*

255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77–96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387–402; Gefter, M. L. et al. (1977) *Somatic Cell Genet.* 3:231–36). Briefly, an immortal cell line (typically a myeloma) is fused to lymphocytes (typically splenocytes) from a mammal immunized with a DHDR immunogen as described above, and the culture supernatants of the resulting hybridoma cells are screened to identify a hybridoma producing a monoclonal antibody that binds DHDR.

Any of the many well known protocols used for fusing lymphocytes and immortalized cell lines can be applied for the purpose of generating an anti-DHDR monoclonal antibody (see, e.g., Galfre, G. et al. (1977) *Nature* 266:55052; Gefter et al. (1977) supra; Lerner (1981) supra; and Kenneth (1980) supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC (Manassas, Va.). Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind DHDR, e.g., using a standard ELISA assay.

Alternative to preparing monoclonal antibody-secreting hybridomas, a monoclonal anti-DHDR antibody can be identified and isolated by screening a recombinant combinatorial immunoglobulin library (e.g., an antibody phage display library) with DHDR to thereby isolate immunoglobulin library members that bind DHDR. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Biotechnology (NY)* 9:1369–1372; Hay et al. (1992) *Hum. Antibod. Hybridomas* 3:81–85; Huse et al. (1989) *Science* 246:1275–1281; Griffiths et al. (1993) *EMBO J.* 12:725–734; Hawkins et al. (1992) *J. Mol. Biol.* 226:889–896; Clackson et al. (1991) *Nature* 352:624–628; Gram et al. (1992) *Proc. Natl. Acad. Sci. USA* 89:3576–3580; Garrard et al. (1991) *Biotechnology* (NY) 9:1373–1377; Hoogenboom et al. (1991) *Nucleic Acids Res.* 19:4133–4137; Barbas et al. (1991) *Proc. Natl. Acad. Sci. USA* 88:7978–7982; and McCafferty et al. (1990) *Nature* 348:552–554.

Additionally, recombinant anti-DHDR antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Cancer Res.* 47:999–1005; Wood et al. (1985) *Nature* 314:446–449; Shaw et al. (1988) *J. Natl. Cancer Inst.* 80:1553–1559; Morrison, S. L. (1985) *Science* 229:1202–1207; Oi et al. (1986) *Biotechniques* 4:214; Winter U.S. Pat. No. 5,225,539; Jones et al. (1986) *Nature* 321:552–525; Verhoeyen et al. (1988) *Science* 239:1534; and Beidler et al. (1988) *J. Immunol.* 141:4053–4060.

An anti-DHDR antibody (e.g., monoclonal antibody) can be used to isolate DHDR by standard techniques, such as affinity chromatography or immunoprecipitation. An anti-DHDR antibody can facilitate the purification of natural DHDR from cells and of recombinantly produced DHDR expressed in host cells. Moreover, an anti-DHDR antibody can be used to detect DHDR protein (e.g., in a cellular lysate or cell supernatant) in order to evaluate the abundance and pattern of expression of the DHDR protein. Anti-DHDR antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid encoding a DHDR protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) Methods Enzymol. 185:3–7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., DHDR proteins, mutant forms of DHDR proteins, fusion proteins, and the like).

The recombinant expression vectors of the invention can be designed for expression of DHDR proteins in prokaryotic or eukaryotic cells. For example, DHDR proteins can be expressed in bacterial cells such as E. coli, insect cells (using baculovirus expression vectors), yeast cells, or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in DHDR activity assays (e.g., direct assays or competitive assays described in detail below), or to generate antibodies specific for DHDR proteins, for example. In a preferred embodiment, a DHDR fusion protein expressed in a retroviral expression vector of the present invention can be utilized to infect bone marrow cells which are subsequently transplanted into irradiated recipients. The pathology of the subject recipient is then examined after sufficient time has passed (e.g., six weeks).

Examples of suitable inducible non-fusion E. coli expression vectors include pTrc (Amann et al. (1988) Gene 69:301–315) and pET 11d (Studier et al. (1990) Methods Enzymol. 185:60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in E. coli is to express the protein in a host bacteria with an impaired capacity to proteolytically cleave the recombinant protein (Gottesman, S. (1990) Methods Enzymol. 185:119–128). Another strategy is to alter the nucleic acid sequence of the nucleic acid to be inserted into an expression vector so that the individual codons for each amino acid are those preferentially utilized in E. coli (Wada et al. (1992) Nucleic Acids Res. 20:2111–2118). Such alteration of nucleic acid sequences of the invention can be carried out by standard DNA synthesis techniques.

In another embodiment, the DHDR expression vector is a yeast expression vector. Examples of vectors for expression in yeast S. cerevisiae include pYepSec1 (Baldari et al. (1987) EMBO J. 6:229–234), pMFa (Kurjan and Herskowitz (1982) Cell 30:933–943), pJRY88 (Schultz et al. (1987) Gene 54:113–123), pYES2 (Invitrogen Corporation, San Diego, Calif.), and picZ (Invitrogen Corp, San Diego, Calif.).

Alternatively, DHDR proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al., *Molecular Cloning: A Laboratory Manual. 2nd ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example by the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to DHDR mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub, H. et al., Antisense RNA as a molecular tool for genetic analysis, *Reviews—Trends in Genetics*, Vol. 1(1) 1986.

Another aspect of the invention pertains to host cells into which a DHDR nucleic acid molecule of the invention is introduced, e.g., a DHDR nucleic acid molecule within a recombinant expression vector or a DHDR nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a DHDR protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual. 2nd ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a DHDR protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a DHDR protein. Accordingly, the invention further provides methods for producing a DHDR protein using the host cells of the invention. In one embodiment, the method comprises culturing the host cell of the invention (into which a recombinant expression vector encoding a DHDR protein has been introduced) in a suitable medium such that a DHDR protein is produced. In another embodiment, the method further comprises isolating a DHDR protein from the medium or the host cell.

The host cells of the invention can also be used to produce non-human transgenic animals. For example, in one embodiment, a host cell of the invention is a fertilized oocyte or an embryonic stem cell into which DHDR-coding sequences have been introduced. Such host cells can then be used to create non-human transgenic animals in which exogenous DHDR sequences have been introduced into their genome or homologous recombinant animals in which endogenous DHDR sequences have been altered. Such animals are useful for studying the function and/or activity of a DHDR and for identifying and/or evaluating modulators of DHDR activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous DHDR gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a DHDR-encoding nucleic acid into the male pronuclei of a fertilized oocyte, e.g., by microinjection, retroviral infection, and allowing the oocyte to develop in a pseudopregnant female foster animal. The DHDR cDNA sequence of SEQ ID NO:10 or 13 can be introduced as a transgene into the genome of a non-human animal. Alternatively, a nonhuman homologuen of a human DHDR gene, such as a mouse or rat DHDR gene, can be used as a transgene. Alternatively, a DHDR gene homologue, such as another DHDR family member, can be isolated based on hybridization to the DHDR cDNA sequences of SEQ ID NO:10, 12, 13, or 15, (described further in subsection I above) and used as a transgene. Intronic sequences and polyadenylation signals can also be included in the transgene to increase the efficiency of expression of the transgene. A tissue-specific regulatory sequence(s) can be operably linked to a DHDR transgene to direct expression of a DHDR protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of a DHDR transgene in its genome and/or expression of DHDR mRNA in tissues or cells of the animals. A transgenic founder animal can then be used to breed additional animals carrying the transgene. Moreover, transgenic animals carrying a transgene encoding a DHDR protein can further be bred to other transgenic animals carrying other transgenes.

To create a homologous recombinant animal, a vector is prepared which contains at least a portion of a DHDR gene into which a deletion, addition or substitution has been introduced to thereby alter, e.g., functionally disrupt, the DHDR gene. The DHDR gene can be a human gene (e.g., the cDNA of SEQ ID NO:12 or 15), but more preferably, is a non-human homologue of a human DHDR gene (e.g., a cDNA isolated by stringent hybridization with the nucleotide sequence of SEQ ID NO:10 or 13). For example, a mouse DHDR gene can be used to construct a homologous recombination nucleic acid molecule, e.g., a vector, suitable for altering an endogenous DHDR gene in the mouse genome. In a preferred embodiment, the homologous recombination nucleic acid molecule is designed such that, upon homologous recombination, the endogenous DHDR gene is functionally disrupted (i.e., no longer encodes a functional protein; also referred to as a "knock out" vector). Alternatively, the homologous recombination nucleic acid molecule can be designed such that, upon homologous recombination, the endogenous DHDR gene is mutated or otherwise altered but still encodes functional protein (e.g., the upstream regulatory region can be altered to thereby alter the expression of the endogenous DHDR protein). In the homologous recombination nucleic acid molecule, the altered portion of the DHDR gene is flanked at its 5' and 3' ends by additional nucleic acid sequence of the DHDR gene to allow for homologous recombination to occur between the exogenous DHDR gene carried by the homologous recombination nucleic acid molecule and an endogenous DHDR gene in a cell, e.g., an embryonic stem cell. The additional flanking DHDR nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced DHDR gene has homologously recombined with the endogenous DHDR gene are selected (see e.g., Li, E. et al. (1992) *Cell* 69:915). The selected cells can then be injected into a blastocyst of an animal (e.g., a mouse) to form aggregation chimeras (see e.g., Bradley, A. in *Teratocarcinomas and Embryonic Stem Cells: A Practical Approach*, Robertson, E. J., ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *S. cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to the morula or blastocyte stage and then transferred to pseudopregnant female foster animal.

The offspring borne of this female foster animal will be a clone of the animal from which the cell, e.g., the somatic cell, is isolated.

IV. Pharmaceutical Compositions

The DHDR nucleic acid molecules, fragments of DHDR proteins, and anti-DHDR antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR® EL solubilizer (BASF, Florham Park, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a DHDR protein or an anti-DHDR antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

In certain embodiments of the invention, a modulator of DHDR activity is administered in combination with other agents (e.g., a small molecule), or in conjunction with another, complementary treatment regime. For example, in one embodiment, a modulator of DHDR activity is used to treat a cellular proliferation, growth, differentiation, and/or migration disorder. Accordingly, modulation of DHDR activity may be used in conjunction with, for example, another agent or treatment used to treat the disorder, e.g., radiation or conventional chemotherapy.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in *Monoclonal Antibodies And Cancer Therapy*, Reisfeld et al. (eds.), pp. 243–56 (Alan R. Liss, Inc. 1985); Hellstrom et al., "Antibodies for Drug Delivery" in *Controlled Drug Delivery* (2nd Ed.), Robinson et al. (eds.), pp. 623–53 (Marcel Dekker, Inc. 1987); Thorpe, "Antibody Carriers of Cytotoxic Agents in Cancer Therapy: A Review", in *Monoclonal Antibodies '84: Biological and Clinical Applications*, Pinchera et al. (eds.), pp. 475–506 (1985); "Analysis, Results, and Future Prospective of the Therapeutic Use of Radiolabeled Antibody in Cancer Therapy", in *Monoclonal Antibodies for Cancer Detection and Therapy*, Baldwin et al. (eds.), pp. 303–16 (Academic Press 1985); and Thorpe et al., "The Preparation And Cytotoxic Properties Of Antibody-Toxin Conjugates" *Immunol. Rev.* 62:119–58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a DHDR protein of the invention has one or more of the following activities: 1) it modulates metabolism or catabolism of biochemical molecules necessary for energy production or storage, 2) it modulates intra- or inter-cellular signaling, 3) it modulates metabolism or catabolism of metabolically important biomolecules, 4) it modulates detoxification of potentially harmful compounds, and 5) it modulates cellular proliferation, growth, differentiation, and/or migration.

The isolated nucleic acid molecules of the invention can be used, for example, to express DHDR protein (e.g., via a recombinant expression vector in a host cell in gene therapy applications), to detect DHDR mRNA (e.g., in a biological sample) or a genetic alteration in a DHDR gene, and to modulate DHDR activity, as described further below. The DHDR proteins can be used to treat disorders characterized by insufficient or excessive production of a DHDR substrate or production of DHDR inhibitors. In addition, the DHDR proteins can be used to screen for naturally occurring DHDR substrates, to screen for drugs or compounds which modulate DHDR activity, as well as to treat disorders characterized by insufficient or excessive production of DHDR protein or production of DHDR protein forms which have decreased, aberrant or unwanted activity compared to DHDR wild type protein (e.g., dehydrogenase-associated disorders, such as cellular proliferation, growth, differentiation, or migration disorders (e.g., lung, breast, brain, ovary, or colon cancer)). Moreover, the anti-DHDR antibodies of the invention can be used to detect and isolate DHDR proteins, regulate the bioavailability of DHDR proteins, and modulate DHDR activity.

A. Screening Assays:

The invention provides a method (also referred to herein as a "screening assay") for identifying modulators, i.e., candidate or test compounds or agents (e.g., peptides, peptidomimetics, small molecules or other drugs) which bind to DHDR proteins, have a stimulatory or inhibitory effect on, for example, DHDR expression or DHDR activity, or have a stimulatory or inhibitory effect on, for example, the expression or activity of DHDR substrate.

In one embodiment, the invention provides assays for screening candidate or test compounds which are substrates of a DHDR protein or polypeptide or biologically active portion thereof (e.g., aldehydes, alcohols, or steroids). In another embodiment, the invention provides assays for screening candidate or test compounds which bind to or modulate the activity of a DHDR protein or polypeptide or biologically active portion thereof (e.g., cofactor or coenzyme analogs, or inhibitory molecules). The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc. Natl. Acad. Sci. USA* 89:1865–1869) or phage (Scott and Smith (1990) *Science* 249:386–390; Devlin (1990) *Science* 249:404–406; Cwirla et al. (1990) *Proc. Natl. Acad. Sci.* 87:6378–6382; Felici (1991) *J. Mol. Biol.* 222:301–310; Ladner supra.).

In one embodiment, an assay is a cell-based assay in which a cell which expresses a DHDR protein or biologically active portion thereof is contacted with a test compound and the ability of the test compound to modulate DHDR activity is determined. Determining the ability of the test compound to modulate DHDR activity can be accomplished by monitoring, for example, the production of one or more specific metabolites in a cell which expresses DHDR (see, e.g., Saada et al. (2000) *Biochem. Biophys. Res. Commun.* 269:382–386). Determining the ability of the test compound to modulate DHDR activity can also be accomplished by monitoring, for example, proliferation of a cell which expresses DHDR. The cell, for example, can be of mammalian origin, e.g., a breast cell or an ovary cell, or a tumor cell.

The ability of the test compound to modulate DHDR binding to a substrate (e.g., an alcohol or an aldehyde) or to bind to DHDR can also be determined. Determining the ability of the test compound to modulate DHDR binding to a substrate can be accomplished, for example, by coupling the DHDR substrate with a radioisotope or enzymatic label such that binding of the DHDR substrate to DHDR can be determined by detecting the labeled DHDR substrate in a complex. Alternatively, DHDR could be coupled with a radioisotope or enzymatic label to monitor the ability of a test compound to modulate DHDR binding to a DHDR substrate in a complex. Determining the ability of the test compound to bind DHDR can be accomplished, for example, by coupling the compound with a radioisotope or enzymatic label such that binding of the compound to DHDR can be determined by detecting the labeled DHDR compound in a complex. For example, compounds (e.g., DHDR substrates) can be labeled with $^{125}I$, $^{35}S$, $^{14}C$, or $^{3}H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., a DHDR substrate) to interact with DHDR without the labeling of any of the interactants. For example, a microphysiometer can be used to detect the interaction of a compound with DHDR without the labeling of either the compound or the DHDR (McConnell, H. M. et al. (1992) *Science* 257:1906–1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and DHDR.

In another embodiment, an assay is a cell-based assay comprising contacting a cell expressing a DHDR target molecule (e.g., a DHDR substrate) with a test compound and determining the ability of the test compound to modulate (e.g., stimulate or inhibit) the activity of the DHDR target molecule. Determining the ability of the test compound to modulate the activity of a DHDR target molecule can be accomplished, for example, by determining the ability of the DHDR protein to bind to or interact with the DHDR target molecule.

Determining the ability of the DHDR protein, or a biologically active fragment thereof, to bind to or interact with a DHDR target molecule can be accomplished by one of the methods described above for determining direct binding. In a preferred embodiment, determining the ability of the DHDR protein to bind to or interact with a DHDR target molecule can be accomplished by determining the activity of the target molecule. For example, the activity of the target molecule can be determined by detecting induction of a cellular response (e.g., changes in cellular proliferation or growth), detecting catalytic/enzymatic activity of the target on an appropriate substrate, detecting the induction of a reporter gene (comprising a target-responsive regulatory element operatively linked to a nucleic acid encoding a detectable marker, e.g., luciferase), or detecting a target-regulated cellular response. Methods for measuring cellular proliferation are well-known to those of skill in the art.

In yet another embodiment, an assay of the present invention is a cell-free assay in which a DHDR protein or biologically active portion thereof is contacted with a test compound and the ability of the test compound to bind to the DHDR protein or biologically active portion thereof is determined. Preferred biologically active portions of the DHDR proteins to be used in assays of the present invention include fragments which participate in interactions with non-DHDR molecules, e.g., fragments with high surface probability scores (see, for example, FIGS. 20 and 28). Binding of the test compound to the DHDR protein can be determined either directly or indirectly as described above. In a preferred embodiment, the assay includes contacting the DHDR protein or biologically active portion thereof with a known compound which binds DHDR to form an assay mixture, contacting the assay mixture with a test compound, and determining the ability of the test compound to interact with a DHDR protein, wherein determining the ability of the test compound to interact with a DHDR protein comprises determining the ability of the test compound to preferentially bind to DHDR or biologically active portion thereof as compared to the known compound.

In another embodiment, the assay is a cell-free assay in which a DHDR protein or biologically active portion thereof is contacted with a test compound and the ability of the test compound to modulate (e.g., stimulate or inhibit) the activity of the DHDR protein or biologically active portion thereof is determined. Determining the ability of the test compound to modulate the activity of a DHDR protein can be accomplished, for example, by determining the ability of the DHDR protein to bind to a DHDR target molecule by one of the methods described above for determining direct binding. Determining the ability of the DHDR protein to bind to a DHDR target molecule can also be accomplished using a technology such as real-time Biomolecular Interaction Analysis (BIA) (Sjolander, S. and Urbaniczky, C. (1991) *Anal. Chem.* 63:2338–2345; Szabo et al. (1995) *Curr. Opin. Struct. Biol.* 5:699–705). As used herein, "BIA" is a technology for studying biospecific interactions in real time, without labeling any of the interactants (e.g., BIACORE™). Changes in the optical phenomenon of surface plasmon resonance (SPR) can be used as an indication of real-time reactions between biological molecules.

In an alternative embodiment, determining the ability of the test compound to modulate the activity of a DHDR protein can be accomplished by determining the ability of the DHDR protein to further modulate the activity of a downstream effector of a DHDR target molecule. For example, the activity of the effector molecule on an appropriate target can be determined or the binding of the effector to an appropriate target can be determined as previously described.

In yet another embodiment, the cell-free assay involves contacting a DHDR protein or biologically active portion thereof with a known compound which binds the DHDR protein to form an assay mixture, contacting the assay mixture with a test compound, and determining the ability of the test compound to interact with the DHDR protein, wherein determining the ability of the test compound to interact with the DHDR protein comprises determining the ability of the DHDR protein to preferentially bind to or catalyze the transfer of a hydride moiety to or from the target substrate.

The cell-free assays of the present invention are amenable to use of both soluble and/or membrane-bound forms of isolated proteins (e.g., DHDR proteins or biologically active portions thereof). In the case of cell-free assays in which a membrane-bound form of an isolated protein is used it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either DHDR or its target molecule to facilitate separation of complexed from uncomplexed forms of one or both of the proteins, as well as to accommodate automation of the assay. Binding of a test compound to a DHDR protein, or interaction of a DHDR protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/DHDR fusion proteins or glutathione-S-transferase/target fusion proteins can be adsorbed onto glutathione SEPHAROSE™ beads (Sigma Chemical, St. Louis, Mo.) or glutathione derivatized microtitre plates, which are then combined with the test compound or the test compound and either the non-adsorbed target protein or DHDR protein, and the mixture incubated under conditions conducive to complex formation (e.g., at physiological conditions for salt and pH). Following incubation, the beads or microtitre plate wells are washed to remove any unbound components, the matrix is immobilized in the case of beads, and complex formation is determined either directly or indirectly, for example, as described above. Alternatively, the complexes can be dissociated from the matrix, and the level of DHDR binding or activity determined using standard techniques.

Other techniques for immobilizing proteins on matrices can also be used in the screening assays of the invention. For example, either a DHDR protein or a DHDR target molecule can be immobilized utilizing conjugation of biotin and streptavidin. Biotinylated DHDR protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies which are reactive with DHDR protein or target molecules but which do not interfere with binding of the DHDR protein to its target molecule can be derivatized to the wells of the plate, and unbound target or DHDR protein is trapped in the wells by antibody conjugation. Methods for detecting such complexes, in addition to those described above for the GST-immobilized complexes, include immunodetection of complexes using antibodies reactive with the DHDR protein or target molecule, as well as enzyme-linked assays which rely on detecting an enzymatic activity associated with the DHDR protein or target molecule.

In another embodiment, modulators of DHDR expression are identified in a method wherein a cell is contacted with a candidate compound and the expression of DHDR mRNA or protein in the cell is determined. The level of expression of DHDR mRNA or protein in the presence of the candidate compound is compared to the level of expression of DHDR mRNA or protein in the absence of the candidate compound. The candidate compound can then be identified as a modulator of DHDR expression based on this comparison. For example, when expression of DHDR mRNA or protein is greater (statistically significantly greater) in the presence of the candidate compound than in its absence, the candidate compound is identified as a stimulator of DHDR mRNA or protein expression. Alternatively, when expression of DHDR mRNA or protein is less (statistically significantly less) in the presence of the candidate compound than in its absence, the candidate compound is identified as an inhibitor of DHDR mRNA or protein expression. The level of DHDR mRNA or protein expression in the cells can be determined by methods described herein for detecting DHDR mRNA or protein.

In yet another aspect of the invention, the DHDR proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with DHDR ("DHDR-binding proteins" or "DHDR-6-bp") and are involved in DHDR activity. Such DHDR-binding proteins are also likely to be involved in the propagation of signals by the DHDR proteins or DHDR targets as, for example, downstream elements of a DHDR-mediated signaling pathway. Alternatively, such DHDR-binding proteins are likely to be DHDR inhibitors.

The two-hybrid system is based on the modular nature of most transcription factors, which consist of separable DNA-binding and activation domains. Briefly, the assay utilizes two different DNA constructs. In one construct, the gene that codes for a DHDR protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a DHDR-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the DHDR protein.

In another aspect, the invention pertains to a combination of two or more of the assays described herein. For example, a modulating agent can be identified using a cell-based or a cell free assay, and the ability of the agent to modulate the activity of a DHDR protein can be confirmed in vivo, e.g., in an animal such as an animal model for cellular transformation and/or tumorigenesis.

For example, the ability of the agent to modulate the activity of a DHDR protein can be tested in an animal such as an animal model for a cellular proliferation disorder, e.g., tumorigenesis. Animal based models for studying tumorigenesis in vivo are well known in the art (reviewed in Animal Models of Cancer Predisposition Syndromes, Hiai, H. and Hino, O. (eds.) 1999, *Progress in Experimental Tumor Research*, Vol. 35; Clarke, A. R. (2000) *Carcinogenesis* 21:435–41) and include, for example, carcinogen-induced tumors (Rithidech, K. et al. (1999) *Mutat. Res.* 428:33–39; Miller, M. L. et al. (2000) *Environ. Mol. Mutagen.* 35:319–327), injection and/or transplantation of tumor cells into an animal, as well as animals bearing mutations in growth regulatory genes, for example, oncogenes (e.g., ras) (Arbeit, J. M. et al. (1993) *Am. J. Pathol.* 142:1187–1197; Sinn, E. et al. (1987) *Cell* 49:465–475; Thorgeirsson, S S et al. *Toxicol Lett* (2000) 112–113:553–555) and tumor suppressor genes (e.g., p53) (Vooijs, M. et al. (1999) *Oncogene* 18:5293–5303; Clark A. R. (1995) *Cancer Metast. Rev.* 14:125–148; Kumar, T. R. et al. (1995) *J. Intern. Med.* 238:233–238; Donehower, L. A. et al. (1992) *Nature* 356215–221). Furthermore, experimental model systems are available for the study of, for example, ovarian cancer (Hamilton, T. C. et al. (1984) *Semin. Oncol.* 11:285–298; Rahman, N. A. et al. (1998) *Mol. Cell. Endocrinol.* 145:167–174; Beamer, W. G. et al. (1998) *Toxicol. Pathol.* 26:704–710), gastric cancer (Thompson, J. et al. (2000) *Int. J. Cancer* 86:863–869; Fodde, R. et al. (1999) *Cytogenet. Cell Genet.* 86:105–111), breast cancer (Li, M. et al. (2000) *Oncogene* 19:1010–1019; Green, J. E. et al. (2000) *Oncogene* 19:1020–1027), melanoma (Satyamoorthy, K. et al. (1999) *Cancer Metast. Rev.* 18:401–405), and prostate cancer (Shirai, T. et al. (2000) *Mutat. Res.* 462: 219–226; Bostwick, D. G. et al. (2000) *Prostate* 43:286–294).

This invention further pertains to novel agents identified by the above-described screening assays. Accordingly, it is within the scope of this invention to further use an agent identified as described herein in an appropriate animal model. For example, an agent identified as described herein (e.g., a DHDR modulating agent, an antisense DHDR nucleic acid molecule, a DHDR-specific antibody, or a DHDR binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

In another aspect, cell-based systems, as described herein, may be used to identify compounds which may act to ameliorate tumorigenic or proliferative disease symptoms. For example, such cell systems may be exposed to a compound, suspected of exhibiting an ability to ameliorate tumorigenic or proliferative disease symptoms, at a sufficient concentration and for a time sufficient to elicit such an amelioration of tumorigenic or proliferative disease symptoms in the exposed cells. After exposure, the cells are examined to determine whether one or more of the tumorigenic or proliferative disease cellular phenotypes has been altered to resemble a more normal or more wild type, non-tumorigenic disease or non-proliferative disease phenotype. Cellular phenotypes that are associated with tumorigenic disease states include aberrant proliferation and migration, angiogenesis, anchorage independent growth, and loss of contact inhibition.

In addition, animal-based tumorigenic disease systems, such as those described herein, may be used to identify compounds capable of ameliorating tumorigenic or proliferative disease symptoms. Such animal models may be used as test substrates for the identification of drugs, pharmaceuticals, therapies, and interventions which may be effective in treating tumorigenic or proliferative disease. For example, animal models may be exposed to a compound, suspected of exhibiting an ability to ameliorate tumorigenic or proliferative disease symptoms, at a sufficient concentration and for a time sufficient to elicit such an amelioration of tumorigenic or apoptotic tumorigenic or proliferative disease symptoms in the exposed animals. The response of the animals to the exposure may be monitored by assessing the reversal of disorders associated with tumorigenic disease, for example, by counting the number of tumors and/or measuring their size before and after treatment. In addition, the animals may be monitored by assessing the reversal of disorders associated with tumorigenic disease, for example, reduction in tumor burden, tumor size, and invasive and/or metastatic potential before and after treatment.

With regard to intervention, any treatments which reverse any aspect of tumorigenic or proliferative disease symptoms should be considered as candidates for human tumorigenic or proliferative disease therapeutic intervention. Dosages of test agents may be determined by deriving dose-response curves.

Additionally, gene expression patterns may be utilized to assess the ability of a compound to ameliorate proliferative or tumorigenic disease symptoms. For example, the expression pattern of one or more genes may form part of a "gene expression profile" or "transcriptional profile" which may be then be used in such an assessment. "Gene expression profile" or "transcriptional profile", as used herein, includes the pattern of mRNA expression obtained for a given tissue or cell type under a given set of conditions. Such conditions may include, but are not limited to, the presence of a tumor, e.g., a breast or ovary tumor or any of the other tumors described herein, including any of control or experimental conditions described herein.

Other conditions may include, for example, cell differentiation, transformation, metastasis, and carcinogen exposure. Gene expression profiles may be generated, for example, by utilizing a differential display procedure, Northern analysis and/or RT-PCR. In one embodiment, DHDR gene sequences may be used as probes and/or PCR primers for the generation and corroboration of such gene expression profiles.

Gene expression profiles may be characterized for known states, either tumorigenic or proliferative disease or normal, within the cell- and/or animal-based model systems. Subsequently, these known gene expression profiles may be compared to ascertain the effect a test compound has to modify such gene expression profiles, and to cause the profile to more closely resemble that of a more desirable profile.

For example, administration of a compound may cause the gene expression profile of a tumorigenic or proliferative disease model system to more closely resemble the control system. Administration of a compound may, alternatively, cause the gene expression profile of a control system to begin to mimic a tumorigenic or proliferative disease state. Such a compound may, for example, be used in further characterizing the compound of interest, or may be used in the generation of additional animal models.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the DHDR nucleotide sequences, described herein, can be used to map the location of the DHDR genes on a chromosome. The mapping of the DHDR sequences to chromosomes is an important first step in correlating these sequences with genes associated with disease.

Briefly, DHDR genes can be mapped to chromosomes by preparing PCR primers (preferably 15–25 bp in length) from the DHDR nucleotide sequences. Computer analysis of the DHDR sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the DHDR sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio, P. et al. (1983) *Science* 220: 919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the DHDR nucleotide sequences to design oligonucleotide primers, sublocalization can be achieved with panels of fragments from specific chromosomes. Other mapping strategies which can similarly be used to map a DHDR sequence to its chromosome include in situ hybridization (described in Fan, Y. et al. (1990) *Proc. Natl. Acad. Sci. USA* 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results in a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridization during chromosomal mapping.

Once a sequence has been mapped to a precise chromosomal location, the physical position of the sequence on the chromosome can be correlated with genetic map data. (Such data are found, for example, in McKusick, V., Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the DHDR gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The DHDR sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the DHDR nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The DHDR nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:10 or 13 can comfortably provide positive individual identification with a panel of perhaps 10 to 1,000 primers which each yield a noncoding amplified sequence of 100 bases. If predicted coding sequences, such as those in SEQ ID NO:12 or 15 are used, a more appropriate number of primers for positive individual identification would be 500–2000.

If a panel of reagents from DHDR nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of DHDR Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:10 or 13 are particularly appropriate for this use as greater numbers of polymorphisms occur in the noncoding regions, making it easier to differentiate individuals using this technique. Examples of polynucleotide reagents include the DHDR nucleotide sequences or portions thereof, e.g., fragments derived from the noncoding regions of SEQ ID NO:10 or 13 having a length of at least 20 bases, preferably at least 30 bases.

The DHDR nucleotide sequences described herein can further be used to provide polynucleotide reagents, e.g., labeled or labelable probes which can be used in, for example, an in situ hybridization technique, to identify a specific tissue, e.g., osteoclasts or trachea tissue. This can be very useful in cases where a forensic pathologist is presented with a tissue of unknown origin. Panels of such DHDR probes can be used to identify tissue by species and/or by organ type.

In a similar fashion, these reagents, e.g., DHDR primers or probes can be used to screen tissue culture for contamination (i.e., screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining DHDR protein and/or nucleic acid expression as well as DHDR activity, in the context of a biological sample (e.g., blood, serum, cells, or tissue) to thereby determine whether an individual is afflicted with a disease or disorder, or is at risk of developing a disorder, associated with aberrant or unwanted DHDR expression or activity. The invention also provides for prognostic (or predictive) assays for determining whether an individual is at risk of developing a disorder associated with DHDR protein, nucleic acid expression or activity. For example, mutations in a DHDR gene can be assayed in a biological sample. Such assays can be used for prognostic or predictive purpose to thereby prophylactically treat an individual prior to the onset of a disorder characterized by or associated with DHDR protein, nucleic acid expression or activity.

Another aspect of the invention pertains to monitoring the influence of agents (e.g., drugs, compounds) on the expression or activity of DHDR in clinical trials.

These and other agents are described in further detail in the following sections.

1. Diagnostic Assays

An exemplary method for detecting the presence or absence of DHDR protein or nucleic acid in a biological sample involves obtaining a biological sample from a test subject and contacting the biological sample with a compound or an agent capable of detecting DHDR protein or nucleic acid (e.g., mRNA or genomic DNA) that encodes DHDR protein such that the presence of DHDR protein or nucleic acid is detected in the biological sample. A preferred agent for detecting DHDR mRNA or genomic DNA is a labeled nucleic acid probe capable of hybridizing to DHDR mRNA or genomic DNA. The nucleic acid probe can be, for example, the DHDR nucleic acid set forth in SEQ ID NO:10, 12, 13, or 15, or a portion thereof, such as an oligonucleotide of at least 15, 30, 50, 100, 250 or 500 nucleotides in length and sufficient to specifically hybridize under stringent conditions to DHDR mRNA or genomic DNA. Other suitable probes for use in the diagnostic assays of the invention are described herein.

A preferred agent for detecting DHDR protein is an antibody capable of binding to DHDR protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells, and biological fluids isolated from a subject, as well as tissues, cells, and fluids present within a subject. That is, the detection method of the invention can be used to detect DHDR mRNA, protein, or genomic DNA in a biological sample in vitro as well as in vivo. For example, in vitro techniques for detection of DHDR mRNA include Northern hybridizations and in situ hybridizations. In vitro techniques for detection of DHDR protein include enzyme linked immunosorbent assays (ELISAs), Western blots, immunoprecipitations and immunofluorescence. In vitro techniques for detection of DHDR genomic DNA include Southern hybridizations. Furthermore, in vivo techniques for detection of DHDR protein include introducing into a subject a labeled anti-DHDR antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting DHDR protein, mRNA, or genomic DNA, such that the presence of DHDR protein, mRNA or genomic DNA is detected in the biological sample, and comparing the presence of DHDR protein, mRNA or genomic DNA in the control sample with the presence of DHDR protein, mRNA or genomic DNA in the test sample.

The invention also encompasses kits for detecting the presence of DHDR in a biological sample. For example, the kit can comprise a labeled compound or agent capable of detecting DHDR protein or mRNA in a biological sample; means for determining the amount of DHDR in the sample; and means for comparing the amount of DHDR in the sample with a standard. The compound or agent can be packaged in a suitable container. The kit can further comprise instructions for using the kit to detect DHDR protein or nucleic acid.

2. Prognostic Assays

The diagnostic methods described herein can furthermore be utilized to identify subjects having or at risk of developing a disease or disorder associated with aberrant or unwanted DHDR expression or activity. As used herein, the term "aberrant" includes a DHDR expression or activity which deviates from the wild type DHDR expression or activity. Aberrant expression or activity includes increased or decreased expression or activity, as well as expression or activity which does not follow the wild type developmental pattern of expression or the subcellular pattern of expression. For example, aberrant DHDR expression or activity is intended to include the cases in which a mutation in the DHDR gene causes the DHDR gene to be under-expressed or over-expressed and situations in which such mutations result in a non-functional DHDR protein or a protein which does not function in a wild-type fashion, e.g., a protein which does not interact with a DHDR substrate, or one which interacts with a non-DHDR substrate. As used herein, the term "unwanted" includes an unwanted phenomenon involved in a biological response such as cellular proliferation. For example, the term unwanted includes a DHDR expression or activity which is undesirable in a subject.

The assays described herein, such as the preceding diagnostic assays or the following assays, can be utilized to identify a subject having or at risk of developing a disorder associated with a misregulation in DHDR protein activity or nucleic acid expression, such as a CNS disorder (e.g., a cognitive or neurodegenerative disorder), a cellular proliferation, growth, differentiation, or migration disorder, a cardiovascular disorder, musculoskeletal disorder, an immune disorder, or a hormonal disorder. Alternatively, the prognostic assays can be utilized to identify a subject having or at risk for developing a disorder associated with a misregulation in DHDR protein activity or nucleic acid expression, such as a CNS disorder, a cellular proliferation, growth, differentiation, or migration disorder, a musculoskeletal disorder, a cardiovascular disorder, an immune disorder, or a hormonal disorder. Thus, the present invention provides a method for identifying a disease or disorder associated with aberrant or unwanted DHDR expression or activity in which a test sample is obtained from a subject and DHDR protein or nucleic acid (e.g., mRNA or genomic DNA) is detected, wherein the presence of DHDR protein or nucleic acid is diagnostic for a subject having or at risk of developing a disease or disorder associated with aberrant or unwanted DHDR expression or activity. As used herein, a "test sample" refers to a biological sample obtained from a subject of interest. For example, a test sample can be a biological fluid (e.g., cerebrospinal fluid or serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted DHDR expression or activity. For example, such methods can be used to determine whether a subject can be effectively treated with an agent for a CNS disorder, a muscular disorder, a cellular proliferation, growth, differentiation, or migration disorder, an immune disorder, or a hormonal disorder. Thus, the present invention provides methods for determining whether a subject can be effectively treated with an agent for a disorder associated with aberrant or unwanted DHDR expression or activity in which a test sample is obtained and DHDR protein or nucleic acid expression or activity is detected (e.g., wherein the abundance of DHDR protein or nucleic acid expression or activity is diagnostic for a subject that can be administered the agent to treat a disorder associated with aberrant or unwanted DHDR expression or activity).

The methods of the invention can also be used to detect genetic alterations in a DHDR gene, thereby determining if a subject with the altered gene is at risk for a disorder characterized by misregulation in DHDR protein activity or nucleic acid expression, such as a CNS disorder, a musculoskeletal disorder, a cellular proliferation, growth, differentiation, or migration disorder, a cardiovascular disorder, an immune disorder, or a hormonal disorder. In preferred embodiments, the methods include detecting, in a sample of cells from the subject, the presence or absence of a genetic alteration characterized by at least one alteration affecting the integrity of a gene encoding a DHDR-protein, or the mis-expression of the DHDR gene. For example, such genetic alterations can be detected by ascertaining the existence of at least one of 1) a deletion of one or more nucleotides from a DHDR gene, 2) an addition of one or more nucleotides to a DHDR gene, 3) a substitution of one or more nucleotides of a DHDR gene, 4) a chromosomal rearrangement of a DHDR gene, 5) an alteration in the level of a messenger RNA transcript of a DHDR gene, 6) aberrant modification of a DHDR gene, such as of the methylation pattern of the genomic DNA, 7) the presence of a non-wild type splicing pattern of a messenger RNA transcript of a DHDR gene, 8) a non-wild type level of a DHDR-protein, 9) allelic loss of a DHDR gene, and 10) inappropriate post-translational modification of a DHDR-protein. As described herein, there are a large number of assays known in the art which can be used for detecting alterations in a DHDR gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in a DHDR gene (see Abravaya et al. (1995) *Nucleic Acids Res.* 23:675–682). This method can include the steps of collecting a sample of cells from a subject, isolating nucleic acid (e.g., genomic, mRNA or both) from the cells of the sample, contacting the nucleic acid sample with one or more primers which specifically hybridize to a DHDR gene under conditions such that hybridization and amplification of the DHDR gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) *Proc. Natl. Acad. Sci. USA* 87:1874–1878), transcriptional amplification system (Kwoh, D. Y. et al. (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a DHDR gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in DHDR can be identified by hybridizing a sample and control nucleic acids, e.g., DNA or RNA, to high density arrays containing hundreds or thousands of oligonucleotide probes (Cronin, M. T. et al. (1996) *Human Mutation* 7:244–255; Kozal, M. J. et al. (1996) *Nature Medicine* 2:753–759). For example, genetic mutations in DHDR can be identified in two dimensional arrays containing light-generated DNA probes as described in Cronin, M. T. et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the DHDR gene and detect mutations by comparing the sequence of the sample DHDR with the corresponding wild-type (control) sequence. Examples of sequencing reactions include those based on techniques developed by Maxam and Gilbert (1977) *Proc. Natl. Acad. Sci. USA* 74:560) or Sanger (1977) *Proc. Natl. Acad. Sci. USA* 74:5463). It is also contemplated that any of a variety of automated sequencing procedures can be utilized when performing the diagnostic assays (Naeve, C. W. (1995) *Biotechniques* 19:448–53), including sequencing by mass spectrometry (see, e.g., PCT International Publication No.

WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the DHDR gene include methods in which protection from cleavage agents is used to detect mismatched bases in RNA/RNA or RNA/DNA heteroduplexes (Myers et al. (1985) *Science* 230: 1242). In general, the art technique of "mismatch cleavage" starts by providing heteroduplexes formed by hybridizing (labeled) RNA or DNA containing the wild-type DHDR sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad. Sci. USA* 85:4397 and Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in DHDR cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a DHDR sequence, e.g., a wild-type DHDR sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in DHDR genes. For example, single strand conformation polymorphism (SSCP) may be used to detect differences in electrophoretic mobility between mutant and wild type nucleic acids (Orita et al. (1989) *Proc Natl. Acad. Sci USA* 86:2766; see also Cotton (1993) *Mutat. Res.* 285:125–144 and Hayashi (1992) *Genet. Anal. Tech. Appl.* 9:73–79). Single-stranded DNA fragments of sample and control DHDR nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6: 1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a DHDR gene.

Furthermore, any cell type or tissue in which DHDR is expressed may be utilized in the prognostic assays described herein.

3. Monitoring of Effects During Clinical Trials

Monitoring the influence of agents (e.g., drugs) on the expression or activity of a DHDR protein (e.g., the modulation of cell proliferation and/or migration) can be applied not only in basic drug screening, but also in clinical trials. For example, the effectiveness of an agent determined by a screening assay as described herein to increase DHDR gene expression, protein levels, or upregulate DHDR activity, can be monitored in clinical trials of subjects exhibiting decreased DHDR gene expression, protein levels, or downregulated DHDR activity. Alternatively, the effectiveness of an agent determined by a screening assay to decrease DHDR gene expression, protein levels, or downregulate DHDR activity, can be monitored in clinical trials of subjects exhibiting increased DHDR gene expression, protein levels, or DHDR activity. In such clinical trials, the expression or activity of a DHDR gene, and preferably, other genes that have been implicated in, for example, a DHDR-associated disorder can be used as a "read out" or marker of the phenotype of a particular cell.

For example, and not by way of limitation, genes, including DHDR, that are modulated in cells by treatment with an agent (e.g., compound, drug or small molecule) which modulates DHDR activity (e.g., identified in a screening assay as described herein) can be identified. Thus, to study the effect of agents on DHDR-associated disorders (e.g., disorders characterized by deregulated cell proliferation and/or migration), for example, in a clinical trial, cells can be isolated and RNA prepared and analyzed for the levels of expression of DHDR and other genes implicated in the DHDR-associated disorder, respectively. The levels of gene expression (e.g., a gene expression pattern) can be quantified by Northern blot analysis or RT-PCR, as described herein, or alternatively by measuring the amount of protein produced, by one of the methods as described herein, or by measuring the levels of activity of DHDR or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a DHDR protein, mRNA, or genomic DNA in the preadministration sample; (iii) obtaining one or more post-administration samples from the subject; (iv) detecting the level of expression or activity of the DHDR protein, mRNA, or genomic DNA in the post-administration samples; (v) comparing the level of expression or activity of the DHDR protein, mRNA, or genomic DNA in the pre-administration sample with the DHDR protein, mRNA, or genomic DNA in the post administration sample or samples; and (vi) altering the administration of the agent to the subject accordingly. For example, increased administration of the agent may be desirable to increase the expression or activity of DHDR to higher levels than detected, i.e., to increase the effectiveness of the agent. Alternatively, decreased administration of the agent may be desirable to decrease expression or activity of DHDR to lower levels than detected, i.e., to decrease the effectiveness of the agent. According to such an embodiment, DHDR expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder or having a disorder associated with aberrant or unwanted DHDR expression or activity, e.g., a dehydrogenase-associated disorder such as a CNS disorder; a cellular proliferation, growth, differentiation, or migration disorder; a, musculoskeletal disorder; a cardiovascular disorder; an immune disorder; or a hormonal disorder. As used herein, "treatment" of a subject includes the application or administration of a therapeutic agent to a subject, or application or administration of a therapeutic agent to a cell or tissue from a subject, who has a diseases or disorder, has a symptom of a disease or disorder, or is at risk of (or susceptible to) a disease or disorder, with the purpose to cure, heal, alleviate, relieve, alter, remedy, ameliorate, improve, or affect the disease or disorder, the symptom of the disease or disorder, or the risk of (or susceptibility to) the disease or disorder. As used herein, a "therapeutic agent" includes, but is not limited to, small molecules, peptides, polypeptides, antibodies, ribozymes, and antisense oligonucleotides.

With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the DHDR molecules of the present invention or DHDR modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted DHDR expression or activity, by administering to the subject a DHDR or an agent which modulates DHDR expression or at least one DHDR activity. Subjects at risk for a disease which is caused or contributed to by aberrant or unwanted DHDR expression or activity can be identified by, for example, any or a combination of diagnostic or prognostic assays as described herein. Administration of a prophylactic agent can occur prior to the manifestation of symptoms characteristic of the DHDR aberrancy, such that a disease or disorder is prevented or, alternatively, delayed in its progression. Depending on the type of DHDR aberrancy, for example, a DHDR, DHDR agonist or DHDR antagonist agent can be used for treating the subject. The appropriate agent can be determined based on screening assays described herein.

2. Therapeutic Methods

Another aspect of the invention pertains to methods of modulating DHDR expression or activity for therapeutic purposes. Accordingly, in an exemplary embodiment, the modulatory method of the invention involves contacting a cell with a DHDR or agent that modulates one or more of the activities of DHDR protein activity associated with the cell. An agent that modulates DHDR protein activity can be an agent as described herein, such as a nucleic acid or a protein, a naturally-occurring target molecule of a DHDR protein (e.g., a DHDR substrate), a DHDR antibody, a DHDR agonist or antagonist, a peptidomimetic of a DHDR agonist or antagonist, or other small molecule. In one embodiment, the agent stimulates one or more DHDR activities. Examples of such stimulatory agents include active DHDR protein and a nucleic acid molecule encoding DHDR that has been introduced into the cell. In another embodiment, the agent inhibits one or more DHDR activities. Examples of such inhibitory agents include antisense DHDR nucleic acid molecules, anti-DHDR antibodies, and DHDR inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a DHDR protein or nucleic acid molecule. In one embodiment, the method involves administering an agent (e.g., an agent identified by a screening assay described herein), or combination of agents that modulates (e.g., upregulates or downregulates) DHDR expression or activity. In another embodiment, the method involves administering a DHDR protein or nucleic acid molecule as therapy to compensate for reduced, aberrant, or unwanted DHDR expression or activity.

Stimulation of DHDR activity is desirable in situations in which DHDR is abnormally downregulated and/or in which increased DHDR activity is likely to have a beneficial effect. Likewise, inhibition of DHDR activity is desirable in situations in which DHDR is abnormally upregulated and/or in which decreased DHDR activity is likely to have a beneficial effect.

3. Pharmacogenomics

The DHDR molecules of the present invention, as well as agents, or modulators which have a stimulatory or inhibitory effect on DHDR activity (e.g., DHDR gene expression) as identified by a screening assay described herein can be administered to individuals to treat (prophylactically or therapeutically) DHDR-associated disorders (e.g., proliferative disorders, CNS disorders, cardiac disorders, metabolic disorders, or muscular disorders) associated with aberrant or unwanted DHDR activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a DHDR molecule or DHDR modulator as well as tailoring the dosage and/or therapeutic regimen of treatment with a DHDR molecule or DHDR modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11):983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach" can be utilized to identify genes that predict drug response. According to this method, if a gene that encodes a drug target is known (e.g., a DHDR protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and the cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling" can be utilized to identify genes that predict drug response. For example, the gene expression of an animal dosed with a drug (e.g., a DHDR molecule or DHDR modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a DHDR molecule or DHDR modulator, such as a modulator identified by one of the exemplary screening assays described herein.

4. Use of DHDR Molecules as Surrogate Markers

The DHDR molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the DHDR molecules of the invention may be detected, and may be correlated with one or more biological states in vivo. For example, the DHDR molecules of the invention may serve as surrogate markers for one or more disorders or disease states or for conditions leading up to disease states.

As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the causation of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35:258–264; and James (1994) *AIDS Treatment News Archive* 209.

The DHDR molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a DHDR marker) transcription or expression, the amplified marker may be in a quantity which is more readily detectable than the drug itself. Also, the marker may be more easily detected due to the nature of the marker itself; for example, using the methods described herein, anti-DHDR antibodies may be employed in an immune-based detection system for a DHDR protein marker, or DHDR-specific radiolabeled probes may be used to detect a DHDR mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90:229–238; Schentag (1999) *Am. J. Health-Syst. Pharm.* 56 Suppl. 3:S21–S24; and Nicolau (1999) *Am. J. Health-Syst. Pharm.* 56 Suppl. 3:S16–S20.

The DHDR molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35(12):1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., DHDR protein or RNA) for specific tumor markers in a subject, a drug or course of treatment may be selected that is optimized for the treatment of the specific tumor likely to be present in the subject. Similarly, the presence or absence of a specific sequence mutation in DHDR DNA may correlate DHDR drug response. The use of pharmacogenomic markers therefore permits the application of the most appropriate treatment for each subject without having to administer the therapy.

E. Electronic Apparatus Readable Media and Arrays

Electronic apparatus readable media comprising DHDR sequence information is also provided. As used herein, "DHDR sequence information" refers to any nucleotide and/or amino acid sequence information particular to the DHDR molecules of the present invention, including but not limited to full-length nucleotide and/or amino acid sequences, partial nucleotide and/or amino acid sequences, polymorphic sequences including single nucleotide polymorphisms (SNPs), epitope sequences, and the like. Moreover, information "related to" said DHDR sequence information includes detection of the presence or absence of a sequence (e.g., detection of expression of a sequence, fragment, polymorphism, etc.), determination of the level of a sequence (e.g., detection of a level of expression, for example, a quantitative detection), detection of a reactivity to a sequence (e.g., detection of protein expression and/or levels, for example, using a sequence-specific antibody), and the like. As used herein, "electronic apparatus readable media" refers to any suitable medium for storing, holding, or containing data or information that can be read and accessed directly by an electronic apparatus. Such media can include, but are not limited to: magnetic storage media, such as floppy discs, hard disc storage medium, and magnetic tape; optical storage media such as compact discs; electronic storage media such as RAM, ROM, EPROM, EEPROM and the like; and general hard disks and hybrids of these categories such as magnetic/optical storage media. The medium is adapted or configured for having recorded thereon DHDR sequence information of the present invention.

As used herein, the term "electronic apparatus" is intended to include any suitable computing or processing apparatus or other device configured or adapted for storing data or information. Examples of electronic apparatus suitable for use with the present invention include stand-alone computing apparatuses; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the DHDR sequence information.

A variety of software programs and formats can be used to store the sequence information on the electronic apparatus readable medium. For example, the sequence information can be represented in a word processing text file, formatted in commercially-available software such as WordPerfect and Microsoft Word, represented in the form of an ASCII file, or stored in a database application, such as DB2, Sybase, Oracle, or the like, as well as in other forms. Any number of dataprocessor structuring formats (e.g., text file or database) may be employed in order to obtain or create a medium having recorded thereon the DHDR sequence information.

By providing DHDR sequence information in readable form, one can routinely access the sequence information for a variety of purposes. For example, one skilled in the art can use the sequence information in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has a DHDR associated disease or disorder or a pre-disposition to a cellular proliferation, growth, differentiation, and/or migration disorder, wherein the method comprises the steps of determining DHDR sequence information associated with the subject and based on the DHDR sequence information, determining whether the subject has a cellular proliferation, growth, differentiation, and/or migration disorder or a pre-disposition to a cellular proliferation, growth, differentiation, and/or migration disorder, and/or recommending a particular treatment for the disease, disorder, or pre-disease condition.

The present invention further provides in an electronic system and/or in a network, a method for determining whether a subject has a cellular proliferation, growth, differentiation, and/or migration disorder or a pre-disposition to a cellular proliferation, growth, differentiation, and/or migration disorder wherein the method comprises the steps of determining DHDR sequence information associated with the subject, and based on the DHDR sequence information, determining whether the subject has a cellular proliferation, growth, differentiation, and/or migration disorder or a pre-disposition to a cellular proliferation, growth, differentiation, and/or migration disorder, and/or recommending a particular treatment for the disease, disorder or pre-disease condition. The method may further comprise the step of receiving phenotypic information associated with the subject and/or acquiring from a network phenotypic information associated with the subject.

The present invention also provides in a network, a method for determining whether a subject has a cellular proliferation, growth, differentiation, and/or migration disorder or a pre-disposition to a cellular proliferation, growth, differentiation, and/or migration disorder associated with DHDR, said method comprising the steps of receiving DHDR sequence information from the subject and/or information related thereto, receiving phenotypic information associated with the subject, acquiring information from the network corresponding to DHDR and/or a cellular proliferation, growth, differentiation, and/or migration disorder, and based on one or more of the phenotypic information, the DHDR information (e.g., sequence information and/or information related thereto), and the acquired information, determining whether the subject has a cellular proliferation, growth, differentiation, and/or migration disorder or a pre-disposition to a cellular proliferation, growth, differentiation, and/or migration disorder. The method may further comprise the step of recommending a particular treatment for the disease, disorder or pre-disease condition.

The present invention also provides a business method for determining whether a subject has a cellular proliferation, growth, differentiation, and/or migration disorder or a pre-disposition to a cellular proliferation, growth, differentiation, and/or migration disorder, said method comprising the steps of receiving information related to DHDR (e.g., sequence information and/or information related thereto), receiving phenotypic information associated with the subject, acquiring information from the network related to DHDR and/or related to a cellular proliferation, growth, differentiation, and/or migration disorder, and based on one or more of the phenotypic information, the DHDR information, and the acquired information, determining whether the subject has a cellular proliferation, growth, differentiation, and/or migration disorder or a pre-disposition to a cellular proliferation, growth, differentiation, and/or migration disorder. The method may further comprise the step of recommending a particular treatment for the disease, disorder or pre-disease condition.

The invention also includes an array comprising a DHDR sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, one of which can be DHDR. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a cellular proliferation, growth, differentiation, and/or migration disorder, progression of a cellular proliferation, growth, differentiation, and/or migration disorder, and processes, such a cellular transformation associated with the cellular proliferation, growth, differentiation, and/or migration disorder.

The array is also useful for ascertaining the effect of the expression of a gene on the expression of other genes in the same cell or in different cells (e.g., ascertaining the effect of DHDR expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including DHDR) that could serve as a molecular target for diagnosis or therapeutic intervention.

This invention is further illustrated by the following examples which should not be construed as limiting. The contents of all references, patents, and published patent applications cited throughout this application, as well as the Figures and the Sequence Listing, are incorporated herein by reference.

EXAMPLES

Example 1

Identification and Characterization of Human DHDR cDNA

In this example, the identification and characterization of the genes encoding human DHDR-5 (clone Fbh22244) and human DHDR-6 (clone Fbh8701) is described.

Isolation of the DHDR cDNA

The invention is based, at least in part, on the discovery of human genes encoding novel proteins, referred to herein as DHDR-5 and DHDR-6. The entire sequences of human clones Fbh22244 and Fbh8701 were determined and found to contain open reading frames termed human "DHDR-5" and "DHDR-6", respectively.

The nucleotide sequence encoding the human DHDR-5 is shown in FIGS. 18A–B and is set forth as SEQ ID NO:10. The protein encoded by this nucleic acid comprises about 330 amino acids and has the amino acid sequence shown in FIGS. 18A–B and set forth as SEQ ID NO:11. The coding region (open reading frame) of SEQ ID NO:10 is set forth as SEQ ID NO:12. Clone Fbh22244 comprises the coding region of human DHDR-5.

The nucleotide sequence encoding the human DHDR-6 is shown in FIGS. 19A–B and is set forth as SEQ ID NO:13. The protein encoded by this nucleic acid comprises about 467 amino acids and has the amino acid sequence shown in FIGS. 19A–B and set forth as SEQ ID NO:14. The coding region (open reading frame) of SEQ ID NO:13 is set forth as SEQ ID NO:15. Clone Fbh8701 comprises the coding region of human DHDR-6.

Analysis of the Human DHDR Molecules

The amino acid sequences of human DHDR-5 and DHDR-6 were analyzed using the program PSORT (available online through the PSORT website) to predict the localization of the proteins within the cell. This program assesses the presence of different targeting and localization amino acid sequences within the query sequence. The results of the analyses show that human DHDR-5 may be localized to the nucleus, to the mitochondria, to the cytoplasm, to secretory vesicles, to vacuoles, to peroxisomes, or to the endoplasmic reticulum. The results of the analyses further show that human DHDR-6 may be localized to the mitochondria, to the cytoplasm, to the nucleus, or to peroxisomes.

Each of the amino acid sequences of DHDR-5 and DHDR-6 was analyzed by the SignalP program (Henrik et al. (1997) *Protein Eng.* 10: 1–6) for the presence of a signal peptide. These analyses revealed the presence of a putative signal peptide in the amino acid sequence of DHDR-6, from residues 1–21.

Searches of each of the amino acid sequences of DHDR-5 and DHDR-6 were performed against the Memsat database. These searches resulted in the identification of two transmembrane domains in the amino acid sequence of human DHDR-5 (SEQ ID NO:11) at about residues 173–193 and 240–257. These searches further identified three transmembrane domains in the amino acid sequence of human DHDR-6 (SEQ ID NO:14) at about residues 181–200, 316–340, and 354–371 in the native molecule, and two transmembrane domains in the amino acid sequence of the presumed mature protein, at about residues 295–319 and 333–350.

Searches of each of the amino acid sequences of DHDR-5 and DHDR-6 were also performed against the HMM database. These searches resulted in the identification of a "short chain dehydrogenase domain" at about residues 68–254 (score=117.6) and a "shikimate/quinate 5-dehydrogenase domain at about residues 10–189 in the amino acid sequence of DHDR-5 (SEQ ID NO:11) (FIGS. 21A–B). These searches further resulted in the identification of two "iron-containing alcohol dehydrogenase domains" at about residues 52–253 (score=119.3) and 276–338 (score=64.1) in the amino acid sequence of DHDR-6 (SEQ ID NO:14) (FIG. 29).

Tissue Distribution of DHDR-5 mRNA

Figure 22:
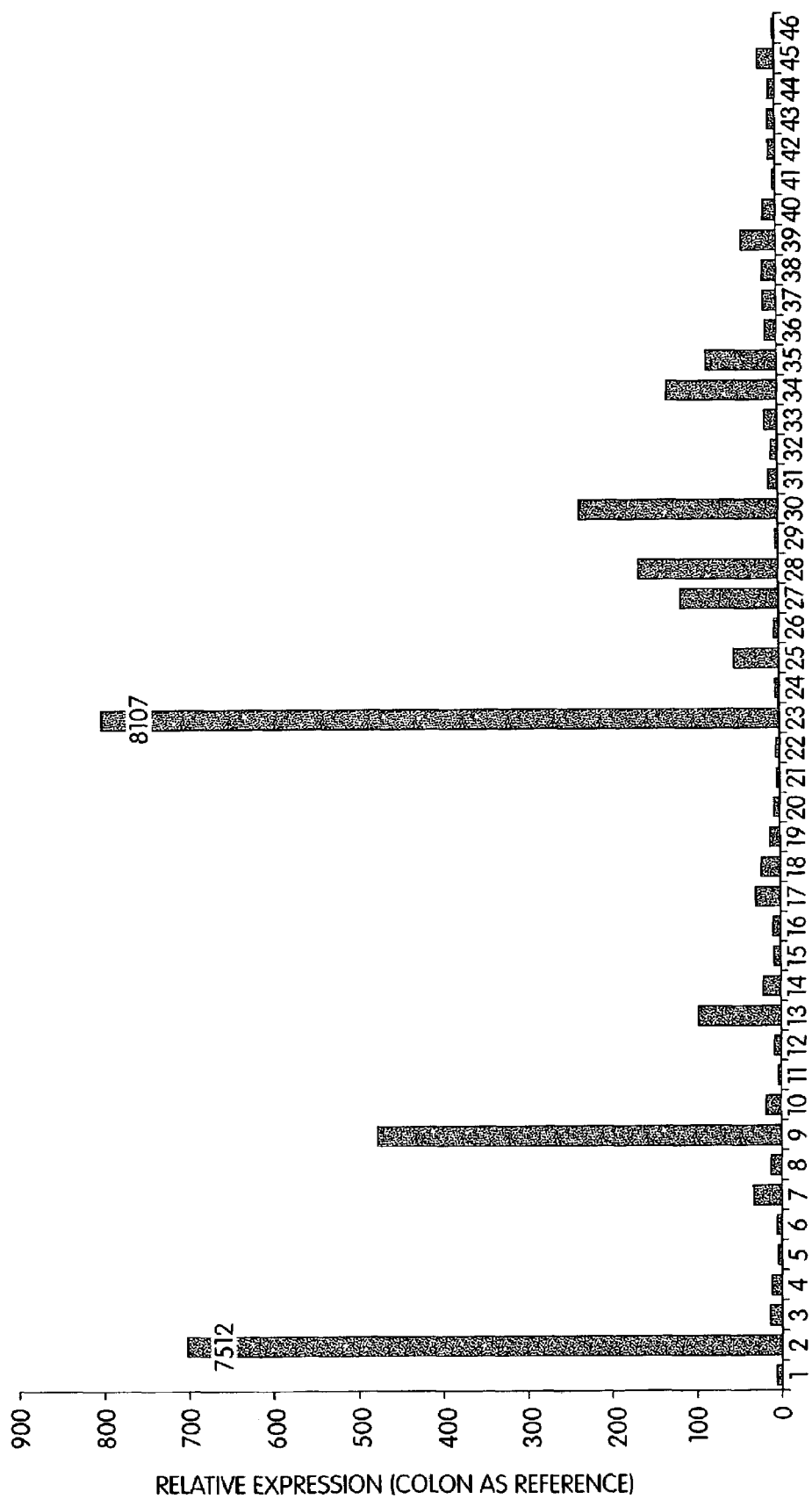
FIG. 22 depicts the expression levels of human DHDR-5 in various normal human tissues, as determined by Taqman analysis. Sample No.: (1) prostate; (2) osteoclast; (3) liver; (4) liver; (5) breast; (6) breast; (7–8) skeletal muscle; (9) brain; (10) hypothalamus; (11–12) colon; (13–14) heart; (15–16) ovary; (17–18) kidney; (19–20) lung; (21 trachea; (24–25) adipose tissue; (26) small intestine; (27–28) thyroid; (29) skin; (30) testis; (31) placenta; (32–33) fetal liver; (34–35) fetal heart; (36–38) osteoblasts; (39) fetal spinal cord; (40) cervix; (41) spleen; (42) spinal cord; (43) thymus; (44) tonsil; (45) lymph node; (46) aorta.

This example describes the tissue distribution of human DHDR-5 mRNA, as was determined by Polymerase Chain Reaction (PCR) on cDNA libraries using oligonucleotide primers based on the human DHDR-5 sequence. The human DHDR-5 gene is highly expressed in osteoclasts, brain, heart, trachea, thyroid, testis, and fetal heart (FIG. 22). Significant expression of DHDR-5 was also observed in the tumorigenic cell lines MCF-7, ZR75, and T47D, and in primary breast tumors (FIG. 24).

The tissue distribution of human DHDR-5 or DHDR-6 mRNA may also be determined using in situ hybridization analysis. For in situ analysis, various tissues, e.g., tissues obtained from brain, are first frozen on dry ice. Ten-micrometer-thick sections of the tissues are postfixed with 4% formaldehyde in DEPC-treated 1× phosphate-buffered saline at room temperature for 10 minutes before being rinsed twice in DEPC 1× phosphate-buffered saline and once in 0.1 M triethanolamine-HCl (pH 8.0). Following incubation in 0.25% acetic anhydride-0.1 M triethanolamine-HCl for 10 minutes, sections are rinsed in DEPC 2×SSC (1×SSC is 0.15 M NaCl plus 0.015 M sodium citrate). Tissue is then dehydrated through a series of ethanol washes, incubated in 100% chloroform for 5 minutes, and then rinsed in 100% ethanol for 1 minute and 95% ethanol for 1 minute and allowed to air dry.

Hybridizations are performed with $^{35}$S-radiolabeled ($5 \times 10^7$ cpm/ml) cRNA probes. Probes are incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1× Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides are washed with 2×SSC. Sections are then sequentially incubated at 37° C. in TNE (a solution containing 10 mM Tris-HCl (pH 7.6), 500 mM NaCl, and 1 mM EDTA), for 10 minutes, in TNE with 10 µg of RNase A per ml for 30 minutes, and finally in TNE for 10 minutes. Slides are then rinsed with 2×SSC at room temperature, washed with 2×SSC at 50° C. for 1 hour, washed with 0.2×SSC at 55° C. for 1 hour, and 0.2×SSC at 60° C. for 1 hour. Sections are then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

Example 2

Further Characterization of DHDR Expression Using Taqman Analysis

This example describes the expression of human DHDR mRNA in various tissues, tumors, cell lines, and disease models, as determined using the TaqMan™ procedure and in situ hybridization analysis.

The Taqman™ procedure is a quantitative, real-time PCR-based approach to detecting mRNA. The RT-PCR reaction exploits the 5' nuclease activity of AmpliTaq Gold™ DNA Polymerase to cleave a TaqMan™ probe during PCR. Briefly, cDNA was generated from the samples of interest and served as the starting material for PCR amplification. In addition to the 5' and 3' gene-specific primers, a gene-specific oligonucleotide probe (complementary to the region being amplified) was included in the reaction (i.e., the Taqman™ probe). The TaqMan™ probe included an oligonucleotide with a fluorescent reporter dye covalently linked to the 5' end of the probe (such as FAM (6-carboxyfluorescein), TET (6-carboxy-4,7,2',7'-tetrachlorofluorescein), JOE (6-carboxy-4,5-dichloro-2,7-dimethoxyfluorescein), or VIC) and a quencher dye (TAMRA (6-carboxy-N,N,N',N'-tetramethylrhodamine) at the 3' end of the probe.

During the PCR reaction, cleavage of the probe separated the reporter dye and the quencher dye, resulting in increased fluorescence of the reporter. Accumulation of PCR products was detected directly by monitoring the increase in fluorescence of the reporter dye. When the probe was intact, the proximity of the reporter dye to the quencher dye resulted in suppression of the reporter fluorescence. During PCR, if the target of interest was present, the probe specifically annealed between the forward and reverse primer sites. The 5'-3' nucleolytic activity of the AmpliTaq™ Gold DNA Polymerase cleaved the probe between the reporter and the quencher only if the probe hybridized to the target. The probe fragments were then displaced from the target, and polymerization of the strand continued. The 3' end of the probe was blocked to prevent extension of the probe during PCR. This process occurred in every cycle and did not interfere with the exponential accumulation of product. RNA was prepared using the trizol method and treated with DNase to remove contaminating genomic DNA. cDNA was synthesized using standard techniques. Mock cDNA synthesis in the absence of reverse transcriptase resulted in samples with no detectable PCR amplification of the control GAPDH or β-actin gene confirming efficient removal of genomic DNA contamination.

Human DHDR-5

Figure 23:
FIG. 23 depicts expression levels of human DHDR-5 in various human tissues and cell types, as determined by Taqman analysis. Sample No.: (1) normal artery; (2) normal vein; (3) aortic smooth muscle cells (SMC) early; (4) coronary smooth muscle cells; (5) human umbilical vein endothelial cells (HUVEC)—static; (6) human umbilical vein endothelial cells (HUVEC)—shear; (7) normal heart; (8) heart—congestive heart failure (CHF); (9) kidney; (10) skeletal muscle; (11) normal adipose tissue; (12) pancreas; (13) primary osteoblasts; (14) osteoclasts (differentiated)

The results of the Taqman analysis showed that human DHDR-5 is highly expressed in human umbilical vein endothelial cells (HUVECs) under conditions of both static and shear, normal brain cortex, hypothalamus, dorsal root ganglion (DRG), glial cells (astrocytes), and prostate epithelial cells (FIG. 23). Human DHDR-5 is also highly expressed in the heart, fetal liver, spleen, normal human lung fibroblasts, pass stell, CD8+ cells, GPA+bone marrow cells, erythroid cells, megakaryocytes, HL60 cells, K562 cells, Molt 4 cells, and Hep3B cells under conditions of both normoxia and hypoxia (FIG. 25).

Taqman analysis of human DHDR-5 expression in tumor cells showed that human DHDR-5 is downregulated in 7/7 ovary tumors (strongly in 5 of the tumors, and moderately in 2 of the tumors), as compared to normal ovary (FIG. 26).

Human DHDR-5 expression is upregulated in 5/8 lung tumors (strongly in 3 of the tumors, moderately in 2 of the tumors), as compared to normal lung (FIG. 26).

Human DHDR-5 expression is upregulated in 2/8 colon tumors, as compared to normal colon (FIG. 27), and is upregulated in 1/4 liver metastases, as compared to normal liver (FIG. 27).

Human DHDR-5 expression is downregulated in proliferating human microvascular endothelial cells (HMVECs), as compared to arrested HMVECs.

Human DHDR-6

The results of the Taqman analysis showed that human DHDR-6 is highly expressed in normal fetal heart, normal heart, heart in congestive heart failure, normal vein, normal spinal cord, normal brain cortex, normal hypothalamus, glial cells (astrocytes), normal breast, infiltrating ductal carcinoma (IDC) breast tumor, normal ovary, normal prostate, prostate tumor, normal colon, normal kidney, normal liver, liver fibrosis, normal fetal liver, normal lung, lung tumor, lung—chronic obstructive pulmonary disease (COPD), normal tonsil, normal lymph node, epithelial cells, skeletal muscle, and differentiated osteoblasts (FIG. 30). The Taqman data in FIG. 30 further indicate that human DHDR-6 expression is upregulated in congestive heart failure (CHF) as compared to normal heart; downregulated in glioblastoma, as compared to normal brain tissues; downregulated in IDC as compared to normal breast; downregulated in ovary tumor as compared to normal ovary; downregulated in colon tumor and inflammatory bowel disease (IBD) as compared to normal colon; upregulated in COPD as compared to normal lung; and upregulated in differentiated osteoblasts as compared to undifferentiated osteoblasts.

Taqman analysis further showed that Human DHDR-6 is downregulated in 3/4 liver metastasis samples, as compared to normal liver samples (FIG. 31).

Human DHDR-6 is also downregulated in 4/5 brain tumors as compared to normal brain (FIG. 31), 8/8 breast tumors as compared to normal breast (FIG. 32), and 7/8 ovary tumors as compared to normal ovary.

Example 3

Expression of Recombinant Human DHDR Protein in Bacterial Cells

In this example, human DHDR-5 or DHDR-6 is expressed as a recombinant glutathione-S-transferase (GST)

fusion polypeptide in E. coli and the fusion polypeptide is isolated and characterized. Specifically, DHDR-5 or DHDR-6 is fused to GST and this fusion polypeptide is expressed in E. coli, e.g., strain PEB199. Expression of the GST-DHDR fusion protein in PEB 199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 4

Expression of Recombinant Human DHDR Protein in COS Cells

To express the human DHDR-5 or DHDR-6 genes in COS cells, the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire DHDR-5 or DHDR-6 protein and an HA tag (Wilson et al. (1984) Cell 37:767) or a FLAG tag fused in-frame to its 3' end is cloned into the polylinker region of the vector, thereby placing the expression of the recombinant protein under the control of the CMV promoter.

To construct the plasmid, the DHDR-5 or DHDR-6 DNA sequence is amplified by PCR using two primers. The 5' primer contains the restriction site of interest followed by approximately twenty nucleotides of the DHDR-5 or DHDR-6 coding sequence starting from the initiation codon; the 3' end sequence contains complementary sequences to the other restriction site of interest, a translation stop codon, the HA tag or FLAG tag and the last 20 nucleotides of the DHDR-5 or DHDR-6 coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably, the two restriction sites chosen are different so that the DHDR-5 or DHDR-6 gene is inserted in the correct orientation. The ligation mixture is transformed into E. coli cells (strains HB101, DH5α, or SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the DHDR-5- or DHDR-6-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J. et al., Molecular Cloning: A Laboratory Manual. 2nd, ed., Cold Spring Harbor Laboratory, Cold Spring Harbor Laboratory Press, Cold Spring Harbor, N.Y., 1989. The expression of the DHDR-5 or DHDR-6 polypeptide is detected by radiolabeling ($^{35}$S-methionine or $^{35}$S-cysteine, available from NEN, Boston, Mass., can be used) and immunoprecipitation (Harlow, E. and Lane, D. Antibodies: A Laboratory Manual, Cold Spring Harbor Laboratory Press, Cold Spring Harbor, N.Y., 1988) using an HA- or FLAG-specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA- or FLAG-specific monoclonal antibody. Precipitated polypeptides are then analyzed by SDS-PAGE.

Alternatively, DNA containing the DHDR-5 or DHDR-6 coding sequence is cloned directly into the polylinker of the pcDNA/Amp vector using the appropriate restriction sites. The resulting plasmid is transfected into COS cells in the manner described above, and the expression of the DHDR-5 or DHDR-6 polypeptide is detected by radiolabeling and immunoprecipitation using a DHDR-specific monoclonal antibody.

IV. 32263, a Novel Human Biotin Enzyme and Uses Thereof

BACKGROUND OF THE INVENTION

Biotin is an essential water-soluble vitamin of the B-complex group which is synthesized by plants, most prokaryotes and virtually all eukaryotes. Also known as vitamin H, biotin is well characterized in its role as a coenzyme or prosthetic group of a number of enzymes. The biotin group can serve as a carrier of activated $CO_2$ and is often covalently attached to enzymes at a biotin-attachment domain through the $\epsilon$-amino group of a lysine residue. The addition of a carboxyl group to an acceptor molecule (carboxylase reaction), a reaction which is catalyzed by such biotin enzymes, generally occurs in two steps:

1. Biotin-enzyme+ATP+$HCO_3^-$⇌$CO_2$~biotin-enzyme+ADP+$P_1$
2. $CO_2$~biotin-enzyme+acceptor⇌biotin-enzyme+acceptor-$CO_2$ Biotin enzymes are also involved in the reverse (decarboxylase) reaction.

The manipulation of biomolecules by addition and removal of carboxyl bonds is of critical importance in most metabolic (e.g., catabolic and anabolic) pathways in cells. A large family of enzymes which catalyze such reactions has been described, generally called biotin carboxylases and biotin decarboxylases in humans (see, e.g., Knowles (1989) Ann. Rev. Biochem. 58:195–221; Samols et al. (1988) J. Biol. Chem. 263:6461–6464). The biotin carboxylases are key enzymes in such pathways as gluconeogenesis, lipogenesis, amino acid metabolism, the urea cycle, and energy transduction. In addition, other biotin enzymes have been identified which are not carboxylases, for example the Biotin Protein Ligases (BPL), which are responsible for specific covalent attachment of biotin to its cognate proteins (Chapman-Smith and Cronan (1999) J. of Nutrition 129: 477S–484S).

Biotin enzymes play important roles in the synthesis and breakdown of a great number of metabolic intermediates, which may implicate them in a number of pathologies.

Several inherited and acquired disorders involving errant biotin metabolism have been described (Baumgartner and Suormala (1997) Int. J. Vitam Nutr Res 67:377–384; Baumgartner and Suormala (1999) Biofactors 10:287–290). These disorders can manifest themselves in a number of symptoms including severe nutritional difficulties, organic aciduria, neurologic abnormalities, and cutaneous distress (rash, alopecia, etc). Accordingly, proteins which are involved with biotin-related metabolism may hold significant therapeutic value.

Given the importance of biotin enzymes in a wide range of cellular processes, there exists a need to identify novel biotin enzymes as well as modulators of such enzymes for use in a variety of processes.

SUMMARY OF THE INVENTION

The present invention is based, at least in part, on the discovery of novel members of the family of biotin proteins, referred to herein as Biotin Enzyme-1 (or BRE) nucleic acid and protein molecules. The BRE nucleic acid and protein molecules of the present invention are useful as modulating agents in regulating a variety of cellular processes, e.g., cellular proliferation, growth, differentiation, protein synthesis, or energy transduction. Accordingly, in one aspect, this invention provides isolated nucleic acid molecules encoding BRE proteins or biologically active portions thereof, as well as nucleic acid fragments suitable as primers or hybridization probes for the detection of BRE-encoding nucleic acids.

In one embodiment, a BRE nucleic acid molecule of the invention is at least 50%, 55%, 60%, 65%, 70%, 75%, 80%, 85%, 90%, 95%, 96%, 97%, 98%, 99% or more identical to the nucleotide sequence (e.g., to the entire length of the nucleotide sequence) shown in SEQ ID NO:16 or 18, or a complement thereof.

In a preferred embodiment, the isolated nucleic acid molecule includes the nucleotide sequence shown in SEQ ID NO:16 or 18, or a complement thereof. In another embodiment, the nucleic acid molecule includes SEQ ID NO:18 and nucleotides 1–166 of SEQ ID NO:16. In yet a further embodiment, the nucleic acid molecule includes SEQ ID NO:18 and nucleotides 2342–2577 of SEQ ID NO:16. In another preferred embodiment, the nucleic acid molecule consists of the nucleotide sequence shown in SEQ ID NO:16 or 18.

In another embodiment, a BRE nucleic acid molecule includes a nucleotide sequence encoding a protein having an amino acid sequence sufficiently identical to the amino acid sequence of SEQ ID NO:17. In a preferred embodiment, a BRE nucleic acid molecule includes a nucleotide sequence encoding a protein having an amino acid sequence at least 50%, 55%, 60%, 65%, 70%, 75%, 80%, 85%, 90%, 95%, 96%, 97%, 98%, 99% or more identical to the entire length of the amino acid sequence of SEQ ID NO:17.

In another preferred embodiment, an isolated nucleic acid molecule encodes the amino acid sequence of human BRE. In yet another preferred embodiment, the nucleic acid molecule includes a nucleotide sequence encoding a protein having the amino acid sequence of SEQ ID NO:17. In yet another preferred embodiment, the nucleic acid molecule is at least 50–100, 100–250, 250–500, 500–750, 750–1000, 1000–1250, 1250–1500, 1500–1750, 1750–2000, 2000–2250, 2250–2500 or more nucleotides in length. In a further preferred embodiment, the nucleic acid molecule is at least 50–100, 100–250, 250–500, 500–750, 750–1000, 1000–1250, 1250–1500, 1500–1750, 1750–2000, 2000–2250, 2250–2500, or more nucleotides in length and encodes a protein having a BRE activity (as described herein).

Another embodiment of the invention features nucleic acid molecules, preferably BRE nucleic acid molecules, which specifically detect BRE nucleic acid molecules relative to nucleic acid molecules encoding non-BRE proteins. For example, in one embodiment, such a nucleic acid molecule is at least 50–100, 100–250, 250–500, 500–750, 750–1000, 1000–1250, 1250–1500, 1500–1750, 1750–2000, 2000–2250, 2250–2500 or more nucleotides in length and hybridizes under stringent conditions to a complement of a nucleic acid molecule comprising the nucleotide sequence shown in SEQ ID NO:16 or 18.

In preferred embodiments, the nucleic acid molecules are at least 15 (e.g., 15 contiguous) nucleotides in length and hybridize under stringent conditions to a complement of the nucleotide molecules set forth in SEQ ID NO:16 or 18.

In other preferred embodiments, the nucleic acid molecule encodes a naturally occurring allelic variant of a polypeptide comprising the amino acid sequence of SEQ ID NO:17, wherein the nucleic acid molecule hybridizes to a complement of a nucleic acid molecule comprising SEQ ID NO:16 or 18, respectively, under stringent conditions.

Another embodiment of the invention provides an isolated nucleic acid molecule which is antisense to a BRE nucleic acid molecule, e.g., the coding strand of a BRE nucleic acid molecule.

Another aspect of the invention provides a vector comprising a BRE nucleic acid molecule. In certain embodiments, the vector is a recombinant expression vector. In another embodiment, the invention provides a host cell containing a vector of the invention. In yet another embodiment, the invention provides a host cell containing a nucleic acid molecule of the invention. The invention also provides a method for producing a protein, preferably a BRE protein, by culturing in a suitable medium, a host cell, e.g., a mammalian host cell such as a non-human mammalian cell, of the invention containing a recombinant expression vector, such that the protein is produced.

Another aspect of this invention features isolated or recombinant BRE proteins and polypeptides. In one embodiment, an isolated BRE protein includes at least one or more of the following domains: a carbamoyl-phosphate synthase L chain, ATP binding domain (or CPSase domain), and/or a biotin-requiring enzyme domain.

In a preferred embodiment, a BRE protein includes at least one or more of the following domains: a CPSase domain, a biotin-requiring enzyme domain, and has an amino acid sequence at least about 50%, 55%, 60%, 65%, 67%, 68%, 70%, 75%, 80%, 85%, 90%, 95%, 96%, 97%, 98%, 99% or more identical to the amino acid sequence of SEQ ID NO:17. In another preferred embodiment, a BRE protein includes at least one or more of the following domains: a CPSase domain, a biotin-requiring enzyme domain and has a BRE activity (as described herein).

In yet another preferred embodiment, a BRE protein includes at least one or more of the following domains: a CPSase domain, a biotin-requiring enzyme domain, and is encoded by a nucleic acid molecule having a nucleotide sequence which hybridizes under stringent hybridization conditions to a complement of a nucleic acid molecule comprising the nucleotide sequence of SEQ ID NO:16 or 18.

In another embodiment, the invention features fragments of the protein having the amino acid sequence of SEQ ID NO:17, wherein the fragment comprises at least 15 amino acids (e.g., contiguous amino acids) of the amino acid sequence of SEQ ID NO:17. In another embodiment, a BRE protein has the amino acid sequence of SEQ ID NO:17.

In another embodiment, the invention features a BRE protein which is encoded by a nucleic acid molecule consisting of a nucleotide sequence at least about 50%, 55%, 60%, 65%, 70%, 75%, 80%, 85%, 90%, 95%, 96%, 97%, 98%, 99% or more identical to a nucleotide sequence of SEQ ID NO:16 or 18, or a complement thereof. This invention further features a BRE protein which is encoded by a nucleic acid molecule consisting of a nucleotide sequence which hybridizes under stringent hybridization conditions to a nucleic acid molecule comprising the nucleotide sequence of SEQ ID NO:16 or 18, or a complement thereof.

The proteins of the present invention or portions thereof, e.g., biologically active portions thereof, can be operatively linked to a non-BRE polypeptide (e.g., heterologous amino acid sequences) to form fusion proteins. The invention further features antibodies, such as monoclonal or polyclonal antibodies, that specifically bind proteins of the invention, preferably BRE proteins. In addition, the BRE proteins or biologically active portions thereof can be incorporated into pharmaceutical compositions, which optionally include pharmaceutically acceptable carriers.

In another aspect, the present invention provides a method for detecting the presence of a BRE nucleic acid molecule, protein, or polypeptide in a biological sample by contacting the biological sample with an agent capable of detecting a BRE nucleic acid molecule, protein, or polypeptide such that the presence of a BRE nucleic acid molecule, protein or polypeptide is detected in the biological sample.

In another aspect, the present invention provides a method for detecting the presence of BRE activity in a biological sample by contacting the biological sample with an agent capable of detecting an indicator of BRE activity such that the presence of BRE activity is detected in the biological sample.

In another aspect, the invention provides a method for modulating BRE activity comprising contacting a cell capable of expressing BRE with an agent that modulates BRE activity such that BRE activity in the cell is modulated. In one embodiment, the agent inhibits BRE activity. In another embodiment, the agent stimulates BRE activity. In one embodiment, the agent is an antibody that specifically binds to a BRE protein. In another embodiment, the agent modulates expression of BRE by modulating transcription of a BRE gene or translation of a BRE mRNA. In yet another embodiment, the agent is a nucleic acid molecule having a nucleotide sequence that is antisense to the coding strand of a BRE mRNA or a BRE gene.

In one embodiment, the methods of the present invention are used to treat a subject having a disorder characterized by aberrant or unwanted BRE protein or nucleic acid expression or activity by administering an agent which is a BRE modulator to the subject. In one embodiment, the BRE modulator is a BRE protein. In another embodiment the BRE modulator is a BRE nucleic acid molecule. In yet another embodiment, the BRE modulator is a peptide, peptidomimetic, or other small molecule. In a preferred embodiment, the disorder characterized by aberrant or unwanted BRE protein or nucleic acid expression is a BRE-associated disorder (e.g., a carboxylase associated disorder, a decarboxylase-associated disorder).

The present invention also provides diagnostic assays for identifying the presence or absence of a genetic alteration characterized by at least one of (i) aberrant modification or mutation of a gene encoding a BRE protein; (ii) misregulation of the gene; and (iii) aberrant post-translational modification of a BRE protein, wherein a wild-type form of the gene encodes a protein with a BRE activity.

In another aspect the invention provides methods for identifying a compound that binds to or modulates the activity of a BRE protein, by providing an indicator composition comprising a BRE protein having BRE activity, contacting the indicator composition with a test compound, and determining the effect of the test compound on BRE activity in the indicator composition to identify a compound that modulates the activity of a BRE protein.

Other features and advantages of the invention will be apparent from the following detailed description and claims.

DETAILED DESCRIPTION OF THE INVENTION

The present invention is based, at least in part, on the discovery of novel molecules, referred to herein as "Biotin Requiring Enzyme" or "BRE" nucleic acid and protein molecules, which are novel members of a family of enzymes which possess the ability to associate with biotin molecules (e.g. to associate covalently with a biotin coenzyme, to associate non-covalently with a biotin cofactor) in order to function in their biological capacity (e.g., to convert BRE substrates and metabolites into their corresponding BRE-mediated products). These novel molecules are capable of participating in metabolic pathways (e.g., as a carboxylase, as a decarboxylase, as a transcarboxylase) and, thus, play a role in or function in a variety of cellular processes, e.g., gluconeogenesis, lipogenesis, amino acid metabolism, nucleic acid metabolism, the urea cycle, and energy transduction.

As used herein, the term "biotin requiring enzyme", also called "biotin enzyme", (referred to herein interchangeably as "BRE") includes a protein, peptide, or enzyme which is able to interact with one or more molecules of biotin in order to carry out its function(s), e.g., specific reactions in catabolic or anabolic pathways. BRE molecules are involved in the anabolism and catabolism of metabolically important biomolecules, including the metabolism of biochemical molecules necessary for energy production or storage (e.g., carbohydrate metabolism, lipid metabolism), important cellular metabolites (e.g. amino acids, nucleic acids, urea cycle intermediates), as well as the detoxification (e.g., catabolism) of potentially harmful compounds (e.g., toxins, carcinogens). Examples of BRE molecules include prokaryotic, plant, and mammalian carboxylases, decarboxylases, transcarboxylases, and biotin protein ligases. As biotin enzymes, the BRE molecules of the present invention provide novel diagnostic targets and therapeutic agents to control BRE-associated disorders.

Preferably such BRE proteins comprise a family of BRE molecules. The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin, e.g., monkey proteins. Members of a family may also have common functional characteristics.

In another embodiment, a BRE molecule of the present invention is identified based on the presence of at least one "CPSase" domain in the protein or corresponding nucleic acid molecule. As used herein, the term "CPSase" or "CPSase domain" includes a protein domain having an amino acid sequence of about 64–669 amino acid residues and a bit score of at least 286 when compared against a CPSase domain Markov Model (HMM), e.g., PFAM accession number PF00289. In a preferred embodiment, a CPSase domain includes a protein domain having an amino acid sequence of about 169–569 amino acid residues and a bit score of at least 386. Preferably, a CPSase domain includes a protein domain having an amino acid sequence of about 269–469 amino acid residues and a bit score of at least about 486 (e.g., 500, 525, 550, 575, 586.6, 600 or more). A CPSase domain preferably includes a sufficient number of amino acid residues for the enzymatic function of the polypeptide sequence Alternatively, in another embodiment, a BRE molecule of the present invention is identified based on the presence of at least one carbamoyl phosphate synthase L chain, N-terminal ("CPSase N-terminal") domain in the protein or corresponding nucleic acid molecule. As used herein, the term "CPSase N-terminal domain" includes a protein domain having an amino acid sequence of about 100–125 amino acid residues and a bit score of at least 144 when compared against a CPSase domain Markov Model (HMM), e.g., PFAM accession number PF00289. In a preferred embodiment, a CPSase N-terminal domain includes a protein domain having an amino acid sequence of about 105–120 amino acid residues and a bit score of at least 164. Preferably, a CPSase domain includes a protein domain having an amino acid sequence of about 100–125 amino acid residues (e.g., 113) and a bit score of at least about 184.

In another embodiment, a BRE molecule of the present invention is identified based on the presence of at least one carbamoyl phosphate synthase ATP-binding ("CPSase ATP-binding") domain in the protein or corresponding nucleic acid molecule. As used herein, the term "CPSase ATP-binding domain" includes a protein domain having an amino acid sequence of about 190–240 amino acid residues and a bit score of at least 190 when compared against a CPSase domain Markov Model (HMM), e.g., PFAM accession number PF02786. In a preferred embodiment, a CPSase domain includes a protein domain having an amino acid sequence of about 200–230 amino acid residues and a bit score of at least 330. Preferably, a CPSase domain includes a protein domain having an amino acid sequence of about 210–220 amino acid residues (e.g.,214 amino acid residues) and a bit score of at least about 550 (e.g., 353 or more). Preferably, a "carbamoyl-phosphate synthase L chain, ATP binding domain" ("CPSase ATP-binding domain") contains a "carbamoyl phosphate synthase subdomain signature". This domain is implicated in ATP binding and/or catalytic activity.

A CPSase domain can include, for example, amino acid residues essential for the enzymatic function of the BRE proteins of the present invention. CPSase domains have been found, for example, in the carbamoylase CPSase (e.g., in duplicate) as well as in a variety of biotin-dependent enzymes (e.g., in single copy) for example acetyl-CoA carboxylase, propionyl-CoA carboxylase, pyruvate carboxylase and urea carboxylase. To identify the presence of a CPSase domain in a BRE protein, the amino acid sequence of the protein is used to search a database of known Hidden Markov Models (HMMs e.g., the PFAM HMM database). The CPSase HMM has been assigned the PFAM Accession PF00289 (see the Pfam website at Washington University is St. Louis pfam.wustl.edu), InterPro accession number IPR000901 (see the Interpro section of the European Bioinformatics Institute website ebi.ac.uk/interpro), and Prosite accession numbers PS00866 and PS00867 (see the Prosite section of the website for ExPASy (Expert Protein Analysis System) proteomics server of the Swiss Institute of Bioinformatics expasy.ch/prosite). For example, a search was performed against the HMM database using the amino acid sequence (SEQ ID NO:17) of human BRE resulting in the identification of a CPSase domain in the amino acid sequence of human BRE (SEQ ID NO:17) at about residues 51–419 having a score of 586.6. The results of the search are set forth in FIGS. 35A–F.

In another embodiment, a BRE molecule of the present invention is identified based on the presence of at least one "biotin-requiring enzyme domain" in the protein or corresponding nucleic acid molecule. As used herein, the term "biotin-requiring enzyme domain" includes a protein domain having an amino acid sequence of about 35–95 amino acid residues and a bit score of at least 38 when compared against a biotin-requiring enzyme domain Markov Model (HMM), e.g., PFAM accession number PF00364. In a preferred embodiment, a biotin-requiring enzyme domain includes a protein domain having an amino acid sequence of about 45–85 amino acid residues and a bit score of at least 48. In another preferred embodiment, a biotin-requiring enzyme domain includes a protein domain having an amino acid sequence of about 55–75 amino acid residues and a bit score of at least 58. Preferably, a biotin-requiring enzyme domain includes a protein domain having an amino acid sequence of about 60–70 amino acid residues and a bit score of at least about 65 (e.g., 66, 67.8, 69, 70, 75, 100 or more). Preferably, the biotin requiring enzyme domain binds biotin and contains, or can be characterized by, the presence of a "biotin requiring enzyme attachment site", which itself is characterized by the inclusion of a conserved lysine residue. To identify the presence of a biotin-requiring enzyme domain in a BRE protein, the amino acid sequence of the protein is used to search a database of known Hidden Markov Models (HMMs e.g., the PFAM HMM database). The biotin-requiring enzyme domain HMM has been assigned the PFAM Accession PF00364 (see the Pfam website at Washington University in St. Louis pfam.wustl.edu), InterPro accession number IPR000089 (see the Interpro section of the European Bioinformatics Institute website ebi.ac.uk/interpro), and Prosite accession number PS00188 (see the Prosite section of the website for ExPASy (Expert Protein Analysis System) proteomics server of the Swiss Institute of Bioinformatics expasy.ch/prosite). For example, a search was performed against the HMM database using the amino acid sequence (SEQ ID NO:17) of human BRE resulting in the identification of a biotin-requiring enzyme domain in the amino acid sequence of human BRE (SEQ ID NO:17) at about residues 650–714 having a score of 67.8. The results of the search are set forth in FIGS. 35A–F.

In a preferred embodiment, a biotin-requiring enzyme domain as described herein is characterized by the presence of a "biotin-requiring enzyme attachment site." As used herein, the term "biotin-requiring enzyme attachment site" includes a motif having the consensus sequence [GN]-[DEQTR]-X-[LIVMFY]-X(2)-[LIVM]-X-[AIV]-M-K-[LMAT]-X(3)-[LIVM]-X-[SAV] and is described under Prosite entry number PS00188 (see the Prosite section of the website for ExPASy (Expert Protein Analysis System) proteomics server of the Swiss Institute of Bioinformatics expasy.ch/prosite). A biotin-requiring enzyme attachment site can be found, for example, within the biotin-requiring enzyme domain of the BRE protein of SEQ ID NO:17 at about residues 671–688. The consensus sequences described herein are described according to standard Prosite Signature designation (e.g., all amino acids are indicated according to their universal single letter designation; X designates any amino acid; X(n) designates any n amino acids, e.g., X (2) designates any 2 amino acids; [LIVM] indicates any one of the amino acids appearing within the brackets, e.g., any one of L, I, V, or M, in the alternative, any one of Leu, Ile, Val, or Met.); and {LIVM} indicates any amino acid except the amino acids appearing within the brackets, e.g., not L, not I, not V, and not M.

Isolated proteins of the present invention, for example BRE proteins, preferably have an amino acid sequence sufficiently identical to the amino acid sequence of SEQ ID NO:17, or are encoded by a nucleotide sequence sufficiently identical to SEQ ID NO:16 or 18. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%–80%, and even more preferably 90%, 91%, 92%, 93%, 94%, 95%, 96%, 97%, 98%, 99% or more homology across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70–80%, or 90–95% homology (and ranges intermediate therein) and share a common functional activity are defined herein as sufficiently identical.

As used interchangeably herein, a "BRE activity", "biological activity of BRE" or "functional activity of BRE", refers to an activity exhibited by a BRE protein, polypeptide or nucleic acid molecule (e.g., in a BRE expressing cell or tissue), on a BRE substrate, as determined in vivo, or in vitro, according to standard techniques. In one embodiment, a BRE activity is a direct activity, such as processing of a BRE-substrate (e.g., carboxylation, decarboxylation). As used herein, a "BRE substrate" is a molecule or a metabolite which is processed by a BRE molecule. Exemplary substrates include, but are not limited to, energy metabolites, lipid metabolism intermediates, activated $CO_2$, carbonyl groups, urea cycle intermediates, amino acid precursors, and nucleic acid precursors. Examples of BRE substrates also include molecules that are essential for BRE function, e.g., biotin, ATP, acetyl CoA. Alternatively, a BRE activity is an indirect activity, such as a cellular signaling or feedback activity mediated by the processing of a BRE substrate by BRE. In a preferred embodiment, the BRE proteins of the present invention have one or more of the following activities: 1) modulate the bioenergetic activities of a cell (e.g., storage or yielding of chemical energy, 2) modulate intra- or intercellular signaling or feedback mechanisms, 3) removal of potentially harmful compounds (e.g., cytotoxic substances) from the cell, or facilitate the neutralization of these molecules through enzymatic alteration (e.g., carboxylation, decarboxylation), 4) modulate the production or breakdown of amino acids or nucleic acids, or modulate the homeostatic balance of available amino acid or nucleic acid pools, 5) specific attachment of biotin to its cognate enzyme, e.g., biotin protein ligase activity.

Accordingly, another embodiment of the invention features isolated BRE proteins and polypeptides having a BRE activity. Other preferred proteins are BRE proteins having one or more of the following domains: a CPSase domain, a biotin-requiring enzyme domain and, preferably, a BRE activity.

Additional preferred proteins have at least one CPSase domain, one biotin-requiring enzyme domain, and are, preferably, encoded by a nucleic acid molecule having a nucleotide sequence which hybridizes under stringent hybridization conditions to a complement of a nucleic acid molecule comprising the nucleotide sequence of SEQ ID NO:16 or 18.

The nucleotide sequence of the isolated human BRE cDNA and the predicted amino acid sequence of the human BRE polypeptide are shown in FIGS. 33A–E and in SEQ ID NOs:16 and 17, respectively.

The human BRE gene, which is approximately 2577 nucleotides in length, encodes a protein having a molecular weight of approximately 79.8 kD and which is approximately 725 amino acid residues in length.

Various aspects of the invention are described in further detail in the following subsections:

I. Isolated Nucleic Acid Molecules

One aspect of the invention pertains to isolated nucleic acid molecules that encode BRE proteins or biologically active portions thereof, as well as nucleic acid fragments sufficient for use as hybridization probes to identify BRE-encoding nucleic acid molecules (e.g., BRE mRNA) and fragments for use as PCR primers for the amplification or mutation of BRE nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated BRE nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:16 or 18, or a portion thereof, can be isolated using standard molecular biology techniques and the sequence information provided herein. Using all or portion of the nucleic acid sequence of SEQ ID NO:16 or 18 as a hybridization probe, BRE nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:16 or 18 can be isolated by the polymerase chain reaction (PCR) using synthetic oligonucleotide primers designed based upon the sequence of SEQ ID NO:16 or 18.

A nucleic acid of the invention can be amplified using cDNA, mRNA or, alternatively, genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to BRE nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:16 or 18. This cDNA may comprise sequences encoding the human BRE protein (i.e., "the coding region", from nucleotides 167–2341), as well as 5' untranslated sequences (nucleotides 1–166) and 3' untranslated sequences (nucleotides 2342–2577) of SEQ ID NO:16. Alternatively, the nucleic acid molecule can comprise only the coding region of SEQ ID NO:16 (e.g., nucleotides 167–2341, corresponding to SEQ ID NO:18). In another embodiment, an isolated nucleic acid molecule of the invention consists of the nucleic acid sequence of SEQ ID NO:16 or 18.

In another preferred embodiment, an isolated nucleic acid molecule of the invention comprises a nucleic acid molecule which is a complement of the nucleotide sequence shown in SEQ ID NO:16 or 18, or a portion of any of these nucleotide sequences. A nucleic acid molecule which is complementary to the nucleotide sequence shown in SEQ ID NO:16 or 18, is one which is sufficiently complementary to the nucleotide sequence shown in SEQ ID NO:16 or 18, such that it can hybridize to the nucleotide sequence shown in SEQ ID NO:16 or 18, respectively, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 90%, 95%, 96%, 97%, 98%, 99% or more identical to the entire length of the nucleotide sequence shown in SEQ ID NO:16 or 18, or a portion of any of these nucleotide sequences.

Moreover, the nucleic acid molecule of the invention can comprise only a portion of the nucleic acid sequence of SEQ ID NO:16 or 18, for example, a fragment which can be used as a probe or primer or a fragment encoding a portion of a BRE protein, e.g., a biologically active portion of a BRE protein. The nucleotide sequence determined from the cloning of the BRE gene allows for the generation of probes and primers designed for use in identifying and/or cloning other BRE family members, as well as BRE homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:16 or 18, of an anti-sense sequence of SEQ ID NO:16 or 18, or of a naturally occurring allelic variant or mutant of SEQ ID NO:16 or 18. In one embodiment, a nucleic acid molecule of the present invention comprises a nucleotide sequence which is greater than 50–100, 100–250, 250–500, 500–750, 750–1000, 1000–1250, 1250–1500, 1500–1750, 1750–2000, 2000–2250, 2250–2500, or more nucleotides in length and hybridizes under stringent hybridization conditions to a nucleic acid molecule of SEQ ID NO:16 or 18.

Probes based on the BRE nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a BRE protein, such as by measuring a level of a BRE-encoding nucleic acid in a sample of cells from a subject e.g., detecting BRE mRNA levels or determining whether a genomic BRE gene has been mutated or deleted.

A nucleic acid fragment encoding a "biologically active portion of a BRE protein" can be prepared by isolating a portion of the nucleotide sequence of SEQ ID NO:16 or 18, which encodes a polypeptide having a BRE biological activity (the biological activities of the BRE proteins are described herein), expressing the encoded portion of the BRE protein (e.g., by recombinant expression in vitro) and assessing the activity of the encoded portion of the BRE protein.

The invention further encompasses nucleic acid molecules that differ from the nucleotide sequence shown in SEQ ID NO:16 or 18, due to degeneracy of the genetic code and thus encode the same BRE proteins as those encoded by the nucleotide sequence shown in SEQ ID NO:16 or 18. In another embodiment, an isolated nucleic acid molecule of the invention has a nucleotide sequence encoding a protein having an amino acid sequence shown in SEQ ID NO:17.

In addition to the BRE nucleotide sequences shown in SEQ ID NO:16 or 18, it will be appreciated by those skilled in the art that DNA sequence polymorphisms that lead to changes in the amino acid sequences of the BRE proteins may exist within a population (e.g., the human population). Such genetic polymorphism in the BRE genes may exist among individuals within a population due to natural allelic variation. As used herein, the terms "gene" and "recombinant gene" refer to nucleic acid molecules which include an open reading frame encoding a BRE protein, preferably a mammalian BRE protein, and can further include non-coding regulatory sequences, and introns.

Allelic variants of human BRE include both functional and non-functional BRE proteins. Functional allelic variants are naturally occurring amino acid sequence variants of the human BRE protein that maintain the ability to process a BRE substrate (e.g., carboxylation, decarboxylation). Functional allelic variants will typically contain only conservative substitution of one or more amino acids of SEQ ID NO:17, or substitution, deletion or insertion of non-critical residues in non-critical regions of the protein.

Non-functional allelic variants are naturally occurring amino acid sequence variants of the human BRE protein that do not have the ability to bind or process a BRE substrate (e.g., carboxylation, decarboxylation), and/or carry out any of the BRE activities described herein. Non-functional allelic variants will typically contain a non-conservative substitution, a deletion, or insertion or premature truncation of the amino acid sequence of SEQ ID NO:17, or a substitution, insertion or deletion in critical residues or critical regions of the protein.

The present invention further provides non-human orthologues of the human BRE protein. Orthologues of the human BRE protein are proteins that are isolated from non-human organisms and possess the same BRE substrate binding and/or modulation of membrane excitability activities of the human BRE protein. Orthologues of the human BRE protein can readily be identified as comprising an amino acid sequence that is substantially identical to SEQ ID NO:17.

Moreover, nucleic acid molecules encoding other BRE family members and, thus, which have a nucleotide sequence which differs from the BRE sequences of SEQ ID NO:16 or 18 are intended to be within the scope of the invention. For example, another BRE cDNA can be identified based on the nucleotide sequence of human BRE. Moreover, nucleic acid molecules encoding BRE proteins from different species, and which, thus, have a nucleotide sequence which differs from the BRE sequences of SEQ ID NO:16 or 18 are intended to be within the scope of the invention. For example, a mouse BRE cDNA can be identified based on the nucleotide sequence of a human BRE.

Nucleic acid molecules corresponding to natural allelic variants and homologues of the BRE cDNAs of the invention can be isolated based on their homology to the BRE nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the BRE cDNAs of the invention can further be isolated by mapping to the same chromosome or locus as the BRE gene.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:16 or 18. In other embodiment, the nucleic acid is at least 50–100, 100–250, 250–500, 500–750, 750–1000, 1000–1250, 1250–1500, 1500–1750, 1750–2000, 2000–2250, 2250–2500, or more nucleotides in length. As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A preferred, non-limiting example of stringent hybridization conditions includes hybridization in 4×sodium chloride/sodium citrate (SSC), at about 65–70° C. (or hybridization in 4×SSC plus 50% formamide at about 42–50° C.) followed by one or more washes in 1×SSC, at about 65–70° C. A preferred, non-limiting example of highly stringent hybridization conditions includes hybridization in 1×SSC, at about 65–70° C. (or hybridization in 1×SSC plus 50% formamide at about 42–50° C.) followed by one or more washes in 0.3×SSC, at about 65–70° C. A preferred, non-limiting example of reduced stringency hybridization conditions includes hybridization in 4×SSC, at about 50–60° C. (or alternatively hybridization in 6×SSC plus 50% formamide at about 40–45° C.) followed by one or more washes in 2×SSC, at about 50–60° C. Ranges intermediate to the above-recited values, e.g., at 65–70° C. or at 42–50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.1 5M NaCl and 15 mM sodium citrate) in the hybridization and wash buffers; washes are performed for 15 minutes each after hybridization is complete. The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m(° C.)=2(\text{\# of A+T bases})+4(\text{\# of G+C bases})$. For hybrids between 18 and 49 base pairs in length, $T_m(° C.)=81.5+16.6(\log_{10}[Na^+])+0.41(\% \text{ G+C})-(600/N)$, where N is the number of bases in the hybrid, and $[Na^+]$ is the concentration of sodium ions in the hybridization buffer ($[Na^+]$ for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25–0.5M $NaH_2PO_4$, 7% SDS at about 65° C., followed by one or more washes at 0.02M $NaH_2PO_4$, 1% SDS at 65° C., see e.g., Church and Gilbert (1984) *Proc. Natl. Acad. Sci. USA* 81:1991–1995, (or alternatively 0.2×SSC, 1% SDS).

Preferably, an isolated nucleic acid molecule of the invention that hybridizes under stringent conditions to the sequence of SEQ ID NO:16 or 18 and corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the BRE sequences that may exist in the population, the skilled artisan will further appreciate that changes can be introduced by mutation into the nucleotide sequences of SEQ ID NO:16 or 18, thereby leading to changes in the amino acid sequence of the encoded BRE proteins, without altering the functional ability of the BRE proteins. For example, nucleotide substitutions leading to amino acid substitutions at "non-essential" amino acid residues can be made in the sequence of SEQ ID NO:16 or 18. A "non-essential" amino acid residue is a residue that can be altered from the wild-type sequence of BRE (e.g., the sequence of SEQ ID NO:17) without altering the biological activity, whereas an "essential" amino acid residue is required for biological activity. For example, amino acid residues that are conserved among the BRE proteins of the present invention (for example, those present in a biotin-requiring enzyme domain or in a carbamoyl-phosphate synthase domain), are predicted to be particularly unamenable to alteration. Furthermore, additional amino acid residues that are conserved between the BRE proteins of the present invention and other members of the BRE family are not likely to be amenable to alteration.

Accordingly, another aspect of the invention pertains to nucleic acid molecules encoding BRE proteins that contain changes in amino acid residues that are not essential for activity. Such BRE proteins differ in amino acid sequence from SEQ ID NO:17, yet retain biological activity. In one embodiment, the isolated nucleic acid molecule comprises a nucleotide sequence encoding a protein, wherein the protein comprises an amino acid sequence at least about 50%, 55%, 60%, 65%, 70%, 75%, 80%, 85%, 90%, 95%, 96%, 97%, 98%, 99% or more identical to SEQ ID NO:17.

An isolated nucleic acid molecule encoding a BRE protein identical to the protein of SEQ ID NO:17 can be created by introducing one or more nucleotide substitutions, additions or deletions into the nucleotide sequence of SEQ ID NO:16 or 18, such that one or more amino acid substitutions, additions or deletions are introduced into the encoded protein. Mutations can be introduced into SEQ ID NO:16 or 18 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a BRE protein is preferably replaced with another amino acid residue from the same side chain family. Alternatively, in another embodiment, mutations can be introduced randomly along all or part of a BRE coding sequence, such as by saturation mutagenesis, and the resultant mutants can be screened for BRE biological activity to identify mutants that retain activity. Following mutagenesis of SEQ ID NO:16 or 18, the encoded protein can be expressed recombinantly and the activity of the protein can be determined.

In a preferred embodiment, a mutant BRE protein can be assayed for the ability to metabolize or catabolize biochemical molecules necessary for energy production or storage, permit intra- or intercellular signaling, metabolize or catabolize metabolically important biomolecules (e.g. amino acids, nucleic acids), and to detoxify potentially harmful compounds, or to facilitate the neutralization of these molecules.

In addition to the nucleic acid molecules encoding BRE proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire BRE coding strand, or to only a portion thereof. In one embodiment, an antisense nucleic acid molecule is antisense to a "coding region" of the coding strand of a nucleotide sequence encoding a BRE. The term "coding region" refers to the region of the nucleotide sequence comprising codons which are translated into amino acid residues (e.g., the coding region of human BRE corresponds to SEQ ID NO:18). In another embodiment, the antisense nucleic acid molecule is antisense to a "noncoding region" of the coding strand of a nucleotide sequence encoding BRE. The term "noncoding region" refers to 5' and 3' sequences which flank the coding region that are not translated into amino acids (i.e., also referred to as 5' and 3' untranslated regions).

Given the coding strand sequences encoding BRE disclosed herein (e.g., SEQ ID NO:18), antisense nucleic acids of the invention can be designed according to the rules of Watson and Crick base pairing. The antisense nucleic acid molecule can be complementary to the entire coding region of BRE mRNA, but more preferably is an oligonucleotide which is antisense to only a portion of the coding or noncoding region of BRE mRNA. For example, the antisense oligonucleotide can be complementary to the region surrounding the translation start site of BRE mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a BRE protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff and Gerlach (1988) *Nature* 334:585–591)) can be used to catalytically cleave BRE mRNA transcripts to thereby inhibit translation of BRE mRNA. A ribozyme having specificity for a BRE-encoding nucleic acid can be designed based upon the nucleotide sequence of a BRE cDNA disclosed herein (i.e., SEQ ID NO:16 or 18). For example, a derivative of a Tetrahymena L-19 IVS RNA can be constructed in which the nucleotide sequence of the active site is complementary to the nucleotide sequence to be cleaved in a BRE-encoding mRNA. See, e.g., Cech et al. U.S. Pat. No. 4,987,071; and Cech et al. U.S. Pat. No. 5,116,742. Alternatively, BRE mRNA can be used to select a catalytic RNA having a specific ribonuclease activity from a pool of RNA molecules. See, e.g., Bartel, D. and Szostak, J. W. (1993) *Science* 261:1411–1418.

Alternatively, BRE gene expression can be inhibited by targeting nucleotide sequences complementary to the regulatory region of the BRE (e.g., the BRE promoter and/or enhancers; e.g., nucleotides 1–166 of SEQ ID NO:16) to form triple helical structures that prevent transcription of the BRE gene in target cells. See generally, Helene, C. (1991) *Anticancer Drug Des.* 6(6): 569–84; Helene, C. et al. (1992) *Ann. N.Y. Acad. Sci.* 660:27–36; and Maher, L. J. (1992) *Bioassays* 14(12):807–15.

In yet another embodiment, the BRE nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. *Proc. Natl. Acad. Sci.* 93: 14670–675.

PNAs of BRE nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of BRE nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of BRE can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of BRE nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

Alternatively, the expression characteristics of an endogenous BRE gene within a cell line or microorganism may be modified by inserting a heterologous DNA regulatory element into the genome of a stable cell line or cloned microorganism such that the inserted regulatory element is operatively linked with the endogenous BRE gene. For example, an endogenous BRE gene which is normally "transcriptionally silent", i.e., a BRE gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous BRE gene may be activated by insertion of a promiscuous regulatory element that works across cell types.

A heterologous regulatory element may be inserted into a stable cell line or cloned microorganism, such that it is operatively linked with an endogenous BRE gene, using techniques, such as targeted homologous recombination, which are well known to those of skill in the art, and described, e.g., in Chappel, U.S. Pat. No. 5,272,071; PCT publication No. WO 91/06667, published May 16, 1991.

II. Isolated BRE Proteins and Anti-BRE Antibodies

One aspect of the invention pertains to isolated BRE proteins, and biologically active portions thereof, as well as polypeptide fragments suitable for use as immunogens to raise anti-BRE antibodies. In one embodiment, native BRE proteins can be isolated from cells or tissue sources by an appropriate purification scheme using standard protein purification techniques. In another embodiment, BRE proteins are produced by recombinant DNA techniques. Alternative to recombinant expression, a BRE protein or polypeptide can be synthesized chemically using standard peptide synthesis techniques.

An "isolated" or "purified" protein or biologically active portion thereof is substantially free of cellular material or other contaminating proteins from the cell or tissue source from which the BRE protein is derived, or substantially free from chemical precursors or other chemicals when chemically synthesized. The language "substantially free of cellular material" includes preparations of BRE protein in which the protein is separated from cellular components of the cells from which it is isolated or recombinantly produced. In one embodiment, the language "substantially free of cellular material" includes preparations of BRE protein having less than about 30% (by dry weight) of non-BRE protein (also referred to herein as a "contaminating protein"), more preferably less than about 20% of non-BRE protein, still more preferably less than about 10% of non-BRE protein, and most preferably less than about 5% non-BRE protein. When the BRE protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of BRE protein in which the protein is separated from chemical precursors or other chemicals which are involved in the synthesis of the protein. In one embodiment, the language "substantially free of chemical precursors or other chemicals" includes preparations of BRE protein having less than about 30% (by dry weight) of chemical precursors or non-BRE chemicals, more preferably less than about 20% chemical precursors or non-BRE chemicals, still more preferably less than about 10% chemical precursors or non-BRE chemicals, and most preferably less than about 5% chemical precursors or non-BRE chemicals.

As used herein, a "biologically active portion" of a BRE protein includes a fragment of a BRE protein which participates in an interaction between a BRE molecule and a non-BRE molecule. Biologically active portions of a BRE protein include peptides comprising amino acid sequences sufficiently identical to or derived from the amino acid sequence of the BRE protein, e.g., the amino acid sequence shown in SEQ ID NO:17, which include less amino acids than the full length BRE protein, and exhibit at least one activity of a BRE protein. Typically, biologically active portions comprise a domain or motif with at least one activity of the BRE protein, e.g., carboxylase activity, decarboxylase activity, transcarboxylase activity. A biologically active portion of a BRE protein can be a polypeptide which is, for example, 25, 50, 75, 100, 125, 150, 175, 200, 250, 300, 325, 350, 375, 400, 425, 450, 475, 500, 525, 550, 575, 600, 625, 650, 675, 700 or more amino acids in length. Biologically active portions of a BRE protein can be used as targets for developing agents which modulate a BRE mediated activity, e.g., intercellular signaling.

It is to be understood that a preferred biologically active portion of a BRE protein of the present invention may contain one or more of the following domains: a CPSase domain, and/or a biotin-requiring enzyme domain. Moreover, other biologically active portions, in which other regions of the protein are deleted, can be prepared by recombinant techniques and evaluated for one or more of the functional activities of a native BRE protein.

In a preferred embodiment, the BRE protein has an amino acid sequence shown in SEQ ID NO:17. In other embodiments, the BRE protein is substantially identical to SEQ ID NO:17, and retains the functional activity of the protein of SEQ ID NO:17, yet differs in amino acid sequence due to natural allelic variation or mutagenesis, as described in detail in subsection I above. Accordingly, in another embodiment, the BRE protein is a protein which comprises an amino acid sequence at least about 50%, 55%, 60%, 65%, 70%, 75%, 80%, 85%, 90%, 95%, 96%, 97%, 98%, 99% or more identical to SEQ ID NO:17.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the BRE amino acid sequence of SEQ ID NO:17 having 725 amino acid residues, at least 218, preferably at least 290, more preferably at least 363, even more preferably at least 435, and even more preferably at least 508, 580, 653 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at the bioinformatics page of the website maintained by Accelrys, Inc., San Diego, Calif., USA), using either a Blosum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*Comput. Appl. Biosci.*, 4: 11–17 (1988)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to BRE nucleic acid molecules of the invention. BLAST protein searches can be performed with the XBLAST program, score=100, wordlength=3 to obtain amino acid sequences homologous to BRE protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used (accessible at the website maintained by National Center for Biotechnology Information, Bethesda, Md., USA).

The invention also provides BRE chimeric or fusion proteins. As used herein, a BRE "chimeric protein" or "fusion protein" comprises a BRE polypeptide operatively linked to a non-BRE polypeptide. An "BRE polypeptide" refers to a polypeptide having an amino acid sequence corresponding to a BRE molecule, whereas a "non-BRE polypeptide" refers to a polypeptide having an amino acid sequence corresponding to a protein which is not substantially homologous to the BRE protein, e.g., a protein which is different from the BRE protein and which is derived from the same or a different organism. Within a BRE fusion protein the BRE polypeptide can correspond to all or a portion of a BRE protein. In a preferred embodiment, a BRE fusion protein comprises at least one biologically active portion of a BRE protein. In another preferred embodiment, a BRE fusion protein comprises at least two biologically active portions of a BRE protein. Within the fusion protein, the term "operatively linked" is intended to indicate that the BRE polypeptide and the non-BRE polypeptide are fused in-frame to each other. The non-BRE polypeptide can be fused to the N-terminus or C-terminus of the BRE polypeptide.

For example, in one embodiment, the fusion protein is a GST-BRE fusion protein in which the BRE sequences are fused to the C-terminus of the GST sequences. Such fusion proteins can facilitate the purification of recombinant BRE.

In another embodiment, the fusion protein is a BRE protein containing a heterologous signal sequence at its N-terminus. In certain host cells (e.g., mammalian host cells), expression and/or secretion of BRE can be increased through use of a heterologous signal sequence.

The BRE fusion proteins of the invention can be incorporated into pharmaceutical compositions and administered to a subject in vivo. The BRE fusion proteins can be used to affect the bioavailability of a BRE substrate. Use of BRE fusion proteins may be useful therapeutically for the treatment of disorders caused by, for example, (i) aberrant modification or mutation of a gene encoding a BRE protein; (ii) mis-regulation of the BRE gene; and (iii) aberrant post-translational modification of a BRE protein.

Moreover, the BRE-fusion proteins of the invention can be used as immunogens to produce anti-BRE antibodies in a subject for use in screening assays to identify molecules which inhibit the interaction of BRE with a BRE substrate.

Preferably, a BRE chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A BRE-encoding nucleic acid can be cloned into such an expression vector such that the fusion moiety is linked in-frame to the BRE protein.

The present invention also pertains to variants of the BRE proteins which function as either BRE agonists (mimetics) or as BRE antagonists. Variants of the BRE proteins can be generated by mutagenesis, e.g., discrete point mutation or truncation of a BRE protein. An agonist of the BRE proteins can retain substantially the same, or a subset, of the biological activities of the naturally occurring form of a BRE protein. An antagonist of a BRE protein can inhibit one or more of the activities of the naturally occurring form of the BRE protein by, for example, competitively modulating a BRE-mediated activity of a BRE protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the BRE protein.

In one embodiment, variants of a BRE protein which function as either BRE agonists (mimetics) or as BRE antagonists can be identified by screening combinatorial libraries of mutants, e.g., truncation mutants, of a BRE protein for BRE protein agonist or antagonist activity. In one embodiment, a variegated library of BRE variants is generated by combinatorial mutagenesis at the nucleic acid level and is encoded by a variegated gene library. A variegated library of BRE variants can be produced by, for example, enzymatically ligating a mixture of synthetic oligonucleotides into gene sequences such that a degenerate set of potential BRE sequences is expressible as individual polypeptides, or alternatively, as a set of larger fusion proteins (e.g., for phage display) containing the set of BRE sequences therein. There are a variety of methods which can be used to produce libraries of potential BRE variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential BRE sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a BRE protein coding sequence can be used to generate a variegated population of BRE fragments for screening and subsequent selection of variants of a BRE protein. In one embodiment, a library of coding sequence fragments can be generated by treating a double stranded PCR fragment of a BRE coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the BRE protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of BRE proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify BRE variants (Arkin and Youvan (1992) *Proc. Natl. Acad. Sci. USA* 89:7811–7815; Delagrave et al. (1993) *Protein Engineering* 6(3): 327–331).

In one embodiment, cell based assays can be exploited to analyze a variegated BRE library. For example, a library of expression vectors can be transfected into a cell line, e.g., a neuronal cell line, which ordinarily responds to a BRE ligand in a particular BRE ligand-dependent manner. The transfected cells are then contacted with a BRE ligand and the effect of expression of the mutant on, e.g., membrane excitability of BRE can be detected. Plasmid DNA can then be recovered from the cells which score for inhibition, or alternatively, potentiation of signaling by the BRE ligand, and the individual clones further characterized.

An isolated BRE protein, or a portion or fragment thereof, can be used as an immunogen to generate antibodies that bind BRE using standard techniques for polyclonal and monoclonal antibody preparation. A full-length BRE protein can be used or, alternatively, the invention provides antigenic peptide fragments of BRE for use as immunogens. The antigenic peptide of BRE comprises at least 8 amino acid residues of the amino acid sequence shown in SEQ ID NO:17 and encompasses an epitope of BRE such that an antibody raised against the peptide forms a specific immune complex with the BRE protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of BRE that are located on the surface of the protein, e.g., hydrophilic regions, as well as regions with high antigenicity.

A BRE immunogen typically is used to prepare antibodies by immunizing a suitable subject, (e.g., rabbit, goat, mouse or other mammal) with the immunogen. An appropriate immunogenic preparation can contain, for example, recombinantly expressed BRE protein or a chemically synthesized BRE polypeptide. The preparation can further include an adjuvant, such as Freund's complete or incomplete adjuvant, or similar immunostimulatory agent. Immunization of a suitable subject with an immunogenic BRE preparation induces a polyclonal anti-BRE antibody response.

Accordingly, another aspect of the invention pertains to anti-BRE antibodies. The term "antibody" as used herein refers to immunoglobulin molecules and immunologically active portions of immunoglobulin molecules, i.e., molecules that contain an antigen binding site which specifically binds (immunoreacts with) an antigen, such as a BRE. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind BRE molecules. The term "monoclonal antibody" or "monoclonal antibody composition", as used herein, refers to a population of antibody molecules that contain only one species of an antigen binding site capable of immunoreacting with a particular epitope of BRE. A monoclonal antibody composition thus typically displays a single binding affinity for a particular BRE protein with which it immunoreacts.

Polyclonal anti-BRE antibodies can be prepared as described above by immunizing a suitable subject with a BRE immunogen. The anti-BRE antibody titer in the immunized subject can be monitored over time by standard techniques, such as with an enzyme linked immunosorbent assay (ELISA) using immobilized BRE. If desired, the antibody molecules directed against BRE can be isolated from the mammal (e.g., from the blood) and further purified by well known techniques, such as protein A chromatography to obtain the IgG fraction. At an appropriate time after immunization, e.g., when the anti-BRE antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a BRE immunogen as described above, and the culture supernatants of the resulting hybridoma cells are screened to identify a hybridoma producing a monoclonal antibody that binds BRE.

Any of the many well known protocols used for fusing lymphocytes and immortalized cell lines can be applied for the purpose of generating an anti-BRE monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of mycloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC (Manassas, Va.). Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind BRE, e.g., using a standard ELISA assay.

Alternative to preparing monoclonal antibody-secreting hybridomas, a monoclonal anti-BRE antibody can be identified and isolated by screening a recombinant combinatorial immunoglobulin library (e.g., an antibody phage display library) with BRE to thereby isolate immunoglobulin library members that bind BRE. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1369–1372; Hay et al. (1992) *Hum. Antibod. Hybridomas* 3:81–85; Huse et al. (1989) *Science* 246:1275–1281; Griffiths et al. (1993) *EMBO J.* 12:725–734; Hawkins et al. (1992) *J. Mol. Biol.* 226: 889–896; Clackson et al. (1991) *Nature* 352:624–628; Gram et al. (1992) *Proc. Natl. Acad. Sci. USA* 89:3576–3580; Garrard et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-BRE antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171, 496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225, 539; Jones et al. (1986) *Nature* 321:552–525; Verhoeyen et al. (1988) *Science* 239:1534; and Beidler et al. (1988) *J. Immunol.* 141:4053–4060.

An anti-BRE antibody (e.g., monoclonal antibody) can be used to isolate BRE by standard techniques, such as affinity chromatography or immunoprecipitation. An anti-BRE antibody can facilitate the purification of natural BRE from cells and of recombinantly produced BRE expressed in host cells. Moreover, an anti-BRE antibody can be used to detect BRE protein (e.g., in a cellular lysate or cell supernatant) in order to evaluate the abundance and pattern of expression of the BRE protein. Anti-BRE antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

III. Recombinant Expression Vectors and Host Cells

Another aspect of the invention pertains to vectors, preferably expression vectors, containing a nucleic acid encoding a BRE protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., BRE proteins, mutant forms of BRE proteins, fusion proteins, and the like).

The recombinant expression vectors of the invention can be designed for expression of BRE proteins in prokaryotic or eukaryotic cells. For example, BRE proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in BRE activity assays, (e.g., direct assays or competitive assays described in detail below), or to generate antibodies specific for BRE proteins, for example. In a preferred embodiment, a BRE fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the BRE expression vector is a yeast expression vector. Examples of vectors for expression in yeast *S. cerevisiae* include pYepSec1 (Baldari, et al., (1987) *EMBO J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (Invitrogen Corporation, San Diego, Calif.).

Alternatively, BRE proteins can be expressed in insect cells using baculovirus expression vectors. Baculovirus vectors available for expression of proteins in cultured insect cells (e.g., Sf9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to BRE mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a BRE nucleic acid molecule of the invention is introduced, e.g., a BRE nucleic acid molecule within a recombinant expression vector or a BRE nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a BRE protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a BRE protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a BRE protein. Accordingly, the invention further provides methods for producing a BRE protein using the host cells of the invention. In one embodiment, the method comprises culturing the host cell of the invention (into which a recombinant expression vector encoding a BRE protein has been introduced) in a suitable medium such that a BRE protein is produced. In another embodiment, the method further comprises isolating a BRE protein from the medium or the host cell.

The host cells of the invention can also be used to produce non-human transgenic animals. For example, in one embodiment, a host cell of the invention is a fertilized oocyte or an embryonic stem cell into which BRE-coding sequences have been introduced. Such host cells can then be used to create non-human transgenic animals in which exogenous BRE sequences have been introduced into their genome or homologous recombinant animals in which endogenous BRE sequences have been altered. Such animals are useful for studying the function and/or activity of a BRE and for identifying and/or evaluating modulators of BRE activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like.

A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous BRE gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a BRE-encoding nucleic acid into the male pronuclei of a fertilized oocyte, e.g., by microinjection, retroviral infection, and allowing the oocyte to develop in a pseudopregnant female foster animal. The BRE cDNA sequence of SEQ ID NO:16 can be introduced as a transgene into the genome of a non-human animal. Alternatively, a nonhuman homologue of a human BRE gene, such as a mouse or rat BRE gene, can be used as a transgene. Alternatively, a BRE gene homologue, such as another BRE family member, can be isolated based on hybridization to the BRE cDNA sequences of SEQ ID NO:16 or 18, and used as a transgene. Intronic sequences and polyadenylation signals can also be included in the transgene to increase the efficiency of expression of the transgene. A tissue-specific regulatory sequence(s) can be operably linked to a BRE transgene to direct expression of a BRE protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a BRE transgene in its genome and/or expression of BRE mRNA in tissues or cells of the animals. A transgenic founder animal can then be used to breed additional animals carrying the transgene. Moreover, transgenic animals carrying a transgene encoding a BRE protein can further be bred to other transgenic animals carrying other transgenes.

To create a homologous recombinant animal, a vector is prepared which contains at least a portion of a BRE gene into which a deletion, addition or substitution has been introduced to thereby alter, e.g., functionally disrupt, the BRE gene. The BRE gene can be a human gene (e.g., the cDNA of SEQ ID NO:18), but more preferably, is a non-human homologue of a human BRE gene (e.g., a cDNA isolated by stringent hybridization with the nucleotide sequence of SEQ ID NO:16). For example, a mouse BRE gene can be used to construct a homologous recombination nucleic acid molecule, e.g., a vector, suitable for altering an endogenous BRE gene in the mouse genome. In a preferred embodiment, the homologous recombination nucleic acid molecule is designed such that, upon homologous recombination, the endogenous BRE gene is functionally disrupted (i.e., no longer encodes a functional protein; also referred to as a "knock out" vector). Alternatively, the homologous recombination nucleic acid molecule can be designed such that, upon homologous recombination, the endogenous BRE gene is mutated or otherwise altered but still encodes functional protein (e.g., the upstream regulatory region can be altered to thereby alter the expression of the endogenous BRE protein). In the homologous recombination nucleic acid molecule, the altered portion of the BRE gene is flanked at its 5' and 3' ends by additional nucleic acid sequence of the BRE gene to allow for homologous recombination to occur between the exogenous BRE gene carried by the homologous recombination nucleic acid molecule and an endogenous BRE gene in a cell, e.g., an embryonic stem cell. The additional flanking BRE nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced BRE gene has homologously recombined with the endogenous BRE gene are selected (see e.g., Li, E. et al. (1992) *Cell* 69:915). The selected cells can then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The BRE nucleic acid molecules, fragments of BRE proteins, and anti-BRE antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR®EL solubilizer (BASF, Florham Park, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a BRE protein or an anti-BRE antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a BRE protein of the invention has one or more of the following activities: 1) modulation the bioenergetic activities of a cell (e.g., storage or yielding of chemical energy) 2) modulation of intra- or intercellular signaling or feedback mechanisms, 3) removal of potentially harmful compounds (e.g., cytotoxic substances) from the cell, or facilitate the neutralization of these molecules through enzymatic alteration (e.g., carboxylation, decarboxylation), 4) modulation the production or breakdown of amino acids or nucleic acids, or modulate the homeostatic balance of available amino acid or nucleic acid pools, 5) the specific attachment of biotin to its cognate enzyme, e.g., biotin protein ligase activity.

In a preferred embodiment, the BRE molecules of the invention are useful for catalyzing carboxylase, decarboxylase, and transcarboxylase reactions. As such, these molecules may be employed in small or large-scale synthesis of either carboxylated moieties or decarboxylated substrate, or in chemical processes that require the production or interconversion of these compounds. Such processes are known in the art (see, e.g., Ullmann et al. (1999) Ullmann's Encyclopedia of Industrial Chemistry, 6th ed. VCH: Weinheim; Gutcho (1983) Chemicals by Fermentation. Park ridge, N.J.: Noyes Data Corporation (ISBN 0818805086); Rehm et al. (eds.) (1993) Biotechnology, 2nd ed. VCH: Weinheim; and Michal, G. (1999) Biochemical Pathways: An Atlas of Biochemistry and Molecular Biology. New York: John Wiley & Sons, and references contained therein.)

The isolated nucleic acid molecules of the invention can be used, for example, to express BRE protein (e.g., via a recombinant expression vector in a host cell in gene therapy applications), to detect BRE mRNA (e.g., in a biological sample) or a genetic alteration in a BRE gene, and to modulate BRE activity, as described further below. The BRE proteins can be used to treat disorders characterized by insufficient or excessive production of a BRE substrate or production of BRE inhibitors. In addition, the BRE proteins can be used to screen for naturally occurring BRE substrates, to screen for drugs or compounds which modulate BRE activity, as well as to treat disorders characterized by insufficient or excessive production of BRE protein or production of BRE protein forms which have decreased, aberrant or unwanted activity compared to BRE wild type protein, preferably a BE-associated disorder. As used herein, a "BE-associated disorder" includes a disorder, disease or condition which is caused or characterized by a misregulation (e.g., downregulation or upregulation) of a biotin enzyme-mediated activity (e.g., BE-mediated activity), for example, carboxylase activity or a decarboxylase activity. Biotin-associated disorders can detrimentally affect cellular functions such as cellular proliferation, growth, differentiation, or migration, cellular regulation of homeostasis, inter- or intra-cellular communication; tissue function, such as cardiac function or musculoskeletal function; systemic responses in an organism, such as nervous system responses, hormonal responses (e.g., insulin response), or immune responses; and protection of cells from toxic compounds (e.g., carcinogens, toxins, mutagens, and toxic byproducts of metabolic activity (e.g., reactive oxygen species)). Examples of biotin-associated disorders include CNS disorders such as cognitive and neurodegenerative disorders, examples of which include, but are not limited to, Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis, progressive supranuclear palsy, epilepsy, and Jakob-Creutzfieldt disease; autonomic function disorders such as hypertension and sleep disorders, and neuropsychiatric disorders, such as depression, schizophrenia, schizoaffective disorder, korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), and bipolar affective neurological disorders, e.g., migraine and obesity. Further CNS-related disorders include, for example, those listed in the American Psychiatric Association's Diagnostic and Statistical manual of Mental Disorders (DSM), the most current version of which is incorporated herein by reference in its entirety.

Further examples of biotin-associated disorders include cardiac-related disorders. Cardiovascular system disorders in which the BRE molecules of the invention may be directly or indirectly involved include arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrilation, Jervell syndrome, Lange-Nielsen syndrome, long-QT syndrome, congestive heart failure, sinus node dysfunction, angina, heart failure, hypertension, atrial fibrillation, atrial flutter, dilated cardiomyopathy, idiopathic cardiomyopathy, myocardial infarction, coronary artery disease, coronary artery spasm, and arrhythmia. BRE-mediated or related disorders also include disorders of the musculoskeletal system such as paralysis and muscle weakness, e.g., ataxia, myotonia, and myokymia.

BRE-associated disorders also include cellular proliferation, growth, differentiation, or migration disorders. Cellular proliferation, growth, differentiation, or migration disorders include those disorders that affect cell proliferation, growth, differentiation, or migration processes. As used herein, a "cellular proliferation, growth, differentiation, or migration process" is a process by which a cell increases in number, size or content, by which a cell develops a specialized set of characteristics which differ from that of other cells, or by which a cell moves closer to or further from a particular location or stimulus. The BRE molecules of the present invention are involved in signal transduction mechanisms, which are known to be involved in cellular growth, differentiation, and migration processes. Thus, the BRE molecules may modulate cellular growth, differentiation, or migration, and may play a role in disorders characterized by aberrantly regulated growth, differentiation, or migration. Such disorders include cancer, e.g., carcinoma, sarcoma, or leukemia; tumor angiogenesis and metastasis; skeletal dysplasia; hepatic disorders; and hematopoietic and/or myeloproliferative disorders.

BRE-associated or related disorders also include hormonal disorders, such as conditions or diseases in which the production and/or regulation of hormones in an organism is aberrant. Examples of such disorders and diseases include type I and type II diabetes mellitus, pituitary disorders (e.g., growth disorders), thyroid disorders (e.g., hypothyroidism or hyperthyroidism), and reproductive or fertility disorders (e.g., disorders which affect the organs of the reproductive system, e.g., the prostate gland, the uterus, or the vagina; disorders which involve an imbalance in the levels of a reproductive hormone in a subject; disorders affecting the ability of a subject to reproduce; and disorders affecting secondary sex characteristic development, e.g., adrenal hyperplasia).

BRE-associated or related disorders also include immune disorders, such as autoimmune disorders or immune deficiency disorders, e.g., congenital X-linked infantile hypogammaglobulinemia, transient hypogammaglobulinemia, common variable immunodeficiency, selective IgA deficiency, chronic mucocutaneous candidiasis, or severe combined immunodeficiency. BRE-associated or related disorders also include disorders affecting tissues in which BRE protein is expressed.

A. Screening Assays:

The invention provides a method (also referred to herein as a "screening assay") for identifying modulators, i.e., candidate or test compounds or agents (e.g., peptides, peptidomimetics, small molecules or other drugs) which bind to BRE proteins, have a stimulatory or inhibitory effect on, for example, BRE expression or BRE activity, or have a stimulatory or inhibitory effect on, for example, the expression or activity of BRE substrate.

These assays are designed to identify compounds that bind to a BRE protein, bind to other inter- or extra-cellular proteins that interact with a BRE protein, and/or interfere with the interaction of the BRE protein with other inter- or extra-cellular proteins. For example, in the case of the BRE protein, such techniques can be used to identify ligands for such a protein. A BRE protein modulator can, for example, be used to ameliorate cellular growth or proliferation diseases or disorders, e.g., cancer, or nutritional difficulties, organic aciduria, neurologic abnormalities, and cutaneous distress. Such compounds may include, but are not limited to BRE peptides, anti-BRE antibodies, or small organic or inorganic compounds. Such compounds may also include other cellular proteins or peptides.

Compounds identified via assays such as those described herein may be useful, for example, for ameliorating cellular growth and proliferation diseases or disorders. In instances whereby a cellular growth or proliferation disease condition results from an overall lower level of BRE gene expression and/or BRE protein in a cell or tissue, compounds that interact with the BRE protein may include compounds which accentuate or amplify the activity of the bound BRE protein. Such compounds would bring about an effective increase in the level of BRE protein activity, thus ameliorating symptoms. In other instances, mutations within the BRE gene may cause aberrant types or excessive amounts of BRE proteins to be made which have a deleterious effect that leads to a cellular growth or proliferation disease or disorder. Similarly, physiological conditions may cause an excessive increase in BRE gene expression leading to a cellular growth or proliferation disease or disorder. In such cases, compounds that bind to a BRE protein may be identified that inhibit the activity of the BRE protein. Assays for testing the effectiveness of compounds identified by techniques such as those described in this section are discussed herein.

In one embodiment, the invention provides assays for screening candidate or test compounds which are substrates of a BRE protein or polypeptide or biologically active portion thereof (e.g., energy transduction metabolites, urea cycle metabolites, lipid metabolism metabolites, amino acid precursors, nucleic acid precursors). In another embodiment, the invention provides assays for screening candidate or test compounds which bind to or modulate the activity of a BRE protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses a BRE protein or biologically active portion thereof is contacted with a test compound and the ability of the test compound to modulate BRE activity is determined. Determining the ability of the test compound to modulate BRE activity can be accomplished by monitoring, for example, the production of one or more specific metabolites in a cell which expresses BRE (see, e.g., Saada et al. (2000) *Biochem Biophys. Res. Commun.* 269: 382–386). The cell, for example, can be of mammalian origin, e.g., an epithelial or neuronal cell. The ability of the test compound to modulate BRE binding to a substrate (e.g., an energy transduction metabolite, a urea cycle metabolite, a lipid metabolism metabolite, an amino acid precursor, a nucleic acid precursor) or to bind to BRE can also be determined. Determining the ability of the test compound to modulate BRE binding to a substrate can be accomplished, for example, by coupling the BRE substrate with a radioisotope or enzymatic label such that binding of the BRE substrate to BRE can be determined by detecting the labeled BRE substrate in a complex. Alternatively, BRE could be coupled with a radioisotope or enzymatic label to monitor the ability of a test compound to modulate BRE binding to a BRE substrate in a complex. Determining the ability of the test compound to bind BRE can be accomplished, for example, by coupling the compound with a radioisotope or enzymatic label such that binding of the compound to BRE can be determined by detecting the labeled compound in a complex. For example, compounds (e.g., BRE substrates) can be labeled with $^{125}I$, $^{35}S$, $^{14}C$, or $^{3}H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., a BRE substrate) to interact with BRE without the labeling of any of the interactants. For example, a microphysiometer can be used to detect the interaction of a compound with BRE without the labeling of either the compound or the BRE. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and BRE.

In another embodiment, an assay is a cell-based assay comprising contacting a cell expressing a BRE target molecule (e.g., a BRE substrate) with a test compound and determining the ability of the test compound to modulate (e.g., stimulate or inhibit) the activity of the BRE target molecule. Determining the ability of the test compound to modulate the activity of a BRE target molecule can be accomplished, for example, by determining the ability of the BRE protein to bind to or interact with the BRE target molecule.

Determining the ability of the BRE protein, or a biologically active fragment thereof, to bind to or interact with a BRE target molecule can be accomplished by one of the methods described above for determining direct binding. In a preferred embodiment, determining the ability of the BRE protein to bind to or interact with a BRE target molecule can be accomplished by determining the activity of the target molecule. For example, the activity of the target molecule can be determined by detecting induction of a cellular response (i.e., cell proliferation, migration and/or metabolic activity), detecting catalytic/enzymatic activity of the target on an appropriate substrate, detecting the induction of a reporter gene (comprising a target-responsive regulatory element operatively linked to a nucleic acid encoding a detectable marker, e.g., luciferase), or detecting a target-regulated cellular response.

In yet another embodiment, an assay of the present invention is a cell-free assay in which a BRE protein or biologically active portion thereof is contacted with a test compound and the ability of the test compound to bind to the BRE protein or biologically active portion thereof is determined. Preferred biologically active portions of the BRE proteins to be used in assays of the present invention include fragments which participate in interactions with non-BRE molecules, e.g., fragments with high surface probability scores (see, for example, FIGS. 34A–B). Binding of the test compound to the BRE protein can be determined either directly or indirectly as described above. In a preferred embodiment, the assay includes contacting the BRE protein or biologically active portion thereof with a known compound which binds BRE to form an assay mixture, contacting the assay mixture with a test compound, and determining the ability of the test compound to interact with a BRE protein, wherein determining the ability of the test compound to interact with a BRE protein comprises determining the ability of the test compound to preferentially bind to BRE or biologically active portion thereof as compared to the known compound.

In another embodiment, the assay is a cell-free assay in which a BRE protein or biologically active portion thereof is contacted with a test compound and the ability of the test compound to modulate (e.g., stimulate or inhibit) the activity of the BRE protein or biologically active portion thereof is determined. Determining the ability of the test compound to modulate the activity of a BRE protein can be accomplished, for example, by determining the ability of the BRE protein to bind to a BRE target molecule by one of the methods described above for determining direct binding. Determining the ability of the BRE protein to bind to a BRE target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIACORE™). Changes in the optical phenomenon of surface plasmon resonance (SPR) can be used as an indication of real-time reactions between biological molecules.

In an alternative embodiment, determining the ability of the test compound to modulate the activity of a BRE protein can be accomplished by determining the ability of the BRE protein to interact with and/or convert a BRE substrate (e.g., to produce a specific metabolite).

In an alternative embodiment, determining the ability of the test compound to modulate the activity of a BRE protein can be accomplished by determining the ability of the BRE protein to further modulate the activity of a downstream effector of a BRE target molecule. For example, the activity of the effector molecule on an appropriate target can be determined or the binding of the effector to an appropriate target can be determined as previously described.

In yet another embodiment, the cell-free assay involves contacting a BRE protein or biologically active portion thereof with a known compound (e.g., a BRE substrate) which binds the BRE protein to form an assay mixture, contacting the assay mixture with a test compound, and determining the ability of the test compound to interact with the BRE protein, wherein determining the ability of the test compound to interact with the BRE protein comprises determining the ability of the BRE protein to preferentially bind to or modulate the activity of a BRE target protein, e.g., catalyze the cleavage, e.g., the hydrolytic cleavage, of a chemical bond within the target protein.

In more than one embodiment of the above assay methods of the present invention, it may be desirable to immobilize either BRE or its target molecule to facilitate separation of complexed from uncomplexed forms of one or both of the proteins, as well as to accommodate automation of the assay. Binding of a test compound to a BRE protein, or interaction of a BRE protein with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/BRE fusion proteins or glutathione-S-transferase/target fusion proteins can be adsorbed onto glutathione SEPHAROSE™ beads (Sigma Chemical, St. Louis, Mo.) or glutathione derivatized microtitre plates, which are then combined with the test compound or the test compound and either the non-adsorbed target protein or BRE protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of BRE binding or activity determined using standard techniques.

Other techniques for immobilizing proteins on matrices can also be used in the screening assays of the invention. For example, either a BRE protein or a BRE target molecule can be immobilized utilizing conjugation of biotin and streptavidin. Biotinylated BRE protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with BRE protein or target molecules but which do not interfere with binding of the BRE protein to its target molecule can be derivatized to the wells of the plate, and unbound target or BRE protein trapped in the wells by antibody conjugation. Methods for detecting such complexes, in addition to those described above for the GST-immobilized complexes, include immunodetection of complexes using antibodies reactive with the BRE protein or target molecule, as well as enzyme-linked assays which rely on detecting an enzymatic activity associated with the BRE protein or target molecule.

In another embodiment, modulators of BRE expression are identified in a method wherein a cell is contacted with a candidate compound and the expression of BRE mRNA or protein in the cell is determined. The level of expression of BRE mRNA or protein in the presence of the candidate compound is compared to the level of expression of BRE mRNA or protein in the absence of the candidate compound. The candidate compound can then be identified as a modulator of BRE expression based on this comparison. For example, when expression of BRE mRNA or protein is greater (statistically significantly greater) in the presence of the candidate compound than in its absence, the candidate compound is identified as a stimulator of BRE mRNA or protein expression. Alternatively, when expression of BRE mRNA or protein is less (statistically significantly less) in the presence of the candidate compound than in its absence, the candidate compound is identified as an inhibitor of BRE mRNA or protein expression. The level of BRE mRNA or protein expression in the cells can be determined by methods described herein for detecting BRE mRNA or protein.

In yet another aspect of the invention, the BRE proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with BRE ("BRE binding proteins" or "HYDL-1-bp") and are involved in BRE activity. Such BRE binding proteins are also likely to be involved in the propagation of signals by the BRE proteins or BRE targets as, for example, downstream elements of a BRE-mediated signaling pathway. Alternatively, such BRE binding proteins are likely to be BRE inhibitors.

The two-hybrid system is based on the modular nature of most transcription factors, which consist of separable DNA-binding and activation domains. Briefly, the assay utilizes two different DNA constructs. In one construct, the gene that codes for a BRE protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a BRE-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the BRE protein.

In another aspect, the invention pertains to a combination of two or more of the assays described herein. For example, a modulating agent can be identified using a cell-based or a cell free assay, and the ability of the agent to modulate the activity of a BRE protein can be confirmed in vivo, e.g., in an animal such as an animal model for cellular transformation and/or tumorigenesis, or an animal model for a metabolic disorder.

This invention further pertains to novel agents identified by the above-described screening assays. Accordingly, it is within the scope of this invention to further use an agent identified as described herein in an appropriate animal model. For example, an agent identified as described herein (e.g., a BRE modulating agent, an antisense BRE nucleic acid molecule, a BRE-specific antibody, or a BRE binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein. In one embodiment, the invention features a method of treating a subject having a cellular growth or proliferation disease or disorder that involves administering to the subject a BRE modulator such that treatment occurs. In another embodiment, the invention features a method of treating a subject having cancer, e.g., colon cancer or lung cancer, that involves treating a subject with a BRE modulator, such that treatment occurs. Preferred BRE modulators include, but are not limited to, BRE proteins or biologically active fragments, BRE nucleic acid molecules, BRE antibodies, ribozymes, and BRE antisense oligonucleotides designed based on the BRE nucleotide sequences disclosed herein, as well as peptides, organic and non-organic small molecules identified as being capable of modulating BRE expression and/or activity, for example, according to at least one of the screening assays described herein.

Any of the compounds, including but not limited to compounds such as those identified in the foregoing assay systems, may be tested for the ability to ameliorate cellular growth or proliferation disease or disorder symptoms. Cell-based and animal model-based assays for the identification of compounds exhibiting such an ability to ameliorate cellular growth or proliferation disease or disorder systems are described herein.

In one aspect, cell-based systems, as described herein, may be used to identify compounds which may act to ameliorate cellular growth or proliferation disease or disorder symptoms. For example, such cell systems may be exposed to a compound, suspected of exhibiting an ability to ameliorate cellular growth or proliferation disease or disorder symptoms, at a sufficient concentration and for a time sufficient to elicit such an amelioration of cellular growth or proliferation disease or disorder symptoms in the exposed cells. After exposure, the cells are examined to determine whether one or more of the cellular growth or proliferation disease or disorder cellular phenotypes has been altered to resemble a more normal or more wild type, non-cellular growth or proliferation disease or disorder phenotype. Cellular phenotypes that are associated with cellular growth and/or proliferation disease states include aberrant proliferation, growth, and migration, anchorage independent growth, and loss of contact inhibition.

In addition, animal-based cellular growth or proliferation disease or disorder systems, such as those described herein, may be used to identify compounds capable of ameliorating cellular growth or proliferation disease or disorder symptoms. Such animal models may be used as test substrates for the identification of drugs, pharmaceuticals, therapies, and interventions which may be effective in treating cellular growth or proliferation disorders or diseases. For example, animal models may be exposed to a compound, suspected of exhibiting an ability to cellular growth or proliferation disease or disorder symptoms, at a sufficient concentration and for a time sufficient to elicit such an amelioration of cellular growth or proliferation disease or disorder symptoms in the exposed animals. The response of the animals to the exposure may be monitored by assessing the reversal of disorders or symptoms associated with cellular growth or proliferation disease, for example, reduction in tumor burden, tumor size, and invasive and/or metastatic potential before and after treatment.

With regard to intervention, any treatments which reverse any aspect of cellular growth or proliferation disease or disorder symptoms should be considered as candidates for human cellular growth or proliferation disease or disorder therapeutic intervention. Dosages of test agents may be determined by deriving dose-response curves.

Additionally, gene expression patterns may be utilized to assess the ability of a compound to ameliorate cellular growth and/or proliferation disease symptoms. For example, the expression pattern of one or more genes may form part of a "gene expression profile" or "transcriptional profile" which may be then be used in such an assessment. "Gene expression profile" or "transcriptional profile", as used herein, includes the pattern of mRNA expression obtained for a given tissue or cell type under a given set of conditions. Such conditions may include, but are not limited to, cell growth, proliferation, differentiation, transformation, tumorigenesis, metastasis, and carcinogen exposure. Gene expression profiles may be generated, for example, by utilizing a differential display procedure, Northern analysis and/or RT-PCR. In one embodiment, BRE gene sequences may be used as probes and/or PCR primers for the generation and corroboration of such gene expression profiles.

Gene expression profiles may be characterized for known states within the cell-and/or animal-based model systems. Subsequently, these known gene expression profiles may be compared to ascertain the effect a test compound has to modify such gene expression profiles, and to cause the profile to more closely resemble that of a more desirable profile.

For example, administration of a compound may cause the gene expression profile of a cellular growth or proliferation disease or disorder model system to more closely resemble the control system. Administration of a compound may, alternatively, cause the gene expression profile of a control system to begin to mimic a cellular growth and/or proliferation disease state. Such a compound may, for example, be used in further characterizing the compound of interest, or may be used in the generation of additional animal models.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the BRE nucleotide sequences, described herein, can be used to map the location of the BRE genes on a chromosome. The mapping of the BRE sequences to chromosomes is an important first step in correlating these sequences with genes associated with disease.

Briefly, BRE genes can be mapped to chromosomes by preparing PCR primers (preferably 15–25 bp in length) from the BRE nucleotide sequences. Computer analysis of the BRE sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the BRE sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220: 919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the BRE nucleotide sequences to design oligonucleotide primers, sublocalization can be achieved with panels of fragments from specific chromosomes. Other mapping strategies which can similarly be used to map a BRE sequence to its chromosome include in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the BRE gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The BRE sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the BRE nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The BRE nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:16 can comfortably provide positive individual identification with a panel of perhaps 10 to 1,000 primers which each yield a noncoding amplified sequence of 100 bases. If predicted coding sequences, such as those in SEQ ID NO:18 or 6 are used, a more appropriate number of primers for positive individual identification would be 500–2,000.

If a panel of reagents from BRE nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of BRE Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:16 are particularly appropriate for this use as greater numbers of polymorphisms occur in the noncoding regions, making it easier to differentiate individuals using this technique. Examples of polynucleotide reagents include the BRE nucleotide sequences or portions thereof, e.g., fragments derived from the noncoding regions of SEQ ID NO:16 having a length of at least 20 bases, preferably at least 30 bases.

The BRE nucleotide sequences described herein can further be used to provide polynucleotide reagents, e.g., labeled or labelable probes which can be used in, for example, an in situ hybridization technique, to identify a specific tissue, e.g., thymus or brain tissue. This can be very useful in cases where a forensic pathologist is presented with a tissue of unknown origin. Panels of such BRE probes can be used to identify tissue by species and/or by organ type.

In a similar fashion, these reagents, e.g., BRE primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining BRE protein and/or nucleic acid expression as well as BRE activity, in the context of a biological sample (e.g., blood, serum, cells, tissue) to thereby determine whether an individual is afflicted with a disease or disorder, or is at risk of developing a disorder, associated with aberrant or unwanted BRE expression or activity. The invention also provides for prognostic (or predictive) assays for determining whether an individual is at risk of developing a disorder associated with BRE protein, nucleic acid expression or activity. For example, mutations in a BRE gene can be assayed in a biological sample. Such assays can be used for prognostic or predictive purpose to thereby prophylactically treat an individual prior to the onset of a disorder characterized by or associated with BRE protein, nucleic acid expression or activity.

Another aspect of the invention pertains to monitoring the influence of agents (e.g., drugs, compounds) on the expression or activity of BRE in clinical trials.

These and other agents are described in further detail in the following sections.

1. Diagnostic Assays

The present invention encompasses methods for diagnostic and prognostic evaluation of cellular growth or proliferation disorders or diseases, e.g., cancer, including, but not limited to colon cancer and lung cancer, and for the identification of subjects exhibiting a predisposition to such conditions.

An exemplary method for detecting the presence or absence of BRE protein or nucleic acid in a biological sample involves obtaining a biological sample from a test subject and contacting the biological sample with a compound or an agent capable of detecting BRE protein or nucleic acid (e.g., mRNA, or genomic DNA) that encodes BRE protein such that the presence of BRE protein or nucleic acid is detected in the biological sample. A preferred agent for detecting BRE mRNA or genomic DNA is a labeled nucleic acid probe capable of hybridizing to BRE mRNA or genomic DNA. The nucleic acid probe can be, for example, the BRE nucleic acid set forth in SEQ ID NO:16 or 18, or a portion thereof, such as an oligonucleotide of at least 15, 30, 50, 100, 250 or 500 nucleotides in length and sufficient to specifically hybridize under stringent conditions to BRE mRNA or genomic DNA. Other suitable probes for use in the diagnostic assays of the invention are described herein.

A preferred agent for detecting BRE protein is an antibody capable of binding to BRE protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect BRE mRNA, protein, or genomic DNA in a biological sample in vitro as well as in vivo. For example, in vitro techniques for detection of BRE mRNA include Northern hybridizations and in situ hybridizations. In vitro techniques for detection of BRE protein include enzyme linked immunosorbent assays (ELISAs), Western blots, immunoprecipitations and immunofluorescence. In vitro techniques for detection of BRE genomic DNA include Southern hybridizations. Furthermore, in vivo techniques for detection of BRE protein include introducing into a subject a labeled anti-BRE antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting BRE protein, mRNA, or genomic DNA, such that the presence of BRE protein, mRNA or genomic DNA is detected in the biological sample, and comparing the presence of BRE protein, mRNA or genomic DNA in the control sample with the presence of BRE protein, mRNA or genomic DNA in the test sample.

The invention also encompasses kits for detecting the presence of BRE in a biological sample. For example, the kit can comprise a labeled compound or agent capable of detecting BRE protein or mRNA in a biological sample; means for determining the amount of BRE in the sample; and means for comparing the amount of BRE in the sample with a standard. The compound or agent can be packaged in a suitable container. The kit can further comprise instructions for using the kit to detect BRE protein or nucleic acid.

In one embodiment, increased levels of BRE protein, mRNA or DNA (e.g., cDNA or genomic DNA) in the test sample as compared to the control sample is determinative or predictive of a BRE-related aberrancy (e.g., a cellular growth or proliferation disease or disorder, for example, cancer). For example, 2-fold levels of expression of BRE in the test sample as compared to the control sample may be determinative or predictive of a BRE-related aberrancy. Preferably, 5-fold, 10-fold, 100-fold, 500-fold or 1000-fold levels of expression of BRE in the test sample as compared to the control sample may be determinative or predictive of a BRE-related aberrancy.

2. Prognostic Assays

The diagnostic methods described herein can furthermore be utilized to identify subjects having or at risk of developing a disease or disorder associated with aberrant or unwanted BRE expression or activity. As used herein, the term "aberrant" includes a BRE expression or activity which deviates from the wild type BRE expression or activity. Aberrant expression or activity includes increased or decreased expression or activity, as well as expression or activity which does riot follow the wild type developmental pattern of expression or the subcellular pattern of expression. For example, aberrant BRE expression or activity is intended to include the cases in which a mutation in the BRE gene causes the BRE gene to be under-expressed or over-expressed and situations in which such mutations result in a non-functional BRE protein or a protein which does not function in a wild-type fashion, e.g., a protein which does not interact with a BRE substrate, or one which interacts with a non-BRE substrate. As used herein, the term "unwanted" includes an unwanted phenomenon involved in a biological response such as cellular proliferation. For example, the term unwanted includes a BRE expression or activity which is undesirable in a subject.

The assays described herein, such as the preceding diagnostic assays or the following assays, can be utilized to identify a subject having or at risk of developing a disorder associated with a misregulation in BRE protein activity or nucleic acid expression, such as a CNS disorder (e.g., a cognitive or neurodegenerative disorder), a cellular proliferation, growth, differentiation, or migration disorder, a cardiovascular disorder, musculoskeletal disorder, an immune disorder, or a hormonal disorder. Alternatively, the prognostic assays can be utilized to identify a subject having or at risk for developing a disorder associated with a misregulation in BRE protein activity or nucleic acid expression, such as a CNS disorder, a cellular proliferation, growth, differentiation, or migration disorder, a musculoskeletal disorder, a cardiovascular disorder, an immune disorder, or a hormonal disorder. Thus, the present invention provides a method for identifying a disease or disorder associated with aberrant or unwanted BRE expression or activity in which a test sample is obtained from a subject and BRE protein or nucleic acid (e.g., mRNA or genomic DNA) is detected, wherein the presence of BRE protein or nucleic acid is diagnostic for a subject having or at risk of developing a disease or disorder associated with aberrant or unwanted BRE expression or activity. As used herein, a "test sample" refers to a biological sample obtained from a subject of interest. For example, a test sample can be a biological fluid (e.g., cerebrospinal fluid or serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted BRE expression or activity. For example, such methods can be used to determine whether a subject can be effectively treated with an agent for a CNS disorder, a muscular disorder, a cellular proliferation, growth, differentiation, or migration disorder, an immune disorder, or a hormonal disorder. Thus, the present invention provides methods for determining whether a subject can be effectively treated with an agent for a disorder associated with aberrant or unwanted BRE expression or activity in which a test sample is obtained and BRE protein or nucleic acid expression or activity is detected (e.g., wherein the abundance of BRE protein or nucleic acid expression or activity is diagnostic for a subject that can be administered the agent to treat a disorder associated with aberrant or unwanted BRE expression or activity).

The methods of the invention can also be used to detect genetic alterations in a BRE gene, thereby determining if a subject with the altered gene is at risk for a disorder characterized by misregulation in BRE protein activity or nucleic acid expression, such as a CNS disorder, a musculoskeletal disorder, a cellular proliferation, growth, differentiation, or migration disorder, a cardiovascular disorder, an immune disorder, or a hormonal disorder. In preferred embodiments, the methods include detecting, in a sample of cells from the subject, the presence or absence of a genetic alteration characterized by at least one of an alteration affecting the integrity of a gene encoding a BRE-protein, or the mis-expression of the BRE gene. For example, such genetic alterations can be detected by ascertaining the existence of at least one of 1) a deletion of one or more nucleotides from a BRE gene; 2) an addition of one or more nucleotides to a BRE gene; 3) a substitution of one or more nucleotides of a BRE gene, 4) a chromosomal rearrangement of a BRE gene; 5) an alteration in the level of a messenger RNA transcript of a BRE gene, 6) aberrant modification of a BRE gene, such as of the methylation pattern of the genomic DNA, 7) the presence of a non-wild type splicing pattern of a messenger RNA transcript of a BRE gene, 8) a non-wild type level of a BRE-protein, 9) allelic loss of a BRE gene, and 10) inappropriate post-translational modification of a BRE-protein. As described herein, there are a large number of assays known in the art which can be used for detecting alterations in a BRE gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in a BRE gene (see Abravaya et al. (1995) *Nucleic Acids Res* 0.23:675–682). This method can include the steps of collecting a sample of cells from a subject, isolating nucleic acid (e.g., genomic, mRNA or both) from the cells of the sample, contacting the nucleic acid sample with one or more primers which specifically hybridize to a BRE gene under conditions such that hybridization and amplification of the BRE gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a BRE gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in BRE can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in BRE can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the BRE gene and detect mutations by comparing the sequence of the sample BRE with the corresponding wild-type (control) sequence.

Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the BRE gene include methods in which protection from cleavage agents is used to detect mismatched bases in RNA/RNA or RNA/DNA heteroduplexes (Myers et al. (1985) *Science* 230: 1242). In general, the art technique of "mismatch cleavage" starts by providing heteroduplexes of formed by hybridizing (labeled) RNA or DNA containing the wild-type BRE sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in BRE cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a BRE sequence, e.g., a wild-type BRE sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in BRE genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125–144; and Hayashi (1992) *Genet. Anal. Tech. Appl.* 9:73–79). Single-stranded DNA fragments of sample and control BRE nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a BRE gene.

Furthermore, any cell type or tissue in which BRE is expressed may be utilized in the prognostic assays described herein.

3. Monitoring of Effects During Clinical Trials

Monitoring the influence of agents (e.g., drugs) on the expression or activity of a BRE protein (e.g., the maintenance of cellular homeostasis) can be applied not only in basic drug screening, but also in clinical trials. For example, the effectiveness of an agent determined by a screening assay as described herein to increase BRE gene expression, protein levels, or upregulate BRE activity, can be monitored in clinical trials of subjects exhibiting decreased BRE gene expression, protein levels, or downregulated BRE activity. Alternatively, the effectiveness of an agent determined by a screening assay to decrease BRE gene expression, protein levels, or downregulate BRE activity, can be monitored in clinical trials of subjects exhibiting increased BRE gene expression, protein levels, or upregulated BRE activity. In such clinical trials, the expression or activity of a BRE gene, and preferably, other genes that have been implicated in, for example, a BRE-associated disorder can be used as a "read out" or markers of the phenotype of a particular cell.

For example, and not by way of limitation, genes, including BRE, that are modulated in cells by treatment with an agent (e.g., compound, drug or small molecule) which modulates BRE activity (e.g., identified in a screening assay as described herein) can be identified. Thus, to study the effect of agents on BRE-associated disorders (e.g., disorders characterized by deregulated cell proliferation and/or migration), for example, in a clinical trial, cells can be isolated and RNA prepared and analyzed for the levels of expression of BRE and other genes implicated in the BRE-associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of BRE or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a BRE protein, mRNA, or genomic DNA in the preadministration sample; (iii) obtaining one or more post-administration samples from the subject; (iv) detecting the level of expression or activity of the BRE protein, mRNA, or genomic DNA in the post-administration samples; (v) comparing the level of expression or activity of the BRE protein, mRNA, or genomic DNA in the pre-administration sample with the BRE protein, mRNA, or genomic DNA in the post administration sample or samples; and (vi) altering the administration of the agent to the subject accordingly. For example, increased administration of the agent may be desirable to increase the expression or activity of BRE to higher levels than detected, i.e., to increase the effectiveness of the agent. Alternatively, decreased administration of the agent may be desirable to decrease expression or activity of BRE to lower levels than detected, i.e. to decrease the effectiveness of the agent. According to such an embodiment, BRE expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder or having a disorder associated with aberrant or unwanted BRE expression or activity, e.g., a biotin-associated disorder such as a CNS disorder; a cellular proliferation, growth, differentiation, or migration disorder; a, musculoskeletal disorder; a cardiovascular disorder; an immune disorder; or a hormonal disorder. With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the BRE molecules of the present invention or BRE modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted BRE expression or activity, by administering to the subject a BRE or an agent which modulates BRE expression or at least one BRE activity. Subjects at risk for a disease which is caused or contributed to by aberrant or unwanted BRE expression or activity can be identified by, for example, any or a combination of diagnostic or prognostic assays as described herein. Administration of a prophylactic agent can occur prior to the manifestation of symptoms characteristic of the BRE aberrancy, such that a disease or disorder is prevented or, alternatively, delayed in its progression. Depending on the type of BRE aberrancy, for example, a BRE, BRE agonist or BRE antagonist agent can be used for treating the subject. The appropriate agent can be determined based on screening assays described herein.

2. Therapeutic Methods

Another aspect of the invention pertains to methods of modulating BRE expression or activity for therapeutic purposes. Accordingly, in an exemplary embodiment, the modulatory method of the invention involves contacting a cell with a BRE or agent that modulates one or more of the activities of BRE protein activity associated with the cell. An agent that modulates BRE protein activity can be an agent as described herein, such as a nucleic acid or a protein, a naturally-occurring substrate molecule of a BRE protein (e.g., energy transduction metabolites, urea cycle metabolites, lipid metabolism metabolites, amino acid precursors, nucleic acid precursors), a BRE antibody, a BRE agonist or antagonist, a peptidomimetic of a BRE agonist or antagonist, or other small molecule. In one embodiment, the agent stimulates one or more BRE activities. Examples of such stimulatory agents include active BRE protein and a nucleic acid molecule encoding BRE that has been introduced into the cell. In another embodiment, the agent inhibits one or more BRE activities. Examples of such inhibitory agents include antisense BRE nucleic acid molecules, anti-BRE antibodies, and BRE inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a BRE protein or nucleic acid molecule. In one embodiment, the method involves administering an agent (e.g., an agent identified by a screening assay described herein), or combination of agents that modulates (e.g., upregulates or downregulates) BRE expression or activity. In another embodiment, the method involves administering a BRE protein or nucleic acid molecule as therapy to compensate for reduced, aberrant, or unwanted BRE expression or activity.

Stimulation of BRE activity is desirable in situations in which BRE is abnormally downregulated and/or in which increased BRE activity is likely to have a beneficial effect. Likewise, inhibition of BRE activity is desirable in situations in which BRE is abnormally upregulated and/or in which decreased BRE activity is likely to have a beneficial effect.

(i) Methods for Inhibiting Target Gene Expression, Synthesis, or Activity

As discussed above, genes involved in cellular growth or proliferation diseases or disorders may cause such disorders via an increased level of gene activity. In some cases, such up-regulation may have a causative or exacerbating effect on the disease state. A variety of techniques may be used to inhibit the expression, synthesis, or activity of such genes and/or proteins.

For example, compounds such as those identified through assays described above, which exhibit inhibitory activity, may be used in accordance with the invention to ameliorate cellular growth or proliferation disease or disorder symptoms. Such molecules may include, but are not limited to, small organic molecules, peptides, antibodies, and the like.

For example, compounds can be administered that compete with endogenous ligand for the BRE protein. The resulting reduction in the amount of ligand-bound BRE protein will modulate endothelial cell physiology. Compounds that can be particularly useful for this purpose include, for example, soluble proteins or peptides, such as peptides comprising one or more of the extracellular domains, or portions and/or analogs thereof, of the BRE protein, including, for example, soluble fusion proteins such as Ig-tailed fusion proteins. (For a discussion of the production of Ig-tailed fusion proteins, see, for example, U.S. Pat. No. 5,116,964). Alternatively, compounds, such as ligand analogs or antibodies, that bind to the BRE receptor site, but do not activate the protein, (e.g., receptor-ligand antagonists) can be effective in inhibiting BRE protein activity.

Further, antisense and ribozyme molecules, as described herein, which inhibit expression of the BRE gene may also be used in accordance with the invention to inhibit aberrant BRE gene activity. Still further, triple helix molecules may be utilized in inhibiting aberrant BRE gene activity.

Antibodies that are both specific for the BRE protein and interfere with its activity may also be used to modulate or inhibit BRE protein function. Such antibodies may be generated using standard techniques described herein, against the BRE protein itself or against peptides corresponding to portions of the protein. Such antibodies include but are not limited to polyclonal, monoclonal, Fab fragments, single chain antibodies, or chimeric antibodies.

In instances where the target gene protein is intracellular and whole antibodies are used, internalizing antibodies may be preferred. Lipofectin liposomes may be used to deliver the antibody or a fragment of the Fab region which binds to the target epitope into cells. Where fragments of the antibody are used, the smallest inhibitory fragment which binds to the target protein's binding domain is preferred. For example, peptides having an amino acid sequence corresponding to the domain of the variable region of the antibody that binds to the target gene protein may be used. Such peptides may be synthesized chemically or produced via recombinant DNA technology using methods well known in the art (described in, for example, Creighton (1983), supra; and Sambrook et al. (1989) supra). Single chain neutralizing antibodies which bind to intracellular target gene epitopes may also be administered. Such single chain antibodies may be administered, for example, by expressing nucleotide sequences encoding single-chain antibodies within the target cell population by utilizing, for example, techniques such as those described in Marasco et al. (1993) *Proc. Natl. Acad. Sci. USA* 90:7889–7893).

Any of the administration techniques described below which are appropriate for peptide administration may be utilized to effectively administer inhibitory target gene antibodies to their site of action.

(ii) Methods for Restoring or Enhancing Target Gene Activity

Genes that cause cellular growth or proliferation diseases or disorders may be underexpressed within cellular growth or proliferative situations. Alternatively, the activity of the protein products of such genes may be decreased, leading to the development of cellular growth or proliferation disease or disorder symptoms. Such down-regulation of gene expression or decrease of protein activity might have a causative or exacerbating effect on the disease state.

In some cases, genes that are up-regulated in the disease state might be exerting a protective effect. A variety of techniques may be used to increase the expression, synthesis, or activity of genes and/or proteins that exert a protective effect in response to cellular growth or proliferation disease or disorder conditions.

Described in this section are methods whereby the level BRE activity may be increased to levels wherein cellular growth or proliferation disease or disorder symptoms are ameliorated. The level of BRE activity may be increased, for example, by either increasing the level of BRE gene expression or by increasing the level of active BRE protein which is present.

For example, a BRE protein, at a level sufficient to ameliorate cellular growth or proliferation disease or disorder symptoms may be administered to a patient exhibiting such symptoms. Any of the techniques discussed below may be used for such administration. One of skill in the art will readily be able to ascertain the concentration of effective, non-toxic doses of the BRE protein, utilizing techniques such as those described above.

Additionally, RNA sequences encoding a BRE protein may be directly administered to a patient exhibiting cellular growth or proliferation disease or disorder symptoms, at a concentration sufficient to produce a level of BRE protein such that cellular growth or proliferation disease or disorder symptoms are ameliorated. Any of the techniques discussed below, which achieve intracellular administration of compounds, such as, for example, liposome administration, may be used for the administration of such RNA molecules. The RNA molecules may be produced, for example, by recombinant techniques such as those described herein.

Further, subjects may be treated by gene replacement therapy. One or more copies of a BRE gene, or a portion thereof, that directs the production of a normal BRE protein with BRE function, may be inserted into cells using vectors which include, but are not limited to adenovirus, adeno-associated virus, and retrovirus vectors, in addition to other particles that introduce DNA into cells, such as liposomes. Additionally, techniques such as those described above may be used for the introduction of BRE gene sequences into human cells.

Cells, preferably, autologous cells, containing BRE expressing gene sequences may then be introduced or reintroduced into the subject at positions which allow for the amelioration of cellular growth or proliferation disease or disorder symptoms. Such cell replacement techniques may be preferred, for example, when the gene product is a secreted, extracellular gene product.

3. Pharmacogenomics

The BRE molecules of the present invention, as well as agents, or modulators which have a stimulatory or inhibitory effect on BRE activity (e.g., BRE gene expression) as identified by a screening assay described herein can be administered to individuals to treat (prophylactically or therapeutically) BRE-associated disorders (e.g., proliferative disorders, CNS disorders, cardiac disorders, metabolic disorders, or muscular disorders) associated with aberrant or unwanted BRE activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a BRE molecule or BRE modulator as well as tailoring the dosage and/or therapeutic regimen of treatment with a BRE molecule or BRE modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11): 983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug target is known (e.g., a BRE protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C 19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a BRE molecule or BRE modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a BRE molecule or BRE modulator, such as a modulator identified by one of the exemplary screening assays described herein.

This invention is further illustrated by the following examples which should not be construed as limiting. The contents of all references, patents and published patent applications cited throughout this application, as well as the Figures and the Sequence Listing, are incorporated herein by reference.

EXAMPLES

Example 1

Identification and Characterization of Human BRE cDNA

In this example, the identification and characterization of the gene encoding human BRE (clone Fbh32263) is described.

Isolation of the BRE cDNA

The invention is based, at least in part, on the discovery of a human genes encoding a novel protein, referred to herein as BRE. The entire sequence of human clones Fbh32263, was determined and found to contain an open reading frame termed human "BRE", set forth in FIGS. 33A–E. The amino acid sequence of the human BRE expression product is set forth in FIGS. 33A–E. The BRE protein sequence set forth in SEQ ID NO:17 comprises about 725 amino acids and is shown in FIGS. 33A–E. The coding region (open reading frame) of SEQ ID NO:16, is set forth as SEQ ID NO:18.

Analysis of the Human BRE Molecule

An analysis of the possible cellular localization of the BRE protein based on its amino acid sequence was performed using the methods and algorithms described in Nakai and Kanehisa (1992) *Genomics* 14:897–911, and at PSORT website maintained by the Human Genome Center at the Institute of Medical Science in the University of Tokyo, Japan (psort.nibb.ac.jp). The results of the analysis predict that human BRE (SEQ ID NO:17) is localized intracellularly (probabilities are shown for localization to e.g., 73.9% in the mitochondria, 13.0% in the cytoplasm, 4.3% in the Golgi apparatus, 4.3% in extracellular spaces (e.g., cell wall), and 4.3% in the endoplasmic reticulum).

A search of the amino acid sequence of BRE was also performed against the HMM database (FIGS. 35A–F). This search resulted in the identification of a "carbamoyl-phosphate synthase L chain, N-terminal domain" ("CPSase N-terminal domain") in the amino acid sequence of BRE (SEQ ID NO:17) at about residues 48–160 (score: 184.0). This search also resulted in the identification of a "carbamoyl-phosphate synthase L chain, ATP binding domain" ("CPSase ATP-binding domain") in the amino acid sequence of BRE (SEQ ID NO:17) at about residues 163–376, which is characterized by a "carbamoyl phosphate synthase subdomain signature". This domain is implicated in ATP binding and/or catalytic activity. This search also resulted in the identification of a "biotin/lipoyl attachment domain" ("Biotin requiring enzyme domain") in the amino acid sequence of BRE (SEQ ID NO:17) at about residues 650–714 (score: 67.8). This domain binds biotin and contains, or can be characterized by, the presence of a "biotin requiring enzyme attachment site", which itself is characterized by the inclusion of a conserved lysine residue. This search also resulted in the identification of a "Biotin carboxylase C-terminal domain" in the amino acid sequence of BRE (SEQ ID NO:17) at about residues 383–490, which is implicated in enzymatic activity. This search also resulted in the identification of a "D-ala D-ala ligase" in the amino acid sequence of BRE (SEQ ID NO:17) at about residues 163–233 (score: 11.1).

Further domain motifs were identified by using the amino acid sequence of BRE (SEQ ID NO:17) to search through the ProDom database (see ProDom website at Institut National de la Recherche Agronomique (INRA)/Central National de la Recherche Scientifique (CNRA), Toulouse, France). Numerous matches against protein domains described as "Biotin synthetase, Acetyl-CoA biotin ligase, Biotin dihydrolipoaide pyruvate dehydrogenase carboxylase, and the like were identified. A search was also performed against the Prosite database, and resulted in the identification of a "biotin requiring enzyme attachment site" at residues 671–688, (Prosite accession number PS00188).

A structural, hydrophobicity, and antigenicity analysis of the human Fbh32263 protein was undertaken. The results of this analysis are set forth in FIGS. 34A–B.

A global comparison of human BRE (SEQ ID NO:17, depicted as "32263.pro") with known transcarboxylases was completed. The results of this alignment are set forth in FIGS. 36A–D. The known transcarboxylases used in the comparison are 3-methylcrotonyl-CoA carboxylase precursor from *Arabidopsis* (GenBank No. AAA67356; depicted as "thal.pro"); a protein similar to propionyl-CoA carboxylase alpha chain from *C. elegans* (GenBank No. AAA93384; depicted as "celegans.pro"); and propionyl-CoA carboxylase alpha chain precursor from *H. sapiens* (GenBank No. PO$_{5165}$; depicted as "human.pro"). The CPSase domain of the human BRE is indicated in italics. The biotin-requiring enzyme domain of the human BRE is underlined.

Example 2

Expression of Recombinant BRE Protein in Bacterial Cells

In this example, BRE is expressed as a recombinant glutathione-S-transferase (GST) fusion polypeptide in *E. coli* and the fusion polypeptide is isolated and characterized. Specifically, BRE is fused to GST and this fusion polypeptide is expressed in *E. coli*, e.g., strain PEB199. Expression of the GST-BRE fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant BRE Protein in COS Cells

To express the BRE gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire BRE protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the BRE DNA sequence is amplified by PCR using two primers. The 5' primer contains the restriction site of interest followed by approximately twenty nucleotides of the BRE coding sequence starting from the initiation codon; the 3' end sequence contains complementary sequences to the other restriction site of interest, a translation stop codon, the HA tag or FLAG tag and the last 20 nucleotides of the BRE coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the BRE gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the BRE-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989. The expression of the BRE polypeptide is detected by radiolabeling ($^{35}$S-methionine or $^{35}$S-cysteine available from NEN, Boston, Mass., can be used) and immunoprecipitation (Harlow, E. and Lane, D. *Antibodies. A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA-specific monoclonal antibody. Precipitated polypeptides are then analyzed by SDS-PAGE.

Alternatively, DNA containing the BRE coding sequence is cloned directly into the polylinker of the pcDNA/Amp vector using the appropriate restriction sites. The resulting plasmid is transfected into COS cells in the manner described above, and the expression of the BRE polypeptide is detected by radiolabeling and immunoprecipitation using a BRE specific monoclonal antibody.

Example 4

Tissue Distribution of BRE by Taqman Expression Analysis

Tissue Expression Analysis of BRE mRNA Using Taqman Analysis

This example describes the tissue distribution of human BRE mRNA (huBRE) in a variety of cells and tissues, as determined using the TaqMan™ procedure. The Taqman™ procedure is a quantitative, reverse transcription PCR-based approach for detecting mRNA. The RT-PCR reaction exploits the 5' nuclease activity of AmpliTaq Gold™ DNA Polymerase to cleave a TaqMan™ probe during PCR. Briefly, cDNA was generated from the samples of interest, e.g., tumor samples and normal samples, cell lines and the like, and used as the starting material for PCR amplification. In addition to the 5' and 3' gene-specific primers, a gene-specific oligonucleotide probe (complementary to the region being amplified) was included in the reaction (i.e., the Taqman™ probe). The TaqMan™ probe includes the oligonucleotide with a fluorescent reporter dye covalently linked to the 5' end of the probe (such as FAM (6-carboxyfluorescein), TET (6-carboxy-4,7,2',7'-tetrachlorofluorescein), JOE (6-carboxy-4,5-dichloro-2,7-dimethoxyfluorescein), or VIC) and a quencher dye (TAMRA (6-carboxy-N,N,N',N'-tetramethylrhodamine) at the 3' end of the probe.

When the fluorescently tagged oligonucleotide is intact, the fluorescent signal from the 5' dye is quenched. As PCR proceeds, the 5' to 3' nucleolytic activity of taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a way of quantitating the initial template concentration. Accumulation of PCR products is detected directly by monitoring the increase in fluorescence of the reporter dye. When the probe is intact, the proximity of the reporter dye to the quencher dye results in suppression of the reporter fluorescence. During PCR, if the target of interest is present, the probe specifically anneals between the forward and reverse primer sites. The 5'-3' nucleolytic activity of the AmpliTaq™ Gold DNA Polymerase cleaves the probe between the reporter and the quencher only if the probe hybridizes to the target. The probe fragments are then displaced from the target, and polymerization of the strand continues. The 3' end of the probe is blocked to prevent extension of the probe during PCR. This process occurs in every cycle and does not interfere with the exponential accumulation of product. Samples can be internally controlled by the addition of a second set of primers/probe specific for a housekeeping gene such as $\beta_2$ microglobulin which has been labeled with a different fluor on the 5' end (typically JOE).

To determine the level of BRE in various tissues a primer/probe set was designed using Primer Express software and primary cDNA sequence information. Total RNA was prepared from a series of tissues using an RNeasy kit from Qiagen First strand cDNA was prepared from one µg total RNA using an oligo dT primer and Superscript II reverse transcriptase (GIBCO-BRL). cDNA obtained from approximately 50 ng total RNA was used per TaqMan reaction. Mock cDNA synthesis in the absence of reverse transcriptase resulted in samples with no detectable PCR amplification of the control gene confirms efficient removal of genomic DNA contamination.

An array of human tissues were tested. The results of one such analysis are depicted in Table I. Expression was greatest in brain, kidney, pancreas, ovary and thymus, and also high in nerve tissues, including dorsal root ganglion and glial cells.

TABLE I

Expression on BRE in various types of human tissues.

| Tissue Type | Mean | β 2 Mean | ∂∂ Ct | Expression |
|---|---|---|---|---|
| Artery normal | 34.07 | 23.3 | 10.77 | 0.57 |
| Vein normal | 35.05 | 21.2 | 13.85 | 0.07 |
| Aortic SMC EARLY | 32.38 | 24.59 | 7.78 | 4.55 |
| Aortic SMC LATE | 31.38 | 24.06 | 7.32 | 6.26 |
| Static HUVEC | 27.61 | 21.66 | 5.94 | 16.29 |
| Shear HUVEC | 28.46 | 21.45 | 7.01 | 7.76 |
| Heart normal | 26.72 | 20.05 | 6.67 | 9.85 |
| Heart CHF | 25.55 | 19.98 | 5.57 | 21.12 |
| Kidney | 25.71 | 21.43 | 4.28 | 51.47 |
| Skeletal Muscle | 30.73 | 21.9 | 8.84 | 2.18 |
| Adipose normal | 27.94 | 20.43 | 7.51 | 5.49 |
| Pancreas | 26.97 | 22.17 | 4.79 | 36.02 |
| primary osteoblasts | 29.45 | 20.08 | 9.37 | 1.52 |
| Osteoclasts (diff) | 34.77 | 18.34 | 16.43 | 0.01 |
| Skin normal | 29.38 | 22.16 | 7.22 | 6.71 |
| Spinal cord normal | 27.71 | 20.54 | 7.17 | 6.92 |
| Brain Cortex normal | 25.59 | 22.18 | 3.42 | 93.75 |
| Brain Hypothalamus normal | 27.25 | 22.13 | 5.12 | 28.76 |
| Nerve | 30.9 | 24.7 | 6.2 | 13.65 |
| DRG (Dorsal Root Ganglion) | 28.98 | 22.91 | 6.07 | 14.88 |
| Glial Cells (Astrocytes) | 26.77 | 21.03 | 5.74 | 18.71 |
| Glioblastoma | 27.18 | 19.04 | 8.14 | 3.54 |
| Breast normal | 30.06 | 21.5 | 8.55 | 2.66 |
| Breast tumor | 26.09 | 19.32 | 6.77 | 9.16 |
| Ovary normal | 26.45 | 20.91 | 5.53 | 21.64 |
| Ovary Tumor | 30.02 | 21.16 | 8.86 | 2.16 |
| Prostate Normal | 27.38 | 20.36 | 7.02 | 7.7 |
| Prostate Tumor | 26.43 | 18.73 | 7.71 | 4.79 |
| Epithelial Cells (Prostate) | 28.87 | 22.16 | 6.71 | 9.59 |
| Colon normal | 29.62 | 18.91 | 10.71 | 0.6 |
| Colon Tumor | 25.76 | 19.77 | 5.99 | 15.79 |
| Lung normal | 30.06 | 19.52 | 10.54 | 0.67 |
| Lung tumor | 25.48 | 19.57 | 5.91 | 16.63 |
| Lung COPD | 27.38 | 19.61 | 7.76 | 4.6 |
| Colon IBD | 33.4 | 19.18 | 14.22 | 0.05 |
| Liver normal | 27.32 | 20.76 | 6.56 | 10.6 |
| Liver fibrosis | 29.02 | 22.59 | 6.42 | 11.64 |
| Dermal Cells-fibroblasts | 28.39 | 20.13 | 8.27 | 3.25 |
| Spleen normal | 29.41 | 19.36 | 10.05 | 0.94 |
| Tonsil normal | 27.07 | 18.26 | 8.81 | 2.23 |
| Lymph node | 27.15 | 19.72 | 7.43 | 5.8 |
| Thymus normal | 27.95 | 22.1 | 5.84 | 17.4 |
| Skin-Decubitus | 30.24 | 21.88 | 8.36 | 3.04 |
| Synovium | 35.66 | 21.22 | 14.45 | 0.04 |
| BM-MNC (Bone marrow mononuclear cells) | 28.1 | 17.94 | 10.16 | 0.87 |
| Activated PBMC | 30.24 | 16.93 | 13.32 | 0.1 |

Moreover, increased expression of BRE was observed in tumors of colon, breast and lung as compared to normal colon, breast and lung respectively. Also, BRE was observed to be decreased in ovary tumors versus non-cancerous ovarian tissue. Therefore, arrays including additional samples of cancerous and non-cancerous human tissues were tested for BRE expression according to the above-described Taqman procedure. The results of such analyses are depicted in Tables II and III

TABLE II

Expression on BRE in various types of cancerous and non-cancerous tissues.

| Tissue Type | Mean | β 2 Mean | ∂∂ Ct | Expression |
|---|---|---|---|---|
| NDR 13 Breast N | 31.05 | 21.69 | 9.36 | 1.53 |
| PIT 400 Breast N | 30.96 | 19.59 | 11.37 | 0.38 |

TABLE II-continued

Expression on BRE in various types of cancerous and non-cancerous tissues.

| Tissue Type | Mean | β 2 Mean | ∂∂ Ct | Expression |
|---|---|---|---|---|
| PIT 56 Breast N | 31.8 | 23.56 | 8.23 | 3.32 |
| MDA 106 Breast T | 30.16 | 22.09 | 8.07 | 3.71 |
| MDA 234 Breast T | 30.01 | 18.56 | 11.45 | 0.36 |
| NDR 57 Breast T | 31.93 | 20.14 | 11.8 | 0.28 |
| MDA 304 Breast T | 31.41 | 20.27 | 11.13 | 0.45 |
| NDR 58 Breast T | 25.96 | 18.64 | 7.33 | 6.24 |
| NDR 132 Breast T | 29.52 | 21.87 | 7.64 | 5 |
| NDR 07 Breast T | 32.48 | 20.31 | 12.18 | 0.22 |
| PIT 208 Ovary N | 27.41 | 20.26 | 7.15 | 7.04 |
| CHT 620 Ovary N | 29.09 | 20.39 | 8.71 | 2.4 |
| CHT 619 Ovary N | 27.24 | 20.6 | 6.64 | 10.03 |
| MDA 293 Ovary N | 31.38 | 24.74 | 6.64 | 10.03 |
| CLN 03 Ovary T | 30.73 | 20.27 | 10.46 | 0.71 |
| CLN 05 Ovary T | 30.66 | 20.01 | 10.65 | 0.62 |
| CLN 17 Ovary T | 29 | 21.06 | 7.95 | 4.04 |
| CLN 07 Ovary T | 31.05 | 19.98 | 11.07 | 0.47 |
| CLN 08 Ovary T | 29.88 | 19.49 | 10.39 | 0.75 |
| MDA 216 Ovary T | 32.1 | 21.74 | 10.36 | 0.76 |
| CLN 012 Ovary T | 29.7 | 22.23 | 7.47 | 5.62 |
| MDA 25 Ovary T | 30.7 | 22.97 | 7.73 | 4.71 |
| MDA 183 Lung N | 36.07 | 18.79 | 17.29 | 0 |
| CLN 930 Lung N | 32.81 | 21.36 | 11.46 | 0.36 |
| MDA 185 Lung N | 32.95 | 20.38 | 12.57 | 0.16 |
| CHT 816 Lung T | 33.88 | 18.11 | 15.77 | 0.02 |
| CHT 814 Lung T | 25.25 | 17.56 | 7.7 | 4.83 |
| MDA 262 Lung T | 29.52 | 23.85 | 5.67 | 19.64 |
| CHT 911 Lung T | 25 | 19.52 | 5.48 | 22.41 |
| CHT 726 Lung T | 30.16 | 18.52 | 11.64 | 0.31 |
| MDA 259 Lung T | 26.82 | 20.36 | 6.46 | 11.32 |
| CHT 845 Lung T | 28.09 | 21.43 | 6.66 | 9.92 |
| CHT 832 Lung T | 29.7 | 19.93 | 9.77 | 1.15 |
| MDA 253 Lung T | 25 | 19.16 | 5.84 | 17.46 |

TABLE III

Expression on BRE in various types of cancerous and non-cancerous tissues.

| Tissue Type | Mean | β 2 Mean | ∂∂ Ct | Expression |
|---|---|---|---|---|
| CHT 396 Colon N | 36.17 | 19.27 | 16.9 | 0 |
| CHT 519 Colon N | 40 | 20.75 | 19.25 | 0 |
| CHT 416 Colon N | 34.14 | 19.88 | 14.27 | 0.05 |
| CHT 452 Colon N | 38.46 | 18.33 | 20.13 | 0 |
| CHT 398 Colon T | 27.14 | 20.11 | 7.02 | 7.7 |
| CHT 807 Colon T | 33.47 | 17.08 | 16.39 | 0.01 |
| CHT 805 Colon T | 32.24 | 18.96 | 13.29 | 0.1 |
| CHT 528 Colon T | 34.58 | 18.27 | 16.31 | 0.01 |
| CHT 368 Colon T | 34.48 | 18.17 | 16.32 | 0.01 |
| CHT 372 Colon T | 32.49 | 20.16 | 12.33 | 0.19 |
| CHT 01 Liver Met | 29.61 | 18.99 | 10.62 | 0.64 |
| CHT 3 Liver Met | 28.56 | 21.02 | 7.54 | 5.39 |
| CHT 896 Liver Met | 29.43 | 19.66 | 9.77 | 1.15 |
| CHT 340 Liver Met | 29.51 | 21.38 | 8.13 | 3.57 |
| PIT 260 Liver N | 28.27 | 18.18 | 10.09 | 0.92 |
| PIT 229 Liver N | 32.4 | 25.54 | 6.86 | 8.61 |
| MGH 16 Brain N | 30.47 | 24.46 | 6 | 15.57 |
| MCL 53 Brain N | 28.64 | 24.29 | 4.36 | 48.87 |
| MCL 377 Brain N | 30.52 | 25.02 | 5.51 | 21.94 |
| MCL 390 Brain N | 28.32 | 23.72 | 4.6 | 41.23 |
| Astrocytes | 27.73 | 20.48 | 7.24 | 6.62 |
| CHT 201 Brain T | 35.27 | 21.15 | 14.12 | 0 |
| CHT 216 Brain T | 27.36 | 17.74 | 9.63 | 1.27 |
| CHT 501 Brain T | 29.84 | 20.98 | 8.86 | 2.15 |
| CHT 1273 Brain T | 27.02 | 22.11 | 4.92 | 33.03 |
| CHT 828 Brain T | 34.14 | 22.36 | 11.79 | 0.28 |
| A24 HMVEC-Arr | 29.25 | 18.73 | 10.53 | 0.68 |
| C48 HMVEC-Prol | 29.18 | 20.4 | 8.79 | 2.27 |
| BWH 54 Fetal Liver | 28.85 | 22.45 | 6.41 | 11.8 |
| BWH 75 Fetal Liver | 27.56 | 20.15 | 7.41 | 5.88 |

Notably, expression was upregulated in 3 of 7 breast tumor samples as compared to normal, in 6 of 8 lung tumor samples versus normal, in one colon tumor sample versus normal, and downregulated in brain, and ovary tumor samples versus normal brain and ovary respectively. Differential expression was also noted in liver metastasis as compared to normal liver samples.

To further investigate the underlying cause of the change in expression in cancerous tissue, e.g. angiogenesis, BRE expression levels were measured in various cancerous samples by quantitative PCR using the Taqman™ procedure as described above. The relative levels of BRE expression in various samples is depicted in Table IV below.

TABLE IV

Expression of BRE in various cancerous samples.

| | | Average 32263 | Average Beta 2 | D Ct | Relative Expression |
|---|---|---|---|---|---|
| ONC 101 | Hemangioma | 31.25 | 18.88 | 12.37 | 0.19 |
| ONC 102 | Hemangioma | 28.17 | 18.32 | 9.85 | 1.08 |
| ONC 103 | Hemangioma | 29.05 | 19.13 | 9.92 | 1.04 |
| NDR 203 | Normal Kidney | 26.77 | 20.60 | 6.17 | 13.94 |
| PIT 213 | Renal Cell Carcinoma | 29.75 | 20.08 | 9.67 | 1.23 |
| CHT 732 | Wilms Tumor | 26.25 | 19.51 | 6.75 | 9.32 |
| CHT 765 | Wilms Tumor | 27.62 | 21.83 | 5.79 | 18.14 |
| NDR 295 | Skin | 29.84 | 21.28 | 8.56 | 2.66 |
| CHT 1424 | Uterine Adenocarcinoma | 26.25 | 18.98 | 7.27 | 6.48 |
| CHT 1238 | Neuroblastoma | 26.96 | 19.10 | 7.87 | 4.29 |
| BWH 78 | Fetal Adrenal | 26.38 | 18.87 | 7.51 | 5.49 |
| BWH 74 | Fetal Kidney | 26.02 | 20.30 | 5 72 | 19.04 |
| BWH 4 | Fetal Heart | 25.26 | 18.00 | 7.26 | 6 55 |
| MPI 849 | Normal Heart | 27.42 | 19.13 | 8.30 | 3.18 |
| NDR 764 | Cartilage | 31.57 | 24.28 | 7.29 | 6 41 |
| CLN 746 | Spinal cord | 28.50 | 21.05 | 7.45 | 5 72 |
| CHT | lymphangioma | 31.71 | 23.66 | 8.05 | 3.77 |

TABLE IV-continued

Expression of BRE in various cancerous samples.

|  |  | Average 32263 | Average Beta 2 | D Ct | Relative Expression |
|---|---|---|---|---|---|
| 1753 CLN 944 | Endometrial polyps | 33.29 | 25.26 | 8.03 | 3.84 |
| NEB 3 | Synovium (RA) | 31.79 | 22.38 | 9.41 | 1.47 |
| CLN 1221 | Hyperkeratotic skin | 30.59 | 22.62 | 7.97 | 3.99 |

Expression was greatest in fetal and normal kidney and Wilm's tumor cells, and also high in tissues such as uterine adenocarcinoma, heart, cartilage and spinal cord.

To further investigate the expression of BRE in tumorigenic cells, BRE expression levels were measured in various cell types suitable for animal transplantation by quantitative PCR using the Taqman™ procedure as described above. The relative levels of BRE expression in various samples is depicted in Table V below.

TABLE V

Expression of BRE in a xenograft panel.

| Tissue Type | 32263 Mean | β 2 Mean | ∂∂ Ct | Expression |
|---|---|---|---|---|
| MCF-7 Breast T | 24.11 | 20.97 | 3.15 | 113.05 |
| ZR75 Breast T | 26.66 | 22.97 | 3.69 | 77.21 |
| T47D Breast T | 23.36 | 20.74 | 2.63 | 162.10 |
| MDA 231 Breast T | 25.32 | 19.5 | 5.83 | 17.58 |
| MDA 435 Breast T | 26.08 | 19.32 | 6.75 | 9.26 |
| SKBr3 Breast | 25.52 | 21.66 | 3.87 | 68.63 |
| DLD 1 Colon T (stage C) | 26.91 | 22.7 | 4.2 | 54.41 |
| SW480 Colon T (stage B) | 27.5 | 23.43 | 4.08 | 59.33 |
| SW620 Colon T (stage C) | 25.39 | 20.7 | 4.69 | 38.74 |
| HCT116 (colon) | 29.17 | 23.45 | 5.71 | 19.04 |
| HT29 (colon) | 26.16 | 19.05 | 7.12 | 7.21 |
| Colo 205 (colon) | 24.72 | 18.06 | 6.66 | 9.89 |
| NCIH125 (lung) | 27.45 | 22.07 | 5.38 | 23.93 |
| NCIH67 (lung) | 27.13 | 22.61 | 4.52 | 43.59 |
| NCIH322 (lung) | 25.93 | 22.41 | 3.52 | 87.47 |
| NCIH460 (lung) | 29.22 | 21.32 | 7.9 | 4.19 |
| A549 (lung) | 28.35 | 23.34 | 5.01 | 31.03 |
| NHBE (lung) | 28.66 | 22.51 | 6.15 | 14.08 |
| SKOV-3 ovary | 29.67 | 20.16 | 9.51 | 1.37 |
| OVCAR-3 ovary | 26.78 | 22.81 | 3.98 | 63.59 |
| 293 Baby Kidney | 27.5 | 22.63 | 4.87 | 34.32 |
| 293T Baby Kidney | 28.33 | 23.92 | 4.41 | 47.04 |

Notably, BRE expression was highest in cells such as breast tumors and breast cancer cell lines and NCIH322. Expression was also noted in colon tumors, ovary and kidney cells.

Example 5

Tissue Distribution of BRE by in situ Analysis

For in situ analysis, various tissues, e.g. tissues obtained from normal lung and colon and lung and colon tumors, were first frozen on dry ice. Ten-micrometer-thick sections of the tissues were post-fixed with 4% formaldehyde in DEPC treated 1× phosphate-buffered saline at room temperature for 10 minutes before being rinsed twice in DEPC 1× phosphate-buffered saline and once in 0.1 M triethanolamine-HCl (pH 8.0). Following incubation in 0.25% acetic anhydride-0.1 M triethanolamine-HCl for 10 minutes, sections were rinsed in DEPC 2×SSC (1×SSC is 0.15M NaCl plus 0.015M sodium citrate). Tissue was then dehydrated through a series of ethanol washes, incubated in 100% chloroform for 5 minutes, and then rinsed in 100% ethanol for 1 minute and 95% ethanol for 1 minute and allowed to air dry.

Hybridizations were performed with $^{35}$S-radiolabeled ($5 \times 10^7$ cpm/ml) cRNA probes. Probes were incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1× Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides were washed with 2×SSC. Sections are then sequentially incubated at 37° C. in TNE (a solution containing 10 mM Tris-HCl (pH 7.6), 500 mM NaCl, and 1 mM EDTA), for 10 minutes, in TNE with 10%g of RNase A per ml for 30 minutes, and finally in TNE for 10 minutes. Slides were then rinsed with 2×SSC at room temperature, washed with 2×SSC at 50° C. for 1 hour, washed with 0.2×SSC at 55° C. for 1 hour, and 0.2×SSC at 60° C. for 1 hour. Sections were then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

As depicted in Table VI below, the in situ hybridization results essentially agreed with the results of the Taqman analysis. In situ hybridization results a moderate signal in 3 of 4 primary colon tumors, and a strong signal in 3 of 4 colon tumors which had metastasized, e.g. to the liver. Similarly, BRE expression was undetectable in 1 normal lung sample tested, and moderate in 5 of 6 lung tumors tested. Ovary and breast tumor samples showed no expression. Expression was also strongly detectable in kidney tumors, e.g. Wilm's tumor and renal cell carcinoma.

| Spectrum | Tissue | Diagnosis | Expression |
|---|---|---|---|
| BREAST: 0/1 normals; 0/2 tumors | | | |
| NDR 17 | Breast | Tumor:WD-IDC, foci of DCIS | (−/−) |
| NDR 7 | Breast | IDC | (−/−) |
| CLN 100 | Breast | Normal | (−/−) |
| COLON: 0/1 normals; 3/4 primary tumors; 2/3 metastases | | | |
| CHT 910 | Colon | Tumor: MD-Invasive AC | (++/+) |
| CHT 890 | Colon | Tumor: M-PD Invasive AC | (+/−) |
| NDR 99 | Colon | Tumor: MD Invasive AC | (+/−) |
| CLN 609 | Colon | Tumor | (−/−) |
| NDR 77 | Colon | Met: Liver mets | (+/+) |
| NDR 100 | Colon | Met: AC in liver | (−) |
| CHT 1 | Colon | Met | (++/+) |
| CHT 72 | Colon | Met: MD-AC | (+/−) |
| CHT 521 | Colon | Normal | (−/−) |

-continued

| Spectrum | Tissue | Diagnosis | Expression |
|---|---|---|---|
| | | LUNG: 0/1 normal; 5/6 tumors | |
| CHT 446 | Lung | Tumor: Adeno M-WD invasive | (−/−) |
| CHT 799 | Lung | Tumor: PD-NSCC, squamous features | (+/−) |
| CHT 800 | Lung | Tumor: PD-NSCC, squamous features | (++/+) |
| MPI 323 | Lung | Tumor: SCLC | (+/−) |
| MPI 215 | Lung | Tumor: PD-SCLC | (++/+) |
| CHT 813 | Lung | Tumor: MD-squamous cell LC | (+/+) |
| MPI 216 | Lung | Normal | (−/−) |
| | | OVARY: 0/1 normal; 0/2 tumors | |
| MDA 300 | Ovary | Tumor: MD-AC | (−/−) |
| MDA 28 | Ovary | Tumor: low-grade serous | (−/−) |
| MDA 201 | Ovary | Normal | (−/−) |
| | | OTHER TISSUES: 2/4 | |
| CHT 734 | Kidney | Wilm's: blue cell tumor | (+++/+) |
| BWH 36 | Adrenal | Fetal: normal developing gland | (−/−) |
| PIT 213 | Kidney | RCC: F grade 3–4 | (++/+) |
| NEB 3 | Synovium | Inflamm: plasma cell infiltrates | (−/−) |

V. 50250, a Novel Human Lipase and uses Thereof

BACKGROUND OF THE INVENTION

Lipid metabolism and storage are important processes not only in normal cellular functioning, but also in such systemic processes as cardiovascular regulation and fat deposition. A family of enzymes that facilitate the hydrolysis of lipids, termed the lipase family, has been identified. These enzymes catalyze the hydrolysis of a variety of lipids and lipid-containing molecules into fatty acids and less-substituted lipid molecules.

Members of the lipase family are ubiquitous, and have been isolated from a wide variety of organisms, including bacteria, yeast, plants and animals. Lipases are serine esterases, and the lipase family is itself a subgroup of the alpha/beta hydrolase superfamily (Ollis et al. (1992) Protein Eng. 5: 197–211). All members of this superfamily share a conserved catalytic triad consisting of a nucleophilic serine, an aspartate and a glutamate residue in a conserved spatial relationship, where the serine is directly involved in the catalytic activity of the enzyme (Ollis et al. (1992), supra). Members of this superfamily also share an "oxyanion hole"—a region of localized oxygen radicals which stabilizes the transition state through hydrogen-bonding with two main chain nitrogen molecules (Dodson et al. (1992) Faraday Discuss 93: 95–105). The lipases are typically highly glycosylated; for example, human gastric lipase has been found to have four N-glycosylation sites located throughout the enzyme (Bodmer et al. (1987) Biochim. Biophys. Acta 909: 147–153).

Different lipases (e.g., human lipases) have different tissue distributions and different specificities, which permits them to be separately regulated depending on the needs of the organism. For example, lipases specific to the pancreas, to the stomach, and to the liver have been identified, having specificity for triglycerides, a variety of dietary lipids, and phospholipids and triglycerides of plasma lipoproteins, respectively. These enzymes are also adapted to different environmental conditions; for example, the gastric lipases only function at low pH, such as that found in the stomach. While lipases have substrate preferences, most of these enzymes will hydrolyze a wider range of substrates, albeit with varying degrees of efficiency (Gotor (1999) Bioorg. Med. Chem. 7: 2189–2197). Recently, lipases have been exploited in the biosynthesis and degradation of biologically important molecules that are otherwise difficult or expensive to synthesize chemically, such as chiral alcohols, lactones, and esters (Gotor (1999), supra).

Lipases play an important role in the breakdown of lipids and lipid-based compounds (e.g., triglycerides, phospholipids, and cholesterol esters) and in the production of fatty acids. These compounds are not only important in the normal functioning of cells (for example, fatty acids are key substituents in a variety of metabolic pathways, and are necessary for membrane biosynthesis, among many other functions), but also in intra- and inter-cellular communication (for example, fatty acids and other lipid degradation products serve as second messengers in a number of signal transduction pathways). As such, their activity contributes to the ability of the cell to grow and differentiate, to proliferate, and to communicate and interact with other cells. Lipases are also critical to the functioning of systemic processes, such as cardiovascular regulation, the ability to take up lipids from ingested food (absorption), and the ability to store lipids (deposition) as energy reserves (e.g., adipocyte formation). Underscoring the importance of this family of enzymes, modulation of the activity of one or more lipases has been linked to a number of human diseases, including Wolman's disease (Anderson et al. (1994) Proc. Natl. Acad. Sci. USA 91: 2718–2722), cholesteryl ester storage disease (CESD) (Pagani et al. (1996) Hum. Molec. Genet. 5: 1611–1617), and hyperlipoproteinemia type I (Ameis et al. (1991) J. Clin. Invest. 87: 1165–1170).

SUMMARY OF THE INVENTION

The present invention is based, at least in part, on the discovery of novel members of the family of lipase molecules, referred to herein as LP nucleic acid and protein molecules. The LP nucleic acid and protein molecules of the present invention are useful as modulating agents in regulating a variety of cellular processes, e.g., cellular proliferation, growth, differentiation, and/or migration. Accordingly, in one aspect, this invention provides isolated nucleic acid molecules encoding LP proteins or biologically active portions thereof, as well as nucleic acid fragments suitable as primers or hybridization probes for the detection of LP-encoding nucleic acids.

In one embodiment, an LP nucleic acid molecule of the invention is at least 50%, 55%, 60%, 65%, 70%, 75%, 80%, 85%, 90%, 95%, 96%, 97%, 98%, 99% or more identical to the nucleotide sequence (e.g., to the entire length of the nucleotide sequence) shown in SEQ ID NO:19, 21, 22, or 24 or a complement thereof.

In a preferred embodiment, the isolated nucleic acid molecule includes the nucleotide sequence shown in SEQ ID NO:19, 21, 22, or 24, or a complement thereof. In another embodiment, the nucleic acid molecule includes SEQ ID NO:21 and nucleotides 1–2 of SEQ ID NO:19. In yet a further embodiment, the nucleic acid molecule includes SEQ ID NO:21 and nucleotides 795–2031 of SEQ ID NO:19. In yet another embodiment, the nucleic acid molecule includes SEQ ID NO:24 and nucleotides 1–47 of SEQ ID NO:22. In yet a further embodiment, the nucleic acid molecule includes SEQ ID NO:24 and nucleotides 795–2031 of SEQ ID NO:22. In another preferred embodiment, the nucleic acid molecule consists of the nucleotide sequence shown in SEQ ID NO:19, 21, 22, or 24.

In another embodiment, the nucleic acid molecule of the present invention includes nucleotides residues 1–62 and/or 928–1049 and/or 1617–1705 and/or 1883–2031 of SEQ ID NO:19.

In another embodiment, an LP nucleic acid molecule includes a nucleotide sequence encoding a protein having an amino acid sequence sufficiently identical to the amino acid sequence of SEQ ID NO:20 or 23. In a preferred embodiment, an LP nucleic acid molecule includes a nucleotide sequence encoding a protein having an amino acid sequence at least 50%, 55%, 60%, 65%, 70%, 75%, 80%, 85%, 90%, 95%, 96%, 97%, 98%, 99% or more identical to the entire length of the amino acid sequence of SEQ ID NO:20 or 23.

In another preferred embodiment, an isolated nucleic acid molecule encodes the amino acid sequence of human LP. In yet another preferred embodiment, the nucleic acid molecule includes a nucleotide sequence encoding a protein having the amino acid sequence of SEQ ID NO:20 or 23. In yet another preferred embodiment, the nucleic acid molecule is at least 50, 100, 150, 177, 200, 250, 300, 350, 400, 450, 500, 550, 600, 650, 700, 750, 756, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000 or more nucleotides in length. In a further preferred embodiment, the nucleic acid molecule is at least 50, 100, 150, 200, 250, 300, 350, 400, 450, 500, 550, 600, 650, 700, 750, 756, 800, 850, 900, 950, 1000, 1021, 1050, 1100, 1150, 1200, 1250, 1300, 1350, 1400, 1450, 1500, 1550, 1600, 1650, 1700, 1750, 1800, 1850, 1900, 1950, 2000 or more nucleotides in length and encodes a protein having an LP activity (as described herein).

Another embodiment of the invention features nucleic acid molecules, preferably LP nucleic acid molecules, which specifically detect LP nucleic acid molecules relative to nucleic acid molecules encoding non-LP proteins. For example, in one embodiment, such a nucleic acid molecule is at least 20, 30, 40, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000 or more nucleotides in length and hybridizes under stringent conditions to a nucleic acid molecule comprising the nucleotide sequence shown in SEQ ID NO:19, 21, 22, or 24, or a complement thereof.

In preferred embodiments, the nucleic acid molecules are at least 15 (e.g., 15 contiguous) nucleotides in length and hybridize under stringent conditions to the nucleotide molecule set forth in SEQ ID NO:19 or 22, or a complement thereof.

In other preferred embodiments, the nucleic acid molecule encodes a naturally occurring allelic variant of a polypeptide comprising the amino acid sequence of SEQ ID NO:20 or 23, wherein the nucleic acid molecule hybridizes to a complement of a nucleic acid molecule comprising SEQ ID NO:19, 21, 22, or 24, respectively, under stringent conditions.

Another embodiment of the invention provides an isolated nucleic acid molecule which is antisense to an LP nucleic acid molecule, e.g., the coding strand of an LP nucleic acid molecule.

Another aspect of the invention provides a vector comprising an LP nucleic acid molecule. In certain embodiments, the vector is a recombinant expression vector. In another embodiment, the invention provides a host cell containing a vector of the invention. In yet another embodiment, the invention provides a host cell containing a nucleic acid molecule of the invention. The invention also provides a method for producing a protein, preferably an LP protein, by culturing in a suitable medium, a host cell, e.g., a mammalian host cell such as a non-human mammalian cell, of the invention containing a recombinant expression vector, such that the protein is produced.

Another aspect of this invention features isolated or recombinant LP proteins and polypeptides. In one embodiment, an isolated LP protein includes at least one or more of the following motifs or domains: a signal peptide, an N-glycosylation site, a lipase/acylhydrolase domain with a GDSL-like motif, and/or an LP signature motif.

In a preferred embodiment, an LP protein includes at least one or more of the following motifs or domains: a signal peptide, an N-glycosylation site, a lipase/acylhydrolase domain with a GDSL-like motif, and/or an LP signature motif, and has an amino acid sequence at least about 50%, 55%, 60%, 65%, 67%, 68%, 70%, 75%, 80%, 85%, 90%, 95%, 96%, 97%, 98%, 99% or more identical to the amino acid sequence of SEQ ID NO:20 or 23.

In another preferred embodiment, an LP protein includes at least one or more of the following motifs or domains: a signal peptide, an N-glycosylation site, a lipase/acylhydrolase domain with a GDSL-like motif, and/or an LP signature motif, and has an LP activity (as described herein).

In yet another preferred embodiment, an LP protein includes at least one or more of the following motifs or domains: a signal peptide, an N-glycosylation site, a lipase/acylhydrolase domain with a GDSL-like motif, and/or an LP signature motif, and is encoded by a nucleic acid molecule having a nucleotide sequence which hybridizes under stringent hybridization conditions to a complement of a nucleic acid molecule comprising the nucleotide sequence of SEQ ID NO:19, 21, 22, or 24.

In another embodiment, the invention features fragments of the protein having the amino acid sequence of SEQ ID NO:20 or 23, wherein the fragment comprises at least 15, 30, 50, 100, 150, 200, 250 or 263 amino acids (e.g., contiguous amino acids) of the amino acid sequence of SEQ ID NO:20 or 23. In another embodiment, an LP protein has the amino acid sequence of SEQ ID NO:20 or 23.

In another embodiment, the invention features an LP protein which is encoded by a nucleic acid molecule consisting of a nucleotide sequence at least about 50%, 55%, 60%, 65%, 70%, 75%, 80%, 85%, 90%, 95%, 96%, 97%, 98%, 99% or more identical to a nucleotide sequence of SEQ ID NO:19, 21, 22, or 24, or a complement thereof. This invention further features an LP protein which is encoded by a nucleic acid molecule consisting of a nucleotide sequence which hybridizes under stringent hybridization conditions to a nucleic acid molecule comprising the nucleotide sequence of SEQ ID NO:19, 21, 22, or 24, or a complement thereof.

The proteins of the present invention or portions thereof, e.g., biologically active portions thereof, can be operatively linked to a non-LP polypeptide (e.g., heterologous amino acid sequences) to form fusion proteins. The invention further features antibodies, such as monoclonal or polyclonal antibodies, that specifically bind proteins of the invention, preferably LP proteins. In addition, the LP proteins or biologically active portions thereof can be incorporated into pharmaceutical compositions, which optionally include pharmaceutically acceptable carriers.

In another aspect, the present invention provides a method for detecting the presence of an LP nucleic acid molecule, protein, or polypeptide in a biological sample by contacting the biological sample with an agent capable of detecting an LP nucleic acid molecule, protein, or polypeptide such that the presence of an LP nucleic acid molecule, protein or polypeptide is detected in the biological sample.

In another aspect, the present invention provides a method for detecting the presence of LP activity in a biological sample by contacting the biological sample with an agent capable of detecting an indicator of LP activity such that the presence of LP activity is detected in the biological sample.

In another aspect, the invention provides a method for modulating LP activity comprising contacting a cell capable of expressing LP with an agent that modulates LP activity such that LP activity in the cell is modulated. In one embodiment, the agent inhibits LP activity. In another embodiment, the agent stimulates LP activity. In one embodiment, the agent is an antibody that specifically binds to an LP protein. In another embodiment, the agent modulates expression of LP by modulating transcription of an LP gene or translation of an LP mRNA. In yet another embodiment, the agent is a nucleic acid molecule having a nucleotide sequence that is antisense to the coding strand of an LP mRNA or an LP gene.

In one embodiment, the methods of the present invention are used to treat a subject having a disorder characterized by aberrant or unwanted LP protein or nucleic acid expression or activity by administering an agent which is an LP modulator to the subject. In one embodiment, the LP modulator is an LP protein. In another embodiment the LP modulator is an LP nucleic acid molecule. In yet another embodiment, the LP modulator is a peptide, peptidomimetic, or other small molecule. In a preferred embodiment, the disorder characterized by aberrant or unwanted LP protein or nucleic acid expression is a lipase-associated disorder, e.g., a cell proliferation, growth, differentiation, or migration disorder, a cardiovascular disorder, or disorders of lipid absorption or deposition.

The present invention also provides diagnostic assays for identifying the presence or absence of a genetic alteration characterized by at least one of (i) aberrant modification or mutation of a gene encoding an LP protein; (ii) mis-regulation of the gene; and (iii) aberrant post-translational modification of an LP protein, wherein a wild-type form of the gene encodes a protein with an LP activity.

In another aspect the invention provides methods for identifying a compound that binds to or modulates the activity of an LP protein, by providing an indicator composition comprising an LP protein having LP activity, contacting the indicator composition with a test compound, and determining the effect of the test compound on LP activity in the indicator composition to identify a compound that modulates the activity of an LP protein.

Other features and advantages of the invention will be apparent from the following detailed description and claims.

DETAILED DESCRIPTION OF THE INVENTION

The present invention is based, at least in part, on the discovery of novel molecules, referred to herein as "lipase" or "LP" nucleic acid and protein molecules (e.g., human LP or LP50250), which are novel members of a family of enzymes possessing lipase activity.

As used herein, the term "lipase" includes a molecule which is involved in catalysis of lipid hydrolysis. Lipases are involved, for example, in the hydrolysis of triglycerides, phospholipids and cholesterol esters to produce fatty acids, and are therefore involved in cellular metabolic and catabolic processes (including respiration, fatty acid biosynthesis, and purine biosynthesis), and intra- and inter-cellular communication (e.g., by producing molecules, such as fatty acids, which are involved in a number of signal transduction pathways) which contribute to the ability of the cell to grow, proliferate, and differentiate. Lipase molecules are also involved in systemic lipid absorption and deposition (e.g., digestion of lipids and adipocyte production), and in cardiovascular regulation. Thus, the LP molecules of the present invention provide novel diagnostic targets and therapeutic agents to control lipase-associated disorders.

As used herein, a "lipase-associated disorder" includes a disorder, disease or condition which is caused or characterized by a misregulation (e.g., downregulation or upregulation) of lipase activity. Lipase-associated disorders can detrimentally affect cellular functions such as cellular proliferation, growth, differentiation, or migration, or systemic responses in an organism, such as cardiovascular function or lipid absorption or deposition.

Examples of lipase-associated disorders include cardiovascular disorders. Cardiovascular system disorders in which the LP molecules of the invention may be directly or indirectly involved include arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrilation, Jervell syndrome, Lange-Nielsen syndrome, long-QT syndrome, congestive heart failure, sinus node dysfunction, angina, heart failure, hypertension, atrial fibrillation, atrial flutter, dilated cardiomyopathy, idiopathic cardiomyopathy, myocardial infarction, coronary artery disease, coronary artery spasm, and arrhythmia.

Lipase disorders also include cellular proliferation, growth, differentiation, or migration disorders. Cellular proliferation, growth, differentiation, or migration disorders include those disorders that affect cell proliferation, growth, differentiation, or migration processes. As used herein, a "cellular proliferation, growth, differentiation, or migration process" is a process by which a cell increases in number, size or content, by which a cell develops a specialized set of characteristics which differ from that of other cells, or by which a cell moves closer to or further from a particular location or stimulus. The LP molecules of the present invention are involved in signal transduction mechanisms, which are known to be involved in cellular growth, differentiation, and migration processes. Thus, the LP molecules may modulate cellular growth, differentiation, or migration, and may play a role in disorders characterized by aberrantly regulated growth, differentiation, or migration. Such disorders include cancer, e.g., carcinoma, sarcoma, or leukemia; tumor angiogenesis and metastasis; skeletal dysplasia; hepatic disorders; and hematopoietic and/or myeloproliferative disorders.

LP-associated or related disorders also include disorders of lipid absorption or deposition. Examples of such disorders include obesity and wasting diseases, Wolman's disease, cholesteryl ester storage disease, hyperlipoproteinemia type I, pancreatic lipase deficiency, combined lipase deficiency, and hepatic lipase deficiency.

LP-associated or related disorders also include disorders affecting tissues in which LP protein is expressed.

As used herein, a "lipase-mediated activity" includes an activity which involves the hydrolysis of lipids to form fatty acids and less-substituted lipid molecules. Lipase-mediated activities include those cellular or systemic activities which require the breakdown of lipids or the production of fatty acids. Such activities include cellular metabolism, modulation or regulation of cellular growth, proliferation, or differentiation, and systemic activities, such as cardiovascular regulation and lipid absorption and deposition.

The term "family" when referring to the protein and nucleic acid molecules of the invention (e.g., the LP family of proteins and/or nucleic acids) is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin, e.g., mouse or monkey proteins. Members of a family may also have common functional characteristics.

For example, the family of LP proteins comprises at least one signal sequence or signal peptide. The prediction of such a signal peptide can be made, for example, utilizing the computer algorithm SignalP (Henrik, et al. (1997) *Protein Engineering* 10:1–6). As used herein, a "signal sequence" or "signal peptide" includes a peptide containing about 15 or more amino acids which occurs at the N-terminus of secretory and membrane bound proteins and which contains a large number of hydrophobic amino acid residues. For example, a signal sequence contains at least about 10–30 amino acid residues, preferably about 15–25 amino acid residues, more preferably about 18–20 amino acid residues, and more preferably about 19 amino acid residues, and has at least about 35–65%, preferably about 38–50%, and more preferably about 40–45% hydrophobic amino acid residues (e.g., Valine, Leucine, Isoleucine or Phenylalanine). Such a "signal sequence", also referred to in the art as a "signal peptide", serves to direct a protein containing such a sequence to a lipid bilayer, and is cleaved in secreted and membrane bound proteins. A potential signal sequence was identified in the amino acid sequence of human $LP_{48-794}$ at about amino acids 1–26 of SEQ ID NO:23.

In another embodiment, an LP molecule of the present invention is identified based on the presence of at least one N-glycosylation site. As used herein, the term "N-glycosylation site" includes an amino acid sequence of about 4 amino acid residues in length which serves as a glycosylation site. More preferably, an N-glycosylation site has the consensus sequence Asn-Xaa-Ser/Thr (where Xaa may be any amino acid). N-glycosylation sites are described in, for example, Prosite PDOC00001 (see the Prosite section of the website for ExPASy (Expert Protein Analysis System) proteomics server of the Swiss Institute of Bioinformatics expasy.ch), the contents of which are incorporated herein by reference. Amino acid residues 101–104 of the LP protein (SEQ ID NO:20) comprise an N-glycosylation site. Amino acid residues 89–92 of the $LP_{48-794}$ protein (SEQ ID NO:23) comprise an N-glycosylation site. Accordingly, LP proteins having at least one N-glycosylation site are within the scope of the invention.

In another embodiment, an LP molecule of the present invention is identified based on the presence of a "lipase/acylhydrolase domain with a GDSL-like motif" in the protein or corresponding nucleic acid molecule. As used herein, the term "lipase/acylhydrolase domain with a GDSL-like motif" includes a protein domain having an amino acid sequence of about 25–125 amino acid residues, and a bit score of at least 10 when compared against a lipase/acylhydrolase domain with a GDSL-like motif Hidden Markov Model (HMM), e.g., PFAM accession number PF00657. In a preferred embodiment, a lipase/acylhydrolase domain with a GDSL-like motif includes a protein domain having an amino acid sequence of about 50–100 amino acid residues and a bit score of at least 15. In another preferred embodiment, a lipase/acylhydrolase domain with a GDSL-like motif includes a protein domain having an amino acid sequence of about 77–79 amino acid residues and a bit score of 22–42. To identify the presence of a lipase/acylhydrolase domain with a GDSL-like motif in an LP protein, the amino acid sequence of the protein is used to search a database of known Hidden Markov Models (HMMs e.g., the PFAM HMM database). The lipase/acylhydrolase domain with a GDSL-like motif (HMM) has been assigned the PFAM Accession PF00657 (see Pfam at the website for Washington University in St. Louis wustl.edu/Pfam/html). For example, a search was performed against the HMM database using the amino acid sequence of human LP (SEQ ID NO:20), resulting in the identification of a lipase/acylhydrolase domain with a GDSL-like motif in the amino acid sequence of human LP (SEQ ID NO:20) at about residues 31–107 of SEQ ID NO:20, having a score of 22.8. A search was also performed against the HMM database using the amino acid sequence of human $LP_{48-794}$ (SEQ ID NO:23), resulting in the identification of a lipase/acylhydrolase domain with a GDSL-like motif in the amino acid sequence of human $LP_{48-794}$ (SEQ ID NO:23) at about residues 17–95 of SEQ ID NO:23, having a score of 42.8.

In another embodiment of the invention, an LP protein is identified based on the presence of at least one "LP signature motif" in the protein or corresponding nucleic acid molecule. As used herein, the term "LP signature motif" includes an amino acid sequence that contains at least about 5–15 amino acid residues that are conserved among LP family members. In one embodiment, an LP signature motif includes an amino acid sequence at least about 7–13 amino acid residues, more preferably about 9–11 amino acid residues, more preferably 10 amino acid residues in length and having the following amino acid sequence: [LIVMFYAG](4)-G-D-S-[LIVM]-X(2), (SEQ ID NO:25), where X indicates any amino acid (see, for example, Upton and Buckley (1995) *Trends Biochem. Sci.* 20:178–179). Accordingly, preferred proteins include the conserved amino acid residues of the above-recited LP signature motif. Proteins including at least 5, 6, 7, 8, 9 or more conserved amino acid residues of the above-recited LP signature motif are also considered to be within the scope of the present invention.

In a preferred embodiment, the LP molecules of the invention include at least one, preferably two or more of the following motifs or domains: a signal peptide, an N-glycosylation site, a lipase/acylhydrolase domain with a GDSL-like motif, and/or an LP signature motif.

Isolated proteins of the present invention, preferably LP proteins, have an amino acid sequence sufficiently identical to the amino acid sequence of SEQ ID NO:20 or 23, or are encoded by a nucleotide sequence sufficiently identical to SEQ ID NO:19, 21, 22, or 24. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%–80%, and even more preferably 90–95% homology across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70–80%, or 90–95% homology and share a common functional activity are defined herein as sufficiently identical.

As used interchangeably herein, an "LP activity", "biological activity of LP" or "functional activity of LP", refers to an activity exerted by an LP protein, polypeptide or nucleic acid molecule on an LP responsive cell or tissue, or on an LP protein substrate, as determined in vivo, or in vitro, according to standard techniques. In one embodiment, an LP activity is a direct activity, such as an association with an LP-target molecule. As used herein, a "target molecule" or "binding partner" is a molecule with which an LP protein binds or interacts in nature, such that LP-mediated function is achieved. An LP target molecule can be a non-LP molecule (e.g., a cofactor) or an LP protein or polypeptide of the present invention. In an exemplary embodiment, an LP target molecule is an LP substrate (e.g., a triglyceride, a phospholipid, a cholesterol ester, or structurally related molecule). Alternatively, an LP activity is an indirect activity, such as a metabolic activity mediated by interaction of the LP protein with an LP substrate. The biological activities of LP are described herein. In an exemplary embodiment, the LP proteins of the present invention have at least one of the following activities: i) interaction with an LP substrate; ii) interaction with a cofactor; and iii) conversion of an LP substrate to product (e.g., catalysis of the conversion of substrate to product). In yet another embodiment, the LP proteins of the present invention have one or more of the following activities: 1) modulate fatty acid production, 2) modulate metabolism and catabolism of important molecules, 3) modulate intra- or inter-cellular communication, 4) modulate cellular growth, proliferation, or differentiation, 5) regulate cardiovascular activity; and 6) modulate lipid absorption or deposition.

Accordingly, another embodiment of the invention features isolated LP proteins and polypeptides having an LP activity. Other preferred proteins are LP proteins having one or more of the following motifs or domains: a signal peptide, an N-glycosylation site, a lipase/acylhydrolase domain with a GDSL-like motif, and/or an LP signature motif and, preferably, an LP activity.

Additional preferred proteins have at least one or more of the following motifs or domains: a signal peptide, an N-glycosylation site, a lipase/acylhydrolase domain with a GDSL-like motif, and/or an LP signature motif, and are, preferably, encoded by a nucleic acid molecule having a nucleotide sequence which hybridizes under stringent hybridization conditions to a complement of a nucleic acid molecule comprising the nucleotide sequence of SEQ ID NO:19, 21, 22, or 24.

The nucleotide sequence of the isolated human LP cDNA and the predicted amino acid sequence of the human LP polypeptide are shown in FIGS. 37A–B and in SEQ ID NOs:19 and 20, respectively. The nucleotide sequence of the isolated cDNA and the predicted amino acid sequence of the $LP_{48-794}$ fragment of the human LP polypeptide are shown in FIGS. 38A–B and in SEQ ID NOs:22 and 23, respectively.

The human LP gene, which is approximately 2031 nucleotides in length, encodes a protein having a molecular weight of approximately 28.9 kD and which is approximately 263 amino acid residues in length. The $LP_{48-794}$ fragment of the human LP gene, the coding region for which is approximately 747 nucleotides in length, encodes a protein having a molecular weight of approximately 27.3 kD and which is approximately 248 amino acid residues in length.

Various aspects of the invention are described in further detail in the following subsections:

I. Isolated Nucleic Acid Molecules

One aspect of the invention pertains to isolated nucleic acid molecules that encode LP proteins or biologically active portions thereof, as well as nucleic acid fragments sufficient for use as hybridization probes to identify LP-encoding nucleic acid molecules (e.g., LP mRNA) and fragments for use as PCR primers for the amplification or mutation of LP nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated LP nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:19, 21, 22, or 24, or a portion thereof, can be isolated using standard molecular biology techniques and the sequence information provided herein. Using all or portion of the nucleic acid sequence of SEQ ID NO:19, 21, 22, or 24, as a hybridization probe, LP nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:19, 21, 22, or 24, can be isolated by the polymerase chain reaction (PCR) using synthetic oligonucleotide primers designed based upon the sequence of SEQ ID NO:19, 21, 22, or 24.

A nucleic acid of the invention can be amplified using cDNA, mRNA or, alternatively, genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to LP nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:19, 21, 22, or 24. This cDNA may comprise sequences encoding the human LP protein (i.e., "the coding region", from nucleotides 3–794), as well as 5' untranslated sequences (nucleotides 1–2) and 3' untranslated sequences (nucleotides 795–2031) of SEQ ID NO:19. Alternatively, the nucleic acid molecule can comprise only the coding region of SEQ ID NO:19 (e.g., nucleotides 3–794, corresponding to SEQ ID NO:21). Alternatively, this cDNA may comprise sequences encoding the $LP_{48-794}$ fragment of the human LP protein (i.e., "the coding region", from nucleotides 48–794), as well as 5' untranslated sequence (nucleotides 1–47) and 3' untranslated sequences (nucleotides 795–2031) of SEQ ID NO:22. Alternatively, the nucleic acid molecule can comprise only the coding region of SEQ ID NO:22 (e.g., nucleotides 48–794, corresponding to SEQ ID NO:24). In another embodiment, an isolated nucleic acid molecule of the invention consists of the nucleic acid sequence of SEQ ID NO:19, 21, 22, or 24.

In another preferred embodiment, an isolated nucleic acid molecule of the invention comprises a nucleic acid molecule which is a complement of the nucleotide sequence shown in SEQ ID NO:19, 21, 22, or 24, or a portion of any of these nucleotide sequences. A nucleic acid molecule which is complementary to the nucleotide sequence shown in SEQ ID NO:19, 21, 22, or 24, is one which is sufficiently complementary to the nucleotide sequence shown in SEQ ID NO:19, 21, 22, or 24, such that it can hybridize to the nucleotide sequence shown in SEQ ID NO:19, 21, 22, or 24, respectively, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 90%, 95%, 96%, 97%, 98%, 99% or more identical to the entire length of the nucleotide sequence shown in SEQ ID NO:19, 21, 22, or 24, or a portion of any of these nucleotide sequences.

Moreover, the nucleic acid molecule of the invention can comprise only a portion of the nucleic acid sequence of SEQ ID NO:19, 21, 22, or 24, for example, a fragment which can be used as a probe or primer or a fragment encoding a portion of an LP protein, e.g., a biologically active portion of an LP protein. The nucleotide sequence determined from the cloning of the LP gene allows for the generation of probes and primers designed for use in identifying and/or cloning other LP family members, as well as LP homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:19, 21, 22, or 24, of an anti-sense sequence of SEQ ID NO:19, 21, 22, or 24, or of a naturally occurring allelic variant or mutant of SEQ ID NO:19, 21, 22, or 24. In one embodiment, a nucleic acid molecule of the present invention comprises a nucleotide sequence which is greater than 50–100, 100–150, 150–200, 200–250, 250–300, 300–350, 350–400, 400–450, 450–500, 500–550, 550–600, 600–650, 650–700, 700–750, 750–800, 800–850, 850–900, 900–950, 950–1000, 1000–1050, 1050–1100, 1100–1150, 1150–1200, 1200–1250, 1250–1300, 1300–1350, 1350–1400, 1400–1450, 1450–1500, 1500–1550, 1550–1600, 1600–1650, 1650–1700, 1700–1750, 1750–1800, 1800–1850, 1850–1900, 1900–1950, 1950–2000 or more nucleotides in length and hybridizes under stringent hybridization conditions to a nucleic acid molecule of SEQ ID NO:19, 21, 22, or 24, or the complement thereof.

Probes based on the LP nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress an LP protein, such as by measuring a level of an LP-encoding nucleic acid in a sample of cells from a subject e.g., detecting LP mRNA levels or determining whether a genomic LP gene has been mutated or deleted.

A nucleic acid fragment encoding a "biologically active portion of an LP protein" can be prepared by isolating a portion of the nucleotide sequence of SEQ ID NO:19, 21, 22, or 24, which encodes a polypeptide having an LP biological activity (the biological activities of the LP proteins are described herein), expressing the encoded portion of the LP protein (e.g., by recombinant expression in vitro) and assessing the activity of the encoded portion of the LP protein.

The invention further encompasses nucleic acid molecules that differ from the nucleotide sequence shown in SEQ ID NO:19, 21, 22, or 24, due to degeneracy of the genetic code and thus encode the same LP proteins as those encoded by the nucleotide sequence shown in SEQ ID NO:19, 21, 22, or 24. In another embodiment, an isolated nucleic acid molecule of the invention has a nucleotide sequence encoding a protein having an amino acid sequence shown in SEQ ID NO:20 or 23.

In addition to the LP nucleotide sequences shown in SEQ ID NO:19, 21, 22, or 24, it will be appreciated by those skilled in the art that DNA sequence polymorphisms that lead to changes in the amino acid sequences of the LP proteins may exist within a population (e.g., the human population). Such genetic polymorphism in the LP genes may exist among individuals within a population due to natural allelic variation. As used herein, the terms "gene" and "recombinant gene" refer to nucleic acid molecules which include an open reading frame encoding an LP protein, preferably a mammalian LP protein, and can further include non-coding regulatory sequences, and introns.

Allelic variants of human LP include both functional and non-functional LP proteins. Functional allelic variants are naturally occurring amino acid sequence variants of the human LP protein that maintain the ability to bind an LP ligand or substrate and/or modulate cell proliferation and/or migration mechanisms. Functional allelic variants will typically contain only conservative substitution of one or more amino acids of SEQ ID NO:20 or 23, or substitution, deletion or insertion of non-critical residues in non-critical regions of the protein.

Non-functional allelic variants are naturally occurring amino acid sequence variants of the human LP protein that do not have the ability to either bind an LP ligand and/or modulate any of the LP activities described herein. Non-functional allelic variants will typically contain a non-conservative substitution, a deletion, or insertion or premature truncation of the amino acid sequence of SEQ ID NO:20 or 23, or a substitution, insertion or deletion in critical residues or critical regions of the protein.

The present invention further provides non-human orthologues of the human LP protein. Orthologues of the human LP protein are proteins that are isolated from non-human organisms and possess the same LP ligand binding and/or modulation of membrane excitability activities of the human LP protein. Orthologues of the human LP protein can readily be identified as comprising an amino acid sequence that is substantially identical to SEQ ID NO:20 or 23.

Moreover, nucleic acid molecules encoding other LP family members and, thus, which have a nucleotide sequence which differs from the LP sequences of SEQ ID NO:19, 21, 22, or 24, are intended to be within the scope of the invention. For example, another LP cDNA can be identified based on the nucleotide sequence of human LP. Moreover, nucleic acid molecules encoding LP proteins from different species, and which, thus, have a nucleotide sequence which differs from the LP sequences of SEQ ID NO:19, 21, 22, or 24, are intended to be within the scope of the invention. For example, a mouse LP cDNA can be identified based on the nucleotide sequence of a human LP.

Nucleic acid molecules corresponding to natural allelic variants and homologues of the LP cDNAs of the invention can be isolated based on their homology to the LP nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the LP cDNAs of the invention can further be isolated by mapping to the same chromosome or locus as the LP gene.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:19, 21, 22, or 24, or a complement thereof. In other embodiment, the nucleic acid is at least 50–100, 100–150, 150–200, 200–250, 250–300, 300–350, 350–400, 400–450, 450–500, 500–550, 550–600, 600–650, 650–700, 700–750, 750–800, 800–850, 850–900, 900–950, 950–1000, 1000–1050, 1050–1100, 1100–1150, 1150–1200, 1200–1250, 1250–1300, 1300–1350, 1350–1400, 1400–1450, 1450–1500, 1500–1550, 1550–1600, 1600–1650, 1650–1700, 1700–1750, 1750–1800, 1800–1850, 1850–1900, 1900–1950, 1950–2000 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A preferred, non-limiting example of stringent hybridization conditions includes hybridization in 4× or 6× sodium chloride/sodium citrate (SSC), at about 65–70° C. (or hybridization in 4×SSC plus 50% formamide at about 42–50° C.) followed by one or more washes in 1×SSC, at about 65–70° C. A further preferred, non-limiting example of stringent hybridization conditions includes hybridization at 6×SSC at 45° C., followed by one or more washes in 0.2×SSC, 0.1% SDS at 65° C. A preferred, non-limiting example of highly stringent hybridization conditions includes hybridization in 1×SSC, at about 65–70° C. (or hybridization in 1×SSC plus 50% formamide at about 42–50° C.) followed by one or more washes in 0.3×SSC, at about 65–70° C. A preferred, non-limiting example of reduced stringency hybridization conditions includes hybridization in 4× or 6×SSC, at about 50–60° C. (or alternatively hybridization in 6×SSC plus 50% formamide at about 40–45° C.) followed by one or more washes in 2×SSC, at about 50–60° C. Ranges intermediate to the above-recited values, e.g., at 65–70° C. or at 42–50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m(° C.)=2(\# \text{ of A+T bases})+4(\# \text{ of G+C bases})$. For hybrids between 18 and 49 base pairs in length, $T_m(° C.)=81.5+16.6(\log_{10}[Na^+])+0.41(\%G+C)-(600/N)$, where N is the number of bases in the hybrid, and [$Na^+$] is the concentration of sodium ions in the hybridization buffer ([$Na^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25–0.5M $NaH_2PO_4$, 7% SDS at about 65° C., followed by one or more washes at 0.02M $NaH_2PO_4$, 1% SDS at 65° C., see e.g., Church and Gilbert (1984) *Proc. Natl. Acad. Sci. USA* 81:1991–1995, (or alternatively 0.2×SSC, 1% SDS).

Preferably, an isolated nucleic acid molecule of the invention that hybridizes under stringent conditions to the sequence of SEQ ID NO:19, 21, 22, or 24, and corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the LP sequences that may exist in the population, the skilled artisan will further appreciate that changes can be introduced by mutation into the nucleotide sequences of SEQ ID NO:19, 21, 22, or 24, thereby leading to changes in the amino acid sequence of the encoded LP proteins, without altering the functional ability of the LP proteins. For example, nucleotide substitutions leading to amino acid substitutions at "non-essential" amino acid residues can be made in the sequence of SEQ ID NO:19, 21, 22, or 24. A "non-essential" amino acid residue is a residue that can be altered from the wild-type sequence of LP (e.g., the sequence of SEQ ID NO:20 or 23) without altering the biological activity, whereas an "essential" amino acid residue is required for biological activity. For example, amino acid residues that are conserved among the LP proteins of the present invention, e.g., those present in a lipase consensus sequence, are predicted to be particularly unamenable to alteration. Furthermore, additional amino acid residues that are conserved between the LP proteins of the present invention and other members of the LP family are not likely to be amenable to alteration.

Accordingly, another aspect of the invention pertains to nucleic acid molecules encoding LP proteins that contain changes in amino acid residues that are not essential for activity. Such LP proteins differ in amino acid sequence from SEQ ID NO:20 or 23, yet retain biological activity. In one embodiment, the isolated nucleic acid molecule comprises a nucleotide sequence encoding a protein, wherein the protein comprises an amino acid sequence at least about 50%, 55%, 60%, 65%, 70%, 75%, 80%, 85%, 90%, 95%, 96%, 97%, 98%, 99% or more identical to SEQ ID NO:20 or 23.

An isolated nucleic acid molecule encoding an LP protein identical to the protein of SEQ ID NO:20 or 23 can be created by introducing one or more nucleotide substitutions, additions or deletions into the nucleotide sequence of SEQ ID NO:19, 21, 22, or 24, such that one or more amino acid substitutions, additions or deletions are introduced into the encoded protein. Mutations can be introduced into SEQ ID NO:19, 21, 22, or 24, by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in an LP protein is preferably replaced with another amino acid residue from the same side chain family. Alternatively, in another embodiment, mutations can be introduced randomly along all or part of an LP coding sequence, such as by saturation mutagenesis, and the resultant mutants can be screened for LP biological activity to identify mutants that retain activity. Following mutagenesis of SEQ ID NO:19, 21, 22, or 24, the encoded protein can be expressed recombinantly and the activity of the protein can be determined.

In a preferred embodiment, a mutant LP protein can be assayed for the ability to metabolize or catabolize important biochemical molecules, to permit intra- or intercellular signaling, to regulate cardiovascular processes, or to modulate lipid absorption or deposition.

In addition to the nucleic acid molecules encoding LP proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire LP coding strand, or to only a portion thereof. In one embodiment, an antisense nucleic acid molecule is antisense to a "coding region" of the coding strand of a nucleotide sequence encoding an LP. The term "coding region" refers to the region of the nucleotide sequence comprising codons which are translated into amino acid residues (e.g., the coding region of human LP corresponds to SEQ ID NO:21, and the coding region of the $LP_{48-794}$ fragment corresponds to SEQ ID NO:24). In another embodiment, the antisense nucleic acid molecule is antisense to a "noncoding region" of the coding strand of a nucleotide sequence encoding LP. The term "noncoding region" refers to 5' and 3' sequences which flank the coding region that are not translated into amino acids (i.e., also referred to as 5' and 3' untranslated regions).

Given the coding strand sequences encoding LP disclosed herein (e.g., SEQ ID NO:21), antisense nucleic acids of the invention can be designed according to the rules of Watson and Crick base pairing. The antisense nucleic acid molecule can be complementary to the entire coding region of LP mRNA, but more preferably is an oligonucleotide which is antisense to only a portion of the coding or noncoding region of LP mRNA. For example, the antisense oligonucleotide can be complementary to the region surrounding the translation start site of LP mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 1-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an LP protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff and Gerlach (1988) *Nature* 334:585–591)) can be used to catalytically cleave LP mRNA transcripts to thereby inhibit translation of LP mRNA. A ribozyme having specificity for an LP-encoding nucleic acid can be designed based upon the nucleotide sequence of an LP cDNA disclosed herein (i.e., SEQ ID NO:19, 21, 22, or 24. For example, a derivative of a *Tetrahymena* L-19 IVS RNA can be constructed in which the nucleotide sequence of the active site is complementary to the nucleotide sequence to be cleaved in an LP-encoding mRNA. See, e.g., Cech et al. U.S. Pat. No. 4,987,071; and Cech et al. U.S. Pat. No. 5,116,742. Alternatively, LP mRNA can be used to select a catalytic RNA having a specific ribonuclease activity from a pool of RNA molecules. See, e.g., Bartel, D. and Szostak, J. W. (1993) *Science* 261:1411–1418.

Alternatively, LP gene expression can be inhibited by targeting nucleotide sequences complementary to the regulatory region of the LP (e.g., the LP promoter and/or enhancers; e.g., nucleotides 1–59 of SEQ ID NO:19) to form triple helical structures that prevent transcription of the LP gene in target cells. See generally, Helene, C. (1991) *Anticancer Drug Des.* 6(6): 569–84; Helene, C. et al. (1992) *Ann. N.Y. Acad. Sci.* 660:2 or 57–36; and Maher, L. J. (1992) *Bioassays* 14(12):807–15.

In yet another embodiment, the LP nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. *Proc. Natl. Acad. Sci.* 93: 14670–675.

PNAs of LP nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of LP nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of LP can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of LP nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

Alternatively, the expression characteristics of an endogenous LP gene within a cell line or microorganism may be modified by inserting a heterologous DNA regulatory element into the genome of a stable cell line or cloned microorganism such that the inserted regulatory element is operatively linked with the endogenous LP gene. For example, an endogenous LP gene which is normally "transcriptionally silent", i.e., an LP gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous LP gene may be activated by insertion of a promiscuous regulatory element that works across cell types.

A heterologous regulatory element may be inserted into a stable cell line or cloned microorganism, such that it is operatively linked with an endogenous LP gene, using techniques, such as targeted homologous recombination, which are well known to those of skill in the art, and described, e.g., in Chappel, U.S. Pat. No. 5,272,071; PCT publication No. WO 91/06667, published May 16, 1991.

II. Isolated LP Proteins and Anti-LP Antibodies

One aspect of the invention pertains to isolated LP proteins, and biologically active portions thereof, as well as polypeptide fragments suitable for use as immunogens to raise anti-LP antibodies. In one embodiment, native LP proteins can be isolated from cells or tissue sources by an appropriate purification scheme using standard protein purification techniques. In another embodiment, LP proteins are produced by recombinant DNA techniques. Alternative to recombinant expression, an LP protein or polypeptide can be synthesized chemically using standard peptide synthesis techniques.

An "isolated" or "purified" protein or biologically active portion thereof is substantially free of cellular material or other contaminating proteins from the cell or tissue source from which the LP protein is derived, or substantially free from chemical precursors or other chemicals when chemically synthesized. The language "substantially free of cellular material" includes preparations of LP protein in which the protein is separated from cellular components of the cells from which it is isolated or recombinantly produced. In one embodiment, the language "substantially free of cellular material" includes preparations of LP protein having less than about 30% (by dry weight) of non-LP protein (also referred to herein as a "contaminating protein"), more preferably less than about 20% of non-LP protein, still more preferably less than about 10% of non-LP protein, and most preferably less than about 5% non-LP protein. When the LP protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of LP protein in which the protein is separated from chemical precursors or other chemicals which are involved in the synthesis of the protein. In one embodiment, the language "substantially free of chemical precursors or other chemicals" includes preparations of LP protein having less than about 30% (by dry weight) of chemical precursors or non-LP chemicals, more preferably less than about 20% chemical precursors or non-LP chemicals, still more preferably less than about 10% chemical precursors or non-LP chemicals, and most preferably less than about 5% chemical precursors or non-LP chemicals.

As used herein, a "biologically active portion" of an LP protein includes a fragment of an LP protein which participates in an interaction between an LP molecule and a non-LP molecule. Biologically active portions of an LP protein include peptides comprising amino acid sequences sufficiently identical to or derived from the amino acid sequence of the LP protein, e.g., the amino acid sequence shown in SEQ ID NO:20 or 23, which include fewer amino acids than the full length LP proteins, and exhibit at least one activity of an LP protein. Typically, biologically active portions comprise a domain or motif with at least one activity of the LP protein, e.g., modulating membrane excitability. A biologically active portion of an LP protein can be a polypeptide which is, for example, 25, 50, 75, 100, 125, 150, 175, 200, 250, 300 or more amino acids in length. Biologically active portions of an LP protein can be used as targets for developing agents which modulate an LP mediated activity, e.g., a proliferative response.

It is to be understood that a preferred biologically active portion of an LP protein of the present invention may contain at least one or more of the following motifs or domains: a signal peptide, an N-glycosylation site, a lipase/acylhydrolase domain with a GDSL-like motif, and/or an LP signature motif. Moreover, other biologically active portions, in which other regions of the protein are deleted, can be prepared by recombinant techniques and evaluated for one or more of the functional activities of a native LP protein.

In a preferred embodiment, the LP protein has an amino acid sequence shown in SEQ ID NO:20 or 23. In other embodiments, the LP protein is substantially identical to SEQ ID NO:20 or 23, and retains the functional activity of the protein of SEQ ID NO:20 or 23, yet differs in amino acid sequence due to natural allelic variation or mutagenesis, as described in detail in subsection I above. Accordingly, in another embodiment, the LP protein is a protein which comprises an amino acid sequence at least about 50%, 55%, 60%, 65%, 70%, 75%, 80%, 85%, 90%, 95%, 96%, 97%, 98%, 99% or more identical to SEQ ID NO:20 or 23.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the LP amino acid sequence of SEQ ID NO:20 or 23 having 248 or 263 amino acid residues, at least 50, preferably at least 100, more preferably at least 150, even more preferably at least 200, and even more preferably at least 225 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at the bioinformatics page of the website maintained by Accelrys, Inc., San Diego, Calif., USA), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*Comput. Appl. Biosci.*, 4: 11–17 (1988)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to LP nucleic acid molecules of the invention. BLAST protein searches can be performed with the XBLAST program, score=100, wordlength=3 to obtain amino acid sequences homologous to LP protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used (accessible at the website maintained by National Center for Biotechnology Information, Bethesda, Md., USA).

The invention also provides LP chimeric or fusion proteins. As used herein, an LP "chimeric protein" or "fusion protein" comprises an LP polypeptide operatively linked to a non-LP polypeptide. An "LP polypeptide" refers to a polypeptide having an amino acid sequence corresponding to an LP molecule, whereas a "non-LP polypeptide" refers to a polypeptide having an amino acid sequence corresponding to a protein which is not substantially homologous to the LP protein, e.g., a protein which is different from the LP protein and which is derived from the same or a different organism. Within an LP fusion protein the LP polypeptide can correspond to all or a portion of an LP protein. In a preferred embodiment, an LP fusion protein comprises at least one biologically active portion of an LP protein. In another preferred embodiment, an LP fusion protein comprises at least two biologically active portions of an LP protein. Within the fusion protein, the term "operatively linked" is intended to indicate that the LP polypeptide and the non-LP polypeptide are fused in-frame to each other. The non-LP polypeptide can be fused to the N-terminus or C-terminus of the LP polypeptide.

For example, in one embodiment, the fusion protein is a GST-LP fusion protein in which the LP sequences are fused to the C-terminus of the GST sequences. Such fusion proteins can facilitate the purification of recombinant LP.

In another embodiment, the fusion protein is an LP protein containing a heterologous signal sequence at its N-terminus. In certain host cells (e.g., mammalian host cells), expression and/or secretion of LP can be increased through use of a heterologous signal sequence.

The LP fusion proteins of the invention can be incorporated into pharmaceutical compositions and administered to a subject in vivo. The LP fusion proteins can be used to affect the bioavailability of an LP substrate. Use of LP fusion proteins may be useful therapeutically for the treatment of disorders caused by, for example, (i) aberrant modification or mutation of a gene encoding an LP protein; (ii) misregulation of the LP gene; and (iii) aberrant post-translational modification of an LP protein.

Moreover, the LP-fusion proteins of the invention can be used as immunogens to produce anti-LP antibodies in a subject, to purify LP ligands and in screening assays to identify molecules which inhibit the interaction of LP with an LP substrate.

Preferably, an LP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). An LP-encoding nucleic acid can be cloned into such an expression vector such that the fusion moiety is linked in-frame to the LP protein.

The present invention also pertains to variants of the LP proteins which function as either LP agonists (mimetics) or as LP antagonists. Variants of the LP proteins can be generated by mutagenesis, e.g., discrete point mutation or truncation of an LP protein. An agonist of the LP proteins can retain substantially the same, or a subset, of the biological activities of the naturally occurring form of an LP protein. An antagonist of an LP protein can inhibit one or more of the activities of the naturally occurring form of the LP protein by, for example, competitively modulating an LP-mediated activity of an LP protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the LP protein.

In one embodiment, variants of an LP protein which function as either LP agonists (mimetics) or as LP antagonists can be identified by screening combinatorial libraries of mutants, e.g., truncation mutants, of an LP protein for LP protein agonist or antagonist activity. In one embodiment, a variegated library of LP variants is generated by combinatorial mutagenesis at the nucleic acid level and is encoded by a variegated gene library. A variegated library of LP variants can be produced by, for example, enzymatically ligating a mixture of synthetic oligonucleotides into gene sequences such that a degenerate set of potential LP sequences is expressible as individual polypeptides, or alternatively, as a set of larger fusion proteins (e.g., for phage display) containing the set of LP sequences therein. There are a variety of methods which can be used to produce libraries of potential LP variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential LP sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of an LP protein coding sequence can be used to generate a variegated population of LP fragments for screening and subsequent selection of variants of an LP protein. In one embodiment, a library of coding sequence fragments can be generated by treating a double stranded PCR fragment of an LP coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the LP protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of LP proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify LP variants (Arkin and Youvan (1992) *Proc. Natl. Acad. Sci. USA* 89:7811–7815; Delagrave et al. (1993) *Protein Engineering* 6(3): 327–331).

In one embodiment, cell based assays can be exploited to analyze a variegated LP library. For example, a library of expression vectors can be transfected into a cell line, e.g., a neuronal cell line, which ordinarily responds to an LP ligand in a particular LP ligand-dependent manner. The transfected cells are then contacted with an LP ligand and the effect of expression of the mutant on, e.g., membrane excitability of LP can be detected. Plasmid DNA can then be recovered from the cells which score for inhibition, or alternatively, potentiation of signaling by the LP ligand, and the individual clones further characterized.

An isolated LP protein, or a portion or fragment thereof, can be used as an immunogen to generate antibodies that bind LP using standard techniques for polyclonal and monoclonal antibody preparation. A full-length LP protein can be used or, alternatively, the invention provides antigenic peptide fragments of LP for use as immunogens. The antigenic peptide of LP comprises at least 8 amino acid residues of the amino acid sequence shown in SEQ ID NO:20 or 23 and encompasses an epitope of LP such that an antibody raised against the peptide forms a specific immune complex with the LP protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of LP that are located on the surface of the protein, e.g., hydrophilic regions, as well as regions with high antigenicity.

An LP immunogen typically is used to prepare antibodies by immunizing a suitable subject, (e.g., rabbit, goat, mouse or other mammal) with the immunogen. An appropriate immunogenic preparation can contain, for example, recombinantly expressed LP protein or a chemically synthesized LP polypeptide. The preparation can further include an adjuvant, such as Freund's complete or incomplete adjuvant, or similar immunostimulatory agent. Immunization of a suitable subject with an immunogenic LP preparation induces a polyclonal anti-LP antibody response.

Accordingly, another aspect of the invention pertains to anti-LP antibodies. The term "antibody" as used herein refers to immunoglobulin molecules and immunologically active portions of immunoglobulin molecules, i.e., molecules that contain an antigen binding site which specifically binds (immunoreacts with) an antigen, such as an LP. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind LP molecules. The term "monoclonal antibody" or "monoclonal antibody composition", as used herein, refers to a population of antibody molecules that contain only one species of an antigen binding site capable of immunoreacting with a particular epitope of LP. A monoclonal antibody composition thus typically displays a single binding affinity for a particular LP protein with which it immunoreacts.

Polyclonal anti-LP antibodies can be prepared as described above by immunizing a suitable subject with an LP immunogen. The anti-LP antibody titer in the immunized subject can be monitored over time by standard techniques, such as with an enzyme linked immunosorbent assay (ELISA) using immobilized LP. If desired, the antibody molecules directed against LP can be isolated from the mammal (e.g., from the blood) and further purified by well known techniques, such as protein A chromatography to obtain the IgG fraction. At an appropriate time after immunization, e.g., when the anti-LP antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem* 0.255:

4980–83; Yeh et al. (1976) *Proc. Natl. Acad. Sci. USA* 76:2 or 5927–31; and Yeh et al. (1982) *Int. J. Cancer* 29:2 or 569–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:2 or 531–36). Briefly, an immortal cell line (typically a myeloma) is fused to lymphocytes (typically splenocytes) from a mammal immunized with an LP immunogen as described above, and the culture supernatants of the resulting hybridoma cells are screened to identify a hybridoma producing a monoclonal antibody that binds LP.

Any of the many well known protocols used for fusing lymphocytes and immortalized cell lines can be applied for the purpose of generating an anti-LP monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4–1, P3-x63-Ag8.653 or Sp2/O-Ag14 myeloma lines. These mycloma lines are available from ATCC (Manassas, Va.). Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind LP, e.g., using a standard ELISA assay.

Alternative to preparing monoclonal antibody-secreting hybridomas, a monoclonal anti-LP antibody can be identified and isolated by screening a recombinant combinatorial immunoglobulin library (e.g., an antibody phage display library) with LP to thereby isolate immunoglobulin library members that bind LP. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1369–1372; Hay et al. (1992) *Hum. Antibod. Hybridomas* 3:81–85; Huse et al. (1989) *Science* 246:1275–1281; Griffiths et al. (1993) *EMBO J.* 12:725–734; Hawkins et al. (1992) *J. Mol. Biol.* 226: 889–896; Clackson et al. (1991) *Nature* 352:624–628; Gram et al. (1992) *Proc. Natl. Acad. Sci. USA* 89:3576–3580; Garrard et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-LP antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171, 496; Morrison et al. European Patent Application 173,494; Neuberger et al. PCT International Publication No. WO 0.86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:2 or 514–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:2 or 514; Winter U.S. Pat. No. 5,225,539; Jones et al. (1986) *Nature* 321:552–525; Verhoeyen et al. (1988) *Science* 239:1534; and Beidler et al. (1988) *J. Immunol.* 141:4053–4060.

An anti-LP antibody (e.g., monoclonal antibody) can be used to isolate LP by standard techniques, such as affinity chromatography or immunoprecipitation. An anti-LP antibody can facilitate the purification of natural LP from cells and of recombinantly produced LP expressed in host cells. Moreover, an anti-LP antibody can be used to detect LP protein (e.g., in a cellular lysate or cell supernatant) in order to evaluate the abundance and pattern of expression of the LP protein. Anti-LP antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

III. Recombinant Expression Vectors and Host Cells

Another aspect of the invention pertains to vectors, preferably expression vectors, containing a nucleic acid encoding an LP protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., LP proteins, mutant forms of LP proteins, fusion proteins, and the like).

The recombinant expression vectors of the invention can be designed for expression of LP proteins in prokaryotic or eukaryotic cells. For example, LP proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in LP activity assays, (e.g., direct assays or competitive assays described in detail below), or to generate antibodies specific for LP proteins, for example. In a preferred embodiment, an LP fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2 or 5111–2118). Such alteration of nucleic acid sequences of the invention can be carried out by standard DNA synthesis techniques.

In another embodiment, the LP expression vector is a yeast expression vector. Examples of vectors for expression in yeast *S. cerevisiae* include pYepSec1 (Baldari, et al., (1987) *EMBO J.* 6:2 or 529–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (Invitrogen Corporation, San Diego, Calif.).

Alternatively, LP proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2 or 5156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:2 or 568–277), lymphoid-specific promoters (Calame and Eaton (1988) *Adv. Immunol.* 43:2 or 535–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to LP mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which an LP nucleic acid molecule of the invention is introduced, e.g., an LP nucleic acid molecule within a recombinant expression vector or an LP nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an LP protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding an LP protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) an LP protein. Accordingly, the invention further provides methods for producing an LP protein using the host cells of the invention. In one embodiment, the method comprises culturing the host cell of the invention (into which a recombinant expression vector encoding an LP protein has been introduced) in a suitable medium such that an LP protein is produced. In another embodiment, the method further comprises isolating an LP protein from the medium or the host cell.

The host cells of the invention can also be used to produce non-human transgenic animals. For example, in one embodiment, a host cell of the invention is a fertilized oocyte or an embryonic stem cell into which LP-coding sequences have been introduced. Such host cells can then be used to create non-human transgenic animals in which exogenous LP sequences have been introduced into their genome or homologous recombinant animals in which endogenous LP sequences have been altered. Such animals are useful for studying the function and/or activity of an LP and for identifying and/or evaluating modulators of LP activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous LP gene has been altered by homologous recombination between the endogenous gene and an exogenous DNA molecule introduced into a cell of the animal, e.g., an embryonic cell of the animal, prior to development of the animal.

A transgenic animal of the invention can be created by introducing an LP-encoding nucleic acid into the male pronuclei of a fertilized oocyte, e.g., by microinjection, retroviral infection, and allowing the oocyte to develop in a pseudopregnant female foster animal. The LP cDNA sequence of SEQ ID NO:19 can be introduced as a transgene into the genome of a non-human animal. Alternatively, a nonhuman homologue of a human LP gene, such as a mouse or rat LP gene, can be used as a transgene. Alternatively, an LP gene homologue, such as another LP family member, can be isolated based on hybridization to the LP cDNA sequences of SEQ ID NO:19, 21, 22, or 24 (described further in subsection I above) and used as a transgene. Intronic sequences and polyadenylation signals can also be included in the transgene to increase the efficiency of expression of the transgene. A tissue-specific regulatory sequence(s) can be operably linked to an LP transgene to direct expression of an LP protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of an LP transgene in its genome and/or expression of LP mRNA in tissues or cells of the animals. A transgenic founder animal can then be used to breed additional animals carrying the transgene. Moreover, transgenic animals carrying a transgene encoding an LP protein can further be bred to other transgenic animals carrying other transgenes.

To create a homologous recombinant animal, a vector is prepared which contains at least a portion of an LP gene into which a deletion, addition or substitution has been introduced to thereby alter, e.g., functionally disrupt, the LP gene. The LP gene can be a human gene (e.g., the cDNA of SEQ ID NO:21 or 24), but more preferably, is a non-human homologue of a human LP gene (e.g., a cDNA isolated by stringent hybridization with the nucleotide sequence of SEQ ID NO:19 or 22). For example, a mouse LP gene can be used to construct a homologous recombination nucleic acid molecule, e.g., a vector, suitable for altering an endogenous LP gene in the mouse genome. In a preferred embodiment, the homologous recombination nucleic acid molecule is designed such that, upon homologous recombination, the endogenous LP gene is functionally disrupted (i.e., no longer encodes a functional protein; also referred to as a "knock out" vector). Alternatively, the homologous recombination nucleic acid molecule can be designed such that, upon homologous recombination, the endogenous LP gene is mutated or otherwise altered but still encodes functional protein (e.g., the upstream regulatory region can be altered to thereby alter the expression of the endogenous LP protein). In the homologous recombination nucleic acid molecule, the altered portion of the LP gene is flanked at its 5' and 3' ends by additional nucleic acid sequence of the LP gene to allow for homologous recombination to occur between the exogenous LP gene carried by the homologous recombination nucleic acid molecule and an endogenous LP gene in a cell, e.g., an embryonic stem cell. The additional flanking LP nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced LP gene has homologously recombined with the endogenous LP gene are selected (see e.g., Li, E. et al. (1992) *Cell* 69:915). The selected cells can then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) Nature 385:810–813 and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The LP nucleic acid molecules, fragments of LP proteins, and anti-LP antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR™EL solubilizer (BASF, Florham Park, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of an LP protein or an anti-LP antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, an LP protein of the invention has one or more of the following activities: 1) modulation of fatty acid production, 2) modulation of metabolism and catabolism of important molecules, 3) modulation of intra- or inter-cellular communication, 4) modulation of cellular growth, proliferation, or differentiation, 5) regulation of cardiovascular activity; and 6) modulation of lipid absorption or deposition and, thus, may be used to: 1) modulate fatty acid production, 2) modulate metabolism and catabolism of important molecules, 3) modulate intra- or inter-cellular communication, 4) modulate cellular growth, proliferation, or differentiation, 5) regulate cardiovascular activity; and 6) modulate lipid absorption or deposition.

The isolated nucleic acid molecules of the invention can be used, for example, to express LP protein (e.g., via a recombinant expression vector in a host cell in gene therapy applications), to detect LP mRNA (e.g., in a biological sample) or a genetic alteration in an LP gene, and to modulate LP activity, as described further below. The LP proteins can be used to treat disorders characterized by insufficient or excessive production of an LP substrate or production of LP inhibitors. In addition, the LP proteins can be used to screen for naturally occurring LP substrates, to screen for drugs or compounds which modulate LP activity, as well as to treat disorders characterized by insufficient or excessive production of LP protein or production of LP protein forms which have decreased, aberrant or unwanted activity compared to LP wild type protein (e.g., lipase-associated disorders).

In a preferred embodiment, the CAH molecules of the invention are useful for catalyzing the hydrolysis of lipids and lipid-containing compounds (e.g., triacylglycerols, phospholipids, and cholesterol esters) to less-substituted lipid compounds and fatty acids. As such, these molecules may be employed in small or large-scale synthesis of either lipids or fatty acids, or in chemical processes that require the production of these compounds. Such processes are known in the art (see, e.g., Ullmann et al. (1999) Ullmann's Encyclopedia of Industrial Chemistry, $6^{th}$ ed. VCH: Weinheim; Gutcho (1983) Chemicals by Fermentation. Park ridge, N.J.: Noyes Data Corporation (ISBN 0818805086); Rehm et al. (eds.) (1993) Biotechnology, $2^{nd}$ ed. VCH: Weinheim; and Michal, G. (1999) Biochemical Pathways: An Atlas of Biochemistry and Molecular Biology. New York: John Wiley & Sons, and references contained therein.)

Furthermore, lipases may be used in biosynthesis of a variety of other compounds, such as chiral alcohols, esters, carboxylic acids, and lactones through hydrolysis and transesterification reactions (Gotor (1999), supra, and references therein).

The isolated nucleic acid molecules of the invention can be used, for example, to express LP protein (e.g., via a recombinant expression vector in a host cell in gene therapy applications), to detect LP mRNA (e.g., in a biological sample) or a genetic alteration in an LP gene, and to modulate LP activity, as described further below. The LP proteins can be used to treat disorders characterized by insufficient or excessive production of an LP substrate or production of LP inhibitors. In addition, the LP proteins can be used to screen for naturally occurring LP substrates, to screen for drugs or compounds which modulate LP activity, as well as to treat disorders characterized by insufficient or excessive production of LP protein or production of LP protein forms which have decreased, aberrant or unwanted activity compared to LP wild type protein (e.g., lipase-associated disorders, such as cardiovascular disorders (e.g., arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrilation, Jervell syndrome, Lange-Nielsen syndrome, long-QT syndrome, congestive heart failure, sinus node dysfunction, angina, heart failure, hypertension, atrial fibrillation, atrial flutter, dilated cardiomyopathy, idiopathic cardiomyopathy, myocardial infarction, coronary artery disease, coronary artery spasm, and arrhythmia); cellular proliferation, growth, differentiation, or migration disorders (e.g., carcinoma, sarcoma, or leukemia; tumor angiogenesis and metastasis; skeletal dysplasia; hepatic disorders; and hematopoietic and/or myeloproliferative disorders); and disorders of lipid absorption or deposition (e.g., obesity and wasting diseases, Wolman's disease, cholesteryl ester storage disease, hyperlipoproteinemia type I, pancreatic lipase deficiency, combined lipase deficiency, and hepatic lipase deficiency). Moreover, the anti-LP antibodies of the invention can be used to detect and isolate LP proteins, regulate the bioavailability of LP proteins, and modulate LP activity.

A. Screening Assays:

The invention provides a method (also referred to herein as a "screening assay") for identifying modulators, i.e., candidate or test compounds or agents (e.g., peptides, peptidomimetics, small molecules or other drugs) which interact with or bind to LP proteins, have a stimulatory or inhibitory effect on, for example, LP expression or LP activity, or have a stimulatory or inhibitory effect on, for example, the availability of LP substrate.

In one embodiment, the invention provides assays for screening candidate or test compounds which are substrates of an LP protein or polypeptide or biologically active portion thereof (e.g., triglycerides, phospholipids and cholesterol esters, or compounds which are structurally related thereto). In another embodiment, the invention provides assays for screening candidate or test compounds which bind to or modulate the activity of an LP protein or polypeptide or biologically active portion thereof (e.g., cofactors or inhibitory molecules). The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2 or 5678; Cho et al. (1993) *Science* 261:1303; Carrell et al. (1994) *Angew. Chem. Int. Ed. Engl.* 33:2 or 5059; Carell et al. (1994) *Angew. Chem. Int. Ed. Engl.* 33:2 or 5061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses an LP protein or biologically active portion thereof is contacted with a test compound and the ability of the test compound to modulate LP activity is determined. Determining the ability of the test compound to modulate LP activity can be accomplished by monitoring, for example, the production of one or more specific LP substrates or products in a cell which expresses LP (see, e.g., Saada et al. (2000) *Biochem Biophys. Res. Commun.* 269: 382–386). The cell, for example, can be of mammalian origin. The ability of the test compound to modulate LP binding to a substrate (e.g., a triglyceride, a phospholipid, or a cholesterol ester, or a compound structurally related to these compounds) or to bind to LP can also be determined. Determining the ability of the test compound to modulate LP binding to a substrate can be accomplished, for example, by coupling the LP substrate with a radioisotope or paramagnetic label such that binding of the LP substrate to LP can be determined by detecting the labeled LP substrate in a complex. Alternatively, LP could be coupled with a radioisotope or enzymatic label to monitor the ability of a test compound to modulate LP binding to an LP substrate in a complex. Determining the ability of the test compound to bind LP can be accomplished, for example, by coupling the compound with a radioisotope or enzymatic label such that binding of the compound to LP can be determined by detecting the labeled LP compound in a complex. For example, compounds (e.g., LP substrates) can be labeled with $^{125}$I, $^{35}$S, $^{14}$C, or $^{3}$H, either directly or indirectly, and the radioisotope detected by direct counting of radioemission or by scintillation counting. Similarly, compounds (e.g., LP substrates) can be labeled with a paramagnetic label, and the label detected by electroparamagnetic resonance. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., an LP substrate) to interact with LP without the labeling of any of the interactants. For example, a microphysiometer can be used to detect the interaction of a compound with LP without the labeling of either the compound or the LP. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and LP.

In another embodiment, an assay is a cell-based assay comprising contacting a cell expressing an LP target molecule (e.g., an LP substrate) with a test compound and determining the ability of the test compound to modulate (e.g., stimulate or inhibit) the activity of the LP target molecule. Determining the ability of the test compound to modulate the activity of an LP target molecule can be accomplished, for example, by determining the ability of the LP protein to bind to or interact with the LP target molecule.

Determining the ability of the LP protein, or a biologically active fragment thereof, to bind to or interact with an LP target molecule (e.g., a substrate or inhibitor) can be accomplished by one of the methods described above for determining direct binding. In a preferred embodiment, determining the ability of the LP protein to bind to or interact with an LP target molecule can be accomplished by determining the activity or availability of the target molecule. For example, a target-regulated cellular activity, such as growth or proliferation, may be monitored.

In yet another embodiment, an assay of the present invention is a cell-free assay in which an LP protein or biologically active portion thereof is contacted with a test compound and the ability of the test compound to associate with, to bind to, or to serve as a substrate for the LP protein or biologically active portion thereof is determined. Preferred biologically active portions of the LP proteins to be used in assays of the present invention include fragments which participate in interactions with non-LP molecules, e.g., fragments with high surface probability scores. Binding of the test compound to the LP protein can be determined either directly or indirectly as described above. In a preferred embodiment, the assay includes contacting the LP protein or biologically active portion thereof with a known compound which interacts with LP to form an assay mixture, contacting the assay mixture with a test compound, and determining the ability of the test compound to interact with an LP protein, wherein determining the ability of the test compound to interact with an LP protein comprises determining the ability of the test compound to preferentially bind to or interact with LP or a biologically active portion thereof as compared to the known compound.

In another embodiment, the assay is a cell-free assay in which an LP protein or biologically active portion thereof is contacted with a test compound and the ability of the test compound to modulate (e.g., stimulate or inhibit) the activity of the LP protein or biologically active portion thereof is determined. Determining the ability of the test compound to modulate the activity of an LP protein can be accomplished, for example, by determining the ability of the LP protein to bind to or associate with an LP target molecule by one of the methods described above for determining direct binding. Determining the ability of the LP protein to bind to an LP target molecule can also be accomplished using a technology such as real-time Biomolecular Interaction Analysis (BIA). Sjolander, S. and Urbaniczky, C. (1991) *Anal. Chem.* 63:2 or 5338–2345 and Szabo et al. (1995) *Curr. Opin. Struct. Biol.* 5:699–705. As used herein, "BIA" is a technology for studying biospecific interactions in real time, without labeling any of the interactants (e.g., BIACORE™). Changes in the optical phenomenon of surface plasmon resonance (SPR) can be used as an indication of real-time reactions between biological molecules.

In an alternative embodiment, determining the ability of the test compound to modulate the activity of an LP protein can be accomplished by determining the ability of the LP protein to further modulate the activity of a downstream effector of an LP target molecule. For example, the activity of the effector molecule on an appropriate target can be determined or the binding of the effector to an appropriate target can be determined as previously described.

In yet another embodiment, the cell-free assay involves contacting an LP protein or biologically active portion thereof with a known compound which binds the LP protein to form an assay mixture, contacting the assay mixture with a test compound, and determining the ability of the test compound to interact with the LP protein, wherein determining the ability of the test compound to interact with the LP protein comprises determining the ability of the LP protein to preferentially hydrolyze a target substrate (e.g., a triglyceride, a phospholipid, a cholesterol ester, or a structurally related compound).

In more than one embodiment of the above assay methods of the present invention, it may be desirable to immobilize either LP or its target molecule to facilitate separation of complexed from uncomplexed forms of either of the interactants, as well as to accommodate automation of the assay. Binding of a test compound to an LP protein, or interaction of an LP protein with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows the LP protein to be bound to a matrix. For example, glutathione-S-transferase/LP fusion proteins can be adsorbed onto glutathione SEPHAROSE™ beads (Sigma Chemical, St. Louis, Mo.) or glutathione derivatized microtitre plates, which are then combined with the test compound or the test compound and either the non-adsorbed target protein or LP protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of LP binding or activity determined using standard techniques.

Other techniques for immobilizing proteins on matrices can also be used in the screening assays of the invention. For example, an LP protein can be immobilized utilizing conjugation of biotin and streptavidin. Biotinylated LP protein can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with LP protein but which do not interfere with binding of the LP protein to its target molecule can be derivatized to the wells of the plate, and unbound target or LP protein trapped in the wells by antibody conjugation. Methods for detecting such complexes, in addition to those described above for the GST-immobilized complexes, include immunodetection of complexes using antibodies reactive with the LP protein or target molecule, as well as enzyme-linked assays which rely on detecting an enzymatic activity associated with the LP protein.

In another embodiment, modulators of LP expression are identified in a method wherein a cell is contacted with a candidate compound and the expression of LP mRNA or protein in the cell is determined. The level of expression of LP mRNA or protein in the presence of the candidate compound is compared to the level of expression of LP mRNA or protein in the absence of the candidate compound. The candidate compound can then be identified as a modulator of LP expression based on this comparison. For example, when expression of LP mRNA or protein is greater (statistically significantly greater) in the presence of the candidate compound than in its absence, the candidate compound is identified as a stimulator of LP mRNA or protein expression. Alternatively, when expression of LP mRNA or protein is less (statistically significantly less) in the presence of the candidate compound than in its absence, the candidate compound is identified as an inhibitor of LP mRNA or protein expression. The level of LP mRNA or protein expression in the cells can be determined by methods described herein for detecting LP mRNA or protein.

In yet another aspect of the invention, the LP proteins can be used as "bait proteins" in a two-hybrid assay or three-hybrid assay (see, e.g., U.S. Pat. No. 5,283,317; Zervos et al. (1993) *Cell* 72:2 or 523–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with LP ("LP-binding proteins" or "LP-6-bp") and are involved in LP activity. Such LP-binding proteins are also likely to be involved in the propagation of signals by the LP proteins or LP targets as, for example, downstream elements of an LP-mediated signaling pathway. Alternatively, such LP-binding proteins are likely to be LP inhibitors.

The two-hybrid system is based on the modular nature of most transcription factors, which consist of separable DNA-binding and activation domains. Briefly, the assay utilizes two different DNA constructs. In one construct, the gene that codes for an LP protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an LP-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene that encodes the protein which interacts with the LP protein.

In another aspect, the invention pertains to a combination of two or more of the assays described herein. For example, a modulating agent can be identified using a cell-based or a cell free assay, and the ability of the agent to modulate the activity of an LP protein can be confirmed in vivo, e.g., in an animal such as an animal model for atherosclerosis.

For example, the ability of the agent to modulate the activity of an LP protein can be tested in an animal such as an animal model for a cellular proliferation disorder, e.g., tumorigenesis. Animal based models for studying tumorigenesis in vivo are well known in the art (reviewed in Animal Models of Cancer Predisposition Syndromes, Hiai, H. and Hino, O. (eds.) 1999, Progress in Experimental Tumor Research, Vol. 35; Clarke, A. R. (2000) Carcinogenesis 21:435–41) and include, for example, carcinogen-induced tumors (Rithidech, K. et al. (1999) Mutat. Res. 428:33–39; Miller, M. L. et al. (2000) Environ. Mol. Mutagen. 35:319–327), injection and/or transplantation of tumor cells into an animal, as well as animals bearing mutations in growth regulatory genes, for example, oncogenes (e.g., ras) (Arbeit, J. M. et al. (1993) Am. J. Pathol. 142:1187–1197; Sinn, E. et al. (1987) Cell 49:465–475; Thorgeirsson, S S et al. Toxicol Lett (2000) 112–113: 553–555) and tumor suppressor genes (e.g., p53) (Vooijs, M. et al. (1999) Oncogene 18:5293–5303; Clark A. R. (1995) Cancer Metast. Rev. 14:125–148; Kumar, T. R. et al. (1995) J. Intern. Med. 238:233–238; Donehower, L. A. et al. (1992) Nature 356215–221). Furthermore, experimental model systems are available for the study of, for example, ovarian cancer (Hamilton, T. C. et al. (1984) Semin. Oncol. 11:285–298; Rahman, N. A. et al. (1998) Mol. Cell. Endocrinol. 145:167–174; Beamer, W. G. et al. (1998) Toxicol. Pathol. 26:704–710), gastric cancer (Thompson, J. et al. (2000) Int. J. Cancer 86:863–869; Fodde, R. et al. (1999) Cytogenet. Cell Genet. 86:105–111), breast cancer (Li, M. et al. (2000) Oncogene 19:1010–1019; Green, J. E. et al. (2000) Oncogene 19:1020–1027), melanoma (Satyamoorthy, K. et al. (1999) Cancer Metast. Rev. 18:401–405), and prostate cancer (Shirai, T. et al. (2000) Mutat. Res. 462: 219–226; Bostwick, D. G. et al. (2000) Prostate 43:286–294).

This invention further pertains to novel agents identified by the above-described screening assays. Accordingly, it is within the scope of this invention to further use an agent identified as described herein in an appropriate animal model. For example, an agent identified as described herein (e.g., an LP modulating agent, an antisense LP nucleic acid molecule, a LP-specific antibody, or an LP binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

In another aspect, cell-based systems, as described herein, may be used to identify compounds which may act to ameliorate tumorigenic or proliferative disease symptoms. For example, such cell systems may be exposed to a compound, suspected of exhibiting an ability to ameliorate tumorigenic or proliferative disease symptoms, at a sufficient concentration and for a time sufficient to elicit such an amelioration of tumorigenic or proliferative disease symptoms in the exposed cells. After exposure, the cells are examined to determine whether one or more of the tumorigenic or proliferative disease cellular phenotypes has been altered to resemble a more normal or more wild type, non-tumorigenic disease or non-proliferative disease phenotype. Cellular phenotypes that are associated with tumorigenic disease states include aberrant proliferation and migration, angiogenesis, anchorage independent growth, and loss of contact inhibition.

In addition, animal-based tumorigenic disease systems, such as those described herein, may be used to identify compounds capable of ameliorating tumorigenic or proliferative disease symptoms. Such animal models may be used as test substrates for the identification of drugs, pharmaceuticals, therapies, and interventions which may be effective in treating tumorigenic or proliferative disease. For example, animal models may be exposed to a compound, suspected of exhibiting an ability to ameliorate tumorigenic or proliferative disease symptoms, at a sufficient concentration and for a time sufficient to elicit such an amelioration of tumorigenic or apoptotic tumorigenic or proliferative disease symptoms in the exposed animals. The response of the animals to the exposure may be monitored by assessing the reversal of disorders associated with tumorigenic disease, for example, by counting the number of tumors and/or measuring their size before and after treatment. In addition, the animals may be monitored by assessing the reversal of disorders associated with tumorigenic disease, for example, reduction in tumor burden, tumor size, and invasive and/or metastatic potential before and after treatment.

With regard to intervention, any treatments which reverse any aspect of tumorigenic or proliferative disease symptoms should be considered as candidates for human tumorigenic or proliferative disease therapeutic intervention. Dosages of test agents may be determined by deriving dose-response curves.

Additionally, gene expression patterns may be utilized to assess the ability of a compound to ameliorate proliferative or tumorigenic disease symptoms. For example, the expression pattern of one or more genes may form part of a "gene expression profile" or "transcriptional profile" which may be then be used in such an assessment. "Gene expression profile" or "transcriptional profile", as used herein, includes the pattern of mRNA expression obtained for a given tissue or cell type under a given set of conditions. Such conditions may include, but are not limited to, the presence of a tumor, e.g., a breast or ovary tumor or any of the other tumors described herein, including any of control or experimental conditions described herein.

Other conditions may include, for example, cell differentiation, transformation, metastasis, and carcinogen exposure. Gene expression profiles may be generated, for example, by utilizing a differential display procedure, Northern analysis and/or RT-PCR. In one embodiment, LP gene sequences may be used as probes and/or PCR primers for the generation and corroboration of such gene expression profiles.

Gene expression profiles may be characterized for known states, either tumorigenic or proliferative disease or normal, within the cell- and/or animal-based model systems. Subsequently, these known gene expression profiles may be compared to ascertain the effect a test compound has to modify such gene expression profiles, and to cause the profile to more closely resemble that of a more desirable profile. For example, administration of a compound may cause the gene expression profile of a tumorigenic or proliferative disease model system to more closely resemble the control system. Administration of a compound may, alternatively, cause the gene expression profile of a control system to begin to mimic a tumorigenic or proliferative disease state. Such a compound may, for example, be used in further characterizing the compound of interest, or may be used in the generation of additional animal models.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the LP nucleotide sequences, described herein, can be used to map the location of the LP genes on a chromosome. The mapping of the LP sequences to chromosomes is an important first step in correlating these sequences with genes associated with disease.

Briefly, LP genes can be mapped to chromosomes by preparing PCR primers (preferably 15–25 bp in length) from the LP nucleotide sequences. Computer analysis of the LP sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the LP sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220: 919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the LP nucleotide sequences to design oligonucleotide primers, sublocalization can be achieved with panels of fragments from specific chromosomes. Other mapping strategies which can similarly be used to map an LP sequence to its chromosome include in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature,* 325:783–787.

Moreover, differences in the DNA sequences between individuals affected and unaffected with a disease associated with the LP gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The LP sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the LP nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The LP nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:19 or 22 can comfortably provide positive individual identification with a panel of perhaps 10 to 1,000 primers which each yield a noncoding amplified sequence of 100 bases. If predicted coding sequences, such as that in SEQ ID NO:21 or 24, are used, a more appropriate number of primers for positive individual identification would be 500–2,000.

If a panel of reagents from LP nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of LP Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:19 or 22 are particularly appropriate for this use as greater numbers of polymorphisms occur in the noncoding regions, making it easier to differentiate individuals using this technique. Examples of polynucleotide reagents include the LP nucleotide sequences or portions thereof, e.g., fragments derived from the noncoding regions of SEQ ID NO:19 or 22 having a length of at least 20 bases, preferably at least 30 bases.

The LP nucleotide sequences described herein can further be used to provide polynucleotide reagents, e.g., labeled or labelable probes which can be used in, for example, an in situ hybridization technique, to identify a specific tissue, e.g., thymus or brain tissue. This can be very useful in cases where a forensic pathologist is presented with a tissue of unknown origin. Panels of such LP probes can be used to identify tissue by species and/or by organ type.

In a similar fashion, these reagents, e.g., LP primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining LP protein and/or nucleic acid expression as well as LP activity, in the context of a biological sample (e.g., blood, serum, cells, tissue) to thereby determine whether an individual is afflicted with a disease or disorder, or is at risk of developing a disorder, associated with aberrant or unwanted LP expression or activity. The invention also provides for prognostic (or predictive) assays for determining whether an individual is at risk of developing a disorder associated with LP protein, nucleic acid expression or activity. For example, mutations in an LP gene can be assayed in a biological sample. Such assays can be used for prognostic or predictive purpose to thereby prophylactically treat an individual prior to the onset of a disorder characterized by or associated with LP protein, nucleic acid expression or activity.

Another aspect of the invention pertains to monitoring the influence of agents (e.g., drugs, compounds) on the expression or activity of LP in clinical trials.

These and other agents are described in further detail in the following sections.

1. Diagnostic Assays

An exemplary method for detecting the presence or absence of LP protein or nucleic acid in a biological sample involves obtaining a biological sample from a test subject and contacting the biological sample with a compound or an agent capable of detecting LP protein or nucleic acid (e.g., mRNA, or genomic DNA) that encodes LP protein such that the presence of LP protein or nucleic acid is detected in the biological sample. A preferred agent for detecting LP mRNA or genomic DNA is a labeled nucleic acid probe capable of hybridizing to LP mRNA or genomic DNA. The nucleic acid probe can be, for example, the LP nucleic acid set forth in SEQ ID NO:19, 21, 22, or 24, or a portion thereof, such as an oligonucleotide of at least 15, 30, 50, 100, 250 or 500 nucleotides in length and sufficient to specifically hybridize under stringent conditions to LP mRNA or genomic DNA. Other suitable probes for use in the diagnostic assays of the invention are described herein.

A preferred agent for detecting LP protein is an antibody capable of binding to LP protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect LP mRNA, protein, or genomic DNA in a biological sample in vitro as well as in vivo. For example, in vitro techniques for detection of LP mRNA include Northern hybridizations and in situ hybridizations. In vitro techniques for detection of LP protein include enzyme linked immunosorbent assays (ELISAs), Western blots, immunoprecipitations and immunofluorescence. In vitro techniques for detection of LP genomic DNA include Southern hybridizations. Furthermore, in vivo techniques for detection of LP protein include introducing into a subject a labeled anti-LP antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting LP protein, mRNA, or genomic DNA, such that the presence of LP protein, mRNA or genomic DNA is detected in the biological sample, and comparing the presence of LP protein, mRNA or genomic DNA in the control sample with the presence of LP protein, mRNA or genomic DNA in the test sample.

The invention also encompasses kits for detecting the presence of LP in a biological sample. For example, the kit can comprise a labeled compound or agent capable of detecting LP protein or mRNA in a biological sample; means for determining the amount of LP in the sample; and means for comparing the amount of LP in the sample with a standard. The compound or agent can be packaged in a suitable container. The kit can further comprise instructions for using the kit to detect LP protein or nucleic acid.

2. Prognostic Assays

The diagnostic methods described herein can furthermore be utilized to identify subjects having or at risk of developing a disease or disorder associated with aberrant or unwanted LP expression or activity. As used herein, the term "aberrant" includes an LP expression or activity which deviates from the wild type LP expression or activity. Aberrant expression or activity includes increased or decreased expression or activity, as well as expression or activity which does not follow the wild type developmental pattern of expression or the subcellular pattern of expression. For example, aberrant LP expression or activity is intended to include the cases in which a mutation in the LP gene causes the LP gene to be under-expressed or over-expressed and situations in which such mutations result in a non-functional LP protein or a protein which does not function in a wild-type fashion, e.g., a protein which does not interact with an LP substrate, or one which interacts with a non-LP substrate. As used herein, the term "unwanted" includes an unwanted phenomenon involved in a biological response such as cellular proliferation. For example, the term unwanted includes an LP expression or activity which is undesirable in a subject.

The assays described herein, such as the preceding diagnostic assays or the following assays, can be utilized to identify a subject having or at risk of developing a disorder associated with a misregulation in LP protein activity or nucleic acid expression, such as a cell proliferation, growth, differentiation, or migration disorder, a cardiovascular disorder, or disorders of lipid absorption or deposition. Alternatively, the prognostic assays can be utilized to identify a subject having or at risk for developing a disorder associated with a misregulation in LP protein activity or nucleic acid expression, such as a cell proliferation, growth, differentiation, or migration disorder, a cardiovascular disorder, or disorders of lipid absorption or deposition. Thus, the present invention provides a method for identifying a disease or disorder associated with aberrant or unwanted LP expression or activity in which a test sample is obtained from a subject and LP protein or nucleic acid (e.g., mRNA or genomic DNA) is detected, wherein the presence of LP protein or nucleic acid is diagnostic for a subject having or at risk of developing a disease or disorder associated with aberrant or unwanted LP expression or activity. As used herein, a "test sample" refers to a biological sample obtained from a subject of interest. For example, a test sample can be a biological fluid (e.g., cerebrospinal fluid or serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted LP expression or activity. For example, such methods can be used to determine whether a subject can be effectively treated with an agent for a cell proliferation, growth, differentiation, or migration disorder, a cardiovascular disorder, or disorders of lipid absorption or deposition. Thus, the present invention provides methods for determining whether a subject can be effectively treated with an agent for a disorder associated with aberrant or unwanted LP expression or activity in which a test sample is obtained and LP protein or nucleic acid expression or activity is detected (e.g., wherein the abundance of LP protein or nucleic acid expression or activity is diagnostic for a subject that can be administered the agent to treat a disorder associated with aberrant or unwanted LP expression or activity).

The methods of the invention can also be used to detect genetic alterations in an LP gene, thereby determining if a subject with the altered gene is at risk for a disorder characterized by misregulation in LP protein activity or nucleic acid expression, such as a cell proliferation, growth, differentiation, or migration disorder, a cardiovascular disorder, or disorders of lipid absorption or deposition. In preferred embodiments, the methods include detecting, in a sample of cells from the subject, the presence or absence of a genetic alteration characterized by at least one of an alteration affecting the integrity of a gene encoding an LP-protein, or the mis-expression of the LP gene. For example, such genetic alterations can be detected by ascertaining the existence of at least one of 1) a deletion of one or more nucleotides from an LP gene; 2) an addition of one or more nucleotides to an LP gene; 3) a substitution of one or more nucleotides of an LP gene, 4) a chromosomal rearrangement of an LP gene; 5) an alteration in the level of a messenger RNA transcript of an LP gene, 6) aberrant modification of an LP gene, such as of the methylation pattern of the genomic DNA, 7) the presence of a non-wild type splicing pattern of a messenger RNA transcript of an LP gene, 8) a non-wild type level of an LP-protein, 9) allelic loss of an LP gene, and 10) inappropriate post-translational modification of an LP-protein. As described herein, there are a large number of assays known in the art which can be used for detecting alterations in an LP gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in an LP gene (see Abravaya et al. (1995) *Nucleic Acids Res.* 23:675–682). This method can include the steps of collecting a sample of cells from a subject, isolating nucleic acid (e.g., genomic, mRNA or both) from the cells of the sample, contacting the nucleic acid sample with one or more primers which specifically hybridize to an LP gene under conditions such that hybridization and amplification of the LP gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an LP gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in LP can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in LP can be identified in two-dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the LP gene and detect mutations by comparing the sequence of the sample LP with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the LP gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type LP sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad Sci USA* 85:4397; Saleeba et al. (1992) *Methods Enzymol.* 217:2 or 586–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in LP cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on an LP sequence, e.g., a wild-type LP sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in LP genes. For example, single strand conformation polymorphism (SSCP) may be used to detect differences in electrophoretic mobility between mutant and wild type nucleic acids (Orita et al. (1989) *Proc Natl. Acad. Sci USA:* 86:2 or 5766, see also Cotton (1993) *Mutat. Res.* 285:125–144; and Hayashi (1992) *Genet. Anal. Tech. Appl.* 9:73–79). Single-stranded DNA fragments of sample and control LP nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2 or 5437–2448) or at the extreme 3' end of one primer where, under appropriate conditions, mismatch can prevent, or reduce polymerase extension (Prossner (1993) *Tibtech* 11:2 or 538). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an LP gene.

Furthermore, any cell type or tissue in which LP is expressed may be utilized in the prognostic assays described herein.

3. Monitoring of Effects During Clinical Trials

Monitoring the influence of agents (e.g., drugs) on the expression or activity of an LP protein (e.g., the modulation of cell proliferation and/or migration) can be applied not only in basic drug screening, but also in clinical trials. For example, the effectiveness of an agent determined by a screening assay as described herein to increase LP gene expression, protein levels, or upregulate LP activity, can be monitored in clinical trials of subjects exhibiting decreased LP gene expression, protein levels, or downregulated LP activity. Alternatively, the effectiveness of an agent determined by a screening assay to decrease LP gene expression, protein levels, or downregulate LP activity, can be monitored in clinical trials of subjects exhibiting increased LP gene expression, protein levels, or upregulated LP activity. In such clinical trials, the expression or activity of an LP gene, and preferably, other genes that have been implicated in, for example, an LP-associated disorder can be used as a "read out" or markers of the phenotype of a particular cell.

For example, and not by way of limitation, genes, including LP, that are modulated in cells by treatment with an agent (e.g., compound, drug or small molecule) which modulates LP activity (e.g., identified in a screening assay as described herein) can be identified. Thus, to study the effect of agents on LP-associated disorders (e.g., disorders characterized by deregulated cell proliferation and/or migration), for example, in a clinical trial, cells can be isolated and RNA prepared and analyzed for the levels of expression of LP and other genes implicated in the LP-associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of LP or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of an LP protein, mRNA, or genomic DNA in the preadministration sample; (iii) obtaining one or more post-administration samples from the subject; (iv) detecting the level of expression or activity of the LP protein, mRNA, or genomic DNA in the post-administration samples; (v) comparing the level of expression or activity of the LP protein, mRNA, or genomic DNA in the pre-administration sample with the LP protein, mRNA, or genomic DNA in the post administration sample or samples; and (vi) altering the administration of the agent to the subject accordingly. For example, increased administration of the agent may be desirable to increase the expression or activity of LP to higher levels than detected, i.e., to increase the effectiveness of the agent. Alternatively, decreased administration of the agent may be desirable to decrease expression or activity of LP to lower levels than detected, i.e. to decrease the effectiveness of the agent. According to such an embodiment, LP expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder or having a disorder associated with aberrant or unwanted LP expression or activity, e.g., a lipase-associated disorder such as a cell proliferation, growth, differentiation, or migration disorder, a cardiovascular disorder, or disorders of lipid absorption or deposition. As used herein, "treatment" of a subject includes the application or administration of a therapeutic agent to a subject, or application or administration of a therapeutic agent to a cell or tissue from a subject, who has a diseases or disorder, has a symptom of a disease or disorder, or is at risk of (or susceptible to) a disease or disorder, with the purpose to cure, heal, alleviate, relieve, alter, remedy, ameliorate, improve, or affect the disease or disorder, the symptom of the disease or disorder, or the risk of (or susceptibility to) the disease or disorder. With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the LP molecules of the present invention or LP modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted LP expression or activity, by administering to the subject an LP or an agent which modulates LP expression or at least one LP activity. Subjects at risk for a disease which is caused or contributed to by aberrant or unwanted LP expression or activity can be identified by, for example, any or a combination of diagnostic or prognostic assays as described herein. Administration of a prophylactic agent can occur prior to the manifestation of symptoms characteristic of the LP aberrancy, such that a disease or disorder is prevented or, alternatively, delayed in its progression. Depending on the type of LP aberrancy, for example, an LP, LP agonist or LP antagonist agent can be used for treating the subject. The appropriate agent can be determined based on screening assays described herein.

2. Therapeutic Methods

Another aspect of the invention pertains to methods of modulating LP expression or activity for therapeutic purposes. Accordingly, in an exemplary embodiment, the modulatory method of the invention involves contacting a cell with an LP or agent that modulates one or more of the activities of LP protein activity associated with the cell. An agent that modulates LP protein activity can be an agent as described herein, such as a nucleic acid or a protein, a naturally-occurring target molecule of an LP protein (e.g., an LP substrate), an LP antibody, an LP agonist or antagonist, a peptidomimetic of an LP agonist or antagonist, or other small molecule. In one embodiment, the agent stimulates one or more LP activities. Examples of such stimulatory agents include active LP protein and a nucleic acid molecule encoding LP that has been introduced into the cell. In another embodiment, the agent inhibits one or more LP activities. Examples of such inhibitory agents include antisense LP nucleic acid molecules, anti-LP antibodies, and LP inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of an LP protein or nucleic acid molecule. In one embodiment, the method involves administering an agent (e.g., an agent identified by a screening assay described herein), or combination of agents that modulates (e.g., upregulates or downregulates) LP expression or activity. In another embodiment, the method involves administering an LP protein or nucleic acid molecule as therapy to compensate for reduced, aberrant, or unwanted LP expression or activity.

Stimulation of LP activity is desirable in situations in which LP is abnormally downregulated and/or in which increased LP activity is likely to have a beneficial effect. Likewise, inhibition of LP activity is desirable in situations in which LP is abnormally upregulated and/or in which decreased LP activity is likely to have a beneficial effect.

3. Pharmacogenomics

The LP molecules of the present invention, as well as agents, or modulators which have a stimulatory or inhibitory effect on LP activity (e.g., LP gene expression) as identified by a screening assay described herein can be administered to individuals to treat (prophylactically or therapeutically) LP-associated disorders (e.g., cell proliferation, growth, differentiation, or migration disorders, cardiovascular disorders, or disorders of lipid absorption or deposition) associated with aberrant or unwanted LP activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an LP molecule or LP modulator as well as tailoring the dosage and/or therapeutic regimen of treatment with an LP molecule or LP modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11): 983–985 and Linder, M. W. et al. (1997) *Clin. Chem.* 43(2):2 or 554–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug target is known (e.g., an LP protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C 19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., an LP molecule or LP modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with an LP molecule or LP modulator, such as a modulator identified by one of the exemplary screening assays described herein.

E. Electronic Apparatus Readable Media and Arrays

Electronic apparatus readable media comprising LP sequence information is also provided. As used herein, "LP sequence information" refers to any nucleotide and/or amino acid sequence information particular to the LP molecules of the present invention, including but not limited to full-length nucleotide and/or amino acid sequences, partial nucleotide and/or amino acid sequences, polymorphic sequences including single nucleotide polymorphisms (SNPs), epitope sequences, and the like. Moreover, information "related to" said LP sequence information includes detection of the presence or absence of a sequence (e.g., detection of expression of a sequence, fragment, polymorphism, etc.), determination of the level of a sequence (e.g., detection of a level of expression, for example, a quantitative detection), detection of a reactivity to a sequence (e.g., detection of protein expression and/or levels, for example, using a sequence-specific antibody), and the like. As used herein, "electronic apparatus readable media" refers to any suitable medium for storing, holding, or containing data or information that can be read and accessed directly by an electronic apparatus. Such media can include, but are not limited to: magnetic storage media, such as floppy discs, hard disc storage medium, and magnetic tape; optical storage media such as compact discs; electronic storage media such as RAM, ROM, EPROM, EEPROM and the like; and general hard disks and hybrids of these categories such as magnetic/optical storage media. The medium is adapted or configured for having recorded thereon LP sequence information of the present invention.

As used herein, the term "electronic apparatus" is intended to include any suitable computing or processing apparatus or other device configured or adapted for storing data or information. Examples of electronic apparatus suitable for use with the present invention include stand-alone computing apparatuses; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the LP sequence information. A variety of software programs and formats can be used to store the sequence information on the electronic apparatus readable medium. For example, the sequence information can be represented in a word processing text file, formatted in commercially-available software such as WordPerfect and Microsoft Word, represented in the form of an ASCII file, or stored in a database application, such as DB2, Sybase, Oracle, or the like, as well as in other forms. Any number of dataprocessor structuring formats (e.g., text file or database) may be employed in order to obtain or create a medium having recorded thereon the LP sequence information.

By providing LP sequence information in readable form, one can routinely access the sequence information for a variety of purposes. For example, one skilled in the art can use the sequence information in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has an LP associated disease or disorder or a pre-disposition to a cellular proliferation, growth, differentiation, and/or migration disorder, wherein the method comprises the steps of determining LP sequence information associated with the subject and based on the LP sequence information, determining whether the subject has a cellular proliferation, growth, differentiation, and/or migration disorder or a pre-disposition to a cellular proliferation, growth, differentiation, and/or migration disorder, and/or recommending a particular treatment for the disease, disorder, or pre-disease condition.

The present invention further provides in an electronic system and/or in a network, a method for determining whether a subject has a cellular proliferation, growth, differentiation, and/or migration disorder or a pre-disposition to a cellular proliferation, growth, differentiation, and/or migration disorder wherein the method comprises the steps of determining LP sequence information associated with the subject, and based on the LP sequence information, determining whether the subject has a cellular proliferation, growth, differentiation, and/or migration disorder or a pre-disposition to a cellular proliferation, growth, differentiation, and/or migration disorder, and/or recommending a particular treatment for the disease, disorder or pre-disease condition. The method may further comprise the step of receiving phenotypic information associated with the subject and/or acquiring from a network phenotypic information associated with the subject.

The present invention also provides in a network, a method for determining whether a subject has a cellular proliferation, growth, differentiation, and/or migration disorder or a pre-disposition to a cellular proliferation, growth, differentiation, and/or migration disorder associated with LP, said method comprising the steps of receiving LP sequence information from the subject and/or information related thereto, receiving phenotypic information associated with the subject, acquiring information from the network corresponding to LP and/or a cellular proliferation, growth, differentiation, and/or migration disorder, and based on one or more of the phenotypic information, the LP information (e.g., sequence information and/or information related thereto), and the acquired information, determining whether the subject has a cellular proliferation, growth, differentiation, and/or migration disorder or a pre-disposition to a cellular proliferation, growth, differentiation, and/or migration disorder. The method may further comprise the step of recommending a particular treatment for the disease, disorder or pre-disease condition.

The present invention also provides a business method for determining whether a subject has a cellular proliferation, growth, differentiation, and/or migration disorder or a pre-disposition to a cellular proliferation, growth, differentiation, and/or migration disorder, said method comprising the steps of receiving information related to LP (e.g., sequence information and/or information related thereto), receiving phenotypic information associated with the subject, acquiring information from the network related to LP and/or related to a cellular proliferation, growth, differentiation, and/or migration disorder, and based on one or more of the phenotypic information, the LP information, and the acquired information, determining whether the subject has a cellular proliferation, growth, differentiation, and/or migration disorder or a pre-disposition to a cellular proliferation, growth, differentiation, and/or migration disorder. The method may further comprise the step of recommending a particular treatment for the disease, disorder or pre-disease condition.

The invention also includes an array comprising an LP sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, one of which can be LP. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a cellular proliferation, growth, differentiation, and/or migration disorder, progression of a cellular proliferation, growth, differentiation, and/or migration disorder, and processes, such a cellular transformation associated with the cellular proliferation, growth, differentiation, and/or migration disorder.

The array is also useful for ascertaining the effect of the expression of a gene on the expression of other genes in the same cell or in different cells (e.g., ascertaining the effect of LP expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including LP) that could serve as a molecular target for diagnosis or therapeutic intervention.

This invention is further illustrated by the following examples which should not be construed as limiting. The contents of all references, patents and published patent applications cited throughout this application, as well as the Figures and the Sequence Listing, are incorporated herein by reference.

EXAMPLES

Example 1

Identification and Characterization of Human LP cDNA

In this example, the identification and characterization of the gene encoding human LP and human $LP_{48-794}$ (clone Fbh50250) is described.

Isolation of the LP cDNA

The invention is based, at least in part, on the discovery of a human gene encoding novel proteins, referred to herein as human LP and human $LP_{48-794}$. The entire sequence of human clone Fbh50250 was determined and found to contain several open reading frames termed human "LP", and human "$LP_{48-794}$", set forth in FIGS. 37A–B and 38A–B, respectively. The amino acid sequences of these human LP expression products are set forth in FIGS. 37A–B and 38A–B, respectively. The human LP protein, the sequence of which is set forth in SEQ ID NO:20, comprises about 263 amino acids and is shown in FIGS. 37A–B. The human $LP_{48-794}$ protein, the sequence of which is set forth in SEQ ID NO:23, comprises about 248 amino acids and is shown in FIGS. 38A–B. The coding regions (open reading frames) of human LP and $LP_{48-794}$ are set forth as SEQ ID NOs:21 and 24, respectively. Clone Fbh50250 comprises the coding regions of human LP and fragment $LP_{48-794}$.

Analysis of the Human LP Molecules

The amino acid sequence of human LP and fragment $LP_{48-794}$ were analyzed using the program PSORT (see PSORT maintained by the Human Genome Center at the Institute of Medical Science in the University of Tokyo, Japan (psort.nibb.acjp)) to predict the localization of the protein within the cell. This program assesses the presence of different targeting and localization amino acid sequences within the query sequence. The results of the analyses show the likelihood of human LP (SEQ ID NO:20) being localized, for example, to the mitochondrion, to the nucleus, to the cell wall or extracellular space, or to the cytoplasm. The results further show the likelihood of fragment $LP_{48-794}$ of human LP (SEQ ID NO:23) being localized, for example, to the cytoplasm, to the mitochondrion, or to the nucleus.

An analysis of the amino acid sequences of human LP and $LP_{48-794}$ using the Signal P program (Henrik, et al. (1997) *Protein Engineering* 10:1–6), identified the potential presence of a signal peptide from amino acids 1–26 of SEQ ID NO:23.

A search of the amino acid sequence of human LP was also performed against the HMM database. This search resulted in the identification of a "lipase/acylhydrolase domain with a GDSL-like motif" in the amino acid sequence of human LP (SEQ ID NO:20) at about residues 31–107 (score=22.8). This search also resulted in the identification of a "lipase/acylhydrolase domain with a GDSL-like motif" in the amino acid sequence of human $LP_{48-794}$ (SEQ ID NO:23) at about residues 17–95 (score=42.8).

A search of the amino acid sequences of human LP and human $LP_{48-794}$ (SEQ ID NOs:20 and 23) was also performed against the ProDom database. The results of this search identified matches against protein domains described as "Isoamyl Acetate-Hydrolyzing Esterase Enzyme" and "Hypothetical 27.6 Kd Lipoprotein in NucB-AroD Intergenic Region". A search was also performed against the Prosite database, resulting in the identification of various sites such as an "N-glycosylation site" at amino acid residues 101–104 of human $LP_{48-794}$, a "cAMP- and cGMP-dependent protein kinase phosphorylation site" at amino acid residues 27 to 230 of human $LP_{48-794}$, a "Protein kinase C phosphorylation site" at amino acid residues 211–213 of human $LP_{48-794}$, as well as multiple casein kinase II phosphorylation sites and multiple N-myristoylation sites.

Tissue Distribution of LP mRNA

This example describes the tissue distribution of human LP mRNA, as determined by Northern analysis, by Polymerase Chain Reaction (PCR) on cDNA libraries using oligonucleotide primers based on the human LP sequence, or by in situ analysis.

Northern blot hybridizations with the various RNA samples are performed under standard conditions and washed under stringent conditions, i.e., 0.2×SSC at 65° C. The DNA probe is radioactively labeled with $^{32}$P-dCTP using the Prime-It kit (Stratagene, La Jolla, Calif.) according to the instructions of the supplier. Filters containing human mRNA (MultiTissue Northern I and MultiTissue Northern II from Clontech, Palo Alto, Calif.) are probed in ExpressHyb hybridization solution (Clontech) and washed at high stringency according to manufacturer's recommendations.

Human LP expression in normal tissues, e.g., human tissues, is assessed by PCR using the Taqman® system (PE Applied Biosystems) according to the manufacturer's instructions.

For in situ analysis, various tissues, e.g. tissues obtained from brain, are first frozen on dry ice. Ten-micrometer-thick sections of the tissues are postfixed with 4% formaldehyde in DEPC treated 1× phosphate-buffered saline at room temperature for 10 minutes before being rinsed twice in DEPC 1× phosphate-buffered saline and once in 0.1 M triethanolamine-HCl (pH 8.0). Following incubation in 0.25% acetic anhydride-0.1 M triethanolamine-HCl for 10 minutes, sections are rinsed in DEPC 2×SSC (1×SSC is 0.15M NaCl plus 0.015M sodium citrate). Tissue is then dehydrated through a series of ethanol washes, incubated in 100% chloroform for 5 minutes, and then rinsed in 100% ethanol for 1 minute and 95% ethanol for 1 minute and allowed to air dry.

Hybridizations are performed with $^{35}$S-radiolabeled (5×10$^7$ cpm/ml) cRNA probes. Probes are incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1× Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides are washed with 2×SSC. Sections are then sequentially incubated at 37° C. in TNE (a solution containing 10 mM Tris-HCl (pH 7.6), 500 mM NaCl, and 1 mM EDTA), for 10 minutes, in TNE with 10 μg of RNase A per ml for 30 minutes, and finally in TNE for 10 minutes. Slides are then rinsed with 2×SSC at room temperature, washed with 2×SSC at 50° C. for 1 hour, washed with 0.2×SSC at 55° C. for 1 hour, and 0.2×SSC at 60° C. for 1 hour. Sections are then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

Example 2

Expression of Recombinant Human LP Protein in Bacterial Cells

In this example, human LP is expressed as a recombinant glutathione-S-transferase (GST) fusion polypeptide in *E. coli* and the fusion polypeptide is isolated and characterized. Specifically, human LP is fused to GST and this fusion polypeptide is expressed in *E. coli*, e.g., strain PEB199. Expression of the GST-LP fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant Human L Protein in COS Cells

To express the human LP gene in COS cells, the pcDNA/ Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire human LP protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the human LP DNA sequence is amplified by PCR using two primers. The 5' primer contains the restriction site of interest followed by approximately twenty nucleotides of the human LP coding sequence starting from the initiation codon; the 3' end sequence contains complementary sequences to the other restriction site of interest, a translation stop codon, the HA tag or FLAG tag and the last 20 nucleotides of the human LP coding sequence. The PCR amplified fragment and the pcDNA/ Amp vector are digested with the appropriate restriction enzymes and the vector is dephosphorylated using the CIAP enzyme (New England Biolabs, Beverly, Mass.). Preferably the two restriction sites chosen are different so that the human LP gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the LP-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989. The expression of the human LP polypeptide is detected by radiolabeling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA-specific, FLAG-specific, or LP-specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA-specific, FLAG-specific, or LP-specific monoclonal antibody. Precipitated polypeptides are then analyzed by SDS-PAGE.

Alternatively, DNA containing the human LP coding sequence is cloned directly into the polylinker of the pcDNA/Amp vector using the appropriate restriction sites. The resulting plasmid is transfected into COS cells in the manner described above, and the expression of the human LP polypeptide is detected by radiolabeling and immunoprecipitation using a human LP-specific monoclonal antibody.

Example 4

Tissue Distribution of Human LP by Taqman Expression Analysis

Tissue Expression Analysis of LP mRNA Using Taqman Analysis

This example describes the tissue distribution of human LP mRNA in a variety of cells and tissues, as determined using the TaqMan™ procedure. The Taqman™ procedure is a quantitative, reverse transcription PCR-based approach for detecting mRNA. The RT-PCR reaction exploits the 5' nuclease activity of AmpliTaq Gold™ DNA Polymerase to cleave a TaqMan™ probe during PCR. Briefly, cDNA was generated from the samples of interest, e.g., tumor samples and normal samples, cell lines and the like, and used as the starting material for PCR amplification. In addition to the 5' and 3' gene-specific primers, a gene-specific oligonucleotide probe (complementary to the region being amplified) was included in the reaction (i.e., the Taqman™ probe). The TaqMan™ probe includes the oligonucleotide with a fluorescent reporter dye covalently linked to the 5' end of the probe (such as FAM (6-carboxyfluorescein), TET (6-carboxy-4,7,2',7'-tetrachlorofluorescein), JOE (6-carboxy-4,5-dichloro-2,7-dimethoxyfluorescein), or VIC) and a quencher dye (TAMRA (6-carboxy-N,N,N',N'-tetramethylrhodamine) at the 3' end of the probe.

When the fluorescently tagged oligonucleotide is intact, the fluorescent signal from the 5' dye is quenched. As PCR proceeds, the 5' to 3' nucleolytic activity of taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a way of quantitating the initial template concentration. Accumulation of PCR products is detected directly by monitoring the increase in fluorescence of the reporter dye. When the probe is intact, the proximity of the reporter dye to the quencher dye results in suppression of the reporter fluorescence. During PCR, if the target of interest is present, the probe specifically anneals between the forward and reverse primer sites. The 5'-3' nucleolytic activity of the AmpliTaq™ Gold DNA Polymerase cleaves the probe between the reporter and the quencher only if the probe hybridizes to the target. The probe fragments are then displaced from the target, and polymerization of the strand continues. The 3' end of the probe is blocked to prevent extension of the probe during PCR. This process occurs in every cycle and does not interfere with the exponential accumulation of product. Samples can be internally controlled by the addition of a second set of primers/probe specific for a housekeeping gene such as P2 microglobulin which has been labeled with a different fluor on the 5' end (typically JOE).

To determine the level of LP in various tissues a primer/probe set was designed using Primer Express software and primary cDNA sequence information. Total RNA was prepared from a series of tissues using an RNeasy kit from Qiagen First strand cDNA was prepared from one μg total RNA using an oligo dT primer and Superscript II reverse transcriptase (GIBCO-BRL). cDNA obtained from approximately 50 ng total RNA was used per TaqMan reaction. Mock cDNA synthesis in the absence of reverse transcriptase resulted in samples with no detectable PCR amplification of the control gene confirms efficient removal of genomic DNA contamination.

An array of human tissues were tested. The results of one such analysis are depicted in FIG. 39. Expression was greatest in brain cortex, heart with coronary heart failure (CHF), prostate epithelial cells, and glial cells. Expression was also high in primary osteoblasts, cardiovascular tissues such as the human umbilical vein epithelial cells, aortic and coronary smooth muscle cells (SMC), normal heart, kidney, liver and dermal fibroblasts, as well as nerve tissues, including the hypothalamus and dorsal root ganglions.

Moreover, as also shown in FIG. 39, increased expression of LP was observed in colon, breast and lung tumors as compared to normal colon, breast and lung tissues, respectively. Also, LP was observed to be decreased in ovary tumors versus non-cancerous ovarian tissue. Therefore, arrays including additional samples of cancerous and non-cancerous human tissues were tested for LP expression according to the above-described Taqman procedure. The results of such analyses are depicted in FIGS. 40 and 41.

Notably, expression was upregulated in 2 out of 6 breast tumor samples as compared to normal tissue samples, in 3 out of 8 lung tumor samples as compared to normal tissue samples, and in 3 out of 6 colon tumor samples as compared to normal tissue samples. Expression was downregulated in 6 out of 8 ovary tumor samples as compared to normal ovary samples.

To investigate the pattern of expression in the liver, LP expression levels were measured in various normal and diseased liver samples by quantitative PCR using the Taqman™ procedure as described above. The relative levels of LP expression in various samples are depicted in FIG. 42. Generally, expression of LP in the diseased state was moderately decreased as compared to normal samples.

To investigate the pattern of expression of LP in cardiovascular tissues, LP expression levels were measured in various tissue samples from normal and diseased cardiovascular vessels, using the Taqman™ procedure described above. The relative levels of LP expression in various samples are depicted in FIG. 43. Notably, LP expression was decreased in one diseased saphenous vein sample as compared to 5 non-diseased saphenous vein samples. A moderate decrease in expression was also noted in diseased arteries as compared to normal arteries.

VI. 55158, a Novel Human Carbonic Anhydrase and uses Thereof

BACKGROUND OF THE INVENTION

Regulation of the availability of carbon dioxide is of critical importance in most metabolic and catabolic pathways in cells. A large family of enzymes that facilitates the interconversion of carbon dioxide to carbonic acid, termed the carbonic anhydrase family, has been identified. In the forward reaction, these enzymes catalyze the reversible hydration of carbon dioxide, thereby forming a carbonyl group on the substrate. These enzymes are also able to participate in the reverse reaction, wherein a carbonyl group on the target molecule, carbonic acid, is reduced by the transfer of a hydride group to the enzyme. In both reaction mechanisms, a coordinated zinc ion mediates the activity of the enzyme. Members of the carbonic anhydrase family are ubiquitous, and have been isolated from nearly all organisms. Family members can be grouped into three different classes: the α-CA, β-CA, and γ-CA, which share little structural similarity, but which all use zinc as a cofactor (Hewett-Emmett and Tashian (1996) *Molec. Phylogenet. Evol.* 5:50–77). The α-CA are exclusively found in animals, while the β-CA and γ-CA have been identified in plants and bacteria, and archaebacteria, respectively (Burnell et al. (1990) *Plant Physiol.* 92: 37–40; Alber and Ferry (1994) *Proc. Natl. Acad. Sci. USA* 91: 6909–6913). In animals, members of the α-CA family have been further classified into seven categories (CA I–CA VII) according to localization and regulation of the enzyme. Subgroups CA I, II, III and VII are localized to the cytosol, CA IV is membrane-bound, CA V enzymes are found in the mitochondria, and CA VI enzymes are most commonly found in the saliva (Lindskog (1997) *Pharmacol. Ther.* 74(1): 1–20). The carbon dioxide hydration turnover rates of these enzymes also differ, with CA II having a high turnover rate (about $10^6$ $sec^{-1}$ at pH 9 and 25° C.) (Khalifah (1971) *J. Biol. Chem.* 246: 2561–2573; Steiner et al. (1975) *Eur. J. Biochem.* 59: 253–259), and CA III having a much lower turnover rate (about $8 \times 10^3$ $sec^{-1}$ at 25° C. (Jewell et al. (1991) *Biochemistry* 30:1484–1490).

Carbonic anhydrases have been well-characterized in terms of function and structure. The crystal structures of many of the α-CA family members are known (Liljas et al. (1972) *Nature New Biol.* 235: 131–137; Kannan et al. (1975) *Proc. Natl. Acad. Sci. USA* 72: 51–55; Eriksson et al. (1988a) Proteins Structure Funct. Genet. 4: 274–282; Håkansson et al. (1992) *J. Mol. Biol.* 227: 1192–1204; Eriksson and Liljas (1993) *Proteins Struc. Funct Genet.* 16: 29–42; Boriack-Sjodin et al. (1995) *Proc. Natl. Acad. Sci. USA* 92: 10949–10953; Stams et al. (1996) *Proc. Natl. Acad. Sci. USA* 93: 13589–13594). Structural similarities between family members are most frequently found in the active site, where the zinc ion is coordinated to the enzyme. Structural studies have found that the zinc ion is physically found near the bottom of the active site cavity, and is coordinated to three nitrogen atoms from three nearby histidines in a tetrahedral geometry, with a hydroxide ion or a water molecule as the fourth ligand (Lidskog (1997), supra). Residues which are conserved among α-CA family members include these three histidine molecules and ten other residues (including Gln-28, Ser-29, Pro-30, Asn-61, Ser-105, Glu-117, Gly-196, Thr-199, Trp-209, and Arg-246), many of which are thought to participate in indirect coordination of the substrate or the zinc ion (Lindskog (1997), supra).

Carbonic anhydrases play an important role in the production and breakdown of carbon dioxide and carbonic acid. Both of these compounds are of vital importance in the normal metabolic pathways and homeostatic regulatory mechanisms of the cell. For example, carbon dioxide is required for metabolic functions as diverse as gluconeogenesis and purine base biosynthesis. Similarly, fatty acid synthesis cannot proceed without carbonic acid (Stryer (1988) *Biochemistry*, $3^{rd}$ ed.). Biologic processes including the formation of various fluids (e.g., cerebrospinal fluid, gastric acid, vitreous humor, and saliva), calcification, bone resorption, respiration, and overall acid-base balance are also closely associated with the activity of carbonic anhydrases (Dodgson et al. (1991) The Carbonic Anhydrases: Cellular Physiology and Molecular Genetics. New York: Plenum). Furthermore, carbonic acid synthesis has been linked to the transport of sodium ions across cellular membranes (Friedland and Maren (1984) Pharmacology of the Eye. Berlin: Springer-Verlag), and is linked to maintenance of cellular pH. As such, their activity contributes to the ability of the cell to grow and differentiate, to proliferate, to communicate and interact with other cells, and to regulate homeostasis. Underscoring the importance of this family of enzymes, modulation of the activity of one or more carbonic anhydrases have been linked to a number of human diseases, including glaucoma (Hoyng and van Beek (2000) *Drugs* 59(3): 411–434), osteoporosis (Hu et al. (1997) *Hum. Mutat.* 9: 383–387); Fathallah et al. (1997) *Hum. Genet.* 99: 634–647), and Sjogren's disease (in which antibodies to carbonic anhydrase have been isolated) (Fox et al. (1998) *Curr. Opin. Rheumatol.* 10(5): 446–456).

SUMMARY OF THE INVENTION

The present invention is based, at least in part, on the discovery of novel members of the family of carbonic anhydrase molecules, referred to herein as CAH nucleic acid and protein molecules. The CAH nucleic acid and protein molecules of the present invention are useful as modulating agents in regulating a variety of cellular processes, e.g., cellular proliferation, growth, differentiation, or migration. Accordingly, in one aspect, this invention provides isolated nucleic acid molecules encoding CAH proteins or biologically active portions thereof, as well as nucleic acid fragments suitable as primers or hybridization probes for the detection of CAH-encoding nucleic acids.

In one embodiment, a CAH nucleic acid molecule of the invention is at least 50%, 55%, 60%, 65%, 70%, 75%, 80%, 85%, 90%, 91%, 92%, 93%, 94%, 95%, 99% or more identical to the nucleotide sequence (e.g., to the entire length of the nucleotide sequence) shown in SEQ ID NO:26 or 28, or a complement thereof.

In a preferred embodiment, the isolated nucleic acid molecule includes the nucleotide sequence shown in SEQ ID NO:26 or 28, or a complement thereof. In another embodiment, the nucleic acid molecule includes SEQ ID NO:28 and nucleotides 1–59 of SEQ ID NO:26. In yet a further embodiment, the nucleic acid molecule includes SEQ ID NO:28 and nucleotides 1047–1855 of SEQ ID NO:26. In another preferred embodiment, the nucleic acid molecule consists of the nucleotide sequence shown in SEQ ID NO:26 or 28.

In another embodiment, a CAH nucleic acid molecule includes a nucleotide sequence encoding a protein having an amino acid sequence sufficiently identical to the amino acid sequence of SEQ ID NO:27. In a preferred embodiment, a CAH nucleic acid molecule includes a nucleotide sequence encoding a protein having an amino acid sequence at least 50%, 55%, 60%, 65%, 70%, 75%, 80%, 85%, 90%, 91%, 92%, 93%, 94%, 95%, 96%, 97%, 98%, 99% or more identical to the entire length of the amino acid sequence of SEQ ID NO:27.

In another preferred embodiment, an isolated nucleic acid molecule encodes the amino acid sequence of human CAH. In yet another preferred embodiment, the nucleic acid molecule includes a nucleotide sequence encoding a protein having the amino acid sequence of SEQ ID NO:27. In yet another preferred embodiment, the nucleic acid molecule is at least 20, 30, 40, 50, 53, 100, 150, 200, 250, 300, 350, 400, 450, 500, 550, 600, 650, 700, 750, 800, 850, 878, 900, 950, 1000, 1050, 1100, 1150, 1200, 1250, 1300, 1350, 1400, 1450, 1500, 1550, 1600, 1650, 1700, 1750, 1800, 1850 or more nucleotides in length. In a further preferred embodiment, the nucleic acid molecule is at least 20, 30, 40, 50, 53, 100, 150, 200, 250, 300, 350, 400, 450, 500, 550, 600, 650, 700, 750, 800, 850, 878, 900, 950, 1000, 1050, 1100, 1150, 1200, 1250, 1300, 1350, 1400, 1450, 1500, 1550, 1600, 1650, 1700, 1750, 1800, 1850 or more nucleotides in length and encodes a protein having a CAH activity (as described herein).

Another embodiment of the invention features nucleic acid molecules, preferably CAH nucleic acid molecules, which specifically detect CAH nucleic acid molecules relative to nucleic acid molecules encoding non-CAH proteins. For example, in one embodiment, such a nucleic acid molecule is at least 20, 30, 40, 50, 53, 100, 150, 200, 250, 300, 350, 400, 450, 500, 550, 600, 650, 700, 750, 800, 850, 878, 900, 950, 1000, 1050, 1100, 1150, 1200, 1250, 1300, 1350, 1400, 1450, 1500, 1550, 1600, 1650, 1700, 1750, 1800, 1850 or more nucleotides in length and hybridizes under stringent conditions to a complement of a nucleic acid molecule comprising the nucleotide sequence shown in SEQ ID NO:26, the nucleotide sequence shown in SEQ ID NO:28, or a complement thereof.

In preferred embodiments, the nucleic acid molecules are at least 15 (e.g., 15 contiguous) nucleotides in length and hybridize under stringent conditions to a complement of the nucleotide molecule set forth in SEQ ID NO:26 or 28.

In other preferred embodiments, the nucleic acid molecule encodes a naturally occurring allelic variant of a polypeptide comprising the amino acid sequence of SEQ ID NO:27, wherein the nucleic acid molecule hybridizes to a complement of a nucleic acid molecule comprising SEQ ID NO:26 or 28, respectively, under stringent conditions.

Another embodiment of the invention provides an isolated nucleic acid molecule which is antisense to a CAH nucleic acid molecule, e.g., the coding strand of a CAH nucleic acid molecule.

Another aspect of the invention provides a vector comprising a CAH nucleic acid molecule. In certain embodiments, the vector is a recombinant expression vector. In another embodiment, the invention provides a host cell containing a vector of the invention. In yet another embodiment, the invention provides a host cell containing a nucleic acid molecule of the invention. The invention also provides a method for producing a protein, preferably a CAH protein, by culturing in a suitable medium, a host cell, e.g., a mammalian host cell such as a non-human mammalian cell, of the invention containing a recombinant expression vector, such that the protein is produced.

Another aspect of this invention features isolated or recombinant CAH proteins and polypeptides. In one embodiment, an isolated CAH protein includes at least one or more of the following motifs or domains: a signal peptide, a CAH signature motif, and/or a carbonic anhydrase domain.

In a preferred embodiment, a CAH protein includes at least one or more of the following motifs or domains: a signal peptide, a CAH signature motif, and/or a carbonic anhydrase domain, and has an amino acid sequence at least about 50%, 55%, 60%, 65%, 67%, 68%, 70%, 75%, 80%, 85%, 90%, 91%, 92%, 93%, 94%, 95%, 96%, 97%, 98%, 99% or more identical to the amino acid sequence of SEQ ID NO:27.

In another preferred embodiment, a CAH protein includes at least one or more of the following motifs or domains: a signal peptide, a CAH signature motif, and/or a carbonic anhydrase domain, and has a CAH activity (as described herein).

In yet another preferred embodiment, a CAH protein includes at least one or more of the following motifs or domains: a signal peptide, a CAH signature motif, and/or a carbonic anhydrase domain, and is encoded by a nucleic acid molecule having a nucleotide sequence which hybridizes under stringent hybridization conditions to a complement of a nucleic acid molecule comprising the nucleotide sequence of SEQ ID NO:26 or 28.

In another embodiment, the invention features fragments of the protein having the amino acid sequence of SEQ ID NO:27, wherein the fragment comprises at least 12 amino acids (e.g., contiguous amino acids) of the amino acid sequence of SEQ ID NO:27. In another embodiment, a CAH protein has the amino acid sequence of SEQ ID NO:27.

In another embodiment, the invention features a CAH protein which is encoded by a nucleic acid molecule consisting of a nucleotide sequence at least about 50%, 55%, 60%, 65%, 70%, 75%, 80%, 85%, 90%, 91%, 92%, 93%, 94%, 95%, 96%, 97%, 98%, 99% or more identical to a nucleotide sequence of SEQ ID NO:26 or 28, or a complement thereof. This invention further features a CAH protein which is encoded by a nucleic acid molecule consisting of a nucleotide sequence which hybridizes under stringent hybridization conditions to a nucleic acid molecule comprising the nucleotide sequence of SEQ ID NO:26 or 28, or a complement thereof.

The proteins of the present invention or portions thereof, e.g., biologically active portions thereof, can be operatively linked to a non-CAH polypeptide (e.g., heterologous amino acid sequences) to form fusion proteins. The invention further features antibodies, such as monoclonal or polyclonal antibodies, that specifically bind proteins of the invention, preferably CAH proteins. In addition, the CAH proteins or biologically active portions thereof can be incorporated into pharmaceutical compositions, which optionally include pharmaceutically acceptable carriers.

In another aspect, the present invention provides a method for detecting the presence of a CAH nucleic acid molecule, protein, or polypeptide in a biological sample by contacting the biological sample with an agent capable of detecting a CAH nucleic acid molecule, protein, or polypeptide such that the presence of a CAH nucleic acid molecule, protein or polypeptide is detected in the biological sample.

In another aspect, the present invention provides a method for detecting the presence of CAH activity in a biological sample by contacting the biological sample with an agent capable of detecting an indicator of CAH activity such that the presence of CAH activity is detected in the biological sample.

In another aspect, the invention provides a method for modulating CAH activity comprising contacting a cell capable of expressing CAH with an agent that modulates CAH activity such that CAH activity in the cell is modulated. In one embodiment, the agent inhibits CAH activity. In another embodiment, the agent stimulates CAH activity. In one embodiment, the agent is an antibody that specifically binds to a CAH protein. In another embodiment, the agent modulates expression of CAH by modulating transcription of a CAH gene or translation of a CAH mRNA. In yet another embodiment, the agent is a nucleic acid molecule having a nucleotide sequence that is antisense to the coding strand of a CAH mRNA or a CAH gene.

In one embodiment, the methods of the present invention are used to treat a subject having a disorder characterized by aberrant or unwanted CAH protein or nucleic acid expression or activity by administering an agent which is a CAH modulator to the subject. In one embodiment, the CAH modulator is a CAH protein. In another embodiment the CAH modulator is a CAH nucleic acid molecule. In yet another embodiment, the CAH modulator is a peptide, peptidomimetic, or other small molecule. In a preferred embodiment, the disorder characterized by aberrant or unwanted CAH protein or nucleic acid expression is a carbonic anhydrase-associated disorder, e.g., a CNS disorder, a cardiovascular disorder, a muscular disorder, a cell proliferation, growth, differentiation, or migration disorder (e.g., cancer), an ocular disorder, or a disorder of bone resorption, or calcification/bone formation.

The present invention also provides diagnostic assays for identifying the presence or absence of a genetic alteration characterized by at least one of (i) aberrant modification or mutation of a gene encoding a CAH protein; (ii) misregulation of the gene; and (iii) aberrant post-translational modification of a CAH protein, wherein a wild-type form of the gene encodes a protein with a CAH activity.

In another aspect the invention provides methods for identifying a compound that binds to or modulates the activity of a CAH protein, by providing an indicator composition comprising a CAH protein having CAH activity, contacting the indicator composition with a test compound, and determining the effect of the test compound on CAH activity in the indicator composition to identify a compound that modulates the activity of a CAH protein.

Other features and advantages of the invention will be apparent from the following detailed description and claims.

DETAILED DESCRIPTION OF THE INVENTION

The present invention is based, at least in part, on the discovery of novel molecules, referred to herein as "carbonic anhydrase" or "CAH" or "CAH55158" nucleic acid and protein molecules, which are novel members of a family of enzymes possessing carbonic anhydrase activity.

As used herein, the term "carbonic anhydrase" includes a molecule which is involved in the interconversion of carbon dioxide and carbonic acid by the reversible transfer of a hydride to carbon dioxide. Carbonic anhydrase molecules are involved in numerous metabolic and catabolic processes in a cell (including respiration, fatty acid biosynthesis, and purine biosynthesis), including those required for energy production or storage, and for metabolism or catabolism of metabolically important biomolecules. Carbonic anhydrase molecules are also involved in regulating homeostasis, (e.g., intracellular pH), in permitting cellular transport and signaling (e.g., sodium ion import), and in systemic processes such as fluid production (e.g., saliva, gastric fluid, intraocular fluid, and cerebrospinal fluid), calcification, and bone resorption. Thus, the CAH molecules of the present invention provide novel diagnostic targets and therapeutic agents to control carbonic anhydrase-associated disorders.

As used herein, a "carbonic anhydrase-mediated activity" includes an activity which involves the catalysis of reversible hydration of carbon dioxide to form carbonic acid (e.g., catalysis of the hydration of carbon dioxide to form carbonic acid and/or catalysis of the reverse reaction). Carbonic anhydrase-mediated activities include those cellular or systemic activities which require carbon dioxide and/or carbonic acid. Such activities include cellular metabolism, intra- or intercellular signaling, maintenance of cellular homeostasis (e.g., cellular pH), and systemic activities, such as calcification, bone resorption, and formation of various biological fluids, including saliva, cerebrospinal fluid, intraocular fluid, and gastric fluid. Such activities also include modulation or regulation of cellular proliferation, growth, differentiation, migration, and inter-or intra-cellular communication.

The term "family" when referring to the protein and nucleic acid molecules of the invention (e.g., the CAH family of proteins and/or nucleic acids) is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin, e.g., mouse or monkey proteins. Members of a family may also have common functional characteristics.

For example, the family of CAH proteins comprises at least one signal sequence or signal peptide. The prediction of such a signal peptide can be made, for example, utilizing the computer algorithm SignalP (Henrik, et al. (1997) *Protein Engineering* 10:1–6). As used herein, a "signal sequence" or "signal peptide" includes a peptide containing about 15 or more amino acids which occurs at the N-terminus of secretory and membrane bound proteins and which contains a large number of hydrophobic amino acid residues. For example, a signal sequence contains at least about 10–30 amino acid residues, preferably about 15–25 amino acid residues, more preferably about 18–20 amino acid residues, and more preferably about 19 amino acid residues, and has at least about 35–65%, preferably about 38–50%, and more preferably about 40–45% hydrophobic amino acid residues (e.g., Valine, Leucine, Isoleucine or Phenylalanine). Such a "signal sequence", also referred to in the art as a "signal peptide", serves to direct a protein containing such a sequence to a lipid bilayer, and is cleaved in secreted and membrane bound proteins. A signal sequence was identified in the amino acid sequence of human CAH at about amino acids 1–21 of SEQ ID NO:27.

In another embodiment, a CAH molecule of the present invention is identified based on the presence of a "carbonic anhydrase domain" in the protein or corresponding nucleic acid molecule. As used herein, the term "carbonic anhydrase domain" includes a protein domain having an amino acid sequence of about 150–300 amino acid residues, and a bit score of at least 70 when compared against a carbonic anhydrase Hidden Markov Model (HMM), e.g., PFAM accession number PF00194. In a preferred embodiment, a carbonic anhydrase domain includes a protein domain having an amino acid sequence of about 200–250 amino acid residues and a bit score of at least 100. In another preferred embodiment, a carbonic anhydrase domain includes a protein domain having an amino acid sequence of about 235–240 amino acid residues and a bit score of at least 125 (e.g., at least 130, 140, 150, 160, 170). To identify the presence of a carbonic anhydrase domain in a CAH protein, the amino acid sequence of the protein is used to search a database of known Hidden Markov Models (HMMs) e.g., the PFAM HMM database. The carbonic anhydrase domain (HMM) has been assigned the PFAM Accession PF00194 (found at Pfam website, genome.wustl.edu/Pfam). For example, a search was performed against the HMM database using the amino acid sequence (SEQ ID NO:27) of human CAH, resulting in the identification of a carbonic anhydrase domain in the amino acid sequence of human CAH (SEQ ID NO:27) at about residues 63–301 of SEQ ID NO:27, having a score of 170.

In another embodiment of the invention, a CAH protein is identified based on the presence of at least one "CAH signature motif" in the protein or corresponding nucleic acid molecule. As used herein, the term "CAH signature motif" includes an amino acid sequence that contains at least about 7–27 amino acid residues that are conserved among CAH family members. In one embodiment, a CAH signature motif includes an amino acid sequence at least about 10–24 amino acid residues, more preferably about 12–22 amino acid residues, even more preferably 15–19 amino acid residues and most preferably 17 amino acid residues in length and having the following amino acid sequence: S-E-[HN]-X-[LIVM]-X(4)-[FYH]-X(2)-E-[LIVMGA]-X-[LIVMFA](2), where X indicates any amino acid (see, for example, Edwards, Y. (1990) *Biochem. Soc. Trans.* 18:171–175). Accordingly, preferred proteins include the conserved amino acid residues of the above-recited CAH signature motif. Proteins including at least 10, 11, 12, 13, 14, 15, or 16 or more conserved amino acid residues of the above-recited CAH signature motif are also considered to be within the scope of the present invention.

In a preferred embodiment, the CAH molecules of the invention include at least one, preferably two or more of the following motifs or domains: a signal peptide, a CAH signature motif, and/or a carbonic anhydrase domain.

Isolated proteins of the present invention, preferably CAH proteins, have an amino acid sequence sufficiently identical to the amino acid sequence of SEQ ID NO:27, or are encoded by a nucleotide sequence sufficiently identical to SEQ ID NO:26 or 28. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%–80%, and even more preferably 90–95% homology across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70–80%, or 90–95% homology and share a common functional activity are defined herein as sufficiently identical.

As used interchangeably herein, an "CAH activity", "biological activity of CAH" or "functional activity of CAH", refers to an activity exerted by a CAH protein, polypeptide or nucleic acid molecule on a CAH responsive cell or tissue, or on a CAH protein substrate, as determined in vivo, or in vitro, according to standard techniques. In one embodiment, a CAH activity is a direct activity, such as an association with a CAH-target molecule. As used herein, a "target molecule" or "binding partner" is a molecule with which a CAH protein binds or interacts in nature, such that CAH-mediated function is achieved. A CAH target molecule can be a non-CAH molecule or a CAH protein or polypeptide of the present invention (e.g., a zinc ion, or other cofactor). In an exemplary embodiment, a CAH target molecule is a CAH substrate (e.g., carbon dioxide or carbonic acid). Alternatively, a CAH activity is an indirect activity, such as a metabolic activity mediated by interaction of the CAH protein with a CAH substrate. The biological activities of CAH are described herein. In an exemplary embodiment, the CAH proteins of the present invention have at least one of the following activities: i) interaction with a CAH substrate; ii) interaction with a cofactor; and iii) conversion of a CAH substrate to product (e.g., catalysis of the conversion of substrate to product). In yet another embodiment, the CAH proteins of the present invention have one or more of the following activities: 1) modulate metabolism and catabolism of biochemical molecules necessary for energy production or storage, or of metabolically important molecules, 2) modulate intra- or intercellular signaling, 3) regulate cellular homeostasis; 4) modulate calcification; 5) modulate bone resorption; 6) modulate fluid production; and 7) modulate cellular proliferation, growth, and/or differentiation.

Accordingly, another embodiment of the invention features isolated CAH proteins and polypeptides having a CAH activity. Other preferred proteins are CAH proteins having one or more of the following motifs or domains: a signal peptide, a CAH signature motif, and/or a carbonic anhydrase domain and, preferably, a CAH activity.

Additional preferred proteins have at least one or more of the following motifs or domains: a signal peptide, a CAH signature motif, and/or a carbonic anhydrase domain, and are, preferably, encoded by a nucleic acid molecule having a nucleotide sequence which hybridizes under stringent hybridization conditions to a complement of a nucleic acid molecule comprising the nucleotide sequence of SEQ ID NO:26 or 28.

The nucleotide sequence of the isolated human CAH cDNA and the predicted amino acid sequence of the human CAH polypeptide are shown in FIGS. 44A–B and in SEQ ID NOs:26 and 27, respectively.

The human CAH gene, which is approximately 1855 nucleotides in length, encodes a protein having a molecular weight of approximately 36.1 kD and which is approximately 328 amino acid residues in length.

Various aspects of the invention are described in further detail in the following subsections:

I. Isolated Nucleic Acid Molecules

One aspect of the invention pertains to isolated nucleic acid molecules that encode CAH proteins or biologically active portions thereof, as well as nucleic acid fragments sufficient for use as hybridization probes to identify CAH-encoding nucleic acid molecules (e.g., CAH mRNA) and fragments for use as PCR primers for the amplification or mutation of CAH nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated CAH nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:26 or 28, or a portion thereof, can be isolated using standard molecular biology techniques and the sequence information provided herein. Using all or portion of the nucleic acid sequence of SEQ ID NO:26 or 28, or the nucleotide sequence of the DNA insert of the plasmid deposited with ATCC as Accession Number _____ as a hybridization probe, CAH nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:26 or 28, can be isolated by the polymerase chain reaction (PCR) using synthetic oligonucleotide primers designed based upon the sequence of SEQ ID NO:26 or 28.

A nucleic acid of the invention can be amplified using cDNA, mRNA or, alternatively, genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to CAH nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:26 or 28. This cDNA may comprise sequences encoding the human CAH protein (i.e., "the coding region", from nucleotides 60–1046), as well as 5' untranslated sequences (nucleotides 1–59) and 3' untranslated sequences (nucleotides 1047–1855) of SEQ ID NO:26. Alternatively, the nucleic acid molecule can comprise only the coding region of SEQ ID NO:26 (e.g., nucleotides 60–1046, corresponding to SEQ ID NO:28). In another embodiment, an isolated nucleic acid molecule of the invention consists of the nucleic acid sequence of SEQ ID NO:26 or 28.

In another preferred embodiment, an isolated nucleic acid molecule of the invention comprises a nucleic acid molecule which is a complement of the nucleotide sequence shown in SEQ ID NO:26 or 28, or a portion of any of these nucleotide sequences. A nucleic acid molecule which is complementary to the nucleotide sequence shown in SEQ ID NO:26 or 28, is one which is sufficiently complementary to the nucleotide sequence shown in SEQ ID NO:26 or 28, such that it can hybridize to the nucleotide sequence shown in SEQ ID NO:26 or 28, respectively, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 90%, 91%, 92%, 93%, 94%, 95%, 96%, 97%, 98%, 99% or more identical to the entire length of the nucleotide sequence shown in SEQ ID NO:26 or 28, or a portion of any of these nucleotide sequences.

Moreover, the nucleic acid molecule of the invention can comprise only a portion of the nucleic acid sequence of SEQ ID NO:26 or 28, for example, a fragment which can be used as a probe or primer or a fragment encoding a portion of a CAH protein, e.g., a biologically active portion of a CAH protein. The nucleotide sequence determined from the cloning of the CAH gene allows for the generation of probes and primers designed for use in identifying and/or cloning other CAH family members, as well as CAH homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO: 26 or 28, of an anti-sense sequence of SEQ ID NO:26 or 28, or of a naturally occurring allelic variant or mutant of SEQ ID NO:26 or 28. In one embodiment, a nucleic acid molecule of the present invention comprises a nucleotide sequence which is greater than 20, 30, 40, 50, 53, 100, 150, 200, 250, 300, 350, 400, 450, 500, 550, 600, 650, 700, 750, 800, 850, 878, 900, 950, 1000, 1050, 1100, 1150, 1200, 1250, 1300, 1350, 1400, 1450, 1500, 1550, 1600, 1650, 1700, 1750, 1800, 1850 or more nucleotides in length and hybridizes under stringent hybridization conditions to a complement of a nucleic acid molecule of SEQ ID NO:26 or 28.

Probes based on the CAH nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a CAH protein, such as by measuring a level of a CAH-encoding nucleic acid in a sample of cells from a subject e.g., detecting CAH mRNA levels or determining whether a genomic CAH gene has been mutated or deleted.

A nucleic acid fragment encoding a "biologically active portion of a CAH protein" can be prepared by isolating a portion of the nucleotide sequence of SEQ ID NO:26 or 28, which encodes a polypeptide having a CAH biological activity (the biological activities of the CAH proteins are described herein), expressing the encoded portion of the CAH protein (e.g., by recombinant expression in vitro) and assessing the activity of the encoded portion of the CAH protein.

The invention further encompasses nucleic acid molecules that differ from the nucleotide sequence shown in SEQ ID NO:26 or 28, due to degeneracy of the genetic code and thus encode the same CAH proteins as those encoded by the nucleotide sequence shown in SEQ ID NO:26 or 28. In another embodiment, an isolated nucleic acid molecule of the invention has a nucleotide sequence encoding a protein having an amino acid sequence shown in SEQ ID NO:27.

In addition to the CAH nucleotide sequences shown in SEQ ID NO:26 or 28, it will be appreciated by those skilled in the art that DNA sequence polymorphisms that lead to changes in the amino acid sequences of the CAH proteins may exist within a population (e.g., the human population). Such genetic polymorphism in the CAH genes may exist among individuals within a population due to natural allelic variation. As used herein, the terms "gene" and "recombinant gene" refer to nucleic acid molecules which include an open reading frame encoding a CAH protein, preferably a mammalian CAH protein, and can further include non-coding regulatory sequences, and introns.

Allelic variants of human CAH include both functional and non-functional CAH proteins. Functional allelic variants are naturally occurring amino acid sequence variants of the human CAH protein that maintain the ability to bind a CAH ligand or substrate and/or modulate cell proliferation and/or migration mechanisms. Functional allelic variants will typically contain only conservative substitution of one or more amino acids of SEQ ID NO:27, or substitution, deletion or insertion of non-critical residues in non-critical regions of the protein.

Non-functional allelic variants are naturally occurring amino acid sequence variants of the human CAH protein that do not have the ability to either bind a CAH ligand and/or modulate any of the CAH activities described herein. Non-functional allelic variants will typically contain a non-conservative substitution, a deletion, or insertion or premature truncation of the amino acid sequence of SEQ ID NO:27, or a substitution, insertion or deletion in critical residues or critical regions of the protein.

The present invention further provides non-human orthologues of the human CAH protein. Orthologues of the human CAH protein are proteins that are isolated from non-human organisms and possess the same CAH ligand binding and/or modulation of membrane excitability activities of the human CAH protein. Orthologues of the human CAH protein can readily be identified as comprising an amino acid sequence that is substantially identical to SEQ ID NO:27.

Moreover, nucleic acid molecules encoding other CAH family members and, thus, which have a nucleotide sequence which differs from the CAH sequences of SEQ ID NO:26 or 28, are intended to be within the scope of the invention. For example, another CAH cDNA can be identified based on the nucleotide sequence of human CAH. Moreover, nucleic acid molecules encoding CAH proteins from different species, and which, thus, have a nucleotide sequence which differs from the CAH sequences of SEQ ID NO:26 or 28, are intended to be within the scope of the invention. For example, a mouse CAH cDNA can be identified based on the nucleotide sequence of a human CAH.

Nucleic acid molecules corresponding to natural allelic variants and homologues of the CAH cDNAs of the invention can be isolated based on their homology to the CAH nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the CAH cDNAs of the invention can further be isolated by mapping to the same chromosome or locus as the CAH gene.

Accordingly, in another embodiment, an isolated nucleic acid molecule of the invention is at least 15, 20, 25, 30 or more nucleotides in length and hybridizes under stringent conditions to a complement of the nucleic acid molecule comprising the nucleotide sequence of SEQ ID NO:26 or 28. In other embodiment, the nucleic acid is at least 20, 30, 40, 50, 53, 100, 150, 200, 250, 300, 350, 400, 450, 500, 550, 600, 650, 700, 750, 800, 850, 878, 900, 950, 1000, 1050, 1100, 1150, 1200, 1250, 1300, 1350, 1400, 1450, 1500, 1550, 1600, 1650, 1700, 1750, 1800, 1850 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chloride/sodium citrate (SSC), at about 65–70° C. (or hybridization in 4×SSC plus 50% formamide at about 42–50° C.) followed by one or more washes in 1×SSC, at about 65–70° C. A preferred, non-limiting example of highly stringent hybridization conditions includes hybridization in 1×SSC, at about 65–70° C. (or hybridization in 1×SSC plus 50% formamide at about 42–50° C.) followed by one or more washes in 0.3×SSC, at about 65–70° C. A preferred, non-limiting example of reduced stringency hybridization conditions includes hybridization in 4×SSC, at about 50–60° C. (or alternatively hybridization in 6× SSC plus 50% formamide at about 40–45° C.) followed by one or more washes in 2×SSC, at about 50–60° C. Ranges intermediate to the above-recited values, e.g., at 65–70° C. or at 42–50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m(° C.)=2(\#\ of\ A+T\ bases)+4(\#\ of\ G+C\ bases)$. For hybrids between 18 and 49 base pairs in length, $T_m(° C.)=81.5+16.6(\log_{10}[Na^+])+0.41(\%G+C)-(600/N)$, where N is the number of bases in the hybrid, and $[Na^+]$ is the concentration of sodium ions in the hybridization buffer ($[Na^+]$ for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25–0.5M $NaH_2PO_4$, 7% SDS at about 65° C., followed by one or more washes at 0.02M $NaH_2PO_4$, 1% SDS at 65° C., see e.g., Church and Gilbert (1984) *Proc. Natl. Acad. Sci. USA* 81:1991–1995, (or alternatively 0.2×SSC, 1% SDS).

Preferably, an isolated nucleic acid molecule of the invention that hybridizes under stringent conditions to the sequence of SEQ ID NO:26 or 28, and corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the CAH sequences that may exist in the population, the skilled artisan will further appreciate that changes can be introduced by mutation into the nucleotide sequences of SEQ ID NO:26 or 28, thereby leading to changes in the amino acid sequence of the encoded CAH proteins, without altering the functional ability of the CAH proteins. For example, nucleotide substitutions leading to amino acid substitutions at "non-essential" amino acid residues can be made in the sequence of SEQ ID NO:26 or 28. A "non-essential" amino acid residue is a residue that can be altered from the wild-type sequence of CAH (e.g., the sequence of SEQ ID NO:27) without altering the biological activity, whereas an "essential" amino acid residue is required for biological activity. For example, amino acid residues that are conserved among the CAH proteins of the present invention, e.g., those present in a carbonic anhydrase consensus sequence, are predicted to be particularly unamenable to alteration. Furthermore, additional amino acid residues that are conserved between the CAH proteins of the present invention and other members of the CAH family are not likely to be amenable to alteration.

Accordingly, another aspect of the invention pertains to nucleic acid molecules encoding CAH proteins that contain changes in amino acid residues that are not essential for activity. Such CAH proteins differ in amino acid sequence from SEQ ID NO:27, yet retain biological activity. In one embodiment, the isolated nucleic acid molecule comprises a nucleotide sequence encoding a protein, wherein the protein comprises an amino acid sequence at least about 50%, 55%, 60%, 65%, 70%, 75%, 80%, 85%, 90%, 91%, 92%, 93%, 94%, 95%, 96%, 97%, 98%, 99% or more identical to SEQ ID NO:27.

An isolated nucleic acid molecule encoding a CAH protein identical to the protein of SEQ ID NO:27 can be created by introducing one or more nucleotide substitutions, additions or deletions into the nucleotide sequence of SEQ ID NO:26 or 28, such that one or more amino acid substitutions, additions or deletions are introduced into the encoded protein. Mutations can be introduced into SEQ ID NO:26 or 28, by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a CAH protein is preferably replaced with another amino acid residue from the same side chain family. Alternatively, in another embodiment, mutations can be introduced randomly along all or part of a CAH coding sequence, such as by saturation mutagenesis, and the resultant mutants can be screened for CAH biological activity to identify mutants that retain activity. Following mutagenesis of SEQ ID NO:26 or 28, the encoded protein can be expressed recombinantly and the activity of the protein can be determined.

In a preferred embodiment, a mutant CAH protein can be assayed for the ability to metabolize or catabolize important biochemical molecules (e.g., those necessary for energy production or storage, or which are themselves metabolically important), to permit intra- or intercellular signaling, to regulate homeostasis (e.g., cellular pH), to modulate calcification or bone resorption, or to modulate fluid production (e.g., saliva, cerebrospinal fluid, gastric fluid, or intraocular fluid).

In addition to the nucleic acid molecules encoding CAH proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire CAH coding strand, or to only a portion thereof. In one embodiment, an antisense nucleic acid molecule is antisense to a "coding region" of the coding strand of a nucleotide sequence encoding a CAH. The term "coding region" refers to the region of the nucleotide sequence comprising codons which are translated into amino acid residues (e.g., the coding region of human CAH corresponds to SEQ ID NO:28). In another embodiment, the antisense nucleic acid molecule is antisense to a "noncoding region" of the coding strand of a nucleotide sequence encoding CAH. The term "noncoding region" refers to 5' and 3' sequences which flank the coding region that are not translated into amino acids (i.e., also referred to as 5' and 3' untranslated regions).

Given the coding strand sequences encoding CAH disclosed herein (e.g., SEQ ID NO:28), antisense nucleic acids of the invention can be designed according to the rules of Watson and Crick base pairing. The antisense nucleic acid molecule can be complementary to the entire coding region of CAH mRNA, but more preferably is an oligonucleotide which is antisense to only a portion of the coding or noncoding region of CAH mRNA. For example, the antisense oligonucleotide can be complementary to the region surrounding the translation start site of CAH mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a CAH protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff and Gerlach (1988) *Nature* 334:585–591)) can be used to catalytically cleave CAH mRNA transcripts to thereby inhibit translation of CAH mRNA. A ribozyme having specificity for a CAH-encoding nucleic acid can be designed based upon the nucleotide sequence of a CAH cDNA disclosed herein (i.e., SEQ ID NO:26 or 28. For example, a derivative of a *Tetrahymena* L-19 IVS RNA can be constructed in which the nucleotide sequence of the active site is complementary to the nucleotide sequence to be cleaved in a CAH-encoding mRNA. See, e.g., Cech et al. U.S. Pat. No. 4,987,071; and Cech et al. U.S. Pat. No. 5,116,742. Alternatively, CAH mRNA can be used to select a catalytic RNA having a specific ribonuclease activity from a pool of RNA molecules. See, e.g., Bartel, D. and Szostak, J. W. (1993) *Science* 261:1411–1418.

Alternatively, CAH gene expression can be inhibited by targeting nucleotide sequences complementary to the regulatory region of the CAH (e.g., the CAH promoter and/or enhancers; e.g., nucleotides 1–59 of SEQ ID NO:26) to form triple helical structures that prevent transcription of the CAH gene in target cells. See generally, Helene, C. (1991) *Anticancer Drug Des.* 6(6): 569–84; Helene, C. et al. (1992) *Ann. N.Y. Acad. Sci.* 660:27–36; and Maher, L. J. (1992) *Bioassays* 14(12):807–15.

In yet another embodiment, the CAH nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. *Proc. Natl. Acad. Sci.* 93: 14670–675.

PNAs of CAH nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of CAH nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of CAH can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of CAH nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

Alternatively, the expression characteristics of an endogenous CAH gene within a cell line or microorganism may be modified by inserting a heterologous DNA regulatory element into the genome of a stable cell line or cloned microorganism such that the inserted regulatory element is operatively linked with the endogenous CAH gene. For example, an endogenous CAH gene which is normally "transcriptionally silent", i.e., a CAH gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous CAH gene may be activated by insertion of a promiscuous regulatory element that works across cell types.

A heterologous regulatory element may be inserted into a stable cell line or cloned microorganism, such that it is operatively linked with an endogenous CAH gene, using techniques, such as targeted homologous recombination, which are well known to those of skill in the art, and described, e.g., in Chappel, U.S. Pat. No. 5,272,071; PCT publication No. WO 91/06667, published May 16, 1991.

II. Isolated CAH Proteins and Anti-CAH Antibodies

One aspect of the invention pertains to isolated CAH proteins, and biologically active portions thereof, as well as polypeptide fragments suitable for use as immunogens to raise anti-CAH antibodies. In one embodiment, native CAH proteins can be isolated from cells or tissue sources by an appropriate purification scheme using standard protein purification techniques. In another embodiment, CAH proteins are produced by recombinant DNA techniques. Alternative to recombinant expression, a CAH protein or polypeptide can be synthesized chemically using standard peptide synthesis techniques.

An "isolated" or "purified" protein or biologically active portion thereof is substantially free of cellular material or other contaminating proteins from the cell or tissue source from which the CAH protein is derived, or substantially free from chemical precursors or other chemicals when chemically synthesized. The language "substantially free of cellular material" includes preparations of CAH protein in which the protein is separated from cellular components of the cells from which it is isolated or recombinantly produced. In one embodiment, the language "substantially free of cellular material" includes preparations of CAH protein having less than about 30% (by dry weight) of non-CAH protein (also referred to herein as a "contaminating protein"), more preferably less than about 20% of non-CAH protein, still more preferably less than about 10% of non-CAH protein, and most preferably less than about 5% non-CAH protein. When the CAH protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of CAH protein in which the protein is separated from chemical precursors or other chemicals which are involved in the synthesis of the protein. In one embodiment, the language "substantially free of chemical precursors or other chemicals" includes preparations of CAH protein having less than about 30% (by dry weight) of chemical precursors or non-CAH chemicals, more preferably less than about 20% chemical precursors or non-CAH chemicals, still more preferably less than about 10% chemical precursors or non-CAH chemicals, and most preferably less than about 5% chemical precursors or non-CAH chemicals.

As used herein, a "biologically active portion" of a CAH protein includes a fragment of a CAH protein which participates in an interaction between a CAH molecule and a non-CAH molecule. Biologically active portions of a CAH protein include peptides comprising amino acid sequences sufficiently identical to or derived from the amino acid sequence of the CAH protein, e.g., the amino acid sequence shown in SEQ ID NO:27, which include less amino acids than the full length CAH proteins, and exhibit at least one activity of a CAH protein. Typically, biologically active portions comprise a domain or motif with at least one activity of the CAH protein, e.g., modulating membrane excitability. A biologically active portion of a CAH protein can be a polypeptide which is, for example, 12, 25, 50, 75, 100, 125, 150, 175, 200, 250, 300 or more amino acids in length. Biologically active portions of a CAH protein can be used as targets for developing agents which modulate a CAH mediated activity, e.g., a proliferative response.

It is to be understood that a preferred biologically active portion of a CAH protein of the present invention may contain at least one or more of the following motifs or domains: a signal peptide, a CAH signature motif, and/or a carbonic anhydrase domain. Moreover, other biologically active portions, in which other regions of the protein are deleted, can be prepared by recombinant techniques and evaluated for one or more of the functional activities of a native CAH protein.

In a preferred embodiment, the CAH protein has an amino acid sequence shown in SEQ ID NO:27. In other embodiments, the CAH protein is substantially identical to SEQ ID NO:27, and retains the functional activity of the protein of SEQ ID NO:27, yet differs in amino acid sequence due to natural allelic variation or mutagenesis, as described in detail in subsection I above. Accordingly, in another embodiment, the CAH protein is a protein which comprises an amino acid sequence at least about 50%, 55%, 60%, 65%, 70%, 75%, 80%, 85%, 90%, 91%, 92%, 93%, 94%, 95%, 96%, 97%, 98%, 99% or more identical to SEQ ID NO:27.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the CAH amino acid sequence of SEQ ID NO:27 having 328 amino acid residues, at least 50, preferably at least 100, more preferably at least 150, even more preferably at least 200, and even more preferably at least 300 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at the bioinformayics page of the website maintained by Accelrys, Inc., San Diego, Calif., USA), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*Comput. Appl. Biosci.*, 4: 11–17 (1988)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to CAH nucleic acid molecules of the invention. BLAST protein searches can be performed with the XBLAST program, score=100, wordlength=3 to obtain amino acid sequences homologous to CAH protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used (accessible at the website maintained by National Center for Biotechnology Information, Bethesda, Md., USA.

The invention also provides CAH chimeric or fusion proteins. As used herein, a CAH "chimeric protein" or "fusion protein" comprises a CAH polypeptide operatively linked to a non-CAH polypeptide. An "CAH polypeptide" refers to a polypeptide having an amino acid sequence corresponding to a CAH molecule, whereas a "non-CAH polypeptide" refers to a polypeptide having an amino acid sequence corresponding to a protein which is not substantially homologous to the CAH protein, e.g., a protein which is different from the CAH protein and which is derived from the same or a different organism. Within a CAH fusion protein the CAH polypeptide can correspond to all or a portion of a CAH protein. In a preferred embodiment, a CAH fusion protein comprises at least one biologically active portion of a CAH protein. In another preferred embodiment, a CAH fusion protein comprises at least two biologically active portions of a CAH protein. Within the fusion protein, the term "operatively linked" is intended to indicate that the CAH polypeptide and the non-CAH polypeptide are fused in-frame to each other. The non-CAH polypeptide can be fused to the N-terminus or C-terminus of the CAH polypeptide.

For example, in one embodiment, the fusion protein is a GST-CAH fusion protein in which the CAH sequences are fused to the C-terminus of the GST sequences. Such fusion proteins can facilitate the purification of recombinant CAH.

In another embodiment, the fusion protein is a CAH protein containing a heterologous signal sequence at its N-terminus. In certain host cells (e.g., mammalian host cells), expression and/or secretion of CAH can be increased through use of a heterologous signal sequence.

The CAH fusion proteins of the invention can be incorporated into pharmaceutical compositions and administered to a subject in vivo. The CAH fusion proteins can be used to affect the bioavailability of a CAH substrate. Use of CAH fusion proteins may be useful therapeutically for the treatment of disorders caused by, for example, (i) aberrant modification or mutation of a gene encoding a CAH protein; (ii) mis-regulation of the CAH gene; and (iii) aberrant post-translational modification of a CAH protein.

Moreover, the CAH-fusion proteins of the invention can be used as immunogens to produce anti-CAH antibodies in a subject, to purify CAH ligands and in screening assays to identify molecules which inhibit the interaction of CAH with a CAH substrate.

Preferably, a CAH chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A CAH-encoding nucleic acid can be cloned into such an expression vector such that the fusion moiety is linked in-frame to the CAH protein.

The present invention also pertains to variants of the CAH proteins which function as either CAH agonists (mimetics) or as CAH antagonists. Variants of the CAH proteins can be generated by mutagenesis, e.g., discrete point mutation or truncation of a CAH protein. An agonist of the CAH proteins can retain substantially the same, or a subset, of the biological activities of the naturally occurring form of a CAH protein. An antagonist of a CAH protein can inhibit one or more of the activities of the naturally occurring form of the CAH protein by, for example, competitively modulating a CAH-mediated activity of a CAH protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the CAH protein.

In one embodiment, variants of a CAH protein which function as either CAH agonists (mimetics) or as CAH antagonists can be identified by screening combinatorial libraries of mutants, e.g., truncation mutants, of a CAH protein for CAH protein agonist or antagonist activity. In one embodiment, a variegated library of CAH variants is generated by combinatorial mutagenesis at the nucleic acid level and is encoded by a variegated gene library. A variegated library of CAH variants can be produced by, for example, enzymatically ligating a mixture of synthetic oligonucleotides into gene sequences such that a degenerate set of potential CAH sequences is expressible as individual polypeptides, or alternatively, as a set of larger fusion proteins (e.g., for phage display) containing the set of CAH sequences therein. There are a variety of methods which can be used to produce libraries of potential CAH variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential CAH sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a CAH protein coding sequence can be used to generate a variegated population of CAH fragments for screening and subsequent selection of variants of a CAH protein. In one embodiment, a library of coding sequence fragments can be generated by treating a double stranded PCR fragment of a CAH coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the CAH protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of CAH proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify CAH variants (Arkin and Youvan (1992) *Proc. Natl. Acad. Sci. USA* 89:7811–7815; Delagrave et al. (1993) *Protein Engineering* 6(3): 327–331).

In one embodiment, cell based assays can be exploited to analyze a variegated CAH library. For example, a library of expression vectors can be transfected into a cell line, e.g., a neuronal cell line, which ordinarily responds to a CAH ligand in a particular CAH ligand-dependent manner. The transfected cells are then contacted with a CAH ligand and the effect of expression of the mutant on, e.g., membrane excitability of CAH can be detected. Plasmid DNA can then be recovered from the cells which score for inhibition, or alternatively, potentiation of signaling by the CAH ligand, and the individual clones further characterized.

An isolated CAH protein, or a portion or fragment thereof, can be used as an immunogen to generate antibodies that bind CAH using standard techniques for polyclonal and monoclonal antibody preparation. A full-length CAH protein can be used or, alternatively, the invention provides antigenic peptide fragments of CAH for use as immunogens. The antigenic peptide of CAH comprises at least 8 amino acid residues of the amino acid sequence shown in SEQ ID NO:27 and encompasses an epitope of CAH such that an antibody raised against the peptide forms a specific immune complex with the CAH protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of CAH that are located on the surface of the protein, e.g., hydrophilic regions, as well as regions with high antigenicity (see, for example, FIG. 45).

A CAH immunogen typically is used to prepare antibodies by immunizing a suitable subject, (e.g., rabbit, goat, mouse or other mammal) with the immunogen. An appropriate immunogenic preparation can contain, for example, recombinantly expressed CAHH protein or a chemically synthesized CAH polypeptide. The preparation can further include an adjuvant, such as Freund's complete or incomplete adjuvant, or similar immunostimulatory agent. Immunization of a suitable subject with an immunogenic CAH preparation induces a polyclonal anti-CAH antibody response.

Accordingly, another aspect of the invention pertains to anti-CAH antibodies. The term "antibody" as used herein refers to immunoglobulin molecules and immunologically active portions of immunoglobulin molecules, i.e., molecules that contain an antigen binding site which specifically binds (immunoreacts with) an antigen, such as a CAH. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind CAH molecules. The term "monoclonal antibody" or "monoclonal antibody composition", as used herein, refers to a population of antibody molecules that contain only one species of an antigen binding site capable of immunoreacting with a particular epitope of CAH. A monoclonal antibody composition thus typically displays a single binding affinity for a particular CAH protein with which it immunoreacts.

Polyclonal anti-CAH antibodies can be prepared as described above by immunizing a suitable subject with a CAH immunogen. The anti-CAH antibody titer in the immunized subject can be monitored over time by standard techniques, such as with an enzyme linked immunosorbent assay (ELISA) using immobilized CAH. If desired, the antibody molecules directed against CAH can be isolated from the mammal (e.g., from the blood) and further purified by well known techniques, such as protein A chromatography to obtain the IgG fraction. At an appropriate time after immunization, e.g., when the anti-CAH antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem* 0.255: 4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a CAH immunogen as described above, and the culture supernatants of the resulting hybridoma cells are screened to identify a hybridoma producing a monoclonal antibody that binds CAH.

Any of the many well known protocols used for fusing lymphocytes and immortalized cell lines can be applied for the purpose of generating an anti-CAH monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. (Manassas, Va.). Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind CAH, e.g., using a standard ELISA assay.

Alternative to preparing monoclonal antibody-secreting hybridomas, a monoclonal anti-CAH antibody can be identified and isolated by screening a recombinant combinatorial immunoglobulin library (e.g., an antibody phage display library) with CAH to thereby isolate immunoglobulin library members that bind CAH. Kits for generating and screening phage display libraries are commercially available (e.g., the Pharmacia *Recombinant Phage Antibody System*, Catalog No. 27-9400-01; and the Stratagene SurfZAP™ *Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1369–1372; Hay et al. (1992) *Hum. Antibod. Hybridomas* 3:81–85; Huse et al. (1989) *Science* 246:1275–1281; Griffiths et al. (1993) *EMBO J.* 12:725–734; Hawkins et al. (1992) *J. Mol. Biol.* 226: 889–896; Clackson et al. (1991) *Nature* 352:624–628; Gram et al. (1992) *Proc. Natl. Acad. Sci. USA* 89:3576–3580; Garrard et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-CAH antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171, 496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225, 539; Jones et al. (1986) *Nature* 321:552–525; Verhoeyen et al. (1988) *Science* 239:1534; and Beidler et al. (1988) *J. Immunol.* 141:4053–4060.

An anti-CAH antibody (e.g., monoclonal antibody) can be used to isolate CAH by standard techniques, such as affinity chromatography or immunoprecipitation. An anti-CAH antibody can facilitate the purification of natural CAH from cells and of recombinantly produced CAH expressed in host cells. Moreover, an anti-CAH antibody can be used to detect CAH protein (e.g., in a cellular lysate or cell supernatant) in order to evaluate the abundance and pattern of expression of the CAH protein. Anti-CAH antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid encoding a CAH protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., CAH proteins, mutant forms of CAH proteins, fusion proteins, and the like).

The recombinant expression vectors of the invention can be designed for expression of CAH proteins in prokaryotic or eukaryotic cells. For example, CAH proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in CAH activity assays, (e.g., direct assays or competitive assays described in detail below), or to generate antibodies specific for CAH proteins, for example. In a preferred embodiment, a CAH fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Meth-* ods in *Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the CAH expression vector is a yeast expression vector. Examples of vectors for expression in yeast *S. cerevisiae* include pYepSec1 (Baldari, et al., (1987) *EMBO J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (Invitrogen Corporation, San Diego, Calif.).

Alternatively, CAH proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to CAH mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a CAH nucleic acid molecule of the invention is introduced, e.g., a CAH nucleic acid molecule within a recombinant expression vector or a CAH nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a CAH protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a CAH protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a CAH protein. Accordingly, the invention further provides methods for producing a CAH protein using the host cells of the invention. In one embodiment, the method comprises culturing the host cell of the invention (into which a recombinant expression vector encoding a CAH protein has been introduced) in a suitable medium such that a CAH protein is produced. In another embodiment, the method further comprises isolating a CAH protein from the medium or the host cell.

The host cells of the invention can also be used to produce non-human transgenic animals. For example, in one embodiment, a host cell of the invention is a fertilized oocyte or an embryonic stem cell into which CAH-coding sequences have been introduced. Such host cells can then be used to create non-human transgenic animals in which exogenous CAH sequences have been introduced into their genome or homologous recombinant animals in which endogenous CAH sequences have been altered. Such animals are useful for studying the function and/or activity of a CAH and for identifying and/or evaluating modulators of CAH activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous CAH gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a CAH-encoding nucleic acid into the male pronuclei of a fertilized oocyte, e.g., by microinjection, retroviral infection, and allowing the oocyte to develop in a pseudopregnant female foster animal. The CAH cDNA sequence of SEQ ID NO:26 can be introduced as a transgene into the genome of a non-human animal. Alternatively, a nonhuman homologue of a human CAH gene, such as a mouse or rat CAH gene, can be used as a transgene. Alternatively, a CAH gene homologue, such as another CAH family member, can be isolated based on hybridization to the CAH cDNA sequences of SEQ ID NO:26 or 28 (described further in subsection I above) and used as a transgene. Intronic sequences and polyadenylation signals can also be included in the transgene to increase the efficiency of expression of the transgene. A tissue-specific regulatory sequence(s) can be operably linked to a CAH transgene to direct expression of a CAH protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a CAH transgene in its genome and/or expression of CAH mRNA in tissues or cells of the animals. A transgenic founder animal can then be used to breed additional animals carrying the transgene. Moreover, transgenic animals carrying a transgene encoding a CAH protein can further be bred to other transgenic animals carrying other transgenes.

To create a homologous recombinant animal, a vector is prepared which contains at least a portion of a CAH gene into which a deletion, addition or substitution has been introduced to thereby alter, e.g., functionally disrupt, the CAH gene. The CAH gene can be a human gene (e.g., the cDNA of SEQ ID NO:28), but more preferably, is a non-human homologue of a human CAH gene (e.g., a cDNA isolated by stringent hybridization with the nucleotide sequence of SEQ ID NO:26). For example, a mouse CAH gene can be used to construct a homologous recombination nucleic acid molecule, e.g., a vector, suitable for altering an endogenous CAH gene in the mouse genome. In a preferred embodiment, the homologous recombination nucleic acid molecule is designed such that, upon homologous recombination, the endogenous CAH gene is functionally disrupted (i.e., no longer encodes a functional protein; also referred to as a "knock out" vector). Alternatively, the homologous recombination nucleic acid molecule can be designed such that, upon homologous recombination, the endogenous CAH gene is mutated or otherwise altered but still encodes functional protein (e.g., the upstream regulatory region can be altered to thereby alter the expression of the endogenous CAE protein). In the homologous recombination nucleic acid molecule, the altered portion of the CAH gene is flanked at its 5' and 3' ends by additional nucleic acid sequence of the CAH gene to allow for homologous recombination to occur between the exogenous CAH gene carried by the homologous recombination nucleic acid molecule and an endogenous CAH gene in a cell, e.g., an embryonic stem cell. The additional flanking CAH nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced CAH gene has homologously recombined with the endogenous CAH gene are selected (see e.g., Li, E. et al. (1992) *Cell* 69:915). The selected cells can then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The CAH nucleic acid molecules, fragments of CAH proteins, and anti-CAH antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, (CREMOPHOR®EL solubilizer (BASF; Florham Park, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a CAH protein or an anti-CAH antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a CAH protein of the invention has one or more of the following activities: 1) it modulates metabolism and catabolism of biochemical molecules necessary for energy production or storage, or of metabolically important molecules, 2) it modulates intra- or intercellular signaling, 3) it regulates cellular homeostasis; 4) it modulates calcification; 5) it modulates bone resorption; and 6) it modulates fluid production.

The isolated nucleic acid molecules of the invention can be used, for example, to express CAH protein (e.g., via a recombinant expression vector in a host cell in gene therapy applications), to detect CAH mRNA (e.g., in a biological sample) or a genetic alteration in a CAH gene, and to modulate CAH activity, as described further below. The CAH proteins can be used to treat disorders characterized by insufficient or excessive production of a CAH substrate or production of CAH inhibitors. In addition, the CAH proteins can be used to screen for naturally occurring CAH substrates, to screen for drugs or compounds which modulate CAH activity, as well as to treat disorders characterized by insufficient or excessive production of CAH protein or production of CAH protein forms which have decreased, aberrant or unwanted activity compared to CAH wild type protein (e.g., carbonic anhydrase-associated disorders).

In a preferred embodiment, the CAH molecules of the invention are useful for catalyzing the reversible hydration of carbon dioxide to carbonic acid. As such, these molecules may be employed in small or large-scale synthesis of either carbon dioxide or carbonic acid, or in chemical processes that require the production or interconversion of these compounds. Such processes are known in the art (see, e.g., Ullmann et al. (1999) Ullmann's Encyclopedia of Industrial Chemistry, $6^{th}$ ed. VCH: Weinheim; Gutcho (1983) Chemicals by Fermentation. Park ridge, N.J.: Noyes Data Corporation (ISBN 0818805086); Rehm et al. (eds.) (1993) Biotechnology, 2$^{nd}$ ed. VCH: Weinheim; and Michal, G. (1999) Biochemical Pathways: An Atlas of Biochemistry and Molecular Biology. New York: John Wiley & Sons, and references contained therein.)

As used herein, a "carbonic anhydrase-associated disorder" includes a disorder, disease or condition which is caused or characterized by a misregulation (e.g., downregulation or upregulation) of carbonic anhydrase activity. Carbonic anhydrase-associated disorders can detrimentally affect cellular functions such as cellular proliferation, growth, differentiation, or migration, inter- or intra-cellular communication; tissue function, such as cardiac function or musculoskeletal function; systemic responses in an organism, such as nervous system responses, ocular function, or bone formation/resorption. Examples of carbonic anhydrase-associated disorders include CNS disorders such as cognitive and neurodegenerative disorders, examples of which include, but are not limited to, Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis, progressive supranuclear palsy, epilepsy, and Jakob-Creutzfieldt disease; autonomic function disorders such as hypertension and sleep disorders, and neuropsychiatric disorders, such as depression, schizophrenia, schizoaffective disorder, korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), and bipolar affective neurological disorders, e.g., migraine and obesity. Further CNS-related disorders include, for example, those listed in the American Psychiatric Association's Diagnostic and Statistical manual of Mental Disorders (DSM), the most current version of which is incorporated herein by reference in its entirety.

Further examples of carbonic anhydrase-associated disorders include cardiac-related disorders. Cardiovascular system disorders in which the CAH molecules of the invention may be directly or indirectly involved include arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrilation, Jervell syndrome, Lange-Nielsen syndrome, long-QT syndrome, congestive heart failure, sinus. node dysfunction, angina, heart failure, hypertension, atrial fibrillation, atrial flutter, dilated cardiomyopathy, idiopathic cardiomyopathy, myocardial infarction, coronary artery disease, coronary artery spasm, and arrhythmia. CAH-mediated or related disorders also include disorders of the musculoskeletal system such as paralysis and muscle weakness, e.g., ataxia, myotonia, and myokymia.

Carbonic anhydrase disorders also include cellular proliferation, growth, differentiation, or migration disorders. Cellular proliferation, growth, differentiation, or migration disorders include those disorders that affect cell proliferation, growth, differentiation, or migration processes. As used herein, a "cellular proliferation, growth, differentiation, or migration process" is a process by which a cell increases in number, size or content, by which a cell develops a specialized set of characteristics which differ from that of other cells, or by which a cell moves closer to or further from a particular location or stimulus. The CAH molecules of the present invention are involved in signal transduction mechanisms, which are known to be involved in cellular growth, differentiation, and migration processes. Thus, the CAH molecules may modulate cellular growth, differentiation, or migration, and may play a role in disorders characterized by aberrantly regulated growth, differentiation, or migration. Such disorders include cancer, e.g., carcinoma, sarcoma, or leukemia; tumor angiogenesis and metastasis; skeletal dysplasia; hepatic disorders; and hematopoietic and/or myeloproliferative disorders.

CAH-associated or related disorders also include ocular disorders, particularly disorders in which intraocular fluid or intraocular pressure is aberrant. Examples of such disorders and diseases include glaucoma and vitreous opacities.

CAH-associated or related disorders also include disorders of bone formation and resorption, including osteoporosis, and osteopetrosis, as well as calcification disorders, such as kidney stone or bone spur formation.

CAH-associated or related disorders also include disorders affecting tissues in which CAH protein is expressed, e.g., cancer, such as lung cancer, ovarian cancer, breast cancer, brain cancer, or colon cancer, or CNS disorders affecting, for example, the brain, hypothalamus, DGR, or the spinal cord.

Moreover, the anti-CAH antibodies of the invention can be used to detect and isolate CAH proteins, regulate the bioavailability of CAH proteins, and modulate CAH activity.

A. Screening Assays:

The invention provides a method (also referred to herein as a "screening assay") for identifying modulators, i.e., candidate or test compounds or agents (e.g., peptides, peptidomimetics, small molecules or other drugs) which interact with or bind to CAH proteins, have a stimulatory or inhibitory effect on, for example, CAH expression or CAH activity, or have a stimulatory or inhibitory effect on, for example, the availability of CAH substrate.

In one embodiment, the invention provides assays for screening candidate or test compounds which are substrates of a CAH protein or polypeptide or biologically active portion thereof (e.g., carbon dioxide or carbonic acid, or compounds which are structurally related thereto). In another embodiment, the invention provides assays for screening candidate or test compounds which bind to or modulate the activity of a CAH protein or polypeptide or biologically active portion thereof (e.g., zinc ions or other cofactors, or inhibitory molecules). The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.*

33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223, 409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses a CAH protein or biologically active portion thereof is contacted with a test compound and the ability of the test compound to modulate CAH activity is determined. Determining the ability of the test compound to modulate CAH activity can be accomplished by monitoring, for example, the production of one or more specific CAH substrates or products in a cell which expresses CAH (see, e.g., Saada et al. (2000) *Biochem Biophys. Res. Commun.* 269:382–386). The cell, for example, can be of mammalian origin. The ability of the test compound to modulate CAH binding to a substrate (e.g., carbon dioxide or carbonic acid) or to bind to CAH can also be determined. Determining the ability of the test compound to modulate CAH binding to a substrate can be accomplished, for example, by coupling the CAH substrate with a radioisotope or paramagnetic label such that binding of the CAH substrate to CAH can be determined by detecting the labeled CAH substrate in a complex. Alternatively, CAH could be coupled with a radioisotope or enzymatic label to monitor the ability of a test compound to modulate CAH binding to a CAH substrate in a complex. Determining the ability of the test compound to bind CAH can be accomplished, for example, by coupling the compound with a radioisotope or enzymatic label such that binding of the compound to CAH can be determined by detecting the labeled CAH compound in a complex. For example, compounds (e.g., CAH substrates) can be labeled with $^{125}I$, $^{35}S$, $^{14}C$, or $^{3}H$, either directly or indirectly, and the radioisotope detected by direct counting of radioemission or by scintillation counting. Similarly, compounds (e.g., CAH substrates) can be labeled with a paramagnetic label, and the label detected by electroparamagnetic resonance. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., a CAH substrate) to interact with CAH without the labeling of any of the interactants. For example, a microphysiometer can be used to detect the interaction of a compound with CAH without the labeling of either the compound or the CAH. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and CAH.

In another embodiment, an assay is a cell-based assay comprising contacting a cell expressing a CAH target molecule (e.g., a CAH substrate) with a test compound and determining the ability of the test compound to modulate (e.g., stimulate or inhibit) the activity of the CAH target molecule. Determining the ability of the test compound to modulate the activity of a CAH target molecule can be accomplished, for example, by determining the ability of the CAH protein to bind to or interact with the CAH target molecule.

Determining the ability of the CAH protein, or a biologically active fragment thereof, to bind to or interact with a CAH target molecule (e.g., a substrate or inhibitor) can be accomplished by one of the methods described above for determining direct binding. In a preferred embodiment, determining the ability of the CAH protein to bind to or interact with a CAH target molecule can be accomplished by determining the activity or availability of the target molecule. For example, a target-regulated cellular activity, such as a biosynthetic pathway which requires the participation of the target molecule (e.g., fatty acid synthesis or purine biosynthesis), may be monitored.

In yet another embodiment, an assay of the present invention is a cell-free assay in which a CAH protein or biologically active portion thereof is contacted with a test compound and the ability of the test compound to associate with, to bind to, or to serve as a substrate for the CAH protein or biologically active portion thereof is determined. Preferred biologically active portions of the CAH proteins to be used in assays of the present invention include fragments which participate in interactions with non-CAH molecules, e.g., fragments with high surface probability scores (see, for example, FIG. 45). Binding of the test compound to the CAH protein can be determined either directly or indirectly as described above. In a preferred embodiment, the assay includes contacting the CAH protein or biologically active portion thereof with a known compound which interacts with CAH to form an assay mixture, contacting the assay mixture with a test compound, and determining the ability of the test compound to interact with a CAH protein, wherein determining the ability of the test compound to interact with a CAH protein comprises determining the ability of the test compound to preferentially bind to or interact with CAH or a biologically active portion thereof as compared to the known compound.

In another embodiment, the assay is a cell-free assay in which a CAH protein or biologically active portion thereof is contacted with a test compound and the ability of the test compound to modulate (e.g., stimulate or inhibit) the activity of the CAH protein or biologically active portion thereof is determined. Determining the ability of the test compound to modulate the activity of a CAH protein can be accomplished, for example, by determining the ability of the CAH protein to bind to or associate with a CAH target molecule by one of the methods described above for determining direct binding. Determining the ability of the CAH protein to bind to a CAH target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIACORE™). Changes in the optical phenomenon of surface plasmon resonance (SPR) can be used as an indication of real-time reactions between biological molecules.

In an alternative embodiment, determining the ability of the test compound to modulate the activity of a CAH protein can be accomplished by determining the ability of the CAH protein to further modulate the activity of a downstream effector of a CAH target molecule. For example, the activity of the effector molecule on an appropriate target can be determined or the binding of the effector to an appropriate target can be determined as previously described.

In yet another embodiment, the cell-free assay involves contacting a CAH protein or biologically active portion thereof with a known compound which binds the CAH protein to form an assay mixture, contacting the assay mixture with a test compound, and determining the ability of the test compound to interact with the CAH protein, wherein determining the ability of the test compound to interact with the CAH protein comprises determining the ability of the CAH protein to preferentially bind to or catalyze the transfer of a hydride moiety to or from the target substrate (e.g., carbon dioxide or carbonic acid).

In more than one embodiment of the above assay methods of the present invention, it may be desirable to immobilize either CAH or its target molecule to facilitate separation of complexed from uncomplexed forms of either of the interactants, as well as to accomodate automation of the assay. Binding of a test compound to a CAH protein, or interaction of a CAH protein with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows the CAH protein to be bound to a matrix. For example, glutathione-S-transferase/CAH fusion proteins can be adsorbed onto glutathione SEPHAROSE™ beads (Sigma Chemical, St. Louis, Mo.) or glutathione derivatized microtitre plates, which are then combined with the test compound or the test compound and either the non-adsorbed target protein or CAH protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of CAH binding or activity determined using standard techniques.

Other techniques for immobilizing proteins on matrices can also be used in the screening assays of the invention. For example, a CAH protein can be immobilized utilizing conjugation of biotin and streptavidin. Biotinylated CAH protein can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with CAH protein but which do not interfere with binding of the CAH protein to its target molecule can be derivatized to the wells of the plate, and unbound target or CAH protein trapped in the wells by antibody conjugation. Methods for detecting such complexes, in addition to those described above for the GST-immobilized complexes, include immunodetection of complexes using antibodies reactive with the CAH protein or target molecule, as well as enzyme-linked assays which rely on detecting an enzymatic activity associated with the CAH protein.

In another embodiment, modulators of CAH expression are identified in a method wherein a cell is contacted with a candidate compound and the expression of CAH mRNA or protein in the cell is determined. The level of expression of CAH mRNA or protein in the presence of the candidate compound is compared to the level of expression of CAH mRNA or protein in the absence of the candidate compound. The candidate compound can then be identified as a modulator of CAH expression based on this comparison. For example, when expression of CAH mRNA or protein is greater (statistically significantly greater) in the presence of the candidate compound than in its absence, the candidate compound is identified as a stimulator of CAH mRNA or protein expression. Alternatively, when expression of CAH mRNA or protein is less (statistically significantly less) in the presence of the candidate compound than in its absence, the candidate compound is identified as an inhibitor of CAH mRNA or protein expression. The level of CAH mRNA or protein expression in the cells can be determined by methods described herein for detecting CAH mRNA or protein.

In yet another aspect of the invention, the CAH proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with CAH ("CAH-binding proteins" or "CAH-6-bp") and are involved in CAH activity. Such CAH-binding proteins are also likely to be involved in the propagation of signals by the CAH proteins or CAH targets as, for example, downstream elements of a CAH-mediated signaling pathway. Alternatively, such CAH-binding proteins are likely to be CAH inhibitors.

The two-hybrid system is based on the modular nature of most transcription factors, which consist of separable DNA-binding and activation domains. Briefly, the assay utilizes two different DNA constructs. In one construct, the gene that codes for a CAH protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a CAH-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene that encodes the protein which interacts with the CAH protein.

In another aspect, the invention pertains to a combination of two or more of the assays described herein. For example, a modulating agent can be identified using a cell-based or a cell free assay, and the ability of the agent to modulate the activity of a CAH protein can be confirmed in vivo, e.g., in an animal such as an animal model for cellular transformation and/or tumorigenesis.

Animal based models for studying tumorigenesis in vivo are well known in the art (reviewed in Animal Models of Cancer Predisposition Syndromes, Hiai, H and Hino, O (eds.) 1999, Progress in Experimental Tumor Research, Vol. 35; Clarke A R Carcinogenesis (2000) 21:435–41) and include, for example, carcinogen-induced tumors (Rithidech, K et al. Mutat Res (1999) 428:33–39; Miller, M L et al. Environ Mol Mutagen (2000) 35:319–327), injection and/or transplantation of tumor cells into an animal, as well as animals bearing mutations in growth regulatory genes, for example, oncogenes (e.g., ras) (Arbeit, J M et al. Am J Pathol (1993) 142:1187–1197; Sinn, E et al. Cell (1987) 49:465–475; Thorgeirsson, S S et al. Toxicol Lett (2000)

112–113:553–555) and tumor suppressor genes (e.g., p53) (Vooijs, M et al. *Oncogene* (1999) 18:5293–5303; Clark A R *Cancer Metast Rev* (1995) 14:125–148; Kumar, T R et al. *J. Intern Med* (1995) 238:233–238; Donehower, L A et al. (1992) *Nature* 356215–221). Furthermore, experimental model systems are available for the study of, for example, colon cancer (Heyer J, et al. (1999) *Oncogene* 18(38): 5325–33), ovarian cancer (Hamilton, T C et al. *Semin Oncol* (1984) 11:285–298; Rahman, N A et al. *Mol Cell Endocrinol* (1998) 145:167–174; Beamer, W G et al. *Toxicol Pathol* (1998) 26:704–710), gastric cancer (Thompson, J et al. *Int J. Cancer* (2000) 86:863–869; Fodde, R et al. *Cytogenet Cell Genet* (1999) 86:105–111), breast cancer (Li, M et al. *Oncogene* (2000) 19:1010–1019; Green, J E et al. *Oncogene* (2000) 19:1020–1027), melanoma (Satyamoorthy, K et al. *Cancer Metast Rev* (1999) 18:401–405), and prostate cancer (Shirai, T et al. *Mutat Res* (2000) 462:219–226; Bostwick, D G et al. *Prostate* (2000) 43:286–294).

This invention further pertains to novel agents identified by the above-described screening assays. Accordingly, it is within the scope of this invention to further use an agent identified as described herein in an appropriate animal model. For example, an agent identified as described herein (e.g., a CAH modulating agent, an antisense CAH nucleic acid molecule, a CAH-specific antibody, a CAH substrate or a CAH-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

In one embodiment, the invention features a method of treating a subject having a cellular growth or proliferation disorder that involves administering to the subject a CAH modulator such that treatment occurs. In another embodiment, the invention features a method of treating a subject having cancer that involves treating a subject with a CAH modulator, such that treatment occurs. Preferred CAH modulators include, but are not limited to, CAH proteins or biologically active fragments, CAH nucleic acid molecules, CAH antibodies, ribozymes, and CAH antisense oligonucleotides designed based on the CAH nucleotide sequences disclosed herein, as well as peptides, organic and non-organic small molecules identified as being capable of modulating CAH expression and/or activity, for example, according to at least one of the screening assays described herein.

Any of the compounds, including but not limited to compounds such as those identified in the foregoing assay systems, may be tested for the ability to ameliorate cellular growth or proliferation disorder symptoms. Cell-based and animal model-based assays for the identification of compounds exhibiting such an ability to ameliorate cellular growth or proliferation disorder systems are described herein.

In one aspect, cell-based systems, as described herein, may be used to identify compounds which may act to ameliorate cellular growth or proliferation disorder symptoms, for example, reduction in tumor burden, tumor size, tumor cell growth, differentiation, and/or proliferation, and invasive and/or metastatic potential before and after treatment. For example, such cell systems may be exposed to a compound, suspected of exhibiting an ability to ameliorate cellular growth or proliferation disorder symptoms, at a sufficient concentration and for a time sufficient to elicit such an amelioration of cellular growth or proliferation disorder symptoms in the exposed cells. After exposure, the cells are examined to determine whether one or more of the cellular growth or proliferation disorder cellular phenotypes has been altered to resemble a more normal or more wild type, non-cellular growth or proliferation disorder phenotype. Cellular phenotypes that are associated with cellular growth and/or proliferation disorders include aberrant proliferation, growth, and migration, anchorage independent growth, and loss of contact inhibition.

In addition, animal-based cellular growth or proliferation disorder systems, such as those described herein, may be used to identify compounds capable of ameliorating cellular growth or proliferation disorder symptoms. Such animal models may be used as test substrates for the identification of drugs, pharmaceuticals, therapies, and interventions which may be effective in treating cellular growth or proliferation disorders. For example, animal models may be exposed to a compound, suspected of exhibiting an ability to ameliorate cellular growth or proliferation disorder symptoms, at a sufficient concentration and for a time sufficient to elicit such an amelioration of cellular growth or proliferation disorder symptoms in the exposed animals. The response of the animals to the exposure may be monitored by assessing the reversal of cellular growth or proliferation disorders, or symptoms associated therewith, for example, reduction in tumor burden, tumor size, and invasive and/or metastatic potential before and after treatment.

With regard to intervention, any treatments which reverse any aspect of cellular growth or proliferation disorder symptoms should be considered as candidates for human cellular growth or proliferation disorder therapeutic intervention. Dosages of test compounds may be determined by deriving dose-response curves.

Additionally, gene expression patterns may be utilized to assess the ability of a compound to ameliorate cellular growth and/or proliferation disorder symptoms. For example, the expression pattern of one or more genes may form part of a "gene expression profile" or "transcriptional profile" which may be then be used in such an assessment. "Gene expression profile" or "transcriptional profile", as used herein, includes the pattern of mRNA expression obtained for a given tissue or cell type under a given set of conditions. Such conditions may include, but are not limited to, cell growth, proliferation, differentiation, transformation, tumorigenesis, metastasis, and carcinogen exposure. Gene expression profiles may be generated, for example, by utilizing a differential display procedure, Northern analysis and/or RT-PCR. In one embodiment, CAH gene sequences may be used as probes and/or PCR primers for the generation and corroboration of such gene expression profiles.

Gene expression profiles may be characterized for known states within the cell-and/or animal-based model systems. Subsequently, these known gene expression profiles may be compared to ascertain the effect a test compound has to modify such gene expression profiles, and to cause the profile to more closely resemble that of a more desirable profile.

For example, administration of a compound may cause the gene expression profile of a cellular growth or proliferation disorder model system to more closely resemble the control system. Administration of a compound may, alternatively, cause the gene expression profile of a control system to begin to mimic a cellular growth and/or proliferation disorder state. Such a compound may, for example, be used in further characterizing the compound of interest, or may be used in the generation of additional animal models.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the CAH nucleotide sequences, described herein, can be used to map the location of the CAH genes on a chromosome. The mapping of the CAH sequences to chromosomes is an important first step in correlating these sequences with genes associated with disease.

Briefly, CAH genes can be mapped to chromosomes by preparing PCR primers (preferably 15–25 bp in length) from the CAH nucleotide sequences. Computer analysis of the CAH sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the CAH sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) Science 220: 919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the CAH nucleotide sequences to design oligonucleotide primers, sublocalization can be achieved with panels of fragments from specific chromosomes. Other mapping strategies which can similarly be used to map a CAH sequence to its chromosome include in situ hybridization (described in Fan, Y. et al. (1990) Proc. Natl. Acad. Sci. USA, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) Nature, 325:783–787.

Moreover, differences in the DNA sequences between individuals affected and unaffected with a disease associated with the CAH gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The CAH sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the CAH nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The CAH nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:26 can comfortably provide positive individual identification with a panel of perhaps 10 to 1,000 primers which each yield a noncoding amplified sequence of 100 bases. If predicted coding sequences, such as that in SEQ ID NO:28, are used, a more appropriate number of primers for positive individual identification would be 500–2,000.

If a panel of reagents from CAH nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of CAH Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:26 are particularly appropriate for this use as greater numbers of polymorphisms occur in the noncoding regions, making it easier to differentiate individuals using this technique. Examples of polynucleotide reagents include the CAH nucleotide sequences or portions thereof, e.g., fragments derived from the noncoding regions of SEQ ID NO:26 having a length of at least 20 bases, preferably at least 30 bases.

The CAH nucleotide sequences described herein can further be used to provide polynucleotide reagents, e.g., labeled or labelable probes which can be used in, for example, an in situ hybridization technique, to identify a specific tissue, e.g., thymus or brain tissue. This can be very useful in cases where a forensic pathologist is presented with a tissue of unknown origin. Panels of such CAH probes can be used to identify tissue by species and/or by organ type.

In a similar fashion, these reagents, e.g., CAH primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining CAH protein and/or nucleic acid expression as well as CAH activity, in the context of a biological sample (e.g., blood, serum, cells, tissue) to thereby determine whether an individual is afflicted with a disease or disorder, or is at risk of developing a disorder, associated with aberrant or unwanted CAH expression or activity. The invention also provides for prognostic (or predictive) assays for determining whether an individual is at risk of developing a disorder associated with CAH protein, nucleic acid expression or activity. For example, mutations in a CAH gene can be assayed in a biological sample. Such assays can be used for prognostic or predictive purpose to thereby prophylactically treat an individual prior to the onset of a disorder characterized by or associated with CAH protein, nucleic acid expression or activity.

Another aspect of the invention pertains to monitoring the influence of agents (e.g., drugs, compounds) on the expression or activity of CAH in clinical trials.

These and other agents are described in further detail in the following sections.

1. Diagnostic Assays

An exemplary method for detecting the presence or absence of CAH protein or nucleic acid in a biological sample involves obtaining a biological sample from a test subject and contacting the biological sample with a compound or an agent capable of detecting CAH protein or nucleic acid (e.g., mRNA, or genomic DNA) that encodes CAH protein such that the presence of CAH protein or nucleic acid is detected in the biological sample. A preferred agent for detecting CAH mRNA or genomic DNA is a labeled nucleic acid probe capable of hybridizing to CAH mRNA or genomic DNA. The nucleic acid probe can be, for example, the CAH nucleic acid set forth in SEQ ID NO:26 or 28, or a portion thereof, such as an oligonucleotide of at least 15, 30, 50, 100, 250 or 500 nucleotides in length and sufficient to specifically hybridize under stringent conditions to CAH mRNA or genomic DNA. Other suitable probes for use in the diagnostic assays of the invention are described herein.

A preferred agent for detecting CAH protein is an antibody capable of binding to CAH protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect CAH mRNA, protein, or genomic DNA in a biological sample in vitro as well as in vivo. For example, in vitro techniques for detection of CAH mRNA include Northern hybridizations and in situ hybridizations. In vitro techniques for detection of CAH protein include enzyme linked immunosorbent assays (ELISAs), Western blots, immunoprecipitations and immunofluorescence. In vitro techniques for detection of CAH genomic DNA include Southern hybridizations. Furthermore, in vivo techniques for detection of CAH protein include introducing into a subject a labeled anti-CAH antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting CAH protein, mRNA, or genomic DNA, such that the presence of CAH protein, mRNA or genomic DNA is detected in the biological sample, and comparing the presence of CAH protein, mRNA or genomic DNA in the control sample with the presence of CAH protein, mRNA or genomic DNA in the test sample.

The invention also encompasses kits for detecting the presence of CAH in a biological sample. For example, the kit can comprise a labeled compound or agent capable of detecting CAH protein or mRNA in a biological sample; means for determining the amount of CAH in the sample; and means for comparing the amount of CAH in the sample with a standard. The compound or agent can be packaged in a suitable container. The kit can further comprise instructions for using the kit to detect CAH protein or nucleic acid.

2. Prognostic Assays

The diagnostic methods described herein can furthermore be utilized to identify subjects having or at risk of developing a disease or disorder associated with aberrant or unwanted CAH expression or activity. As used herein, the term "aberrant" includes a CAH expression or activity which deviates from the wild type CAH expression or activity. Aberrant expression or activity includes increased or decreased expression or activity, as well as expression or activity which does not follow the wild type developmental pattern of expression or the subcellular pattern of expression. For example, aberrant CAH expression or activity is intended to include the cases in which a mutation in the CAH gene causes the CAH gene to be under-expressed or over-expressed and situations in which such mutations result in a non-functional CAH protein or a protein which does not function in a wild-type fashion, e.g., a protein which does not interact with a CAH substrate, or one which interacts with a non-CAH substrate. As used herein, the term "unwanted" includes an unwanted phenomenon involved in a biological response such as cellular proliferation. For example, the term unwanted includes a CAH expression or activity which is undesirable in a subject.

The assays described herein, such as the preceding diagnostic assays or the following assays, can be utilized to identify a subject having or at risk of developing a disorder associated with a misregulation in CAH protein activity or nucleic acid expression, such as a CNS disorder (e.g., a cognitive or neurodegenerative disorder), a cellular proliferation, growth, differentiation, or migration disorder (e.g., cancer), a cardiovascular disorder, musculoskeletal disorder, an ocular disorder, or a disorder of bone resorption, or calcification/bone formation. Alternatively, the prognostic assays can be utilized to identify a subject having or at risk for developing a disorder associated with a misregulation in CAH protein activity or nucleic acid expression, such as a CNS disorder, a cellular proliferation, growth, differentiation, or migration disorder (e.g., cancer), a musculoskeletal disorder, a cardiovascular disorder, an ocular disorder, or a disorder of bone resorption, or calcification/bone formation. Thus, the present invention provides a method for identifying a disease or disorder associated with aberrant or unwanted CAH expression or activity in which a test sample is obtained from a subject and CAH protein or nucleic acid (e.g., mRNA or genomic DNA) is detected, wherein the presence of CAH protein or nucleic acid is diagnostic for a subject having or at risk of developing a disease or disorder associated with aberrant or unwanted CAH expression or activity. As used herein, a "test sample" refers to a biological sample obtained from a subject of interest. For example, a test sample can be a biological fluid (e.g., cerebrospinal fluid or serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted CAH expression or activity. For example, such methods can be used to determine whether a subject can be effectively treated with an agent for a CNS disorder, a muscular disorder, a cellular proliferation, growth, differentiation, or migration disorder (e.g., cancer), an ocular disorder, or a disorder of bone resorption, or calcification/bone formation. Thus, the present invention provides methods for determining whether a subject can be effectively treated with an agent for a disorder associated with aberrant or unwanted CAH expression or activity in which a test sample is obtained and CAH protein or nucleic acid expression or activity is detected (e.g., wherein the abundance of CAH protein or nucleic acid expression or activity is diagnostic for a subject that can be administered the agent to treat a disorder associated with aberrant or unwanted CAH expression or activity).

The methods of the invention can also be used to detect genetic alterations in a CAH gene, thereby determining if a subject with the altered gene is at risk for a disorder characterized by misregulation in CAH protein activity or nucleic acid expression, such as a CNS disorder, a musculoskeletal disorder, a cellular proliferation, growth, differentiation, or migration disorder (e.g., cancer), a cardiovascular disorder, an ocular disorder, or a disorder of bone resorption, or calcification/bone formation. In preferred embodiments, the methods include detecting, in a sample of cells from the subject, the presence or absence of a genetic alteration characterized by at least one of an alteration affecting the integrity of a gene encoding a CAH-protein, or the mis-expression of the CAH gene. For example, such genetic alterations can be detected by ascertaining the existence of at least one of 1) a deletion of one or more nucleotides from a CAH gene; 2) an addition of one or more nucleotides to a CAH gene; 3) a substitution of one or more nucleotides of a CAH gene, 4) a chromosomal rearrangement of a CAH gene; 5) an alteration in the level of a messenger RNA transcript of a CAH gene, 6) aberrant modification of a CAH gene, such as of the methylation pattern of the genomic DNA, 7) the presence of a non-wild type splicing pattern of a messenger RNA transcript of a CAH gene, 8) a non-wild type level of a CAH-protein, 9) allelic loss of a CAH gene, and 10) inappropriate post-translational modification of a CAH-protein. As described herein, there are a large number of assays known in the art which can be used for detecting alterations in a CAH gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in a CAH gene (see Abravaya et al. (1995) *Nucleic Acids Res.* 23:675–682). This method can include the steps of collecting a sample of cells from a subject, isolating nucleic acid (e.g., genomic, mRNA or both) from the cells of the sample, contacting the nucleic acid sample with one or more primers which specifically hybridize to a CAH gene under conditions such that hybridization and amplification of the CAH gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a CAH gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in CAH can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in CAH can be identified in two-dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the CAH gene and detect mutations by comparing the sequence of the sample CAH with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the CAH gene include methods in which protection from cleavage agents is used to detect mismatched bases in RNA/RNA or RNA/DNA heteroduplexes (Myers et al. (1985) *Science* 230: 1242). In general, the art technique of "mismatch cleavage" starts by providing heteroduplexes of formed by hybridizing (labeled) RNA or DNA containing the wild-type CAH sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in CAH cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a CAH sequence, e.g., a wild-type CAH sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in CAH genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125–144; and Hayashi (1992) *Genet. Anal. Tech. Appl.* 9:73–79). Single-stranded DNA fragments of sample and control CAH nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (*J*989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a CAH gene.

Furthermore, any cell type or tissue in which CAH is expressed may be utilized in the prognostic assays described herein.

3. Monitoring of Effects During Clinical Trials

Monitoring the influence of agents (e.g., drugs) on the expression or activity of a CAH protein (e.g., the modulation of cell proliferation and/or migration) can be applied not only in basic drug screening, but also in clinical trials. For example, the effectiveness of an agent determined by a screening assay as described herein to increase CAH gene expression, protein levels, or upregulate CAH activity, can be monitored in clinical trials of subjects exhibiting decreased CAH gene expression, protein levels, or down-regulated CAH activity. Alternatively, the effectiveness of an agent determined by a screening assay to decrease CAH gene expression, protein levels, or downregulate CAH activity, can be monitored in clinical trials of subjects exhibiting increased CAH gene expression, protein levels, or upregulated CAH activity. In such clinical trials, the expression or activity of a CAH gene, and preferably, other genes that have been implicated in, for example, a CAH-associated disorder can be used as a "read out" or markers of the phenotype of a particular cell.

For example, and not by way of limitation, genes, including CAH, that are modulated in cells by treatment with an agent (e.g., compound, drug or small molecule) which modulates CAH activity (e.g., identified in a screening assay as described herein) can be identified. Thus, to study the effect of agents on CAH-associated disorders (e.g., disorders characterized by deregulated cell proliferation and/or migration), for example, in a clinical trial, cells can be isolated and RNA prepared and analyzed for the levels of expression of CAH and other genes implicated in the CAH-associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of CAH or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a CAH protein, mRNA, or genomic DNA in the preadministration sample; (iii) obtaining one or more post-administration samples from the subject; (iv) detecting the level of expression or activity of the CAH protein, mRNA, or genomic DNA in the post-administration samples; (v) comparing the level of expression or activity of the CAH protein, mRNA, or genomic DNA in the pre-administration sample with the CAH protein, mRNA, or genomic DNA in the post administration sample or samples; and (vi) altering the administration of the agent to the subject accordingly. For example, increased administration of the agent may be desirable to increase the expression or activity of CAH to higher levels than detected, i.e., to increase the effectiveness of the agent. Alternatively, decreased administration of the agent may be desirable to decrease expression or activity of CAH to lower levels than detected, i.e. to decrease the effectiveness of the agent. According to such an embodiment, CAH expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder or having a disorder associated with aberrant or unwanted CAH expression or activity, e.g., a carbonic anhydrase-associated disorder such as a CNS disorder; a cellular proliferation, growth, differentiation, or migration disorder (e.g., cancer); a, musculoskeletal disorder; a cardiovascular disorder; an ocular disorder, or a disorder of bone resorption, or calcification/bone formation.

"Treatment", as used herein, is defined as the application or administration of a therapeutic agent to a patient, or application or administration of a therapeutic agent to an isolated tissue or cell line from a patient, who has a disease or disorder, a symptom of disease or disorder or a predisposition toward a disease or disorder, with the purpose of curing, healing, alleviating, relieving, altering, remedying, ameliorating, improving or affecting the disease or disorder, the symptoms of disease or disorder or the predisposition toward a disease or disorder. A therapeutic agent includes, but is not limited to, small molecules, peptides, antibodies, ribozymes and antisense oligonucleotides. With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the CAH molecules of the present invention or CAH modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted CAH expression or activity, by administering to the subject a CAH or an agent which modulates CAH expression or at least one CAH activity. Subjects at risk for a disease which is caused or contributed to by aberrant or unwanted CAH expression or activity can be identified by, for example, any or a combination of diagnostic or prognostic assays as described herein. Administration of a prophylactic agent can occur prior to the manifestation of symptoms characteristic of the CAH aberrancy, such that a disease or disorder is prevented or, alternatively, delayed in its progression. Depending on the type of CAH aberrancy, for example, a CAH, CAH agonist or CAH antagonist agent can be used for treating the subject. The appropriate agent can be determined based on screening assays described herein.

2. Therapeutic Methods

Another aspect of the invention pertains to methods of modulating CAH expression or activity for therapeutic purposes. Accordingly, in an exemplary embodiment, the modulatory method of the invention involves contacting a cell with a CAH or agent that modulates one or more of the activities of CAH protein activity associated with the cell. An agent that modulates CAH protein activity can be an agent as described herein, such as a nucleic acid or a protein, a naturally-occurring target molecule of a CAH protein (e.g., a CAH substrate), a CAH antibody, a CAH agonist or antagonist, a peptidomimetic of a CAH agonist or antagonist, or other small molecule. In one embodiment, the agent stimulates one or more CAH activities. Examples of such stimulatory agents include active CAH protein and a nucleic acid molecule encoding CAH that has been introduced into the cell. In another embodiment, the agent inhibits one or more CAH activities. Examples of such inhibitory agents include antisense CAH nucleic acid molecules, anti-CAH antibodies, and CAH inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a CAH protein or nucleic acid molecule. In one embodiment, the method involves administering an agent (e.g., an agent identified by a screening assay described herein), or combination of agents that modulates (e.g., upregulates or downregulates) CAH expression or activity. In another embodiment, the method involves administering a CAH protein or nucleic acid molecule as therapy to compensate for reduced, aberrant, or unwanted CAH expression or activity.

Stimulation of CAH activity is desirable in situations in which CAH is abnormally downregulated and/or in which increased CAH activity is likely to have a beneficial effect. Likewise, inhibition of CAH activity is desirable in situations in which CAH is abnormally upregulated and/or in which decreased CAH activity is likely to have a beneficial effect.

3. Pharmacogenomics

The CAH molecules of the present invention, as well as agents, or modulators which have a stimulatory or inhibitory effect on CAH activity (e.g., CAH gene expression) as identified by a screening assay described herein can be administered to individuals to treat (prophylactically or therapeutically) CAH-associated disorders (e.g., proliferative disorders (e.g., cancer), CNS disorders, cardiac disorders, metabolic disorders, muscular disorders, ocular disorders, or disorders of bone resorption, or calcification/bone formation) associated with aberrant or unwanted CAH activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a CAH molecule or CAH modulator as well as tailoring the dosage and/or therapeutic regimen of treatment with a CAH molecule or CAH modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11): 983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug target is known (e.g., a CAH protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a CAH molecule or CAH modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a CAH molecule or CAH modulator, such as a modulator identified by one of the exemplary screening assays described herein.

VI. Electronic Apparatus Readable Media and Arrays

Electronic apparatus readable media comprising CAH sequence information is also provided. As used herein, "CAH sequence information" refers to any nucleotide and/or amino acid sequence information particular to the CAH molecules of the present invention, including but not limited to full-length nucleotide and/or amino acid sequences, partial nucleotide and/or amino acid sequences, polymorphic sequences including single nucleotide polymorphisms (SNPs), epitope sequences, and the like. Moreover, information "related to" said CAH sequence information includes detection of the presence or absence of a sequence (e.g., detection of expression of a sequence, fragment, polymorphism, etc.), determination of the level of a sequence (e.g., detection of a level of expression, for example, a quantitative detection), detection of a reactivity to a sequence (e.g., detection of protein expression and/or levels, for example, using a sequence-specific antibody), and the like. As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon CAH sequence information of the present invention.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the CAH sequence information.

A variety of software programs and formats can be used to store the sequence information on the electronic apparatus readable medium. For example, the sequence information can be represented in a word processing text file, formatted in commercially-available software such as WordPerfect and Microsoft Word, or represented in the form of an ASCII file, stored in a database application, such as DB2, Sybase, Oracle, or the like, as well as in other forms. Any number of data processor structuring formats (e.g., text file or database) may be employed in order to obtain or create a medium having recorded thereon the CAH sequence information.

By providing CAH sequence information in readable form, one can routinely access the sequence information for a variety of purposes. For example, one skilled in the art can use the sequence information in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has a CAH-associated disease or disorder or a pre-disposition to a CAH-associated disease or disorder, wherein the method comprises the steps of determining CAH sequence information associated with the subject and based on the CAH sequence information, determining whether the subject has a CAH-associated disease or disorder or a pre-disposition to a CAH-associated disease or disorder and/or recommending a particular treatment for the disease, disorder or pre-disease condition.

The present invention further provides in an electronic system and/or in a network, a method for determining whether a subject has a CAH-associated disease or disorder or a pre-disposition to a disease associated with a CAH wherein the method comprises the steps of determining CAH sequence information associated with the subject, and based on the CAH sequence information, determining whether the subject has a CAH-associated disease or disorder or a pre-disposition to a CAH-associated disease or disorder, and/or recommending a particular treatment for the disease, disorder or pre-disease condition. The method may further comprise the step of receiving phenotypic information associated with the subject and/or acquiring from a network phenotypic information associated with the subject.

The present invention also provides in a network, a method for determining whether a subject has a CAH-associated disease or disorder or a pre-disposition to a CAH associated disease or disorder associated with CAH, said method comprising the steps of receiving CAH sequence information from the subject and/or information related thereto, receiving phenotypic information associated with the subject, acquiring information from the network corresponding to CAH and/or a CAH-associated disease or disorder, and based on one or more of the phenotypic information, the CAH information (e.g., sequence information and/or information related thereto), and the acquired information, determining whether the subject has a CAH-associated disease or disorder or a pre-disposition to a CAH-associated disease or disorder (e.g., a carbonic anhydrase-associated disorder such as a CNS disorder; a cellular proliferation, growth, differentiation, or migration disorder; a, musculoskeletal disorder; a cardiovascular disorder; an ocular disorder, or a disorder of bone resorption, or calcification/bone formation). The method may further comprise the step of recommending a particular treatment for the disease, disorder or pre-disease condition.

The present invention also provides a business method for determining whether a subject has a CAH-associated disease or disorder or a pre-disposition to a CAH-associated disease or disorder, said method comprising the steps of receiving information related to CAH (e.g., sequence information and/or information related thereto), receiving phenotypic information associated with the subject, acquiring information from the network related to CAH and/or related to a CAH-associated disease or disorder, and based on one or more of the phenotypic information, the CAH information, and the acquired information, determining whether the subject has a CAH-associated disease or disorder or a pre-disposition to a CAH-associated disease or disorder. The method may further comprise the step of recommending a particular treatment for the disease, disorder or pre-disease condition.

The invention also includes an array comprising a CAH sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, one of which can be CAH. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a CAH-associated disease or disorder, progression of CAH-associated disease or disorder, and processes, such a cellular transformation associated with the CAH-associated disease or disorder.

The array is also useful for ascertaining the effect of the expression of a gene on the expression of other genes in the same cell or in different cells (e.g., ascertaining the effect of CAH expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including CAH) that could serve as a molecular target for diagnosis or therapeutic intervention.

This invention is further illustrated by the following examples which should not be construed as limiting. The contents of all references, patents and published patent applications cited throughout this application, as well as the Figures and the Sequence Listing, are incorporated herein by reference.

EXAMPLES

Example 1

Identification and Characterization of Human CAH cDNA

In this example, the identification and characterization of the gene encoding human CAH (clone Fbh55158) is described.

Isolation of the CAH cDNA

The invention is based, at least in part, on the discovery of a human gene encoding a novel protein, referred to herein as CAH. The entire sequence of human clone Fbh55158, was determined and found to contain an open reading frame termed human "CAH", set forth in FIGS. 44A–B. The amino acid sequence of this human CAH expression product is set forth in FIGS. 44A–B. The CAH protein sequence set forth in SEQ ID NO:27 comprises about 328 amino acids and is shown in FIGS. 44A–B. The coding region (open reading frame) of SEQ ID NO:26 is set forth as SEQ ID NO:28.

Analysis of the Human CAH Molecules

The amino acid sequence of human CAH was analyzed using the program PSORT (see PSORT maintained by the Human Genome Center at the Institute of Medical Science in the University of Tokyo, Japan (psort.nibb.acjp) to predict the localization of the protein within the cell. This program assesses the presence of different targeting and localization amino acid sequences within the query sequence. The results of the analyses show that the human CAH (SEQ ID NO:27) may be localized, for example, to the nucleus, to the mitochondrion, to the cytoplasm, to the plasma membrane, or to secretory vesicles. Results also show the presence of several dileucine motifs in the tail of the amino acid sequence of the human CAH (SEQ ID NO:27) at amino acids 10–11, 146–147, 216–217, 269–270, and 326–327.

An analysis of the amino acid sequence of human CAH using the Signal P program (Henrik, et al. (1997) *Protein Engineering* 10:1–6), identified the presence of a signal peptide from amino acids 1–21.

A search of the amino acid sequence of CAH was also performed against the HMM database (FIG. 46). This search resulted in the identification of a "eukaryotic-type carbonic anhydrase domain" in the amino acid sequence of CAH (SEQ ID NO:27) at about residues 63–301 (score=170.6) (FIG. 46).

A search of the amino acid sequence of CAH was also performed against the ProDom database. This search resulted in the identification of a domain "similar to carbonic anhydrase I" in the amino acid sequence of human CAH (SEQ ID NO:27) at about residues 15–85 (score=114), a "carbonic anhydrase dehydratase lyase carbonate zinc precursor signal protein glycoprotein domain" in the amino acid sequence of human CAH (SEQ ID NO:27) at about residues 47–300, a "carbonic anhydrase lyase carbonate dehydratase zinc precursor signal II domain" in the amino acid sequence of human CAH (SEQ ID NO:27) at about residues 33–300 (score=476), an "anhydrase-related carbonic carp CA-XI II CA-RP precursor signal unnamed product domain" in the amino acid sequence of human CAH (SEQ ID NO:27) at about residues 1–62 (score=293), and a "carbonic anhydrase domain" in the amino acid sequence of human CAH (SEQ ID NO:27) at about residues 11–72 (score=71).

A search of the amino acid sequence of CAH was also performed against the ProSite database. This search resulted in the identification of several "N-glycosylation sites" in the amino acid sequence of CAH (SEQ ID NO:27) at about residues 116–119, 168–171, and 302–305, two "cAMP- and cGMP-dependent protein kinase phosphorylation sites" at residues 64–67 and 92–95, several "protein kinase C phosphorylation sites" at amino acids 25–27, 101–103, 106–108, 125–127, 209–211, and 266–268, a "casein kinase II phosphorylation site" at residues 281–284, several "N-myristoylation sites" at residues 51–56, 96–101, 119–124, 136–141, and 149–154, and two "amidation sites" at residues 62–65 and 90–93.

The CAH proteins of the present invention include many features indicative of the carbonic anhydrase family of proteins. For instance, the CAH proteins of the present invention contain conserved residues known to be located in the active site and/or to coordinate the zinc ion in most carbonic anhydrases of the a class. These residues include Gln66, Ser67, and Pro68, Ser143 and Glu155. Additionally, a number of the other conserved residues are present, but shifted by one (Asn100) or three (Gly234, Thr237, Trp247, or Arg 284) residues from their location in the typical α-CAH molecule. As such, the CAH family of proteins are referred to herein as carbonic anhydrase proteins.

Tissue Distribution of CAH mRNA by Taqman™ Analysis

This example describes the tissue distribution of human CAH mRNA in a variety of cells and tissues, as determined using the TaqMan™ procedure. The Taqman™ procedure is a quantitative, reverse transcription PCR-based approach for detecting mRNA. The RT-PCR reaction exploits the 5' nuclease activity of AmpliTaq Gold™ DNA Polymerase to cleave a TaqMan™ probe during PCR. Briefly, cDNA was generated from the samples of interest, e.g., various human normal and tumor tissues, and used as the starting material for PCR amplification. In addition to the 5' and 3' gene-specific primers, a gene-specific oligonucleotide probe (complementary to the region being amplified) was included in the reaction (i.e., the Taqman™ probe). The TaqMan™ probe includes the oligonucleotide with a fluorescent reporter dye covalently linked to the 5' end of the probe (such as FAM (6-carboxyfluorescein), TET (6-carboxy-4,7,2',7'-tetrachlorofluorescein), JOE (6-carboxy-4,5-dichloro-2,7-dimethoxyfluorescein), or VIC) and a quencher dye (TAMRA (6-carboxy-N,N,N',N'-tetramethylrhodamine) at the 3' end of the probe.

During the PCR reaction, cleavage of the probe separates the reporter dye and the quencher dye, resulting in increased fluorescence of the reporter. Accumulation of PCR products is detected directly by monitoring the increase in fluorescence of the reporter dye. When the probe is intact, the proximity of the reporter dye to the quencher dye results in suppression of the reporter fluorescence. During PCR, if the target of interest is present, the probe specifically anneals between the forward and reverse primer sites. The 5'-3' nucleolytic activity of the AmpliTaq™ Gold DNA Polymerase cleaves the probe between the reporter and the quencher only if the probe hybridizes to the target. The probe fragments are then displaced from the target, and polymerization of the strand continues. The 3' end of the probe is blocked to prevent extension of the probe during PCR. This process occurs in every cycle and does not interfere with the exponential accumulation of product. RNA was prepared using the trizol method and treated with DNase to remove contaminating genomic DNA. cDNA was synthesized using standard techniques. Mock cDNA synthesis in the absence of reverse transcriptase resulted in samples with no detectable PCR amplification of the control gene confirms efficient removal of genomic DNA contamination.

A human tissue panel was tested revealing highest expression of human CAH mRNA in the brain, hypothalamus, dorsal root ganglia (DRG), kidney tissue, and spinal cord (see FIG. 47).

A panel containing various human lung, ovary, and breast normal and tumor tissue samples indicated highest expression of human CAH mRNA in lung tumor tissue, with weak expression in normal lung tissue (see FIG. 48). High expression was also detected in normal ovary tissue, with weak expression detected in ovary tumor tissue (see FIG. 49). Weak expression was also detected in normal breast tissue with higher expression detected in breast tumor tissue (see FIG. 50).

A panel containing various human colon, liver, and brain normal and tumor tissue samples indicated highest expression of human CAH mRNA in normal brain tissue, with weak expression in brain tumor tissue. Weak expression was also detected in astrocytes, HMVEC, placental tissue, fetal adrenal gland, and fetal liver tissue (see FIG. 51). Expression was also detected in normal colon tissue, with weaker expression detected in colon tumor tissue. Expression was also detected in colon tumor metastases to the liver, with weaker expression detected in a normal liver tissue sample (see FIG. 52).

Various normal and cancer cell lines were also tested for CAH mRNA expression, including human breast carcinoma cell lines, human colon carcinoma cell lines, and human lung carcinoma cell lines. Relative expression of human CAH mRNA is shown in Table 1, below.

TABLE 1

| Cell lines | 55158.2 (CAH) | B-2 | Average 55158.2 (CAH) | Average Beta-2 | ΔCt | Relative Expression |
|---|---|---|---|---|---|---|
| MCF-7 | 39.02 | 18.75 | 38.96 | 18.545 | 20.415 | 0.00 |
|  | 38.9 | 18.34 |  |  |  |  |
| ZR75 | 34.71 | 18.33 | 34.73 | 18.31 | 16.42 | 0.01 |
|  | 34.75 | 18.29 |  |  |  |  |
| T47D | 36.03 | 17.28 | 36.03 | 17.28 | 18.75 | 0.00 |
| MDA 231 | 38.98 | 16.83 | 38.495 | 17 | 21.495 | 0.00 |
|  | 38.01 | 17.17 |  |  |  |  |
| MDA 435 | 33.47 | 15.44 | 33.505 | 15.47 | 18.035 | 0.00 |
|  | 33.54 | 15.5 |  |  |  |  |
| DLD-1 | 34.86 | 18.91 | 34.735 | 18.84 | 15.895 | 0.02 |
|  | 34.61 | 18.77 |  |  |  |  |
| SW 480 | 38.01 | 16.4 | 38.01 | 16.4 | 21.61 | 0.00 |
| SW 620 |  |  |  |  |  |  |
| HCT 116 |  |  |  |  |  |  |
| HT 29 | 39.04 | 15.26 | 39.52 | 15.315 | 24.205 | 0.00 |
|  | 40 | 15.37 |  |  |  |  |
| Colo 205 | 37.1 | 14.55 | 37.345 | 14.535 | 22.81 | 0.00 |
|  | 37.59 | 14.52 |  |  |  |  |

TABLE 1-continued

| Cell lines | 55158.2 (CAH) | B-2 | Average 55158.2 (CAH) | Average Beta-2 | ΔCt | Relative Expression |
|---|---|---|---|---|---|---|
| NCIH 125 | 40 | 17.28 | 38.605 | 17.31 | 21.295 | 0.00 |
|  | 37.21 | 17.34 |  |  |  |  |
| NCIH 67 | 36.7 | 18.38 | 36.665 | 18.375 | 18.29 | 0.00 |
|  | 36.63 | 18.37 |  |  |  |  |
| NCIH 322 |  |  |  |  |  |  |
| NCIH 460 |  |  | 37.34 | 17.22 | 20.12 | 0.00 |
|  | 37.34 | 17.22 |  |  |  |  |
| A549 | 38.67 | 18.24 | 38.625 | 18.155 | 20.47 | 0.00 |
|  | 38.58 | 18.07 |  |  |  |  |
| NHBE | 34.75 | 18.17 | 34.82 | 18.315 | 16.505 | 0.01 |
|  | 34.89 | 18.46 |  |  |  |  |
| NTC | 40 | 39.98 | 39.14 | 39.99 |  |  |
|  | 38.28 | 40 |  |  |  |  |

Tissue Distribution of CAH mRNA by Northern Analysis

This example describes the tissue distribution of CAH mRNA, as determined by Northern analysis.

Northern blot hybridizations with the various RNA samples are performed under standard conditions and washed under stringent conditions, i.e., 0.2×SSC at 65° C. The DNA probe is radioactively labeled with $^{32}$P-dCTP using the Prime-It kit (Stratagene, La Jolla, Calif.) according to the instructions of the supplier. Filters containing human mRNA (MultiTissue Northern I and MultiTissue Northern II from Clontech, Palo Alto, Calif.) are probed in ExpressHyb hybridization solution (Clontech) and washed at high stringency according to manufacturer's recommendations.

Tissue Distribution of CAH mRNA by in situ Analysis

For in situ analysis, various tissues, e.g. tissues obtained from brain, are first frozen on dry ice. Ten-micrometer-thick sections of the tissues are postfixed with 4% formaldehyde in DEPC treated 1× phosphate-buffered saline at room temperature for 10 minutes before being rinsed twice in DEPC 1× phosphate-buffered saline and once in 0.1 M triethanolamine-HCl (pH 8.0). Following incubation in 0.25% acetic anhydride-0.1 M triethanolamine-HCl for 10 minutes, sections are rinsed in DEPC 2×SSC (1×SSC is 0.15M NaCl plus 0.015M sodium citrate). Tissue is then dehydrated through a series of ethanol washes, incubated in 100% chloroform for 5 minutes, and then rinsed in 100% ethanol for 1 minute and 95% ethanol for 1 minute and allowed to air dry.

Hybridizations are performed with $^{35}$S-radiolabeled (5×10$^7$ cpm/ml) cRNA probes. Probes are incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1× Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides are washed with 2×SSC. Sections are then sequentially incubated at 37° C. in TNE (a solution containing 10 mM Tris-HCl (pH 7.6), 500 mM NaCl, and 1 mM EDTA), for 10 minutes, in TNE with 10 μg of RNase A per ml for 30 minutes, and finally in TNE for 10 minutes. Slides are then rinsed with 2×SSC at room temperature, washed with 2×SSC at 50° C. for 1 hour, washed with 0.2×SSC at 55° C. for 1 hour, and 0.2×SSC at 60° C. for 1 hour. Sections are then dehydrated rapidly through serial ethanol-0.3 M sodium acetate concentrations before being air dried and exposed to Kodak Biomax MR scientific imaging film for 24 hours and subsequently dipped in NB-2

Example 2

Expression of Recombinant CAH Protein in Bacterial Cells

In this example, CAH is expressed as a recombinant glutathione-S-transferase (GST) fusion polypeptide in *E. coli* and the fusion polypeptide is isolated and characterized. Specifically, CAH is fused to GST and this fusion polypeptide is expressed in *E. coli*, e.g., strain PEB 199. Expression of the GST-CAH fusion protein in PEB 199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant CAH Protein in COS Cells

To express the CAH gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire CAH protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the CAH DNA sequence is amplified by PCR using two primers. The 5' primer contains the restriction site of interest followed by approximately twenty nucleotides of the CAH coding sequence starting from the initiation codon; the 3' end sequence contains complementary sequences to the other restriction site of interest, a translation stop codon, the HA tag or FLAG tag and the last 20 nucleotides of the CAH coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the CAH gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the CAH-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. The expression of the CAH polypeptide is detected by radiolabeling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA-specific monoclonal antibody. Precipitated polypeptides are then analyzed by SDS-PAGE.

Alternatively, DNA containing the CAH coding sequence is cloned directly into the polylinker of the pcDNA/Amp vector using the appropriate restriction sites. The resulting plasmid is transfected into COS cells in the manner described above, and the expression of the CAH polypeptide is detected by radiolabeling and immunoprecipitation using a CAH-specific monoclonal antibody.

VII. 47765, a Novel Human Lysyl Oxidase and Uses Thereof

BACKGROUND OF THE INVENTION

Biogenesis of connective tissue matrices is a prerequisite for the production and functioning of a number of human tissues, including skin, muscle, and bone. A family of enzymes that facilitates the covalent cross-linking of the molecular units of collagen and elastin, termed the lysyl oxidase family, has been identified. These enzymes catalyze the oxidation of peptidyl lysine in these extracellular matrix proteins to peptidyl α-aminoadipic-δ-semialdehyde, which is able to condense with neighboring amino groups or peptidyl aldehydes to form covalent crosslinkages (Kagan (1986) in: Biology of the Extracellular Matrix, Mecham, ed. Vol. 1: Regulation of Matrix Accumulation. Academic Press: Orlando, Fla.: 321–398).

Members of the lysyl oxidase family have been isolated from a wide variety of animal species, including human, rodent, avian, mammalian, and piscine sources. A protein having activity and structure similar to that of lysyl oxidase has also been isolated from yeast (Dove et al. (1996) *FEBS Lett.* 398: 231–234). Family members vary widely in structure, having between 48 and 100% homology (Smith-Mungo and Kagan (1998) *Matrix Biology* 16: 387–398). The region of the protein which has been found to share the greatest identity (90–95%) between family members is the C-terminal segment of the preproprotein amino acid sequence (Smith-Mungo and Kagan (1998), supra). This region is believed to include the active site, as well as sequences involved in the octahedral coordination of the copper ion (Gacheru et al. (1990) *J. Biol. Chem.* 265: 19022–19027), and a binding site for another cofactor, lysyltyrosine quinone (Wang et al. (1996). Lysyl oxidases are also characterized by an N-terminal signal peptide (70–72% identical), which is thought to mediate the secretion of these proteins into the surrounding extracellular matrix (Smith-Mungo and Kagan (1998), supra).

Studies of lysyl oxidase have indicated that this enzyme undergoes significant trafficking and processing prior to becoming fully functional in the cell. For example, bovine lysyl oxidase is synthesized as a 46 kDa sequence having an N-terminal 21 residue signal peptide. The N-terminal portion of the protein is N-glycosylated at two or three sites and undergoes signal peptide cleavage to yield an inactive 50 kD proenzyme, which is secreted into the extracellular matrix (Trackman et al. (1990) *Biochemistry* 29: 4863–4870; Trackman et al. (1991) *Biochemistry* 30: 8282). The proenzyme is cleaved at a Gly-Asp bond by a metalloproteinase (also present in the extracellular matrix) to the fully-active 32 kD species, lacking the N-glycosylated N-terminal region (Trackman et al. (1992) *J. Biol. Chem.* 267: 8666–8671). It is thought that this process prevents lysyl oxidase from catalyzing the cross-linking of nascent matrix macromolecules prior to their export from the cell (Smith-Mungo and Kagan (1998), supra).

The mechanism by which lysyl oxidases catalyze the covalent cross-linking of the molecular subunits of elastin and collagen has also been characterized. Lysyl oxidase first forms a Schiff base with its carbonyl cofactor (lysyltyrosine quinone in the case of animal lysyl oxidase; trihydroxyphenylalanine quinone in the case of yeast lysyl oxidase (Dove et al. (1996), supra). The rate-limiting step is the general base (histidine residue)-facilitated α-proton abstraction from the substrate (Gacheru et al. (1988) *J. Biol. Chem.* 265: 19022–19027; Williamson and Kagan (1987) *J. Biol. Chem.* 261: 9477–9482). The carbonyl cofactor is reduced by electron migration from the substrate carbanion, and the aldehyde product is released. The reduced enzyme, still bound to the amino group of the substrate, is reoxidized by molecular oxygen to produce hydrogen peroxide and ammonia (Smith-Mungo and Kagan (1998), supra). While elastin and collagen subunits are typically the substrates for lysyl oxidase, in vitro studies have demonstrated that this enzyme is able to oxidize peptidyl lysine in a number of different basic, globular proteins (Kagan et al. (1984) *J. Biol. Chem.* 259: 11203–11207). A coordinated copper ion mediates the activity of the enzyme in this reaction mechanism.

Lysyl oxidases play an important role in the production of connective matrices, such as elastin or collagen matrices. Such matrices are of vital importance in maintaining the structure of the cell (e.g., the extracellular matrix, or cell wall). As such, their activity contributes to the ability of the cell to grow, differentiate and proliferate. On a larger scale, such matrices are also critical for the formation of various tissues, such as skin, muscle, bone, and cartilage. Underscoring the importance of this family of enzymes, modulation of the activity of one or more lysyl oxidases has been linked to a number of human diseases, including cutis laxa and Ehlers-Danlos syndrome type V (both skin elasticity disorders) (Khakoo et al. (1997) *Clin. Genet.* 51: 109–114; DiFerrante et al. (1975) *Connect. Tissue Res.* 3: 49–53), and Menkes' disease (Kuivaniemi et al. (1985) *Am. J. Hum. Genet.* 37: 798–808). The human lysyl oxidase gene has been mapped to human chromosome 5q23.3–31.2 (Hamalainen et al. (1991) *Genomics* 11: 508–516; Svinarich et al. (1992) *J. Biol. Chem.* 267: 14382–14387; and Mariani et al. (1992)) *Matrix* 12: 242–248), and disorders linked to this region may also involve lysyl oxidase activity.

SUMMARY OF THE INVENTION

The present invention is based, at least in part, on the discovery of novel members of the family of lysyl oxidase molecules, referred to herein as LSO nucleic acid and protein molecules. The LSO nucleic acid and protein molecules of the present invention are useful as modulating agents in regulating a variety of cellular processes, e.g., cellular proliferation, growth, differentiation, or migration. Accordingly, in one aspect, this invention provides isolated nucleic acid molecules encoding LSO proteins or biologically active portions thereof, as well as nucleic acid fragments suitable as primers or hybridization probes for the detection of LSO-encoding nucleic acids.

In one embodiment, an LSO nucleic acid molecule of the invention is at least 42%, 48%, 50%, 55%, 60%, 65%, 70%, 75%, 80%, 85%, 90%, 95%, 96%, 97%, 98%, 99% or more identical to the nucleotide sequence (e.g., to the entire length of the nucleotide sequence) shown in SEQ ID NO:29 or 31, or a complement thereof.

In a preferred embodiment, the isolated nucleic acid molecule includes the nucleotide sequence shown in SEQ ID NO:29 or 31, or a complement thereof. In another embodiment, the nucleic acid molecule includes SEQ ID NO:31 and nucleotides 1–94 of SEQ ID NO:29. In yet a further embodiment, the nucleic acid molecule includes SEQ ID NO:31 and nucleotides 2366–2976 of SEQ ID NO:29. In another preferred embodiment, the nucleic acid molecule consists of the nucleotide sequence shown in SEQ ID NO:29 or 31, or a complement thereof. In another preferred embodiment, the nucleic acid molecule includes a fragment of at least 1243 or 1412 nucleotides of the nucleotide sequence of SEQ ID NO:29, SEQ ID NO:31, or a complement thereof.

In preferred embodiments, the nucleic acid molecules are at least 15 (e.g., contiguous) nucleotides in length and hybridize under stringent conditions to nucleotides 1–32 and 556–571 of SEQ ID NO:29. In other preferred embodiments, the nucleic acid molecules comprise nucleotides 1–32 and 556–572 of SEQ ID NO:29. In another preferred embodiment, the nucleic acid molecules consist of nucleotides 1–32 and 556–572 of SEQ ID NO:29.

In another embodiment, an LSO nucleic acid molecule includes a nucleotide sequence encoding a protein having an amino acid sequence sufficiently identical to the amino acid sequence of SEQ ID NO:30. In a preferred embodiment, an LSO nucleic acid molecule includes a nucleotide sequence encoding a protein having an amino acid sequence at least 42%, 50%, 55%, 60%, 65%, 70%, 75%, 80%, 85%, 90%, 95%, 96%, 97%, 98%, 99% or more identical to the entire length of the amino acid sequence of SEQ ID NO:30.

In another preferred embodiment, an isolated nucleic acid molecule encodes the amino acid sequence of human LSO. In yet another preferred embodiment, the nucleic acid molecule includes a nucleotide sequence encoding a protein having the amino acid sequence of SEQ ID NO:30. In yet another preferred embodiment, the nucleic acid molecule is at least 50, 100, 150, 200, 250, 300, 350, 400, 450, 500, 550, 600, 650, 700, 750, 800, 850, 900, 950, 1000, 1050, 1100, 1150, 1200, 1242, 1250, 1300, 1350, 1400, 1412, 1450, 1500, 1550, 1600, 1650, 1700, 1750, 1800, 1900, 2000, 2100, 2200, 2300, 2400, 2500, 2600, 2700, 2800, 2900 or more nucleotides in length. In a further preferred embodiment, the nucleic acid molecule is at least 50, 100, 150, 200, 250, 300, 350, 400, 450, 500, 550, 600, 650, 700, 750, 800, 850, 900, 950, 1000, 1050, 1100, 1150, 1200, 1242, 1250, 1300, 1350, 1400, 1412, 1450, 1500, 1550, 1600, 1650, 1700, 1750, 1800, 1900, 2000, 2100, 2200, 2300, 2400, 2500, 2600, 2700, 2800, 2900 or more nucleotides in length and encodes a protein having an LSO activity (as described herein).

Another embodiment of the invention features nucleic acid molecules, preferably LSO nucleic acid molecules, which specifically detect LSO nucleic acid molecules relative to nucleic acid molecules encoding non-LSO proteins. For example, in one embodiment, such a nucleic acid molecule is at least 20, 30, 40, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1900, 2000, 2100, 2200, 2300, 2400, 2500, 2600, 2700, 2800, 2900 or more nucleotides in length and hybridizes under stringent conditions to a nucleic acid molecule comprising the nucleotide sequence shown in SEQ ID NO:29 or 31, or a complement thereof, In preferred embodiments, the nucleic acid molecules are at least 15 (e.g., 15 contiguous) nucleotides in length and hybridize under stringent conditions to the nucleotide molecule set forth in SEQ ID NO:29 or 31, or a complement thereof.

In other preferred embodiments, the nucleic acid molecule encodes a naturally occurring allelic variant of a polypeptide comprising the amino acid sequence of SEQ ID NO:30, wherein the nucleic acid molecule hybridizes to a complement of a nucleic acid molecule comprising SEQ ID NO:29 or 31, respectively, under stringent conditions.

Another embodiment of the invention provides an isolated nucleic acid molecule which is antisense to an LSO nucleic acid molecule, e.g., the coding strand of an LSO nucleic acid molecule.

Another aspect of the invention provides a vector comprising an LSO nucleic acid molecule. In certain embodiments, the vector is a recombinant expression vector. In another embodiment, the invention provides a host cell containing a vector of the invention. In yet another embodiment, the invention provides a host cell containing a nucleic acid molecule of the invention. The invention also provides a method for producing a protein, preferably an LSO protein, by culturing in a suitable medium, a host cell, e.g., a mammalian host cell such as a non-human mammalian cell, of the invention containing a recombinant expression vector, such that the protein is produced.

Another aspect of this invention features isolated or recombinant LSO proteins and polypeptides. In one embodiment, an isolated LSO protein includes at least one or more of the following motifs or domains: a signal peptide, an N-glycosylation site, a lysyl oxidase domain, an LSO signature motif, and/or a scavenger receptor cysteine-rich domain.

In a preferred embodiment, an LSO protein includes at least one or more of the following motifs or domains: a signal peptide, an N-glycosylation site, a lysyl oxidase domain, an LSO signature motif, and/or a scavenger receptor cysteine-rich domain, and has an amino acid sequence at least about 42%, 50%, 55%, 60%, 65%, 67%, 68%, 70%, 75%, 80%, 85%, 90%, 95%, 96%, 97%, 98%, 99% or more identical to the amino acid sequence of SEQ ID NO:30.

In another preferred embodiment, an LSO protein includes at least one or more of the following motifs or domains: a signal peptide, an N-glycosylation site, a lysyl oxidase domain, an LSO signature motif, and/or a scavenger receptor cysteine-rich domain, and has an LSO activity (as described herein).

In yet another preferred embodiment, an LSO protein includes at least one or more of the following motifs or domains: a signal peptide, an N-glycosylation site, a lysyl oxidase domain, an LSO signature motif, and/or a scavenger receptor cysteine-rich domain, and is encoded by a nucleic acid molecule having a nucleotide sequence which hybridizes under stringent hybridization conditions to a complement of a nucleic acid molecule comprising the nucleotide sequence of SEQ ID NO:29 or 31.

In another embodiment, the invention features fragments of the protein having the amino acid sequence of SEQ ID NO:30, wherein the fragment comprises at least 412 amino acids (e.g., contiguous amino acids) of the amino acid sequence of SEQ ID NO:30. In another embodiment, an LSO protein has the amino acid sequence of SEQ ID NO:30.

In yet another embodiment, an LSO protein comprises or consists of amino acid residues 1–31 and/or 85–90 of SEQ ID NO:30.

In another embodiment, the invention features an LSO protein which is encoded by a nucleic acid molecule consisting of a nucleotide sequence at least about 42%, 48%, 50%, 55%, 60%, 65%, 70%, 75%, 80%, 85%, 90%, 95%, 96%, 97%, 98%, 99% or more identical to a nucleotide sequence of SEQ ID NO:29 or 31, or a complement thereof. This invention further features an LSO protein which is encoded by a nucleic acid molecule consisting of a nucleotide sequence which hybridizes under stringent hybridization conditions to a nucleic acid molecule comprising the nucleotide sequence of SEQ ID NO:29 or 31, or a complement thereof.

The proteins of the present invention or portions thereof, e.g., biologically active portions thereof, can be operatively linked to a non-LSO polypeptide (e.g., heterologous amino acid sequences) to form fusion proteins. The invention further features antibodies, such as monoclonal or polyclonal antibodies, that specifically bind proteins of the invention, preferably LSO proteins. In addition, the LSO proteins or biologically active portions thereof can be incorporated into pharmaceutical compositions, which optionally include pharmaceutically acceptable carriers.

In another aspect, the present invention provides a method for detecting the presence of an LSO nucleic acid molecule, protein, or polypeptide in a biological sample by contacting the biological sample with an agent capable of detecting an LSO nucleic acid molecule, protein, or polypeptide such that the presence of an LSO nucleic acid molecule, protein or polypeptide is detected in the biological sample.

In another aspect, the present invention provides a method for detecting the presence of LSO activity in a biological sample by contacting the biological sample with an agent capable of detecting an indicator of LSO activity such that the presence of LSO activity is detected in the biological sample.

In another aspect, the invention provides a method for modulating LSO activity comprising contacting a cell capable of expressing LSO with an agent that modulates LSO activity such that LSO activity in the cell is modulated. In one embodiment, the agent inhibits LSO activity. In another embodiment, the agent stimulates LSO activity. In one embodiment, the agent is an antibody that specifically binds to an LSO protein. In another embodiment, the agent modulates expression of LSO by modulating transcription of an LSO gene or translation of an LSO mRNA. In yet another embodiment, the agent is a nucleic acid molecule having a nucleotide sequence that is antisense to the coding strand of an LSO mRNA or an LSO gene.

In one embodiment, the methods of the present invention are used to treat a subject having a disorder characterized by aberrant or unwanted LSO protein or nucleic acid expression or activity by administering an agent which is an LSO modulator to the subject. In one embodiment, the LSO modulator is an LSO protein. In another embodiment the LSO modulator is an LSO nucleic acid molecule. In yet another embodiment, the LSO modulator is a peptide, peptidomimetic, or other small molecule. In a preferred embodiment, the disorder characterized by aberrant or unwanted LSO protein or nucleic acid expression is a lysyl oxidase-associated disorder, e.g., a cell proliferation, growth, or differentiation disorder, a muscular disorder, a bone disorder, a skin elasticity disorder, or a cartilage-based disorder.

The present invention also provides diagnostic assays for identifying the presence or absence of a genetic alteration characterized by at least one of (i) aberrant modification or mutation of a gene encoding an LSO protein; (ii) misregulation of the gene; and (iii) aberrant post-translational modification of an LSO protein, wherein a wild-type form of the gene encodes a protein with an LSO activity.

In another aspect the invention provides methods for identifying a compound that binds to or modulates the activity of an LSO protein, by providing an indicator composition comprising an LSO protein having LSO activity, contacting the indicator composition with a test compound, and determining the effect of the test compound on LSO activity in the indicator composition to identify a compound that modulates the activity of an LSO protein.

Other features and advantages of the invention will be apparent from the following detailed description and claims.

DETAILED DESCRIPTION OF THE INVENTION

The present invention is based, at least in part, on the discovery of novel molecules, referred to interchangeably herein as "lysyl oxidase" or "LSO" nucleic acid and protein molecules (e.g., human LSO or LSO47765), which are novel members of a family of enzymes possessing lysyl oxidase activity.

As used herein, the term "lysyl oxidase" includes a molecule which is involved in the oxidation of peptidyl lysine to peptidyl α-aminoadipic-δ semialdehyde, thereby catalyzing the covalent crosslinking between and within the molecular units of extracellular matrix proteins, e.g., elastin or collagen. Lysyl oxidase molecules are involved in the biogenesis of connective tissue matrices, and therefore are involved in cellular growth, proliferation, and differentiation. Lysyl oxidase molecules are also involved in systemic processes such as skin, bone, cartilage and muscle formation and function, and in tumor formation. Thus, the LSO molecules of the present invention provide novel diagnostic targets and therapeutic agents to control lysyl oxidase-associated disorders.

As used herein, a "lysyl oxidase-associated disorder" includes a disorder, disease or condition which is caused or characterized by a misregulation (e.g., downregulation or upregulation) of lysyl oxidase activity. Lysyl oxidase-associated disorders can detrimentally affect cellular functions such as cellular proliferation, growth, differentiation, or migration; or systemic responses in an organism, such as bone, skin, cartilage, or muscle formation, structure, or elasticity, or tumor formation. Examples of lysyl oxidase-associated disorders include muscular disorders, such as cardiac muscle-related disorders. Cardiovascular system disorders in which the LSO molecules of the invention may be directly or indirectly involved include arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrillation, Jervell syndrome, Lange-Nielsen syndrome, long-QT syndrome, congestive heart failure, sinus node dysfunction, angina, heart failure, hypertension, atrial fibrillation, atrial flutter, dilated cardiomyopathy, idiopathic cardiomyopathy, myocardial infarction, coronary artery disease, coronary artery spasm, and arrhythmia. LSO-mediated or related disorders also include disorders of the musculoskeletal system such as paralysis and muscle weakness, e.g., ataxia, myotonia, and myokymia.

Lysyl oxidase disorders also include cellular proliferation, growth, differentiation, or migration disorders. Cellular proliferation, growth, differentiation, or migration disorders include those disorders that affect cell proliferation, growth, differentiation, or migration processes. As used herein, a "cellular proliferation, growth, differentiation, or migration process" is a process by which a cell increases in number, size or content, by which a cell develops a specialized set of characteristics which differ from that of other cells, or by which a cell moves closer to or further from a particular location or stimulus. The LSO molecules of the invention are known to be involved in production/maintenance of the extracellular matrix, which is of vital importance in maintaining the structure of the cell. Thus, the LSO molecules may modulate cellular growth, differentiation, or migration, and may play a role in disorders characterized by aberrantly regulated growth, differentiation, or migration. Such disorders include cancer, e.g., carcinoma, sarcoma, or leukemia; tumor angiogenesis and metastasis; skeletal dysplasia; hepatic disorders; and hematopoietic and/or myeloproliferative disorders.

LSO-associated or related disorders also include disorders of bone formation and resorption, including osteoporosis, osteochondrosis, and osteopetrosis.

LSO-associated or related disorders also include disorders of skin formation and elasticity, including cutis laxa and Ehlers-Danlos type V syndrome.

LSO-associated or related disorders also include disorders of cartilage formation and structure, including chondromalacia and polychondritis.

LSO-associated or related disorders also include disorders affecting tissues in which LSO protein is expressed.

As used herein, a "lysyl oxidase-mediated activity" includes an activity mediated by a lysyl oxidase polypeptide. A lysyl oxidase-mediated activity includes the catalysis of the oxidation of peptidyl lysine to peptidyl α-aminoadipic-δ semialdehyde, thereby catalyzing the covalent crosslinking between and within the molecular units of extracellular matrix proteins, e.g., elastin and of collagen. Lysyl oxidase-mediated activities include those cellular or systemic activities which require the cross-linking of extracellular matrix proteins, e.g., collagen or elastin. Such activities include cellular growth, proliferation, and differentiation, and also systemic activities, such as bone, skin, cartilage and muscle biosynthesis and function, or tumor formation.

The term "family" when referring to the protein and nucleic acid molecules of the invention (e.g., the LSO family of proteins and/or nucleic acids) is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin, e.g., mouse or monkey proteins. Members of a family may also have common functional characteristics.

For example, proteins that belong to the family of LSO proteins comprise at least one signal sequence or signal peptide. The prediction of such a signal peptide can be made, for example, utilizing the computer algorithm SignalP (Henrik, et al. (1997) *Protein Engineering* 10:1–6). As used herein, a "signal sequence" or "signal peptide" includes a peptide containing about 15 or more amino acids which occurs at the N-terminus of secretory and membrane bound proteins and which contains a large number of hydrophobic amino acid residues. For example, a signal sequence contains at least about 10–30 amino acid residues, preferably about 15–25 amino acid residues, more preferably about 18–20 amino acid residues, and more preferably about 19 amino acid residues, and has at least about 35–65%, preferably about 38–50%, and more preferably about 40–45% hydrophobic amino acid residues (e.g., Valine, Leucine, Isoleucine or Phenylalanine). Such a "signal sequence", also referred to in the art as a "signal peptide", serves to direct a protein containing such a sequence to a lipid bilayer, and is cleaved in secreted and membrane bound proteins. A signal sequence was identified in the amino acid sequence of human LSO at about amino acids 1–24 of SEQ ID NO:30.

In another embodiment, an LSO molecule of the present invention is identified based on the presence of at least one N-glycosylation site. As used herein, the term "N-glycosylation site" includes an amino acid sequence of about 4 amino acid residues in length which serves as a glycosylation site. More preferably, an N-glycosylation site has the consensus sequence Asn-Xaa-Ser/Thr (where Xaa may be any amino acid). N-glycosylation sites are described in, for example, Prosite PDOC00001 (see the Prosite entry PDOC00001 at the website for ExPASy (Expert Protein Analysis System) proteomics server of the Swiss Institute of Bioinformayics expasy.ch), the contents of which are incorporated herein by reference. Amino acid residues 198–201 and 629–632 of the LSO protein comprise N-glycosylation sites. Accordingly, LSO proteins having at least one N-glycosylation site are within the scope of the invention.

In another embodiment, an LSO molecule of the present invention is identified based on the presence of a "lysyl oxidase domain" in the protein or corresponding nucleic acid molecule. As used herein, the term "lysyl oxidase domain" includes a protein domain having an amino acid sequence of about 100–300 amino acid residues, and a bit score of at least 200 when compared against a lysyl oxidase Hidden Markov Model (HMM), e.g., PFAM accession number PF01186. In a preferred embodiment, a lysyl oxidase domain includes a protein domain having an amino acid sequence of about 150–250 amino acid residues and a bit score of at least 300. In another preferred embodiment, a lysyl oxidase domain includes a protein domain having an amino acid sequence of about 202–205 amino acid residues and a bit score of at least 475 (e.g., 480, 490, 500, 510, 513 or more). To identify the presence of a lysyl oxidase domain in an LSO protein, the amino acid sequence of the protein is used to search a database of known Hidden Markov Models (HMMs e.g., the PFAM HMM database). The lysyl oxidase domain (HMM) has been assigned the PFAM Accession PF01186 (found at a Pfam website, genome.wustl.edu/Pfam). For example, a search was performed against the HMM database using the amino acid sequence (SEQ ID NO:30) of human LSO, resulting in the identification of a lysyl oxidase domain in the amino acid sequence of human LSO (SEQ ID NO:30) at about residues 533–736 of SEQ ID NO:30, having a score of 513.1.

In another embodiment of the invention, an LSO protein is identified based on the presence of at least one "LSO signature motif" in the protein or corresponding nucleic acid molecule. As used herein, the term "LSO signature motif" includes an amino acid sequence that contains at least about 5–20 amino acid residues that are conserved among LSO family members. In one embodiment, an LSO signature motif includes an amino acid sequence at least about 7–17 amino acid residues, more preferably about 9–15 amino acid residues, more preferably 10–13 amino acid residues and still more preferably 11 amino acid residues in length and having the following amino acid sequence: W-X-W-H-X-C-H-X-H-Y-H, (SEQ ID NO:32), where X indicates any amino acid (see, for example, Krebs and Krawetz (1993) Biochim. Biophys. Acta 1202: 7–12). Accordingly, preferred proteins include the conserved amino acid residues of the above-recited LSO signature motif. Proteins including at least 7, 8, 9, 10 or more conserved amino acid residues of the above-recited LSO signature motif are also considered to be within the scope of the present invention.

In another embodiment, an LSO molecule of the present invention is identified based on the presence of a "scavenger receptor cysteine-rich domain" in the protein or corresponding nucleic acid molecule. As used herein, the term "scavenger receptor cysteine-rich domain" includes a protein domain having an amino acid sequence of about 50–150 amino acid residues, and a bit score of at least 25 when compared against a scavenger receptor cysteine-rich domain Hidden Markov Model (HMM), e.g., PFAM accession number PF00530. In a preferred embodiment, a scavenger receptor cysteine-rich domain includes a protein domain having an amino acid sequence of about 75–125 amino acid residues and a bit score of at least 35. In another preferred embodiment, a scavenger receptor cysteine-rich domain includes a protein domain having an amino acid sequence of about 97–119 amino acid residues and a bit score of at least 40 (e.g., 41, 42, 43, 44, 45, 46 or higher). To identify the presence of a scavenger receptor cysteine-rich domain in an LSO protein, the amino acid sequence of the protein may be used to search a database of known Hidden Markov Models (HMMs e.g., the PFAM HMM database). The scavenger receptor cysteine-rich domain (HMM) has been assigned the PFAM Accession PF00530 (found at a Pfam website, genome.wustl.edu/Pfam). For example, a search was performed against the HMM database using the amino acid sequence (SEQ ID NO:30) of human LSO, resulting in the identification of four scavenger receptor cysteine-rich domains in the amino acid sequence of human LSO (SEQ ID NO:30) at about residues 37–133, 169–287, 314–411, and 424–529 of SEQ ID NO:30, having scores of 98.1, 30.4, 115.8, and 46.3, respectively.

In a preferred embodiment, the LSO molecules of the invention include at least one, preferably two or more of the following motifs or domains: a signal peptide, an N-glycosylation site, a lysyl oxidase domain, an LSO signature motif, and/or a scavenger receptor cysteine-rich domain.

Isolated proteins of the present invention, preferably LSO proteins, have an amino acid sequence sufficiently identical to the amino acid sequence of SEQ ID NO:30, or are encoded by a nucleotide sequence sufficiently identical to SEQ ID NO:29 or 31. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%–80%, and even more preferably 90–95% homology across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70–80%, or 90–95% homology and share a common functional activity are defined herein as sufficiently identical.

As used interchangeably herein, an "LSO activity", "biological activity of LSO" or "functional activity of LSO", refers to an activity exerted by an LSO protein, polypeptide or nucleic acid molecule on an LSO responsive cell or tissue, or on an LSO protein substrate, as determined in vivo, or in vitro, according to standard techniques. In one embodiment, an LSO activity is a direct activity, such as an association with an LSO-target molecule. As used herein, a "target molecule" or "binding partner" is a molecule with which an LSO protein binds or interacts in nature, such that LSO-mediated function is achieved. An LSO target molecule can be a non-LSO molecule (e.g., a copper ion, lysyltyrosine quinone, trihydroxyphenylalanine quinone, or other cofactor) or an LSO protein or polypeptide of the present invention. In an exemplary embodiment, an LSO target molecule is an LSO substrate (e.g., elastin or collagen). Alternatively, an LSO activity is an indirect activity, such as a metabolic activity mediated by interaction of the LSO protein with an LSO substrate. The biological activities of LSO are described herein. In an exemplary embodiment, the LSO proteins of the present invention have at least one of the following activities: i) interaction with an LSO substrate; ii) interaction with a cofactor (e.g., a copper ion, lysyltyrosine quinone, trihydroxyphenylalanine quinone, or other cofactor); and iii) conversion of an LSO substrate to product (e.g., catalysis of the conversion of substrate to product). In yet another embodiment, the LSO proteins of the present invention have one or more of the following activities: 1) modulate cellular growth, proliferation, or differentiation, 2) modulate skin formation or elasticity 3) modulate bone formation or structure; 4) modulate muscle formation or elasticity; 5) modulate cartilage formation or structure; and 6) modulate tumor formation.

Accordingly, another embodiment of the invention features isolated LSO proteins and polypeptides having an LSO activity. Other preferred proteins are LSO proteins having one or more of the following motifs or domains: a signal peptide, an N-glycosylation site, a lysyl oxidase domain, an LSO signature motif, and/or a scavenger receptor cysteine-rich domain and, preferably, an LSO activity.

Additional preferred proteins have at least one or more of the following motifs or domains: a signal peptide, an N-glycosylation site, a lysyl oxidase domain, an LSO signature motif, and/or a scavenger receptor cysteine-rich domain, and are, preferably, encoded by a nucleic acid molecule having a nucleotide sequence which hybridizes under stringent hybridization conditions to a complement of a nucleic acid molecule comprising the nucleotide sequence of SEQ ID NO:29 or 31.

The nucleotide sequence of the isolated human LSO cDNA and the predicted amino acid sequence of the human LSO polypeptide are shown in FIGS. 53A–E and in SEQ ID NOs:29 and 30, respectively.

The human LSO gene, which is approximately 2976 nucleotides in length, encodes a protein having a molecular weight of approximately 83.2 kD and which is approximately 756 amino acid residues in length.

Various aspects of the invention are described in further detail in the following subsections:

I. Isolated Nucleic Acid Molecules

One aspect of the invention pertains to isolated nucleic acid molecules that encode LSO proteins or biologically active portions thereof, as well as nucleic acid fragments sufficient for use as hybridization probes to identify LSO-encoding nucleic acid molecules (e.g., LSO mRNA) and fragments for use as PCR primers for the amplification or mutation of LSO nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated LSO nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:29 or 31, or a portion thereof, can be isolated using standard molecular biology techniques and the sequence information provided herein. Using all or portion of the nucleic acid sequence of SEQ ID NO:29 or 31, as a hybridization probe, LSO nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:29 or 31, can be isolated by the polymerase chain reaction (PCR) using synthetic oligonucleotide primers designed based upon the sequence of SEQ ID NO:29 or 31.

A nucleic acid of the invention can be amplified using cDNA, mRNA or, alternatively, genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to LSO nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:29 or 31. This cDNA may comprise sequences encoding the human LSO protein (i.e., "the coding region", from nucleotides 95–2365), as well as 5' untranslated sequences (nucleotides 1–94) and 3' untranslated sequences (nucleotides 2366–2976) of SEQ ID NO:29. Alternatively, the nucleic acid molecule can comprise only the coding region of SEQ ID NO:29 (e.g., nucleotides 95–2365, corresponding to SEQ ID NO:31). In another embodiment, an isolated nucleic acid molecule of the invention consists of SEQ ID NO:29 or 31.

In another preferred embodiment, an isolated nucleic acid molecule of the invention comprises a nucleic acid molecule which is a complement of the nucleotide sequence shown in SEQ ID NO:29 or 31, or a portion of any of these nucleotide sequences. A nucleic acid molecule which is complementary to the nucleotide sequence shown in SEQ ID NO:29 or 31, is one which is sufficiently complementary to the nucleotide sequence shown in SEQ ID NO:29 or 31, such that it can hybridize to the nucleotide sequence shown in SEQ ID NO:29 or 31, respectively, thereby forming a stable duplex.

In still another preferred embodiment, an isolated nucleic acid molecule of the present invention comprises a nucleotide sequence which is at least about 42%, 48%, 50%, 55%, 60%, 65%, 70%, 75%, 80%, 85%, 90%, 95%, 96%, 97%, 98%, 99% or more identical to the entire length of the nucleotide sequence shown in SEQ ID NO:29 or 31, or a portion of any of these nucleotide sequences.

Moreover, the nucleic acid molecule of the invention can comprise only a portion of the nucleic acid sequence of SEQ ID NO:29 or 31, for example, a fragment which can be used as a probe or primer or a fragment encoding a portion of an LSO protein, e.g., a biologically active portion of an LSO protein. The nucleotide sequence determined from the cloning of the LSO gene allows for the generation of probes and primers designed for use in identifying and/or cloning other LSO family members, as well as LSO homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:29 or 31, of an anti-sense sequence of SEQ ID NO:29 or 31, or of a naturally occurring allelic variant or mutant of SEQ ID NO:29 or 31. In one embodiment, a nucleic acid molecule of the present invention comprises a nucleotide sequence which is greater than 20–50, 50–100, 100–150, 150–200, 200–250, 250–300, 300–350, 350–400, 400–450, 450–500, 500–550, 550–600, 600–650, 650–700, 700–750, 750–800, 800–850, 850–900, 900–950, 950–1000, 1000–1050, 1050–1100, 1100–1150, 1150–1200, 1200–1250, 1250–1300, 1300–1350, 1350–1400, 1400–1450, 1450–1500, 1500–1550, 1550–1600, 1600–1650, 1650–1700, 1700–1750, 1750–1800, 1800–1850, 1850–1900, 1900–1950, 1950–2000, 2000–2050, 2050–2100, 2100–2150, 2150–2200, 2200–2250, 2250–2300, 2300–2350, 2350–2400, 2400–2450, 2450–2500, 2500–2550, 2550–2600, 2600–2650, 2650–2700, 2700–2750, 2750–2800, 2800–2850, 2850–2900, 2900–2950 or more nucleotides in length and hybridizes under stringent hybridization conditions to a complement of a nucleic acid molecule of SEQ ID NO:29 or 31.

Ranges intermediate to the above-recited values, e.g., nucleic acid molecules comprising the nucleic acid sequence which is 50–60, 60–70, 70–80, 80–90, 90–100 or more nucleotides in length and hybridizes under stringent hybridization conditions to a complement of a nucleic acid molecule of SEQ ID NO:29 or 31, are also intended to be encompassed by the present invention. Values and ranges included and/or intermediate within the ranges set forth herein are also intended to be within the scope of the present invention. For example, nucleic acid molecules comprising the nucleic acid sequence which is 51, 52, 53, 54, 55, 56, 57, 58, and 59 or more nucleotides in length and hybridizes under stringent hybridization conditions to a complement of a nucleic acid molecule of SEQ ID NO:29 or 31, are intended to be included within the range of 50–60 or more nucleotides in length and hybridizes under stringent hybridization conditions to a complement of a nucleic acid molecule of SEQ ID NO:29 or 31.

Probes based on the LSO nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress an LSO protein, such as by measuring a level of an LSO-encoding nucleic acid in a sample of cells from a subject e.g., detecting LSO mRNA levels or determining whether a genomic LSO gene has been mutated or deleted.

A nucleic acid fragment encoding a "biologically active portion of an LSO protein" can be prepared by isolating a portion of the nucleotide sequence of SEQ ID NO:29 or 31, which encodes a polypeptide having an LSO biological activity (the biological activities of the LSO proteins are described herein), expressing the encoded portion of the LSO protein (e.g., by recombinant expression in vitro) and assessing the activity of the encoded portion of the LSO protein.

The invention further encompasses nucleic acid molecules that differ from the nucleotide sequence shown in SEQ ID NO:29 or 31, due to degeneracy of the genetic code and thus encode the same LSO proteins as those encoded by the nucleotide sequence shown in SEQ ID NO:29 or 31. In another embodiment, an isolated nucleic acid molecule of the invention has a nucleotide sequence encoding a protein having an amino acid sequence shown in SEQ ID NO:30.

In addition to the LSO nucleotide sequences shown in SEQ ID NO:29 or 31, it will be appreciated by those skilled in the art that DNA sequence polymorphisms that lead to changes in the amino acid sequences of the LSO proteins may exist within a population (e.g., the human population). Such genetic polymorphism in the LSO genes may exist among individuals within a population due to natural allelic variation. As used herein, the terms "gene" and "recombinant gene" refer to nucleic acid molecules which include an open reading frame encoding an LSO protein, preferably a mammalian LSO protein, and can further include non-coding regulatory sequences, and introns.

Allelic variants of human LSO include both functional and non-functional LSO proteins. Functional allelic variants are naturally occurring amino acid sequence variants of the human LSO protein that maintain the ability, for example, to bind an LSO ligand or substrate and/or to modulate cell growth, proliferation and/or differentiation mechanisms. Functional allelic variants will typically contain only conservative substitution of one or more amino acids of SEQ ID NO:30, or substitution, deletion or insertion of non-critical residues in non-critical regions of the protein.

Non-functional allelic variants are naturally occurring amino acid sequence variants of the human LSO protein that do not have the ability to either bind an LSO ligand and/or modulate any of the LSO activities described herein. Non-functional allelic variants will typically contain a non-conservative substitution, a deletion, or insertion or premature truncation of the amino acid sequence of SEQ ID NO:30, or a substitution, insertion or deletion in critical residues or critical regions of the protein.

The present invention further provides non-human orthologues of the human LSO protein. Orthologues of the human LSO protein are proteins that are isolated from non-human organisms and possess the same LSO ligand binding and/or modulation of membrane excitability activities of the human LSO protein. Orthologues of the human LSO protein can readily be identified as comprising an amino acid sequence that is substantially identical to SEQ ID NO:30.

Moreover, nucleic acid molecules encoding other LSO family members and, thus, which have a nucleotide sequence which differs from the LSO sequences of SEQ ID NO:29 or 31, are intended to be within the scope of the invention. For example, another LSO cDNA can be identified based on the nucleotide sequence of human LSO. Moreover, nucleic acid molecules encoding LSO proteins from different species, and which, thus, have a nucleotide sequence which differs from the LSO sequences of SEQ ID NO:29 or 31, are intended to be within the scope of the invention. For example, a mouse LSO cDNA can be identified based on the nucleotide sequence of a human LSO.

Nucleic acid molecules corresponding to natural allelic variants and homologues of the LSO cDNAs of the invention can be isolated based on their homology to the LSO nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the LSO cDNAs of the invention can further be isolated by mapping to the same chromosome or locus as the LSO gene.

Accordingly, in another embodiment, an isolated nucleic acid molecule of the invention is at least 15, 20, 25, 30 or more nucleotides in length and hybridizes under stringent conditions to a complement of the nucleic acid molecule comprising the nucleotide sequence of SEQ ID NO:29 or 31. In other embodiment, the nucleic acid is at least 20–50, 50–100, 100–150, 150–200, 200–250, 250–300, 300–350, 350–400, 400–450, 450–500, 500–550, 550–600, 600–650, 650–700, 700–750, 750–800, 800–850, 850–900, 900–950, 950–1000, 1000–1050, 1050–1100, 1100–1150, 1150–1200, 1200–1250, 1250–1300, 1300–1350, 1350–1400, 1400–1450, 1450–1500, 1500–1550, 1550–1600, 1600–1650, 1650–1700, 1700–1750, 1750–1800, 1800–1850, 1850–1900, 1900–1950, 1950–2000, 2000–2050, 2050–2100, 2100–2150, 2150–2200, 2200–2250, 2250–2300, 2300–2350, 2350–2400, 2400–2450, 2450–2500, 2500–2550, 2550–2600, 2600–2650, 2650–2700, 2700–2750, 2750–2800, 2800–2850, 2850–2900, 2900–2950 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A preferred, non-limiting example of stringent hybridization conditions includes hybridization in 4× or 6× sodium chloride/sodium citrate (SSC), at about 65–70° C. (or hybridization in 4×SSC plus 50% formamide at about 42–50° C.) followed by one or more washes in 1×SSC, at about 65–70° C. A further preferred, non-limiting example of stringent hybridization conditions includes hybridization at 6×SSC at 45° C., followed by one or more washes in 0.2×SSC, 0.1% SDS at 65° C. A preferred, non-limiting example of highly stringent hybridization conditions includes hybridization in 1×SSC, at about 65–70° C. (or hybridization in 1×SSC plus 50% formamide at about 42–50° C.) followed by one or more washes in 0.3×SSC, at about 65–70° C. A preferred, non-limiting example of reduced stringency hybridization conditions includes hybridization in 4× or 6×SSC, at about 50–60° C. (or alternatively hybridization in 6×SSC plus 50% formamide at about 40–45° C.) followed by one or more washes in 2× SSC, at about 50–60° C. Ranges intermediate to the above-recited values, e.g., at 65–70° C. or at 42–50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m(° C.)=2(\# \text{ of A+T bases})+4(\# \text{ of G+C bases})$. For hybrids between 18 and 49 base pairs in length, $T_m(° C.)=81.5+16.6(\log_{10}[Na^+])+0.41 (\%G+C)-(600/N)$, where N is the number of bases in the hybrid, and $[Na^+]$ is the concentration of sodium ions in the hybridization buffer ($[Na^+]$ for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25–0.5M $NaH_2PO_4$, 7% SDS at about 65° C., followed by one or more washes at 0.02M $NaH_2PO_4$, 1% SDS at 65° C., see e.g., Church and Gilbert (1984) *Proc. Natl. Acad. Sci. USA* 81:1991–1995, (or alternatively 0.2×SSC, 1% SDS).

Preferably, an isolated nucleic acid molecule of the invention that hybridizes under stringent conditions to the sequence of SEQ ID NO:29 or 31 and corresponds to a naturally-occurring nucleic acid molecule. As used herein, a "naturally-occurring" nucleic acid molecule refers to an RNA or DNA molecule having a nucleotide sequence that occurs in nature (i.e., encodes a natural protein).

In addition to naturally-occurring allelic variants of the LSO sequences that may exist in the population, the skilled artisan will further appreciate that changes can be introduced by mutation into the nucleotide sequences of SEQ ID NO:29 or 31, thereby leading to changes in the amino acid sequence of the encoded LSO proteins, without altering the functional ability of the LSO proteins. For example, nucleotide substitutions leading to amino acid substitutions at "non-essential" amino acid residues can be made in the sequence of SEQ ID NO:29 or 31. A "non-essential" amino acid residue is a residue that can be altered from the wild-type sequence of LSO (e.g., the sequence of SEQ ID NO:30) without altering the biological activity, whereas an "essential" amino acid residue is required for biological activity. For example, amino acid residues that are conserved among the LSO proteins of the present invention, e.g., those present in a lysyl oxidase consensus sequence, are predicted to be particularly unamenable to alteration.

Accordingly, another aspect of the invention pertains to nucleic acid molecules encoding LSO proteins that contain changes in amino acid residues that are not essential for activity. Such LSO proteins differ in amino acid sequence from SEQ ID NO:30, yet retain biological activity. In one embodiment, the isolated nucleic acid molecule comprises a nucleotide sequence encoding a protein, wherein the protein comprises an amino acid sequence at least about 42%, 50%, 55%, 60%, 65%, 70%, 75%, 80%, 85%, 90%, 95%, 96%, 97%, 98%, 99% or more identical to SEQ ID NO:30.

An isolated nucleic acid molecule encoding an LSO protein identical to the protein of SEQ ID NO:30 can be created by introducing one or more nucleotide substitutions, additions or deletions into the nucleotide sequence of SEQ ID NO:29 or 31, such that one or more amino acid substitutions, additions or deletions are introduced into the encoded protein. Mutations can be introduced into SEQ ID NO:29 or 31, by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in an LSO protein is preferably replaced with another amino acid residue from the same side chain family. Alternatively, in another embodiment, mutations can be introduced randomly along all or part of an LSO coding sequence, such as by saturation mutagenesis, and the resultant mutants can be screened for LSO biological activity to identify mutants that retain activity. Following mutagenesis of SEQ ID NO:29 or 31, the encoded protein can be expressed recombinantly and the activity of the protein can be determined.

In a preferred embodiment, a mutant LSO protein can be assayed for the ability to modulate cellular growth, proliferation, or differentiation, to modulate bone, skin, cartilage, or muscle growth, structure, or elasticity, or to modulate tumor formation.

In addition to the nucleic acid molecules encoding LSO proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire LSO coding strand, or to only a portion thereof. In one embodiment, an antisense nucleic acid molecule is antisense to a "coding region" of the coding strand of a nucleotide sequence encoding an LSO. The term "coding region" refers to the region of the nucleotide sequence comprising codons which are translated into amino acid residues (e.g., the coding region of human LSO corresponds to SEQ ID NO:31). In another embodiment, the antisense nucleic acid molecule is antisense to a "noncoding region" of the coding strand of a nucleotide sequence encoding LSO. The term "noncoding region" refers to 5' and 3' sequences which flank the coding region that are not translated into amino acids (i.e., also referred to as 5' and 3' untranslated regions).

Given the coding strand sequences encoding LSO disclosed herein (e.g., SEQ ID NO:31), antisense nucleic acids of the invention can be designed according to the rules of Watson and Crick base pairing. The antisense nucleic acid molecule can be complementary to the entire coding region of LSO mRNA, but more preferably is an oligonucleotide which is antisense to only a portion of the coding or noncoding region of LSO mRNA. For example, the antisense oligonucleotide can be complementary to the region surrounding the translation start site of LSO mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an LSO protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff and Gerlach (1988) *Nature* 334:585–591)) can be used to catalytically cleave LSO mRNA transcripts to thereby inhibit translation of LSO mRNA. A ribozyme having specificity for an LSO-encoding nucleic acid can be designed based upon the nucleotide sequence of an LSO cDNA disclosed herein (i.e., SEQ ID NO:29 or 31. For example, a derivative of a *Tetrahymena* L-19 IVS RNA can be constructed in which the nucleotide sequence of the active site is complementary to the nucleotide sequence to be cleaved in an LSO-encoding mRNA. See, e.g., Cech et al. U.S. Pat. No. 4,987,071; and Cech et al. U.S. Pat. No. 5,116,742. Alternatively, LSO mRNA can be used to select a catalytic RNA having a specific ribonuclease activity from a pool of RNA molecules. See, e.g., Bartel, D. and Szostak, J. W. (1993) *Science* 261:1411–1418.

Alternatively, LSO gene expression can be inhibited by targeting nucleotide sequences complementary to the regulatory region of the LSO (e.g., the LSO promoter and/or enhancers; e.g., nucleotides 1–94 of SEQ ID NO:29) to form triple helical structures that prevent transcription of the LSO gene in target cells. See generally, Helene, C. (1991) *Anticancer Drug Des.* 6(6): 569–84; Helene, C. et al. (1992) *Ann. N.Y. Acad. Sci.* 660:27–36; and Maher, L. J. (1992) *Bioassays* 14(12):807–15.

In yet another embodiment, the LSO nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. *Proc. Natl. Acad. Sci.* 93: 14670–675.

PNAs of LSO nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of LSO nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of LSO can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of LSO nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

Alternatively, the expression characteristics of an endogenous LSO gene within a cell line or microorganism may be modified by inserting a heterologous DNA regulatory element into the genome of a stable cell line or cloned microorganism such that the inserted regulatory element is operatively linked with the endogenous LSO gene. For example, an endogenous LSO gene which is normally "transcriptionally silent", i.e., an LSO gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous LSO gene may be activated by insertion of a promiscuous regulatory element that works across cell types.

A heterologous regulatory element may be inserted into a stable cell line or cloned microorganism, such that it is operatively linked with an endogenous LSO gene, using techniques, such as targeted homologous recombination, which are well known to those of skill in the art, and described, e.g., in Chappel, U.S. Pat. No. 5,272,071; PCT publication No. WO 91/06667, published May 16, 1991.

II. Isolated LSO Proteins and Anti-LSO Antibodies

One aspect of the invention pertains to isolated LSO proteins, and biologically active portions thereof, as well as polypeptide fragments suitable for use as immunogens to raise anti-LSO antibodies. In one embodiment, native LSO proteins can be isolated from cells or tissue sources by an appropriate purification scheme using standard protein purification techniques. In another embodiment, LSO proteins are produced by recombinant DNA techniques. Alternative to recombinant expression, an LSO protein or polypeptide can be synthesized chemically using standard peptide synthesis techniques.

An "isolated" or "purified" protein or biologically active portion thereof is substantially free of cellular material or other contaminating proteins from the cell or tissue source from which the LSO protein is derived, or substantially free from chemical precursors or other chemicals when chemically synthesized. The language "substantially free of cellular material" includes preparations of LSO protein in which the protein is separated from cellular components of the cells from which it is isolated or recombinantly produced. In one embodiment, the language "substantially free of cellular material" includes preparations of LSO protein having less than about 30% (by dry weight) of non-LSO protein (also referred to herein as a "contaminating protein"), more preferably less than about 20% of non-LSO protein, still more preferably less than about 10% of non-LSO protein, and most preferably less than about 5% non-LSO protein. When the LSO protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of LSO protein in which the protein is separated from chemical precursors or other chemicals which are involved in the synthesis of the protein. In one embodiment, the language "substantially free of chemical precursors or other chemicals" includes preparations of LSO protein having less than about 30% (by dry weight) of chemical precursors or non-LSO chemicals, more preferably less than about 20% chemical precursors or non-LSO chemicals, still more preferably less than about 10% chemical precursors or non-LSO chemicals, and most preferably less than about 5% chemical precursors or non-LSO chemicals.

As used herein, a "biologically active portion" of an LSO protein includes a fragment of an LSO protein which participates in an interaction between an LSO molecule and a non-LSO molecule. Biologically active portions of an LSO protein include peptides comprising amino acid sequences sufficiently identical to or derived from the amino acid sequence of the LSO protein, e.g., the amino acid sequence shown in SEQ ID NO:30, which include less amino acids than the full length LSO proteins, and exhibit at least one activity of an LSO protein. Typically, biologically active portions comprise a domain or motif with at least one activity of the LSO protein, e.g., modulating membrane excitability. A biologically active portion of an LSO protein can be a polypeptide which is, for example, 25, 50, 75, 100, 125, 150, 175, 200, 250, 300, 350, 400, 450, 500, 550, 600, 650, 700, 725, 750 or more amino acids in length. Biologically active portions of an LSO protein can be used as targets for developing agents which modulate an LSO mediated activity, e.g., a proliferative response.

It is to be understood that a preferred biologically active portion of an LSO protein of the present invention may contain at least one or more of the following motifs or domains: a signal peptide, an N-glycosylation site, a lysyl oxidase domain, an LSO signature motif, and/or a scavenger receptor cysteine-rich domain. Moreover, other biologically active portions, in which other regions of the protein are deleted, can be prepared by recombinant techniques and evaluated for one or more of the functional activities of a native LSO protein.

In a preferred embodiment, the LSO protein has an amino acid sequence shown in SEQ ID NO:30. In other embodiments, the LSO protein is substantially identical to SEQ ID NO:30, and retains the functional activity of the protein of SEQ ID NO:30, yet differs in amino acid sequence due to natural allelic variation or mutagenesis, as described in detail in subsection I above. Accordingly, in another embodiment, the LSO protein is a protein which comprises an amino acid sequence at least about 42%, 50%, 55%, 60%, 65%, 70%, 75%, 80%, 85%, 90%, 95%, 96%, 97%, 98%, 99% or more identical to SEQ ID NO:30.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the LSO amino acid sequence of SEQ ID NO:30 having 328 amino acid residues, at least 50, preferably at least 100, more preferably at least 200, even more preferably at least 300, at least 400, at least 500, at least 600, and even more preferably at least 700 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at the bioinformatics page of the website maintained by Accelrys, Inc., San Diego, Calif., USA), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*Comput. Appl. Biosci.*, 4: 11–17 (1988)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to LSO nucleic acid molecules of the invention. BLAST protein searches can be performed with the XBLAST program, score=100, wordlength=3 to obtain amino acid sequences homologous to LSO protein molecules of the invention. To obtain gapped alignments for comparison purposes, Gapped BLAST can be utilized as described in Altschul et al., (1997) *Nucleic Acids Res.* 25(17): 3389–3402. When utilizing BLAST and Gapped BLAST programs, the default parameters of the respective programs (e.g., XBLAST and NBLAST) can be used (accessible at the website maintained by National Center for Biotechnology Information, Betesda, Md., USA.

The invention also provides LSO chimeric or fusion proteins. As used herein, an LSO "chimeric protein" or "fusion protein" comprises an LSO polypeptide operatively linked to a non-LSO polypeptide. An "LSO polypeptide" refers to a polypeptide having an amino acid sequence corresponding to an LSO molecule, whereas a "non-LSO polypeptide" refers to a polypeptide having an amino acid sequence corresponding to a protein which is not substantially homologous to the LSO protein, e.g., a protein which is different from the LSO protein and which is derived from the same or a different organism. Within an LSO fusion protein the LSO polypeptide can correspond to all or a portion of an LSO protein. In a preferred embodiment, an LSO fusion protein comprises at least one biologically active portion of an LSO protein. In another preferred embodiment, an LSO fusion protein comprises at least two biologically active portions of an LSO protein. Within the fusion protein, the term "operatively linked" is intended to indicate that the LSO polypeptide and the non-LSO polypeptide are fused in-frame to each other. The non-LSO polypeptide can be fused to the N-terminus or C-terminus of the LSO polypeptide.

For example, in one embodiment, the fusion protein is a GST-LSO fusion protein in which the LSO sequences are fused to the C-terminus of the GST sequences. Such fusion proteins can facilitate the purification of recombinant LSO.

In another embodiment, the fusion protein is an LSO protein containing a heterologous signal sequence at its N-terminus. In certain host cells (e.g., mammalian host cells), expression and/or secretion of LSO can be increased through use of a heterologous signal sequence.

The LSO fusion proteins of the invention can be incorporated into pharmaceutical compositions and administered to a subject in vivo. The LSO fusion proteins can be used to affect the bioavailability of an LSO substrate. Use of LSO fusion proteins may be useful therapeutically for the treatment of disorders caused by, for example, (i) aberrant modification or mutation of a gene encoding an LSO protein; (ii) mis-regulation of the LSO gene; and (iii) aberrant post-translational modification of an LSO protein.

Moreover, the LSO-fusion proteins of the invention can be used as immunogens to produce anti-LSO antibodies in a subject, to purify LSO ligands and in screening assays to identify molecules which inhibit the interaction of LSO with an LSO substrate.

Preferably, an LSO chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). An LSO-encoding nucleic acid can be cloned into such an expression vector such that the fusion moiety is linked in-frame to the LSO protein.

The present invention also pertains to variants of the LSO proteins which function as either LSO agonists (mimetics) or as LSO antagonists. Variants of the LSO proteins can be generated by mutagenesis, e.g., discrete point mutation or truncation of an LSO protein. An agonist of the LSO proteins can retain substantially the same, or a subset, of the biological activities of the naturally occurring form of an LSO protein. An antagonist of an LSO protein can inhibit one or more of the activities of the naturally occurring form of the LSO protein by, for example, competitively modulating an LSO-mediated activity of an LSO protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the LSO protein.

In one embodiment, variants of an LSO protein which function as either LSO agonists (mimetics) or as LSO antagonists can be identified by screening combinatorial libraries of mutants, e.g., truncation mutants, of an LSO protein for LSO protein agonist or antagonist activity. In one embodiment, a variegated library of LSO variants is generated by combinatorial mutagenesis at the nucleic acid level and is encoded by a variegated gene library. A variegated library of LSO variants can be produced by, for example, enzymatically ligating a mixture of synthetic oligonucleotides into gene sequences such that a degenerate set of potential LSO sequences is expressible as individual polypeptides, or alternatively, as a set of larger fusion proteins (e.g., for phage display) containing the set of LSO sequences therein. There are a variety of methods which can be used to produce libraries of potential LSO variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential LSO sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of an LSO protein coding sequence can be used to generate a variegated population of LSO fragments for screening and subsequent selection of variants of an LSO protein. In one embodiment, a library of coding sequence fragments can be generated by treating a double stranded PCR fragment of an LSO coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the LSO protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of LSO proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify LSO variants (Arkin and Youvan (1992) *Proc. Natl. Acad. Sci. USA* 89:7811–7815; Delagrave et al. (1993) *Protein Engineering* 6(3): 327–331).

In one embodiment, cell based assays can be exploited to analyze a variegated LSO library. For example, a library of expression vectors can be transfected into a cell line, e.g., a neuronal cell line, which ordinarily responds to an LSO ligand in a particular LSO ligand-dependent manner. The transfected cells are then contacted with an LSO ligand and the effect of expression of the mutant on, e.g., membrane excitability of LSO can be detected. Plasmid DNA can then be recovered from the cells which score for inhibition, or alternatively, potentiation of signaling by the LSO ligand, and the individual clones further characterized.

An isolated LSO protein, or a portion or fragment thereof, can be used as an immunogen to generate antibodies. that bind LSO using standard techniques for polyclonal and monoclonal antibody preparation. A full-length LSO protein can be used or, alternatively, the invention provides antigenic peptide fragments of LSO for use as immunogens. The antigenic peptide of LSO comprises at least 8 amino acid residues of the amino acid sequence shown in SEQ ID NO:30 and encompasses an epitope of LSO such that an antibody raised against the peptide forms a specific immune complex with the LSO protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of LSO that are located on the surface of the protein, e.g., hydrophilic regions, as well as regions with high antigenicity (see FIG. 54).

An LSO immunogen typically is used to prepare antibodies by immunizing a suitable subject, (e.g., rabbit, goat, mouse or other mammal) with the immunogen. An appropriate immunogenic preparation can contain, for example, recombinantly expressed LSO protein or a chemically synthesized LSO polypeptide. The preparation can further include an adjuvant, such as Freund's complete or incomplete adjuvant, or similar immunostimulatory agent. Immunization of a suitable subject with an immunogenic LSO preparation induces a polyclonal anti-LSO antibody response.

Accordingly, another aspect of the invention pertains to anti-LSO antibodies. The term "antibody" as used herein refers to immunoglobulin molecules and immunologically active portions of immunoglobulin molecules, i.e., molecules that contain an antigen binding site which specifically binds (immunoreacts with) an antigen, such as an LSO. Examples of immunologically active portions of immunoglobulin molecules include F(ab) and $F(ab')_2$ fragments which can be generated by treating the antibody with an enzyme such as pepsin. The invention provides polyclonal and monoclonal antibodies that bind LSO molecules. The term "monoclonal antibody" or "monoclonal antibody composition", as used herein, refers to a population of antibody molecules that contain only one species of an antigen binding site capable of immunoreacting with a particular epitope of LSO. A monoclonal antibody composition thus typically displays a single binding affinity for a particular LSO protein with which it immunoreacts.

Polyclonal anti-LSO antibodies can be prepared as described above by immunizing a suitable subject with an LSO immunogen. The anti-LSO antibody titer in the immunized subject can be monitored over time by standard techniques, such as with an enzyme linked immunosorbent assay (ELISA) using immobilized LSO. If desired, the antibody molecules directed against LSO can be isolated from the mammal (e.g., from the blood) and further purified by well known techniques, such as protein A chromatography to obtain the IgG fraction. At an appropriate time after immunization, e.g., when the anti-LSO antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem* 0.255: 4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with an LSO immunogen as described above, and the culture supernatants of the resulting hybridoma cells are screened to identify a hybridoma producing a monoclonal antibody that binds LSO.

Any of the many well known protocols used for fusing lymphocytes and immortalized cell lines can be applied for the purpose of generating an anti-LSO monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4–1, P3-x63-Ag8.653 or Sp2/O-Ag14 myeloma lines. These myeloma lines are available from ATCC (Manassas, Va.). Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind LSO, e.g., using a standard ELISA assay.

Alternative to preparing monoclonal antibody-secreting hybridomas, a monoclonal anti-LSO antibody can be identified and isolated by screening a recombinant combinatorial immunoglobulin library (e.g., an antibody phage display library) with LSO to thereby isolate immunoglobulin library members that bind LSO. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1369–1372; Hay et al. (1992) *Hum. Antibod. Hybridomas* 3:81–85; Huse et al. (1989) *Science* 246:1275–1281; Griffiths et al. (1993) *EMBO J.* 12:725–734; Hawkins et al. (1992) *J. Mol. Biol.* 226:889–896; Clackson et al. (1991) *Nature* 352:624–628; Gram et al. (1992) *Proc. Natl. Acad. Sci. USA* 89:3576–3580; Garrard et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-LSO antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171, 496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225, 539; Jones et al. (1986) *Nature* 321:552–525; Verhoeyen et al. (1988) *Science* 239:1534; and Beidler et al. (1988) *J. Immunol.* 141:4053–4060.

An anti-LSO antibody (e.g., monoclonal antibody) can be used to isolate LSO by standard techniques, such as affinity chromatography or immunoprecipitation. An anti-LSO antibody can facilitate the purification of natural LSO from cells and of recombinantly produced LSO expressed in host cells. Moreover, an anti-LSO antibody can be used to detect LSO protein (e.g., in a cellular lysate or cell supernatant) in order to evaluate the abundance and pattern of expression of the LSO protein. Anti-LSO antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

III. Recombinant Expression Vectors and Host Cells

Another aspect of the invention pertains to vectors, preferably expression vectors, containing a nucleic acid encoding an LSO protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., LSO proteins, mutant forms of LSO proteins, fusion proteins, and the like).

The recombinant expression vectors of the invention can be designed for expression of LSO proteins in prokaryotic or eukaryotic cells. For example, LSO proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in LSO activity assays, (e.g., direct assays or competitive assays described in detail below), or to generate antibodies specific for LSO proteins, for example. In a preferred embodiment, an LSO fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS5174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the LSO expression vector is a yeast expression vector. Examples of vectors for expression in yeast *S. cerevisiae* include pYepSec1 (Baldari, et al., (1987) *EMBO J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (Invitrogen Corporation, San Diego, Calif.).

Alternatively, LSO proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to LSO mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which an LSO nucleic acid molecule of the invention is introduced, e.g., an LSO nucleic acid molecule within a recombinant expression vector or an LSO nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an LSO protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding an LSO protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) an LSO protein. Accordingly, the invention further provides methods for producing an LSO protein using the host cells of the invention. In one embodiment, the method comprises culturing the host cell of the invention (into which a recombinant expression vector encoding an LSO protein has been introduced) in a suitable medium such that an LSO protein is produced. In another embodiment, the method further comprises isolating an LSO protein from the medium or the host cell.

The host cells of the invention can also be used to produce non-human transgenic animals. For example, in one embodiment, a host cell of the invention is a fertilized oocyte or an embryonic stem cell into which LSO-coding sequences have been introduced. Such host cells can then be used to create non-human transgenic animals in which exogenous LSO sequences have been introduced into their genome or homologous recombinant animals in which endogenous LSO sequences have been altered. Such animals are useful for studying the function and/or activity of an LSO and for identifying and/or evaluating modulators of LSO activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous LSO gene has been altered by homologous recombination between the endogenous gene and an exogenous DNA molecule introduced into a cell of the animal, e.g., an embryonic cell of the animal, prior to development of the animal.

A transgenic animal of the invention can be created by introducing an LSO-encoding nucleic acid into the male pronuclei of a fertilized oocyte, e.g., by microinjection, retroviral infection, and allowing the oocyte to develop in a pseudopregnant female foster animal. The LSO cDNA sequence of SEQ ID NO:29 can be introduced as a transgene into the genome of a non-human animal. Alternatively, a nonhuman homologue of a human LSO gene, such as a mouse or rat LSO gene, can be used as a transgene. Alternatively, an LSO gene homologue, such as another LSO family member, can be isolated based on hybridization to the LSO cDNA sequences of SEQ ID NO:29 or 31 (described further in subsection I above) and used as a transgene. Intronic sequences and polyadenylation signals can also be included in the transgene to increase the efficiency of expression of the transgene. A tissue-specific regulatory sequence(s) can be operably linked to an LSO transgene to direct expression of an LSO protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of an LSO transgene in its genome and/or expression of LSO mRNA in tissues or cells of the animals. A transgenic founder animal can then be used to breed additional animals carrying the transgene. Moreover, transgenic animals carrying a transgene encoding an LSO protein can further be bred to other transgenic animals carrying other transgenes.

To create a homologous recombinant animal, a vector is prepared which contains at least a portion of an LSO gene into which a deletion, addition or substitution has been introduced to thereby alter, e.g., functionally disrupt, the LSO gene. The LSO gene can be a human gene (e.g., the cDNA of SEQ ID NO:31), but more preferably, is a non-human homologue of a human LSO gene (e.g., a cDNA isolated by stringent hybridization with the nucleotide sequence of SEQ ID NO:29). For example, a mouse LSO gene can be used to construct a homologous recombination nucleic acid molecule, e.g., a vector, suitable for altering an endogenous LSO gene in the mouse genome. In a preferred embodiment, the homologous recombination nucleic acid molecule is designed such that, upon homologous recombination, the endogenous LSO gene is functionally disrupted (i.e., no longer encodes a functional protein; also referred to as a "knock out" vector). Alternatively, the homologous recombination nucleic acid molecule can be designed such that, upon homologous recombination, the endogenous LSO gene is mutated or otherwise altered but still encodes functional protein (e.g., the upstream regulatory region can be altered to thereby alter the expression of the endogenous LSO protein). In the homologous recombination nucleic acid molecule, the altered portion of the LSO gene is flanked at its 5' and 3' ends by additional nucleic acid sequence of the LSO gene to allow for homologous recombination to occur between the exogenous LSO gene carried by the homologous recombination nucleic acid molecule and an endogenous LSO gene in a cell, e.g., an embryonic stem cell. The additional flanking LSO nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced LSO gene has homologously recombined with the endogenous LSO gene are selected (see e.g., Li, E. et al. (1992) *Cell* 69:915). The selected cells can then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of

*Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The LSO nucleic acid molecules, fragments of LSO proteins, and anti-LSO antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR® EL solubilizer (BASF, Florham Park, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of an LSO protein or an anti-LSO antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, an LSO protein of the invention has one or more of the following activities: 1) it modulates cellular growth, proliferation, or differentiation, 2) it modulates skin formation or elasticity 3) it modulates bone formation or structure; 4) it modulates muscle formation or elasticity; 5) it modulates cartilage formation or structure; and 6) it modulates tumor formation and, thus, may be used to 1) modulate cellular growth, proliferation, or differentiation, 2) modulate skin formation or elasticity 3) modulate bone formation or structure; 4) modulate muscle formation or elasticity; 5) modulate cartilage formation or structure; and 6) modulate tumor formation The isolated nucleic acid molecules of the invention can be used, for example, to express LSO protein (e.g., via a recombinant expression vector in a host cell in gene therapy applications), to detect LSO mRNA (e.g., in a biological sample) or a genetic alteration in an LSO gene, and to modulate LSO activity, as described further below. The LSO proteins can be used to treat disorders characterized by insufficient or excessive production of an LSO substrate or production of LSO inhibitors. In addition, the LSO proteins can be used to screen for naturally occurring LSO substrates, to screen for drugs or compounds which modulate LSO activity, as well as to treat disorders characterized by insufficient or excessive production of LSO protein or production of LSO protein forms which have decreased, aberrant or unwanted activity compared to LSO wild type protein (e.g., lysyl oxidase-associated disorders).

In a preferred embodiment, the LSO molecules of the invention are useful for catalyzing the covalent cross-linking of the molecular units of elastin or collagen. As such, these molecules may be employed in small or large-scale synthesis of either elastin or collagen, or in chemical processes that require the production of these compounds. Such processes are known in the art (see, e.g., Ullmann et al. (1999) Ullmann's Encyclopedia of Industrial Chemistry, $6^{th}$ ed. VCH: Weinheim; Gutcho (1983) Chemicals by Fermentation. Park ridge, N.J.: Noyes Data Corporation (ISBN 0818805086); Rehm et al. (eds.) (1993) Biotechnology, $2^{nd}$ ed. VCH: Weinheim; and Michal, G. (1999) Biochemical Pathways: An Atlas of Biochemistry and Molecular Biology. New York: John Wiley & Sons, and references contained therein.)

The isolated nucleic acid molecules of the invention can be used, for example, to express LSO protein (e.g., via a recombinant expression vector in a host cell in gene therapy applications), to detect LSO mRNA (e.g., in a biological sample) or a genetic alteration in an LSO gene, and to modulate LSO activity, as described further below. The LSO proteins can be used to treat disorders characterized by insufficient or excessive production of an LSO substrate or production of LSO inhibitors. In addition, the LSO proteins can be used to screen for naturally occurring LSO substrates, to screen for drugs or compounds which modulate LSO activity, as well as to treat disorders characterized by insufficient or excessive production of LSO protein or production of LSO protein forms which have decreased, aberrant or unwanted activity compared to LSO wild type protein (e.g., lysyl oxidase-associated disorders, such as muscular disorders (e.g., paralysis, muscle weakness (e.g., ataxia, myotonia, and myokymia), muscular dystrophy (e.g., Duchenne muscular dystrophy or myotonic dystrophy), spinal muscular atrophy, congenital myopathies, central core disease, rod myopathy, central nuclear myopathy, Lambert-Eaton syndrome, denervation, and infantile spinal muscular atrophy (Werdnig-Hoffman disease); cellular growth, differentiation, or migration disorders (e.g., cancer, e.g., carcinoma, sarcoma, or leukemia; tumor angiogenesis and metastasis; skeletal dysplasia; neuronal deficiencies resulting from impaired neural induction and patterning); disorders of bone formation and resorption (e.g., osteoporosis, osteochondrosis, and osteopetrosis); disorders of skin formation and elasticity (e.g., cutis laxa and Ehlers-Danlos type V syndrome); or disorders of cartilage formation and structure (e.g., chondromalacia and polychondritis). Moreover, the anti-LSO antibodies of the invention can be used to detect and isolate LSO proteins, regulate the bioavailability of LSO proteins, and modulate LSO activity.

A. Screening Assays:

The invention provides a method (also referred to herein as a "screening assay") for identifying modulators, i.e., candidate or test compounds or agents (e.g., peptides, peptidomimetics, small molecules or other drugs) which interact with or bind to LSO proteins, have a stimulatory or inhibitory effect on, for example, LSO expression or LSO activity, or have a stimulatory or inhibitory effect on, for example, the availability of LSO substrate.

In one embodiment, the invention provides assays for screening candidate or test compounds which are substrates of an LSO protein or polypeptide or biologically active portion thereof (e.g., subunits of elastin or collagen, or compounds which are structurally related thereto). In another embodiment, the invention provides assays for screening candidate or test compounds which bind to or modulate the activity of an LSO protein or polypeptide or biologically active portion thereof (e.g., copper ions, lysyl-tyrosine quinone, trihydroxyphenylalanine quinone, or other cofactors, or inhibitory molecules). The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds may be presented in solution (e.g., Houghten (1992) Biotechniques 13:412–421), or on beads (Lam (1991) Nature 354:82–84), chips (Fodor (1993) Nature 364:555–556), bacteria (Ladner U.S. Pat. No. 5,223,409), spores (Ladner U.S. Pat. No. '409), plasmids (Cull et al. (1992) Proc Natl Acad Sci USA 89:1865–1869) or on phage (Scott and Smith (1990) Science 249:386–390); (Devlin (1990) Science 249:404–406); (Cwirla et al. (1990) Proc. Natl. Acad. Sci. 87:6378–6382); (Felici (1991) J. Mol. Biol. 222:301–310); (Ladner supra.).

In one embodiment, an assay is a cell-based assay in which a cell which expresses an LSO protein or biologically active portion thereof is contacted with a test compound and the ability of the test compound to modulate LSO activity is determined. Determining the ability of the test compound to modulate LSO activity can be accomplished by monitoring, for example, the production of one or more specific LSO substrates or products in a cell which expresses LSO (see, e.g., Saada et al. (2000) Biochem Biophys. Res. Commun. 269: 382–386). The cell, for example, can be of mammalian origin. The ability of the test compound to modulate LSO binding to a substrate (e.g., subunits of elastin or collagen) or to bind to LSO can also be determined. Determining the ability of the test compound to modulate LSO binding to a substrate can be accomplished, for example, by coupling the LSO substrate or test compound with a radioisotope or fluorigenic label such that binding of the LSO substrate or test compound to LSO can be determined by detecting the labeled LSO substrate in a complex. Alternatively, LSO or a test compound could be coupled with a radioisotope or enzymatic label to monitor the ability of a test compound to modulate LSO binding to an LSO substrate in a complex. Determining the ability of the test compound to bind LSO can be accomplished, for example, by coupling the compound with a radioisotope or enzymatic or otherwise detectable label such that binding of the compound to LSO can be determined by detecting the labeled LSO compound in a complex. For example, compounds (e.g., LSO substrates) can be labeled with $^{125}I$, $^{35}S$, $^{14}C$, or $^{3}H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., an LSO substrate) to interact with LSO without the labeling of any of the interactants. For example, a microphysiometer can be used to detect the interaction of a compound with LSO without the labeling of either the compound or the LSO. McConnell, H. M. et al. (1992) Science 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and LSO.

In another embodiment, an assay is a cell-based assay comprising contacting a cell expressing an LSO target molecule (e.g., an LSO substrate) with a test compound and determining the ability of the test compound to modulate (e.g., stimulate or inhibit) the activity of the LSO target molecule. Determining the ability of the test compound to modulate the activity of an LSO target molecule can be accomplished, for example, by determining the ability of the LSO protein to bind to or interact with the LSO target molecule.

Determining the ability of the LSO protein, or a biologically active fragment thereof, to bind to or interact with an LSO target molecule (e.g., a substrate or inhibitor) can be accomplished by one of the methods described above for determining direct binding. In a preferred embodiment, determining the ability of the LSO protein to bind to or interact with an LSO target molecule can be accomplished by determining the activity or availability of the target molecule. For example, a target-regulated cellular activity, such as a biosynthetic pathway which requires the participation of the target molecule (e.g., elastin or collagen synthesis), may be monitored.

In yet another embodiment, an assay of the present invention is a cell-free assay in which an LSO protein or biologically active portion thereof is contacted with a test compound and the ability of the test compound to associate with, to bind to, or to serve as a substrate for the LSO protein or biologically active portion thereof is determined. Preferred biologically active portions of the LSO proteins to be used in assays of the present invention include fragments which participate in interactions with non-LSO molecules, e.g., fragments with high surface probability scores (see FIG. 54). Binding of the test compound to the LSO protein can be determined either directly or indirectly as described above. In a preferred embodiment, the assay includes contacting the LSO protein or biologically active portion thereof with a known compound which interacts with LSO to form an assay mixture, contacting the assay mixture with a test compound, and determining the ability of the test compound to interact with an LSO protein, wherein determining the ability of the test compound to interact with an LSO protein comprises determining the ability of the test compound to preferentially bind to or interact with LSO or a biologically active portion thereof as compared to the known compound.

In another embodiment, the assay is a cell-free assay in which an LSO protein or biologically active portion thereof is contacted with a test compound and the ability of the test compound to modulate (e.g., stimulate or inhibit) the activity of the LSO protein or biologically active portion thereof is determined. Determining the ability of the test compound to modulate the activity of an LSO protein can be accomplished, for example, by determining the ability of the LSO protein to bind to or associate with an LSO target molecule by one of the methods described above for determining direct binding. Determining the ability of the LSO protein to bind to an LSO target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIACORE™). Changes in the optical phenomenon of surface plasmon resonance (SPR) can be used as an indication of real-time reactions between biological molecules.

In an alternative embodiment, determining the ability of the test compound to modulate the activity of an LSO protein can be accomplished by determining the ability of the LSO protein to further modulate the activity of a downstream effector of an LSO target molecule. For example, the activity of the effector molecule on an appropriate target can be determined or the binding of the effector to an appropriate target can be determined as previously described.

In yet another embodiment, the cell-free assay involves contacting an LSO protein or biologically active portion thereof with a known compound which binds the LSO protein to form an assay mixture, contacting the assay mixture with a test compound, and determining the ability of the test compound to interact with the LSO protein, wherein determining the ability of the test compound to interact with the LSO protein comprises determining the ability of the LSO protein to preferentially bind to or catalyze the oxidation of peptidyl lysine in the target substrate (e.g., subunits of elastin or collagen).

In more than one embodiment of the above assay methods of the present invention, it may be desirable to immobilize either LSO or its target molecule to facilitate separation of complexed from uncomplexed forms of either of the interactants, as well as to accommodate automation of the assay. Binding of a test compound to an LSO protein, or interaction of an LSO protein with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows the LSO protein to be bound to a matrix. For example, glutathione-S-transferase/LSO fusion proteins can be adsorbed onto glutathione SEPHAROSE™ beads (Sigma Chemical, St. Louis, Mo.) or glutathione derivatized microtitre plates, which are then combined with the test compound or the test compound and either the non-adsorbed target protein or LSO protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of LSO binding or activity determined using standard techniques.

Other techniques for immobilizing proteins on matrices can also be used in the screening assays of the invention. For example, an LSO protein can be immobilized utilizing conjugation of biotin and streptavidin. Biotinylated LSO protein can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with LSO protein but which do not interfere with binding of the LSO protein to its target molecule can be derivatized to the wells of the plate, and unbound target or LSO protein trapped in the wells by antibody conjugation. Methods for detecting such complexes, in addition to those described above for the GST-immobilized complexes, include immunodetection of complexes using antibodies reactive with the LSO protein or target molecule, as well as enzyme-linked assays which rely on detecting an enzymatic activity associated with the LSO protein.

In another embodiment, modulators of LSO expression are identified in a method wherein a cell is contacted with a candidate compound and the expression of LSO mRNA or protein in the cell is determined. The level of expression of LSO mRNA or protein in the presence of the candidate compound is compared to the level of expression of LSO mRNA or protein in the absence of the candidate compound. The candidate compound can then be identified as a modulator of LSO expression based on this comparison. For example, when expression of LSO mRNA or protein is greater (statistically significantly greater) in the presence of the candidate compound than in its absence, the candidate compound is identified as a stimulator of LSO mRNA or protein expression. Alternatively, when expression of LSO mRNA or protein is less (statistically significantly less) in the presence of the candidate compound than in its absence, the candidate compound is identified as an inhibitor of LSO mRNA or protein expression. The level of LSO mRNA or protein expression in the cells can be determined by methods described herein for detecting LSO mRNA or protein.

In yet another aspect of the invention, the LSO proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with LSO ("LSO-binding proteins" or "LSO-6-bp") and are involved in LSO activity. Such LSO-binding proteins are also likely to be involved in the propagation of signals by the LSO proteins or LSO targets as, for example, downstream elements of an LSO-mediated signaling pathway. Alternatively, such LSO-binding proteins are likely to be LSO inhibitors.

The two-hybrid system is based on the modular nature of most transcription factors, which consist of separable DNA-binding and activation domains. Briefly, the assay utilizes two different DNA constructs. In one construct, the gene that codes for an LSO protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an LSO-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene that encodes the protein which interacts with the LSO protein.

In another aspect, the invention pertains to a combination of two or more of the assays described herein. For example, a modulating agent can be identified using a cell-based or a cell free assay, and the ability of the agent to modulate the activity of an LSO protein can be confirmed in vivo, e.g., in an animal such as an animal model for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein (e.g., an LSO modulating agent, an antisense LSO nucleic acid molecule, an LSO-specific antibody, an LSO substrate or an LSO-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the LSO nucleotide sequences, described herein, can be used to map the location of the LSO genes on a chromosome. The mapping of the LSO sequences to chromosomes is an important first step in correlating these sequences with genes associated with disease.

Briefly, LSO genes can be mapped to chromosomes by preparing PCR primers (preferably 15–25 bp in length) from the LSO nucleotide sequences. Computer analysis of the LSO sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the LSO sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220: 919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the LSO nucleotide sequences to design oligonucleotide primers, sublocalization can be achieved with panels of fragments from specific chromosomes. Other mapping strategies which can similarly be used to map an LSO sequence to its chromosome include in situ hybridization (described in Fan, Y. et al. (1990) *Proc. Natl. Acad. Sci. USA,* 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature,* 325:783–787.

Moreover, differences in the DNA sequences between individuals affected and unaffected with a disease associated with the LSO gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The LSO sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult.

The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the LSO nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The LSO nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:29 can comfortably provide positive individual identification with a panel of perhaps 10 to 1,000 primers which each yield a noncoding amplified sequence of 100 bases. If predicted coding sequences, such as that in SEQ ID NO:31, are used, a more appropriate number of primers for positive individual identification would be 500–2,000.

If a panel of reagents from LSO nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of LSO Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:29 are particularly appropriate for this use as greater numbers of polymorphisms occur in the noncoding regions, making it easier to differentiate individuals using this technique. Examples of polynucleotide reagents include the LSO nucleotide sequences or portions thereof, e.g., fragments derived from the noncoding regions of SEQ ID NO:29 having a length of at least 20 bases, preferably at least 30 bases.

The LSO nucleotide sequences described herein can further be used to provide polynucleotide reagents, e.g., labeled or labelable probes which can be used in, for example, an in situ hybridization technique, to identify a specific tissue, e.g., thymus or brain tissue. This can be very useful in cases where a forensic pathologist is presented with a tissue of unknown origin. Panels of such LSO probes can be used to identify tissue by species and/or by organ type.

In a similar fashion, these reagents, e.g., LSO primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining LSO protein and/or nucleic acid expression as well as LSO activity, in the context of a biological sample (e.g., blood, serum, cells, tissue) to thereby determine whether an individual is afflicted with a disease or disorder, or is at risk of developing a disorder, associated with aberrant or unwanted LSO expression or activity. The invention also provides for prognostic (or predictive) assays for determining whether an individual is at risk of developing a disorder associated with LSO protein, nucleic acid expression or activity. For example, mutations in an LSO gene can be assayed in a biological sample. Such assays can be used for prognostic or predictive purpose to thereby prophylactically treat an individual prior to the onset of a disorder characterized by or associated with LSO protein, nucleic acid expression or activity.

Another aspect of the invention pertains to monitoring the influence of agents (e.g., drugs, compounds) on the expression or activity of LSO in clinical trials.

These and other agents are described in further detail in the following sections.

1. Diagnostic Assays

An exemplary method for detecting the presence or absence of LSO protein or nucleic acid in a biological sample involves obtaining a biological sample from a test subject and contacting the biological sample with a compound or an agent capable of detecting LSO protein or nucleic acid (e.g., mRNA, or genomic DNA) that encodes LSO protein such that the presence of LSO protein or nucleic acid is detected in the biological sample. A preferred agent for detecting LSO mRNA or genomic DNA is a labeled nucleic acid probe capable of hybridizing to LSO mRNA or genomic DNA. The nucleic acid probe can be, for example, the LSO nucleic acid set forth in SEQ ID NO:29 or 31, or a portion thereof, such as an oligonucleotide of at least 15, 30, 50, 100, 250 or 500 nucleotides in length and sufficient to specifically hybridize under stringent conditions to LSO mRNA or genomic DNA. Other suitable probes for use in the diagnostic assays of the invention are described herein.

A preferred agent for detecting LSO protein is an antibody capable of binding to LSO protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect LSO mRNA, protein, or genomic DNA in a biological sample in vitro as well as in vivo. For example, in vitro techniques for detection of LSO mRNA include Northern hybridizations and in situ hybridizations. In vitro techniques for detection of LSO protein include enzyme linked immunosorbent assays (ELISAs), Western blots, immunoprecipitations and immunofluorescence. In vitro techniques for detection of LSO genomic DNA include Southern hybridizations. Furthermore, in vivo techniques for detection of LSO protein include introducing into a subject a labeled anti-LSO antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting LSO protein, mRNA, or genomic DNA, such that the presence of LSO protein, mRNA or genomic DNA is detected in the biological sample, and comparing the presence of LSO protein, mRNA or genomic DNA in the control sample with the presence of LSO protein, mRNA or genomic DNA in the test sample.

The invention also encompasses kits for detecting the presence of LSO in a biological sample. For example, the kit can comprise a labeled compound or agent capable of detecting LSO protein or mRNA in a biological sample; means for determining the amount of LSO in the sample; and means for comparing the amount of LSO in the sample with a standard. The compound or agent can be packaged in a suitable container. The kit can further comprise instructions for using the kit to detect LSO protein or nucleic acid.

2. Prognostic Assays

The diagnostic methods described herein can furthermore be utilized to identify subjects having or at risk of developing a disease or disorder associated with aberrant or unwanted LSO expression or activity. As used herein, the term "aberrant" includes an LSO expression or activity which deviates from the wild type LSO expression or activity. Aberrant expression or activity includes increased or decreased expression or activity, as well as expression or activity which does not follow the wild type developmental pattern of expression or the subcellular pattern of expression. For example, aberrant LSO expression or activity is intended to include the cases in which a mutation in the LSO gene causes the LSO gene to be under-expressed or over-expressed and situations in which such mutations result in a non-functional LSO protein or a protein which does not function in a wild-type fashion, e.g., a protein which does not interact with an LSO substrate, or one which interacts with a non-LSO substrate. As used herein, the term "unwanted" includes an unwanted phenomenon involved in a biological response such as cellular proliferation. For example, the term unwanted includes an LSO expression or activity which is undesirable in a subject.

The assays described herein, such as the preceding diagnostic assays or the following assays, can be utilized to identify a subject having or at risk of developing a disorder associated with a misregulation in LSO protein activity or nucleic acid expression, such as a cellular proliferation, growth, differentiation, or migration disorder, a muscular disorder, a disorder of bone formation or structure, a disorder of cartilage formation or structure, a disorder of skin elasticity or formation, or a tumor formation disorder. Alternatively, the prognostic assays can be utilized to identify a subject having or at risk for developing a disorder associated with a misregulation in LSO protein activity or nucleic acid expression, such as a cellular proliferation, growth, differentiation, or migration disorder, a muscular disorder, a disorder of bone formation or structure, a disorder of cartilage formation or structure, a disorder of skin elasticity or formation, or a tumor formation disorder. Thus, the present invention provides a method for identifying a disease or disorder associated with aberrant or unwanted LSO expression or activity in which a test sample is obtained from a subject and LSO protein or nucleic acid (e.g., mRNA or genomic DNA) is detected, wherein the presence of LSO protein or nucleic acid is diagnostic for a subject having or at risk of developing a disease or disorder associated with aberrant or unwanted LSO expression or activity. As used herein, a "test sample" refers to a biological sample obtained from a subject of interest. For example, a test sample can be a biological fluid (e.g., cerebrospinal fluid or serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted LSO expression or activity. For example, such methods can be used to determine whether a subject can be effectively treated with an agent for a cellular proliferation, growth, differentiation, or migration disorder, a muscular disorder, a disorder of bone formation or structure, a disorder of cartilage formation or structure, a disorder of skin elasticity or formation, or a tumor formation disorder. Thus, the present invention provides methods for determining whether a subject can be effectively treated with an agent for a disorder associated with aberrant or unwanted LSO expression or activity in which a test sample is obtained and LSO protein or nucleic acid expression or activity is detected (e.g., wherein the abundance of LSO protein or nucleic acid expression or activity is diagnostic for a subject that can be administered the agent to treat a disorder associated with aberrant or unwanted LSO expression or activity).

The methods of the invention can also be used to detect genetic alterations in an LSO gene, thereby determining if a subject with the altered gene is at risk for a disorder characterized by misregulation in LSO protein activity or nucleic acid expression, such as a cellular proliferation, growth, differentiation, or migration disorder, a muscular disorder, a disorder of bone formation or structure, a disorder of cartilage formation or structure, a disorder of skin elasticity or formation, or a tumor formation disorder. In preferred embodiments, the methods include detecting, in a sample of cells from the subject, the presence or absence of a genetic alteration characterized by at least one of an alteration affecting the integrity of a gene encoding an LSO-protein, or the mis-expression of the LSO gene. For example, such genetic alterations can be detected by ascertaining the existence of at least one of 1) a deletion of one or more nucleotides from an LSO gene; 2) an addition of one or more nucleotides to an LSO gene; 3) a substitution of one or more nucleotides of an LSO gene, 4) a chromosomal rearrangement of an LSO gene; 5) an alteration in the level of a messenger RNA transcript of an LSO gene, 6) aberrant modification of an LSO gene, such as of the methylation pattern of the genomic DNA, 7) the presence of a non-wild type splicing pattern of a messenger RNA transcript of an LSO gene, 8) a non-wild type level of an LSO-protein, 9) allelic loss of an LSO gene, and 10) inappropriate post-translational modification of an LSO-protein. As described herein, there are a large number of assays known in the art which can be used for detecting alterations in an LSO gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in an LSO gene (see Abravaya et al. (1995) *Nucleic Acids Res.* 23:675–682). This method can include the steps of collecting a sample of cells from a subject, isolating nucleic acid (e.g., genomic, mRNA or both) from the cells of the sample, contacting the nucleic acid sample with one or more primers which specifically hybridize to an LSO gene under conditions such that hybridization and amplification of the LSO gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an LSO gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in LSO can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in LSO can be identified in two-dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the LSO gene and detect mutations by comparing the sequence of the sample LSO with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the LSO gene include methods in which protection from cleavage agents is used to detect mismatched bases in RNA/RNA or RNA/DNA heteroduplexes (Myers et al. (1985) *Science* 230: 1242). In general, the art technique of "mismatch cleavage" starts by providing heteroduplexes of formed by hybridizing (labeled) RNA or DNA containing the wild-type LSO sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in LSO cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on an LSO sequence, e.g., a wild-type LSO sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in LSO genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125–144; and Hayashi (1992) *Genet. Anal. Tech. Appl.* 9:73–79). Single-stranded DNA fragments of sample and control LSO nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an LSO gene.

Furthermore, any cell type or tissue in which LSO is expressed may be utilized in the prognostic assays described herein.

3. Monitoring of Effects During Clinical Trials

Monitoring the influence of agents (e.g., drugs) on the expression or activity of an LSO protein (e.g., the modulation of cell proliferation and/or migration) can be applied not only in basic drug screening, but also in clinical trials. For example, the effectiveness of an agent determined by a screening assay as described herein to increase LSO gene expression, protein levels, or upregulate LSO activity, can be monitored in clinical trials of subjects exhibiting decreased LSO gene expression, protein levels, or downregulated LSO activity. Alternatively, the effectiveness of an agent determined by a screening assay to decrease LSO gene expression, protein levels, or downregulate LSO activity, can be monitored in clinical trials of subjects exhibiting increased LSO gene expression, protein levels, or upregulated LSO activity. In such clinical trials, the expression or activity of an LSO gene, and preferably, other genes that have been implicated in, for example, an LSO-associated disorder can be used as a "read out" or markers of the phenotype of a particular cell.

For example, and not by way of limitation, genes, including LSO, that are modulated in cells by treatment with an agent (e.g., compound, drug or small molecule) which modulates LSO activity (e.g., identified in a screening assay as described herein) can be identified. Thus, to study the effect of agents on LSO-associated disorders (e.g., disorders characterized by deregulated cell proliferation and/or migration), for example, in a clinical trial, cells can be isolated and RNA prepared and analyzed for the levels of expression of LSO and other genes implicated in the LSO-associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of LSO or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of an LSO protein, mRNA, or genomic DNA in the preadministration sample; (iii) obtaining one or more post-administration samples from the subject; (iv) detecting the level of expression or activity of the LSO protein, mRNA, or genomic DNA in the post-administration samples; (v) comparing the level of expression or activity of the LSO protein, mRNA, or genomic DNA in the pre-administration sample with the LSO protein, mRNA, or genomic DNA in the post administration sample or samples; and (vi) altering the administration of the agent to the subject accordingly. For example, increased administration of the agent may be desirable to increase the expression or activity of LSO to higher levels than detected, i.e., to increase the effectiveness of the agent. Alternatively, decreased administration of the agent may be desirable to decrease expression or activity of LSO to lower levels than detected, i.e. to decrease the effectiveness of the agent. According to such an embodiment, LSO expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder or having a disorder associated with aberrant or unwanted LSO expression or activity, e.g., a lysyl oxidase-associated disorder such as a cellular proliferation, growth, differentiation, or migration disorder, a muscular disorder, a disorder of bone formation or structure, a disorder of cartilage formation or structure, a disorder of skin elasticity or formation, or a tumor formation disorder. With regard to both prophylactic and therapeutic methods of treatment, such treatments may be specifically tailored or modified, based on knowledge obtained from the field of pharmacogenomics.

As used herein, "treatment" of a subject includes the application or administration of a therapeutic agent to a subject, or application or administration of a therapeutic agent to a cell or tissue from a subject, who has a diseases or disorder, has a symptom of a disease or disorder, or is at risk of (or susceptible to) a disease or disorder, with the purpose to cure, heal, alleviate, relieve, alter, remedy, ameliorate, improve, or affect the disease or disorder, the symptom of the disease or disorder, or the risk of (or susceptibility to) the disease or disorder. As used herein, a "therapeutic agent" includes, but is not limited to, small molecules, peptides, polypeptides, antibodies, ribozymes, and antisense oligonucleotides.

"Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the LSO molecules of the present invention or LSO modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted LSO expression or activity, by administering to the subject an LSO or an agent which modulates LSO expression or at least one LSO activity. Subjects at risk for a disease which is caused or contributed to by aberrant or unwanted LSO expression or activity can be identified by, for example, any or a combination of diagnostic or prognostic assays as described herein. Administration of a prophylactic agent can occur prior to the manifestation of symptoms characteristic of the LSO aberrancy, such that a disease or disorder is prevented or, alternatively, delayed in its progression. Depending on the type of LSO aberrancy, for example, an LSO, LSO agonist or LSO antagonist agent can be used for treating the subject. The appropriate agent can be determined based on screening assays described herein.

2. Therapeutic Methods

Another aspect of the invention pertains to methods of modulating LSO expression or activity for therapeutic purposes. Accordingly, in an exemplary embodiment, the modulatory method of the invention involves contacting a cell with an LSO or agent that modulates one or more of the activities of LSO protein activity associated with the cell. An agent that modulates LSO protein activity can be an agent as described herein, such as a nucleic acid or a protein, a naturally-occurring target molecule of an LSO protein (e.g., an LSO substrate), an LSO antibody, an LSO agonist or antagonist, a peptidomimetic of an LSO agonist or antagonist, or other small molecule. In one embodiment, the agent stimulates one or more LSO activities. Examples of such stimulatory agents include active LSO protein and a nucleic acid molecule encoding LSO that has been introduced into the cell. In another embodiment, the agent inhibits one or more LSO activities. Examples of such inhibitory agents include antisense LSO nucleic acid molecules, anti-LSO antibodies, and LSO inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of an LSO protein or nucleic acid molecule. In one embodiment, the method involves administering an agent (e.g., an agent identified by a screening assay described herein), or combination of agents that modulates (e.g., upregulates or downregulates) LSO expression or activity. In another embodiment, the method involves administering an LSO protein or nucleic acid molecule as therapy to compensate for reduced, aberrant, or unwanted LSO expression or activity.

Stimulation of LSO activity is desirable in situations in which LSO is abnormally downregulated and/or in which increased LSO activity is likely to have a beneficial effect. Likewise, inhibition of LSO activity is desirable in situations in which LSO is abnormally upregulated and/or in which decreased LSO activity is likely to have a beneficial effect.

3. Pharmacogenomics

The LSO molecules of the present invention, as well as agents, or modulators which have a stimulatory or inhibitory effect on LSO activity (e.g., LSO gene expression) as identified by a screening assay described herein can be administered to individuals to treat (prophylactically or therapeutically) LSO-associated disorders (e.g., proliferative disorders, muscular disorders, bone disorders, skin disorders, cartilage disorders, or tumor disorders) associated with aberrant or unwanted LSO activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an LSO molecule or LSO modulator as well as tailoring the dosage and/or therapeutic regimen of treatment with an LSO molecule or LSO modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11): 983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug target is known (e.g., an LSO protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., an LSO molecule or LSO modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with an LSO molecule or LSO modulator, such as a modulator identified by one of the exemplary screening assays described herein.

E. Electronic Apparatus Readable Media and Arrays

Electronic apparatus readable media comprising LSO sequence information is also provided. As used herein, "LSO sequence information" refers to any nucleotide and/or amino acid sequence information particular to the LSO molecules of the present invention, including but not limited to full-length nucleotide and/or amino acid sequences, partial nucleotide and/or amino acid sequences, polymorphic sequences including single nucleotide polymorphisms (SNPs), epitope sequences, and the like. Moreover, information "related to" said LSO sequence information includes detection of the presence or absence of a sequence (e.g., detection of expression of a sequence, fragment, polymorphism, etc.), determination of the level of a sequence (e.g., detection of a level of expression, for example, a quantitative detection), detection of a reactivity to a sequence (e.g., detection of protein expression and/or levels, for example, using a sequence-specific antibody), and the like. As used herein, "electronic apparatus readable media" refers to any suitable medium for storing, holding, or containing data or information that can be read and accessed directly by an electronic apparatus. Such media can include, but are not limited to: magnetic storage media, such as floppy discs, hard disc storage medium, and magnetic tape; optical storage media such as compact discs; electronic storage media such as RAM, ROM, EPROM, EEPROM and the like; and general hard disks and hybrids of these categories such as magnetic/optical storage media. The medium is adapted or configured for having recorded thereon LSO sequence information of the present invention.

As used herein, the term "electronic apparatus" is intended to include any suitable computing or processing apparatus or other device configured or adapted for storing data or information. Examples of electronic apparatus suitable for use with the present invention include stand-alone computing apparatuses; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the LSO sequence information.

A variety of software programs and formats can be used to store the sequence information on the electronic apparatus readable medium. For example, the sequence information can be represented in a word processing text file, formatted in commercially-available software such as WordPerfect and Microsoft Word, represented in the form of an ASCII file, or stored in a database application, such as DB2, Sybase, Oracle, or the like, as well as in other forms. Any number of dataprocessor structuring formats (e.g., text file or database) may be employed in order to obtain or create a medium having recorded thereon the LSO sequence information.

By providing LSO sequence information in readable form, one can routinely access the sequence information for a variety of purposes. For example, one skilled in the art can use the sequence information in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has a lysyl oxidase associated disorder or a pre-disposition to lysyl oxidase-associated disorder, wherein the method comprises the steps of determining LSO sequence information associated with the subject and based on the LSO sequence information, determining whether the subject has a lysyl oxidase-associated disorder or a pre-disposition to a lysyl oxidase-associated disorder, and/or recommending a particular treatment for the disease, disorder, or pre-disease condition.

The present invention further provides in an electronic system and/or in a network, a method for determining whether a subject has a lysyl oxidase-associated disorder or a pre-disposition to a lysyl oxidase-associated disorder wherein the method comprises the steps of determining LSO sequence information associated with the subject, and based on the LSO sequence information, determining whether the subject has a lysyl oxidase-associated disorder or a pre-disposition to a lysyl oxidase-associated disorder, and/or recommending a particular treatment for the disease, disorder or pre-disease condition. The method may further comprise the step of receiving phenotypic information associated with the subject and/or acquiring from a network phenotypic information associated with the subject.

The present invention also provides in a network, a method for determining whether a subject has a lysyl oxidase-associated disorder or a pre-disposition to a lysyl oxidase-associated disorder associated with LSO, said method comprising the steps of receiving LSO sequence information from the subject and/or information related thereto, receiving phenotypic information associated with the subject, acquiring information from the network corresponding to LSO and/or a lysyl oxidase-associated disorder, and based on one or more of the phenotypic information, the LSO information (e.g., sequence information and/or information related thereto), and the acquired information, determining whether the subject has a lysyl oxidase-associated disorder or a pre-disposition to a lysyl oxidase-associated disorder. The method may further comprise the step of recommending a particular treatment for the disease, disorder or pre-disease condition.

The present invention also provides a business method for determining whether a subject has lysyl oxidase-associated disorder or a pre-disposition to a lysyl oxidase-associated disorder, said method comprising the steps of receiving information related to LSO (e.g., sequence information and/or information related thereto), receiving phenotypic information associated with the subject, acquiring information from the network related to LSO and/or related to a lysyl oxidase-associated disorder, and based on one or more of the phenotypic information, the LSO information, and the acquired information, determining whether the subject has a lysyl oxidase-associated disorder or a pre-disposition to a lysyl oxidase-associated disorder. The method may further comprise the step of recommending a particular treatment for the disease, disorder or pre-disease condition.

The invention also includes an array comprising a LSO sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, one of which can be LSO. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a lysyl oxidase-associated disorder, progression of a lysyl oxidase-associated disorder, and processes associated with the lysyl oxidase-associated disorder.

The array is also useful for ascertaining the effect of the expression of a gene on the expression of other genes in the same cell or in different cells (e.g., ascertaining the effect of LSO expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including LSO) that could serve as a molecular target for diagnosis or therapeutic intervention.

This invention is further illustrated by the following examples which should not be construed as limiting. The contents of all references, patents and published patent applications cited throughout this application, as well as the Figures and Sequence Listing, are incorporated herein by reference.

EXAMPLES

Example 1

Identification and Characterization of Human LSO cDNA

In this example, the identification and characterization of the gene encoding human LSO (clone Fbh47765) is described.

Isolation of the LSO cDNA

The invention is based, at least in part, on the discovery of a human gene encoding a novel protein, referred to herein as human LSO. The entire sequence of human clone Fbh47765, was determined and found to contain an open reading frame termed human "LSO".

The nucleotide sequence encoding the human LSO protein is shown in FIGS. 53A–E and is set forth as SEQ ID NO:29. The protein encoded by this nucleic acid comprises about 756 amino acids and has the amino acid sequence shown in FIGS. 53A–E and set forth as SEQ ID NO:30. The coding region (open reading frame) of SEQ ID NO:29 is set forth as SEQ ID NO:31. Clone Fbh55158 comprises the coding region of human LSO.

Analysis of the Human LSO Molecules

The amino acid sequence of human LSO was analyzed using the program PSORT (see PSORT maintained by the Human Genome Center at the Institute of Medical Science in the University of Tokyo, Japan (psort.nibb.ac.jp) to predict the localization of the protein within the cell. This program assesses the presence of different targeting and localization amino acid sequences within the query sequence. The results of the analyses show the likelihood of the human LSO (SEQ ID NO:30) being localized, for example, extracellularly, in the mitochondrion, in vacuoles, and in the endoplasmic reticulum.

An analysis of the amino acid sequence of human LSO using the Signal P program (Henrik, et al. (1997) *Protein Engineering* 10:1–6), identified the presence of a signal peptide from amino acids 1–24.

A search was also performed against the Prosite database resulting in the identification of two N-glycosylation sites in the amino acid sequence of human LSO (SEQ ID NO:30) at about residues 198–201 and 629–632.

A search of the amino acid sequence of human LSO was also performed against the HMM database. This search resulted in the identification of a "lysyl oxidase domain" in the amino acid sequence of human LSO (SEQ ID NO:30) at about residues 533–736 (score 513.1). This search further resulted in the identification of four "scavenger receptor cysteine-rich domains" in the amino acid sequence of human LSO (SEQ ID NO:30) at about residues 37–133 (score=98.1), 169–287 (score=30.4), 314–411 (score=115.8), and 424–529 (score=46.3).

A search of the amino acid sequence of human LSO was also performed against the ProDom database, resulting in the identification of a "lysyl oxidase protein-lysine precursor signal 6-oxidase oxireductase copper glycoprotein homolog" domain at amino acid residues 533–731 of human LSO.

Tissue Distribution of LSO mRNA

This example describes the tissue distribution of human LSO mRNA, as determined by Northern analysis, by Polymerase Chain Reaction (PCR) on cDNA libraries using oligonucleotide primers based on the human LSO sequence, or by in situ analysis.

Northern blot hybridizations with the various RNA samples are performed under standard conditions and washed under stringent conditions, i.e., 0.2×SSC at 65° C. The DNA probe is radioactively labeled with $^{32}$P-dCTP using the Prime-It kit (Stratagene, La Jolla, Calif.) according to the instructions of the supplier. Filters containing human mRNA (MultiTissue Northern I and MultiTissue Northern II from Clontech, Palo Alto, Calif.) are probed in ExpressHyb hybridization solution (Clontech) and washed at high stringency according to manufacturer's recommendations.

Human LSO expression in normal tissues, e.g., human tissues, is assessed by PCR using the Taqman® system (PE Applied Biosystems) according to the manufacturer's instructions.

For in situ analysis, various tissues, e.g. tissues obtained from brain, are first frozen on dry ice. Ten-micrometer-thick sections of the tissues are postfixed with 4% formaldehyde in DEPC treated 1× phosphate-buffered saline at room temperature for 10 minutes before being rinsed twice in DEPC 1× phosphate-buffered saline and once in 0.1 M triethanolamine-HCl (pH 8.0). Following incubation in 0.25% acetic anhydride-0.1 M triethanolamine-HCl for 10 minutes, sections are rinsed in DEPC 2×SSC (1×SSC is 0.15M NaCl plus 0.015M sodium citrate). Tissue is then dehydrated through a series of ethanol washes, incubated in 100% chloroform for 5 minutes, and then rinsed in 100% ethanol for 1 minute and 95% ethanol for 1 minute and allowed to air dry.

Hybridizations are performed with $^{35}$S-radiolabeled ($5×10^7$ cpm/ml) cRNA probes. Probes are incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1× Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides are washed with 2×SSC. Sections are then sequentially incubated at 37° C. in TNE (a solution containing 10 mM Tris-HCl (pH 7.6), 500 mM NaCl, and 1 mM EDTA), for 10 minutes, in TNE with 10 µg of RNase A per ml for 30 minutes, and finally in TNE for 10 minutes. Slides are then rinsed with 2×SSC at room temperature, washed with 2×SSC at 50° C. for 1 hour, washed with 0.2×SSC at 55° C. for 1 hour, and 0.2×SSC at 60° C. for 1 hour. Sections are then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

Example 2

Expression of Recombinant Human LSO Protein in Bacterial Cells

In this example, human LSO is expressed as a recombinant glutathione-S-transferase (GST) fusion polypeptide in E. coli and the fusion polypeptide is isolated and characterized. Specifically, human LSO is fused to GST and this fusion polypeptide is expressed in E. coli, e.g., strain PEB199. Expression of the GST-LSO fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant Human LSO Protein in COS Cells

To express the human LSO gene in COS cells, the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire human LSO protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the human LSO DNA sequence is amplified by PCR using two primers. The 5' primer contains the restriction site of interest followed by approximately twenty nucleotides of the human LSO coding sequence starting from the initiation codon; the 3' end sequence contains complementary sequences to the other restriction site of interest, a translation stop codon, the HA tag or FLAG tag and the last 20 nucleotides of the human LSO coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the human LSO gene is inserted in the correct orientation. The ligation mixture is transformed into E. coli cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the human LSO-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989. The expression of the LSO polypeptide is detected by radiolabeling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA-specific, a FLAG-specific, or a human LSO-specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA-specific, a FLAG-specific, or a human LSO-specific monoclonal antibody. Precipitated polypeptides are then analyzed by SDS-PAGE.

Alternatively, DNA containing the human LSO coding sequence is cloned directly into the polylinker of the pcDNA/Amp vector using the appropriate restriction sites. The resulting plasmid is transfected into COS cells in the manner described above, and the expression of the human LSO polypeptide is detected by radiolabeling and immunoprecipitation using a human LSO-specific monoclonal antibody.

VIII. 62088, a Novel Human Nucleoside Phosphatase Family Member and uses Thereof

BACKGROUND OF THE INVENTION

The family of nucleoside phosphatases includes proteins from a wide array of organisms ranging from peas to toxiplasma, yeast, and mammals (Handa et al. (1996) *Biochem. Biophys. Res. Commun.* 218:916–923; Vasconcelos et al. (1996) *J. Biol. Chem.* 271:22139–22145). Members of this family share several very conserved domains and are membrane-bound. These proteins are highly glycosylated and exist as homooligomers (e.g., dimers, trimers, and tetramers). Nucleoside phosphatase members include nucleotide triphosphatases (NTPases, e.g., ATPases, GTPases, and UTPases) and nucleotide diphosphatases (NDPases, e.g., ADPases, GDPases, and UDPases) which function to hydrolyze ATP to ADP, ADP to AMP, GTP to GDP, GDP to GMP, UTP to UDP, and/or UDP to UMP. Enzymes included in this family have a broad tissue distribution and have been identified in heart, placenta, lung, liver, skeletal muscle, thymus, kidney, pancreas, testis, ovary, prostate, colon, and brain tissues (Zimmermann (1999) *Trends Pharm. Sci.* 20:231–236).

Nucleotides, such as ATP, ADP, GTP, GDP, UTP, and UDP, act as signaling substances in nearly all tissues (Zimmermann, supra). For example, extracellular ATP is though to induce cell permeabilization and cell necrosis or apoptosis, triggering of accumulation of second messengers, and effect cell proliferation (Redegeld (1999) *Trends Pharm. Sci.* 20:453–459). GTP is thought to induce cell motility and invasion as well as signaling via G proteins (Keely et al. (1998) *Trends Cell Biol.* 8:101–107; Vale (1999) *Trends Biochem. Sci.* 24:M38–M42). UTP has been shown to be involved with extracellular signaling, mobilization of intracellular Ca$^{2+}$, and initiation of cytokine production (Lazarowski et al. (1997) *J. Biol. Chem.* 272:24348–24354; Marriott et al. (1999) *Cell Immunol.* 195:147–156). Nucleoside phosphatases play an important role in signal transduction via the hydrolysis and subsequent termination of signaling mediated by extracellular nucleotides. In addition to modifying cell signaling, nucleoside phosphatases have also been implicated in protecting the cell from invading organisms by destroying incoming DNA or RNA, inhibiting platelet-mediated thrombotic diatheses, neurotransmission, blood pressure regulation, and slowing the progression of vascular injury (Gao et al. (1999) *J. Biol. Chem.* 274: 21450–21456; Zimmerman, supra).

Several nucleoside phosphatases have been identified to date, including CD39L1 (rat, mouse, human, and chicken) (Zimmerman, supra), CD39L3 (human and chicken) (Zimmerman, supra), CD39 (human, rat, mouse, and bovine) (Birks, et al. (1994) *J. Immunol.* 153:3574–3583; Zimmerman, supra), *S. cerevisiae* GDA1 (Abeijon et al. (1993) *J. Cell Biol.* 122:307–323), T. Gondii NTP1 (Asai et al. (1995) *J. Biol. Chem.* 270:11391–11397), and pea NTPA (Hsieh et al. (1996) *Plant Mol. Biol.* 30:135–147).

SUMMARY OF THE INVENTION

The present invention is based, at least in part, on the discovery of novel nucleoside phosphatase family members, referred to herein as nucleoside phosphatase family member-1 or "NPM-1" nucleic acid and polypeptide molecules. The NPM-1 nucleic acid and polypeptide molecules of the present invention are useful as modulating agents in regulating a variety of cellular and/or biological processes, e.g., cell signaling, neurotransmission and neuromodulation, nociception, tumor inhibition, endocrine gland secretion control, modulation of platelet aggregation, Cl$^-$ transport, renal function, molecular motor function, cytoskeletal organization, and vesicle transport. Accordingly, in one aspect, this invention provides isolated nucleic acid molecules encoding NPM-1 polypeptides or biologically active portions thereof, as well as nucleic acid fragments suitable as primers or hybridization probes for the detection of NPM-1-encoding nucleic acids.

In one embodiment, the invention features an isolated nucleic acid molecule that includes the nucleotide sequence set forth in SEQ ID NO:33 or 35. In another embodiment, the invention features an isolated nucleic acid molecule that encodes a polypeptide including the amino acid sequence set forth in SEQ ID NO:34.

In still other embodiments, the invention features isolated nucleic acid molecules including nucleotide sequences that are substantially identical (e.g., 60% identical) to the nucleotide sequence set forth as SEQ ID NO:33 or 35. The invention further features isolated nucleic acid molecules including at least 30 contiguous nucleotides of the nucleotide sequence set forth as SEQ ID NO:33 or 35. In another embodiment, the invention features isolated nucleic acid molecules which encode a polypeptide including an amino acid sequence that is substantially identical (e.g., 60% identical) to the amino acid sequence set forth as SEQ ID NO:34. The present invention also features nucleic acid molecules which encode allelic variants of the polypeptide having the amino acid sequence set forth as SEQ ID NO:34. In addition to isolated nucleic acid molecules encoding full-length polypeptides, the present invention also features nucleic acid molecules which encode fragments, for example, biologically active or antigenic fragments, of the full-length polypeptides of the present invention (e.g., fragments including at least 10 contiguous amino acid residues of the amino acid sequence of SEQ ID NO:34). In still other embodiments, the invention features nucleic acid molecules that are complementary to, antisense to, or hybridize under stringent conditions to the isolated nucleic acid molecules described herein.

In a related aspect, the invention provides vectors including the isolated nucleic acid molecules described herein (e.g., NPM-1-encoding nucleic acid molecules). Such vectors can optionally include nucleotide sequences encoding heterologous polypeptides. Also featured are host cells including such vectors (e.g., host cells including vectors suitable for producing NPM-1 nucleic acid molecules and polypeptides).

In another aspect, the invention features isolated NPM-1 polypeptides and/or biologically active or antigenic fragments thereof. Exemplary embodiments feature a polypeptide including the amino acid sequence set forth as SEQ ID NO:34, a polypeptide including an amino acid sequence at least 60% identical to the amino acid sequence set forth as SEQ ID NO:34, a polypeptide encoded by a nucleic acid molecule including a nucleotide sequence at least 60% identical to the nucleotide sequence set forth as SEQ ID NO:33 or 35. Also featured are fragments of the full-length polypeptides described herein (e.g., fragments including at least 10 contiguous amino acid residues of the sequence set forth as SEQ ID NO:34) as well as allelic variants of the polypeptide having the amino acid sequence set forth as SEQ ID NO:34.

The NPM-1 polypeptides and/or biologically active or antigenic fragments thereof, are useful, for example, as reagents or targets in assays applicable to treatment and/or diagnosis of NPM-1 mediated or related disorders. In one embodiment, an NPM-1 polypeptide or fragment thereof, has an NPM-1 activity. In another embodiment, an NPM-1 polypeptide or fragment thereof, has a transmembrane domain, a nucleoside phosphatase family domain, and optionally, has an NPM-1 activity. In a related aspect, the invention features antibodies (e.g., antibodies which specifically bind to any one of the polypeptides described herein) as well as fusion polypeptides including all or a fragment of a polypeptide described herein.

The present invention further features methods for detecting NPM-1 polypeptides and/or NPM-1 nucleic acid molecules, such methods featuring, for example, a probe, primer or antibody described herein. Also featured are kits for the detection of NPM-1 polypeptides and/or NPM-1 nucleic acid molecules. In a related aspect, the invention features methods for identifying compounds which bind to and/or modulate the activity of an NPM-1 polypeptide or NPM-1 nucleic acid molecule described herein. Further featured are methods for modulating an NPM-1 activity.

Other features and advantages of the invention will be apparent from the following detailed description and claims.

DETAILED DESCRIPTION OF THE INVENTION

The present invention is based, at least in part, on the discovery of novel molecules, referred to herein as "nucleoside phosphatase family member-1" or "NPM-1" nucleic acid and polypeptide molecules, which are novel members of the nucleoside phosphatase family. These novel molecules are capable of, for example, modulating a nucleoside phosphatase-mediated activity (e.g., diphosphate and triphosphate hydrolase-mediated activity) in a cell, e.g., a heart, placenta, lung, liver, skeletal muscle, thymus, kidney, pancreas, testis, ovary, prostate, colon, or brain cell.

As used herein, a "nucleoside phosphatase family member" includes a protein or polypeptide which is involved in triphosphate and/or diphosphate hydrolysis and regulation of, e.g., ATP, ADP, GTP, GDP, UTP, and/or UDP. As used herein, the term "nucleoside hydrolysis" includes the dephosphorylation of ATP, ADP, GTP, GDP, UTP, and/or UDP, resulting in the formation of ADP, AMP, GDP, GMP, UDP, and/or UMP or other forms of nucleoside. Nucleoside hydrolysis is mediated by nucleoside phosphatases, e.g., NTPases and NDPases, e.g., ATPases, ADPases, GTPases, GDPases, UTPases, and UDPases. As used herein, the term "regulation of ATP, ADP, GTP, GDP, UTP, and/or UDP levels" includes cellular mechanisms involved in regulating and influencing the levels, e.g., intracellular and/or extracellular levels, of ATP, ADP, GTP, GDP, UTP, and/or UDP. Such mechanisms include the hydrolysis of ATP to ADP, ADP to AMP, GTP to GDP, GDP to GMP, UTP to UDP, and/or UDP to UMP (i.e., nucleoside hydrolysis) in response to biological cues, e.g., by a nucleoside phosphatase. The maintenance of ATP, ADP, GTP, GDP, UTP, and/or UDP levels is particularly important for a cell's signaling needs. Thus, the NPM-1 molecules, by participating in ATP, ADP, GTP, GDP, UTP, and/or UDP hydrolysis and regulation of ADP, AMP, GDP, GMP, UDP, and/or UMP levels, may modulate ATP, ADP, GTP, GDP, UTP, and/or UDP hydrolysis and ADP, AMP, GDP, GMP, UDP, and/or UMP levels and provide novel diagnostic targets and therapeutic agents to control ATP, ADP, GTP, GDP, UTP, and/or UDP hydrolysis-related disorders. As the NPM-1 molecules of the present invention are nucleoside phosphatases modulating nucleoside-phosphatase mediated activities (e.g., diphosphate and triphosphate hydrolase activities), they may also be useful for developing novel diagnostic and therapeutic agents for nucleoside-phosphatase associated disorders (e.g., diphosphate and triphosphate hydrolase associated disorders).

The term "family" when referring to the polypeptide and nucleic acid molecules of the invention is intended to mean two or more polypeptides or nucleic acid molecules having a common structural domain or motif and having sufficient amino acid or nucleotide sequence homology as defined herein. Such family members can be naturally or non-naturally occurring and can be from either the same or different species. For example, a family can contain a first polypeptide of human origin, as well as other, distinct polypeptides of human origin or alternatively, can contain homologues of non-human origin, e.g., mouse or monkey polypeptides. Members of a family may also have common functional characteristics.

For example, the family of NPM-1 polypeptides comprise at least one "transmembrane domain" and preferably two transmembrane domains. As used herein, the term "transmembrane domain" includes an amino acid sequence of about 20–45 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, alanines, valines, phenylalanines, prolines or methionines. Transmembrane domains are described in, for example, Zagotta W. N. et al., (1996) *Annual Rev. Neurosci.* 19: 235–263, the contents of which are incorporated herein by reference. Amino acid residues 29–47 and 552–570 of the NPM-1 polypeptide comprise transmembrane domains (see FIGS. 56 and 58). Accordingly, NPM-1 polypeptides having at least 50–60% homology, preferably about 60–70%, more preferably about 70–80%, or about 80–90% homology with a transmembrane domain of human NPM-1 are within the scope of the invention.

To identify the presence of a transmembrane domain in an NPM-1 protein, and make the determination that a protein of interest has a particular profile, the amino acid sequence of the protein may be subjected to MEMSAT analysis. A MEMSAT analysis resulting in the identification of two transmembrane domains in the amino acid sequence of human NPM-1 (SEQ ID NO:34) at about residues 29–47 and 552–570 are set forth in FIG. 58.

In another embodiment, an NPM-1 molecule of the present invention is identified based on the presence of at least one "nucleoside phosphatase family domain", also referred to interchangeably as an "NTPase domain". As used herein, the term "nucleoside phosphatase family domain" or "NTPase domain" includes a protein domain having an amino acid sequence of about 350–550 amino acid residues and has a bit score of at least 150 when compared against a nucleoside phosphatase Hidden Markov Model (HMM), e.g., a GDA1_CD39 (nucleoside phosphatase) family HMM having PFAM Accession No. PF0150. Preferably, a "nucleoside phosphatase family domain" of "NTPase domain" has an amino acid sequence of about 400–500, 425–475, or more preferably about 461 amino acid residues, and a bit score of at least 200, 250, 300, 320, or more preferably 324.9. In a preferred embodiment, a "nucleoside phosphatase family domain" or "NTPase domain" includes a protein which has an amino acid sequence of about 390–510 amino acid residues, and serves to hydrolyze diphosphate or triphosphate nucleotides, and optionally is an ectoenzymatic domain (e.g., acts extracellularly), and lies between amino- and carboxy-terminal cytoplasmic domains. To identify the presence of a nucleoside phosphatase family domain in an NPM-1 protein, and make the determination that a protein of interest has a particular profile, the amino acid sequence of the protein may be searched against a database of known protein domains (e.g., the HMM database). The nucleoside phosphatase family domain (HMM) has been assigned the PFAM Accession PF01150 (found at a Pfam website, genome.wustl.edu/Pfam). A search was performed against the HMM database resulting in the identification of a nucleoside phosphatase family domain in the amino acid sequence of human NPM-1 (SEQ ID NO:34) at about residues 75–536 of SEQ ID NO:34. The results of the search are set forth in FIGS. 57A–D.

A description of the Pfam database can be found in Sonhammer et al. (1997) *Proteins* 28:405–420 and a detailed description of HMMs can be found, for example, in Gribskov et al. (1990) *Meth. Enzymol.* 183:146–159; Gribskov et al. (1987) *Proc. Natl. Acad. Sci. USA* 84:4355–4358; Krogh et al. (1994) *J. Mol. Biol.* 235:1501–1531; and Stultz et al. (1993) *Protein Sci.* 2:305–314, the contents of which are incorporated herein by reference.

In a preferred embodiment, the NPM-1 molecules of the invention include at least one, preferably two, transmembrane domain(s) and/or at least one nucleoside phosphatase family domain.

Isolated polypeptides of the present invention, preferably NPM-1 polypeptides, have an amino acid sequence sufficiently identical to the amino acid sequence of SEQ ID NO:34 or are encoded by a nucleotide sequence sufficiently identical to SEQ ID NO:33 or 35. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains having at least 50%, 55%, 60%, 65%, 70%, 75%, 80%, 85%, 85%, 90%, 95%, 96%, 97%, 98%, 99% or more homology or identity across the amino acid sequences of the domains and contain at least one and preferably two structural domains or motifs, are defined herein as sufficiently identical. Furthermore, amino acid or nucleotide sequences which share at least 50%, 55%, 60%, 65%, 70%, 75%, 80%, 85%, 85%, 90%, 95%, 96%, 97%, 98%, 99% or more homology or identity and share a common functional activity are defined herein as sufficiently identical.

In a preferred embodiment, an NPM-1 polypeptide includes at least one or more of the following domains: a transmembrane domain, a nucleoside phosphatase family domain, and has an amino acid sequence at least about 50%, 55%, 60%, 65%, 70%, 75%, 80%, 85%, 85%, 90%, 95%, 96%, 97%, 98%, 99% or more homologous or identical to the amino acid sequence of SEQ ID NO:34. In yet another preferred embodiment, an NPM-1 polypeptide includes at least one or more of the following domains: a transmembrane domain and/or a nucleoside phosphatase family domain, and is encoded by a nucleic acid molecule having a nucleotide sequence which hybridizes under stringent hybridization conditions to a complement of a nucleic acid molecule comprising the nucleotide sequence of SEQ ID NO:33 or 35. In another preferred embodiment, an NPM-1 polypeptide includes at least one or more of the following domains: a transmembrane domain, a nucleoside phosphatase family domain, and has an NPM-1 activity.

As used interchangeably herein, an "NPM-1 activity", "biological activity of NPM-1" or "functional activity of NPM-1", refers to an activity exerted by an NPM-1 polypeptide or nucleic acid molecule on an NPM-1 responsive cell or tissue, or on an NPM-1 polypeptide substrate, as determined in vivo, or in vitro, according to standard techniques.

In one embodiment, an NPM-1 activity is a direct activity, such as an association with an NPM-1-target molecule. As used herein, a "target molecule" or "binding partner" is a molecule with which an NPM-1 polypeptide binds or interacts in nature, such that NPM-1-mediated function is achieved. An NPM-1 target molecule can be a non-NPM-1 molecule, for example, a non-NPM-1 polypeptide or polypeptide. In an exemplary embodiment, an NPM-1 target molecule is an NPM-1 ligand, e.g., a nucleoside phosphatase family domain ligand e.g., nucleoside triphosphates and/or nucleoside diphosphates. For example, an NPM-1 target molecule can have one or more of the following activities: (1) interact with nucleotide triphosphates (e.g., ATP, GTP, UTP, and the like) (2) interact with nucleoside diphosphates (e.g., ADP, GDP, UDP, and the like), (3) hydrolysis of nucleoside triphosphates (e.g., ATP, GTP, UTP, and the like), (4) hydrolysis of nucleoside diphosphates (e.g., ADP, GDP, UDP, and the like), and (5) interact with and/or hydrolysis of thiamine pyrophosphate. Alternatively, an NPM-1 activity is an indirect activity, such as a cellular signaling activity mediated by interaction of the NPM-1 polypeptide with an NPM-1 ligand. The biological activities of NPM-1 are described herein. For example, the NPM-1 polypeptides of the present invention can have one or more of the following activities: (1) hydrolyze nucleoside triphosphates, (2) hydrolyze nucleoside diphosphates, (3) modulate signal transduction, (4) modulate neurotransmission and neuromodulation (e.g., in the central and peripheral nervous systems), (5) modulate tumor inhibition, (6) modulate endocrine gland secretion, (7) modulate platelet aggregation, (8) modulate $Cl^-$ transport (e.g., in airway epithelia), (9) modulate renal function, (10) modulate molecular motor function, (11) modulate cytoskeletal organization, (12) modulate vesicle transport, (13) participate in nociception, (14) modulate cellular growth and/or proliferation, and (15) modulate angiogenesis.

Accordingly, another embodiment of the invention features isolated NPM-1 polypeptides and polypeptides having an NPM-1 activity. Preferred polypeptides are NPM-1 polypeptides having at least one or more of the following domains: a transmembrane domain, a nucleoside phosphatase family domain, and, preferably, an NPM-1 activity.

Additional preferred polypeptides have one or more of the following domains: a transmembrane domain and/or a nucleoside phosphatase family domain, and are, preferably, encoded by a nucleic acid molecule having a nucleotide sequence which hybridizes under stringent hybridization conditions to a complement of a nucleic acid molecule comprising the nucleotide sequence of SEQ ID NO:33 or 35.

The nucleotide sequence of the isolated human NPM-1 cDNA and the predicted amino acid sequence of the human NPM-1 polypeptide are shown in FIGS. 55A–E and in SEQ ID NOs:33 and 34, respectively.

The human NPM-1 gene, which is approximately 3296 nucleotides in length, encodes a polypeptide which is approximately 604 amino acid residues in length.

Various aspects of the invention are described in further detail in the following subsections:

I. Isolated Nucleic Acid Molecules

One aspect of the invention pertains to isolated nucleic acid molecules that encode NPM-1 polypeptides or biologically active portions thereof, as well as nucleic acid fragments sufficient for use as hybridization probes to identify NPM-1-encoding nucleic acid molecules (e.g., NPM-1 mRNA) and fragments for use as PCR primers for the amplification or mutation of NPM-1 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regard to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated NPM-1 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:33 or 35, or a portion thereof, can be isolated using standard molecular biology techniques and the sequence information provided herein. Using all or a portion of the nucleic acid sequence of SEQ ID NO:33 or 35, as a hybridization probe, NPM-1 nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:33 or 35, can be isolated by the polymerase chain reaction (PCR) using synthetic oligonucleotide primers designed based upon the sequence of SEQ ID NO:33 or 35.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to NPM-1 nucleotide sequences can be prepared by standard synthetic techniques, e.g., using an automated DNA synthesizer.

In one embodiment, an isolated nucleic acid molecule of the invention comprises the nucleotide sequence shown in SEQ ID NO:33. The sequence of SEQ ID NO:33 corresponds to the human NPM-1 cDNA. This cDNA comprises sequences encoding the human NPM-1 polypeptide (i.e., "the coding region", from nucleotides 217–2031) as well as 5' untranslated sequences (nucleotides 1–216) and 3' untranslated sequences (nucleotides 2032–3296). Alternatively, the nucleic acid molecule can comprise only the coding region of SEQ ID NO:33 (e.g., nucleotides 217–2031, corresponding to SEQ ID NO:35). Accordingly, in another embodiment, the isolated nucleic acid molecule comprises SEQ ID NO:35 and nucleotides 1–216 and 2032–3296 of SEQ ID NO:33. In yet another embodiment, the nucleic acid molecule consists of the nucleotide sequence set forth as SEQ ID NO:33 or 35.

In still another embodiment, an isolated nucleic acid molecule of the invention comprises a nucleic acid molecule which is a complement of the nucleotide sequence shown in SEQ ID NO:33 or 35, or a portion of any of these nucleotide sequences. A nucleic acid molecule which is complementary to the nucleotide sequence shown in SEQ ID NO:33 or 35, is one which is sufficiently complementary to the nucleotide sequence shown in SEQ ID NO:33 or 35, such that it can hybridize to the nucleotide sequence shown in SEQ ID NO:33 or 35, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 90%, 95%, 96%, 97%, 98%, 99% or more identical to the nucleotide sequence shown in SEQ ID NO:33 or 35 (e.g., to the entire length of the nucleotide sequence), or to a portion or complement of any of these nucleotide sequences. In one embodiment, a nucleic acid molecule of the present invention comprises a nucleotide sequence which is at least (or no greater than) 50–100, 100–250, 250–500, 500–750, 750–1000, 1000–1250, 1250–1500, 1500–1750, 1750–2000, 2000–2250, 2250–2500, 2500–2750, 2750–3000, 3000–3296 or more nucleotides in length and hybridizes under stringent hybridization conditions to a complement of a nucleic acid molecule of SEQ ID NO:33 or 35.

Moreover, the nucleic acid molecule of the invention can comprise only a portion of the nucleic acid sequence of SEQ ID NO:33 or 35, for example, a fragment which can be used as a probe or primer or a fragment encoding a portion of an NPM-1 polypeptide, e.g., a biologically active portion of an NPM-1 polypeptide. The nucleotide sequence determined from the cloning of the NPM-1 gene allows for the generation of probes and primers designed for use in identifying and/or cloning other NPM-1 family members, as well as NPM-1 homologues from other species. The probe/primer typically comprises substantially purified oligonucleotide. The probe/primer (e.g., oligonucleotide) typically comprises a region of nucleotide sequence that hybridizes under stringent conditions to at least about 12 or 15, preferably about 20 or 25, more preferably about 30, 35, 40, 45, 50, 55, 60, 65, 75, 80, 85, 90, 95, or 100 or more consecutive nucleotides of a sense sequence of SEQ ID NO:33 or 35, of an anti-sense sequence of SEQ ID NO:33 or 35, or of a naturally occurring allelic variant or mutant of SEQ ID NO:33 or 35.

Exemplary probes or primers are at least (or no greater than) 12 or 15, 20 or 25, 30, 35, 40, 45, 50, 55, 60, 65, 70, 75 or more nucleotides in length and/or comprise consecutive nucleotides of an isolated nucleic acid molecule described herein. Also included within the scope of the present invention are probes or primers comprising contiguous or consecutive nucleotides of an isolated nucleic acid molecule described herein, but for the difference of 1, 2, 3, 4, 5, 6, 7, 8, 9 or 10 bases within the probe or primer sequence. Probes based on the NPM-1 nucleotide sequences can be used to detect (e.g., specifically detect) transcripts or genomic sequences encoding the same or homologous polypeptides. In preferred embodiments, the probe further comprises a label group attached thereto, e.g., the label group can be a radioisotope, a fluorescent compound, an enzyme, or an enzyme co-factor. In another embodiment a set of primers is provided, e.g., primers suitable for use in a PCR, which can be used to amplify a selected region of an NPM-1 sequence, e.g., a domain, region, site or other sequence described herein. The primers should be at least 5, 10, or 50 base pairs in length and less than 100, or less than 200, base pairs in length. The primers should be identical, or differs by no greater than 1, 2, 3, 4, 5, 6, 7, 8, 9 or 10 bases when compared to a sequence disclosed herein or to the sequence of a naturally occurring variant. Such probes can be used as a part of a diagnostic test kit for identifying cells or tissue which misexpress an NPM-1 polypeptide, such as by measuring a level of an NPM-1-encoding nucleic acid in a sample of cells from a subject e.g., detecting NPM-1 mRNA levels or determining whether a genomic NPM-1 gene has been mutated or deleted.

A nucleic acid fragment encoding a "biologically active portion of an NPM-1 polypeptide" can be prepared by isolating a portion of the nucleotide sequence of SEQ ID NO:33 or 35, which encodes a polypeptide having an NPM-1 biological activity (the biological activities of the NPM-1 polypeptides are described herein), expressing the encoded portion of the NPM-1 polypeptide (e.g., by recombinant expression in vitro) and assessing the activity of the encoded portion of the NPM-1 polypeptide. In an exemplary embodiment, the nucleic acid molecule is at least 50–100, 100–250, 250–500, 500–750, 750–1000, 1000–1250, 1250–1500, 1500–1750, 1750–2000, 2000–2250, 2250–2500, 2500–2750, 2750–3000, 3000–3296 or more nucleotides in length and encodes a polypeptide having an NPM-1 activity (as described herein).

The invention further encompasses nucleic acid molecules that differ from the nucleotide sequence shown in SEQ ID NO:33 or 35. Such differences can be due to due to degeneracy of the genetic code, thus resulting in a nucleic acid which encodes the same NPM-1 polypeptides as those encoded by the nucleotide sequence shown in SEQ ID NO:33 or 35. In another embodiment, an isolated nucleic acid molecule of the invention has a nucleotide sequence encoding a polypeptide having an amino acid sequence which differs by at least 1, but no greater than 5, 10, 20, 50 or 100 amino acid residues from the amino acid sequence shown in SEQ ID NO:34. In yet another embodiment, the nucleic acid molecule encodes the amino acid sequence of human NPM-1. If an alignment is needed for this comparison, the sequences should be aligned for maximum homology.

Nucleic acid variants can be naturally occurring, such as allelic variants (same locus), homologues (different locus), and orthologues (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

Allelic variants result, for example, from DNA sequence polymorphisms within a population (e.g., the human population) that lead to changes in the amino acid sequences of the NPM-1 polypeptides. Such genetic polymorphisms in the NPM-1 genes may exist among individuals within a population due to natural allelic variation. As used herein, the terms "gene" and "recombinant gene" refer to nucleic acid molecules which include an open reading frame encoding an NPM-1 polypeptide, preferably a mammalian NPM-1 polypeptide, and can further include non-coding regulatory sequences, and introns.

Accordingly, in one embodiment, the invention features isolated nucleic acid molecules which encode a naturally occurring allelic variant of a polypeptide comprising the amino acid sequence of SEQ ID NO:34, wherein the nucleic acid molecule hybridizes to a complement of a nucleic acid molecule comprising SEQ ID NO:33 or 35, for example, under stringent hybridization conditions.

Allelic variants of human NPM-1 include both functional and non-functional NPM-1 polypeptides. Functional allelic variants are naturally occurring amino acid sequence variants of the human NPM-1 polypeptide that maintain the ability to bind an NPM-1 ligand or substrate and/or modulate hydrolysis and/or signal transduction. Functional allelic variants will typically contain only conservative substitution of one or more amino acids of SEQ ID NO:34, or substitution, deletion or insertion of non-critical residues in non-critical regions of the polypeptide.

Non-functional allelic variants are naturally occurring amino acid sequence variants of the human NPM-1 polypeptide that do not have the ability to mediate nucleoside hydrolysis. Non-functional allelic variants will typically contain a non-conservative substitution, a deletion, or insertion or premature truncation of the amino acid sequence of SEQ ID NO:34, or a substitution, insertion or deletion in critical residues or critical regions.

The present invention further provides non-human orthologues (e.g., non-human orthologues of the human NPM-1 polypeptide). Orthologues of the human NPM-1 polypeptides are polypeptides that are isolated from non-human organisms and possess the same NPM-1 ligand binding and/or modulation of membrane excitation mechanisms of the human NPM-1 polypeptide. Orthologues of the human NPM-1 polypeptide can readily be identified as comprising an amino acid sequence that is substantially identical to SEQ ID NO:34.

Moreover, nucleic acid molecules encoding other NPM-1 family members and, thus, which have a nucleotide sequence which differs from the NPM-1 sequences of SEQ ID NO:33 or 35, are intended to be within the scope of the invention. For example, another NPM-1 cDNA can be identified based on the nucleotide sequence of human NPM-1. Moreover, nucleic acid molecules encoding NPM-1 polypeptides from different species, and which, thus, have a nucleotide sequence which differs from the NPM-1 sequences of SEQ ID NO:33 or 35, are intended to be within the scope of the invention. For example, a mouse NPM-1 cDNA can be identified based on the nucleotide sequence of a human NPM-1.

Nucleic acid molecules corresponding to natural allelic variants and homologues of the NPM-1 cDNAs of the invention can be isolated based on their homology to the NPM-1 nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the NPM-1 cDNAs of the invention can further be isolated by mapping to the same chromosome or locus as the NPM-1 gene.

Orthologues, homologues and allelic variants can be identified using methods known in the art (e.g., by hybridization to an isolated nucleic acid molecule of the present invention, for example, under stringent hybridization conditions). In one embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:33 or 35. In other embodiment, the nucleic acid is at least 100, 100–150, 150–200, 200–250, 250–300, 300–350, 350–400, 400–450, 450–500, 500–550, 550–600, 600–650, 650–700, 700–750, 750–800, 800–850, 850–900, 900–950, 950–1000, 1000–1050, 1050–1070, 1070–1100, 1100–1150, 1150–1200, 1200–1250, 1250–1300, 1300–1350, 1350–1400, 1400–1450, 1450–1500, 1500–1550, 1550–1600, 1600–1650, 1650–1700, 1700–1750, 1750–1800, 1800–2000, 2000–2250, 2250–2500, 2500–2750, 2750–3000, 3000–3296 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A preferred, non-limiting example of stringent hybridization conditions includes hybridization in 4×sodium chloride/sodium citrate (SSC), at about 65–70° C. (or hybridization in 4×SSC plus 50% formamide at about 42–50° C.) followed by one or more washes in 1×SSC, at about 65–70° C. A preferred, non-limiting example of highly stringent hybridization conditions includes hybridization in 1×SSC, at about 65–70° C. (or hybridization in 1×SSC plus 50% formamide at about 42–50° C.) followed by one or more washes in 0.3×SSC, at about 65–70° C. A preferred, non-limiting example of reduced stringency hybridization conditions includes hybridization in 4×SSC, at about 50–60° C. (or alternatively hybridization in 6×SSC plus 50% formamide at about 40–45° C.) followed by one or more washes in 2×SSC, at about 50–60° C. Ranges intermediate to the above-recited values, e.g., at 65–70° C. or at 42–50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m(°C.) = 2(\# \text{ of A+T bases}) + 4(\# \text{ of G+C bases})$. For hybrids between 18 and 49 base pairs in length, $T_m(°C.) = 81.5 + 16.6(\log_{10}[Na^+]) + 0.41(\% \text{ G+C}) - (600/N)$, where N is the number of bases in the hybrid, and $[Na^+]$ is the concentration of sodium ions in the hybridization buffer ($[Na^+]$ for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25–0.5M $NaH_2PO_4$, 7% SDS at about 65° C., followed by one or more washes at 0.02M $NaH_2PO_4$, 1% SDS at 65° C., see e.g., Church and Gilbert (1984) *Proc. Natl. Acad. Sci. USA* 81:1991–1995, (or, alternatively, 0.2×SSC, 1% SDS).

Preferably, an isolated nucleic acid molecule of the invention that hybridizes under stringent conditions to the sequence of SEQ ID NO:33 or 35 and corresponds to a naturally-occurring nucleic acid molecule. As used herein, a "naturally-occurring" nucleic acid molecule refers to an RNA or DNA molecule having a nucleotide sequence that occurs in nature (e.g., encodes a natural polypeptide).

In addition to naturally-occurring allelic variants of the NPM-1 sequences that may exist in the population, the skilled artisan will further appreciate that changes can be introduced by mutation into the nucleotide sequences of SEQ ID NO:33 or 35, thereby leading to changes in the amino acid sequence of the encoded NPM-1 polypeptides, without altering the functional ability of the NPM-1 polypeptides. For example, nucleotide substitutions leading to amino acid substitutions at "non-essential" amino acid residues can be made in the sequence of SEQ ID NO:33 or 35. A "non-essential" amino acid residue is a residue that can be altered from the wild-type sequence of NPM-1 (e.g., the sequence of SEQ ID NO:34) without altering the biological activity, whereas an "essential" amino acid residue is required for biological activity. For example, amino acid residues that are conserved among the NPM-1 polypeptides of the present invention, e.g., those present in a nucleoside phosphatase family domain, are predicted to be particularly unamenable to alteration. Furthermore, additional amino acid residues that are conserved between the NPM-1 polypeptides of the present invention and other members of the NPM-1 family are not likely to be amenable to alteration.

Accordingly, another aspect of the invention pertains to nucleic acid molecules encoding NPM-1 polypeptides that contain changes in amino acid residues that are not essential for activity. Such NPM-1 polypeptides differ in amino acid sequence from SEQ ID NO:34, yet retain biological activity. In one embodiment, the isolated nucleic acid molecule comprises a nucleotide sequence encoding a polypeptide, wherein the polypeptide comprises an amino acid sequence at least about 50%, 55%, 60%, 65%, 70%, 75%, 80%, 85%, 90%, 95%, 96%, 97%, 98%, 99% or more identical to SEQ ID NO:34 (e.g., to the entire length of SEQ ID NO:34).

An isolated nucleic acid molecule encoding an NPM-1 polypeptide identical to the polypeptide of SEQ ID NO:34, can be created by introducing one or more nucleotide substitutions, additions or deletions into the nucleotide sequence of SEQ ID NO:33 or 35, such that one or more amino acid substitutions, additions or deletions are introduced into the encoded polypeptide. Mutations can be introduced into SEQ ID NO:33 or 35, by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in an NPM-1 polypeptide is preferably replaced with another amino acid residue from the same side chain family. Alternatively, in another embodiment, mutations can be introduced randomly along all or part of an NPM-1 coding sequence, such as by saturation mutagenesis, and the resultant mutants can be screened for NPM-1 biological activity to identify mutants that retain activity. Following mutagenesis of SEQ ID NO:33 or 35, the encoded polypeptide can be expressed recombinantly and the activity of the polypeptide can be determined.

In a preferred embodiment, a mutant NPM-1 polypeptide can be assayed for the ability to (1) hydrolyze nucleoside triphosphates, (2) hydrolyze nucleoside diphosphates, (3) modulate signal transduction, (4) modulate neurotransmission and neuromodulation (e.g., in the central and peripheral nervous systems), (5) modulate tumor inhibition, (6) modulate endocrine gland secretion, (7) modulate platelet aggregation, (8) modulate Cl⁻ transport (e.g., in airway epithelia), (9) modulate renal function, (10) modulate molecular motor function, (11) modulate cytoskeletal organization, (12) modulate vesicle transport, (13) participate in nociception, (14) modulate cellular growth and/or proliferation, and (15) modulate angiogenesis.

In addition to the nucleic acid molecules encoding NPM-1 polypeptides described above, another aspect of the invention pertains to isolated nucleic acid molecules which are antisense thereto. In an exemplary embodiment, the invention provides an isolated nucleic acid molecule which is antisense to an NPM-1 nucleic acid molecule (e.g., is antisense to the coding strand of an NPM-1 nucleic acid molecule). An "antisense" nucleic acid comprises a nucleotide sequence which is complementary to a "sense" nucleic acid encoding a polypeptide, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire NPM-1 coding strand, or to only a portion thereof. In one embodiment, an antisense nucleic acid molecule is antisense to a "coding region" of the coding strand of a nucleotide sequence encoding NPM-1. The term "coding region" refers to the region of the nucleotide sequence comprising codons which are translated into amino acid residues (e.g., the coding region of human NPM-1 corresponds to SEQ ID NO:35). In another embodiment, the antisense nucleic acid molecule is antisense to a "noncoding region" of the coding strand of a nucleotide sequence encoding NPM-1. The term "noncoding region" refers to 5' and 3' sequences which flank the coding region that are not translated into amino acids (i.e., also referred to as 5' and 3' untranslated regions).

Given the coding strand sequences encoding NPM-1 disclosed herein (e.g., SEQ ID NO:35), antisense nucleic acids of the invention can be designed according to the rules of Watson and Crick base pairing. The antisense nucleic acid molecule can be complementary to the entire coding region of NPM-1 mRNA, but more preferably is an oligonucleotide which is antisense to only a portion of the coding or noncoding region of NPM-1 mRNA. For example, the antisense oligonucleotide can be complementary to the region surrounding the translation start site of NPM-1 mRNA (e.g., between the −10 and +10 regions of the start site of a gene nucleotide sequence). An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an NPM-1 polypeptide to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff and Gerlach (1988) *Nature* 334:585–591)) can be used to catalytically cleave NPM-1 mRNA transcripts to thereby inhibit translation of NPM-1 mRNA. A ribozyme having specificity for an NPM-1-encoding nucleic acid can be designed based upon the nucleotide sequence of an NPM-1 cDNA disclosed herein (i.e., SEQ ID NO:33 or 35. For example, a derivative of a Tetrahymena L-19 IVS RNA can be constructed in which the nucleotide sequence of the active site is complementary to the nucleotide sequence to be cleaved in an NPM-1-encoding mRNA. See, e.g., Cech et al. U.S. Pat. No. 4,987,071; and Cech et al. U.S. Pat. No. 5,116,742. Alternatively, NPM-1 mRNA can be used to select a catalytic RNA having a specific ribonuclease activity from a pool of RNA molecules. See, e.g., Bartel, D. and Szostak, J. W. (1993) *Science* 261:1411–1418.

Alternatively, NPM-1 gene expression can be inhibited by targeting nucleotide sequences complementary to the regulatory region of the NPM-1 (e.g., the NPM-1 promoter and/or enhancers) to form triple helical structures that prevent transcription of the NPM-1 gene in target cells. See generally, Helene, C. (1991) *Anticancer Drug Des.* 6(6): 569–84; Helene, C. et al. (1992) *Ann. N.Y. Acad. Sci.* 660:27–36; and Maher, L. J. (1992) *Bioassays* 14(12): 807–15.

In yet another embodiment, the NPM-1 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. *Proc. Natl. Acad. Sci.* 93: 14670–675.

PNAs of NPM-1 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of NPM-1 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of NPM-1 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of NPM-1 nucleic acid molecules can be generated which may combine the advantageous properties of PNA and DNA. Such chimeras allow DNA recognition enzymes, (e.g., RNase H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al.

(1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

Alternatively, the expression characteristics of an endogenous NPM-1 gene within a cell line or microorganism may be modified by inserting a heterologous DNA regulatory element into the genome of a stable cell line or cloned microorganism such that the inserted regulatory element is operatively linked with the endogenous NPM-1 gene. For example, an endogenous NPM-1 gene which is normally "transcriptionally silent", i.e., an NPM-1 gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous NPM-1 gene may be activated by insertion of a promiscuous regulatory element that works across cell types.

A heterologous regulatory element may be inserted into a stable cell line or cloned microorganism, such that it is operatively linked with an endogenous NPM-1 gene, using techniques, such as targeted homologous recombination, which are well known to those of skill in the art, and described, e.g., in Chappel, U.S. Pat. No. 5,272,071; PCT publication No. WO 91/06667, published May 16, 1991.

II. Isolated NPM-1 Polypeptides and Anti-NPM-1 Antibodies

One aspect of the invention pertains to isolated NPM-1 or recombinant polypeptides, and biologically active portions thereof, as well as polypeptide fragments suitable for use as immunogens to raise anti-NPM-1 antibodies. In one embodiment, native NPM-1 polypeptides can be isolated from cells or tissue sources by an appropriate purification scheme using standard protein purification techniques. In another embodiment, NPM-1 polypeptides are produced by recombinant DNA techniques. Alternative to recombinant expression, an NPM-1 polypeptide or polypeptide can be synthesized chemically using standard peptide synthesis techniques.

An "isolated" or "purified" polypeptide or biologically active portion thereof is substantially free of cellular material or other contaminating proteins from the cell or tissue source from which the NPM-1 polypeptide is derived, or substantially free from chemical precursors or other chemicals when chemically synthesized. The language "substantially free of cellular material" includes preparations of NPM-1 polypeptide in which the polypeptide is separated from cellular components of the cells from which it is isolated or recombinantly produced. In one embodiment, the language "substantially free of cellular material" includes preparations of NPM-1 polypeptide having less than about 30% (by dry weight) of non-NPM-1 polypeptide (also referred to herein as a "contaminating protein"), more preferably less than about 20% of non-NPM-1 polypeptide, still more preferably less than about 10% of non-NPM-1 polypeptide, and most preferably less than about 5% non-NPM-1 polypeptide. When the NPM-1 polypeptide or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of NPM-1 polypeptide in which the polypeptide is separated from chemical precursors or other chemicals which are involved in the synthesis of the polypeptide. In one embodiment, the language "substantially free of chemical precursors or other chemicals" includes preparations of NPM-1 polypeptide having less than about 30% (by dry weight) of chemical precursors or non-NPM-1 chemicals, more preferably less than about 20% chemical precursors or non-NPM-1 chemicals, still more preferably less than about 10% chemical precursors or non-NPM-1 chemicals, and most preferably less than about 5% chemical precursors or non-NPM-1 chemicals.

As used herein, a "biologically active portion" of an NPM-1 polypeptide includes a fragment of an NPM-1 polypeptide which participates in an interaction between an NPM-1 molecule and a non-NPM-1 molecule. Biologically active portions of an NPM-1 polypeptide include peptides comprising amino acid sequences sufficiently identical to or derived from the amino acid sequence of the NPM-1 polypeptide, e.g., the amino acid sequence shown in SEQ ID NO:34, which include less amino acids than the fill length NPM-1 polypeptides, and exhibit at least one activity of an NPM-1 polypeptide. Typically, biologically active portions comprise a domain or motif with at least one activity of the NPM-1 polypeptide, e.g., modulating triphosphate and/or diphosphate hydrolysis. A biologically active portion of an NPM-1 polypeptide can be a polypeptide which is, for example, 25, 30, 35, 40, 45, 50, 75, 100, 125, 150, 175, 200, 225, 250, 275, 300, 325, 350, 375, 400, 425, 450, 475, 500, 525, 550, 575, or 600 or more amino acids in length. Biologically active portions of an NPM-1 polypeptide can be used as targets for developing agents which modulate an NPM-1 mediated activity, e.g., triphosphate and/or diphosphate hydrolysis.

In one embodiment, a biologically active portion of an NPM-1 polypeptide comprises at least one nucleoside phosphatase family domain. It is to be understood that a preferred biologically active portion of an NPM-1 polypeptide of the present invention comprises at least one or more of the following domains: a transmembrane domain and/or a nucleoside phosphatase family domain. Moreover, other biologically active portions, in which other regions of the polypeptide are deleted, can be prepared by recombinant techniques and evaluated for one or more of the functional activities of a native NPM-1 polypeptide.

Another aspect of the invention features fragments of the polypeptide having the amino acid sequence of SEQ ID NO:34, for example, for use as immunogens. In one embodiment, a fragment comprises at least 5 amino acids (e.g., contiguous or consecutive amino acids) of the amino acid sequence of SEQ ID NO:34. In another embodiment, a fragment comprises at least 10, 15, 20, 25, 30, 35, 40, 45, 50, 100, 200, 300, 400, 500, 600 or more amino acids (e.g., contiguous or consecutive amino acids) of the amino acid sequence of SEQ ID NO:34.

In a preferred embodiment, an NPM-1 polypeptide has an amino acid sequence shown in SEQ ID NO:34. In other embodiments, the NPM-1 polypeptide is substantially identical to SEQ ID NO:34, and retains the functional activity of the polypeptide of SEQ ID NO:34, yet differs in amino acid sequence due to natural allelic variation or mutagenesis, as described in detail in subsection I above. In another embodiment, the NPM-1 polypeptide is a polypeptide which comprises an amino acid sequence at least about 50%, 55%, 60%, 65%, 70%, 75%, 80%, 85%, 90%, 95%, 96%, 97%, 98%, 99% or more identical to SEQ ID NO:34.

In another embodiment, the invention features an NPM-1 polypeptide which is encoded by a nucleic acid molecule consisting of a nucleotide sequence at least about 50%, 55%, 60%, 65%, 70%, 75%, 80%, 85%, 90%, 95%, 96%, 97%, 98%, 99% or more identical to a nucleotide sequence of SEQ ID NO:33 or 35, or a complement thereof. This invention further features an NPM-1 polypeptide which is encoded by a nucleic acid molecule consisting of a nucleotide sequence which hybridizes under stringent hybridization conditions to a complement of a nucleic acid molecule comprising the nucleotide sequence of SEQ ID NO:33 or 35, or a complement thereof.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the NPM-1 amino acid sequence of SEQ ID NO:34 having 604 amino acid residues, at least 181, preferably at least 241, more preferably at least 302, more preferably at least 362, even more preferably at least 423, and even more preferably at least 483 or 543 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at the bioinformatics page of the website maintained by Accelrys, Inc., San Diego, Calif. USA), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A preferred, non-limiting example of parameters to be used in conjunction with the GAP program include a Blosum 62 scoring matrix with a gap penalty of 12, a gap extend penalty of 4, and a frameshift gap penalty of 5.

In another embodiment, the percent identity between two amino acid or nucleotide sequences is determined using the algorithm of E. Meyers and W. Miller (*Comput. Appl. Biosci.*, 4:11–17 (1988)) which has been incorporated into the ALIGN program (version 2.0 or version 2.0U), using a PAM120 weight residue table, a gap length penalty of 12 and a gap penalty of 4.

The nucleic acid and polypeptide sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to NPM-1 nucleic acid molecules of the invention. BLAST protein searches can be performed with the XBLAST program, score=100, wordlength=3, and a Blosum62 matrix to obtain amino acid sequences homologous to NPM-1 polypeptide molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used (accessible at the website maintained by National Center for Biotechnology Information, Bethesda, Md. USA.

The invention also provides NPM-1 chimeric or fusion proteins. As used herein, an NPM-1 "chimeric protein" or "fusion protein" comprises an NPM-1 polypeptide operatively linked to a non-NPM-1 polypeptide. An "NPM-1 polypeptide" refers to a polypeptide having an amino acid sequence corresponding to NPM-1, whereas a "non-NPM-1 polypeptide" refers to a polypeptide having an amino acid sequence corresponding to a polypeptide which is not substantially homologous to the NPM-1 polypeptide, e.g., a polypeptide which is different from the NPM-1 polypeptide and which is derived from the same or a different organism. Within an NPM-1 fusion protein the NPM-1 polypeptide can correspond to all or a portion of an NPM-1 polypeptide. In a preferred embodiment, an NPM-1 fusion protein comprises at least one biologically active portion of an NPM-1 polypeptide. In another preferred embodiment, an NPM-1 fusion protein comprises at least two biologically active portions of an NPM-1 polypeptide. Within the fusion protein, the term "operatively linked" is intended to indicate that the NPM-1 polypeptide and the non-NPM-1 polypeptide are fused in-frame to each other. The non-NPM-1 polypeptide can be fused to the N-terminus or C-terminus of the NPM-1 polypeptide.

For example, in one embodiment, the fusion protein is a GST-NPM-1 fusion protein in which the NPM-1 sequences are fused to the C-terminus of the GST sequences. Such fusion proteins can facilitate the purification of recombinant NPM-1. In another embodiment, the fusion protein is an NPM-1 polypeptide containing a heterologous signal sequence at its N-terminus. In certain host cells (e.g., mammalian host cells), expression and/or secretion of NPM-1 can be increased through the use of a heterologous signal sequence.

The NPM-1 fusion proteins of the invention can be incorporated into pharmaceutical compositions and administered to a subject in vivo. The NPM-1 fusion proteins can be used to affect the bioavailability of an NPM-1 substrate. Use of NPM-1 fusion proteins may be useful therapeutically for the treatment of disorders caused by, for example, (i)

aberrant modification or mutation of a gene encoding an NPM-1 polypeptide; (ii) mis-regulation of the NPM-1 gene; and (iii) aberrant post-translational modification of an NPM-1 polypeptide.

Moreover, the NPM-1-fusion proteins of the invention can be used as immunogens to produce anti-NPM-1 antibodies in a subject, to purify NPM-1 ligands and in screening assays to identify molecules which inhibit the interaction of NPM-1 with an NPM-1 substrate.

Preferably, an NPM-1 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a GST polypeptide). An NPM-1-encoding nucleic acid can be cloned into such an expression vector such that the fusion moiety is linked in-frame to the NPM-1 polypeptide.

The present invention also pertains to variants of the NPM-1 polypeptides which function as either NPM-1 agonists (mimetics) or as NPM-1 antagonists. Variants of the NPM-1 polypeptides can be generated by mutagenesis, e.g., discrete point mutation or truncation of an NPM-1 polypeptide. An agonist of the NPM-1 polypeptides can retain substantially the same, or a subset, of the biological activities of the naturally occurring form of an NPM-1 polypeptide. An antagonist of an NPM-1 polypeptide can inhibit one or more of the activities of the naturally occurring form of the NPM-1 polypeptide by, for example, competitively modulating an NPM-1-mediated activity of an NPM-1 polypeptide. Thus, specific biological effects can be elicited by treatment with a variant of limited function. In one embodiment, treatment of a subject with a variant having a subset of the biological activities of the naturally occurring form of the polypeptide has fewer side effects in a subject relative to treatment with the naturally occurring form of the NPM-1 polypeptide.

In one embodiment, variants of an NPM-1 polypeptide which function as either NPM-1 agonists (mimetics) or as NPM-1 antagonists can be identified by screening combinatorial libraries of mutants, e.g., truncation mutants, of an NPM-1 polypeptide for NPM-1 polypeptide agonist or antagonist activity. In one embodiment, a variegated library of NPM-1 variants is generated by combinatorial mutagenesis at the nucleic acid level and is encoded by a variegated gene library. A variegated library of NPM-1 variants can be produced by, for example, enzymatically ligating a mixture of synthetic oligonucleotides into gene sequences such that a degenerate set of potential NPM-1 sequences is expressible as individual polypeptides, or alternatively, as a set of larger fusion proteins (e.g., for phage display) containing the set of NPM-1 sequences therein. There are a variety of methods which can be used to produce libraries of potential NPM-1 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential NPM-1 sequences. Methods for synthesizing degenerate oligonucleotides are known in the art (see, e.g., Narang, S. A. (1983) Tetrahedron 39:3; Itakura et al. (1984) Annu. Rev. Biochem. 53:323; Itakura et al. (1984) Science 198:1056; Ike et al. (1983) Nucleic Acid Res. 11:477.

In addition, libraries of fragments of an NPM-1 polypeptide coding sequence can be used to generate a variegated population of NPM-1 fragments for screening and subsequent selection of variants of an NPM-1 polypeptide. In one embodiment, a library of coding sequence fragments can be generated by treating a double stranded PCR fragment of an NPM-1 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the NPM-1 polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of NPM-1 polypeptides. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify NPM-1 variants (Arkin and Youvan (1992) Proc. Natl. Acad. Sci. USA 89:7811–7815; Delagrave et al. (1993) Protein Engineering 6(3):327–331).

In one embodiment, cell based assays can be exploited to analyze a variegated NPM-1 library. For example, a library of expression vectors can be transfected into a cell line, e.g., an endothelial cell line, which ordinarily responds to NPM-1 in a particular NPM-1 substrate-dependent manner. The transfected cells are then contacted with NPM-1 and the effect of expression of the mutant on signaling by the NPM-1 substrate can be detected, e.g., by monitoring extracellular nucleoside phosphate concentrations, e.g., ATP, ADP, AMP, GTP, GDP, GMP, UTP, and/or UDP concentrations. Plasmid DNA can then be recovered from the cells which score for inhibition, or alternatively, potentiation of signaling by the NPM-1 substrate, and the individual clones further characterized.

An isolated NPM-1 polypeptide, or a portion or fragment thereof, can be used as an immunogen to generate antibodies that bind NPM-1 using standard techniques for polyclonal and monoclonal antibody preparation. A full-length NPM-1 polypeptide can be used or, alternatively, the invention provides antigenic peptide fragments of NPM-1 for use as immunogens. The antigenic peptide of NPM-1 comprises at least 8 amino acid residues of the amino acid sequence shown in SEQ ID NO:34 and encompasses an epitope of NPM-1 such that an antibody raised against the peptide forms a specific immune complex with NPM-1. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of NPM-1 that are located on the surface of the polypeptide, e.g., hydrophilic regions, as well as regions with high antigenicity (see, for example, FIG. 56).

An NPM-1 immunogen typically is used to prepare antibodies by immunizing a suitable subject, (e.g., rabbit, goat, mouse or other mammal) with the immunogen. An appropriate immunogenic preparation can contain, for example, recombinantly expressed NPM-1 polypeptide or a chemically synthesized NPM-1 polypeptide. The preparation can further include an adjuvant, such as Freund's complete or incomplete adjuvant, or similar immunostimulatory agent. Immunization of a suitable subject with an immunogenic NPM-1 preparation induces a polyclonal anti-NPM-1 antibody response.

Accordingly, another aspect of the invention pertains to anti-NPM-1 antibodies. The term "antibody" as used herein refers to immunoglobulin molecules and immunologically active portions of immunoglobulin molecules, i.e., molecules that contain an antigen binding site which specifically binds (immunoreacts with) an antigen, such as NPM-1. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind NPM-1. The term "monoclonal antibody" or "monoclonal antibody composition", as used herein, refers to a population of antibody molecules that contain only one species of an antigen binding site capable of immunoreacting with a particular epitope of NPM-1. A monoclonal antibody composition thus typically displays a single binding affinity for a particular NPM-1 polypeptide with which it immunoreacts.

Polyclonal anti-NPM-1 antibodies can be prepared as described above by immunizing a suitable subject with an NPM-1 immunogen. The anti-NPM-1 antibody titer in the immunized subject can be monitored over time by standard techniques, such as with an enzyme linked immunosorbent assay (ELISA) using immobilized NPM-1. If desired, the antibody molecules directed against NPM-1 can be isolated from the mammal (e.g., from the blood) and further purified by well known techniques, such as protein A chromatography to obtain the IgG fraction. At an appropriate time after immunization, e.g., when the anti-NPM-1 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with an NPM-1 immunogen as described above, and the culture supernatants of the resulting hybridoma cells are screened to identify a hybridoma producing a monoclonal antibody that binds NPM-1.

Any of the many well known protocols used for fusing lymphocytes and immortalized cell lines can be applied for the purpose of generating an anti-NPM-1 monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC (Manassas Va.). Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind NPM-1, e.g., using a standard ELISA assay.

Alternative to preparing monoclonal antibody-secreting hybridomas, a monoclonal anti-NPM-1 antibody can be identified and isolated by screening a recombinant combinatorial immunoglobulin library (e.g., an antibody phage display library) with NPM-1 to thereby isolate immunoglobulin library members that bind NPM-1. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1369–1372; Hay et al.

(1992) *Hum. Antibod. Hybridomas* 3:81–85; Huse et al. (1989) *Science* 246:1275–1281; Griffiths et al. (1993) *EMBO J.* 12:725–734; Hawkins et al. (1992) *J. Mol. Biol.* 226:889–896; Clackson et al. (1991) *Nature* 352:624–628; Gram et al. (1992) *Proc. Natl. Acad. Sci. USA* 89:3576–3580; Garrard et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-NPM-1 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyen et al. (1988) *Science* 239:1534; and Beidler et al. (1988) *J. Immunol.* 141:4053–4060.

An anti-NPM-1 antibody (e.g., monoclonal antibody) can be used to isolate NPM-1 by standard techniques, such as affinity chromatography or immunoprecipitation. An anti-NPM-1 antibody can facilitate the purification of natural NPM-1 from cells and of recombinantly produced NPM-1 expressed in host cells. Moreover, an anti-NPM-1 antibody can be used to detect NPM-1 polypeptide (e.g., in a cellular lysate or cell supernatant) in order to evaluate the abundance and pattern of expression of the NPM-1 polypeptide. Anti-NPM-1 antibodies can be used diagnostically to monitor polypeptide levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

III. Recombinant Expression Vectors and Host Cells

Another aspect of the invention pertains to vectors, for example recombinant expression vectors, containing a nucleic acid containing an NPM-1 nucleic acid molecule or vectors containing a nucleic acid molecule which encodes an NPM-1 polypeptide (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of polypeptide desired, and the like. The expression vectors of the invention can be introduced into host cells to thereby produce proteins or peptides, including fusion proteins or peptides, encoded by nucleic acids as described herein (e.g., NPM-1 polypeptides, mutant forms of NPM-1 polypeptides, fusion proteins, and the like).

Accordingly, an exemplary embodiment provides a method for producing a polypeptide, preferably an NPM-1 polypeptide, by culturing in a suitable medium a host cell of the invention (e.g., a mammalian host cell such as a nonhuman mammalian cell) containing a recombinant expression vector, such that the polypeptide is produced.

The recombinant expression vectors of the invention can be designed for expression of NPM-1 polypeptides in prokaryotic or eukaryotic cells. For example, NPM-1 polypeptides can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in NPM-1 activity assays, (e.g., direct assays or competitive assays described in detail below), or to generate antibodies specific for NPM-1 polypeptides, for example. In a preferred embodiment, an NPM-1 fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the NPM-1 expression vector is a yeast expression vector. Examples of vectors for expression in yeast *S. cerevisiae* include pYepSec1 (Baldari, et al., (1987) *EMBO J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (Invitrogen Corporation, San Diego, Calif.).

Alternatively, NPM-1 polypeptides can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to NPM-1 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which an NPM-1 nucleic acid molecule of the invention is introduced, e.g., an NPM-1 nucleic acid molecule within a vector (e.g., a recombinant expression vector) or an NPM-1 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an NPM-1 polypeptide can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual*. 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding an NPM-1 polypeptide or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) an NPM-1 polypeptide. Accordingly, the invention further provides methods for producing an NPM-1 polypeptide using the host cells of the invention. In one embodiment, the method comprises culturing the host cell of the invention (into which a recombinant expression vector encoding an NPM-1 polypeptide has been introduced) in a suitable medium such that an NPM-1 polypeptide is produced. In another embodiment, the method further comprises isolating an NPM-1 polypeptide from the medium or the host cell.

The host cells of the invention can also be used to produce non-human transgenic animals. For example, in one embodiment, a host cell of the invention is a fertilized oocyte or an embryonic stem cell into which NPM-1-coding sequences have been introduced. Such host cells can then be used to create non-human transgenic animals in which exogenous NPM-1 sequences have been introduced into their genome or homologous recombinant animals in which endogenous NPM-1 sequences have been altered. Such animals are useful for studying the function and/or activity of an NPM-1 and for identifying and/or evaluating modulators of NPM-1 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous NPM-1 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing an NPM-1-encoding nucleic acid into the male pronuclei of a fertilized oocyte, e.g., by microinjection, retroviral infection, and allowing the oocyte to develop in a pseudopregnant female foster animal. The NPM-1 cDNA sequence of SEQ ID NO:33 can be introduced as a transgene into the genome of a non-human animal. Alternatively, a nonhuman homologue of a human NPM-1 gene, such as a mouse or rat NPM-1 gene, can be used as a transgene. Alternatively, an NPM-1 gene homologue, such as another NPM-1 family member, can be isolated based on hybridization to the NPM-1 cDNA sequences of SEQ ID NO:33 or 35 (described further in subsection I above) and used as a transgene. Intronic sequences and polyadenylation signals can also be included in the transgene to increase the efficiency of expression of the transgene. A tissue-specific regulatory sequence(s) can be operably linked to an NPM-1 transgene to direct expression of an NPM-1 polypeptide to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of an NPM-1 transgene in its genome and/or expression of NPM-1 mRNA in tissues or cells of the animals. A transgenic founder animal can then be used to breed additional animals carrying the transgene. Moreover, transgenic animals carrying a transgene encoding an NPM-1 polypeptide can further be bred to other transgenic animals carrying other transgenes.

To create a homologous recombinant animal, a vector is prepared which contains at least a portion of an NPM-1 gene into which a deletion, addition or substitution has been introduced to thereby alter, e.g., functionally disrupt, the NPM-1 gene. The NPM-1 gene can be a human gene (e.g., the cDNA of SEQ ID NO:35), but more preferably, is a non-human homologue of a human NPM-1 gene (e.g., a cDNA isolated by stringent hybridization with the nucleotide sequence of SEQ ID NO:33). For example, a mouse NPM-1 gene can be used to construct a homologous recombination nucleic acid molecule, e.g., a vector, suitable for altering an endogenous NPM-1 gene in the mouse genome. In a preferred embodiment, the homologous recombination nucleic acid molecule is designed such that, upon homologous recombination, the endogenous NPM-1 gene is functionally disrupted (i.e., no longer encodes a functional protein; also referred to as a "knock out" vector). Alternatively, the homologous recombination nucleic acid molecule can be designed such that, upon homologous recombination, the endogenous NPM-1 gene is mutated or otherwise altered but still encodes functional polypeptide (e.g., the upstream regulatory region can be altered to thereby alter the expression of the endogenous NPM-1 polypeptide). In the homologous recombination nucleic acid molecule, the altered portion of the NPM-1 gene is flanked at its 5' and 3' ends by additional nucleic acid sequence of the NPM-1 gene to allow for homologous recombination to occur between the exogenous NPM-1 gene carried by the homologous recombination nucleic acid molecule and an endogenous NPM-1 gene in a cell, e.g., an embryonic stem cell. The additional flanking NPM-1 nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) Cell 51:503 for a description of homologous recombination vectors). The homologous recombination nucleic acid molecule is introduced into a cell, e.g., an embryonic stem cell line (e.g., by electroporation) and cells in which the introduced NPM-1 gene has homologously recombined with the endogenous NPM-1 gene are selected (see e.g., Li, E. et al. (1992) Cell 69:915). The selected cells can then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The NPM-1 nucleic acid molecules, NPM-1 polypeptides, fragments of NPM-1 polypeptides, NPM-1 modulators, and anti-NPM-1 antibodies (also referred to herein as "active compounds") of the invention can be incorporated into pharmaceutical compositions suitable for administration. Such compositions typically comprise the nucleic acid molecule, polypeptide, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR® EL solubilizer (BASF, Florham Park, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of an NPM-1 polypeptide, NPM-1 modulator or an anti-NPM-1 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a polypeptide or antibody can include a single treatment or, preferably, can include a series of treatments.

In a preferred example, a subject is treated with antibody or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

In certain embodiments of the invention, a modulator of NPM-1 activity is administered in combination with other agents (e.g., a small molecule), or in conjunction with another, complementary treatment regime. For example, in one embodiment, a modulator of NPM-1 activity is used to treat a NPM-1 associated disorder. Accordingly, modulation of NPM-1 activity may be used in conjunction with, for example, another agent used to treat the NPM-1 associated disorder, e.g., another known agent used to treat cancer, in particular, lung, breast or ovary cancer.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin, or *diphtheria* toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985);

Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, an NPM-1 polypeptide of the invention has one or more of the following activities: (1) hydrolysis of nucleoside triphosphates, (2) hydrolysis of nucleoside diphosphates, (3) modulation of signal transduction, (4) neurotransmission and neuromodulation (e.g., in the central and peripheral nervous systems), (5) modulation of tumor inhibition, (6) modulation of endocrine gland secretion, (7) modulation of platelet aggregation, (8) modulation of $Cl^-$ transport (e.g., in airway epithelia), (9) modulation of renal function, (10) modulation of molecular motor function, (11) modulation of cytoskeletal organization, (12) modulation of vesicle transport, (13) participation in nociception, (14) modulate cellular growth and/or proliferation, and (15) modulate angiogenesis.

The isolated nucleic acid molecules of the invention can be used, for example, to express NPM-1 polypeptide (e.g., via a recombinant expression vector in a host cell in gene therapy applications), to detect NPM-1 mRNA (e.g., in a biological sample) or a genetic alteration in an NPM-1 gene, and to modulate NPM-1 activity, as described further below. The NPM-1 polypeptides can be used to treat disorders characterized by insufficient or excessive levels of production of an NPM-1 substrate (e.g., levels of nucleoside di- or tri-phosphates) or production of NPM-1 inhibitors. In addition, the NPM-1 polypeptides can be used to screen for naturally occurring NPM-1 substrates, to screen for drugs or compounds which modulate NPM-1 activity, as well as to treat disorders characterized by insufficient or excessive production of NPM-1 polypeptide or production of NPM-1 polypeptide forms which have decreased, aberrant or unwanted activity compared to NPM-1 wild type polypeptide (e.g., nucleoside phosphatase associated disorders, for example cell permeabilization, cell necrosis or apoptosis, triggering of second messengers, cell proliferation, cell motility, or signal transduction disorders). Moreover, the anti-NPM-1 antibodies of the invention can be used to detect and isolate NPM-1 polypeptides, to regulate the bioavailability of NPM-1 polypeptides, and modulate NPM-1 activity.

A. Screening Assays:

The invention provides a method (also referred to herein as a "screening assay") for identifying modulators, i.e., candidate or test compounds or agents (e.g., peptides, peptidomimetics, small molecules or other drugs) which bind to NPM-1 polypeptides, have a stimulatory or inhibitory effect on, for example, NPM-1 expression or NPM-1 activity, or have a stimulatory or inhibitory effect on, for example, the expression or activity of an NPM-1 substrate.

In one embodiment, the invention provides assays for screening candidate or test compounds which are substrates of an NPM-1 polypeptide or polypeptide or biologically active portion thereof. In another embodiment, the invention provides assays for screening candidate or test compounds which bind to or modulate the activity of an NPM-1 polypeptide or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses an NPM-1 polypeptide or biologically active portion thereof is contacted with a test compound and the ability of the test compound to modulate NPM-1 activity is determined. Determining the ability of the test compound to modulate NPM-1 activity can be accomplished by monitoring, for example, extracellular nucleoside phosphate concentrations, e.g., ATP, ADP, AMP, GTP, GDP, GMP, UTP, UDP, and/or UMP concentrations. The cell, for example, can be of mammalian origin, e.g., a heart, placenta, lung, liver, skeletal muscle, thymus, kidney, pancreas, testis, ovary, prostate, colon, or brain cell.

The ability of the test compound to modulate NPM-1 binding to a substrate or to bind to NPM-1 can also be determined. Determining the ability of the test compound to modulate NPM-1 binding to a substrate can be accomplished, for example, by coupling the NPM-1 substrate with a radioisotope or enzymatic label such that binding of the NPM-1 substrate to NPM-1 can be determined by detecting the labeled NPM-1 substrate in a complex. Alternatively, NPM-1 could be coupled with a radioisotope or enzymatic label to monitor the ability of a test compound to modulate NPM-1 binding to an NPM-1 substrate in a complex. Determining the ability of the test compound to bind NPM-1 can be accomplished, for example, by coupling the compound with a radioisotope or enzymatic label such that binding of the compound to NPM-1 can be determined by detecting the labeled NPM-1 compound in a complex. For example, compounds (e.g., NPM-1 substrates) can be labeled with $^{125}I$, $^{35}S$, $^{14}C$, or $^{3}H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., an NPM-1 substrate) to interact with NPM-1 without the labeling of any of the interactants. For example, a microphysiometer can be used to detect the interaction of a compound with NPM-1 without the labeling of either the compound or the NPM-1. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and NPM-1.

In another embodiment, an assay is a cell-based assay comprising contacting a cell expressing an NPM-1 target molecule (e.g., an NPM-1 substrate) with a test compound and determining the ability of the test compound to modulate (e.g., stimulate or inhibit) the activity of the NPM-1 target molecule. Determining the ability of the test compound to modulate the activity of an NPM-1 target molecule can be accomplished, for example, by determining the ability of the NPM-1 polypeptide to bind to or interact with the NPM-1 target molecule.

Determining the ability of the NPM-1 polypeptide, or a biologically active fragment thereof, to bind to or interact with an NPM-1 target molecule can be accomplished by one of the methods described above for determining direct binding. In a preferred embodiment, determining the ability of the NPM-1 polypeptide to bind to or interact with an NPM-1 target molecule can be accomplished by determining the activity of the target molecule. For example, the activity of the target molecule can be determined by detecting induction of a cellular second messenger of the target (i.e., intracellular $Ca^{2+}$, diacylglycerol, $IP_3$, and the like), detecting catalytic/enzymatic activity of the target using an appropriate substrate, detecting the induction of a reporter gene (comprising a target-responsive regulatory element operatively linked to a nucleic acid encoding a detectable marker, e.g., luciferase), or detecting a target-regulated cellular response.

In yet another embodiment, an assay of the present invention is a cell-free assay in which an NPM-1 polypeptide or biologically active portion thereof is contacted with a test compound and the ability of the test compound to bind to the NPM-1 polypeptide or biologically active portion thereof is determined. Preferred biologically active portions of the NPM-1 polypeptides to be used in assays of the present invention include fragments which participate in interactions with non-NPM-1 molecules, e.g., fragments with high surface probability scores (see, for example, FIG. 56). Binding of the test compound to the NPM-1 polypeptide can be determined either directly or indirectly as described above. In a preferred embodiment, the assay includes contacting the NPM-1 polypeptide or biologically active portion thereof with a known compound which binds NPM-1 to form an assay mixture, contacting the assay mixture with a test compound, and determining the ability of the test compound to interact with an NPM-1 polypeptide, wherein determining the ability of the test compound to interact with an NPM-1 polypeptide comprises determining the ability of the test compound to preferentially bind to NPM-1 or biologically active portion thereof as compared to the known compound.

In another embodiment, the assay is a cell-free assay in which an NPM-1 polypeptide or biologically active portion thereof is contacted with a test compound and the ability of the test compound to modulate (e.g., stimulate or inhibit) the activity of the NPM-1 polypeptide or biologically active portion thereof is determined. Determining the ability of the test compound to modulate the activity of an NPM-1 polypeptide can be accomplished, for example, by determining the ability of the NPM-1 polypeptide to bind to an NPM-1 target molecule by one of the methods described above for determining direct binding. Determining the ability of the NPM-1 polypeptide to bind to an NPM-1 target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIACORE®). Changes in the optical phenomenon of surface plasmon resonance (SPR) can be used as an indication of real-time reactions between biological molecules.

In an alternative embodiment, determining the ability of the test compound to modulate the activity of an NPM-1 polypeptide can be accomplished by determining the ability of the NPM-1 polypeptide to further modulate the activity of a downstream effector of an NPM-1 target molecule. For example, the activity of the effector molecule on an appropriate target can be determined or the binding of the effector to an appropriate target can be determined as previously described.

In yet another embodiment, the cell-free assay involves contacting an NPM-1 polypeptide or biologically active portion thereof with a known compound which binds the NPM-1 polypeptide to form an assay mixture, contacting the assay mixture with a test compound, and determining the ability of the test compound to interact with the NPM-1 polypeptide, wherein determining the ability of the test compound to interact with the NPM-1 polypeptide comprises determining the ability of the NPM-1 polypeptide to preferentially bind to or modulate the activity of an NPM-1 target molecule.

In more than one embodiment of the above assay methods of the present invention, it may be desirable to immobilize either NPM-1 or its target molecule to facilitate separation of complexed from uncomplexed forms of one or both of the proteins, as well as to accommodate automation of the assay. Binding of a test compound to an NPM-1 polypeptide, or interaction of an NPM-1 polypeptide with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/NPM-1 fusion proteins or glutathione-S-transferase/target fusion proteins can be adsorbed onto glutathione SEPHAROSE® beads (Sigma Chemical, St. Louis, Mo.) or glutathione derivatized micrometer plates, which are then combined with the test compound or the test compound and either the non-adsorbed target protein or NPM-1 polypeptide, and the mixture incubated under conditions conducive to complex formation (e.g., at physiological conditions for salt and pH). Following incubation, the beads or micrometer plate wells are washed to remove any unbound components, the matrix immobilized in the case of beads, complex determined either directly or indirectly, for example, as described above. Alternatively, the complexes can be dissociated from the matrix, and the level of NPM-1 binding or activity determined using standard techniques.

Other techniques for immobilizing proteins on matrices can also be used in the screening assays of the invention. For example, either an NPM-1 polypeptide or an NPM-1 target molecule can be immobilized utilizing conjugation of biotin and streptavidin. Biotinylated NPM-1 polypeptide or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with NPM-1 polypeptide or target molecules but which do not interfere with binding of the NPM-1 polypeptide to its target molecule can be derivatized to the wells of the plate, and unbound target or NPM-1 polypeptide trapped in the wells by antibody conjugation. Methods for detecting such complexes, in addition to those described above for the GST-immobilized complexes, include immunodetection of complexes using antibodies reactive with the NPM-1 polypeptide or target molecule, as well as enzyme-linked assays which rely on detecting an enzymatic activity associated with the NPM-1 polypeptide or target molecule.

In another embodiment, modulators of NPM-1 expression are identified in a method wherein a cell is contacted with a candidate compound and the expression of NPM-1 mRNA or polypeptide in the cell is determined. The level of expression of NPM-1 mRNA or polypeptide in the presence of the candidate compound is compared to the level of expression of NPM-1 mRNA or polypeptide in the absence of the candidate compound. The candidate compound can then be identified as a modulator of NPM-1 expression based on this comparison. For example, when expression of NPM-1 mRNA or polypeptide is greater (statistically significantly greater) in the presence of the candidate compound than in its absence, the candidate compound is identified as a stimulator of NPM-1 mRNA or polypeptide expression. Alternatively, when expression of NPM-1 mRNA or polypeptide is less (statistically significantly less) in the presence of the candidate compound than in its absence, the candidate compound is identified as an inhibitor of NPM-1 mRNA or polypeptide expression. The level of NPM-1 mRNA or polypeptide expression in the cells can be determined by methods described herein for detecting NPM-1 mRNA or polypeptide.

In yet another aspect of the invention, the NPM-1 polypeptides can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with NPM-1 ("NPM-1-binding proteins" or "NPM-1-bp") and are involved in NPM-1 activity. Such NPM-1-binding proteins are also likely to be involved in the propagation of signals by the NPM-1 polypeptides or NPM-1 targets as, for example, downstream elements of an NPM-1-mediated signaling pathway. Alternatively, such NPM-1-binding proteins are likely to be NPM-1 inhibitors.

The two-hybrid system is based on the modular nature of most transcription factors, which consist of separable DNA-binding and activation domains. Briefly, the assay utilizes two different DNA constructs. In one construct, the gene that codes for an NPM-1 polypeptide is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an NPM-1-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the NPM-1 polypeptide.

In another aspect, the invention pertains to a combination of two or more of the assays described herein. For example, a modulating agent can be identified using a cell-based or a cell free assay, and the ability of the agent to modulate the activity of an NPM-1 polypeptide can be confirmed in vivo, e.g., in an animal such as an animal model for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein (e.g., an NPM-1 modulating agent, an antisense NPM-1 nucleic acid molecule, an NPM-1-specific antibody, or an NPM-1-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the NPM-1 nucleotide sequences, described herein, can be used to map the location of the NPM-1 genes on a chromosome. The mapping of the NPM-1 sequences to chromosomes is an important first step in correlating these sequences with genes associated with disease.

Briefly, NPM-1 genes can be mapped to chromosomes by preparing PCR primers (preferably 15–25 bp in length) from the NPM-1 nucleotide sequences. Computer analysis of the NPM-1 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the NPM-1 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220: 919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the NPM-1 nucleotide sequences to design oligonucleotide primers, sublocalization can be achieved with panels of fragments from specific chromosomes. Other mapping strategies which can similarly be used to map an NPM-1 sequence to its chromosome include in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the NPM-1 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The NPM-1 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the NPM-1 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The NPM-1 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:33 can comfortably provide positive individual identification with a panel of perhaps 10 to 1,000 primers which each yield a noncoding amplified sequence of 100 bases. If predicted coding sequences, such as those in SEQ ID NO:35 are used, a more appropriate number of primers for positive individual identification would be 500–2,000.

If a panel of reagents from NPM-1 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of NPM-1 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:33 are particularly appropriate for this use as greater numbers of polymorphisms occur in the noncoding regions, making it easier to differentiate individuals using this technique. Examples of polynucleotide reagents include the NPM-1 nucleotide sequences or portions thereof, e.g., fragments derived from the noncoding regions of SEQ ID NO:33 having a length of at least 20 bases, preferably at least 30 bases.

The NPM-1 nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such NPM-1 probes can be used to identify tissue by species and/or by organ type.

In a similar fashion, these reagents, e.g., NPM-1 primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining NPM-1 polypeptide and/or nucleic acid expression as well as NPM-1 activity, in the context of a biological sample (e.g., blood, serum, cells, tissue) to thereby determine whether an individual is afflicted with a disease or disorder, or is at risk of developing a disorder, associated with aberrant or unwanted NPM-1 expression or activity. The invention also provides for prognostic (or predictive) assays for determining whether an individual is at risk of developing a disorder associated with NPM-1 polypeptide, nucleic acid expression or activity. For example, mutations in an NPM-1 gene can be assayed in a biological sample. Such assays can be used for prognostic or predictive purpose to thereby prophylactically treat an individual prior to the onset of a disorder characterized by or associated with NPM-1 polypeptide, nucleic acid expression or activity.

Another aspect of the invention pertains to monitoring the influence of agents (e.g., drugs, compounds) on the expression or activity of NPM-1 in clinical trials.

These and other agents are described in further detail in the following sections.

1. Diagnostic Assays

An exemplary method for detecting the presence or absence of NPM-1 polypeptide or nucleic acid in a biological sample involves obtaining a biological sample from a test subject and contacting the biological sample with a compound or an agent capable of detecting NPM-1 polypeptide or nucleic acid (e.g., mRNA, or genomic DNA) that encodes NPM-1 polypeptide such that the presence of NPM-1 polypeptide or nucleic acid is detected in the biological sample. In another aspect, the present invention provides a method for detecting the presence of NPM-1 activity in a biological sample by contacting the biological sample with an agent capable of detecting an indicator of NPM-1 activity such that the presence of NPM-1 activity is detected in the biological sample. A preferred agent for detecting NPM-1 mRNA or genomic DNA is a labeled nucleic acid probe capable of hybridizing to NPM-1 mRNA or genomic DNA. The nucleic acid probe can be, for example, the NPM-1 nucleic acid set forth in SEQ ID NO:33 or 35, or a portion thereof, such as an oligonucleotide of at least 15, 30, 50, 100, 250 or 500 nucleotides in length and sufficient to specifically hybridize under stringent conditions to NPM-1 mRNA or genomic DNA. Other suitable probes for use in the diagnostic assays of the invention are described herein.

A preferred agent for detecting NPM-1 polypeptide is an antibody capable of binding to NPM-1 polypeptide, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect NPM-1 mRNA, polypeptide, or genomic DNA in a biological sample in vitro as well as in vivo. For example, in vitro techniques for detection of NPM-1 mRNA include Northern hybridizations and in situ hybridizations. In vitro techniques for detection of NPM-1 polypeptide include enzyme linked immunosorbent assays (ELISAs), Western blots, immunoprecipitations and immunofluorescence. In vitro techniques for detection of NPM-1 genomic DNA include Southern hybridizations. Furthermore, in vivo techniques for detection of NPM-1 polypeptide include introducing into a subject a labeled anti-NPM-1 antibody. For example, the antibody can be labeled with a radioactive marker whose presence and location in a subject can be detected by standard imaging techniques.

The present invention also provides diagnostic assays for identifying the presence or absence of a genetic alteration characterized by at least one of (i) aberrant modification or mutation of a gene encoding an NPM-1 polypeptide; (ii) aberrant expression of a gene encoding an NPM-1 polypeptide; (iii) mis-regulation of the gene; and (iv) aberrant post-translational modification of an NPM-1 polypeptide, wherein a wild-type form of the gene encodes a polypeptide with an NPM-1 activity. "Misexpression or aberrant expression", as used herein, refers to a non-wild type pattern of gene expression, at the RNA or protein level. It includes, but is not limited to, expression at non-wild type levels (e.g., over or under expression); a pattern of expression that differs from wild type in terms of the time or stage at which the gene is expressed (e.g., increased or decreased expression (as compared with wild type) at a predetermined developmental period or stage); a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene (e.g., a pattern of increased or decreased expression (as compared with wild type) in the presence of an increase or decrease in the strength of the stimulus).

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting NPM-1 polypeptide, mRNA, or genomic DNA, such that the presence of NPM-1 polypeptide, mRNA or genomic DNA is detected in the biological sample, and comparing the presence of NPM-1 polypeptide, mRNA or genomic DNA in the control sample with the presence of NPM-1 polypeptide, mRNA or genomic DNA in the test sample.

The invention also encompasses kits for detecting the presence of NPM-1 in a biological sample. For example, the kit can comprise a labeled compound or agent capable of detecting NPM-1 polypeptide or mRNA in a biological sample; means for determining the amount of NPM-1 in the sample; and means for comparing the amount of NPM-1 in the sample with a standard. The compound or agent can be packaged in a suitable container. The kit can further comprise instructions for using the kit to detect NPM-1 polypeptide or nucleic acid.

2. Prognostic Assays

The diagnostic methods described herein can furthermore be utilized to identify subjects having or at risk of developing a disease or disorder associated with aberrant or unwanted NPM-1 expression or activity. As used herein, the term "aberrant" includes an NPM-1 expression or activity which deviates from the wild type NPM-1 expression or activity. Aberrant expression or activity includes increased or decreased expression or activity, as well as expression or activity which does not follow the wild type developmental pattern of expression or the subcellular pattern of expression. For example, aberrant NPM-1 expression or activity is intended to include the cases in which a mutation in the NPM-1 gene causes the NPM-1 gene to be under-expressed or over-expressed and situations in which such mutations result in a non-functional NPM-1 polypeptide or a polypeptide which does not function in a wild-type fashion, e.g., a polypeptide which does not interact with an NPM-1 substrate, e.g., a non-nucleoside phosphatase subunit or ligand, or one which interacts with a non-NPM-1 substrate, e.g. a non-nucleoside phosphatase subunit or ligand. As used herein, the term "unwanted" includes an unwanted phenomenon involved in a biological response, such as cellular proliferation. For example, the term unwanted includes an NPM-1 expression or activity which is undesirable in a subject.

The assays described herein, such as the preceding diagnostic assays or the following assays, can be utilized to identify a subject having or at risk of developing a disorder associated with a misregulation in NPM-1 polypeptide activity or nucleic acid expression, such as a nucleoside phosphatase associated disorder (e.g., a cell permeabilization, cell necrosis or apoptosis, triggering of second messenger, cell proliferation, cell motility, or signal transduction disorder). Alternatively, the prognostic assays can be utilized to identify a subject having or at risk for developing a disorder associated with a misregulation in NPM-1 polypeptide activity or nucleic acid expression, such as a nucleoside phosphatase associated disorder, or a cell permeabilization, cell necrosis or apoptosis, triggering of second messenger, cell proliferation, cell motility, or signal transduction disorder. Thus, the present invention provides a method for identifying a disease or disorder associated with aberrant or unwanted NPM-1 expression or activity in which a test sample is obtained from a subject and NPM-1 polypeptide or nucleic acid (e.g., mRNA or genomic DNA) is detected, wherein the presence of NPM-1 polypeptide or nucleic acid is diagnostic for a subject having or at risk of developing a disease or disorder associated with aberrant or unwanted NPM-1 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted NPM-1 expression or activity. For example, such methods can be used to determine whether a subject can be effectively treated with an agent for a nucleoside phosphatase associated disorder, or a cell permeabilization, cell necrosis or apoptosis, triggering of second messenger, cell proliferation, cell motility, or signal transduction disorder. Thus, the present invention provides methods for determining whether a subject can be effectively treated with an agent for a disorder associated with aberrant or unwanted NPM-1 expression or activity in which a test sample is obtained and NPM-1 polypeptide or nucleic acid expression or activity is detected (e.g., wherein the abundance of NPM-1 polypeptide or nucleic acid expression or activity is diagnostic for a subject that can be administered the agent to treat a disorder associated with aberrant or unwanted NPM-1 expression or activity).

The methods of the invention can also be used to detect genetic alterations in an NPM-1 gene, thereby determining if a subject with the altered gene is at risk for a disorder characterized by misregulation in NPM-1 polypeptide activity or nucleic acid expression, such as a nucleoside phosphatase associated disorder, or a cell permeabilization, cell necrosis or apoptosis, triggering of second messenger, cell proliferation, cell motility, or signal transduction disorder. In preferred embodiments, the methods include detecting, in a sample of cells from the subject, the presence or absence of a genetic alteration characterized by at least one of an alteration affecting the integrity of a gene encoding an NPM-1-polypeptide, or the mis-expression of the NPM-1 gene. For example, such genetic alterations can be detected by ascertaining the existence of at least one of 1) a deletion of one or more nucleotides from an NPM-1 gene; 2) an addition of one or more nucleotides to an NPM-1 gene; 3) a substitution of one or more nucleotides of an NPM-1 gene, 4) a chromosomal rearrangement of an NPM-1 gene; 5) an alteration in the level of a messenger RNA transcript of an NPM-1 gene, 6) aberrant modification of an NPM-1 gene, such as of the methylation pattern of the genomic DNA, 7) the presence of a non-wild type splicing pattern of a messenger RNA transcript of an NPM-1 gene, 8) a non-wild type level of an NPM-1-polypeptide, 9) allelic loss of an NPM-1 gene, and 10) inappropriate post-translational modification of an NPM-1-polypeptide. As described herein, there are a large number of assays known in the art which can be used for detecting alterations in an NPM-1 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the NPM-1-gene (see Abravaya et al. (1995) *Nucleic Acids Res* 0.23:675–682). This method can include the steps of collecting a sample of cells from a subject, isolating nucleic acid (e.g., genomic, mRNA or both) from the cells of the sample, contacting the nucleic acid sample with one or more primers which specifically hybridize to an NPM-1 gene under conditions such that hybridization and amplification of the NPM-1-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an NPM-1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in NPM-1 can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in NPM-1 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the NPM-1 gene and detect mutations by comparing the sequence of the sample NPM-1 with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the NPM-1 gene include methods in which protection from cleavage agents is used to detect mismatched bases in RNA/RNA or RNA/DNA heteroduplexes (Myers et al. (1985) *Science* 230: 1242). In general, the art technique of "mismatch cleavage" starts by providing heteroduplexes of formed by hybridizing (labeled) RNA or DNA containing the wild-type NPM-1 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in NPM-1 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on an NPM-1 sequence, e.g., a wild-type NPM-1 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in NPM-1 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125–144; and Hayashi (1992) *Genet. Anal. Tech. Appl.* 9:73–79). Single-stranded DNA fragments of sample and control NPM-1 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an NPM-1 gene.

Furthermore, any cell type or tissue in which NPM-1 is expressed may be utilized in the prognostic assays described herein.

3. Monitoring of Effects During Clinical Trials

Monitoring the influence of agents (e.g., drugs) on the expression or activity of an NPM-1 polypeptide (e.g., the modulation of membrane excitability) can be applied not only in basic drug screening, but also in clinical trials. For example, the effectiveness of an agent determined by a screening assay as described herein to increase NPM-1 gene expression, polypeptide levels, or upregulate NPM-1 activity, can be monitored in clinical trials of subjects exhibiting decreased NPM-1 gene expression, polypeptide levels, or downregulated NPM-1 activity. Alternatively, the effectiveness of an agent determined by a screening assay to decrease NPM-1 gene expression, polypeptide levels, or downregulate NPM-1 activity, can be monitored in clinical trials of subjects exhibiting increased NPM-1 gene expression, polypeptide levels, or upregulated NPM-1 activity. In such clinical trials, the expression or activity of an NPM-1 gene, and preferably, other genes that have been implicated in, for example, an NPM-1-associated disorder can be used as a "read out" or markers of the phenotype of a particular cell.

For example, and not by way of limitation, genes, including NPM-1, that are modulated in cells by treatment with an agent (e.g., compound, drug or small molecule) which modulates NPM-1 activity (e.g., identified in a screening assay as described herein) can be identified. Thus, to study the effect of agents on NPM-1-associated disorders (e.g., disorders characterized by deregulated nucleoside phosphatase activity), for example, in a clinical trial, cells can be isolated and RNA prepared and analyzed for the levels of expression of NPM-1 and other genes implicated in the NPM-1-associated disorder, respectively. The levels of gene expression (e.g., a gene expression pattern) can be quantified by northern blot analysis or RT-PCR, as described herein, or alternatively by measuring the amount of polypeptide produced, by one of the methods as described herein, or by measuring the levels of activity of NPM-1 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of an NPM-1 polypeptide, mRNA, or genomic DNA in the preadministration sample; (iii) obtaining one or more post-administration samples from the subject; (iv) detecting the level of expression or activity of the NPM-1 polypeptide, mRNA, or genomic DNA in the post-administration samples; (v) comparing the level of expression or activity of the NPM-1 polypeptide, mRNA, or genomic DNA in the pre-administration sample with the NPM-1 polypeptide, mRNA, or genomic DNA in the post administration sample or samples; and (vi) altering the administration of the agent to the subject accordingly. For example, increased administration of the agent may be desirable to increase the expression or activity of NPM-1 to higher levels than detected, i.e., to increase the effectiveness of the agent. Alternatively, decreased administration of the agent may be desirable to decrease expression or activity of NPM-1 to lower levels than detected, i.e. to decrease the effectiveness of the agent. According to such an embodiment, NPM-1 expression or activity may be used as an indicator of the effectiveness of an agent, even in the absence of an observable phenotypic response.

D. Methods of Treatment:

As used herein, the term "nucleoside phosphatase associated disorder" includes disorders, diseases, or conditions which are characterized by aberrant, e.g., upregulated or downregulated, nucleoside hydrolysis and/or aberrant, e.g., upregulated or downregulated, ATP, ADP, GTP, GDP, UTP, and/or UDP levels. Examples of such disorders may include cardiovascular disorders, e.g., arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrillation, long-QT syndrome, congestive heart failure, sinus node dysfunction, angina, heart failure, hypertension, atrial fibrillation, atrial flutter, dilated cardiomyopathy, idiopathic cardiomyopathy, myocardial infarction, coronary artery disease, coronary artery spasm, or arrhythmia.

Other examples of nucleoside phosphatase-associated disorders include disorders of the central nervous system, e.g., cystic fibrosis, type 1 neurofibromatosis, cognitive and neurodegenerative disorders, examples of which include, but are not limited to, Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis, progressive supranuclear palsy, epilepsy, and Creutzfeldt-Jakob disease; autonomic function disorders such as hypertension and sleep disorders, and neuropsychiatric disorders, such as depression, schizophrenia, schizoaffective disorder, korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), and bipolar affective neurological disorders, e.g., migraine and obesity. Further nucleoside phosphatase-associated include, for example, those listed in the American Psychiatric Association's Diagnostic and Statistical manual of Mental Disorders (DSM), the most current version of which is incorporated herein by reference in its entirety.

Still other examples of nucleoside phosphatase-associated disorders include cellular proliferation, growth, differentiation, or migration disorders. Cellular proliferation, growth, differentiation, or migration disorders include those disorders that affect cell proliferation, growth, differentiation, or migration processes. As used herein, a "cellular proliferation, growth, differentiation, or migration process" is a process by which a cell increases in number, size or content, by which a cell develops a specialized set of characteristics which differ from that of other cells, or by which a cell moves closer to or further from a particular location or stimulus. Such disorders include cancer, e.g., carcinoma, sarcoma, or leukemia; tumor angiogenesis and metastasis; skeletal dysplasia; hepatic disorders; and hematopoietic and/or myeloproliferative disorders.

Still other examples of nucleoside phosphatase-associated include disorders of the immune system, such as Wiskott-Aldrich syndrome, viral infection, autoimmune disorders or immune deficiency disorders, e.g., congenital X-linked infantile hypogammaglobulinemia, transient hypogammaglobulinemia, common variable immunodeficiency, selective IgA deficiency, chronic mucocutaneous candidiasis, or severe combined immunodeficiency. Other examples of nucleoside phosphatase-associated disorders include congenital malformalities, including facio-genital dysplasia; and skin disorders, including microphthalmia with linear skin defects syndrome.

The present invention provides for both prophylactic and therapeutic methods of treating a subject at risk of (or susceptible to) a disorder or having a disorder associated with aberrant or unwanted NPM-1 expression or activity, e.g. a nucleoside phosphatase associated disorder, or a cell permeabilization, cell necrosis or apoptosis, triggering of second messenger, cell proliferation, cell motility, or signal transduction disorder). With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the NPM-1 molecules of the present invention or NPM-1 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Treatment is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

A therapeutic agent includes, but is not limited to, small molecules, peptides, antibodies, ribozymes and antisense oligonucleotides.

1. Prophylactic Methods

In one aspect, the invention provides a method for preventing in a subject, a disease or condition associated with an aberrant or unwanted NPM-1 expression or activity, by administering to the subject an NPM-1 or an agent which modulates NPM-1 expression or at least one NPM-1 activity. Subjects at risk for a disease which is caused or contributed to by aberrant or unwanted NPM-1 expression or activity can be identified by, for example, any or a combination of diagnostic or prognostic assays as described herein. Administration of a prophylactic agent can occur prior to the manifestation of symptoms characteristic of the NPM-1 aberrancy, such that a disease or disorder is prevented or, alternatively, delayed in its progression. Depending on the type of NPM-1 aberrancy, for example, an NPM-1, NPM-1 agonist or NPM-1 antagonist agent can be used for treating the subject. The appropriate agent can be determined based on screening assays described herein.

2. Therapeutic Methods

Another aspect of the invention pertains to methods of modulating NPM-1 expression or activity for therapeutic purposes. Accordingly, in an exemplary embodiment, the modulatory method of the invention involves contacting a cell capable of expressing NPM-1 with an agent that modulates one or more of the activities of NPM-1 polypeptide activity associated with the cell, such that NPM-1 activity in the cell is modulated. An agent that modulates NPM-1 polypeptide activity can be an agent as described herein, such as a nucleic acid or a polypeptide, a naturally-occurring target molecule of an NPM-1 polypeptide (e.g., an NPM-1 substrate), an NPM-1 antibody, an NPM-1 agonist or antagonist, a peptidomimetic of an NPM-1 agonist or antagonist, or other small molecule. In one embodiment, the agent stimulates one or more NPM-1 activities. Examples of such stimulatory agents include active NPM-1 polypeptide and a nucleic acid molecule encoding NPM-1 that has been introduced into the cell. In another embodiment, the agent inhibits one or more NPM-1 activities. Examples of such inhibitory agents include antisense NPM-1 nucleic acid molecules, anti-NPM-1 antibodies, and NPM-1 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of an NPM-1 polypeptide or nucleic acid molecule. In one embodiment, the method involves administering an agent (e.g., an agent identified by a screening assay described herein), or combination of agents that modulates (e.g., upregulates or downregulates) NPM-1 expression or activity. In another embodiment, the method involves administering an NPM-1 polypeptide or nucleic acid molecule as therapy to compensate for reduced, aberrant, or unwanted NPM-1 expression or activity.

Stimulation of NPM-1 activity is desirable in situations in which NPM-1 is abnormally downregulated and/or in which increased NPM-1 activity is likely to have a beneficial effect. Likewise, inhibition of NPM-1 activity is desirable in situations in which NPM-1 is abnormally upregulated and/or in which decreased NPM-1 activity is likely to have a beneficial effect.

3. Pharmacogenomics

The NPM-1 molecules of the present invention, as well as agents, or modulators which have a stimulatory or inhibitory effect on NPM-1 activity (e.g., NPM-1 gene expression) as identified by a screening assay described herein can be administered to individuals to treat (prophylactically or therapeutically) NPM-1-associated disorders (e.g., proliferative disorders) associated with aberrant or unwanted NPM-1 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an NPM-1 molecule or NPM-1 modulator as well as tailoring the dosage and/or therapeutic regimen of treatment with an NPM-1 molecule or NPM-1 modulator.

Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23(10–11): 983–985 and Linder, M. W. et al. (1997) Clin. Chem. 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., an NPM-1 polypeptide of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., an NPM-1 molecule or NPM-1 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with an NPM-1 molecule or NPM-1 modulator, such as a modulator identified by one of the exemplary screening assays described herein.

4. Use of NPM-1 Molecules as Surrogate Markers

The NPM-1 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the NPM-1 molecules of the invention may be detected, and may be correlated with one or more biological states in vivo. For example, the NPM-1 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258–264; and James (1994) *AIDS Treatment News Archive* 209.

The NPM-1 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., an NPM-1 marker) transcription or expression, the amplified marker may be in a quantity which is more readily detectable than the drug itself. Also, the marker may be more easily detected due to the nature of the marker itself; for example, using the methods described herein, anti-NPM-1 antibodies may be employed in an immune-based detection system for an NPM-1 polypeptide marker, or NPM-1- specific radiolabeled probes may be used to detect an NPM-1 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229–238; Schentag (1999) *Am. J. Health-Syst. Pharm.* 56 Suppl. 3: S21–S24; and Nicolau (1999) *Am. J. Health-Syst. Pharm.* 56 Suppl. 3: S16–S20. The NPM-1 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35(12): 1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or polypeptide (e.g., NPM-1 polypeptide or RNA) for specific tumor markers in a subject, a drug or course of treatment may be selected that is optimized for the treatment of the specific tumor likely to be present in the subject. Similarly, the presence or absence of a specific sequence mutation in NPM-1 DNA may correlate NPM-1 drug response. The use of pharmacogenomic markers therefore permits the application of the most appropriate treatment for each subject without having to administer the therapy.

VI. Electronic Apparatus Readable Media and Arrays

Electronic apparatus readable media comprising NPM-1 sequence information is also provided. As used herein, "NPM-1 sequence information" refers to any nucleotide and/or amino acid sequence information particular to the NPM-1 molecules of the present invention, including but not limited to full-length nucleotide and/or amino acid sequences, partial nucleotide and/or amino acid sequences, polymorphic sequences including single nucleotide polymorphisms (SNPs), epitope sequences, and the like. Moreover, information "related to" said NPM-1 sequence information includes detection of the presence or absence of a sequence (e.g., detection of expression of a sequence, fragment, polymorphism, etc.), determination of the level of a sequence (e.g., detection of a level of expression, for example, a quantitative detection), detection of a reactivity to a sequence (e.g., detection of protein expression and/or levels, for example, using a sequence-specific antibody), and the like. As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon NPM-1 sequence information of the present invention.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the NPM-1 sequence information.

A variety of software programs and formats can be used to store the sequence information on the electronic apparatus readable medium. For example, the sequence information can be represented in a word processing text file, formatted in commercially-available software such as WordPerfect and Microsoft Word, or represented in the form of an ASCII file, stored in a database application, such as DB2, Sybase, Oracle, or the like, as well as in other forms. Any number of dataprocessor structuring formats (e.g., text file or database) may be employed in order to obtain or create a medium having recorded thereon the NPM-1 sequence information.

By providing NPM-1 sequence information in readable form, one can routinely access the sequence information for a variety of purposes. For example, one skilled in the art can use the sequence information in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has a NPM-1-associated disease or disorder or a pre-disposition to a NPM-1-associated disease or disorder, wherein the method comprises the steps of determining NPM-1 sequence information associated with the subject and based on the NPM-1 sequence information, determining whether the subject has a NPM-1-associated disease or disorder or a pre-disposition to a NPM-1-associated disease or disorder and/or recommending a particular treatment for the disease, disorder or pre-disease condition.

The present invention further provides in an electronic system and/or in a network, a method for determining whether a subject has a NPM-1-associated disease or disorder or a pre-disposition to a disease associated with a NPM-1 wherein the method comprises the steps of determining NPM-1 sequence information associated with the subject, and based on the NPM-1 sequence information, determining whether the subject has a NPM-1-associated disease or disorder or a pre-disposition to a NPM-1-associated disease or disorder, and/or recommending a particular treatment for the disease, disorder or pre-disease condition. The method may further comprise the step of receiving phenotypic information associated with the subject and/or acquiring from a network phenotypic information associated with the subject.

The present invention also provides in a network, a method for determining whether a subject has a NPM-1-associated disease or disorder or a pre-disposition to a NPM-1-associated disease or disorder associated with NPM-1, said method comprising the steps of receiving NPM-1 sequence information from the subject and/or information related thereto, receiving phenotypic information associated with the subject, acquiring information from the network corresponding to NPM-1 and/or a NPM-1-associated disease or disorder, and based on one or more of the phenotypic information, the NPM-1 information (e.g., sequence information and/or information related thereto), and the acquired information, determining whether the subject has a NPM-1-associated disease or disorder or a pre-disposition to a NPM-1-associated disease or disorder. The method may further comprise the step of recommending a particular treatment for the disease, disorder or pre-disease condition.

The present invention also provides a business method for determining whether a subject has a NPM-1-associated disease or disorder or a pre-disposition to a NPM-1-associated disease or disorder, said method comprising the steps of receiving information related to NPM-1 (e.g., sequence information and/or information related thereto), receiving phenotypic information associated with the subject, acquiring information from the network related to NPM-1 and/or related to a NPM-1-associated disease or disorder, and based on one or more of the phenotypic information, the NPM-1 information, and the acquired information, determining whether the subject has a NPM-1-associated disease or disorder or a pre-disposition to a NPM-1-associated disease or disorder. The method may further comprise the step of recommending a particular treatment for the disease, disorder or pre-disease condition.

The invention also includes an array comprising a NPM-1 sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, one of which can be NPM-1. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a NPM-1-associated disease or disorder, progression of NPM-1-associated disease or disorder, and processes, such a cellular transformation associated with the NPM-1-associated disease or disorder.

The array is also useful for ascertaining the effect of the expression of a gene on the expression of other genes in the same cell or in different cells (e.g., ascertaining the effect of NPM-1 expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including NPM-1) that could serve as a molecular target for diagnosis or therapeutic intervention.

This invention is further illustrated by the following examples which should not be construed as limiting. The contents of all references, patents and published patent applications cited throughout this application, as well as the Figures and the Sequence Listing, are incorporated herein by reference.

EXAMPLES

Example 1

Identification and Characterization of Human NPM-1 cDNA

In this example, the identification and characterization of the gene encoding human NPM-1 (clone 62088) is described.

Isolation of the Human NPM-1 cDNA

The invention is based, at least in part, on the discovery of a human gene encoding a novel polypeptide, referred to herein as human NPM-1. The entire sequence of the human clone 62088 was determined and found to contain an open reading frame termed human "NPM-1." The nucleotide sequence of the human NPM-1 gene is set forth in FIGS. 55A–E and in the Sequence Listing as SEQ ID NO:33. The amino acid sequence of the human NPM-1 expression product is set forth in FIGS. 55A–E and in the Sequence Listing as SEQ ID NO:34. The NPM-1 polypeptide comprises about 604 amino acids. The coding region (open reading frame) of SEQ ID NO:33 is set forth as SEQ ID NO:35.

Analysis of the Human NPM-1 Molecules

A search using the polypeptide sequence of SEQ ID NO:34 was performed against the HMM database in PFAM (FIGS. 57A–D) resulting in the identification of a nucleoside phosphatase family domain in the amino acid sequence of human NPM-1 at about residues 75–536 of SEQ ID NO:34 (score=324.9).

A search using the polypeptide sequence of SEQ ID NO:34 was also performed against the Memsat database (FIG. 58), resulting in the identification of three potential transmembrane domains in the amino acid sequence of human NPM-1 (SEQ ID NO:34) at about residues 29–47, 84–102, and 552–570, and the identification of a potential signal peptide in the amino acid sequence of human NPM-1 at about residues 1–54 of SEQ ID NO:34.

The second predicted transmembrane domain (i.e., amino acids 84–102 of SEQ ID NO:34) having a score of 0.7 is not presumed to be a physiological domain based the low score and on further analysis of NPM-1 as a nucleoside phosphatase family member. Members of the family (e.g., CD39) typically contain two transmembrane domains and a large ectoplasmic domain.

The prredicted signal peptide (i.e., within the region of amino acids 1–54 of SEQ ID NO:34) falls within the first region of the predicted transmembrane domain (i.e., amino acids 29–47 of SEQ ID NO:34 and is not presumed to be a physiological domain based on its location within the first transmembrane domain, analogy to nucleoside phosphatase family members, and analogy to signal anchor sequences. A singal peptide (e.g., TNF) may function not as a cleavable signal sequence but, instead, serve as a signal anchor sequence.

The amino acid sequence of human NPM-1 was analyzed using the program PSORT (see the PSORT website maintained by the Human Genome Center at the Institute of Medical Science in the University of Tokyo, Japan (psort.nibb.ac.jp)) to predict the localization of the proteins within the cell. This program assesses the presence of different targeting and localization amino acid sequences within the query sequence. The results of the analyses show that human NPM-1 may be localized to the mitochondria, endoplasmic reticulum, or to the nucleus.

Searches of the amino acid sequence of human NPM-1 were further performed against the Prosite database. These searches resulted in the identification in the amino acid sequence of human NPM-1 of a number of potential N-glycosylation sites, a potential protein kinase C phosphorylation site, a number of potential protein kinase C phosphorylation sites, a number of potential casein kinase II phosphorylation sites, a potential tyrosine kinase phosphorylation site, a number of potential N-myristoylation sites, a potential amidation site, a potential prokaryotic membrane lipoprotein lipid attachment site, and a potential cell attachment sequence.

Further hits were identified by using the amino acid sequence of NPM-1 (SEQ ID NO:34) to search through the ProDom database. Numerous matches against proteins and/or protein domains described as "lysosomal apyrase-like plasmid LALP1 guanosine-diphosphatase hydrolase", "hydrolase lysosomal apyrase-like chromosome transmembrane", "hydrolase antigen transmembrane apyrase ecto-ATPase glycoprotein ATP-diphosphohydrolase nucleoside lymphoid", "antigen hydrolase ecto-ATPase transmembrane glycoprotein ATP-diphosphohydrolase activation lymphoid vascular", "lysosomal apyrase-like plasmid LALP1 guanosine-diphosphatase hydrolase", "chromosome transmembrane hydrolase X", and "hydrolase nucleoside-triphosphatase multigene family triphosphate NTPase precursor signal II", and the like were identified.

Example 2

Expression of Recombinant NPM-1 Polypeptide in Bacterial Cells

In this example, human NPM-1 is expressed as a recombinant glutathione-S-transferase (GST) fusion polypeptide in *E. coli* and the fusion polypeptide is isolated and characterized. Specifically, NPM-1 is fused to GST and this fusion polypeptide is expressed in *E. coli*, e.g., strain PEB199. Expression of the GST-NPM-1 fusion polypeptide in PEB 199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant NPM-1 Polypeptide in COS Cells

To express the human NPM-1 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire NPM-1 polypeptide and an HA tag (Wilson et al. (1984) *Cell* 37:767) or a FLAG tag fused in-frame to its 3' end of the fragment is cloned into the polylinker region of the vector, thereby placing the expression of the recombinant polypeptide under the control of the CMV promoter.

To construct the plasmid, the human NPM-1 DNA sequence is amplified by PCR using two primers. The 5' primer contains the restriction site of interest followed by approximately twenty nucleotides of the NPM-1 coding sequence starting from the initiation codon; the 3' end sequence contains complementary sequences to the other restriction site of interest, a translation stop codon, the HA tag or FLAG tag and the last 20 nucleotides of the NPM-1 coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the NPM-1 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the human NPM-1-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual*. 2nd, ed., Cold Spring Harbor Laboratory, Cold Spring Harbor Laboratory Press, Cold Spring Harbor, N.Y., 1989. The expression of the IC54420 polypeptide is detected by radiolabeling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the human NPM-1 coding sequence is cloned directly into the polylinker of the pcDNA/Amp vector using the appropriate restriction sites. The resulting plasmid is transfected into COS cells in the manner described above, and the expression of the NPM-1 polypeptide is detected by radiolabeling and immunoprecipitation using an NPM-1-specific monoclonal antibody.

Example 4

Tissue Distribution of Human NPM-1 mRNA Using Taqman™ Analysis

This example describes the tissue distribution of human NPM-1 mRNA in a variety of cells and tissues, as determined using the TaqMan™ procedure. The Taqman™ procedure is a quantitative, reverse transcription PCR-based approach for detecting mRNA. The RT-PCR reaction exploits the 5' nuclease activity of AmpliTaq Gold™ DNA Polymerase to cleave a TaqMan™ probe during PCR. Briefly, cDNA was generated from the samples of interest, e.g., various tumor and normal tissue samples, and used as the starting material for PCR amplification. In addition to the 5' and 3' gene-specific primers, a gene-specific oligonucleotide probe (complementary to the region being amplified) was included in the reaction (i.e., the Taqman™ probe). The TaqMan™ probe includes the oligonucleotide with a fluorescent reporter dye covalently linked to the 5' end of the probe (such as FAM (6-carboxyfluorescein), TET (6-carboxy-4,7,2',7'-tetrachlorofluorescein), JOE (6-carboxy-4,5-dichloro-2,7-dimethoxyfluorescein), or VIC) and a quencher dye (TAMRA (6-carboxy-N,N,N',N'-tetramethylrhodamine) at the 3' end of the probe.

During the PCR reaction, cleavage of the probe separates the reporter dye and the quencher dye, resulting in increased fluorescence of the reporter. Accumulation of PCR products is detected directly by monitoring the increase in fluorescence of the reporter dye. When the probe is intact, the proximity of the reporter dye to the quencher dye results in suppression of the reporter fluorescence. During PCR, if the target of interest is present, the probe specifically anneals between the forward and reverse primer sites. The 5'–3' nucleolytic activity of the AmpliTaq™ Gold DNA Polymerase cleaves the probe between the reporter and the quencher only if the probe hybridizes to the target. The probe fragments are then displaced from the target, and polymerization of the strand continues. The 3' end of the probe is blocked to prevent extension of the probe during PCR. This process occurs in every cycle and does not interfere with the exponential accumulation of product. RNA was prepared using the trizol method and treated with DNase to remove contaminating genomic DNA. cDNA was synthesized using standard techniques. Mock cDNA synthesis in the absence of reverse transcriptase resulted in samples with no detectable PCR amplification of the control gene confirms efficient removal of genomic DNA contamination.

An array of human tissues were tested. The results of one such analysis are depicted in Table I. NPM-1 expression was strong in astrocytes and coronary smooth muscle cells from normal tissues, and was elevated in early aortic smooth muscle cells, shear HUVEC, static HUVEC, and prostate epithelial cells from normal tissues.

TABLE I

Human NPM-1 Taqman Data

| Tissue Type | Mean | β 2 Mean | ∂∂ Ct | Expression |
|---|---|---|---|---|
| Artery normal | 40 | 22.32 | 17.68 | 0 |
| Vein normal | 40 | 21.32 | 18.68 | 0 |
| Aortic SMC EARLY | 29.98 | 22.62 | 7.36 | 6.0872 |
| Coronary SMC | 29.98 | 23.89 | 6.09 | 14.731 |
| Static HUVEC | 29.59 | 21.26 | 8.34 | 3.0968 |
| Shear HUVEC | 28.86 | 21.55 | 7.32 | 6.2584 |
| Heart normal | 32.98 | 19.4 | 13.58 | 0.0817 |
| Heart CHF | 39.98 | 20.07 | 19.91 | 0 |

TABLE I-continued

Human NPM-1 Taqman Data

| Tissue Type | Mean | β 2 Mean | ∂∂ Ct | Expression |
|---|---|---|---|---|
| Kidney | 30.55 | 21.14 | 9.41 | 1.47 |
| Skeletal Muscle | 40 | 22.4 | 17.61 | 0 |
| Adipose normal | 40 | 20.63 | 19.37 | 0 |
| Pancreas | 31.95 | 22.45 | 9.49 | 1.3907 |
| primary osteoblasts | 33.91 | 20.19 | 13.73 | 0.0739 |
| Osteoclasts (diff) | 36.52 | 18.56 | 17.97 | 0 |
| Skin normal | 38.36 | 22.01 | 16.35 | 0 |
| Spinal cord normal | 40 | 20.41 | 19.59 | 0 |
| Brain Cortex normal | 32.13 | 21.99 | 10.15 | 0.8832 |
| Brain Hypothalamus normal | 40 | 22.25 | 17.75 | 0 |
| Nerve | 40 | 24.47 | 15.54 | 0 |
| DRG (Dorsal Root Ganglion) | 40 | 22.59 | 17.41 | 0 |
| Glial Cells (Astrocytes) | 28.46 | 22.9 | 5.57 | 21.1236 |
| Glioblastoma | 40 | 18.32 | 21.68 | 0 |
| Breast normal | 40 | 21.66 | 18.34 | 0 |
| Breast tumor | 38.72 | 19.13 | 19.59 | 0 |
| Ovary normal | 35.84 | 21.06 | 14.79 | 0 |
| Ovary Tumor | 39.88 | 20.77 | 19.11 | 0 |
| Prostate Normal | 39.52 | 20.31 | 19.21 | 0 |
| Prostate Tumor | 38.94 | 18.32 | 20.62 | 0 |
| Epithelial Cells (Prostate) | 29.85 | 21.74 | 8.11 | 3.6195 |
| Colon normal | 34.2 | 19.26 | 14.94 | 0.0318 |
| Colon Tumor | 29.68 | 19.56 | 10.12 | 0.9017 |
| Lung normal | 37.66 | 19.2 | 18.47 | 0 |
| Lung tumor | 30.59 | 19.09 | 11.51 | 0.3441 |
| Lung COPD | 39.99 | 19.58 | 20.41 | 0 |
| Colon IBD | 37.73 | 19.22 | 18.52 | 0 |
| Liver normal | 33.96 | 21.09 | 12.88 | 0.1331 |
| Liver fibrosis | 33.37 | 22.85 | 10.52 | 0.6834 |
| Dermal Cells-fibroblasts | 31.61 | 21.57 | 10.05 | 0.9466 |
| Spleen normal | 40 | 20.22 | 19.79 | 0 |
| Tonsil normal | 36.46 | 17.95 | 18.52 | 0 |
| Lymph node | 40 | 19.47 | 20.53 | 0 |
| Small Intestine | 30.55 | 20.52 | 10.03 | 0.9565 |
| Skin-Decubitus | 35.11 | 21.52 | 13.6 | 0 |
| Synovium | 40 | 21.25 | 18.75 | 0 |
| BM-MNC (Bone marrow mononuclear cells) | 28.32 | 17.54 | 10.78 | 0.5707 |
| Activated PBMC | 37.41 | 16.7 | 20.71 | 0 |

Increased expression of NPM-1 was observed in tumors of the breast, lung, and colon as compared to normal breast, lung, and colon tissues. Furthermore, NPM-1 expression was observed in both normal ovary tissue samples as well as ovary tissue samples derived from tumors. The results of such analyses are depicted in Tables II-V below.

TABLE II

NPM-1 Expression In Clinical Breast Samples

| | Average 62088 | Average Beta 2 | Relative Expression |
|---|---|---|---|
| Breast N | 35.9 | 22.5 | 0.36 |
| Breast N | 39.5 | 21.2 | 0.01 |
| Breast N | 34.5 | 17.6 | 0.03 |
| Breast N | 34.0 | 19.4 | 0.16 |
| Breast T | 29.5 | 17.7 | 1.10 |
| Breast T | 30.2 | 17.9 | 0.81 |
| Breast T | 27.3 | 16.9 | 2.75 |
| Breast T | 31.2 | 19.9 | 1.55 |
| Breast T | 30.8 | 18.6 | 0.85 |
| Breast T | 29.2 | 19.7 | 5.51 |

TABLE III

NPM-1 Expression In Clinical Lung Samples

|  | Average 62088 | Average Beta 2 | Relative Expression |
|---|---|---|---|
| Lung N | 32.0 | 17.0 | 0.12 |
| Lung N | 35.4 | 19.0 | 0.05 |
| Lung N | 28.8 | 16.2 | 0.64 |
| Lung N | 34.3 | 16.3 | 0.02 |
| Lung T | 24.7 | 16.2 | 11.40 |
| Lung T | 26.4 | 17.1 | 6.62 |
| Lung T | 26.7 | 18.2 | 10.31 |
| Lung T | 28.4 | 16.9 | 1.38 |
| Lung T | 27.3 | 18.7 | 10.53 |
| Lung T | 27.6 | 19.1 | 10.78 |
| Lung T | 25.7 | 17.5 | 13.05 |

TABLE IV

NPM-1 Expression In Clinical Colon Samples

|  | Average 62088 | Average Beta 2 | Relative Expression |
|---|---|---|---|
| Colon N | 36.1 | 22.4 | 0.8 |
| Colon N | 33.2 | 18.4 | 0.4 |
| Colon N | 28.5 | 18.0 | 7.8 |
| Colon N | 30.4 | 16.4 | 0.7 |
| Colon T | 28.8 | 16.1 | 1.7 |
| Colon T | 29.8 | 17.4 | 2.1 |
| Colon T | 28.8 | 15.9 | 1.4 |
| Colon T | 27.2 | 16.7 | 7.8 |
| Colon T | 29.5 | 16.3 | 1.2 |
| Colon T | 28.1 | 15.7 | 2.1 |
| Liver Met | 28.1 | 17.1 | 5.2 |
| Liver Met | 28.3 | 19.1 | 19.2 |
| Liver Met | 26.2 | 17.2 | 21.9 |
| Liver Met | 28.1 | 17.3 | 6.0 |
| Liver Nor | 26.3 | 16.2 | 10.1 |
| Liver Nor | 31.8 | 22.4 | 15.8 |

TABLE V

NPM-1 Expression In Clinical Ovary Samples

|  | Average 62088 | Average Beta 2 | Relative Expression |
|---|---|---|---|
| Ovary N | 28.5 | 17.9 | 2.60 |
| Ovary N | 33.0 | 19.4 | 0.33 |
| Ovary N | 35.4 | 22.5 | 0.53 |
| Ovary T | 31.3 | 18.5 | 0.55 |
| Ovary T | 29.1 | 18.0 | 1.75 |
| Ovary T | 29.4 | 17.1 | 0.76 |
| Ovary T | 32.0 | 17.9 | 0.24 |
| Ovary T | 31.8 | 17.5 | 0.19 |
| Ovary T | 32.4 | 19.2 | 0.43 |
| Ovary T | 32.2 | 20.3 | 1.03 |
| Ovary T | 31.5 | 16.7 | 0.14 |

To further investigate the observed increase in NPM-1 expression in cancerous tissue, NPM-1 expression levels were measured in various angiogenesis samples by quantitative PCR using the Taqman™ procedure as described above. The relative levels of NPM-1 expression in various tissue samples is depicted in Table VI below.

TABLE VI

NPM-1 Expression In Clinical Angiogenic Samples

|  | 62088 | Beta 2 | Expression |
|---|---|---|---|
| Brain N | 29.6 | 19.6 | 10.2 |
| Brain N | 29.1 | 20.5 | 27.5 |
| Astrocyt | 27.5 | 21.1 | 125.0 |
| Brain T | 29.1 | 16.4 | 1.6 |
| Brain T | 28.2 | 16.1 | 2.6 |
| Brain T | 29.2 | 16.2 | 1.4 |
| Brain T | 28.7 | 16.9 | 3.2 |
| Brain T | 33.8 | 18.7 | 0.3 |
| HMVEC | 24.3 | 16.0 | 34.1 |
| HMVEC | 24.0 | 16.5 | 62.7 |
| Placenta | 30.8 | 22.2 | 29.8 |
| Fetal Adrenal | 31.9 | 23.4 | 29.0 |
| Fetal Adrenal | 28.2 | 23.1 | 320.9 |
| Fetal Liver | 28.1 | 19.1 | 21.3 |
| Fetal Liver | 29.2 | 18.0 | 4.7 |

Expression was greatest in astrocytes, and high in HMVEC, placental, fetal adrenal, fetal liver, and normal brain tissue samples.

To further investigate the expression of NPM-1 in tumorigenic cells, NPM-1 expression levels were measured in various cell types suitable for animal transplantation by quantitative PCR using the Taqman™ procedure as described above. The relative levels of NPM-1 expression in various samples is depicted in Table VII below.

TABLE VII

Human NPM-1 Taqman Data In Xenograft Cells

|  | Average 62088 | Average 18S | Relative Expression |
|---|---|---|---|
| MCF-7 | 28.81 | 12.01 | 0.44 |
| ZR75 | 27.87 | 9.87 | 0.19 |
| T47D | 27.83 | 11.11 | 0.46 |
| MDA 231 | 28.97 | 10.30 | 0.12 |
| MDA 435 | 28.07 | 11.12 | 0.40 |
| DLD-1 | 28.33 | 10.55 | 0.22 |
| SW 480 | 30.49 | 11.11 | 0.07 |
| SW 620 | 27.93 | 10.66 | 0.32 |
| HCT 116 | 27.38 | 9.52 | 0.21 |
| HT 29 | 27.85 | 11.00 | 0.43 |
| Colo 205 | 25.90 | 9.10 | 0.44 |
| NCIH 125 | 27.64 | 10.05 | 0.26 |
| NCIH 67 | 27.21 | 7.66 | 0.07 |
| NCIH 322 | 28.71 | 11.33 | 0.29 |
| NCIH 460 | 27.32 | 8.84 | 0.14 |
| A549 | 28.19 | 9.47 | 0.12 |
| NHBE | 27.94 | 8.65 | 0.08 |

Notably, NPM-1 expression was highest in the human breast cancer cell lines MCF-7, T47D, and MDA 435, and the human colon cancer cell lines HT29, and Colo 205. Expression was also elevated in the human colon cancer cell line DLD-1, the human breast cancer cell line SW 620, and the human lung cancer cell lines NCIH 125 and NCIH 322.

Example 5

Tissue Distribution of NPM-1 by in situ Analysis

This example describes the tissue distribution of human NPM-1 mRNA, as determined by in situ hybridization analysis using oligonucleotide probes based on the human NPM-1 sequence.

For in situ analysis, various tissues, e.g. tissues obtained from lung, ovary, colon, and breast, were first frozen on dry ice. Ten-micrometer-thick sections of the tissues were then postfixed with 4% formaldehyde in DEPC treated 1× phosphate-buffered saline at room temperature for 10 minutes before being rinsed twice in DEPC 1× phosphate-buffered saline and once in 0.1 M triethanolamine-HCl (pH 8.0). Following incubation in 0.25% acetic anhydride-0.1 M triethanolamine-HCl for 10 minutes, sections were rinsed in DEPC 2×SSC (1×SSC is 0.15M NaCl plus 0.015M sodium citrate). Tissue was then dehydrated through a series of ethanol washes, incubated in 100% chloroform for 5 minutes, and then rinsed in 100% ethanol for 1 minute and 95% ethanol for 1 minute and allowed to air dry.

Hybridizations were performed with $^{35}$S-radiolabeled ($5×10^7$ cpm/ml) cRNA probes. Probes were incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1× Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides were washed with 2×SSC. Sections were then sequentially incubated at 37° C. in TNE (a solution containing 10 mM Tris-HCl (pH 7.6), 500 mM NaCl, and 1 mM EDTA), for 10 minutes, in TNE with 10 µg of RNase A per ml for 30 minutes, and finally in TNE for 10 minutes. Slides were then rinsed with 2×SSC at room temperature, washed with 2×SSC at 50° C. for 1 hour, washed with 0.2×SSC at 55° C. for 1 hour, and 0.2×SSC at 60° C. for 1 hour. Sections were then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

As depicted in Tables VIII and IX below, the in situ hybridization results essentially agreed with the results of the Taqman™ analysis. In situ hybridization data with probe e/f indicated weak expression in a lung tumor. Normal and malignant epithelium of the breast, colon, and ovary were negative for NPM-1 expression. In situ hybridization data with probe a/b indicated weak but specific expression in breast tumors (DCIS and IDC), positive expression in a subset of ovary tumors, and was negative for normal and malignant epithelium of the colon.

TABLE VIII

Human NPM-1 In Situ Hybridization Data (Probe E/F)

| Specimen # | Tissue | Diagnosis | Results |
|---|---|---|---|
| LUNG: 0/2 normal; 1/3 tumor | | | |
| CHT 457 | Lung | normal | (−) |
| CHT 213 | Lung | normal | (−) |
| CHT 799 | Lung | tumor: NSCCL [SCC] | (−) |
| CHT 344 | Lung | tumor: WD/MD SCC | (−) |
| CHT 846 | Lung | tumor: NSCCL [SCC] | (+) |
| BREAST: 0/3; 0/3 tumor | | | |

TABLE VIII-continued

Human NPM-1 In Situ Hybridization Data (Probe E/F)

| Specimen # | Tissue | Diagnosis | Results |
|---|---|---|---|
| CHT 561 | Breast | normal | (−) |
| PIT 723 | Breast | normal | (−) |
| PIT 34 | Breast | normal | (−) |
| NDR 137 | Breast | tumor: DCIS/hyperplasia | (−) |
| NDR 16 | Breast | tumor: IDC | (−) |
| MDA 91 | Breast | tumor: IDC/ILC | (−) |
| COLON: 0/1 normal; 0/1 tumor | | | |
| NDR 118 | Colon | normal | (−) |
| CHT 372 | Colon | tumor | (−) |
| OVARY: 0/2 normal; 0/3 tumor | | | |
| MDA 203 | Ovary | normal | (−) |
| MDA 197 | Ovary | normal | (−) |
| MDA 62 | Ovary | tumor: PD-PS | (−) |
| MDA 29 | Ovary | tumor: LMP-PS | (−) |
| MDA 210 | Ovary | tumor: PD-PS | (−) |

TABLE IX

Human NPM-1 In Situ Hybridization Data (Probe A/B)

| Specimen # | Tissue | Diagnosis | Results |
|---|---|---|---|
| BREAST: 0/1 normals; 2/2 tumors | | | |
| PIT 35 | Breast | normal | (−) |
| NDR 6 | Breast | tumor: IDC | (+) |
| CLN 186 | Breast | tumor: DCIS/IDC | (+) |
| COLON: 0/2 normals; 0/1 tumor; 0/1 metastasis | | | |
| CHT 231 | Colon | normal | (−) |
| CHT 818 | Colon | normal | (−) |
| CHT 907 | Colon | tumor | (−) |
| CHT 77 | Colon | metastasis | (−) |
| OVARY: 0/2 normals; 1/3 tumors | | | |
| MDA 202 | Ovary | normal | (−) |
| MDA 217 | Ovary | normal | (−) |
| CLN 5 | Ovary | tumor: MD-PS | (−) |
| CLN 346 | Ovary | tumor: LMP-mucinous | (−) |
| MDA 300 | Ovary | tumor: MD-AC [endometrioid] | (+) |

IX. 50566, a Novel Human Glyoxalase II Related Factor and uses Thereof

BACKGROUND OF THE INVENTION

In bacterial and eukaryotic cells, 2-oxaloaldehydes are potentially toxic compounds which can arise through normally functioning metabolic pathways and which must be maintained in proper equilibrium to avoid cellular damage. In bacterial and eukaryotic cells there exists a glyoxalase system that catalyzes the conversion of 2-oxaloaldehydes into 2-hydrocarboxylic acids using glutathione (GSH) as a co-enzyme. The glyoxalase system comprises two distinct enzymes, glyoxalase I (EC 4.4.1.5 lactoylglutathione lyase) and glyoxalase II (EC 3.1.2.6 hydroxyacylglutathione hydrolase), homologs of which are known to exist in virtually all prokaryotic and eukaryotic organisms (Bito et al. (1997) *J. Biol. Chem.* 272:21509–21519; Ridderstöm et al. (1996) *J. Biol. Chem.* 271:319–3123). The glyoxalase reactions initiate when GSH reacts non-enzymatically with a 2-oxaloaldehyde, yielding a thiohemiacetyl compound (Reaction A below; see, e.g., Cameron et al. (1999) *Structure*

7:1067–1078). Glyoxalase I catalyzes the isomerization of the thiohemiacetyl to produce a 2-hydroxycarboxylic acid (Reaction B below). Glyoxalase II catalyzes the hydrolysis of the thioester to produce GSH and a 2-hydrocarboxylic acid (Reaction C below).

Reaction A (non-enzymatic)

Reaction B (Glyoxalase I)

Reaction C (Glyoxalase II)

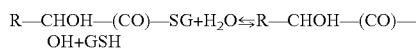

The primary biological function of the glyoxalase system appears to be the conversion of methylglyoxal ($H_3C$—(CO)—CHO) into D-lactate. methylglyoxal is formed in higher eukaryotes primarily from the normal glycolytic conversion of triose-phosphates by the enzyme triose-phosphate isomerase (Richard (1993) *Biochem. Soc. Trans.* 21:549–553). In yeast and bacteria, methylglyoxal arises mainly from the metabolism of dihydroxyacetone phosphate by methylglyoxal synthase (Bito et al. (1997) *J. Biol. Chem.* 272:21509–21519).

Methylglyoxal can produce covalent DNA adducts and will react with arginine and lysine residues in proteins. While this property may potentially play a biological role, it is clear that high levels of methylglyoxal and other oxaloaldehydes are cytotoxic and, thus, must be maintained at controlled levels (Abordo et al. (999) *Biochem. Pharmacol.* 58:641–648). Accordingly, the detoxification activity of the glyoxalase system has been implicated in a wide array of general cellular functions including proliferation, differentiation, and cell division. For example, a recent report indicates that glyoxalase II plays a role in the regulation of spermatogenesis (Ji et al. (1997) *Biochem. Biophys. Res. Comm.* 241:714–719). The glyoxalase system has also been the focus of some oncological research (Hooper et al. (1988) *Cell Mol. Biol.* 34:399–405; Liotti et al. (1993) *Bull. Cancer* 80:62–68; Thornalley (1995) *Crit Rev Oncol Hematol.* 20:99–128; Murthy et al. (1994) *J. Med. Chem.* 37:2161–2166). Linkage of the glyoxalase system has also been established for other disorders including diabetes (McLellan et al. (1993) *Biochem. Soc. Trans.* 21:172S; Beisswenger et al. (1999) *Diabetes* 48:198–202; Thornalley (1991) *Heredity* 67:139–142), atherosclerosis, the immune response, aging, and oxidative stress (Thornalley (1996) *Gen. Pharmacol.* 27:565–573; Thornalley (1993) *Mol. Aspects Med.* 14:287–371). Studies of pathological states associated with protozoan infection have also focussed on the glyoxalase system (Thornalley et al. (1994) *Biochem. Pharmacol.* 47:418–420).

SUMMARY OF THE INVENTION

The present invention is based, at least in part, on the discovery of novel family members of the glyoxalase enzyme system, referred to herein as "Glyoxalase II Related Factor" or "G2RF" nucleic acid and polypeptide molecules. The G2RF nucleic acid and polypeptide molecules of the present invention are useful as modulating agents in regulating a variety of cellular and/or biological processes, e.g., detoxification, maintenance of metabolite equilibrium, cellular proliferation, tissue differentiation, control of cell cycle, and immune response. Accordingly, in one aspect, this invention provides isolated nucleic acid molecules encoding G2RF polypeptides or biologically active portions thereof, as well as nucleic acid fragments suitable as primers or hybridization probes for the detection of G2RF-encoding nucleic acids.

In one embodiment, the invention features an isolated nucleic acid molecule that includes the nucleotide sequence set forth in SEQ ID NO:36 or 38. In another embodiment, the invention features an isolated nucleic acid molecule that encodes a polypeptide including the amino acid sequence set forth in SEQ ID NO:37.

In still other embodiments, the invention features isolated nucleic acid molecules including nucleotide sequences that are substantially identical (e.g., 60%, 65%, 70%, 75%, 80%, 85%, 90%, 95%, 96%, 97%, 98% or 99% identical) to the nucleotide sequence set forth as SEQ ID NO:36 or 38. The invention further features isolated nucleic acid molecules including at least 428, 450, 500, 521, 550, 600, 650, 700 or more contiguous nucleotides of the nucleotide sequence set forth as SEQ ID NO:36 or 38. In another embodiment, the invention features isolated nucleic acid molecules which encode a polypeptide including an amino acid sequence that is substantially identical (e.g., 60%, 65%, 70%, 75%, 80%, 85%, 90%, 95%, 96%, 97%, 98% or 99% identical) to the amino acid sequence set forth as SEQ ID NO:37. The present invention also features nucleic acid molecules which encode allelic variants of the polypeptide having the amino acid sequence set forth as SEQ ID NO:37. In addition to isolated nucleic acid molecules encoding full-length polypeptides, the present invention also features nucleic acid molecules which encode fragments, for example, biologically active or antigenic fragments, of the full-length polypeptides of the present invention (e.g., fragments including at least 10 contiguous amino acid residues of the amino acid sequence of SEQ ID NO:37). In still other embodiments, the invention features nucleic acid molecules that are complementary to, antisense to, or hybridize under stringent conditions to the isolated nucleic acid molecules described herein.

In a related aspect, the invention provides vectors including the isolated nucleic acid molecules described herein (e.g., G2RF-encoding nucleic acid molecules). Such vectors can optionally include nucleotide sequences encoding heterologous polypeptides. Also featured are host cells including such vectors (e.g., host cells including vectors suitable for producing G2RF nucleic acid molecules and polypeptides).

In another aspect, the invention features isolated G2RF polypeptides and/or biologically active or antigenic fragments thereof. Exemplary embodiments feature a polypeptide including the amino acid sequence set forth as SEQ ID NO:37, a polypeptide including an amino acid sequence at least 60%, 65%, 70%, 75%, 80%, 85%, 90%, 95%, 96%, 97%, 98% or 99% identical to the amino acid sequence set forth as SEQ ID NO:37, a polypeptide encoded by a nucleic acid molecule including a nucleotide sequence at least 60%, 65%, 70%, 75%, 80%, 85%, 90%, 95%, 96%, 97%, 98% or 99% identical to the nucleotide sequence set forth as SEQ ID NO:36 or 38. Also featured are fragments of the full-length polypeptides described herein (e.g., fragments including at least 10, 20, 30, 40, 50, 60, 70, 80, 90, 100, 110, 120, 130, 140, 150 or more contiguous amino acid residues of the sequence set forth as SEQ ID NO:37) as well as allelic variants of the polypeptide having the amino acid sequence set forth as SEQ ID NO:37.

The G2RF polypeptides and/or biologically active or antigenic fragments thereof, are useful, for example, as reagents or targets in assays applicable to treatment and/or diagnosis of G2RF mediated or related disorders. In one embodiment, a G2RF polypeptide or fragment thereof, has a G2RF activity. In another embodiment, a G2RF polypeptide or fragment thereof, has a transmembrane domain, a metallo-beta lactamase superfamily domain, and, optionally, has a G2RF activity. In a related aspect, the invention features antibodies (e.g., antibodies which specifically bind to any one of the polypeptides described herein) as well as fusion polypeptides including all or a fragment of a polypeptide described herein.

The present invention further features methods for detecting G2RF polypeptides and/or G2RF nucleic acid molecules, such methods featuring, for example, a probe, primer or antibody described herein. Also featured are kits for the detection of G2RF polypeptides and/or G2RF nucleic acid molecules. In a related aspect, the invention features methods for identifying compounds which bind to and/or modulate the activity of a G2RF polypeptide or G2RF nucleic acid molecule described herein. Further featured are methods for modulating a G2RF activity.

Other features and advantages of the invention will be apparent from the following detailed description and claims.

DETAILED DESCRIPTION OF THE INVENTION

The present invention is based, at least in part, on the discovery of novel molecules, referred to herein as "Glyoxalase II Related Factor" or "G2RF" nucleic acid and polypeptide molecules, which are novel members of the glyoxalase system enzyme family. These novel molecules are capable of metabolizing toxic compounds (e.g., cytotoxin or other metabolites) in a cell, e.g., a heart, placenta, lung, liver, skeletal muscle, thymus, kidney, pancreas, testis, ovary, prostate, colon, or brain cell. By doing so, these molecules help maintain a proper equilibrium of toxic compounds in a cell, thus preventing the occurrence of cellular damage.

As used herein, a "glyoxalase II related factor" includes a protein or polypeptide which is involved in the metabolism of cytotoxins and other metabolites, as well as in the regulation of their cellular levels. As used herein, the terms "cytotoxins" and "metabolites" include compounds which can be harmful or detrimental to a cell when present in sufficient concentrations or quantities. Cytotoxins and metabolites include those which arise from endogenous sources, e.g., the normal metabolic processes of the cell such as the energetic metabolic pathways. Cytotoxins and metabolites may also enter the cell from the extracellular milieu. Cytotoxins and metabolites which enter the cell include those which originate from outside the organism (xenobiotic compounds). Examples of cytotoxins and metabolites include oxaloaldehydes, hydroxycarboxylic acids, pharmacological compounds (e.g., chemotherapeutic compounds and anti-cancer drugs), oxidative compounds, glutathione-conjugates, energy metabolites, methylglyoxal, and the like.

As used herein, the phrase "regulation of cellular levels" includes cellular mechanisms involved in regulating and influencing the levels (e.g., intracellular and/or extracellular levels) of cytotoxins and metabolites (e.g., oxaloaldehydes and hydroxycarboxylic acids or glutathione-conjugates). Such mechanisms include the conversion of potentially cytotoxic compounds into non-toxic or less toxic compounds, e.g., conversion of oxaloaldehydes (such as methylglyoxal or glutathione conjugates) into hydrocarboxylic acids (such as lactate) in response to biological cues, such as formation of nucleotide adjunct, modification of amino acids, and oxidative stress. The maintenance of regulation of cytotoxin and metabolite levels is particularly important for a cell's ability to function properly. Thus, the G2RF molecules, by participating in the regulation of cytotoxin and metabolite levels, may provide novel diagnostic targets and therapeutic agents for controlling cytotoxin- and metabolite-associated disorders (e.g., glyoxalase-associated disorders, oxaloaldehyde- and methylglyoxal-associated disorders).

As used herein, the terms "cytotoxin-associated disorders" and "metabolite-associated disorders" include disorders, diseases, or conditions which are characterized by aberrant, e.g., upregulated, downregulated, or misregulated, cytotoxin and/or metabolite levels (e.g., oxaloacetate, hydroxycarboxylic acid, thioester compound, or glutathione-conjugated compound levels). Examples of such disorders may include cardiovascular disorders, e.g., arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrillation, long-QT syndrome, congestive heart failure, sinus node dysfunction, angina, heart failure, hypertension, atrial fibrillation, atrial flutter, dilated cardiomyopathy, idiopathic cardiomyopathy, myocardial infarction, coronary artery disease, coronary artery spasm, or arrhythmia.

Other examples of cytotoxin- and metabolite-associated disorders include disorders of the central nervous system, e.g., cystic fibrosis, type 1 neurofibromatosis, cognitive and neurodegenerative disorders, examples of which include, but are not limited to, Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis, progressive supranuclear palsy, epilepsy, and Creutzfeldt-Jakob disease; autonomic function disorders such as hypertension and sleep disorders, and neuropsychiatric disorders, such as depression, schizophrenia, schizoaffective disorder, korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), and bipolar affective neurological disorders, e.g., migraine and obesity. Further cytotoxin- and metabolite-associated disorders include, for example, those listed in the American Psychiatric Association's Diagnostic and Statistical manual of Mental Disorders (DSM), the most current version of which is incorporated herein by reference in its entirety.

Still other examples of cytotoxin- and metabolite-associated disorders include cellular proliferation, growth, differentiation, or migration disorders. Cellular proliferation, growth, differentiation, or migration disorders include those disorders that affect cell proliferation, growth, differentiation, or migration processes. As used herein, a "cellular proliferation, growth, differentiation, or migration process" is a process by which a cell increases in number, size or content, by which a cell develops a specialized set of characteristics which differ from that of other cells (e.g., spermatogenesis), or by which a cell moves closer to or further from a particular location or stimulus. Such disorders include cancer, e.g., carcinoma, sarcoma, or leukemia; tumor angiogenesis and metastasis; skeletal dysplasia; hepatic disorders; and hematopoietic and/or myeloproliferative disorders.

Still other examples of cytotoxin- and metabolite-associated disorders include disorders of the immune system, such as the immune response during starvation, Wiskott-Aldrich syndrome, viral infection, autoimmune disorders or immune deficiency disorders, e.g., congenital X-linked infantile hypogammaglobulinemia, transient hypogammaglobulinemia, common variable immunodeficiency, selective IgA deficiency, chronic mucocutaneous candidiasis, or severe combined immunodeficiency. Other examples of cytotoxin- and metabolite-associated disorders include congenital malformities, including facio-genital dysplasia; and skin disorders, including microphthalmia with linear skin defects syndrome.

The term "family" when referring to the polypeptide and nucleic acid molecules of the invention is intended to mean two or more polypeptides or nucleic acid molecules having a common structural domain or motif and having sufficient amino acid or nucleotide sequence homology as defined herein. Such family members can be naturally or non-naturally occurring and can be from either the same or different species. For example, a family can contain a first polypeptide of human origin, as well as other, distinct polypeptides of human origin or alternatively, can contain homologues of non-human origin, e.g., mouse or monkey polypeptides. Members of a family may also have common functional characteristics.

For example, the family of G2RF polypeptides comprise at least one "transmembrane domain." As used herein, the term "transmembrane domain" includes an amino acid sequence of about 20–45 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, alanines, valines, phenylalanines, prolines or methionines. Transmembrane domains are described in, for example, Zagotta W. N. et al., (1996) Annual Rev. Neurosci. 19: 235–263, the contents of which are incorporated herein by reference. Amino acid residues 129–145 of the human G2RF polypeptide (SEQ ID NO:37) comprise a transmembrane domain (FIG. 60). Accordingly, G2RF polypeptides having at least 50–60% homology, preferably about 60–70%, more preferably about 70–80%, or about 80–90% homology with a transmembrane domain of human G2RF are within the scope of the invention.

To identify the presence of a transmembrane domain in a G2RF protein, and make the determination that a protein of interest has a particular profile, the amino acid sequence of the protein may be subjected to MEMSAT analysis. A MEMSAT analysis resulting in the identification of a transmembrane domain in the amino acid sequence of human G2RF (SEQ ID NO:37) at about residues 129–145 are set forth in FIG. 60.

In another embodiment, a G2RF molecule of the present invention is identified based on the presence of at least one "metallo-beta-lactamase superfamily domain", also referred to interchangeably herein as a "lactamase-B domain." As used herein, the term "metallo-beta-lactamase superfamily domain" or "lactamase-B domain" includes a protein domain having an amino acid sequence of about 80–250 amino acid residues and has a bit score of at least 80 when compared against a metallo-beta-lactamase superfamily domain Hidden Markov Model (HMM). Preferably, a "metallo-beta-lactamase superfamily domain" has an amino acid sequence of about 90–240, 100–220, 120–200, 140–180, or more preferably, about 165 amino acid residues, and a bit score of at least 90, 100, 110, 120, or more preferably about 133.3. In a preferred embodiment, a "metallo-beta-lactamase superfamily domain" includes a domain which has an amino acid sequence of about 80–250 amino acid residues, and serves to catalyze the hydrolysis of a thioester (e.g. the thioester in a lactoylglutathione compound). Metallo-beta lactamase superfamily domains are described in, for example, Carfi et al., (1995) EMBO Journal 14:4914–4921, the contents of which are incorporated herein by reference. To identify the presence of a metallo-beta-lactamase superfamily domain in a G2RF protein, and make the determination that a protein of interest has a particular profile, the amino acid sequence of the protein may be searched against a database of known protein domains (e.g., the HMM database). The metallo-beta-lactamase superfamily domain has been assigned the PFAM Accession No. PF00753 (found at Pfam website, genome.wustl.edu) and InterPro Accession No. IPR001279 (see the the European Bioinformatics Institute websitehttp ebi.ac.uk). A search was performed against the HMM database resulting in the identification of a metallo-beta-lactamase superfamily domain in the amino acid sequence of human G2RF (SEQ ID NO:37) at about residues 7–172 of SEQ ID NO:37. The results of the search are set forth in FIG. 61.

A description of the Pfam database can be found in Sonhammer et al. (1997) Proteins 28:405–420 and a detailed description of HMMs can be found, for example, in Gribskov et al. (1990) Meth. Enzymol. 183:146–159; Gribskov et al. (1987) Proc. Natl. Acad. Sci. USA 84:4355–4358; Krogh et al. (1994) J. Mol. Biol. 235:1501–1531; and Stultz et al. (1993) Protein Sci. 2:305–314, the contents of which are incorporated herein by reference.

In a preferred embodiment, the G2RF molecules of the invention include at least one transmembrane domain and/or at least one a metallo-beta-lactamase superfamily domain.

Isolated G2DF polypeptides of the present invention, have an amino acid sequence sufficiently identical to the amino acid sequence of SEQ ID NO:37 or are encoded by a nucleotide sequence sufficiently identical to SEQ ID NO:36 or 38. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains having at least 50%, 55%, 60%, 65%, 70%, 75%, 80%, 85%, 85%, 90%, 95%, 96%, 97%, 98%, 99% or more homology or identity across the amino acid sequences of the domains and contain at least one and preferably two structural domains or motifs, are defined herein as sufficiently identical. Furthermore, amino acid or nucleotide sequences which share at least 50%, 52%, 53%, 54%, 55%, 60%, 65%, 70%, 75%, 80%, 85%, 85%, 90%, 95%, 96%, 97%, 98%, 99% or more homology or identity and share a common functional activity are defined herein as sufficiently identical.

In a preferred embodiment, a G2RF polypeptide includes at least one or more of the following domains: a transmembrane domain and/or a metallo-beta-lactamase superfamily domain, and has an amino acid sequence at least about 50%, 53%, 54%, 55%, 60%, 65%, 70%, 75%, 80%, 85%, 85%, 90%, 95%, 96%, 97%, 98%, 99% or more homologous or identical to the amino acid sequence of SEQ ID NO:37. In yet another preferred embodiment, a G2RF polypeptide includes at least one or more of the following domains: a transmembrane domain and/or a metallo-beta-lactamase superfamily domain, and is encoded by a nucleic acid molecule having a nucleotide sequence which hybridizes under stringent hybridization conditions to a complement of a nucleic acid molecule comprising the nucleotide sequence of SEQ ID NO:36 or 38. In another preferred embodiment, a G2RF polypeptide includes at least one or more of the following domains: a transmembrane domain and/or a metallo-beta-lactamase superfamily domain, and has a G2RF activity.

As used interchangeably herein, "G2RF activity", "biological activity of G2RF" or "functional activity of G2RF", includes an activity exerted by a G2RF polypeptide or nucleic acid molecule on a G2RF responsive cell or tissue, or on a G2RF polypeptide substrate, as determined in vivo, or in vitro, according to standard techniques. In one embodiment, a G2RF activity is a direct activity, such as an association with a G2RF-target molecule. As used herein, a "target molecule" or "binding partner" is a molecule with which a G2RF polypeptide binds or interacts in nature, such that G2RF-mediated function is achieved. A G2RF target molecule can be a non-G2RF molecule, for example, a non-G2RF polypeptide. In an exemplary embodiment, a G2RF target molecule is a G2RF ligand, e.g., a cytotoxin, a metabolite, glutathione, a glutathione-conjugated compound such as lactoylglutathione, or a thioester-containing compound. For example, a G2RF target molecule can have one or more of the following activities: (1) it may interact with cytotoxins and metabolites (e.g., lactoylglutathione, a glutathione-conjugated metabolite, a hydroxycarboxylic acid, and the like), (2) it may catalyze the metabolism of a cytotoxin or metabolite (e.g., lactoylglutathione, a glutathione-conjugated metabolite, a hydroxycarboxylic acid, and the like), (3) it may hydrolyze a thioester containing compound (e.g., lactoylglutathione, and the like), (4) it may catalyze the formation of a thioester conjugation on a substrate (e.g., lactate or a hydroxycarboxylic acid). Moreover, a G2RF activity is an indirect activity, such as a cellular signaling activity mediated by interaction of the G2RF polypeptide with a G2RF ligand. The biological activities of G2RF are described herein. For example, the G2RF polypeptides of the present invention can have one or more of the following activities: (1) modulation of signal transduction in a cell, (2) modulation of cytotoxin and/or metabolite levels (e.g., detoxification), (3) maintenance of equilibrium of cytotoxins and/or metabolites, (4) modulation of cancer or tumor progression, (5) modulation of cellular proliferation, (6) modulation of tissue development (e.g. embryogenesis), (7) modulation of differentiation, (8) modulation of apoptosis, and (9) modulation of energy metabolism.

The nucleotide sequence of the isolated human G2RF cDNA and the predicted amino acid sequence of the human G2RF polypeptide are shown in FIG. 59 and in SEQ ID NOs:36 and 37, respectively.

The human G2RF gene, which is approximately 1154 nucleotides in length, encodes a polypeptide which is approximately 282 amino acid residues in length.

Various aspects of the invention are described in further detail in the following subsections:

I. Isolated Nucleic Acid Molecules

One aspect of the invention pertains to isolated nucleic acid molecules that encode G2RF polypeptides or biologically active portions thereof, as well as nucleic acid fragments sufficient for use as hybridization probes to identify G2RF-encoding nucleic acid molecules (e.g., G2RF mRNA) and fragments for use as PCR primers for the amplification or mutation of G2RF nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regard to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated G2RF nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:36 or 38, or a portion thereof, can be isolated using standard molecular biology techniques and the sequence information provided herein. Using all or a portion of the nucleic acid sequence of SEQ ID NO:36 or 38, as a hybridization probe, G2RF nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:36 or 38, can be isolated by the polymerase chain reaction (PCR) using synthetic oligonucleotide primers designed based upon the sequence of SEQ ID NO:36 or 38.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to G2RF nucleotide sequences can be prepared by standard synthetic techniques, e.g., using an automated DNA synthesizer.

In one embodiment, an isolated nucleic acid molecule of the invention comprises the nucleotide sequence shown in SEQ ID NO:36. The sequence of SEQ ID NO:36 corresponds to the human G2RF cDNA. This cDNA comprises sequences encoding the human G2RF polypeptide (i.e., "the coding region", from nucleotides 22–870) as well as 5' untranslated sequences (nucleotides 1–21) and 3' untranslated sequences (nucleotides 871–1154). Alternatively, the nucleic acid molecule can comprise only the coding region of SEQ ID NO:36 (e.g., nucleotides 22–870, corresponding to SEQ ID NO:38). Accordingly, in another embodiment, the isolated nucleic acid molecule comprises SEQ ID NO:38 and nucleotides 1–21 and 871–1154 of SEQ ID NO:36. In yet another embodiment, the nucleic acid molecule consists of the nucleotide sequence set forth as SEQ ID NO:36 or 38.

In still another embodiment, an isolated nucleic acid molecule of the invention comprises a nucleic acid molecule which is a complement of the nucleotide sequence shown in SEQ ID NO:36 or 38, or a portion of any of these nucleotide sequences. A nucleic acid molecule which is complementary to the nucleotide sequence shown in SEQ ID NO:36 or 38, is one which is sufficiently complementary to the nucleotide sequence shown in SEQ ID NO:36 or 38, such that it can hybridize to the nucleotide sequence shown in SEQ ID NO:36 or 38, thereby forming a stable duplex.

In still another preferred embodiment, an isolated nucleic acid molecule of the present invention comprises a nucleotide sequence which is at least about 50%, 53%, 54%, 55%, 60%, 65%, 70%, 75%, 80%, 85%, 90%, 95%, 96%, 97%, 98%, 99% or more identical to the nucleotide sequence shown in SEQ ID NO:36 or 38 (e.g., to the entire length of the nucleotide sequence), or to a portion or complement of any of these nucleotide sequences. In one embodiment, a nucleic acid molecule of the present invention comprises a nucleotide sequence which is at least (or no greater than) 50–100, 100–200, 200–300, 300–400, 400–500, 500–600, 600–700, 700–800, 800–900, 900–1000, 1000–1100, or more nucleotides in length and hybridizes under stringent hybridization conditions to a complement of a nucleic acid molecule of SEQ ID NO:36 or 38.

Moreover, the nucleic acid molecule of the invention can comprise only a portion of the nucleic acid sequence of SEQ ID NO:36 or 38, for example, a fragment which can be used as a probe or primer or a fragment encoding a portion of a G2RF polypeptide, e.g., a biologically active portion of a G2RF polypeptide. The nucleotide sequence determined from the cloning of the G2RF gene allows for the generation of probes and primers designed for use in identifying and/or cloning other G2RF family members, as well as G2RF homologues from other species. The probe/primer typically comprises substantially purified oligonucleotide. The probe/primer (e.g., oligonucleotide) typically comprises a region of nucleotide sequence that hybridizes under stringent conditions to at least about 12 or 15, preferably about 20 or 25, more preferably about 30, 35, 40, 45, 50, 55, 60, 65, 75, 80, 85, 90, 95, or 100 or more consecutive nucleotides of a sense sequence of SEQ ID NO:36 or 38, of an anti-sense sequence of SEQ ID NO:36 or 38, or of a naturally occurring allelic variant or mutant of SEQ ID NO:36 or 38.

Exemplary probes or primers are at least (or no greater than) 12 or 15, 20 or 25, 30, 35, 40, 45, 50, 55, 60, 65, 70, 75 or more nucleotides in length and/or comprise consecutive nucleotides of an isolated nucleic acid molecule described herein. Also included within the scope of the present invention are probes or primers comprising contiguous or consecutive nucleotides of an isolated nucleic acid molecule described herein, but for the difference of 1, 2, 3, 4, 5, 6, 7, 8, 9 or 10 bases within the probe or primer sequence. Probes based on the G2RF nucleotide sequences can be used to detect (e.g., specifically detect) transcripts or genomic sequences encoding the same or homologous polypeptides. In preferred embodiments, the probe further comprises a label group attached thereto, e.g., the label group can be a radioisotope, a fluorescent compound, an enzyme, or an enzyme co-factor. In another embodiment a set of primers is provided, e.g., primers suitable for use in a PCR, which can be used to amplify a selected region of a G2RF sequence, e.g., a domain, region, site or other sequence described herein. The primers should be at least 5, 10, or 50 base pairs in length and less than 100, or less than 200, base pairs in length. The primers should be identical, or differs by no greater than 1, 2, 3, 4, 5, 6, 7, 8, 9 or 10 bases when compared to a sequence disclosed herein or to the sequence of a naturally occurring variant. Such probes can be used as a part of a diagnostic test kit for identifying cells or tissue which misexpress a G2RF polypeptide, such as by measuring a level of a G2RF-encoding nucleic acid in a sample of cells from a subject e.g., detecting G2RF mRNA levels or determining whether a genomic G2RF gene has been mutated or deleted.

A nucleic acid fragment encoding a "biologically active portion of a G2RF polypeptide" can be prepared by isolating a portion of the nucleotide sequence of SEQ ID NO:36 or 38, which encodes a polypeptide having a G2RF biological activity (the biological activities of the G2RF polypeptides are described herein), expressing the encoded portion of the G2RF polypeptide (e.g., by recombinant expression in vitro) and assessing the activity of the encoded portion of the G2RF polypeptide. In an exemplary embodiment, the nucleic acid molecule is at least 50–100, 100–200, 200–300, 300–400, 400–500, 500–600, 600–700, 700–800, 800–900, 900–1000, 1000–1100, or more nucleotides in length and encodes a polypeptide having a G2RF activity (as described herein).

The invention further encompasses nucleic acid molecules that differ from the nucleotide sequence shown in SEQ ID NO:36 or 38. Such differences can be due to due to degeneracy of the genetic code, thus resulting in a nucleic acid which encodes the same G2RF polypeptides as those encoded by the nucleotide sequence shown in SEQ ID NO:36 or 38. In another embodiment, an isolated nucleic acid molecule of the invention has a nucleotide sequence encoding a polypeptide having an amino acid sequence which differs by at least 1, but no greater than 5, 10, 20, 50 or 100 amino acid residues from the amino acid sequence shown in SEQ ID NO:37. In yet another embodiment, the nucleic acid molecule encodes the amino acid sequence of human G2RF. If an alignment is needed for this comparison, the sequences should be aligned for maximum homology.

Nucleic acid variants can be naturally occurring, such as allelic variants (same locus), homologues (different locus), and orthologues (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

Allelic variants result, for example, from DNA sequence polymorphisms within a population (e.g., the human population) that lead to changes in the amino acid sequences of the G2RF polypeptides. Such genetic polymorphisms in the G2RF genes may exist among individuals within a population due to natural allelic variation. As used herein, the terms "gene" and "recombinant gene" refer to nucleic acid molecules which include an open reading frame encoding a G2RF polypeptide, preferably a mammalian G2RF polypeptide, and can further include non-coding regulatory sequences, and introns.

Accordingly, in one embodiment, the invention features isolated nucleic acid molecules which encode a naturally occurring allelic variant of a polypeptide comprising the amino acid sequence of SEQ ID NO:37, wherein the nucleic acid molecule hybridizes to a complement of a nucleic acid molecule comprising SEQ ID NO:36 or 38, for example, under stringent hybridization conditions.

Allelic variants of human G2RF include both functional and non-functional G2RF polypeptides. Functional allelic variants are naturally occurring amino acid sequence variants of the human G2RF polypeptide that maintain the ability to bind a G2RF ligand or substrate and/or modulate hydrolysis and/or signal transduction. Functional allelic variants will typically contain only conservative substitution of one or more amino acids of SEQ ID NO:37, or substitution, deletion or insertion of non-critical residues in non-critical regions of the polypeptide.

Non-functional allelic variants are naturally occurring amino acid sequence variants of the human G2RF polypeptide that do not have the ability to modulate cytotoxin and/or metabolite levels (e.g., oxaloacetate, hydroxycarboxylic acid, thioester compound, or glutathione-conjugated compound levels). Non-functional allelic variants will typically contain a non-conservative substitution, a deletion, or insertion or premature truncation of the amino acid sequence of SEQ ID NO:37, or a substitution, insertion or deletion in critical residues or critical regions.

The present invention further provides non-human orthologues (e.g., non-human orthologues of the human G2RF polypeptide). Orthologues of the human G2RF polypeptides are polypeptides that are isolated from non-human organisms and possess the same ability to regulate cytotoxin and metabolite levels as the human G2RF polypeptide. Orthologues of the human G2RF polypeptide can readily be identified as comprising an amino acid sequence that is substantially identical to SEQ ID NO:37.

Moreover, nucleic acid molecules encoding other G2RF family members and, thus, which have a nucleotide sequence which differs from the G2RF sequences of SEQ ID NO:36 or 38, are intended to be within the scope of the invention. For example, another G2RF cDNA can be identified based on the nucleotide sequence of human G2RF. Moreover, nucleic acid molecules encoding G2RF polypeptides from different species, and which, thus, have a nucleotide sequence which differs from the G2RF sequences of SEQ ID NO:36 or 38, are intended to be within the scope of the invention. For example, a mouse G2RF cDNA can be identified based on the nucleotide sequence of a human G2RF.

Nucleic acid molecules corresponding to natural allelic variants and homologues of the G2RF cDNAs of the invention can be isolated based on their homology to the G2RF nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the G2RF cDNAs of the invention can further be isolated by mapping to the same chromosome or locus as the G2RF gene.

Orthologues, homologues and allelic variants can be identified using methods known in the art (e.g., by hybridization to an isolated nucleic acid molecule of the present invention, for example, under stringent hybridization conditions). In one embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:36 or 38. In other embodiment, the nucleic acid is at least 50, 100, 200, 300, 400, 420, 427, 428, 429, 500, 600, 700, 800, 900, 1000, 1100 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A preferred, non-limiting example of stringent hybridization conditions includes hybridization in 4×sodium chloride/sodium citrate (SSC), at about 65–70° C. (or hybridization in 4×SSC plus 50% formamide at about 42–50° C.) followed by one or more washes in 1×SSC, at about 65–70° C. A preferred, non-limiting example of highly stringent hybridization conditions includes hybridization in 1×SSC, at about 65–70° C. (or hybridization in 1×SSC plus 50% formamide at about 42–50° C.) followed by one or more washes in 0.3×SSC, at about 65–70° C. A preferred, non-limiting example of reduced stringency hybridization conditions includes hybridization in 4 SSC, at about 50–60° C. (or alternatively hybridization in 6×SSC plus 50% formamide at about 40–45° C.) followed by one or more washes in 2×SSC, at about 50–60° C. Ranges intermediate to the above-recited values, e.g., at 65–70° C. or at 42–50° C. are also intended to be encompassed by the present invention. SSPE (1×SSPE is 0.15M NaCl, 10 mM NaH$_2$PO$_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m$(° C.)=2(# of A+T bases)+4(# of G+C bases). For hybrids between 18 and 49 base pairs in length, $T_m$(° C.)=81.5+16.6(log$_{10}$[Na$^+$])+0.41(% G+C)−(600/N), where N is the number of bases in the hybrid, and [Na$^+$] is the concentration of sodium ions in the hybridization buffer ([Na$^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25–0.5M NaH$_2$PO$_4$, 7% SDS at about 65° C., followed by one or more washes at 0.02M NaH$_2$PO$_4$, 1% SDS at 65° C., see e.g., Church and Gilbert (1984) *Proc. Natl. Acad. Sci. USA* 81:1991–1995, (or, alternatively, 0.2×SSC, 1% SDS).

Preferably, an isolated nucleic acid molecule of the invention that hybridizes under stringent conditions to the sequence of SEQ ID NO:36 or 38 and corresponds to a naturally-occurring nucleic acid molecule. As used herein, a "naturally-occurring" nucleic acid molecule refers to an RNA or DNA molecule having a nucleotide sequence that occurs in nature (e.g., encodes a natural polypeptide).

In addition to naturally-occurring allelic variants of the G2RF sequences that may exist in the population, the skilled artisan will further appreciate that changes can be introduced by mutation into the nucleotide sequences of SEQ ID NO:36 or 38, thereby leading to changes in the amino acid sequence of the encoded G2RF polypeptides, without altering the functional ability of the G2RF polypeptides. For example, nucleotide substitutions leading to amino acid substitutions at "non-essential" amino acid residues can be made in the sequence of SEQ ID NO:36 or 38. A "non-essential" amino acid residue is a residue that can be altered from the wild-type sequence of G2RF (e.g., the sequence of SEQ ID NO:37) without altering the biological activity, whereas an "essential" amino acid residue is required for biological activity. For example, amino acid residues that are conserved among the G2RF polypeptides of the present invention, e.g., those present in a metallo-beta-lactamase superfamily domain, are predicted to be particularly unamenable to alteration. Furthermore, additional amino acid residues that are conserved between the G2RF polypeptides of the present invention and other members of the G2RF family are not likely to be amenable to alteration.

Accordingly, another aspect of the invention pertains to nucleic acid molecules encoding G2RF polypeptides that contain changes in amino acid residues that are not essential for activity. Such G2RF polypeptides differ in amino acid sequence from SEQ ID NO:37, yet retain biological activity. In one embodiment, the isolated nucleic acid molecule comprises a nucleotide sequence encoding a polypeptide, wherein the polypeptide comprises an amino acid sequence at least about 50%, 55%, 60%, 65%, 70%, 75%, 80%, 85%, 90%, 95%, 96%, 97%, 98%, 99% or more identical to SEQ ID NO:37 (e.g., to the entire length of SEQ ID NO:37).

An isolated nucleic acid molecule encoding a G2RF polypeptide identical to the polypeptide of SEQ ID NO:37, can be created by introducing one or more nucleotide substitutions, additions or deletions into the nucleotide sequence of SEQ ID NO:36 or 38, such that one or more amino acid substitutions, additions or deletions are introduced into the encoded polypeptide. Mutations can be introduced into SEQ ID NO:36 or 38, by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a G2RF polypeptide is preferably replaced with another amino acid residue from the same side chain family. Alternatively, in another embodiment, mutations can be introduced randomly along all or part of a G2RF coding sequence, such as by saturation mutagenesis, and the resultant mutants can be screened for G2RF biological activity to identify mutants that retain activity. Following mutagenesis of SEQ ID NO:36 or 38, the encoded polypeptide can be expressed recombinantly and the activity of the polypeptide can be determined.

In a preferred embodiment, a mutant G2RF polypeptide can be assayed for the ability to: (1) interact with cytotoxins and metabolites (e.g., lactoylglutathione, a glutathione-conjugated metabolite, a hydroxycarboxylic acid, and the like), (2) catalyze the metabolism of a cytotoxin or metabolite (e.g., lactoylglutathione, a glutathione-conjugated metabolite, a hydroxycarboxylic acid, and the like), (3) hydrolyze of a thioester compound (e.g., lactoylglutathione, and the like), (4) catalyze the formation of a thioester conjugation on a substrate (e.g., lactate, a hydroxycarboxylic acid), (5) modulate signal transduction in a cell, (6) modulate levels of cytotoxins and/or metabolites (e.g., detoxify), (7) maintain equilibrium of cytotoxins and/or metabolites, (8) modulate cancer or tumor progression, (9) modulate cellular proliferation, (10) modulate tissue development (e.g., embryogenesis), (11) modulate differentiation, (12) modulate apoptosis, or (13) modulate energy metabolism.

In addition to the nucleic acid molecules encoding G2RF polypeptides described above, another aspect of the invention pertains to isolated nucleic acid molecules which are antisense thereto. In an exemplary embodiment, the invention provides an isolated nucleic acid molecule which is antisense to a G2RF nucleic acid molecule (e.g., is antisense to the coding strand of a G2RF nucleic acid molecule). An "antisense" nucleic acid comprises a nucleotide sequence which is complementary to a "sense" nucleic acid encoding a polypeptide, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire G2RF coding strand, or to only a portion thereof. In one embodiment, an antisense nucleic acid molecule is antisense to a "coding region" of the coding strand of a nucleotide sequence encoding G2RF. The term "coding region" refers to the region of the nucleotide sequence comprising codons which are translated into amino acid residues (e.g., the coding region of human G2RF corresponds to SEQ ID NO:38). In another embodiment, the antisense nucleic acid molecule is antisense to a "noncoding region" of the coding strand of a nucleotide sequence encoding G2RF. The term "noncoding region" refers to 5' and 3' sequences which flank the coding region that are not translated into amino acids (i.e., also referred to as 5' and 3' untranslated regions).

Given the coding strand sequences encoding G2RF disclosed herein (e.g., SEQ ID NO:38), antisense nucleic acids of the invention can be designed according to the rules of Watson and Crick base pairing. The antisense nucleic acid molecule can be complementary to the entire coding region of G2RF mRNA, but more preferably is an oligonucleotide which is antisense to only a portion of the coding or noncoding region of G2RF mRNA. For example, the antisense oligonucleotide can be complementary to the region surrounding the translation start site of G2RF mRNA (e.g., between the −10 and +10 regions of the start site of a gene nucleotide sequence). An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothiG2RFe derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a G2RF polypeptide to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff and Gerlach (1988) *Nature* 334:585–591)) can be used to catalytically cleave G2RF mRNA transcripts to thereby inhibit translation of G2RF mRNA. A ribozyme having specificity for a G2RF-encoding nucleic acid can be designed based upon the nucleotide sequence of a G2RF cDNA disclosed herein (i.e., SEQ ID NO:36 or 38, For example, a derivative of a *Tetrahymena* L-19 IVS RNA can be constructed in which the nucleotide sequence of the active site is complementary to the nucleotide sequence to be cleaved in a G2RF-encoding mRNA. See, e.g., Cech et al. U.S. Pat. No. 4,987,071; and Cech et al. U.S. Pat. No. 5,116,742. Alternatively, G2RF mRNA can be used to select a catalytic RNA having a specific ribonuclease activity from a pool of RNA molecules. See, e.g., Bartel, D. and Szostak, J. W. (1993) *Science* 261:1411–1418.

Alternatively, G2RF gene expression can be inhibited by targeting nucleotide sequences complementary to the regulatory region of the G2RF (e.g., the G2RF promoter and/or enhancers) to form triple helical structures that prevent transcription of the G2RF gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12):807–15.

In yet another embodiment, the G2RF nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. *Proc. Natl. Acad. Sci.* 93: 14670–675.

PNAs of G2RF nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of G2RF nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of G2RF can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of G2RF nucleic acid molecules can be generated which may combine the advantageous properties of PNA and DNA. Such chimeras allow DNA recognition enzymes, (e.g., RNase H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) Nucleic Acids Res. 24 (17): 3357–63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag, M. et al. (1989) Nucleic Acid Res. 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3'PNA segment (Peterser, K. H. et al. (1975) Bioorganic Med. Chem. Lett. 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553–6556; Lemaitre et al. (1987) Proc. Natl. Acad. Sci. USA 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) Bio-Techniques 6:958–976) or intercalating agents. (See, e.g., Zon (1988) Pharm. Res. 5:539–549). To this end, the oligonucleotide may be conjugated to another molecule, (e.g., a peptide, hybridization triggered cross-linking agent, transport agent, or hybridization-triggered cleavage agent).

Alternatively, the expression characteristics of an endogenous G2RF gene within a cell line or microorganism may be modified by inserting a heterologous DNA regulatory element into the genome of a stable cell line or cloned microorganism such that the inserted regulatory element is operatively linked with the endogenous G2RF gene. For example, an endogenous G2RF gene which is normally "transcriptionally silent", i.e., a G2RF gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous G2RF gene may be activated by insertion of a promiscuous regulatory element that works across cell types.

A heterologous regulatory element may be inserted into a stable cell line or cloned microorganism, such that it is operatively linked with an endogenous G2RF gene, using techniques, such as targeted homologous recombination, which are well known to those of skill in the art, and described, e.g., in Chappel, U.S. Pat. No. 5,272,071; PCT publication No. WO 91/06667, published May 16, 1991.

II. Isolated G2RF Polypeptides and Anti-G2RF Antibodies

One aspect of the invention pertains to isolated G2RF or recombinant polypeptides, and biologically active portions thereof, as well as polypeptide fragments suitable for use as immunogens to raise anti-G2RF antibodies. In one embodiment, native G2RF polypeptides can be isolated from cells or tissue sources by an appropriate purification scheme using standard protein purification techniques. In another embodiment, G2RF polypeptides are produced by recombinant DNA techniques. Alternative to recombinant expression, a G2RF polypeptide or polypeptide can be synthesized chemically using standard peptide synthesis techniques.

An "isolated" or "purified" polypeptide or biologically active portion thereof is substantially free of cellular material or other contaminating proteins from the cell or tissue source from which the G2RF polypeptide is derived, or substantially free from chemical precursors or other chemicals when chemically synthesized. The language "substantially free of cellular material" includes preparations of G2RF polypeptide in which the polypeptide is separated from cellular components of the cells from which it is isolated or recombinantly produced. In one embodiment, the language "substantially free of cellular material" includes preparations of G2RF polypeptide having less than about 30% (by dry weight) of non-G2RF polypeptide (also referred to herein as a "contaminating protein"), more preferably less than about 20% of non-G2RF polypeptide, still more preferably less than about 10% of non-G2RF polypeptide, and most preferably less than about 5% non-G2RF polypeptide. When the G2RF polypeptide or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of G2RF polypeptide in which the polypeptide is separated from chemical precursors or other chemicals which are involved in the synthesis of the polypeptide. In one embodiment, the language "substantially free of chemical precursors or other chemicals" includes preparations of G2RF polypeptide having less than about 30% (by dry weight) of chemical precursors or non-G2RF chemicals, more preferably less than about 20% chemical precursors or non-G2RF chemicals, still more preferably less than about 10% chemical precursors or non-G2RF chemicals, and most preferably less than about 5% chemical precursors or non-G2RF chemicals.

As used herein, a "biologically active portion" of a G2RF polypeptide includes a fragment of a G2RF polypeptide which participates in an interaction between a G2RF molecule and a non-G2RF molecule. Biologically active portions of a G2RF polypeptide include peptides comprising amino acid sequences sufficiently identical to or derived from the amino acid sequence of the G2RF polypeptide, e.g., the amino acid sequence shown in SEQ ID NO:37, which include less amino acids than the fill length G2RF polypeptides, and exhibit at least one activity of a G2RF polypeptide. Typically, biologically active portions comprise a domain or motif with at least one activity of the G2RF polypeptide, e.g., modulating cytotoxin and/or metabolite levels. A biologically active portion of a G2RF polypeptide can be a polypeptide which is, for example, 25, 30, 35, 40, 45, 50, 75, 100, 125, 150, 175, 200, 225, 250, 275, 300, 325, 350, 375, 400, 425, 450, 475, 500, 525, 550, 575, or 600 or more amino acids in length. Biologically active portions of a G2RF polypeptide can be used as targets for developing agents which modulate a G2RF mediated activity, e.g., modulating cytotoxin and/or metabolite levels.

In one embodiment, a biologically active portion of a G2RF polypeptide comprises at least metallo-beta-lactamase superfamily domain. It is to be understood that a preferred biologically active portion of a G2RF polypeptide of the present invention comprises at least one or more of the following domains: a transmembrane domain and/or a metallo-beta-lactamase superfamily domain. Moreover, other biologically active portions, in which other regions of the polypeptide are deleted, can be prepared by recombinant techniques and evaluated for one or more of the functional activities of a native G2RF polypeptide.

Another aspect of the invention features fragments of the polypeptide having the amino acid sequence of SEQ ID NO:37, for example, for use as immunogens. In one embodiment, a fragment comprises at least 5 amino acids (e.g., contiguous or consecutive amino acids) of the amino acid sequence of SEQ ID NO:37, In another embodiment, a fragment comprises at least 10, 15, 20, 25, 30, 35, 40, 45, 50, 100, 200, 300, 400, 500, 600 or more amino acids (e.g., contiguous or consecutive amino acids) of the amino acid sequence of SEQ ID NO:37.

In a preferred embodiment, a G2RF polypeptide has an amino acid sequence shown in SEQ ID NO:37. In other embodiments, the G2RF polypeptide is substantially identical to SEQ ID NO:37, and retains the functional activity of the polypeptide of SEQ ID NO:37, yet differs in amino acid sequence due to natural allelic variation or mutagenesis, as described in detail in subsection I above. In another embodiment, the G2RF polypeptide is a polypeptide which comprises an amino acid sequence at least about 50%, 55%, 60%, 65%, 70%, 75%, 80%, 85%, 90%, 95%, 96%, 97%, 98%, 99% or more identical to SEQ ID NO:37.

In another embodiment, the invention features a G2RF polypeptide which is encoded by a nucleic acid molecule consisting of a nucleotide sequence at least about 50%, 55%, 60%, 65%, 70%, 75%, 80%, 85%, 90%, 95%, 96%, 97%, 98%, 99% or more identical to a nucleotide sequence of SEQ ID NO:36 or 38, or a complement thereof. This invention further features a G2RF polypeptide which is encoded by a nucleic acid molecule consisting of a nucleotide sequence which hybridizes under stringent hybridization conditions to a complement of a nucleic acid molecule comprising the nucleotide sequence of SEQ ID NO:36 or 38, or a complement thereof.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the G2RF amino acid sequence of SEQ ID NO:37 having 282 amino acid residues, at least 85, preferably at least 113, more preferably at least 142, more preferably at least 170, even more preferably at least 198, and even more preferably at least 226 or 255 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at the bioinformatics page of the website by Accelrys, Inc., San Diego, Calif, USA), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A preferred, non-limiting example of parameters to be used in conjunction with the GAP program include a Blosum 62 scoring matrix with a gap penalty of 12, a gap extend penalty of 4, and a frameshift gap penalty of 5.

In another embodiment, the percent identity between two amino acid or nucleotide sequences is determined using the algorithm of E. Meyers and W. Miller (*Comput. Appl. Biosci.*, 4:11–17 (1988)) which has been incorporated into the ALIGN program (version 2.0 or version 2.0U), using a PAM120 weight residue table, a gap length penalty of 12 and a gap penalty of 4.

The nucleic acid and polypeptide sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to G2RF nucleic acid molecules of the invention. BLAST protein searches can be performed with the XBLAST program, score=100, wordlength=3, and a Blosum62 matrix to obtain amino acid sequences homologous to G2RF polypeptide molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used (accessible at the website maintained by National Center for Biotechnology Information, Bethesda, Md. USA).

The invention also provides G2RF chimeric or fusion proteins. As used herein, a G2RF "chimeric protein" or "fusion protein" comprises a G2RF polypeptide operatively linked to a non-G2RF polypeptide. An "G2RF polypeptide" refers to a polypeptide having an amino acid sequence corresponding to G2RF, whereas a "non-G2RF polypeptide" refers to a polypeptide having an amino acid sequence corresponding to a polypeptide which is not substantially homologous to the G2RF polypeptide, e.g., a polypeptide which is different from the G2RF polypeptide and which is derived from the same or a different organism. Within a G2RF fusion protein the G2RF polypeptide can correspond to all or a portion of a G2RF polypeptide. In a preferred embodiment, a G2RF fusion protein comprises at least one biologically active portion of a G2RF polypeptide. In another preferred embodiment, a G2RF fusion protein comprises at least two biologically active portions of a G2RF polypeptide. Within the fusion protein, the term "operatively linked" is intended to indicate that the G2RF polypeptide and the non-G2RF polypeptide are fused in-frame to each other. The non-G2RF polypeptide can be fused to the N-terminus or C-terminus of the G2RF polypeptide.

For example, in one embodiment, the fusion protein is a GST-G2RF fusion protein in which the G2RF sequences are fused to the C-terminus of the GST sequences. Such fusion proteins can facilitate the purification of recombinant G2RF.

In another embodiment, the fusion protein is a G2RF polypeptide containing a heterologous signal sequence at its N-terminus. In certain host cells (e.g., mammalian host cells), expression and/or secretion of G2RF can be increased through the use of a heterologous signal sequence.

The G2RF fusion proteins of the invention can be incorporated into pharmaceutical compositions and administered to a subject in vivo. The G2RF fusion proteins can be used to affect the bioavailability of a G2RF substrate. Use of G2RF fusion proteins may be useful therapeutically for the treatment of disorders caused by, for example, (i) aberrant modification or mutation of a gene encoding a G2RF polypeptide; (ii) mis-regulation of the G2RF gene; and (iii) aberrant post-translational modification of a G2RF polypeptide.

Moreover, the G2RF-fusion proteins of the invention can be used as immunogens to produce anti-G2RF antibodies in a subject, to purify G2RF ligands and in screening assays to identify molecules which inhibit the interaction of G2RF with a G2RF substrate.

Preferably, a G2RF chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A G2RF-encoding nucleic acid can be cloned into such an expression vector such that the fusion moiety is linked in-frame to the G2RF polypeptide.

The present invention also pertains to variants of the G2RF polypeptides which function as either G2RF agonists (mimetics) or as G2RF antagonists. Variants of the G2RF polypeptides can be generated by mutagenesis, e.g., discrete point mutation or truncation of a G2RF polypeptide. An agonist of the G2RF polypeptides can retain substantially the same, or a subset, of the biological activities of the naturally occurring form of a G2RF polypeptide. An antagonist of a G2RF polypeptide can inhibit one or more of the activities of the naturally occurring form of the G2RF polypeptide by, for example, competitively modulating a G2RF-mediated activity of a G2RF polypeptide. Thus, specific biological effects can be elicited by treatment with a variant of limited function. In one embodiment, treatment of a subject with a variant having a subset of the biological activities of the naturally occurring form of the polypeptide has fewer side effects in a subject relative to treatment with the naturally occurring form of the G2RF polypeptide.

In one embodiment, variants of a G2RF polypeptide which function as either G2RF agonists (mimetics) or as G2RF antagonists can be identified by screening combinatorial libraries of mutants, e.g., truncation mutants, of a G2RF polypeptide for G2RF polypeptide agonist or antagonist activity. In one embodiment, a variegated library of G2RF variants is generated by combinatorial mutagenesis at the nucleic acid level and is encoded by a variegated gene library. A variegated library of G2RF variants can be produced by, for example, enzymatically ligating a mixture of synthetic oligonucleotides into gene sequences such that a degenerate set of potential G2RF sequences is expressible as individual polypeptides, or alternatively, as a set of larger fusion proteins (e.g., for phage display) containing the set of G2RF sequences therein. There are a variety of methods which can be used to produce libraries of potential G2RF variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential G2RF sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a G2RF polypeptide coding sequence can be used to generate a variegated population of G2RF fragments for screening and subsequent selection of variants of a G2RF polypeptide. In one embodiment, a library of coding sequence fragments can be generated by treating a double stranded PCR fragment of a G2RF coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the G2RF polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of G2RF polypeptides. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify G2RF variants (Arkin and Youvan (1992) *Proc. Natl. Acad. Sci. USA* 89:7811–7815; Delagrave et al. (1993) *Protein Engineering* 6(3):327–331).

In one embodiment, cell based assays can be exploited to analyze a variegated G2RF library. For example, a library of expression vectors can be transfected into a cell line, e.g., an endothelial cell line, which ordinarily responds to G2RF in a particular G2RF substrate-dependent manner. The transfected cells are then contacted with G2RF and the effect of expression of the mutant on signaling by the G2RF substrate can be detected, e.g., by monitoring cytotoxin and/or metabolite (e.g., oxaloaldehydes, hydroxycarboxylic) concentrations. Plasmid DNA can then be recovered from the cells which score for inhibition, or alternatively, potentiation of signaling by the G2RF substrate, and the individual clones further characterized.

An isolated G2RF polypeptide, or a portion or fragment thereof, can be used as an immunogen to generate antibodies that bind G2RF using standard techniques for polyclonal and monoclonal antibody preparation. A full-length G2RF polypeptide can be used or, alternatively, the invention provides antigenic peptide fragments of G2RF for use as immunogens. The antigenic peptide of G2RF comprises at least 8 amino acid residues of the amino acid sequence shown in SEQ ID NO:37 and encompasses an epitope of G2RF such that an antibody raised against the peptide forms a specific immune complex with G2RF. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of G2RF that are located on the surface of the polypeptide, e.g., hydrophilic regions, as well as regions with high antigenicity (see, for example, FIG. 60).

A G2RF immunogen typically is used to prepare antibodies by immunizing a suitable subject, (e.g., rabbit, gG2RF, mouse or other mammal) with the immunogen. An appropriate immunogenic preparation can contain, for example, recombinantly expressed G2RF polypeptide or a chemically synthesized G2RF polypeptide. The preparation can further include an adjuvant, such as Freund's complete or incomplete adjuvant, or similar immunostimulatory agent. Immunization of a suitable subject with an immunogenic G2RF preparation induces a polyclonal anti-G2RF antibody response.

Accordingly, another aspect of the invention pertains to anti-G2RF antibodies. The term "antibody" as used herein refers to immunoglobulin molecules and immunologically active portions of immunoglobulin molecules, i.e., molecules that contain an antigen binding site which specifically binds (immunoreacts with) an antigen, such as G2RF. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind G2RF. The term "monoclonal antibody" or "monoclonal antibody composition", as used herein, refers to a population of antibody molecules that contain only one species of an antigen binding site capable of immunoreacting with a particular epitope of G2RF. A monoclonal antibody composition thus typically displays a single binding affinity for a particular G2RF polypeptide with which it immunoreacts.

Polyclonal anti-G2RF antibodies can be prepared as described above by immunizing a suitable subject with a G2RF immunogen. The anti-G2RF antibody titer in the immunized subject can be monitored over time by standard techniques, such as with an enzyme linked immunosorbent assay (ELISA) using immobilized G2RF. If desired, the antibody molecules directed against G2RF can be isolated from the mammal (e.g., from the blood) and further purified by well known techniques, such as protein A chromatography to obtain the IgG fraction. At an appropriate time after immunization, e.g., when the anti-G2RF antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem* 0.255: 4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a G2RF immunogen as described above, and the culture supernatants of the resulting hybridoma cells are screened to identify a hybridoma producing a monoclonal antibody that binds G2RF.

Any of the many well known protocols used for fusing lymphocytes and immortalized cell lines can be applied for the purpose of generating an anti-G2RF monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC (Manassas, Va.). Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind G2RF, e.g., using a standard ELISA assay.

Alternative to preparing monoclonal antibody-secreting hybridomas, a monoclonal anti-G2RF antibody can be identified and isolated by screening a recombinant combinatorial immunoglobulin library (e.g., an antibody phage display library) with G2RF to thereby isolate immunoglobulin library members that bind G2RF. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1369–1372; Hay et al. (1992) *Hum. Antibod. Hybridomas* 3:81–85; Huse et al. (1989) *Science* 246:1275–1281; Griffiths et al. (1993) *EMBO J.* 12:725–734; Hawkins et al. (1992) *J. Mol. Biol.* 226: 889–896; Clackson et al. (1991) *Nature* 352:624–628; Gram et al. (1992) *Proc. Natl. Acad. Sci. USA* 89:3576–3580; Garrard et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-G2RF antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171, 496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225, 539; Jones et al. (1986) *Nature* 321:552–525; Verhoeyen et al. (1988) *Science* 239:1534; and Beidler et al. (1988) *J. Immunol.* 141:4053–4060.

An anti-G2RF antibody (e.g., monoclonal antibody) can be used to isolate G2RF by standard techniques, such as affinity chromatography or immunoprecipitation. An anti-G2RF antibody can facilitate the purification of natural G2RF from cells and of recombinantly produced G2RF expressed in host cells. Moreover, an anti-G2RF antibody can be used to detect G2RF polypeptide (e.g., in a cellular lysate or cell supernatant) in order to evaluate the abundance and pattern of expression of the G2RF polypeptide. Anti-G2RF antibodies can be used diagnostically to monitor polypeptide levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, for example recombinant expression vectors, containing a nucleic acid containing a G2RF nucleic acid molecule or vectors containing a nucleic acid molecule which encodes a G2RF polypeptide (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Meth-*

*ods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of polypeptide desired, and the like. The expression vectors of the invention can be introduced into host cells to thereby produce proteins or peptides, including fusion proteins or peptides, encoded by nucleic acids as described herein (e.g., G2RF polypeptides, mutant forms of G2RF polypeptides, fusion proteins, and the like).

Accordingly, an exemplary embodiment provides a method for producing a polypeptide, preferably a G2RF polypeptide, by culturing in a suitable medium a host cell of the invention (e.g., a mammalian host cell such as a non-human mammalian cell) containing a recombinant expression vector, such that the polypeptide is produced.

The recombinant expression vectors of the invention can be designed for expression of G2RF polypeptides in prokaryotic or eukaryotic cells. For example, G2RF polypeptides can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in G2RF activity assays, (e.g., direct assays or competitive assays described in detail below), or to generate antibodies specific for G2RF polypeptides, for example. In a preferred embodiment, a G2RF fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the G2RF expression vector is a yeast expression vector. Examples of vectors for expression in yeast *S. cerevisiae* include pYepSec1 (Baldari, et al., (1987) *EMBO J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (Invitrogen Corporation, San Diego, Calif.).

Alternatively, G2RF polypeptides can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA*

86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to G2RF mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a G2RF nucleic acid molecule of the invention is introduced, e.g., a G2RF nucleic acid molecule within a vector (e.g., a recombinant expression vector) or a G2RF nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a G2RF polypeptide can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a G2RF polypeptide or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a G2RF polypeptide. Accordingly, the invention further provides methods for producing a G2RF polypeptide using the host cells of the invention. In one embodiment, the method comprises culturing the host cell of the invention (into which a recombinant expression vector encoding a G2RF polypeptide has been introduced) in a suitable medium such that a G2RF polypeptide is produced. In another embodiment, the method further comprises isolating a G2RF polypeptide from the medium or the host cell.

The host cells of the invention can also be used to produce non-human transgenic animals. For example, in one embodiment, a host cell of the invention is a fertilized oocyte or an embryonic stem cell into which G2RF-coding sequences have been introduced. Such host cells can then be used to create non-human transgenic animals in which exogenous G2RF sequences have been introduced into their genome or homologous recombinant animals in which endogenous G2RF sequences have been altered. Such animals are useful for studying the function and/or activity of a G2RF and for identifying and/or evaluating modulators of G2RF activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, gG2RFs, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous G2RF gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a G2RF-encoding nucleic acid into the male pronuclei of a fertilized oocyte, e.g., by microinjection, retroviral infection, and allowing the oocyte to develop in a pseudopregnant female foster animal. The G2RF cDNA sequence of SEQ ID NO:36 can be introduced as a transgene into the genome of a non-human animal. Alternatively, a nonhuman homologue of a human G2RF gene, such as a mouse or rat G2RF gene, can be used as a transgene. Alternatively, a G2RF gene homologue, such as another G2RF family member, can be isolated based on hybridization to the G2RF cDNA sequences of SEQ ID NO:36 or 38, (described further in subsection I above) and used as a transgene. Intronic sequences and polyadenylation signals can also be included in the transgene to increase the efficiency of expression of the transgene. A tissue-specific regulatory sequence(s) can be operably linked to a G2RF transgene to direct expression of a G2RF polypeptide to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a G2RF transgene in its genome and/or expression of G2RF mRNA in tissues or cells of the animals. A transgenic founder animal can then be used to breed additional animals carrying the transgene. Moreover, transgenic animals carrying a transgene encoding a G2RF polypeptide can further be bred to other transgenic animals carrying other transgenes.

To create a homologous recombinant animal, a vector is prepared which contains at least a portion of a G2RF gene into which a deletion, addition or substitution has been introduced to thereby alter, e.g., functionally disrupt, the G2RF gene. The G2RF gene can be a human gene (e.g., the cDNA of SEQ ID NO:38), but more preferably, is a non-human homologue of a human G2RF gene (e.g., a cDNA isolated by stringent hybridization with the nucleotide sequence of SEQ ID NO:36). For example, a mouse G2RF gene can be used to construct a homologous recombination nucleic acid molecule, e.g., a vector, suitable for altering an endogenous G2RF gene in the mouse genome. In a preferred embodiment, the homologous recombination nucleic acid molecule is designed such that, upon homologous recombination, the endogenous G2RF gene is functionally disrupted (i.e., no longer encodes a functional protein; also referred to as a "knock out" vector). Alternatively, the homologous recombination nucleic acid molecule can be designed such that, upon homologous recombination, the endogenous G2RF gene is mutated or otherwise altered but still encodes functional polypeptide (e.g., the upstream regulatory region can be altered to thereby alter the expression of the endogenous G2RF polypeptide). In the homologous recombination nucleic acid molecule, the altered portion of the G2RF gene is flanked at its 5' and 3' ends by additional nucleic acid sequence of the G2RF gene to allow for homologous recombination to occur between the exogenous G2RF gene carried by the homologous recombination nucleic acid molecule and an endogenous G2RF gene in a cell, e.g., an embryonic stem cell. The additional flanking G2RF nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced G2RF gene has homologously recombined with the endogenous G2RF gene are selected (see e.g., Li, E. et al. (1992) *Cell* 69:915). The selected cells can then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The G2RF nucleic acid molecules, G2RF polypeptides, fragments of G2RF polypeptides, G2RF modulators, and anti-G2RF antibodies (also referred to herein as "active compounds") of the invention can be incorporated into pharmaceutical compositions suitable for administration. Such compositions typically comprise the nucleic acid molecule, polypeptide, or antibody and a pharmaceutically acceptable carrier. As used herein the language "pharmaceutically acceptable carrier" is intended to include any and all solvents, dispersion media, cG2RFings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR® EL solubilizer (BASF; Florham Park, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a cG2RFing such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a G2RF polypeptide, G2RF modulator or an anti-G2RF antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a polypeptide or antibody can include a single treatment or, preferably, can include a series of treatments.

In a preferred example, a subject is treated with antibody or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin, or *diphtheria* toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a G2RF polypeptide of the invention has one or more of the following activities: (1) interactions with cytotoxins and metabolites (e.g., lactoylglutathione, a glutathione-conjugated metabolite, a hydroxycarboxylic acid, and the like), (2) catalyze the metabolism of a cytotoxin or metabolite (e.g., lactoylglutathione, a glutathione-conjugated metabolite, a hydroxycarboxylic acid, and the like), (3) hydrolyze a thioester compound (e.g., lactoylglutathione, and the like), (4) catalysis of the formation of a thioester conjugation on a substrate (e.g., lactate, a hydroxycarboxylic acid), (5) modulation of signal transduction in a cell, (6) modulation of levels of cytotoxins and/or metabolites (e.g., detoxify), (7) maintenance of equilibrium of cytotoxins and/or metabolites, (8) modulation of tumor growth, (9) modulation of cellular proliferation, (10) modulation of tissue development (e.g. embryogenesis), (11) modulation of differentiation, (12) modulation of apoptosis, or (13) modulation of energy metabolism.

The isolated nucleic acid molecules of the invention can be used, for example, to express G2RF polypeptide (e.g., via a recombinant expression vector in a host cell in gene therapy applications), to detect G2RF mRNA (e.g., in a biological sample) or a genetic alteration in a G2RF gene, and to modulate G2RF activity, as described further below. The G2RF polypeptides can be used to treat disorders characterized by insufficient or excessive levels of production of a G2RF substrate (e.g., levels of cytotoxins and/or substrates) or production of G2RF inhibitors. In addition, the G2RF polypeptides can be used to screen for naturally occurring G2RF substrates, to screen for drugs or compounds which modulate G2RF activity, as well as to treat disorders characterized by insufficient or excessive production of G2RF polypeptide or production of G2RF polypeptide forms which have decreased, aberrant or unwanted activity compared to G2RF wild type polypeptide (e.g., cytotoxin- and metabolite-associated disorders such as cytotoxin and/or metabolite imbalance, cell necrosis, apoptosis, cell proliferation, cell differentiation, and/or signal transduction disorders). Moreover, the anti-G2RF antibodies of the invention can be used to detect and isolate G2RF polypeptides, to regulate the bioavailability of G2RF polypeptides, and modulate G2RF activity.

A. Screening Assays:

The invention provides a method (also referred to herein as a "screening assay") for identifying modulators, i.e., candidate or test compounds or agents (e.g., peptides, peptidomimetics, small molecules or other drugs) which bind to G2RF polypeptides, have a stimulatory or inhibitory effect on, for example, G2RF expression or G2RF activity, or have a stimulatory or inhibitory effect on, for example, the expression or activity of a G2RF substrate.

In one embodiment, the invention provides assays for screening candidate or test compounds which are substrates of a G2RF polypeptide or polypeptide or biologically active portion thereof. In another embodiment, the invention provides assays for screening candidate or test compounds which bind to or modulate the activity of a G2RF polypeptide or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds may be presented in solution (e.g., Houghten (1992) Biotechniques 13:412–421), or on beads (Lam (1991) Nature 354:82–84), chips (Fodor (1993) Nature 364:555–1556), bacteria (Ladner U.S. Pat. No. 5,223,409), spores (Ladner U.S. Pat. No. '409), plasmids (Cull et al. (1992) Proc Natl Acad Sci USA 89:1865–1869) or on phage (Scott and Smith (1990) Science 249:386–390); (Devlin (1990) Science 249:404–406); (Cwirla et al. (1990) Proc. Natl. Acad. Sci. 87:6378–6382); (Felici (1991) J. Mol. Biol. 222:301–310); (Ladner supra.).

In one embodiment, an assay is a cell-based assay in which a cell which expresses a G2RF polypeptide or biologically active portion thereof is contacted with a test compound and the ability of the test compound to modulate G2RF activity is determined. Determining the ability of the test compound to modulate G2RF activity can be accomplished by monitoring, for example, cytotoxin and/or metabolite levels (e.g., oxaloacetate, hydroxycarboxylic acid, thioester compound, or glutathione-conjugated compound levels). The cell, for example, can be of mammalian origin, e.g., a heart, placenta, lung, liver, skeletal muscle, thymus, kidney, pancreas, testis, ovary, prostate, colon, or brain cell.

The ability of the test compound to modulate G2RF binding to a substrate or to bind to G2RF can also be determined. Determining the ability of the test compound to modulate G2RF binding to a substrate can be accomplished, for example, by coupling the G2RF substrate with a radioisotope or enzymatic label such that binding of the G2RF substrate to G2RF can be determined by detecting the labeled G2RF substrate in a complex. Alternatively, G2RF could be coupled with a radioisotope or enzymatic label to monitor the ability of a test compound to modulate G2RF binding to a G2RF substrate in a complex. Determining the ability of the test compound to bind G2RF can be accomplished, for example, by coupling the compound with a radioisotope or enzymatic label such that binding of the compound to G2RF can be determined by detecting the labeled G2RF compound in a complex. For example, compounds (e.g., G2RF substrates such as cytotoxins and/or metabolites) can be labeled with $^{125}I$, $^{35}S$, $^{14}C$, $^{3}H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., G2RF substrates such as cytotoxins and/or metabolites) to interact with G2RF without the labeling of any of the interactants. For example, a microphysiometer can be used to detect the interaction of a compound with G2RF without the labeling of either the compound or the G2RF. McConnell, H. M. et al. (1992) Science 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and G2RF.

In another embodiment, an assay is a cell-based assay comprising contacting a cell expressing a G2RF target molecule (e.g., G2RF substrates such as a cytotoxin and/or a metabolite) with a test compound and determining the ability of the test compound to modulate (e.g., stimulate or inhibit) the activity of the G2RF target molecule. Determining the ability of the test compound to modulate the activity of a G2RF target molecule can be accomplished, for example, by determining the ability of the G2RF polypeptide to bind to or interact with the G2RF target molecule.

Determining the ability of the G2RF polypeptide, or a biologically active fragment thereof, to bind to or interact with a G2RF target molecule can be accomplished by one of the methods described above for determining direct binding. In a preferred embodiment, determining the ability of the G2RF polypeptide to bind to or interact with a G2RF target molecule can be accomplished by determining the activity of the target molecule. For example, the activity of the target molecule can be determined by detecting induction of a cellular second messenger of the target, detecting catalytic/enzymatic activity of the target using an appropriate substrate, detecting the induction of a reporter gene (comprising a target-responsive regulatory element operatively linked to a nucleic acid encoding a detectable marker, e.g., luciferase), or detecting a target-regulated cellular response.

In yet another embodiment, an assay of the present invention is a cell-free assay in which a G2RF polypeptide or biologically active portion thereof is contacted with a test compound and the ability of the test compound to bind to the G2RF polypeptide or biologically active portion thereof is determined. Preferred biologically active portions of the G2RF polypeptides to be used in assays of the present invention include fragments which participate in interactions with non-G2RF molecules, e.g., fragments with high surface probability scores (see, for example, FIG. 60). Binding of the test compound to the G2RF polypeptide can be determined either directly or indirectly as described above. In a preferred embodiment, the assay includes contacting the G2RF polypeptide or biologically active portion thereof with a known compound which binds G2RF to form an assay mixture, contacting the assay mixture with a test compound, and determining the ability of the test compound to interact with a G2RF polypeptide, wherein determining the ability of the test compound to interact with a G2RF polypeptide comprises determining the ability of the test compound to preferentially bind to G2RF or biologically active portion thereof as compared to the known compound.

In another embodiment, the assay is a cell-free assay in which a G2RF polypeptide or biologically active portion thereof is contacted with a test compound and the ability of the test compound to modulate (e.g., stimulate or inhibit) the activity of the G2RF polypeptide or biologically active portion thereof is determined. Determining the ability of the test compound to modulate the activity of a G2RF polypeptide can be accomplished, for example, by determining the ability of the G2RF polypeptide to bind to a G2RF target molecule by one of the methods described above for determining direct binding. Determining the ability of the G2RF polypeptide to bind to a G2RF target molecule can also be accomplished using a technology such as real-time Biomolecular Interaction Analysis (BIA). Sjolander, S. and Urbaniczky, C. (1991) Anal. Chem. 63:2338–2345 and Szabo et al. (1995) Curr. Opin. Struct. Biol. 5:699–705. As used herein, "BIA" is a technology for studying biospecific interactions in real time, without labeling any of the interactants (e.g., BIACORE™). Changes in the optical phenomenon of surface plasmon resonance (SPR) can be used as an indication of real-time reactions between biological molecules.

In an alternative embodiment, determining the ability of the test compound to modulate the activity of a G2RF polypeptide can be accomplished by determining the ability of the G2RF polypeptide to further modulate the activity of a downstream effector of a G2RF target molecule. For example, the activity of the effector molecule on an appropriate target can be determined or the binding of the effector to an appropriate target can be determined as previously described.

In yet another embodiment, the cell-free assay involves contacting a G2RF polypeptide or biologically active portion thereof with a known compound which binds the G2RF polypeptide to form an assay mixture, contacting the assay mixture with a test compound, and determining the ability of the test compound to interact with the G2RF polypeptide, wherein determining the ability of the test compound to interact with the G2RF polypeptide comprises determining the ability of the G2RF polypeptide to preferentially bind to or modulate the activity of a G2RF target molecule.

In more than one embodiment of the above assay methods of the present invention, it may be desirable to immobilize either G2RF or its target molecule to facilitate separation of complexed from uncomplexed forms of one or both of the proteins, as well as to accommodate automation of the assay. Binding of a test compound to a G2RF polypeptide, or interaction of a G2RF polypeptide with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/G2RF fusion proteins or glutathione-S-transferase/target fusion proteins can be adsorbed onto glutathione SEPHAROSE™ beads (Sigma Chemical, St. Louis, Mo.) or glutathione derivatized micrometer plates, which are then combined with the test compound or the test compound and either the non-adsorbed target protein or G2RF polypeptide, and the mixture incubated under conditions conducive to complex formation (e.g., at physiological conditions for salt and pH). Following incubation, the beads or micrometer plate wells are washed to remove any unbound components, the matrix immobilized in the case of beads, complex determined either directly or indirectly, for example, as described above. Alternatively, the complexes can be dissociated from the matrix, and the level of G2RF binding or activity determined using standard techniques.

Other techniques for immobilizing proteins on matrices can also be used in the screening assays of the invention. For example, either a G2RF polypeptide or a G2RF target molecule can be immobilized utilizing conjugation of biotin and streptavidin. Biotinylated G2RF polypeptide or target molecules can be prepared from biotin-NHS (N-hydroxy-succinimide) using techniques known in the art (e.g., biotinylation kit, Pierce Chemicals, Rockford, Ill.), and immobilized in the wells of streptavidin-cG2RFed 96 well plates (Pierce Chemical). Alternatively, antibodies reactive with G2RF polypeptide or target molecules but which do not interfere with binding of the G2RF polypeptide to its target molecule can be derivatized to the wells of the plate, and unbound target or G2RF polypeptide trapped in the wells by antibody conjugation. Methods for detecting such complexes, in addition to those described above for the GST-immobilized complexes, include immunodetection of complexes using antibodies reactive with the G2RF polypeptide or target molecule, as well as enzyme-linked assays which rely on detecting an enzymatic activity associated with the G2RF polypeptide or target molecule.

In another embodiment, modulators of G2RF expression are identified in a method wherein a cell is contacted with a candidate compound and the expression of G2RF mRNA or polypeptide in the cell is determined. The level of expression of G2RF mRNA or polypeptide in the presence of the candidate compound is compared to the level of expression of G2RF mRNA or polypeptide in the absence of the candidate compound. The candidate compound can then be identified as a modulator of G2RF expression based on this comparison. For example, when expression of G2RF mRNA or polypeptide is greater (statistically significantly greater) in the presence of the candidate compound than in its absence, the candidate compound is identified as a stimulator of G2RF mRNA or polypeptide expression. Alternatively, when expression of G2RF mRNA or polypeptide is less (statistically significantly less) in the presence of the candidate compound than in its absence, the candidate compound is identified as an inhibitor of G2RF mRNA or polypeptide expression. The level of G2RF mRNA or polypeptide expression in the cells can be determined by methods described herein for detecting G2RF mRNA or polypeptide.

In yet another aspect of the invention, the G2RF polypeptides can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with G2RF ("G2RF-binding proteins" or "G2RF-bp") and are involved in G2RF activity. Such G2RF-binding proteins are also likely to be involved in the propagation of signals by the G2RF polypeptides or G2RF targets as, for example, downstream elements of a G2RF-mediated signaling pathway. Alternatively, such G2RF-binding proteins are likely to be G2RF inhibitors.

The two-hybrid system is based on the modular nature of most transcription factors, which consist of separable DNA-binding and activation domains. Briefly, the assay utilizes two different DNA constructs. In one construct, the gene that codes for a G2RF polypeptide is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a G2RF-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the G2RF polypeptide.

In another aspect, the invention pertains to a combination of two or more of the assays described herein. For example, a modulating agent can be identified using a cell-based or a cell free assay, and the ability of the agent to modulate the activity of a G2RF polypeptide can be confirmed in vivo, e.g., in an animal such as an animal model for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein (e.g., a G2RF modulating agent, an antisense G2RF nucleic acid molecule, a G2RF-specific antibody, or a G2RF-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the G2RF nucleotide sequences, described herein, can be used to map the location of the G2RF genes on a chromosome. The mapping of the G2RF sequences to chromosomes is an important first step in correlating these sequences with genes associated with disease.

Briefly, G2RF genes can be mapped to chromosomes by preparing PCR primers (preferably 15–25 bp in length) from the G2RF nucleotide sequences. Computer analysis of the G2RF sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the G2RF sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220: 919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the G2RF nucleotide sequences to design oligonucleotide primers, sublocalization can be achieved with panels of fragments from specific chromosomes. Other mapping strategies which can similarly be used to map a G2RF sequence to its chromosome include in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the G2RF gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The G2RF sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the G2RF nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The G2RF nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:36 can comfortably provide positive individual identification with a panel of perhaps 10 to 1,000 primers which each yield a noncoding amplified sequence of 100 bases. If predicted coding sequences, such as those in SEQ ID NO:38 are used, a more appropriate number of primers for positive individual identification would be 500–2,000.

If a panel of reagents from G2RF nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of G2RF Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:36 are particularly appropriate for this use as greater numbers of polymorphisms occur in the noncoding regions, making it easier to differentiate individuals using this technique. Examples of polynucleotide reagents include the G2RF nucleotide sequences or portions thereof, e.g., fragments derived from the noncoding regions of SEQ ID NO:36 having a length of at least 20 bases, preferably at least 30 bases.

The G2RF nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such G2RF probes can be used to identify tissue by species and/or by organ type.

In a similar fashion, these reagents, e.g., G2RF primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining G2RF polypeptide and/or nucleic acid expression as well as G2RF activity, in the context of a biological sample (e.g., blood, serum, cells, tissue) to thereby determine whether an individual is afflicted with a disease or disorder, or is at risk of developing a disorder, associated with aberrant or unwanted G2RF expression or activity. The invention also provides for prognostic (or predictive) assays for determining whether an individual is at risk of developing a disorder associated with G2RF polypeptide, nucleic acid expression or activity. For example, mutations in a G2RF gene can be assayed in a biological sample. Such assays can be used for prognostic or predictive purpose to thereby prophylactically treat an individual prior to the onset of a disorder characterized by or associated with G2RF polypeptide, nucleic acid expression or activity.

Another aspect of the invention pertains to monitoring the influence of agents (e.g., drugs, compounds) on the expression or activity of G2RF in clinical trials.

These and other agents are described in further detail in the following sections.

1. Diagnostic Assays

An exemplary method for detecting the presence or absence of G2RF polypeptide or nucleic acid in a biological sample involves obtaining a biological sample from a test subject and contacting the biological sample with a compound or an agent capable of detecting G2RF polypeptide or nucleic acid (e.g., mRNA, or genomic DNA) that encodes G2RF polypeptide such that the presence of G2RF polypeptide or nucleic acid is detected in the biological sample. In another aspect, the present invention provides a method for detecting the presence of G2RF activity in a biological sample by contacting the biological sample with an agent capable of detecting an indicator of G2RF activity such that the presence of G2RF activity is detected in the biological sample. A preferred agent for detecting G2RF mRNA or genomic DNA is a labeled nucleic acid probe capable of hybridizing to G2RF mRNA or genomic DNA. The nucleic acid probe can be, for example, the G2RF nucleic acid set forth in SEQ ID NO:36 or 38, or a portion thereof, such as an oligonucleotide of at least 15, 30, 50, 100, 250 or 500 nucleotides in length and sufficient to specifically hybridize under stringent conditions to G2RF mRNA or genomic DNA. Other suitable probes for use in the diagnostic assays of the invention are described herein.

A preferred agent for detecting G2RF polypeptide is an antibody capable of binding to G2RF polypeptide, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect G2RF mRNA, polypeptide, or genomic DNA in a biological sample in vitro as well as in vivo. For example, in vitro techniques for detection of G2RF mRNA include Northern hybridizations and in situ hybridizations. In vitro techniques for detection of G2RF polypeptide include enzyme linked immunosorbent assays (ELISAs), Western blots, immunoprecipitations and immunofluorescence. In vitro techniques for detection of G2RF genomic DNA include Southern hybridizations. Furthermore, in vivo techniques for detection of G2RF polypeptide include introducing into a subject a labeled anti-G2RF antibody. For example, the antibody can be labeled with a radioactive marker whose presence and location in a subject can be detected by standard imaging techniques.

The present invention also provides diagnostic assays for identifying the presence or absence of a genetic alteration characterized by at least one of (i) aberrant modification or mutation of a gene encoding a G2RF polypeptide; (ii) aberrant expression of a gene encoding a G2RF polypeptide; (iii) mis-regulation of the gene; and (iii) aberrant post-translational modification of a G2RF polypeptide, wherein a wild-type form of the gene encodes a polypeptide with a G2RF activity. "Misexpression or aberrant expression", as used herein, refers to a non-wild type pattern of gene expression, at the RNA or protein level. It includes, but is not limited to, expression at non-wild type levels (e.g., over or under expression); a pattern of expression that differs from wild type in terms of the time or stage at which the gene is expressed (e.g., increased or decreased expression (as compared with wild type) at a predetermined developmental period or stage); a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene (e.g., a pattern of increased or decreased expression (as compared with wild type) in the presence of an increase or decrease in the strength of the stimulus).

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting G2RF polypeptide, mRNA, or genomic DNA, such that the presence of G2RF polypeptide, mRNA or genomic DNA is detected in the biological sample, and comparing the presence of G2RF polypeptide, mRNA or genomic DNA in the control sample with the presence of G2RF polypeptide, mRNA or genomic DNA in the test sample.

The invention also encompasses kits for detecting the presence of G2RF in a biological sample. For example, the kit can comprise a labeled compound or agent capable of detecting G2RF polypeptide or mRNA in a biological sample; means for determining the amount of G2RF in the sample; and means for comparing the amount of G2RF in the sample with a standard. The compound or agent can be packaged in a suitable container. The kit can further comprise instructions for using the kit to detect G2RF polypeptide or nucleic acid.

2. Prognostic Assays

The diagnostic methods described herein can furthermore be utilized to identify subjects having or at risk of developing a disease or disorder associated with aberrant or unwanted G2RF expression or activity. As used herein, the term "aberrant" includes a G2RF expression or activity which deviates from the wild type G2RF expression or activity. Aberrant expression or activity includes increased or decreased expression or activity, as well as expression or activity which does not follow the wild type developmental pattern of expression or the subcellular pattern of expression. For example, aberrant G2RF expression or activity is intended to include the cases in which a mutation in the G2RF gene causes the G2RF gene to be under-expressed or over-expressed and situations in which such mutations result in a non-functional G2RF polypeptide or a polypeptide which does not function in a wild-type fashion, e.g., a polypeptide which does not interact with a G2RF substrate such as a cytotoxin and/or a metabolite (e.g., oxaloacetates, hydroxycarboxylic acids, thioester compounds, glutathione-conjugated compounds). As used herein, the term "unwanted" includes an unwanted phenomenon involved in a biological response, such as cellular proliferation. For example, the term unwanted includes a G2RF expression or activity which is undesirable in a subject.

The assays described herein, such as the preceding diagnostic assays or the following assays, can be utilized to identify a subject having or at risk of developing a disorder associated with a misregulation in G2RF polypeptide activity or nucleic acid expression, such as cytotoxin- and metabolite-associated disorders (e.g., a cell permeabilization, cell necrosis or apoptosis, triggering of second messenger, cell proliferation, cell motility, or signal transduction disorder). Alternatively, the prognostic assays can be utilized to identify a subject having or at risk for developing a disorder associated with a misregulation in G2RF polypeptide activity or nucleic acid expression, such as a cytotoxin- and a metabolite-associated disorder (e.g., a cell permeabilization, cell necrosis or apoptosis, triggering of second messenger, cell proliferation, cell motility, or signal transduction disorder). Thus, the present invention provides a method for identifying a disease or disorder associated with aberrant or unwanted G2RF expression or activity in which a test sample is obtained from a subject and G2RF polypeptide or nucleic acid (e.g., mRNA or genomic DNA) is detected, wherein the presence of G2RF polypeptide or nucleic acid is diagnostic for a subject having or at risk of developing a disease or disorder associated with aberrant or unwanted G2RF expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted G2RF expression or activity. For example, such methods can be used to determine whether a subject can be effectively treated with an agent for a cytotoxin- and metabolite-associated disorder (e.g., glyoxalase-associated disorders such as cytotoxin and/or metabolite imbalance, cell necrosis, apoptosis, cell proliferation, cell differentiation, and/or signal transduction disorders). Thus, the present invention provides methods for determining whether a subject can be effectively treated with an agent for a disorder associated with aberrant or unwanted G2RF expression or activity in which a test sample is obtained and G2RF polypeptide or nucleic acid expression or activity is detected (e.g., wherein the abundance of G2RF polypeptide or nucleic acid expression or activity is diagnostic for a subject that can be administered the agent to treat a disorder associated with aberrant or unwanted G2RF expression or activity).

The methods of the invention can also be used to detect genetic alterations in a G2RF gene, thereby determining if a subject with the altered gene is at risk for a disorder characterized by misregulation in G2RF polypeptide activity or nucleic acid expression, such as a cytotoxin- and metabolite-associated disorder (e.g., glyoxalase-associated disorders such as cytotoxin and/or metabolite imbalance, cell necrosis, apoptosis, cell proliferation, cell differentiation, and/or signal transduction disorders). In preferred embodiments, the methods include detecting, in a sample of cells from the subject, the presence or absence of a genetic alteration characterized by at least one of an alteration affecting the integrity of a gene encoding a G2RF-polypeptide, or the mis-expression of the G2RF gene. For example, such genetic alterations can be detected by ascertaining the existence of at least one of 1) a deletion of one or more nucleotides from a G2RF gene; 2) an addition of one or more nucleotides to a G2RF gene; 3) a substitution of one or more nucleotides of a G2RF gene, 4) a chromosomal rearrangement of a G2RF gene; 5) an alteration in the level of a messenger RNA transcript of a G2RF gene, 6) aberrant modification of a G2RF gene, such as of the methylation pattern of the genomic DNA, 7) the presence of a non-wild type splicing pattern of a messenger RNA transcript of a G2RF gene, 8) a non-wild type level of a G2RF-polypeptide, 9) allelic loss of a G2RF gene, and 10) inappropriate post-translational modification of a G2RF-polypeptide. As described herein, there are a large number of assays known in the art which can be used for detecting alterations in a G2RF gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the G2RF-gene (see Abravaya et al. (1995) *Nucleic Acids Res.* 23:675–682). This method can include the steps of collecting a sample of cells from a subject, isolating nucleic acid (e.g., genomic, mRNA or both) from the cells of the sample, contacting the nucleic acid sample with one or more primers which specifically hybridize to a G2RF gene under conditions such that hybridization and amplification of the G2RF-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a G2RF gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in G2RF can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in G2RF can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the G2RF gene and detect mutations by comparing the sequence of the sample G2RF with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the G2RF gene include methods in which protection from cleavage agents is used to detect mismatched bases in RNA/RNA or RNA/DNA heteroduplexes (Myers et al. (1985) *Science* 230:

1242). In general, the art technique of "mismatch cleavage" starts by providing heteroduplexes of formed by hybridizing (labeled) RNA or DNA containing the wild-type G2RF sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in G2RF cDNAs obtained from samples of cells. For example, the meutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a G2RF sequence, e.g., a wild-type G2RF sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in G2RF genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125–144; and Hayashi (1992) *Genet. Anal. Tech. Appl.* 9:73–79). Single-stranded DNA fragments of sample and control G2RF nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6: 1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a G2RF gene.

Furthermore, any cell type or tissue in which G2RF is expressed may be utilized in the prognostic assays described herein.

3. Monitoring of Effects During Clinical Trials

Monitoring the influence of agents (e.g., drugs) on the expression or activity of a G2RF polypeptide (e.g., the modulation of membrane excitability) can be applied not only in basic drug screening, but also in clinical trials. For example, the effectiveness of an agent determined by a screening assay as described herein to increase G2RF gene expression, polypeptide levels, or upregulate G2RF activity, can be monitored in clinical trials of subjects exhibiting decreased G2RF gene expression, polypeptide levels, or downregulated G2RF activity. Alternatively, the effectiveness of an agent determined by a screening assay to decrease G2RF gene expression, polypeptide levels, or downregulate G2RF activity, can be monitored in clinical trials of subjects exhibiting increased G2RF gene expression, polypeptide levels, or upregulated G2RF activity. In such clinical trials, the expression or activity of a G2RF gene, and preferably, other genes that have been implicated in, for example, a G2RF-associated disorder can be used as a "read out" or markers of the phenotype of a particular cell.

For example, and not by way of limitation, genes, including G2RF, that are modulated in cells by treatment with an agent (e.g., compound, drug or small molecule) which modulates G2RF activity (e.g., identified in a screening assay as described herein) can be identified. Thus, to study the effect of agents on G2RF-associated disorders (e.g., disorders characterized by deregulated glycolase activity), for example, in a clinical trial, cells can be isolated and RNA prepared and analyzed for the levels of expression of G2RF and other genes implicated in the G2RF-associated disorder, respectively. The levels of gene expression (e.g., a gene expression pattern) can be quantified by northern blot analysis or RT-PCR, as described herein, or alternatively by measuring the amount of polypeptide produced, by one of the methods as described herein, or by measuring the levels of activity of G2RF or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a G2RF polypeptide, mRNA, or genomic DNA in the preadministration sample; (iii) obtaining one or more post-administration samples from the subject; (iv) detecting the level of expression or activity of the G2RF polypeptide, mRNA, or genomic DNA in the post-administration samples; (v) comparing the level of expression or activity of the G2RF polypeptide, mRNA, or genomic DNA in the pre-administration sample with the G2RF polypeptide, mRNA, or genomic DNA in the post administration sample or samples; and (vi) altering the administration of the agent to the subject accordingly. For example, increased administration of the agent may be desirable to increase the expression or activity of G2RF to higher levels than detected, i.e., to increase the effectiveness of the agent. Alternatively, decreased administration of the agent may be desirable to decrease expression or activity of G2RF to lower levels than detected, i.e. to decrease the effectiveness of the agent. According to such an embodiment, G2RF expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder or having a disorder associated with aberrant or unwanted G2RF expression or activity (e.g., glyoxalase-associated disorders such as cytotoxin and/or metabolite imbalance, cell necrosis, apoptosis, cell proliferation, cell differentiation, and/or signal transduction disorders). As used herein, "treatment" of a subject includes the application or administration of a therapeutic agent to a subject, or application or administration of a therapeutic agent to a cell or tissue from a subject, who has a diseases or disorder, has a symptom of a disease or disorder, or is at risk of (or susceptible to) a disease or disorder, with the purpose to cure, heal, alleviate, relieve, alter, remedy, ameliorate, improve, or affect the disease or disorder, the symptom of the disease or disorder, or the risk of (or susceptibility to) the disease or disorder. As used herein, a "therapeutic agent" includes, but is not limited to, small molecules, peptides, polypeptides, antibodies, ribozymes, and antisense oligonucleotides. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the G2RF molecules of the present invention or G2RF modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted G2RF expression or activity, by administering to the subject a G2RF or an agent which modulates G2RF expression or at least one G2RF activity. Subjects at risk for a disease which is caused or contributed to by aberrant or unwanted G2RF expression or activity can be identified by, for example, any or a combination of diagnostic or prognostic assays as described herein. Administration of a prophylactic agent can occur prior to the manifestation of symptoms characteristic of the G2RF aberrancy, such that a disease or disorder is prevented or, alternatively, delayed in its progression. Depending on the type of G2RF aberrancy, for example, a G2RF, G2RF agonist or G2RF antagonist agent can be used for treating the subject. The appropriate agent can be determined based on screening assays described herein.

2. Therapeutic Methods

Another aspect of the invention pertains to methods of modulating G2RF expression or activity for therapeutic purposes. Accordingly, in an exemplary embodiment, the modulatory method of the invention involves contacting a cell capable of expressing G2RF with an agent that modulates one or more of the activities of G2RF polypeptide activity associated with the cell, such that G2RF activity in the cell is modulated. An agent that modulates G2RF polypeptide activity can be an agent as described herein, such as a nucleic acid or a polypeptide, a naturally-occurring target molecule of a G2RF polypeptide (e.g., a G2RF substrate), a G2RF antibody, a G2RF agonist or antagonist, a peptidomimetic of a G2RF agonist or antagonist, or other small molecule. In one embodiment, the agent stimulates one or more G2RF activities. Examples of such stimulatory agents include active G2RF polypeptide and a nucleic acid molecule encoding G2RF that has been introduced into the cell. In another embodiment, the agent inhibits one or more G2RF activities. Examples of such inhibitory agents include antisense G2RF nucleic acid molecules, anti-G2RF antibodies, and G2RF inhibitors. These modulatory methods can be performed in vitro (e.g., by culturing the cell with the agent) or, alternatively, in vivo (e.g., by administering the agent to a subject). By way of example, glycolase enzyme inhibitors and substrates and their contemplated use in cancer therapy are discussed in Lo and Thornalley (1993) *Biochem. Soc. Trans.* 21:159S, and Murthy et al. (1994) *J. Med. Chem.* 37:2161–2166. As such, the present invention provides methods of treating an individual afflicted with a disease or disorder characterized by aberrant or unwanted expression or activity of a G2RF polypeptide or nucleic acid molecule. In one embodiment, the method involves administering an agent (e.g., an agent identified by a screening assay described herein), or combination of agents that modulates (e.g., upregulates or downregulates) G2RF expression or activity. In another embodiment, the method involves administering a G2RF polypeptide or nucleic acid molecule as therapy to compensate for reduced, aberrant, or unwanted G2RF expression or activity.

Stimulation of G2RF activity is desirable in situations in which G2RF is abnormally downregulated and/or in which increased G2RF activity is likely to have a beneficial effect.

Likewise, inhibition of G2RF activity is desirable in situations in which G2RF is abnormally upregulated and/or in which decreased G2RF activity is likely to have a beneficial effect.

3. Pharmacogenomics

The G2RF molecules of the present invention, as well as agents, or modulators which have a stimulatory or inhibitory effect on G2RF activity (e.g., G2RF gene expression) as identified by a screening assay described herein can be administered to individuals to treat (prophylactically or therapeutically) G2RF-associated disorders (e.g., cytotoxin- and metabolite-associated disorders such as cytotoxin and/or metabolite imbalance, cell necrosis, apoptosis, cell proliferation, cell differentiation, and/or signal transduction disorders) associated with aberrant or unwanted G2RF activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a G2RF molecule or G2RF modulator as well as tailoring the dosage and/or therapeutic regimen of treatment with a G2RF molecule or G2RF modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11): 983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a G2RF polypeptide of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a G2RF molecule or G2RF modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a G2RF molecule or G2RF modulator, such as a modulator identified by one of the exemplary screening assays described herein.

4. Use of G2RF Molecules as Surrogate Markers

The G2RF molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the G2RF molecules of the invention may be detected, and may be correlated with one or more biological states in vivo. For example, the G2RF molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrum.* 35:258–264; and James (1994) *AIDS Treatment News Archive* 209.

The G2RF molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a G2RF marker) transcription or expression, the amplified marker may be in a quantity which is more readily detectable than the drug itself. Also, the marker may be more easily detected due to the nature of the marker itself; for example, using the methods described herein, anti-G2RF antibodies may be employed in an immune-based detection system for a G2RF polypeptide marker, or G2RF-specific radiolabeled probes may be used to detect a G2RF mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *En. Health Perspex.* 90: 229–238; Schentag (1999) *Am. J. Health-Syst. Pharm.* 56: S21–S24; and Nicolau (1999) *Am, J. Health-Syst. Pharm.* 56 Suppl. 3: S16–S20.

The G2RF molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35(12): 1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or polypeptide (e.g., G2RF polypeptide or G2RF RNA) which can function as specific tumor markers in a subject, a drug or course of treatment may be selected that is optimized for the treatment of the specific tumor likely to be present in the subject. Similarly, the presence or absence of a specific sequence mutation in G2RF DNA may correlate G2RF drug response. The use of pharmacogenomic markers therefore permits the application of the most appropriate treatment for each subject without having to administer the therapy.

VI. Electronic Apparatus Readable Media and Arrays

Electronic apparatus readable media comprising G2RF sequence information is also provided. As used herein, "G2RF sequence information" refers to any nucleotide and/or amino acid sequence information particular to the G2RF molecules of the present invention, including but not limited to full-length nucleotide and/or amino acid sequences, partial nucleotide and/or amino acid sequences, polymorphic sequences including single nucleotide polymorphisms (SNPs), epitope sequences, and the like. Moreover, information "related to" said G2RF sequence information includes detection of the presence or absence of a sequence (e.g., detection of expression of a sequence, fragment, polymorphism, etc.), determination of the level of a sequence (e.g., detection of a level of expression, for example, a quantitative detection), detection of a reactivity to a sequence (e.g., detection of protein expression and/or levels, for example, using a sequence-specific antibody), and the like. As used herein, "electronic apparatus readable media" refers to any suitable medium for storing, holding, or containing data or information that can be read and accessed directly by an electronic apparatus. Such media can include, but are not limited to: magnetic storage media, such as floppy discs, hard disc storage medium, and magnetic tape; optical storage media such as compact discs; electronic storage media such as RAM, ROM, EPROM, EEPROM and the like; and general hard disks and hybrids of these categories such as magnetic/optical storage media. The medium is adapted or configured for having recorded thereon G2RF sequence information of the present invention.

As used herein, the term "electronic apparatus" is intended to include any suitable computing or processing apparatus or other device configured or adapted for storing data or information. Examples of electronic apparatus suitable for use with the present invention include stand-alone computing apparatuses; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the G2RF sequence information.

A variety of software programs and formats can be used to store the sequence information on the electronic apparatus readable medium. For example, the sequence information can be represented in a word processing text file, formatted in commercially-available software such as WordPerfect and Microsoft Word, represented in the form of an ASCII file, or stored in a database application, such as DB2, Sybase, Oracle, or the like, as well as in other forms. Any number of dataprocessor structuring formats (e.g., text file or database) may be employed in order to obtain or create a medium having recorded thereon the G2RF sequence information.

By providing G2RF sequence information in readable form, one can routinely access the sequence information for a variety of purposes. For example, one skilled in the art can use the sequence information in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has a G2RF associated disease or disorder or a pre-disposition to a G2RF associated disease or disorder, wherein the method comprises the steps of determining G2RF sequence information associated with the subject and based on the G2RF sequence information, determining whether the subject has a G2RF associated disease or disorder or a pre-disposition to a G2RF associated disease or disorder, and/or recommending a particular treatment for the disease, disorder, or pre-disease condition.

The present invention further provides in an electronic system and/or in a network, a method for determining whether a subject has a G2RF associated disease or disorder or a pre-disposition to a disease associated with G2RF wherein the method comprises the steps of determining G2RF sequence information associated with the subject, and based on the G2RF sequence information, determining whether the subject has a G2RF associated disease or disorder or a pre-disposition to a G2RF associated disease or disorder, and/or recommending a particular treatment for the disease, disorder or pre-disease condition. The method may further comprise the step of receiving phenotypic information associated with the subject and/or acquiring from a network phenotypic information associated with the subject.

The present invention also provides in a network, a method for determining whether a subject has a G2RF associated disease or disorder or a pre-disposition to a G2RF associated disease or disorder associated with G2RF, said method comprising the steps of receiving G2RF sequence information from the subject and/or information related thereto, receiving phenotypic information associated with the subject, acquiring information from the network corresponding to G2RF and/or a G2RF associated disease or disorder, and based on one or more of the phenotypic information, the G2RF information (e.g., sequence information and/or information related thereto), and the acquired information, determining whether the subject has a G2RF associated disease or disorder or a pre-disposition to a G2RF associated disease or disorder. The method may further comprise the step of recommending a particular treatment for the disease, disorder or pre-disease condition.

The present invention also provides a business method for determining whether a subject has a G2RF associated disease or disorder or a pre-disposition to a G2RF associated disease or disorder, said method comprising the steps of receiving information related to G2RF (e.g., sequence information and/or information related thereto), receiving phenotypic information associated with the subject, acquiring information from the network related to G2RF and/or related to a G2RF associated disease or disorder, and based on one or more of the phenotypic information, the G2RF information, and the acquired information, determining whether the subject has a G2RF associated disease or disorder or a pre-disposition to a G2RF associated disease or disorder. The method may further comprise the step of recommending a particular treatment for the disease, disorder or pre-disease condition.

The invention also includes an array comprising a G2RF sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, one of which can be G2RF. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a G2RF associated disease or disorder, progression of G2RF associated disease or disorder, and processes, such a cellular transformation associated with the G2RF associated disease or disorder.

The array is also useful for ascertaining the effect of the expression of a gene on the expression of other genes in the same cell or in different cells (e.g., ascertaining the effect of G2RF expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including G2RF) that could serve as a molecular target for diagnosis or therapeutic intervention.

This invention is further illustrated by the following examples which should not be construed as limiting. The contents of all references, patents and published patent applications cited throughout this application, as well as the Figures and the Sequence Listing, are incorporated herein by reference.

EXAMPLES

Example 1

Identification and Characterization of Human G2RF cDNA

In this example, the identification and characterization of the gene encoding human G2RF (clone 50566) is described.

Isolation of the Human G2RF cDNA

The invention is based, at least in part, on the discovery of a human gene encoding a novel polypeptide, referred to herein as human G2RF. The entire sequence of the human clone 50566 was determined and found to contain an open reading frame termed human "G2RF." The nucleotide sequence of the human G2RF gene is set forth in FIG. 59 and in the Sequence Listing as SEQ ID NO:36. The amino acid sequence of the human G2RF expression product is set forth in FIG. 59 and in the Sequence Listing as SEQ ID NO:37. The G2RF polypeptide comprises about 282 amino acids. The coding region (open reading frame) of SEQ ID NO:36 is set forth as SEQ ID NO:38.

Analysis of the Human G2RF Molecules

A search using the polypeptide sequence of SEQ ID NO:37 was performed against the HMM database in PFAM (FIG. 61) resulting in the identification of a metallo-beta-lactamase superfamily domain in the amino acid sequence of human G2RF at about residues 7–172 of SEQ ID NO:37 (score=133.3).

A search using the polypeptide sequence of SEQ ID NO:37 was also performed against the Memsat database (FIG. 60), resulting in the identification of a potential transmembrane domain in the amino acid sequence of human G2RF (SEQ ID NO:37) at about residues 129–145, and the identification of a potential signal peptide in the amino acid sequence of human G2RF at about residues 1–54 of SEQ ID NO:37.

Further domain motifs were identified by using the amino acid sequence of 50566 (SEQ ID NO:37) to search the ProDom database (for ProDom information, refer to Institute National de la Recherche Agronomique (INRA)/Central National de la Recherche Scientifique (CNRS), Toulouse, France).

Numerous matches against protein domains described as "Hydrolase II Hydroxyacylglutathione Glyoxalase Glx Zinc Cytoplasmic Plasmid Peptide Multigene", Hydrolase Similar Flavoprotein Rv2260 Tuberculosis Mycobacterium PH1213", "Hydrolase II Hydroxyacylglutathione Zinc Glyoxalase Glx Precursor Family", "II Hydrolase Glyoxalase Glx Hydroxyacylglutathione Zinc Precursor Specific MNCB-5687 Peptide" and the like were identified. A search was also performed against the Prosite database, which resulted in the identification of a potential "cAMP- and cGMP-dependent protein kinase phosphorylation site" at residues 232–235 (Prosite accession number PS00004), two potential "Protein kinase C phosphorylation sites" at residues 86–88 and 235–237 (Prosite accession number PS00005), multiple potential "Casein kinase II phosphorylation sites" at residues 143–146, 155–158, 177–180 and 213–216 (Prosite accession number PS00006), and multiple potential N-myristoylation sites at residues 44–49, 140–145 and 274–279 (Prosite accession number PS00008).

The amino acid sequence of human G2RF was analyzed using the program PSORT (see the PSORT website maintained by the Human Genome at the Institute of Medical Science in the University of Tokyo, Japan (psort.nibb.ac.jp)) to predict the localization of the proteins within the cell. This program assesses the presence of different targeting and localization amino acid sequences within the query sequence. The results of the analyses show that human G2RF may be localized to the cytoplasm, nucleus, mitochondria, or golgi.

Tissue Distribution of Human G2RF mRNA

This example describes the tissue distribution of human G2RF mRNA, as may be determined by in situ hybridization analysis using oligonucleotide probes based on the human G2RF sequence.

For in situ analysis, various tissues, e.g. tissues obtained from brain, are first frozen on dry ice. Ten-micrometer-thick sections of the tissues are postfixed with 4% formaldehyde in DEPC treated 1× phosphate-buffered saline at room temperature for 10 minutes before being rinsed twice in DEPC 1× phosphate-buffered saline and once in 0.1 M triethanolamine-HCl (pH 8.0). Following incubation in 0.25% acetic anhydride-0.1 M triethanolamine-HCl for 10 minutes, sections are rinsed in DEPC 2×SSC (1×SSC is 0.15M NaCl plus 0.015M sodium citrate). Tissue is then dehydrated through a series of ethanol washes, incubated in 100% chloroform for 5 minutes, and then rinsed in 100% ethanol for 1 minute and 95% ethanol for 1 minute and allowed to air dry.

Hybridizations are performed with $^{35}$S-radiolabeled ($5\times10^7$ cpm/ml) cRNA probes. Probes are incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1× Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides are washed with 2×SSC. Sections are then sequentially incubated at 37° C. in TNE (a solution containing 10 mM Tris-HCl (pH 7.6), 500 mM NaCl, and 1 mM EDTA), for 10 minutes, in TNE with 10 μg of RNase A per ml for 30 minutes, and finally in TNE for 10 minutes. Slides are then rinsed with 2×SSC at room temperature, washed with 2×SSC at 50° C. for 1 hour, washed with 0.2×SSC at 55° C. for 1 hour, and 0.2×SSC at 60° C. for 1 hour. Sections are then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

Example 2

Expression of Recombinant G2RF Polypeptide in Bacterial Cells

In this example, human G2RF is expressed as a recombinant glutathione-S-transferase (GST) fusion polypeptide in E. coli and the fusion polypeptide is isolated and characterized. Specifically, G2RF is fused to GST and this fusion polypeptide is expressed in E. coli, e.g., strain PEB199. Expression of the GST-G2RF fusion polypeptide in PEB199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant G2RF Polypeptide in COS Cells

To express the human G2RF gene in COS cells, the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire G2RF polypeptide and an HA tag (Wilson et al. (1984) *Cell* 37:767) or a FLAG tag fused in-frame to its 3' end of the fragment is cloned into the polylinker region of the vector, thereby placing the expression of the recombinant polypeptide under the control of the CMV promoter.

To construct the plasmid, the human G2RF DNA sequence is amplified by PCR using two primers. The 5' primer contains the restriction site of interest followed by approximately twenty nucleotides of the G2RF coding sequence starting from the initiation codon; the 3' end sequence contains complementary sequences to the other restriction site of interest, a translation stop codon, the HA tag or FLAG tag and the last 20 nucleotides of the G2RF coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the G2RF gene is inserted in the correct orientation. The ligation mixture is transformed into E. coli cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the human G2RF-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual*. 2nd, ed., Cold Spring Harbor Laboratory, Cold Spring Harbor Laboratory Press, Cold Spring Harbor, N.Y., 1989. The expression of the IC54420 polypeptide is detected by radiolabeling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the human G2RF coding sequence is cloned directly into the polylinker of the pcDNA/Amp vector using the appropriate restriction sites. The resulting plasmid is transfected into COS cells in the manner described above, and the expression of the G2RF polypeptide is detected by radiolabeling and immunoprecipitation using a G2RF-specific monoclonal antibody.

Example 4

Tissue Distribution of Human G2RF by Taqman Expression Analysis

Tissue Expression Analysis of G2RF mRNA Using Taqman Analysis

This example describes the tissue distribution of human G2RF mRNA in a variety of cells and tissues, as determined using the TaqMan™ procedure. The Taqman™ procedure is a quantitative, reverse transcription PCR-based approach for detecting mRNA. The RT-PCR reaction exploits the 5' nuclease activity of AmpliTaq Gold™ DNA Polymerase to cleave a TaqMan™ probe during PCR. Briefly, cDNA was generated from the samples of interest, e.g., tumor samples and normal samples, cell lines and the like, and used as the starting material for PCR amplification. In addition to the 5' and 3' gene-specific primers, a gene-specific oligonucleotide probe (complementary to the region being amplified) was included in the reaction (i.e., the Taqman™ probe). The TaqMan™ probe includes the oligonucleotide with a fluorescent reporter dye covalently linked to the 5' end of the probe (such as FAM (6-carboxyfluorescein), TET (6-carboxy-4,7,2',7'-tetrachlorofluorescein), JOE (6-carboxy-4,5-dichloro-2,7-dimethoxyfluorescein), or VIC) and a quencher dye (TAMRA (6-carboxy-N,N,N',N'-tetramethylrhodamine) at the 3' end of the probe.

When the fluorescently tagged oligonucleotide is intact, the fluorescent signal from the 5' dye is quenched. As PCR proceeds, the 5' to 3' nucleolytic activity of taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a way of quantitating the initial template concentration. Accumulation of PCR products is detected directly by monitoring the increase in fluorescence of the reporter dye. When the probe is intact, the proximity of the reporter dye to the quencher dye results in suppression of the reporter fluorescence. During PCR, if the target of interest is present, the probe specifically anneals between the forward and reverse primer sites. The 5'-3' nucleolytic activity of the AmpliTaq™ Gold DNA Polymerase cleaves the probe between the reporter and the quencher only if the probe hybridizes to the target. The probe fragments are then displaced from the target, and polymerization of the strand continues. The 3' end of the probe is blocked to prevent extension of the probe during PCR. This process occurs in every cycle and does not interfere with the exponential accumulation of product. Samples can be internally controlled by the addition of a second set of primers/probe specific for a housekeeping gene such as P2 microglobulin which has been labeled with a different fluor on the 5' end (typically JOE).

To determine the level of G2RF in various tissues a primer/probe set was designed using Primer Express software and primary cDNA sequence information. Total RNA was prepared from a series of tissues using an RNeasy kit from Qiagen First strand cDNA was prepared from one µg total RNA using an oligo dT primer and Superscript II reverse transcriptase (GIBCO-BRL). cDNA obtained from approximately 50 ng total RNA was used per TaqMan reaction. Mock cDNA synthesis in the absence of reverse transcriptase resulted in samples with no detectable PCR amplification of the control gene confirms efficient removal of genomic DNA contamination.

An array of human tissues were tested. The results of one such analysis are depicted in FIG. 62. Expression was greatest in the brain cortex and hypothalamus, normal skin, heart with coronary heart failure (CHF) and erythroid cells. Expression was also high in the kidney, coronary smooth muscle cells (SMC), human umbilical vein epithelial cells (HUVEC), normal spinal cord tissue, dorsal root ganglions and colon tumor.

X. 48118, a Human Ubiquitin Carboxyl Terminal Hydrolase and uses Therefor

BACKGROUND OF THE INVENTION

The hydrolysis of chemical bonds within molecules is of critical importance in most metabolic (e.g., catabolic and anabolic) pathways in cells. A large family of enzymes which catalyze the cleavage of a bond with the addition of water, termed hydrolases, has been identified. Members of the hydrolase family are found in nearly all organisms, from microbes to plants to humans. Different classes of hydrolases are specific for an array of biological and chemical substrates. Members of the hydrolase family of enzymes include enzymes that hydrolyze ester bonds (e.g., phosphatases, sulfatases, exonucleases, and endonucleases), glycosidases, enzymes that act on ether bonds, peptidases (e.g., exopeptidases and endopeptidases), as well as enzymes that hydrolyze carbon-nitrogen bonds, acid anhydrides, carbon-carbon bonds, halide bonds, phosphorous-nitrogen bonds, sulfur-nitrogen bonds, carbon-phosphorous bonds, and sulfur-sulfur bonds (E. C. Webb ed., *Enzyme Nomenclature*, pp. 306–450, © 1992 Academic Press, Inc. San Diego, Calif.).

Hydrolases play important roles in the synthesis and breakdown of nearly all major metabolic intermediates, including polypeptides, nucleic acids, and lipids. As such, their activity contributes to the ability of the cell to grow and differentiate, to proliferate, to adhere and move, and to interact and communicate with other cells. Hydrolases also are important in the conversion of pro-proteins and pro-hormones to their active forms, the inactivation of peptides, the biotransformation of compounds (e.g., a toxin or a carcinogen), antigen presentation, and the regulation of synaptic transmission.

Ubiquitin carboxyl terminal hydrolases are responsible for de-ubiquitination in the cell and are critical in ubiquitin biosynthesis and proteosomal degradation. Because these proteins modulate ubiquitination, they are thought to be involved in numerous cellular processes which are mediated by ubiquitin including cell-cycle control, oncoprotein degradation, receptor function, regulation of transcription, stress responses, signaling pathways, antigen presentation, and the degradation of abnormal proteins (Johnston et al. (1999) *EMBO J.* 18:3877–3887).

SUMMARY OF THE INVENTION

The present invention is based, at least in part, on the discovery of novel members of the family of ubiquitin carboxyl-terminal hydrolase molecules, referred to herein as "human ubiquitin carboxyl-terminal hydrolase-1" or "HUCH-1" nucleic acid and protein molecules. The HUCH-1 nucleic acid and protein molecules of the present invention are useful as modulating agents in regulating a variety of cellular processes, e.g., processing poly-ubiquitin precursors, ubiquitin biosynthesis, and protease degradation. Accordingly, in one aspect, this invention provides isolated nucleic acid molecules encoding HUCH-1 proteins or biologically active portions thereof, as well as nucleic acid fragments suitable as primers or hybridization probes for the detection of HUCH-1-encoding nucleic acids.

In one embodiment, a HUCH-1 nucleic acid molecule of the invention is at least 50%, 55%, 60%, 65%, 70%, 74%, 75%, 80%, 85%, 89%, 90%, 95%, 96%, 97%, 98%, 99% or more identical to the nucleotide sequence (e.g., to the entire length of the nucleotide sequence) shown in SEQ ID NO:39 or 41, or a complement thereof.

In a preferred embodiment, the isolated nucleic acid molecule includes the nucleotide sequence shown in SEQ ID NO:39 or 41, or a complement thereof. In another embodiment, the nucleic acid molecule includes SEQ ID NO:41 and nucleotides 1–127 of SEQ ID NO:39. In yet a further embodiment, the nucleic acid molecule includes SEQ ID NO:41 and nucleotides 128–1229 of SEQ ID NO:39. In another preferred embodiment, the nucleic acid molecule consists of the nucleotide sequence shown in SEQ ID NO:39 or 41.

In another embodiment, a HUCH-1 nucleic acid molecule includes a nucleotide sequence encoding a protein having an amino acid sequence sufficiently identical to the amino acid sequence of SEQ ID NO:40. In a preferred embodiment, a HUCH-1 nucleic acid molecule includes a nucleotide sequence encoding a protein having an amino acid sequence at least 50%, 55%, 60%, 65%, 70%, 74%, 75%, 80%, 85%, 89%, 90%, 95%, 96%, 97%, 98%, 99% or more identical to the entire length of the amino acid sequence of SEQ ID NO:40.

In another preferred embodiment, an isolated nucleic acid molecule encodes the amino acid sequence of HUCH-1. In yet another preferred embodiment, the nucleic acid molecule includes a nucleotide sequence encoding a protein having the amino acid sequence of SEQ ID NO:40. In yet another preferred embodiment, the nucleic acid molecule is at least 50, 100, 150, 200, 250, 300, 350, 400, 450, 500, 550, 600, 650, 653, 700, 750, 800, 850, 900, 950, 1000, 1100, 1200, 1300, 1400, 1500, 1600, 1700 or more nucleotides in length. In a further preferred embodiment, the nucleic acid molecule is at least 50, 100, 150, 200, 250, 300, 350, 400, 450, 500, 550, 600, 650, 653, 700, 750, 800, 850, 900, 950, 1000, 1100, 1200, 1300, 1400, 1500, 1600, 1700 or more nucleotides in length and encodes a protein having a HUCH-1 activity (as described herein).

Another embodiment of the invention features nucleic acid molecules, preferably HUCH-1 nucleic acid molecules, which specifically detect HUCH-1 nucleic acid molecules relative to nucleic acid molecules encoding non-HUCH-1 proteins. For example, in one embodiment, such a nucleic acid molecule is at least 20, 30, 40, 50, 100, 150, 200, 250, 300, 350, 400, 450, 500, 550, 600, 650, 653, 700, 750, 800, 850, 900, 950, 1000, 1100, 1200, 1300, 1400, 1500, 1600, 1700 or more nucleotides in length and hybridizes under stringent conditions to a nucleic acid molecule comprising the nucleotide sequence shown in SEQ ID NO:39 or 41, or a complement thereof.

In preferred embodiments, the nucleic acid molecules are at least 15 nucleotides (e.g., 15 contiguous nucleotides) in length and hybridize under stringent conditions to the nucleotide molecules set forth in SEQ ID NO:39 or 41 or a complement thereof. In certain embodiments, the nucleic acid molecules are at least 15 nucleotides in length and hybridize under stringent conditions to nucleotides 1–127 and 1230–1791 of SEQ ID NO:39. In another embodiment, the nucleic acid molecules comprise nucleotides 1–127 and 1230–1791 of SEQ ID NO:39. In yet another embodiment, the nucleic acid molecules consist of nucleotides 1–23 and 1002–1332 of SEQ ID NO:39.

In other preferred embodiments, the nucleic acid molecule encodes a naturally occurring allelic variant of a polypeptide comprising the amino acid sequence of SEQ ID NO:40, wherein the nucleic acid molecule hybridizes to a nucleic acid molecule comprising SEQ ID NO:39 or 41 under stringent conditions.

Another embodiment of the invention provides an isolated nucleic acid molecule which is antisense to a HUCH-1 nucleic acid molecule, e.g., the coding strand of a HUCH-1 nucleic acid molecule.

Another aspect of the invention provides a vector comprising a HUCH-1 nucleic acid molecule. In certain embodiments, the vector is a recombinant expression vector. In another embodiment, the invention provides a host cell containing a vector of the invention. In yet another embodiment, the invention provides a host cell containing a nucleic acid molecule of the invention. The invention also provides a method for producing a protein, preferably a HUCH-1 protein, by culturing in a suitable medium, a host cell, e.g., a mammalian host cell such as a non-human mammalian cell, of the invention containing a recombinant expression vector, such that the protein is produced.

Another aspect of this invention features isolated or recombinant HUCH-1 proteins and polypeptides. In one embodiment, an isolated HUCH-1 protein includes at least one or more of the following domains: a ubiquitin carboxyl terminal hydrolase domain and/or a transmembrane domain. In a preferred embodiment, an isolated HUCH-1 protein includes at least one ubiquitin carboxyl terminal hydrolase domain.

In a preferred embodiment, a HUCH-1 protein includes at least one or more of the following domains: a ubiquitin carboxyl-terminal hydrolase family domain, and/or a transmembrane domain, and has an amino acid sequence at least about 50%, 55%, 60%, 65%, 67%, 68%, 70%, 72%, 75%, 80%, 85%, 87%, 90%, 95%, 96%, 97%, 98%, 99% or more identical to the amino acid sequence of SEQ ID NO:40.

In another preferred embodiment, a HUCH-1 protein includes at least one or more of the following domains: a ubiquitin carboxyl-terminal hydrolase family domain, and/or a transmembrane domain, and has a HUCH-1 activity (as described herein).

In yet another preferred embodiment, a HUCH-1 protein includes at least one or more of the following domains: a ubiquitin carboxyl-terminal hydrolase family domain or a transmembrane domain, and is encoded by a nucleic acid molecule having a nucleotide sequence which hybridizes under stringent hybridization conditions to a nucleic acid molecule comprising the nucleotide sequence of SEQ ID NO:39 or 41.

In another embodiment, the invention features fragments of the protein having the amino acid sequence of SEQ ID NO:40, wherein the fragment comprises at least 15 amino acids (e.g., contiguous amino acids) of the amino acid sequence of SEQ ID NO:40, In another embodiment, a HUCH-1 protein has the amino acid sequence of SEQ ID NO:40.

In another embodiment, the invention features a HUCH-1 protein which is encoded by a nucleic acid molecule consisting of a nucleotide sequence at least about 50%, 55%, 60%, 65%, 70%, 72%, 75%, 80%, 85%, 87%, 90%, 95%, 96%, 97%, 98%, 99% or more identical to a nucleotide sequence of SEQ ID NO:39 or 41, or a complement thereof. This invention further features a HUCH-1 protein which is encoded by a nucleic acid molecule consisting of a nucleotide sequence which hybridizes under stringent hybridization conditions to a nucleic acid molecule comprising the nucleotide sequence of SEQ ID NO:39 or 41, or a complement thereof.

The proteins of the present invention or portions thereof, e.g., biologically active portions thereof, can be operatively linked to a non-HUCH-1 polypeptide (e.g., heterologous amino acid sequences) to form fusion proteins. The invention further features antibodies, such as monoclonal or polyclonal antibodies, that specifically bind proteins of the invention, preferably HUCH-1 proteins. In addition, the HUCH-1 proteins or biologically active portions thereof can be incorporated into pharmaceutical compositions, which optionally include pharmaceutically acceptable carriers.

In another aspect, the present invention provides a method for detecting the presence of a HUCH-1 nucleic acid molecule, protein, or polypeptide in a biological sample by contacting the biological sample with an agent capable of detecting a HUCH-1 nucleic acid molecule, protein, or polypeptide such that the presence of a HUCH-1 nucleic acid molecule, protein or polypeptide is detected in the biological sample.

In another aspect, the present invention provides a method for detecting the presence of HUCH-1 activity in a biological sample by contacting the biological sample with an agent capable of detecting an indicator of HUCH-1 activity such that the presence of HUCH-1 activity is detected in the biological sample.

In another aspect, the invention provides a method for modulating HUCH-1 activity comprising contacting a cell capable of expressing HUCH-1 with an agent that modulates HUCH-1 activity such that HUCH-1 activity in the cell is modulated. In one embodiment, the agent inhibits HUCH-1 activity. In another embodiment, the agent stimulates HUCH-1 activity. In one embodiment, the agent is an antibody that specifically binds to a HUCH-1 protein. In another embodiment, the agent modulates expression of HUCH-1 by modulating transcription of a HUCH-1 gene or translation of a HUCH-1 mRNA. In yet another embodiment, the agent is a nucleic acid molecule having a nucleotide sequence that is antisense to the coding strand of a HUCH-1 mRNA or a HUCH-1 gene.

In one embodiment, the methods of the present invention are used to treat a subject having a disorder characterized by aberrant or unwanted HUCH-1 protein or nucleic acid expression or activity by administering an agent which is a HUCH-1 modulator to the subject. In one embodiment, the HUCH-1 modulator is a HUCH-1 protein. In another embodiment the HUCH-1 modulator is a HUCH-1 nucleic acid molecule. In yet another embodiment, the HUCH-1 modulator is a peptide, peptidomimetic, or other small molecule.

In a preferred embodiment, the disorder characterized by aberrant or unwanted HUCH-1 protein or nucleic acid expression is a hydrolase-associated disorder, e.g., a central nervous system (CNS) disorder, a cardiovascular disorder, a muscular disorder, a hormonal disorder, a gastrointestinal disorder, a metabolic disorder, an inflammatory or immune system disorder, or a cell proliferation, growth, differentiation, or migration disorder.

The present invention also provides diagnostic assays for identifying the presence or absence of a genetic alteration characterized by at least one of (i) aberrant modification or mutation of a gene encoding a HUCH-1 protein; (ii) misregulation of the gene; and (iii) aberrant post-translational modification of a HUCH-1 protein, wherein a wild-type form of the gene encodes a protein with a HUCH-1 activity.

In another aspect the invention provides methods for identifying a compound that binds to or modulates the activity of a HUCH-1 protein, by providing an indicator composition comprising a HUCH-1 protein having HUCH-1 activity, contacting the indicator composition with a test compound, and determining the effect of the test compound on HUCH-1 activity in the indicator composition to identify a compound that modulates the activity of a HUCH-1 protein.

Other features and advantages of the invention will be apparent from the following detailed description and claims.

DETAILED DESCRIPTION OF THE INVENTION

The present invention is based, at least in part, on the discovery of novel molecules, referred to herein as "human ubiquitin carboxyl-terminal hydrolase-1" or "HUCH-1" nucleic acid and protein molecules, which are novel members of a family of thiol proteases which are capable of hydrolyzing the peptide bond at the C-terminal glycine of ubiquitin. Thus, these novel HUCH-1 molecules may play a role in or function in a variety of metabolic and cellular processes, e.g., processing of poly-ubiquitin precursors, ubiquitin biosynthesis, and protease degradation.

As used herein, the term "ubiquitin carboxyl-terminal hydrolase" includes a molecule which is involved in the hydrolytic cleavage of a bond within a ubiquitin-containing molecule (e.g., a peptide). Ubiquitin carboxyl-terminal hydrolase molecules are involved in the anabolism and catabolism of metabolically important biomolecules, including the metabolism of biochemical molecules necessary for energy production or storage, and for intra- or inter-cellular signaling, as well as the detoxification of potentially harmful compounds (e.g., toxins, carcinogens). Examples of hydrolases include fungal, bacterial and pancreatic lipases, acetylcholinesterases, serine carboxypeptidases, haloalkane dehalogenases, dienelactone hydrolases, $A_2$ bromoperoxidases, and thioesterases. As hydrolases, the HUCH-1 molecules of the present invention provide novel diagnostic targets and therapeutic agents to control hydrolase-associated disorders, e.g., ubiquitin carboxyl-terminal hydrolase-associated disorder.

As used herein, a "ubiquitin carboxyl-terminal hydrolase-associated disorder" or a "HUCH-1 associated disorder" includes a disorder, disease or condition which is caused or characterized by a misregulation (e.g., downregulation or upregulation) of a HUCH-1-mediated activity. Ubiquitin carboxyl-terminal hydrolase-associated disorders can detrimentally affect cellular functions such as cellular proliferation, growth, differentiation, or migration, inter- or intracellular communication; tissue function, such as cardiac function or musculoskeletal function; systemic responses in an organism, such as nervous system responses, hormonal responses (e.g., insulin response), or immune responses; and protection of cells from toxic compounds (e.g., carcinogens, toxins, or mutagens). Examples of hydrolase-associated (e.g., ubiquitin carboxyl-terminal hydrolase-associated) disorders include central nervous system disorders. Central nervous system disorders include those disorders that are affected by aberrant ubiquitination. Thus, the HUCH-1 molecules of the present invention may play a role in disorders characterized by aberrantly regulated ubiquitination. Such disorders include cognitive and neurodegenerative disorders, examples of which include, but are not limited to, Alzheimer's disease, Parkinson's disease, Huntington's disease, progressive supranuclear palsy, Pick's disease, Kuf's disease, Lewy body disease, neurofibrillary tangles, Rosenthal fibers, Mallory's hyaline, senile dementia, myasthenia gravis, Gilles de la Tourette's syndrome, multiple sclerosis, amyotrophic lateral sclerosis, progressive supranuclear palsy, epilepsy, and Creutzfeldt-Jakob disease; autonomic function disorders such as hypertension and sleep disorders, and neuropsychiatric disorders, such as depression, schizophrenia, schizoaffective disorder, korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), and bipolar affective neurological disorders, e.g., migraine and obesity. Further CNS-related disorders include, for example, those listed in the American Psychiatric Association's Diagnostic and Statistical manual of Mental Disorders (DSM), the most current version of which is incorporated herein by reference in its entirety.

Further examples of ubiquitin carboxyl-terminal hydrolase-associated disorders include cardiovascular disorders. Cardiovascular system disorders in which the HUCH-1 molecules of the invention may be directly or indirectly involved include arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrillation, Jervell syndrome, Lange-Nielsen syndrome, long-QT syndrome, congestive heart failure, sinus node dysfunction, angina, heart failure, hypertension, atrial fibrillation, atrial flutter, dilated cardiomyopathy, idiopathic cardiomyopathy, myocardial infarction, coronary artery disease, coronary artery spasm, and arrhythmia. HUCH-1 associated disorders also include disorders of the musculoskeletal system such as paralysis and muscle weakness, e.g., ataxia, myotonia, and myokymia.

HUCH-1 associated disorders also include hormonal disorders, such as conditions or diseases in which the production and/or regulation of hormones in an organism is aberrant.

Examples of such disorders and diseases include type I and type II diabetes mellitus, pituitary disorders (e.g., growth disorders), thyroid disorders (e.g., hypothyroidism or hyperthyroidism), and reproductive or fertility disorders (e.g., disorders which affect the organs of the reproductive system, e.g., the prostate gland, the uterus, or the vagina;

disorders which involve an imbalance in the levels of a reproductive hormone in a subject; disorders affecting the ability of a subject to reproduce; and disorders affecting secondary sex characteristic development, e.g., adrenal hyperplasia).

HUCH-1-associated disorders also include inflammatory or immune system disorders, examples of which include, but are not limited to viral infection, inflammatory bowel disease, ulcerative colitis, Crohn's disease, leukocyte adhesion deficiency II syndrome, peritonitis, chronic obstructive pulmonary disease, lung inflammation, asthma, acute appendicitis, septic shock, nephritis, amyloidosis, rheumatoid arthritis, chronic bronchitis, sarcoidosis, scleroderma, lupus, polymyositis, Reiter's syndrome, psoriasis, pelvic inflammatory disease, inflammatory breast disease, orbital inflammatory disease, immune deficiency disorders (e.g., HIV, common variable immunodeficiency, congenital X-linked infantile hypogammaglobulinemia, transient hypogammaglobulinemia, selective IgA deficiency, chronic mucocutaneous candidiasis, severe combined immunodeficiency), autoimmune disorders.

An HUCH-1 associated disorder also includes a hematopoietic or thrombotic disorder, for example, disseminated intravascular coagulation, thromboembolic vascular disease, anemia, lymphoma, leukemia, neutrophilia, neutropenia, myeloproliferative disorders, thrombocytosis, thrombocytopenia, von Willebrand disease, and hemophilia.

In addition, HUCH-1 associated disorders include gastrointestinal and digestive disorders including, but not limited to, esophageal disorders such as atresia and fistulas, stenosis, achalasia, esophageal rings and webs, hiatal hernia, lacerations, esophagitis, diverticula, systemic sclerosis (scleroderma), varices, esophageal tumors such as squamous cell carcinomas and adenocarcinomas, stomach disorders such as diaphragmatic hernias, pyloric stenosis, dyspepsia, gastritis, acute gastric erosion and ulceration, peptic ulcers, stomach tumors such as carcinomas and sarcomas, small intestine disorders such as congenital atresia and stenosis, diverticula, Meckel's diverticulum, pancreatic rests, ischemic bowel disease, infective enterocolitis, Crohn's disease, tumors of the small intestine such as carcinomas and sarcomas, disorders of the colon such as malabsorption, obstructive lesions such as hernias, megacolon, diverticular disease, melanosis coli, ischemic injury, hemorrhoids, angiodysplasia of right colon, inflammations of the colon such as ulcerative colitis, and tumors of the colon such as polyps and sarcomas; as well as metabolic disorders (e.g., lysosomal storage disease, type II glycogenolysis, Fabry's disease, enzyme deficiencies, and inborn errors of metabolism); hepatic disorders and renal disorders (e.g., renal failure and glomerulonephritis).

HUCH-1-associated disorders also include disorders affecting tissues in which HUCH-1 protein is expressed.

As used herein, a "ubiquitin carboxyl-terminal hydrolase-mediated activity" or a "HUCH-1-mediated activity" includes an activity which involves the cleavage, e.g., hydrolytic cleavage, of a peptide bond within a biochemical molecule containing ubiquitin, e.g., a protein. Ubiquitin carboxyl-terminal hydrolase-mediated activities include the anabolism and catabolism of metabolically important biomolecules, including the metabolism of ubiquitin, and the processing of ubiqutinated peptides and/or proteins (i.e., proteosomal degradation).

The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin, e.g., monkey proteins. Members of a family may also have common functional characteristics.

For example, the family of HUCH-1 proteins comprises at least one "ubiquitin carboxyl-terminal hydrolase family domain" in the protein or corresponding nucleic acid molecule. As used herein, the term "ubiquitin carboxyl-terminal hydrolase family domain" includes both ubiquitin carboxyl-terminal hydrolase family-1 and ubiquitin carboxyl-terminal hydrolase family-2 domains. The term ubiquitin carboxyl-terminal hydrolase family-1 domain includes a protein domain having an amino acid sequence of about 10–100 amino acid residues, preferably about 20–50 amino acid residues, and more preferably about 31 amino acid residues, and having a bit score for the alignment of the sequence to the ubiquitin carboxyl-terminal hydrolase family-1 domain (HMM) of at least about 20, 30, 40, or 50, more preferably 60 or greater. The term ubiquitin carboxyl-terminal hydrolase family-2 domain includes a protein domain having an amino acid sequence of about 40–100 amino acid residues, preferably about 50–90 amino acid residues, and more preferably about 72 amino acid residues, and having a bit score for the alignment of the sequence to the ubiquitin carboxyl-terminal hydrolase family-2 domain (HMM) of at least about 50, 60, 70, 80, 90, 100, more preferably 106 or greater. To identify the presence of a ubiquitin carboxyl-terminal hydrolase family domain in a HUCH-1 protein, and to make the determination that a protein of interest has a particular profile, the amino acid sequence of the protein is searched against a database of known protein domains (e.g., the HMM database). The ubiquitin carboxyl-terminal hydrolase family-1 domain (HMM) has been assigned the PFAM Accession PF00442 (see the PFAM website). The ubiquitin carboxyl-terminal hydrolase family-2 domain (HMM) has been assigned the PFAM Accession PF00443 (see the PFAM website). A search was performed against the HMM database resulting in the identification of a ubiquitin carboxyl-terminal hydrolase family-1 domain in the amino acid sequence of HUCH-1 at about residues 35–66 of SEQ ID NO:40 and a ubiquitin carboxyl-terminal hydrolase family-2 domain in the amino acid sequence of HUCH-1 at about residues 292–364 of SEQ ID NO:40. The results of the search are set forth in FIG. 66.

In one embodiment, a carboxyl-terminal hydrolase family-1 domain includes at least about 40–100 amino acid residues and has at least about 50–60% homology with a carboxyl-terminal hydrolase family-1 domain of HUCH-1 (e.g., residues 35–66 of SEQ ID NO:40). Preferably, a carboxyl-terminal hydrolase family-1 domain includes at least about 50–90 amino acid residues, or about 70–75 amino acid residues, and has at least 60–70% homology, preferably about 70–80%, or about 80–90% homology with an alpha/beta hydrolase fold of HUCH-1 (e.g., residues 35–66 of SEQ ID NO:40).

In another embodiment, a ubiquitin carboxyl-terminal hydrolase family-2 domain includes at least about 50–90 amino acid residues and has at least about 50–60% homology with a ubiquitin carboxyl-terminal hydrolase family-2 domain of HUCH-1 (e.g., residues 292–364 of SEQ ID NO:40). Preferably, a ubiquitin carboxyl-terminal hydrolase family-2 domain includes at least about 60–80 amino acid residues, or about 70–75 amino acid residues, and has at least 60–70% homology, preferably about 70–80%, or about 80–90% homology with a ubiquitin carboxyl-terminal hydrolase family-2 of HUCH-1 (e.g., residues 292–364 of SEQ ID NO:40).

Accordingly, HUCH-1 proteins having at least 50–60% homology, preferably about 60–70%, more preferably about 70–80%, or about 80–90% homology with a ubiquitin carboxyl-terminal hydrolase family domain (e.g., a ubiquitin carboxyl-terminal hydrolase family-1 or a ubiquitin carboxyl-terminal hydrolase family-2 domain) of HUCH-1 are within the scope of the invention.

In another embodiment, a HUCH-1 protein of the present invention is identified based on the presence of at least one "transmembrane domain". As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta W. N. et al., (1996) *Annual Rev. Neurosci.* 19: 235–263, the contents of which are incorporated herein by reference. Amino acid residues 34–56 of the native HUCH-1 protein are predicted to comprise a transmembrane domain (see FIG. 65).

Accordingly, HUCH-1 proteins having at least 50–60% homology, preferably about 60–70%, more preferably about 70–80%, or about 80–90% homology with a transmembrane domain of HUCH-1 are within the scope of the invention.

In a preferred embodiment, the HUCH-1 molecules of the invention include at least one or more of the following domains: a ubiquitin carboxyl-terminal hydrolase family domain or a transmembrane domain. In a further preferred embodiment, the HUCH-1 molecules of the invention include at least one ubiquitin carboxyl-terminal hydrolase family domain.

Isolated proteins of the present invention, preferably HUCH-1 proteins, have an amino acid sequence sufficiently identical to the amino acid sequence of SEQ ID NO:40, or are encoded by a nucleotide sequence sufficiently identical to SEQ ID NO:39 or 41. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%–80%, and even more preferably 90–95% homology across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70–80%, or 90–95% homology and share a common functional activity are defined herein as sufficiently identical.

As used interchangeably herein, a "HUCH-1 activity", "biological activity of HUCH-1" or "HUCH-1-mediated activity", includes an activity exerted by a HUCH-1 protein, polypeptide or nucleic acid molecule on a HUCH-1 responsive cell or tissue, or on a HUCH-1 protein substrate, as determined in vivo, or in vitro, according to standard techniques. In one embodiment, a HUCH-1 activity is a direct activity, such as an association with a HUCH-1 target molecule. As used herein, a "target molecule" or "binding partner" is a molecule with which a HUCH-1 protein binds or interacts in nature, such that HUCH-1 mediated function is achieved. A HUCH-1 target molecule can be a non-HUCH-1 molecule or a HUCH-1 protein or polypeptide of the present invention. In an exemplary embodiment, a HUCH-1 target molecule is a HUCH-1 substrate (e.g., a peptide). Alternatively, a HUCH-1 activity is an indirect activity, such as a cellular signaling activity mediated by interaction of the HUCH-1 protein with a HUCH-1 ligand or substrate. The biological activities of HUCH-1 are described herein. For example, the HUCH-1 proteins of the present invention can have one or more of the following activities: 1) modulation of the metabolism of biochemical molecules necessary for energy production or storage, 2) modulation of the conversion of pro-proteins and/or pro-hormones to their active forms; 3) modulation of the inactivation of peptides; 4) modulation of intra- or inter-cellular signaling; 5) modulation of the biotransformation and detoxification of potentially harmful compounds; and 6) modulation of the anabolism and/or catabolism of metabolically important biomolecules (e.g., ubiquitin containing proteins).

In one embodiment, a HUCH-1 activity is a hydrolase activity. In another embodiment, a HUCH-1 activity is a thiol protease activity.

Accordingly, another embodiment of the invention features isolated HUCH-1 proteins and polypeptides having a HUCH-1 activity. Other preferred proteins are HUCH-1 proteins having one or more of the following domains: ubiquitin carboxyl-terminal hydrolase family domain, and/or a transmembrane domain, and, preferably, a HUCH-1 activity.

Additional preferred proteins have at least one ubiquitin carboxyl-terminal hydrolase family domain, and a transmembrane domain, and are, preferably, encoded by a nucleic acid molecule having a nucleotide sequence which hybridizes under stringent hybridization conditions to a nucleic acid molecule comprising the nucleotide sequence of SEQ ID NO:39 or 41.

The nucleotide sequence of the isolated HUCH-1 cDNA and the predicted amino acid sequence of the HUCH-1 polypeptide are shown in FIG. 63 and in SEQ ID NOs:39 and 40, respectively.

The HUCH-1 gene, which is approximately 1791 nucleotides in length, encodes a protein of approximately 366 amino acid residues in length.

Various aspects of the invention are described in further detail in the following subsections:

I. Isolated Nucleic Acid Molecules

One aspect of the invention pertains to isolated nucleic acid molecules that encode HUCH-1 proteins or biologically active portions thereof, as well as nucleic acid fragments sufficient for use as hybridization probes to identify HUCH-1-encoding nucleic acid molecules (e.g., HUCH-1 mRNA) and fragments for use as PCR primers for the amplification or mutation of HUCH-1 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated HUCH-1 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:39 or 41, or a portion thereof, can be isolated using standard molecular biology techniques and the sequence information provided herein. Using all or portion of the nucleic acid sequence of SEQ ID NO:39 or 41, as a hybridization probe, HUCH-1 nucleic acid molecules can be isolated using standard hybridization and cloning techniques (e.g., as described in Sambrook, J., Fritsh, E. F., and Maniatis, T. *Molecular Cloning: A Laboratory Manual*. 2nd, ed., *Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:39 or 41, can be isolated by the polymerase chain reaction (PCR) using synthetic oligonucleotide primers designed based upon the sequence of SEQ ID NO:39 or 41.

A nucleic acid of the invention can be amplified using cDNA, mRNA or, alternatively, genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to HUCH-1 nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:39 or 41. This cDNA may comprise sequences encoding the HUCH-1 protein (i.e., "the coding region", from nucleotides 128–1229), as well as 5' untranslated sequences (nucleotides 1–127) and 3' untranslated sequences (nucleotides 1230–1791) of SEQ ID NO:39. Alternatively, the nucleic acid molecule can comprise only the coding region of SEQ ID NO:39 (e.g., nucleotides 128–1229, corresponding to SEQ ID NO:3). In yet another embodiment, an isolated nucleic acid molecule of the invention consists of the nucleic acid sequence of SEQ ID NO:39 or 41.

In another preferred embodiment, an isolated nucleic acid molecule of the invention comprises a nucleic acid molecule which is a complement of the nucleotide sequence shown in SEQ ID NO:39 or 41, or a portion of any of these nucleotide sequences. A nucleic acid molecule which is complementary to the nucleotide sequence shown in SEQ ID NO:39 or 41, is one which is sufficiently complementary to the nucleotide sequence shown in SEQ ID NO:39 or 41, such that it can hybridize to the nucleotide sequence shown in SEQ ID NO:39 or 41, respectively, thereby forming a stable duplex.

In still another preferred embodiment, an isolated nucleic acid molecule of the present invention comprises a nucleotide sequence which is at least about 50%, 55%, 60%, 65%, 70%, 74%, 75%, 80%, 85%, 89%, 90%, 95%, 96%, 97%, 98%, 99% or more identical to the entire length of the nucleotide sequence shown in SEQ ID NO:39 or 41, or a portion of any of these nucleotide sequences.

Moreover, the nucleic acid molecule of the invention can comprise only a portion of the nucleic acid sequence of SEQ ID NO:39 or 41, for example, a fragment which can be used as a probe or primer or a fragment encoding a portion of a HUCH-1 protein, e.g., a biologically active portion of a HUCH-1 protein. The nucleotide sequences determined from the cloning of the HUCH-1 gene allows for the generation of probes and primers designed for use in identifying and/or cloning other HUCH-1 family members, as well as HUCH-1 homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:39 or 41, of an anti-sense sequence of SEQ ID NO:39 or 41, or of a naturally occurring allelic variant or mutant of SEQ ID NO:39 or 41, In one embodiment, a nucleic acid molecule of the present invention comprises a nucleotide sequence which is greater than 50–100, 100–150, 150–200, 200–250, 250–300, 300–350, 350–400, 400–450, 450–500, 500–550, 550–600, 600–650, 653, 653–700, 700–750, 750–800, 800–850, 850–900, 900–950, 950–1000, 1000–1050, 1050–1100, 1100–1150, 1150–1200, 1200–1250, 1250–1300, 1300–1350, 1350–1400, 1400–1450, 1450–1500, 1500–1550, 1550–1600, 1600–1650, 1650–1700, 1700–1750 or more nucleotides in length and hybridizes under stringent hybridization conditions to a nucleic acid molecule of SEQ ID NO:39 or 41.

Probes based on the HUCH-1 nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a HUCH-1 protein, such as by measuring a level of a HUCH-1-encoding nucleic acid in a sample of cells from a subject e.g., detecting HUCH-1 mRNA levels or determining whether a genomic HUCH-1 gene has been mutated or deleted.

A nucleic acid fragment encoding a "biologically active portion of a HUCH-1 protein" can be prepared by isolating a portion of the nucleotide sequence of SEQ ID NO:39 or 41, which encodes a polypeptide having a HUCH-1 biological activity (the biological activities of the HUCH-1 proteins are described herein), expressing the encoded portion of the HUCH-1 protein (e.g., by recombinant expression in vitro) and assessing the activity of the encoded portion of the HUCH-1 protein.

The invention further encompasses nucleic acid molecules that differ from the nucleotide sequence shown in SEQ ID NO:39 or 41, due to degeneracy of the genetic code and thus encode the same HUCH-1 proteins as those encoded by the nucleotide sequence shown in SEQ ID NO:39 or 41, In another embodiment, an isolated nucleic acid molecule of the invention has a nucleotide sequence encoding a protein having an amino acid sequence shown in SEQ ID NO:40.

In addition to the HUCH-1 nucleotide sequences shown in SEQ ID NO:39 or 41, it will be appreciated by those skilled in the art that DNA sequence polymorphisms that lead to changes in the amino acid sequences of the HUCH-1 proteins may exist within a population (e.g., the human population). Such genetic polymorphism in the HUCH-1 genes may exist among individuals within a population due to natural allelic variation. As used herein, the terms "gene" and "recombinant gene" refer to nucleic acid molecules which include an open reading frame encoding a HUCH-1 protein, preferably a mammalian HUCH-1 protein, and can further include non-coding regulatory sequences, and introns.

Allelic variants of HUCH-1 include both functional and non-functional HUCH-1 proteins. Functional allelic variants are naturally occurring amino acid sequence variants of the HUCH-1 protein that maintain the ability to bind a HUCH-1 ligand or substrate and/or modulate cell proliferation and/or migration mechanisms, or metabolism of biochemical molecules (e.g., a peptide). Functional allelic variants will typically contain only conservative substitution of one or more amino acids of SEQ ID NO:40, or substitution, deletion or insertion of non-critical residues in non-critical regions of the protein.

Non-functional allelic variants are naturally occurring amino acid sequence variants of the HUCH-1 protein that do not have the ability to either bind a HUCH-1 ligand or substrate and/or modulate any of the HUCH-1 activities described herein. Non-functional allelic variants will typically contain a non-conservative substitution, a deletion, or insertion or premature truncation of the amino acid sequence of SEQ ID NO:40, or a substitution, insertion or deletion in critical residues or critical regions of the protein.

The present invention further provides non-human orthologues of the HUCH-1 protein. Orthologues of the HUCH-1 protein are proteins that are isolated from non-human organisms and possess the same HUCH-1 ligand or substrate binding and/or modulation of cell proliferation and/or migration mechanisms, or metabolism of biochemical molecules of the HUCH-1 protein. Orthologues of the HUCH-1 protein can readily be identified as comprising an amino acid sequence that is substantially identical to SEQ ID NO:40.

Moreover, nucleic acid molecules encoding other HUCH-1 family members and, thus, which have a nucleotide sequence which differs from the HUCH-1 sequence of SEQ ID NO:39 or 41, are intended to be within the scope of the invention. For example, another HUCH-1 cDNA can be identified based on the nucleotide sequence of HUCH-1. Moreover, nucleic acid molecules encoding HUCH-1 proteins from different species, and which thus, have a nucleotide sequence which differs from the HUCH-1 sequence of SEQ ID NO:39 or 41, are intended to be within the scope of the invention. For example, a mouse HUCH-1 cDNA can be identified based on the nucleotide sequence of a human HUCH-1.

Nucleic acid molecules corresponding to natural allelic variants and homologues of the HUCH-1 cDNA of the invention can be isolated based on their homology to the HUCH-1 nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the HUCH-1 cDNA of the invention can further be isolated by mapping to the same chromosome or locus as the HUCH-1 gene.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:39 or 41, In other embodiment, the nucleic acid is at least 50–100, 100–150, 150–200, 200–250, 250–300, 300–350, 350–400, 400–450, 450–500, 500–550, 550–600, 600–650, 650–700, 700–750, 750–800, 800–850, 850–900, 900–950, 950–1000, 1000–1050, 1050–1100, 1100–1150, 1150–1200, 1200–1250, 1250–1300, 1300–1350, 1350–1400, 1400–1450, 1450–1500, 1500–1550, 1550–1600, 1600–1650, 1650–1700, 1700–1750 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A preferred, non-limiting example of stringent hybridization conditions includes hybridization in 4×sodium chloride/sodium citrate (SSC), at about 65–70° C. (or hybridization in 4×SSC plus 50% formamide at about 42–50° C.) followed by one or more washes in 1×SSC, at about 65–70° C. A preferred, non-limiting example of highly stringent hybridization conditions includes hybridization in 1×SSC, at about 65–70° C. (or hybridization in 1×SSC plus 50% formamide at about 42–50° C.) followed by one or more washes in 0.3×SSC, at about 65–70° C. A preferred, non-limiting example of reduced stringency hybridization conditions includes hybridization in 4×SSC, at about 50–60° C. (or alternatively hybridization in 6×SSC plus 50% formamide at about 40–45° C.) followed by one or more washes in 2×SSC, at about 50–60° C. Ranges intermediate to the above-recited values, e.g., at 65–70° C. or at 42–50° C. are also intended to be encompassed by the present invention. SSPE (1×SSPE is 0.15M NaCl, 10 mM NaH$_2$PO$_4$, and 1.25 mM EDTA, pH 7.4) can be substituted for SSC (1×SSC is 0.1 5M NaCl and 15 mM sodium citrate) in the hybridization and wash buffers; washes are performed for 15 minutes each after hybridization is complete. The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m(°C.) = 2(\# \text{ of A+T bases}) + 4(\# \text{ of G+C bases})$. For hybrids between 18 and 49 base pairs in length, $T_m(°C.) = 81.5 + 16.6(\log_{10}[Na^+]) + 0.41(\% \text{ G+C}) - (600/N)$, where N is the number of bases in the hybrid, and [Na$^+$] is the concentration of sodium ions in the hybridization buffer ([Na$^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25–0.5M $NaH_2PO_4$, 7% SDS at about 65° C., followed by one or more washes at 0.02M $NaH_2PO_4$, 1% SDS at 65° C., see e.g., Church and Gilbert (1984) *Proc. Natl. Acad. Sci. USA* 81:1991–1995, (or, alternatively, 0.2×SSC, 1% SDS).

In addition to naturally-occurring allelic variants of the HUCH-1 sequences that may exist in the population, the skilled artisan will further appreciate that changes can be introduced by mutation into the nucleotide sequences of SEQ ID NO:39 or 41, thereby leading to changes in the amino acid sequence of the encoded HUCH-1 protein, without altering the functional ability of the HUCH-1 protein. For example, nucleotide substitutions leading to amino acid substitutions at "non-essential" amino acid residues can be made in the sequence of SEQ ID NO:39 or 41. A "non-essential" amino acid residue is a residue that can be altered from the wild-type sequence of HUCH-1 (e.g., the sequence of SEQ ID NO:40) without altering the biological activity, whereas an "essential" amino acid residue is required for biological activity. For example, amino acid residues that are conserved among the HUCH-1 proteins of the present invention, e.g., those present in an alpha/beta hydrolase fold or a catalytic triad, are predicted to be particularly unamenable to alteration. Furthermore, additional amino acid residues that are conserved between the HUCH-1 proteins of the present invention and other members of the HUCH-1 family are not likely to be amenable to alteration.

Accordingly, another aspect of the invention pertains to nucleic acid molecules encoding HUCH-1 proteins that contain changes in amino acid residues that are not essential for activity. Such HUCH-1 proteins differ in amino acid sequence from SEQ ID NO:40, yet retain biological activity. In one embodiment, the isolated nucleic acid molecule comprises a nucleotide sequence encoding a protein, wherein the protein comprises an amino acid sequence at least about 50%, 55%, 60%, 65%, 70%, 75%, 80%, 85%, 90%, 95%, 96%, 97%, 98%, 99% or more identical to SEQ ID NO:40.

An isolated nucleic acid molecule encoding a HUCH-1 protein identical to the protein of SEQ ID NO:40 can be created by introducing one or more nucleotide substitutions, additions or deletions into the nucleotide sequence of SEQ ID NO:39 or 41, such that one or more amino acid substitutions, additions or deletions are introduced into the encoded protein. Mutations can be introduced into SEQ ID NO:39 or 41, by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a HUCH-1 protein is preferably replaced with another amino acid residue from the same side chain family. Alternatively, in another embodiment, mutations can be introduced randomly along all or part of a HUCH-1 coding sequence, such as by saturation mutagenesis, and the resultant mutants can be screened for HUCH-1 biological activity to identify mutants that retain activity. Following mutagenesis of SEQ ID NO:39 or 41, the encoded protein can be expressed recombinantly and the activity of the protein can be determined.

In a preferred embodiment, a mutant HUCH-1 protein can be assayed for the ability to: 1) modulate the metabolism of biochemical molecules necessary for energy production or storage, 2) modulate the conversion of proproteins and/or prohormones to their active forms; 3) modulate the inactivation of peptides; 4) modulate intra- or intercellular signaling; 5) modulate the biotransformation and detoxification of potentially harmful compounds; and 6) modulate the anabolism and/or catabolism of metabolically important biomolecules.

In addition to the nucleic acid molecules encoding HUCH-1 proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire HUCH-1 coding strand, or to only a portion thereof. In one embodiment, an antisense nucleic acid molecule is antisense to a "coding region" of the coding strand of a nucleotide sequence encoding HUCH-1. The term "coding region" refers to the region of the nucleotide sequence comprising codons which are translated into amino acid residues (e.g., the coding region of HUCH-1 corresponds to SEQ ID NO:41). In another embodiment, the antisense nucleic acid molecule is antisense to a "noncoding region" of the coding strand of a nucleotide sequence encoding HUCH-1. The term "noncoding region" refers to 5' and 3' sequences which flank the coding region that are not translated into amino acids (i.e., also referred to as 5' and 3' untranslated regions).

Given the coding strand sequences encoding HUCH-1 disclosed herein (e.g., SEQ ID NO:41), antisense nucleic acids of the invention can be designed according to the rules of Watson and Crick base pairing. The antisense nucleic acid molecule can be complementary to the entire coding region of HUCH-1 mRNA, but more preferably is an oligonucleotide which is antisense to only a portion of the coding or noncoding region of HUCH-1 mRNA. For example, the antisense oligonucleotide can be complementary to the region surrounding the translation start site of HUCH-1 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a HUCH-1 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff and Gerlach (1988) *Nature* 334:585–591)) can be used to catalytically cleave HUCH-1 mRNA transcripts to thereby inhibit translation of HUCH-1 mRNA. A ribozyme having specificity for a HUCH-1-encoding nucleic acid can be designed based upon the nucleotide sequence of a HUCH-1 cDNA disclosed herein (i.e., SEQ ID NO:39 or 41. For example, a derivative of a *Tetrahymena* L-19 IVS RNA can be constructed in which the nucleotide sequence of the active site is complementary to the nucleotide sequence to be cleaved in a HUCH-1-encoding mRNA. See, e.g., Cech et al. U.S. Pat. No. 4,987,071; and Cech et al. U.S. Pat. No. 5,116,742. Alternatively, HUCH-1 mRNA can be used to select a catalytic RNA having a specific ribonuclease activity from a pool of RNA molecules. See, e.g., Bartel, D. and Szostak, J. W. (1993) *Science* 261:1411–1418.

Alternatively, HUCH-1 gene expression can be inhibited by targeting nucleotide sequences complementary to the regulatory region of the HUCH-1 (e.g., the HUCH-1 promoter and/or enhancers; e.g., nucleotides 1–366 of SEQ ID NO:39) to form triple helical structures that prevent transcription of the HUCH-1 gene in target cells. See generally, Helene, C. (1991) *Anticancer Drug Des.* 6(6): 569–84; Helene, C. et al. (1992) *Ann. N.Y. Acad. Sci.* 660:27–36; and Maher, L. J. (1992) *Bioassays* 14(12):807–15.

In yet another embodiment, the HUCH-1 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. *Proc. Natl. Acad. Sci.* 93: 14670–675.

PNAs of HUCH-1 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of HUCH-1 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of HUCH-1 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of HUCH-1 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

Alternatively, the expression characteristics of an endogenous HUCH-1 gene within a cell line or microorganism may be modified by inserting a heterologous DNA regulatory element into the genome of a stable cell line or cloned microorganism such that the inserted regulatory element is operatively linked with the endogenous HUCH-1 gene. For example, an endogenous HUCH-1 gene which is normally "transcriptionally silent", i.e., a HUCH-1 gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous HUCH-1 gene may be activated by insertion of a promiscuous regulatory element that works across cell types.

A heterologous regulatory element may be inserted into a stable cell line or cloned microorganism, such that it is operatively linked with an endogenous HUCH-1 gene, using techniques, such as targeted homologous recombination, which are well known to those of skill in the art, and described, e.g., in Chappel, U.S. Pat. No. 5,272,071; PCT publication No. WO 91/06667, published May 16, 1991.

II. Isolated HUCH-1 Proteins and Anti-HUCH-1 Antibodies

One aspect of the invention pertains to isolated HUCH-1 proteins, and biologically active portions thereof, as well as polypeptide fragments suitable for use as immunogens to raise anti-HUCH-1 antibodies. In one embodiment, native HUCH-1 proteins can be isolated from cells or tissue sources by an appropriate purification scheme using standard protein purification techniques. In another embodiment, HUCH-1 proteins are produced by recombinant DNA techniques. Alternative to recombinant expression, a HUCH-1 protein or polypeptide can be synthesized chemically using stand peptide synthesis techniques.

An "isolated" or "purified" protein or biologically active portion thereof is substantially free of cellular material or other contaminating proteins from the cell or tissue source from which the HUCH-1 protein is derived, or substantially free from chemical precursors or other chemicals when chemically synthesized. The language "substantially free of cellular material" includes preparations of HUCH-1 protein in which the protein is separated from cellular components of the cells from which it is isolated or recombinantly produced. In one embodiment, the language "substantially free of cellular material" includes preparations of HUCH-1 protein having less than about 30% (by dry weight) of non-HUCH-1 protein (also referred to herein as a "contaminating protein"), more preferably less than about 20% of non-HUCH-1 protein, still more preferably less than about 10% of non-HUCH-1 protein, and most preferably less than about 5% non-HUCH-1 protein. When the HUCH-1 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of HUCH-1 protein in which the protein is separated from chemical precursors or other chemicals which are involved in the synthesis of the protein. In one embodiment, the language "substantially free of chemical precursors or other chemicals" includes preparations of HUCH-1 protein having less than about 30% (by dry weight) of chemical precursors or non-HUCH-1 chemicals, more preferably less than about 20% chemical precursors or non-HUCH-1 chemicals, still more preferably less than about 10% chemical precursors or non-HUCH-1 chemicals, and most preferably less than about 5% chemical precursors or non-HUCH-1 chemicals.

As used herein, a "biologically active portion" of a HUCH-1 protein includes a fragment of a HUCH-1 protein which participates in an interaction between a HUCH-1 molecule and a non-HUCH-1 molecule. Biologically active portions of a HUCH-1 protein include peptides comprising amino acid sequences sufficiently identical to or derived from the amino acid sequence of the HUCH-1 protein, e.g., the amino acid sequence shown in SEQ ID NO:40, which include less amino acids than the full length HUCH-1 protein, and exhibit at least one activity of a HUCH-1 protein. Typically, biologically active portions comprise a domain or motif with at least one activity of the HUCH-1 protein, e.g., modulation of ubiquitin biosynthesis, proteosomal degradation, or metabolism of biochemical molecules. A biologically active portion of a HUCH-1 protein can be a polypeptide which is, for example, 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, 1275, 1300, 1325, 1350, 1375, 1400, 1425, 1450, 1475, 1500, 1525, 1550, 1575, 1600, 1625, 1650, 1675, 1700, 1725, 1750, 1775 or more amino acids in length. Biologically active portions of a HUCH-1 protein can be used as targets for developing agents which modulate a HUCH-1 mediated activity, e.g., modulation of ubiquitin biosynthesis, proteosomal degradation, or metabolism of biochemical molecules.

In one embodiment, a biologically active portion of a HUCH-1 protein comprises at least one ubiquitin carboxyl-terminal hydrolase family domain. In another embodiment, a biologically active portion of a HUCH-1 protein of the present invention may contain at least one ubiquitin carboxyl-terminal hydrolase family domain and one or more transmembrane domains. Moreover, other biologically active portions, in which other regions of the protein are deleted, can be prepared by recombinant techniques and evaluated for one or more of the functional activities of a native HUCH-1 protein.

In a preferred embodiment, the HUCH-1 protein has an amino acid sequence shown in SEQ ID NO:40. In other embodiments, the HUCH-1 protein is substantially identical to SEQ ID NO:40 and retains the functional activity of the protein of SEQ ID NO:40, yet differs in amino acid sequence due to natural allelic variation or mutagenesis, as described in detail in subsection I above. Accordingly, in another embodiment, the HUCH-1 protein is a protein which comprises an amino acid sequence at least about 50%, 55%, 60%, 65%, 70%, 75%, 80%, 85%, 90%, 95%, 96%, 97%, 98%, 99% or more identical to SEQ ID NO:40.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the HUCH-1 amino acid sequence of SEQ ID NO:40 having 366 amino acid residues, at least 110, preferably at least 146, more preferably at least 183, even more preferably at least 220, even more preferably at least 293, and even more preferably at least 330 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at the GCG website), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at the GCG website), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*Comput. Appl. Biosci.*, 4: 11–17 (1988)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to HUCH-1 nucleic acid molecules of the invention. BLAST protein searches can be performed with the XBLAST program, score=100, wordlength=3 to obtain amino acid sequences homologous to HUCH-1 protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See the NCBI website.

The invention also provides HUCH-1 chimeric or fusion proteins. As used herein, a HUCH-1 "chimeric protein" or "fusion protein" comprises a HUCH-1 polypeptide operatively linked to a non-HUCH-1 polypeptide. A "HUCH-1 polypeptide" refers to a polypeptide having an amino acid sequence corresponding to a HUCH-1 molecule, whereas a "non-HUCH-1 polypeptide" refers to a polypeptide having an amino acid sequence corresponding to a protein which is not substantially homologous to the HUCH-1 protein, e.g., a protein which is different from the HUCH-1 protein and which is derived from the same or a different organism. Within a HUCH-1 fusion protein the HUCH-1 polypeptide can correspond to all or a portion of a HUCH-1 protein. In a preferred embodiment, a HUCH-1 fusion protein comprises at least one biologically active portion of a HUCH-1 protein. In another preferred embodiment, a HUCH-1 fusion protein comprises at least two biologically active portions of a HUCH-1 protein. Within the fusion protein, the term "operatively linked" is intended to indicate that the HUCH-1 polypeptide and the non-HUCH-1 polypeptide are fused in-frame to each other. The non-HUCH-1 polypeptide can be fused to the N-terminus or C-terminus of the HUCH-1 polypeptide.

For example, in one embodiment, the fusion protein is a GST-HUCH-1 fusion protein in which the HUCH-1 sequences are fused to the C-terminus of the GST sequences. Such fusion proteins can facilitate the purification of recombinant HUCH-1.

In another embodiment, the fusion protein is a HUCH-1 protein containing a heterologous signal sequence at its N-terminus. In certain host cells (e.g., mammalian host cells), expression and/or secretion of HUCH-1 can be increased through use of a heterologous signal sequence.

The HUCH-1 fusion proteins of the invention can be incorporated into pharmaceutical compositions and administered to a subject in vivo. The HUCH-1 fusion proteins can be used to affect the bioavailability of a HUCH-1 substrate. Use of HUCH-1 fusion proteins may be useful therapeutically for the treatment of disorders caused by, for example, (i) aberrant modification or mutation of a gene encoding a HUCH-1 protein; (ii) mis-regulation of the HUCH-1 gene; and (iii) aberrant post-translational modification of a HUCH-1 protein.

Moreover, the HUCH-1 fusion proteins of the invention can be used as immunogens to produce anti-HUCH-1 antibodies in a subject, to purify HUCH-1 ligands and in screening assays to identify molecules which inhibit the interaction of HUCH-1 with a HUCH-1 substrate.

Preferably, a HUCH-1 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A HUCH-1-encoding nucleic acid can be cloned into such an expression vector such that the fusion moiety is linked in-frame to the HUCH-1 protein.

The present invention also pertains to variants of the HUCH-1 proteins which function as either HUCH-1 agonists (mimetics) or as HUCH-1 antagonists. Variants of the HUCH-1 proteins can be generated by mutagenesis, e.g., discrete point mutation or truncation of a HUCH-1 protein. An agonist of the HUCH-1 proteins can retain substantially the same, or a subset, of the biological activities of the naturally occurring form of a HUCH-1 protein. An antagonist of a HUCH-1 protein can inhibit one or more of the activities of the naturally occurring form of the HUCH-1 protein by, for example, competitively modulating a HUCH-1-mediated activity of a HUCH-1 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the HUCH-1 protein.

In one embodiment, variants of a HUCH-1 protein which function as either HUCH-1 agonists (mimetics) or as HUCH-1 antagonists can be identified by screening combinatorial libraries of mutants, e.g., truncation mutants, of a HUCH-1 protein for HUCH-1 protein agonist or antagonist activity. In one embodiment, a variegated library of HUCH-1 variants is generated by combinatorial mutagenesis at the nucleic acid level and is encoded by a variegated gene library. A variegated library of HUCH-1 variants can be produced by, for example, enzymatically ligating a mixture of synthetic oligonucleotides into gene sequences such that a degenerate set of potential HUCH-1 sequences is expressible as individual polypeptides, or alternatively, as a set of larger fusion proteins (e.g., for phage display) containing the set of HUCH-1 sequences therein. There are a variety of methods which can be used to produce libraries of potential HUCH-1 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential HUCH-1 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a HUCH-1 protein coding sequence can be used to generate a variegated population of HUCH-1 fragments for screening and subsequent selection of variants of a HUCH-1 protein. In one embodiment, a library of coding sequence fragments can be generated by treating a double stranded PCR fragment of a HUCH-1 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the HUCH-1 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of HUCH-1 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify HUCH-1 variants (Arkin and Youvan (1992) *Proc. Natl. Acad. Sci. USA* 89:7811–7815; Delagrave et al. (1993) *Protein Engineering* 6(3): 327–331).

In one embodiment, cell based assays can be exploited to analyze a variegated HUCH-1 library. For example, a library of expression vectors can be transfected into a cell line, e.g., a mammalian cell line, which ordinarily responds to a HUCH-1 ligand in a particular HUCH-1 ligand-dependent manner. The transfected cells are then contacted with a HUCH-1 ligand and the effect of expression of the mutant on, e.g., modulation of cell proliferation and/or migration mechanisms, or HUCH-1 dependent metabolism of biochemical molecules can be detected. Plasmid DNA can then be recovered from the cells which score for inhibition, or alternatively, potentiation of signaling by the HUCH-1 ligand, and the individual clones further characterized.

An isolated HUCH-1 protein, or a portion or fragment thereof, can be used as an immunogen to generate antibodies that bind HUCH-1 using standard techniques for polyclonal and monoclonal antibody preparation. A full-length HUCH-1 protein can be used or, alternatively, the invention provides antigenic peptide fragments of HUCH-1 for use as immunogens. The antigenic peptide of HUCH-1 comprises at least 8 amino acid residues of the amino acid sequence shown in SEQ ID NO:40 and encompasses an epitope of HUCH-1 such that an antibody raised against the peptide forms a specific immune complex with the HUCH-1 protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of HUCH-1 that are located on the surface of the protein, e.g., hydrophilic regions, as well as regions with high antigenicity (see, for example, FIG. 64).

A HUCH-1 immunogen typically is used to prepare antibodies by immunizing a suitable subject, (e.g., rabbit, goat, mouse or other mammal) with the immunogen. An appropriate immunogenic preparation can contain, for example, recombinantly expressed HUCH-1 protein or a chemically synthesized HUCH-1 polypeptide. The preparation can further include an adjuvant, such as Freund's complete or incomplete adjuvant, or similar immunostimulatory agent. Immunization of a suitable subject with an immunogenic HUCH-1 preparation induces a polyclonal anti-HUCH-1 antibody response.

Accordingly, another aspect of the invention pertains to anti-HUCH-1 antibodies. The term "antibody" as used herein refers to immunoglobulin molecules and immunologically active portions of immunoglobulin molecules, i.e., molecules that contain an antigen binding site which specifically binds (immunoreacts with) an antigen, such as HUCH-1. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind HUCH-1 molecules. The term "monoclonal antibody" or "monoclonal antibody composition", as used herein, refers to a population of antibody molecules that contain only one species of an antigen binding site capable of immunoreacting with a particular epitope of HUCH-1. A monoclonal antibody composition thus typically displays a single binding affinity for a particular HUCH-1 protein with which it immunoreacts.

Polyclonal anti-HUCH-1 antibodies can be prepared as described above by immunizing a suitable subject with a HUCH-1 immunogen. The anti-HUCH-1 antibody titer in the immunized subject can be monitored over time by standard techniques, such as with an enzyme linked immunosorbent assay (ELISA) using immobilized HUCH-1. If desired, the antibody molecules directed against HUCH-1 can be isolated from the mammal (e.g., from the blood) and further purified by well known techniques, such as protein A chromatography to obtain the IgG fraction. At an appropriate time after immunization, e.g., when the anti-HUCH-1 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a HUCH-1 immunogen as described above, and the culture supernatants of the resulting hybridoma cells are screened to identify a hybridoma producing a monoclonal antibody that binds HUCH-1.

Any of the many well known protocols used for fusing lymphocytes and immortalized cell lines can be applied for the purpose of generating an anti-HUCH-1 monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC (Manassa, Va.). Typically, HAT-sensitive mouse myecloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind HUCH-1, e.g., using a standard ELISA assay.

Alternative to preparing monoclonal antibody-secreting hybridomas, a monoclonal anti-HUCH-1 antibody can be identified and isolated by screening a recombinant combinatorial immunoglobulin library (e.g., an antibody phage display library) with HUCH-1 to thereby isolate immunoglobulin library members that bind HUCH-1. Kits for generating and screening phage display libraries are commercially available (e.g., the Pharmacia *Recombinant Phage Antibody System*, Catalog No. 27-9400-01; and the Stratagene *SurfZAP*™ *Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1369–1372; Hay et al. (1992) *Hum. Antibod. Hybridomas* 3:81–85; Huse et al. (1989) *Science* 246:1275–1281; Griffiths et al. (1993) *EMBO J.* 12:725–734; Hawkins et al. (1992) *J. Mol. Biol.* 226:889–896; Clackson et al. (1991)

*Nature* 352:624–628; Gram et al. (1992) *Proc. Natl. Acad. Sci. USA* 89:3576–3580; Garrard et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-HUCH-1 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by, recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyen et al. (1988) *Science* 239:1534; and Beidler et al. (1988) *J. Immunol.* 141:4053–4060.

An anti-HUCH-1 antibody (e.g., monoclonal antibody) can be used to isolate HUCH-1 by standard techniques, such as affinity chromatography or immunoprecipitation. An anti-HUCH-1 antibody can facilitate the purification of natural HUCH-1 from cells and of recombinantly produced HUCH-1 expressed in host cells. Moreover, an anti-HUCH-1 antibody can be used to detect HUCH-1 protein (e.g., in a cellular lysate or cell supernatant) in order to evaluate the abundance and pattern of expression of the HUCH-1 protein. Anti-HUCH-1 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and acquorin, and examples of suitable radioactive material include $^{125}$I, $^{131}$I, $^{35}$S or $^{3}$H.

III. Recombinant Expression Vectors and Host Cells

Another aspect of the invention pertains to vectors, preferably expression vectors, containing a nucleic acid encoding a HUCH-1 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., HUCH-1 proteins, mutant forms of HUCH-1 proteins, fusion proteins, and the like).

The recombinant expression vectors of the invention can be designed for expression of HUCH-1 proteins in prokaryotic or eukaryotic cells. For example, HUCH-1 proteins can be expressed in bacterial cells such as *E. Coli*, insect cells (using baculovirus expression vectors) yeast cells or mammalian cells. Suitable host cells are discussed further in Goeddel, *Gene Expression Technology: Methods in Etymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. Coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in HUCH-1 activity assays, (e.g., direct assays or competitive assays described in detail below), or to generate antibodies specific for HUCH-1 proteins, for example. In a preferred embodiment, a HUCH-1 fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. Coli* expression vectors include pTrc (Amann et al., (1988) *Gene* 69:301–315) and pET 11d (Studier et al., *Gene Expression Technology: Methods in Etymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. Coli* is to express the protein in a host bacteria with an impaired capacity to proteolytically cleave the recombinant protein (Gottesman, S., *Gene Expression Technology: Methods in Etymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. Coli* (Wada et al., (1992) *Nucleic Acids Res.* 20:2111–2118). Such alteration of nucleic acid sequences of the invention can be carried out by standard DNA synthesis techniques.

In another embodiment, the HUCH-1 expression vector is a yeast expression vector. Examples of vectors for expression in yeast *S. cerevisiae* include pYepSec1 (Baldari, et al., (1987) *EMBO J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (Invitrogen Corporation, San Diego, Calif.).

Alternatively, HUCH-1 proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), lung specific promoters, and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to HUCH-1 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a HUCH-1 nucleic acid molecule of the invention is introduced, e.g., a HUCH-1 nucleic acid molecule within a recombinant expression vector or a HUCH-1 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a HUCH-1 protein can be expressed in bacterial cells such as E. Coli, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a HUCH-1 protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a HUCH-1 protein. Accordingly, the invention further provides methods for producing a HUCH-1 protein using the host cells of the invention. In one embodiment, the method comprises culturing the host cell of the invention (into which a recombinant expression vector encoding a HUCH-1 protein has been introduced) in a suitable medium such that a HUCH-1 protein is produced. In another embodiment, the method further comprises isolating a HUCH-1 protein from the medium or the host cell.

The host cells of the invention can also be used to produce non-human transgenic animals. For example, in one embodiment, a host cell of the invention is a fertilized oocyte or an embryonic stem cell into which HUCH-1 coding sequences have been introduced. Such host cells can then be used to create non-human transgenic animals in which exogenous HUCH-1 sequences have been introduced into their genome or homologous recombinant animals in which endogenous HUCH-1 sequences have been altered. Such animals are useful for studying the function and/or activity of a HUCH-1 and for identifying and/or evaluating modulators of HUCH-1 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous HUCH-1 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a HUCH-1-encoding nucleic acid into the male pronuclei of a fertilized oocyte, e.g., by microinjection, retroviral infection, and allowing the oocyte to develop in a pseudopregnant female foster animal. The HUCH-1 cDNA sequence of SEQ ID NO:39 can be introduced as a transgene into the genome of a non-human animal. Alternatively, a nonhuman homologue of a HUCH-1 gene, such as a mouse or rat HUCH-1 gene, can be used as a transgene. Alternatively, a HUCH-1 gene homologue, such as another HUCH-1 family member, can be isolated based on hybridization to the HUCH-1 cDNA sequences of SEQ ID NO:39 or 41, (described further in subsection I above) and used as a transgene. Intronic sequences and polyadenylation signals can also be included in the transgene to increase the efficiency of expression of the transgene. A tissue-specific regulatory sequence(s) can be operably linked to a HUCH-1 transgene to direct expression of a HUCH-1 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a HUCH-1 transgene in its genome and/or expression of HUCH-1 mRNA in tissues or cells of the animals. A transgenic founder animal can then be used to breed additional animals carrying the transgene. Moreover, transgenic animals carrying a transgene encoding a HUCH-1 protein can further be bred to other transgenic animals carrying other transgenes.

To create a homologous recombinant animal, a vector is prepared which contains at least a portion of a HUCH-1 gene into which a deletion, addition or substitution has been introduced to thereby alter, e.g., functionally disrupt, the HUCH-1 gene. The HUCH-1 gene can be a human gene (e.g., the cDNA of SEQ ID NO:41), but more preferably, is a non-human homologue of a HUCH-1 gene (e.g., a cDNA isolated by stringent hybridization with the nucleotide sequence of SEQ ID NO:39). For example, a mouse HUCH-1 gene can be used to construct a homologous recombination nucleic acid molecule, e.g., a vector, suitable for altering an endogenous HUCH-1 gene in the mouse genome. In a preferred embodiment, the homologous recombination nucleic acid molecule is designed such that, upon homologous recombination, the endogenous HUCH-1 gene is functionally disrupted (i.e., no longer encodes a functional protein; also referred to as a "knock out" vector). Alternatively, the homologous recombination nucleic acid molecule can be designed such that, upon homologous recombination, the endogenous HUCH-1 gene is mutated or otherwise altered but still encodes functional protein (e.g., the upstream regulatory region can be altered to thereby alter the expression of the endogenous HUCH-1 protein). In the homologous recombination nucleic acid molecule, the altered portion of the HUCH-1 gene is flanked at its 5' and 3' ends by additional nucleic acid sequence of the HUCH-1 gene to allow for homologous recombination to occur between the exogenous HUCH-1 gene carried by the homologous recombination nucleic acid molecule and an endogenous HUCH-1 gene in a cell, e.g., an embryonic stem cell. The additional flanking HUCH-1 nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced HUCH-1 gene has homologously recombined with the endogenous HUCH-1 gene are selected (see e.g., Li, E. et al. (1992) *Cell* 69:915). The selected cells can then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The HUCH-1 nucleic acid molecules, fragments of HUCH-1 proteins, and anti-HUCH-1 antibodies (also referred to herein as "active compounds") of the invention can be incorporated into pharmaceutical compositions suitable for administration. Active compounds may include, but are not limited to, peptides, nucleic acids, antibodies, and small inorganic or inorganic compounds. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR® EL solubilizer (BASF; Florham Park, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fingi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a HUCH-1 protein or an anti-HUCH-1 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

In certain embodiments of the invention, a modulator of HUCH-1 activity is administered in combination with other agents (e.g., a small molecule), or in conjunction with another, complementary treatment regime. For example, in one embodiment, a modulator of HUCH-1 activity is used to treat a cellular proliferative disorder, e.g., a cancer. Accordingly, modulation of HUCH-1 activity may be used in conjunction with, for example, chemotherapeutic agents and/or anti-angiogenesis agents.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, coichicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin, or *diphtheria* toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a HUCH-1 protein of the invention has one or more of the following activities: 1) modulation of the metabolism of biochemical molecules necessary for energy production or storage, 2) modulation of the conversion of pro-proteins and/or pro-hormones to their active forms; 3) modulation of the inactivation of peptides; 4) modulation of intra- or intercellular signaling; 5) modulation of the biotransformation and detoxification of potentially harmful compounds; and 6) modulation of the anabolism and/or catabolism of metabolically important biomolecules.

The isolated nucleic acid molecules of the invention can be used, for example, to express HUCH-1 protein (e.g., via a recombinant expression vector in a host cell in gene therapy applications), to detect HUCH-1 mRNA (e.g., in a biological sample) or a genetic alteration in a HUCH-1 gene, and to modulate HUCH-1 activity, as described further below. The HUCH-1 proteins can be used to treat disorders characterized by insufficient or excessive production of a HUCH-1 substrate or production of HUCH-1 inhibitors. In addition, the HUCH-1 proteins can be used to screen for naturally occurring HUCH-1 substrates, to screen for drugs or compounds which modulate HUCH-1 activity, as well as to treat disorders characterized by insufficient or excessive production of HUCH-1 protein or production of HUCH-1 protein forms which have decreased, aberrant or unwanted activity compared to HUCH-1 wild type protein (e.g., hydrolase-associated disorders, such as CNS disorders; cardiovascular system disorders; cellular proliferation, growth, differentiation, or migration disorders; hormonal disorders; inflammatory or immune system disorders; hematopoietic or thrombotic disorders; gastrointestinal and digestive disorders; metabolic disorders; hepatic disorders; and renal disorders).

Moreover, the anti-HUCH-1 antibodies of the invention can be used to detect and isolate HUCH-1 proteins, regulate the bioavailability of HUCH-1 proteins, and modulate HUCH-1 activity.

A. Screening Assays:

The invention provides a method (also referred to herein as a "screening assay") for identifying modulators, i.e., candidate or test compounds or agents (e.g., peptides, peptidomimetics, small molecules or other drugs) which bind to HUCH-1 proteins, have a stimulatory or inhibitory effect on, for example, HUCH-1 expression or HUCH-1 activity, or have a stimulatory or inhibitory effect on, for example, the expression or activity of a HUCH-1 substrate.

Compounds identified via assays such as those described herein may be useful, for example, for ameliorating a HUCH-1 associated disorder, such as, a cellular proliferative disorder, e.g., cancer. In instances whereby a cellular proliferative disorder results from an overall lower level of HUCH-1 gene expression and/or HUCH-1 protein in a cell or tissue, compounds which accentuate or amplify the expression and/or activity of the HUCH-1 protein may ameliorate symptoms. In other instances, mutations within the HUCH-1 gene may cause aberrant types or excessive amounts of HUCH-1 proteins to be made which have a deleterious effect that leads to a cellular proliferative disease. Similarly, physiological conditions may cause an increase in HUCH-1 gene expression leading to a cellular proliferative disease. In such cases, compounds that inhibit or decrease the expression and/or activity of HUCH-1 may ameliorate symptoms. Assays for testing the effectiveness of compounds identified by techniques are discussed herein.

In one embodiment, the invention provides assays for screening candidate or test compounds which are substrates of a HUCH-1 protein or polypeptide or biologically active portion thereof (e.g., peptides). In another embodiment, the invention provides assays for screening candidate or test compounds which bind to or modulate the activity of a HUCH-1 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses a HUCH-1 protein or biologically active portion thereof is contacted with a test compound and the ability of the test compound to modulate HUCH-1 activity is determined. Determining the ability of the test compound to modulate HUCH-1 activity can be accomplished by monitoring, for example, cell progression through the cell cycle, or the production of one or more specific metabolites in a cell which expresses HUCH-1. The cell, for example, can be of mammalian origin, e.g., an epithelial or neuronal cell. The ability of the test compound to modulate HUCH-1 binding to a substrate (e.g., a peptide, lipid or nucleic acid) or to bind to HUCH-1 can also be determined. Determining the ability of the test compound to modulate HUCH-1 binding to a substrate can be accomplished, for example, by coupling the HUCH-1 substrate with a radioisotope or enzymatic label such that binding of the HUCH-1 substrate to HUCH-1 can be determined by detecting the labeled HUCH-1 substrate in a complex. Alternatively, HUCH-1 could be coupled with a radioisotope or enzymatic label to monitor the ability of a test compound to modulate HUCH-1 binding to a HUCH-1 substrate in a complex. Determining the ability of the test compound to bind HUCH-1 can be accomplished, for example, by coupling the compound with a radioisotope or enzymatic label such that binding of the compound to HUCH-1 can be determined by detecting the labeled compound in a complex. For example, compounds (e.g., HUCH-1 substrates) can be labeled with $^{125}I$, $^{35}S$, $^{14}C$, or $^{3}H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., a HUCH-1 substrate) to interact with HUCH-1 without the labeling of any of the interactants. For example, a microphysiometer can be used to detect the interaction of a compound with HUCH-1 without the labeling of either the compound or the HUCH-1. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and HUCH-1.

In another embodiment, an assay is a cell-based assay comprising contacting a cell expressing a HUCH-1 target molecule (e.g., a HUCH-1 substrate) with a test compound and determining the ability of the test compound to modulate (e.g., stimulate or inhibit) the activity of the HUCH-1 target molecule. Determining the ability of the test compound to modulate the activity of a HUCH-1 target molecule can be accomplished, for example, by determining the ability of the HUCH-1 protein to bind to or interact with the HUCH-1 target molecule.

Determining the ability of the HUCH-1 protein, or a biologically active fragment thereof, to bind to or interact with a HUCH-1 target molecule can be accomplished by one of the methods described above for determining direct binding. In a preferred embodiment, determining the ability of the HUCH-1 protein to bind to or interact with a HUCH-1 target molecule can be accomplished by determining the activity of the target molecule. For example, the activity of the target molecule can be determined by detecting induction of a cellular response (i.e., cell proliferation, migration and/or metabolic activity), detecting catalytic/enzymatic activity of the target on an appropriate substrate, detecting the induction of a reporter gene (comprising a target-responsive regulatory element operatively linked to a nucleic acid encoding a detectable marker, e.g., luciferase), or detecting a target-regulated cellular response.

In yet another embodiment, an assay of the present invention is a cell-free assay in which a HUCH-1 protein or biologically active portion thereof is contacted with a test compound and the ability of the test compound to bind to the HUCH-1 protein or biologically active portion thereof is determined. Preferred biologically active portions of the HUCH-1 proteins to be used in assays of the present invention include fragments which participate in interactions with non-HUCH-1 molecules, e.g., fragments with high surface probability scores (see, for example, FIG. 64). Binding of the test compound to the HUCH-1 protein can be determined either directly or indirectly as described above. In a preferred embodiment, the assay includes contacting the HUCH-1 protein or biologically active portion thereof with a known compound which binds HUCH-1 to form an assay mixture, contacting the assay mixture with a test compound, and determining the ability of the test compound to interact with a HUCH-1 protein, wherein determining the ability of the test compound to interact with a HUCH-1 protein comprises determining the ability of the test compound to preferentially bind to HUCH-1 or biologically active portion thereof as compared to the known compound.

In another embodiment, the assay is a cell-free assay in which a HUCH-1 protein or biologically active portion thereof is contacted with a test compound and the ability of the test compound to modulate (e.g., stimulate or inhibit) the activity of the HUCH-1 protein or biologically active portion thereof is determined. Determining the ability of the test compound to modulate the activity of a HUCH-1 protein can be accomplished, for example, by determining the ability of the HUCH-1 protein to bind to a HUCH-1 target molecule by one of the methods described above for determining direct binding. Determining the ability of the HUCH-1 protein to bind to a HUCH-1 target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIACORE™). Changes in the optical phenomenon of surface plasmon resonance (SPR) can be used as an indication of real-time reactions between biological molecules.

In an alternative embodiment, determining the ability of the test compound to modulate the activity of a HUCH-1 protein can be accomplished by determining the ability of the HUCH-1 protein to further modulate the activity of a downstream effector of a HUCH-1 target molecule. For example, the activity of the effector molecule on an appropriate target can be determined or the binding of the effector to an appropriate target can be determined as previously described.

In yet another embodiment, the cell-free assay involves contacting a HUCH-1 protein or biologically active portion thereof with a known compound (e.g., a HUCH-1 substrate) which binds the HUCH-1 protein to form an assay mixture, contacting the assay mixture with a test compound, and determining the ability of the test compound to interact with the HUCH-1 protein, wherein determining the ability of the test compound to interact with the HUCH-1 protein comprises determining the ability of the HUCH-1 protein to preferentially bind to or modulate the activity of a HUCH-1 target protein, e.g., catalyze the cleavage, e.g., the hydrolytic cleavage, of a chemical bond within the target protein.

In more than one embodiment of the above assay methods of the present invention, it may be desirable to immobilize either HUCH-1 or its target molecule to facilitate separation of complexed from uncomplexed forms of one or both of the proteins, as well as to accommodate automation of the assay. Binding of a test compound to a HUCH-1 protein, or interaction of a HUCH-1 protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/HUCH-1 fusion proteins or glutathione-S-transferase/target fusion proteins can be adsorbed onto glutathione SEPHAROSE™ beads (Sigma Chemical, St. Louis, Mo.) or glutathione derivatized microtitre plates, which are then combined with the test compound or the test compound and either the non-adsorbed target protein or HUCH-1 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of HUCH-1 binding or activity determined using standard techniques.

Other techniques for immobilizing proteins on matrices can also be used in the screening assays of the invention. For example, either a HUCH-1 protein or a HUCH-1 target molecule can be immobilized utilizing conjugation of biotin and streptavidin. Biotinylated HUCH-1 protein or target molecules can be prepared from biotin-NHS (N-hydroxysuccinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with HUCH-1 protein or target molecules but which do not interfere with binding of the HUCH-1 protein to its target molecule can be derivatized to the wells of the plate, and unbound target or HUCH-1 protein trapped in the wells by antibody conjugation. Methods for detecting such complexes, in addition to those described above for the GST-immobilized complexes, include immunodetection of complexes using antibodies reactive with the HUCH-1 protein or target molecule, as well as enzyme-linked assays which rely on detecting an enzymatic activity associated with the HUCH-1 protein or target molecule.

In another embodiment, modulators of HUCH-1 expression are identified in a method wherein a cell is contacted with a candidate compound and the expression of HUCH-1 mRNA or protein in the cell is determined. The level of expression of HUCH-1 mRNA or protein in the presence of the candidate compound is compared to the level of expression of HUCH-1 mRNA or protein in the absence of the candidate compound. The candidate compound can then be identified as a modulator of HUCH-1 expression based on this comparison. For example, when expression of HUCH-1 mRNA or protein is greater (statistically significantly greater) in the presence of the candidate compound than in its absence, the candidate compound is identified as a stimulator of HUCH-1 mRNA or protein expression. Alternatively, when expression of HUCH-1 mRNA or protein is less (statistically significantly less) in the presence of the candidate compound than in its absence, the candidate compound is identified as an inhibitor of HUCH-1 mRNA or protein expression. The level of HUCH-1 mRNA or protein expression in the cells can be determined by methods described herein for detecting HUCH-1 mRNA or protein.

In yet another aspect of the invention, the HUCH-1 proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with HUCH-1 ("HUCH-1 binding proteins" or "HUCH-1-bp") and are involved in HUCH-1 activity. Such HUCH-1 binding proteins are also likely to be involved in the propagation of signals by the HUCH-1 proteins or HUCH-1 targets as, for example, downstream elements of a HUCH-1-mediated signaling pathway. Alternatively, such HUCH-1 binding proteins are likely to be HUCH-1 inhibitors.

The two-hybrid system is based on the modular nature of most transcription factors, which consist of separable DNA-binding and activation domains. Briefly, the assay utilizes two different DNA constructs. In one construct, the gene that codes for a HUCH-1 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a HUCH-1-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the HUCH-1 protein.

In another aspect, the invention pertains to a combination of two or more of the assays described herein. For example, a modulating agent can be identified using a cell-based or a cell free assay, and the ability of the agent to modulate the activity of a HUCH-1 protein can be confirmed in vivo, e.g., in an animal such as an animal model for cellular transformation and/or tumorigenesis, or an animal model for a metabolic disorder.

This invention further pertains to novel agents identified by the above-described screening assays. Accordingly, it is within the scope of this invention to further use an agent identified as described herein in an appropriate animal model. For example, an agent identified as described herein (e.g., a HUCH-1 modulating agent, an antisense HUCH-1 nucleic acid molecule, a HUCH-1-specific antibody, or a HUCH-1 binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

Any of the compounds, including but not limited to compounds such as those identified in the foregoing assay systems, may be tested for the ability to ameliorate symptoms of, for example, a central nervous system disorder. Cell-based and animal model-based assays for the identification of compounds exhibiting an ability to ameliorate the symptoms of a cellular proliferative disorder are described herein.

In one aspect, cell-based systems, as described herein, may be used to identify compounds which may act to ameliorate symptoms of a cellular proliferative disorder. For example, such cell systems may be exposed to a test compound (e.g., suspected of exhibiting an ability to ameliorate symptoms of a central nervous system disorder), at a sufficient concentration and for a time sufficient to elicit amelioration of symptoms of a cellular proliferative disorder in the exposed cells. After exposure, the cells are examined to determine whether one or more of the cellular phenotypes associated with a central nervous system disorder has been altered to resemble a normal or wild type, non-central nervous system disorder phenotype.

In addition, animal-based models of central nervous system disorders, such as those described herein, may be used to identify compounds capable of ameliorating symptoms of a cellular proliferative disorder. Such animal models may be used as test substrates for the identification of drugs, pharmaceuticals, therapies, and interventions which may be effective in treating a cellular proliferative disorder. For example, animal models may be exposed to a test compound at a sufficient concentration and for a time sufficient to ameliorate symptoms of a central nervous system disorder in the exposed animals. The response of the animals to the exposure may be monitored by assessing amelioration of symptoms of a central nervous system disorder.

With regard to intervention, any treatments which reverse any aspect of a central nervous system disorder should be considered as candidates for human disease therapeutic intervention. Dosages of test agents may be determined by deriving dose-response curves.

Additionally, gene expression patterns may be utilized to assess the ability of a compound to ameliorate symptoms of a central nervous system disorder. For example, the expression pattern of one or more genes may form part of a "gene expression profile" or "transcriptional profile" which may be then in such an assessment. "Gene expression profile" or "transcriptional profile", as used herein, includes the pattern of mRNA expression obtained for a given tissue or cell type under a given set of conditions. Such conditions may include, but are not limited to, cell proliferation, differentiation, transformation, tumorigenesis and metastasis. Gene expression profiles may be generated, for example, by utilizing a differential display procedure, Northern analysis and/or RT-PCR. In one embodiment, HUCH-1 gene sequences may be used as probes and/or PCR primers for the generation and corroboration of such gene expression profiles.

Gene expression profiles may be characterized for known states, for example, a central nervous system disease state or normal state, within the cell- and/or animal-based model systems. Subsequently, these known gene expression profiles may be compared to ascertain the effect of a test compound on modifying such gene expression profiles.

For example, administration of a test compound may cause the gene expression profile of a cellular proliferative disorder model system to more closely resemble the control system. Administration of a test compound may, alternatively, cause the gene expression profile of a control system to begin to mimic a central nervous system disorder state. Such a test compound may, for example, be used in further characterizing the test compound of interest, or may be used in the generation of additional animal models.

Cells that contain and express HUCH-1 gene sequences which encode a HUCH-1 protein, and further, exhibit cellular phenotypes associated with a central nervous system disorder, may be used to identify compounds that exhibit cellular growth modulatory activity. Such cells include tumor cell lines, such as those exemplified herein, as well as generic mammalian cell lines such as COS cells. Further, such cells may include recombinant cell lines derived from a transgenic animal. For example, animal models of central nervous system disorders may be used to generate cell lines that can be used as cell culture models for this disorder. While primary cultures derived from transgenic animals may be utilized, the generation of continuous cell lines is preferred. For examples of techniques which may be used to derive a continuous cell line from the transgenic animals, see Small et al., (1985) *Mol. Cell Biol.* 5:642–648.

Alternatively, cells of a cell type known to be involved in central nervous system disorders may be transfected with sequences capable of increasing or decreasing the amount of HUCH-1 gene expression within the cell. For example, HUCH-1 gene sequences may be introduced into, and overexpressed in, the genome of the cell of interest, or, if endogenous HUCH-1 gene sequences are present, they may be either overexpressed or, alternatively, disrupted in order to underexpress or inactivate HUCH-1 gene expression.

In order to overexpress a HUCH-1 gene, the coding portion of the HUCH-1 gene may be ligated to a regulatory sequence which is capable of driving gene expression in the cell type of interest. Such regulatory regions will be well known to those of skill in the art, and may be utilized in the absence of undue experimentation. Recombinant methods for expressing target genes are described above.

For underexpression of an endogenous HUCH-1 gene sequence, such a sequence may be isolated and engineered such that when reintroduced into the genome of the cell type of interest, the endogenous HUCH-1 alleles will be inactivated. Preferably, the engineered HUCH-1 sequence is introduced via gene targeting such that the endogenous HUCH-1 sequence is disrupted upon integration of the engineered HUCH-1 sequence into the cell's genome. Transfection of host cells with HUCH-1 genes is discussed, above.

Cells treated with test compounds or transfected with HUCH-1 genes can be examined for phenotypes associated with a central nervous system disorders.

Transfection of a HUCH-1 nucleic acid may be accomplished by using standard techniques (described herein and in, for example, Ausubel (1989) supra). Transfected cells should be evaluated for the presence of the recombinant HUCH-1 gene sequences, for expression and accumulation of HUCH-1 mRNA, and for the presence of recombinant HUCH-1 protein production. In instances wherein a decrease in HUCH-1 gene expression is desired, standard techniques may be used to demonstrate whether a decrease in endogenous HUCH-1 gene expression and/or in HUCH-1 protein production is achieved.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the HUCH-1 nucleotide sequences, described herein, can be used to map the location of the HUCH-1 genes on a chromosome. The mapping of the HUCH-1 sequences to chromosomes is an important first step in correlating these sequences with genes associated with disease.

Briefly, HUCH-1 genes can be mapped to chromosomes by preparing PCR primers (preferably 15–25 bp in length) from the HUCH-1 nucleotide sequences. Computer analysis of the HUCH-1 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the HUCH-1 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220: 919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the HUCH-1 nucleotide sequences to design oligonucleotide primers, sublocalization can be achieved with panels of fragments from specific chromosomes. Other mapping strategies which can similarly be used to map a HUCH-1 sequence to its chromosome include in situ hybridization (described in Fan, Y. et al. (1990) *Proc. Natl. Acad. Sci. USA,* 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature,* 325:783–787.

Moreover, differences in the DNA sequences between individuals affected and unaffected with a disease associated with the HUCH-1 gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The HUCH-1 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the HUCH-1 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The HUCH-1 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:39 can comfortably provide positive individual identification with a panel of perhaps 10 to 1,000 primers which each yield a noncoding amplified sequence of 100 bases. If predicted coding sequences, such as those in SEQ ID NO:41 are used, a more appropriate number of primers for positive individual identification would be 500–2,000.

If a panel of reagents from HUCH-1 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of HUCH-1 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:39 are particularly appropriate for this use as greater numbers of polymorphisms occur in the noncoding regions, making it easier to differentiate individuals using this technique. Examples of polynucleotide reagents include the HUCH-1 nucleotide sequences or portions thereof, e.g., fragments derived from the noncoding regions of SEQ ID NO:39 having a length of at least 20 bases, preferably at least 30 bases.

The HUCH-1 nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such HUCH-1 probes can be used to identify tissue by species and/or by organ type.

In a similar fashion, these reagents, e.g., HUCH-1 primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining HUCH-1 protein and/or nucleic acid expression as well as HUCH-1 activity, in the context of a biological sample (e.g., blood, serum, cells, tissue) to thereby determine whether an individual is afflicted with a disease or disorder, or is at risk of developing a disorder, associated with aberrant or unwanted HUCH-1 expression or activity, e.g., a central nervous system disorder. The invention also provides for prognostic (or predictive) assays for determining whether an individual is at risk of developing a disorder associated with HUCH-1 protein, nucleic acid expression or activity. For example, mutations in a HUCH-1 gene can be assayed in a biological sample. Such assays can be used for prognostic or predictive purpose to thereby prophylactically treat an individual prior to the onset of a disorder characterized by or associated with HUCH-1 protein, nucleic acid expression or activity.

Another aspect of the invention pertains to monitoring the influence of agents (e.g., drugs, compounds) on the expression or activity of HUCH-1 in clinical trials.

These and other agents are described in further detail in the following sections.

1. Diagnostic Assays

An exemplary method for detecting the presence or absence of HUCH-1 protein or nucleic acid in a biological sample involves obtaining a biological sample from a test subject and contacting the biological sample with a compound or an agent capable of detecting HUCH-1 protein or nucleic acid (e.g., mRNA, or genomic DNA) that encodes HUCH-1 protein such that the presence of HUCH-1 protein or nucleic acid is detected in the biological sample. A preferred agent for detecting HUCH-1 mRNA or genomic DNA is a labeled nucleic acid probe capable of hybridizing to HUCH-1 mRNA or genomic DNA. The nucleic acid probe can be, for example, the HUCH-1 nucleic acid set forth in SEQ ID NO:39 or 41, or a portion thereof, such as an oligonucleotide of at least 15, 30, 50, 100, 250 or 500 nucleotides in length and sufficient to specifically hybridize under stringent conditions to HUCH-1 mRNA or genomic DNA. Other suitable probes for use in the diagnostic assays of the invention are described herein.

A preferred agent for detecting HUCH-1 protein is an antibody capable of binding to HUCH-1 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect HUCH-1 mRNA, protein, or genomic DNA in a biological sample in vitro as well as in vivo. For example, in vitro techniques for detection of HUCH-1 mRNA include Northern hybridizations and in situ hybridizations. In vitro techniques for detection of HUCH-1 protein include enzyme linked immunosorbent assays (ELISAs), Western blots, immunoprecipitations and immunofluorescence. In vitro techniques for detection of HUCH-1 genomic DNA include Southern hybridizations. Furthermore, in vivo techniques for detection of HUCH-1 protein include introducing into a subject a labeled anti-HUCH-1 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting HUCH-1 protein, mRNA, or genomic DNA, such that the presence of HUCH-1 protein, mRNA or genomic DNA is detected in the biological sample, and comparing the presence of HUCH-1 protein, mRNA or genomic DNA in the control sample with the presence of HUCH-1 protein, mRNA or genomic DNA in the test sample.

The invention also encompasses kits for detecting the presence of HUCH-1 in a biological sample. For example, the kit can comprise a labeled compound or agent capable of detecting HUCH-1 protein or mRNA in a biological sample; means for determining the amount of HUCH-1 in the sample; and means for comparing the amount of HUCH-1 in the sample with a standard. The compound or agent can be packaged in a suitable container.

The kit can further comprise instructions for using the kit to detect HUCH-1 protein or nucleic acid.

2. Prognostic Assays

The diagnostic methods described herein can furthermore be utilized to identify subjects having or at risk of developing a disease or disorder associated with aberrant or unwanted HUCH-1 expression or activity, e.g., a central nervous system disorder. As used herein, the term "aberrant" includes a HUCH-1 expression or activity which deviates from the wild type HUCH-1 expression or activity. Aberrant expression or activity includes increased or decreased expression or activity, as well as expression or activity which does not follow the wild type developmental pattern of expression or the subcellular pattern of expression. For example, aberrant HUCH-1 expression or activity is intended to include the cases in which a mutation in the HUCH-1 gene causes the HUCH-1 gene to be under-expressed or over-expressed and situations in which such mutations result in a non-functional HUCH-1 protein or a protein which does not function in a wild-type fashion, e.g., a protein which does not interact with a HUCH-1 substrate, or one which interacts with a non-HUCH-1 substrate. As used herein, the term "unwanted" includes an unwanted phenomenon involved in a biological response such as cellular proliferation. For example, the term unwanted includes a HUCH-1 expression or activity which is undesirable in a subject.

The assays described herein, such as the preceding diagnostic assays or the following assays, can be utilized to identify a subject having or at risk of developing a disorder associated with a misregulation in HUCH-1 protein activity or nucleic acid expression, such as a CNS disorder, a cardiovascular disorder, a muscular disorder, a hormonal disorder, a gastrointestinal disorder, a metabolic disorder, an inflammatory or immune system disorder, or a cell proliferation, growth, differentiation, or migration disorder. Alternatively, the prognostic assays can be utilized to identify a subject having or at risk for developing a disorder associated with a misregulation in HUCH-1 protein activity or nucleic acid expression, such as a CNS disorder, a cardiovascular disorder, a muscular disorder, a hormonal disorder, a gastrointestinal disorder, a metabolic disorder, an inflammatory or immune system disorder, or a cell proliferation, growth, differentiation, or migration disorder. Thus, the present invention provides a method for identifying a disease or disorder associated with aberrant or unwanted HUCH-1 expression or activity in which a test sample is obtained from a subject and HUCH-1 protein or nucleic acid (e.g., mRNA or genomic DNA) is detected, wherein the presence of HUCH-1 protein or nucleic acid is diagnostic for a subject having or at risk of developing a disease or disorder associated with aberrant or unwanted HUCH-1 expression or activity. As used herein, a "test sample" refers to a biological sample obtained from a subject of interest. For example, a test sample can be a biological fluid (e.g., cerebrospinal fluid or serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted HUCH-1 expression or activity. For example, such methods can be used to determine whether a subject can be effectively treated with an agent for a CNS disorder, a cardiovascular disorder, a muscular disorder, a hormonal disorder, a gastrointestinal disorder, a metabolic disorder, an inflammatory or immune system disorder, or a cell proliferation, growth, differentiation, or migration disorder. Thus, the present invention provides methods for determining whether a subject can be effectively treated with an agent for a disorder associated with aberrant or unwanted HUCH-1 expression or activity in which a test sample is obtained and HUCH-1 protein or nucleic acid expression or activity is detected (e.g., wherein the abundance of HUCH-1 protein or nucleic acid expression or activity is diagnostic for a subject that can be administered the agent to treat a disorder associated with aberrant or unwanted HUCH-1 expression or activity).

The methods of the invention can also be used to detect genetic alterations in a HUCH-1 gene, thereby determining if a subject with the altered gene is at risk for a disorder characterized by misregulation in HUCH-1 protein activity or nucleic acid expression, such as a CNS disorder, a cardiovascular disorder, a muscular disorder, a hormonal disorder, a gastrointestinal disorder, an inflammatory or immune system disorder, or a cell proliferation, growth, differentiation, or migration disorder. In preferred embodiments, the methods include detecting, in a sample of cells from the subject, the presence or absence of a genetic alteration characterized by at least one of an alteration affecting the integrity of a gene encoding a HUCH-1 protein, or the mis-expression of the HUCH-1 gene. For example, such genetic alterations can be detected by ascertaining the existence of at least one of 1) a deletion of one or more nucleotides from a HUCH-1 gene; 2) a addition of one or more nucleotides to a HUCH-1 gene; 3) a substitution of one or more nucleotides of a HUCH-1 gene, 4) a chromosomal rearrangement of a HUCH-1 gene; 5) an alteration in the level of a messenger RNA transcript of a HUCH-1 gene, 6) aberrant modification of a HUCH-1 gene, such as of the methylation pattern of the genomic DNA, 7) the presence of a non-wild type splicing pattern of a messenger RNA transcript of a HUCH-1 gene, 8) a non-wild type level of a HUCH-1 protein, 9) allelic loss of a HUCH-1 gene, and 10) inappropriate post-translational modification of a HUCH-1 protein. As described herein, there are a large number of assays known in the art which can be used for detecting alterations in a HUCH-1 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1994) Proc. Natl. Acad. Sci. USA 91:360–364), the latter of which can be particularly useful for detecting point mutations in a HUCH-1 gene (see Abravaya et al. (1995) Nucleic Acids Res. 23:675–682). This method can include the steps of collecting a sample of cells from a subject, isolating nucleic acid (e.g., genomic, mRNA or both) from the cells of the sample, contacting the nucleic acid sample with one or more primers which specifically hybridize to a HUCH-1 gene under conditions such that hybridization and amplification of the HUCH-1 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) Proc. Natl. Acad. Sci. USA 87:1874–1878), transcriptional amplification system (Kwoh, D. Y. et al., (1989) Proc. Natl. Acad. Sci. USA 86:1173–1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a HUCH-1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in HUCH-1 can be identified by hybridizing a sample and control nucleic acids, e.g., DNA or RNA, to high density arrays containing hundreds or thousands of oligonucleotides probes (Cronin, M. T. et al. (1996) Human Mutation 7: 244–255; Kozal, M. J. et al. (1996) Nature Medicine 2: 753–759). For example, genetic mutations in HUCH-1 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the HUCH-1 gene and detect mutations by comparing the sequence of the sample HUCH-1 with the corresponding wild-type (control) sequence. Examples of sequencing reactions include those based on techniques developed by Maxam and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Biotechniques 19:448), including sequencing by mass spectrometry (see, e.g., PCT International Publication No. WO 94/16101; Cohen et al. (1996) Adv. Chromatogr. 36:127–162; and Griffin et al. (1993) Appl. Biochem. Biotechnol. 38:147–159).

Other methods for detecting mutations in the HUCH-1 gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes of formed by hybridizing (labeled) RNA or DNA containing the wild-type HUCH-1 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl Acad Sci USA 85:4397; Saleeba et al. (1992) Methods Enzymol. 217: 286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in HUCH-1 cDNAs obtained from samples of cells. For example, the mutY enzyme of E. Coli cleaves A at G/A mismatches and the thymidine DNA glycosylase from HeLa cells cleaves T at G/T mismatches (Hsu et al. (1994) Carcinogenesis 15:1657–1662). According to an exemplary embodiment, a probe based on a HUCH-1 sequence, e.g., a wild-type HUCH-1 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in HUCH-1 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125–144; and Hayashi (1992) *Genet. Anal. Tech. Appl.* 9:73–79). Single-stranded DNA fragments of sample and control HUCH-1 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a HUCH-1 gene.

Furthermore, any cell type or tissue in which HUCH-1 is expressed may be utilized in the prognostic assays described herein.

3. Monitoring of Effects During Clinical Trials

Monitoring the influence of agents (e.g., drugs) on the expression or activity of a HUCH-1 protein (e.g., the modulation of cell proliferation and/or migration) can be applied not only in basic drug screening, but also in clinical trials. For example, the effectiveness of an agent determined by a screening assay as described herein to increase HUCH-1 gene expression, protein levels, or upregulate HUCH-1 activity, can be monitored in clinical trials of subjects exhibiting decreased HUCH-1 gene expression, protein levels, or downregulated HUCH-1 activity. Alternatively, the effectiveness of an agent determined by a screening assay to decrease HUCH-1 gene expression, protein levels, or downregulate HUCH-1 activity, can be monitored in clinical trials of subjects exhibiting increased HUCH-1 gene expression, protein levels, or upregulated HUCH-1 activity. In such clinical trials, the expression or activity of a HUCH-1 gene, and preferably, other genes that have been implicated in, for example, an HUCH-1-associated disorder can be used as a "read out" or markers of the phenotype of a particular cell.

For example, and not by way of limitation, genes, including HUCH-1, that are modulated in cells by treatment with an agent (e.g., compound, drug or small molecule) which modulates HUCH-1 activity (e.g., identified in a screening assay as described herein) can be identified. Thus, to study the effect of agents on HUCH-1-associated disorders (e.g., disorders characterized by deregulated central nervous system function), for example, in a clinical trial, cells can be isolated and RNA prepared and analyzed for the levels of expression of HUCH-1 and other genes implicated in the HUCH-1-associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of HUCH-1 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a HUCH-1 protein, mRNA, or genomic DNA in the preadministration sample; (iii) obtaining one or more post-administration samples from the subject; (iv) detecting the level of expression or activity of the HUCH-1 protein, mRNA, or genomic DNA in the post-administration samples; (v) comparing the level of expression or activity of the HUCH-1 protein, mRNA, or genomic DNA in the pre-administration sample with the HUCH-1 protein, mRNA, or genomic DNA in the post administration sample or samples; and (vi) altering the administration of the agent to the subject accordingly. For example, increased administration of the agent may be desirable to increase the expression or activity of HUCH-1 to higher levels than detected, i.e., to increase the effectiveness of the agent. Alternatively, decreased administration of the agent may be desirable to decrease expression or activity of HUCH-1 to lower levels than detected, i.e. to decrease the effectiveness of the agent. According to such an embodiment, HUCH-1 expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder or having a disorder associated with aberrant or unwanted HUCH-1 expression or activity, e.g., a hydrolase-associated disorder such as a CNS disorder, a cardiovascular disorder, a muscular disorder, a hormonal disorder, a gastrointestinal disorder, a metabolic disorder, an inflammatory or immune system disorder, or a cell proliferation, growth, differentiation, or migration disorder. With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the HUCH-1 molecules of the present invention or HUCH-1 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Treatment is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

A therapeutic agent includes, but is not limited to, small molecules, peptides, antibodies, ribozymes and antisense oligonucleotides.

1. Prophylactic Methods

In one aspect, the invention provides a method for preventing in a subject, a disease or condition associated with an aberrant or unwanted HUCH-1 expression or activity, by administering to the subject a HUCH-1 or an agent which modulates HUCH-1 expression or at least one HUCH-1 activity. Subjects at risk for a disease which is caused or contributed to by aberrant or unwanted HUCH-1 expression or activity can be identified by, for example, any or a combination of diagnostic or prognostic assays as described herein. Administration of a prophylactic agent can occur prior to the manifestation of symptoms characteristic of the HUCH-1 aberrancy, such that a disease or disorder is prevented or, alternatively, delayed in its progression. Depending on the type of HUCH-1 aberrancy, for example, a HUCH-1, HUCH-1 agonist or HUCH-1 antagonist agent can be used for treating the subject. The appropriate agent can be determined based on screening assays described herein.

2. Therapeutic Methods

Another aspect of the invention pertains to methods of modulating HUCH-1 expression or activity for therapeutic purposes. Accordingly, in an exemplary embodiment, the modulatory method of the invention involves contacting a cell with a HUCH-1 or agent that modulates one or more of the activities of HUCH-1 protein activity associated with the cell. An agent that modulates HUCH-1 protein activity can be an agent as described herein, such as a nucleic acid or a protein, a naturally-occurring target molecule of a HUCH-1 protein (e.g., a HUCH-1 substrate), a HUCH-1 antibody, a HUCH-1 agonist or antagonist, a peptidomimetic of a HUCH-1 agonist or antagonist, or other small molecule. In one embodiment, the agent stimulates one or more HUCH-1 activities. Examples of such stimulatory agents include active HUCH-1 protein and a nucleic acid molecule encoding HUCH-1 that has been introduced into the cell. In another embodiment, the agent inhibits one or more HUCH-1 activities. Examples of such inhibitory agents include antisense HUCH-1 nucleic acid molecules, anti-HUCH-1 antibodies, and HUCH-1 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a HUCH-1 protein or nucleic acid molecule. In one embodiment, the method involves administering an agent (e.g., an agent identified by a screening assay described herein), or combination of agents that modulates (e.g., upregulates or downregulates) HUCH-1 expression or activity. In another embodiment, the method involves administering a HUCH-1 protein or nucleic acid molecule as therapy to compensate for reduced, aberrant, or unwanted HUCH-1 expression or activity.

Stimulation of HUCH-1 activity is desirable in situations in which HUCH-1 is abnormally downregulated and/or in which increased HUCH-1 activity is likely to have a beneficial effect. Likewise, inhibition of HUCH-1 activity is desirable in situations in which HUCH-1 is abnormally upregulated and/or in which decreased HUCH-1 activity is likely to have a beneficial effect.

3. Pharmacogenomics

The HUCH-1 molecules of the present invention, as well as agents, or modulators which have a stimulatory or inhibitory effect on HUCH-1 activity (e.g., HUCH-1 gene expression) as identified by a screening assay described herein can be administered to individuals to treat (prophylactically or therapeutically) HUCH-1-associated disorders (e.g., CNS disorders, cardiovascular disorders, muscular disorders, hormonal disorders, gastrointestinal disorders, metabolic disorders, inflammatory or immune system disorders, or cell proliferation, growth, differentiation, or migration disorders) associated with aberrant or unwanted HUCH-1 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a HUCH-1 molecule or HUCH-1 modulator as well as tailoring the dosage and/or therapeutic regimen of treatment with a HUCH-1 molecule or HUCH-1 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11): 983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a HUCH-1 protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a HUCH-1 molecule or HUCH-1 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a HUCH-1 molecule or HUCH-1 modulator, such as a modulator identified by one of the exemplary screening assays described herein.

VI. Electronic Apparatus Readable Media and Arrays

Electronic apparatus readable media comprising HUCH-1 sequence information is also provided. As used herein, "HUCH-1 sequence information" refers to any nucleotide and/or amino acid sequence information particular to the HUCH-1 molecules of the present invention, including but not limited to full-length nucleotide and/or amino acid sequences, partial nucleotide and/or amino acid sequences, polymorphic sequences including single nucleotide polymorphisms (SNPs), epitope sequences, and the like. Moreover, information "related to" said HUCH-1 sequence information includes detection of the presence or absence of a sequence (e.g., detection of expression of a sequence, fragment, polymorphism, etc.), determination of the level of a sequence (e.g., detection of a level of expression, for example, a quantitative detection), detection of a reactivity to a sequence (e.g., detection of protein expression and/or levels, for example, using a sequence-specific antibody), and the like. As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon HUCH-1 sequence information of the present invention.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the HUCH-1 sequence information.

A variety of software programs and formats can be used to store the sequence information on the electronic apparatus readable medium. For example, the sequence information can be represented in a word processing text file, formatted in commercially-available software such as WordPerfect and Microsoft Word, or represented in the form of an ASCII file, stored in a database application, such as DB2, Sybase, Oracle, or the like, as well as in other forms. Any number of dataprocessor structuring formats (e.g., text file or database) may be employed in order to obtain or create a medium having recorded thereon the HUCH-1 sequence information.

By providing HUCH-1 sequence information in readable form, one can routinely access the sequence information for a variety of purposes. For example, one skilled in the art can use the sequence information in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has a HUCH-1-associated disease or disorder or a pre-disposition to a HUCH-1-associated disease or disorder, wherein the method comprises the steps of determining HUCH-1 sequence information associated with the subject and based on the HUCH-1 sequence information, determining whether the subject has a HUCH-1-associated disease or disorder or a pre-disposition to a HUCH-1-associated disease or disorder and/or recommending a particular treatment for the disease, disorder or pre-disease condition.

The present invention further provides in an electronic system and/or in a network, a method for determining whether a subject has a HUCH-1-associated disease or disorder or a pre-disposition to a disease associated with a HUCH-1 wherein the method comprises the steps of determining HUCH-1 sequence information associated with the subject, and based on the HUCH-1 sequence information, determining whether the subject has a HUCH-1-associated disease or disorder or a pre-disposition to a HUCH-1-associated disease or disorder, and/or recommending a particular treatment for the disease, disorder or pre-disease condition. The method may further comprise the step of receiving phenotypic information associated with the subject and/or acquiring from a network phenotypic information associated with the subject.

The present invention also provides in a network, a method for determining whether a subject has a HUCH-1-associated disease or disorder or a pre-disposition to a HUCH-1-associated disease or disorder associated with HUCH-1, said method comprising the steps of receiving HUCH-1 sequence information from the subject and/or information related thereto, receiving phenotypic information associated with the subject, acquiring information from the network corresponding to HUCH-1 and/or a HUCH-1-associated disease or disorder, and based on one or more of the phenotypic information, the HUCH-1 information (e.g., sequence information and/or information related thereto), and the acquired information, determining whether the subject has a HUCH-1-associated disease or disorder or a pre-disposition to a HUCH-1-associated disease or disorder. The method may further comprise the step of recommending a particular treatment for the disease, disorder or pre-disease condition.

The present invention also provides a business method for determining whether a subject has a HUCH-1-associated disease or disorder or a pre-disposition to a HUCH-1-associated disease or disorder, said method comprising the steps of receiving information related to HUCH-1 (e.g., sequence information and/or information related thereto), receiving phenotypic information associated with the subject, acquiring information from the network related to HUCH-1 and/or related to a HUCH-1-associated disease or disorder, and based on one or more of the phenotypic information, the HUCH-1 information, and the acquired information, determining whether the subject has a HUCH-1-associated disease or disorder or a pre-disposition to a HUCH-1-associated disease or disorder. The method may further comprise the step of recommending a particular treatment for the disease, disorder or pre-disease condition.

The invention also includes an array comprising a HUCH-1 sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, one of which can be HUCH-1. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a HUCH-1-associated disease or disorder, progression of HUCH-1-associated disease or disorder, and processes, such a cellular transformation associated with the HUCH-1-associated disease or disorder.

The array is also useful for ascertaining the effect of the expression of a gene on the expression of other genes in the same cell or in different cells (e.g., ascertaining the effect of HUCH-1 expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including HUCH-1) that could serve as a molecular target for diagnosis or therapeutic intervention.

This invention is further illustrated by the following examples which should not be construed as limiting. The contents of all references, patents and published patent applications cited throughout this application, as well as the Figures and Sequence Listing, are incorporated herein by reference.

EXAMPLES

Example 1

Identification and Characterization of HUCH-1 cDNA

In this example, the identification and characterization of the gene encoding the HUCH-1 (clone Fbh48118fl) is described.

Isolation of the HUCH-1 cDNA

The invention is based, at least in part, on the discovery of a human gene encoding a novel protein, referred to herein as HUCH-1. The entire sequence of human clone Fbh48118fl was determined and found to contain an open reading frame termed "HUCH-1."

The nucleotide sequence encoding the HUCH-1 protein is shown in FIG. 63 and is set forth as SEQ ID NO:39. The protein encoded by this nucleic acid comprises about 366 amino acids and has the amino acid sequence shown in FIG. 63 and set forth as SEQ ID NO:40. The coding region (open reading frame) of SEQ ID NO:39 is set forth as SEQ ID NO:41. Clone Fbh48118fl comprises the coding region of HUCH.

Analysis of the HUCH-1 Molecules

A search using the polypeptide sequence of SEQ ID NO:40 was performed against the Memsat database (FIG. 65), resulting in the identification of one potential transmembrane domain in the amino acid sequence of HUCH-1 (SEQ ID NO:40) at about residues 34–56.

The amino acid sequence of HUCH-1 was analyzed using the program PSORT (see the PSORT website) to predict the localization of the proteins within the cell. This program assesses the presence of different targeting and localization amino acid sequences within the query sequence. The results of the analyses show that HUCH-1 may be localized to the nucleus, the mitochondria, extracellularly, or to the cytoplasm.

Searches of the amino acid sequence of HUCH-1 were further performed against the Prosite database. These searches resulted in the identification in the amino acid sequence of HUCH-1 of a number of potential N-glycosylation sites, a number of potential protein kinase C phosphorylation sites, a number of potential casein kinase II phosphorylation sites, a potential tyrosine kinase phosphorylation site, a number of potential N-myristoylation sites, and a number of potential ubiquitin carboxyl-terminal hydrolases family 2 signature sites.

A search of the amino acid sequence of HUCH-1 was also performed against the HMM database (FIG. 66). This search resulted in the identification of an "ubiquitin carboxyl-terminal hydrolase family domains" in the amino acid sequence of HUCH-1 (SEQ ID NO:40) at about residues 35–66 (score=60.8), and at about residues 292–364 (score=106.4).

Further hits were identified by using the amino acid sequence of HUCH-1 (SEQ ID NO:40) to search through the ProDom database. Numerous matches against proteins and/or protein domains described as "ubiquitin hydrolase carboxyl-terminal ubiquitin-specific processing protease deubiquitinating enzyme thiolesterase conjugation", "ubiquitin protease hydrolase carboxyl-terminal ubiquitin-specific enzyme FIS hydrolyzing cDNA deubiquitinating", "ubiquitin hydrolase protease enzyme carboxyl-terminal ubiquitin-specific deubiquitinating processing thiolesterase FAF-X", "ubiquitin hydrolase protease enzyme carboxyl-terminal ubiquitin-specific deubiquitinating processing thiolesterase conjugation", "protease ubiquitin ubiquitin-specific BcDNA:LD22910 conjugation deubiquitinating thiolesterase enzyme carboxyl-terminal", "CG8830", "ubiquitin hydrolase carboxyl-terminal protease conjugation deubiquitinating enzyme thiolesterase ubiquitin-specific processing", "CG4165", "C34F6.9", "chromosome F3 1E3.4 I subunit hydrolase nuclease PAN2 PAB-dependent C22G7.04 PABIP-dependent" and the like were identified.

Tissue Distribution of HUCH-1 mRNA

This example describes the tissue distribution of HUCH-1 mRNA, as may be determined by Polymerase Chain Reaction (PCR) on cDNA libraries using oligonucleotide primers based on the HUCH-1 sequence.

For in situ analysis, various tissues, e.g. tissues obtained from brain, are first frozen on dry ice. Ten-micrometer-thick sections of the tissues are postfixed with 4% formaldehyde in DEPC treated 1× phosphate-buffered saline at room temperature for 10 minutes before being rinsed twice in DEPC 1× phosphate-buffered saline and once in 0.1 M triethanolamine-HCl (pH 8.0). Following incubation in 0.25% acetic anhydride-0.1 M triethanolamine-HCl for 10 minutes, sections are rinsed in DEPC 2×SSC (1×SSC is 0.15M NaCl plus 0.015M sodium citrate). Tissue is then dehydrated through a series of ethanol washes, incubated in 100% chloroform for 5 minutes, and then rinsed in 100% ethanol for 1 minute and 95% ethanol for 1 minute and allowed to air dry.

Hybridizations are performed with $^{35}$S-radiolabeled (5×10$^7$ cpm/ml) cRNA probes. Probes are incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1× Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides are washed with 2×SSC. Sections are then sequentially incubated at 37° C. in TNE (a solution containing 10 mM Tris-HCl (pH 7.6), 500 mM NaCl, and 1 mM EDTA), for 10 minutes, in TNE with 10 µg of RNase A per ml for 30 minutes, and finally in TNE for 10 minutes. Slides are then rinsed with 2×SSC at room temperature, washed with 2×SSC at 50° C. for 1 hour, washed with 0.2×SSC at 55° C. for 1 hour, and 0.2×SSC at 60° C. for 1 hour. Sections are then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

Example 2

Expression of Recombinant HUCH-1 Polypeptide in Bacterial Cells

In this example, HUCH-1 is expressed as a recombinant glutathione-S-transferase (GST) fusion polypeptide in *E. Coli* and the fusion polypeptide is isolated and characterized. Specifically, HUCH-1 is fused to GST and this fusion polypeptide is expressed in *E. Coli*, e.g., strain PEB199. Expression of the GST-HUCH-1 fusion polypeptide in PEB199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant HUCH-1 Polypeptide in COS Cells

To express the HUCH-1 gene in COS cells, the pcDNA/Amp vector by Invitrogen Corporation (San Diego, Calif.) is used. This vector contains an SV40 origin of replication, an ampicillin resistance gene, an *E. Coli* replication origin, a CMV promoter followed by a polylinker region, and an SV40 intron and polyadenylation site. A DNA fragment encoding the entire HUCH-1 polypeptide and an HA tag (Wilson et al. (1984) *Cell* 37:767) or a FLAG tag fused in-frame to its 3' end of the fragment is cloned into the polylinker region of the vector, thereby placing the expression of the recombinant polypeptide under the control of the CMV promoter.

To construct the plasmid, the HUCH-1 DNA sequence is amplified by PCR using two primers. The 5' primer contains the restriction site of interest followed by approximately twenty nucleotides of the HUCH-1 coding sequence starting from the initiation codon; the 3' end sequence contains complementary sequences to the other restriction site of interest, a translation stop codon, the HA tag or FLAG tag and the last 20 nucleotides of the HUCH-1 coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the HUCH-1 gene is inserted in the correct orientation. The ligation mixture is transformed into *E. Coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the HUCH-1-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989. The expression of the IC54420 polypeptide is detected by radiolabeling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the HUCH-1 coding sequence is cloned directly into the polylinker of the pcDNA/Amp vector using the appropriate restriction sites. The resulting plasmid is transfected into COS cells in the manner described above, and the expression of the HUCH-1 polypeptide is detected by radiolabeling and immunoprecipitation using a HUCH-1-specific monoclonal antibody. are then analyzed by SDS-PAGE.

EQUIVALENTS

Those skilled in the art will recognize, or be able to ascertain using no more than routine experimentation, many equivalents to the specific embodiments of the invention described herein. Such equivalents are intended to be encompassed by the following claims.

SEQUENCE LISTING

```
<160> NUMBER OF SEQ ID NOS: 41

<210> SEQ ID NO 1
<211> LENGTH: 1808
<212> TYPE: DNA
<213> ORGANISM: Homo sapiens
<220> FEATURE:
<221> NAME/KEY: CDS
<222> LOCATION: (285)...(1418)

<400> SEQUENCE: 1
ggagtcgacc cacgcgtccg ggagcagcgg ccggggcggc agcggtcccc aggccgggac     60
acccggggtg gtgcgcccgg gttcgcgggg gctgcgccgg cgccggggag gcgggggag    120
```

```
                                    -continued cgggagcggg cgacgcgggg aaggggggag ccaggggggag gcgccggcc ggaggagggg        180 cggacccgcc gccctagccg agcagagcac agccgagccg agcggccggg gcggggccg         240 accccggcca gcgtcggcgc agagagcggg cggaggcgca ggcc atg ctg cgg ctg         296
                                                Met Leu Arg Leu
                                                  1 gtg ccc acc ggg gcc cgg gcc atc gtg gac atg tcg tac gcc cgc cac         344
Val Pro Thr Gly Ala Arg Ala Ile Val Asp Met Ser Tyr Ala Arg His
  5              10                  15                  20 ttc ctg gac ttc cag ggc tcc gcc att ccc caa gcc atg cag aag ctg         392
Phe Leu Asp Phe Gln Gly Ser Ala Ile Pro Gln Ala Met Gln Lys Leu
             25                  30                  35 gtg gtg acc cgg ctg agc ccc aac ttc cgc gag gcc gtc acc ctg agc         440
Val Val Thr Arg Leu Ser Pro Asn Phe Arg Glu Ala Val Thr Leu Ser
         40                  45                  50 cgg gac tgc ccg gtg ccg ctc ccc ggg gac gga gac ctc ctc gtc cgg         488
Arg Asp Cys Pro Val Pro Leu Pro Gly Asp Gly Asp Leu Leu Val Arg
         55                  60                  65 aac cga ttt gtt ggt gtt aac gca tct gac atc aac tat tca gca ggc         536
Asn Arg Phe Val Gly Val Asn Ala Ser Asp Ile Asn Tyr Ser Ala Gly
 70                  75                  80 cgc tat gac ccc tca gtt aag cct ccc ttt gac ata ggt ttc gaa ggc         584
Arg Tyr Asp Pro Ser Val Lys Pro Pro Phe Asp Ile Gly Phe Glu Gly
 85                  90                  95                 100 att ggg gag gtg gtg gcc cta ggc ctc tct gct agt gcc aga tac aca         632
Ile Gly Glu Val Val Ala Leu Gly Leu Ser Ala Ser Ala Arg Tyr Thr
                105                 110                 115 gtt ggc caa gct gtg gct tac atg gca cct ggt tct ttt gct gag tac         680
Val Gly Gln Ala Val Ala Tyr Met Ala Pro Gly Ser Phe Ala Glu Tyr
            120                 125                 130 aca gtt gtg cct gcc agc att gca act cca gtg ccc tca gtg aaa ccc         728
Thr Val Val Pro Ala Ser Ile Ala Thr Pro Val Pro Ser Val Lys Pro
            135                 140                 145 gag tat ctt acc ctg ctg gta agt ggc acc acc gca tac atc agc ctg         776
Glu Tyr Leu Thr Leu Leu Val Ser Gly Thr Thr Ala Tyr Ile Ser Leu
150                 155                 160 aaa gag ctc gga gga ctg tcg gaa ggg aaa aaa gtt ttg gtg aca gca         824
Lys Glu Leu Gly Gly Leu Ser Glu Gly Lys Lys Val Leu Val Thr Ala
165                 170                 175                 180 gca gct ggg gga acg ggc cag ttt gcc atg cag ctt tca aag aag gca         872
Ala Ala Gly Gly Thr Gly Gln Phe Ala Met Gln Leu Ser Lys Lys Ala
                185                 190                 195 aag tgc cat gta att gga acc tgc tct tct gat gaa aag tct gct ttt         920
Lys Cys His Val Ile Gly Thr Cys Ser Ser Asp Glu Lys Ser Ala Phe
            200                 205                 210 ctg aaa tct ctt ggc tgt gat cgt cct atc aac tat aaa act gaa ccc         968
Leu Lys Ser Leu Gly Cys Asp Arg Pro Ile Asn Tyr Lys Thr Glu Pro
            215                 220                 225 gta ggt acc gtc ctt aag cag gag tac cct gaa ggt gtc gat gtg gtc        1016
Val Gly Thr Val Leu Lys Gln Glu Tyr Pro Glu Gly Val Asp Val Val
            230                 235                 240 tat gaa tct gtt ggg gga gcc atg ttt gac ttg gct gta gac gcc ctg        1064
Tyr Glu Ser Val Gly Gly Ala Met Phe Asp Leu Ala Val Asp Ala Leu
245                 250                 255                 260 gct acg aaa ggc cgc ttg ata gta ata ggg ttt atc tct ggc tac caa        1112
Ala Thr Lys Gly Arg Leu Ile Val Ile Gly Phe Ile Ser Gly Tyr Gln
                265                 270                 275 act cct act ggc ctt tcg cct gtg aaa gca gga aca ttg cca gcc aaa        1160
Thr Pro Thr Gly Leu Ser Pro Val Lys Ala Gly Thr Leu Pro Ala Lys
            280                 285                 290
```

-continued

```
ctg ctc aag aaa tct gcc agc gta cag ggc ttc ttc ctg aac cat tac    1208
Leu Leu Lys Lys Ser Ala Ser Val Gln Gly Phe Phe Leu Asn His Tyr
        295                 300                 305 ctt tct aag tat caa gca gcc atg agc cac ttg ctc gag atg tgt gtg    1256
Leu Ser Lys Tyr Gln Ala Ala Met Ser His Leu Leu Glu Met Cys Val
    310                 315                 320 agc gga gac ctg gtt tgt gag gtg gac ctt gga gat ctg tct cca gag    1304
Ser Gly Asp Leu Val Cys Glu Val Asp Leu Gly Asp Leu Ser Pro Glu
325                 330                 335                 340 ggc agg ttt act ggc ctg gag tcc ata ttc cgt gct gtc aat tat atg    1352
Gly Arg Phe Thr Gly Leu Glu Ser Ile Phe Arg Ala Val Asn Tyr Met
                345                 350                 355 tac atg gga aaa aac act gga aaa att gta gtt gaa tta cct cac tct    1400
Tyr Met Gly Lys Asn Thr Gly Lys Ile Val Val Glu Leu Pro His Ser
            360                 365                 370 gtc aac agt aag ctg taa aaacagaaca atgacataaa tcaagggaga            1448
Val Asn Ser Lys Leu *
            375 aagaaaatgg gcactttatg tctcagaatt actcaaatca atttattttt agttggtaat   1508 ggatataata tttcttaaaa caaaagtaag gtgttaatga ataggtctct ccttctcctc   1568 ctcctcctcc tcttcccttg ggggaaaaaa aaaaatgtgc taataaaact tccctccatg   1628 gctaagaggg aaaacgctta cattcaattc tttagtcatg gatggtctcg ttccagatgt   1688 tattgttcca gggaactaaa ttcattcctg atgccagatc tgatcgagkc agtatgtctt   1748 cagcttggat caggatttta aaatcagttt tgaaagtggg ttcccgactt ctttggcttt   1808

<210> SEQ ID NO 2
<211> LENGTH: 377
<212> TYPE: PRT
<213> ORGANISM: Homo sapiens

<400> SEQUENCE: 2

Met Leu Arg Leu Val Pro Thr Gly Ala Arg Ala Ile Val Asp Met Ser
 1               5                  10                  15

Tyr Ala Arg His Phe Leu Asp Phe Gln Gly Ser Ala Ile Pro Gln Ala
            20                  25                  30

Met Gln Lys Leu Val Val Thr Arg Leu Ser Pro Asn Phe Arg Glu Ala
        35                  40                  45

Val Thr Leu Ser Arg Asp Cys Pro Val Pro Leu Pro Gly Asp Gly Asp
    50                  55                  60

Leu Leu Val Arg Asn Arg Phe Val Gly Val Asn Ala Ser Asp Ile Asn
65                  70                  75                  80

Tyr Ser Ala Gly Arg Tyr Asp Pro Ser Val Lys Pro Pro Phe Asp Ile
                85                  90                  95

Gly Phe Glu Gly Ile Gly Glu Val Val Ala Leu Gly Leu Ser Ala Ser
            100                 105                 110

Ala Arg Tyr Thr Val Gly Gln Ala Val Ala Tyr Met Ala Pro Gly Ser
        115                 120                 125

Phe Ala Glu Tyr Thr Val Val Pro Ala Ser Ile Ala Thr Pro Val Pro
    130                 135                 140

Ser Val Lys Pro Glu Tyr Leu Thr Leu Leu Val Ser Gly Thr Thr Ala
145                 150                 155                 160

Tyr Ile Ser Leu Lys Glu Leu Gly Gly Leu Ser Glu Gly Lys Lys Val
                165                 170                 175

Leu Val Thr Ala Ala Ala Gly Gly Thr Gly Gln Phe Ala Met Gln Leu
```

```
                    180                 185                 190
Ser Lys Lys Ala Lys Cys His Val Ile Gly Thr Cys Ser Ser Asp Glu
        195                 200                 205

Lys Ser Ala Phe Leu Lys Ser Leu Gly Cys Asp Arg Pro Ile Asn Tyr
    210                 215                 220

Lys Thr Glu Pro Val Gly Thr Val Leu Lys Gln Glu Tyr Pro Glu Gly
225                 230                 235                 240

Val Asp Val Val Tyr Glu Ser Val Gly Gly Ala Met Phe Asp Leu Ala
                245                 250                 255

Val Asp Ala Leu Ala Thr Lys Gly Arg Leu Ile Val Ile Gly Phe Ile
            260                 265                 270

Ser Gly Tyr Gln Thr Pro Thr Gly Leu Ser Pro Val Lys Ala Gly Thr
        275                 280                 285

Leu Pro Ala Lys Leu Leu Lys Lys Ser Ala Ser Val Gln Gly Phe Phe
    290                 295                 300

Leu Asn His Tyr Leu Ser Lys Tyr Gln Ala Ala Met Ser His Leu Leu
305                 310                 315                 320

Glu Met Cys Val Ser Gly Asp Leu Val Cys Glu Val Asp Leu Gly Asp
                325                 330                 335

Leu Ser Pro Glu Gly Arg Phe Thr Gly Leu Glu Ser Ile Phe Arg Ala
            340                 345                 350

Val Asn Tyr Met Tyr Met Gly Lys Asn Thr Gly Lys Ile Val Val Glu
        355                 360                 365

Leu Pro His Ser Val Asn Ser Lys Leu
    370                 375

<210> SEQ ID NO 3
<211> LENGTH: 1134
<212> TYPE: DNA
<213> ORGANISM: Homo sapiens
<220> FEATURE:
<221> NAME/KEY: CDS
<222> LOCATION: (1)...(1134)

<400> SEQUENCE: 3 atg ctg cgg ctg gtg ccc acc ggg gcc cgg gcc atc gtg gac atg tcg    48
Met Leu Arg Leu Val Pro Thr Gly Ala Arg Ala Ile Val Asp Met Ser
1               5                  10                  15 tac gcc cgc cac ttc ctg gac ttc cag ggc tcc gcc att ccc caa gcc    96
Tyr Ala Arg His Phe Leu Asp Phe Gln Gly Ser Ala Ile Pro Gln Ala
                20                  25                  30 atg cag aag ctg gtg gtg acc cgg ctg agc ccc aac ttc cgc gag gcc   144
Met Gln Lys Leu Val Val Thr Arg Leu Ser Pro Asn Phe Arg Glu Ala
            35                  40                  45 gtc acc ctg agc cgg gac tgc ccg gtg ccg ctc ccc ggg gac gga gac   192
Val Thr Leu Ser Arg Asp Cys Pro Val Pro Leu Pro Gly Asp Gly Asp
        50                  55                  60 ctc ctc gtc cgg aac cga ttt gtt ggt gtt aac gca tct gac atc aac   240
Leu Leu Val Arg Asn Arg Phe Val Gly Val Asn Ala Ser Asp Ile Asn
65                  70                  75                  80 tat tca gca ggc cgc tat gac ccc tca gtt aag cct ccc ttt gac ata   288
Tyr Ser Ala Gly Arg Tyr Asp Pro Ser Val Lys Pro Pro Phe Asp Ile
                85                  90                  95 ggt ttc gaa ggc att ggg gag gtg gtg gcc cta ggc ctc tct gct agt   336
Gly Phe Glu Gly Ile Gly Glu Val Val Ala Leu Gly Leu Ser Ala Ser
            100                 105                 110 gcc aga tac aca gtt ggc caa gct gtg gct tac atg gca cct ggt tct   384
Ala Arg Tyr Thr Val Gly Gln Ala Val Ala Tyr Met Ala Pro Gly Ser
```

|  |  |  |  |  |  |  |  |  |  |  |  |  |  |  |  |  |
|---|---|---|---|---|---|---|---|---|---|---|---|---|---|---|---|---|
|  |  |  | 115 |  |  |  | 120 |  |  |  | 125 |  |  |  |  |  |
| ttt | gct | gag | tac | aca | gtt | gtg | cct | gcc | agc | att | gca | act | cca | gtg | ccc | 432 |
| Phe | Ala | Glu | Tyr | Thr | Val | Val | Pro | Ala | Ser | Ile | Ala | Thr | Pro | Val | Pro |  |
|  | 130 |  |  |  | 135 |  |  |  | 140 |  |  |  |  |  |  |  |
| tca | gtg | aaa | ccc | gag | tat | ctt | acc | ctg | ctg | gta | agt | ggc | acc | acc | gca | 480 |
| Ser | Val | Lys | Pro | Glu | Tyr | Leu | Thr | Leu | Leu | Val | Ser | Gly | Thr | Thr | Ala |  |
| 145 |  |  |  |  | 150 |  |  |  |  | 155 |  |  |  |  | 160 |  |
| tac | atc | agc | ctg | aaa | gag | ctc | gga | gga | ctg | tcg | gaa | ggg | aaa | aaa | gtt | 528 |
| Tyr | Ile | Ser | Leu | Lys | Glu | Leu | Gly | Gly | Leu | Ser | Glu | Gly | Lys | Lys | Val |  |
|  |  |  |  | 165 |  |  |  |  | 170 |  |  |  |  | 175 |  |  |
| ttg | gtg | aca | gca | gca | gct | ggg | gga | acg | ggc | cag | ttt | gcc | atg | cag | ctt | 576 |
| Leu | Val | Thr | Ala | Ala | Ala | Gly | Gly | Thr | Gly | Gln | Phe | Ala | Met | Gln | Leu |  |
|  |  |  | 180 |  |  |  |  | 185 |  |  |  |  | 190 |  |  |  |
| tca | aag | aag | gca | aag | tgc | cat | gta | att | gga | acc | tgc | tct | tct | gat | gaa | 624 |
| Ser | Lys | Lys | Ala | Lys | Cys | His | Val | Ile | Gly | Thr | Cys | Ser | Ser | Asp | Glu |  |
|  |  | 195 |  |  |  |  | 200 |  |  |  |  | 205 |  |  |  |  |
| aag | tct | gct | ttt | ctg | aaa | tct | ctt | ggc | tgt | gat | cgt | cct | atc | aac | tat | 672 |
| Lys | Ser | Ala | Phe | Leu | Lys | Ser | Leu | Gly | Cys | Asp | Arg | Pro | Ile | Asn | Tyr |  |
|  | 210 |  |  |  |  | 215 |  |  |  |  | 220 |  |  |  |  |  |
| aaa | act | gaa | ccc | gta | ggt | acc | gtc | ctt | aag | cag | gag | tac | cct | gaa | ggt | 720 |
| Lys | Thr | Glu | Pro | Val | Gly | Thr | Val | Leu | Lys | Gln | Glu | Tyr | Pro | Glu | Gly |  |
| 225 |  |  |  |  | 230 |  |  |  |  | 235 |  |  |  |  | 240 |  |
| gtc | gat | gtg | gtc | tat | gaa | tct | gtt | ggg | gga | gcc | atg | ttt | gac | ttg | gct | 768 |
| Val | Asp | Val | Val | Tyr | Glu | Ser | Val | Gly | Gly | Ala | Met | Phe | Asp | Leu | Ala |  |
|  |  |  |  | 245 |  |  |  |  | 250 |  |  |  |  | 255 |  |  |
| gta | gac | gcc | ctg | gct | acg | aaa | ggg | cgc | ttg | ata | gta | ata | ggg | ttt | atc | 816 |
| Val | Asp | Ala | Leu | Ala | Thr | Lys | Gly | Arg | Leu | Ile | Val | Ile | Gly | Phe | Ile |  |
|  |  |  | 260 |  |  |  |  | 265 |  |  |  |  | 270 |  |  |  |
| tct | ggc | tac | caa | act | cct | act | ggc | ctt | tcg | cct | gtg | aaa | gca | gga | aca | 864 |
| Ser | Gly | Tyr | Gln | Thr | Pro | Thr | Gly | Leu | Ser | Pro | Val | Lys | Ala | Gly | Thr |  |
|  |  | 275 |  |  |  |  | 280 |  |  |  |  | 285 |  |  |  |  |
| ttg | cca | gcc | aaa | ctg | ctc | aag | aaa | tct | gcc | agc | gta | cag | ggc | ttc | ttc | 912 |
| Leu | Pro | Ala | Lys | Leu | Leu | Lys | Lys | Ser | Ala | Ser | Val | Gln | Gly | Phe | Phe |  |
|  | 290 |  |  |  |  | 295 |  |  |  |  | 300 |  |  |  |  |  |
| ctg | aac | cat | tac | ctt | tct | aag | tat | caa | gca | gcc | atg | agc | cac | ttg | ctc | 960 |
| Leu | Asn | His | Tyr | Leu | Ser | Lys | Tyr | Gln | Ala | Ala | Met | Ser | His | Leu | Leu |  |
| 305 |  |  |  |  | 310 |  |  |  |  | 315 |  |  |  |  | 320 |  |
| gag | atg | tgt | gtg | agc | gga | gac | ctg | gtt | tgt | gag | gtg | gac | ctt | gga | gat | 1008 |
| Glu | Met | Cys | Val | Ser | Gly | Asp | Leu | Val | Cys | Glu | Val | Asp | Leu | Gly | Asp |  |
|  |  |  |  | 325 |  |  |  |  | 330 |  |  |  |  | 335 |  |  |
| ctg | tct | cca | gag | ggc | agg | ttt | act | ggc | ctg | gag | tcc | ata | ttc | cgt | gct | 1056 |
| Leu | Ser | Pro | Glu | Gly | Arg | Phe | Thr | Gly | Leu | Glu | Ser | Ile | Phe | Arg | Ala |  |
|  |  |  | 340 |  |  |  |  | 345 |  |  |  |  | 350 |  |  |  |
| gtc | aat | tat | atg | tac | atg | gga | aaa | aac | act | gga | aaa | att | gta | gtt | gaa | 1104 |
| Val | Asn | Tyr | Met | Tyr | Met | Gly | Lys | Asn | Thr | Gly | Lys | Ile | Val | Val | Glu |  |
|  |  | 355 |  |  |  |  | 360 |  |  |  |  | 365 |  |  |  |  |
| tta | cct | cac | tct | gtc | aac | agt | aag | ctg | taa |  |  |  |  |  |  | 1134 |
| Leu | Pro | His | Ser | Val | Asn | Ser | Lys | Leu | * |  |  |  |  |  |  |  |
|  | 370 |  |  |  |  | 375 |  |  |  |  |  |  |  |  |  |  |

<210> SEQ ID NO 4
<211> LENGTH: 3238
<212> TYPE: DNA
<213> ORGANISM: Homo sapiens
<220> FEATURE:
<221> NAME/KEY: CDS
<222> LOCATION: (150)...(2540)

<400> SEQUENCE: 4
gcacgaggaa cagaagcagc agaagcaaca gcagtagcag cggcagcagc aacagcagca     60

```
gcccctactg aagtccaata gaggagactt gatctctagt tcattctgga actccgcctg     120
ggattgtgca ctgtccaggg tcctgaaac atg aac caa act gcc agc gtg tcc      173
                                 Met Asn Gln Thr Ala Ser Val Ser
                                  1               5 cat cac atc aag tgt caa ccc tca aaa aca atc aag gaa ctg gga agt      221
His His Ile Lys Cys Gln Pro Ser Lys Thr Ile Lys Glu Leu Gly Ser
     10              15                  20 aac agc cct cca cag aga aac tgg aag gga att gct att gct ctg ctg      269
Asn Ser Pro Pro Gln Arg Asn Trp Lys Gly Ile Ala Ile Ala Leu Leu
 25              30                  35                  40 gtg att tta gtt gta tgc tca ctc atc act atg tca gtc atc ctc tta      317
Val Ile Leu Val Val Cys Ser Leu Ile Thr Met Ser Val Ile Leu Leu
                 45                  50                  55 acc cca gat gaa ctc aca aat tcg tca gaa acc aga ttg tct ttg gaa      365
Thr Pro Asp Glu Leu Thr Asn Ser Ser Glu Thr Arg Leu Ser Leu Glu
             60                  65                  70 gac ctc ttt agg aaa gac ttt gtg ctt cac gat cca gag gct cgg tgg      413
Asp Leu Phe Arg Lys Asp Phe Val Leu His Asp Pro Glu Ala Arg Trp
         75                  80                  85 atc aat gat aca gat gtg gtg tat aaa agc gag aat gga cat gtc att      461
Ile Asn Asp Thr Asp Val Val Tyr Lys Ser Glu Asn Gly His Val Ile
     90                  95                 100 aaa ctg aat ata gaa aca aat gct acc aca tta tta ttg gaa aac aca      509
Lys Leu Asn Ile Glu Thr Asn Ala Thr Thr Leu Leu Leu Glu Asn Thr
105             110                 115                 120 act ttt gta acc ttc aaa gca tca aga cat tca gtt tca cca gat tta      557
Thr Phe Val Thr Phe Lys Ala Ser Arg His Ser Val Ser Pro Asp Leu
                125                 130                 135 aaa tat gtc ctt ctg gca tat gat gtc aaa cag att ttt cat tat tcg      605
Lys Tyr Val Leu Leu Ala Tyr Asp Val Lys Gln Ile Phe His Tyr Ser
            140                 145                 150 tat act gct tca tat gtg att tac aac ata cac act agg gaa gtt tgg      653
Tyr Thr Ala Ser Tyr Val Ile Tyr Asn Ile His Thr Arg Glu Val Trp
        155                 160                 165 gag tta aat cct cca gaa gta gag gac tcc gtc ttg cag tac gcg gcc      701
Glu Leu Asn Pro Pro Glu Val Glu Asp Ser Val Leu Gln Tyr Ala Ala
170                 175                 180 tgg ggt gtc caa ggg cag cag ctg att tat att ttt gaa aat aat atc      749
Trp Gly Val Gln Gly Gln Gln Leu Ile Tyr Ile Phe Glu Asn Asn Ile
185                 190                 195                 200 tac tat caa cct gat ata aag agc agt tca ttg cga ctg aca tct tct      797
Tyr Tyr Gln Pro Asp Ile Lys Ser Ser Ser Leu Arg Leu Thr Ser Ser
                205                 210                 215 gga aaa gaa gaa ata att ttt aat ggg att gct gac tgg tta tat gaa      845
Gly Lys Glu Glu Ile Ile Phe Asn Gly Ile Ala Asp Trp Leu Tyr Glu
            220                 225                 230 gag gaa ctc ctg cat tct cac atc gcc cac tgg tgg tca cca gat gga      893
Glu Glu Leu Leu His Ser His Ile Ala His Trp Trp Ser Pro Asp Gly
        235                 240                 245 gaa aga ctt gcc ttc ctg atg ata aat gac tct ttg gta ccc acc atg      941
Glu Arg Leu Ala Phe Leu Met Ile Asn Asp Ser Leu Val Pro Thr Met
250                 255                 260 gtt atc cct cgg ttt act gga gcg ttg tat ccc aaa gga aag cag tat      989
Val Ile Pro Arg Phe Thr Gly Ala Leu Tyr Pro Lys Gly Lys Gln Tyr
265                 270                 275                 280 ccg tat cct aag gca ggt caa gtg aac cca aca ata aaa tta tat gtt     1037
Pro Tyr Pro Lys Ala Gly Gln Val Asn Pro Thr Ile Lys Leu Tyr Val
                285                 290                 295 gta aac ctg tat gga cca act cac act ttg gag ctc atg cca cct gac     1085
Val Asn Leu Tyr Gly Pro Thr His Thr Leu Glu Leu Met Pro Pro Asp
```

-continued

```
Val Asn Leu Tyr Gly Pro Thr His Thr Leu Glu Leu Met Pro Pro Asp
                300                 305                 310 agc ttt aaa tca aga gaa tac tat atc act atg gtt aaa tgg gta agc     1133
Ser Phe Lys Ser Arg Glu Tyr Tyr Ile Thr Met Val Lys Trp Val Ser
            315                 320                 325 aat acc aag act gtg gta aga tgg tta aac cga cct cag aac atc tcc     1181
Asn Thr Lys Thr Val Val Arg Trp Leu Asn Arg Pro Gln Asn Ile Ser
        330                 335                 340 atc ctc aca gtc tgt gag acc act aca ggt gct tgt agt aaa aaa tat     1229
Ile Leu Thr Val Cys Glu Thr Thr Thr Gly Ala Cys Ser Lys Lys Tyr
345                 350                 355                 360 gag atg aca tca gat acg tgg ctc tct cag cag aat gag gag ccc gtg     1277
Glu Met Thr Ser Asp Thr Trp Leu Ser Gln Gln Asn Glu Glu Pro Val
                365                 370                 375 ttt tct aga gac ggc agc aaa ttc ttt atg aca gtg cct gtt aag caa     1325
Phe Ser Arg Asp Gly Ser Lys Phe Phe Met Thr Val Pro Val Lys Gln
            380                 385                 390 ggg gga cgt gga gaa ttt cac cac ata gct atg ttc ctc atc cag agt     1373
Gly Gly Arg Gly Glu Phe His His Ile Ala Met Phe Leu Ile Gln Ser
        395                 400                 405 aaa agt gag caa att acc gtg cgg cat ctg aca tca gga aac tgg gaa     1421
Lys Ser Glu Gln Ile Thr Val Arg His Leu Thr Ser Gly Asn Trp Glu
410                 415                 420 gtg ata aag atc ttg gca tac gat gaa act act caa aaa att tac ttt     1469
Val Ile Lys Ile Leu Ala Tyr Asp Glu Thr Thr Gln Lys Ile Tyr Phe
425                 430                 435                 440 ctg agc act gaa tct tct ccc aga gga agg cag ctg tac agt gct tct     1517
Leu Ser Thr Glu Ser Ser Pro Arg Gly Arg Gln Leu Tyr Ser Ala Ser
                445                 450                 455 act gaa gga tta ttg aat cgc caa tgc att tca tgt aat ttc atg aaa     1565
Thr Glu Gly Leu Leu Asn Arg Gln Cys Ile Ser Cys Asn Phe Met Lys
            460                 465                 470 gaa caa tgt aca tat ttt gat gcc agt ttt agt ccc atg aat caa cat     1613
Glu Gln Cys Thr Tyr Phe Asp Ala Ser Phe Ser Pro Met Asn Gln His
        475                 480                 485 ttc tta tta ttc tgt gaa ggt cca agg gtc cca gtg gtc agc cta cat     1661
Phe Leu Leu Phe Cys Glu Gly Pro Arg Val Pro Val Val Ser Leu His
490                 495                 500 agt acg gac aac cca gca aaa tat ttt ata ttg gaa agc aat tct atg     1709
Ser Thr Asp Asn Pro Ala Lys Tyr Phe Ile Leu Glu Ser Asn Ser Met
505                 510                 515                 520 ctg aag gaa gct atc ctg aag aag aag ata gga aag cca gaa att aaa     1757
Leu Lys Glu Ala Ile Leu Lys Lys Lys Ile Gly Lys Pro Glu Ile Lys
                525                 530                 535 atc ctt cat att gac gac tat gaa ctt cct tta cag ttg tcc ctt ccc     1805
Ile Leu His Ile Asp Asp Tyr Glu Leu Pro Leu Gln Leu Ser Leu Pro
            540                 545                 550 aaa gat ttt atg gac cga aac cag tat gct ctt ctg tta ata atg gat     1853
Lys Asp Phe Met Asp Arg Asn Gln Tyr Ala Leu Leu Leu Ile Met Asp
        555                 560                 565 gaa gaa cca gga ggc cag ctg gtt aca gat aag ttc cat att gac tgg     1901
Glu Glu Pro Gly Gly Gln Leu Val Thr Asp Lys Phe His Ile Asp Trp
570                 575                 580 gat tcc gta ctc att gac atg gat aat gtc att gta gca aga ttt gat     1949
Asp Ser Val Leu Ile Asp Met Asp Asn Val Ile Val Ala Arg Phe Asp
585                 590                 595                 600 ggc aga gga agt gga ttc cag ggt ctg aaa att ttg cag gag att cat     1997
Gly Arg Gly Ser Gly Phe Gln Gly Leu Lys Ile Leu Gln Glu Ile His
                605                 610                 615
```

-continued

```
cga aga tta ggt tca gta gaa gta aag gac caa ata aca gct gtg aaa      2045
Arg Arg Leu Gly Ser Val Glu Val Lys Asp Gln Ile Thr Ala Val Lys
        620                 625                 630 ttt ttg ctg aaa ctg cct tac att gac tcc aaa aga tta agc att ttt      2093
Phe Leu Leu Lys Leu Pro Tyr Ile Asp Ser Lys Arg Leu Ser Ile Phe
635                 640                 645 gga aag ggt tat ggt ggc tat att gca tca atg atc tta aaa tca gat      2141
Gly Lys Gly Tyr Gly Gly Tyr Ile Ala Ser Met Ile Leu Lys Ser Asp
    650                 655                 660 gaa aag ctt ttt aaa tgt gga tcc gtg gtt gca cct atc aca gac ttg      2189
Glu Lys Leu Phe Lys Cys Gly Ser Val Val Ala Pro Ile Thr Asp Leu
665                 670                 675                 680 aaa ttg tat gcc tca gct ttc tct gaa aga tac ctt ggg atg cca tct      2237
Lys Leu Tyr Ala Ser Ala Phe Ser Glu Arg Tyr Leu Gly Met Pro Ser
                685                 690                 695 aag gaa gaa agc act tac cag gca gcc agt gtg cta cat aat gtt cat      2285
Lys Glu Glu Ser Thr Tyr Gln Ala Ala Ser Val Leu His Asn Val His
            700                 705                 710 ggc ttg aaa gaa gaa aat ata tta ata att cat gga act gct gac aca      2333
Gly Leu Lys Glu Glu Asn Ile Leu Ile Ile His Gly Thr Ala Asp Thr
        715                 720                 725 aaa gtt cat ttc caa cac tca gca gaa tta atc aag cac cta ata aaa      2381
Lys Val His Phe Gln His Ser Ala Glu Leu Ile Lys His Leu Ile Lys
    730                 735                 740 gct gga gtg aat tat act atg cag gtc tac cca gat gaa ggt cat aac      2429
Ala Gly Val Asn Tyr Thr Met Gln Val Tyr Pro Asp Glu Gly His Asn
745                 750                 755                 760 gta tct gag aag agc aag tat cat ctc tac agc aca atc ctc aaa ttc      2477
Val Ser Glu Lys Ser Lys Tyr His Leu Tyr Ser Thr Ile Leu Lys Phe
                765                 770                 775 ttc agt gat tgt ttg aag gaa gaa ata tct gtg cta cca cag gaa cca      2525
Phe Ser Asp Cys Leu Lys Glu Glu Ile Ser Val Leu Pro Gln Glu Pro
            780                 785                 790 gaa gaa gat gaa taa tggaccgtat ttatacagaa ctgaagggaa tattgaggct      2580
Glu Glu Asp Glu *
        795 caatgaaacc tgacaaagag actgtaatat tgtagttgct ccagaatgtc aagggcagct      2640 tacggagatg tcactggagc agcacgctca gagacagtga actagcattt gaatacacaa      2700 gtccaagtct actgtgttgc tagggtgca gaacccgttt ctttgtatga gagaggtcaa       2760 agggttggtt tcctgggaga aattagtttt gcattaaagt aggagtagtg catgtttttct     2820 tctgttatcc ccctgtttgt tctgtaacta gttgctctca ttttaatttc actggccacc     2880 atcatctttg catataatgc acaatctatc atctgtccta cagtccctga tctttcatgg     2940 ctgagctgca atctaacact ttactgtacc tttataataa gtgcaattct ttcattgtct     3000 attattatgc ttaagaaaat attcagttaa taaaaacag agtatttat gtaatttctg       3060 ttttaaaaa gacattatta aatgggtcaa aggacatata gaaatgtggr wttcagcacc      3120 ttccaaagtt cagccagtta tcagtagata caatatcttt aaatgaacac acgagtgtat    3180 gtctcacaat atatatacac cagtgtgcat atacagttaa tgaaactatc tttaaatg     3238

<210> SEQ ID NO 5
<211> LENGTH: 796
<212> TYPE: PRT
<213> ORGANISM: Homo sapiens

<400> SEQUENCE: 5

Met Asn Gln Thr Ala Ser Val Ser His His Ile Lys Cys Gln Pro Ser
```

-continued

```
  1               5                  10                 15
Lys Thr Ile Lys Glu Leu Gly Ser Asn Ser Pro Gln Arg Asn Trp
             20                  25                 30
Lys Gly Ile Ala Ile Ala Leu Leu Val Ile Leu Val Val Cys Ser Leu
             35                  40                 45
Ile Thr Met Ser Val Ile Leu Leu Thr Pro Asp Glu Leu Thr Asn Ser
             50                  55                 60
Ser Glu Thr Arg Leu Ser Leu Glu Asp Leu Phe Arg Lys Asp Phe Val
 65                  70                 75                 80
Leu His Asp Pro Glu Ala Arg Trp Ile Asn Asp Thr Asp Val Val Tyr
                 85                  90                 95
Lys Ser Glu Asn Gly His Val Ile Lys Leu Asn Ile Glu Thr Asn Ala
                100                 105                110
Thr Thr Leu Leu Leu Glu Asn Thr Thr Phe Val Thr Phe Lys Ala Ser
                115                 120                125
Arg His Ser Val Ser Pro Asp Leu Lys Tyr Val Leu Leu Ala Tyr Asp
                130                 135                140
Val Lys Gln Ile Phe His Tyr Ser Tyr Thr Ala Ser Tyr Val Ile Tyr
145                 150                 155                160
Asn Ile His Thr Arg Glu Val Trp Glu Leu Asn Pro Pro Glu Val Glu
                165                 170                175
Asp Ser Val Leu Gln Tyr Ala Ala Trp Gly Val Gln Gly Gln Gln Leu
                180                 185                190
Ile Tyr Ile Phe Glu Asn Asn Ile Tyr Tyr Gln Pro Asp Ile Lys Ser
                195                 200                205
Ser Ser Leu Arg Leu Thr Ser Ser Gly Lys Glu Glu Ile Ile Phe Asn
210                 215                 220
Gly Ile Ala Asp Trp Leu Tyr Glu Glu Glu Leu Leu His Ser His Ile
225                 230                 235                240
Ala His Trp Trp Ser Pro Asp Gly Glu Arg Leu Ala Phe Leu Met Ile
                245                 250                255
Asn Asp Ser Leu Val Pro Thr Met Val Ile Pro Arg Phe Thr Gly Ala
                260                 265                270
Leu Tyr Pro Lys Gly Lys Gln Tyr Pro Tyr Pro Lys Ala Gly Gln Val
                275                 280                285
Asn Pro Thr Ile Lys Leu Tyr Val Val Asn Leu Tyr Gly Pro Thr His
                290                 295                300
Thr Leu Glu Leu Met Pro Pro Asp Ser Phe Lys Ser Arg Glu Tyr Tyr
305                 310                 315                320
Ile Thr Met Val Lys Trp Val Ser Asn Thr Lys Thr Val Val Arg Trp
                325                 330                335
Leu Asn Arg Pro Gln Asn Ile Ser Ile Leu Thr Val Cys Glu Thr Thr
                340                 345                350
Thr Gly Ala Cys Ser Lys Lys Tyr Glu Met Thr Ser Asp Thr Trp Leu
                355                 360                365
Ser Gln Gln Asn Glu Glu Pro Val Phe Ser Arg Asp Gly Ser Lys Phe
                370                 375                380
Phe Met Thr Val Pro Val Lys Gln Gly Gly Arg Gly Glu Phe His His
385                 390                 395                400
Ile Ala Met Phe Leu Ile Gln Ser Lys Ser Glu Gln Ile Thr Val Arg
                405                 410                415
His Leu Thr Ser Gly Asn Trp Glu Val Ile Lys Ile Leu Ala Tyr Asp
                420                 425                430
```

Glu Thr Thr Gln Lys Ile Tyr Phe Leu Ser Thr Glu Ser Pro Arg
            435                 440                 445

Gly Arg Gln Leu Tyr Ser Ala Ser Thr Glu Gly Leu Leu Asn Arg Gln
    450                 455                 460

Cys Ile Ser Cys Asn Phe Met Lys Glu Gln Cys Thr Tyr Phe Asp Ala
465                 470                 475                 480

Ser Phe Ser Pro Met Asn Gln His Phe Leu Leu Phe Cys Glu Gly Pro
                485                 490                 495

Arg Val Pro Val Val Ser Leu His Ser Thr Asp Asn Pro Ala Lys Tyr
            500                 505                 510

Phe Ile Leu Glu Ser Asn Ser Met Leu Lys Glu Ala Ile Leu Lys Lys
            515                 520                 525

Lys Ile Gly Lys Pro Glu Ile Lys Ile Leu His Ile Asp Asp Tyr Glu
    530                 535                 540

Leu Pro Leu Gln Leu Ser Leu Pro Lys Asp Phe Met Asp Arg Asn Gln
545                 550                 555                 560

Tyr Ala Leu Leu Leu Ile Met Asp Glu Glu Pro Gly Gly Gln Leu Val
                565                 570                 575

Thr Asp Lys Phe His Ile Asp Trp Asp Ser Val Leu Ile Asp Met Asp
            580                 585                 590

Asn Val Ile Val Ala Arg Phe Asp Gly Arg Gly Ser Gly Phe Gln Gly
            595                 600                 605

Leu Lys Ile Leu Gln Glu Ile His Arg Arg Leu Gly Ser Val Glu Val
    610                 615                 620

Lys Asp Gln Ile Thr Ala Val Lys Phe Leu Leu Lys Leu Pro Tyr Ile
625                 630                 635                 640

Asp Ser Lys Arg Leu Ser Ile Phe Gly Lys Gly Tyr Gly Gly Tyr Ile
                645                 650                 655

Ala Ser Met Ile Leu Lys Ser Asp Glu Lys Leu Phe Lys Cys Gly Ser
            660                 665                 670

Val Val Ala Pro Ile Thr Asp Leu Lys Leu Tyr Ala Ser Ala Phe Ser
            675                 680                 685

Glu Arg Tyr Leu Gly Met Pro Ser Lys Glu Glu Ser Thr Tyr Gln Ala
    690                 695                 700

Ala Ser Val Leu His Asn Val His Gly Leu Lys Glu Glu Asn Ile Leu
705                 710                 715                 720

Ile Ile His Gly Thr Ala Asp Thr Lys Val His Phe Gln His Ser Ala
                725                 730                 735

Glu Leu Ile Lys His Leu Ile Lys Ala Gly Val Asn Tyr Thr Met Gln
            740                 745                 750

Val Tyr Pro Asp Glu Gly His Asn Val Ser Glu Lys Ser Lys Tyr His
    755                 760                 765

Leu Tyr Ser Thr Ile Leu Lys Phe Phe Ser Asp Cys Leu Lys Glu Glu
    770                 775                 780

Ile Ser Val Leu Pro Gln Glu Pro Glu Glu Asp Glu
785                 790                 795

<210> SEQ ID NO 6
<211> LENGTH: 2388
<212> TYPE: DNA
<213> ORGANISM: Homo sapiens
<220> FEATURE:
<221> NAME/KEY: CDS
<222> LOCATION: (1)...(2388)

```
<400> SEQUENCE: 6 atg aac caa act gcc agc gtg tcc cat cac atc aag tgt caa ccc tca        48
Met Asn Gln Thr Ala Ser Val Ser His His Ile Lys Cys Gln Pro Ser
1               5                  10                  15 aaa aca atc aag gaa ctg gga agt aac agc cct cca cag aga aac tgg        96
Lys Thr Ile Lys Glu Leu Gly Ser Asn Ser Pro Pro Gln Arg Asn Trp
            20                  25                  30 aag gga att gct att gct ctg ctg gtg att tta gtt gta tgc tca ctc       144
Lys Gly Ile Ala Ile Ala Leu Leu Val Ile Leu Val Val Cys Ser Leu
        35                  40                  45 atc act atg tca gtc atc ctc tta acc cca gat gaa ctc aca aat tcg       192
Ile Thr Met Ser Val Ile Leu Leu Thr Pro Asp Glu Leu Thr Asn Ser
    50                  55                  60 tca gaa acc aga ttg tct ttg gaa gac ctc ttt agg aaa gac ttt gtg       240
Ser Glu Thr Arg Leu Ser Leu Glu Asp Leu Phe Arg Lys Asp Phe Val
65                  70                  75                  80 ctt cac gat cca gag gct cgg tgg atc aat gat aca gat gtg gtg tat       288
Leu His Asp Pro Glu Ala Arg Trp Ile Asn Asp Thr Asp Val Val Tyr
                85                  90                  95 aaa agc gag aat gga cat gtc att aaa ctg aat ata gaa aca aat gct       336
Lys Ser Glu Asn Gly His Val Ile Lys Leu Asn Ile Glu Thr Asn Ala
            100                 105                 110 acc aca tta tta ttg gaa aac aca act ttt gta acc ttc aaa gca tca       384
Thr Thr Leu Leu Leu Glu Asn Thr Thr Phe Val Thr Phe Lys Ala Ser
        115                 120                 125 aga cat tca gtt tca cca gat tta aaa tat gtc ctt ctg gca tat gat       432
Arg His Ser Val Ser Pro Asp Leu Lys Tyr Val Leu Leu Ala Tyr Asp
    130                 135                 140 gtc aaa cag att ttt cat tat tcg tat act gct tca tat gtg att tac       480
Val Lys Gln Ile Phe His Tyr Ser Tyr Thr Ala Ser Tyr Val Ile Tyr
145                 150                 155                 160 aac ata cac act agg gaa gtt tgg gag tta aat cct cca gaa gta gag       528
Asn Ile His Thr Arg Glu Val Trp Glu Leu Asn Pro Pro Glu Val Glu
                165                 170                 175 gac tcc gtc ttg cag tac gcg gcc tgg ggt gtc caa ggg cag cag ctg       576
Asp Ser Val Leu Gln Tyr Ala Ala Trp Gly Val Gln Gly Gln Gln Leu
            180                 185                 190 att tat att ttt gaa aat aat atc tac tat caa cct gat ata aag agc       624
Ile Tyr Ile Phe Glu Asn Asn Ile Tyr Tyr Gln Pro Asp Ile Lys Ser
        195                 200                 205 agt tca ttg cga ctg aca tct tct gga aaa gaa gaa ata att ttt aat       672
Ser Ser Leu Arg Leu Thr Ser Ser Gly Lys Glu Glu Ile Ile Phe Asn
    210                 215                 220 ggg att gct gac tgg tta tat gaa gag gaa ctc ctg cat tct cac atc       720
Gly Ile Ala Asp Trp Leu Tyr Glu Glu Glu Leu Leu His Ser His Ile
225                 230                 235                 240 gcc cac tgg tgg tca cca gat gga gaa aga ctt gcc ttc ctg atg ata       768
Ala His Trp Trp Ser Pro Asp Gly Glu Arg Leu Ala Phe Leu Met Ile
                245                 250                 255 aat gac tct ttg gta ccc acc atg gtt atc cct cgg ttt act gga gcg       816
Asn Asp Ser Leu Val Pro Thr Met Val Ile Pro Arg Phe Thr Gly Ala
            260                 265                 270 ttg tat ccc aaa gga aag cag tat ccg tat cct aag gca ggt caa gtg       864
Leu Tyr Pro Lys Gly Lys Gln Tyr Pro Tyr Pro Lys Ala Gly Gln Val
        275                 280                 285 aac cca aca ata aaa tta tat gtt gta aac ctg tat gga cca act cac       912
Asn Pro Thr Ile Lys Leu Tyr Val Val Asn Leu Tyr Gly Pro Thr His
    290                 295                 300 act ttg gag ctc atg cca cct gac agc ttt aaa tca aga gaa tac tat       960
```

```
                    Thr Leu Glu Leu Met Pro Pro Asp Ser Phe Lys Ser Arg Glu Tyr Tyr
                    305                 310                 315                 320 atc act atg gtt aaa tgg gta agc aat acc aag act gtg gta aga tgg       1008
Ile Thr Met Val Lys Trp Val Ser Asn Thr Lys Thr Val Val Arg Trp
                325                 330                 335 tta aac cga cct cag aac atc tcc atc ctc aca gtc tgt gag acc act       1056
Leu Asn Arg Pro Gln Asn Ile Ser Ile Leu Thr Val Cys Glu Thr Thr
            340                 345                 350 aca ggt gct tgt agt aaa aaa tat gag atg aca tca gat acg tgg ctc       1104
Thr Gly Ala Cys Ser Lys Lys Tyr Glu Met Thr Ser Asp Thr Trp Leu
        355                 360                 365 tct cag cag aat gag gag ccc gtg ttt tct aga gac ggc agc aaa ttc       1152
Ser Gln Gln Asn Glu Glu Pro Val Phe Ser Arg Asp Gly Ser Lys Phe
    370                 375                 380 ttt atg aca gtg cct gtt aag caa ggg gga cgt gga gaa ttt cac cac       1200
Phe Met Thr Val Pro Val Lys Gln Gly Gly Arg Gly Glu Phe His His
385                 390                 395                 400 ata gct atg ttc ctc atc cag agt aaa agt gag caa att acc gtg cgg       1248
Ile Ala Met Phe Leu Ile Gln Ser Lys Ser Glu Gln Ile Thr Val Arg
                405                 410                 415 cat ctg aca tca gga aac tgg gaa gtg ata aag atc ttg gca tac gat       1296
His Leu Thr Ser Gly Asn Trp Glu Val Ile Lys Ile Leu Ala Tyr Asp
            420                 425                 430 gaa act act caa aaa att tac ttt ctg agc act gaa tct tct ccc aga       1344
Glu Thr Thr Gln Lys Ile Tyr Phe Leu Ser Thr Glu Ser Ser Pro Arg
        435                 440                 445 gga agg cag ctg tac agt gct tct act gaa gga tta ttg aat cgc caa       1392
Gly Arg Gln Leu Tyr Ser Ala Ser Thr Glu Gly Leu Leu Asn Arg Gln
    450                 455                 460 tgc att tca tgt aat ttc atg aaa gaa caa tgt aca tat ttt gat gcc       1440
Cys Ile Ser Cys Asn Phe Met Lys Glu Gln Cys Thr Tyr Phe Asp Ala
465                 470                 475                 480 agt ttt agt ccc atg aat caa cat ttc tta tta ttc tgt gaa ggt cca       1488
Ser Phe Ser Pro Met Asn Gln His Phe Leu Leu Phe Cys Glu Gly Pro
                485                 490                 495 agg gtc cca gtg gtc agc cta cat agt acg gac aac cca gca aaa tat       1536
Arg Val Pro Val Val Ser Leu His Ser Thr Asp Asn Pro Ala Lys Tyr
            500                 505                 510 ttt ata ttg gaa agc aat tct atg ctg aag gaa gct atc ctg aag aag       1584
Phe Ile Leu Glu Ser Asn Ser Met Leu Lys Glu Ala Ile Leu Lys Lys
        515                 520                 525 aag ata gga aag cca gaa att aaa atc ctt cat att gac gac tat gaa       1632
Lys Ile Gly Lys Pro Glu Ile Lys Ile Leu His Ile Asp Asp Tyr Glu
    530                 535                 540 ctt cct tta cag ttg tcc ctt ccc aaa gat ttt atg gac cga aac cag       1680
Leu Pro Leu Gln Leu Ser Leu Pro Lys Asp Phe Met Asp Arg Asn Gln
545                 550                 555                 560 tat gct ctt ctg tta ata atg gat gaa gaa cca gga ggc cag ctg gtt       1728
Tyr Ala Leu Leu Leu Ile Met Asp Glu Glu Pro Gly Gly Gln Leu Val
                565                 570                 575 aca gat aag ttc cat att gac tgg gat tcc gta ctc att gac atg gat       1776
Thr Asp Lys Phe His Ile Asp Trp Asp Ser Val Leu Ile Asp Met Asp
            580                 585                 590 aat gtc att gta gca aga ttt gat ggc aga gga agt gga ttc cag ggt       1824
Asn Val Ile Val Ala Arg Phe Asp Gly Arg Gly Ser Gly Phe Gln Gly
        595                 600                 605 ctg aaa att ttg cag gag att cat cga aga tta ggt tca gta gaa gta       1872
Leu Lys Ile Leu Gln Glu Ile His Arg Arg Leu Gly Ser Val Glu Val
    610                 615                 620
```

| | | |
|---|---|---|
| aag gac caa ata aca gct gtg aaa ttt ttg ctg aaa ctg cct tac att<br>Lys Asp Gln Ile Thr Ala Val Lys Phe Leu Leu Lys Leu Pro Tyr Ile<br>625                        630                       635                    640 | 1920 |
| gac tcc aaa aga tta agc att ttt gga aag ggt tat ggt ggc tat att<br>Asp Ser Lys Arg Leu Ser Ile Phe Gly Lys Gly Tyr Gly Gly Tyr Ile<br>                        645                       650                      655 | 1968 |
| gca tca atg atc tta aaa tca gat gaa aag ctt ttt aaa tgt gga tcc<br>Ala Ser Met Ile Leu Lys Ser Asp Glu Lys Leu Phe Lys Cys Gly Ser<br>          660                       665                       670 | 2016 |
| gtg gtt gca cct atc aca gac ttg aaa ttg tat gcc tca gct ttc tct<br>Val Val Ala Pro Ile Thr Asp Leu Lys Leu Tyr Ala Ser Ala Phe Ser<br>675                        680                       685 | 2064 |
| gaa aga tac ctt ggg atg cca tct aag gaa gaa agc act tac cag gca<br>Glu Arg Tyr Leu Gly Met Pro Ser Lys Glu Glu Ser Thr Tyr Gln Ala<br>690                        695                       700 | 2112 |
| gcc agt gtg cta cat aat gtt cat ggc ttg aaa gaa gaa aat ata tta<br>Ala Ser Val Leu His Asn Val His Gly Leu Lys Glu Glu Asn Ile Leu<br>705                        710                       715                    720 | 2160 |
| ata att cat gga act gct gac aca aaa gtt cat ttc caa cac tca gca<br>Ile Ile His Gly Thr Ala Asp Thr Lys Val His Phe Gln His Ser Ala<br>                        725                       730                       735 | 2208 |
| gaa tta atc aag cac cta ata aaa gct gga gtg aat tat act atg cag<br>Glu Leu Ile Lys His Leu Ile Lys Ala Gly Val Asn Tyr Thr Met Gln<br>          740                       745                       750 | 2256 |
| gtc tac cca gat gaa ggt cat aac gta tct gag aag agc aag tat cat<br>Val Tyr Pro Asp Glu Gly His Asn Val Ser Glu Lys Ser Lys Tyr His<br>                 755                       760                    765 | 2304 |
| ctc tac agc aca atc ctc aaa ttc ttc agt gat tgt ttg aag gaa gaa<br>Leu Tyr Ser Thr Ile Leu Lys Phe Phe Ser Asp Cys Leu Lys Glu Glu<br>770                        775                       780 | 2352 |
| ata tct gtg cta cca cag gaa cca gaa gaa gat gaa<br>Ile Ser Val Leu Pro Gln Glu Pro Glu Glu Asp Glu<br>785                        790                       795 | 2388 |

```
<210> SEQ ID NO 7
<211> LENGTH: 1626
<212> TYPE: DNA
<213> ORGANISM: Homo sapiens
<220> FEATURE:
<221> NAME/KEY: CDS
<222> LOCATION: (218)...(808)
<220> FEATURE:
<221> NAME/KEY: misc_feature
<222> LOCATION: 96-148, 1462, 1549
<223> OTHER INFORMATION: n = A,T,C or G

<400> SEQUENCE: 7
```

| | |
|---|---|
| aggtcccggg atccggtggg tggtgcaaat caaagaacct gctcctcagt ggatgttgcc | 60 |
| ctttactttc taggccttgt ccgggaagtg ttactnnnnn nnnnnnnnnn nnnnnnnnnn | 120 |
| nnnnnnnnnn nnnnnnnnnn nnnnnnnnac gcgtccgccg gccgctgggc cgctgcctga | 180 |
| gccagggagg cgcagcgcga gctcccactt cgtcttc atg gat tcc cag ccc agc<br>                                                   Met Asp Ser Gln Pro Ser<br>                                                     1                   5 | 235 |
| tgc gtg gtg gtg act ggt ttt ggg ccc ttc cgg cag cac ttg gtg aat<br>Cys Val Val Val Thr Gly Phe Gly Pro Phe Arg Gln His Leu Val Asn<br>          10                       15                       20 | 283 |
| tcc agc tgg gaa gca gtg aag gag ctc tcc aag ctg ggc ctg ggg aat<br>Ser Ser Trp Glu Ala Val Lys Glu Leu Ser Lys Leu Gly Leu Gly Asn<br>                 25                       30                    35 | 331 |
| gaa aca gtg gtg cag ctg cgg act ctg gag ctg cct gta gat tac agg<br>Glu Thr Val Val Gln Leu Arg Thr Leu Glu Leu Pro Val Asp Tyr Arg | 379 |

-continued

```
                40                   45                   50
gag gct aag cgg agg gtc acc gga atc tgg gaa gat cat cag ccg caa      427
Glu Ala Lys Arg Arg Val Thr Gly Ile Trp Glu Asp His Gln Pro Gln
 55                   60                   65                   70 ctc gtc gtg cat gtg ggc atg gac acc gcc gcc aag gcg atc att ctg      475
Leu Val Val His Val Gly Met Asp Thr Ala Ala Lys Ala Ile Ile Leu
                 75                   80                   85 gaa cag tct ggc aag aac caa ggc tac cgg gac gcc gac atc cgc agc      523
Glu Gln Ser Gly Lys Asn Gln Gly Tyr Arg Asp Ala Asp Ile Arg Ser
                 90                   95                  100 ttc tgg ccc gag ggc ggc gtg tgc cta cct ggc agc cca gac gtg ctg      571
Phe Trp Pro Glu Gly Gly Val Cys Leu Pro Gly Ser Pro Asp Val Leu
            105                  110                  115 gag tca ggg gtc tgc atg aag gca gtc tgc aag cgc gta gct gtg gag      619
Glu Ser Gly Val Cys Met Lys Ala Val Cys Lys Arg Val Ala Val Glu
        120                  125                  130 ggt gtc gac gtg atc ttt tcc cga gat gca ggc aga tac gtc tgt gat      667
Gly Val Asp Val Ile Phe Ser Arg Asp Ala Gly Arg Tyr Val Cys Asp
135                  140                  145                  150 tat acc tat tac ctg tct ctg cat cat gga aag ggc tgc gcg gca ctc      715
Tyr Thr Tyr Tyr Leu Ser Leu His His Gly Lys Gly Cys Ala Ala Leu
                155                  160                  165 atc cat gtc cct cca cta tcg cgc ggg ctc ccg gcc agc ctg ctg gga      763
Ile His Val Pro Pro Leu Ser Arg Gly Leu Pro Ala Ser Leu Leu Gly
            170                  175                  180 aga gcc ttg aga ggt cat cat cca gca aat gct gga aga ggg tga          808
Arg Ala Leu Arg Gly His His Pro Ala Asn Ala Gly Arg Gly  *
        185                  190                  195 ttgtgaacat ctggtgagag aatggatgtg aaggtctttt tagcaacatt agaacactac    868
aaaaatcaca catctgaatg atttaatgga gggagaaaca gatagcttcc ctgtcgtctt    928
tactggcaat ttgcatgctg agaaagctca gctgtcagag aagaggcaat gcttttctgg    988
agaacgcttc caggcaacat gcgtgaacac acgtgcccca catagctcag cttccctgcc    1048
accaaagtgt agtgatgctt ccaggaggga caaaaccaaa ccagagacag aaatgcatac    1108
agaattattt tatttaactt aaaccatgta gtactttact agaaaaaagc agagtaagag    1168
aaactaacgt tgccttagct tcagccattc aaaatagaca gtttcttttt tccattatgt    1228
aaagaatcca gagtatatcg caataacagg aataaattct tacaacagaa tatacaaaaa    1288
cattttgaaa ttttttttcat ctactgattt tttatataaa caggattttt taggaataat    1348
ttatacacag aaagtcattt tatgtaacaa attggccatg ttattacctt ttttttttctt    1408 acttaaaaaa attttttttt aacaagaaaa ctcagaaaat gcattatttg cggngcatcc    1468
attccatccc gccttctggt tgatttttt ttatcccaga caaagggata cccagaggta    1528
gacaaactct ggcaaaccct ntcaccttaa cctcactggg cttaaaaaag cagacagggg    1588
gttttcaccc gggcggtctc ttccacccgg tggatgtg                           1626
```

<210> SEQ ID NO 8
<211> LENGTH: 196
<212> TYPE: PRT
<213> ORGANISM: Homo sapiens

<400> SEQUENCE: 8

```
Met Asp Ser Gln Pro Ser Cys Val Val Thr Gly Phe Gly Pro Phe
 1               5                   10                  15

Arg Gln His Leu Val Asn Ser Ser Trp Glu Ala Val Lys Glu Leu Ser
                20                  25                  30
```

```
Lys Leu Gly Leu Gly Asn Glu Thr Val Val Gln Leu Arg Thr Leu Glu
            35                  40                  45

Leu Pro Val Asp Tyr Arg Glu Ala Lys Arg Arg Val Thr Gly Ile Trp
        50                  55                  60

Glu Asp His Gln Pro Gln Leu Val Val His Val Gly Met Asp Thr Ala
 65                  70                  75                  80

Ala Lys Ala Ile Ile Leu Glu Gln Ser Gly Lys Asn Gln Gly Tyr Arg
                85                  90                  95

Asp Ala Asp Ile Arg Ser Phe Trp Pro Glu Gly Val Cys Leu Pro
            100                 105                 110

Gly Ser Pro Asp Val Leu Glu Ser Gly Val Cys Met Lys Ala Val Cys
            115                 120                 125

Lys Arg Val Ala Val Glu Gly Val Asp Val Ile Phe Ser Arg Asp Ala
            130                 135                 140

Gly Arg Tyr Val Cys Asp Tyr Thr Tyr Tyr Leu Ser Leu His His Gly
145                 150                 155                 160

Lys Gly Cys Ala Ala Leu Ile His Val Pro Pro Leu Ser Arg Gly Leu
                165                 170                 175

Pro Ala Ser Leu Leu Gly Arg Ala Leu Arg Gly His His Pro Ala Asn
            180                 185                 190

Ala Gly Arg Gly
        195

<210> SEQ ID NO 9
<211> LENGTH: 588
<212> TYPE: DNA
<213> ORGANISM: Homo sapiens
<220> FEATURE:
<221> NAME/KEY: CDS
<222> LOCATION: (1)...(588)

<400> SEQUENCE: 9 atg gat tcc cag ccc agc tgc gtg gtg gtg act ggt ttt ggg ccc ttc      48
Met Asp Ser Gln Pro Ser Cys Val Val Val Thr Gly Phe Gly Pro Phe
  1               5                  10                  15 cgg cag cac ttg gtg aat tcc agc tgg gaa gca gtg aag gag ctc tcc      96
Arg Gln His Leu Val Asn Ser Ser Trp Glu Ala Val Lys Glu Leu Ser
                 20                  25                  30 aag ctg ggc ctg ggg aat gaa aca gtg gtg cag ctg cgg act ctg gag     144
Lys Leu Gly Leu Gly Asn Glu Thr Val Val Gln Leu Arg Thr Leu Glu
             35                  40                  45 ctg cct gta gat tac agg gag gct aag cgg agg gtc acc gga atc tgg     192
Leu Pro Val Asp Tyr Arg Glu Ala Lys Arg Arg Val Thr Gly Ile Trp
         50                  55                  60 gaa gat cat cag ccg caa ctc gtc gtg cat gtg ggc atg gac acc gcc     240
Glu Asp His Gln Pro Gln Leu Val Val His Val Gly Met Asp Thr Ala
 65                  70                  75                  80 gcc aag gcg atc att ctg gaa cag tct ggc aag aac caa ggc tac cgg     288
Ala Lys Ala Ile Ile Leu Glu Gln Ser Gly Lys Asn Gln Gly Tyr Arg
                 85                  90                  95 gac gcc gac atc cgc agc ttc tgg ccc gag ggc ggc gtg tgc cta cct     336
Asp Ala Asp Ile Arg Ser Phe Trp Pro Glu Gly Gly Val Cys Leu Pro
            100                 105                 110 ggc agc cca gac gtg ctg gag tca ggg gtc tgc atg aag gca gtc tgc     384
Gly Ser Pro Asp Val Leu Glu Ser Gly Val Cys Met Lys Ala Val Cys
            115                 120                 125 aag cgc gta gct gtg gag ggt gtc gac gtg atc ttt tcc cga gat gca     432
Lys Arg Val Ala Val Glu Gly Val Asp Val Ile Phe Ser Arg Asp Ala
```

|  |  |
|---|---|
| ggc aga tac gtc tgt gat tat acc tat tac ctg tct ctg cat cat gga<br>Gly Arg Tyr Val Cys Asp Tyr Thr Tyr Tyr Leu Ser Leu His His Gly<br>145                            150                           155                          160 | 480 |
| aag ggc tgc gcg gca ctc atc cat gtc cct cca cta tcg cgc ggg ctc<br>Lys Gly Cys Ala Ala Leu Ile His Val Pro Pro Leu Ser Arg Gly Leu<br>                            165                           170                           175 | 528 |
| ccg gcc agc ctg ctg gga aga gcc ttg aga ggt cat cat cca gca aat<br>Pro Ala Ser Leu Leu Gly Arg Ala Leu Arg Gly His His Pro Ala Asn<br>                180                           185                           190 | 576 |
| gct gga aga ggg<br>Ala Gly Arg Gly<br>        195 | 588 |

<210> SEQ ID NO 10
<211> LENGTH: 1498
<212> TYPE: DNA
<213> ORGANISM: Homo sapiens
<220> FEATURE:
<221> NAME/KEY: CDS
<222> LOCATION: (118)...(1107)

<400> SEQUENCE: 10

|  |  |
|---|---|
| gccgcgcggg tctggcggga ccggtttgga agactttgcc ggcctgcaga ttggccttaa | 60 |
| gagaaggacg gagccacata ctgctgacgg cccagaactg gcagagagaa ggttgcc atg<br>                                                                                                                                                  Met<br>                                                                                                                                                  1 | 120 |
| gct gct gtt gac agt ttc tac ctc ttg tac agg gaa atc gcc agg tct<br>Ala Ala Val Asp Ser Phe Tyr Leu Leu Tyr Arg Glu Ile Ala Arg Ser<br>                   5                               10                          15 | 168 |
| tgc aat tgc tat atg gaa gct cta gct ttg gtt gga gcc tgg tat acg<br>Cys Asn Cys Tyr Met Glu Ala Leu Ala Leu Val Gly Ala Trp Tyr Thr<br>                  20                            25                           30 | 216 |
| gcc aga aaa agc atc act gtc atc tgt gac ttt tac agc ctg atc agg<br>Ala Arg Lys Ser Ile Thr Val Ile Cys Asp Phe Tyr Ser Leu Ile Arg<br> 35                          40                           45 | 264 |
| ctg cat ttt atc ccc cgc ctg ggg agc aga gca gac ttg atc aag cag<br>Leu His Phe Ile Pro Arg Leu Gly Ser Arg Ala Asp Leu Ile Lys Gln<br> 50                          55                           60                           65 | 312 |
| tat gga aga tgg gcc gtt gtc agc ggt gca aca gat ggg att gga aaa<br>Tyr Gly Arg Trp Ala Val Val Ser Gly Ala Thr Asp Gly Ile Gly Lys<br>                  70                            75                           80 | 360 |
| gcc tac gct gaa gag tta gca agc cga ggt ctc aat ata atc ctg att<br>Ala Tyr Ala Glu Glu Leu Ala Ser Arg Gly Leu Asn Ile Ile Leu Ile<br>                            85                           90                           95 | 408 |
| agt cgg aac gag gag aag ttg cag gtt gtt gct aaa gac ata gcc gac<br>Ser Arg Asn Glu Glu Lys Leu Gln Val Val Ala Lys Asp Ile Ala Asp<br>                100                           105                           110 | 456 |
| acg tac aaa gtg gaa act gat att ata gtt gcg gac ttc agc agc ggt<br>Thr Tyr Lys Val Glu Thr Asp Ile Ile Val Ala Asp Phe Ser Ser Gly<br>        115                           120                           125 | 504 |
| cgt gag atc tac ctt cca att cga gaa gcc ctg aag gac aaa gac gtt<br>Arg Glu Ile Tyr Leu Pro Ile Arg Glu Ala Leu Lys Asp Lys Asp Val<br>130                            135                           140                           145 | 552 |
| ggc atc ttg gta aat aac gtg ggt gtg ttt tat ccc tac ccg cag tat<br>Gly Ile Leu Val Asn Asn Val Gly Val Phe Tyr Pro Tyr Pro Gln Tyr<br>                  150                           155                           160 | 600 |
| ttc act cag ctg tcc gag gac aag ctc tgg gac atc ata aat gtg aac<br>Phe Thr Gln Leu Ser Glu Asp Lys Leu Trp Asp Ile Ile Asn Val Asn<br>                         165                           170                           175 | 648 |

-continued

| | | | | | | | | | | | | | | | |
|---|---|---|---|---|---|---|---|---|---|---|---|---|---|---|---|
| att | gcc | gcc | gct | agt | ttg | atg | gtc | cat | gtt | gtg | tta | ccg | gga | atg | gtg |
| Ile | Ala | Ala | Ala | Ser | Leu | Met | Val | His | Val | Val | Leu | Pro | Gly | Met | Val |
| | | | 180 | | | | | 185 | | | | | 190 | | |

696

| gag | aga | aag | aaa | ggt | gcc | atc | gtc | acg | atc | tct | tct | ggc | tcc | tgc | tgc |
|---|---|---|---|---|---|---|---|---|---|---|---|---|---|---|---|
| Glu | Arg | Lys | Lys | Gly | Ala | Ile | Val | Thr | Ile | Ser | Ser | Gly | Ser | Cys | Cys |
| 195 | | | | | 200 | | | | | 205 | | | | | |

744

| aaa | ccc | act | cct | cag | ctg | gct | gca | ttt | tct | gct | tct | aag | gct | tat | tta |
|---|---|---|---|---|---|---|---|---|---|---|---|---|---|---|---|
| Lys | Pro | Thr | Pro | Gln | Leu | Ala | Ala | Phe | Ser | Ala | Ser | Lys | Ala | Tyr | Leu |
| 210 | | | | | 215 | | | | | 220 | | | | | 225 |

792

| gac | cac | ttc | agc | aga | gcc | ttg | caa | tat | gaa | tat | gcc | tct | aaa | gga | atc |
|---|---|---|---|---|---|---|---|---|---|---|---|---|---|---|---|
| Asp | His | Phe | Ser | Arg | Ala | Leu | Gln | Tyr | Glu | Tyr | Ala | Ser | Lys | Gly | Ile |
| | | | | 230 | | | | | 235 | | | | | 240 | |

840

| ttt | gta | cag | agt | cta | atc | cct | ttc | tat | gta | gcc | acc | agc | atg | aca | gca |
|---|---|---|---|---|---|---|---|---|---|---|---|---|---|---|---|
| Phe | Val | Gln | Ser | Leu | Ile | Pro | Phe | Tyr | Val | Ala | Thr | Ser | Met | Thr | Ala |
| | | | | 245 | | | | | 250 | | | | | 255 | |

888

| ccc | agc | aac | ttt | ctg | cac | agg | tgc | tcg | tgg | ttg | gtg | cct | tcg | cca | aaa |
|---|---|---|---|---|---|---|---|---|---|---|---|---|---|---|---|
| Pro | Ser | Asn | Phe | Leu | His | Arg | Cys | Ser | Trp | Leu | Val | Pro | Ser | Pro | Lys |
| | | 260 | | | | | 265 | | | | | 270 | | | |

936

| gtc | tat | gca | cat | cat | gct | gtt | tct | act | ctt | ggg | att | tcc | aaa | agg | acc |
|---|---|---|---|---|---|---|---|---|---|---|---|---|---|---|---|
| Val | Tyr | Ala | His | His | Ala | Val | Ser | Thr | Leu | Gly | Ile | Ser | Lys | Arg | Thr |
| 275 | | | | | 280 | | | | | 285 | | | | | |

984

| aca | gga | tat | tgg | tcc | cat | tct | att | cag | ttt | ctt | ttt | gca | cag | tat | atg |
|---|---|---|---|---|---|---|---|---|---|---|---|---|---|---|---|
| Thr | Gly | Tyr | Trp | Ser | His | Ser | Ile | Gln | Phe | Leu | Phe | Ala | Gln | Tyr | Met |
| 290 | | | | | 295 | | | | | 300 | | | | | 305 |

1032

| cct | gaa | tgg | ctc | tgg | gtg | tgg | gga | gca | aat | att | ctc | aac | cgt | tca | cta |
|---|---|---|---|---|---|---|---|---|---|---|---|---|---|---|---|
| Pro | Glu | Trp | Leu | Trp | Val | Trp | Gly | Ala | Asn | Ile | Leu | Asn | Arg | Ser | Leu |
| | | | 310 | | | | | 315 | | | | | 320 | | |

1080

| cgt | aag | gaa | gcc | tta | tcc | tgc | aca | gcc | tgagtctgga | tggccacttg | | | | | |
|---|---|---|---|---|---|---|---|---|---|---|---|---|---|---|---|
| Arg | Lys | Glu | Ala | Leu | Ser | Cys | Thr | Ala | | | | | | | |
| | | | 325 | | | | | 330 | | | | | | | |

1127 agaagttttg ccaactcctg ggaacctcga tattctgaca tttggaaaaa cacatttaat    1187 ttatctcctg tgtttcattg ctgattattc agcatactgt tgattcgtca tttgcaaaac    1247 acacataata ccgtcagagt gctgtgaaaa accttaaggg tgtgtggatg gcacaggatc    1307 aataatgcct gaggctgatt gacgacatct cattttcggt gcttttttccc taagctgttt    1367 gaaagttacg cttttctgtt gttctagagc cacagcagtc taatattgaa atataatatg    1427 atttgtcagg tcttataaaa aaaaaaaaaa aaaaaattg cggccgcaag cttattccct    1487 ttagtrrggg t    1498

<210> SEQ ID NO 11
<211> LENGTH: 330
<212> TYPE: PRT
<213> ORGANISM: Homo sapiens

<400> SEQUENCE: 11

| Met | Ala | Ala | Val | Asp | Ser | Phe | Tyr | Leu | Leu | Tyr | Arg | Glu | Ile | Ala | Arg |
|---|---|---|---|---|---|---|---|---|---|---|---|---|---|---|---|
| 1 | | | | 5 | | | | | 10 | | | | | 15 | |

| Ser | Cys | Asn | Cys | Tyr | Met | Glu | Ala | Leu | Ala | Leu | Val | Gly | Ala | Trp | Tyr |
|---|---|---|---|---|---|---|---|---|---|---|---|---|---|---|---|
| | | | 20 | | | | | 25 | | | | | 30 | | |

| Thr | Ala | Arg | Lys | Ser | Ile | Thr | Val | Ile | Cys | Asp | Phe | Tyr | Ser | Leu | Ile |
|---|---|---|---|---|---|---|---|---|---|---|---|---|---|---|---|
| | | | 35 | | | | | 40 | | | | | 45 | | |

| Arg | Leu | His | Phe | Ile | Pro | Arg | Leu | Gly | Ser | Arg | Ala | Asp | Leu | Ile | Lys |
|---|---|---|---|---|---|---|---|---|---|---|---|---|---|---|---|
| | 50 | | | | | 55 | | | | | 60 | | | | |

| Gln | Tyr | Gly | Arg | Trp | Ala | Val | Val | Ser | Gly | Ala | Thr | Asp | Gly | Ile | Gly |
|---|---|---|---|---|---|---|---|---|---|---|---|---|---|---|---|
| 65 | | | | | 70 | | | | | 75 | | | | | 80 |

| Lys | Ala | Tyr | Ala | Glu | Glu | Leu | Ala | Ser | Arg | Gly | Leu | Asn | Ile | Ile | Leu |
|---|---|---|---|---|---|---|---|---|---|---|---|---|---|---|---|
| | | | | 85 | | | | | 90 | | | | | 95 | |

```
Ile Ser Arg Asn Glu Glu Lys Leu Gln Val Val Ala Lys Asp Ile Ala
            100                 105                 110

Asp Thr Tyr Lys Val Glu Thr Asp Ile Ile Val Ala Asp Phe Ser Ser
        115                 120                 125

Gly Arg Glu Ile Tyr Leu Pro Ile Arg Glu Ala Leu Lys Asp Lys Asp
    130                 135                 140

Val Gly Ile Leu Val Asn Asn Val Gly Val Phe Tyr Pro Tyr Pro Gln
145                 150                 155                 160

Tyr Phe Thr Gln Leu Ser Glu Asp Lys Leu Trp Asp Ile Ile Asn Val
                165                 170                 175

Asn Ile Ala Ala Ala Ser Leu Met Val His Val Val Leu Pro Gly Met
            180                 185                 190

Val Glu Arg Lys Lys Gly Ala Ile Val Thr Ile Ser Ser Gly Ser Cys
        195                 200                 205

Cys Lys Pro Thr Pro Gln Leu Ala Ala Phe Ser Ala Ser Lys Ala Tyr
    210                 215                 220

Leu Asp His Phe Ser Arg Ala Leu Gln Tyr Glu Tyr Ala Ser Lys Gly
225                 230                 235                 240

Ile Phe Val Gln Ser Leu Ile Pro Phe Tyr Val Ala Thr Ser Met Thr
                245                 250                 255

Ala Pro Ser Asn Phe Leu His Arg Cys Ser Trp Leu Val Pro Ser Pro
            260                 265                 270

Lys Val Tyr Ala His His Ala Val Ser Thr Leu Gly Ile Ser Lys Arg
        275                 280                 285

Thr Thr Gly Tyr Trp Ser His Ser Ile Gln Phe Leu Phe Ala Gln Tyr
    290                 295                 300

Met Pro Glu Trp Leu Trp Val Trp Gly Ala Asn Ile Leu Asn Arg Ser
305                 310                 315                 320

Leu Arg Lys Glu Ala Leu Ser Cys Thr Ala
                325                 330

<210> SEQ ID NO 12
<211> LENGTH: 990
<212> TYPE: DNA
<213> ORGANISM: Homo sapiens
<220> FEATURE:
<221> NAME/KEY: CDS
<222> LOCATION: (1)...(990)

<400> SEQUENCE: 12 atg gct gct gtt gac agt ttc tac ctc ttg tac agg gaa atc gcc agg      48
Met Ala Ala Val Asp Ser Phe Tyr Leu Leu Tyr Arg Glu Ile Ala Arg
  1               5                  10                  15 tct tgc aat tgc tat atg gaa gct cta gct ttg gtt gga gcc tgg tat      96
Ser Cys Asn Cys Tyr Met Glu Ala Leu Ala Leu Val Gly Ala Trp Tyr
                 20                  25                  30 acg gcc aga aaa agc atc act gtc atc tgt gac ttt tac agc ctg atc     144
Thr Ala Arg Lys Ser Ile Thr Val Ile Cys Asp Phe Tyr Ser Leu Ile
         35                  40                  45 agg ctg cat ttt atc ccc cgc ctg ggg agc aga gca gac ttg atc aag     192
Arg Leu His Phe Ile Pro Arg Leu Gly Ser Arg Ala Asp Leu Ile Lys
     50                  55                  60 cag tat gga aga tgg gcc gtt gtc agc ggt gca aca gat ggg att gga     240
Gln Tyr Gly Arg Trp Ala Val Val Ser Gly Ala Thr Asp Gly Ile Gly
 65                  70                  75                  80 aaa gcc tac gct gaa gag tta gca agc cga ggt ctc aat ata atc ctg     288
Lys Ala Tyr Ala Glu Glu Leu Ala Ser Arg Gly Leu Asn Ile Ile Leu
```

```
                        85                 90                  95
att agt cgg aac gag gag aag ttg cag gtt gtt gct aaa gac ata gcc      336
Ile Ser Arg Asn Glu Glu Lys Leu Gln Val Val Ala Lys Asp Ile Ala
            100                 105                 110 gac acg tac aaa gtg gaa act gat att ata gtt gcg gac ttc agc agc      384
Asp Thr Tyr Lys Val Glu Thr Asp Ile Ile Val Ala Asp Phe Ser Ser
        115                 120                 125 ggt cgt gag atc tac ctt cca att cga gaa gcc ctg aag gac aaa gac      432
Gly Arg Glu Ile Tyr Leu Pro Ile Arg Glu Ala Leu Lys Asp Lys Asp
    130                 135                 140 gtt ggc atc ttg gta aat aac gtg ggt gtg ttt tat ccc tac ccg cag      480
Val Gly Ile Leu Val Asn Asn Val Gly Val Phe Tyr Pro Tyr Pro Gln
145                 150                 155                 160 tat ttc act cag ctg tcc gag gac aag ctc tgg gac atc ata aat gtg      528
Tyr Phe Thr Gln Leu Ser Glu Asp Lys Leu Trp Asp Ile Ile Asn Val
                165                 170                 175 aac att gcc gcc gct agt ttg atg gtc cat gtt gtg tta ccg gga atg      576
Asn Ile Ala Ala Ala Ser Leu Met Val His Val Val Leu Pro Gly Met
            180                 185                 190 gtg gag aga aag aaa ggt gcc atc gtc acg atc tct tct ggc tcc tgc      624
Val Glu Arg Lys Lys Gly Ala Ile Val Thr Ile Ser Ser Gly Ser Cys
        195                 200                 205 tgc aaa ccc act cct cag ctg gct gca ttt tct gct tct aag gct tat      672
Cys Lys Pro Thr Pro Gln Leu Ala Ala Phe Ser Ala Ser Lys Ala Tyr
    210                 215                 220 tta gac cac ttc agc aga gcc ttg caa tat gaa tat gcc tct aaa gga      720
Leu Asp His Phe Ser Arg Ala Leu Gln Tyr Glu Tyr Ala Ser Lys Gly
225                 230                 235                 240 atc ttt gta cag agt cta atc cct ttc tat gta gcc acc agc atg aca      768
Ile Phe Val Gln Ser Leu Ile Pro Phe Tyr Val Ala Thr Ser Met Thr
                245                 250                 255 gca ccc agc aac ttt ctg cac agg tgc tcg tgg ttg gtg cct tcg cca      816
Ala Pro Ser Asn Phe Leu His Arg Cys Ser Trp Leu Val Pro Ser Pro
            260                 265                 270 aaa gtc tat gca cat cat gct gtt tct act ctt ggg att tcc aaa agg      864
Lys Val Tyr Ala His His Ala Val Ser Thr Leu Gly Ile Ser Lys Arg
        275                 280                 285 acc aca gga tat tgg tcc cat tct att cag ttt ctt ttt gca cag tat      912
Thr Thr Gly Tyr Trp Ser His Ser Ile Gln Phe Leu Phe Ala Gln Tyr
    290                 295                 300 atg cct gaa tgg ctc tgg gtg tgg gga gca aat att ctc aac cgt tca      960
Met Pro Glu Trp Leu Trp Val Trp Gly Ala Asn Ile Leu Asn Arg Ser
305                 310                 315                 320 cta cgt aag gaa gcc tta tcc tgc aca gcc                              990
Leu Arg Lys Glu Ala Leu Ser Cys Thr Ala
                325                 330

<210> SEQ ID NO 13
<211> LENGTH: 1981
<212> TYPE: DNA
<213> ORGANISM: Homo sapiens
<220> FEATURE:
<221> NAME/KEY: CDS
<222> LOCATION: (15)...(1415)

<400> SEQUENCE: 13
ggactccaag cgcc atg gcc gct gcc gcc cga gcc cgg gtc gcg tac ttg       50
                Met Ala Ala Ala Ala Arg Ala Arg Val Ala Tyr Leu
                  1               5                  10 ctg agg caa ctg caa cgc gca gcg tgc cag tgc cca act cat tct cat       98
Leu Arg Gln Leu Gln Arg Ala Ala Cys Gln Cys Pro Thr His Ser His
```

```
                15                  20                  25
act tac tcc caa gcc cct gga ctt tca cct tct ggg aaa aca aca gat       146
Thr Tyr Ser Gln Ala Pro Gly Leu Ser Pro Ser Gly Lys Thr Thr Asp
         30                  35                  40 tat gcc ttt gag atg gct gtt tca aat att aga tat gga gca gca gtt       194
Tyr Ala Phe Glu Met Ala Val Ser Asn Ile Arg Tyr Gly Ala Ala Val
 45                  50                  55                  60 aca aag gaa gta gga atg gac cta aaa aac atg ggt gct aaa aat gtg       242
Thr Lys Glu Val Gly Met Asp Leu Lys Asn Met Gly Ala Lys Asn Val
                 65                  70                  75 tgc ttg atg aca gac aag aac ctc tcc aag ctc cct cct gtg caa gta       290
Cys Leu Met Thr Asp Lys Asn Leu Ser Lys Leu Pro Pro Val Gln Val
             80                  85                  90 gct atg gat tcc cta gtg aag aat ggc atc ccc ttt acg gtt tat gat       338
Ala Met Asp Ser Leu Val Lys Asn Gly Ile Pro Phe Thr Val Tyr Asp
         95                 100                 105 aat gtg aga gtg gaa cca acg gat tca agc ttc atg gaa gct att gag       386
Asn Val Arg Val Glu Pro Thr Asp Ser Ser Phe Met Glu Ala Ile Glu
110                 115                 120 ttt gcc caa aag gga gct ttt gat gcc tat gtt gct gtc ggt ggt ggc       434
Phe Ala Gln Lys Gly Ala Phe Asp Ala Tyr Val Ala Val Gly Gly Gly
125                 130                 135                 140 tct acc atg gac acc tgt aag gct gct aat ctg tat gca tcc agc cct       482
Ser Thr Met Asp Thr Cys Lys Ala Ala Asn Leu Tyr Ala Ser Ser Pro
                145                 150                 155 cat tct gat ttc cta gat tat gtc agt gcc ccc att ggc aag gga aag       530
His Ser Asp Phe Leu Asp Tyr Val Ser Ala Pro Ile Gly Lys Gly Lys
            160                 165                 170 cct gtg tct gtg cct ctt aag cct ctg att gca gtg cca act acc tca       578
Pro Val Ser Val Pro Leu Lys Pro Leu Ile Ala Val Pro Thr Thr Ser
        175                 180                 185 gga acc ggg agt gaa act act ggg gtt gcc att ttt gac tat gaa cac       626
Gly Thr Gly Ser Glu Thr Thr Gly Val Ala Ile Phe Asp Tyr Glu His
    190                 195                 200 ttg aaa gta aaa att ggc atc act tcg aga gcc atc aaa ccc aca ctg       674
Leu Lys Val Lys Ile Gly Ile Thr Ser Arg Ala Ile Lys Pro Thr Leu
205                 210                 215                 220 gga ctg att gat cct ctg cac acc ctc cac atg cct gcc cga gtg gtc       722
Gly Leu Ile Asp Pro Leu His Thr Leu His Met Pro Ala Arg Val Val
                225                 230                 235 gcc aac agt ggc ttt gat gtg ctt tgc cat gcc ctg gag tca tac acc       770
Ala Asn Ser Gly Phe Asp Val Leu Cys His Ala Leu Glu Ser Tyr Thr
            240                 245                 250 acc ctg ccc tac cac ctg cgg agc ccc tgc cct tca aat ccc atc aca       818
Thr Leu Pro Tyr His Leu Arg Ser Pro Cys Pro Ser Asn Pro Ile Thr
        255                 260                 265 cgg cct gcg tac cag ggc agc aac cca atc agt gac att tgg gct atc       866
Arg Pro Ala Tyr Gln Gly Ser Asn Pro Ile Ser Asp Ile Trp Ala Ile
    270                 275                 280 cac gcg ctg cgg atc gtg gct aag tat ctg aag agg gct gtc aga aat       914
His Ala Leu Arg Ile Val Ala Lys Tyr Leu Lys Arg Ala Val Arg Asn
285                 290                 295                 300 ccc gat gat ctt gaa gca agg tct cat atg cac ttg gca agt gct ttt       962
Pro Asp Asp Leu Glu Ala Arg Ser His Met His Leu Ala Ser Ala Phe
                305                 310                 315 gct ggc atc ggc ttt gga aat gct ggt gtt cat ctg tgc cat gga atg      1010
Ala Gly Ile Gly Phe Gly Asn Ala Gly Val His Leu Cys His Gly Met
            320                 325                 330 tct tac cca att tca ggt tta gtg aag atg tat aaa gca aag gat tac      1058
```

```
                Ser Tyr Pro Ile Ser Gly Leu Val Lys Met Tyr Lys Ala Lys Asp Tyr
                        335                 340                 345 aat gtg gat cac cca ctg gtg ccc cat ggc ctt tct gtg gtg ctc acg              1106
Asn Val Asp His Pro Leu Val Pro His Gly Leu Ser Val Val Leu Thr
        350                 355                 360 tcc cca gcg gtg ttc act ttc acg gcc cag atg ttt cca gag cga cac              1154
Ser Pro Ala Val Phe Thr Phe Thr Ala Gln Met Phe Pro Glu Arg His
365                 370                 375                 380 ctg gag atg gca gaa ata ctg gga gcc gac acc cgc act gcc agg atc              1202
Leu Glu Met Ala Glu Ile Leu Gly Ala Asp Thr Arg Thr Ala Arg Ile
                385                 390                 395 caa gat gca ggg ctg gtg ttg gca gac acg ctc cgg aaa ttc tta ttc              1250
Gln Asp Ala Gly Leu Val Leu Ala Asp Thr Leu Arg Lys Phe Leu Phe
            400                 405                 410 gat ctg gat gtt gat gat ggc cta gca gct gtt ggt tac tcc aaa gct              1298
Asp Leu Asp Val Asp Asp Gly Leu Ala Ala Val Gly Tyr Ser Lys Ala
        415                 420                 425 gat atc ccc gca cta gtg aaa gga acg ctg ccc cag gaa agg gtc acc              1346
Asp Ile Pro Ala Leu Val Lys Gly Thr Leu Pro Gln Glu Arg Val Thr
    430                 435                 440 aag ctt gca ccc tgt ccc cag tca gaa gag gat ctg gct gct ctg ttt              1394
Lys Leu Ala Pro Cys Pro Gln Ser Glu Glu Asp Leu Ala Ala Leu Phe
445                 450                 455                 460 gaa gct tca atg aaa ctg tat taattgtcat tttaactgaa agaattaccg                 1445
Glu Ala Ser Met Lys Leu Tyr
                465 ctggccattg tagtgctgag agcaagagct gatctagcta gggctttgtc ttttcatctt            1505 tgcgcataac ttacctgtta ccagtatagg tgggatatac atttatcttg caggaaattc            1565 cccaaagctc agagtccagt tccttccata aaacaggctg acaaatgac cactatgtta             1625 gacccccagg ctcgacttca ggggtcagtg ttcctgtccc aaacccacca cagaatactc            1685 tgcctctgyt tcatgtagca aatgagcaaa aactcagtat ctatcaaaag tgtaaattat            1745 atttcctatg cctagtaatt cacttcatgt ctaaaaattt atctgataga aacactagca            1805 ccagtacata cagaagcatg gcaaggatgt ttctggcagc acttttctaa taataaaaga            1865 tttgaaacaa cmwwaarwaw wmawwawwrr wawawaraks acttatagta tactagacag            1925 tggaatacta tggtactgtt aataaagatg aagtaaatct cttggaaaaa aaaaaa               1981

<210> SEQ ID NO 14
<211> LENGTH: 467
<212> TYPE: PRT
<213> ORGANISM: Homo sapiens

<400> SEQUENCE: 14

Met Ala Ala Ala Arg Ala Arg Val Ala Tyr Leu Leu Arg Gln Leu
 1               5                  10                  15

Gln Arg Ala Ala Cys Gln Cys Pro Thr His Ser His Thr Tyr Ser Gln
                20                  25                  30

Ala Pro Gly Leu Ser Pro Ser Gly Lys Thr Thr Asp Tyr Ala Phe Glu
            35                  40                  45

Met Ala Val Ser Asn Ile Arg Tyr Gly Ala Ala Val Thr Lys Glu Val
        50                  55                  60

Gly Met Asp Leu Lys Asn Met Gly Ala Lys Asn Val Cys Leu Met Thr
65                  70                  75                  80

Asp Lys Asn Leu Ser Lys Leu Pro Pro Val Gln Val Ala Met Asp Ser
                85                  90                  95
```

-continued

```
Leu Val Lys Asn Gly Ile Pro Phe Thr Val Tyr Asp Asn Val Arg Val
            100                 105                 110
Glu Pro Thr Asp Ser Ser Phe Met Glu Ala Ile Glu Phe Ala Gln Lys
        115                 120                 125
Gly Ala Phe Asp Ala Tyr Val Ala Val Gly Gly Ser Thr Met Asp
130                 135                 140
Thr Cys Lys Ala Ala Asn Leu Tyr Ala Ser Ser Pro His Ser Asp Phe
145                 150                 155                 160
Leu Asp Tyr Val Ser Ala Pro Ile Gly Lys Gly Lys Pro Val Ser Val
            165                 170                 175
Pro Leu Lys Pro Leu Ile Ala Val Pro Thr Thr Ser Gly Thr Gly Ser
            180                 185                 190
Glu Thr Thr Gly Val Ala Ile Phe Asp Tyr Glu His Leu Lys Val Lys
        195                 200                 205
Ile Gly Ile Thr Ser Arg Ala Ile Lys Pro Thr Leu Gly Leu Ile Asp
210                 215                 220
Pro Leu His Thr Leu His Met Pro Ala Arg Val Val Ala Asn Ser Gly
225                 230                 235                 240
Phe Asp Val Leu Cys His Ala Leu Glu Ser Tyr Thr Thr Leu Pro Tyr
            245                 250                 255
His Leu Arg Ser Pro Cys Pro Ser Asn Pro Ile Thr Arg Pro Ala Tyr
            260                 265                 270
Gln Gly Ser Asn Pro Ile Ser Asp Ile Trp Ala Ile His Ala Leu Arg
        275                 280                 285
Ile Val Ala Lys Tyr Leu Lys Arg Ala Val Arg Asn Pro Asp Asp Leu
290                 295                 300
Glu Ala Arg Ser His Met His Leu Ala Ser Ala Phe Ala Gly Ile Gly
305                 310                 315                 320
Phe Gly Asn Ala Gly Val His Leu Cys His Gly Met Ser Tyr Pro Ile
            325                 330                 335
Ser Gly Leu Val Lys Met Tyr Lys Ala Lys Asp Tyr Asn Val Asp His
            340                 345                 350
Pro Leu Val Pro His Gly Leu Ser Val Val Leu Thr Ser Pro Ala Val
        355                 360                 365
Phe Thr Phe Thr Ala Gln Met Phe Pro Glu Arg His Leu Glu Met Ala
370                 375                 380
Glu Ile Leu Gly Ala Asp Thr Arg Thr Ala Arg Ile Gln Asp Ala Gly
385                 390                 395                 400
Leu Val Leu Ala Asp Thr Leu Arg Lys Phe Leu Phe Asp Leu Asp Val
            405                 410                 415
Asp Asp Gly Leu Ala Ala Val Gly Tyr Ser Lys Ala Asp Ile Pro Ala
            420                 425                 430
Leu Val Lys Gly Thr Leu Pro Gln Glu Arg Val Thr Lys Leu Ala Pro
        435                 440                 445
Cys Pro Gln Ser Glu Glu Asp Leu Ala Ala Leu Phe Glu Ala Ser Met
450                 455                 460
Lys Leu Tyr
465

<210> SEQ ID NO 15
<211> LENGTH: 1401
<212> TYPE: DNA
<213> ORGANISM: Homo sapiens
<220> FEATURE:
<221> NAME/KEY: CDS
```

-continued

<222> LOCATION: (1)...(1401)

<400> SEQUENCE: 15

| | | | | | | | | | | | | | | | | |
|---|---|---|---|---|---|---|---|---|---|---|---|---|---|---|---|---|
| atg | gcc | gct | gcc | gcc | cga | gcc | cgg | gtc | gcg | tac | ttg | ctg | agg | caa | ctg | 48 |
| Met | Ala | Ala | Ala | Ala | Arg | Ala | Arg | Val | Ala | Tyr | Leu | Leu | Arg | Gln | Leu | |
| 1 | | | | 5 | | | | | 10 | | | | | 15 | | |
| caa | cgc | gca | gcg | tgc | cag | tgc | cca | act | cat | tct | cat | act | tac | tcc | caa | 96 |
| Gln | Arg | Ala | Ala | Cys | Gln | Cys | Pro | Thr | His | Ser | His | Thr | Tyr | Ser | Gln | |
| | | | 20 | | | | | 25 | | | | | 30 | | | |
| gcc | cct | gga | ctt | tca | cct | tct | ggg | aaa | aca | aca | gat | tat | gcc | ttt | gag | 144 |
| Ala | Pro | Gly | Leu | Ser | Pro | Ser | Gly | Lys | Thr | Thr | Asp | Tyr | Ala | Phe | Glu | |
| | | | | 35 | | | | | 40 | | | | | 45 | | |
| atg | gct | gtt | tca | aat | att | aga | tat | gga | gca | gca | gtt | aca | aag | gaa | gta | 192 |
| Met | Ala | Val | Ser | Asn | Ile | Arg | Tyr | Gly | Ala | Ala | Val | Thr | Lys | Glu | Val | |
| | 50 | | | | | 55 | | | | | 60 | | | | | |
| gga | atg | gac | cta | aaa | aac | atg | ggt | gct | aaa | aat | gtg | tgc | ttg | atg | aca | 240 |
| Gly | Met | Asp | Leu | Lys | Asn | Met | Gly | Ala | Lys | Asn | Val | Cys | Leu | Met | Thr | |
| 65 | | | | | 70 | | | | | 75 | | | | | 80 | |
| gac | aag | aac | ctc | tcc | aag | ctc | cct | cct | gtg | caa | gta | gct | atg | gat | tcc | 288 |
| Asp | Lys | Asn | Leu | Ser | Lys | Leu | Pro | Pro | Val | Gln | Val | Ala | Met | Asp | Ser | |
| | | | | 85 | | | | | 90 | | | | | 95 | | |
| cta | gtg | aag | aat | ggc | atc | ccc | ttt | acg | gtt | tat | gat | aat | gtg | aga | gtg | 336 |
| Leu | Val | Lys | Asn | Gly | Ile | Pro | Phe | Thr | Val | Tyr | Asp | Asn | Val | Arg | Val | |
| | | | 100 | | | | | 105 | | | | | 110 | | | |
| gaa | cca | acg | gat | tca | agc | ttc | atg | gaa | gct | att | gag | ttt | gcc | caa | aag | 384 |
| Glu | Pro | Thr | Asp | Ser | Ser | Phe | Met | Glu | Ala | Ile | Glu | Phe | Ala | Gln | Lys | |
| | | | | 115 | | | | | 120 | | | | | 125 | | |
| gga | gct | ttt | gat | gcc | tat | gtt | gct | gtc | ggt | ggt | ggc | tct | acc | atg | gac | 432 |
| Gly | Ala | Phe | Asp | Ala | Tyr | Val | Ala | Val | Gly | Gly | Gly | Ser | Thr | Met | Asp | |
| | 130 | | | | | 135 | | | | | 140 | | | | | |
| acc | tgt | aag | gct | gct | aat | ctg | tat | gca | tcc | agc | cct | cat | tct | gat | ttc | 480 |
| Thr | Cys | Lys | Ala | Ala | Asn | Leu | Tyr | Ala | Ser | Ser | Pro | His | Ser | Asp | Phe | |
| 145 | | | | | 150 | | | | | 155 | | | | | 160 | |
| cta | gat | tat | gtc | agt | gcc | ccc | att | ggc | aag | gga | aag | cct | gtg | tct | gtg | 528 |
| Leu | Asp | Tyr | Val | Ser | Ala | Pro | Ile | Gly | Lys | Gly | Lys | Pro | Val | Ser | Val | |
| | | | | 165 | | | | | 170 | | | | | 175 | | |
| cct | ctt | aag | cct | ctg | att | gca | gtg | cca | act | acc | tca | gga | acc | ggg | agt | 576 |
| Pro | Leu | Lys | Pro | Leu | Ile | Ala | Val | Pro | Thr | Thr | Ser | Gly | Thr | Gly | Ser | |
| | | | 180 | | | | | 185 | | | | | 190 | | | |
| gaa | act | act | ggg | gtt | gcc | att | ttt | gac | tat | gaa | cac | ttg | aaa | gta | aaa | 624 |
| Glu | Thr | Thr | Gly | Val | Ala | Ile | Phe | Asp | Tyr | Glu | His | Leu | Lys | Val | Lys | |
| | | | | 195 | | | | | 200 | | | | | 205 | | |
| att | ggc | atc | act | tcg | aga | gcc | atc | aaa | ccc | aca | ctg | gga | ctg | att | gat | 672 |
| Ile | Gly | Ile | Thr | Ser | Arg | Ala | Ile | Lys | Pro | Thr | Leu | Gly | Leu | Ile | Asp | |
| | 210 | | | | | 215 | | | | | 220 | | | | | |
| cct | ctg | cac | acc | ctc | cac | atg | cct | gcc | cga | gtg | gtc | gcc | aac | agt | ggc | 720 |
| Pro | Leu | His | Thr | Leu | His | Met | Pro | Ala | Arg | Val | Val | Ala | Asn | Ser | Gly | |
| 225 | | | | | 230 | | | | | 235 | | | | | 240 | |
| ttt | gat | gtg | ctt | tgc | cat | gcc | ctg | gag | tca | tac | acc | acc | ctg | ccc | tac | 768 |
| Phe | Asp | Val | Leu | Cys | His | Ala | Leu | Glu | Ser | Tyr | Thr | Thr | Leu | Pro | Tyr | |
| | | | | 245 | | | | | 250 | | | | | 255 | | |
| cac | ctg | cgg | agc | ccc | tgc | cct | tca | aat | ccc | atc | aca | cgg | cct | gcg | tac | 816 |
| His | Leu | Arg | Ser | Pro | Cys | Pro | Ser | Asn | Pro | Ile | Thr | Arg | Pro | Ala | Tyr | |
| | | | 260 | | | | | 265 | | | | | 270 | | | |
| cag | ggc | agc | aac | cca | atc | agt | gac | att | tgg | gct | atc | cac | gcg | ctg | cgg | 864 |
| Gln | Gly | Ser | Asn | Pro | Ile | Ser | Asp | Ile | Trp | Ala | Ile | His | Ala | Leu | Arg | |
| | | | | 275 | | | | | 280 | | | | | 285 | | |
| atc | gtg | gct | aag | tat | ctg | aag | agg | gct | gtc | aga | aat | ccc | gat | gat | ctt | 912 |
| Ile | Val | Ala | Lys | Tyr | Leu | Lys | Arg | Ala | Val | Arg | Asn | Pro | Asp | Asp | Leu | |
| | 290 | | | | | 295 | | | | | 300 | | | | | |

```
gaa gca agg tct cat atg cac ttg gca agt gct ttt gct ggc atc ggc      960
Glu Ala Arg Ser His Met His Leu Ala Ser Ala Phe Ala Gly Ile Gly
305                 310                 315                 320 ttt gga aat gct ggt gtt cat ctg tgc cat gga atg tct tac cca att     1008
Phe Gly Asn Ala Gly Val His Leu Cys His Gly Met Ser Tyr Pro Ile
                325                 330                 335 tca ggt tta gtg aag atg tat aaa gca aag gat tac aat gtg gat cac     1056
Ser Gly Leu Val Lys Met Tyr Lys Ala Lys Asp Tyr Asn Val Asp His
            340                 345                 350 cca ctg gtg ccc cat ggc ctt tct gtg gtg ctc acg tcc cca gcg gtg     1104
Pro Leu Val Pro His Gly Leu Ser Val Val Leu Thr Ser Pro Ala Val
        355                 360                 365 ttc act ttc acg gcc cag atg ttt cca gag cga cac ctg gag atg gca     1152
Phe Thr Phe Thr Ala Gln Met Phe Pro Glu Arg His Leu Glu Met Ala
    370                 375                 380 gaa ata ctg gga gcc gac acc cgc act gcc agg atc caa gat gca ggg     1200
Glu Ile Leu Gly Ala Asp Thr Arg Thr Ala Arg Ile Gln Asp Ala Gly
385                 390                 395                 400 ctg gtg ttg gca gac acg ctc cgg aaa ttc tta ttc gat ctg gat gtt     1248
Leu Val Leu Ala Asp Thr Leu Arg Lys Phe Leu Phe Asp Leu Asp Val
                405                 410                 415 gat gat ggc cta gca gct gtt ggt tac tcc aaa gct gat atc ccc gca     1296
Asp Asp Gly Leu Ala Ala Val Gly Tyr Ser Lys Ala Asp Ile Pro Ala
            420                 425                 430 cta gtg aaa gga acg ctg ccc cag gaa agg gtc acc aag ctt gca ccc     1344
Leu Val Lys Gly Thr Leu Pro Gln Glu Arg Val Thr Lys Leu Ala Pro
        435                 440                 445 tgt ccc cag tca gaa gag gat ctg gct gct ctg ttt gaa gct tca atg     1392
Cys Pro Gln Ser Glu Glu Asp Leu Ala Ala Leu Phe Glu Ala Ser Met
    450                 455                 460 aaa ctg tat                                                         1401
Lys Leu Tyr
465

<210> SEQ ID NO 16
<211> LENGTH: 2577
<212> TYPE: DNA
<213> ORGANISM: Homo sapiens
<220> FEATURE:
<221> NAME/KEY: CDS
<222> LOCATION: (167)..(2341)

<400> SEQUENCE: 16
gtagcgaggc ttgggtggcg aactcggcac gaggcccaaa ggtaggctca ggctccgacg      60
gtggccggcg ggggtcacga ggcttcgtag tggaggaacg ggtttggcgt gtgggacgca     120
gctgcctctg tactggggag tcacggagtg gccgggctcc agggac atg gcg gcg       175
                                                 Met Ala Ala
                                                   1 gcc tct gcg gtg tcg gtg ctg ctg gtg gcg gcg gag agg aac cgg tgg      223
Ala Ser Ala Val Ser Val Leu Leu Val Ala Ala Glu Arg Asn Arg Trp
  5                  10                  15 cat cgt ctc ccg agc ctg ctc ctg ccg ccg agg aca tgg gtg tgg agg      271
His Arg Leu Pro Ser Leu Leu Leu Pro Pro Arg Thr Trp Val Trp Arg
 20                  25                  30                  35 caa aga acc atg aag tac aca aca gcc aca gga aga aac att acc aag      319
Gln Arg Thr Met Lys Tyr Thr Thr Ala Thr Gly Arg Asn Ile Thr Lys
                 40                  45                  50 gtc ctc att gca aac aga gga gaa att gcc tgc agg gtg atg cgc aca      367
Val Leu Ile Ala Asn Arg Gly Glu Ile Ala Cys Arg Val Met Arg Thr
             55                  60                  65
```

```
gcc aaa aaa ctg ggt gta cag act gtg gcg gtt tat agt gag gct gac      415
Ala Lys Lys Leu Gly Val Gln Thr Val Ala Val Tyr Ser Glu Ala Asp
         70                  75                  80 aga aat tcc atg cat gta gat atg gca gat gaa gca tat tcc atc ggc      463
Arg Asn Ser Met His Val Asp Met Ala Asp Glu Ala Tyr Ser Ile Gly
     85                  90                  95 ccc gct ccc tcc cag cag agc tac cta tct atg gag aaa atc att caa      511
Pro Ala Pro Ser Gln Gln Ser Tyr Leu Ser Met Glu Lys Ile Ile Gln
100                 105                 110                 115 gtg gcc aag acc tct gct gca cag gct atc cat cca gga tgc ggt ttt      559
Val Ala Lys Thr Ser Ala Ala Gln Ala Ile His Pro Gly Cys Gly Phe
            120                 125                 130 ctt tca gaa aac atg gaa ttt gct gaa ctt tgt aag caa gaa gga att      607
Leu Ser Glu Asn Met Glu Phe Ala Glu Leu Cys Lys Gln Glu Gly Ile
        135                 140                 145 att ttt ata ggc cct cct cca tct gca att aga gac atg ggt ata aag      655
Ile Phe Ile Gly Pro Pro Pro Ser Ala Ile Arg Asp Met Gly Ile Lys
    150                 155                 160 agc aca tcc aaa tcc ata atg gct gct gct gga gta cct gtt gtg gag      703
Ser Thr Ser Lys Ser Ile Met Ala Ala Ala Gly Val Pro Val Val Glu
165                 170                 175 ggt tat cat ggt gag gac caa tca gac cag tgc ctg aag gaa cac gcc      751
Gly Tyr His Gly Glu Asp Gln Ser Asp Gln Cys Leu Lys Glu His Ala
180                 185                 190                 195 agg aga att ggc tat cct gtc atg att aaa gcc gtc cgg ggt gga gga      799
Arg Arg Ile Gly Tyr Pro Val Met Ile Lys Ala Val Arg Gly Gly Gly
            200                 205                 210 gga aaa gga atg agg att gtt aga tca gaa caa gaa ttt caa gaa cag      847
Gly Lys Gly Met Arg Ile Val Arg Ser Glu Gln Glu Phe Gln Glu Gln
        215                 220                 225 tta gag tca gca cgg aga gaa gct aag aag tct ttc aat gat gat gct      895
Leu Glu Ser Ala Arg Arg Glu Ala Lys Lys Ser Phe Asn Asp Asp Ala
    230                 235                 240 atg ctg atc gag aag ttt gta gac aca ccg agg cat gta gaa gtc cag      943
Met Leu Ile Glu Lys Phe Val Asp Thr Pro Arg His Val Glu Val Gln
245                 250                 255 gtg ttt ggt gat cac cat ggc aat gct gtg tac ttg ttt gaa aga gac      991
Val Phe Gly Asp His His Gly Asn Ala Val Tyr Leu Phe Glu Arg Asp
260                 265                 270                 275 tgt agt gtg cag agg cga cat cag aag atc att gag gag gcc cca gcg     1039
Cys Ser Val Gln Arg Arg His Gln Lys Ile Ile Glu Glu Ala Pro Ala
            280                 285                 290 cct ggt att aaa tct gaa gta aga aaa aag ctg gga gaa gct gca gtc     1087
Pro Gly Ile Lys Ser Glu Val Arg Lys Lys Leu Gly Glu Ala Ala Val
        295                 300                 305 aga gct gct aaa gct gta aat tat gtt gga gca ggg act gtg gag ttt     1135
Arg Ala Ala Lys Ala Val Asn Tyr Val Gly Ala Gly Thr Val Glu Phe
    310                 315                 320 att atg gac tca aaa cat aat ttc tgt ttc atg gag atg aat aca agg     1183
Ile Met Asp Ser Lys His Asn Phe Cys Phe Met Glu Met Asn Thr Arg
325                 330                 335 ctg caa gtg gaa cat cct gtt act gag atg atc aca gga act gac ttg     1231
Leu Gln Val Glu His Pro Val Thr Glu Met Ile Thr Gly Thr Asp Leu
340                 345                 350                 355 gtg gag tgg cag ctt aga att gca gca gga gag aag att cct ttg agc     1279
Val Glu Trp Gln Leu Arg Ile Ala Ala Gly Glu Lys Ile Pro Leu Ser
            360                 365                 370 cag gaa gaa ata act ctg cag ggc cat gcc ttc gaa gct aga ata tat     1327
Gln Glu Glu Ile Thr Leu Gln Gly His Ala Phe Glu Ala Arg Ile Tyr
        375                 380                 385
```

```
gca gaa gat cct agc aat aac ttc atg cct gtg gca ggc cca tta gtg      1375
Ala Glu Asp Pro Ser Asn Asn Phe Met Pro Val Ala Gly Pro Leu Val
        390                 395                 400 cac ctc tct act cct cga gca gac cct tcc acc agg att gaa act gga      1423
His Leu Ser Thr Pro Arg Ala Asp Pro Ser Thr Arg Ile Glu Thr Gly
405                 410                 415 gta cgg caa gga gac gaa gtt tcc gtg cat tat gac ccc atg att gcg      1471
Val Arg Gln Gly Asp Glu Val Ser Val His Tyr Asp Pro Met Ile Ala
420                 425                 430                 435 aag ctg gtc gtg tgg gca gca gat cgc cag gcg gca ttg aca aaa ctg      1519
Lys Leu Val Val Trp Ala Ala Asp Arg Gln Ala Ala Leu Thr Lys Leu
                440                 445                 450 agg tac agc ctt cgt cag tac aat att gtt gga ctg ccc acc aac att      1567
Arg Tyr Ser Leu Arg Gln Tyr Asn Ile Val Gly Leu Pro Thr Asn Ile
            455                 460                 465 gac ttc tta ctc aac ctg tct ggc cac cca gag ttt gaa gct ggg aac      1615
Asp Phe Leu Leu Asn Leu Ser Gly His Pro Glu Phe Glu Ala Gly Asn
        470                 475                 480 gtg cac act gat ttc atc cct caa cac cac aaa cag ttg ttg ctc agt      1663
Val His Thr Asp Phe Ile Pro Gln His His Lys Gln Leu Leu Leu Ser
485                 490                 495 cgg aag gct gca gcc aaa gag tct tta tgc cag gca gcc ctg ggt ctc      1711
Arg Lys Ala Ala Ala Lys Glu Ser Leu Cys Gln Ala Ala Leu Gly Leu
500                 505                 510                 515 atc ctc aag gag aaa gcc atg acc gac act ttc act ctt cag gca cat      1759
Ile Leu Lys Glu Lys Ala Met Thr Asp Thr Phe Thr Leu Gln Ala His
                520                 525                 530 gat caa ttc tct cca ttt tcg tct agc agt gga aga aga ctg aat atc      1807
Asp Gln Phe Ser Pro Phe Ser Ser Ser Ser Gly Arg Arg Leu Asn Ile
            535                 540                 545 tcg tat acc aga aac atg act ctt aaa gat ggt aaa aac aat gta gcc      1855
Ser Tyr Thr Arg Asn Met Thr Leu Lys Asp Gly Lys Asn Asn Val Ala
        550                 555                 560 ata gct gta acg tat aac cat gat ggg tct tat agc atg cag att gaa      1903
Ile Ala Val Thr Tyr Asn His Asp Gly Ser Tyr Ser Met Gln Ile Glu
565                 570                 575 gat aaa act ttc caa gtc ctt ggt aat ctt tac agc gag gga gac tgc      1951
Asp Lys Thr Phe Gln Val Leu Gly Asn Leu Tyr Ser Glu Gly Asp Cys
580                 585                 590                 595 act tac ctg aaa tgt tct gtt aat gga gtt gct agt aaa gcg aag ctg      1999
Thr Tyr Leu Lys Cys Ser Val Asn Gly Val Ala Ser Lys Ala Lys Leu
                600                 605                 610 att atc ctg gaa aac act att tac cta ttt tcc aag gaa gga agt att      2047
Ile Ile Leu Glu Asn Thr Ile Tyr Leu Phe Ser Lys Glu Gly Ser Ile
            615                 620                 625 gag att gac att cca gtc ccc aaa tac tta tct tct gtg agc tca caa      2095
Glu Ile Asp Ile Pro Val Pro Lys Tyr Leu Ser Ser Val Ser Ser Gln
        630                 635                 640 gaa act cag ggc ggc ccc tta gct cct atg act gga acc att gaa aag      2143
Glu Thr Gln Gly Gly Pro Leu Ala Pro Met Thr Gly Thr Ile Glu Lys
645                 650                 655 gtg ttt gtc aaa gct gga gac aaa gtg aaa gcg gga gat tcc ctc atg      2191
Val Phe Val Lys Ala Gly Asp Lys Val Lys Ala Gly Asp Ser Leu Met
660                 665                 670                 675 gtt atg atc gcc atg aag atg gag cat acc ata aag tct cca aag gat      2239
Val Met Ile Ala Met Lys Met Glu His Thr Ile Lys Ser Pro Lys Asp
                680                 685                 690 ggc aca gta aag aaa gtg ttc tac aga gaa ggt gct cag gcc aac aga      2287
Gly Thr Val Lys Lys Val Phe Tyr Arg Glu Gly Ala Gln Ala Asn Arg
```

-continued

```
                       695                 700                 705
cac act cct tta gtc gag ttt gag gag gaa gaa tca gac aaa agg gaa      2335
His Thr Pro Leu Val Glu Phe Glu Glu Glu Glu Ser Asp Lys Arg Glu
        710                 715                 720 tcg gaa taaactccag caaggaaatg gccagttaag tagtgtcttc tctctccacc       2391
Ser Glu
725 aaaaagagga agtgcctcca gctttctgg gggtctcata agagcagtt ttactaaatg      2451 attgtatgct tatgctgaac acctttcata ttggagaatc atgcatttgg gtcactaatt   2511 atctcaaaat atttcatact aataagttg aattattttt tattggaagc caaaaaaaaa    2571 aaaagg                                                              2577

<210> SEQ ID NO 17
<211> LENGTH: 725
<212> TYPE: PRT
<213> ORGANISM: Homo sapiens

<400> SEQUENCE: 17

Met Ala Ala Ala Ser Ala Val Ser Val Leu Leu Val Ala Ala Glu Arg
 1               5                  10                  15

Asn Arg Trp His Arg Leu Pro Ser Leu Leu Leu Pro Pro Arg Thr Trp
                20                  25                  30

Val Trp Arg Gln Arg Thr Met Lys Tyr Thr Thr Ala Thr Gly Arg Asn
             35                  40                  45

Ile Thr Lys Val Leu Ile Ala Asn Arg Gly Glu Ile Ala Cys Arg Val
         50                  55                  60

Met Arg Thr Ala Lys Lys Leu Gly Val Gln Thr Val Ala Val Tyr Ser
 65                  70                  75                  80

Glu Ala Asp Arg Asn Ser Met His Val Asp Met Ala Asp Glu Ala Tyr
                 85                  90                  95

Ser Ile Gly Pro Ala Pro Ser Gln Gln Ser Tyr Leu Ser Met Glu Lys
            100                 105                 110

Ile Ile Gln Val Ala Lys Thr Ser Ala Ala Gln Ala Ile His Pro Gly
        115                 120                 125

Cys Gly Phe Leu Ser Glu Asn Met Glu Phe Ala Glu Leu Cys Lys Gln
    130                 135                 140

Glu Gly Ile Ile Phe Ile Gly Pro Pro Ser Ala Ile Arg Asp Met
145                 150                 155                 160

Gly Ile Lys Ser Thr Ser Lys Ser Ile Met Ala Ala Gly Val Pro
                165                 170                 175

Val Val Glu Gly Tyr His Gly Glu Asp Gln Ser Asp Gln Cys Leu Lys
            180                 185                 190

Glu His Ala Arg Arg Ile Gly Tyr Pro Val Met Ile Lys Ala Val Arg
        195                 200                 205

Gly Gly Gly Gly Lys Gly Met Arg Ile Val Arg Ser Glu Gln Glu Phe
    210                 215                 220

Gln Glu Gln Leu Glu Ser Ala Arg Arg Glu Ala Lys Lys Ser Phe Asn
225                 230                 235                 240

Asp Asp Ala Met Leu Ile Glu Lys Phe Val Asp Thr Pro Arg His Val
                245                 250                 255

Glu Val Gln Val Phe Gly Asp His His Gly Asn Ala Val Tyr Leu Phe
            260                 265                 270

Glu Arg Asp Cys Ser Val Gln Arg Arg His Gln Lys Ile Ile Glu Glu
        275                 280                 285
```

```
Ala Pro Ala Pro Gly Ile Lys Ser Glu Val Arg Lys Lys Leu Gly Glu
    290                 295                 300

Ala Ala Val Arg Ala Ala Lys Ala Val Asn Tyr Val Gly Ala Gly Thr
305                 310                 315                 320

Val Glu Phe Ile Met Asp Ser Lys His Asn Phe Cys Phe Met Glu Met
                325                 330                 335

Asn Thr Arg Leu Gln Val Glu His Pro Val Thr Glu Met Ile Thr Gly
            340                 345                 350

Thr Asp Leu Val Glu Trp Gln Leu Arg Ile Ala Ala Gly Glu Lys Ile
        355                 360                 365

Pro Leu Ser Gln Glu Glu Ile Thr Leu Gln Gly His Ala Phe Glu Ala
    370                 375                 380

Arg Ile Tyr Ala Glu Asp Pro Ser Asn Asn Phe Met Pro Val Ala Gly
385                 390                 395                 400

Pro Leu Val His Leu Ser Thr Pro Arg Ala Asp Pro Ser Thr Arg Ile
                405                 410                 415

Glu Thr Gly Val Arg Gln Gly Asp Glu Val Ser Val His Tyr Asp Pro
            420                 425                 430

Met Ile Ala Lys Leu Val Val Trp Ala Ala Asp Arg Gln Ala Ala Leu
        435                 440                 445

Thr Lys Leu Arg Tyr Ser Leu Arg Gln Tyr Asn Ile Val Gly Leu Pro
    450                 455                 460

Thr Asn Ile Asp Phe Leu Leu Asn Leu Ser Gly His Pro Glu Phe Glu
465                 470                 475                 480

Ala Gly Asn Val His Thr Asp Phe Ile Pro Gln His Lys Gln Leu
                485                 490                 495

Leu Leu Ser Arg Lys Ala Ala Lys Glu Ser Leu Cys Gln Ala Ala
            500                 505                 510

Leu Gly Leu Ile Leu Lys Glu Lys Ala Met Thr Asp Thr Phe Thr Leu
        515                 520                 525

Gln Ala His Asp Gln Phe Ser Pro Phe Ser Ser Ser Gly Arg Arg
    530                 535                 540

Leu Asn Ile Ser Tyr Thr Arg Asn Met Thr Leu Lys Asp Gly Lys Asn
545                 550                 555                 560

Asn Val Ala Ile Ala Val Thr Tyr Asn His Asp Gly Ser Tyr Ser Met
                565                 570                 575

Gln Ile Glu Asp Lys Thr Phe Gln Val Leu Gly Asn Leu Tyr Ser Glu
            580                 585                 590

Gly Asp Cys Thr Tyr Leu Lys Cys Ser Val Asn Gly Val Ala Ser Lys
        595                 600                 605

Ala Lys Leu Ile Ile Leu Glu Asn Thr Ile Tyr Leu Phe Ser Lys Glu
    610                 615                 620

Gly Ser Ile Glu Ile Asp Ile Pro Val Pro Lys Tyr Leu Ser Ser Val
625                 630                 635                 640

Ser Ser Gln Glu Thr Gln Gly Gly Pro Leu Ala Pro Met Thr Gly Thr
                645                 650                 655

Ile Glu Lys Val Phe Val Lys Ala Gly Asp Lys Val Lys Ala Gly Asp
            660                 665                 670

Ser Leu Met Val Met Ile Ala Met Lys Met Glu His Thr Ile Lys Ser
        675                 680                 685

Pro Lys Asp Gly Thr Val Lys Lys Val Phe Tyr Arg Glu Gly Ala Gln
    690                 695                 700
```

```
Ala Asn Arg His Thr Pro Leu Val Glu Phe Glu Glu Glu Ser Asp
705                 710                 715                 720

Lys Arg Ser Glu
            725

<210> SEQ ID NO 18
<211> LENGTH: 2175
<212> TYPE: DNA
<213> ORGANISM: Homo sapiens
<220> FEATURE:
<221> NAME/KEY: CDS
<222> LOCATION: (1)..(2175)

<400> SEQUENCE: 18 atg gcg gcg gcc tct gcg gtg tcg gtg ctg ctg gtg gcg gcg gag agg      48
Met Ala Ala Ala Ser Ala Val Ser Val Leu Leu Val Ala Ala Glu Arg
1               5                   10                  15 aac cgg tgg cat cgt ctc ccg agc ctg ctc ctg ccg ccg agg aca tgg      96
Asn Arg Trp His Arg Leu Pro Ser Leu Leu Leu Pro Pro Arg Thr Trp
                20                  25                  30 gtg tgg agg caa aga acc atg aag tac aca aca gcc aca gga aga aac     144
Val Trp Arg Gln Arg Thr Met Lys Tyr Thr Thr Ala Thr Gly Arg Asn
            35                  40                  45 att acc aag gtc ctc att gca aac aga gga gaa att gcc tgc agg gtg     192
Ile Thr Lys Val Leu Ile Ala Asn Arg Gly Glu Ile Ala Cys Arg Val
        50                  55                  60 atg cgc aca gcc aaa aaa ctg ggt gta cag act gtg gcg gtt tat agt     240
Met Arg Thr Ala Lys Lys Leu Gly Val Gln Thr Val Ala Val Tyr Ser
65                  70                  75                  80 gag gct gac aga aat tcc atg cat gta gat atg gca gat gaa gca tat     288
Glu Ala Asp Arg Asn Ser Met His Val Asp Met Ala Asp Glu Ala Tyr
                85                  90                  95 tcc atc ggc ccc gct ccc tcc cag cag agc tac cta tct atg gag aaa     336
Ser Ile Gly Pro Ala Pro Ser Gln Gln Ser Tyr Leu Ser Met Glu Lys
            100                 105                 110 atc att caa gtg gcc aag acc tct gct gca cag gct atc cat cca gga     384
Ile Ile Gln Val Ala Lys Thr Ser Ala Ala Gln Ala Ile His Pro Gly
        115                 120                 125 tgc ggt ttt ctt tca gaa aac atg gaa ttt gct gaa ctt tgt aag caa     432
Cys Gly Phe Leu Ser Glu Asn Met Glu Phe Ala Glu Leu Cys Lys Gln
    130                 135                 140 gaa gga att att ttt ata ggc cct cct cca tct gca att aga gac atg     480
Glu Gly Ile Ile Phe Ile Gly Pro Pro Pro Ser Ala Ile Arg Asp Met
145                 150                 155                 160 ggt ata aag agc aca tcc aaa tcc ata atg gct gct gct gga gta cct     528
Gly Ile Lys Ser Thr Ser Lys Ser Ile Met Ala Ala Ala Gly Val Pro
                165                 170                 175 gtt gtg gag ggt tat cat ggt gag gac caa tca gac cag tgc ctg aag     576
Val Val Glu Gly Tyr His Gly Glu Asp Gln Ser Asp Gln Cys Leu Lys
            180                 185                 190 gaa cac gcc agg aga att ggc tat cct gtc atg att aaa gcc gtc cgg     624
Glu His Ala Arg Arg Ile Gly Tyr Pro Val Met Ile Lys Ala Val Arg
        195                 200                 205 ggt gga gga gga aaa gga atg agg att gtt aga tca gaa caa gaa ttt     672
Gly Gly Gly Gly Lys Gly Met Arg Ile Val Arg Ser Glu Gln Glu Phe
    210                 215                 220 caa gaa cag tta gag tca gca cgg aga gaa gct aag aag tct ttc aat     720
Gln Glu Gln Leu Glu Ser Ala Arg Arg Glu Ala Lys Lys Ser Phe Asn
225                 230                 235                 240 gat gat gct atg ctg atc gag aag ttt gta gac aca ccg agg cat gta     768
Asp Asp Ala Met Leu Ile Glu Lys Phe Val Asp Thr Pro Arg His Val
```

-continued

```
                245                 250                 255
gaa gtc cag gtg ttt ggt gat cac cat ggc aat gct gtg tac ttg ttt      816
Glu Val Gln Val Phe Gly Asp His His Gly Asn Ala Val Tyr Leu Phe
            260                 265                 270 gaa aga gac tgt agt gtg cag agg cga cat cag aag atc att gag gag      864
Glu Arg Asp Cys Ser Val Gln Arg Arg His Gln Lys Ile Ile Glu Glu
            275                 280                 285 gcc cca gcg cct ggt att aaa tct gaa gta aga aaa aag ctg gga gaa      912
Ala Pro Ala Pro Gly Ile Lys Ser Glu Val Arg Lys Lys Leu Gly Glu
            290                 295                 300 gct gca gtc aga gct gct aaa gct gta aat tat gtt gga gca ggg act      960
Ala Ala Val Arg Ala Ala Lys Ala Val Asn Tyr Val Gly Ala Gly Thr
305                 310                 315                 320 gtg gag ttt att atg gac tca aaa cat aat ttc tgt ttc atg gag atg     1008
Val Glu Phe Ile Met Asp Ser Lys His Asn Phe Cys Phe Met Glu Met
                325                 330                 335 aat aca agg ctg caa gtg gaa cat cct gtt act gag atg atc aca gga     1056
Asn Thr Arg Leu Gln Val Glu His Pro Val Thr Glu Met Ile Thr Gly
                340                 345                 350 act gac ttg gtg gag tgg cag ctt aga att gca gca gga gag aag att     1104
Thr Asp Leu Val Glu Trp Gln Leu Arg Ile Ala Ala Gly Glu Lys Ile
                355                 360                 365 cct ttg agc cag gaa gaa ata act ctg cag ggc cat gcc ttc gaa gct     1152
Pro Leu Ser Gln Glu Glu Ile Thr Leu Gln Gly His Ala Phe Glu Ala
370                 375                 380 aga ata tat gca gaa gat cct agc aat aac ttc atg cct gtg gca ggc     1200
Arg Ile Tyr Ala Glu Asp Pro Ser Asn Asn Phe Met Pro Val Ala Gly
385                 390                 395                 400 cca tta gtg cac ctc tct act cct cga gca gac cct tcc acc agg att     1248
Pro Leu Val His Leu Ser Thr Pro Arg Ala Asp Pro Ser Thr Arg Ile
                405                 410                 415 gaa act gga gta cgg caa gga gac gaa gtt tcc gtg cat tat gac ccc     1296
Glu Thr Gly Val Arg Gln Gly Asp Glu Val Ser Val His Tyr Asp Pro
                420                 425                 430 atg att gcg aag ctg gtc gtg tgg gca gca gat cgc cag gcg gca ttg     1344
Met Ile Ala Lys Leu Val Val Trp Ala Ala Asp Arg Gln Ala Ala Leu
                435                 440                 445 aca aaa ctg agg tac agc ctt cgt cag tac aat att gtt gga ctg ccc     1392
Thr Lys Leu Arg Tyr Ser Leu Arg Gln Tyr Asn Ile Val Gly Leu Pro
                450                 455                 460 acc aac att gac ttc tta ctc aac ctg tct ggc cac cca gag ttt gaa     1440
Thr Asn Ile Asp Phe Leu Leu Asn Leu Ser Gly His Pro Glu Phe Glu
465                 470                 475                 480 gct ggg aac gtg cac act gat ttc atc cct caa cac cac aaa cag ttg     1488
Ala Gly Asn Val His Thr Asp Phe Ile Pro Gln His His Lys Gln Leu
                485                 490                 495 ttg ctc agt cgg aag gct gca gcc aaa gag tct tta tgc cag gca gcc     1536
Leu Leu Ser Arg Lys Ala Ala Ala Lys Glu Ser Leu Cys Gln Ala Ala
                500                 505                 510 ctg ggt ctc atc ctc aag gag aaa gcc atg acc gac act ttc act ctt     1584
Leu Gly Leu Ile Leu Lys Glu Lys Ala Met Thr Asp Thr Phe Thr Leu
                515                 520                 525 cag gca cat gat caa ttc tct cca ttt tcg tct agc agt gga aga aga     1632
Gln Ala His Asp Gln Phe Ser Pro Phe Ser Ser Ser Ser Gly Arg Arg
530                 535                 540 ctg aat atc tcg tat acc aga aac atg act ctt aaa gat ggt aaa aac     1680
Leu Asn Ile Ser Tyr Thr Arg Asn Met Thr Leu Lys Asp Gly Lys Asn
545                 550                 555                 560 aat gta gcc ata gct gta acg tat aac cat gat ggg tct tat agc atg     1728
```

-continued

| | | |
|---|---|---|
| Asn Val Ala Ile Ala Val Thr Tyr Asn His Asp Gly Ser Tyr Ser Met<br>565 570 575 | | |
| cag att gaa gat aaa act ttc caa gtc ctt ggt aat ctt tac agc gag<br>Gln Ile Glu Asp Lys Thr Phe Gln Val Leu Gly Asn Leu Tyr Ser Glu<br>580 585 590 | 1776 | |
| gga gac tgc act tac ctg aaa tgt tct gtt aat gga gtt gct agt aaa<br>Gly Asp Cys Thr Tyr Leu Lys Cys Ser Val Asn Gly Val Ala Ser Lys<br>595 600 605 | 1824 | |
| gcg aag ctg att atc ctg gaa aac act att tac cta ttt tcc aag gaa<br>Ala Lys Leu Ile Ile Leu Glu Asn Thr Ile Tyr Leu Phe Ser Lys Glu<br>610 615 620 | 1872 | |
| gga agt att gag att gac att cca gtc ccc aaa tac tta tct tct gtg<br>Gly Ser Ile Glu Ile Asp Ile Pro Val Pro Lys Tyr Leu Ser Ser Val<br>625 630 635 640 | 1920 | |
| agc tca caa gaa act cag ggc ggc ccc tta gct cct atg act gga acc<br>Ser Ser Gln Glu Thr Gln Gly Gly Pro Leu Ala Pro Met Thr Gly Thr<br>645 650 655 | 1968 | |
| att gaa aag gtg ttt gtc aaa gct gga gac aaa gtg aaa gcg gga gat<br>Ile Glu Lys Val Phe Val Lys Ala Gly Asp Lys Val Lys Ala Gly Asp<br>660 665 670 | 2016 | |
| tcc ctc atg gtt atg atc gcc atg aag atg gag cat acc ata aag tct<br>Ser Leu Met Val Met Ile Ala Met Lys Met Glu His Thr Ile Lys Ser<br>675 680 685 | 2064 | |
| cca aag gat ggc aca gta aag aaa gtg ttc tac aga gaa ggt gct cag<br>Pro Lys Asp Gly Thr Val Lys Lys Val Phe Tyr Arg Glu Gly Ala Gln<br>690 695 700 | 2112 | |
| gcc aac aga cac act cct tta gtc gag ttt gag gag gaa gaa tca gac<br>Ala Asn Arg His Thr Pro Leu Val Glu Phe Glu Glu Glu Glu Ser Asp<br>705 710 715 720 | 2160 | |
| aaa agg gaa tcg gaa<br>Lys Arg Glu Ser Glu<br>725 | 2175 | |

<210> SEQ ID NO 19
<211> LENGTH: 2031
<212> TYPE: DNA
<213> ORGANISM: Homo sapiens
<220> FEATURE:
<221> NAME/KEY: CDS
<222> LOCATION: (3)...(792)
<220> FEATURE:
<221> NAME/KEY: misc_feature
<222> LOCATION: 1617, 1618, 1625
<223> OTHER INFORMATION: n = A,T,C or G

<400> SEQUENCE: 19

| | | |
|---|---|---|
| cc acg cgt ccg ccc acg cgt ccg cgc ccc gcc ccg ccc ggc tgc tcc<br>Thr Arg Pro Pro Thr Arg Pro Arg Pro Ala Pro Pro Gly Cys Ser<br>1 5 10 15 | 47 | |
| atg gcg ctg tgc gag gcc gcg ggc tgc ggg agt gcc ctg ctc tgg cct<br>Met Ala Leu Cys Glu Ala Ala Gly Cys Gly Ser Ala Leu Leu Trp Pro<br>20 25 30 | 95 | |
| cgc ttg ttg ctc ttc ggg gac tcc atc acc cag ttt tcc ttc cag cag<br>Arg Leu Leu Leu Phe Gly Asp Ser Ile Thr Gln Phe Ser Phe Gln Gln<br>35 40 45 | 143 | |
| ggt gga tgg gga gca tcg ctg gct gac agg ctg gtc aga aaa tgt gat<br>Gly Gly Trp Gly Ala Ser Leu Ala Asp Arg Leu Val Arg Lys Cys Asp<br>50 55 60 | 191 | |
| gtt ctg aat cgt gga ttt tca ggt tac aat acc agg tgg gcc aaa att<br>Val Leu Asn Arg Gly Phe Ser Gly Tyr Asn Thr Arg Trp Ala Lys Ile<br>65 70 75 | 239 | |
| atc ctt cca aga tta atc agg aaa gga aac agt ttg gac atc cca gta | 287 | |

-continued

| | | |
|---|---|---|
| Ile Leu Pro Arg Leu Ile Arg Lys Gly Asn Ser Leu Asp Ile Pro Val<br>80                        85                          90                           95 | | |
| gca gtt aca att ttc ttt ggg gcc aat gac agt gca cta aaa gat gag<br>Ala Val Thr Ile Phe Phe Gly Ala Asn Asp Ser Ala Leu Lys Asp Glu<br>                          100                     105                     110 | 335 | |
| aat ccc aag cag cac att ccc ctg gag gag tac gct gcg aac cta aag<br>Asn Pro Lys Gln His Ile Pro Leu Glu Glu Tyr Ala Ala Asn Leu Lys<br>            115                        120                     125 | 383 | |
| agc atg gtg cag tac ctg aag tcc gtg gac atc cct gag aat cga gtc<br>Ser Met Val Gln Tyr Leu Lys Ser Val Asp Ile Pro Glu Asn Arg Val<br>        130                        135                     140 | 431 | |
| att ctc atc acg ccg acc cca ctt tgt gaa aca gcc tgg gaa gaa cag<br>Ile Leu Ile Thr Pro Thr Pro Leu Cys Glu Thr Ala Trp Glu Glu Gln<br>145                        150                     155 | 479 | |
| tgc atc ata caa ggt tgc aaa cta aat cgc ctg aac tct gtt gtt ggt<br>Cys Ile Ile Gln Gly Cys Lys Leu Asn Arg Leu Asn Ser Val Val Gly<br>160                        165                     170                   175 | 527 | |
| gaa tat gcc aat gcg tgt tta caa gtg gcc caa gac tgt ggg act gac<br>Glu Tyr Ala Asn Ala Cys Leu Gln Val Ala Gln Asp Cys Gly Thr Asp<br>                 180                        185                     190 | 575 | |
| gta ctt gac ctg tgg acc ctg atg cag gac agc cag gac ttc tca tct<br>Val Leu Asp Leu Trp Thr Leu Met Gln Asp Ser Gln Asp Phe Ser Ser<br>            195                        200                     205 | 623 | |
| tat tta tca gat gga cta cat ttg tct cca aag ggg aat gaa ttt ttg<br>Tyr Leu Ser Asp Gly Leu His Leu Ser Pro Lys Gly Asn Glu Phe Leu<br>        210                        215                     220 | 671 | |
| ttc tcg cat ctc tgg cct ttg ata gag aaa aag gtc tct tct cta cct<br>Phe Ser His Leu Trp Pro Leu Ile Glu Lys Lys Val Ser Ser Leu Pro<br>225                        230                     235 | 719 | |
| ttg ctg ctt cct tac tgg cgg gat gta gca gaa gca aaa cct gaa tta<br>Leu Leu Leu Pro Tyr Trp Arg Asp Val Ala Glu Ala Lys Pro Glu Leu<br>240                        245                     250                   255 | 767 | |
| agt ctg ctg gga gat gga gac cat t agccaatcac aggagaccca<br>Ser Leu Leu Gly Asp Gly Asp His<br>                260 | 812 | |
| aatctgcttg ttatctacag aactcaaagt tgtcaatacg tagaggtacg ctttttttcct | 872 | |
| caggcttaaa cctttgccac tgatattaat aataaaagta ttagatgatt tttcagggaa | 932 | |
| gttttatact taggtccatt gtgtttcgac agtatttatt aatgcagata tcagtgctac | 992 | |
| agctataaaa tataccctga gcagcttgtt aattctataa atgacaaaga ctatgttttt | 1052 | |
| aaaaagtcac aattttataa aaatggtttt tcttacattc ttttgagaac tgtttcactc | 1112 | |
| atacatacac ccacacaccc cactcaacct tgtatcaaat tccaaaagtg taactaaagt | 1172 | |
| ataagaatat catgactagt taaaagatag caaataccat aaggtacaag ttcaagtatt | 1232 | |
| agtataacaa gtatctgagt aacaaatgtc cttggaaatg gggggtagga ggagatatga | 1292 | |
| ttagtcacag gtttggttaa ctgccctcaa aatttacaag ttaaaatgtt ttggctggtg | 1352 | |
| agcacatttc agttcttagg ggaaaaaaag cttttaatgg caatttatag aaatcagaat | 1412 | |
| ccaggctaat gattttttatc cttcacacag taaatgcagc ccatccagaa tcctggagca | 1472 | |
| ataaagtaag aagtaattca aatatctgct tgtgggtcaa taaaaagggt ttctgaagta | 1532 | |
| tcaagtcttg tggggacagc ccccaacccct aagggcaggt agtattctat ctcctggctg | 1592 | |
| gctcatcaca ttcaaaacaa cctgnntttt ttnttgttgt tgttgttgtt aagaaatatc | 1652 | |
| tcaccctctt attcaatagt gtttgaaaac aggcaatctt tgtattttaa atattctagg | 1712 | |
| tttgtagata gtgaattttt tttttttttt ttttttttttg aggcagagtc tcactctgtc | 1772 | |

-continued

```
acccaggctg gagtgtagtg gcgcaacctc agcctctcca agtgctggga ttacaggcat    1832
gagccaccac tcccagccaa tagtgaattt tctaagagca tgtatcccta tcagtaacag    1892
ggatacatga agatacttat aaaatacaga aaaactgccc agcaaatcag ggccctaaac    1952
agttggtaga ttccataaat tcaactggct accatgtata gccctcactg taaggtaggt    2012
ggttaggttt ctagagagc                                                  2031
```

```
<210> SEQ ID NO 20
<211> LENGTH: 263
<212> TYPE: PRT
<213> ORGANISM: Homo sapiens

<400> SEQUENCE: 20
```

Thr Arg Pro Pro Thr Arg Pro Arg Pro Ala Pro Pro Gly Cys Ser Met
1               5                   10                  15

Ala Leu Cys Glu Ala Ala Gly Cys Gly Ser Ala Leu Leu Trp Pro Arg
            20                  25                  30

Leu Leu Leu Phe Gly Asp Ser Ile Thr Gln Phe Ser Phe Gln Gln Gly
        35                  40                  45

Gly Trp Gly Ala Ser Leu Ala Asp Arg Leu Val Arg Lys Cys Asp Val
    50                  55                  60

Leu Asn Arg Gly Phe Ser Gly Tyr Asn Thr Arg Trp Ala Lys Ile Ile
65                  70                  75                  80

Leu Pro Arg Leu Ile Arg Lys Gly Asn Ser Leu Asp Ile Pro Val Ala
                85                  90                  95

Val Thr Ile Phe Phe Gly Ala Asn Asp Ser Ala Leu Lys Asp Glu Asn
            100                 105                 110

Pro Lys Gln His Ile Pro Leu Glu Glu Tyr Ala Ala Asn Leu Lys Ser
        115                 120                 125

Met Val Gln Tyr Leu Lys Ser Val Asp Ile Pro Glu Asn Arg Val Ile
    130                 135                 140

Leu Ile Thr Pro Thr Pro Leu Cys Glu Thr Ala Trp Glu Glu Gln Cys
145                 150                 155                 160

Ile Ile Gln Gly Cys Lys Leu Asn Arg Leu Asn Ser Val Val Gly Glu
                165                 170                 175

Tyr Ala Asn Ala Cys Leu Gln Val Ala Gln Asp Cys Gly Thr Asp Val
            180                 185                 190

Leu Asp Leu Trp Thr Leu Met Gln Asp Ser Gln Asp Phe Ser Ser Tyr
        195                 200                 205

Leu Ser Asp Gly Leu His Leu Ser Pro Lys Gly Asn Glu Phe Leu Phe
    210                 215                 220

Ser His Leu Trp Pro Leu Ile Glu Lys Lys Val Ser Ser Leu Pro Leu
225                 230                 235                 240

Leu Leu Pro Tyr Trp Arg Asp Val Ala Glu Ala Lys Pro Glu Leu Ser
                245                 250                 255

Leu Leu Gly Asp Gly Asp His
            260

```
<210> SEQ ID NO 21
<211> LENGTH: 789
<212> TYPE: DNA
<213> ORGANISM: Homo sapiens
<220> FEATURE:
<221> NAME/KEY: CDS
<222> LOCATION: (1)...(789)

<400> SEQUENCE: 21
```

| | | |
|---|---|---|
| acg cgt ccg ccc acg cgt ccg cgc ccc gcc ccg ccc ggc tgc tcc atg<br>Thr Arg Pro Pro Thr Arg Pro Arg Pro Ala Pro Pro Gly Cys Ser Met<br>1                         5                          10                     15 | 48 |
| gcg ctg tgc gag gcc gcg ggc tgc ggg agt gcc ctg ctc tgg cct cgc<br>Ala Leu Cys Glu Ala Ala Gly Cys Gly Ser Ala Leu Leu Trp Pro Arg<br>           20                     25                     30 | 96 |
| ttg ttg ctc ttc ggg gac tcc atc acc cag ttt tcc ttc cag cag ggt<br>Leu Leu Leu Phe Gly Asp Ser Ile Thr Gln Phe Ser Phe Gln Gln Gly<br>        35                     40                    45 | 144 |
| gga tgg gga gca tcg ctg gct gac agg ctg gtc aga aaa tgt gat gtt<br>Gly Trp Gly Ala Ser Leu Ala Asp Arg Leu Val Arg Lys Cys Asp Val<br>50                      55                     60 | 192 |
| ctg aat cgt gga ttt tca ggt tac aat acc agg tgg gcc aaa att atc<br>Leu Asn Arg Gly Phe Ser Gly Tyr Asn Thr Arg Trp Ala Lys Ile Ile<br>65                      70                     75                   80 | 240 |
| ctt cca aga tta atc agg aaa gga aac agt ttg gac atc cca gta gca<br>Leu Pro Arg Leu Ile Arg Lys Gly Asn Ser Leu Asp Ile Pro Val Ala<br>                 85                     90                    95 | 288 |
| gtt aca att ttc ttt ggg gcc aat gac agt gca cta aaa gat gag aat<br>Val Thr Ile Phe Phe Gly Ala Asn Asp Ser Ala Leu Lys Asp Glu Asn<br>           100                     105                    110 | 336 |
| ccc aag cag cac att ccc ctg gag gag tac gct gcg aac cta aag agc<br>Pro Lys Gln His Ile Pro Leu Glu Glu Tyr Ala Ala Asn Leu Lys Ser<br>           115                     120                    125 | 384 |
| atg gtg cag tac ctg aag tcc gtg gac atc cct gag aat cga gtc att<br>Met Val Gln Tyr Leu Lys Ser Val Asp Ile Pro Glu Asn Arg Val Ile<br>130                      135                     140 | 432 |
| ctc atc acg ccg acc cca ctt tgt gaa aca gcc tgg gaa gaa cag tgc<br>Leu Ile Thr Pro Thr Pro Leu Cys Glu Thr Ala Trp Glu Glu Gln Cys<br>145                      150                     155                  160 | 480 |
| atc ata caa ggt tgc aaa cta aat cgc ctg aac tct gtt gtt ggt gaa<br>Ile Ile Gln Gly Cys Lys Leu Asn Arg Leu Asn Ser Val Val Gly Glu<br>                  165                     170                    175 | 528 |
| tat gcc aat gcg tgt tta caa gtg gcc caa gac tgt ggg act gac gta<br>Tyr Ala Asn Ala Cys Leu Gln Val Ala Gln Asp Cys Gly Thr Asp Val<br>                 180                     185                    190 | 576 |
| ctt gac ctg tgg acc ctg atg cag gac agc cag gac ttc tca tct tat<br>Leu Asp Leu Trp Thr Leu Met Gln Asp Ser Gln Asp Phe Ser Ser Tyr<br>           195                     200                    205 | 624 |
| tta tca gat gga cta cat ttg tct cca aag ggg aat gaa ttt ttg ttc<br>Leu Ser Asp Gly Leu His Leu Ser Pro Lys Gly Asn Glu Phe Leu Phe<br>210                      215                     220 | 672 |
| tcg cat ctc tgg cct ttg ata gag aaa aag gtc tct tct cta cct ttg<br>Ser His Leu Trp Pro Leu Ile Glu Lys Lys Val Ser Ser Leu Pro Leu<br>225                      230                     235                  240 | 720 |
| ctg ctt cct tac tgg cgg gat gta gca gaa gca aaa cct gaa tta agt<br>Leu Leu Pro Tyr Trp Arg Asp Val Ala Glu Ala Lys Pro Glu Leu Ser<br>                 245                     250                    255 | 768 |
| ctg ctg gga gat gga gac cat<br>Leu Leu Gly Asp Gly Asp His<br>260 | 789 |

<210> SEQ ID NO 22
<211> LENGTH: 1984
<212> TYPE: DNA
<213> ORGANISM: Homo sapiens
<220> FEATURE:
<221> NAME/KEY: CDS
<222> LOCATION: (1)...(744)
<220> FEATURE:
<221> NAME/KEY: misc_feature
<222> LOCATION: 1570, 1571, 1578
<223> OTHER INFORMATION: n = A,T,C or G

<400> SEQUENCE: 22

```
atg gcg ctg tgc gag gcc gcg ggc tgc ggg agt gcc ctg ctc tgg cct        48
Met Ala Leu Cys Glu Ala Ala Gly Cys Gly Ser Ala Leu Leu Trp Pro
 1               5                  10                  15 cgc ttg ttg ctc ttc ggg gac tcc atc acc cag ttt tcc ttc cag cag        96
Arg Leu Leu Leu Phe Gly Asp Ser Ile Thr Gln Phe Ser Phe Gln Gln
             20                  25                  30 ggt gga tgg gga gca tcg ctg gct gac agg ctg gtc aga aaa tgt gat       144
Gly Gly Trp Gly Ala Ser Leu Ala Asp Arg Leu Val Arg Lys Cys Asp
         35                  40                  45 gtt ctg aat cgt gga ttt tca ggt tac aat acc agg tgg gcc aaa att       192
Val Leu Asn Arg Gly Phe Ser Gly Tyr Asn Thr Arg Trp Ala Lys Ile
     50                  55                  60 atc ctt cca aga tta atc agg aaa gga aac agt ttg gac atc cca gta       240
Ile Leu Pro Arg Leu Ile Arg Lys Gly Asn Ser Leu Asp Ile Pro Val
 65                  70                  75                  80 gca gtt aca att ttc ttt ggg gcc aat gac agt gca cta aaa gat gag       288
Ala Val Thr Ile Phe Phe Gly Ala Asn Asp Ser Ala Leu Lys Asp Glu
                 85                  90                  95 aat ccc aag cag cac att ccc ctg gag gag tac gct gcg aac cta aag       336
Asn Pro Lys Gln His Ile Pro Leu Glu Glu Tyr Ala Ala Asn Leu Lys
            100                 105                 110 agc atg gtg cag tac ctg aag tcc gtg gac atc cct gag aat cga gtc       384
Ser Met Val Gln Tyr Leu Lys Ser Val Asp Ile Pro Glu Asn Arg Val
        115                 120                 125 att ctc atc acg ccg acc cca ctt tgt gaa aca gcc tgg gaa gaa cag       432
Ile Leu Ile Thr Pro Thr Pro Leu Cys Glu Thr Ala Trp Glu Glu Gln
    130                 135                 140 tgc atc ata caa ggt tgc aaa cta aat cgc ctg aac tct gtt gtt ggt       480
Cys Ile Ile Gln Gly Cys Lys Leu Asn Arg Leu Asn Ser Val Val Gly
145                 150                 155                 160 gaa tat gcc aat gcg tgt tta caa gtg gcc caa gac tgt ggg act gac       528
Glu Tyr Ala Asn Ala Cys Leu Gln Val Ala Gln Asp Cys Gly Thr Asp
                165                 170                 175 gta ctt gac ctg tgg acc ctg atg cag gac agc cag gac ttc tca tct       576
Val Leu Asp Leu Trp Thr Leu Met Gln Asp Ser Gln Asp Phe Ser Ser
            180                 185                 190 tat tta tca gat gga cta cat ttg tct cca aag ggg aat gaa ttt ttg       624
Tyr Leu Ser Asp Gly Leu His Leu Ser Pro Lys Gly Asn Glu Phe Leu
        195                 200                 205 ttc tcg cat ctc tgg cct ttg ata gag aaa aag gtc tct tct cta cct       672
Phe Ser His Leu Trp Pro Leu Ile Glu Lys Lys Val Ser Ser Leu Pro
    210                 215                 220 ttg ctg ctt cct tac tgg cgg gat gta gca gaa gca aaa cct gaa tta       720
Leu Leu Leu Pro Tyr Trp Arg Asp Val Ala Glu Ala Lys Pro Glu Leu
225                 230                 235                 240 agt ctg ctg gga gat gga gac cat tagccaatca caggagaccc aaatctgctt     774
Ser Leu Leu Gly Asp Gly Asp His
                245 gttatctaca gaactcaaag ttgtcaatac gtagaggtac gcttttttcc tcaggcttaa     834 acctttgcca ctgatattaa taataaaagt attagatgat ttttcaggga agttttatac     894 ttaggtccat tgtgtttcga cagtatttat taatgcagat atcagtgcta cagctataaa     954 atatacccctg agcagcttgt taattctata aatgacaaag actatgtttt taaaaagtca    1014 caatttata aaaatggttt ttcttacatt cttttgagaa ctgtttcact catacataca     1074
```

```
cccacacacc ccactcaacc ttgtatcaaa ttccaaaagt gtaactaaag tataagaata    1134
tcatgactag ttaaaagata gcaaatacca taaggtacaa gttcaagtat tagtataaca    1194
agtatctgag taacaaatgt ccttggaaat ggggggtagg aggagatatg attagtcaca    1254
ggtttggtta actgccctca aaatttacaa gttaaaatgt tttggctggt gagcacattt    1314
cagttcttag gggaaaaaaa gcttttaatg gcaatttata gaaatcagaa tccaggctaa    1374 tgattttat ccttcacaca gtaaatgcag cccatccaga atcctggagc aataaagtaa    1434
gaagtaattc aaatatctgc ttgtgggtca ataaaaaggg tttctgaagt atcaagtctt    1494
gtggggacag cccccaaccc taagggcagg tagtattcta tctcctggct ggctcatcac    1554
attcaaaaca acctgnnttt tttnttgttg ttgttgttgt taagaaatat ctcaccctct    1614
tattcaatag tgtttgaaaa caggcaatct ttgtatttta aatattctag gtttgtagat    1674
agtgaatttt ttttttttttt tttttttttt gaggcagagt ctcactctgt cacccaggct    1734
ggagtgtagt ggcgcaacct cagcctctcc aagtgctggg attacaggca tgagccacca    1794
ctcccagcca atagtgaatt ttctaagagc atgtatccct atcagtaaca gggatacatg    1854
aagatactta taaaatacag aaaaactgcc cagcaaatca gggccctaaa cagttggtag    1914
attccataaa ttcaactggc taccatgtat agccctcact gtaaggtagg tggttaggtt    1974
tctagagagc                                                           1984
```

<210> SEQ ID NO 23
<211> LENGTH: 248
<212> TYPE: PRT
<213> ORGANISM: Homo sapiens

<400> SEQUENCE: 23

```
Met Ala Leu Cys Glu Ala Ala Gly Cys Gly Ser Ala Leu Leu Trp Pro
 1               5                  10                  15

Arg Leu Leu Phe Gly Asp Ser Ile Thr Gln Phe Ser Phe Gln Gln
            20                  25                  30

Gly Gly Trp Gly Ala Ser Leu Ala Asp Arg Leu Val Arg Lys Cys Asp
        35                  40                  45

Val Leu Asn Arg Gly Phe Ser Gly Tyr Asn Thr Arg Trp Ala Lys Ile
    50                  55                  60

Ile Leu Pro Arg Leu Ile Arg Lys Gly Asn Ser Leu Asp Ile Pro Val
65                  70                  75                  80

Ala Val Thr Ile Phe Phe Gly Ala Asn Asp Ser Ala Leu Lys Asp Glu
                85                  90                  95

Asn Pro Lys Gln His Ile Pro Leu Glu Glu Tyr Ala Ala Asn Leu Lys
            100                 105                 110

Ser Met Val Gln Tyr Leu Lys Ser Val Asp Ile Pro Glu Asn Arg Val
        115                 120                 125

Ile Leu Ile Thr Pro Thr Pro Leu Cys Glu Thr Ala Trp Glu Gln
    130                 135                 140

Cys Ile Ile Gln Gly Cys Lys Leu Asn Arg Leu Asn Ser Val Val Gly
145                 150                 155                 160

Glu Tyr Ala Asn Ala Cys Leu Gln Val Ala Gln Asp Cys Gly Thr Asp
                165                 170                 175

Val Leu Asp Leu Trp Thr Leu Met Gln Asp Ser Gln Asp Phe Ser Ser
            180                 185                 190

Tyr Leu Ser Asp Gly Leu His Leu Ser Pro Lys Gly Asn Glu Phe Leu
        195                 200                 205
```

```
Phe Ser His Leu Trp Pro Leu Ile Glu Lys Lys Val Ser Ser Leu Pro
    210                 215                 220

Leu Leu Leu Pro Tyr Trp Arg Asp Val Ala Glu Ala Lys Pro Glu Leu
225                 230                 235                 240

Ser Leu Leu Gly Asp Gly Asp His
                245
```

<210> SEQ ID NO 24
<211> LENGTH: 744
<212> TYPE: DNA
<213> ORGANISM: Homo sapiens
<220> FEATURE:
<221> NAME/KEY: CDS
<222> LOCATION: (1)...(744)

<400> SEQUENCE: 24

```
atg gcg ctg tgc gag gcc gcg ggc tgc ggg agt gcc ctg ctc tgg cct      48
Met Ala Leu Cys Glu Ala Ala Gly Cys Gly Ser Ala Leu Leu Trp Pro
1               5                   10                  15 cgc ttg ttg ctc ttc ggg gac tcc atc acc cag ttt tcc ttc cag cag      96
Arg Leu Leu Leu Phe Gly Asp Ser Ile Thr Gln Phe Ser Phe Gln Gln
                20                  25                  30 ggt gga tgg gga gca tcg ctg gct gac agg ctg gtc aga aaa tgt gat     144
Gly Gly Trp Gly Ala Ser Leu Ala Asp Arg Leu Val Arg Lys Cys Asp
            35                  40                  45 gtt ctg aat cgt gga ttt tca ggt tac aat acc agg tgg gcc aaa att     192
Val Leu Asn Arg Gly Phe Ser Gly Tyr Asn Thr Arg Trp Ala Lys Ile
        50                  55                  60 atc ctt cca aga tta atc agg aaa gga aac agt ttg gac atc cca gta     240
Ile Leu Pro Arg Leu Ile Arg Lys Gly Asn Ser Leu Asp Ile Pro Val
65                  70                  75                  80 gca gtt aca att ttc ttt ggg gcc aat gac agt gca cta aaa gat gag     288
Ala Val Thr Ile Phe Phe Gly Ala Asn Asp Ser Ala Leu Lys Asp Glu
                85                  90                  95 aat ccc aag cag cac att ccc ctg gag gag tac gct gcg aac cta aag     336
Asn Pro Lys Gln His Ile Pro Leu Glu Glu Tyr Ala Ala Asn Leu Lys
            100                 105                 110 agc atg gtg cag tac ctg aag tcc gtg gac atc cct gag aat cga gtc     384
Ser Met Val Gln Tyr Leu Lys Ser Val Asp Ile Pro Glu Asn Arg Val
        115                 120                 125 att ctc atc acg ccg acc cca ctt tgt gaa aca gcc tgg gaa gaa cag     432
Ile Leu Ile Thr Pro Thr Pro Leu Cys Glu Thr Ala Trp Glu Glu Gln
    130                 135                 140 tgc atc ata caa ggt tgc aaa cta aat cgc ctg aac tct gtt gtt ggt     480
Cys Ile Ile Gln Gly Cys Lys Leu Asn Arg Leu Asn Ser Val Val Gly
145                 150                 155                 160 gaa tat gcc aat gcg tgt tta caa gtg gcc caa gac tgt ggg act gac     528
Glu Tyr Ala Asn Ala Cys Leu Gln Val Ala Gln Asp Cys Gly Thr Asp
                165                 170                 175 gta ctt gac ctg tgg acc ctg atg cag gac agc cag gac ttc tca tct     576
Val Leu Asp Leu Trp Thr Leu Met Gln Asp Ser Gln Asp Phe Ser Ser
            180                 185                 190 tat tta tca gat gga cta cat ttg tct cca aag ggg aat gaa ttt ttg     624
Tyr Leu Ser Asp Gly Leu His Leu Ser Pro Lys Gly Asn Glu Phe Leu
        195                 200                 205 ttc tcg cat ctc tgg cct ttg ata gag aaa aag gtc tct tct cta cct     672
Phe Ser His Leu Trp Pro Leu Ile Glu Lys Lys Val Ser Ser Leu Pro
    210                 215                 220 ttg ctg ctt cct tac tgg cgg gat gta gca gaa gca aaa cct gaa tta     720
Leu Leu Leu Pro Tyr Trp Arg Asp Val Ala Glu Ala Lys Pro Glu Leu
225                 230                 235                 240
```

```
agt ctg ctg gga gat gga gac cat                                      744
Ser Leu Leu Gly Asp Gly Asp His
            245

<210> SEQ ID NO 25
<211> LENGTH: 10
<212> TYPE: PRT
<213> ORGANISM: Artificial Sequence
<220> FEATURE:
<223> OTHER INFORMATION: LP signature motif
<220> FEATURE:
<221> NAME/KEY: VARIANT
<222> LOCATION: 1-4
<223> OTHER INFORMATION: Xaa may be Leu, Ile, Val, Met, Phe, Tyr, Ala,
      or
<220> FEATURE:
<221> NAME/KEY: VARIANT
<222> LOCATION: 8
<223> OTHER INFORMATION: Gly
<220> FEATURE:
<221> NAME/KEY: VARIANT
<222> LOCATION: 9, 10
<223> OTHER INFORMATION: Xaa may be Leu, Ile, Val, or Met
<220> FEATURE:
<223> OTHER INFORMATION: Xaa may be any amino acid

<400> SEQUENCE: 25

Xaa Xaa Xaa Xaa Gly Asp Ser Xaa Xaa Xaa
 1               5                  10

<210> SEQ ID NO 26
<211> LENGTH: 1855
<212> TYPE: DNA
<213> ORGANISM: Homo sapiens
<220> FEATURE:
<221> NAME/KEY: CDS
<222> LOCATION: (60)...(1046)
<220> FEATURE:
<221> NAME/KEY: misc_feature
<222> LOCATION: 3, 14, 20, 21
<223> OTHER INFORMATION: n = A,T,C or G

<400> SEQUENCE: 26
aantcgagaa attntaatan ncactcacta tagggagtcg acccacgcga ccgcagagg      59 atg gaa ata gtc tgg gag gtg ctt ttt ctt ctt caa gcc aat ttc atc     107
Met Glu Ile Val Trp Glu Val Leu Phe Leu Leu Gln Ala Asn Phe Ile
 1               5                  10                  15 gtc tgc ata tca gct caa cag aat tca cca aaa atc cat gaa ggc tgg     155
Val Cys Ile Ser Ala Gln Gln Asn Ser Pro Lys Ile His Glu Gly Trp
             20                  25                  30 tgg gca tac aag gag gtg gtc cag gga agc ttt gtt cca gtt cct tct     203
Trp Ala Tyr Lys Glu Val Val Gln Gly Ser Phe Val Pro Val Pro Ser
         35                  40                  45 ttc tgg gga ttg gtg aac tca gct tgg aat ctt tgc tct gtg ggg aaa     251
Phe Trp Gly Leu Val Asn Ser Ala Trp Asn Leu Cys Ser Val Gly Lys
     50                  55                  60 cgg cag tcg cca gtc aac ata gag acc agt cac atg atc ttc gac ccc     299
Arg Gln Ser Pro Val Asn Ile Glu Thr Ser His Met Ile Phe Asp Pro
 65                  70                  75                  80 ttt ctg aca cct ctt cgc atc aac acg ggg ggc agg aag gtc agt ggg     347
Phe Leu Thr Pro Leu Arg Ile Asn Thr Gly Gly Arg Lys Val Ser Gly
                 85                  90                  95 acc atg tac aac act gga aga cac gta tcc cct cgc ctg gac aag gag     395
Thr Met Tyr Asn Thr Gly Arg His Val Ser Pro Arg Leu Asp Lys Glu
            100                 105                 110 cac ttg gtc aac ata tct gga ggg ccc atg aca tac agc cac cgg ctg     443
```

```
                His Leu Val Asn Ile Ser Gly Gly Pro Met Thr Tyr Ser His Arg Leu
                            115                 120                 125 gag gag atc cga cta cac ttt ggg agt gag gac agc caa ggg tcg gag                491
Glu Glu Ile Arg Leu His Phe Gly Ser Glu Asp Ser Gln Gly Ser Glu
        130                 135                 140 cac ctc ctc aat gga cag gcc ttc tct ggg gag gtg cag ctc atc cac                539
His Leu Leu Asn Gly Gln Ala Phe Ser Gly Glu Val Gln Leu Ile His
145                 150                 155                 160 tat aac cat gag cta tat acg aat gtc aca gaa gct gca aag agt cca                587
Tyr Asn His Glu Leu Tyr Thr Asn Val Thr Glu Ala Ala Lys Ser Pro
                165                 170                 175 aat gga ttg gtg gta gtt tct ata ttt ata aaa gtt tct gat tca tca                635
Asn Gly Leu Val Val Val Ser Ile Phe Ile Lys Val Ser Asp Ser Ser
            180                 185                 190 aac cca ttt ctt aat cga atg ctc aac aga gat act atc aca aga ata                683
Asn Pro Phe Leu Asn Arg Met Leu Asn Arg Asp Thr Ile Thr Arg Ile
        195                 200                 205 aca tat aaa aat gat gca tat tta cta cag ggg ctt aat ata gag gaa                731
Thr Tyr Lys Asn Asp Ala Tyr Leu Leu Gln Gly Leu Asn Ile Glu Glu
    210                 215                 220 cta tat cca gag acc tct agt ttc atc act tac gat ggg tcg atg act                779
Leu Tyr Pro Glu Thr Ser Ser Phe Ile Thr Tyr Asp Gly Ser Met Thr
225                 230                 235                 240 atc cca ccc tgc tat gag aca gca agt tgg atc ata atg aac aaa cct                827
Ile Pro Pro Cys Tyr Glu Thr Ala Ser Trp Ile Ile Met Asn Lys Pro
                245                 250                 255 gtc tat ata acc agg atg cag atg cat tcc ttg cgc ctg ctc agc cag                875
Val Tyr Ile Thr Arg Met Gln Met His Ser Leu Arg Leu Leu Ser Gln
            260                 265                 270 aac cag cca tct cag atc ttt ctg agc atg agt gac aac ttc agg cct                923
Asn Gln Pro Ser Gln Ile Phe Leu Ser Met Ser Asp Asn Phe Arg Pro
        275                 280                 285 gtc cag cca ctc aac aac cgc tgc atc cgc acc aat atc aac ttc agt                971
Val Gln Pro Leu Asn Asn Arg Cys Ile Arg Thr Asn Ile Asn Phe Ser
    290                 295                 300 tta cag ggg aag gac tgt cca aac aac cga gcc cag aag ctt cag tat               1019
Leu Gln Gly Lys Asp Cys Pro Asn Asn Arg Ala Gln Lys Leu Gln Tyr
305                 310                 315                 320 aga gta aat gaa tgg ctc ctc aag tag ggaacaaagc caagaagaat                     1066
Arg Val Asn Glu Trp Leu Leu Lys  *
                325 cccacctcag tgaaatgcta caactgtgaa ttgacgtaac ctagaatgtc cccCttcttg             1126 cttctctctc cttctttccc ccaagcctca ttcattcttg ggattggccc tttcttcatg             1186 aaaagtgtct gcaaaaccat ggcagaggaa tacatctctc acacatactc acaaacacac             1246 acacaagcac ttgcacatac atacaaacac atgcaaacat acctacacac acacacactc             1306 ttacaacctc catcatggga agtcaagttt cagaaacaaa agtctcattc ataagaggtc             1366 ttagaagaaa ataaccagtt aacctgattt caattttgat accgttttcc tgaactaata             1426 aatctaccca atgagacttt tcagcctttg tacatacaaa attcttccaa aagagagagg             1486 agaaaataca gctctgatgg catcaaacgg actttgcatc aagtaatttc agatagtgtc             1546 ctaggatcct ttgagggtgc tggtagcagg tgagcaggac aaagttgacc aaggacactt             1606 atttctagat tatgattctt ctgtttactc aacaatttac aaagaaaaaa aagacagaca             1666 ttgaagagct acacattgta tatatatcac cacagactat aaggaaatgg aattattttcc           1726 ctctttgtca catatctgta gtaggatttg ccaagatcag aaatgatcca tttgctgttt             1786
```

```
cttgttttcc aaaggtcata cattgtgttt ggttattgtt accagctcaa taaatgtgtt     1846
taacgagtt                                                              1855

<210> SEQ ID NO 27
<211> LENGTH: 328
<212> TYPE: PRT
<213> ORGANISM: Homo sapiens

<400> SEQUENCE: 27

Met Glu Ile Val Trp Glu Val Leu Phe Leu Leu Gln Ala Asn Phe Ile
1               5                   10                  15

Val Cys Ile Ser Ala Gln Gln Asn Ser Pro Lys Ile His Glu Gly Trp
            20                  25                  30

Trp Ala Tyr Lys Glu Val Val Gln Gly Ser Phe Val Pro Val Pro Ser
        35                  40                  45

Phe Trp Gly Leu Val Asn Ser Ala Trp Asn Leu Cys Ser Val Gly Lys
    50                  55                  60

Arg Gln Ser Pro Val Asn Ile Glu Thr Ser His Met Ile Phe Asp Pro
65                  70                  75                  80

Phe Leu Thr Pro Leu Arg Ile Asn Thr Gly Gly Arg Lys Val Ser Gly
                85                  90                  95

Thr Met Tyr Asn Thr Gly Arg His Val Ser Pro Arg Leu Asp Lys Glu
            100                 105                 110

His Leu Val Asn Ile Ser Gly Gly Pro Met Thr Tyr Ser His Arg Leu
        115                 120                 125

Glu Glu Ile Arg Leu His Phe Gly Ser Glu Asp Ser Gln Gly Ser Glu
    130                 135                 140

His Leu Leu Asn Gly Gln Ala Phe Ser Gly Glu Val Gln Leu Ile His
145                 150                 155                 160

Tyr Asn His Glu Leu Tyr Thr Asn Val Thr Glu Ala Ala Lys Ser Pro
                165                 170                 175

Asn Gly Leu Val Val Ser Ile Phe Ile Lys Val Ser Asp Ser Ser
            180                 185                 190

Asn Pro Phe Leu Asn Arg Met Leu Asn Arg Asp Thr Ile Thr Arg Ile
        195                 200                 205

Thr Tyr Lys Asn Asp Ala Tyr Leu Leu Gln Gly Leu Asn Ile Glu Glu
    210                 215                 220

Leu Tyr Pro Glu Thr Ser Ser Phe Ile Thr Tyr Asp Gly Ser Met Thr
225                 230                 235                 240

Ile Pro Pro Cys Tyr Glu Thr Ala Ser Trp Ile Ile Met Asn Lys Pro
                245                 250                 255

Val Tyr Ile Thr Arg Met Gln Met His Ser Leu Arg Leu Leu Ser Gln
            260                 265                 270

Asn Gln Pro Ser Gln Ile Phe Leu Ser Met Ser Asp Asn Phe Arg Pro
        275                 280                 285

Val Gln Pro Leu Asn Asn Arg Cys Ile Arg Thr Asn Ile Asn Phe Ser
    290                 295                 300

Leu Gln Gly Lys Asp Cys Pro Asn Asn Arg Ala Gln Lys Leu Gln Tyr
305                 310                 315                 320

Arg Val Asn Glu Trp Leu Leu Lys
                325

<210> SEQ ID NO 28
<211> LENGTH: 984
<212> TYPE: DNA
```

<213> ORGANISM: Homo sapiens
<220> FEATURE:
<221> NAME/KEY: CDS
<222> LOCATION: (1)...(984)

<400> SEQUENCE: 28

| | | | | | | | | | | | | | | | | |
|---|---|---|---|---|---|---|---|---|---|---|---|---|---|---|---|---|
| atg | gaa | ata | gtc | tgg | gag | gtg | ctt | ttt | ctt | ctt | caa | gcc | aat | ttc | atc | 48 |
| Met | Glu | Ile | Val | Trp | Glu | Val | Leu | Phe | Leu | Leu | Gln | Ala | Asn | Phe | Ile | |
| 1 | | | | 5 | | | | | 10 | | | | | 15 | | |
| gtc | tgc | ata | tca | gct | caa | cag | aat | tca | cca | aaa | atc | cat | gaa | ggc | tgg | 96 |
| Val | Cys | Ile | Ser | Ala | Gln | Gln | Asn | Ser | Pro | Lys | Ile | His | Glu | Gly | Trp | |
| | | | 20 | | | | | 25 | | | | | 30 | | | |
| tgg | gca | tac | aag | gag | gtg | gtc | cag | gga | agc | ttt | gtt | cca | gtt | cct | tct | 144 |
| Trp | Ala | Tyr | Lys | Glu | Val | Val | Gln | Gly | Ser | Phe | Val | Pro | Val | Pro | Ser | |
| | | 35 | | | | | 40 | | | | | 45 | | | | |
| ttc | tgg | gga | ttg | gtg | aac | tca | gct | tgg | aat | ctt | tgc | tct | gtg | ggg | aaa | 192 |
| Phe | Trp | Gly | Leu | Val | Asn | Ser | Ala | Trp | Asn | Leu | Cys | Ser | Val | Gly | Lys | |
| | 50 | | | | | 55 | | | | | 60 | | | | | |
| cgg | cag | tcg | cca | gtc | aac | ata | gag | acc | agt | cac | atg | atc | ttc | gac | ccc | 240 |
| Arg | Gln | Ser | Pro | Val | Asn | Ile | Glu | Thr | Ser | His | Met | Ile | Phe | Asp | Pro | |
| 65 | | | | | 70 | | | | | 75 | | | | | 80 | |
| ttt | ctg | aca | cct | ctt | cgc | atc | aac | acg | ggg | ggc | agg | aag | gtc | agt | ggg | 288 |
| Phe | Leu | Thr | Pro | Leu | Arg | Ile | Asn | Thr | Gly | Gly | Arg | Lys | Val | Ser | Gly | |
| | | | | 85 | | | | | 90 | | | | | 95 | | |
| acc | atg | tac | aac | act | gga | aga | cac | gta | tcc | cct | cgc | ctg | gac | aag | gag | 336 |
| Thr | Met | Tyr | Asn | Thr | Gly | Arg | His | Val | Ser | Pro | Arg | Leu | Asp | Lys | Glu | |
| | | | 100 | | | | | 105 | | | | | 110 | | | |
| cac | ttg | gtc | aac | ata | tct | gga | ggg | ccc | atg | aca | tac | agc | cac | cgg | ctg | 384 |
| His | Leu | Val | Asn | Ile | Ser | Gly | Gly | Pro | Met | Thr | Tyr | Ser | His | Arg | Leu | |
| | | 115 | | | | | 120 | | | | | 125 | | | | |
| gag | gag | atc | cga | cta | cac | ttt | ggg | agt | gag | gac | agc | caa | ggg | tcg | gag | 432 |
| Glu | Glu | Ile | Arg | Leu | His | Phe | Gly | Ser | Glu | Asp | Ser | Gln | Gly | Ser | Glu | |
| | 130 | | | | | 135 | | | | | 140 | | | | | |
| cac | ctc | ctc | aat | gga | cag | gcc | ttc | tct | ggg | gag | gtg | cag | ctc | atc | cac | 480 |
| His | Leu | Leu | Asn | Gly | Gln | Ala | Phe | Ser | Gly | Glu | Val | Gln | Leu | Ile | His | |
| 145 | | | | | 150 | | | | | 155 | | | | | 160 | |
| tat | aac | cat | gag | cta | tat | acg | aat | gtc | aca | gaa | gct | gca | aag | agt | cca | 528 |
| Tyr | Asn | His | Glu | Leu | Tyr | Thr | Asn | Val | Thr | Glu | Ala | Ala | Lys | Ser | Pro | |
| | | | | 165 | | | | | 170 | | | | | 175 | | |
| aat | gga | ttg | gtg | gta | gtt | tct | ata | ttt | ata | aaa | gtt | tct | gat | tca | tca | 576 |
| Asn | Gly | Leu | Val | Val | Val | Ser | Ile | Phe | Ile | Lys | Val | Ser | Asp | Ser | Ser | |
| | | | 180 | | | | | 185 | | | | | 190 | | | |
| aac | cca | ttt | ctt | aat | cga | atg | ctc | aac | aga | gat | act | atc | aca | aga | ata | 624 |
| Asn | Pro | Phe | Leu | Asn | Arg | Met | Leu | Asn | Arg | Asp | Thr | Ile | Thr | Arg | Ile | |
| | | 195 | | | | | 200 | | | | | 205 | | | | |
| aca | tat | aaa | aat | gat | gca | tat | tta | cta | cag | ggg | ctt | aat | ata | gag | gaa | 672 |
| Thr | Tyr | Lys | Asn | Asp | Ala | Tyr | Leu | Leu | Gln | Gly | Leu | Asn | Ile | Glu | Glu | |
| | 210 | | | | | 215 | | | | | 220 | | | | | |
| cta | tat | cca | gag | acc | tct | agt | ttc | atc | act | tac | gat | ggg | tcg | atg | act | 720 |
| Leu | Tyr | Pro | Glu | Thr | Ser | Ser | Phe | Ile | Thr | Tyr | Asp | Gly | Ser | Met | Thr | |
| 225 | | | | | 230 | | | | | 235 | | | | | 240 | |
| atc | cca | ccc | tgc | tat | gag | aca | gca | agt | tgg | atc | ata | atg | aac | aaa | cct | 768 |
| Ile | Pro | Pro | Cys | Tyr | Glu | Thr | Ala | Ser | Trp | Ile | Ile | Met | Asn | Lys | Pro | |
| | | | | 245 | | | | | 250 | | | | | 255 | | |
| gtc | tat | ata | acc | agg | atg | cag | atg | cat | tcc | ttg | cgc | ctg | ctc | agc | cag | 816 |
| Val | Tyr | Ile | Thr | Arg | Met | Gln | Met | His | Ser | Leu | Arg | Leu | Leu | Ser | Gln | |
| | | | 260 | | | | | 265 | | | | | 270 | | | |
| aac | cag | cca | tct | cag | atc | ttt | ctg | agc | atg | agt | gac | aac | ttc | agg | cct | 864 |
| Asn | Gln | Pro | Ser | Gln | Ile | Phe | Leu | Ser | Met | Ser | Asp | Asn | Phe | Arg | Pro | |
| | | 275 | | | | | 280 | | | | | 285 | | | | |

-continued

```
gtc cag cca ctc aac aac cgc tgc atc cgc acc aat atc aac ttc agt       912
Val Gln Pro Leu Asn Asn Arg Cys Ile Arg Thr Asn Ile Asn Phe Ser
    290                 295                 300 tta cag ggg aag gac tgt cca aac aac cga gcc cag aag ctt cag tat       960
Leu Gln Gly Lys Asp Cys Pro Asn Asn Arg Ala Gln Lys Leu Gln Tyr
305                 310                 315                 320 aga gta aat gaa tgg ctc ctc aag                                       984
Arg Val Asn Glu Trp Leu Leu Lys
                325
```

<210> SEQ ID NO 29
<211> LENGTH: 2976
<212> TYPE: DNA
<213> ORGANISM: Homo sapiens
<220> FEATURE:
<221> NAME/KEY: CDS
<222> LOCATION: (95)...(2362)
<220> FEATURE:
<221> NAME/KEY: misc_feature
<222> LOCATION: 2947, 2950
<223> OTHER INFORMATION: n = A,T,C or G

<400> SEQUENCE: 29

```
cacgcgtccg cgctgctccg ccgcggcgcc cgcccagccc cggactgtcc gcgctccatc      60
tggtatcttg gcctcagctg tccttgaagt cacc atg gcg tgg tcc cca cca gcc     115
                                     Met Ala Trp Ser Pro Pro Ala
                                      1               5 acc ctc ttt ctg ttc ctg ctg ctg cta ggc cag ccc cct ccc agc agg       163
Thr Leu Phe Leu Phe Leu Leu Leu Leu Gly Gln Pro Pro Pro Ser Arg
         10                  15                  20 cca cag tca ctg ggc acc act aag ctc cgg ctg gtg ggc cca gag agc       211
Pro Gln Ser Leu Gly Thr Thr Lys Leu Arg Leu Val Gly Pro Glu Ser
 25                  30                  35 aag cca gag gag ggc cgc ctg gag gtg ctg cac cag ggc cag tgg ggc       259
Lys Pro Glu Glu Gly Arg Leu Glu Val Leu His Gln Gly Gln Trp Gly
 40                  45                  50                  55 acc gtg tgt gat gac aac ttt gct atc cag gag gcc aca gtg gct tgc       307
Thr Val Cys Asp Asp Asn Phe Ala Ile Gln Glu Ala Thr Val Ala Cys
             60                  65                  70 cgc cag ctg ggc ttc gaa gct gcc ttg acc tgg gcc cac agt gcc aag       355
Arg Gln Leu Gly Phe Glu Ala Ala Leu Thr Trp Ala His Ser Ala Lys
     75                  80                  85 tac ggc caa ggg gag gga ccc atc tgg ctg gac aat gtg cgc tgt gtg       403
Tyr Gly Gln Gly Glu Gly Pro Ile Trp Leu Asp Asn Val Arg Cys Val
 90                  95                 100 ggc aca gag agc tcc ttg gac cag tgc ggg tct aat ggc tgg gga gtc       451
Gly Thr Glu Ser Ser Leu Asp Gln Cys Gly Ser Asn Gly Trp Gly Val
105                 110                 115 agt gac tgc agt cac tca gaa gac gta ggg gtg ata tgc cac ccc cgg       499
Ser Asp Cys Ser His Ser Glu Asp Val Gly Val Ile Cys His Pro Arg
120                 125                 130                 135 cgc cat cgt ggc tac ctt tct gaa act gtc tcc aat gcc ctt ggg ccc       547
Arg His Arg Gly Tyr Leu Ser Glu Thr Val Ser Asn Ala Leu Gly Pro
             140                 145                 150 cag ggc cgg cgg ctg gag gag gtg cgg ctc aag ccc atc ctt gcc agt       595
Gln Gly Arg Arg Leu Glu Glu Val Arg Leu Lys Pro Ile Leu Ala Ser
     155                 160                 165 gcc aag cag cat agc cca gtg acc gag gga gcc gtg gag gtg aag tat       643
Ala Lys Gln His Ser Pro Val Thr Glu Gly Ala Val Glu Val Lys Tyr
170                 175                 180 gag ggc cac tgg cgg cag gtg tgt gac cag ggc tgg acc atg aac aac       691
Glu Gly His Trp Arg Gln Val Cys Asp Gln Gly Trp Thr Met Asn Asn
```

-continued

```
            185                 190                 195
agc agg gtg gtg tgc ggg atg ctg ggc ttc ccc agc gag gtg cct gtc      739
Ser Arg Val Val Cys Gly Met Leu Gly Phe Pro Ser Glu Val Pro Val
200                 205                 210                 215 gac agc cac tac tac agg aaa gtc tgg gat ctg aag atg agg gac cct      787
Asp Ser His Tyr Tyr Arg Lys Val Trp Asp Leu Lys Met Arg Asp Pro
                220                 225                 230 aag tct agg ctg aag agc ctg acg aat aag aac tcc ttc tgg atc cac      835
Lys Ser Arg Leu Lys Ser Leu Thr Asn Lys Asn Ser Phe Trp Ile His
            235                 240                 245 cag gtc acc tgc ctg ggg aca gag ccc cac atg gcc aac tgc cag gtg      883
Gln Val Thr Cys Leu Gly Thr Glu Pro His Met Ala Asn Cys Gln Val
        250                 255                 260 cag gtg gct cca gcc cgg ggc aag ctg cgg cca gcc tgc cca ggt ggc      931
Gln Val Ala Pro Ala Arg Gly Lys Leu Arg Pro Ala Cys Pro Gly Gly
    265                 270                 275 atg cac gct gtg gtc agc tgt gtg gca ggg cct cac ttc cgc cca ccg      979
Met His Ala Val Val Ser Cys Val Ala Gly Pro His Phe Arg Pro Pro
280                 285                 290                 295 aag aca aag cca caa cgc aaa ggg tcc tgg gca gag gag ccg agg gtg     1027
Lys Thr Lys Pro Gln Arg Lys Gly Ser Trp Ala Glu Glu Pro Arg Val
                300                 305                 310 cgc ctg cgc tcc ggg gcc cag gtg ggc gag ggc cgg gtg gaa gtg ctc     1075
Arg Leu Arg Ser Gly Ala Gln Val Gly Glu Gly Arg Val Glu Val Leu
            315                 320                 325 atg aac cgc cag tgg ggc acg gtc tgt gac cac agg tgg aac ctc atc     1123
Met Asn Arg Gln Trp Gly Thr Val Cys Asp His Arg Trp Asn Leu Ile
        330                 335                 340 tct gcc agt gtc gtg tgt cgt cag ctg ggc ttt ggc tct gct cgg gag     1171
Ser Ala Ser Val Val Cys Arg Gln Leu Gly Phe Gly Ser Ala Arg Glu
    345                 350                 355 gcc ctc ttt ggg gcc cgg ctg ggc caa ggg cta ggg ccc atc cac ctg     1219
Ala Leu Phe Gly Ala Arg Leu Gly Gln Gly Leu Gly Pro Ile His Leu
360                 365                 370                 375 agt gag gtg cgc tgc agg gga tat gag cgg acc ctc agc gac tgc cct     1267
Ser Glu Val Arg Cys Arg Gly Tyr Glu Arg Thr Leu Ser Asp Cys Pro
                380                 385                 390 gcc ctg gaa ggg tcc cag aat ggt tgc caa cat gag aat gat gct gct     1315
Ala Leu Glu Gly Ser Gln Asn Gly Cys Gln His Glu Asn Asp Ala Ala
            395                 400                 405 gtc agg tgc aat gtc cct aac atg ggc ttt cag aat cag gtg cgc ttg     1363
Val Arg Cys Asn Val Pro Asn Met Gly Phe Gln Asn Gln Val Arg Leu
        410                 415                 420 gct ggt ggg cgt atc cct gag gag ggg cta ttg gag gtg cag gtg gag     1411
Ala Gly Gly Arg Ile Pro Glu Glu Gly Leu Leu Glu Val Gln Val Glu
    425                 430                 435 gtg aac ggg gtc cca cgc tgg ggg agc gtg tgc agt gaa aac tgg ggg     1459
Val Asn Gly Val Pro Arg Trp Gly Ser Val Cys Ser Glu Asn Trp Gly
440                 445                 450                 455 ctc acc gaa gcc atg gtg gcc tgc cga cag ctc ggc ctg ggt ttt gcc     1507
Leu Thr Glu Ala Met Val Ala Cys Arg Gln Leu Gly Leu Gly Phe Ala
                460                 465                 470 atc cat gcc tac aag gaa acc tgg ttc tgg tcg ggg acg cca agg gcc     1555
Ile His Ala Tyr Lys Glu Thr Trp Phe Trp Ser Gly Thr Pro Arg Ala
            475                 480                 485 cag gag gtg gtg atg agt ggg gtg cgc tgc tca ggc aca gag ctg gcc     1603
Gln Glu Val Val Met Ser Gly Val Arg Cys Ser Gly Thr Glu Leu Ala
        490                 495                 500 ctg cag cag tgc cag agg cac ggg ccg gtg cac tgc tcc cac ggt ggc     1651
```

-continued

```
                Leu Gln Gln Cys Gln Arg His Gly Pro Val His Cys Ser His Gly Gly
                    505                 510                 515 ggg cgc ttc ctg gct gga gtc tcc tgc atg gac agt gca cca gac ctg           1699
Gly Arg Phe Leu Ala Gly Val Ser Cys Met Asp Ser Ala Pro Asp Leu
520                 525                 530                 535 gtg atg aac gcc cag cta gtg cag gag acg gcc tac ttg gag gac cgc           1747
Val Met Asn Ala Gln Leu Val Gln Glu Thr Ala Tyr Leu Glu Asp Arg
                540                 545                 550 ccg ctc agc cag ctg tat tgt gcc cac gag gag aac tgc ctc tcc aag           1795
Pro Leu Ser Gln Leu Tyr Cys Ala His Glu Glu Asn Cys Leu Ser Lys
            555                 560                 565 tct gca gat cac atg gac tgg ccc tac gga tac cgc cgc cta ttg cgc           1843
Ser Ala Asp His Met Asp Trp Pro Tyr Gly Tyr Arg Arg Leu Leu Arg
        570                 575                 580 ttc tcc aca cag atc tac aat ctg ggc cgg act gac ttt cgt cca aag           1891
Phe Ser Thr Gln Ile Tyr Asn Leu Gly Arg Thr Asp Phe Arg Pro Lys
    585                 590                 595 act gga cgc gat agc tgg gtt tgg cac cag tgc cac agg cat tac cac           1939
Thr Gly Arg Asp Ser Trp Val Trp His Gln Cys His Arg His Tyr His
600                 605                 610                 615 agc att gag gtc ttc acc cac tac gac ctc ctc act ctc aat ggc tcc           1987
Ser Ile Glu Val Phe Thr His Tyr Asp Leu Leu Thr Leu Asn Gly Ser
                620                 625                 630 aag gtg gct gag ggg cac aag gcc agc ttc tgt ctg gag gac aca aac           2035
Lys Val Ala Glu Gly His Lys Ala Ser Phe Cys Leu Glu Asp Thr Asn
            635                 640                 645 tgc ccc aca gga ctg cag cgg cgc tac gca tgt gcc aac ttt gga gaa           2083
Cys Pro Thr Gly Leu Gln Arg Arg Tyr Ala Cys Ala Asn Phe Gly Glu
        650                 655                 660 cag gga gtg act gta ggc tgc tgg gac acc tac cgg cat gac att gat           2131
Gln Gly Val Thr Val Gly Cys Trp Asp Thr Tyr Arg His Asp Ile Asp
    665                 670                 675 tgc cag tgg gtg gat atc aca gat gtg ggc ccc ggg aat tat atc ttc           2179
Cys Gln Trp Val Asp Ile Thr Asp Val Gly Pro Gly Asn Tyr Ile Phe
680                 685                 690                 695 cag gtg att gtg aac ccc cac tat gaa gtg gca gag tca gat ttc tcc           2227
Gln Val Ile Val Asn Pro His Tyr Glu Val Ala Glu Ser Asp Phe Ser
                700                 705                 710 aac aat atg ctg cag tgc cgc tgc aag tat gat ggg cac cgg gtc tgg           2275
Asn Asn Met Leu Gln Cys Arg Cys Lys Tyr Asp Gly His Arg Val Trp
            715                 720                 725 ctg cac aac tgc cac aca ggg aat tca tac cca gcc aat gca gaa ctc           2323
Leu His Asn Cys His Thr Gly Asn Ser Tyr Pro Ala Asn Ala Glu Leu
        730                 735                 740 tcc ctg gag cag gaa cag cgt ctc agg aac aac ctc atc tgaagctgtc           2372
Ser Leu Glu Gln Glu Gln Arg Leu Arg Asn Asn Leu Ile
    745                 750                 755 actgcacact cctagctgct gccgatacac cagatacctc agcttattgg agccatgccc        2432
ttcacagagt cccaactcag aggaaaaggg ccagtgccaa ggggcaccaa gaacctgctc        2492
aggaagcctt tgatggcaa gatcaccaat ccagatggta ttgctccctc aggatggctc        2552
tgggcctgcc cctaagggcc tgtggcctat ggaatatgtc ctccaggctt tgcttagctg        2612
agctcctctt ctgtaaggaa acccagtcat ccctgaatct tgccacagag atccgggatt       2672
caggagctct cagtttctta gggatggact atggcccagt cccccatcta agtggtgctt       2732
tgcaaatgtc ttggaggagt ataggacaga ggaccaaaat acacagcagg tagtgktagc      2792
tctctgctag gagctcaaag caacacaact tgtatcaaaa tcacaactgg cagaaaaact      2852
```

-continued

```
gggtggatcc aatcctttct ttcatctgtg tatttaagaa yyaaccytta mactctggtc    2912
tttaggggcc ttamctttat ttwmcacama maatnggngg ttttattatc yttggaagca    2972
caaa                                                                2976
```

<210> SEQ ID NO 30
<211> LENGTH: 756
<212> TYPE: PRT
<213> ORGANISM: Homo sapiens

<400> SEQUENCE: 30

```
Met Ala Trp Ser Pro Ala Thr Leu Phe Leu Phe Leu Leu Leu Leu
  1               5                  10                  15

Gly Gln Pro Pro Ser Arg Pro Gln Ser Leu Gly Thr Thr Lys Leu
                 20                  25                  30

Arg Leu Val Gly Pro Glu Ser Lys Pro Glu Glu Gly Arg Leu Glu Val
             35                  40                  45

Leu His Gln Gly Gln Trp Gly Thr Val Cys Asp Asp Asn Phe Ala Ile
 50                  55                  60

Gln Glu Ala Thr Val Ala Cys Arg Gln Leu Gly Phe Glu Ala Ala Leu
 65                  70                  75                  80

Thr Trp Ala His Ser Ala Lys Tyr Gly Gln Gly Glu Gly Pro Ile Trp
                 85                  90                  95

Leu Asp Asn Val Arg Cys Val Gly Thr Glu Ser Ser Leu Asp Gln Cys
            100                 105                 110

Gly Ser Asn Gly Trp Gly Val Ser Asp Cys Ser His Ser Glu Asp Val
            115                 120                 125

Gly Val Ile Cys His Pro Arg Arg His Arg Gly Tyr Leu Ser Glu Thr
            130                 135                 140

Val Ser Asn Ala Leu Gly Pro Gln Gly Arg Arg Leu Glu Glu Val Arg
145                 150                 155                 160

Leu Lys Pro Ile Leu Ala Ser Ala Lys Gln His Ser Pro Val Thr Glu
                165                 170                 175

Gly Ala Val Glu Val Lys Tyr Glu Gly His Trp Arg Gln Val Cys Asp
            180                 185                 190

Gln Gly Trp Thr Met Asn Asn Ser Arg Val Val Cys Gly Met Leu Gly
            195                 200                 205

Phe Pro Ser Glu Val Pro Val Asp Ser His Tyr Tyr Arg Lys Val Trp
            210                 215                 220

Asp Leu Lys Met Arg Asp Pro Leu Ser Arg Leu Lys Ser Leu Thr Asn
225                 230                 235                 240

Lys Asn Ser Phe Trp Ile His Gln Val Thr Cys Leu Gly Thr Glu Pro
                245                 250                 255

His Met Ala Asn Cys Gln Val Gln Val Ala Pro Ala Arg Gly Lys Leu
            260                 265                 270

Arg Pro Ala Cys Pro Gly Gly Met His Ala Val Val Ser Cys Val Ala
            275                 280                 285

Gly Pro His Phe Arg Pro Pro Lys Thr Lys Pro Gln Arg Lys Gly Ser
            290                 295                 300

Trp Ala Glu Glu Pro Arg Val Arg Leu Arg Ser Gly Ala Gln Val Gly
305                 310                 315                 320

Glu Gly Arg Val Glu Val Leu Met Asn Arg Gln Trp Gly Thr Val Cys
                325                 330                 335

Asp His Arg Trp Asn Leu Ile Ser Ala Ser Val Val Cys Arg Gln Leu
            340                 345                 350
```

-continued

```
Gly Phe Gly Ser Ala Arg Glu Ala Leu Phe Gly Ala Arg Leu Gly Gln
            355                 360                 365

Gly Leu Gly Pro Ile His Leu Ser Glu Val Arg Cys Arg Gly Tyr Glu
            370                 375                 380

Arg Thr Leu Ser Asp Cys Pro Ala Leu Glu Gly Ser Gln Asn Gly Cys
385                 390                 395                 400

Gln His Glu Asn Asp Ala Ala Val Arg Cys Asn Val Pro Asn Met Gly
                405                 410                 415

Phe Gln Asn Gln Val Arg Leu Ala Gly Gly Arg Ile Pro Glu Glu Gly
            420                 425                 430

Leu Leu Glu Val Gln Val Glu Val Asn Gly Val Pro Arg Trp Gly Ser
            435                 440                 445

Val Cys Ser Glu Asn Trp Gly Leu Thr Glu Ala Met Val Ala Cys Arg
        450                 455                 460

Gln Leu Gly Leu Gly Phe Ala Ile His Ala Tyr Lys Glu Thr Trp Phe
465                 470                 475                 480

Trp Ser Gly Thr Pro Arg Ala Gln Glu Val Val Met Ser Gly Val Arg
                485                 490                 495

Cys Ser Gly Thr Glu Leu Ala Leu Gln Gln Cys Gln Arg His Gly Pro
            500                 505                 510

Val His Cys Ser His Gly Gly Arg Phe Leu Ala Gly Val Ser Cys
            515                 520                 525

Met Asp Ser Ala Pro Asp Leu Val Met Asn Ala Gln Leu Val Gln Glu
        530                 535                 540

Thr Ala Tyr Leu Glu Asp Arg Pro Leu Ser Gln Leu Tyr Cys Ala His
545                 550                 555                 560

Glu Glu Asn Cys Leu Ser Lys Ser Ala Asp His Met Asp Trp Pro Tyr
                565                 570                 575

Gly Tyr Arg Arg Leu Leu Arg Phe Ser Thr Gln Ile Tyr Asn Leu Gly
            580                 585                 590

Arg Thr Asp Phe Arg Pro Lys Thr Gly Arg Asp Ser Trp Val Trp His
            595                 600                 605

Gln Cys His Arg His Tyr His Ser Ile Glu Val Phe Thr His Tyr Asp
        610                 615                 620

Leu Leu Thr Leu Asn Gly Ser Lys Val Ala Glu Gly His Lys Ala Ser
625                 630                 635                 640

Phe Cys Leu Glu Asp Thr Asn Cys Pro Thr Gly Leu Gln Arg Arg Tyr
                645                 650                 655

Ala Cys Ala Asn Phe Gly Glu Gln Gly Val Thr Val Gly Cys Trp Asp
            660                 665                 670

Thr Tyr Arg His Asp Ile Asp Cys Gln Trp Val Asp Ile Thr Asp Val
            675                 680                 685

Gly Pro Gly Asn Tyr Ile Phe Gln Val Ile Val Asn Pro His Tyr Glu
        690                 695                 700

Val Ala Glu Ser Asp Phe Ser Asn Asn Met Leu Gln Cys Arg Cys Lys
705                 710                 715                 720

Tyr Asp Gly His Arg Val Trp Leu His Asn Cys His Thr Gly Asn Ser
                725                 730                 735

Tyr Pro Ala Asn Ala Glu Leu Ser Leu Glu Gln Glu Gln Arg Leu Arg
            740                 745                 750

Asn Asn Leu Ile
            755
```

-continued

<210> SEQ ID NO 31
<211> LENGTH: 2268
<212> TYPE: DNA
<213> ORGANISM: Homo sapiens
<220> FEATURE:
<221> NAME/KEY: CDS
<222> LOCATION: (1)...(2268)

<400> SEQUENCE: 31

```
atg gcg tgg tcc cca cca gcc acc ctc ttt ctg ttc ctg ctg ctg cta      48
Met Ala Trp Ser Pro Pro Ala Thr Leu Phe Leu Phe Leu Leu Leu Leu
 1               5                  10                  15 ggc cag ccc cct ccc agc agg cca cag tca ctg ggc acc act aag ctc      96
Gly Gln Pro Pro Pro Ser Arg Pro Gln Ser Leu Gly Thr Thr Lys Leu
             20                  25                  30 cgg ctg gtg ggc cca gag agc aag cca gag gag ggc cgc ctg gag gtg     144
Arg Leu Val Gly Pro Glu Ser Lys Pro Glu Glu Gly Arg Leu Glu Val
         35                  40                  45 ctg cac cag ggc cag tgg ggc acc gtg tgt gat gac aac ttt gct atc     192
Leu His Gln Gly Gln Trp Gly Thr Val Cys Asp Asp Asn Phe Ala Ile
     50                  55                  60 cag gag gcc aca gtg gct tgc cgc cag ctg ggc ttc gaa gct gcc ttg     240
Gln Glu Ala Thr Val Ala Cys Arg Gln Leu Gly Phe Glu Ala Ala Leu
 65                  70                  75                  80 acc tgg gcc cac agt gcc aag tac ggc caa ggg gag gga ccc atc tgg     288
Thr Trp Ala His Ser Ala Lys Tyr Gly Gln Gly Glu Gly Pro Ile Trp
                 85                  90                  95 ctg gac aat gtg cgc tgt gtg ggc aca gag agc tcc ttg gac cag tgc     336
Leu Asp Asn Val Arg Cys Val Gly Thr Glu Ser Ser Leu Asp Gln Cys
            100                 105                 110 ggg tct aat ggc tgg gga gtc agt gac tgc agt cac tca gaa gac gta     384
Gly Ser Asn Gly Trp Gly Val Ser Asp Cys Ser His Ser Glu Asp Val
        115                 120                 125 ggg gtg ata tgc cac ccc cgg cgc cat cgt ggc tac ctt tct gaa act     432
Gly Val Ile Cys His Pro Arg Arg His Arg Gly Tyr Leu Ser Glu Thr
    130                 135                 140 gtc tcc aat gcc ctt ggg ccc cag ggc cgg cgg ctg gag gag gtg cgg     480
Val Ser Asn Ala Leu Gly Pro Gln Gly Arg Arg Leu Glu Glu Val Arg
145                 150                 155                 160 ctc aag ccc atc ctt gcc agt gcc aag cag cat agc cca gtg acc gag     528
Leu Lys Pro Ile Leu Ala Ser Ala Lys Gln His Ser Pro Val Thr Glu
                165                 170                 175 gga gcc gtg gag gtg aag tat gag ggc cac tgg cgg cag gtg tgt gac     576
Gly Ala Val Glu Val Lys Tyr Glu Gly His Trp Arg Gln Val Cys Asp
            180                 185                 190 cag ggc tgg acc atg aac aac agc agg gtg gtg tgc ggg atg ctg ggc     624
Gln Gly Trp Thr Met Asn Asn Ser Arg Val Val Cys Gly Met Leu Gly
        195                 200                 205 ttc ccc agc gag gtg cct gtc gac agc cac tac tac agg aaa gtc tgg     672
Phe Pro Ser Glu Val Pro Val Asp Ser His Tyr Tyr Arg Lys Val Trp
    210                 215                 220 gat ctg aag atg agg gac cct aag tct agg ctg aag agc ctg acg aat     720
Asp Leu Lys Met Arg Asp Pro Lys Ser Arg Leu Lys Ser Leu Thr Asn
225                 230                 235                 240 aag aac tcc ttc tgg atc cac cag gtc acc tgc ctg ggg aca gag ccc     768
Lys Asn Ser Phe Trp Ile His Gln Val Thr Cys Leu Gly Thr Glu Pro
                245                 250                 255 cac atg gcc aac tgc cag gtg cag gtg gct cca gcc cgg ggc aag ctg     816
His Met Ala Asn Cys Gln Val Gln Val Ala Pro Ala Arg Gly Lys Leu
            260                 265                 270
```

```
cgg cca gcc tgc cca ggt ggc atg cac gct gtg gtc agc tgt gtg gca      864
Arg Pro Ala Cys Pro Gly Gly Met His Ala Val Val Ser Cys Val Ala
        275                 280                 285 ggg cct cac ttc cgc cca ccg aag aca aag cca caa cgc aaa ggg tcc      912
Gly Pro His Phe Arg Pro Pro Lys Thr Lys Pro Gln Arg Lys Gly Ser
290                 295                 300 tgg gca gag gag ccg agg gtg cgc ctg cgc tcc ggg gcc cag gtg ggc      960
Trp Ala Glu Glu Pro Arg Val Arg Leu Arg Ser Gly Ala Gln Val Gly
305                 310                 315                 320 gag ggc cgg gtg gaa gtg ctc atg aac cgc cag tgg ggc acg gtc tgt     1008
Glu Gly Arg Val Glu Val Leu Met Asn Arg Gln Trp Gly Thr Val Cys
                325                 330                 335 gac cac agg tgg aac ctc atc tct gcc agt gtc gtg tgt cgt cag ctg     1056
Asp His Arg Trp Asn Leu Ile Ser Ala Ser Val Val Cys Arg Gln Leu
            340                 345                 350 ggc ttt ggc tct gct cgg gag gcc ctc ttt ggg gcc cgg ctg ggc caa     1104
Gly Phe Gly Ser Ala Arg Glu Ala Leu Phe Gly Ala Arg Leu Gly Gln
        355                 360                 365 ggg cta ggg ccc atc cac ctg agt gag gtg cgc tgc agg gga tat gag     1152
Gly Leu Gly Pro Ile His Leu Ser Glu Val Arg Cys Arg Gly Tyr Glu
370                 375                 380 cgg acc ctc agc gac tgc cct gcc ctg gaa ggg tcc cag aat ggt tgc     1200
Arg Thr Leu Ser Asp Cys Pro Ala Leu Glu Gly Ser Gln Asn Gly Cys
385                 390                 395                 400 caa cat gag aat gat gct gct gtc agg tgc aat gtc cct aac atg ggc     1248
Gln His Glu Asn Asp Ala Ala Val Arg Cys Asn Val Pro Asn Met Gly
                405                 410                 415 ttt cag aat cag gtg cgc ttg gct ggt ggg cgt atc cct gag gag ggg     1296
Phe Gln Asn Gln Val Arg Leu Ala Gly Gly Arg Ile Pro Glu Glu Gly
            420                 425                 430 cta ttg gag gtg cag gtg gag gtg aac ggg gtc cca cgc tgg ggg agc     1344
Leu Leu Glu Val Gln Val Glu Val Asn Gly Val Pro Arg Trp Gly Ser
        435                 440                 445 gtg tgc agt gaa aac tgg ggg ctc acc gaa gcc atg gtg gcc tgc cga     1392
Val Cys Ser Glu Asn Trp Gly Leu Thr Glu Ala Met Val Ala Cys Arg
450                 455                 460 cag ctc ggc ctg ggt ttt gcc atc cat gcc tac aag gaa acc tgg ttc     1440
Gln Leu Gly Leu Gly Phe Ala Ile His Ala Tyr Lys Glu Thr Trp Phe
465                 470                 475                 480 tgg tcg ggg acg cca agg gcc cag gag gtg gtg atg agt ggg gtg cgc     1488
Trp Ser Gly Thr Pro Arg Ala Gln Glu Val Val Met Ser Gly Val Arg
                485                 490                 495 tgc tca ggc aca gag ctg gcc ctg cag cag tgc cag agg cac ggg ccg     1536
Cys Ser Gly Thr Glu Leu Ala Leu Gln Gln Cys Gln Arg His Gly Pro
            500                 505                 510 gtg cac tgc tcc cac ggt ggc ggg cgc ttc ctg gct gga gtc tcc tgc     1584
Val His Cys Ser His Gly Gly Gly Arg Phe Leu Ala Gly Val Ser Cys
        515                 520                 525 atg gac agt gca cca gac ctg gtg atg aac gcc cag cta gtg cag gag     1632
Met Asp Ser Ala Pro Asp Leu Val Met Asn Ala Gln Leu Val Gln Glu
530                 535                 540 acg gcc tac ttg gag gac cgc ccg ctc agc cag ctg tat tgt gcc cac     1680
Thr Ala Tyr Leu Glu Asp Arg Pro Leu Ser Gln Leu Tyr Cys Ala His
545                 550                 555                 560 gag gag aac tgc ctc tcc aag tct gca gat cac atg gac tgg ccc tac     1728
Glu Glu Asn Cys Leu Ser Lys Ser Ala Asp His Met Asp Trp Pro Tyr
                565                 570                 575 gga tac cgc cgc cta ttg cgc ttc tcc aca cag atc tac aat ctg ggc     1776
Gly Tyr Arg Arg Leu Leu Arg Phe Ser Thr Gln Ile Tyr Asn Leu Gly
            580                 585                 590
```

```
cgg act gac ttt cgt cca aag act gga cgc gat agc tgg gtt tgg cac     1824
Arg Thr Asp Phe Arg Pro Lys Thr Gly Arg Asp Ser Trp Val Trp His
        595                 600                 605 cag tgc cac agg cat tac cac agc att gag gtc ttc acc cac tac gac     1872
Gln Cys His Arg His Tyr His Ser Ile Glu Val Phe Thr His Tyr Asp
    610                 615                 620 ctc ctc act ctc aat ggc tcc aag gtg gct gag ggg cac aag gcc agc     1920
Leu Leu Thr Leu Asn Gly Ser Lys Val Ala Glu Gly His Lys Ala Ser
625                 630                 635                 640 ttc tgt ctg gag gac aca aac tgc ccc aca gga ctg cag cgg cgc tac     1968
Phe Cys Leu Glu Asp Thr Asn Cys Pro Thr Gly Leu Gln Arg Arg Tyr
                645                 650                 655 gca tgt gcc aac ttt gga gaa cag gga gtg act gta ggc tgc tgg gac     2016
Ala Cys Ala Asn Phe Gly Glu Gln Gly Val Thr Val Gly Cys Trp Asp
            660                 665                 670 acc tac cgg cat gac att gat tgc cag tgg gtg gat atc aca gat gtg     2064
Thr Tyr Arg His Asp Ile Asp Cys Gln Trp Val Asp Ile Thr Asp Val
        675                 680                 685 ggc ccc ggg aat tat atc ttc cag gtg att gtg aac ccc cac tat gaa     2112
Gly Pro Gly Asn Tyr Ile Phe Gln Val Ile Val Asn Pro His Tyr Glu
    690                 695                 700 gtg gca gag tca gat ttc tcc aac aat atg ctg cag tgc cgc tgc aag     2160
Val Ala Glu Ser Asp Phe Ser Asn Asn Met Leu Gln Cys Arg Cys Lys
705                 710                 715                 720 tat gat ggg cac cgg gtc tgg ctg cac aac tgc cac aca ggg aat tca     2208
Tyr Asp Gly His Arg Val Trp Leu His Asn Cys His Thr Gly Asn Ser
                725                 730                 735 tac cca gcc aat gca gaa ctc tcc ctg gag cag gaa cag cgt ctc agg     2256
Tyr Pro Ala Asn Ala Glu Leu Ser Leu Glu Gln Glu Gln Arg Leu Arg
            740                 745                 750 aac aac ctc atc                                                     2268
Asn Asn Leu Ile
        755

<210> SEQ ID NO 32
<211> LENGTH: 9
<212> TYPE: PRT
<213> ORGANISM: Artificial Sequence
<220> FEATURE:
<223> OTHER INFORMATION: LSO signature motif
<220> FEATURE:
<221> NAME/KEY: VARIANT
<222> LOCATION: 2, 5
<223> OTHER INFORMATION: Xaa= any amino acid

<400> SEQUENCE: 32

Trp Xaa Trp His Xaa Cys His Tyr His
 1               5

<210> SEQ ID NO 33
<211> LENGTH: 3296
<212> TYPE: DNA
<213> ORGANISM: Homo sapiens
<220> FEATURE:
<221> NAME/KEY: CDS
<222> LOCATION: (217)...(2031)
<220> FEATURE:
<221> NAME/KEY: misc_feature
<222> LOCATION: 6, 21, 47
<223> OTHER INFORMATION: n = A,T,C or G

<400> SEQUENCE: 33
cgcgtncgcg tggcgyccsc gnmcgsgysg gcccccgcgt ccgggcngga crcgkggscg     60

-continued

| | |
|---|---|
| cggggagcag ctcgggactg aaccgagagg tgccgaagga accggcgggc cgcttgatcc | 120 |
| cgctgcagac gtaggagatg cctgggacaa ggaggccacc ttctcagggc aaaagaaaaa | 180 |

| | | |
|---|---|---|
| gaaggtgaca ggcgttgaga ccaccgaagg gaaccc atg gct agg atc agt ttt<br>                                                                  Met Ala Arg Ile Ser Phe<br>                                                                     1               5 | 234 |
| tcc tac ctc tgc cca gcc tcc tgg tac ttc act gtg ccc aca gtg agt<br>Ser Tyr Leu Cys Pro Ala Ser Trp Tyr Phe Thr Val Pro Thr Val Ser<br>              10                 15                 20 | 282 |
| cca ttt ctc cgt cag cgg gtg gca ttc ctg gga ctc ttc ttc ata tcc<br>Pro Phe Leu Arg Gln Arg Val Ala Phe Leu Gly Leu Phe Phe Ile Ser<br>       25                 30                 35 | 330 |
| tgt ctc ctt tta ctt atg tta atc ata gac ttt cga cat tgg agt gct<br>Cys Leu Leu Leu Leu Met Leu Ile Ile Asp Phe Arg His Trp Ser Ala<br>   40                 45                 50 | 378 |
| tca tta cca cga gat agg caa tac gaa agg tat ttg gct cga gta ggg<br>Ser Leu Pro Arg Asp Arg Gln Tyr Glu Arg Tyr Leu Ala Arg Val Gly<br>55                 60                 65                 70 | 426 |
| gag ctt gaa gct act gac act gaa gac cca aat ctg aat tat gga ctt<br>Glu Leu Glu Ala Thr Asp Thr Glu Asp Pro Asn Leu Asn Tyr Gly Leu<br>              75                 80                 85 | 474 |
| gtt gtt gac tgt ggc agc agt ggt tcc cgg att ttt gtt tat ttc tgg<br>Val Val Asp Cys Gly Ser Ser Gly Ser Arg Ile Phe Val Tyr Phe Trp<br>            90                 95                100 | 522 |
| cca aga cat aat ggg aac ccc cat gac ttg ctg gac atc aaa cag atg<br>Pro Arg His Asn Gly Asn Pro His Asp Leu Leu Asp Ile Lys Gln Met<br>     105                110                115 | 570 |
| aga gac cgc aac agc caa cca gtg gtt aaa aaa atc aag cca gga atc<br>Arg Asp Arg Asn Ser Gln Pro Val Val Lys Lys Ile Lys Pro Gly Ile<br>120                  125                130 | 618 |
| tct gca atg gca gac act cca gaa cat gcc agt gat tac ctt cgt cct<br>Ser Ala Met Ala Asp Thr Pro Glu His Ala Ser Asp Tyr Leu Arg Pro<br>135                  140                145                150 | 666 |
| ctg ctg agc ttt gct gct gct cat gtg cct gtg aag aag cac aag gag<br>Leu Leu Ser Phe Ala Ala Ala His Val Pro Val Lys Lys His Lys Glu<br>              155                160                165 | 714 |
| acc cct ctt tac atc ctc tgc aca gca ggc atg agg ctt ctc cct gag<br>Thr Pro Leu Tyr Ile Leu Cys Thr Ala Gly Met Arg Leu Leu Pro Glu<br>                170                175                180 | 762 |
| agg aag cag ttg gct atc ttg gct gac cta gtg aaa gat tta cca ctg<br>Arg Lys Gln Leu Ala Ile Leu Ala Asp Leu Val Lys Asp Leu Pro Leu<br>            185                190                195 | 810 |
| gag ttt gac ttc ctc ttt tca cag tct caa gca gaa gtg atc tct ggg<br>Glu Phe Asp Phe Leu Phe Ser Gln Ser Gln Ala Glu Val Ile Ser Gly<br>200                  205                210 | 858 |
| aag cag gaa ggg gtt tat gca tgg att gga atc aac ttt gtt ttg gga<br>Lys Gln Glu Gly Val Tyr Ala Trp Ile Gly Ile Asn Phe Val Leu Gly<br>215                  220                225                230 | 906 |
| aga ttc gac cac gag gat gaa tca gat gct gag gct acc cag gaa ttg<br>Arg Phe Asp His Glu Asp Glu Ser Asp Ala Glu Ala Thr Gln Glu Leu<br>              235                240                245 | 954 |
| gca gca gga cgg aga agg aca gta ggg ata ctg gat atg gga gga gcc<br>Ala Ala Gly Arg Arg Arg Thr Val Gly Ile Leu Asp Met Gly Gly Ala<br>            250                255                260 | 1002 |
| tct ctc caa att gct tat gaa gtt cct acc tca acc tct gtc ctt cct<br>Ser Leu Gln Ile Ala Tyr Glu Val Pro Thr Ser Thr Ser Val Leu Pro<br>            265                270                275 | 1050 |
| gca aag cag gaa gaa gct gcc aag atc ctg ctg gct gag ttc aac ctg<br>Ala Lys Gln Glu Glu Ala Ala Lys Ile Leu Leu Ala Glu Phe Asn Leu<br>280                  285                290 | 1098 |

```
                                                          -continued ggc tgt gat gtg caa cac act gaa cac gtg tac agg gtt tat gtc aca       1146
Gly Cys Asp Val Gln His Thr Glu His Val Tyr Arg Val Tyr Val Thr
295                 300                 305                 310 act ttt ctg ggt ttc gga ggc aac ttt gcc cgg cag cgc tac gaa gac       1194
Thr Phe Leu Gly Phe Gly Gly Asn Phe Ala Arg Gln Arg Tyr Glu Asp
                315                 320                 325 ctt gtt ctg aat gaa act ctt aac aaa aac aga ttg ctt ggt cag aag       1242
Leu Val Leu Asn Glu Thr Leu Asn Lys Asn Arg Leu Leu Gly Gln Lys
        330                 335                 340 aca ggt ctg agt ccc gac aat cca ttt ctg gat ccc tgc ctg cca gtg       1290
Thr Gly Leu Ser Pro Asp Asn Pro Phe Leu Asp Pro Cys Leu Pro Val
    345                 350                 355 gga ctc aca gat gtg gtg gag agg aac agc caa gtc tta cat gtc cga       1338
Gly Leu Thr Asp Val Val Glu Arg Asn Ser Gln Val Leu His Val Arg
360                 365                 370 gga aga gga gac tgg gtg tct tgt ggg gca atg ctg agc ccc ctg ctg       1386
Gly Arg Gly Asp Trp Val Ser Cys Gly Ala Met Leu Ser Pro Leu Leu
375                 380                 385                 390 gct cgc tcc aac acc agc cag gcc tca ctc aat ggc ata tat caa tcg       1434
Ala Arg Ser Asn Thr Ser Gln Ala Ser Leu Asn Gly Ile Tyr Gln Ser
                395                 400                 405 cct att gac ttc aac aac agc gag ttc tac ggc ttc tct gag ttt ttt       1482
Pro Ile Asp Phe Asn Asn Ser Glu Phe Tyr Gly Phe Ser Glu Phe Phe
        410                 415                 420 tat tgt aca gag gat gtg ttg cgc att ggt ggc cgc tac cat ggg cca       1530
Tyr Cys Thr Glu Asp Val Leu Arg Ile Gly Gly Arg Tyr His Gly Pro
    425                 430                 435 aca ttt gcc aag gct gct cag gat tac tgt ggc atg gct tgg tcg gta       1578
Thr Phe Ala Lys Ala Ala Gln Asp Tyr Cys Gly Met Ala Trp Ser Val
440                 445                 450 cta act cag aga ttc aag aat ggc ctc ttt tca tca cat gca gat gag       1626
Leu Thr Gln Arg Phe Lys Asn Gly Leu Phe Ser Ser His Ala Asp Glu
455                 460                 465                 470 cat cga ctc aaa tat cag tgt ttt aaa tcg gct tgg atg tac caa gtc       1674
His Arg Leu Lys Tyr Gln Cys Phe Lys Ser Ala Trp Met Tyr Gln Val
                475                 480                 485 tta cat gaa gga ttc cac ttt ccc tat gac tac cca aac ctg cgg aca       1722
Leu His Glu Gly Phe His Phe Pro Tyr Asp Tyr Pro Asn Leu Arg Thr
        490                 495                 500 gcc cag ctg gtg tat gac cga gag gtt cag tgg acg ctg gga gcc att       1770
Ala Gln Leu Val Tyr Asp Arg Glu Val Gln Trp Thr Leu Gly Ala Ile
    505                 510                 515 cta tat aaa aca cga ttc tta cca ctc agg gat ctt cgg cag gaa ggt       1818
Leu Tyr Lys Thr Arg Phe Leu Pro Leu Arg Asp Leu Arg Gln Glu Gly
520                 525                 530 gtc cga caa gcc cat ggt agc tgg ttc cgt ctc tcc ttt gta tac aac       1866
Val Arg Gln Ala His Gly Ser Trp Phe Arg Leu Ser Phe Val Tyr Asn
535                 540                 545                 550 cac tat ctc ttc ttt gcc tgt atc ctg gtg gtg cta ctg gcc atc ttc       1914
His Tyr Leu Phe Phe Ala Cys Ile Leu Val Val Leu Leu Ala Ile Phe
                555                 560                 565 cta tac ctt ctg cgg cta cgc cga att cac cac cga caa aca cga gcc       1962
Leu Tyr Leu Leu Arg Leu Arg Arg Ile His His Arg Gln Thr Arg Ala
        570                 575                 580 tca gct cca ttg gac ttg ctg tgg ctt gaa gag gtg gtg ccc atg atg       2010
Ser Ala Pro Leu Asp Leu Leu Trp Leu Glu Glu Val Val Pro Met Met
    585                 590                 595 gga gta cag gtg ggg ccg tga ggctggacca ggactagaga agcttgagca          2061
Gly Val Gln Val Gly Pro  *
```

```
                                                                        600
ccccgagtt gctgctcatt gaattcctcc actttcttat atagcctcag atgctgtgat    2121
gtctgacctt gtggatattt gcccttggaa tttctacttt actttctacc gtaattcctt    2181
ctccgtaccc aggtcttctc tgagagaagc tataatttaa tctgtgagga actaaatgac    2241
aggagattgg tgctaatacg ggggaccaag ctttgtccaa gtgaagcagg cttcgactcc    2301
ttctgagagg tctggtgtgt tcctagaatc tcaccttttc ttcccttgct aaagcatgaa    2361
gtttggcatt tggcacactg gaagcctggt tgaaatgaaa tttgtagcat ctgatacaaa    2421
gccagagaca ttctagcaag tgcagcagcc ccttctttct ctgtaacaga gatatcattt    2481
atgtggagat ccacaacctt aacagggat ccaagatctt tgcagttcaa tcgaccacat    2541
aggaatttcc aggcaccaaa atgatataac ttccttgctt ccttgacaaa gaagccatca    2601
tgggtgtgat ccaagatccc tgtcgtagtg ttgatgatgt tagtacatga ttttaaaggt    2661
tagaacccct tctaaatgaa tggtctgtgg aagattttag tatcttatct gatgcctggt    2721
atgatgagga tagaaaattt ttccattttt atgtgcctca caggctgttt gggcattaat    2781
tttgcttttt gagccttaag tgtgttagta ggatggagaa actgtgatgg ggactgggaa    2841
cctggatttg tctgatttta ggtcactgtt ccctgggcct gtttttgtga gcccttacac    2901
aggaagatat aaagagagtt ctttcatttc actgctaaaa tcagtatgta gtatggggaa    2961
tgtatttggg ttgtttttaa agaaaagggg aacagaatca ggagagtggg caaaggcaat    3021
aaaatcaaag ttcttattaa ttatttctga gaaatagaag tttctcaatt tatgactctt    3081
ggaatgtctg aaagggagca aatttggaat agatcaatct gttaataagc catctggcaa    3141
ctttcagaac ctctattaag agactgctga gtcacaaaca gcacttccat taatgaagcg    3201
agaggaaaag ccataataat tacatcttca cccactaccc ttccagagct ttgcttctcc    3261
tccacattta gccattaaat tgcatgagga tttct                              3296
```

<210> SEQ ID NO 34
<211> LENGTH: 604
<212> TYPE: PRT
<213> ORGANISM: Homo sapiens

<400> SEQUENCE: 34

Met Ala Arg Ile Ser Phe Ser Tyr Leu Cys Pro Ala Ser Trp Tyr Phe
 1               5                  10                  15

Thr Val Pro Thr Val Ser Pro Phe Leu Arg Gln Arg Val Ala Phe Leu
             20                  25                  30

Gly Leu Phe Phe Ile Ser Cys Leu Leu Leu Met Leu Ile Ile Asp
         35                  40                  45

Phe Arg His Trp Ser Ala Ser Leu Pro Arg Asp Arg Gln Tyr Glu Arg
     50                  55                  60

Tyr Leu Ala Arg Val Gly Glu Leu Glu Ala Thr Asp Thr Glu Asp Pro
 65                  70                  75                  80

Asn Leu Asn Tyr Gly Leu Val Val Asp Cys Gly Ser Ser Gly Ser Arg
                 85                  90                  95

Ile Phe Val Tyr Phe Trp Pro Arg His Asn Gly Asn Pro His Asp Leu
            100                 105                 110

Leu Asp Ile Lys Gln Met Arg Asp Arg Asn Ser Gln Pro Val Val Lys
        115                 120                 125

Lys Ile Lys Pro Gly Ile Ser Ala Met Ala Asp Thr Pro Glu His Ala
    130                 135                 140

-continued

```
Ser Asp Tyr Leu Arg Pro Leu Leu Ser Phe Ala Ala Ala His Val Pro
145                 150                 155                 160

Val Lys Lys His Lys Glu Thr Pro Leu Tyr Ile Leu Cys Thr Ala Gly
                165                 170                 175

Met Arg Leu Leu Pro Glu Arg Lys Gln Leu Ala Ile Leu Ala Asp Leu
            180                 185                 190

Val Lys Asp Leu Pro Leu Glu Phe Asp Phe Leu Phe Ser Gln Ser Gln
        195                 200                 205

Ala Glu Val Ile Ser Gly Lys Gln Glu Gly Val Tyr Ala Trp Ile Gly
    210                 215                 220

Ile Asn Phe Val Leu Gly Arg Phe Asp His Glu Asp Glu Ser Asp Ala
225                 230                 235                 240

Glu Ala Thr Gln Glu Leu Ala Ala Gly Arg Arg Thr Val Gly Ile
                245                 250                 255

Leu Asp Met Gly Gly Ala Ser Leu Gln Ile Ala Tyr Glu Val Pro Thr
            260                 265                 270

Ser Thr Ser Val Leu Pro Ala Lys Gln Glu Glu Ala Ala Lys Ile Leu
        275                 280                 285

Leu Ala Glu Phe Asn Leu Gly Cys Asp Val Gln His Thr Glu His Val
    290                 295                 300

Tyr Arg Val Tyr Val Thr Thr Phe Leu Gly Phe Gly Asn Phe Ala
305                 310                 315                 320

Arg Gln Arg Tyr Glu Asp Leu Val Leu Asn Glu Thr Leu Asn Lys Asn
                325                 330                 335

Arg Leu Leu Gly Gln Lys Thr Gly Leu Ser Pro Asp Asn Pro Phe Leu
            340                 345                 350

Asp Pro Cys Leu Pro Val Gly Leu Thr Asp Val Val Glu Arg Asn Ser
        355                 360                 365

Gln Val Leu His Val Arg Gly Arg Gly Asp Trp Val Ser Cys Gly Ala
    370                 375                 380

Met Leu Ser Pro Leu Leu Ala Arg Ser Asn Thr Ser Gln Ala Ser Leu
385                 390                 395                 400

Asn Gly Ile Tyr Gln Ser Pro Ile Asp Phe Asn Asn Ser Glu Phe Tyr
                405                 410                 415

Gly Phe Ser Glu Phe Phe Tyr Cys Thr Glu Asp Val Leu Arg Ile Gly
            420                 425                 430

Gly Arg Tyr His Gly Pro Thr Phe Ala Lys Ala Ala Gln Asp Tyr Cys
        435                 440                 445

Gly Met Ala Trp Ser Val Leu Thr Gln Arg Phe Lys Asn Gly Leu Phe
    450                 455                 460

Ser Ser His Ala Asp Glu His Arg Leu Lys Tyr Gln Cys Phe Lys Ser
465                 470                 475                 480

Ala Trp Met Tyr Gln Val Leu His Glu Gly Phe His Phe Pro Tyr Asp
                485                 490                 495

Tyr Pro Asn Leu Arg Thr Ala Gln Leu Val Tyr Asp Arg Glu Val Gln
            500                 505                 510

Trp Thr Leu Gly Ala Ile Leu Tyr Lys Thr Arg Phe Leu Pro Leu Arg
        515                 520                 525

Asp Leu Arg Gln Glu Gly Val Arg Gln Ala His Gly Ser Trp Phe Arg
    530                 535                 540

Leu Ser Phe Val Tyr Asn His Tyr Leu Phe Phe Ala Cys Ile Leu Val
545                 550                 555                 560

Val Leu Leu Ala Ile Phe Leu Tyr Leu Leu Arg Leu Arg Arg Ile His
```

His Arg Gln Thr Arg Ala Ser Ala Pro Leu Asp Leu Leu Trp Leu Glu
            565                 570                 575
Glu Val Val Pro Met Met Gly Val Gln Val Gly Pro
    580                 585                 590
         595                 600

<210> SEQ ID NO 35
<211> LENGTH: 1815
<212> TYPE: DNA
<213> ORGANISM: Homo sapiens
<220> FEATURE:
<221> NAME/KEY: CDS
<222> LOCATION: (1)...(1815)

<400> SEQUENCE: 35

```
atg gct agg atc agt ttt tcc tac ctc tgc cca gcc tcc tgg tac ttc      48
Met Ala Arg Ile Ser Phe Ser Tyr Leu Cys Pro Ala Ser Trp Tyr Phe
1               5                  10                  15 act gtg ccc aca gtg agt cca ttt ctc cgt cag cgg gtg gca ttc ctg      96
Thr Val Pro Thr Val Ser Pro Phe Leu Arg Gln Arg Val Ala Phe Leu
                20                  25                  30 gga ctc ttc ttc ata tcc tgt ctc ctt tta ctt atg tta atc ata gac     144
Gly Leu Phe Phe Ile Ser Cys Leu Leu Leu Leu Met Leu Ile Ile Asp
            35                  40                  45 ttt cga cat tgg agt gct tca tta cca cga gat agg caa tac gaa agg     192
Phe Arg His Trp Ser Ala Ser Leu Pro Arg Asp Arg Gln Tyr Glu Arg
        50                  55                  60 tat ttg gct cga gta ggg gag ctt gaa gct act gac act gaa gac cca     240
Tyr Leu Ala Arg Val Gly Glu Leu Glu Ala Thr Asp Thr Glu Asp Pro
65                  70                  75                  80 aat ctg aat tat gga ctt gtt gtt gac tgt ggc agc agt ggt tcc cgg     288
Asn Leu Asn Tyr Gly Leu Val Val Asp Cys Gly Ser Ser Gly Ser Arg
                85                  90                  95 att ttt gtt tat ttc tgg cca aga cat aat ggg aac ccc cat gac ttg     336
Ile Phe Val Tyr Phe Trp Pro Arg His Asn Gly Asn Pro His Asp Leu
            100                 105                 110 ctg gac atc aaa cag atg aga gac cgc aac agc caa cca gtg gtt aaa     384
Leu Asp Ile Lys Gln Met Arg Asp Arg Asn Ser Gln Pro Val Val Lys
        115                 120                 125 aaa atc aag cca gga atc tct gca atg gca gac act cca gaa cat gcc     432
Lys Ile Lys Pro Gly Ile Ser Ala Met Ala Asp Thr Pro Glu His Ala
    130                 135                 140 agt gat tac ctt cgt cct ctg ctg agc ttt gct gct gct cat gtg cct     480
Ser Asp Tyr Leu Arg Pro Leu Leu Ser Phe Ala Ala Ala His Val Pro
145                 150                 155                 160 gtg aag aag cac aag gag acc cct ctt tac atc ctc tgc aca gca ggc     528
Val Lys Lys His Lys Glu Thr Pro Leu Tyr Ile Leu Cys Thr Ala Gly
                165                 170                 175 atg agg ctt ctc cct gag agg aag cag ttg gct atc ttg gct gac cta     576
Met Arg Leu Leu Pro Glu Arg Lys Gln Leu Ala Ile Leu Ala Asp Leu
            180                 185                 190 gtg aaa gat tta cca ctg gag ttt gac ttc ctc ttt tca cag tct caa     624
Val Lys Asp Leu Pro Leu Glu Phe Asp Phe Leu Phe Ser Gln Ser Gln
        195                 200                 205 gca gaa gtg atc tct ggg aag cag gaa ggg gtt tat gca tgg att gga     672
Ala Glu Val Ile Ser Gly Lys Gln Glu Gly Val Tyr Ala Trp Ile Gly
    210                 215                 220 atc aac ttt gtt ttg gga aga ttc gac cac gag gat gaa tca gat gct     720
Ile Asn Phe Val Leu Gly Arg Phe Asp His Glu Asp Glu Ser Asp Ala
225                 230                 235                 240
```

-continued

| | | |
|---|---|---|
| gag gct acc cag gaa ttg gca gca gga cgg aga agg aca gta ggg ata<br>Glu Ala Thr Gln Glu Leu Ala Ala Gly Arg Arg Arg Thr Val Gly Ile<br>    245                 250                 255 | | 768 |
| ctg gat atg gga gga gcc tct ctc caa att gct tat gaa gtt cct acc<br>Leu Asp Met Gly Gly Ala Ser Leu Gln Ile Ala Tyr Glu Val Pro Thr<br>260                 265                 270 | | 816 |
| tca acc tct gtc ctt cct gca aag cag gaa gaa gct gcc aag atc ctg<br>Ser Thr Ser Val Leu Pro Ala Lys Gln Glu Glu Ala Ala Lys Ile Leu<br>            275                 280                 285 | | 864 |
| ctg gct gag ttc aac ctg ggc tgt gat gtg caa cac act gaa cac gtg<br>Leu Ala Glu Phe Asn Leu Gly Cys Asp Val Gln His Thr Glu His Val<br>290                 295                 300 | | 912 |
| tac agg gtt tat gtc aca act ttt ctg ggt ttc gga ggc aac ttt gcc<br>Tyr Arg Val Tyr Val Thr Thr Phe Leu Gly Phe Gly Gly Asn Phe Ala<br>305                 310                 315                 320 | | 960 |
| cgg cag cgc tac gaa gac ctt gtt ctg aat gaa act ctt aac aaa aac<br>Arg Gln Arg Tyr Glu Asp Leu Val Leu Asn Glu Thr Leu Asn Lys Asn<br>            325                 330                 335 | | 1008 |
| aga ttg ctt ggt cag aag aca ggt ctg agt ccc gac aat cca ttt ctg<br>Arg Leu Leu Gly Gln Lys Thr Gly Leu Ser Pro Asp Asn Pro Phe Leu<br>340                 345                 350 | | 1056 |
| gat ccc tgc ctg cca gtg gga ctc aca gat gtg gtg gag agg aac agc<br>Asp Pro Cys Leu Pro Val Gly Leu Thr Asp Val Val Glu Arg Asn Ser<br>            355                 360                 365 | | 1104 |
| caa gtc tta cat gtc cga gga aga gga gac tgg gtg tct tgt ggg gca<br>Gln Val Leu His Val Arg Gly Arg Gly Asp Trp Val Ser Cys Gly Ala<br>370                 375                 380 | | 1152 |
| atg ctg agc ccc ctg ctg gct cgc tcc aac acc agc cag gcc tca ctc<br>Met Leu Ser Pro Leu Leu Ala Arg Ser Asn Thr Ser Gln Ala Ser Leu<br>385                 390                 395                 400 | | 1200 |
| aat ggc ata tat caa tcg cct att gac ttc aac aac agc gag ttc tac<br>Asn Gly Ile Tyr Gln Ser Pro Ile Asp Phe Asn Asn Ser Glu Phe Tyr<br>            405                 410                 415 | | 1248 |
| ggc ttc tct gag ttt ttt tat tgt aca gag gat gtg ttg cgc att ggt<br>Gly Phe Ser Glu Phe Phe Tyr Cys Thr Glu Asp Val Leu Arg Ile Gly<br>420                 425                 430 | | 1296 |
| ggc cgc tac cat ggg cca aca ttt gcc aag gct gct cag gat tac tgt<br>Gly Arg Tyr His Gly Pro Thr Phe Ala Lys Ala Ala Gln Asp Tyr Cys<br>            435                 440                 445 | | 1344 |
| ggc atg gct tgg tcg gta cta act cag aga ttc aag aat ggc ctc ttt<br>Gly Met Ala Trp Ser Val Leu Thr Gln Arg Phe Lys Asn Gly Leu Phe<br>450                 455                 460 | | 1392 |
| tca tca cat gca gat gag cat cga ctc aaa tat cag tgt ttt aaa tcg<br>Ser Ser His Ala Asp Glu His Arg Leu Lys Tyr Gln Cys Phe Lys Ser<br>465                 470                 475                 480 | | 1440 |
| gct tgg atg tac caa gtc tta cat gaa gga ttc cac ttt ccc tat gac<br>Ala Trp Met Tyr Gln Val Leu His Glu Gly Phe His Phe Pro Tyr Asp<br>            485                 490                 495 | | 1488 |
| tac cca aac ctg cgg aca gcc cag ctg gtg tat gac cga gag gtt cag<br>Tyr Pro Asn Leu Arg Thr Ala Gln Leu Val Tyr Asp Arg Glu Val Gln<br>500                 505                 510 | | 1536 |
| tgg acg ctg gga gcc att cta tat aaa aca cga ttc tta cca ctc agg<br>Trp Thr Leu Gly Ala Ile Leu Tyr Lys Thr Arg Phe Leu Pro Leu Arg<br>            515                 520                 525 | | 1584 |
| gat ctt cgg cag gaa ggt gtc cga caa gcc cat ggt agc tgg ttc cgt<br>Asp Leu Arg Gln Glu Gly Val Arg Gln Ala His Gly Ser Trp Phe Arg<br>530                 535                 540 | | 1632 |
| ctc tcc ttt gta tac aac cac tat ctc ttc ttt gcc tgt atc ctg gtg<br>Leu Ser Phe Val Tyr Asn His Tyr Leu Phe Phe Ala Cys Ile Leu Val<br>545                 550                 555                 560 | | 1680 |

-continued

| | | |
|---|---|---|
| gtg cta ctg gcc atc ttc cta tac ctt ctg cgg cta cgc cga att cac<br>Val Leu Leu Ala Ile Phe Leu Tyr Leu Leu Arg Leu Arg Arg Ile His<br>                      565                    570                    575 | 1728 |

```
gtg cta ctg gcc atc ttc cta tac ctt ctg cgg cta cgc cga att cac    1728
Val Leu Leu Ala Ile Phe Leu Tyr Leu Leu Arg Leu Arg Arg Ile His
                565                 570                 575 cac cga caa aca cga gcc tca gct cca ttg gac ttg ctg tgg ctt gaa    1776
His Arg Gln Thr Arg Ala Ser Ala Pro Leu Asp Leu Leu Trp Leu Glu
            580                 585                 590 gag gtg gtg ccc atg atg gga gta cag gtg ggg ccg tga                1815
Glu Val Val Pro Met Met Gly Val Gln Val Gly Pro *
        595                 600

<210> SEQ ID NO 36
<211> LENGTH: 1154
<212> TYPE: DNA
<213> ORGANISM: Homo sapiens
<220> FEATURE:
<221> NAME/KEY: CDS
<222> LOCATION: (22)..(870)

<400> SEQUENCE: 36
cggacgcgtg ggtccgtgac c atg aag gtc aag gtc atc ccc gtg ctc gag    51
                       Met Lys Val Lys Val Ile Pro Val Leu Glu
                         1               5                  10 gac aac tac atg tac ctg gtc atc gag gag ctc acg cgc gag gcg gtg    99
Asp Asn Tyr Met Tyr Leu Val Ile Glu Glu Leu Thr Arg Glu Ala Val
                15                  20                  25 gcc gtg gac gtg gct gtg ccc aag agg ctg ctg gag atc gtg ggc cgg    147
Ala Val Asp Val Ala Val Pro Lys Arg Leu Leu Glu Ile Val Gly Arg
            30                  35                  40 gag ggg gtg tct ctg acc gct gtg ctg acc acc cac cat cac tgg gac    195
Glu Gly Val Ser Leu Thr Ala Val Leu Thr Thr His His His Trp Asp
        45                  50                  55 cac gcg cgg gga aac ccg gag ctg gcg cgg ctt cgt ccc ggg ctg gcg    243
His Ala Arg Gly Asn Pro Glu Leu Ala Arg Leu Arg Pro Gly Leu Ala
    60                  65                  70 gtg ctg ggc gcg gac gag cgc atc ttc tcg ctg acg cgc agg ctg gcg    291
Val Leu Gly Ala Asp Glu Arg Ile Phe Ser Leu Thr Arg Arg Leu Ala
75                  80                  85                  90 cac ggc gag gag ctg cgg ttc ggg gcc atc cac gtg cgt tgc ctc ctg    339
His Gly Glu Glu Leu Arg Phe Gly Ala Ile His Val Arg Cys Leu Leu
                95                 100                 105 acg ccc ggc cac acc gcc ggc cac atg agc tac ttc ctg tgg gag gac    387
Thr Pro Gly His Thr Ala Gly His Met Ser Tyr Phe Leu Trp Glu Asp
            110                 115                 120 gat tgc ccg gac cca ccc gcc ctg ttc tcg ggc gac gcg ctg tcg gtg    435
Asp Cys Pro Asp Pro Pro Ala Leu Phe Ser Gly Asp Ala Leu Ser Val
        125                 130                 135 gcc ggc tgc ggc tcg tgc ctg gag ggc agc gcc cag cag atg tac cag    483
Ala Gly Cys Gly Ser Cys Leu Glu Gly Ser Ala Gln Gln Met Tyr Gln
    140                 145                 150 agc ctg gcc gag ctg ggt acc ctg ccc ccc gag acg aag gtg ttc tgc    531
Ser Leu Ala Glu Leu Gly Thr Leu Pro Pro Glu Thr Lys Val Phe Cys
155                 160                 165                 170 ggc cac gag cac acg ctt agc aac ctg gag ttt gcc cag aaa gtg gag    579
Gly His Glu His Thr Leu Ser Asn Leu Glu Phe Ala Gln Lys Val Glu
                175                 180                 185 ccc tgc aac gac cac gtg aga gcc aag ctg tcc tgg gct aag aag agg    627
Pro Cys Asn Asp His Val Arg Ala Lys Leu Ser Trp Ala Lys Lys Arg
            190                 195                 200 gat gag gat gac gtg ccc act gtg ccg tcg act ctg ggc gag gag cgc    675
Asp Glu Asp Asp Val Pro Thr Val Pro Ser Thr Leu Gly Glu Glu Arg
        205                 210                 215
```

```
ctc tac aac ccc ttc ctg cgg gtg gca gag gag ccg gtg cgc aag ttc      723
Leu Tyr Asn Pro Phe Leu Arg Val Ala Glu Glu Pro Val Arg Lys Phe
        220                 225                 230 acg ggc aag gcg gtc ccc gcc gac gtc ctg gag gcg cta tgc aag gag      771
Thr Gly Lys Ala Val Pro Ala Asp Val Leu Glu Ala Leu Cys Lys Glu
235                 240                 245                 250 cgg gcg cgc ttc gaa cag gcg ggc gag ccg cgg cag cca cag gcg cgg      819
Arg Ala Arg Phe Glu Gln Ala Gly Glu Pro Arg Gln Pro Gln Ala Arg
                    255                 260                 265 gcc ctc ctt gcg ctg cag tgg ggg ctc ctg agt gca gcc cca cac gac      867
Ala Leu Leu Ala Leu Gln Trp Gly Leu Leu Ser Ala Ala Pro His Asp
            270                 275                 280 tga ccacccaga ccctcacagg gctggggcct gcgtccctcc tcgtgacctc            920
ggccagctgg acccacatga gggccacctc tggaaccttc ttcgaggccc tggccagcca    980
tctgcccagc ctcggagggt gggcaacctg gtgcttcccg ggtggacaca caggaccact   1040
cagtggggcc tgtgtgggcg ccagacctg ggtgtctggg aagtgggca cacggggcct    1100 ccgaactatg aataaagctt tgaaagccgt tgtcaaaaaa aaaaaaaaa aaaa          1154

<210> SEQ ID NO 37
<211> LENGTH: 282
<212> TYPE: PRT
<213> ORGANISM: Homo sapiens

<400> SEQUENCE: 37

Met Lys Val Lys Val Ile Pro Val Leu Glu Asp Asn Tyr Met Tyr Leu
 1               5                  10                  15

Val Ile Glu Glu Leu Thr Arg Glu Ala Val Ala Val Asp Val Ala Val
                20                  25                  30

Pro Lys Arg Leu Leu Glu Ile Val Gly Arg Glu Gly Val Ser Leu Thr
            35                  40                  45

Ala Val Leu Thr Thr His His His Trp Asp His Ala Arg Gly Asn Pro
        50                  55                  60

Glu Leu Ala Arg Leu Arg Pro Gly Leu Ala Val Leu Gly Ala Asp Glu
 65                  70                  75                  80

Arg Ile Phe Ser Leu Thr Arg Arg Leu Ala His Gly Glu Glu Leu Arg
                85                  90                  95

Phe Gly Ala Ile His Val Arg Cys Leu Leu Thr Pro Gly His Thr Ala
            100                 105                 110

Gly His Met Ser Tyr Phe Leu Trp Glu Asp Asp Cys Pro Asp Pro Pro
        115                 120                 125

Ala Leu Phe Ser Gly Asp Ala Leu Ser Val Ala Gly Cys Gly Ser Cys
    130                 135                 140

Leu Glu Gly Ser Ala Gln Gln Met Tyr Gln Ser Leu Ala Glu Leu Gly
145                 150                 155                 160

Thr Leu Pro Pro Glu Thr Lys Val Phe Cys Gly His Glu His Thr Leu
                165                 170                 175

Ser Asn Leu Glu Phe Ala Gln Lys Val Glu Pro Cys Asn Asp His Val
            180                 185                 190

Arg Ala Lys Leu Ser Trp Ala Lys Lys Arg Asp Glu Asp Val Pro
        195                 200                 205

Thr Val Pro Ser Thr Leu Gly Glu Glu Arg Leu Tyr Asn Pro Phe Leu
    210                 215                 220

Arg Val Ala Glu Glu Pro Val Arg Lys Phe Thr Gly Lys Ala Val Pro
225                 230                 235                 240
```

```
Ala Asp Val Leu Glu Ala Leu Cys Lys Glu Arg Ala Arg Phe Glu Gln
            245                 250                 255

Ala Gly Glu Pro Arg Gln Pro Gln Ala Arg Ala Leu Leu Ala Leu Gln
        260                 265                 270

Trp Gly Leu Leu Ser Ala Ala Pro His Asp
        275                 280

<210> SEQ ID NO 38
<211> LENGTH: 846
<212> TYPE: DNA
<213> ORGANISM: Homo sapiens
<220> FEATURE:
<221> NAME/KEY: CDS
<222> LOCATION: (1)..(846)

<400> SEQUENCE: 38 atg aag gtc aag gtc atc ccc gtg ctc gag gac aac tac atg tac ctg        48
Met Lys Val Lys Val Ile Pro Val Leu Glu Asp Asn Tyr Met Tyr Leu
  1               5                  10                  15 gtc atc gag gag ctc acg cgc gag gcg gtg gcc gtg gac gtg gct gtg        96
Val Ile Glu Glu Leu Thr Arg Glu Ala Val Ala Val Asp Val Ala Val
             20                  25                  30 ccc aag agg ctg ctg gag atc gtg ggc cgg gag ggg gtg tct ctg acc       144
Pro Lys Arg Leu Leu Glu Ile Val Gly Arg Glu Gly Val Ser Leu Thr
         35                  40                  45 gct gtg ctg acc acc cac cat cac tgg gac cac gcg cgg gga aac ccg       192
Ala Val Leu Thr Thr His His His Trp Asp His Ala Arg Gly Asn Pro
     50                  55                  60 gag ctg gcg cgg ctt cgt ccc ggg ctg gcg gtg ctg ggc gcg gac gag       240
Glu Leu Ala Arg Leu Arg Pro Gly Leu Ala Val Leu Gly Ala Asp Glu
 65                  70                  75                  80 cgc atc ttc tcg ctg acg cgc agg ctg gcg cac ggc gag gag ctg cgg       288
Arg Ile Phe Ser Leu Thr Arg Arg Leu Ala His Gly Glu Glu Leu Arg
                 85                  90                  95 ttc ggg gcc atc cac gtg cgt tgc ctc ctg acg ccc ggc cac acc gcc       336
Phe Gly Ala Ile His Val Arg Cys Leu Leu Thr Pro Gly His Thr Ala
            100                 105                 110 ggc cac atg agc tac ttc ctg tgg gag gac gat tgc ccg gac cca ccc       384
Gly His Met Ser Tyr Phe Leu Trp Glu Asp Asp Cys Pro Asp Pro Pro
        115                 120                 125 gcc ctg ttc tcg ggc gac gcg ctg tcg gtg gcc ggc tgc ggc tcg tgc       432
Ala Leu Phe Ser Gly Asp Ala Leu Ser Val Ala Gly Cys Gly Ser Cys
    130                 135                 140 ctg gag ggc agc gcc cag cag atg tac cag agc ctg gcc gag ctg ggt       480
Leu Glu Gly Ser Ala Gln Gln Met Tyr Gln Ser Leu Ala Glu Leu Gly
145                 150                 155                 160 acc ctg ccc ccc gag acg aag gtg ttc tgc ggc cac gag cac acg ctt       528
Thr Leu Pro Pro Glu Thr Lys Val Phe Cys Gly His Glu His Thr Leu
                165                 170                 175 agc aac ctg gag ttt gcc cag aaa gtg gag ccc tgc aac gac cac gtg       576
Ser Asn Leu Glu Phe Ala Gln Lys Val Glu Pro Cys Asn Asp His Val
            180                 185                 190 aga gcc aag ctg tcc tgg gct aag aag agg gat gag gat gac gtg ccc       624
Arg Ala Lys Leu Ser Trp Ala Lys Lys Arg Asp Glu Asp Asp Val Pro
        195                 200                 205 act gtg ccg tcg act ctg ggc gag gag cgc ctc tac aac ccc ttc ctg       672
Thr Val Pro Ser Thr Leu Gly Glu Glu Arg Leu Tyr Asn Pro Phe Leu
    210                 215                 220 cgg gtg gca gag gag ccg gtg cgc aag ttc acg ggc aag gcg gtc ccc       720
Arg Val Ala Glu Glu Pro Val Arg Lys Phe Thr Gly Lys Ala Val Pro
```

-continued

```
             225                 230                 235                 240 gcc gac gtc ctg gag gcg cta tgc aag gag cgg gcg cgc ttc gaa cag      768
Ala Asp Val Leu Glu Ala Leu Cys Lys Glu Arg Ala Arg Phe Glu Gln
                245                 250                 255 gcg ggc gag ccg cgg cag cca cag gcg cgg gcc ctc ctt gcg ctg cag      816
Ala Gly Glu Pro Arg Gln Pro Gln Ala Arg Ala Leu Leu Ala Leu Gln
                260                 265                 270 tgg ggg ctc ctg agt gca gcc cca cac gac                              846
Trp Gly Leu Leu Ser Ala Ala Pro His Asp
            275                 280

<210> SEQ ID NO 39
<211> LENGTH: 1791
<212> TYPE: DNA
<213> ORGANISM: Homo sapiens
<220> FEATURE:
<221> NAME/KEY: CDS
<222> LOCATION: (128)...(1225)

<400> SEQUENCE: 39
gaaaactgaa agccggaccc caggccgccg cgctgccgcc cggcctcccc gccagcgcgc     60
caccatgggc agtcccggtt tccccttgta aagatggcgg tgagggatcg ctgcaacctt    120 tagacta atg act gtc cga aac atc gcc tcc atc tgt aat atg ggc acc      169
        Met Thr Val Arg Asn Ile Ala Ser Ile Cys Asn Met Gly Thr
          1               5                  10 aat gcc tct gct ctg gaa aaa gac att ggt cca gag cag ttt cca atc      217
Asn Ala Ser Ala Leu Glu Lys Asp Ile Gly Pro Glu Gln Phe Pro Ile
 15                  20                  25                  30 aat gaa cac tat ttc gga ttg gtc aat ttt gga aac aca tgc tac tgt      265
Asn Glu His Tyr Phe Gly Leu Val Asn Phe Gly Asn Thr Cys Tyr Cys
                 35                  40                  45 aac tcc gtg ctt cag gca ttg tac ttc tgc cgt cca ttc cgg gag aat      313
Asn Ser Val Leu Gln Ala Leu Tyr Phe Cys Arg Pro Phe Arg Glu Asn
             50                  55                  60 gtg ttg gca tac aag gcc cag caa aag aag aag gaa aac ttg ctg acg      361
Val Leu Ala Tyr Lys Ala Gln Gln Lys Lys Lys Glu Asn Leu Leu Thr
         65                  70                  75 tgc ctg gcg gac ctt ttc cac agc att gcc aca cag aag aag aag gtt      409
Cys Leu Ala Asp Leu Phe His Ser Ile Ala Thr Gln Lys Lys Lys Val
     80                  85                  90 ggc gtc atc cca cca aag aag ttc att tca agg ctg aga aaa gag aat      457
Gly Val Ile Pro Pro Lys Lys Phe Ile Ser Arg Leu Arg Lys Glu Asn
 95                 100                 105                 110 gat ctc ttt gat aac tac atg cag cag gat gct cat gaa ttt tta aat      505
Asp Leu Phe Asp Asn Tyr Met Gln Gln Asp Ala His Glu Phe Leu Asn
                115                 120                 125 tat ttg cta aac act att gcg gac atc ctt cag gag gag aag aaa cag      553
Tyr Leu Leu Asn Thr Ile Ala Asp Ile Leu Gln Glu Glu Lys Lys Gln
            130                 135                 140 gaa aaa caa aat gga aaa tta aaa aat ggc aac atg aac gaa cct gcg      601
Glu Lys Gln Asn Gly Lys Leu Lys Asn Gly Asn Met Asn Glu Pro Ala
        145                 150                 155 gaa aat aat aaa cca gaa ctc acc tgg gtc cat gag att ttt cag gga      649
Glu Asn Asn Lys Pro Glu Leu Thr Trp Val His Glu Ile Phe Gln Gly
    160                 165                 170 acg ctt acc aat gaa act cga tgc ttg aac tgt gaa act gtt agt agc      697
Thr Leu Thr Asn Glu Thr Arg Cys Leu Asn Cys Glu Thr Val Ser Ser
175                 180                 185                 190 aaa gat gaa gat ttt ctt gac ctt tct gtt gat gtg gag cag aat aca      745
Lys Asp Glu Asp Phe Leu Asp Leu Ser Val Asp Val Glu Gln Asn Thr
```

```
                195                 200                 205
tcc att acc cac tgt cta aga gac ttc agc aac aca gaa aca ctg tgt       793
Ser Ile Thr His Cys Leu Arg Asp Phe Ser Asn Thr Glu Thr Leu Cys
            210                 215                 220 agt gaa caa aaa tat tat tgt gaa aca tgc tgc agc aaa caa gaa gcc       841
Ser Glu Gln Lys Tyr Tyr Cys Glu Thr Cys Cys Ser Lys Gln Glu Ala
            225                 230                 235 cag aaa agg atg agg gta aaa aag ctg ccc atg atc ttg gcc ctg cac       889
Gln Lys Arg Met Arg Val Lys Lys Leu Pro Met Ile Leu Ala Leu His
    240                 245                 250 cta aag cgg ttc aag tac atg gag cag ctg cac aga tac acc aag ctg       937
Leu Lys Arg Phe Lys Tyr Met Glu Gln Leu His Arg Tyr Thr Lys Leu
255                 260                 265                 270 tct tac cgt gtg gtc ttc cct ctg gaa ctc cgg ctc ttc aac acc tcc       985
Ser Tyr Arg Val Val Phe Pro Leu Glu Leu Arg Leu Phe Asn Thr Ser
                275                 280                 285 agt gat gca gtg aac ctg gac cgc atg tat gac ttg gtt gcg gtg gtc      1033
Ser Asp Ala Val Asn Leu Asp Arg Met Tyr Asp Leu Val Ala Val Val
            290                 295                 300 gtt cac tgt ggc agt ggt cct aat cgt ggg cat tat atc act att gtg      1081
Val His Cys Gly Ser Gly Pro Asn Arg Gly His Tyr Ile Thr Ile Val
        305                 310                 315 aaa agt cac ggc ttc tgg ctt ttg ttt gat gat gac att gta gag aaa      1129
Lys Ser His Gly Phe Trp Leu Leu Phe Asp Asp Asp Ile Val Glu Lys
    320                 325                 330 ata gat gct caa gct att gaa gaa ttc tat ggc ctg acg tca gat ata      1177
Ile Asp Ala Gln Ala Ile Glu Glu Phe Tyr Gly Leu Thr Ser Asp Ile
335                 340                 345                 350 tca aaa aat tca gaa tct gga tat att tta ttc tat cag tca aga gag      1225
Ser Lys Asn Ser Glu Ser Gly Tyr Ile Leu Phe Tyr Gln Ser Arg Glu
                355                 360                 365 taactgaaag acctgcggga ctgattcacg tggggagaat gttcacagca ctgtcacccg    1285
gcttctccgc aggctttcct cttccccagt ggcccactaa tggtatcact ccgagtctca    1345
atggtctggc tgtgttagac tctctccttt tgtgttttta catgcagcac tactcttggt    1405
tttatttcag tctgacatag agttaactgc aatcagattg tagtctgatt tatatgaata    1465
acggttgcta atttaggac tgggtgaaag ctatgccatt cattatgtct ggctgtatta     1525
gaatgacatt tcctatgaat gtctacggtc tgttttaggt gtttgctaaa cttctatggc    1585
ttccagggtc ttcttacaat gcattccttt aacttgtccc tggaagcatt gctacccatt    1645
ttcagcttct ctgcctctct tctgatacaa ggacagaaga attgggtaga tattcacctt    1705 ttagggggtgc aagtatagct ttaagtttgt gcaagtgaaa atgttgaaaa gtgagtaacc    1765
tcgatattaa aatcatcctt gacatg                                         1791

<210> SEQ ID NO 40
<211> LENGTH: 366
<212> TYPE: PRT
<213> ORGANISM: Homo sapiens

<400> SEQUENCE: 40

Met Thr Val Arg Asn Ile Ala Ser Ile Cys Asn Met Gly Thr Asn Ala
 1               5                  10                  15

Ser Ala Leu Glu Lys Asp Ile Gly Pro Glu Gln Phe Pro Ile Asn Glu
            20                  25                  30

His Tyr Phe Gly Leu Val Asn Phe Gly Asn Thr Cys Tyr Cys Asn Ser
        35                  40                  45
```

```
Val Leu Gln Ala Leu Tyr Phe Cys Arg Pro Phe Arg Glu Asn Val Leu
     50                  55                  60

Ala Tyr Lys Ala Gln Gln Lys Lys Glu Asn Leu Leu Thr Cys Leu
 65              70                  75                  80

Ala Asp Leu Phe His Ser Ile Ala Thr Gln Lys Lys Val Gly Val
                 85                  90                  95

Ile Pro Pro Lys Lys Phe Ile Ser Arg Leu Arg Lys Glu Asn Asp Leu
                100                 105                 110

Phe Asp Asn Tyr Met Gln Gln Asp Ala His Glu Phe Leu Asn Tyr Leu
            115                 120                 125

Leu Asn Thr Ile Ala Asp Ile Leu Gln Glu Glu Lys Lys Gln Glu Lys
    130                 135                 140

Gln Asn Gly Lys Leu Lys Asn Gly Asn Met Asn Glu Pro Ala Glu Asn
145                 150                 155                 160

Asn Lys Pro Glu Leu Thr Trp Val His Glu Ile Phe Gln Gly Thr Leu
                165                 170                 175

Thr Asn Glu Thr Arg Cys Leu Asn Cys Glu Thr Val Ser Ser Lys Asp
                180                 185                 190

Glu Asp Phe Leu Asp Leu Ser Val Asp Val Glu Gln Asn Thr Ser Ile
            195                 200                 205

Thr His Cys Leu Arg Asp Phe Ser Asn Thr Glu Thr Leu Cys Ser Glu
    210                 215                 220

Gln Lys Tyr Tyr Cys Glu Thr Cys Cys Ser Lys Gln Glu Ala Gln Lys
225                 230                 235                 240

Arg Met Arg Val Lys Lys Leu Pro Met Ile Leu Ala Leu His Leu Lys
                245                 250                 255

Arg Phe Lys Tyr Met Glu Gln Leu His Arg Tyr Thr Lys Leu Ser Tyr
                260                 265                 270

Arg Val Val Phe Pro Leu Glu Leu Arg Leu Phe Asn Thr Ser Ser Asp
            275                 280                 285

Ala Val Asn Leu Asp Arg Met Tyr Asp Leu Val Ala Val Val His
    290                 295                 300

Cys Gly Ser Gly Pro Asn Arg Gly His Tyr Ile Thr Ile Val Lys Ser
305                 310                 315                 320

His Gly Phe Trp Leu Leu Phe Asp Asp Ile Val Glu Lys Ile Asp
                325                 330                 335

Ala Gln Ala Ile Glu Glu Phe Tyr Gly Leu Thr Ser Asp Ile Ser Lys
            340                 345                 350

Asn Ser Glu Ser Gly Tyr Ile Leu Phe Tyr Gln Ser Arg Glu
    355                 360                 365

<210> SEQ ID NO 41
<211> LENGTH: 1098
<212> TYPE: DNA
<213> ORGANISM: Homo sapiens
<220> FEATURE:
<221> NAME/KEY: CDS
<222> LOCATION: (1)...(1098)

<400> SEQUENCE: 41 atg act gtc cga aac atc gcc tcc atc tgt aat atg ggc acc aat gcc    48
Met Thr Val Arg Asn Ile Ala Ser Ile Cys Asn Met Gly Thr Asn Ala
 1               5                  10                  15 tct gct ctg gaa aaa gac att ggt cca gag cag ttt cca atc aat gaa    96
Ser Ala Leu Glu Lys Asp Ile Gly Pro Glu Gln Phe Pro Ile Asn Glu
             20                  25                  30
```

```
cac tat ttc gga ttg gtc aat ttt gga aac aca tgc tac tgt aac tcc         144
His Tyr Phe Gly Leu Val Asn Phe Gly Asn Thr Cys Tyr Cys Asn Ser
             35                  40                  45 gtg ctt cag gca ttg tac ttc tgc cgt cca ttc cgg gag aat gtg ttg         192
Val Leu Gln Ala Leu Tyr Phe Cys Arg Pro Phe Arg Glu Asn Val Leu
     50                  55                  60 gca tac aag gcc cag caa aag aag aag gaa aac ttg ctg acg tgc ctg         240
Ala Tyr Lys Ala Gln Gln Lys Lys Lys Glu Asn Leu Leu Thr Cys Leu
 65                  70                  75                  80 gcg gac ctt ttc cac agc att gcc aca cag aag aag aag gtt ggc gtc         288
Ala Asp Leu Phe His Ser Ile Ala Thr Gln Lys Lys Lys Val Gly Val
                 85                  90                  95 atc cca cca aag aag ttc att tca agg ctg aga aaa gag aat gat ctc         336
Ile Pro Pro Lys Lys Phe Ile Ser Arg Leu Arg Lys Glu Asn Asp Leu
             100                 105                 110 ttt gat aac tac atg cag cag gat gct cat gaa ttt tta aat tat ttg         384
Phe Asp Asn Tyr Met Gln Gln Asp Ala His Glu Phe Leu Asn Tyr Leu
         115                 120                 125 cta aac act att gcg gac atc ctt cag gag gag aag aaa cag gaa aaa         432
Leu Asn Thr Ile Ala Asp Ile Leu Gln Glu Glu Lys Lys Gln Glu Lys
     130                 135                 140 caa aat gga aaa tta aaa aat ggc aac atg aac gaa cct gcg gaa aat         480
Gln Asn Gly Lys Leu Lys Asn Gly Asn Met Asn Glu Pro Ala Glu Asn
145                 150                 155                 160 aat aaa cca gaa ctc acc tgg gtc cat gag att ttt cag gga acg ctt         528
Asn Lys Pro Glu Leu Thr Trp Val His Glu Ile Phe Gln Gly Thr Leu
                 165                 170                 175 acc aat gaa act cga tgc ttg aac tgt gaa act gtt agt agc aaa gat         576
Thr Asn Glu Thr Arg Cys Leu Asn Cys Glu Thr Val Ser Ser Lys Asp
             180                 185                 190 gaa gat ttt ctt gac ctt tct gtt gat gtg gag cag aat aca tcc att         624
Glu Asp Phe Leu Asp Leu Ser Val Asp Val Glu Gln Asn Thr Ser Ile
         195                 200                 205 acc cac tgt cta aga gac ttc agc aac aca gaa aca ctg tgt agt gaa         672
Thr His Cys Leu Arg Asp Phe Ser Asn Thr Glu Thr Leu Cys Ser Glu
     210                 215                 220 caa aaa tat tat tgt gaa aca tgc tgc agc aaa caa gaa gcc cag aaa         720
Gln Lys Tyr Tyr Cys Glu Thr Cys Cys Ser Lys Gln Glu Ala Gln Lys
225                 230                 235                 240 agg atg agg gta aaa aag ctg ccc atg atc ttg gcc ctg cac cta aag         768
Arg Met Arg Val Lys Lys Leu Pro Met Ile Leu Ala Leu His Leu Lys
                 245                 250                 255 cgg ttc aag tac atg gag cag ctg cac aga tac acc aag ctg tct tac         816
Arg Phe Lys Tyr Met Glu Gln Leu His Arg Tyr Thr Lys Leu Ser Tyr
             260                 265                 270 cgt gtg gtc ttc cct ctg gaa ctc cgg ctc ttc aac acc tcc agt gat         864
Arg Val Val Phe Pro Leu Glu Leu Arg Leu Phe Asn Thr Ser Ser Asp
         275                 280                 285 gca gtg aac ctg gac cgc atg tat gac ttg gtt gcg gtg gtc gtt cac         912
Ala Val Asn Leu Asp Arg Met Tyr Asp Leu Val Ala Val Val His
     290                 295                 300 tgt ggc agt ggt cct aat cgt ggg cat tat atc act att gtg aaa agt         960
Cys Gly Ser Gly Pro Asn Arg Gly His Tyr Ile Thr Ile Val Lys Ser
305                 310                 315                 320 cac ggc ttc tgg ctt ttg ttt gat gat gac att gta gag aaa ata gat         1008
His Gly Phe Trp Leu Leu Phe Asp Asp Asp Ile Val Glu Lys Ile Asp
                 325                 330                 335 gct caa gct att gaa gaa ttc tat ggc ctg acg tca gat ata tca aaa         1056
Ala Gln Ala Ile Glu Glu Phe Tyr Gly Leu Thr Ser Asp Ile Ser Lys
             340                 345                 350
```

```
aat tca gaa tct gga tat att tta ttc tat cag tca aga gag          1098
Asn Ser Glu Ser Gly Tyr Ile Leu Phe Tyr Gln Ser Arg Glu
    355                 360                 365
```

What is claimed:

1. An isolated nucleic acid molecule selected from the group consisting of:
   (a) a nucleic acid molecule comprising the nucleotide sequence set forth in SEQ ID NO: 33, or the entire complement thereof; and
   (b) a nucleic acid molecule comprising the nucleotide sequence set forth in SEQ ID NO:35, or the entire complement thereof.

2. An isolated nucleic acid molecule comprising the nucleic acid molecule of claim 1, and a nucleotide sequence encoding a heterologous polypeptide.

3. A vector comprising the nucleic acid molecule of claim 1.

4. A host cell transfected with the vector of claim 3.

5. A method of producing a polypeptide comprising culturing the host cell of claim 4 in an appropriate culture medium to, thereby, produce the polypeptide.

6. An isolated nucleic acid molecule, or the entire complement thereof, wherein the nucleic acid molecule encodes a polypeptide comprising the amino acid sequence set forth in SEQ ID NO: 34.

7. An isolated nucleic acid molecule comprising the nucleic acid molecule of claim 6, and a nucleotide sequence encoding a heterologous polypeptide.

8. A vector comprising the nucleic acid molecule of claim 6.

9. A host cell transfected with the vector of claim 8.

10. A method of producing a polypeptide comprising culturing the host cell of claim 9 in an appropriate culture medium to, thereby, produce the polypeptide.

11. An isolated nucleic acid molecule selected from the group consisting of:
    (a) a nucleic acid molecule comprising a nucleotide sequence which is at least 95% identical to the nucleotide sequence of SEQ ID NO:33, SEQ ID NO:35, or the entire complement of either of the foregoing, wherein the nucleic acid molecule encodes a polypeptide having a nucleoside phosphatase family member-1 (NPM-1) activity;
    (b) a nucleic acid molecule comprising a nucleic acid sequence, or the entire complement thereof, wherein the nucleic acid sequence encodes a polypeptide comprising an amino acid sequence at least 95% identical to the amino acid sequence of SEQ ID NO: 34, wherein the polypeptide has an NPM-1 activity; and
    (c) a nucleic acid molecule which hybridizes under hybridization conditions of 4×sodium chloride/sodium citrate (SSC), at 65–70° C. or 4×SSC plus 50% formamide at 42–50° C., followed by one or more washes in 1×SSC, at about 65–70° C., to the SEQ ID NO:33, SEQ ID NO:35, or the entire complement of either of the foregoing, wherein the nucleic acid molecule encodes a polypeptide which has an NPM-1 activity.

12. An isolated nucleic acid molecule comprising the nucleic acid molecule of claim 11, and a nucleotide sequence encoding a heterologous polypeptide.

13. A vector comprising the nucleic acid molecule of claim 11.

14. The vector of claim 13, which is an expression vector.

15. A host cell transfected with the expression vector of claim 14.

16. A method of producing a polypeptide comprising culturing the host cell of claim 15 in an appropriate culture medium to, thereby, produce the polypeptide.

17. An isolated nucleic acid molecule comprising a nucleic acid sequence encoding a polypeptide comprising the nucleoside phosphatase family domain of 62088, wherein the nucleoside phosphatase family domain of 62088 consists of amino acid residues 75–536 of SEQ ID NO:34, wherein the polypeptide has an NPM-1 activity.

18. The nucleic acid molecule of claim 17, further comprising sequences encoding a heterologous polypeptide.

19. An isolated nucleic acid molecule selected from the group consisting of:
    a) SEQ ID NQ:33;
    b) SEQ ID NO:35; and
    c) a nucleic acid encoding SEQ ID NQ:34.

20. A host cell in culture, wherein the host cell expresses the nucleic acid of claim 19.

21. A method for detecting the presence of a nucleic acid molecule of any one of claims 1, 6, or 11 in a sample comprising:
    a) contacting the sample with a nucleic acid probe or primer which selectively hybridizes under hybridization conditions of 4×sodium chloride/sodium citrate (SSC), at 65–70° C. or 4×SSC plus 50% formamide at 42–50° C. to the nucleic acid molecule; and
    b) determining whether the nucleic acid probe or primer binds to a nucleic acid molecule in the sample to thereby detect the presence of a nucleic acid molecule of any one of claims 1, 2, or 5 in the sample.

22. The method of claim 21, wherein the sample comprises mRNA molecules and is contacted with a nucleic acid probe.

23. A kit comprising a nucleic acid which selectively hybridizes under hybridization conditions of 4×sodium chloride/sodium citrate (SSC), at 65–70° C. or 4×SSC plus 50% formamide at 42–50° C. to a nucleic acid molecule of any one of claims 1, 6, or 11 and instructions for use.

* * * * *